US009783536B2

(12) United States Patent
Furuyama et al.

(10) Patent No.: US 9,783,536 B2
(45) Date of Patent: Oct. 10, 2017

(54) NITROGEN-CONTAINING HETEROCYCLIC COMPOUND OR SALT THEREOF

(71) Applicant: FUJIFILM Corporation, Minato-ku, Tokyo (JP)

(72) Inventors: Hidetomo Furuyama, Kanagawa (JP); Hideki Kurihara, Kanagawa (JP); Takahiro Terao, Kanagawa (JP); Daisuke Nakagawa, Kanagawa (JP); Shintaro Tanabe, Kanagawa (JP); Takayuki Kato, Kanagawa (JP); Masahiko Yamamoto, Kanagawa (JP); Shinichiro Sekine, Kanagawa (JP); Tomoyuki Mashiko, Kanagawa (JP); Shinsuke Inuki, Kanagawa (JP); Satoshi Ueda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/795,568

(22) Filed: Jul. 9, 2015

(65) Prior Publication Data

US 2015/0322063 A1 Nov. 12, 2015

Related U.S. Application Data

(63) Continuation of application No. PCT/JP2014/050873, filed on Jan. 14, 2014.

(30) Foreign Application Priority Data

Jan. 11, 2013 (JP) ................................. 2013-003832

(51) Int. Cl.
*C07D 519/00* (2006.01)
*C07D 471/04* (2006.01)

(52) U.S. Cl.
CPC ......... *C07D 471/04* (2013.01); *C07D 519/00* (2013.01)

(58) Field of Classification Search
CPC ........................... C07D 519/00; C07D 471/04
See application file for complete search history.

(56) References Cited

U.S. PATENT DOCUMENTS

| 6,180,631 | B1 | 1/2001 | McMahon et al. | |
| 6,727,252 | B1* | 4/2004 | McMahon ........... | C07D 471/04 514/249 |
| 2011/0150831 | A1 | 6/2011 | Schuster et al. | |
| 2012/0245178 | A1 | 9/2012 | Su et al. | |

FOREIGN PATENT DOCUMENTS

| EP | 1 990 342 A1 | 11/2008 |
| JP | 2001-518496 A | 10/2001 |
| JP | 2009-515854 A | 4/2009 |
| JP | 2016-506367 A | 3/2016 |
| WO | 99/17759 A2 | 4/1999 |
| WO | 2009/155156 A1 | 12/2009 |
| WO | 2011/064250 A1 | 6/2011 |
| WO | 2011/079804 A | 7/2011 |
| WO | 2014/074657 A1 | 5/2014 |

OTHER PUBLICATIONS

McMahon et al., 1999, caplus an 1999:244571.*
Gerlach et al., 2008, caplus an 2008:1399006.*
Bhide et al., caplus an 2014:786679, 2014.*
Hodgetts et al., Bioorganic & Medicinal Chemistry Letters, 2010, 20, 4359-4363.*
Cleator et al., Organic Process Research & Development, 2013, 17, 1561-1567.*
Jeffrey A. Engelman, et al., "Effective use of PI3K and MEK inhibitors to treat mutant *Kras* G12D and *PIK3CA* H1047R murine lung cancers", Nature medicine, Dec. 2008, pp. 1351-1356, vol. 14, No. 12.
Office Action dated Feb. 1, 2016, issued by the State Intellectual Property Office of the P.R.C. in corresponding Chinese Application No. 201480004295.8.
Extended European Search Report dated Sep. 22, 2015, from the European Patent Office in counterpart European Application No. 14737606.5.
Office Action dated May 24, 2016 from the Japanese Patent Office in counterpart Japanese Application No. 2014-556461.
Response to Extended European Search Report dated Apr. 18, 2016, submitted in counterpart European Application No. 14737606.5.
Office Action dated Oct. 24, 2016 from the State Intellectual Property Office of the P.R.C. in counterpart Chinese Application No. 201480004295.8.
Office Action dated Nov. 28, 2016, from the Russian Patent Office in corresponding Russian Application No. 2015127995/04.
Marian Wozniak, et al., "Amination and Synthesis of Some Nitronaphthyridines", Liebigs Annalen der Chemie, 1993, pp. 471-475, No. 5.
Pixu Liu, et al., "Targeting the phosphoinositide 3-kinase pathway in cancer", Nature Reviews Drug Discovery, Aug. 2009, pp. 627-644, vol. 8.
Romina Marone, et al., "Targeting phosphoinositide 3-kinase—Moving towards therapy", Biochimica et Biophysica Acta, Oct. 12, 2007, pp. 159-185, vol. 1784, No. 1.

(Continued)

*Primary Examiner* — Sun Jae Yoo
(74) *Attorney, Agent, or Firm* — Sughrue Mion, PLLC

(57) ABSTRACT

A compound represented by Formula [1](in the formula, $Z^1$ represents N, CH, or the like; $X^1$ represents NH or the like; $R^1$ represents a heteroaryl group or the like; each of $R^2$, $R^3$, and $R^4$ represents a hydrogen atom, a halogen atom, an alkoxy group, or the like; and $R^5$ represents a heteroaryl group or the like) or salt thereof.

[1]

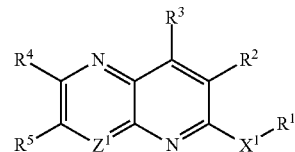

19 Claims, No Drawings

(56) References Cited

OTHER PUBLICATIONS

Jeremy L. Yap, et al., "Small Molecule Inhibitors of the ERK Signalling Pathway:Towards Novel Anti-cancer Therapeutics", ChemMedChem, Jan. 3, 2011, pp. 38-48, vol. 6, No. 1.

Ker Yu, et al., "Response and determinants of cancer cell susceptibility to P13K inhibitors: Combined targeting of P13K and Mek1 as an effective anticancer strategy", Cancer Biology & Therapy, Feb. 4, 2008, pp. 307-315, vol. 7, No. 2.

Jeffrey A. Engelman, et al., "Effective use of P13K and MEK inhibitors to treat mutant *Kras* G12D and *PIK3CA* H1047R murine lung cancers", Nature medicine, Dec. 2008, pp. 1351-1356, vol. 14, No. 12.

International Search Report for PCT/JP2014/050873 dated Feb. 10, 2014 [PCT/ISA/210], 7 pages in English and Japanese.

Written Opinion for PCT/JP2014/050873 dated Feb. 10, 2014 [PCT/ISA/237].

International Preliminary Report on Patentability for PCT/JP2014/050873 dated Apr. 22, 2015 [PCT/IPEA/409], 10 pages in English and Japanese.

Office Action dated Apr. 19, 2017, from the European Patent Office in counterpart European Application No. 14 737 606.5.

\* cited by examiner

NITROGEN-CONTAINING HETEROCYCLIC COMPOUND OR SALT THEREOF

CROSS-REFERENCE TO RELATED APPLICATIONS

This application is a continuation application of International Application No. PCT/JP2014/050873, filed Jan. 14, 2014, which is incorporated herein by reference. Further, this application claims priority from Japanese Patent Application No. 2013-003832, filed Jan. 11, 2013, which is incorporated herein by reference.

TECHNICAL FIELD

The present invention relates to a nitrogen-containing heterocyclic compound or salt thereof.

BACKGROUND ART

The PI3K (phosphatidylinositol 3-kinase)-AKT(protein kinase B) pathway is an important signal transduction pathway that plays a central role in cell growth, proliferation, differentiation, invasion, migration, apoptosis, glucose metabolism, or the like. It is known that the PI3K-AKT pathway is constantly activated in plural malignant tumors (Nature Reviews Drug Discovery, Vol. 8, No. 8, pp. 627-644, 2009) by activation of a receptor on the upstream of the PI3K-AKT pathway, or mutation, defect, or amplification of molecules constituting the PI3K-AKT pathway.

It is reported that the PI3K-AKT pathway is involved in not only malignant tumors but also in other diseases, for example, a cell proliferative disease, an allergic disease, an autoimmune disease, a neurodegenerative disease, a circulatory system disease, an inflammatory disease, an endocrine disorder, a metabolic disorder, or an infection (Biochimica et Biophysica Acta Vol. 1784, No. 1, pp. 159-185, 2008).

Therefore, it is considered that regulating the PI3K-AKT pathway is beneficial in a treatment for various diseases.

In addition, the Ras-Raf-MEK (MAP kinase kinase)-ERK (extracellular signal-regulated kinase) pathway is located on the downstream of various receptors, and plays an important role in cell physiological functions, for example, cell proliferation, apoptosis, or cell differentiation (ChemMedChem Vol. 6, No. 1, pp. 38-48, 2011).

Examples of diseases in which the Ras-Raf-MEK-ERK pathway is involved include a malignant tumor, an allergic disease, an autoimmune disease, a neurodegenerative disease, and a circulatory system disease.

Therefore, it is expected that regulating the Ras-Raf-MEK-ERK pathway is beneficial in a treatment for various diseases.

Here, it is reported that the PI3K-AKT pathway and the Ras-Raf-MEK-ERK pathway complementarily functions regarding cell proliferation, and regulating both the pathways at the same time is beneficial in a treatment for malignant tumors (Cancer Biology & Therapy Vol. 7, No. 2, pp. 307-315, 2008 and Nature medicine, Vol. 14, No. 12, pp. 1351-1356, 2008).

In the treatment of diseases, since the PI3K-AKT pathway and the Ras-Raf-MEK-ERK pathway are very important, PI3K-AKT pathway inhibitors or Ras-Raf-MEK-ERK pathway inhibitors have been developed thus far. However, the number thereof which became commercially available is very small (Pamphlet of International Publication No. WO2011/064250). In addition, regarding compounds that inhibit both the signal pathways directly and at the same time, there are only a few reports (Japanese National-Phase Publication (JP-A) No. 2009-515854) thus far.

On the other hand, 1,5-naphthyridine derivatives having a urea structure in the molecule that inhibits AurolaB, the Ras-Raf-MEK-ERK pathway, and Erk2 have been known (Pamphlet of International Publication No. WO2011/064250).

SUMMARY OF INVENTION

Technical Problem

A compound or a pharmaceutical composition having excellent inhibitory activity with respect to the PI3K-AKT pathway and/or the Ras-Raf-MEK-ERK pathway is desired.

Solution to Problem

Under such circumstances, the present inventors have conducted extensive studies. As a result, they have found that the nitrogen-containing heterocyclic compound represented by the following Formula [1] or salt thereof has excellent inhibitory activity with respect to the PI3K-AKT pathway and/or the Ras-Raf-MEK-ERK pathway, and completed the invention.

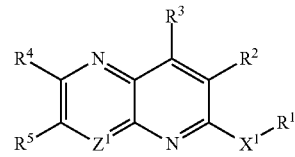

[1]

(In the formula:

$Z^1$ represents N or $CR^6$;

$R^6$ represents a hydrogen atom, a halogen atom, a hydroxyl group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted, a $C_{1-6}$ alkoxy group which may be substituted, an aryloxy group which may be substituted, a $C_{1-6}$ alkylthio group which may be substituted, an arylthio group which may be substituted, a heteroaryl group which may be substituted, a heteroaryloxy group which may be substituted, a heteroarylthio group which may be substituted, a heterocyclyl group which may be substituted, or $NR^7R^8$;

each of $R^7$ and $R^8$ independently represents a hydrogen atom, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted, a heteroaryl group which may be substituted, a heterocyclyl group which may be substituted, or an amino protecting group;

$X^1$ represents $NR^9$, O, S, or $CR^{10}R^{11}$;

$R^9$ represents a hydrogen atom, a $C_{1-6}$ alkyl group which may be substituted, or an amino protecting group;

each of $R^{10}$ and $R^{11}$ independently represents a hydrogen atom or a $C_{1-6}$ alkyl group which may be substituted;

$R^1$ represents a monocyclic nitrogen-containing heteroaryl group which may be substituted, a monocyclic nitrogen- and oxygen-containing heteroaryl group which may be substituted, a monocyclic nitrogen- and sulfur-containing heteroaryl group which may be substituted, a bicyclic nitrogen-containing heteroaryl group which may be substituted, a bicyclic nitrogen- and oxygen-containing heteroaryl group which may be substituted, or a bicyclic nitrogen- and sulfur-containing heteroaryl group which may be substituted;

$R^2$ represents a hydrogen atom or a halogen atom;

$R^3$ represents a hydrogen atom or a halogen atom;

$R^4$ represents a hydrogen atom, a halogen atom, an amino group which may be protected, a hydroxyl group which may be protected, a $C_{1-6}$ alkyl group which may be substituted, or a $C_{1-6}$ alkoxy group which may be substituted;

$R^5$ represents a hydrogen atom, a halogen atom, a hydroxyl group which may be protected, a carbamoyl group which may be substituted, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted, a $C_{1-6}$ alkoxy group which may be substituted, an aryloxy group which may be substituted, a $C_{1-6}$ alkylthio group which may be substituted, an arylthio group which may be substituted, a heteroaryl group which may be substituted, a heteroaryloxy group which may be substituted, a heteroarylthio group which may be substituted, a heterocyclyl group which may be substituted, or $NR^{12}R^{13}$;

each of $R^{12}$ and $R^{13}$ independently represents a hydrogen atom, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted, a heteroaryl group which may be substituted, a heterocyclyl group which may be substituted, or an amino-protecting group; and wherein, in a case in which $Z^1$ represents N and $R^4$ represents a hydrogen atom, $R^5$ represents a halogen atom, a hydroxyl group which may be protected, a carbamoyl group which may be substituted, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, an aryloxy group which may be substituted, a $C_{1-6}$ alkylthio group which may be substituted, an arylthio group which may be substituted, a heteroaryl group which may be substituted, a heteroaryloxy group which may be substituted, a heteroarylthio group which may be substituted, a heterocyclyl group which may be substituted, or $NR^{12}R^{13}$, and $R^{12}$ represents a hydrogen atom, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted, a heteroaryl group which may be substituted, a heterocyclyl group which may be substituted, or an amino protecting group, and $R^{13}$ represents a $C_{3-8}$ cycloalkyl group which may be substituted, an aryl group which may be substituted, a heteroaryl group which may be substituted, or a heterocyclyl group which may be substituted.)

Another aspect of the invention provides a pharmaceutical composition containing the nitrogen-containing heterocyclic compound or salt thereof of the invention, in particular, a pharmaceutical composition for treating a disease in which the PI3K and/or the ERK is involved, containing the nitrogen-containing heterocyclic compound or salt thereof of the invention, and a pharmaceutical composition for treating a disease selected from the group consisting of a malignant tumor, a cell proliferative disease, an allergic disease, an autoimmune disease, a neurodegenerative disease, a circulatory system disease, an inflammatory disease, an endocrine disorder, a metabolic disorder, and an infection, containing the nitrogen-containing heterocyclic compound or salt thereof of the invention.

Still another aspect of the invention provides an agent for treating a disease selected from the group consisting of a malignant tumor, a cell proliferative disease, an allergic disease, an autoimmune disease, a neurodegenerative disease, a circulatory system disease, an inflammatory disease, an endocrine disorder, a metabolic disorder, and an infection, containing the nitrogen-containing heterocyclic compound or salt thereof of the inventiond.

Still another aspect of the invention provides a PI3K and/or an ERK inhibitor containing the nitrogen-containing heterocyclic compound or salt thereof of the invention.

Still another aspect of the invention provides a prodrug of the nitrogen-containing heterocyclic compound or salt thereof of the invention.

Still another aspect of the invention provides a use of the nitrogen-containing heterocyclic compound or salt thereof of the invention for preparing of the pharmaceutical composition of the invention; a method of treating a disease in which the PI3K and/or the ERK is involved, the method including administering a therapeutically effective amount of the nitrogen-containing heterocyclic compound or salt thereof of the invention to a mammal including humans; and a method of treating a disease selected from the group consisting of a malignant tumor, a cell proliferative disease, an allergic disease, an autoimmune disease, a neurodegenerative disease, a circulatory system disease, an inflammatory disease, an endocrine disorder, a metabolic disorder, and an infection, the method including administering a therapeutically effective amount of the nitrogen-containing heterocyclic compound or salt thereof of the invention to a mammal including humans.

That is, the invention is as follows.

(1) A nitrogen-containing heterocyclic compound represented by Formula [1] or salt thereof.

(2) The nitrogen-containing heterocyclic compound or salt thereof according to (1), in which $R^4$ represents a hydrogen atom, a halogen atom, an amino group which may be protected, or a $C_{1-6}$ alkoxy group which may be substituted.

(3) The nitrogen-containing heterocyclic compound or salt thereof according to (1) or (2), in which $Z^1$ represents $CR^6$ (in the formula, $R^6$ has the same meaning as that described above).

(4) The nitrogen-containing heterocyclic compound or salt thereof according to any one of (1) to (3), in which $R^2$ is a hydrogen atom.

(5) The nitrogen-containing heterocyclic compound or salt thereof according to any one of (1) to (4), in which $R^3$ is a hydrogen atom.

(6) The nitrogen-containing heterocyclic compound or salt thereof according to any one of (1) to (5), in which $X^1$ represents $NR^{9a}$ (in the formula, $R^{9a}$ represents a hydrogen atom or an amino protecting group) or S.

(7) The nitrogen-containing heterocyclic compound or salt thereof according to any one of (1) to (6), in which $R^1$ represents a pyrazolyl group which may be substituted, an imidazolyl group which may be substituted, a triazolyl group which may be substituted, a thiazolyl group which may be substituted, an oxadiazolyl group which may be substituted, a thiadiazolyl group which may be substituted, a pyridyl group which may be substituted, or a pyridazinyl group which may be substituted.

(8) The nitrogen-containing heterocyclic compound or salt thereof according to any one of (1) to (6), in which $R^1$ represents a pyrazolyl group which may be substituted with one or more substituents selected from a substituent group $A_1$, an imidazolyl group which may be substituted with one or more substituents selected from the substituent group $A_1$, a triazolyl group which may be substituted with one or more substituents selected from the substituent group $A_1$, a thiazolyl group which may be substituted with one or more substituents selected from the substituent group $A_1$, an oxadiazolyl group which may be substituted with one or more substituents selected from the substituent group $A_1$, a thiadiazolyl group which may be substituted with one or more substituents selected from the substituent group $A_1$, a pyridyl group which may be substituted with one or more substituents selected from the substituent group $A_1$, or a pyridazinyl group which may be substituted with one or more substituents selected from the substituent group $A_1$.

(9) The nitrogen-containing heterocyclic compound or salt thereof according to any one of (1) to (6), in which $R^1$ represents a pyrazolyl group which may be substituted with one or more substituents selected from a substituent group $\alpha_1$, an imidazolyl group which may be substituted with one or more substituents selected from the substituent group $\alpha_1$, a triazolyl group which may be substituted with one or more substituents selected from the substituent group $\alpha_1$, a thiazolyl group which may be substituted with one or more substituents selected from the substituent group $\alpha_1$, an oxadiazolyl group which may be substituted with one or more substituents selected from the substituent group $\alpha_1$, a thiadiazolyl group which may be substituted with one or more substituents selected from the substituent group $\alpha_1$, a pyridyl group which may be substituted with one or more substituents selected from the substituent group $\alpha_1$, or a pyridazinyl group which may be substituted with one or more substituents selected from the substituent group $\alpha_1$.

(10) The nitrogen-containing heterocyclic compound or salt thereof according to any one of (1) to (9), in which: $R^5$ represents a hydrogen atom or a halogen atom; and $Z^1$ represents $CR^{6a}$ (in the formula, $R^{6a}$ represents an aryl group which may be substituted, a heteroaryl group which may be substituted, a heterocyclyl group which may be substituted, or $NHR^{8a}$ (in the formula, $R^{8a}$ represents an aryl group which may be substituted, a heteroaryl group which may be substituted, or a heterocyclyl group which may be substituted)).

(11) The nitrogen-containing heterocyclic compound or salt thereof according to any one of (1) to (9), in which: $R^5$ represents a hydrogen atom or a halogen atom; and $Z^1$ represents $CR^{6b}$ (in the formula, $R^{6b}$ represents an aryl group which may be substituted with one or more substituents selected from a substituent group $\alpha_2$, a heteroaryl group which may be substituted with one or more substituents selected from the substituent group $\alpha_2$, a heterocyclyl group which may be substituted with one or more substituents selected from the substituent group $\alpha_2$, or $NHR^{8b}$ (in the formula, $R^{8b}$ represents an aryl group which may be substituted with one or more substituents selected from the substituent group $\alpha_2$, a heteroaryl group which may be substituted with one or more substituents selected from the substituent group $\alpha_2$, or a heterocyclyl group which may be substituted with one or more substituents selected from the substituent group $\alpha_2$)).

(12) The nitrogen-containing heterocyclic compound or salt thereof according to any one of (1) to (9), in which: $R^5$ represents a hydrogen atom or a halogen atom; and $Z^1$ represents $CR^{6c}$ (in the formula, $R^{6c}$ represents a phenyl group which may be substituted with one or more substituents selected from a substituent group $\alpha_2$, a pyrazolyl group which may be substituted with one or more substituents selected from the substituent group $\alpha_2$, a pyridyl group which may be substituted with one or more substituents selected from the substituent group $\alpha_2$, a pyrimidinyl group which may be substituted with one or more substituents selected from the substituent group $\alpha_2$, a pyrazinyl group which may be substituted with one or more substituents selected from the substituent group $\alpha_2$, a pyridazinyl group which may be substituted with one or more substituents selected from the substituent group $\alpha_2$, a morpholinyl group which may be substituted with one or more substituents selected from the substituent group $\alpha_2$, or $NHR^{8c}$ (in the formula, $R^{8c}$ represents a phenyl group which may be substituted with one or more substituents selected from the substituent group $\alpha_2$, a pyridyl group which may be substituted with one or more substituents selected from the substituent group $\alpha_2$, a pyrimidinyl group which may be substituted with one or more substituents selected from the substituent group $\alpha_2$, a pyrazinyl group which may be substituted with one or more substituents selected from the substituent group $\alpha_2$, or a pyridazinyl group which may be substituted with one or more substituents selected from the substituent group $\alpha_2$)).

(13) The nitrogen-containing heterocyclic compound or salt thereof according to any one of (1), (2), or (4) to (9), in which $Z^1$ represents N or $CR^{6d}$ (in the formula, $R^{6d}$ represents a hydrogen atom, a halogen atom, a $C_{1-6}$ alkyl group which may be substituted, a $C_{1-6}$ alkoxy group which may be substituted, or $NHR^{8d}$ (in the formula, $R^{8d}$ represents a hydrogen atom or a $C_{1-6}$ alkyl group which may be substituted)); and $R^5$ represents a $C_{3-8}$ cycloalkyl group which may be substituted, an aryl group which may be substituted, a heteroaryl group which may be substituted, a heterocyclyl group which may be substituted, or $NR^{12a}R^{13a}$ (in the formula, $R^{12a}$ represents a hydrogen atom or a $C_{1-6}$ alkyl group which may be substituted; and $R^{13a}$ represents a $C_{3-8}$ cycloalkyl group which may be substituted, an aryl group which may be substituted, a heteroaryl group which may be substituted, or a heterocyclyl group which may be substituted).

(14) The nitrogen-containing heterocyclic compound or salt thereof according to any one of (1), (2), or (4) to (9), in which: $Z^1$ represents N or CH; and $R^5$ represents a $C_{3-8}$ cycloalkyl group which may be substituted with one or more substituents selected from a substituent group $A_3$, an aryl group which may be substituted with one or more substituents selected from the substituent group $A_3$, a heteroaryl group which may be substituted with one or more substituents selected from the substituent group $A_3$, a heterocyclyl group which may be substituted with one or more substituents selected from the substituent group $A_3$, or $NR^{12b}R^{13b}$ (in the formula, $R^{12b}$ represents a hydrogen atom or a $C_{1-6}$ alkyl group; and $R^{13b}$ represents a $C_{3-8}$ cycloalkyl group which may be substituted with one or more substituents selected from the substituent group $A_3$, an aryl group which may be substituted with one or more substituents selected from the substituent group $A_3$, a heteroaryl group which may be substituted with one or more substituents selected from the substituent group $A_3$, or a heterocyclyl group which may be substituted with one or more substituents selected from the substituent group $A_3$).

(15) The nitrogen-containing heterocyclic compound or salt thereof according to any one of (1), (2), or (4) to (9), in which: $Z^1$ represents N or CH; and $R^5$ represents a $C_{3-8}$ cycloalkyl group which may be substituted with one or more substituents selected from a substituent group $\alpha_3$, an aryl group which may be substituted with one or more substituents selected from the substituent group $\alpha_3$, a heteroaryl group which may be substituted with one or more substituents selected from the substituent group $\alpha_3$, a heterocyclyl group which may be substituted with one or more substituents selected from the substituent group $\alpha_3$, or $NR^{12b}R^{13c}$ (in the formula, $R^{12b}$ represents a hydrogen atom or a $C_{1-6}$ alkyl group; and $R^{13c}$ represents a $C_{3-8}$ cycloalkyl group which may be substituted with one or more substituents selected from the substituent group $\alpha_3$, an aryl group which may be substituted with one or more substituents selected from the substituent group $\alpha_3$, a heteroaryl group which may be substituted with one or more substituents selected from the substituent group $\alpha_3$, or a heterocyclyl group which may be substituted with one or more substituents selected from the substituent group $\alpha_3$).

(16) The nitrogen-containing heterocyclic compound or salt thereof according to any one of (1), (2), or (4) to (9), in which: $Z^1$ represents N or CH; and $R^5$ represents a phenyl group which may be substituted with one or more substituents selected from a substituent group $\alpha_3$, a pyrazolyl group which may be substituted with one or more substituents selected from the substituent group $\alpha_3$, an isoxazolyl group which may be substituted with one or more substituents selected from the substituent group $\alpha_3$, a pyridyl group which may be substituted with one or more substituents selected from the substituent group $\alpha_3$, a pyrimidinyl group which may be substituted with one or more substituents selected from the substituent group $\alpha_3$, a pyrazinyl group which may be substituted with one or more substituents selected from the substituent group $\alpha_3$, a pyridazinyl group which may be substituted with one or more substituents selected from the substituent group $\alpha_3$, an azetidinyl which may be substituted with one or more substituents selected from the substituent group $\alpha_3$, a pyrrolidinyl group which may be substituted with one or more substituents selected from the substituent group $\alpha_3$, a piperidinyl group which may be substituted with one or more substituents selected from the substituent group $\alpha_3$, a piperazinyl group which may be substituted with one or more substituents selected from the substituent group $\alpha_3$, a morpholinyl group which may be substituted with one or more substituents selected from the substituent group $\alpha_3$, a homopiperazinyl group which may be substituted with one or more substituents selected from the substituent group $\alpha_3$, or $NR^{12b}R^{13d}$ (in the formula, $R^{13d}$ represents a phenyl group which may be substituted with one or more substituents selected from the substituent group $\alpha_3$, a pyrazolyl group which may be substituted with one or more substituents selected from the substituent group $\alpha_3$, an isoxazolyl group which may be substituted with one or more substituents selected from the substituent group $\alpha_3$, a pyridyl group which may be substituted with one or more substituents selected from the substituent group $\alpha_3$, a pyrimidinyl group which may be substituted with one or more substituents selected from the substituent group $\alpha_3$, a pyrazinyl group which may be substituted with one or more substituents selected from the substituent group $\alpha_3$, a pyridazinyl group which may be substituted with one or more substituents selected from the substituent group $\alpha_3$, a pyrrolidinyl group which may be substituted with one or more substituents selected from the substituent group $\alpha_3$, a piperidinyl group which may be substituted with one or more substituents selected from the substituent group $\alpha_3$, or a tetrahydropyridyl group which may be substituted with one or more substituents selected from the substituent group $\alpha_3$; and $R^{12b}$ has the same meaning as that described above).

(17) A nitrogen-containing heterocyclic compound represented by Formula [1a] or salt thereof.

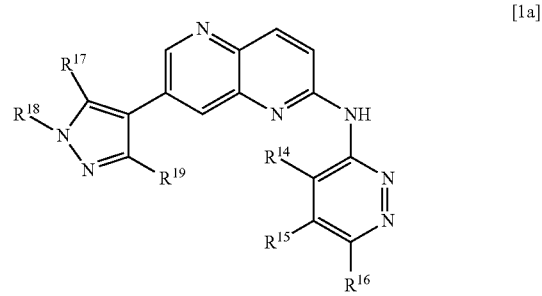

[1a]

(In the formula, each of $R^{14}$, $R^{15}$, and $R^{16}$ independently represents a hydrogen atom, a halogen atom, a hydroxyl group which may be protected, an amino group which may be protected, a carboxyl group which may be protected, a cyano group, a carbamoyl group which may be substituted with one or more substituents selected from a substituent group $B_1$, a sulfamoyl group which may be substituted with one or more substituents selected from the substituent group $B_1$, a $C_{1-6}$ alkyl group which may be substituted with one or more substituents selected from the substituent group $B_1$, a $C_{2-6}$ alkenyl group which may be substituted with one or more substituents selected from the substituent group $B_1$, a $C_{3-8}$ cycloalkyl group which may be substituted with one or more substituents selected from the substituent group $B_1$, an aryl group which may be substituted with one or more substituents selected from the substituent group $B_1$, a $C_{1-6}$ alkoxy group which may be substituted with one or more substituents selected from the substituent group $B_1$, a $C_{3-8}$ cycloalkoxy group which may be substituted with one or more substituents selected from the substituent group $B_1$, an aryloxy group which may be substituted with one or more substituents selected from the substituent group $B_1$, a $C_{1-6}$ alkylthio group which may be substituted with one or more substituents selected from the substituent group $B_1$, an arylthio group which may be substituted with one or more substituents selected from the substituent group $B_1$, a $C_{1-6}$ alkylamino group which may be substituted with one or more substituents selected from the substituent group $B_1$, a di($C_{1-6}$ alkyl)amino group which may be substituted with one or more substituents selected from the substituent group $B_1$, an acyl group which may be substituted with one or more substituents selected from the substituent group $B_1$, a heteroaryl group which may be substituted with one or more substituents selected from the substituent group $B_1$, or a heterocyclyl group which may be substituted with one or more substituents selected from the substituent group $B_1$; and each of $R^{17}$, $R^{18}$, and $R^{19}$ independently represents a hydrogen atom, a halogen atom, a hydroxyl group which may be protected, an amino group which may be protected, an amino group which may be substituted with one or more substituents selected from a substituent group $E_3$, a carboxyl group which may be protected, a cyano group, a carbamoyl group which may be substituted with one or more substituents selected from a substituent group $B_3$, a sulfamoyl group which may be substituted with one or more substituents selected from the substituent group $B_3$, a $C_{1-6}$ alkyl group which may be substituted with one or more substituents selected from the substituent group $B_3$, a $C_{2-6}$ alkenyl group which may be substituted with one or more substituents selected from the substituent group $B_3$, a $C_{3-8}$ cycloalkyl group which may be substituted with one or more substituents selected from the substituent group $B_3$, an aryl group which may be substituted with one or more substituents selected from the substituent group $B_3$, a $C_{1-6}$ alkoxy group which may be substituted with one or more substituents selected from the substituent group $B_3$, an aryloxy group which may be substituted with one or more substituents selected from the substituent group $B_3$, a $C_{1-6}$ alkylthio group which may be substituted with one or more substituents selected from the substituent group $B_3$, an arylthio group which may be substituted with one or more substituents selected from the substituent group $B_3$, a $C_{1-6}$ alkyl amino group which may be substituted with one or more substituents selected from the substituent group $B_3$, a di($C_{1-6}$ alkyl)amino group which may be substituted with one or more substituents selected from the substituent group $B_3$, a $C_{1-6}$ alkylsulfonyl group which may be substituted with one or more substituents selected from the substituent group $B_3$, an arylsulfonyl group which may be substituted with one or more substituents selected from the substituent group $B_3$, an acyl group which may be substituted with one or more substituents selected from the substituent group $B_3$, a heteroaryl group which may be substituted with one or more substituents selected from the substituent group $B_3$, a heterocyclyl group which may be substituted with one or more substituents selected from the substituent group $B_3$, or a heterocyclyloxy group which may be substituted with one or more substituents selected from the substituent group $B_3$.)

(18) The nitrogen-containing heterocyclic compound or salt thereof according to (17), in which each of $R^{14}$ and $R^{16}$ represents a hydrogen atom, and $R^{17}$ represents a hydrogen atom.

(19) A pharmaceutical composition comprising the nitrogen-containing heterocyclic compound or salt thereof according to any one of (1) to (18).

(20) An agent for treating a disease selected from the group consisting of a malignant tumor, a cell proliferative disease, an allergic disease, an autoimmune disease, a neurodegenerative disease, a circulatory system disease, an inflammatory disease, an endocrine disorder, a metabolic disorder, and an infection, the agent comprising the nitrogen-containing heterocyclic compound or salt thereof according to any one of (1) to (18).

(21) A PI3K- and/or ERK-inhibitor comprising the nitrogen-containing heterocyclic compound or salt thereof according to any one of (1) to (18).

In addition, the invention provides the following (a) to (d).

(a) The compound represented by Formula [1] or Formula [1a] defined above or salt thereof, for use as a medicine.

(b) A pharmaceutical composition including a pharmacologically acceptable additive together with the compound represented by Formula [1] or Formula [1a] or salt thereof.

(c) A use of the compound represented by Formula [1] or Formula [1a] or salt thereof in preparing a medicine for use in a treatment for a disease or a condition in which the PI3K and/or the ERK is involved, which is preferably for use in a treatment for a malignant tumor, a cell proliferative disease, an allergic disease, an autoimmune disease, a neurodegenerative disease, a circulatory system disease, an inflammatory disease, an endocrine disorder, a metabolic disorder, or an infection.

(d) A method for use in a treatment for a disease associated with the PI3K and/or the ERK, which is preferably for use in a treatment for a malignant tumor, a cell proliferative disease, an allergic disease, an autoimmune disease, a neurodegenerative disease, a circulatory system disease, an inflammatory disease, an endocrine disorder, a metabolic disorder, or an infection, and includes a step of administering a therapeutically effective amount of the compound represented by Formula [1] or Formula [1a] or salt thereof to a subject (mammal including humans) that requires such a treatment.

Effects of Invention

The nitrogen-containing heterocyclic compound or salt thereof of the invention has excellent inhibitory activity with respect to the PI3K-AKT pathway and/or the Ras-Raf-MEK-ERK pathway, is useful for a treatment such as prevention of or a cure for a disease such as a malignant tumor, a cell proliferative disease, an allergic disease, an autoimmune disease, a neurodegenerative disease, a circulatory system disease, an inflammatory disease, an endocrine disorder, a metabolic disorder, or an infection, and, is particularly useful for a treatment such as prevention of or cure for a malignant tumor.

In addition, the PI3K and/or the ERK inhibitor of the invention has excellent inhibitory activity with respect to the PI3K-AKT pathway and/or the Ras-Raf-MEK-ERK pathway, is useful for a treatment such as prevention of or cure for a disease such as a malignant tumor, a cell proliferative disease, an allergic disease, an autoimmune disease, a neurodegenerative disease, a circulatory system disease, an inflammatory disease, an endocrine disorder, a metabolic disorder, or an infection, and, is particularly useful for a treatment such as prevention of or cure for a malignant tumor.

DESCRIPTION OF EMBODIMENTS

In the present specification, "A and/or B" means "A and B, or A or B".

Hereinafter, the invention will be described in detail.

In the specification, each term has the following meaning, unless specified otherwise.

A "halogen atom" means a fluorine atom, a chlorine atom, a bromine atom, or an iodine atom.

A $C_{1-6}$ alkyl group means a linear or branched $C_{1-6}$ alkyl group such as a methyl group, an ethyl group, a propyl group, an isopropyl group, a butyl group, a sec-butyl group, an isobutyl group, a tert-butyl group, a pentyl group, an isopentyl group, or a hexyl group.

A $C_{2-6}$ alkenyl group means a linear or branched $C_{2-6}$ alkenyl group such as a vinyl group, an allyl group, a propenyl group, an isopropenyl group, a butenyl group, an isobutenyl group, a 1,3-butadienyl group, a pentenyl group, or a hexenyl group.

A $C_{2-6}$ alkynyl group means a linear or branched $C_{2-6}$ alkynyl group such as an ethynyl group, a propynyl group, a butynyl group, a pentynyl group, or a hexynyl group.

A $C_{3-8}$ cycloalkyl group means a monocyclic $C_{3-8}$ cycloalkyl group such as a cyclopropyl group, a cyclobutyl group, a cyclopentyl group, or a cyclohexyl group, or a $C_{4-8}$ crosslinked cyclic hydrocarbon ring group such as a bicyclo[2.1.0]pentyl group, a bicyclo[2.2.0]hexyl group, or a bicyclo[3.2.1]octyl group.

A condensed polycyclic hydrocarbon ring group means a bi- to tetra-cyclic hydrocarbon ring group such as a naphthyl group, an anthryl group, a phenanthryl group, a pyrenyl group, a fluorenyl group, an indenyl group, or an acenaphthylenyl group.

A partially-saturated condensed polycyclic hydrocarbon ring group is a condensed polycyclic hydrocarbon ring group which was partially hydrogenated, and means an indanyl group, an acenaphthenyl group, or the like.

An aryl group means a phenyl group, a condensed polycyclic hydrocarbon ring group, or a partially saturated condensed polycyclic hydrocarbon ring group.

An ar $C_{1-6}$ alkyl group means an ar $C_{1-6}$ alkyl group such as a benzyl group, a diphenylmethyl group, a trityl group, a phenethyl group, or a naphthylmethyl group.

A $C_{1-6}$ alkylene group means a linear or branched $C_{1-6}$ alkylene group such as a methylene group, an ethylene group, a propylene group, a butylene group, or a hexylene group.

A $C_{1-6}$ alkoxy group means a linear or branched $C_{1-6}$ alkyloxy group such as a methoxy group, an ethoxy group, a propyl oxy group, an isopropyl oxy group, a butoxy group, an isobutoxy group, a sec-butoxy group, a tert-butoxy group, a pentyloxy group, or a hexyloxy group.

A $C_{3-8}$ cycloalkoxy group means a $C_{3-8}$ cyclobulyloxy group such as a cyclopropyloxy group, a cyclobutyloxy group, a cyclopentyloxy group, or a cyclohexyloxy group.

A $C_{1-6}$ alkoxy $C_{1-6}$ alkyl group means a $C_{1-6}$ alkyloxy $C_{1-6}$ alkyl group such as a methoxymethyl group or a 1-ethoxyethyl group.

The aryloxy group means a phenyloxy group, a naphthyloxy group, an indanyloxy group, or an indenyloxy group.

A $C_{1-6}$ alkylthio group means a linear or branched $C_{1-6}$ alkylthio group such as a methylthio group, an ethylthio group, a propylthio group, an isopropylthio group, a butylthio group, an isobutylthio group, a sec-butylthio group, a tert-butylthio group, a pentylthio group, or a hexylthio group.

An arylthio group means a phenylthio group, a naphthylthio group, an indanylthio group, or an indenylthio group.

A $C_{1-6}$ alkylsulfonyl group means a linear or branched $C_{1-6}$ alkylsulfonyl group such as a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group, or a hexylsulfonyl group.

An arylsulfonyl group means a benzenesulfonyl group, a p-toluenesulfonyl group, a naphthylsulfonyl group, an indanylsulfonyl group, or an indenylsulfonyl group.

A $C_{1-6}$ alkylsulfonyloxy group means a $C_{1-6}$ alkylsulfonyloxy group such as a methylsulfonyloxy group or an ethylsulfonyloxy group.

An arylsulfonyloxy group means a benzenesulfonyloxy group or a p-toluenesulfonyloxy group.

A $C_{2-6}$ alkanoyl group means a linear or branched $C_{2-6}$ alkanoyl group such as an acetyl group, a propionyl group, a valeryl group, an isovaleryl group, or a pivaloyl group.

An aroyl group means a benzoyl group, or a naphthoyl group.

A heterocyclic carbonyl group means a nicotinoyl group, a thenyl group, a pyrrolidinocarbonyl group, or a furoyl group.

An (α-substituted) aminoacetyl group means an (α-substituted) aminoacetyl group of which the N-terminal may be protected, derived from an amino acid (glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline, or hydroxyproline).

An acyl group means a formyl group, a succinyl group, a glutaryl group, a maleoyl group, a phthaloyl group, a $C_{2-6}$ alkanoyl group, an aroyl group, a heterocyclic carbonyl group, or an (α-substituted) aminoacetyl group.

A $C_{1-6}$ alkoxycarbonyl group means a linear or branched $C_{1-6}$ alkyloxycarbonyl group such as a methoxycarbonyl group, an ethoxycarbonyl group, an isopropyloxycarbonyl group, a tert-butoxycarbonyl group, or a 1,1-dimethylpropoxycarbonyl group.

An aryloxycarbonyl group means a phenyloxycarbonyl group or a naphthyloxycarbonyl group.

An ar $C_{1-6}$ alkoxycarbonyl group means an ar $C_{1-6}$ alkyloxycarbonyl group such as a benzyloxycarbonyl group or a phenethyloxycarbonyl group.

A $C_{1-6}$ alkylamino group means a linear or branched $C_{1-6}$ alkylamino group such as a methylamino group, an ethylamino group, a propylamino group, an isopropylamino group, a butylamino group, a sec-butylamino group, a tert-butylamino group, a pentylamino group, or a hexylamino group.

A di($C_{1-6}$ alkyl)amino group means a linear or branched di($C_{1-6}$ alkyl)amino group such as a dimethylamino group, a diethylamino group, a dipropylamino group, a diisopropylamino group, a dibutylamino group, a di(tert-butyl)amino group, a dipentylamino group, a dihexylamino group, an (ethyl)(methyl)amino group, a (methyl)(propyl)amino group, an (ethyl)(propyl)amino group, or an (ethyl)(isopropyl)amino group.

A nitrogen-containing heterocyclyl group means a heterocyclyl group of which a ring including at least one nitrogen atom does not have aromatic properties, and examples thereof include an azetidinyl group, a pyrrolidinyl group, a piperidinyl group, a homopiperidinyl group, an octahydroazocinyl group, an imidazolidinyl group, a pyrazolidinyl group, a piperazinyl group, and a homopiperazinyl group. The heterocyclyl group may be further condensed with another aromatic ring or another aliphatic ring.

An oxygen-containing heterocyclyl group means a tetrahydrofuranyl group, a tetrahydropyranyl group, an oxetanyl group, a 1,3-dioxanyl group or the like. The heterocyclyl group may be further condensed with another aromatic ring or another aliphatic ring.

A sulfur-containing heterocyclyl group means a tetrahydrothienyl group, a tetrahydrothiopyranyl group or the like. This heterocyclyl group includes a group of which the sulfur atom is oxidized, and may be further condensed with another aromatic ring or another aliphatic ring.

A nitrogen- and oxygen-containing heterocyclyl group means a morpholinyl group, a 1,4-oxazepanyl group or the like. This heterocyclyl group may be further condensed with another aromatic ring or another aliphatic ring.

A nitrogen- and sulfur-containing heterocyclyl group means a thiomorpholinyl or the like. This heterocyclyl group includes a group of which the sulfur atom is oxidized, and may be further condensed with another aromatic ring or another aliphatic ring.

A hetero, crosslinked ring group means a hetero, crosslinked ring group including at least one heteroatom (for example, an oxygen atom, a nitrogen atom, or a sulfur atom), and examples thereof include a 3-aza-6-oxabicyclo[3.1.1]heptyl group, a 3-aza-8-oxabicyclo[3.2.1]octyl group, and a 8-aza-3-oxabicyclo[3.2.1]octyl group.

A heterospiro ring group means a heterospiro ring group including at least one heteroatom (for example, an oxygen atom, a nitrogen atom, or a sulfur atom), and examples thereof include a 2-azaspiro[3.3]heptyl group, a 2-oxaspiro

[3.3]heptyl group, a 6-aza-2-oxaspiro[3.3]heptyl group, a 1-azaspiro[4.5]decyl group, and a 1-oxaspiro[4.5]decyl group.

A heterocyclyl group means the nitrogen-containing heterocyclyl group, the oxygen-containing heterocyclyl group, the sulfur-containing heterocyclyl group, the nitrogen- and oxygen-containing heterocyclyl group, the nitrogen- and sulfur-containing heterocyclyl group, the hetero, crosslinked ring group, or the heterospiro ring group.

A heterocyclyloxy group means a group in which an oxy group is bonded to a heterocyclyl group, and examples thereof include an azetidinyloxy group, an oxetanyloxy group, a pyrrolidinyloxy group, a piperidinyloxy group, and a tetrahydropyranyloxy group.

A monocyclic, nitrogen-containing heteroaryl group means a heteroaryl group (which may be partially saturated) of which a ring including at least one nitrogen atom has aromatic properties, and examples thereof include a pyrrolinyl group, a pyrrolyl group, a tetrahydropyridyl group, a pyridyl group, an imidazolinyl group, an imidazolyl group, a pyrazolinyl group, a pyrazolyl group, a pyrazinyl group, a pyridazinyl group, a pyrimidinyl group, a triazolyl group, and a tetrazolyl group. This heteroaryl group may be further condensed with another aromatic ring or another aliphatic ring.

A monocyclic, oxygen-containing heteroaryl group means a heteroaryl group (which may be partially saturated) of which a ring including at least one oxygen atom has aromatic properties, and examples thereof include a furanyl group and a pyranyl group. This heteroaryl group may be further condensed with another aromatic ring or another aliphatic ring.

A monocyclic, sulfur-containing heteroaryl group means a heteroaryl group (which may be partially saturated) of which a ring including at least one sulfur atom has aromatic properties, and examples thereof include a thienyl group. This heteroaryl group may be further condensed with another aromatic ring or another aliphatic ring.

A monocyclic, nitrogen- and oxygen-containing heteroaryl group means an oxazolyl group, an isoxazolyl group, an oxadiazolyl group or the like. This heteroaryl group may be further condensed with another aromatic ring or another aliphatic ring.

A monocyclic, nitrogen- and sulfur-containing heteroaryl group means a thiazolyl group, an isothiazolyl group, a thiadiazolyl group or the like. This heteroaryl group may be further condensed with another aromatic ring or another aliphatic ring.

A bicyclic, nitrogen-containing heteroaryl group means a bicyclic heteroaryl group (which may be partially saturated) of which a ring including at least one nitrogen atom has aromatic properties, and examples thereof include an indolyl group, an isoindolyl group, a benzimidazolyl group, an indazolyl group, a benzotriazolyl group, a quinolyl group, an isoquinolyl group, a tetrahydroquinolyl group, a tetrahydroisoquinolyl group, a quinolizinyl group, a cinnolinyl group, a phthalazinyl group, a quinazolinyl group, a quinoxalinyl group, a naphthyridinyl group, a pyrrolopyridyl group, an imidazopyridyl group, a pyrazolopyridyl group, a pyridopyrazyl group, a purinyl group, a pteridinyl group, a 5,6,7,8-tetrahydrophthalazinyl group, a 5,6,7,8-tetrahydrocinnolinyl group, a 1,2,3,4-tetrahydropyrido[2,3-d]pyridazinyl group, a 5,6,7,8-tetrahydro-[1,2,4]triazolo[4,3-a]pyrazinyl group, a 5,6,7,8-tetrahydropyrido[3,4-d]pyridazinyl group, a 5,6,7,8-tetrahydropyrido[3,2-c]pyridazinyl group, a 5,6,7,8-tetrahydropyrido[4,3-c]pyridazinyl group, a 6,7-dihydro-5H-cyclopenta[d]pyridazinyl group, a 6,7-dihydro-5H-cyclopenta[c]pyridazinyl group, a 2,3-dihydro-1H-pyrrolo[2,3-d]pyridazinyl group, a 6,7-dihydro-5H-pyrrolo[3,4-d]pyridazinyl group, a 6,7-dihydro-5H-pyrrolo[3,2-c]pyridazinyl group, a 6,7-dihydro-5H-pyrrolo[3,4-c]pyridazinyl group, and a 6,7-dihydro-5H-pyrrolo[2,3-c]pyridazinyl group.

A bicyclic, oxygen-containing heteroaryl group means a bicyclic heteroaryl group (which may be partially saturated) of which a ring including at least one oxygen atom has aromatic properties, and examples thereof include a benzofuranyl group, an isobenzofuranyl group, and a chromenyl group.

A bicyclic, sulfur-containing heteroaryl group means a bicyclic heteroaryl group (which may be partially saturated) of which a ring including at least one sulfur atom has aromatic properties, and examples thereof include a benzothienyl group.

A bicyclic, nitrogen- and oxygen-containing heteroaryl group means a bicyclic heteroaryl group (which may be partially saturated) of which a ring including at least one nitrogen atom and at least one oxygen atom has aromatic properties, and examples thereof include a benzoxazolyl group, a benzoisoxazolyl group, a benzoxadiazolyl group, a dihydropyranopyridyl group, a dihydrodioxynopyridyl group, a dihydropyridooxadienyl group, a 3,4-dihydro-2H-pyrano[2,3-d]pyridazinyl group, a 7,8-dihydro-5H-pyrano[3,4-d]pyridazinyl group, a 7,8-dihydro-6H-pyrano[3,2-c]pyridazinyl group, a 7,8-dihydro-5H-pyrano[4,3-c]pyridazinyl group, a 2,3-dihydrofuro[2,3-d]pyridazinyl group, a 5,7-dihydrofuro[3,4-d]pyridazinyl group, a 6,7-dihydrofuro[3,2-c]pyridazinyl group, a 5,7-dihydrofuro[3,4-c]pyridazinyl group, and a 5,6-dihydrofuro[2,3-c]pyridazinyl group.

A bicyclic, nitrogen- and sulfur-containing heteroaryl group means a bicyclic heteroaryl group (which may be partially saturated) of which a ring including at least one nitrogen atom and at least one sulfur atom has aromatic properties, and examples thereof include a benzothiazolyl group, a benzoisothiazolyl group, a benzothiadiazolyl group, and a thiazolopyridyl group.

A heteroaryl group means the monocyclic, nitrogen-containing heteroaryl group, the monocyclic, oxygen-containing heteroaryl group, the monocyclic, sulfur-containing heteroaryl group, the monocyclic, nitrogen- and oxygen-containing heteroaryl group, the monocyclic, nitrogen- and sulfur-containing heteroaryl group, the bicyclic, nitrogen-containing heteroaryl group, the bicyclic, oxygen-containing heteroaryl group, the bicyclic, sulfur-containing heteroaryl group, the bicyclic, nitrogen- and oxygen-containing heteroaryl group, or the bicyclic, nitrogen- and sulfur-containing heteroaryl group.

A heteroaryloxy group means a group in which an oxy group is bonded to a heteroaryl group, and examples thereof include a pyridyloxy group, a pyridazinyloxy group, and a pyrimidinyloxy group.

A heteroarylthio group means a group in which a thio group is bonded to a heteroaryl group, and examples thereof include a pyridylthio group, a pyridazinylthio group, andr a pyrimidinylthio group.

A silyl group means a trimethylsilyl group, a triethylsilyl group, a tributylsilyl group, a tert-butyldimethylsilyl group or the like.

A leaving group means a halogen atom, a $C_{1-6}$ alkylsulfonyloxy group, an arylsulfonyloxy group or the like. The $C_{1-6}$ alkylsulfonyloxy group or the arylsulfonyloxy group may have a substituent.

Examples of a hydroxyl protecting group include any group that can be usually used as a protecting group of a hydroxyl group, and examples thereof include the groups described in "Protective Groups in Organic Synthesis" written by W. Greene et al., 4th edition, pp. 16-366, 2007 (John Wiley & Sons, INC.).

Specific examples thereof include a $C_{1-6}$ alkyl group, a $C_{2-6}$ alkenyl group, an ar $C_{1-6}$ alkyl group, a $C_{1-6}$ alkoxy $C_{1-6}$ alkyl group, an acyl group, a $C_{1-6}$ alkoxycarbonyl group, an ar $C_{1-6}$ alkoxycarbonyl group, a $C_{1-6}$ alkylsulfonyl group, an arylsulfonyl group, a silyl group, a tetrahydrofuranyl group, and a tetrahydropyranyl group. These groups may have a substituent.

Examples of an amino protecting group include any group that can be usually used as a protecting group of a amino group, and examples thereof include the groups described in "Protective Groups in Organic Synthesis" written by W. Greene et al., 4th edition, pp. 696-926, 2007 (John Wiley & Sons, INC.).

Specific examples thereof include an ar $C_{1-6}$ alkyl group, a $C_{1-6}$ alkoxy $C_{1-6}$ alkyl group, an acyl group, a $C_{1-6}$ alkoxycarbonyl group, an ar $C_{1-6}$ alkoxycarbonyl group, an aryloxycarbonyl group, a $C_{1-6}$ alkylsulfonyl group, an arylsulfonyl group, and a silyl group. These groups may have a substituent.

Examples of a carboxyl protecting group include any group that can be usually used as a protecting group of a carboxyl group, and examples thereof include the groups described in "Protective Groups in Organic Synthesis" written by W. Greene et al., 4th edition, pp. 533-646, 2007 (John Wiley & Sons, INC.).

Specific examples thereof include a $C_{1-6}$ alkyl group, a $C_{2-6}$ alkenyl group, an aryl group, an ar $C_{1-6}$ alkyl group, a $C_{1-6}$ alkoxy $C_{1-6}$ alkyl group, and a silyl group. These groups may have a substituent.

An aliphatic hydrocarbon means pentane, hexane, cyclohexane or the like.

A halogenated hydrocarbon means methylene chloride, chloroform, dichloroethane or the like.

An alcohol means methanol, ethanol, propanol, 2-propanol, butanol, 2-methyl-2-propanol, ethylene glycol, diethylene glycol, triethylene glycol, propylene glycol or the like.

An ether means diethyl ether, diisopropyl ether, 1,4-dioxane, tetrahydrofuran, anisole, ethylene glycol dimethyl ether, diethylene glycol dimethyl ether, diethylene glycol diethyl ether or the like.

A ketone means acetone, 2-butanone, 4-methyl-2-pentanone or the like.

An ester means methyl acetate, ethyl acetate, propyl acetate, butyl acetate, cyclohexyl acetate, amyl acetate or the like.

An amide means N,N-dimethylformamide, N,N-dimethylacetamide, N-methylpyrrolidone or the like.

A sulfoxide means dimethyl sulfoxide or the like.

A carboxylic acid means formic acid, acetic acid, trifluoroacetic acid or the like.

An aromatic hydrocarbon means benzene, toluene, xylene or the like.

A palladium catalyst means a metal palladium such as palladium-carbon or palladium black; an inorganic palladium salt such as palladium chloride; an organic palladium salt such as palladium acetate; an organic palladium complex such as tetrakis(triphenylphosphine)palladium(0), bis(tri-tert-butylphosphine)palladium(0), bis(triphenylphosphine)palladium(II) dichloride, (1,1'-bis(diphenylphosphino)ferrocene)palladium(II) dichloride, bis(di-tert-butyl(4-dimethylaminophenyl)phosphine)dichloropalladium(II), (E)-di(μ-acetate)bis(o-(di-o-tolylphosphino)benzyl)dipalladium(II), or tris(dibenzylideneacetone)dipalladium(0); a ploymer-immobilized organic palladium complex such as polymer-supported bis(acetate)triphenylphosphine palladium(II) or polymer-supported di(acetate)dicyclohexylphenylphosphine palladium(II); or the like. These may be used in combination.

Examples of a ligand include: a trialkylphosphine such as trimethylphosphine or tri-tert-butylphosphine; a tricycloalkylphosphine such as tricyclohexylphosphine; a triarylphosphine such as triphenylphosphine or tritolylphosphine; a trialkylphosphite such as trimethylphosphite, triethylphosphite, or tributylphosphite; a tricycloalkylphosphite such as tricyclohexylphosphite; a triarylphosphite such as triphenylphosphite; a imidazolium salt such as 1,3-bis(2,4,6-trimethylphenyl)imidazolium chloride; a diketone such as acetylacetone or octafluoroacetyl acetone; an amine such as trimethylamine, triethylamine, tripropylamine, or triisopropylamine; and 1,1'-bis(diphenylphosphino)ferrocene, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, 2-(di-tert-butylphosphino)-2',4',6'-triisopropylbiphenyl, 4,5-bis(diphenylphosphino)-9,9-dimethylxanthene, and 2-(di-tert-butylphosphino)biphenyl. These may be used in combination.

The monocyclic, nitrogen-containing heteroaryl group, the monocyclic, nitrogen- and oxygen-containing heteroaryl group, the monocyclic, nitrogen- and sulfur-containing heteroaryl group, the bicyclic, nitrogen-containing heteroaryl group, the bicyclic, nitrogen- and oxygen-containing heteroaryl group, or the bicyclic, nitrogen- and sulfur-containing heteroaryl group of $R^1$ may be substituted with one or more substituents selected from the substituent group $A_1$.

Preferably, the monocyclic, nitrogen-containing heteroaryl group, the monocyclic, nitrogen- and oxygen-containing heteroaryl group, the monocyclic, nitrogen- and sulfur-containing heteroaryl group, the bicyclic, nitrogen-containing heteroaryl group, the bicyclic, nitrogen- and oxygen-containing heteroaryl group, or the bicyclic, nitrogen- and sulfur-containing heteroaryl group of $R^1$ may be substituted with one or more substituents selected from the substituent group $\alpha_1$.

The $C_{1-6}$ alkyl group or the $C_{1-6}$ alkoxy group of $R^4$ may be substituted with one or more substituents selected from the substituent group $\alpha_2$.

The carbamoyl group, the $C_{1-6}$ alkyl group, the $C_{2-6}$ alkenyl group, the $C_{2-6}$ alkynyl group, the $C_{3-8}$ cycloalkyl group, the aryl group, the $C_{1-6}$ alkoxy group, the aryloxy group, the $C_{1-6}$ alkylthio group, the arylthio group, the heteroaryl group, the heteroaryloxy group, the heteroarylthio group, or the heterocyclyl group of $R^5$ may be substituted with one or more substituents selected from the substituent group $A_3$.

Preferably, the carbamoyl group, the $C_{1-6}$ alkyl group, the $C_{2-6}$ alkenyl group, the $C_{2-6}$ alkynyl group, the $C_{3-8}$ cycloalkyl group, the aryl group, the $C_{1-6}$ alkoxy group, the aryloxy group, the $C_{1-6}$ alkylthio group, the arylthio group, the heteroaryl group, the heteroaryloxy group, the heteroarylthio group, or the heterocyclyl group of $R^5$ may be substituted with one or more substituents selected from the substituent group $\alpha_3$.

The $C_{1-6}$ alkyl group, the $C_{2-6}$ alkenyl group, the $C_{2-6}$ alkynyl group, the $C_{3-8}$ cycloalkyl group, the aryl group, the $C_{1-6}$ alkoxy group, the aryloxy group, the $C_{1-6}$ alkylthio group, the arylthio group, the heteroaryl group, the heteroaryloxy group, the heteroarylthio group, or the heterocyclyl group of $R^6$ may be substituted with one or more substituents selected from the substituent group $\alpha_2$.

The $C_{1-6}$ alkyl group, the $C_{2-6}$ alkenyl group, the $C_{2-6}$ alkynyl group, the $C_{3-8}$ cycloalkyl group, the aryl group, the heteroaryl group, or the heterocyclyl group of $R^7$ or $R^8$ may be substituted with one or more substituents selected from the substituent group $\alpha_2$.

The $C_{1-6}$ alkyl group of $R^9$ may be substituted with one or more substituents selected from the substituent group $\alpha_2$.

The $C_{1-6}$ alkyl group of $R^{10}$ or $R^{11}$ may be substituted with one or more substituents selected from the substituent group $\alpha_2$.

The $C_{1-6}$ alkyl group, the $C_{2-6}$ alkenyl group, the $C_{2-6}$ alkynyl group, the $C_{3-8}$ cycloalkyl group, the aryl group, the heteroaryl group, or the heterocyclyl group of $R^{12}$ or $R^{13}$ may be substituted with one or more substituents selected from the substituent group $A_3$.

Preferably, the $C_{1-6}$ alkyl group, the $C_{2-6}$ alkenyl group, the $C_{2-6}$ alkynyl group, the $C_{3-8}$ cycloalkyl group, the aryl group, the heteroaryl group, or the heterocyclyl group of $R^{12}$ or $R^{13}$ may be substituted with one or more substituents selected from the substituent group $\alpha_3$.

Substituent group $A_1$: A halogen atom, a hydroxyl group which may be protected, an amino group which may be protected, a carboxyl group which may be protected, a cyano group, a carbamoyl group which may be substituted with one or more substituents selected from a substituent group $B_1$, a sulfamoyl group which may be substituted with one or more substituents selected from the substituent group $B_1$, a $C_{1-6}$ alkyl group which may be substituted with one or more substituents selected from the substituent group $B_1$, a $C_{2-6}$ alkenyl group which may be substituted with one or more substituents selected from the substituent group $B_1$, a $C_{3-8}$ cycloalkyl group which may be substituted with one or more substituents selected from the substituent group $B_1$, an aryl group which may be substituted with one or more substituents selected from the substituent group $B_1$, a $C_{1-6}$ alkoxy group which may be substituted with one or more substituents selected from the substituent group $B_1$, a $C_{3-8}$ cycloalkoxy group which may be substituted with one or more substituents selected from the substituent group $B_1$, an aryloxy group which may be substituted with one or more substituents selected from the substituent group $B_1$, a $C_{1-6}$ alkylthio group which may be substituted with one or more substituents selected from the substituent group $B_1$, an arylthio group which may be substituted with one or more substituents selected from the substituent group $B_1$, a $C_{1-6}$ alkylamino group which may be substituted with one or more substituents selected from the substituent group $B_1$, a di($C_{1-6}$ alkyl)amino group which may be substituted with one or more substituents selected from the substituent group $B_1$, an acyl group which may be substituted with one or more substituents selected from the substituent group $B_1$, a heteroaryl group which may be substituted with one or more substituents selected from the substituent group $B_1$, a heterocyclyl group which may be substituted with one or more substituents selected from the substituent group $B_1$, and an oxo group.

Substituent group $B_1$: A halogen atom, a hydroxyl group which may be protected, an amino group which may be protected, a carboxyl group which may be protected, a cyano group, a carbamoyl group which may be substituted with one or more substituents selected from a substituent group $C_1$, a sulfamoyl group which may be substituted with one or more substituents selected from the substituent group $C_1$, a $C_{1-6}$ alkyl group which may be substituted with one or more substituents selected from the substituent group $C_1$, a $C_{3-8}$ cycloalkyl group which may be substituted with one or more substituents selected from the substituent group $C_1$, an aryl group which may be substituted with one or more substituents selected from the substituent group $C_1$, a $C_{1-6}$ alkoxy group which may be substituted with one or more substituents selected from the substituent group $C_1$, a $C_{1-6}$ alkylamino group which may be substituted with one or more substituents selected from the substituent group $C_1$, a di($C_{1-6}$ alkyl)amino group which may be substituted with one or more substituents selected from the substituent group $C_1$, a $C_{1-6}$ alkylsulfonyl group which may be substituted with one or more substituents selected from the substituent group $C_1$, an arylsulfonyl group which may be substituted with one or more substituents selected from the substituent group $C_1$, an acyl group which may be substituted with one or more substituents selected from the substituent group $C_1$, a heteroaryl group which may be substituted with one or more substituents selected from the substituent group $C_1$, a heterocyclyl group which may be substituted with one or more substituents selected from the substituent group $C_1$, and an oxo group.

Substituent group $C_1$: A halogen atom, a hydroxyl group which may be protected, an amino group which may be protected, a carboxyl group which may be protected, a cyano group, a carbamoyl group which may be substituted with a $C_{1-6}$ alkyl group, a $C_{1-6}$ alkyl group which may be substituted with a halogen atom, an aryl group which may be substituted with a halogen atom or a $C_{1-6}$ alkyl group, a $C_{1-6}$ alkoxy group which may be substituted with a halogen atom, and an oxo group.

Substituent group $\alpha_1$: A halogen atom, a hydroxyl group which may be protected, an amino group which may be protected, a carboxyl group which may be protected, a cyano group, a carbamoyl group which may be substituted with one or more substituents selected from a substituent group $\beta_1$, a sulfamoyl group which may be substituted with one or more substituents selected from the substituent group $\beta_1$, a $C_{1-6}$ alkyl group which may be substituted with one or more substituents selected from the substituent group $\beta_1$, a $C_{3-8}$ cycloalkyl group which may be substituted with one or more substituents selected from the substituent group $\beta_1$, an aryl group which may be substituted with one or more substituents selected from the substituent group $\beta_1$, a $C_{1-6}$ alkoxy group which may be substituted with one or more substituents selected from the substituent group $\beta_1$, an aryloxy group which may be substituted with one or more substituents selected from the substituent group $\beta_1$, a $C_{1-6}$ alkylthio group which may be substituted with one or more substituents selected from the substituent group $\beta_1$, an arylthio group which may be substituted with one or more substituents selected from the substituent group $\beta_1$, a $C_{1-6}$ alkylamino group which may be substituted with one or more substituents selected from the substituent group $\beta_1$, a di($C_{1-6}$ alkyl)amino group which may be substituted with one or more substituents selected from the substituent group $\beta_1$, an acyl group which may be substituted with one or more substituents selected from the substituent group $\beta_1$, a heteroaryl group which may be substituted with one or more substituents selected from the substituent group $\beta_1$, a heterocyclyl group which may be substituted with one or more substituents selected from the substituent group $\beta_1$, and an oxo group.

Substituent group $\beta_1$: A halogen atom, a hydroxyl group which may be protected, an amino group which may be protected, a carboxyl group which may be protected, a cyano group, a carbamoyl group which may be substituted with one or more substituents selected from a substituent group $\gamma_1$, a $C_{1-6}$ alkyl group which may be substituted with one or more substituents selected from the substituent group $\gamma_1$, a $C_{3-8}$ cycloalkyl group which may be substituted with one or more substituents selected from the substituent group $\gamma_1$, an aryl group which may be substituted with one or more substituents selected from the substituent group $\gamma_1$, a $C_{1-6}$ alkoxy group which may be substituted with one or more substituents selected from the substituent group $\gamma_1$, a $C_{1-6}$ alkylamino group which may be substituted with one or more substituents selected from the substituent group $\gamma_1$, a di($C_{1-6}$ alkyl)amino group which may be substituted with one or more substituents selected from the substituent group $\gamma_1$, a $C_{1-6}$ alkylsulfonyl group which may be substituted with one or more substituents selected from the substituent group $\gamma_1$, an arylsulfonyl group which may be substituted with one or more substituents selected from the substituent group $\gamma_1$, an acyl group which may be substituted with one or more substituents selected from the substituent group $\gamma_1$, a heteroaryl group which may be substituted with one or more substituents selected from the substituent group $\gamma_1$, a heterocyclyl group which may be substituted with one or more substituents selected from the substituent group $\gamma_1$, and an oxo group.

Substituent group $\gamma_1$: A halogen atom, a hydroxyl group which may be protected, an amino group which may be protected, a carboxyl group which may be protected, a cyano group, a carbamoyl group which may be substituted with a $C_{1-6}$ alkyl group, a $C_{1-6}$ alkyl group which may be substituted with a halogen atom, a $C_{1-6}$ alkoxy group which may be substituted with a halogen atom, and an oxo group.

Substituent group $\alpha_2$: A halogen atom, a hydroxyl group which may be protected, an amino group which may be protected, a carboxyl group which may be protected, a cyano group, a carbamoyl group which may be substituted with one or more substituents selected from the substituent group $\beta_2$, a $C_{1-6}$ alkyl group which may be substituted with one or more substituents selected from the substituent group $\beta_2$, a $C_{1-6}$ alkoxy group which may be substituted with one or more substituents selected from the substituent group $\beta_2$, and an oxo group.

Substituent group $\beta_2$: A halogen atom, a $C_{1-6}$ alkyl group which may be substituted with one or more substituents selected from the substituent group $\gamma_2$, a $C_{3-8}$ cycloalkyl group which may be substituted with one or more substituents selected from the substituent group $\gamma_2$, an aryl group which may be substituted with one or more substituents selected from the substituent group $\gamma_2$, a heteroaryl group which may be substituted with one or more substituents selected from the substituent group $\gamma_2$, and a heterocyclyl group which may be substituted with one or more substituents selected from the substituent group $\gamma_2$.

Substituent group $\gamma_2$: A halogen atom, a hydroxyl group which may be protected, an amino group which may be protected, a carboxyl group which may be protected, a cyano group, a $C_{1-6}$ alkyl group which may be substituted with a halogen atom, a $C_{1-6}$ alkoxy group which may be substituted with a halogen atom, and an oxo group.

Substituent group $A_3$: A halogen atom, a hydroxyl group which may be protected, an amino group which may be protected, an amino group which may be substituted with one or more substituents selected from a substituent group $E_3$, a carboxyl group which may be protected, a cyano group, a carbamoyl group which may be substituted with one or more substituents selected from a substituent group $B_3$, a sulfamoyl group which may be substituted with one or more substituents selected from the substituent group $B_3$, a $C_{1-6}$ alkyl group which may be substituted with one or more substituents selected from the substituent group $B_3$, a $C_{2-6}$ alkenyl group which may be substituted with one or more substituents selected from the substituent group $B_3$, a $C_{3-8}$ cycloalkyl group which may be substituted with one or more substituents selected from the substituent group $B_3$, an aryl group which may be substituted with one or more substituents selected from the substituent group $B_3$, a $C_{1-6}$ alkoxy group which may be substituted with one or more substituents selected from the substituent group $B_3$, an aryloxy group which may be substituted with one or more substituents selected from the substituent group $B_3$, a $C_{1-6}$ alkylthio group which may be substituted with one or more substituents selected from the substituent group $B_3$, an arylthio group which may be substituted with one or more substituents selected from the substituent group $B_3$, a $C_{1-6}$ alkyl amino group which may be substituted with one or more substituents selected from the substituent group $B_3$, a di($C_{1-6}$ alkyl)amino group which may be substituted with one or more substituents selected from the substituent group $B_3$, a $C_{1-6}$ alkylsulfonyl group which may be substituted with one or more substituents selected from the substituent group $B_3$, an arylsulfonyl group which may be substituted with one or more substituents selected from the substituent group $B_3$, an acyl group which may be substituted with one or more substituents selected from the substituent group $B_3$, a heteroaryl group which may be substituted with one or more substituents selected from the substituent group $B_3$, a heterocyclyl group which may be substituted with one or more substituents selected from the substituent group $B_3$, a heterocyclyloxy group which may be substituted with one or more substituents selected from the substituent group $B_3$, and an oxo group.

Substituent group $B_3$: A halogen atom, a hydroxyl group which may be protected, an amino group which may be protected, a carboxyl group which may be protected, a cyano group, a carbamoyl group which may be substituted with one or more substituents selected from a substituent group $C_3$, a $C_{1-6}$ alkyl group which may be substituted with one or more substituents selected from the substituent group $C_3$, a $C_{3-8}$ cycloalkyl group which may be substituted with one or more substituents selected from the substituent group $C_3$, an aryl group which may be substituted with one or more substituents selected from the substituent group $C_3$, a $C_{1-6}$ alkoxy group which may be substituted with one or more substituents selected from the substituent group $C_3$, an aryloxy group which may be substituted with one or more substituents selected from the substituent group $C_3$, a $C_{1-6}$ alkylamino group which may be substituted with one or more substituents selected from the substituent group $C_3$, a di($C_{1-6}$ alkyl)amino group which may be substituted with one or more substituents selected from the substituent group $C_3$, a $C_{1-6}$ alkylsulfonyl group which may be substituted with one or more substituents selected from the substituent group $C_3$, an arylsulfonyl group which may be substituted with one or more substituents selected from the substituent group $C_3$, an acyl group which may be substituted with one or more substituents selected from the substituent group $C_3$, a heteroaryl group which may be substituted with one or more substituents selected from the substituent group $C_3$, a heterocyclyl group which may be substituted with one or more substituents selected from the substituent group $C_3$, a heteroaryloxy group which may be substituted with one or more substituents selected from the substituent group $C_3$, a heterocyclyloxy group which may be substituted with one or more substituents selected from the substituent group $C_3$, and an oxo group.

Substituent group $C_3$: A halogen atom, a hydroxyl group which may be protected, an amino group which may be protected, a carboxyl group which may be protected, a nitro group, cyano group, a carbamoyl group which may be substituted with one or more substituents selected from a substituent group $D_3$, a $C_{1-6}$ alkyl group which may be substituted with one or more substituents selected from the substituent group $D_3$, a $C_{3-8}$ cycloalkyl group which may be substituted with one or more substituents selected from the substituent group $D_3$, an aryl group which may be substituted with one or more substituents selected from the substituent group $D_3$, a $C_{1-6}$ alkoxy group which may be substituted with one or more substituents selected from the substituent group $D_3$, an aryloxy group which may be substituted with one or more substituents selected from the substituent group $D_3$, a $C_{1-6}$ alkylamino group which may be substituted with one or more substituents selected from the substituent group $D_3$, a di($C_{1-6}$ alkyl)amino group which may be substituted with one or more substituents selected from the substituent group $D_3$, a $C_{1-6}$ alkylsulfonyl group which may be substituted with one or more substituents selected from the substituent group $D_3$, an acyl group which may be substituted with one or more substituents selected from the substituent group $D_3$, a heteroaryl group which may be substituted with one or more substituents selected from the substituent group $D_3$, a heterocyclyl group which may be substituted with one or more substituents selected from the substituent group $D_3$, a silyl group which may be substituted with one or more substituents selected from the substituent group $D_3$, and an oxo group.

Substituent group $D_3$: A halogen atom, a hydroxyl group which may be protected, a $C_{1-6}$ alkyl group, a $C_{3-8}$ cycloalkyl group, an aryl group, a $C_{1-6}$ alkoxy group, a $C_{1-6}$ alkylamino group, a di($C_{1-6}$ alkyl)amino group, a $C_{1-6}$ alkylsulfonyl group, a heteroaryl group, a heterocyclyl group, and an oxo group.

Substituent group $E_3$: A $C_{3-8}$ cycloalkyl group which may be substituted with one or more substituents selected from a substituent group $F_3$, an aryl group which may be substituted with one or more substituents selected from the substituent group $F_3$, a heteroaryl group which may be substituted with one or more substituents selected from the substituent group $F_3$, and a heterocyclyl group which may be substituted with one or more substituents selected from the substituent group $F_3$.

Substituent group $F_3$: A halogen atom, a carboxyl group which may be protected, and a $C_{1-6}$ alkyl group.

Substituent group $\alpha_3$: A halogen atom, a hydroxyl group which may be protected, an amino group which may be protected, a carboxyl group which may be protected, a cyano group, a carbamoyl group which may be substituted with one or more substituents selected from a substituent group $\beta_3$, a $C_{1-6}$ alkyl group which may be substituted with one or more substituents selected from the substituent group $\beta_3$, a $C_{3-8}$ cycloalkyl group which may be substituted with one or more substituents selected from the substituent group $\beta_3$, an aryl group which may be substituted with one or more substituents selected from the substituent group $\beta_3$, a $C_{1-6}$ alkoxy group which may be substituted with one or more substituents selected from the substituent group $\beta_3$, an aryloxy group which may be substituted with one or more substituents selected from the substituent group $\beta_3$, a $C_{1-6}$ alkylthio group which may be substituted with one or more substituents selected from the substituent group $\beta_3$, an arylthio group which may be substituted with one or more substituents selected from the substituent group $\beta_3$, a $C_{1-6}$ alkylamino group which may be substituted with one or more substituents selected from the substituent group $\beta_3$, a di($C_{1-6}$ alkyl)amino group which may be substituted with one or more substituents selected from the substituent group $\beta_3$, a $C_{1-6}$ alkylsulfonyl group which may be substituted with one or more substituents selected from the substituent group $\beta_3$, an arylsulfonyl group which may be substituted with one or more substituents selected from the substituent group $\beta_3$, an acyl group which may be substituted with one or more substituents selected from the substituent group $\beta_3$, a heteroaryl group which may be substituted with one or more substituents selected from the substituent group $\beta_3$, a heterocyclyl group which may be substituted with one or more substituents selected from the substituent group $\beta_3$, a heterocyclyloxy group which may be substituted with one or more substituents selected from the substituent group $\beta_3$, and an oxo group.

Substituent group $\beta_3$: A halogen atom, a hydroxyl group which may be protected, an amino group which may be protected, a carboxyl group which may be protected, a cyano group, a carbamoyl group which may be substituted with one or more substituents selected from a substituent group $\gamma_3$, a $C_{1-6}$ alkyl group which may be substituted with one or more substituents selected from the substituent group $\gamma_3$, a $C_{3-8}$ cycloalkyl group which may be substituted with one or more substituents selected from the substituent group $\gamma_3$, an aryl group which may be substituted with one or more substituents selected from the substituent group $\gamma_3$, a $C_{1-6}$ alkoxy group which may be substituted with one or more substituents selected from the substituent group $\gamma_3$, a $C_{1-6}$ alkylamino group which may be substituted with one or more substituents selected from the substituent group $\gamma_3$, a di($C_{1-6}$ alkyl)amino group which may be substituted with one or more substituents selected from the substituent group $\gamma_3$, a $C_{1-6}$ alkylsulfonyl group which may be substituted with one or more substituents selected from the substituent group $\gamma_3$, an arylsulfonyl group which may be substituted with one or more substituents selected from the substituent group $\gamma_3$, a heteroaryl group which may be substituted with one or more substituents selected from the substituent group $\gamma_3$, a heterocyclyl group which may be substituted with one or more substituents selected from the substituent group $\gamma_3$, a heterocyclyloxy group which may be substituted with one or more substituents selected from the substituent group $\gamma_3$, and an oxo group.

Substituent group $\gamma_3$: A halogen atom, a hydroxyl group which may be protected, an amino group which may be protected, a carboxyl group which may be protected, a cyano group, a $C_{1-6}$ alkyl group which may be substituted with a halogen atom, a $C_{1-6}$ alkoxy group which may be substituted with a halogen atom, and an oxo group.

As the compound represented by Formula [1], the following compound is preferable.

$X^1$ is $NR^9$ (in the formula, $R^9$ has the same meaning as that described above), O, S, or $CR^{10}R^{11}$ (in the formula, each of $R^{10}$ and $R^{11}$ has the same meaning as that described above).

$X^1$ is preferably $NR^9$ (in the formula, $R^9$ has the same meaning as that described above) or S, more preferably $NR^{9a}$ (in the formula, $R^{9a}$ represents a hydrogen atom or an amino protecting group) or S, still more preferably $NR^{9a}$ (in the formula, $R^{9a}$ has the same meaning as that described above), and most preferably NH.

$Z^1$ is N or $CR^6$ (in the formula, $R^6$ has the same meaning as that described above).

$Z^1$ is preferably $CR^6$ (in the formula, $R^6$ has the same meaning as that described above), more preferably $CR^{6a}$ (in the formula, $R^{6a}$ represents an aryl group which may be substituted, a heteroaryl group which may be substituted, a heterocyclyl group which may be substituted, or NHR$^{8a}$ (in the formula, R$^{8a}$ represents an aryl group which may be substituted, a heteroaryl group which may be substituted, or a heterocyclyl group which may be substituted)), still more preferably CR$^{6b}$ (in the formula, R$^{6b}$ represents an aryl group which may be substituted with one or more substituents selected from a substituent group $\alpha_2$, a heteroaryl group which may be substituted with one or more substituents selected from a substituent group $\alpha_2$, a heterocyclyl group which may be substituted with one or more substituents selected from a substituent group $\alpha_2$, or NHR$^{8b}$ (in the formula, R$^{8b}$ represents an aryl group which may be substituted with one or more substituents selected from a substituent group $\alpha_2$, a heteroaryl group which may be substituted with one or more substituents selected from a substituent group $\alpha_2$, or a heterocyclyl group which may be substituted with one or more substituents selected from a substituent group $\alpha_2$)), and most preferably CR$^{6a}$ (in the formula, R$^{6a}$ represents a phenyl group which may be substituted with one or more substituents selected from a substituent group $\alpha_2$, a pyrazolyl group which may be substituted with one or more substituents selected from a substituent group $\alpha_2$, a pyridyl group which may be substituted with one or more substituents selected from a substituent group $\alpha_2$, a pyrimidinyl group which may be substituted with one or more substituents selected from a substituent group $\alpha_2$, a pyrazinyl group which may be substituted with one or more substituents selected from a substituent group $\alpha_2$, a pyridazinyl group which may be substituted with one or more substituents selected from a substituent group $\alpha_2$, a morpholinyl group which may be substituted with one or more substituents selected from a substituent group $\alpha_2$, or NHR$^{8c}$ (in the formula, R$^{8c}$ represents a phenyl group which may be substituted with one or more substituents selected from a substituent group $\alpha_2$, a pyridyl group which may be substituted with one or more substituents selected from a substituent group $\alpha_2$, a pyrimidinyl group which may be substituted with one or more substituents selected from a substituent group $\alpha_2$, a pyrazinyl group which may be substituted with one or more substituents selected from a substituent group $\alpha_2$, a pyridazinyl group which may be substituted with one or more substituents selected from a substituent group $\alpha_2$)).

In a case in which Z$^1$ is CR$^{6a}$ (in the formula, R$^{6a}$ has the same meaning as that described above), CR$^{6b}$ (in the formula, R$^{6b}$ has the same meaning as that described above), or CR$^{6c}$ (in the formula, R$^{6c}$ has the same meaning as that described above), R$^5$ is preferably a hydrogen atom or a halogen atom, and more preferably a hydrogen atom.

In another aspect, Z$^1$ is preferably N or CR$^{6d}$ (in the formula, R$^{6d}$ represents a hydrogen atom, a halogen atom, a C$_{1-6}$ alkyl group which may be substituted, a C$_{1-6}$ alkoxy group which may be substituted, or NHR$^{8d}$ (in the formula, R$^{8d}$ represents a hydrogen atom or a C$_{1-6}$ alkyl group which may be substituted)), more preferably N or CR$^{6e}$ (in the formula, R$^{6e}$ represents a hydrogen atom, a halogen atom, or a C$_{1-6}$ alkoxy group which may be substituted), and still more preferably N or CH.

In a case in which Z$^1$ is N or CR$^{6d}$ (in the formula, R$^{6d}$ has the same meaning as that described above), N or CR$^{6e}$ (in the formula, R$^{6e}$ has the same meaning as that described above), or N or CH, R$^5$ is preferably a C$_{3-8}$ cycloalkyl group which may be substituted, an aryl group which may be substituted, a heteroaryl group which may be substituted, a heterocyclyl group which may be substituted, or NR$^{12a}$R$^{13a}$ (in the formula, R$^{12a}$ represents a hydrogen atom or a C$_{1-6}$ alkyl group which may be substituted; and R$^{13a}$ represents a C$_{3-8}$ cycloalkyl group which may be substituted, an aryl group which may be substituted, a heteroaryl group which may be substituted, or a heterocyclyl group which may be substituted), more preferably a C$_{3-8}$ cycloalkyl group which may be substituted with one or more substituents selected from the substituent group A$_3$, an aryl group which may be substituted with one or more substituents selected from the substituent group A$_3$, a heteroaryl group which may be substituted with one or more substituents selected from the substituent group A$_3$, a heterocyclyl group which may be substituted with one or more substituents selected from the substituent group A$_3$, or NR$^{12b}$R$^{13b}$ (in the formula, R$^{12b}$ represents a hydrogen atom or a C$_{1-6}$ alkyl group; and R$^{13b}$ represents a C$_{3-8}$ cycloalkyl group which may be substituted with one or more substituents selected from the substituent group A$_3$, an aryl group which may be substituted with one or more substituents selected from the substituent group A$_3$, a heteroaryl group which may be substituted with one or more substituents selected from the substituent group A$_3$, or a heterocyclyl group which may be substituted with one or more substituents selected from the substituent group A$_3$), still more preferably a C$_{3-8}$ cycloalkyl group which may be substituted with one or more substituents selected from the substituent group $\alpha_3$, an aryl group which may be substituted with one or more substituents selected from the substituent group $\alpha_3$, a heteroaryl group which may be substituted with one or more substituents selected from the substituent group $\alpha_3$, a heterocyclyl group which may be substituted with one or more substituents selected from the substituent group $\alpha_3$, or NR$^{12b}$R$^{13c}$ (in the formula, R$^{12b}$ represents a hydrogen atom or a C$_{1-6}$ alkyl group; and R$^{13c}$ represents a C$_{3-8}$ cycloalkyl group which may be substituted with one or more substituents selected from the substituent group $\alpha_3$, an aryl group which may be substituted with one or more substituents selected from the substituent group $\alpha_3$, a heteroaryl group which may be substituted with one or more substituents selected from the substituent group $\alpha_3$, or a heterocyclyl group which may be substituted with one or more substituents selected from the substituent group $\alpha_3$), most preferably a phenyl group which may be substituted with one or more substituents selected from the substituent group $\alpha_3$, a pyrazolyl group which may be substituted with one or more substituents selected from the substituent group $\alpha_3$, an isoxazolyl group which may be substituted with one or more substituents selected from the substituent group $\alpha_3$, a pyridyl group which may be substituted with one or more substituents selected from the substituent group $\alpha_3$, a pyrimidinyl group which may be substituted with one or more substituents selected from the substituent group $\alpha_3$, a pyrazinyl group which may be substituted with one or more substituents selected from the substituent group $\alpha_3$, a pyridazinyl group which may be substituted with one or more substituents selected from the substituent group $\alpha_3$, an aziridinyl group which may be substituted with one or more substituents selected from the substituent group $\alpha_3$, a pyrrolidinyl group which may be substituted with one or more substituents selected from the substituent group $\alpha_3$, a piperidinyl group which may be substituted with one or more substituents selected from the substituent group $\alpha_3$, a piperazinyl group which may be substituted with one or more substituents selected from the substituent group $\alpha_3$, a morpholinyl group which may be substituted with one or more substituents selected from the substituent group $\alpha_3$, a homopiperazinyl group which may be substituted with one or more substituents selected from the substituent group $\alpha_3$, or NR$^{12b}$R$^{13d}$ (in the formula, R$^{12b}$ represents a hydrogen atom or a $C_{1-6}$ alkyl group; and $R^{13d}$ represents a phenyl group which may be substituted with one or more substituents selected from the substituent group $\alpha_3$, a pyrazolyl group which may be substituted with one or more substituents selected from the substituent group $\alpha_3$, an isoxazolyl group which may be substituted with one or more substituents selected from the substituent group $\alpha_3$, a pyridyl group which may be substituted with one or more substituents selected from the substituent group $\alpha_3$, a pyrimidinyl group which may be substituted with one or more substituents selected from the substituent group $\alpha_3$, a pyrazinyl group which may be substituted with one or more substituents selected from the substituent group $\alpha_3$, a pyridazinyl group which may be substituted with one or more substituents selected from the substituent group $\alpha_3$, a pyrrolidinyl group which may be substituted with one or more substituents selected from the substituent group $\alpha_3$, a piperidinyl group which may be substituted with one or more substituents selected from the substituent group $\alpha_3$, or a tetrahydropyridyl group which may be substituted with one or more substituents selected from the substituent group $\alpha_3$).

$R^1$ is a monocyclic, nitrogen-containing heteroaryl group which may be substituted, a monocyclic, nitrogen- and oxygen-containing heteroaryl group which may be substituted, a monocyclic, nitrogen- and sulfur-containing heteroaryl group which may be substituted, a bicyclic, nitrogen-containing heteroaryl group which may be substituted, a bicyclic, nitrogen- and oxygen-containing heteroaryl group which may be substituted, or a bicyclic, nitrogen- and sulfur-containing heteroaryl group which may be substituted.

$R^1$ is preferably a pyrazolyl group which may be substituted, an imidazolyl group which may be substituted, a triazolyl group which may be substituted, a thiazolyl group which may be substituted, an oxadiazolyl group which may be substituted, a thiadiazolyl group which may be substituted, a pyridyl group which may be substituted, or a pyridazinyl group which may be substituted, more preferably a pyrazolyl group which may be substituted with one or more substituents selected from a substituent group $A_1$, an imidazolyl group which may be substituted with one or more substituents selected from the substituent group $A_1$, a triazolyl group which may be substituted with one or more substituents selected from the substituent group $A_1$, a thiazolyl group which may be substituted with one or more substituents selected from the substituent group $A_1$, an oxadiazolyl group which may be substituted with one or more substituents selected from the substituent group $A_1$, a thiadiazolyl group which may be substituted with one or more substituents selected from the substituent group $A_1$, a pyridyl group which may be substituted with one or more substituents selected from the substituent group $A_1$, or a pyridazinyl group which may be substituted with one or more substituents selected from the substituent group $A_1$, still more preferably a pyrazolyl group which may be substituted with one or more substituents selected from the substituent group $\alpha_1$, an imidazolyl group which may be substituted with one or more substituents selected from the substituent group $\alpha_1$, a triazolyl group which may be substituted with one or more substituents selected from the substituent group $\alpha_1$, a thiazolyl group which may be substituted with one or more substituents selected from the substituent group $\alpha_1$, an oxadiazolyl group which may be substituted with one or more substituents selected from the substituent group $\alpha_1$, a thiadiazolyl group which may be substituted with one or more substituents selected from the substituent group $\alpha_1$, a pyridyl group which may be substituted with one or more substituents selected from the substituent group $\alpha_1$, or a pyridazinyl group which may be substituted with one or more substituents selected from the substituent group $\alpha_1$, and most preferably a thiadiazolyl group which may be substituted with one or more substituents selected from the substituent group $\alpha_1$ or a pyridazinyl group which may be substituted with one or more substituents selected from the substituent group $\alpha_1$.

$R^2$ is a hydrogen atom or a halogen atom.
$R^2$ is preferably a hydrogen atom.
$R^3$ is a hydrogen atom or a halogen atom.
$R^3$ is preferably a hydrogen atom.
$R^4$ is a hydrogen atom, a halogen atom, a hydroxyl group which may be protected, an amino group which may be protected, a $C_{1-6}$ alkyl group which may be substituted, or a $C_{1-6}$ alkoxy group which may be substituted.

$R^4$ is preferably a hydrogen atom, a halogen atom, an amino group which may be protected, or a $C_{1-6}$ alkoxy group which may be substituted, more preferably a hydrogen atom or an amino group which may be protected, and still more preferably a hydrogen atom.

$R^5$ is a hydrogen atom, a halogen atom, a hydroxyl group which may be protected, a carbamoyl group which may be substituted, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted, a $C_{1-6}$ alkoxy group which may be substituted, an aryloxy group which may be substituted, a $C_{1-6}$ alkylthio group which may be substituted, an arylthio group which may be substituted, a heteroaryl group which may be substituted, a heteroaryloxy group which may be substituted, a heteroarylthio group which may be substituted, a heterocyclyl group which may be substituted, or $NR^{12}R^{13}$ (in the formula, each of $R^{12}$ and $R^{13}$ has the same meaning as that described above).

$R^5$ is preferably a hydrogen atom, a halogen atom, a hydroxyl group which may be protected, a carbamoyl group which may be substituted, a $C_{1-6}$ alkyl group which may be substituted, a $C_{2-6}$ alkenyl group which may be substituted, a $C_{2-6}$ alkynyl group which may be substituted, an aryl group which may be substituted, a $C_{1-6}$ alkoxy group which may be substituted, a heteroaryl group which may be substituted, a heteroaryloxy group which may be substituted, a heterocyclyl group which may be substituted, or $NR^{12}R^{13}$ (in the formula, each of $R^{12}$ and $R^{13}$ has the same meaning as that described above).

Here, in a case in which $Z^1$ represents N, and $R^4$ is a hydrogen atom, $R^5$ is a halogen atom, a hydroxyl group which may be protected, a carbamoyl group which may be substituted, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, an aryloxy group which may be substituted, a $C_{1-6}$ alkylthio group which may be substituted, an arylthio group which may be substituted, a heteroaryl group which may be substituted, a heteroaryloxy group which may be substituted, a heteroarylthio group which may be substituted, a heterocyclyl group which may be substituted, or $NR^{12}R^{13}$ (in the formula, $R^{12}$ represents a hydrogen atom, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted, a heteroaryl group which may be substituted, a heterocyclyl group which may be substituted, or an amino protecting group; and $R^{13}$ represents a $C_{3-8}$ cycloalkyl group which may be substituted, an aryl group which may be substituted, a heteroaryl group which may be substituted, or a heterocyclyl group which may be substituted).

As the compound represented by Formula [1], the compound represented by Formula [1a] is preferable.

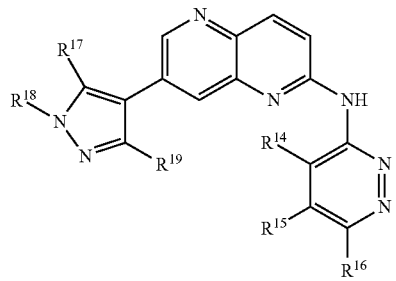

[1a]

(In the formula, each of $R^{14}$, $R^{15}$, $R^{16}$, $R^{17}$, $R^{18}$, and $R^{19}$ has the same meaning as that described above.)

More preferably, each of $R^{14}$ and $R^{16}$ is a hydrogen atom, and $R^{17}$ represents a hydrogen atom in the compound.

Examples of a salt of the compound represented by Formula [1] include salts of a basic group such as an amino group or an acidic group such as a phenolic hydroxyl group or a carboxyl group, which are typically known.

Examples of the salt of the basic group include a salt of a mineral acid such as hydrochloric acid, hydrogen bromide, or sulfuric acid, a salt of an organic carboxylic acid such as tartaric acid, formic acid, acetic acid, citric acid, trichloroacetic acid, or trifluoroacetic acid, and a salt of a sulfonic acid such as methanesulfonic acid, benzenesulfonic acid, p-toluenesulfonic acid, mesitylenesulfonic acid, or naphthalene sulfonic acid.

Examples of the salt of the acidic group include a salt of an alkali metal such as sodium or potassium; a salt of an alkali earth metal such as calcium or magnesium; an ammonium salt; and a salt of a nitrogen-containing organic base such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, or N,N'-dibenzylethylenediamine.

Furthermore, among the above-described salts, preferable examples of the compound represented by Formula[1] include pharmacologically acceptable salts.

In a case in which an isomer (for example, a tautomer, an optical isomes, or a geometric isomer) of the compound represented by Formula [1] or salt thereof is present, the invention includes the isomer, and further includes a solvate, a hydrate, and various shapes of crystal of the compound represented by Formula [1] or salt thereof.

Furthermore, the invention includes a prodrug of the compound represented by Formula [1].

The prodrug of the compound represented by Formula [1] may have characteristics such as the followings.

(1) The prodrug of the compound represented by Formula [1] may have excellent inhibitory activity with respect to the PI3K-AKT pathway and/or the Ras-Raf-MEK-ERK pathway, while this is not necessary.

(2) The prodrug of the compound represented by Formula [1] is converted to the compound represented by Formula [1] by cleavage of a functional group that functions as a prodrug by an enzyme in a body after administration. In this case, the compound represented by Formula [1] and the prodrug thereof may be coexist in a mixed manner.

(3) To the prodrug of the compound represented by Formula [1], for example, enhancement of a drug efficacy action, duration of a drug efficacy action, reduction of side effects, reduction of toxicity and/or improvement of stability are expected.

Next, the method of preparing the compound of the invention will be described.

The compound of the invention is prepared by combining known methods, and for example, can be prepared according to the following preparation method.

[Preparation Method 1]

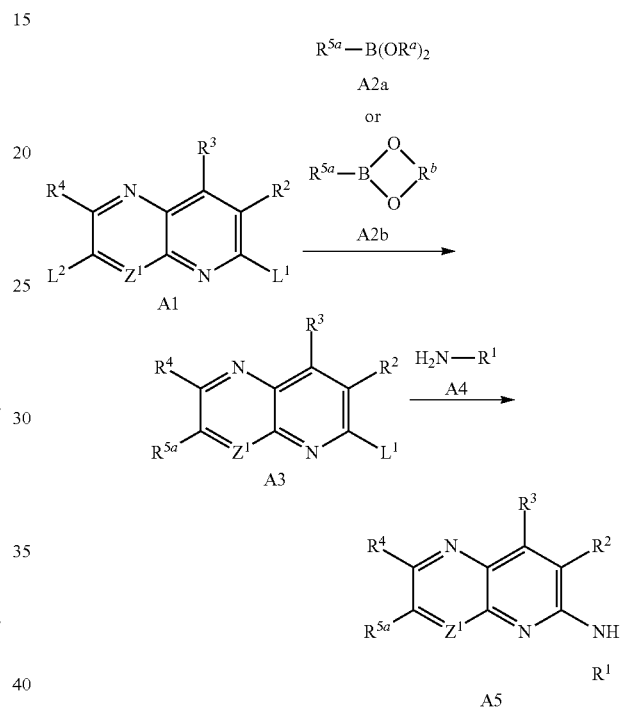

(In the formulae, $R^a$ represents a hydrogen atom or a $C_{1-6}$ alkyl group which may be substituted, $R^b$ represents a $C_{1-6}$ alkylene group which may be substituted, $R^{5a}$ represents an aryl group which may be substituted or a heteroaryl group which may be substituted, $L^1$ represents a leaving group, $L^2$ represents a leaving group, and each of $R^1$, $R^2$, $R^3$, $R^4$, and $Z^1$ has the same meaning as that described above.)

(1-1)

As the compound represented by Formula A2a, for example, pyridine-3-boronic acid, 3-(methanesulfonamide) phenylboronic acid, thiophene-2-boronic acid, benzofuran-2-boronic acid, and 3-methoxyphenylboronic acid are known.

As the compound represented by Formula A2b, for example, 1-(3-(pyrrolidin-1-yl)propyl)-4-(4,4,5,5-tetramethyl-1,3,2-dioxaborolan-2-yl)-1H-pyrazole, and 3-(4,4,5,5-tetramethyl-1,3,2-dioxaborolan-2-yl)furan are known.

The compound represented by Formula A2a and the compound represented by Formula A2b can be prepared from a corresponding halogeno material, for example, according to the method described in Japanese Patent Application Laid-Open (JP-A) No. 2003-206290, or "The Journal of Organic Chemistry", vol. 60, pp. 7508-7510, 1995.

The compound represented by Formula A3 can be prepared by reacting the compound represented by Formula A1 with the compound represented by Formula A2a or the compound represented by Formula A2b in the presence of a base, in the presence of a palladium catalyst, and in the presence or absence of a ligand.

A solvent used in the reaction is not particularly limited as long as the solvent does not adversely affect the reaction. Examples thereof include an aliphatic hydrocarbon, a halogenated hydrocarbon, an ether, a ketone, an ester, an alcohol, an amide, a sulfoxide, an aromatic hydrocarbon, acetonitrile, and water. These may be used in a mixed manner.

Examples of the base used in the reaction include an inorganic base such as sodium hydrogen carbonate, sodium carbonate, potassium carbonate, cesium carbonate, sodium hydroxide, potassium hydroxide, potassium acetate, or tripotassium phosphate, and an organic base such as 1,8-diazabicyclo[5.4.0]-7-undecene, triethylamine, or N,N-diisopropylethylamine.

An amount of the base used is from 1-fold by mole to 50-fold by mole, preferably from 1-fold by mole to 10-fold by mole, and more preferably from 2-fold by mole to 5-fold by mole, with respect to the compound represented by Formula A1.

An amount of the palladium catalyst used in the reaction is from 0.00001-fold by mole to 1-fold by mole, and preferably from 0.001-fold by mole to 0.1-fold by mole, with respect to the compound represented by Formula A1.

An amount of the ligand, which is used in the reaction if desired, is from 0.00001-fold by mole to 1-fold by mole, and preferably from 0.001-fold by mole to 0.1-fold by mole, with respect to the compound represented by Formula A1.

An amount of the compound represented by Formula A2a or the compound represented by Formula A2b used is from 1-fold by mole to 50-fold by mole, and preferably from 1-fold by mole to 2-fold by mole, with respect to the compound represented by Formula A1.

Preferably, the reaction may be performed at a temperature of from room temperature to 250° C. for from 10 minutes to 24 hours in an inert gas (for example, nitrogen or argon) atmosphere.

The reaction can also be performed using a tin reagent or a zinc reagent instead of the compound represented by Formula A2a or the compound represented by Formula A2b. The reaction may be performed, for example, according to the method described in "Organometallics in Synthesis)" written by M. Schlosser et al., 2nd edition, pp. 1123-1217, 2002 (John Wiley & Sons, INC.).

(1-2)

As the compound represented by Formula A4, for example, 2-aminothiazole, 2-aminopyridine, 3-aminopyridazine, or 2-aminothiadiazole is known.

The compound represented by Formula A5 can be prepared by reacting the compound represented by Formula A3 with the compound represented by Formula A4 in the presence of a base, in the presence of a palladium catalyst, and in the presence or absence of a ligand.

A solvent used in the reaction is not particularly limited as long as the solvent does not adversely affect the reaction. Examples thereof include an aliphatic hydrocarbon, a halogenated hydrocarbon, an ether, an ester, a sulfoxide, an aromatic hydrocarbon, and acetonitrile. These may be used in a mixed manner.

Examples of the base used in the reaction include an inorganic base such as sodium hydrogen carbonate, sodium carbonate, potassium carbonate, cesium carbonate, or tripotassium phosphate, and an organic base such as 1,8-diazabicyclo[5.4.0]-7-undecene, triethylamine, N,N-diisopropylethylamine, sodium tert-butoxide, potassium tert-butoxide, lithium bis(trimethylsilyl)amide, or lithium 2,2,6,6-tetramethylpiperidide.

An amount of the base used is from 1-fold by mole to 50-fold by mole, preferably from 1-fold by mole to 10-fold by mole, and more preferably from 2-fold by mole to 5-fold by mole, with respect to the compound represented by Formula A3.

An amount of the palladium catalyst used in the reaction is from 0.00001-fold by mole to 1-fold by mole, and preferably from 0.001-fold by mole to 0.1-fold by mole, with respect to the compound represented by Formula A3.

An amount of the ligand, which is used in the reaction if desired, is from 0.00001-fold by mole to 1-fold by mole, and preferably from 0.001-fold by mole to 0.1-fold by mole, with respect to the compound represented by Formula A3.

An amount of the compound represented by Formula A4 used is from 1-fold by mole to 50-fold by mole, and preferably from 1-fold by mole to 2-fold by mole, with respect to the compound represented by Formula A3.

Preferably, the reaction may be performed at a temperature of from room temperature to 250° C. for from 10 minutes to 24 hours in an inert gas (for example, nitrogen or argon) atmosphere.

[Preparation Method 2]

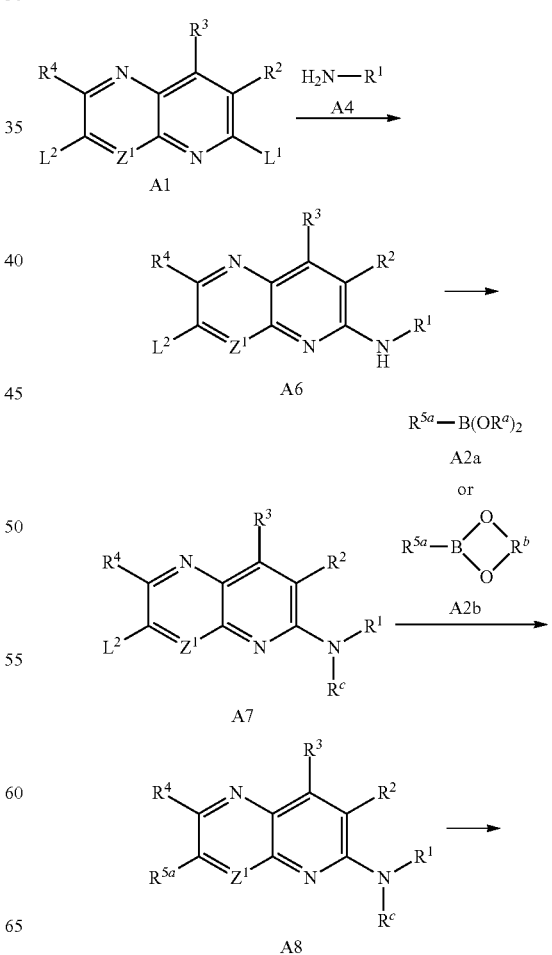

-continued

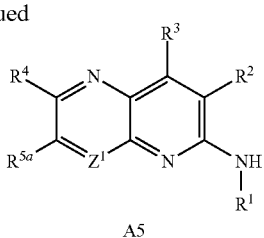

A5

(In the formulae, $R^c$ represents an amino protecting group, and each of $R^a$, $R^b$, $R^1$, $R^2$, $R^3$, $R^4$, $R^{5a}$, $L^1$, $L^2$, and $Z^1$ has the same meaning as that described above.)

(2-1)

The compound represented by Formula A6 can be prepared by reacting the compound represented by Formula A1 with the compound represented by Formula A4 in the presence of a base or in the absence thereof, or in the presence of an acid or in the absence thereof.

A solvent used in the reaction is not particularly limited as long as the solvent does not adversely affect the reaction. Examples thereof include an aliphatic hydrocarbon, a halogenated hydrocarbon, an ether, an ester, a sulfoxide, an aromatic hydrocarbon, an amide, and acetonitrile. These may be used in a mixed manner.

Examples of the base, which is used in the reaction if desired, include an inorganic base such as sodium hydride, potassium carbonate, or cesium carbonate, and an organic base such as 1,8-diazabicyclo[5.4.0]-7-undecene, triethylamine, or N,N-diisopropylethylamine.

A amount of the base used is from 1-fold by mole to 50-fold by mole, preferably from 1-fold by mole to 10-fold by mole, and more preferably from 2-fold by mole to 5-fold by mole, with respect to the compound represented by Formula A1.

Examples of the acid, which is used in the reaction if desired, include an inorganic acid such as hydrochloric acid or sulfuric acid, and an organic acid such as p-toluenesulfonic acid, acetic acid, or trifluoroacetic acid.

An amount of the acid used is from 0.001-fold by mole to 10-fold by mole with respect to the compound represented by Formula A1.

An amount of the compound represented by Formula A4 used is from 1-fold by mole to 50-fold by mole, and preferably from 1-fold by mole to 2-fold by mole, with respect to the compound represented by Formula A1.

Preferably, the reaction may be performed at a temperature of from room temperature to 250° C. for from 10 minutes to 24 hours.

(2-2)

The compound represented by Formula A7 can be prepared by protecting the amino group of the compound represented by Formula 6 in the presence of a base.

The reaction may be performed, for example, according to the method described in "Protective Groups in Organic Synthesis" written by W. Greene et al., 4th edition, pp. 696-926, 2007 (John Wiley & Sons, INC.).

(2-3)

The compound represented by Formula A8 can be prepared by reacting the compound represented by Formula A7 with the compound represented by Formula A2a or the compound represented by Formula A2b in the presence of a base, in the presence of a palladium catalyst, and in the presence or absence of a ligand.

The reaction may be performed according to Preparation Method (1-1).

(2-4)

The compound represented by Formula A5 can be prepared by deprotecting the compound represented by Formula A8.

The reaction may be performed, for example, according to the method described in "Protective Groups in Organic Synthesis" written by W. Greene et al., 4th edition, pp. 696-926, 2007 (John Wiley & Sons, INC.).

[Preparation Method 3]

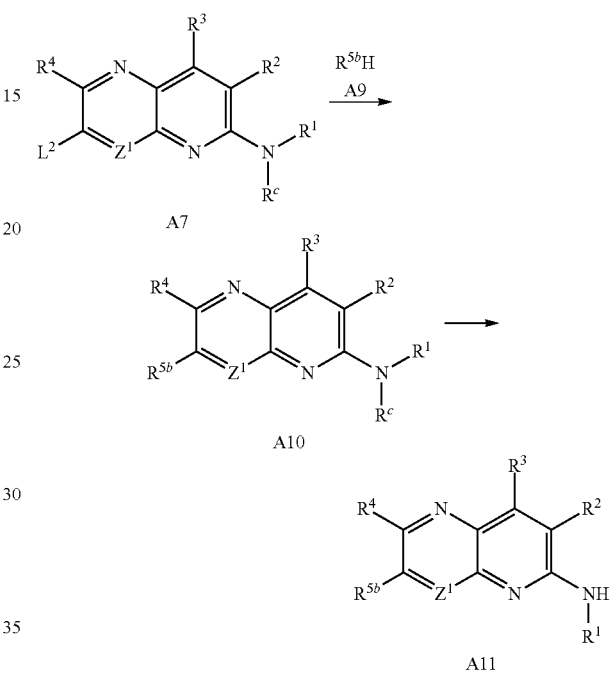

(In the formulae, $R^{5b}$ represents a heterocyclyl group which may be substituted or $NR^{12a}R^{13a}$, in which each of $R^{12a}$ and $R^{13a}$ has the same meaning as that described above, and each of $R^C$, $R^1$, $R^2$, $R^3$, $R^4$, $L^2$, and $Z^1$ has the same meaning as that described above.)

(3-1)

As the compound represented by Formula A9, for example, morpholine, 1-methylpiperazine, 4-aminopyridine, or 4-methoxyaniline is known.

The compound represented by Formula A10 can be prepared by reacting the compound represented by Formula A7 with the compound represented by Formula A9 in the presence of a base, in the presence of a palladium catalyst, and in the presence or absence of a ligand.

The solvent used in the reaction is not particularly limited as long as the solvent does not adversely affect the reaction. Examples thereof include an aliphatic hydrocarbon, an ether, an ester, an aromatic hydrocarbon, and acetonitrile. These may be used in a mixed manner.

Examples of the base used in the reaction include an inorganic base such as sodium hydrogen carbonate, sodium carbonate, potassium carbonate, cesium carbonate, or tripotassium phosphate, and an organic base such as 1,8-diazabicyclo[5.4.0]-7-undecene, triethylamine, sodium tert-butoxide, potassium tert-butoxide, or N,N-diisopropylethylamine.

An amount of the base used is from 1-fold by mole to 50-fold by mole, preferably from 1-fold by mole to 10-fold by mole, and more preferably from 2-fold by mole to 5-fold by mole, with respect to the compound represented by Formula A7.

An amount of the palladium catalyst used in the reaction is from 0.00001-fold by mole to 1-fold by mole, and preferably from 0.001-fold by mole to 0.1-fold by mole, with respect to the compound represented by Formula A7.

An amount of the ligand, which is used in the reaction if desired, is from 0.00001-fold by mole to 1-fold by mole, and preferably from 0.001-fold by mole to 0.1-fold by mole, with respect to the compound represented by Formula A7.

An amount of the compound represented by Formula A9 used is from 1-fold by mole to 50-fold by mole, and preferably from 1-fold by mole to 2-fold by mole, with respect to the compound represented by Formula A7.

Preferably, the reaction may be performed at a temperature of from room temperature to 250° C. for from 10 minutes to 24 hours in an inert gas (for example, nitrogen or argon) atmosphere.

(3-2)

The compound represented by Formula A11 can be prepared by deprotecting the compound represented by Formula A10.

The reaction may be performed according to Preparation Method (2-4).

[Preparation Method 4]

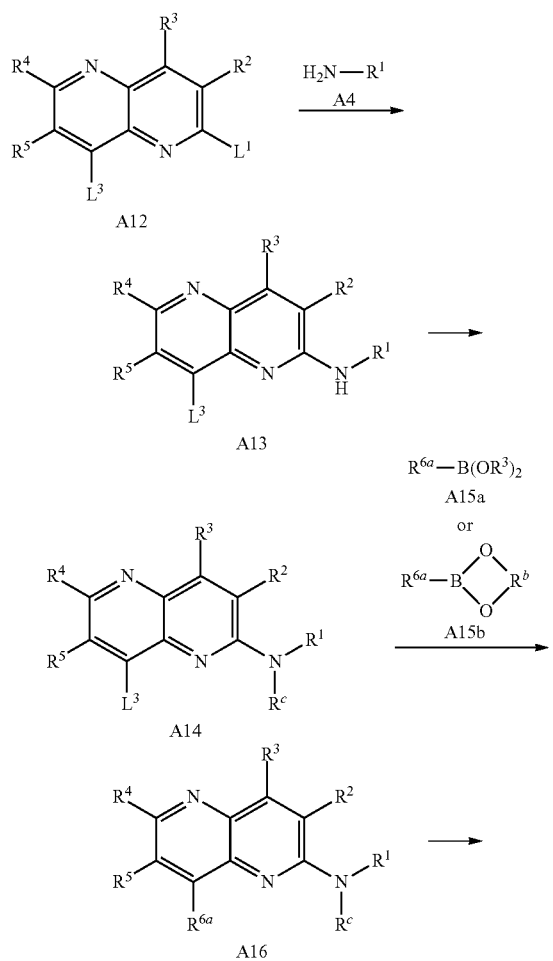

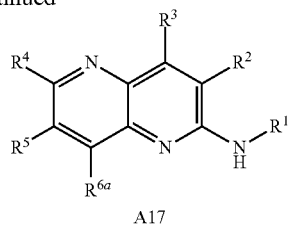

(In the formulae, $R^{6a}$ represents an aryl group which may be substituted or a heteroaryl group which may be substituted, $L^3$ represents a leaving group, and each of $R^a$, $R^b$, $R^c$, $R^1$, $R^2$, $R^3$, $R^4$, $R^5$, and $L^1$ has the same meaning as that described above.)

(4-1)

The compound represented by Formula A13 can be prepared by reacting the compound represented by Formula A12 with the compound represented by Formula A4 in the presence of a base and a palladium catalyst.

The reaction may be performed according to Preparation Method (1-2).

(4-2)

The compound represented by Formula A14 can be prepared by protecting the amino group of the compound represented by Formula A13.

The reaction may be performed according to Preparation Method (2-2).

(4-3)

As the compound represented by Formula A15a, for example, 3-aminocarbonylphenylboronic acid, and 3-methoxypyridine-4-boronic acid are known.

As the compound represented by Formula A15b, for example, 5-(4,4,5,5-tetramethyl-1,3,2-dioxaborolan-2-yl) pyrimidine, and 1-(tert-butoxycarbonyl)-4-(4,4,5,5-tetramethyl-1,3,2-dioxaborolan-2-yl)pyrazole are known.

In addition, the compound represented by Formula A15a and the compound represented by Formula A15b can be prepared from a corresponding halogeno material, for example, according to the method described in JP-A No. 2003-206290, or "The Journal of Organic Chemistry", vol. 60, pp. 7508-7510, 1995.

The compound represented by Formula A16 can be prepared by reacting the compound represented by Formula A14 with the compound represented by Formula A15a or the compound represented by Formula A15b in the presence of a base, in the presence of a palladium catalyst, and in the presence or absence of a ligand.

The reaction may be performed according to Preparation Method (1-1).

(4-4)

The compound represented by Formula A17 can be prepared by deprotecting the compound represented by Formula A16.

The reaction may be performed according to Preparation Method (2-4).

[Preparation Method 5]

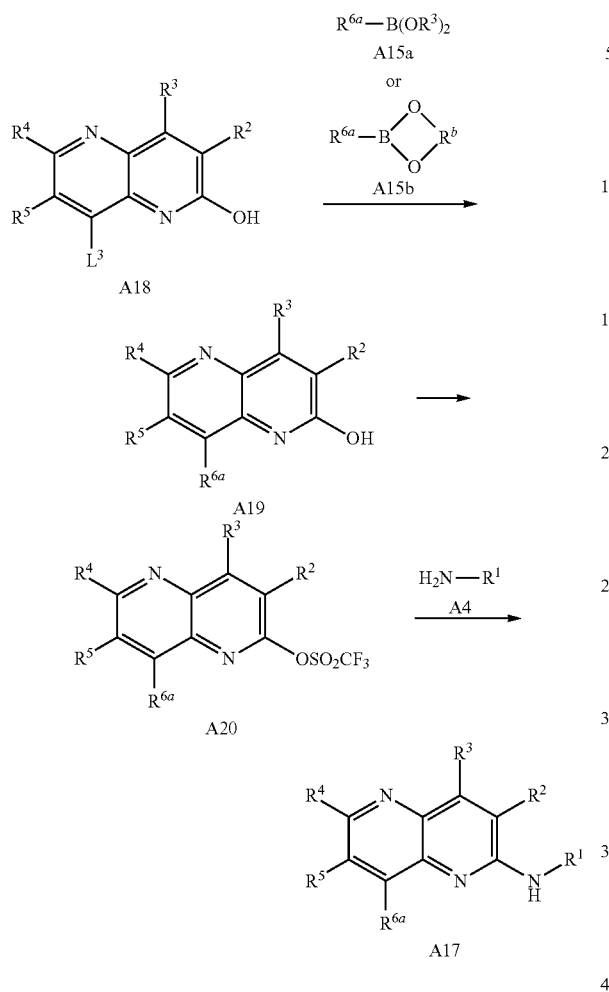

(In the formulae, each of $R^a$, $R^b$, $R^1$, $R^2$, $R^3$, $R^4$, $R^5$, $R^{6a}$, and $L^3$ has the same meaning as that described above.)

(5-1)

The compound represented by Formula A19 can be prepared by reacting the compound represented by Formula A18 with the compound represented by Formula A15a or the compound represented by Formula A15b in the presence of a base, in the presence of a palladium catalyst, and in the presence or absence of a ligand.

The reaction may be performed according to Preparation Method (1-1).

(5-2)

The compound represented by Formula A20 can be prepared by reacting the compound represented by Formula A19 with trifluoromethanesulfonic acid anhydride or N-phenyl-bis(trifluoromethanesulfonimide) in the presence of a base.

The solvent used in the reaction is not particularly limited as long as the solvent does not adversely affect the reaction. Examples thereof include an aliphatic hydrocarbon, a halogenated hydrocarbon, an ether, a ketone, an ester, an amide, a sulfoxide, and an aromatic hydrocarbon. These may be used in a mixed manner.

Examples of the base used in the reaction include an inorganic base such as potassium carbonate or sodium hydride, and an organic base such as pyridine 2,6-lutidine, triethylamine, or N,N-diisopropylethylamine.

An amount of the base used is from 1-fold by mole to 50-fold by mole, preferably from 1-fold by mole to 10-fold by mole, and more preferably from 2-fold by mole to 5-fold by mole, with respect to the compound represented by Formula A19.

An amount of trifluoromethanesulfonic acid anhydride or N-phenyl-bis(trifluoromethanesulfonimide) used in the reaction is from 1-fold by mole to 10-fold by mole, and preferably from 1-fold by mole to 2-fold by mole, with respect to the compound represented by Formula A19.

Preferably, the reaction may be performed at a temperature of from 0° C. to 30° C. for from 30 minutes to 24 hours in an inert gas (for example, nitrogen or argon) atmosphere.

(5-3)

The compound represented by Formula A17 can be prepared by reacting the compound represented by Formula A20 with the compound represented by Formula A4 in the presence of a base and a palladium catalyst.

The reaction may be performed according to Preparation Method (1-2).

[Preparation Method 6]

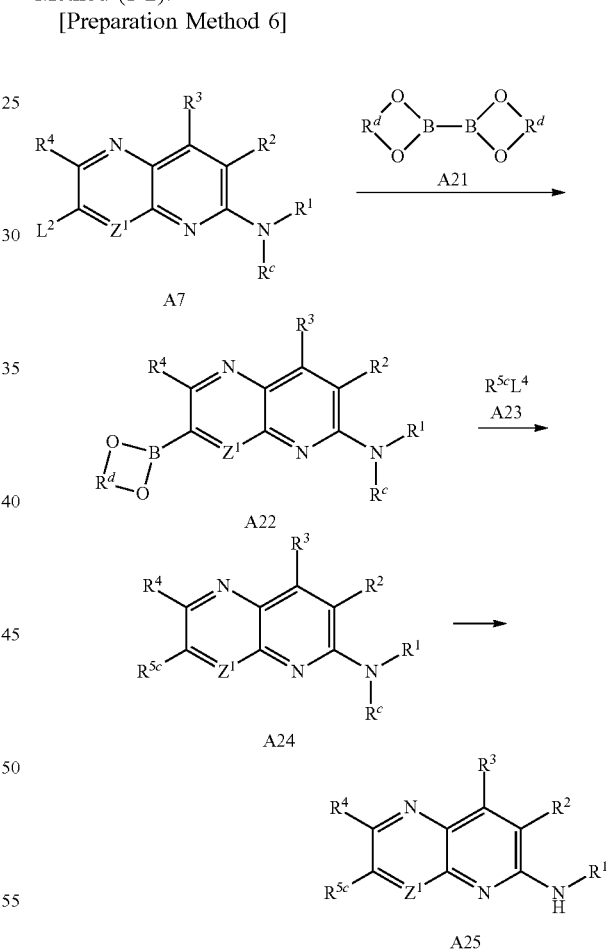

(In the formulae, $R^d$ represents a $C_{1-6}$ alkylene group which may be substituted; $R^{5c}$ represents an aryl group which may be substituted or a heteroaryl group which may be substituted; $L^4$ represents a leaving group; and each of $R^c$, $R^1$, $R^2$, $R^3$, $R^4$, $L^2$, and $Z^1$ has the same meaning as that described above.)

(6-1)

As the compound represented by Formula A21, for example, bis(pinacolato)diboron is known.

The compound represented by Formula A22 can be prepared by reacting the compound represented by Formula A7 with the compound represented by Formula A21 in the presence of a base, in the presence of a palladium catalyst, and in the presence or absence of a ligand.

The reaction may be performed according to Preparation Method (1-1).

The compound represented by Formula A22 may be used in the following reaction as it is without being isolated.

(6-2)

As the compound represented by Formula A23, for example, 4-iodo-3-(2-methoxyethyl)-1-methyl-1H-pyrazole is known.

The compound represented by Formula A24 can be prepared by reacting the compound represented by Formula A22 with the compound represented by Formula A23 in the presence of a base, in the presence of a palladium catalyst, and in the presence or absence of a ligand.

The solvent used in the reaction is not particularly limited as long as the solvent does not adversely affect the reaction. Examples thereof include an aliphatic hydrocarbon, a halogenated hydrocarbon, an ether, a ketone, an ester, a sulfoxide, an aromatic hydrocarbon, acetonitrile, an alcohol, an amide, and water. These may be used in a mixed manner.

Examples of the base used in the reaction include an inorganic base such as sodium hydrogen carbonate, sodium carbonate, potassium carbonate, cesium carbonate, or tripotassium phosphate, and an organic base such as 1,8-diazabicyclo[5.4.0]-7-undecene, triethylamine, or N,N-diisopropylethylamine.

An amount of the base used is from 1-fold by mole to 50-fold by mole, preferably from 1-fold by mole to 10-fold by mole, and more preferably from 2-fold by mole to 5-fold by mole, with respect to the compound represented by Formula A22.

An amount of the palladium catalyst used in the reaction is from 0.00001-fold by mole to 1-fold by mole, and preferably from 0.001-fold by mole to 0.1-fold by mole, with respect to the compound represented by Formula A22.

An amount of the ligand, which is used in the reaction if desired, is from 0.00001-fold by mole to 1-fold by mole, and preferably from 0.001-fold by mole to 0.1-fold by mole, with respect to the compound represented by Formula A22.

An amount of the compound represented by Formula A23 used is from 1-fold by mole to 5-fold by mole, and preferably from 1-fold by mole to 2-fold by mole, with respect to the compound represented by Formula A22.

Preferably, the reaction may be performed at a temperature of from room temperature to 250° C. for from 1 hour to 24 hours in an inert gas (for example, nitrogen or argon) atmosphere.

(6-3)

The compound represented by Formula A25 can be prepared by deprotecting the compound represented by Formula A24.

The reaction may be performed according to Preparation Method (2-4).

[Preparation Method 7]

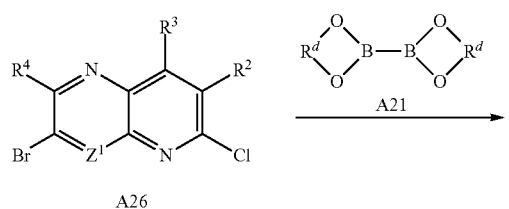

(In the formulae, each of $R^d$, $R^1$, $R^2$, $R^3$, $R^4$, $R^{5c}$, $L^4$, and $Z^1$ has the same meaning as that described above.)

(7-1)

The compound represented by Formula A27 can be prepared by reacting the compound represented by Formula A26 with the compound represented by Formula A21 in the presence of a base, in the presence of a palladium catalyst, and in the presence or absence of a ligand.

The reaction may be performed according to Preparation Method (6-1).

(7-2)

The compound represented by Formula A28 can be prepared by reacting the compound represented by Formula A27 with the compound represented by Formula A23 in the presence of a base, in the presence of a palladium catalyst, and in the presence or absence of a ligand.

The reaction may be performed according to Preparation Method (6-2).

(7-3)

The compound represented by Formula A29 can be prepared by reacting the compound represented by Formula A28 with the compound represented by Formula A4 in the presence of a base and a palladium catalyst.

The reaction may be performed according to Preparation Method (1-2).

Next, methods for preparing a compound which is a raw material for the compound of the invention will be described.

39

[Preparation Method A]

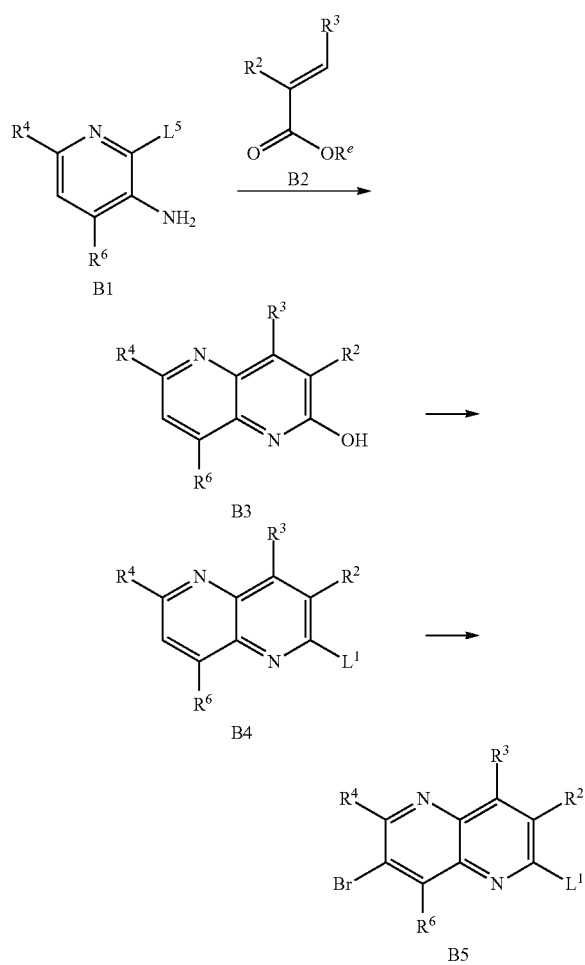

(In the formulae, $R^e$ represents a $C_{1-6}$ alkyl group, $L^5$ represents a leaving group; and each of $R^2$, $R^3$, $R^4$, $R^6$, and $L^1$ has the same meaning as that described above.)

(A-1)

As the compound represented by Formula B1, for example, 2-chloro-3-aminopyridine is known.

As the compound represented by Formula B2, for example, butyl acrylate, methyl acrylate, ethyl acrylate, and tert-butyl acrylate is known.

The compound represented by Formula B3 can be prepared by reacting the compound represented by Formula B1 with the compound represented by Formula B2 in the presence of a base, in the presence of a palladium catalyst, and in the presence or absence of a ligand.

The solvent used in the reaction is not particularly limited as long as the solvent does not adversely affect the reaction. Examples thereof include an aliphatic hydrocarbon, a halogenated hydrocarbon, an alcohol, an ether, a ketone, an ester, an amide, a sulfoxide, an aromatic hydrocarbon, and water. These may be used in a mixed manner.

Preferable examples of the solvent include an ester, and a more preferable example thereof is cyclohexyl acetate.

Examples of the base used in the reaction include an inorganic base such as sodium hydrogen carbonate, sodium carbonate, potassium carbonate, cesium carbonate, or tripotassium phosphate, and an organic base such as pyridine,

40

4-(dimethylamino)pyridine, triethylamine, N,N-diisopropylethylamine, or sodium tert-butoxide.

Preferable examples of the base include an organic base, and a more preferable example thereof is triethylamine.

An amount of the base used is from 1-fold by mole to 50-fold by mole, preferably from 1-fold by mole to 10-fold by mole, and more preferably from 1-fold by mole to 4-fold by mole, with respect to the compound represented by Formula B1.

Preferable examples of the palladium catalyst used in the reaction include an organic palladium complex, and a more preferable example thereof is bis(tri-tert-butylphosphine) palladium(0).

An amount of the palladium catalyst used is from 0.001-fold by mole to 1-fold by mole, preferably from 0.002-fold by mole to 0.5-fold by mole, and more preferably from 0.005-fold by mole to 0.1-fold by mole, with respect to the compound represented by Formula B1.

An amount of the ligand, which is used in the reaction if desired, is from 0.00001-fold by mole to 1-fold by mole, preferably from 0.0001-fold by mole to 0.5-fold by mole, and more preferably from 0.001-fold by mole to 0.5-fold by mole, with respect to the compound represented by Formula B1.

An amount of the compound represent by Formula B2 used is from 1-fold by mole to 10-fold by mole, preferably from 1-fold by mole to 5-fold by mole, and more preferably from 1-fold by mole to 2-fold by mole, with respect to the compound represented by Formula B1.

Preferably, the reaction may be performed at a temperature of from room temperature to 180° C. for from 30 minutes to 96 hours in an inert gas (for example, nitrogen or argon) atmosphere.

(A-2)

The compound represented by Formula B4 can be prepared by reacting the compound represented by Formula B3 with a halogenating agent, sulfonic acid anhydride, or a sulfonic halide.

The solvent used in the reaction is not particularly limited as long as the solvent does not adversely affect the reaction. Examples thereof include an aliphatic hydrocarbon, a halogenated hydrocarbon, and an aromatic hydrocarbon. These may be used in a mixed manner.

A halogenating agent or sulfonic acid anhydride may be used as the solvent.

Examples of the halogenating agent used in the reaction include phosphorus oxychloride, thionyl chloride, phosphorus tribromide, and thionyl bromide.

Preferable examples of the halogenating agent include phosphorus oxychloride and thionyl chloride, and a more preferable example thereof is phosphorus oxychloride.

An amount of the halogenating agent used is from 1-fold by mole to 10-fold by mole, preferably from 2-fold by mole to 8-fold by mole, and more preferably from 4-fold by mole to 6-fold by mole, with respect to the compound represented by Formula B3.

Examples of the sulfonic acid anhydride used in the reaction include trifluoromethanesulfonic acid anhydride.

Examples of the sulfonic halide used in the reaction include trifluoromethanesulfonyl chloride.

In the case of using the sulfonic halide, the reaction is preferably performed in the presence of a base.

Examples of the base used in the reaction include an organic base such as pyridine, 4-(dimethylamino)pyridine, triethylamine, or N,N-diisopropylethylamine.

An amount of the base used is from 1-fold by mole to 50-fold by mole, preferably from 1-fold by mole to 10-fold by mole, and more preferably from 1-fold by mole to 4-fold by mole, with respect to the compound represented by Formula B3.

In the reaction, the halogenating agent is preferably used as the solvent, and more preferably, phosphorus oxychloride is used as the solvent.

The reaction may be performed at a temperature of from room temperature to the boiling temperature of the solvent, that is preferably at the boiling temperature of the solvent, for from 30 minutes to 24 hours.

(A-3)

The compound represented by Formula B5 can be prepared by reacting the compound represented by Formula B4 with a brominating agent in the presence or absence of a base.

A solvent used in the reaction is not particularly limited as long as the solvent does not adversely affect the reaction. Examples thereof include an aliphatic hydrocarbon, a halogenated hydrocarbon, a carboxylic acid, and water. These may be used in a mixed manner.

Preferable examples of the solvent include a carboxylic acid, and a more preferable example thereof is acetic acid.

Examples of the brominating agent used in the reaction include bromine and thionyl bromide, and a more preferable example thereof is bromine.

An amount of the brominating agent used in the reaction is from 1-fold by mole to 2-fold by mole, and preferably from 1.0-fold by mole to 1.2-fold by mole, with respect to the compound represented by Formula B4.

Examples of the base, which is used in the reaction if desired, include preferably sodium acetate and potassium acetate, and a more preferable example thereof is sodium acetate.

An amount of the base used is from 1-fold by mole to 5-fold by mole, preferably from 1-fold by mole to 2-fold by mole, and more preferably from 1.0-fold by mole to 1.2-fold by mole, with respect to the compound represented by Formula B4.

The reaction may be performed at a temperature of from 60° C. to 120° C., that is preferably at a temperature of from 80° C. to 100° C., for from 30 minutes to 24 hours.

[Preparation Method B]

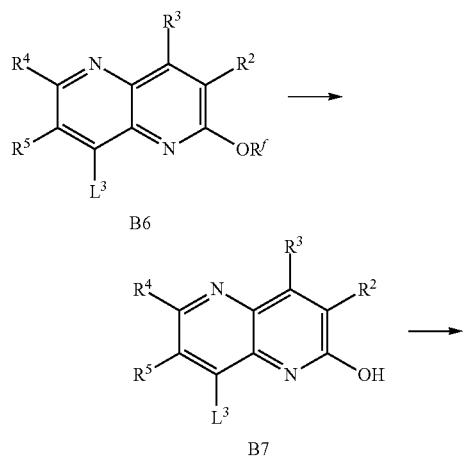

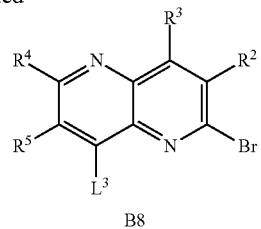

(In the formulae, $R^f$ represents a $C_{1-6}$ alkyl group, and each of $R^2$, $R^3$, $R^4$, $R^5$, and $L^3$ has the same meaning as that described above.)

(B-1)

As the compound represented by Formula B6, for example, 6-methoxy-1,5-naphthyridin-4(1H)-one is known.

The compound represented by Formula B7 can be prepared by reacting the compound represented by Formula B6 with an acid.

A solvent used in the reaction is not particularly limited as long as the solvent does not adversely affect the reaction. Examples thereof include an aliphatic hydrocarbon, a halogenated hydrocarbon, an alcohol, an ether, a ketone, an ester, an amide, a sulfoxide, an aromatic hydrocarbon, and water. These may be used in a mixed manner.

Examples of the acid used in the reaction include an inorganic acid such as hydrobromic acid, hydrochloric acid, sulfuric acid, nitric acid, or phosphoric acid, and an organic acid such as acetic acid or trifluoroacetic acid.

An amount of the acid used is from 0.001-fold by mole to 50-fold by mole with respect to the compound represented by Formula B6.

Preferably, the reaction may be performed at a temperature of from 50° C. to 180° C. for from 10 minutes to 24 hours.

(B-2)

The compound represented by Formula B8 can be prepared by reacting the compound represented by Formula B7 with a brominating agent.

A solvent used in the reaction is not particularly limited as long as the solvent does not adversely affect the reaction. Examples thereof include an aliphatic hydrocarbon, a halogenated hydrocarbon, and an aromatic hydrocarbon. These may be used in a mixed manner.

Examples of the brominating agent used in the reaction include phosphorous oxybromide and phosphorus tribromide, and a more preferable example thereof is phosphorous oxybromide.

An amount of the brominating agent used in the reaction is from 1-fold by mole to 2-fold by mole, and preferably from 1.0-fold by mole to 1.2-fold by mole, with respect to the compound represented by Formula B7.

Preferably, the reaction may be performed at a temperature of from 50° C. to 180° C. for from 10 minutes to 24 hours in an inert gas (for example, nitrogen or argon) atmosphere.

The compounds obtained in the preparation methods described above can be derived to other compounds by a known reaction such as condensation, addition, oxidation, reduction, rearrangement, substitution, halogenation, dehydration, or hydrolysis, or by appropriately combining these reactions.

In a case in which an amino group, a hydroxyl group, or a carboxyl group is present in the compounds obtained by the preparation methods described above, the reaction can be performed after appropriately changing the protecting group thereof. In addition, in a case in which two or more protecting groups are present, the protecting groups can be selectively deprotected by a known reaction.

In a case in which isomers (for example, optical isomers, geometric isomers, or tautomers) are present in compounds used in the preparation methods described above, these isomers can also be used. In addition, in a case in which a solvate, a hydrate, or various shapes of crystal are present, the solvate, hydrate, or various shapes of crystal can also be used.

In a case in which the compound represented by Formula [1] or salt thereof is used as a medicine, a pharmaceutic aid such as an excipient, a carrier, or a diluent which is typically used in formulation may be used in an appropriately mixing manner.

Examples of an additive include an excipient, a disintegrating agent, a binding agent, a lubricant, a flavoring agent, a colorant, an aromatizer, a surfactant, a coating agent, and a plasticizer.

Examples of the excipient include a sugar alcohol such as erythritol, mannitol, xylitol, or sorbitol; a sugar such as white sugar, powdered sugar, lactose, or glucose; a cyclodextrin such as α-cyclodextrin, β-cyclodextrin, γ-cyclodextrin, hydroxypropyl β-cyclodextrin, or sodium sulfobutylether β-cyclodextrin; a cellulose such as crystalline cellulose or microcrystalline cellulose; and a starch such as a corn starch, a potato starch, or a pregelatinized starch.

Examples of the disintegrating agent include carmellose, carmellose calcium, croscarmellose sodium, sodium carboxymethyl starch, crospovidone, low substituted hydroxypropyl cellulose, and a partly pregelatinized starch.

Examples of the binding agent include hydroxypropyl cellulose, croscarmellose sodium, and methylcellulose.

Examples of the lubricant include stearic acid, magnesium stearate, calcium stearate, talc, hydrated silicon dioxide, light anhydrous silicic acid, and sucrose fatty acid ester.

Examples of the flavoring agent include aspartame, saccharin, stevia, thaumatin, and acesulfame potassium.

Examples of the colorant include titanium dioxide, ferric oxide, yellow ferric oxide, black iron oxide, Food Red No. 102, Food Yellow No. 4, and Food Yellow No. 5.

Examples of the aromatizer include an essential oil such as an orange oil, a lemon oil, a peppermint oil, or a pine oil; an essence such as an orange essence or a peppermint essence; a flavor such as a cherry flavor, a vanilla flavor, or a fruit flavor; a powder fragrance such as an apple micron, a banana micron, a peach micron, a strawberry micron, or an orange micron; vanillin; and ethyl vanillin.

Examples of the surfactant include sodium lauryl sulfate, dioctyl sodium sulfosuccinate, polysorbate, and polyoxyethylene hydrogenated castor oil.

Examples of the coating agent include hydroxypropyl methyl cellulose, aminoalkyl methacrylate copolymer E, aminoalkyl methacrylate copolymer RS, ethyl cellulose, cellulose acetate phthalate, hydroxypropyl methyl cellulose phthalate, a methacrylic acid copolymer L, a methacrylic acid copolymer LD, and a methacrylic acid copolymer S.

Examples of the plasticizer include triethyl citrate, macrogol, triacetin, and propylene glycol.

These additives may be used singly, or in combination of two or more kinds thereof.

A blending amount thereof is not particularly limited, and the additives may be appropriately blended such that the effect thereof is sufficiently exhibited depending on the respective purposes.

These additives can be administered orally or parenterally according to a usual method in a form such as a tablet, a capsule, a powder, a syrup, a granule, a pill, a suspension, an emulsion, a solution, a powdered formulation, a suppository, an eye drop, a nasal drop, an ear drop, a patch, an ointment, or an injection. In addition, an administration method, a dose, and a number of administration can be appropriately selected depending on a patient's age, body weight, and symptom. Typically, for an adult, 0.01 mg/kg to 1000 mg/kg may be administered orally or parenterally once or several times per day.

The compound or salt thereof of the invention can be used in a treatment such as prevention of or cure for diseases associated with PI3K and/or ERK.

Examples of the diseases associated with PI3K and/or ERK include a cell proliferative disease, an allergic disease, an autoimmune disease, a neurodegenerative disease, a circulatory system disease, an inflammatory disease, an endocrine disorder, a metabolic disorder, and an infection.

Preferable examples of diseases to which the compound or salt thereof of the invention can be applied include malignant tumors in which the PI3K-AKT pathway and/or the Ras-Raf-MEK-ERK pathway is accelerated.

Specifically, the compound or salt thereof of the invention can be used in a treatment such as prevention of or cure for malignant tumors which exhibit resistance with respect to a PI3K-AKT pathway inhibitor and/or a Ras-Raf-MEK-ERK pathway inhibitor.

EXAMPLES

The invention will be described with reference to Reference Examples, Examples, and Test Examples, but the invention is not limited thereto.

Unless otherwise specified, in purification by column chromatography, an automated purification apparatus ISOLERA (manufactured by Biotage Japan Ltd.) or a medium-pressure liquid chromatograph YFLC W-PREP 2XY (manufactured by YAMAZEN CORPORATION) was used.

Unless otherwise specified, as a carrier in silica gel column chromatography, SNAP KP-Sil CARTRIDGE (manufactured by Biotage Japan Ltd.), or HIGH FLASH COLUMN W001, W002, W003, W004, or W005 (manufactured by YAMAZEN CORPORATION) was used.

As NH silica, SNAP KP-NH CARTRIDGE (manufactured by Biotage Japan Ltd.) was used.

In preparative thin layer silica gel chromatography, PLC GLASS PLATE SILICA GEL $F_{60}$ (manufactured by Merck KGaA) was used.

As a microwave reaction apparatus, INITIATOR SIXTY (manufactured by Biotage Japan Ltd.) was used.

As a flow-type hydrogenation reaction apparatus, H-CUBE (manufactured by ThalesNano Inc.) was used.

In preparative reversed phase HPLC, WATERS 2998 PHOTODIODE ARRAY (PDA) DETECTOR (manufactured by Waters), WATERS 600 CONTROLLER (manufactured by Waters), a WATERS 2767 SAMPLE MANAGER (manufactured by Waters) set, and a YMC-ACTUS PROC18 (30×50 mm column) (manufactured by YMC Co., Ltd.) were used.

A MS spectrum was measured by an ionization method in which ACQUITY SQD LC/MS SYSTEM (manufactured by Waters, ionization method: ElectroSpray Ionization (ESI) method) and LCMS-2010EV (manufactured by Shimadzu Corporation, ionization method: ESI and Atmospheric Pressure Chemical Ionization (APCI)) were performed at the same time.

In the measurement of an NMR spectrum, tetramethylsilane was used as an internal standard, BRUKER AV300 (manufactured by Bruker Corporation) was used, and all δ values were shown in ppm.

Abbreviations in NMR measurement have the following meanings.

s: Singlet
br: Broad
d: Doublet
dd: Double doublet
t: Triplet
q: Quartet
quin: Quintet
sext: Sextet
sep: Septet
m: Multiplet
DMSO-$d_6$: Hexadeuterodimethylsulfoxide Abbreviations in Reference Examples and Examples have the following meanings.

Ac: Acetyl
Bn: Benzyl
Boc: tert-Butoxycarbonyl
Bu: Butyl
$^t$Bu: tert-Butyl
Et: Ethyl
Fmoc: 9-Fluorenylmethyloxycarbonyl
Me: Methyl
Ms: Methylsulfonyl
Ph: Phenyl
SEM: (2-(Trimethylsilyl)ethoxy)methyl
TBS: tert-Butyldimethylsilyl
Tf: Trifluoromethylsulfonyl
TFA: Trifluoroacetic acid
THP: Tetrahydropyranyl
TMS: Trimethylsilyl
Ts: Toluenesulfonyl Example 0001

0001-1

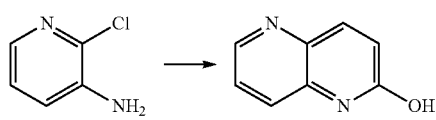 [SMILES: Nc1cccnc1Cl ; Oc1ccc2ncccc2n1]

Triethylamine (13 mL), butyl acrylate (10 mL), and bis(tri-tert-butylphosphine)palladium(0) (350 mg) were added to a solution of 2-chloro-3-aminopyridine (6.00 g) in cyclohexyl acetate (60 mL), followed by stirring at 150° C. for 40 hours in a nitrogen atmosphere. Water (30 ml) was added to the reaction mixture at 70° C., and the resultant product was cooled to room temperature while stirring. The reaction mixture was subjected to an ultrasonic treatment for 30 minutes, and the solid matter was collected by filtration and washed with water. Ethyl acetate (3 mL)/2-propanol (4 mL) was added to the obtained solid matter, and the resultant product was subjected to an ultrasonic treatment. The solid matter was collected by filtration, thereby obtaining 1,5-naphthyridin-2-ol (2.51 g) as a pale yellow solid.
MSm/z(M+H):147.

0001-2

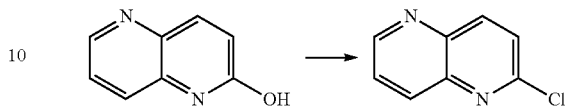

Phosphorus oxychloride (8.3 mL) was added to 1,5-naphthyridin-2-ol (2.76 g), followed by stirring at 100° C. for 5 hours. The reaction mixture was cooled to room temperature, and added dropwise to a mixture of ethyl acetate (30 mL), water (30 mL), and sodium carbonate (9.57 g) over a period of 1 hour in an ice bath. Water (10 mL) was added thereto, and sodium carbonate was added thereto, followed by adjusting the pH of the resultant product to 8.3. The resultant product was stirred at room temperature for 10 minutes, and ethyl acetate (270 mL) and water (200 mL) were added thereto. The organic layer was collected by separation, and the aqueous layer was extracted two times with ethyl acetate (200 mL). The organic layer and the extraction liquid were combined, the resultant product was dried over anhydrous sodium sulfate, and the solvent was distilled off under reduced pressure, thereby obtaining 2-chloro-1,5-naphthyridine (2.86 g) as a pale yellow solid.
MSm/z(M+H):165.

0001-3

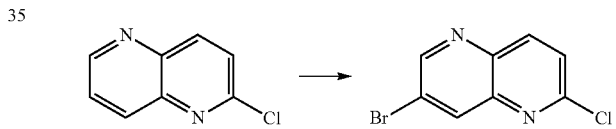

A solution of bromine (0.99 mL) in acetic acid (2.5 mL) was added dropwise to a mixture of 2-chloro-1,5-naphthyridine (2.88 g) and sodium acetate (2.89 g) in acetic acid (15 mL) at 85° C., and acetic acid (2 mL) was added thereto, followed by stirring at 85° C. for 3 hours. The reaction mixture was cooled to room temperature, and added dropwise to a 6 mol/L sodium hydroxide aqueous solution (60 mL) under ice-cooling. The solid matter was collected by filtration, suspended in methanol (5 mL), and subjected to an ultrasonic treatment. The solid matter was collected by filtration, and washed with methanol (3 mL). The obtained solid was suspended in a 75 v/v % methanol aqueous solution (8 mL), the resultant product was subjected to an ultrasonic treatment, and the solid matter was collected by filtration, thereby obtaining 7-bromo-2-chloro-1,5-naphthyridine (3.33 g) as a pale yellow solid.
MSm/z(M+H):243.

0001-4

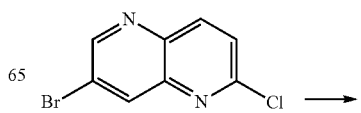

47
-continued

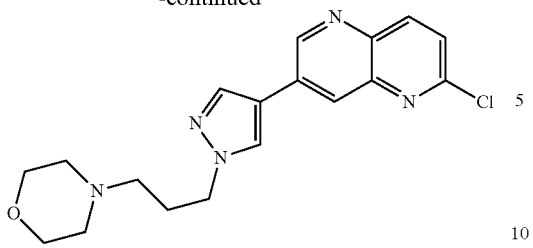

A mixture of 7-bromo-2-chloro-1,5-naphthyridine (30 mg), 1-(3-morpholinopropyl)-1H-pyrazole-4-boronic acid pinacol ester (59 mg), bis(di-tert-butyl(4-dimethylaminophenyl)phosphine)dichloropalladium(II) (5 mg) and sodium carbonate (20 mg) in 1,4-dioxane (1.9 mL) and water (0.1 mL) was stirred at 100° C. for 7.5 hours in a nitrogen atmosphere. The reaction mixture was cooled to room temperature, ethanol (4 mL) was added thereto, and the solvent was distilled off under reduced pressure. The obtained residue was purified by silica gel column chromatography (chloroform-ethyl acetate, NH silica), thereby obtaining 4-(3-(4-(6-chloro-1,5-naphthyridin-3-yl)-1H-pyrazol-1-yl)propyl)morpholine (45.6 mg) as a white solid.

MSm/z(M+H):358.

0001-5

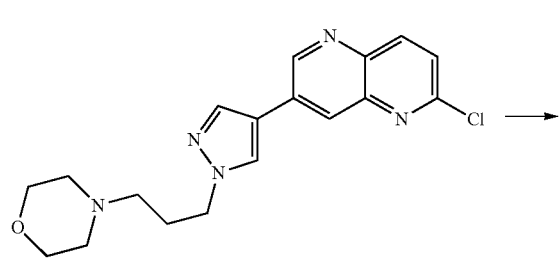

48
-continued

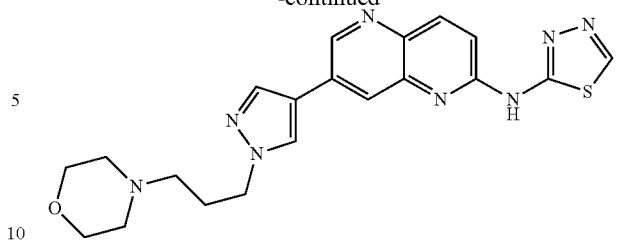

A mixture of 4-(3-(4-(6-chloro-1,5-naphthyridin-3-yl)-1H-pyrazol-1-yl)propyl)morpholine (45.6 mg), 1,3,4-thiadiazole-2-amine (19 mg), tris(dibenzylideneacetone)dipalladium(0) (23 mg), 4,5-bis(diphenylphosphino)-9,9-dimethylxanthene (28 mg) and cesium carbonate (120 mg) in 1,4-dioxane (1.9 mL) was stirred at 150° C. for 30 minutes using a microwave reaction apparatus. The reaction mixture was cooled to room temperature, and ethanol was added thereto. The insolubles were filtered off using celite, the filtrate was concentrated under reduced pressure, and the obtained residue was purified by silica gel column chromatography (chloroform-methanol, NH silica), thereby obtaining N-(7-(1-(3-morpholinopropyl)-1H-pyrazol-4-yl)-1,5-naphthyridin-2-yl)-1,3,4-thiadiazole-2-amine (11 mg) as a white solid.

$^1$H-NMR(DMSO-d$_6$)δ:12.23(1H,s),9.17(1H,s),9.09(1H, d,J=2.0 Hz),8.57(1H,s),8.33(1H,d,J=2.0 Hz),8.28(1H,d, J=9.2 Hz),8.21(1H,s),7.44(1H,d,J=9.2 Hz),4.21(2H,t,J=7.1 Hz),3.58(4H,t,J=4.6 Hz),2.36-2.28(6H,m),2.05-1.99(2H,m).

MSm/z(M+H):423.

Example 0002

The following compounds were obtained in the same manner as in Examples 0001-4 and 0001-5.

| Example No. | | |
|---|---|---|
| 0002 | | |
| 0002-1 | 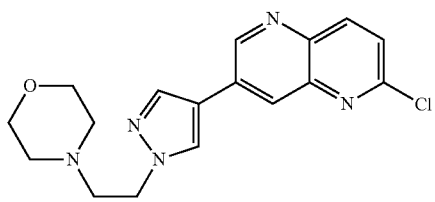 [SMILES: Clc1ccc2ncc(-c3cnn(CCN4CCOCC4)c3)cc2n1] | MS m/z (M + H): 344 |
| 0002-2 | 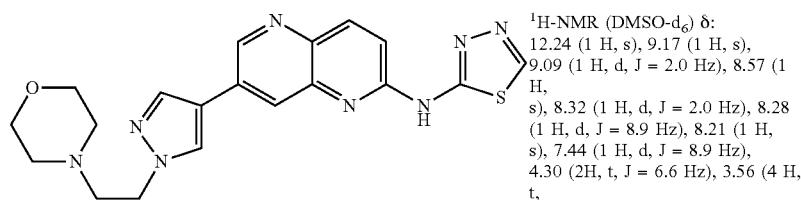 | $^1$H-NMR (DMSO-d$_6$) δ: 12.24 (1 H, s), 9.17 (1 H, s), 9.09 (1 H, d, J = 2.0 Hz), 8.57 (1 H, s), 8.32 (1 H, d, J = 2.0 Hz), 8.28 (1 H, d, J = 8.9 Hz), 8.21 (1 H, s), 7.44 (1 H, d, J = 8.9 Hz), 4.30 (2H, t, J = 6.6 Hz), 3.56 (4 H, t, J = 4.5 Hz ), 2.79 (2H, t, J = 6.6 Hz ), 2.50-2.40 (4H, m). MS m/z (M + H): 409. |

Example 0003

0003-1

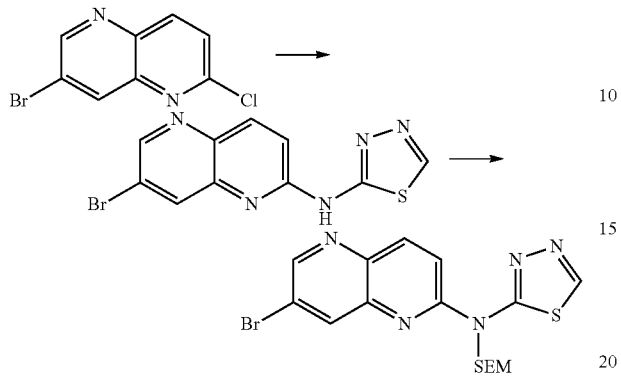

A mixture of 7-bromo-2-chloro-1,5-naphthyridine (30 mg), 1,3,4-thiadiazole-2-amine (25 mg) and potassium carbonate (17 mg) in dimethylsulfoxide (0.5 mL) was stirred at 150° C. for 30 minutes using a microwave reaction apparatus. The reaction mixture was cooled to room temperature, and water was added thereto. The solid matter was collected by filtration, thereby obtaining N-(7-bromo-1,5-naphthyridin-2-yl)-1,3,4-thiadiazole-2-amine.

The same reaction was performed using 7-bromo-2-chloro-1,5-naphthyridine (60 mg), thereby obtaining N-(7-bromo-1,5-naphthyridin-2-yl)-1,3,4-thiadiazole-2-amine.

The obtained N-(7-bromo-1,5-naphthyridin-2-yl)-1,3,4-thiadiazole-2-amines were combined, and N,N-dimethylformamide (1.8 mL), 2-(chloromethoxy)ethyltrimethylsilane (86 μL), and N,N-diisopropylethylamine (172 μL) were added thereto, followed by stirring at room temperature for 18 hours. 2-(Chloromethoxy)ethyltrimethylsilane (36 μL) was added thereto, followed by stirring at 50° C. for 2 hours. Water was added to the reaction mixture, the solid matter was collected by filtration, and washed with water and methanol, thereby obtaining N-(7-bromo-1,5-naphthyridin-2-yl)-N-((2-(trimethylsilyl)ethoxy)methyl)-1,3,4-thiadiazole-2-amine (78.9 mg) as a pale yellow solid.

MSm/z(M+H):438.

0003-2

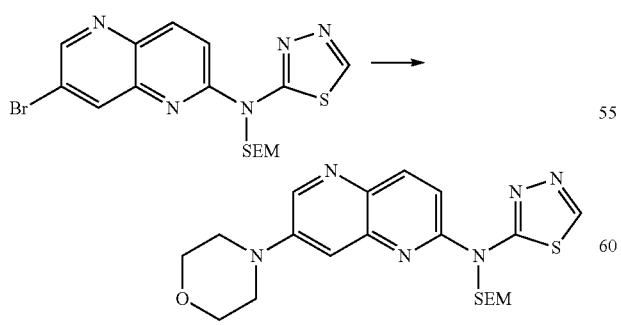

1,4-Dioxane (1 mL) and toluene (3 mL) were added to a mixture of N-(7-bromo-1,5-naphthyridin-2-yl)-N-((2-(trimethylsilyl)ethoxy)methyl)-1,3,4-thiadiazole-2-amine (78.9 mg), morpholine (47 μL), tris(dibenzylideneacetone)dipalladium(0) (33 mg), 4,5-bis(diphenylphosphino)-9,9-dimethylxanthene (42 mg), and cesium carbonate (175 mg), followed by stirring at 100° C. for 5 hours. The reaction mixture was cooled to room temperature, and water and ethyl acetate were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate, NH silica), thereby obtaining N-(7-morpholino-1,5-naphthyridin-2-yl)-N-((2-(trimethylsilyl)ethoxy)methyl)-1,3,4-thiadiazole-2-amine (17.1 mg) as a pale yellow solid.

MSm/z(M+H):445.

0003-3

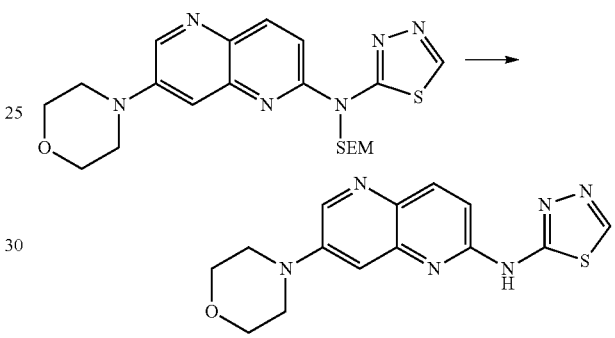

Concentrated hydrochloric acid (1 mL) was added to a solution of N-(7-morpholino-1,5-naphthyridin-2-yl)-N-((2-(trimethylsilyl)ethoxy)methyl)-1,3,4-thiadiazole-2-amine (50 mg) in ethanol (3 mL), followed by stirring at 90° C. for 17 hours. The reaction mixture was cooled to room temperature, and neutralized by the addition of a 6.0 mol/L sodium hydroxide aqueous solution under ice-cooling. The solvent was distilled off under reduced pressure, and the obtained residue was purified by silica gel column chromatography (chloroform-ethyl acetate, chloroform-methanol, NH silica), thereby obtaining N-(7-morpholino-1,5-naphthyridin-2-yl)-1,3,4-thiadiazole-2-amine (1.4 mg) as a pale yellow solid.

$^1$H-NMR(DMSO-$d_6$)δ:12.07(1H,s),9.09(1H,s),8.74(1H, d,J=2.6 Hz),8.16(1H,d,J=8.9 Hz),7.37(1H,d,J=2.6 Hz),7.24 (1H,d,J=8.9 Hz),3.81(4H,t,J=4.8 Hz),3.40-3.35(4H,m).

MSm/z(M+H):315.

Example 0004

0004-1

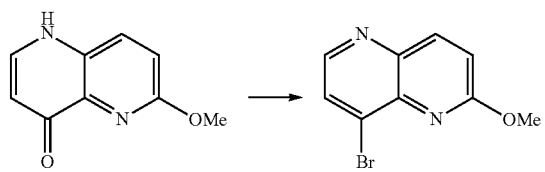 [SMILES: COc1ccc2[nH]ccc(=O)c2n1 ; COc1ccc2nccc(Br)c2n1]

Phosphorous oxybromide (5.60 g) was added to a solution of 6-methoxy-1,5-naphthyridin-4(1H)-one (3.51 g) in N,N-dimethylformamide (20 mL), followed by stirring at 80° C. for 30 minutes. The reaction mixture was cooled to room temperature, and added dropwise to a mixture solution of methanol-water (1:10). The resultant product was neutralized by the addition of a sodium hydroxide aqueous solution, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 8-bromo-2-methoxy-1,5-naphthyridine (3.20 g) as a yellow solid.

MSm/z(M+H):239,241.

0004-2

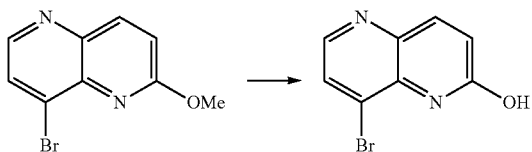 [SMILES: COc1ccc2nccc(Br)c2n1 ; Oc1ccc2nccc(Br)c2n1]

A mixture of 8-bromo-2-methoxy-1,5-naphthyridine (500 mg) in 5.1 mol/L hydrobromic acid (5 mL) was stirred at 80° C. for 3 hours. The reaction mixture was allowed to cool to room temperature, and the solvent was distilled off under reduced pressure. The residue was neutralized by the addition of a saturated sodium hydrogen carbonate aqueous solution, and the solvent was distilled off under reduced pressure. The obtained residue was washed with water, thereby obtaining 8-bromo-1,5-naphthyridin-2-ol (360 mg) as a white solid.

MSm/z(M+H):225,227.

0004-3

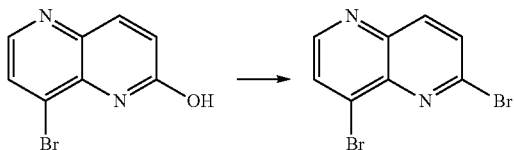 [SMILES: Oc1ccc2nccc(Br)c2n1 ; Brc1ccc2nccc(Br)c2n1]

A mixture solution of 8-bromo-1,5-naphthyridin-2-ol (6.0 g) in toluene (100 mL)/N,N-dimethylformamide (10 mL) was heated to 110° C., and a suspension of phosphorous oxybromide (10.13 g) in toluene (50 mL) was added dropwise thereto. The reaction mixture was stirred at 110° C. for 30 minutes, allowed to cool to room temperature, added dropwise to water, and neutralized by the addition of a sodium hydroxide aqueous solution, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 2,8-dibromo-1,5-naphthyridine (3.53 g) as a pale yellow solid.

MSm/z(M+H):287, 289, 291.

0004-4

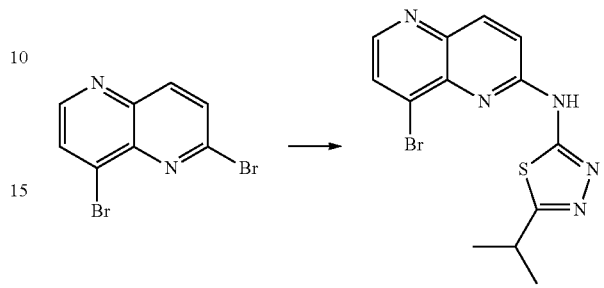

A mixture of 2,8-dibromo-1,5-naphthyridine (3.54 g), 5-isopropyl-1,3,4-thiadiazole-2-amine (1.85 g), tris(dibenzylideneacetone)dipalladium(0) (0.56 g), 4,5-bis(diphenylphosphino)-9,9-dimethylxanthene (0.71 g) and cesium carbonate (8.03 g) in 1,4-dioxane (17.6 mL) was reacted at 130° C. for 20 minutes using a microwave reaction apparatus. Ethyl acetate and water were added to the reaction mixture. The organic layer was collected by separation, washed with a saturated sodium chloride aqueous solution, and dried over anhydrous sodium sulfate, and the solvent was distilled off under reduced pressure. The obtained residue was purified by silica gel column chromatography (methanol-ethyl acetate), and the resultant product was washed with methanol and chloroform, thereby obtaining N-(8-bromo-1,5-naphthyridin-2-yl)-5-isopropyl-1,3,4-thiadiazole-2-amine (333 mg) as a pale yellow solid.

MSm/z(M+H):350,352.

0004-5

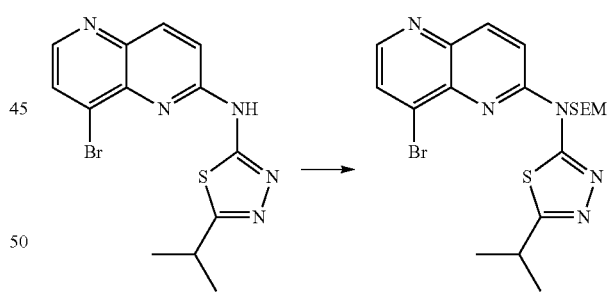

(2-(Chloromethoxy)ethyl)trimethylsilane (0.43 mL) was added to a suspension of N-(8-bromo-1,5-naphthyridin-2-yl)-5-isopropyl-1,3,4-thiadiazole-2-amine (564 mg) in N-methylpyrrolidone (16.1 mL), and 60% sodium hydride (136 mg) was added thereto under ice-cooling, followed by stirring for 2 hours in a nitrogen atmosphere. The reaction was stopped by the addition of ethanol to the reaction mixture, and ethyl acetate and water were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (methanol-ethyl acetate), thereby obtaining N-(8-bromo-1,5-naphthyridin-2- yl)-5-isopropyl-N-((2-trimethylsilyl)ethoxy)methyl)-1,3,4-thiadiazole-2-amine (398 mg) as a pale yellow solid.

MSm/z(M+H):480,482.

0004-6

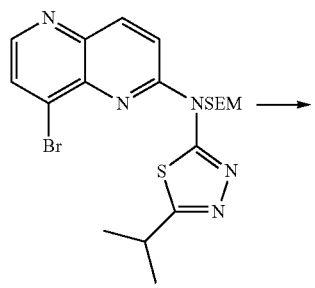

4-Aminopyridine (4.8 mg), tris(dibenzylideneacetone)dipalladium(0) (3.1 mg), 2-(dicyclohexylphosphino)-2',4',6'-triisopropylbiphenyl (3.3 mg), and sodium tert-butoxide (8.1 mg) were added to a solution of N-(8-bromo-1,5-naphthyridin-2-yl)-5-isopropyl-N-((2-(trimethylsilyl)ethoxy)methyl)-1,3,4-thiadiazole-2-amine (16.5 mg) in 1,4-dioxane (1.4 mL), followed by reacting at 150° C. for 30 minutes using a microwave reaction apparatus. Ethyl acetate and water were added to the reaction mixture. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane, methanol-ethyl acetate), thereby obtaining $N^2$-(5-isopropyl-1,3,4-thiadiazol-2-yl)-$N^8$-(pyridin-4-yl)-$N^2$-((2-(trimethylsilyl)ethoxy)methyl)-1,5-naphthyridine-2,8-diamine (8.0 mg) as an orange solid.

MSm/z(M+H):494.

0004-7

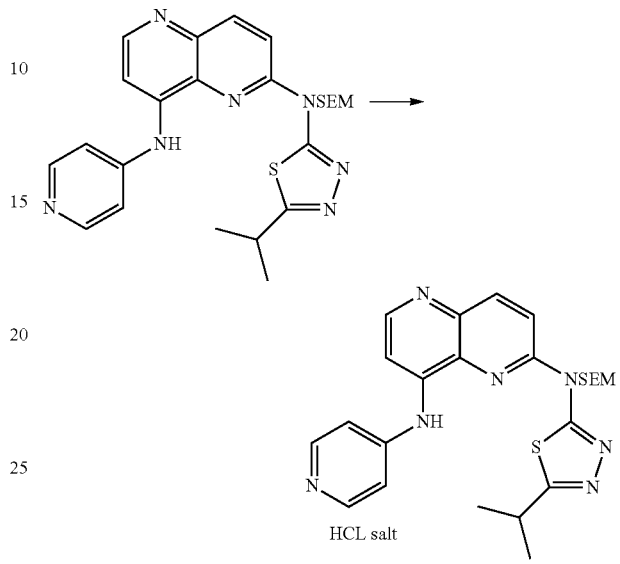

A solution (3.0 mL) of 4.0 mol/L hydrogen chloride/1,4-dioxane was added to $N^2$-(5-isopropyl-1,3,4-thiadiazol-2-yl)-$N^8$-(pyridin-4-yl)-$N^2$-((2-(trimethylsilyl)ethoxy)methyl)-1,5-naphthyridine-2,8-diamine (8.0 mg), followed by stirring at room temperature for 1 hour. The solvent was distilled off under reduced pressure, thereby obtaining $N^2$-(5-isopropyl-1,3,4-thiadiazol-2-yl)-$N^8$-(pyridin-4-yl)-1,5-naphthyridine-2,8-diamine (5.1 mg) hydrochloride as a yellow solid.

$^1$H-NMR(CD$_3$OD)δ:8.93(1H,d,J=5.9 Hz),8.68(2H,d,J=6.6 Hz),8.48(1H,d,J=9.2 Hz),8.20(1H,d,J=5.9 Hz),7.84 (3H,m,J=16.2,7.6 Hz),3.41(1H,t,J=6.9 Hz),1.47(6H,d,J=14.9 Hz).

MSm/z(M+H):364.

Examples 0005 to 0009

The following compounds were obtained in the same manner as in Examples 0004-6 and 0004-7.

| Example No. | | |
|---|---|---|
| 0005 | | |
| 0005-1 | 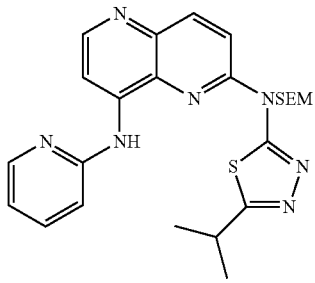 [SMILES: CC(C)c1nnc(N(COCC[Si](C)(C)C)c2ccc3nccc(Nc4ccccn4)c3n2)s1] | MS m/z (M + H): 494. |

| Example No. | | |
|---|---|---|
| 0005-2 | 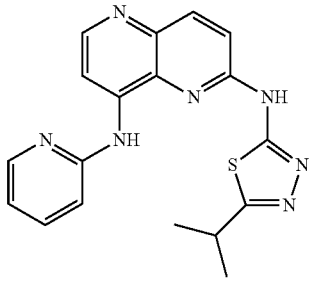 [SMILES: CC(C)c1nnc(Nc2ccc3nccc(Nc4ccccn4)c3n2)s1]<br>TFA salt | ¹H-NMR (DMSO-d₆) δ: 9.57 (1H, s), 8.85-8.75 (2H, m), 8.52 (1H, d, J = 5.3 Hz), 8.40 (1H, d, J = 9.2 Hz), 7.98 (1H, t, J = 6.9 Hz), 7.73 (1H, d, J = 9.2 Hz), 7.43 (1H, d, J = 8.6 Hz), 7.25 (1H, t, J = 5.9 Hz), 1.46 (6H, d, J = 6.6 Hz).<br>MS m/z (M + H): 364. |
| 0006 | | |
| 0006-1 | 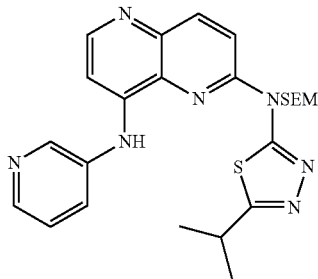 [SMILES: CC(C)c1nnc(N(COCC[Si](C)(C)C)c2ccc3nccc(Nc4cccnc4)c3n2)s1] | MS m/z (M + H): 494. |
| 0006-2 | 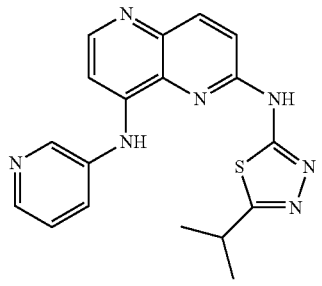 [SMILES: CC(C)c1nnc(Nc2ccc3nccc(Nc4cccnc4)c3n2)s1]<br>Formic acid salt | ¹H-NMR (CD₃OD) δ:<br>8.88 (1H, s), 8.65 (1H, d, J = 4.6 Hz), 8.49 (1H, d, J = 7.3 Hz), 8.32 (1H, d, J = 9.2 Hz), 8.20 (1H, d, J = 7.9 Hz), 7.79-7.75 (2H, m), 7.36 (1H, d, J = 7.3 Hz), 2.18 (1H, d, J = 7.9 Hz), 1.45 (6H, d, J = 7.3 Hz).<br>MS m/z (M + H): 364. |
| 0007 | | |
| 0007-1 | 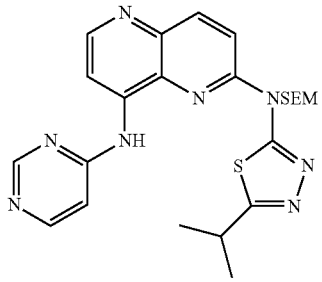 [SMILES: CC(C)c1nnc(N(COCC[Si](C)(C)C)c2ccc3nccc(Nc4ccncn4)c3n2)s1] | MS m/z (M + H): 495. |

-continued
| Example No. | | |
|---|---|---|
| 0007-2 | 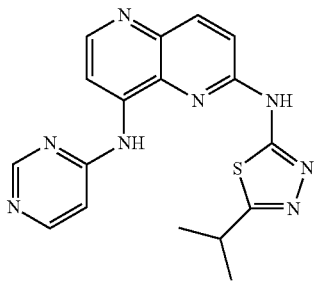 [SMILES: CC(C)c1nnc(Nc2ccc3nccc(Nc4ccncn4)c3n2)s1]<br>TFA salt | ¹H-NMR (CD₃OD) δ:<br>9.19 (1H, d, J = 6.6 Hz), 9.09 (1H, s), 8.80-<br>8.76 (2H, m), 8.39 (1H, d, J = 9.2 Hz), 7.77 (1H, d, J = 9.2 Hz),<br>7.42 (1H, d, J = 5.3 Hz), 3.54-<br>3.51 (1H, m), 1.54 (6H, d, J = 6.6 Hz).<br>MS m/z (M + H): 365. |
| 0008 | | |
| 0008-1 | 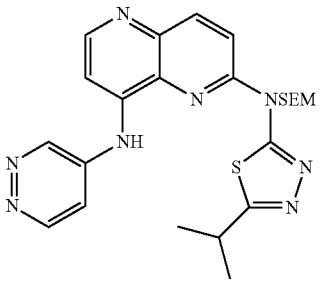 [SMILES: CC(C)c1nnc(N(COCC[Si](C)(C)C)c2ccc3nccc(Nc4ccnnc4)c3n2)s1] | MS m/z (M + H): 495. |
| 0008-2 | 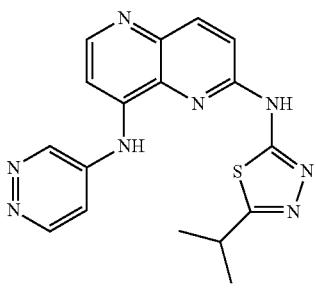 [SMILES: CC(C)c1nnc(Nc2ccc3nccc(Nc4ccnnc4)c3n2)s1]<br>TFA salt | ¹H-NMR (CD₃OD) δ:<br>9.02 (1H, d, J = 3.3 Hz), 8.86-<br>8.84 (2H, m), 8.39 (1H, d, J = 9.2 Hz), 7.82 (1H, d, J = 5.3 Hz),<br>7.59 (1H, d, J = 8.6 Hz), 7.33-<br>7.31 (1H, m), 2.19 (1H, t, J = 7.6 Hz), 1.39 (6H, d, J = 7.3 Hz).<br>MS m/z (M + H): 365. |
| 0009 | | |
| 0009-1 | 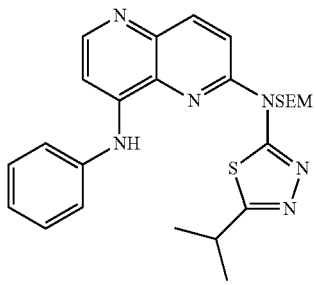 [SMILES: CC(C)c1nnc(N(COCC[Si](C)(C)C)c2ccc3nccc(Nc4ccccc4)c3n2)s1] | MS m/z (M + H): 493. |

| Example No. | | |
|---|---|---|
| 0009-2 | 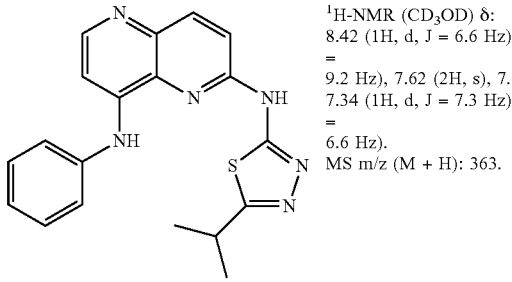<br>TFA salt | $^1$H-NMR (CD$_3$OD) δ:<br>8.42 (1H, d, J = 6.6 Hz), 8.29 (1H, d, J = 9.2 Hz), 7.76 (1H, d, J = 9.2 Hz), 7.62 (2H, s), 7.61 (2H, s), 7.47 (1H, d, J = 4.6 Hz), 7.34 (1H, d, J = 7.3 Hz), 3.44 (1H, t, J = 6.9 Hz), 1.45 (6H, d, J = 6.6 Hz).<br>MS m/z (M + H): 363. |

Example 0010

0010-1

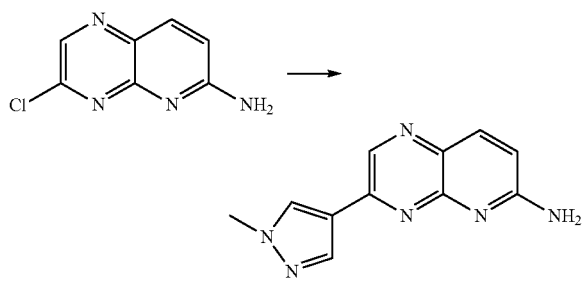

1-Methyl-4-(4,4,5,5-tetramethyl-1,3,2-dioxaborolan-2-yl)-1H-pyrazole (866 mg), tris(dibenzylideneacetone)dipalladium(0) (79.1 mg), tricyclohexylphosphine (92.5 mg), and potassium phosphate (1 g) were added to a mixture solution of 3-chloropyrido[2,3-b]pyrazine-6-amine (500 mg) in 1,4-dioxane (12.4 mL)/water (1.4 mL), followed by reacting at 120° C. for 10 minutes using a microwave reaction apparatus. Ethyl acetate/chloroform was added to the reaction mixture, the solid matter was collected by filtration, and washed with ethyl acetate, thereby obtaining 3-(1-methyl-1H-pyrazol-4-yl)pyrido[2,3-b]pyrazine-6-amine (326.6 mg).

MSm/z(M+H):227.

0010-2

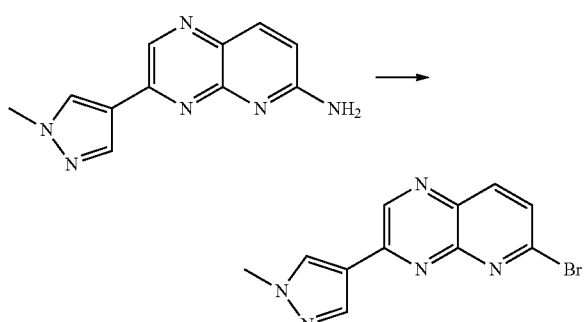

Antimony bromide (127.8 mg) and tert-butyl nitrite (0.26 mL) were added to a solution of 3-(1-methyl-1H-pyrazol-4-yl)pyrido[2,3-b]pyrazine-6-amine (50 mg) in dibromomethane (1.26 mL) at 0° C. in a nitrogen atmosphere, followed by stirring at room temperature for 7 hours. The insolubles were filtered off, and the solid was washed with ethyl acetate/water. The filtrate and the washings were combined, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane, methanol-ethyl acetate), thereby obtaining 6-bromo-3-(1-methyl-1H-pyrazol-4-yl)pyrido[2,3-b]pyrazine (10.8 mg) as a pale yellow solid.

MSm/z(M+H):290,292.

0010-3

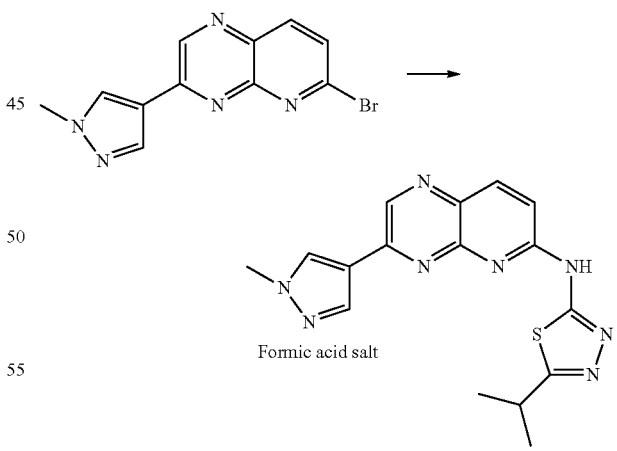

5-Isopropyl-1,3,4-thiadiazole-2-amine (2.5 mg) and potassium carbonate (3.6 mg) were added to a solution of 6-bromo-3-(1-methyl-1H-pyrazol-4-yl)pyrido[2,3-b]pyrazine (5.0 mg) in dimethylsulfoxide (0.35 mL), followed by stirring at 130° C. for 8 hours. After the reaction mixture was cooled to room temperature, ethyl acetate and water were added thereto. The organic layer was collected by separation, washed with a saturated sodium chloride aqueous solution, and dried over anhydrous sodium sulfate, and the solvent was distilled off under reduced pressure. The obtained residue was purified by preparative reversed phase HPLC (a 0.1% formic acid aqueous solution-a 0.1% formic acid acetonitrile solution), and the solvent was distilled off under reduced pressure, thereby obtaining 5-isopropyl-N-(3-(1-methyl-1H-pyrazol-4-yl)pyrido[2,3-b]pyrazine-6-yl)-1,3,4-thiadiazole-2-amineformate (1.1 mg) as a yellow solid.

¹H-NMR(CD₃OD)δ:9.09(1H,s),8.56(1H,s),8.36(1H,s), 8.29(1H,d,J=9.2 Hz),7.41(1H,d,J=8.6 Hz),4.03(3H,s),3.98-3.96(1H,m),1.50(6H,d,J=6.6 Hz).
MSm/z(M+H):353.

Examples 0011 to 0013

The following compounds were obtained in the same manner as in Examples 0004-6 and 0004-7.

| Example No. | | |
|---|---|---|
| 0011 | | |
| 0011-1 | 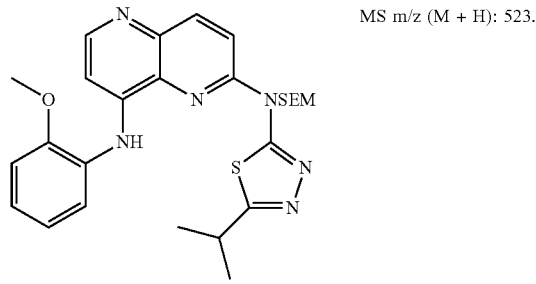 | MS m/z (M + H): 523. |
| 0011-2 | 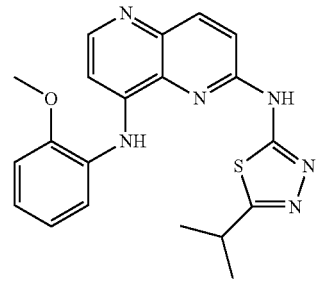 [SMILES: COc1ccccc1Nc1ccnc2ccc(Nc3nnc(C(C)C)s3)nc12] | ¹H-NMR (CD₃OD) δ: 8.41 (1H, d, J = 6.6 Hz), 8.28 (1H, d, J = 9.2 Hz), 7.73-7.68 (2H, m), 7.40-7.37 (2H, m), 7.29 (1H, d, J = 8.6 Hz), 7.21-7.15 (1H, m), 3.97 (3H, s), 3.43 (1H, t, J = 6.9 Hz), 1.45 (6H, d, J = 7.3 Hz). MS m/z (M + H): 393. |
| 0012 | | |
| 0012-1 | 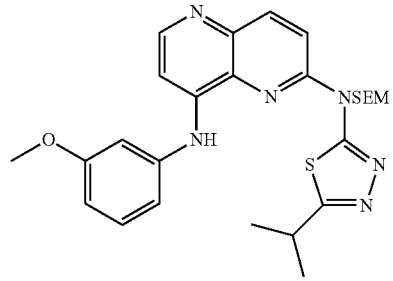 [SMILES: COc1cccc(Nc2ccnc3ccc(N(COCC[Si](C)(C)C)c4nnc(C(C)C)s4)nc23)c1] | MS m/z (M + H): 523. |
| 0012-2 | 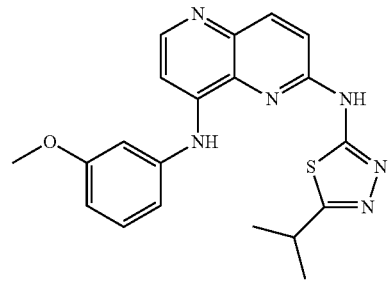 [SMILES: COc1cccc(Nc2ccnc3ccc(Nc4nnc(C(C)C)s4)nc23)c1] TFA salt | ¹H-NMR (CD₃OD) δ: 8.42 (1H, d, J = 7.3 Hz), 8.29 (1H, d, J = 9.2 Hz), 7.74 (1H, d, J = 9.2 Hz), 7.52 (1H, t, J = 7.9 Hz), 7.40 (1H, d, J = 6.6 Hz), 7.18 (2H, m, J = 4.6 Hz), 7.02 (1H, dd, J = 8.3, 1.7 Hz), 3.88 (3H, d, J = 2.0 Hz), 3.44 (1H, t, J = 6.9 Hz), 1.45 (6H, d, J = 6.9 Hz). MS m/z (M + H): 393. |

| Example No. | | |
|---|---|---|
| 0013 | | |
| 0013-1 | 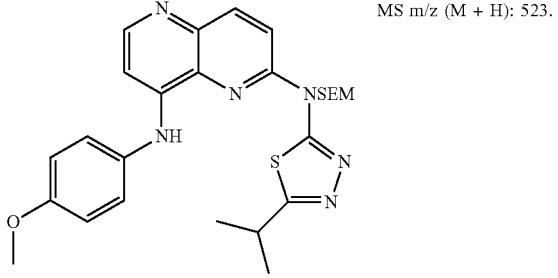 | MS m/z (M + H): 523. |
| 0013-2 | | $^1$H-NMR (DMSO-$d_6$) δ:<br>8.40 (1H, d, J = 5.3 Hz), 8.24 (1H, d, J = 9.2 Hz), 8.12 (1H, s), 7.52 (1H, d, J = 9.2 Hz), 7.45 (2H, d, J = 9.2 Hz), 7.07 (3H, m, J = 7.9, 3.7 Hz), 3.80 (3H, s), 3.41 (1H, t, J = 6.9 Hz), 1.38 (6H, d, J = 6.6 Hz).<br>MS m/z (M + H): 393. |

Example 0014

0014-1

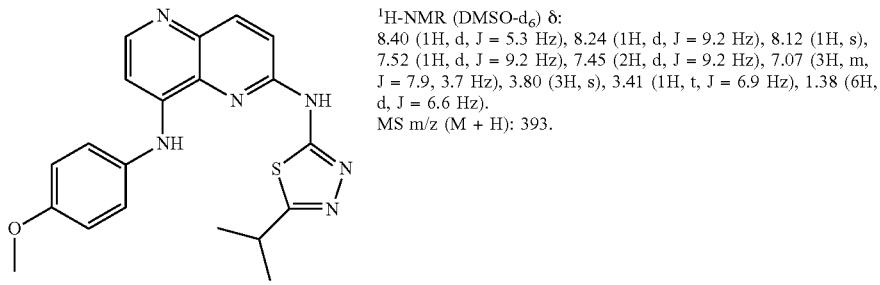

Isobutyric acid (4.67 mL) and silver nitrate (1.15 g) were added to a solution of 3,6-dichloropyridazine (5 g) in water (168 mL)/sulfuric acid (7.4 mL), and a solution of ammonium peroxodisulfate (26 g) in water (84 mL) was added dropwise thereto at room temperature over a period of 20 minutes, followed by stirring at 70° C. for 30 minutes. The reaction mixture was cooled to room temperature, adjusted to have a pH of 8 by the addition of ammonia water, and ethyl acetate was added thereto. The organic layer was collected by separation, washed with a saturated sodium chloride aqueous solution, and dried over anhydrous sodium sulfate, and the solvent was distilled off under reduced pressure, thereby obtaining 3,6-dichloro-4-isopropylpyridazine (6.33 g) as pale yellow oily substance.

MS m/z (M+H):191.

0014-2

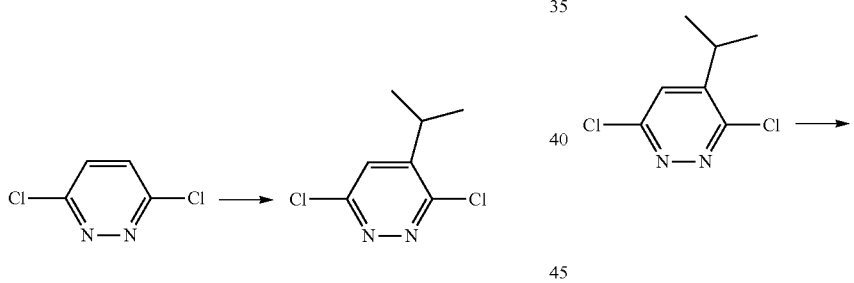

2,4-Dimethoxybenzylamine (10 mL) and 1,8-diazabicyclo[5.4.0]undeca-7-ene (14.9 mL) were added to a solution of 3,6-dichloro-4-isopropylpyridazine (6.33 g) in 1,4-dioxane (66 mL), followed by stirring at 100° C. for 19 hours. The reaction mixture was cooled to room temperature, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 6-chloro-N-(2,4-dimethoxybenzyl)-5-isopropylpyridazine-3-amine (2.64 g) as pale yellow oily substance.

MSm/z(M+H):322.

0014-3

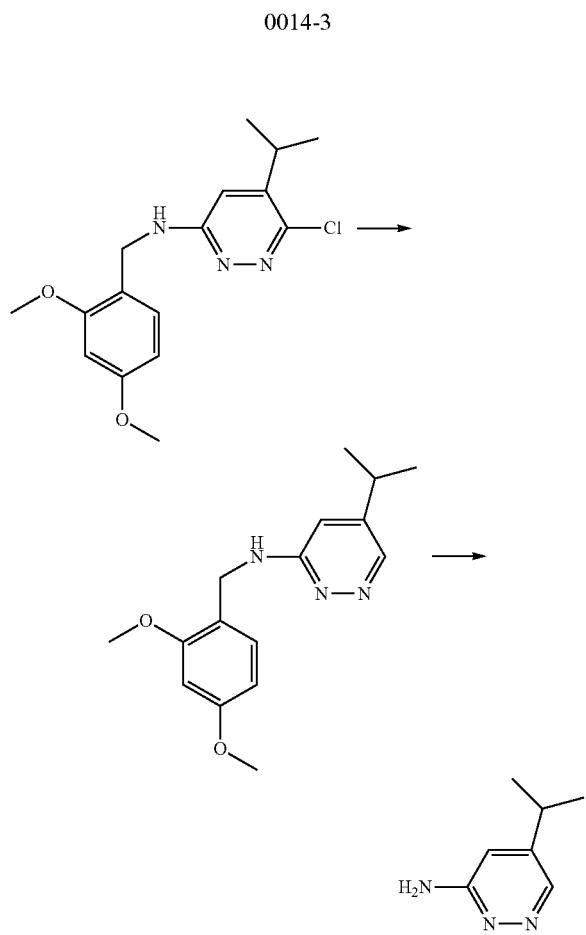

A mixture of 10% palladium/carbon (0.5 g), 6-chloro-N-(2,4-dimethoxybenzyl)-5-isopropylpyridazine-3-amine (2.64 g) and methanol (27.3 mL) in acetic acid (0.94 mL) was stirred at room temperature for 3 hours under pressurized hydrogen (0.8 MPa). Furthermore, acetic acid (3.76 mL) was added thereto, followed by stirring at 50° C. for 2.5 hours under pressurized hydrogen (0.8 MPa). The insolubles were filtered off using celite, and the solvent was distilled off under reduced pressure, thereby obtaining orange oily substance (4.33 g).

Water (0.82 mL) and trifluoroacetic acid (8.2 mL) were added to the obtained orange oily substance (4.33 g), followed by stirring at room temperature for 30 minutes. The insolubles were filtered off using celite, and the solid was washed with ethyl acetate/methanol. The filtrate and the washings were combined, and the solvent was distilled off under reduced pressure. The obtained residue was purified by silica gel column chromatography (methanol-ethyl acetate, NH silica), thereby obtaining 5-isopropylpyridazine-3-amine (0.97 g) as a pale yellow solid.

MSm/z(M+H):138.

0014-4

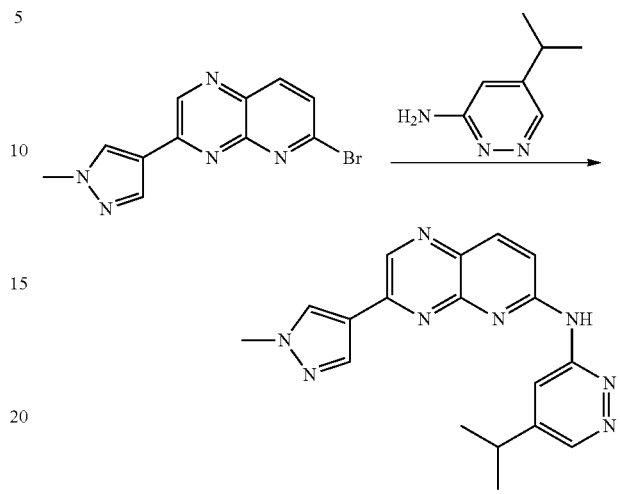

1,4-Dioxane (0.79 mL) was added to a mixture of 6-bromo-3-(1-methyl-1H-pyrazol-4-yl)pyrido[2,3-b]pyrazine (11.4 mg), 5-isopropylpyridazine-3-amine (8.1 mg), tris(dibenzylideneacetone)dipalladium(0) (3.6 mg), 4,5-bis(diphenylphosphino)-9,9-dimethylxanthene (4.5 mg), and cesium carbonate (32 mg), followed by reacting at 150° C. for 30 minutes using a microwave reaction apparatus. Ethyl acetate and water were added to the reaction mixture. The organic layer was collected by separation, washed with a saturated sodium chloride aqueous solution, and dried over anhydrous sodium sulfate, and the solvent was distilled off under reduced pressure. The obtained residue was purified by silica gel column chromatography (methanol-ethyl acetate), thereby obtaining N-(5-isopropylpyridazin-3-yl)-3-(1-methyl-1H-pyrazol-4-yl)pyrido[2,3-b]pyrazine-6-amine (1.3 mg) as a yellow solid.

$^1$H-NMR(DMSO-$d_6$)δ:10.93(1H,s),9.13(1H,s),8.91(1H, d,J=2.0 Hz),8.69(1H,s),8.60(1H,s),8.28(2H,m,J=4.6 Hz), 7.82(1H,d,J=9.2 Hz),3.96(3H,s),1.33(6H,d,J=6.6 Hz).

MSm/z(M+H):347.

Example 0015

0015-1

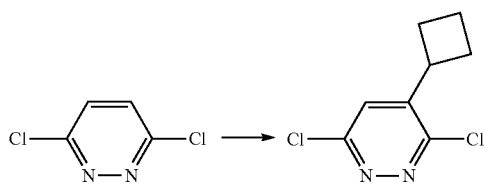 [SMILES: Clc1ccc(Cl)nn1 ; Clc1cc(C2CCC2)c(Cl)nn1]

3,6-Dichloro-4-cyclobutylpyridazine was obtained as pale yellow oily substance in the same manner as in Example 0014-1.

MSm/z(M+H):204.

0015-2

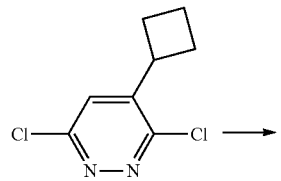

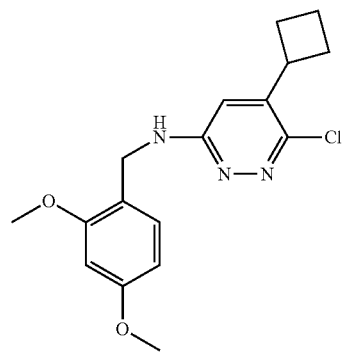

2,4-Dimethoxybenzylamine (1.48 mL) and 1,8-diazabicyclo[5.4.0]undeca-7-ene (2.2 mL) were added to a solution of 3,6-dichloro-4-cyclobutylpyridazine (0.99 g) in 1,4-dioxane (7 mL), followed by reacting at 145° C. for 45 minutes using a microwave reaction apparatus. Ethyl acetate and water were added to the reaction mixture. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 6-chloro-N-(2,4-dimethoxybenzyl)-5-cyclobutylpyridazine-3-amine (274 mg).

MSm/z(M+H):334.

0015-3

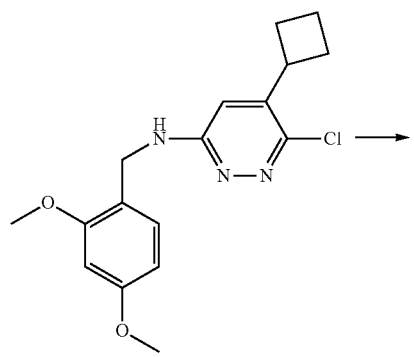

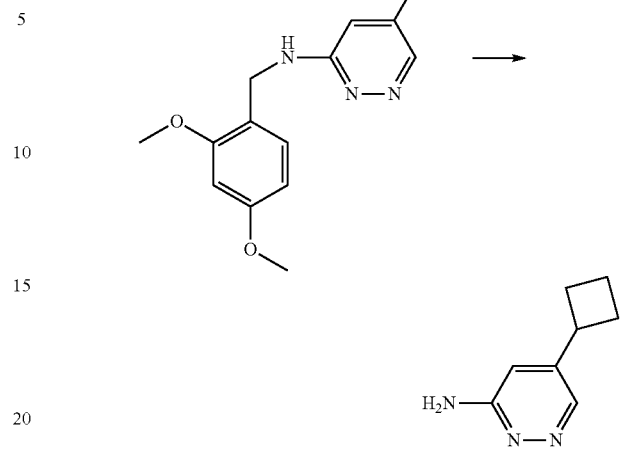

A mixture solution of 6-chloro-N-(2,4-dimethoxybenzyl)-5-cyclobutylpyridazine-3-amine (274 mg) in methanol (20.5 mL)/acetic acid (2 mL) was reacted using a flow-type hydrogenation reaction apparatus (30 bar, 1.0 mL/min, 55° C., 10% Pd/C). The solvent was distilled off under reduced pressure, thereby obtaining pale yellow oily substance.

Water (0.25 mL) and trifluoroacetic acid (5 mL) were added to the obtained pale yellow oily substance, followed by stirring at room temperature for 30 minutes. The insolubles were filtered off using celite, and the solid was washed with ethyl acetate/methanol. The filtrate and the washings were combined, and the solvent was distilled off under reduced pressure. The obtained residue was purified by silica gel column chromatography (methanol-chloroform, NH silica), thereby obtaining 5-cyclobutylpyridazine-3-amine (129 mg) as a pale yellow solid.

MSm/z(M+H):150.

0015-4

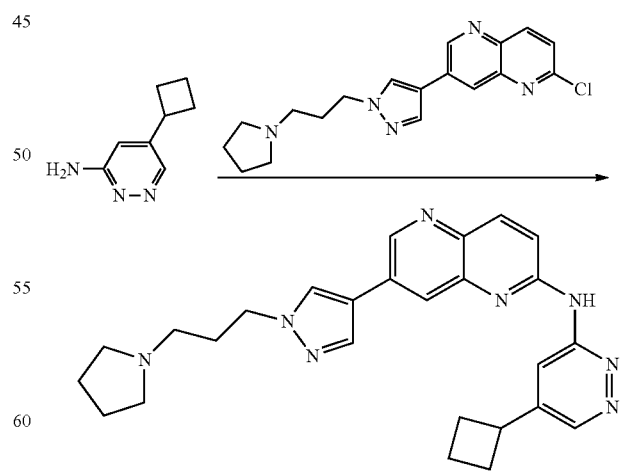

1,4-Dioxane (0.89 mL) was added to a mixture of 2-chloro-7-(1-(3-(pyrrolidin-1-yl)propyl)-1H-pyrazol-4-yl)-1,5-naphthyridine (15.2 mg), 5-cyclobutylpyridazine-3-amine (10.1 mg), tris(dibenzylideneacetone)dipalladium(0)

(4.2 mg), 4,5-bis(diphenylphosphino)-9,9-dimethylxanthene (5.3 mg), and cesium carbonate (36.3 mg), followed by reacting at 150° C. for 30 minutes using a microwave reaction apparatus. Ethyl acetate and water were added to the reaction mixture. The organic layer was collected by separation, washed with a saturated sodium chloride aqueous solution, and dried over anhydrous sodium sulfate, and the solvent was distilled off under reduced pressure. The obtained residue was purified by silica gel column chromatography (methanol-ethyl acetate, NH silica) and preparative reversed phase HPLC (a 0.1% formic acid aqueous solution-a 0.1% formic acid acetonitrile solution), and the solvent was distilled off under reduced pressure, thereby obtaining N-(5-cyclobutylpyridazin-3-yl)-7-(1-(3-(pyrrolidin-1-yl)propyl)-1H-pyrazol-4-yl)-1,5-naphthyridine-2-amineformate (0.8 mg) as a brown solid.

$^1$H-NMR(DMSO-$d_6$) δ 10.71(1H,s),9.05(1H,d,J=2.0 Hz), 8.83(1H,d,J=1.3 Hz),8.69(1H,d,J=1.3 Hz),8.52(1H,s),8.21 (3H,d,J=2.0 Hz),7.70(1H,d,J=9.2 Hz),4.24(2H,t,J=6.6 Hz), 3.67(1H,t,J=8.6 Hz),2.71(8H,d,J=9.2 Hz),2.47-2.41(2H,m), 2.24(2H,m,J=9.1,2.2 Hz),2.11-2.05(4H,m),1.78-1.75(2H,m).
MS m/z(M+H):455.

Examples 0016 to 0018

The following compounds were obtained in the same manner as in Examples 0015-1 to 0015-4.

| Example No. | | |
|---|---|---|
| 0016 | | |
| 0016-1 | 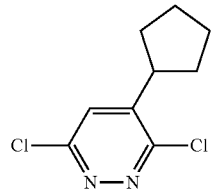 [SMILES: Clc1cc(C2CCCC2)c(Cl)nn1] | MS m/z (M + H): 217. |
| 0016-2 | 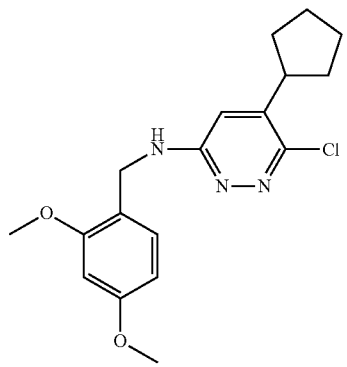 [SMILES: COc1ccc(CNc2cc(C3CCCC3)c(Cl)nn2)c(OC)c1] | MS m/z (M + H): 348. |
| 0016-3 | 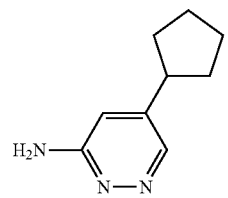 [SMILES: Nc1cc(C2CCCC2)cnn1] | MS m/z (M + H): 164. |
| 0016-4 | 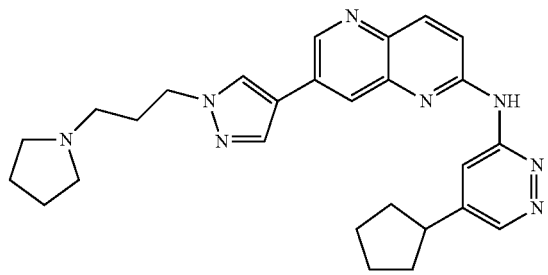 [SMILES: c1nc2ccc(Nc3cc(C4CCCC4)cnn3)nc2cc1-c1cnn(CCCN2CCCC2)c1] | $^1$H-NMR (DMSO-$d_6$) δ: 10.69 (1H, s), 9.04 (1H, d, J = 2.0 Hz), 8.84 (1H, d, J = 2.0 Hz), 8.70 (1H, d, J = 2.0 Hz), 8.50 (1H, s), 8.23-8.19 (3H, m), 7.71 (1H, d, J = 8.6 Hz), 4.32 (2H, t, J = 6.9 Hz), 3.12 (1H, t, J = 7.9 Hz), 2.55-2.52 (6H, m), 2.17-1.63 (14H, m). MS m/z (M + H): 469. |

| Example No. | | |
|---|---|---|
| 0017 | | |
| 0017-1 | 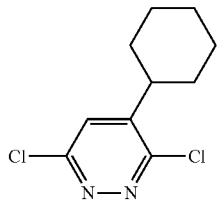 [SMILES: Clc1cc(C2CCCCC2)c(Cl)nn1] | MS m/z (M + H): 231. |
| 0017-2 | 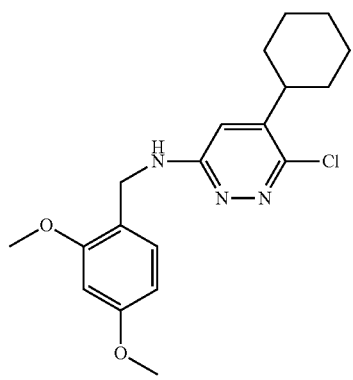 [SMILES: COc1ccc(CNc2cc(C3CCCCC3)c(Cl)nn2)c(OC)c1] | MS m/z (M + H): 362. |
| 0017-3 | 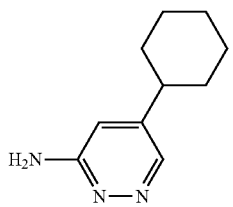 [SMILES: Nc1cc(C2CCCCC2)cnn1] | MS m/z (M + H): 178. |
| 0017-4 | 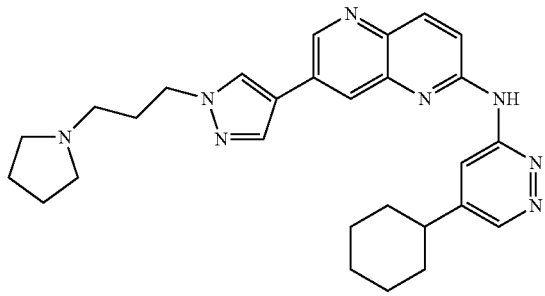 [SMILES: c1nc2ccc(Nc3cc(C4CCCCC4)cnn3)nc2cc1-c1cnn(CCCN2CCCC2)c1] | $^1$H-NMR (CDCl$_3$) δ: 8.93 (1H, d, J = 2.0 Hz), 8.75 (1H, brs), 8.48 (1H, s), 8.24 (1H, d, J = 9.2 Hz), 8.13 (1H, d, J = 2.0 Hz), 7.96 (2H, d, J = 5.9 Hz), 7.54 (1H, d, J = 9.2 Hz), 4.36 (2H, t, J = 6.6 Hz), 3.10-3.06 (3H, m), 2.96 (2H, t, J = 7.6 Hz), 2.62 (2H, s), 2.45-2.35 (2H, m), 2.25-1.82 (14H, m), 1.50-1.37 (3H, m). MS m/z (M + H): 483. |
| 0018 | | |
| 0018-1 | 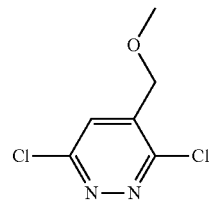 | MS m/z (M + H): 193. |

| Example No. | | |
|---|---|---|
| 0018-2 | 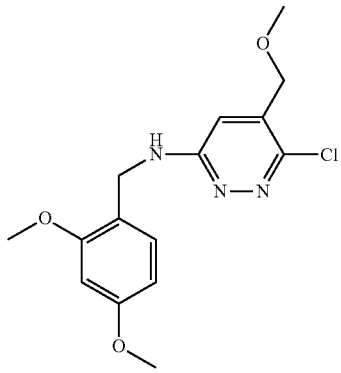 [SMILES: COCc1cc(NCc2ccc(OC)cc2OC)nnc1Cl] | MS m/z (M + H): 324. |
| 0018-3 | 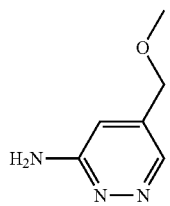 | MS m/z (M + H): 140. |
| 0018-4 | 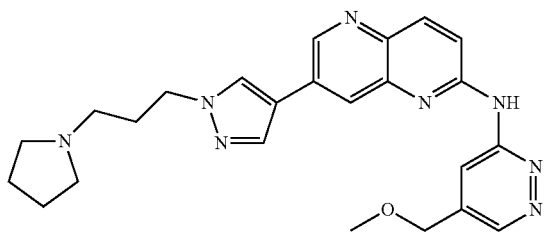 [SMILES: COCc1cnnc(Nc2ccc3ncc(-c4cnn(CCCN5CCCC5)c4)cc3n2)c1] | $^1$H-NMR (DMSO-d$_6$) δ: 10.81 (1H, s), 9.05 (1H, d, J = 2.0 Hz), 8.83 (1H, d, J = 2.0 Hz), 8.79 (1H, s), 8.51 (1H, s), 8.23 (2H, m), 8.18 (1H, s), 7.70 (1H, d, J = 9.2 Hz), 4.61 (2H, s), 4.22 (2H, t, J = 6.9 Hz), 3.44 (3H, s), 2.41-2.39 (6H, m), 2.01 (2H, t, J = 6.9 Hz), 1.71-1.67 (4H, m). MS m/z (M + H): 445. |
Example 0019
0019-1
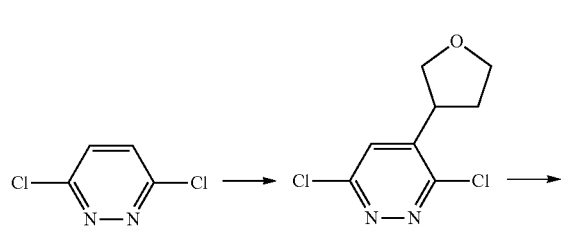
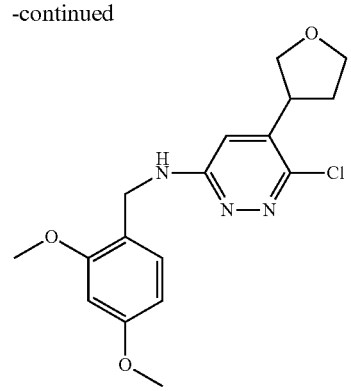
Brown oily substance (1.54 g) was obtained in the same manner as in Example 0014 except that tetrahydrofuran-3-carboxylic acid was used instead of the isobutyric acid used in Example 0014.

2,4-Dimethoxybenzylamine (2.1 mL) and 1,8-diazabicyclo[5.4.0]undeca-7-ene (3.2 mL) were added to a solution of the obtained brown oily substance (1.54 g) in 1,4-dioxane (14 mL), followed by stirring at 100° C. overnight. Ethyl acetate and water were added to the reaction mixture. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 6-chloro-N-(2,4-dimethoxybenzyl)-5-(tetrahydrofuran-3-yl)pyridazine-3-amine (348 mg) as an orange solid.

MSm/z(M+H):350.

0019-2

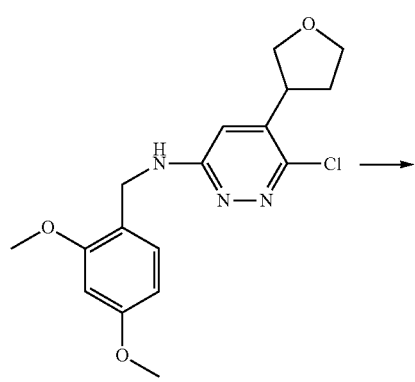

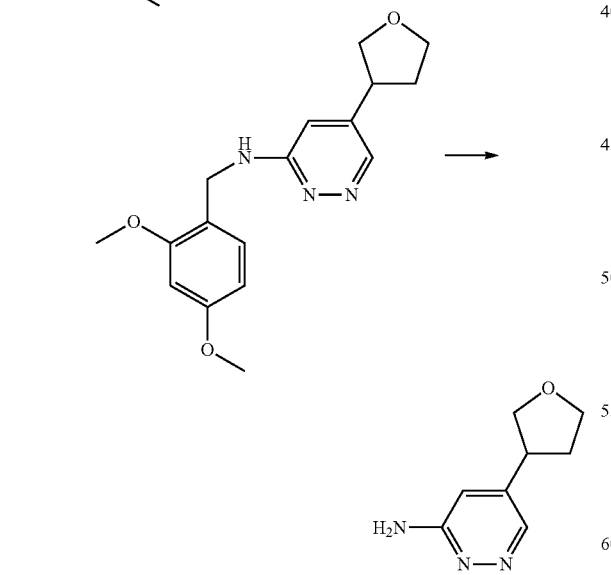

5-(Tetrahydrofuran-3-yl)pyridazine-3-amine was obtained as a pale orange solid in the same manner as in Example 0016-3.

MSm/z(M+H):166.

0019-3

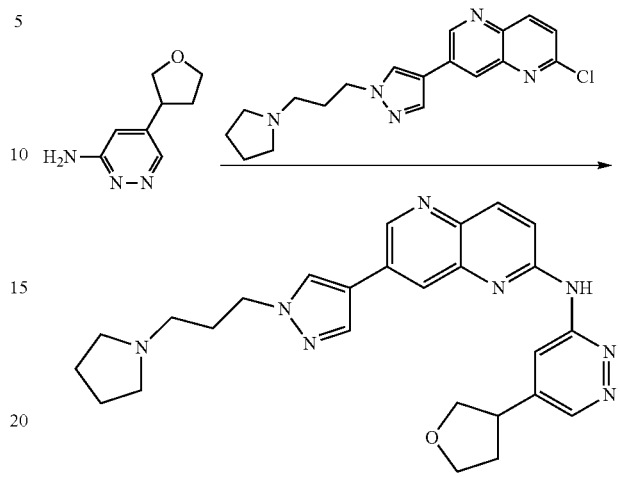

7-(1-(3-(Pyrrolidin-1-yl)propyl)-1H-pyrazol-4-yl)-N-(5-(tetrahydrofuran-3-yl)pyridazin-3-yl)-1,5-naphthyridine-2-amine was obtained as an orange solid in the same manner as in Example 0015-4.

$^1$H-NMR(CDCl$_3$)δ:8.96(2H,m),8.84(1H,d,J=2.0 Hz), 8.25(1H,d,J=9.2 Hz),8.11(1H,d,J=2.0 Hz),7.97(1H,s),7.89 (1H,s),7.51(1H,d,J=8.6 Hz),4.29-4.24(4H,m),4.07-3.93(3H, m),2.57-2.47(7H,m),2.16-2.13(3H,m),1.82-1.80(4H,m).
MSm/z(M+H):471.

Example 0020

0020-1

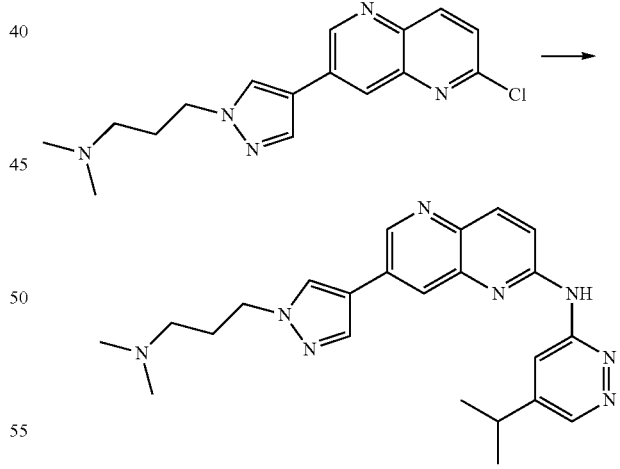

7-(1-(3-(Dimethylamino)propyl)-1H-pyrazol-4-yl)-N-(5-isopropylpyridazin-3-yl)-1,5-naphthyridine-2-amine (0.7 mg) was obtained as an orange solid in the same manner as in Example 0018 except that 3-(4-(6-chloro-1,5-naphthyridin-3-yl)-1H-pyrazol-1-yl)-N,N-dimethylpropane-1-amine was used instead of the 2-chloro-7-(1-(3-(pyrrolidin-1-yl)propyl)-1H-pyrazol-4-yl)-1,5-naphthyridine used in Example 0018, and 5-isopropylpyridazine-3-amine was used instead of the 5-(methoxymethyl)pyridazine-3-amine used in Example 0018.

$^1$H-NMR(CDCl$_3$)δ:8.93-8.81(3H,m),8.24(1H,d,J=8.6 Hz),8.10(1H,d,J=1.3 Hz),7.97(1H,s),7.90(1H,s),7.53(1H,d,J=8.6 Hz),5.34(1H,t,J=5.6 Hz),4.31(3H,t,J=6.9 Hz),3.45 (1H,s),3.06-3.03(1H,m),2.41-2.37(2H,m),2.32(6H,s),1.42 (6H,d,J=7.3 Hz).

MSm/z(M+H):417.

Example 0021

0021-1

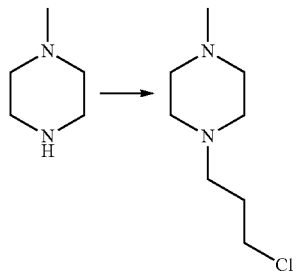

1-Bromo-3-chloropropane (0.25 mL) was added to a solution of 1-methylpiperazine (0.55 mL) in toluene (2.5 mL), followed by stirring at 80° C. for 2 hours. The reaction mixture was cooled to room temperature, and 2 mol/L hydrochloric acid was added thereto. The aqueous layer was collected by separation, adjusted to have a pH of 12 by the addition of a 2 mol/L sodium hydroxide aqueous solution, and ethyl acetate was added thereto. The organic layer was collected by separation, washed with a saturated sodium chloride aqueous solution, and dried over anhydrous sodium sulfate, and the solvent was distilled off under reduced pressure, thereby obtaining 1-(3-chloropropyl)-4-methyl-piperazine (187 mg) as a white solid.

$^1$H-NMR(CDCl$_3$)δ:3.59(2H,t,J=6.6 Hz),2.49(8H,t,J=7.3 Hz),2.29(3H,s),1.95(2H,t,J=6.9 Hz).

0021-2

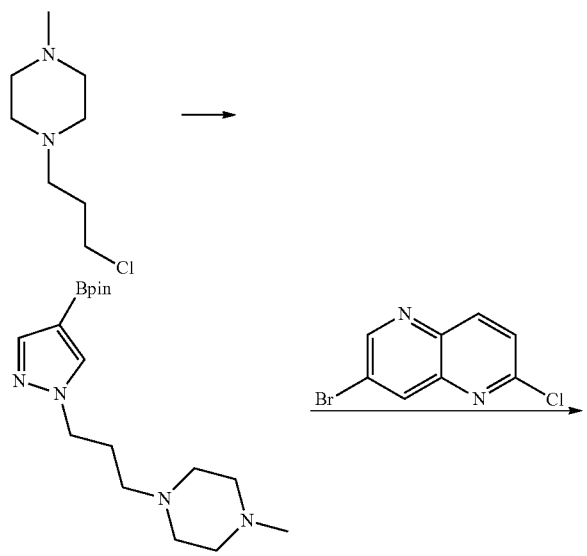

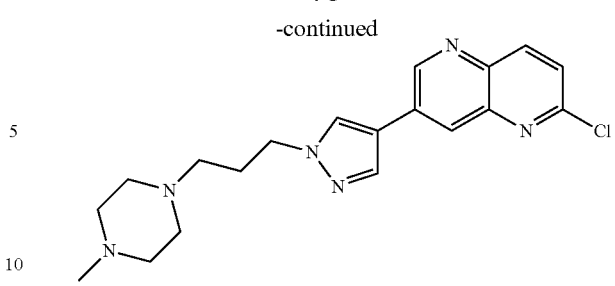

4-(4,4,5,5-Tetramethyl-1,3,2-dioxaborolan-2-yl)-1H-pyrazole (351.4 mg), cesium carbonate (1.17 g), and sodium iodide (58.0 mg) were added to a mixture solution of 1-(3-chloropropyl)-4-methylpiperazine (0.64 g) in acetonitrile (2.4 mL)/tetrahydrofuran (1.0 mL), followed by reacting at 80° C. for 19 hours. After the reaction mixture was cooled to room temperature, the insolubles were filtered off, and the residue was washed with ethyl acetate. The filtrate and the washings were combined, and the solvent was distilled off under reduced pressure, thereby obtaining orange oily substance (137 mg).

7-Bromo-2-chloro-1,5-naphthyridine (50 mg), bis(di-tert-butyl(4-dimethylaminophenyl)phosphine)dichloropalladium(II) (14.5 mg), and sodium carbonate (43.4 mg) were added to a mixture solution of the obtained orange oily substance (137 mg) in 1,4-dioxane (2.0 mL)/water (0.2 mL), followed by stirring at 100° C. for 2 hours. After the reaction mixture was cooled to room temperature, the insolubles were filtered off using celite, and the residue was washed with ethyl acetate. The filtrate and the washings were combined, and the solvent was distilled off under reduced pressure. The obtained residue was purified by silica gel column chromatography (ethyl acetate-hexane, methanol-ethyl acetate, NH silica), thereby obtaining 2-chloro-7-(1-(3-(4-methylpiperazin-1-yl)propyl)-1H-pyrazol-4-yl)-1,5-naphthyridine (44.1 mg) as a pale yellow solid.

MSm/z(M+H):371.

0021-3

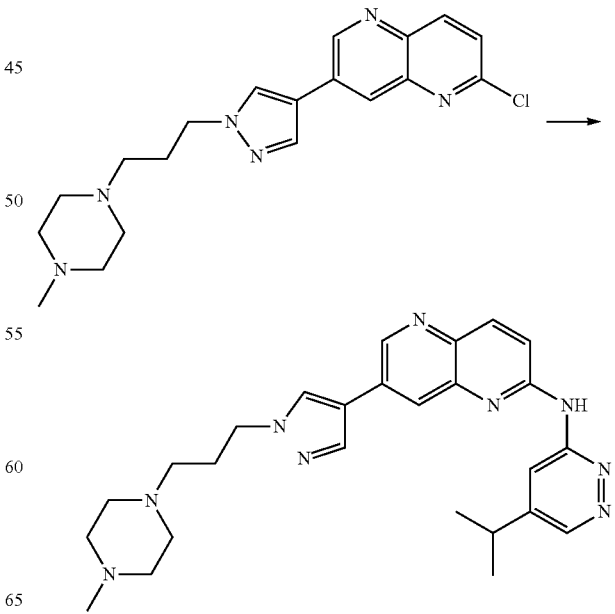

N-(5-isopropylpyridazin-3-yl)-7-(1-(3-(4-methylpiperazin-1-yl)propyl)-1H-pyrazol-4-yl)-1,5-naphthyridine-2-amine was obtained as a pale yellow solid in the same manner as in Example 0015-4.

$^1$H-NMR(CDCl$_3$)δ:8.93(1H,d,J=2.0 Hz),8.83-8.81(2H, m),8.24(1H,d,J=9.2 Hz),8.10(1H,s),7.97(1H,s),7.87(1H,s),7.52(1H,d,J=9.2 Hz),4.29(2H,t,J=6.6 Hz),3.06(1H,t,J=6.9 Hz),2.51-2.47(7H,m),2.38(3H,t,J=6.9 Hz),2.31(3H,s),2.13(2H,q,J=6.8 Hz),1.42(6H,d,J=7.3 Hz).

MSm/z(M+H):472.

Example 0022

0022-1

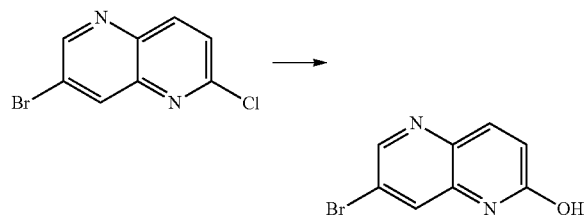

Several drops of a 4 mol/L hydrogen chloride-1,4-dioxane solution (3 mL) and water were added to 7-bromo-2-chloro-1,5-naphthyridine (250 mg), followed by stirring at 100° C. overnight. The reaction mixture was cooled to room temperature, and water was added thereto. The solid matter was collected by filtration, and washed with a mixture solution of water and hexane-ethyl acetate (1:1), thereby obtaining 7-bromo-1,5-naphthyridin-2-ol (190 mg) as a grey solid.

$^1$H-NMR(DMSO-d$_6$)δ:11.96(1H,brs),8.56(1H,d,J=2.3 Hz),7.93(1H,d,J=9.9 Hz),7.85(1H,d,J=2.30 Hz),6.79(1H,d,J=9.9 Hz).

0022-2

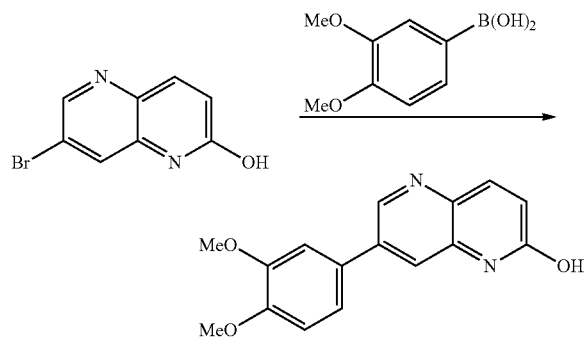

1,4-Dioxane (5 mL), 2 mol/L sodium carbonate aqueous solution (0.99 mL), and bis(di-tert-butyl(4-dimethylaminophenyl)phosphine)dichloropalladium(II) (46 mg) were added to a mixture of 7-bromo-1,5-naphthyridin-2-ol (150 mg) and 3,4-dimethoxyphenylboronic acid (150 mg) in a nitrogen atmosphere, followed by stirring at 100° C. for 2 days. The reaction mixture was cooled to room temperature, a mixed solvent of chloroform-methanol (10:1) was added thereto, and the solid matter was collected by filtration, thereby obtaining 7-(3,4-dimethoxyphenyl)-1,5-naphthyridin-2-ol (137 mg) as a yellow solid.

MSm/z(M+H):283.

0022-3

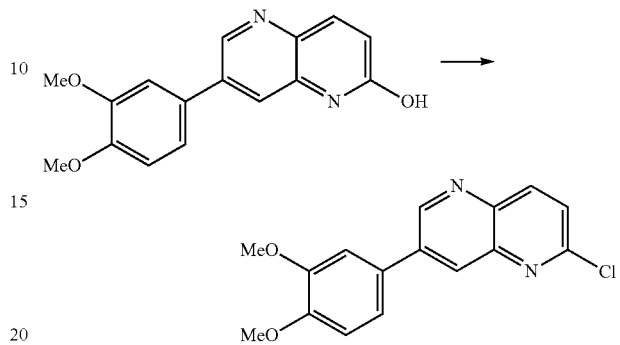

Phosphorus oxychloride (4 g) was added to 7-(3,4-dimethoxyphenyl)-1,5-naphthyridin-2-ol (134 mg), followed by stirring at 100° C. for 2 hours. After the reaction mixture was cooled to room temperature, water was added dropwise thereto, the resultant product was neutralized with a 5 mol/L sodium hydroxide aqueous solution, and chloroform was added thereto. The organic layer was collected by separation, and dried over anhydrous sodium sulfate, and the solvent was distilled off under reduced pressure. The obtained residue was purified by silica gel column chromatography (hexane-ethyl acetate), thereby obtaining 2-chloro-7-(3,4-dimethoxyphenyl)-1,5-naphthyridine (134 mg) as an orange solid.

$^1$H-NMR(CDCl$_3$)δ:9.24(1H,d,J=2.6 Hz),8.43(1H,d,J=2.6 Hz),8.37(1H,d,J=9.2 Hz),7.60(1H,d,J=9.2 Hz),7.33(1H,dd,J=8.3,2.1 Hz),7.24(1H,d,J=2.1 Hz),7.05(1H,d,J=8.3 Hz),3.99(3H,s),3.97(3H,s).

0022-4

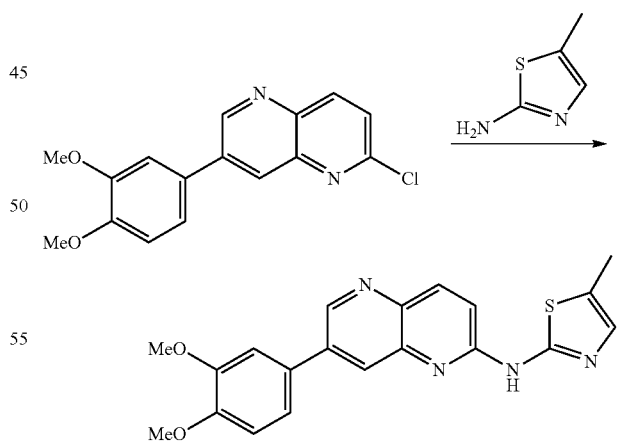

1,4-Dioxane (2 mL) was added to a mixture of 2-chloro-7-(3,4-dimethoxyphenyl)-1,5-naphthyridine (30 mg), 5-methylthiazole-2-amine (17 mg), tris(dibenzylideneacetone)dipalladium(0) (9.2 mg), 4,5-bis(diphenylphosphino)-9,9-dimethylxanthene (12 mg), and cesium carbonate (98 mg) in a nitrogen atmosphere, and the reaction vessel was sealed, followed by stirring at 100° C. overnight. The reaction mixture was cooled to room temperature, and water was added thereto. The solid matter was collected by filtration, and purified by silica gel column chromatography (chloroform-methanol), thereby obtaining N-(7-(3,4-dimethoxyphenyl)-1,5-naphthyridin-2-yl)-5-methylthiazole-2-amine (32 mg) as a yellow solid.

$^1$H-NMR(CDCl$_3$)δ:10.58(1H,brs),9.00(1H,d,J=2.0 Hz), 8.35(1H,d,J=2.0 Hz),8.25(1H,d,J=8.6 Hz),7.35(1H,dd, J=8.6,2.0 Hz),7.30-7.27(1H,m),7.24-7.18(2H,m),7.05(1H,d, J=8.6 Hz),4.03(3H,s),3.98(3H,s),2.51(3H,s).

MSm/z(M+H):379.

Example 0023

0023-1

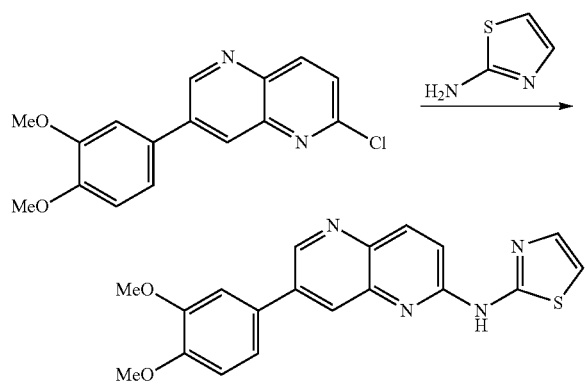

1,4-Dioxane (2 mL) was added to a mixture of 2-chloro-7-(3,4-dimethoxyphenyl)-1,5-naphthyridine (30 mg), thiazole-2-amine (15 mg), tris(dibenzylideneacetone)dipalladium(0) (9.2 mg), 4,5-bis(diphenylphosphino)-9,9-dimethylxanthene (12 mg), and cesium carbonate (98 mg) in a nitrogen atmosphere, and the reaction vessel was sealed, followed by stirring at 100° C. overnight. The reaction mixture was cooled to room temperature, and water was added thereto. The solid matter was collected by filtration, and purified by silica gel column chromatography (chloroform-methanol), thereby obtaining N-(7-(3,4-dimethoxyphenyl)-1,5-naphthyridin-2-yl)thiazole-2-amine (10 mg) as a yellow solid.

$^1$H-NMR(CDCl$_3$)δ:10.60(1H,brs),9.02(1H,d,J=2.0 Hz), 8.36(1H,d,J=2.0 Hz),8.28(1H,d,J=9.2 Hz),7.59(1H,d,J=3.7 Hz),7.36-7.22(3H,m),7.05(1H,d,J=7.9 Hz),7.00(1H,d,J=3.7 Hz),4.03(3H,s),3.98(3H,s).

MSm/z(M+H):365.

Example 0024

0024-1

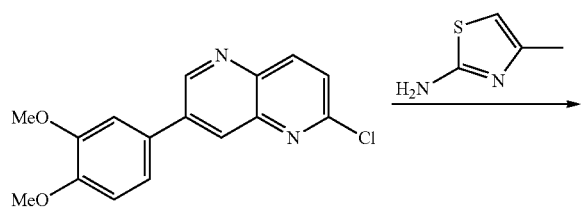

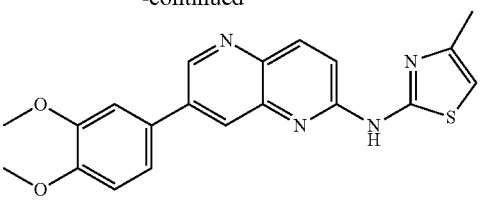

1,4-Dioxane (2 mL) was added to a mixture of 2-chloro-7-(3,4-dimethoxyphenyl)-1,5-naphthyridine (30 mg), 4-methylthiazole-2-amine (17 mg), tris(dibenzylideneacetone)dipalladium(0) (9.2 mg), 4,5-bis(diphenylphosphino)-9,9-dimethylxanthene (12 mg), and cesium carbonate (98 mg) in a nitrogen atmosphere, and the reaction vessel was sealed, followed by stirring at 100° C. overnight. The reaction mixture was cooled to room temperature, water was added thereto, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (chloroform-methanol), thereby obtaining N-(7-(3,4-dimethoxyphenyl)-1,5-naphthyridin-2-yl)-4-methylthiazole-2-amine (10 mg) as a yellow solid.

$^1$H-NMR(CDCl$_3$)δ:9.01(1H,s),8.33(1H,s),8.24(1H,d, J=8.3 Hz),7.33(1H,d,J=8.3 Hz),7.13(1H,d,J=8.6 Hz),7.04 (1H,d,J=8.6 Hz),6.52(1H,s),6.09(1H,s),4.02(3H,s),3.97(4H, s),2.40(3H,s).

MSm/z(M+H):379.

Example 0025

0025-1>

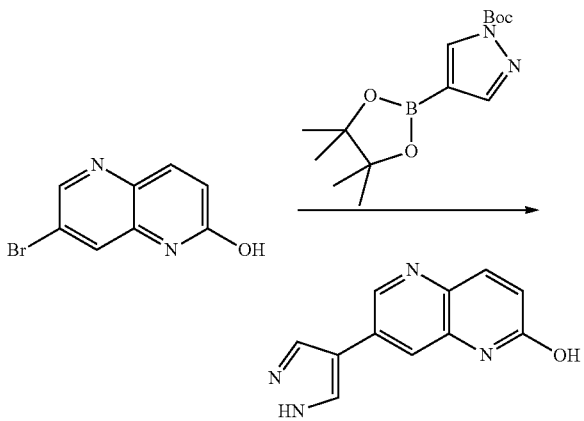

A 2 mol/L sodium carbonate aqueous solution (1.3 mL) and 1,4-dioxane (6.0 mL) were added to a mixture of 7-bromo-1,5-naphthyridin-2-ol (190 mg), tert-butyl 4-(4,4,5,5-tetramethyl-1,3,2-dioxaborolan-2-yl)-1H-pyrazole-1-carboxylate (376 mg), and bis(di-tert-butyl(4-dimethylaminophenyl)phosphine)dichloropalladium(II) (60 mg) in a nitrogen atmosphere, followed by stirring at 100° C. overnight. The reaction mixture was cooled to room temperature, and water was added thereto. The solid matter was collected by filtration, thereby obtaining 7-(1H-pyrazol-4-yl)-1,5-naphthyridin-2-ol (190 mg) as a grey solid.

¹H-NMR(DMSO-d₆)δ:13.23(1H,brs),11.84(1H,brs),8.79 (1H,d,J=2.0 Hz),8.20(2H,brs),7.90(1H,d,J=9.9 Hz),7.73 (1H,d,J=2.0 Hz),6.66(1H,d,J=9.9 Hz).

0025-2

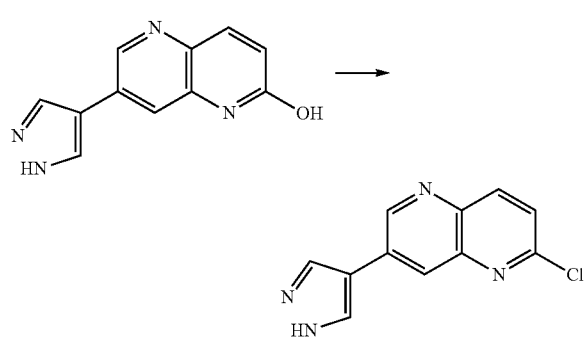

Phosphorus oxychloride (1.7 g) was added to 7-(1H-pyrazol-4-yl)-1,5-naphthyridin-2-ol (50 mg) at room temperature, followed by stirring at 80° C. for 30 minutes, and stirring at 100° C. for 1.5 hours. The reaction mixture was cooled to room temperature, water was added thereto, and the resultant product was neutralized with a 5 mol/L sodium hydroxide aqueous solution. The solid matter was collected by filtration, thereby obtaining 2-chloro-7-(1H-pyrazol-4-yl)-1,5-naphthyridine (40 mg) as a grey solid.

MSm/z(M+H):231,233.

0025-3

N,N-dimethylformamide (2 mL) was added to 2-chloro-7-(1H-pyrazol-4-yl)-1,5-naphthyridine (15 mg) in a nitrogen atmosphere, and 60% sodium hydride (3 mg) was added thereto under ice-cooling, followed by stirring at the same temperature for 30 minutes. (2-(Chloromethoxy)ethyl)trimethylsilane (14 µL) was added to the reaction mixture under ice-cooling, followed by stirring at room temperature for 1 hour. Water and ethyl acetate were added to the reaction mixture. The organic layer was collected by separation, washed with water and a saturated sodium chloride aqueous solution, and dried over anhydrous sodium sulfate, and the solvent was distilled off under reduced pressure. The obtained residue was purified by preparative thin layer silica gel chromatography (hexane-ethyl acetate), thereby obtaining 2-chloro-7-(1-((2-(trimethylsilyl)ethoxy)methyl)-1H-pyrazol-4-yl)-1,5-naphthyridine (6 mg) as a white solid.

MSm/z(M+H):361,363.

0025-4

N-(7-(1-((2-(trimethylsilyl)ethoxy)methyl)-1H-pyrazol-4-yl)-1,5-naphthyridin-2-yl)-1,3,4-thiadiazole-2-amine was obtained as a white solid in the same manner as in Example 0015-4.

¹H-NMR(CDCl₃)δ:13.10(1H,brs),8.98(1H,d,J=2.0 Hz), 8.85(1H,s),8.35(1H,d,J=9.2 Hz),8.28(1H,d,J=2.0 Hz),8.06 (1H,s),8.03(1H,s),7.80(1H,d,J=9.2 Hz),5.53(2H,s),3.68-3.63(2H,m),0.99-0.94(2H,m),0.01(9H,s).

MSm/z(M+H):426.

Example 0026

0026-1

2-Chloro-7-(1H-pyrazol-4-yl)-1,5-naphthyridine (65 mg) was dissolved in N,N-dimethylformamide in a nitrogen atmosphere, and 60% sodium hydride (17 mg) was added thereto under ice-cooling, followed by stirring for 30 minutes under ice-cooling. Methyl iodide (36 µL) was added to the reaction mixture, followed by stirring at room temperature for 50 minutes. Water and ethyl acetate were added to the reaction mixture. The organic layer was collected by separation, washed with water and a saturated sodium chloride aqueous solution, and dried over anhydrous sodium sulfate, and the solvent was distilled off under reduced pressure. The obtained residue was purified by silica gel column chromatography (chloroform-methanol), thereby obtaining 2-chloro-7-(1-methyl-1H-pyrazol-4-yl)-1,5-naphthyridine (20 mg) as a pale yellow solid.

MSm/z(M+H):245,247.

0026-2

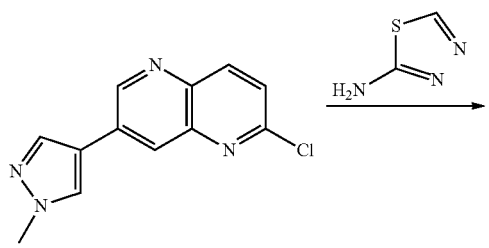

N-(7-(1-methyl-1H-pyrazol-4-yl)-1,5-naphthyridin-2-yl)-1,3,4-thiadiazole-2-amine was obtained as a pale yellow solid in the same manner as in Example 0015-4.

$^1$H-NMR(DMSO-d$_6$)δ:9.17(1H,s),9.08(1H,d,J=2.6 Hz), 8.52(1H,s),8.32(1H,d,J=2.6 Hz),8.28(1H,d,J=9.2 Hz),8.20 (1H,s),7.44(1H,d,J=9.2 Hz),3.93(3H,s).

MSm/z(M+H):310.

Examples 0027 to 0029

The following compounds were obtained in the same manner as in Example 0015-4.

| Example No. | | |
|---|---|---|
| 0027 | | |
| 0027-1 | 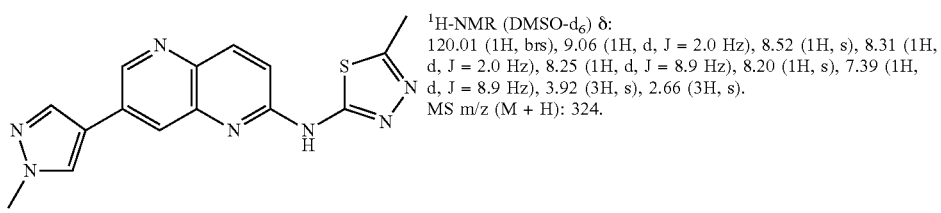 | $^1$H-NMR (DMSO-d$_6$) δ: 120.01 (1H, brs), 9.06 (1H, d, J = 2.0 Hz), 8.52 (1H, s), 8.31 (1H, d, J = 2.0 Hz), 8.25 (1H, d, J = 8.9 Hz), 8.20 (1H, s), 7.39 (1H, d, J = 8.9 Hz), 3.92 (3H, s), 2.66 (3H, s). MS m/z (M + H): 324. |
| 0028 | | |
| 0028-1 | 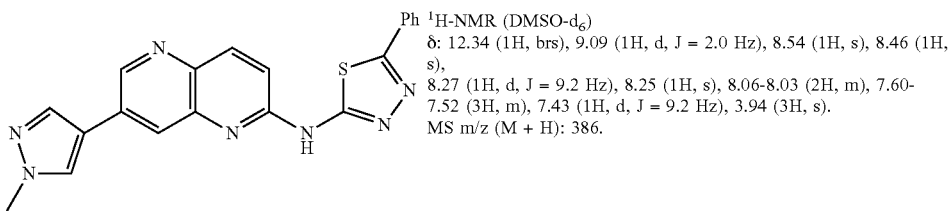 | $^1$H-NMR (DMSO-d$_6$) δ: 12.34 (1H, brs), 9.09 (1H, d, J = 2.0 Hz), 8.54 (1H, s), 8.46 (1H, s), 8.27 (1H, d, J = 9.2 Hz), 8.25 (1H, s), 8.06-8.03 (2H, m), 7.60-7.52 (3H, m), 7.43 (1H, d, J = 9.2 Hz), 3.94 (3H, s). MS m/z (M + H): 386. |
| 0029 | | |
| 0029-1 | 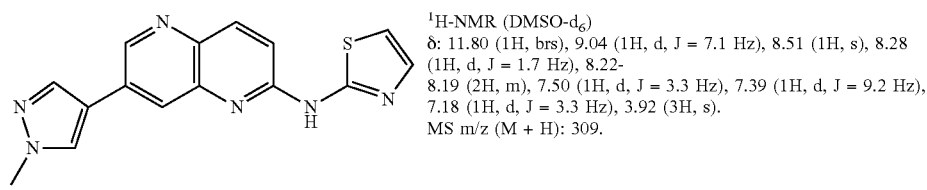 | $^1$H-NMR (DMSO-d$_6$) δ: 11.80 (1H, brs), 9.04 (1H, d, J = 7.1 Hz), 8.51 (1H, s), 8.28 (1H, d, J = 1.7 Hz), 8.22-8.19 (2H, m), 7.50 (1H, d, J = 3.3 Hz), 7.39 (1H, d, J = 9.2 Hz), 7.18 (1H, d, J = 3.3 Hz), 3.92 (3H, s). MS m/z (M + H): 309. |

-continued

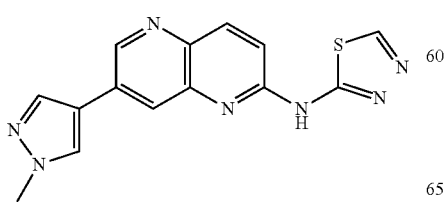

Example 0030

0030-1

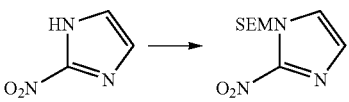

Tetrahydrofuran (10 mL) was added to 2-nitro-1H-imidazole (226 mg) in a nitrogen atmosphere, 60% sodium hydride (96 mg) was added thereto under ice-cooling, followed by stirring for 30 minutes under ice-cooling, and, thereafter, (2-(chloromethoxy)ethyl)trimethylsilane (421 μL) was added thereto, followed by stirring at room temperature for 2 hours. Water and ethyl acetate were added to the reaction mixture. The organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate), thereby obtaining 2-nitro-1-((2-(trimethylsilyl)ethoxy)methyl)-1H-imidazole (460 mg) as a yellow solid.

¹H-NMR(CDCl₃)δ:7.37-7.36(2H,m),5.84(2H,s),3.73-3.68(2H,m),1.06-1.003(2H,m),0.07(9H,s).

0030-2

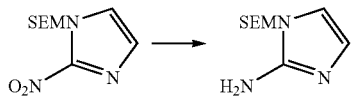

2-Nitro-1-((2-(trimethylsilyl)ethoxy)methyl)-1H-imidazole (176 mg) was dissolved in methanol (15 mL), and the resultant product was reacted using a flow-type hydrogenation reaction apparatus (atmospheric pressure, 1.0 mL/min, room temperature, 10% Pd/C). The solvent was distilled off under reduced pressure, thereby obtaining 1-((2-(trimethylsilyl)ethoxy)methyl)-1H-imidazole-2-amine (150 mg) as brown oily substance.

¹H-NMR(CDCl₃)δ:6.61(1H,d,J=1.7 Hz),6.56(1H,d,J=1.7 Hz),5.07(2H,s),4.19(2H,brs),3.54-4.48(2H,m),0.93-0.87 (2H,m),0.00(9H,s).

0030-3

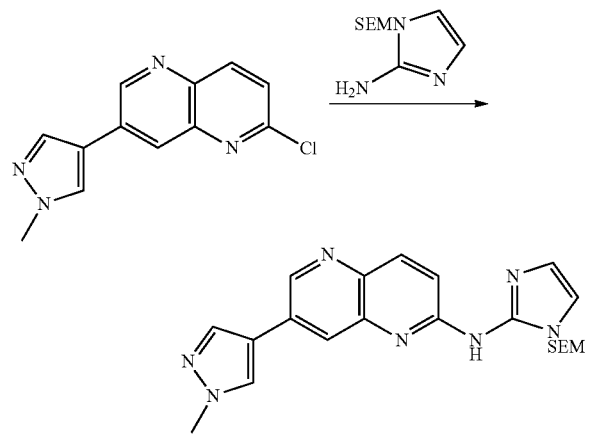

1,4-Dioxane (2 mL) was added to a mixture of 2-chloro-7-(1-methyl-1H-pyrazol-4-yl)-1,5-naphthyridine (20 mg), 1-((2-(trimethylsilyl)ethoxy)methyl)-1H-imidazole-2-amine (26 mg), tris(dibenzylideneacetone)dipalladium(0) (7.5 mg), 4,5-bis(diphenylphosphino)-9,9-dimethylxanthene (9.5 mg), and cesium carbonate (80 mg) in a nitrogen atmosphere, and the reaction vessel was sealed, followed by stirring at 150° C. for 30 minutes using a microwave reaction apparatus. The reaction mixture was cooled to room temperature, and water and ethyl acetate were added thereto.

The organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate, NH silica), thereby obtaining 7-(1-methyl-1H-pyrazol-4-yl)-N-(1-((2-(trimethylsilyl)ethoxy)methyl)-1H-imidazol-2-yl)-1,5-naphthyridine-2-amine (15 mg) as an orange solid.

MSm/z(M+H):422.

0030-4

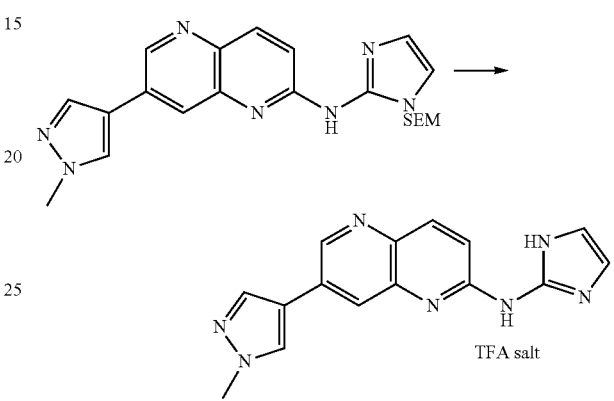

7-(1-Methyl-1H-pyrazol-4-yl)-N-(1-((2-(trimethylsilyl)ethoxy)methyl)-1H-imidazol-2-yl)-1,5-naphthyridine-2-amine (15 mg) was dissolved in a mixed solvent (4.1 mL) of methylene chloride-ethanol-trifluoroacetic acid (3:0.1:1), followed by stirring at room temperature for 7 hours. The reaction mixture was distilled off under reduced pressure, thereby obtaining trifluoroacetate (1.8 mg) of N-(1H-imidazol-2-yl)-7-(1-methyl-1H-pyrazol-4-yl)-1,5-naphthyridine-2-amine as a pale yellow solid.

¹H-NMR(CD₃OD)δ:9.10(1H,d,J=2.0 Hz),8.69(1H,d,J=2.0 Hz),8.35(1H,d,J=9.2 Hz),8.28(1H,s),8.08(1H,s),7.40 (1H,d,J=9.2 Hz),7.23(2H,s),4.01(3H,s).

MSm/z(M+H):292.

Example 0031

0031-1

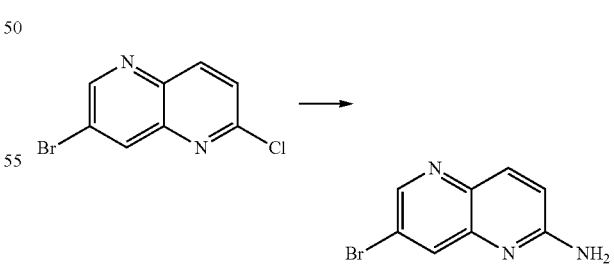

A mixture solution of 7-bromo-2-chloro-1,5-naphthyridine (100 mg) in 1,4-dioxane (2 mL) and a 25% ammonia aqueous solution was stirred at 120° C. for 3 hours using a microwave reaction apparatus. The reaction mixture was cooled to room temperature, and a saturated sodium chloride aqueous solution and ethyl acetate were added thereto. The organic layer was collected by separation, and dried over anhydrous sodium sulfate, and the solvent was distilled off under reduced pressure, thereby obtaining 7-bromo-1,5-naphthyridine-2-amine (90 mg) as a white solid.

$^1$H-NMR(DMSO-d$_6$)δ:8.53(1H,d),8.02(1H,d),7.92(1H,d),7.01(1H,d),6.94(1H,s).

MSm/z(M+H):224,226.

0031-2

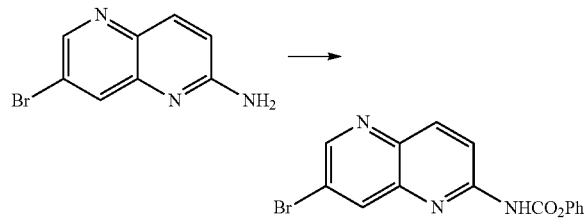

Pyridine (9 mL) was added to a mixture of 7-bromo-1,5-naphthyridine-2-amine (300 mg) and phenyl chloroformate (280 μL), followed by stirring at room temperature for 2 hours. Phenyl chloroformate (140 μL) was added thereto, followed by stirring at room temperature for 1 hour. The reaction mixture was distilled off under reduced pressure, and the obtained residue was purified by silica gel column chromatography (chloroform-methanol), thereby obtaining phenyl (7-bromo-1,5-naphthyridin-2-yl)carbamate (310 mg) as a white solid.

MSm/z(M+H):344,346.

0031-3

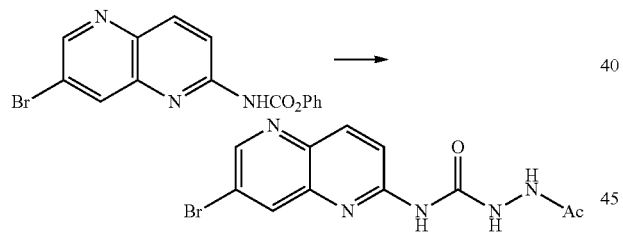

Phenyl (7-bromo-1,5-naphthyridin-2-yl)carbamate (20 mg) was dissolved in 1,4-dioxane (2 mL), and acetohydrazide (6.5 mg) was added thereto, followed by stirring at 150° C. for 30 minutes using a microwave reaction apparatus. The reaction mixture was cooled to room temperature, the solid matter was collected by filtration, thereby obtaining 2-acetyl-N-(7-bromo-1,5-naphthyridin-2-yl)hydrazinecarboxamide (14 mg) as a white solid.

MSm/z(M+H):324,326.

0031-4

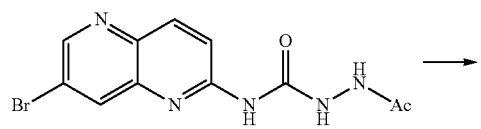

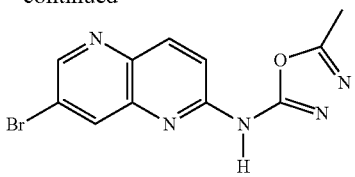

Phosphorus oxychloride (2.5 g) was added to 2-acetyl-N-(7-bromo-1,5-naphthyridin-2-yl)hydrazinecarboxamide (50 mg), followed by stirring at 80° C. for 2 hours. The reaction mixture was cooled to room temperature, and water was added dropwise thereto. The resultant product was neutralized with a 5 mol/L sodium hydroxide aqueous solution, and chloroform was added thereto. The organic layer was collected by separation, and dried over anhydrous sodium sulfate, and the solvent was distilled off under reduced pressure, thereby obtaining N-(7-bromo-1,5-naphthyridin-2-yl)-5-methyl-1,3,4-oxadiazole-2-amine (34 mg) as a yellow solid.

MSm/z(M+H):306,308.

0031-5

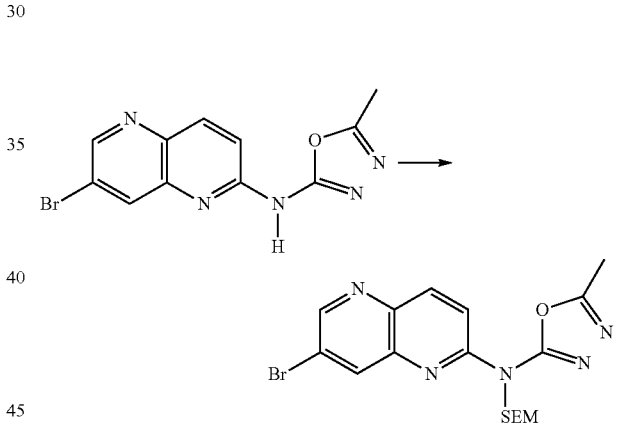

N-(7-bromo-1,5-naphthyridin-2-yl)-5-methyl-1,3,4-oxadiazole-2-amine (31 mg) was dissolved in N,N-dimethylformamide (2 mL) in a nitrogen atmosphere, and 60% sodium hydride (6 mg) was added thereto under ice-cooling, followed by stirring for 1 hour. (2-(Chloromethoxy)ethyl)trimethylsilane (14 μL) was added to the reaction mixture, followed by stirring at room temperature for 1 hour. Water and ethyl acetate were added to the reaction mixture. The organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate), thereby obtaining N-(7-bromo-1,5-naphthyridin-2-yl)-5-methyl-N-((2-(trimethylsilyl)ethoxy)methyl)-1,3,4-oxadiazole-2-amine (20 mg).

$^1$H-NMR(CDCl$_3$)δ:8.85(1H,d,J=2.0 Hz),8.35(1H,d,J=2.0 Hz),8.32(1H,d,J=9.9 Hz),8.19(1H,d,J=9.9 Hz),5.77(2H,s),3.82-3.75(2H,m),2.56(3H,s),0.99-0.94(2H,m),−0.05(9H,s).

0031-6

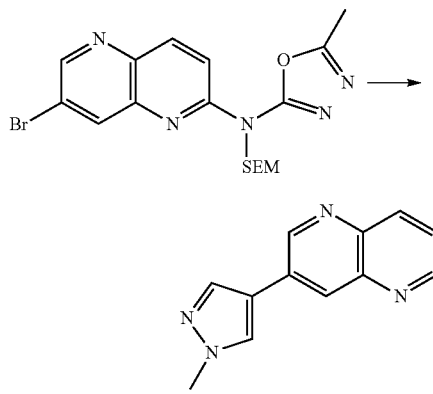

1,4-Dioxane (2 mL) and a 2 mol/L sodium carbonate aqueous solution (69 μL) were added to a mixture of N-(7-bromo-1,5-naphthyridin-2-yl)-5-methyl-N-((2-(trimethylsilyl)ethoxy)methyl)-1,3,4-oxadiazole-2-amine (20 mg), 1-methyl-4-(4,4,5,5-tetramethyl-1,3,2-dioxaborolan-2-yl)-1H-pyrazole (14 mg), and bis(di-tert-butyl(4-dimethylaminophenyl)phosphine)dichloropalladium(II) (3.2 mg) in a nitrogen atmosphere, and the reaction vessel was sealed, followed by stirring at 100° C. overnight. The reaction mixture was cooled to room temperature, and water and ethyl acetate were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate, NH silica), thereby obtaining 5-methyl-N-(7-(1-methyl-1H-pyrazol-4-yl)-1,5-naphthyridin-2-yl)-N-((2-(trimethylsilyl)ethoxy)methyl)-1,3,4-oxadiazole-2-amine (18 mg) as a white solid.

MSm/z(M+H):438.

0031-7

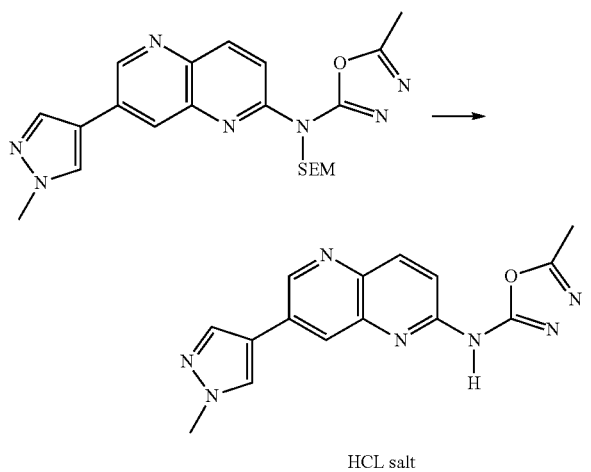

HCL salt

A mixed solvent (4.1 mL) of chloroform-ethanol-trifluoroacetic acid (3:0.1:1) was added to 5-methyl-N-(7-(1-methyl-1H-pyrazol-4-yl)-1,5-naphthyridin-2-yl)-N-((2-(trimethylsilyl)ethoxy)methyl)-1,3,4-oxadiazole-2-amine (18 mg), followed by stirring at room temperature for 3 hours. The solvent was distilled off under reduced pressure, and a mixed solvent of methanol-ethyl acetate was added to the obtained residue. The solid matter was collected by filtration, thereby obtaining 5-methyl-N-(7-(1-methyl-1H-pyrazol-4-yl)-1,5-naphthyridin-2-yl)-1,3,4-oxadiazole-2-amine hydrochloride (5 mg) as a yellow solid.

$^1$H-NMR(DMSO-d$_6$)δ:9.07(1H,d,J=2.0 Hz),8.49(1H,s),8.29-8.26(2H,m),8.18(1H,s),7.96-7.84(1H,m),3.92(3H,s),2.46(3H,s).

MSm/z(M+H):308.

Example 0032

0032-1

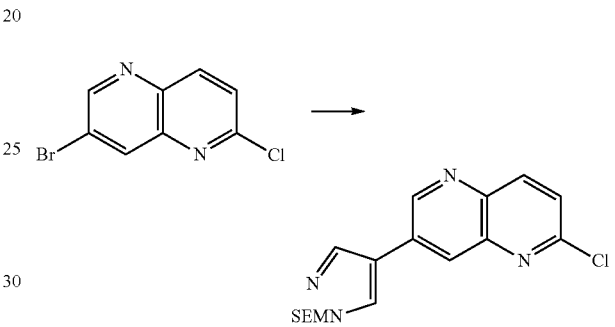

1,4-Dioxane (2 mL) and a 2 mol/L sodium carbonate aqueous solution (315 μL) were added to a mixture of 7-bromo-2-chloro-1,5-naphthyridine (50 mg), 4-(4,4,5,5-tetramethyl-1,3,2-dioxaborolan-2-yl)-1-((2-(trimethylsilyl)ethoxy)methyl)-1H-pyrazole (77 mg), and bis(di-tert-butyl(4-dimethylaminophenyl)phosphino)dichloropalladium(II) (15 mg) in a nitrogen atmosphere, and the reaction vessel was sealed, followed by stirring at 100° C. for 5 hours. The reaction mixture was cooled to room temperature, and water and ethyl acetate were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate), thereby obtaining 2-chloro-7-(1-((2-(trimethylsilyl)ethoxy)methyl)-1H-pyrazol-4-yl)-1,5-naphthyridine (57 mg) as a white solid.

$^1$H-NMR(CDCl$_3$)δ:9.15(1H,d,J=2.0 Hz),8.35-8.31(2H,m),8.04(1H,s),8.00(1H,s),7.57(1H,d,J=8.6 Hz),5.53(2H,s),3.68-3.63(2H,m),0.99-0.93(2H,m),0.00(9H,s).

0032-2

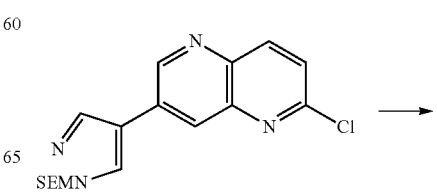

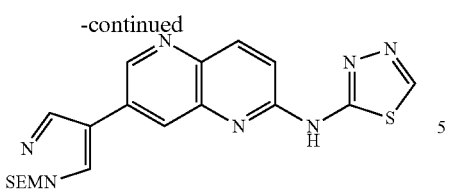

1,4-Dioxane (3 mL) was added to a mixture of 2-chloro-7-(1-((2-(trimethylsilyl)ethoxy)methyl)-1H-pyrazol-4-yl)-1,5-naphthyridine (57 mg), 1,3,4-thiadiazole-2-amine (24 mg), tris(dibenzylideneacetone)dipalladium(0) (14 mg), 4,5-bis(diphenylphosphino)-9,9-dimethylxanthene (18 mg), and cesium carbonate (154 mg) in a nitrogen atmosphere, followed by stirring at 100° C. for 7 hours. The reaction mixture was cooled to room temperature, and water and ethyl acetate were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (chloroform-methanol, NH silica), thereby obtaining N-(7-(1-((2-trimethylsilyl)ethoxy)methyl)-1H-pyrazol-4-yl)-1,5-naphthyridin-2-yl)-1,3,4-thiadiazole-2-amine (23 mg).

MS m/z(M+H):426.

0032-3

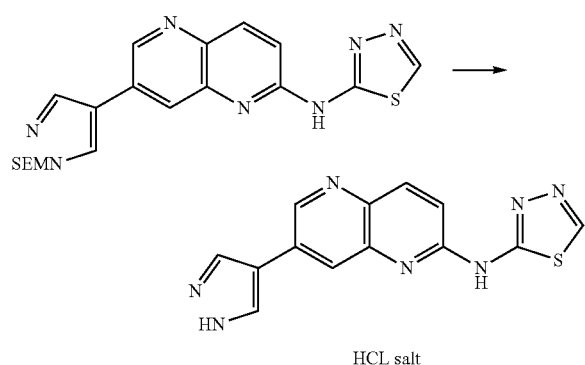

HCL salt

Ethanol (3 mL) and 3 mol/L hydrochloric acid (3 mL) were added to N-(7-(1-((2-(trimethylsilyl)ethoxy)methyl)-1H-pyrazol-4-yl)-1,5-naphthyridin-2-yl)-1,3,4-thiadiazole-2-amine (23 mg), followed by stirring at 80° C. for 4 hours. The reaction mixture was cooled to room temperature, and the solvent was concentrated under reduced pressure. Methanol and ethyl acetate were added to the obtained residue, and the produced solid matter was collected by filtration, thereby obtaining N-(7-(1H-pyrazol-4-yl)-1,5-naphthyridin-2-yl)-1,3,4-thiadiazole-2-amine hydrochloride (6 mg) as a pale yellow solid.

$^1$H-NMR(DMSO-$d_6$)δ:12.30(1H,brs),9.19-9.18(2H,m),8.46(1H,d,J=1.2 Hz),8.44(2H,s),8.33(1H,d,J=9.2 Hz),7.49 (1H,d,J=9.2 Hz).

MS m/z(M+H):296.

Example 0033

0033-1

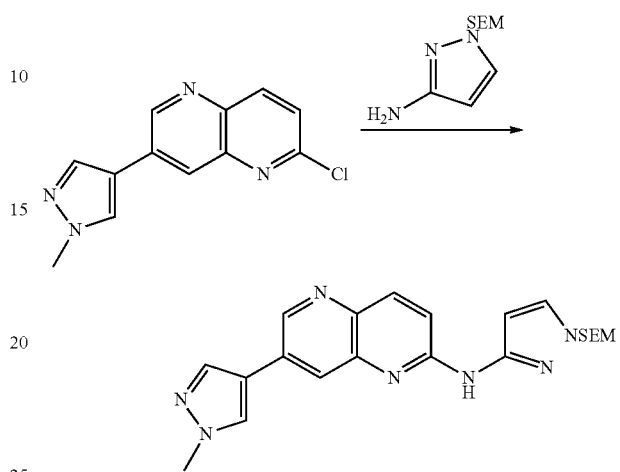

1,4-Dioxane (3 mL) was added to a mixture of 2-chloro-7-(1-methyl-1H-pyrazol-4-yl)-1,5-naphthyridine (15 mg), 1-((2-(trimethylsilyl)ethoxy)methyl)-1H-pyrazole-3-amine (20 mg), tris(dibenzylideneacetone)dipalladium(0) (5.5 mg), 4,5-bis(diphenylphosphino)-9,9-dimethylxanthene (6.9 mg), and cesium carbonate (59 mg) in a nitrogen atmosphere, and the reaction vessel was sealed, followed by stirring at 150° C. for 30 minutes using a microwave reaction apparatus. Tris(dibenzylideneacetone)dipalladium (0) (11 mg) and 4,5-bis(diphenylphosphino)-9,9-dimethylxanthene (14 mg) were added thereto, followed by stirring at 150° C. for 1 hour using a microwave reaction apparatus. The reaction mixture was cooled to room temperature, and water and ethyl acetate were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate, chloroform-methanol, NH silica), and further purified by preparative thin layer silica gel chromatography (chloroform-methanol), thereby obtaining 7-(1-methyl-1H-pyrazol-4-yl)-N-(1-((2-(trimethylsilyl)ethoxy)methyl)-1H-pyrazol-3-yl)-1,5-naphthyridine-2-amine (4 mg) as oily substance.

MS m/z(M+H):422.

0033-2

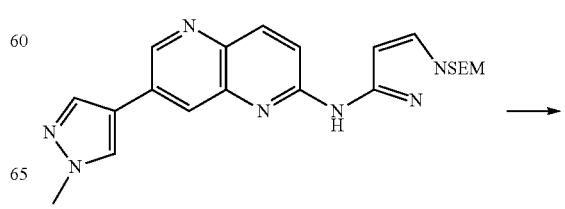

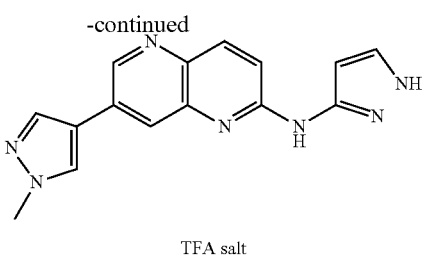

TFA salt 7-(1-Methyl-1H-pyrazol-4-yl)-N-(1-((2-(trimethylsilyl)ethoxy)methyl)-1H-pyrazol-3-yl)-1,5-naphthyridine-2-amine (4 mg) was dissolved in a mixed solvent (2.3 mL) of chloroform-trifluoroacetic acid-ethanol (1:1:0.3), followed by stirring at 50° C. for 6 hours. The reaction mixture was cooled to room temperature, and the solvent was distilled off under reduced pressure. The obtained residue was washed with ethyl acetate, thereby obtaining 7-(1-methyl-1H-pyrazol-4-yl)-N-(1H-pyrazol-3-yl)-1,5-naphthyridine-2-aminetrifluoroacetate (2 mg) as a yellow solid.

$^1$H-NMR(DMSO-d$_6$)δ:10.84(1H,brs),9.02(1H,d,J=2.0 Hz),8.48(1H,s),8.39(1H,br),8.20-8.17(2H,m),7.78(1H,d, J=2.0 Hz),7.40(1H,d,J=9.2 Hz),6.75(1H,s),3.95(3H,s).

MSm/z(M+H):292.

Example 0034

0034-1

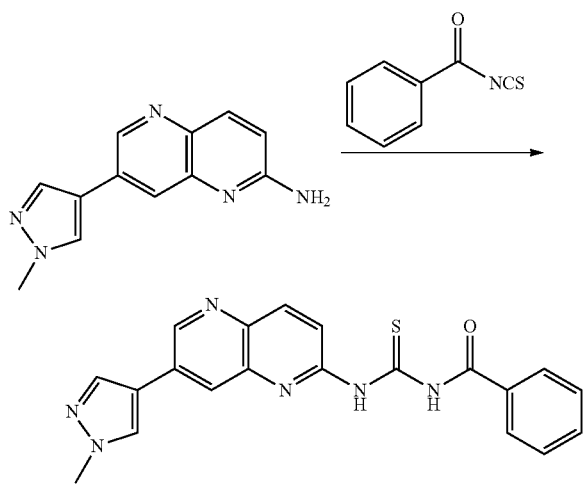

7-(1-Methyl-1H-pyrazol-4-yl)-1,5-naphthyridine-2-amine (201 mg) was dissolved in 1,4-dioxane (8.9 mL), and benzoyl isothiocyanate (0.24 mL) was added thereto under ice-cooling, followed by stirring at room temperature for 1 hour, and stirring at 55° C. for 2 hours. The reaction mixture was cooled to room temperature, and the solvent was distilled off under reduced pressure. Ethyl acetate was added to the obtained residue, and the solid matter was collected by filtration, thereby obtaining N-((7-(1-methyl-1H-pyrazol-4-yl)-1,5-naphthyridin-2-yl)carbamothioyl)benzamide (232 mg) as a yellow solid.

MSm/z(M+H):389.

0034-2

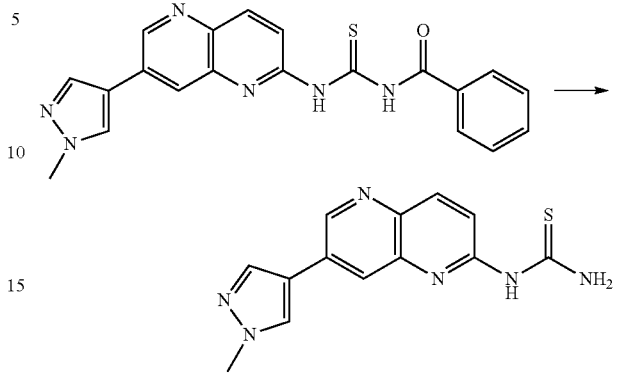

N-((7-(1-methyl-1H-pyrazol-4-yl)-1,5-naphthyridin-2-yl)carbamothioyl)benzamide (50 mg) was dissolved in 1,4-dioxane (1.3 mL), and a 2 mol/L sodium hydroxide aqueous solution (0.14 mL) was added thereto, followed by stirring at 80° C. for 1.5 hours. The reaction mixture was cooled to room temperature, and water was added thereto. The solid matter was collected by filtration, thereby obtaining 1-(7-(1-methyl-1H-pyrazol-4-yl)-1,5-naphthyridin-2-yl)thiourea (22 mg) as a pale yellow solid.

MSm/z(M+H):285.

0034-3

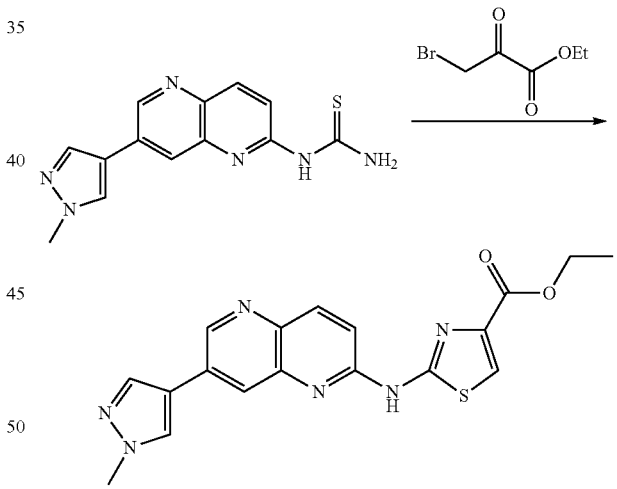

1-(7-(1-Methyl-1H-pyrazol-4-yl)-1,5-naphthyridin-2-yl)thiourea (20 mg) and ethyl 3-bromo-2-oxopropanoate (8.8 mL) were dissolved in N,N-dimethylformamide (2 mL), followed by stirring at 60° C. for 2 hours. The reaction mixture was cooled to room temperature, and water and ethyl acetate were added thereto. The organic layer was collected by separation, washed sequentially with water and a saturated sodium chloride aqueous solution, and dried over anhydrous sodium sulfate, and the solvent was distilled off under reduced pressure. The obtained residue was purified by silica gel column chromatography (chloroform-methanol), thereby obtaining ethyl 2-((7-(1-methyl-1H-pyrazol-4-yl)-1,5-naphthyridin-2-yl)amino)thiazole-4-carboxylate (16 mg) as a yellow solid.

¹H-NMR(DMSO-d₆)δ:12.28(1H,s),9.07(1H,d,J=2.3 Hz), 8.51(1H,s),8.31(1H,d,J=2.3 Hz),8.24(1H,d,J=9.2 Hz),8.19 (1H,s),8.04(1H,s),7.33(1H,d,J=9.2 Hz),4.30(2H,q,J=7.0 Hz),3.92(3H,s),1.32(3H,t,J=7.0 Hz).
MSm/z(M+H):381.

Example 0035

0035-1

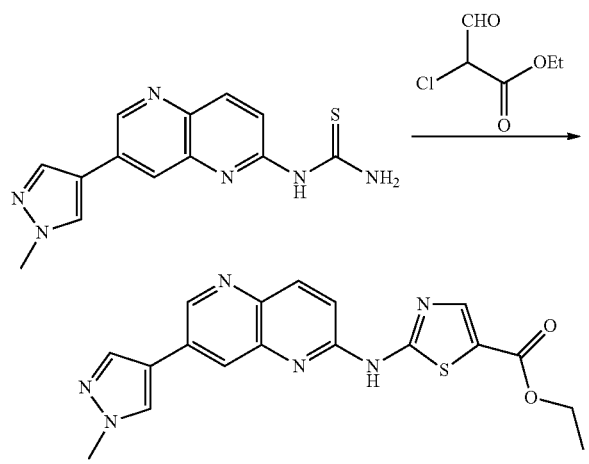

1-(7-(1-Methyl-1H-pyrazol-4-yl)-1,5-naphthyridin-2-yl) thiourea (20 mg) and ethyl 2-chloro-3-oxopropanoate (10 mg) were dissolved in N,N-dimethylformamide (2 mL), followed by stirring at 80° C. overnight. The reaction mixture was cooled to room temperature, and water and ethyl acetate were added thereto. The organic layer was collected by separation, washed sequentially with water and a saturated sodium chloride aqueous solution, and dried over anhydrous sodium sulfate, and the solvent was distilled off under reduced pressure. The obtained residue was dissolved in a mixed solvent of chloroform-methanol, and ethyl acetate was added thereto. The solid matter was collected by filtration, thereby obtaining ethyl 2-((7-(1-methyl-1H-pyrazol-4-yl)-1,5-naphthyridin-2-yl)amino)thiazole-5-carboxylate (8 mg) as a pale yellow solid.

¹H-NMR(DMSO-d₆)δ:12.35(1H,s),9.12(1H,d,J=2.0 Hz), 8.58(1H,s),8.34(1H,d,J=2.0 Hz),8.30(1H,d,J=9.2 Hz),8.24 (1H,s),8.17(1H,s),7.45(1H,d,J=9.2 Hz),4.33(2H,q,J=7.0 Hz),3.93(3H,s),1.34(3H,t,J=7.0 Hz).
MSm/z(M+H):381.

Example 0036

0036-1

1,4-Dioxane (2 mL) was added to a mixture of 2-chloro-7-(1-methyl-1H-pyrazol-4-yl)-1,5-naphthyridine (12 mg), 2-aminopyridine (7 mg), potassium tert-butoxide (16 mg), tris(dibenzylideneacetone)dipalladium(0) (4.5 mg), and 4,5-bis(diphenylphosphino)-9,9-dimethylxanthene (5.6 mg) in a nitrogen atmosphere, and the reaction vessel was sealed, followed by stirring at 150° C. for 30 minutes using a microwave reaction apparatus. The reaction mixture was cooled to room temperature, and water and ethyl acetate were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (chloroform-methanol), thereby obtaining 7-(1-methyl-1H-pyrazol-4-yl)-N-(pyridin-2-yl)-1,5-naphthyridine-2-amine (4 mg) as a pale yellow solid.

¹H-NMR(DMSO-d₆)δ:10.25(1H,s),9.00(1H,d,J=2.0 Hz), 8.62(1H,d,J=8.6 Hz),8.48(1H,s),8.32-8.30(1H,m),8.25(1H, d,J=2.0 Hz),8.17(1H,s),8.15(1H,d,J=9.2 Hz),7.83-7.77(1H, m),7.67(1H,d,J=9.2 Hz),7.03-6.99(1H,m),3.92(3H,s).
MSm/z(M+H):303.

Examples 0037 and 0038

The following compounds were obtained in the same manner as in Example 0036-1.

| Example No. | | |
|---|---|---|
| 0037 | | |
| 0037-1 | 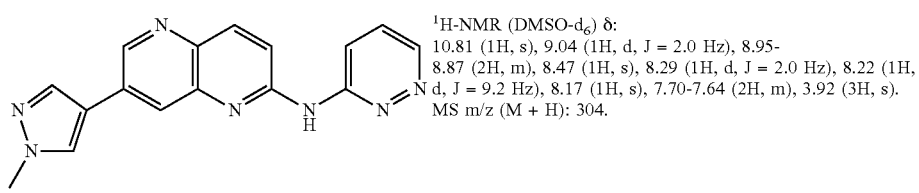 | ¹H-NMR (DMSO-d₆) δ: 10.81 (1H, s), 9.04 (1H, d, J = 2.0 Hz), 8.95-8.87 (2H, m), 8.47 (1H, s), 8.29 (1H, d, J = 2.0 Hz), 8.22 (1H, d, J = 9.2 Hz), 8.17 (1H, s), 7.70-7.64 (2H, m), 3.92 (3H, s). MS m/z (M + H): 304. |

| Example No. | | |
|---|---|---|
| 0038 | | |
| 0038-1 | 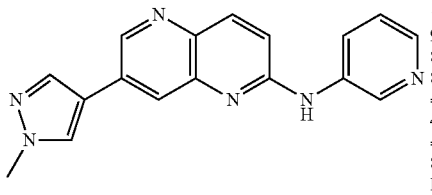 | ¹H-NMR (DMSO-d₆) δ:<br>9.82 (1H, s), 9.11 (1H, d, J = 2.6 Hz), 8.96 (1H, d, J = 2.0 Hz), 8.57-<br>8.53 (1H, m), 8.48 (1H, s) 8.24 (1H, d, J = 2.0 Hz), 8.21 (1H, dd, J = 4.6, 3.1 Hz), 8.17 (1H, s), 8.11 (1H, d, J = 9.2 Hz), 7.38 (1H, dd, J = 8.6, 4.6 Hz), 7.24 (1H, d, J = 9.2 Hz), 3.91 (3H, s).<br>MS m/z (M + H): 303. |

Example 0039

0039-1

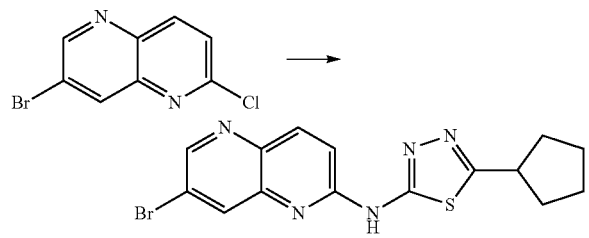

A solution of 7-bromo-2-chloro-1,5-naphthyridine (2.04 g), 5-cyclopentyl-1,3,4-thiadiazole-2-amine (1.41 g), and potassium carbonate (1.73 g) in dimethylsulfoxide (16 mL) was stirred at 130° C. for 3 hours. After the reaction mixture was cooled to room temperature, water was added thereto, and the solid matter was collected by filtration, thereby obtaining N-(7-bromo-1,5-naphthyridin-2-yl)-5-cyclopentyl-1,3,4-thiadiazole-2-amine (1.92 g).

¹H-NMR(DMSO-d₆)δ:12.20(1H,s),8.84(1H,d,J=2.7 Hz), 8.56(1H,d,J=2.7 Hz),8.31(1H,d,J=9.3 Hz),7.51(1H,d,J=9.3 Hz),3.56-3.40(1H,m),2.22-2.08(2H,m),1.94-1.34(6H,m).

MSm/z(M+H):376,378.

Example 0040

0040-1

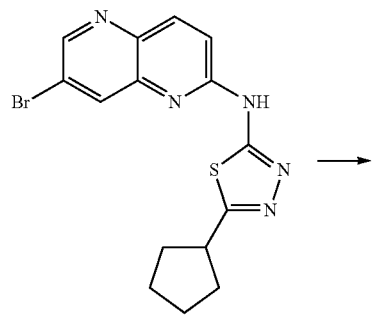

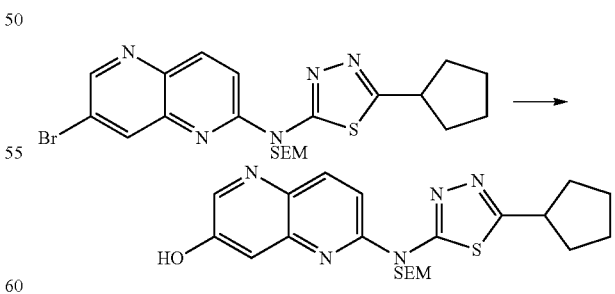

60% sodium hydride (256 mg) was added to a solution of N-(7-bromo-1,5-naphthyridin-2-yl)-5-cyclopentyl-1,3,4-thiadiazole-2-amine (1.21 g) and 2-(chloromethoxy)ethyltrimethylsilane (0.846 mL) in N-methylpyrrolidone (32 mL) under ice-cooling, followed by stirring at the same temperature for 1 hour, and stirring at room temperature for 1 hour. Ethyl acetate and water were added to the reaction mixture. The organic layer was collected by separation, washed with a saturated sodium chloride aqueous solution, and and dried over anhydrous sodium sulfate. The obtained residue was purified by silica gel column chromatography (ethyl acetate-hexane), thereby obtaining N-(7-bromo-1,5-naphthyridin-2-yl)-5-cyclopentyl-N-((2-(trimethylsilyl)ethoxy)methyl)-1,3,4-thiadiazole-2-amine (601 mg) and (Z)-7-bromo-N-(5-cyclopentyl-3-((2-(trimethylsilyl)ethoxy)methyl)-1,3,4-thiadiazol-2(3H)-ylidene)-1,5-naphthyridine-2-amine (206 mg).

MSm/z(M+H):506,508, 506,508.

0040-2

A mixture of N-(7-bromo-1,5-naphthyridin-2-yl)-5-cyclopentyl-N-((2-(trimethylsilyl)ethoxy)methyl)-1,3,4-thiadiazole-2-amine (200 mg), bis(pinacolato)diboron (150 mg), (1,1'-bis(diphenylphosphino)ferrocene)palladium(II) dichloride (32 mg) and potassium acetate (77 mg) in 1,4-dioxane (2.0 mL) was stirred at 80° C. for 2 hours in a nitrogen atmosphere. The reaction mixture was cooled to room temperature, and 30% hydrogen peroxide water (0.1 mL) and a saturated sodium hydrogen carbonate aqueous solution (1.5 mL) were added thereto, followed by stirring at room temperature for 3 hours. A saturated sodium chloride aqueous solution and ethyl acetate were added to the reaction mixture. The organic layer was collected by separation, and dried over anhydrous sodium sulfate, and the solvent was distilled off under reduced pressure. The obtained residue was purified by silica gel column chromatography (ethyl acetate-hexane), thereby obtaining 6-((5-cyclopentyl-1,3,4-thiadiazol-2-yl)((2-(trimethylsilyl)ethoxy)methyl)amino)-1,5-naphthyridin-3-ol (99 mg) as a white solid.
MSm/z(M+H):444.

0040-3

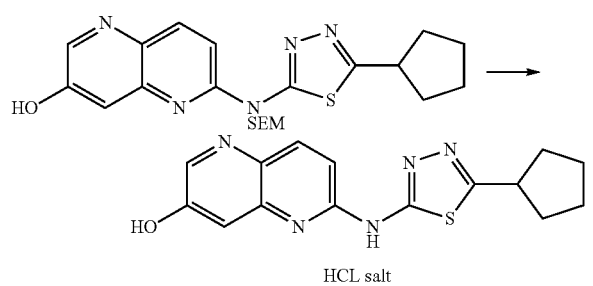

HCL salt

Methanol (0.5 mL), 12 mol/L hydrochloric acid (0.5 mL), 1,4-dioxane (0.25 mL), N-methylpyrrolidone (0.125 mL), and methanol (0.5 mL) were added to 6-((5-cyclopentyl-1,3,4-thiadiazol-2-yl)((2-(trimethylsilyl)ethoxy)methyl)amino)-1,5-naphthyridin-3-ol (10 mg), followed by stirring at 50° C. for 1 hour. The reaction mixture was cooled to room temperature, and the solvent was distilled off under reduced pressure. Diisopropyl ether and water were added to the obtained residue, and the solid matter was collected by filtration, thereby obtaining 6-((5-cyclopentyl-1,3,4-thiadiazol-2-yl)amino)-1,5-naphthyridin-3-ol hydrochloride (2.9 mg).
$^1$H-NMR(DMSO-$d_6$)δ:12.06-11.80(1H,brs),10.74-10.56 (1H,brs),8.44(1H,d,J=2.1 Hz),8.17(1H,d,J=9.0 Hz),7.43 (1H,d,J=2.1 Hz),7.25(1H,d,J=9.0 Hz),3.54-3.38(1H,m), 2.22-2.08(2H,m),1.90-1.62(6H,m).
MSm/z(M+H):314.

Example 0041

0041-1

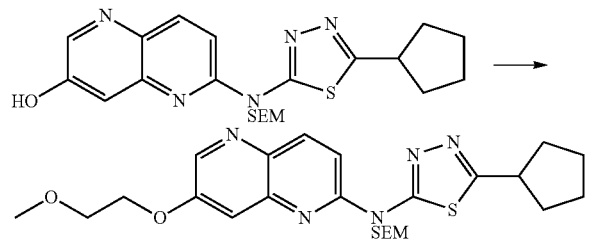

1-Bromo-2-methoxyethane (0.0064 mL) was added to a mixture of 6-((5-cyclopentyl-1,3,4-thiadiazol-2-yl)((2-(trimethylsilyl)ethoxy)methyl)amino)-1,5-naphthyridin-3-ol (20 mg) and potassium carbonate (19 mg) in N-methylpyrrolidone (0.5 mL), followed by stirring at 70° C. for 3 hours. The reaction mixture was cooled to room temperature, and ethyl acetate and water were added thereto. The organic layer was collected by separation, washed sequentially with water and a saturated sodium chloride aqueous solution, and dried over anhydrous sodium sulfate, and the solvent was distilled off under reduced pressure, thereby obtaining 5-cyclopentyl-N-(7-(2-methoxyethoxy)-1,5-naphthyridin-2-yl)-N-((2-(trimethylsilyl)ethoxy)methyl)-1,3,4-thiadiazole-2-amine (13 mg).
MSm/z(M+H):502.

0041-2

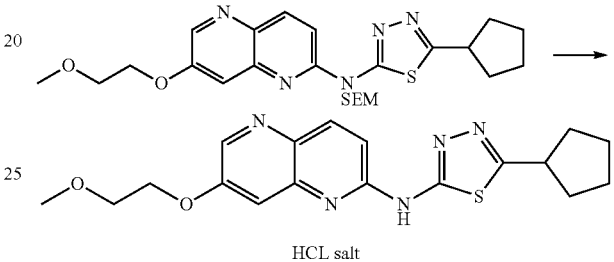

HCL salt 12 mol/L hydrochloric acid (0.4 mL) was added to a solution of 5-cyclopentyl-N-(7-(2-methoxyethoxy)-1,5-naphthyridin-2-yl)-N-((2-trimethylsilyl)ethoxy)methyl)-1,3, 4-thiadiazole-2-amine (13 mg) in methanol (1.2 mL), followed by stirring at room temperature for 1.5 hours. The solvent was distilled off under reduced pressure, and diisopropyl ether and water were added to the obtained residue. The solid matter was collected by filtration, thereby obtaining 5-cyclopentyl-N-(7-(2-methoxyethoxy)-1,5-naphthyridin-2-yl)-1,3,4-thiadiazole-2-amine hydrochloride (3.3 mg).
$^1$H-NMR(DMSO-$d_6$)δ:11.98(1H,brs),8.52(1H,d,J=2.7 Hz),8.21(1H,d,J=9.3 Hz),7.63(1H,d,J=2.7 Hz),7.30(1H,d, J=9.3 Hz),4.38-4.33(2H,m),3.78-3.73(2H,m),3.52-3.36(1H, m),3.38(3H,s),2.22-2.08(2H,m),1.94-1.64(6H,m).
MSm/z(M+H):372.

Example 0042

0042-1

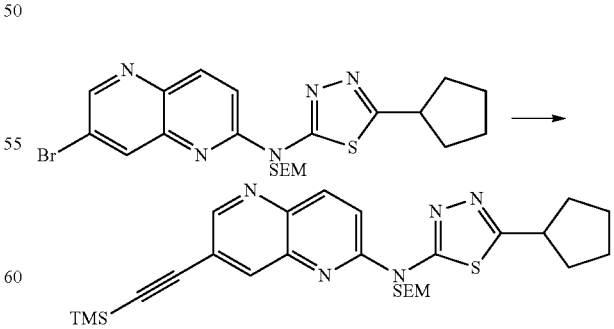

Tetrakis(triphenylphosphine)palladium(0) (16 mg), copper iodide (I) (5 mg), triethylamine (0.049 mL), and trimethylsilylacetylene (0.039 mL) were added to a solution of N-(7-bromo-1,5-naphthyridin-2-yl)-5-cyclopentyl-N-((2-

(trimethylsilyl)ethoxy)methyl)-1,3,4-thiadiazole-2-amine (70 mg) in tetrahydrofuran (1.5 mL), followed by stirring for 1.5 hours under heating to reflux. N-methylpyrrolidone (0.75 mL) and trimethylsilylacetylene (0.2 mL) were added thereto, followed by stirring at the same temperature for 1 hour. The reaction mixture was cooled to room temperature, and ethyl acetate and water were added thereto. The organic layer was collected by separation, washed sequentially with water and a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 5-cyclopentyl-N-((2-(trimethylsilyl)ethoxy)methyl)-N-(7-((trimethylsilyl)ethynyl)-1,5-naphthyridin-2-yl)-1,3,4-thiadiazole-2-amine (65 mg).

MSm/z(M+H):524.

0042-2

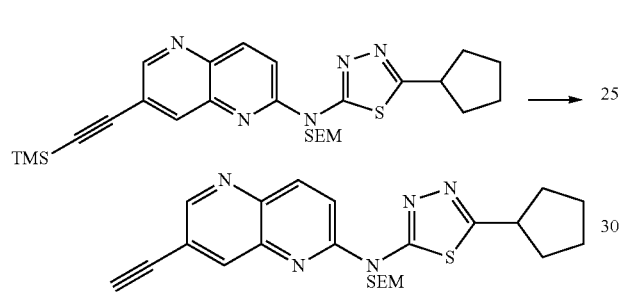

Methanol (1.2 mL) was added to 5-cyclopentyl-N-((2-(trimethylsilyl)ethoxy)methyl)-N-(7-((trimethylsilyl)ethynyl)-1,5-naphthyridin-2-yl)-1,3,4-thiadiazole-2-amine (65 mg) and potassium carbonate (34 mg), followed by stirring at room temperature for 2 hours. Ethyl acetate and a saturated sodium chloride aqueous solution were added to the reaction mixture. The organic layer was collected by separation, and dried over anhydrous sodium sulfate. The obtained solution was purified by silica gel column chromatography (ethyl acetate-hexane), thereby obtaining 5-cyclopentyl-N-(7-ethynyl-1,5-naphthyridin-2-yl)-N-((2-(trimethylsilyl)ethoxy)methyl)-1,3,4-thiadiazole-2-amine (30 mg).

MSm/z(M+H):452.

0042-3

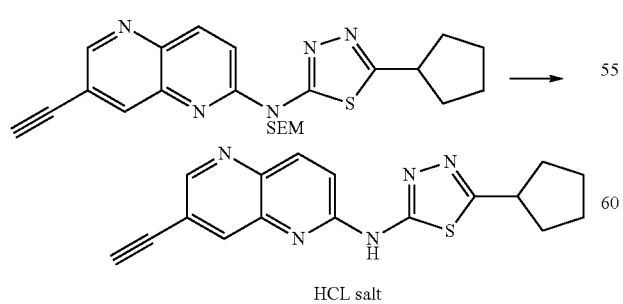

12 mol/L hydrochloric acid (0.4 mL) was added to a solution of 5-cyclopentyl-N-(7-ethynyl-1,5-naphthyridin-2-yl)-N-((2-(trimethylsilyl)ethoxy)methyl)-1,3,4-thiadiazole-2-amine (13 mg) in methanol (1.2 mL), followed by stirring at room temperature for 1.5 hours. The solvent was distilled off under reduced pressure, diisopropyl ether and water were added to the obtained residue, and the solid matter was collected by filtration, thereby obtaining 5-cyclopentyl-N-(7-ethynyl-1,5-naphthyridin-2-yl)-1,3,4-thiadiazole-2-amine hydrochloride (2.3 mg).

$^1$H-NMR(DMSO-$d_6$)δ:12.15(1H,brs),8.78(1H,d,J=1.8 Hz),8.36(1H,d,1.8 Hz),8.31(1H,J=9.3 Hz),7.49(1H,d,J=9.3 Hz),4.64(1H,s),3.54-3.38(1H,m),2.22-2.08(2H,m),1.92-1.64(6H,m).

MSm/z(M+H):322.

Example 0043

0043-1

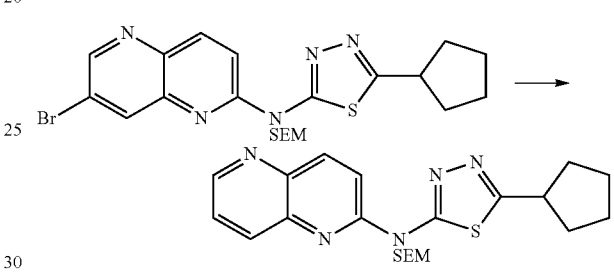

A mixture of N-(7-bromo-1,5-naphthyridin-2-yl)-5-cyclopentyl-N-((2-(trimethylsilyl)ethoxy)methyl)-1,3,4-thiadiazole-2-amine (37 mg), tetrakis(triphenylphosphine)palladium(0) (8 mg), ammonium formate (18 mg) and triethylamine (0.082 mL) in N-methylpyrrolidone (1 mL) was stirred at 120° C. for 60 minutes using a microwave reaction apparatus. The reaction mixture was cooled to room temperature, and ethyl acetate and water were added thereto. The organic layer was collected by separation, washed sequentially with water and a saturated sodium chloride aqueous solution, and dried over anhydrous sodium sulfate. The obtained solution was purified by silica gel column chromatography (ethyl acetate-hexane), thereby obtaining 5-cyclopentyl-N-(1,5-naphthyridin-2-yl)-N-((2-(trimethylsilyl)ethoxy)methyl)-1,3,4-thiadiazole-2-amine (21 mg).

MSm/z(M+H):427.

0043-2

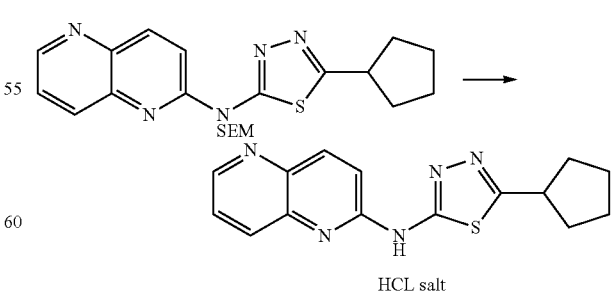

12 mol/L hydrochloric acid (0.4 mL) was added to a solution of 5-cyclopentyl-N-(1,5-naphthyridin-2-yl)-N-((2-(trimethylsilyl)ethoxy)methyl)-1,3,4-thiadiazole-2-amine (21 mg) in methanol (1.2 mL), followed by stirring at room temperature for 2 hours. The solvent was distilled off under reduced pressure, diisopropyl ether and water were added thereto, and the solid matter was collected by filtration, thereby obtaining 5-cyclopentyl-N-(1,5-naphthyridin-2-yl)-1,3,4-thiadiazole-2-amine hydrochloride (3.3 mg).

$^1$H-NMR(DMSO-d$_6$)δ:12.07(1H,brs),8.79-8.76(1H,m), 8.30(1H,d,J=9.0 Hz),8.24(1H,d,8.1 Hz),7.72-7.67(1H,m), 7.49(1H,d,9.3 Hz),3.54-3.38(1H,m),2.22-2.08(2H,m),1.92-1.64(6H,m).

MSm/z(M+H):298.

Example 0044

0044-1

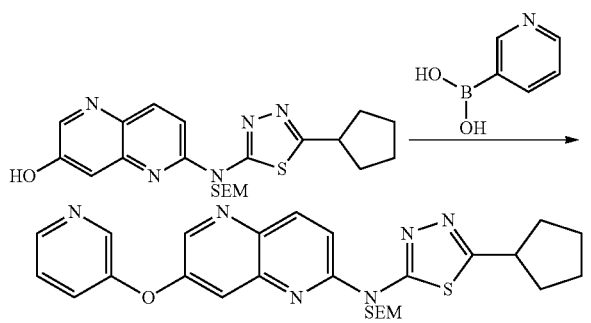

A mixture of 6-((5-cyclopentyl-1,3,4-thiadiazol-2-yl)((2-(trimethylsilyl)ethoxy)methyl)amino)-1,5-naphthyridin-3-ol (20 mg), 3-pyridylboronic acid (8 mg), copper(II) acetate (25 mg), molecular sieve 4A (20 mg) and triethylamine (0.063 mL) in dichloromethane (0.5 mL) was stirred at room temperature for 3 hours, and stirred at 50° C. for 5 days. After the reaction mixture was cooled to room temperature, the insolubles were filtered off using celite, and ethyl acetate and water were added thereto. The organic layer was collected by separation, washed with a saturated sodium chloride aqueous solution, and dried over anhydrous sodium sulfate. The obtained solution was purified by silica gel column chromatography (ethyl acetate-hexane), thereby obtaining 5-cyclopentyl-N-(7-((pyridin-3-yl)oxy)-1,5-naphthyridin-2-yl)-N-((2-(trimethylsilyl)ethoxy)methyl)-1,3,4-thiadiazole-2-amine (3.5 mg).

MSm/z(M+H):521.

0044-2

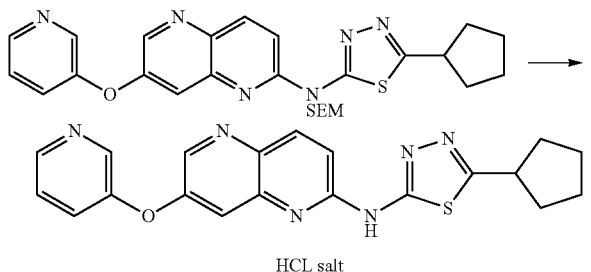

HCL salt 12 mol/L hydrochloric acid (0.4 mL) was added to a solution of 5-cyclopentyl-N-(7-((pyridin-3-yl)oxy)-1,5-naphthyridin-2-yl)-N-((2-(trimethylsilyl)ethoxy)methyl)-1,3,4-thiadiazole-2-amine (3.5 mg) in methanol (1.2 mL), followed by stirring at room temperature for 1.5 hours. The solvent was distilled off under reduced pressure, and diisopropyl ether, water, sodium hydroxide aqueous solution, and dichloromethane were added thereto. The organic layer was collected by separation, and dried over anhydrous sodium sulfate, and the solvent was distilled off under reduced pressure, thereby obtaining 5-cyclopentyl-N-(7-((pyridin-3-yl)oxy)-1,5-naphthyridin-2-yl)-1,3,4-thiadiazole-2-amine hydrochloride (1.68 mg).

$^1$H-NMR(CDCl$_3$)δ:8.69(1H,d,J=2.7 Hz),8.60-8.52(2H, m),8.31(1H,d,J=9.3 Hz),7.65-7.60(2H,m),7.50-7.38(2H,m), 3.58-3.50(1H,m), 2.32-2.18(2H,m),2.00-1.72(6H,m).

MSm/z(M+H):391.

Example 0045

0045-1

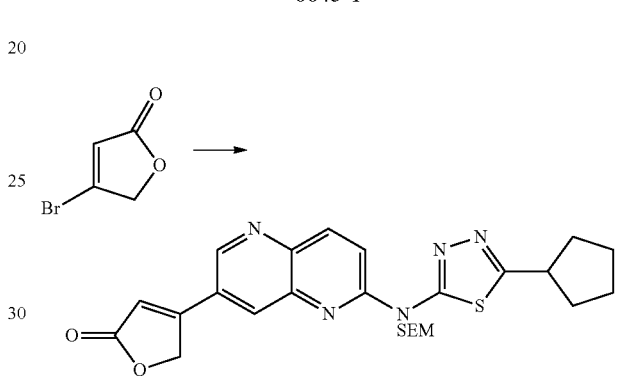

A mixture of N-(7-bromo-1,5-naphthyridin-2-yl)-5-cyclopentyl-N-((2-(trimethylsilyl)ethoxy)methyl)-1,3,4-thiadiazole-2-amine (20 mg), bis(pinacolato)diboron (15 mg), (1,1'-bis(diphenylphosphino)ferrocene)palladium(II) dichloride (3 mg) and potassium acetate (8 mg) in 1,4-dioxane (0.6 mL) was stirred at 120° C. for 50 minutes using a microwave reaction apparatus. 4-Bromofuran-2(5H)-one (13 mg), sodium carbonate (8 mg), and bis(di-tert-butyl(4-dimethylaminophenyl)phosphine)dichloropalladium(II) (7 mg) were added to the reaction mixture, followed by stirring at 120° C. for 30 minutes using a microwave reaction apparatus. After the reaction mixture was cooled to room temperature, the insolubles were filtered off using celite, and ethyl acetate and water were added thereto. The organic layer was collected by separation, washed with a saturated sodium chloride aqueous solution, and dried over anhydrous sodium sulfate. The obtained solution was purified by silica gel column chromatography (ethyl acetate-hexane), thereby obtaining 4-(6-((5-cyclopentyl-1,3,4-thiadiazol-2-yl)((2-(trimethylsilyl)ethoxy)methyl)amino)-1,5-naphthyridin-3-yl)furan-2(5H)-one (20 mg).

MSm/z(M+H):510.

0045-2

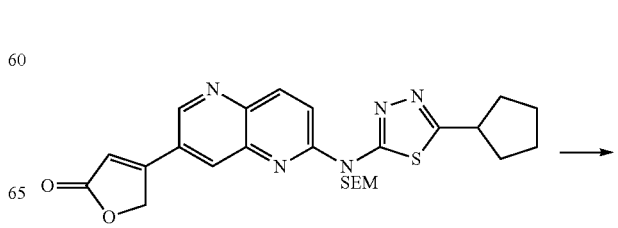

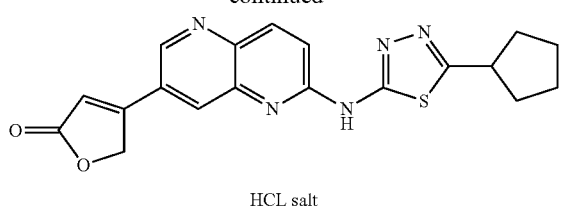

HCL salt

A 4 mol/L hydrogen chloride/1,4-dioxane solution (0.4 mL) was added to a solution of 4-(6-((5-cyclopentyl-1,3,4-thiadiazol-2-yl)((2-(trimethylsilyl)ethoxy)methyl)amino)-1,5-naphthyridin-3-yl)furan-2(5H)-one (20 mg) in 1,4-dioxane (1.2 mL), followed by stirring at room temperature for 6 hours. The solvent was distilled off under reduced pressure, diisopropyl ether was added thereto, and the solid matter was collected by filtration, thereby obtaining 4-(6-((5-cyclopentyl-1,3,4-thiadiazol-2-yl)amino)-1,5-naphthyridin-3-yl)furan-2(5H)-one hydrochloride (8.0 mg).

$^1$H-NMR(DMSO-$d_6$)δ:9.16(1H,d,J=2.7 Hz),8.46(1H,d,J=2.7 Hz),8.36(1H,d,9.3 Hz),7.57(1H,d,J=9.3 Hz),7.14(1H,s),5.61(2H,s),3.54-3.44(1H,m),2.22-2.10(2H,m),1.94-1.66 (6H,m).

MSm/z(M+H):380.

Example 0046

0046-1

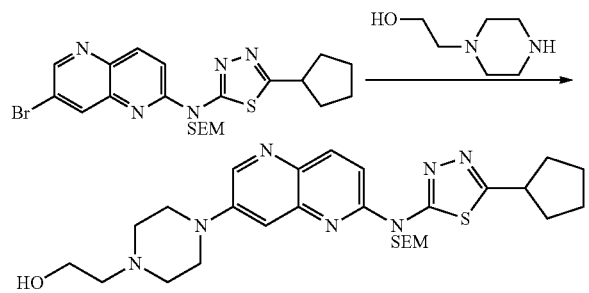

A mixture of N-(7-bromo-1,5-naphthyridin-2-yl)-5-cyclopentyl-N-((2-(trimethylsilyl)ethoxy)methyl)-1,3,4-thiadiazole-2-amine (27 mg), 2-(piperazin-1-yl)ethanol (0.013 mL), tris(dibenzylideneacetone)dipalladium(0) (5 mg), 2-(dicyclohexylphosphino)-2',4',6'-triisopropylbiphenyl (5 mg) and sodium tert-butoxide (20 mg) in 1,4-dioxane (1 mL) was stirred at 100° C. for 7 hours. After the reaction mixture was cooled to room temperature, the insolubles were filtered off using celite, and ethyl acetate and water were added thereto. The organic layer was collected by separation, washed with a saturated sodium chloride aqueous solution, and dried over anhydrous sodium sulfate. The obtained solution was purified by silica gel column chromatography (methanol-ethyl acetate), thereby obtaining 2-(4-(6-((5-cyclopentyl-1,3,4-thiadiazol-2-yl)((2-(trimethylsilyl)ethoxy)methyl)amino)-1,5-naphthyridin-3-yl)piperazin-1-yl)ethanol (10 mg).

MSm/z(M+H):556.

0046-2

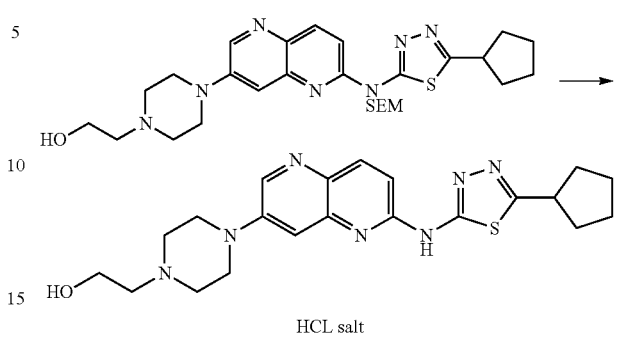

HCL salt 12 mol/L hydrochloric acid (0.4 mL) was added to a solution of 2-(4-(6-((5-cyclopentyl-1,3,4-thiadiazol-2-yl)((2-(trimethylsilyl)ethoxy)methyl)amino)-1,5-naphthyridin-3-yl)piperazin-1-yl)ethanol (10 mg) in methanol (1.2 mL), followed by stirring at room temperature for 3 hours. The solvent was distilled off under reduced pressure, diisopropyl ether and water were added to the obtained residue, and the solvent was distilled off under reduced pressure. Chloroform, methanol, and ethyl acetate were added to the obtained residue. The solid matter was collected by filtration, thereby obtaining 2-(4-(6-((5-cyclopentyl-1,3,4-thiadiazol-2-yl)amino)-1,5-naphthyridin-3-yl)piperazin-1-yl)ethanol hydrochloride (2.4 mg).

$^1$H-NMR(DMSO-$d_6$)δ:8.76(1H,d,J=2.7 Hz),8.16(1H,d,J=8.7 Hz),7.49(1H,d,J=2.7 Hz),7.25(1H,d,J=8.7 Hz),4.23-4.15(2H,m),3.84-3.77(2H,m),3.66-3.52(3H,m),3.36-3.52 (6H,m),2.22-2.10(2H,m),1.94-1.66(6H,m).

MSm/z(M+H):426.

Example 0047

0047-1

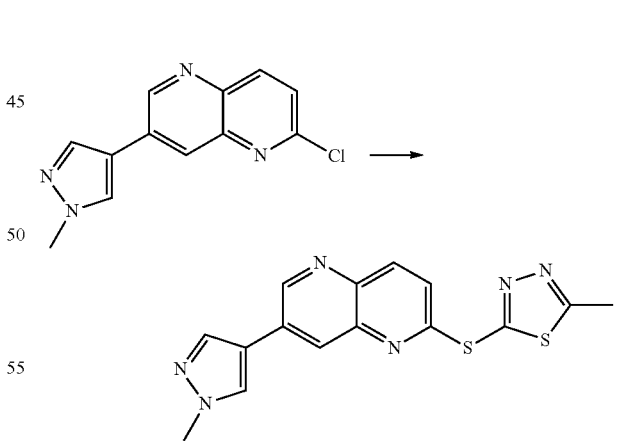

A mixture of 2-chloro-7-(1-methyl-1H-pyrazol-4-yl)-1,5-naphthyridine (10 mg), 5-methyl-1,3,4-thiadiazole-2-thiol (17 mg) and potassium carbonate (23 mg) in dimethylsulfoxide (0.5 mL) was stirred at 50° C. for 4.5 hours, and stirred at 100° C. for 4.5 hours. The reaction mixture was cooled to room temperature, and ethyl acetate and water were added thereto. The organic layer was collected by separation, washed sequentially with water and a saturated sodium chloride aqueous solution, and dried over anhydrous sodium sulfate. The obtained solution was purified by silica gel column chromatography (methanol-ethyl acetate), thereby obtaining 2-methyl-5-((7-(1-methyl-1H-pyrazol-4-yl)-1,5-naphthyridin-2-yl)thio)-1,3,4-thiadiazole (5.9 mg).

$^1$H-NMR(DMSO-d$_6$)δ:9.31(1H,d,J=2.1 Hz),8.57(1H,s),8.52(1H,d,J=2.1 Hz),8.39(1H,d,J=8.4 Hz),8.26(1H,s),7.83(1H,d,J=8.4 Hz),3.93(3H,s),2.83(3H,s)

MSm/z(M+H):341. .

Examples 0048 to 0052

The following compounds were obtained in the same manner as in Examples 0046-1 and 0046-2.

| Example No. | | |
|---|---|---|
| 0048 | | |
| 0048-1 | 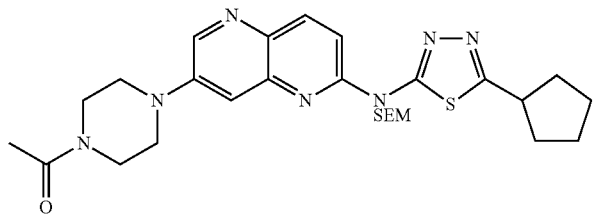 [SMILES: CC(=O)N1CCN(c2cnc3ccc(N(COCC[Si](C)(C)C)c4nnc(C5CCCC5)s4)nc3c2)CC1] | MS m/z (M + H): 554. |
| 0048-2 | 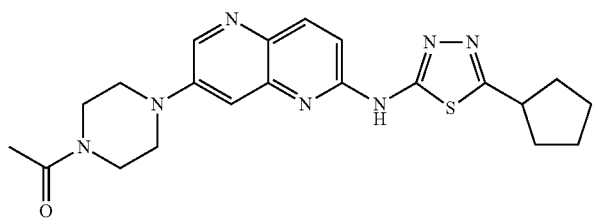 [SMILES: CC(=O)N1CCN(c2cnc3ccc(Nc4nnc(C5CCCC5)s4)nc3c2)CC1]<br>HCL salt | $^1$H-NMR (DMSO-d$_6$) δ:<br>8.78 (1H, d, J = 2.7 Hz), 8.18 (1H, d, J = 9.3 Hz), 7.52 (1H, d, J = 2.7 Hz), 7.26 (1H, d, J = 9.3 Hz), 3.69-3.28 (9H, m), 2.22-2.08 (2H, m), 2.08 (3H, s), 1.93-1.66 (6H. m).<br>MS m/z (M + H): 424. |
| 0049 | | |
| 0049-1 | 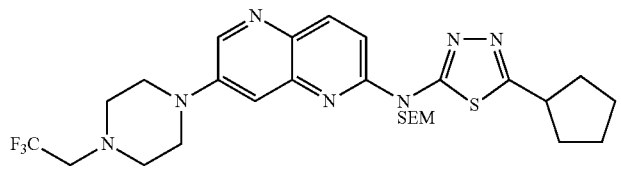 [SMILES: C[Si](C)(C)CCOCN(c1ccc2ncc(N3CCN(CC(F)(F)F)CC3)cc2n1)c1nnc(C2CCCC2)s1] | MS m/z (M + H): 595. |
| 0049-2 | 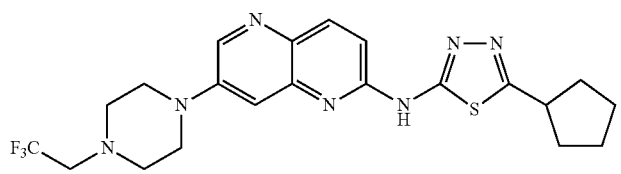 [SMILES: FC(F)(F)CN1CCN(c2cnc3ccc(Nc4nnc(C5CCCC5)s4)nc3c2)CC1]<br>HCL salt | $^1$H-NMR (DMSO-d$_6$) δ:<br>8.75 (1H, d, J = 2.7 Hz), 8.16 (1H, d, J = 9.3 Hz), 7.47 (1H, d, J = 2.7 Hz), 7.24 (1H, d, J = 9.3 Hz), 3.66-3.28 (7H, m), 2.88-2.83 (4H, m), 2.22-2.06 (2H, m), 1.93-1.66 (6H. m).<br>MS m/z (M + H): 464. |
| 0050 | | |
| 0050-1 | 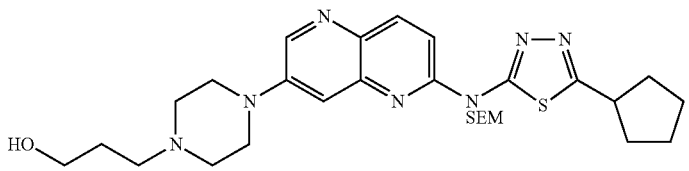 [SMILES: C[Si](C)(C)CCOCN(c1ccc2ncc(N3CCN(CCCO)CC3)cc2n1)c1nnc(C2CCCC2)s1] | MS m/z (M + H): 570. |

| Example No. | | |
|---|---|---|
| 0050-2 | 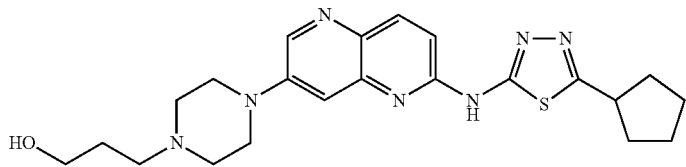 [SMILES: OCCCN1CCN(c2cnc3ccc(Nc4nnc(C5CCCC5)s4)nc3c2)CC1] HCL salt | ¹H-NMR (CD₃OD) δ: 8.64 (1H, d, J = 2.7 Hz), 8.09 (1H, d, J = 9.3 Hz), 7.53 (1H, d, J = 2.7 Hz), 7.16 (1H, d, J = 9.3 Hz), 3.70-3.45 (8H, m), 2.81-2.74 (4H, m), 2.65-2.58 (2H, m), 2.30-2.18 (2H, m), 1.96-1.74 (8H, m). MS m/z (M + H): 440. |
| 0051 | | |
| 0051-1 | 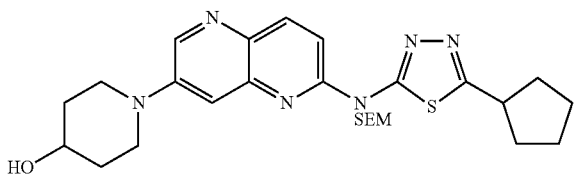 [SMILES: C[Si](C)(C)CCOCN(c1ccc2ncc(N3CCC(O)CC3)cc2n1)c1nnc(C2CCCC2)s1] | MS m/z (M + H): 527. |
| 0051-2 | 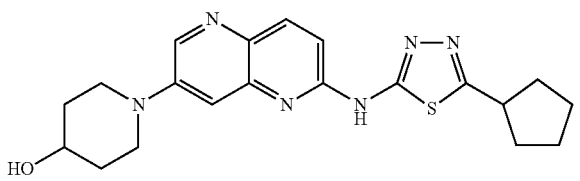 [SMILES: OC1CCN(c2cnc3ccc(Nc4nnc(C5CCCC5)s4)nc3c2)CC1] HCL salt | ¹H-NMR (DMSO-d₆) δ: 11.83 (1H, brs), 8.69 (1H, d, J = 2.7 Hz), 8.09 (1Hd, J = 8.4 Hz), 8.34 (1H, d, J = 2.7 Hz), 7.16 (1H, d, J = 8.4 Hz), 4.77 (1H, d, J = 4.5 Hz), 3.83-3.66 (4H, m), 3.54-3.33 (1H, m), 3.16-3.03 (1H, m), 2.20-2.08 (2H, m), 1.94-1.46 (10H, m). MS m/z (M + H): 397. |
| 0052 | | |
| 0052-1 | 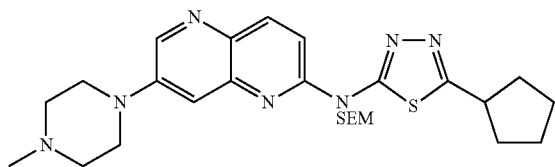 [SMILES: CN1CCN(c2cnc3ccc(N(COCC[Si](C)(C)C)c4nnc(C5CCCC5)s4)nc3c2)CC1] | MS m/z (M + H): 526. |
| 0052-2 | 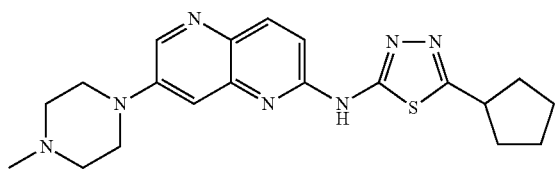 [SMILES: CN1CCN(c2cnc3ccc(Nc4nnc(C5CCCC5)s4)nc3c2)CC1] HCL salt | ¹H-NMR (DMSO-d₆) δ: 10.72 (1H, brs), 8.78 (1H, d, J = 2.7 Hz), 8.19 (1H, d, J = 9.0 Hz), 7.58 (1H, d, J = 2.7 Hz), 7.28 (1H, d, J = 9.0 Hz), 4.25-4.16 (2H, m), 3.66-3.14 (7H, m), 2.86 (3H, s), 2.23-2.08 (2H, m), 1.92-1.64 (6H, m). MS m/z (M + H): 396. |

Example 0053

0053-1

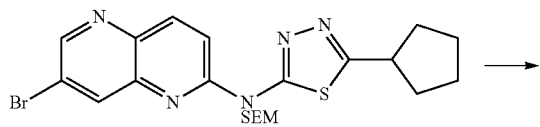 →

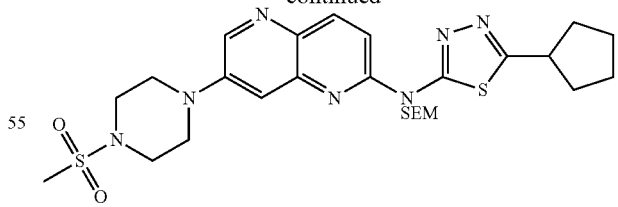

A mixture of N-(7-bromo-1,5-naphthyridin-2-yl)-5-cyclopentyl-N-((2-(trimethylsilyl)ethoxy)methyl)-1,3,4-thiadiazole-2-amine (20 mg), 1-(methylsulfonyl)piperazine (15 mg), tris(dibenzylideneacetone)dipalladium(0) (6 mg), 2-(dicyclohexylphosphino)-2',4',6'-triisopropylbiphenyl (7 mg) and cesium carbonate (32 mg) in 1,4-dioxane (1 mL) was stirred at 100° C. for 19 hours. After the reaction mixture was cooled to room temperature, the insolubles were filtered off using celite, and ethyl acetate and water were added thereto. The organic layer was collected by separation, washed with a saturated sodium chloride aqueous solution, and dried over anhydrous sodium sulfate. The obtained solution was purified by silica gel column chromatography (methanol-ethyl acetate), thereby obtaining 5-cyclopentyl-N-(7-(4-(methylsulfonyl)piperazin-1-yl)-1,5-naphthyridin-2-yl)-N-((2-(trimethylsilyl)ethoxy)methyl)-1,3,4-thiadiazole-2-amine (12 mg).

MSm/z(M+H):590.

0053-2

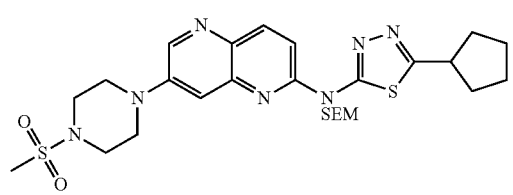

12 mol/L hydrochloric acid (0.4 mL) was added to a solution of 5-cyclopentyl-N-(7-(4-(methylsulfonyl)piperazin-1-yl)-1,5-naphthyridin-2-yl)-N-((2-(trimethylsilyl)ethoxy)methyl)-1,3,4-thiadiazole-2-amine (12 mg) in methanol (1.2 mL), followed by stirring at room temperature for 14 hours. The solvent was distilled off under reduced pressure, diisopropyl ether and methanol were added to the obtained residue, and the solid matter was collected by filtration, thereby obtaining 5-cyclopentyl-N-(7-(4-(methylsulfonyl)piperazin-1-yl)-1,5-naphthyridin-2-yl)-1,3,4-thiadiazole-2-amine hydrochloride (10 mg).

$^1$H-NMR(DMSO-d$_6$)δ:8.76(1H,d,J=2.7 Hz),8.15(1H,d,J=9.3 Hz),7.46(1H,d,J=2.7 Hz),7.23(1H,d,J=9.3 Hz),3.58-3.22(9H,m),2.96(3H,s),2.20-2.08(2H,m),1.94-1.64(6H,m).
MSm/z(M+H):460.

Examples 0054 to 0057

The following compounds were obtained in the same manner as in Examples 0053-1 and 0053-2.

| Example No. | | |
|---|---|---|
| 0054 | | |
| 0054-1 | 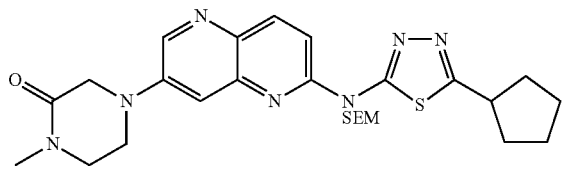 [SMILES: CN1CCN(c2cnc3ccc(N(COCC[Si](C)(C)C)c4nnc(C5CCCC5)s4)nc3c2)CC1=O] | MS m/z (M + H): 540. |
| 0054-2 | 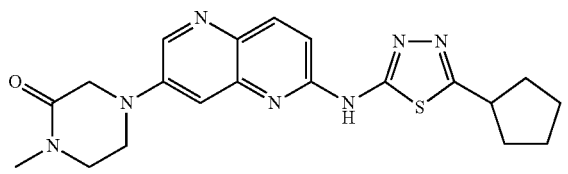 [SMILES: CN1CCN(c2cnc3ccc(Nc4nnc(C5CCCC5)s4)nc3c2)CC1=O]<br>HCL salt | $^1$H-NMR (DMSO-d$_6$) δ:<br>8.76 (1H, d, J = 2.7 Hz), 8.17 (1H, d, J = 8.7 Hz), 7.49 (1H, d, J = 2.7 Hz), 7.24 (1H, d, J = 8.7 Hz), 4.06 (2H, brs),<br>3.81-3.75 (2H, m), 3.57-3.44 (3H, m), 2.94 (3H, s), 2.21-2.08 (2H, m), 1.94-1.64 (6H, m).<br>MS m/z (M + H): 410. |
| 0055 | | |
| 0055-1 | 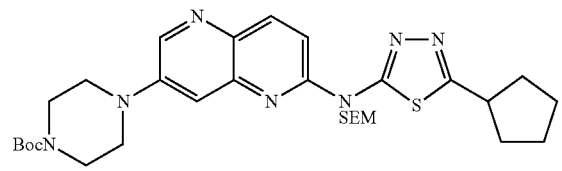 [SMILES: CC(C)(C)OC(=O)N1CCN(c2cnc3ccc(N(COCC[Si](C)(C)C)c4nnc(C5CCCC5)s4)nc3c2)CC1] | MS m/z (M + H): 612. |

| Example No. | | |
|---|---|---|
| 0055-2 | 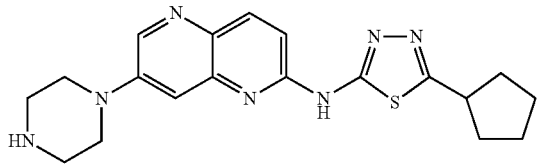 [SMILES: c1nc2ccc(Nc3nnc(C4CCCC4)s3)nc2cc1N1CCNCC1] HCL salt | ¹H-NMR (DMSO-d₆) δ: 9.02 (1H, brs), 8.76 (1H, d, J = 2.7 Hz), 8.17 (1H, d, J = 8.4 Hz), 7.51 (1H, d, J = 2.7 Hz), 7.26 (1H, d, J = 8.4 Hz), 3.68-3.26 (9H, m), 2.21-2.08 (2H, m), 1.94-1.64 (6H, m). MS m/z (M + H): 381. |
| 0056 | | |
| 0056-1 | 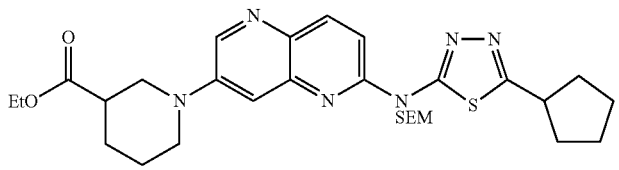 [SMILES: CCOC(=O)C1CCCN(c2cnc3ccc(N(COCC[Si](C)(C)C)c4nnc(C5CCCC5)s4)nc3c2)C1] | MS m/z (M + H): 583. |
| 0056-2 | 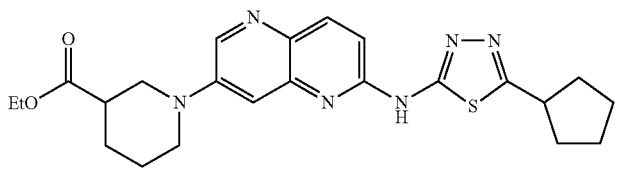 [SMILES: CCOC(=O)C1CCCN(c2cnc3ccc(Nc4nnc(C5CCCC5)s4)nc3c2)C1] HCL salt | ¹H-NMR (DMSO-d₆) δ: 8.76 (1H, d, J = 2.7 Hz), 8.17 (1H, d, J = 9.0 Hz), 7.52 (1H, d, J = 2.7 Hz), 7.25 (1H, d, J = 9.0 Hz), 4.10 (2H, q, J = 7.5 Hz), 3.95-3.20 (6H, m), 2.30-1.58 (10H, m), 2.08 (3H, s), 1./21 (3H, t, J = 7.5 Hz). MS m/z (M + H): 453. |
| 0057 | | |
| 0057-1 | 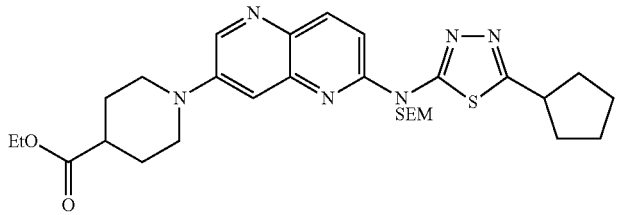 [SMILES: CCOC(=O)C1CCN(c2cnc3ccc(N(COCC[Si](C)(C)C)c4nnc(C5CCCC5)s4)nc3c2)CC1] | MS m/z (M + H): 583. |
| 0057-2 | 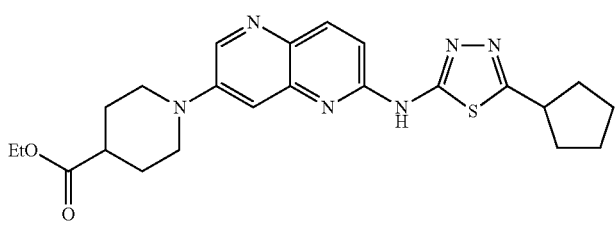 [SMILES: CCOC(=O)C1CCN(c2cnc3ccc(Nc4nnc(C5CCCC5)s4)nc3c2)CC1] HCL salt | ¹H-NMR (DMSO-d₆) δ: 8.79 (1H, d, J = 2.7 Hz), 8.19 (1H, d, J = 8.4 Hz), 7.57 (1H, d, J = 2.7 Hz), 7.26 (1H, d, J = 8.4 Hz), 4.10 (2H, q, J = 7.5 Hz), 4.02-3.94 (2H, m), 3.64-3.50 (1H, m), 3.12-3.00 (2H, m), 2.22-1.64 (13H, m), 1.21 (3H, t, J = 7.5 Hz). MS m/z (M + H): 453. |

Example 0058

0058-1

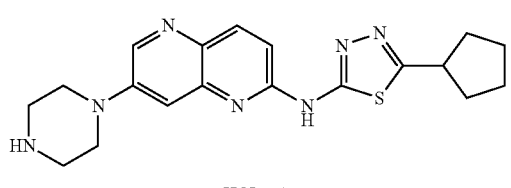

HCL salt

-continued

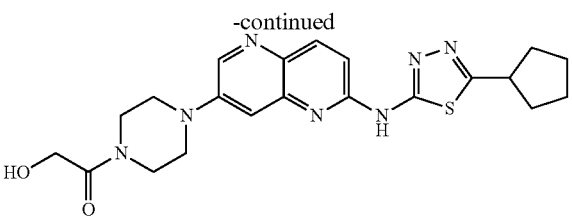

After a solution of 2-hydroxyacetic acid (6 mg), 1-ethyl-3-(3-dimethylaminopropyl)carbodiimide hydrochloride (15 mg), and 1-hydroxy-1H-benzotriazolemonohydrate (11 mg) in N,N-dimethylformamide (0.5 mL) was stirred at room temperature for 15 minutes, 5-cyclopentyl-N-(7-(piperazin- 1-yl)-1,5-naphthyridin-2-yl)-1,3,4-thiadiazole-2-amine (10 mg) and triethylamine (0.037 mL) were added thereto, followed by stirring at room temperature for 2 days. Water was added to the reaction mixture, the solid matter was collected by filtration, thereby obtaining 1-(4-(6-((5-cyclopentyl-1,3,4-thiadiazol-2-yl)amino)-1,5-naphthyridin-3-yl)piperazin-1-yl)-2-hydroxyethanone (5.7 mg).

¹H-NMR(CD₃OD)δ:8.66(1H,d,2.7 Hz),8.10(1H,d,J=9.3 Hz),7.55(1H,d,2.7 Hz),7.18(1H,d,J=9.3 Hz),4.60(2H,brs), 3.87-3.81(2H,m),3.70-3.64(2H,m),3.54-3.44(5H,m),2.32-2.18(2H,m),1.98-1.74(6H,m).

MSm/z(M+H):440.

Example 0059

0059-1

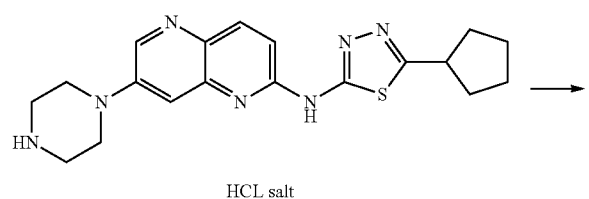

HCL salt

↓


After a solution of 2-dimethylaminoacetic acid (8 mg), 1-ethyl-3-(3-dimethylaminopropyl)carbodiimide hydrochloride (15 mg), and 1-hydroxy-1H-benzotriazolemonohydrate (11 mg) in N,N-dimethylformamide (0.5 mL) was stirred at room temperature for 15 minutes, 5-cyclopentyl-N-(7-(piperazin-1-yl)-1,5-naphthyridin-2-yl)-1,3,4-thiadiazole-2-amine (10 mg) and triethylamine (0.037 mL) were added thereto, followed by stirring at room temperature for 2 days. Water was added to the reaction mixture, the solid matter was collected by filtration, thereby obtaining 1-(4-(6-((5-cyclopentyl-1,3,4-thiadiazol-2-yl)amino)-1,5-naphthyridin-3-yl)piperazin-1-yl)-2-(dimethylamino)ethanone (3.7 mg).

¹H-NMR(CD₃OD)δ:8.65(1H,brs),8.09(1H,d,J=8.7 Hz), 7.53(1H,brs),7.16(1H,d,J=8.7 Hz),4.06(2H,s),3.86-3.78(4H,m),3.56-3.42(5H,m),2.35(6H,s),2.31-2.18(2H,m),1.98-1.72 (6H,m).

MSm/z(M+H):467.

Examples 0060 to 0063

The following compounds were obtained in the same manner as in Examples 0053-1 and 0053-2.

| Example No. | | |
|---|---|---|
| 0060 | | |
| 0060-1 | 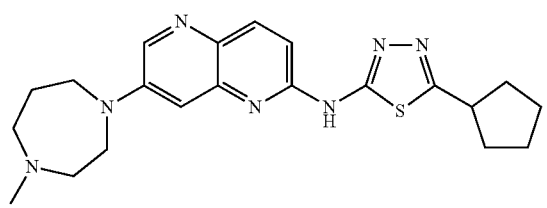 | MS m/z (M + H): 540. |
| 0060-2 | 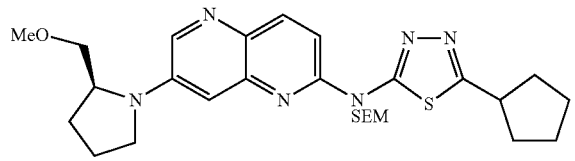 [SMILES: COC[C@@H]1CCCN1c1cnc2ccc(N(COCC[Si](C)(C)C)c3nnc(C4CCCC4)s3)nc2c1] HCL salt | ¹H-NMR (CD₃OD) δ: 8.48 (1H, d, J = 2.7 Hz), 8.04 (1H, d, J = 8.7 Hz), 7.30 (1H, d, J = 2.7 Hz), 7.06 (1H, d, J = 8.7 Hz), 3.81-3.75 (2H, m), 3.73-3.64 (2H, m), 3.57-3.44 (1H, m), 2.89-2.83 (2H, m), 2.71-2.65 (2H, m), 2.41 (3H, s), 2.29-1.76 (10H, m). MS m/z (M + H): 410. |
| 0061 | | |
| 0061-1 | [structure with MeO-, SEM] | MS m/z (M + H): 541. |

| Example No. | | |
|---|---|---|
| 0061-2 | 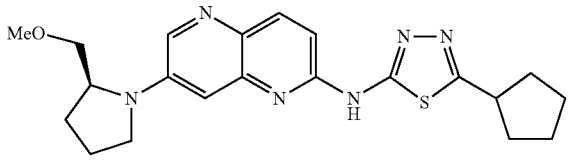 [SMILES: COC[C@@H]1CCCN1c1cnc2ccc(Nc3nnc(C4CCCC4)s3)nc2c1] | $^1$H-NMR (CD$_3$OD) δ: 8.53 (1H, d, J = 2.7 Hz), 8.17 (1H, d, J = 9.3 Hz), 7.26 (1H, d, J = 2.7 Hz), 7.19 (1H, d, J = 9.3 Hz), 4.31-4.23 (1H, m), 3.30 (3H, s), 2.21-1.64 (17H, m). MS m/z (M + H): 411. |
| 0062 | | |
| 0062-1 | 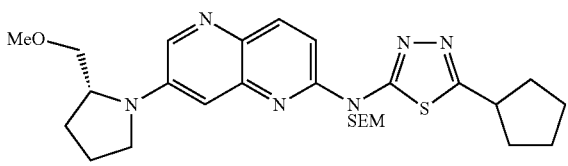 [SMILES: COC[C@H]1CCCN1c1cnc2ccc(N(COCC[Si](C)(C)C)c3nnc(C4CCCC4)s3)nc2c1] | MS m/z (M + H): 411. |
| 0062-2 | 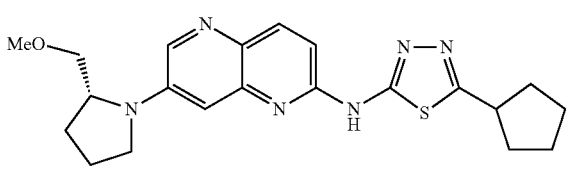 [SMILES: COC[C@H]1CCCN1c1cnc2ccc(Nc3nnc(C4CCCC4)s3)nc2c1] HCL salt | $^1$H-NMR (CD$_3$OD) δ: 8.53 (1H, d, J = 2.7 Hz), 8.17 (1H, d, J = 9.3 Hz), 7.26 (1H, d, J = 2.7 Hz), 7.19 (1H, d, J = 9.3 Hz), 4.31-4.23 (1H, m), 3.30 (3H, s), 2.21-1.64 (17H, m). MS m/z (M + H): 411. |
| 0063 | | |
| 0063-1 | 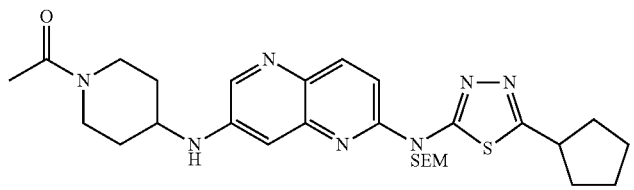 [SMILES: CC(=O)N1CCC(Nc2cnc3ccc(N(COCC[Si](C)(C)C)c4nnc(C5CCCC5)s4)nc3c2)CC1] | MS m/z (M + H): 568. |
| 0063-2 | 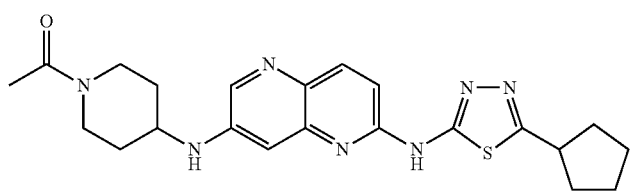 [SMILES: CC(=O)N1CCC(Nc2cnc3ccc(Nc4nnc(C5CCCC5)s4)nc3c2)CC1] HCL salt | $^1$H-NMR (DMSO-d$_6$) δ: 8.37 (1H, d, J = 2.7 Hz), 8.07 (1H, d, J = 8.4 Hz), 7.17 (1H, d, J = 2.7 Hz), 7.11 (1H, d, J = 8.4 Hz), 4.28-4.17 (2H, m), 3.86-3.74 (4H, m), 2.99-2.87 (2H, m), 2.22-1.64 (10H, m), 2.03 (3H, s). MS m/z (M + H): 438. |

Example 0064

0064-1

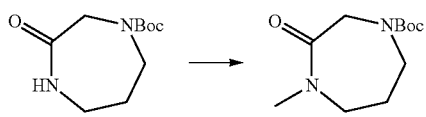

Iodomethane (0.078 mL) and 60% sodium hydride (50 mg) were added sequentially to a mixture solution of tert-butyl 3-oxo-1,4-diazepane-1-carboxylate (180 mg) in tetrahydrofuran (2 mL) and acetonitrile (2 mL) at room temperature, followed by stirring for 5 hours. Ethyl acetate and water were added sequentially to the reaction mixture. The organic layer was collected by separation, washed with a saturated sodium chloride aqueous solution, and dried over anhydrous sodium sulfate, and the solvent was distilled off under reduced pressure, thereby obtaining tert-butyl 4-methyl-3-oxo-1,4-diazepane-1-carboxylate (225 mg).

$^1$H-NMR(CDCl$_3$)δ:3.62-3.53(4H,m),3.41(2H,t,J=4.8 Hz),3.01(3H,s),2.65(2H,t,J=5.4 Hz),1.47(9H,s).

0064-2

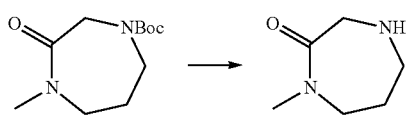

Water (0.4 mL) and trifluoroacetic acid (4 mL) were added sequentially to a solution of tert-butyl 4-methyl-3-oxo-1,4-diazepane-1-carboxylate (225 mg) in dichloromethane (4 mL) at room temperature, followed by stirring for 21 hours. The solvent was distilled off under reduced pressure, and the obtained residue was purified by silica gel column chromatography (methanol-ethyl acetate-hexane, NH silica), thereby obtaining 1-methyl-1,4-diazepan-2-one (85 mg).

$^1$H-NMR(CDCl$_3$)δ:3.45-3.40(2H,m),3.00(3H,s),2.97-2.92(4H,m),2.69-2.64(2H,m).

0064-3

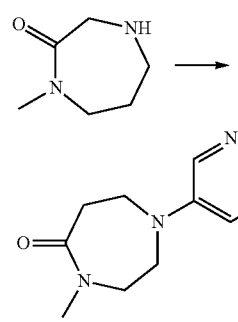

1-(6-((5-cyclopentyl-1,3,4-thiadiazol-2-yl)((2-(trimethylsilyl)ethoxy)methyl)amino)-1,5-naphthyridin-3-yl)-4-methyl-1,4-diazepan-5-one was obtained in the same manner as in Example 0053-1.
MSm/z(M+H):554.

0064-4

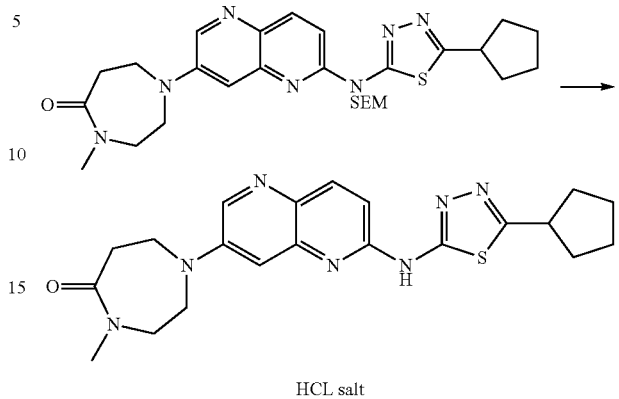

HCL salt 1-(6-((5-cyclopentyl-1,3,4-thiadiazol-2-yl)amino)-1,5-naphthyridin-3-yl)-4-methyl-1,4-diazepan-5-one hydrochloride was obtained in the same manner as in Example 0053-2.
$^1$H-NMR(DMSO-d$_6$)δ:8.71(1H,2.4 Hz),8.15(1H,d,J=9.3 Hz),7.43(1H,d,J=2.4 Hz),7.20(1H,d,J=9.3 Hz),3.76-3.42 (7H,m),2.80-2.71(2H,m),2.22-2.08(2H,m),2.89(3H,s),1.94-1.64(6H,m).
MSm/z(M+H):424.

Examples 0065 to 0081

The following compounds were obtained in the same manner as in Examples 0046-1 snd 0046-2.

| Example No. | | |
|---|---|---|
| 0065 | | |
| 0065-1 | 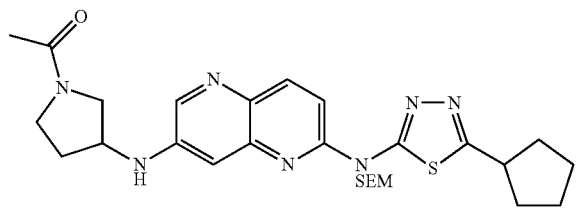 [SMILES: CC(=O)N1CCC(Nc2cnc3ccc(N(COCC[Si](C)(C)C)c4nnc(C5CCCC5)s4)nc3c2)C1] | MS m/z (M + H): 554. |
| 0065-2 | 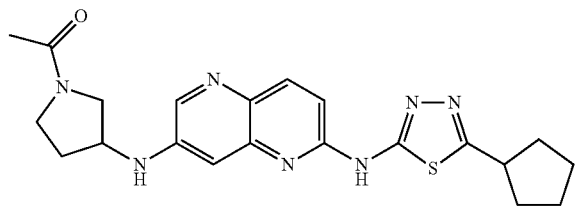 [SMILES: CC(=O)N1CCC(Nc2cnc3ccc(Nc4nnc(C5CCCC5)s4)nc3c2)C1] HCL salt | $^1$H-NMR (DMSO-d$_6$) δ: 8.38-8.33 (1H, m), 8.08 (1H, d, J = 9.3 Hz), 7.15-7.11 (1H, m), 7.13 (1H, d, J = 9.3 Hz), 3.68-3.42 (6H, m), 2.22-2.08 (2H, m), 1.97 (3H, s), 1.92-1.64 (8H, m). MS m/z (M + H): 424. |
| 0066 | | |
| 0066-1 | 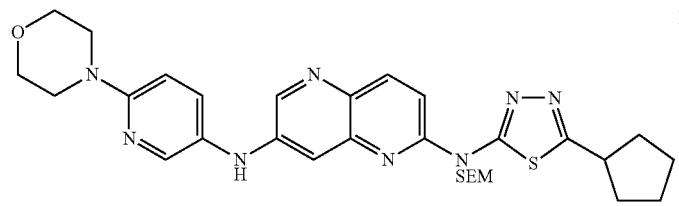 [SMILES: C[Si](C)(C)CCOCN(c1ccc2ncc(Nc3ccc(N4CCOCC4)nc3)cc2n1)c1nnc(C2CCCC2)s1] | MS m/z (M + H): 605. |

-continued
| Example No. | | |
|---|---|---|
| 0066-2 | 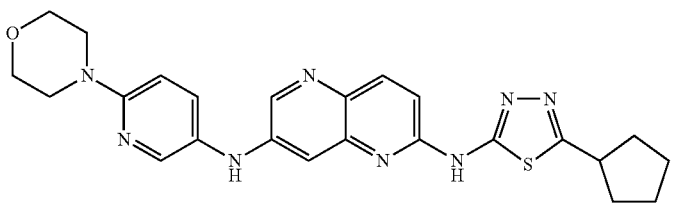 [SMILES: c1cc(N2CCOCC2)ncc1Nc1cnc2ccc(Nc3nnc(C4CCCC4)s3)nc2c1]      HCL salt | ¹H-NMR (DMSO-d₆) δ: 8.97 (1H, brs), 8.52 (1H, d, J = 2.7 Hz), 8.16 (1H, d, J = 9.3 Hz), 8.07 (1H, d, J = 2.7 Hz), 7.90 (1H, dd, J = 9.9, 2.7 Hz), 7.41 (1H, d, J = 2.7 Hz), 7.28 (1H, d, J = 9.9 Hz), 7.22 (1H, d, J = 9.3 Hz), 3.80-3.68 (7H, m), 2.18-2.04 (2H, m), 1.88-1.62 (8H, m). MS m/z (M + H): 475. |
| 0067 | | |
| 0067-1 | 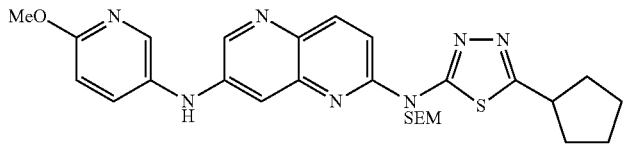 [SMILES: COc1ccc(Nc2cnc3ccc(N(COCC[Si](C)(C)C)c4nnc(C5CCCC5)s4)nc3c2)cn1] | MS m/z (M + H): 550. |
| 0067-2 | 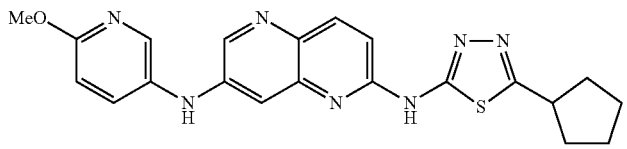 [SMILES: COc1ccc(Nc2cnc3ccc(Nc4nnc(C5CCCC5)s4)nc3c2)cn1]      HCL salt | ¹H-NMR (DMSO-d₆) δ: 8.75 (1H, brs), 8.49 (1H, d, 2.4 Hz), 8.16 (1H, d, J = 2.7 Hz), 8.11 (1H, d, J = 8.4 Hz), 7.73 (1H, dd, J = 8.7, 2.7 Hz), 7.32 (1H, d, 2.4 Hz), 7.17 (1H, d, J = 8.7 Hz), 6.93 (1H, d, J = 8.4 Hz), 3.87 (3H, s), 3.54-3.42 (1H, m), 2.16-2.04 (2H, m), 1.88-1.60 (6H, m). MS m/z (M + H): 420. |
| 0068 | | |
| 0068-1 | 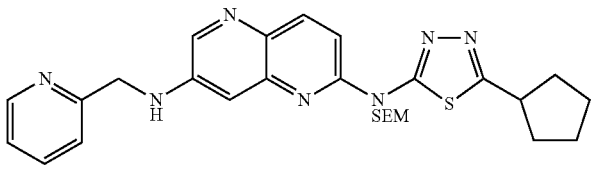 [SMILES: C[Si](C)(C)CCOCN(c1ccc2ncc(NCc3ccccn3)cc2n1)c1nnc(C2CCCC2)s1] | MS m/z (M + H): 534. |
| 0068-2 | 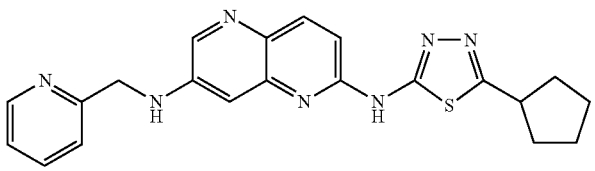 [SMILES: c1ccc(CNc2cnc3ccc(Nc4nnc(C5CCCC5)s4)nc3c2)nc1]      HCL salt | ¹H-NMR (DMSO-d₆) δ: 8.67-8.63 (1H, m), 8.45 (1H, d, J = 2.4 Hz), 8.05 (1H, d, J = 8.7 Hz), 7.99-7.93 (1H, m), 7.63-7.38 (2H, m), 7.08 (1H, d, J = 8.7 Hz), 7.02 (1H, d, J = 2.4 Hz), 3.54-3.42 (3H, m), 2.20-2.06 (2H, m), 1.88-1.62 (6H, m). MS m/z (M + H): 404. |
| 0069 | | |
| 0069-1 | 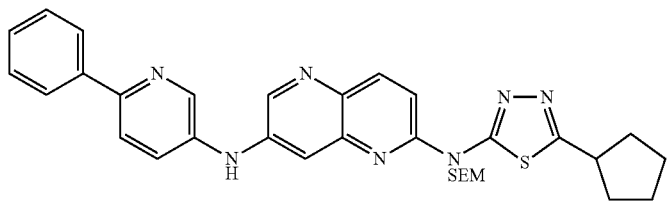 [SMILES: C[Si](C)(C)CCOCN(c1ccc2ncc(Nc3ccc(-c4ccccc4)nc3)cc2n1)c1nnc(C2CCCC2)s1] | MS m/z (M + H): 596. |

-continued
| Example No. | | |
|---|---|---|
| 0069-2 | 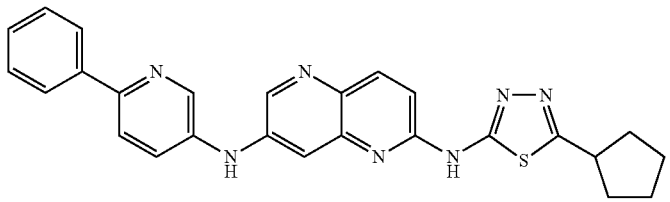 [SMILES: c1ccc(-c2ccc(Nc3cnc4ccc(Nc5nnc(C6CCCC6)s5)nc4c3)cn2)cc1] HCL salt | ¹H-NMR (DMSO-d₆) δ: 13.85 (1H, brs), 11.72 (1H, brs), 9.90 (1H, brs), 9.69 (1H, brs), 8.71-8.61 (2H, m), 8.35-8.17 (3H, m), 8.10-8.00 (2H, m), 7.58-7.42 (3H, m), 4.31-4.23 (1H, m), 1.92-1.58 (8H, m). MS m/z (M + H): 466. |
| 0070 | | |
| 0070-1 | 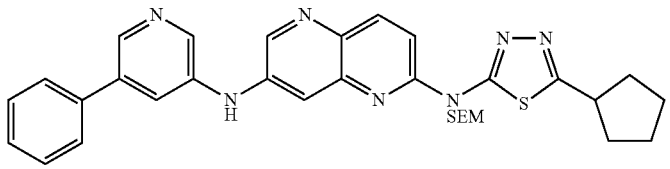 [SMILES: C[Si](C)(C)CCOCN(c1ccc2ncc(Nc3cncc(-c4ccccc4)c3)cc2n1)c1nnc(C2CCCC2)s1] | MS m/z (M + H): 596. |
| 0070-2 | 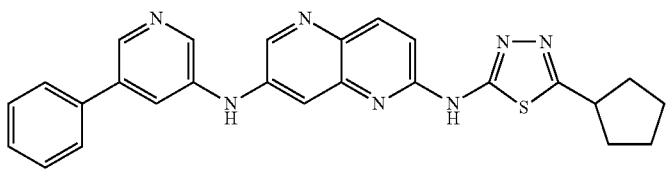 [SMILES: c1ccc(-c2cncc(Nc3cnc4ccc(Nc5nnc(C6CCCC6)s5)nc4c3)c2)cc1] HCL salt | ¹H-NMR (DMSO-d₆) δ: 9.60 (1H, brs), 8.72-8.62 (3H, m), 8.21 (1H, d, J = 9.0 Hz), 7.92-7.78 (3H, m), 7.60-7.46 (4H, m), 7.29 (1H, d, J = 9.0 Hz), 4.31-4.23 (1H, m), 1.92-1.58 (8H, m). MS m/z (M + H): 466. |
| 0071 | | |
| 0071-1 | 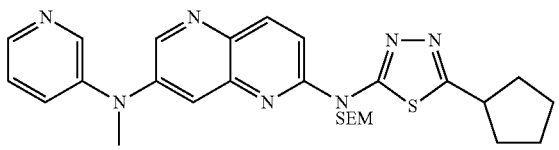 [SMILES: CN(c1cccnc1)c1cnc2ccc(N(COCC[Si](C)(C)C)c3nnc(C4CCCC4)s3)nc2c1] | MS m/z (M + H): 534. |
| 0071-2 | 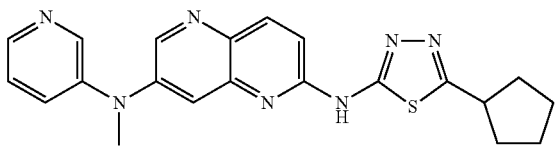 [SMILES: CN(c1cccnc1)c1cnc2ccc(Nc3nnc(C4CCCC4)s3)nc2c1] | ¹H-NMR (CDCl₃) δ: 8.60-8.42 (3H, m), 8.26-8.16 (2H, m), 7.64-7.50 (2H, m), 7.40-7.32 (1H, m), 3.56-3.48 (1H, m), 3.54 (3H, s), 2.30-2.18 (2H, m), 2.04-1.66 (6H, m). MS m/z (M + H): 404. |
| 0072 | | |
| 0072-1 | 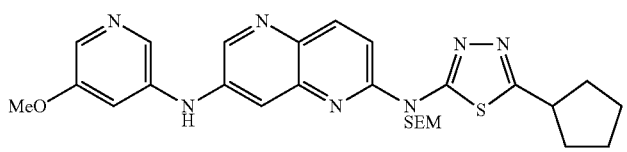 [SMILES: COc1cncc(Nc2cnc3ccc(N(COCC[Si](C)(C)C)c4nnc(C5CCCC5)s4)nc3c2)c1] | MS m/z (M + H): 550. |
| 0072-2 | 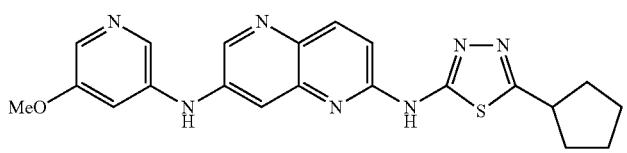 [SMILES: COc1cncc(Nc2cnc3ccc(Nc4nnc(C5CCCC5)s4)nc3c2)c1] | ¹H-NMR (CDCl₃/CD₃OD = 4/1) δ: 8.50 (1H, brs), 8.14 (1H, brs), 8.11 (1H, d, J = 9.3 Hz), 7.93 (1H, brs), 7.86 (1H, brs), 7.40 (1H, brs), 7.18 (1H, d, J = 9.3 Hz), 3.91 (3H, s), 3.55-3.46 (1H, m), 2.32-2.18 (2H, m), 1.94-1.72 (6H, m). MS m/z (M + H): 420. |

-continued
| Example No. | | |
|---|---|---|
| 0073 | | |
| 0073-1 | 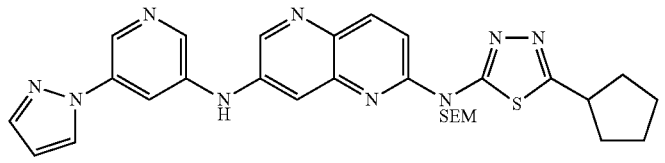 [SMILES: C[Si](C)(C)CCOCN(c1ccc2ncc(Nc3cncc(-n4cccn4)c3)cc2n1)c1nnc(C2CCCC2)s1] | MS m/z (M + H): 586. |
| 0073-2 | 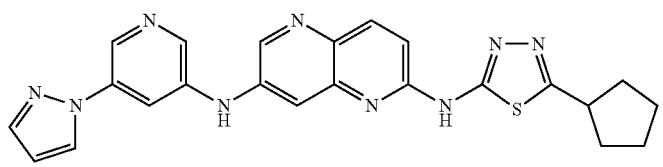 [SMILES: c1cnn(-c2cncc(Nc3cnc4ccc(Nc5nnc(C6CCCC6)s5)nc4c3)c2)c1] | ¹H-NMR (DMSO-d₆) δ: 11.96 (1H, brs), 9.33 (1H, brs), 8.73 (1H, d, 1.8 Hz), 8.65 (1H, s), 8.64 (1H, s), 8.45 (1H, d, J = 2.1 Hz), 8.18 (1H, d, J = 9.0 Hz), 8.17 (1H, d, J = 2.1 Hz), 7.81 (1H, d, J = 1.8 Hz), 7.78 (1H, d, J = 2.7 Hz), 7.26 (1H, 9.0 Hz), 6.63-6.60 (1H, m), 3.50-3.33 (1H, m), 2.16-2.04 (2H, m), 1.84-1.62 (6H, m). MS m/z (M + H): 456. |
| 0074 | | |
| 0074-1 | 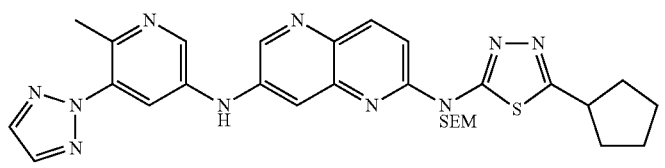 [SMILES: Cc1ncc(Nc2cnc3ccc(N(COCC[Si](C)(C)C)c4nnc(C5CCCC5)s4)nc3c2)cc1-n1nccn1] | MS m/z (M + H): 601. |
| 0074-2 |  | ¹H-NMR (DMSO-d₆) δ: 11.94 (brs, 1H), 9.26 (1H, brs), 8.61 (1H, d, J = 2.7 Hz), 8.57 (1H, d, J = 2.7 Hz), 8.18 (2H, s), 8.16 (1H, d, J = 9.3 Hz), 7.95 (1H, d, J = 2.4 Hz), 7.71 (1H, d, J = 2.4 Hz), 7.24 (1H, d, J = 9.3 Hz), 3.50-3.33 (1H, m), 2.33 (3H, s), 2.16-2.04 (2H, m), 1.84-1.62 (6H, m). MS m/z (M + H): 471. |
| 0075 | | |
| 0075-1 | 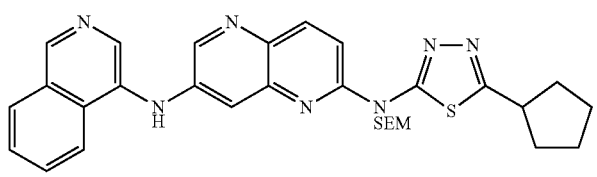 [SMILES: C[Si](C)(C)CCOCN(c1ccc2ncc(Nc3cncc4ccccc34)cc2n1)c1nnc(C2CCCC2)s1] | MS m/z (M + H): 570. |
| 0075-2 | 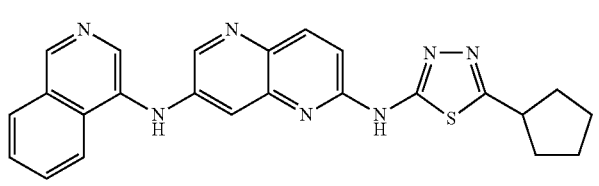 [SMILES: c1ccc2c(Nc3cnc4ccc(Nc5nnc(C6CCCC6)s5)nc4c3)cncc2c1] | ¹H-NMR (DMSO-d₆) δ: 11.88 (1H, brs), 9.15 (1H, s), 9.00 (1H, brs), 8.68 (1H, d, 1.8 Hz), 8.61 (1H, s), 8.24-8.12 (3H, m), 7.88-7.74 (2H, m), 7.38 (1H, d, J = 2.7 Hz), 7.20 (1H, d, J = 9.3 Hz), 3.50-3.33 (1H, m), 2.16-2.04 (2H, m), 1.84-1.62 (6H, m). MS m/z (M + H): 440. |
| 0076 | | |
| 0076-1 | 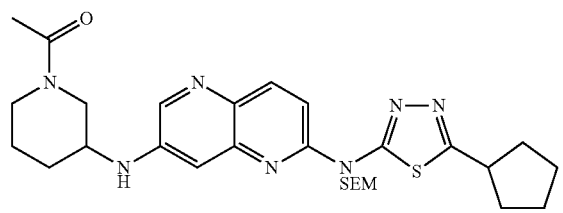 [SMILES: CC(=O)N1CCCC(Nc2cnc3ccc(N(COCC[Si](C)(C)C)c4nnc(C5CCCC5)s4)nc3c2)C1] | MS m/z (M + H): 568. |

| Example No. | | |
|---|---|---|
| 0076-2 | 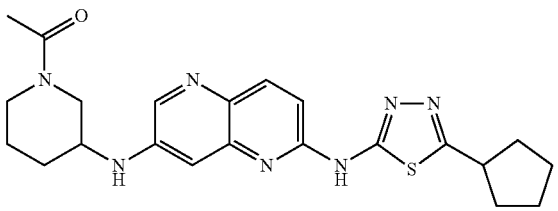 [SMILES: CC(=O)N1CCCC(Nc2cnc3ccc(Nc4nnc(C5CCCC5)s4)nc3c2)C1]
HCL salt | ¹H-NMR (DMSO-d₆) δ:
8.38 (1H, dd, J = 12 Hz, 2.7 Hz), 8.07 (1H, d, J = 8.7 Hz), 7.25 (1H, ddd, J = 12 Hz, 2.7 Hz, 2.1 Hz), 7.11 (1H, dd, J = 8.7 Hz, 2.1 Hz), 3.96-3.44 (6H, m), 2.16-2.04 (2H, m), 2.08 (3H, s), 1.84-1.62 (10H, m).
MS m/z (M + H): 438. |
| 0077 | | |
| 0077-1 | 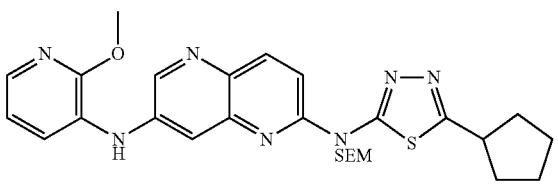 [SMILES: COc1ncccc1Nc1cnc2ccc(N(COCC[Si](C)(C)C)c3nnc(C4CCCC4)s3)nc2c1] | MS m/z (M + H): 550. |
| 0077-2 | 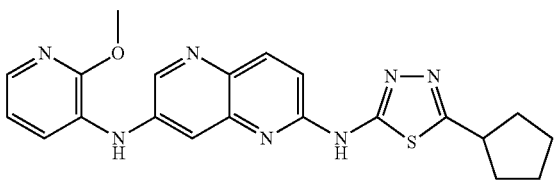 [SMILES: COc1ncccc1Nc1cnc2ccc(Nc3nnc(C4CCCC4)s3)nc2c1] | ¹H-NMR (DMSO-d₆) δ:
11.88 (1H, brs), 8.62 (1H, d, J = 2.4 Hz), 8.43 (1H, brs), 8.12 (1H, d, J = 8.7 Hz), 7.90-7.87 (1H, m), 7.76-7.72 (1H, m), 7.45 (1H, d, J = 2.7 Hz), 7.20 (1H, d, J = 9.3 Hz), 7.06-7.00 (1H, m), 3.95 (3H, s), 3.50-3.33 (1H, m), 2.16-2.04 (2H, m), 1.84-1.62 (6H, m).
MS m/z (M + H): 420. |
| 0078 | | |
| 0078-1 | 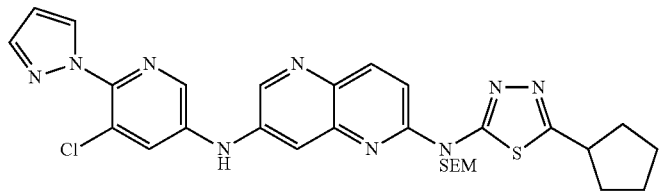 [SMILES: C[Si](C)(C)CCOCN(c1ccc2ncc(Nc3cnc(-n4cccn4)c(Cl)c3)cc2n1)c1nnc(C2CCCC2)s1] | MS m/z (M + H): 620. |
| 0078-2 | 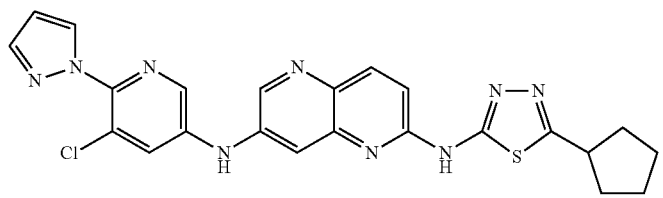 [SMILES: Clc1cc(Nc2cnc3ccc(Nc4nnc(C5CCCC5)s4)nc3c2)cnc1-n1cccn1] | ¹H-NMR ((CD₃)₂CO) δ:
8.72 (1H, d, J = 2.1 Hz), 8.64 (1H, brs), 8.47 (1H, d, 2.4 Hz), 8.22 (1H, d, J = 9.3 Hz), 8.12 (1H, d, J = 2.4 Hz), 8.03-7.95 (1H, m), 7.74 (1H, brs), 7.44 (1H, d, J = 9.3 Hz), 6.53-6.50 (1H, m), 3.50-3.33 (1H, m), 2.16-2.04 (2H, m), 1.84-1.62 (6H, m).
MS m/z (M + H): 490. |
| 0079 | | |
| 0079-1 | 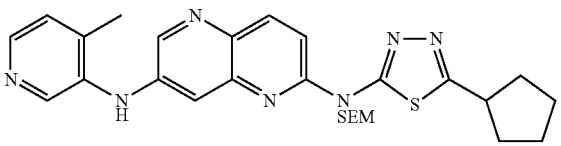 [SMILES: Cc1ccncc1Nc1cnc2ccc(N(COCC[Si](C)(C)C)c3nnc(C4CCCC4)s3)nc2c1] | MS m/z (M + H): 534. |
| 0079-2 | 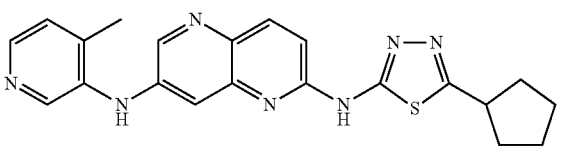 [SMILES: Cc1ccncc1Nc1cnc2ccc(Nc3nnc(C4CCCC4)s3)nc2c1] | ¹H-NMR (CDCl₃) δ:
8.56 (1H, brs), 8.47 (1H, d, J = 2.7 Hz), 8.31-8.27 (1H, m), 8.09 (1H, d, J = 9.3 Hz), 7.38-7.32 (2H, m), 7.10 (1H, d, J = 9.3 Hz), 3.71-3.62 (1H, m), 2.35 (3H, s), 1.92-1.68 (8H, m).
MS m/z (M + H): 404. |

| Example No. | | |
|---|---|---|
| 0080 | | |
| 0080-1 | 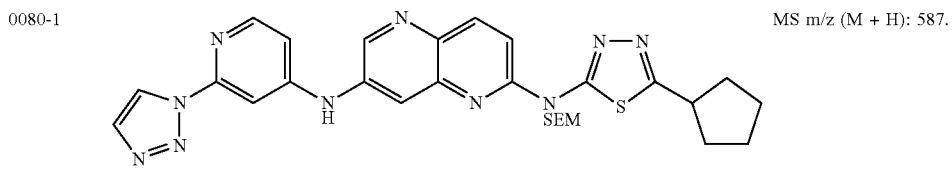 | MS m/z (M + H): 587. |
| 0080-2 | 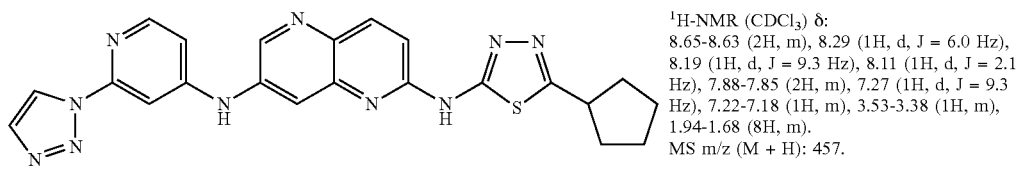 | $^1$H-NMR (CDCl$_3$) δ:<br>8.65-8.63 (2H, m), 8.29 (1H, d, J = 6.0 Hz),<br>8.19 (1H, d, J = 9.3 Hz), 8.11 (1H, d, J = 2.1 Hz), 7.88-7.85 (2H, m), 7.27 (1H, d, J = 9.3 Hz), 7.22-7.18 (1H, m), 3.53-3.38 (1H, m), 1.94-1.68 (8H, m).<br>MS m/z (M + H): 457. |
| 0081 | | |
| 0081-1 | 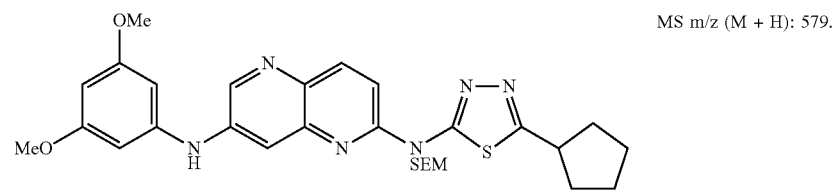 | MS m/z (M + H): 579. |
| 0082-2 | 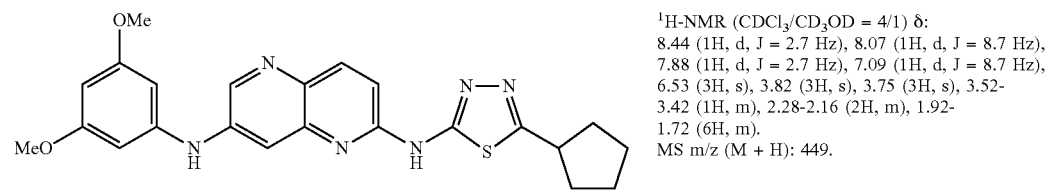 | $^1$H-NMR (CDCl$_3$/CD$_3$OD = 4/1) δ:<br>8.44 (1H, d, J = 2.7 Hz), 8.07 (1H, d, J = 8.7 Hz), 7.88 (1H, d, J = 2.7 Hz), 7.09 (1H, d, J = 8.7 Hz), 6.53 (3H, s), 3.82 (3H, s), 3.75 (3H, s), 3.52-3.42 (1H, m), 2.28-2.16 (2H, m), 1.92-1.72 (6H, m).<br>MS m/z (M + H): 449. |

Example 0082

0082-1

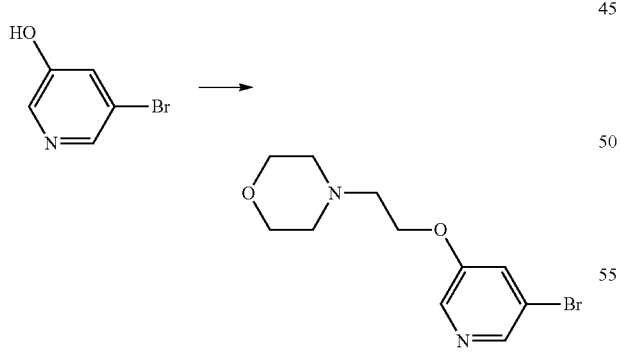

A mixture of 5-bromopyridin-3-ol (500 mg), 4-(2-bromoethyl)morpholine hydrochloride (641 mg) and potassium carbonate (1.18 g) in acetonitrile (6 mL) was stirred for 5 hours under heating to reflux. The reaction mixture was cooled to room temperature, and ethyl acetate and water were added thereto. The organic layer was collected by separation, and the aqueous layer was extracted with chloroform. The organic layer and the extraction liquid were combined, the resultant product was dried over anhydrous sodium sulfate, and the solvent was distilled off under reduced pressure, thereby obtaining 4-(2-((5-bromopyridin-3-yl)oxy)ethyl)morpholine (0.75 g).

MS m/z (M+H): 287, 289.

0082-2

A 25% ammonia aqueous solution (2 mL) was added to a mixture of 4-(2-((5-bromopyridin-3-yl)oxy)ethyl)morpholine (0.75 g) and copper(I) oxide (205 mg) in N-methylpyrrolidone (2 mL), followed by stirring at 120° C. for 30 minutes using a microwave reaction apparatus. The insolubles were filtered off using celite, and chloroform was added thereto. The organic layer was collected by separation, and dried over anhydrous sodium sulfate, and the obtained solution was purified by silica gel column chromatography (methanol-ethyl acetate), thereby obtaining 5-(2-morpholinoethoxy)pyridine-3-amine (226 mg).

MSm/z(M+H):224.

0082-3 and 0082-4

The following compounds were obtained in the same manner as in Examples 0046-1 and 0046-2.

carbonate (1.18 g) in acetonitrile (6 mL) was stirred for 5 hours under heating to reflux. The reaction mixture was cooled to room temperature, and ethyl acetate and water were added thereto. The organic layer was collected by separation, and the aqueous layer was extracted with chloroform. The organic layer and the extraction liquid were combined, the resultant product was dried over anhydrous sodium sulfate, and the solvent was distilled off under reduced pressure, thereby obtaining 3-bromo-5-(2-(pyrrolidin-1-yl)ethoxy)pyridine (0.54 g).

MSm/z(M+H):271,273.

| Example No. | | |
|---|---|---|
| 0082 | | |
| 0082-3 | 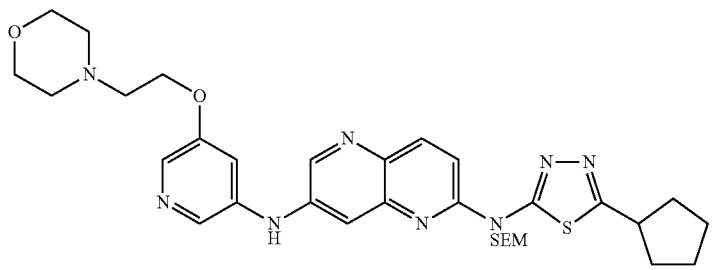 [SMILES: C[Si](C)(C)CCOCN(c1ccc2ncc(Nc3cncc(OCCN4CCOCC4)c3)cc2n1)c1nnc(C2CCCC2)s1] | MS m/z (M + H): 649. |
| 0082-4 | 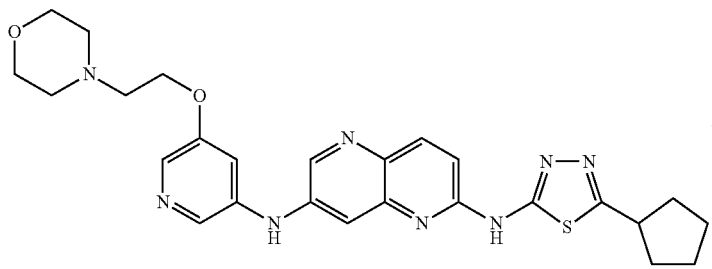 [SMILES: c1ncc(OCCN2CCOCC2)cc1Nc1cnc2ccc(Nc3nnc(C4CCCC4)s3)nc2c1] | $^1$H-NMR (DMSO-$d_6$) δ: 11.93 (1H, brs), 9.07 (1H, brs), 8.59 (1H, d, J = 2.7 Hz), 8.15 (1H, d, J = 9.3 Hz), 8.13 (1H, s), 7.96 (1H, d, J = 2.7 Hz), 7.68 (1H, d, J = 2.7 Hz), 7.29 (1H, brs), 7.22 (1H, d, J = 9.3 Hz), 4.19 (2H, t, J = 5.1 Hz), 3.56-3.28 (7H, m), 2.75-2.68 (4H, m), 2.18-2.06 (2H, m), 1.88-1.62 (6H, m). MS m/z (M + H): 519. |

Example 0083

0083-1

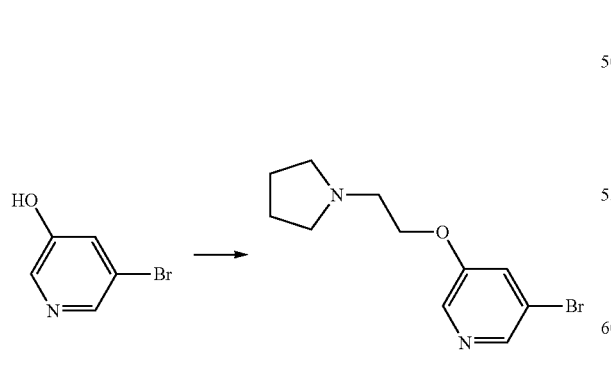

0083-2

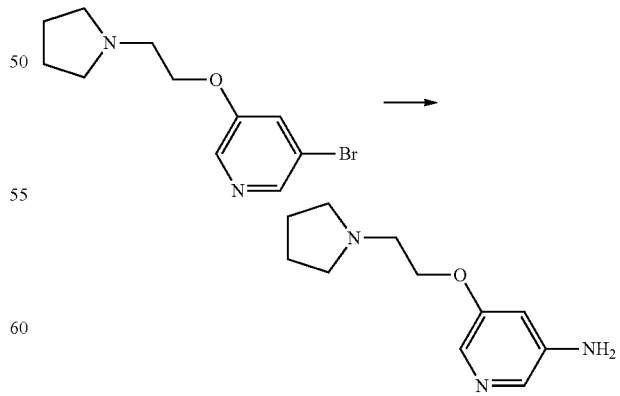

A mixture of 5-bromopyridin-3-ol (500 mg), 1-(2-bromoethyl)pyrrolidine hydrochloride (585 mg) and potassium A 25% ammonia aqueous solution (2 mL) was added to a mixture of 3-bromo-5-(2-(pyrrolidin-1-yl)ethoxy)pyridine (0.54 g), copper(I) oxide (205 mg), and N-methylpyrrolidone (2 mL), followed by stirring at 120° C. for 30 minutes using a microwave reaction apparatus. The insolubles were filtered off using celite, and dichloromethane was added thereto. The organic layer was collected by separation, and dried over anhydrous sodium sulfate, and the obtained solution was purified by silica gel column chromatography (methanol-ethyl acetate, NH silica), thereby obtaining 5-(2-(pyrrolidin-1-yl)ethoxy)pyridine-3-amine (104 mg).

MSm/z(M+H):208.

0083-3 and 0083-4

The following compounds were obtained in the same manner as in Examples 0046-1 and 0046-2.

bonate (2.80 g) in acetonitrile (8 mL) and tetrahydrofuran (4 mL) was stirred for 1.5 hours under heating to reflux. The reaction mixture was cooled to room temperature, and ethyl acetate and water were added thereto. The organic layer was collected by separation, and dried over anhydrous sodium sulfate, and the solvent was distilled off under reduced pressure, thereby obtaining 4-(3-((5-bromopyridin-3-yl)oxy)propyl)morpholine (788 mg).

MSm/z(M+H):301,303.

| Example No. | | |
|---|---|---|
| 0083 | | |
| 0083-3 | 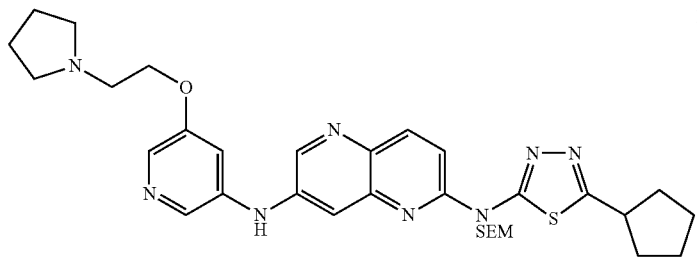 [SMILES: C[Si](C)(C)CCOCN(c1ccc2ncc(Nc3cncc(OCCN4CCCC4)c3)cc2n1)c1nnc(C2CCCC2)s1] | MS m/z (M + H): 633. |
| 0083-4 | 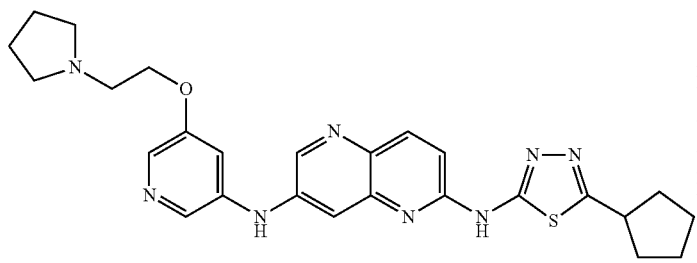 [SMILES: c1ncc(OCCN2CCCC2)cc1Nc1cnc2ccc(Nc3nnc(C4CCCC4)s3)nc2c1] | $^1$H-NMR (DMSO-d$_6$) δ: 11.94 (1H, brs), 9.08 (1H, brs), 8.59 (1H, d, J = 2.7 Hz), 8.15 (1H, d, J = 9.3 Hz), 8.13 (1H, s), 7.96 (1H, d, J = 2.7 Hz), 7.68 (1H, brs), 7.29 (1H, brs), 7.23 (1H, d, J = 9.3 Hz), 4.20-4.14 (2H, m), 2.85-2.48 (5H, m), 2.29-2.25 (2H, m), 2.18-2.06 (2H, m), 1.88-1.62 (10H, m). MS m/z (M + H): 503. |

Example 0084

0084-1

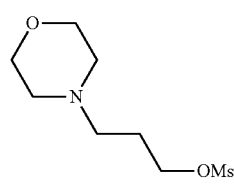

A mixture of 5-bromopyridin-3-ol (500 mg), 3-morpholinopropyl methanesulfonate (832 mg) and cesium car- 0084-2

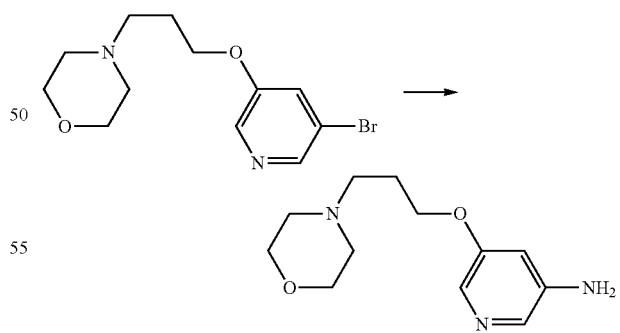

A 25% ammonia aqueous solution (2 mL) was added to a mixture of 4-(3-((5-bromopyridin-3-yl)oxy)propyl)morpholine (788 mg) and copper(I) oxide (186 mg) in N-methylpyrrolidone (2 mL), followed by stirring at 120° C. for 60 minutes using a microwave reaction apparatus. Dichloromethane and water were added to the reaction mixture. The organic layer was collected by separation, and dried over anhydrous sodium sulfate, and the obtained solution was purified by silica gel column chromatography (methanol-ethyl acetate), thereby obtaining 5-(3-morpholinopropoxy)pyridine-3-amine (297 mg).

MSm/z(M+H):238.

0084-3 and 0084-4

The following compounds were obtained in the same manner as in Examples 0046-1 and 0046-2.

Morpholine (0.117 mL) was added to half the amount of the reaction mixture, followed by stirring at room temperature for 9 hours. Water and ethyl acetate were added to the reaction mixture. The organic layer was collected by separation, washed with a saturated sodium chloride aqueous solution, and dried over anhydrous sodium sulfate, and the solvent was distilled off under reduced pressure, thereby obtaining tert-butyl (6-(morpholinomethyl)pyridin-3-yl)carbamate (121 mg).

MSm/z(M+H):294.

| Example No. | | |
|---|---|---|
| 0084 | | |
| 0084-3 | 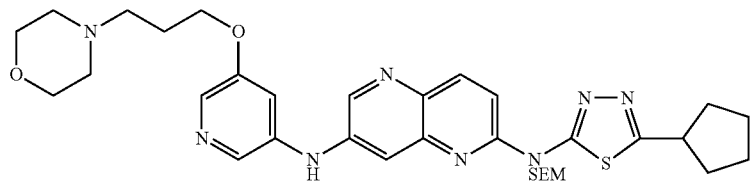 [SMILES: C[Si](C)(C)CCOCN(c1ccc2ncc(Nc3cncc(OCCCN4CCOCC4)c3)cc2n1)c1nnc(C2CCCC2)s1] | MS m/z (M + H): 663. |
| 0084-4 | 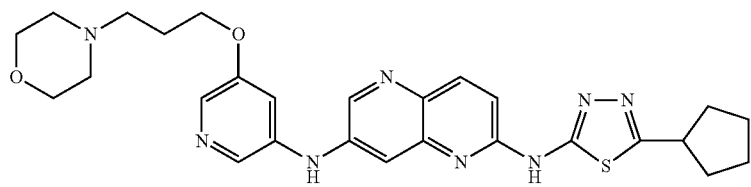 [SMILES: c1ncc(OCCCN2CCOCC2)cc1Nc1cnc2ccc(Nc3nnc(C4CCCC4)s3)nc2c1] | $^1$H-NMR (CDCl$_3$/CD$_3$OD = 4/1) δ: 8.51 (1 H, brs), 8.18-8.08 (2H, m), 7.93 (1 H, brs), 7.84 (1 H, brs), 7.23-7 16 (2H, m), 4.15-4.08 (2H, m), 3.98-3.91 (7H, m), 3.77-3.71 (4H, m), 2.32-1.72 (10H, m). MS m/z (M + H): 533. |

Example 0085

0085-1

0085-2

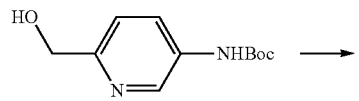

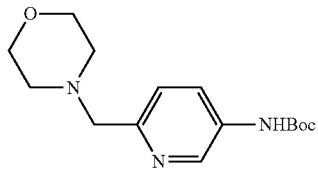

Methanesulfonyl chloride (0.104 mL) was added to a solution of tert-butyl (6-(hydroxymethyl)pyridin-3-yl)carbamate (202 mg) and triethylamine (0.189 mL) in dichloromethane (9 mL) under ice-cooling, followed by stirring at the same temperature for 30 minutes. The reaction mixture was divided into two.

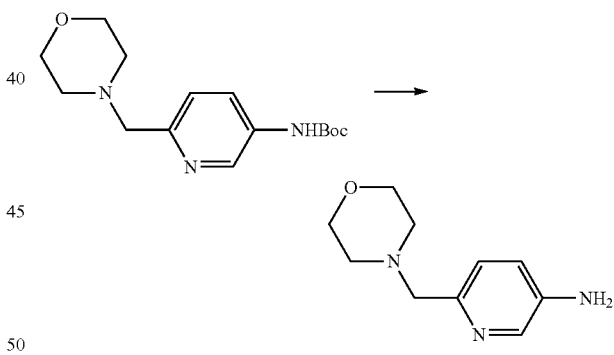

Water (0.1 mL) and trifluoroacetic acid (1 mL) were added to a solution of tert-butyl (6-(morpholinomethyl)pyridin-3-yl)carbamate (42 mg) in dichloromethane (1 mL), followed by stirring at room temperature for 3 hours. The solvent was distilled off under reduced pressure, and the obtained residue was purified by silica gel column chromatography (methanol-ethyl acetate, NH silica), thereby obtaining 6-(morpholinomethyl)pyridine-3-amine (20 mg).

MSm/z(M+H):194.

0085-3 and 0085-4

The following compounds were obtained in the same manner as in Examples 0046-1 and 0046-2.

| Example No. | | |
|---|---|---|
| 0085 | | |
| 0085-3 | 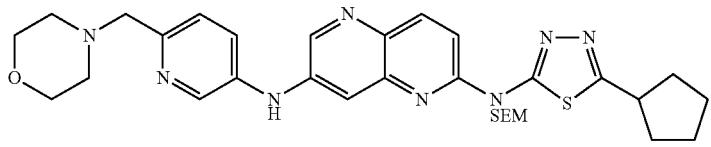 [SMILES: C[Si](C)(C)CCOCN(c1ccc2ncc(Nc3ccc(CN4CCOCC4)nc3)cc2n1)c1nnc(C2CCCC2)s1] | MS m/z (M + H): 619. |
| 0085-4 | 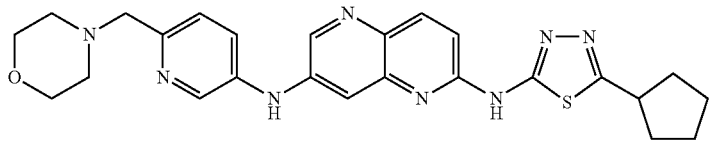 [SMILES: c1cc(CN2CCOCC2)ncc1Nc1cnc2ccc(Nc3nnc(C4CCCC4)s3)nc2c1] | ¹H-NMR (CDCl₃/CD₃OD = 4/1) δ: 8.48 (2H, brs), 8.13-8.07 (1H, m), 7.82-7.78 (1H, m), 7.75-7.67 (1H, m), 7.50-7.44 (1H, m), 7.16-7.10 (1H, m), 3.81-3.75 (5H, m), 3.68-3.65 (2H, m), 2.62-2.55 (4H, m), 2.31-2.18 (2H, m), 1.96-1.72 (6H, m). MS m/z (M + H): 489. |

Example 0086

0086-1

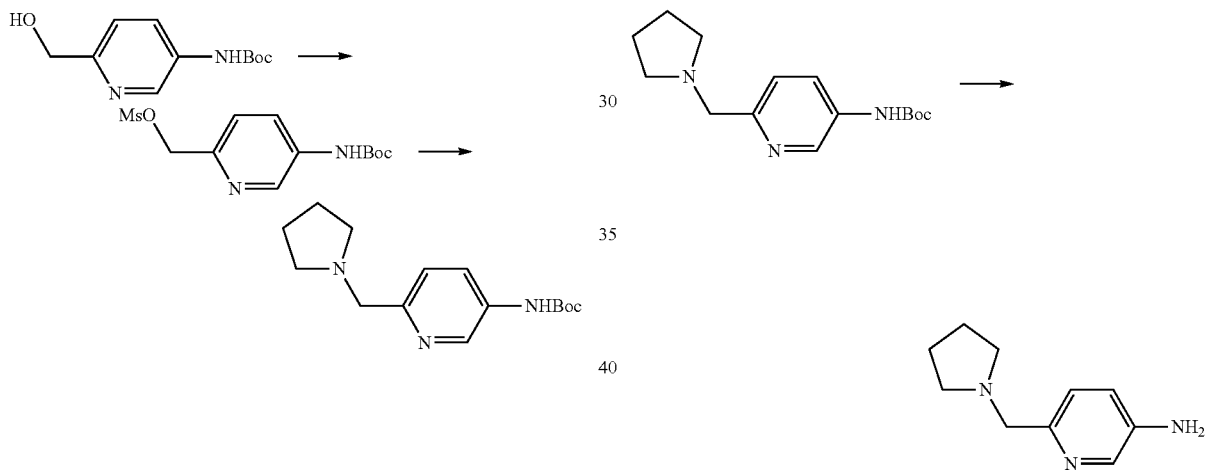

0086-2

Methanesulfonyl chloride (0.104 mL) was added to a solution of tert-butyl (6-(hydroxymethyl)pyridin-3-yl)carbamate (202 mg) and triethylamine (0.189 mL) in dichloromethane (9 mL) under ice-cooling, followed by stirring at the same temperature for 30 minutes. The reaction mixture was divided into two.

Pyrrolidine (0.111 mL) was added to half the amount of the reaction mixture, followed by stirring at room temperature for 9 hours. Water and ethyl acetate were added to the reaction mixture. The organic layer was collected by separation, washed with a saturated sodium chloride aqueous solution, and dried over anhydrous sodium sulfate, and the solvent was distilled off under reduced pressure, thereby obtaining tert-butyl (6-(pyrrolidin-1-ylmethyl)pyridin-3-yl)carbamate (94 mg).

MSm/z(M+H):278.

Water (0.1 mL) and trifluoroacetic acid (1 mL) were added to a solution of tert-butyl (6-(pyrrolidin-1-ylmethyl)pyridin-3-yl)carbamate (49 mg) in dichloromethane (1 mL), followed by stirring at room temperature for 1 hour. The solvent was distilled off under reduced pressure, and the obtained residue was purified by silica gel column chromatography (methanol-ethyl acetate, NH silica), thereby obtaining 6-(pyrrolidin-1-ylmethyl)pyridine-3-amine (15 mg).

MSm/z(M+H):178.

0086-3 and 0086-4

The following compounds were obtained in the same manner as in Examples 0046-1 and 0046-2.

| Example No. | | |
|---|---|---|
| 0086 | | |
| 0086-3 | 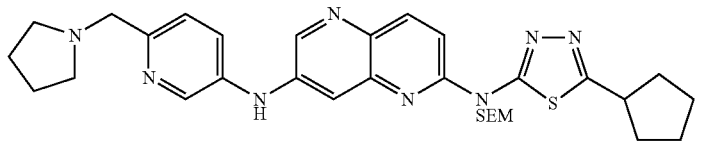 [SMILES: C[Si](C)(C)CCOCN(c1ccc2ncc(Nc3ccc(CN4CCCC4)nc3)cc2n1)c1nnc(C2CCCC2)s1] | MS m/z (M + H): 603. |
| 0086-4 |  | ¹H-NMR (CDCl₃/CD₃OD = 4/1) δ:<br>8.48 (1H, d, J = 2.7 Hz), 8.46 (1H, d, J = 2.7 Hz), 8.10 (1H, d, J = 8.4 Hz), 7.79 (1H, d, J = 2.7 Hz), 7.72 (1H, dd, J = 8.7, 2.7 Hz), 7.47 (1H, d, J = 8.4 Hz), 7.13 (1H, d, J = 8.7 Hz), 3.80 (2H, brs), 3.53-3.40 (1H, m), 2.69-2.61 (4H, m), 2.28-2.17 (2H, m), 1.94-1.68 (10H, m).<br>MS m/z (M + H): 473. |

Example 0087

0087-1

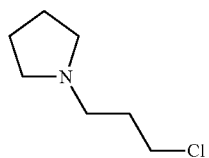

0087-2

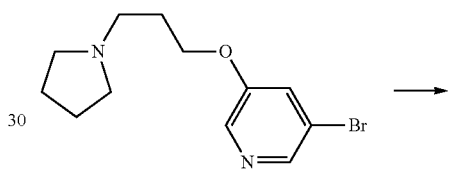

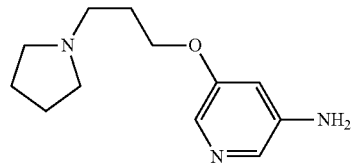

A mixture of 5-bromopyridin-3-ol (500 mg), 1-(3-chloropropyl)pyrrolidine (1.0 g) and potassium carbonate (1.18 g) in acetonitrile (4 mL) and tetrahydrofuran (4 mL) was stirred for 5 hours under heating to reflux. The reaction mixture was cooled to room temperature, and ethyl acetate and water were added thereto. The organic layer was collected by separation, and dried over anhydrous sodium sulfate, and the solvent was distilled off under reduced pressure, thereby obtaining 3-bromo-5-(3-(pyrrolidin-1-yl)propoxy)pyridine (740 mg).

MSm/z(M+H):285,287.

A 25% ammonia aqueous solution (2 mL) was added to a mixture of 3-bromo-5-(3-(pyrrolidin-1-yl)propoxy)pyridine (740 mg) and copper(I) oxide (185 mg) in N-methylpyrrolidone (2 mL), followed by stirring at 120° C. for 60 minutes using a microwave reaction apparatus. The reaction mixture was cooled to room temperature, and dichloromethane and water were added thereto. The organic layer was collected by separation, and dried over anhydrous sodium sulfate. The obtained solution was purified by silica gel column chromatography (methanol-ethyl acetate), thereby obtaining 5-(3-(pyrrolidin-1-yl)propoxy)pyridine-3-amine (139 mg).

MSm/z(M+H):222.

0087-3 and 0087-4

The following compounds were obtained in the same manner as in Examples 0046-1 and 0046-2.

| Example No. | | |
|---|---|---|
| 0087 | | |
| 0087-3 | 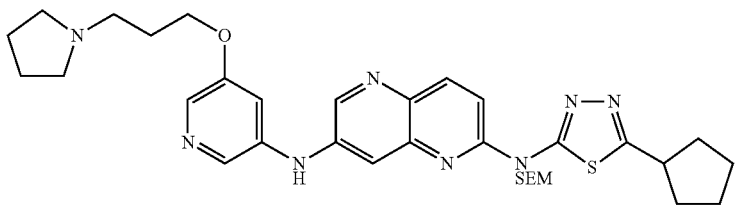 | MS m/z (M + H): 647. |
| 0087-4 | 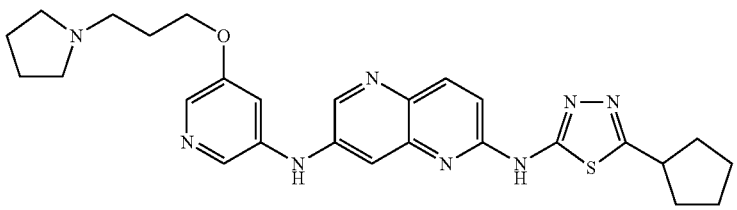 [SMILES: c1ncc(OCCCN2CCCC2)cc1Nc1cnc2ccc(Nc3nnc(C4CCCC4)s3)nc2c1] | ¹H-NMR (CDCl₃/CD₃OD = 4/1) δ: 8.50 (1H, brs), 8.18 (1H, brs), 8.11 (1H, d, J = 9.3 Hz), 7.92 (1H, brs), 7.83 (1H, brs), 7.16 (1H, brs), 7.15 (1H, d, J = 9.3 Hz), 4.10 (1H, t, J = 6.0 Hz), 2.84-2.61 (7H, m), 2.26-2.04 (4H, m), 1.94-1.70 (12H, m). MS m/z (M + H): 517. |

Examples 0088 and 0089

The following compounds were obtained in the same manner as in Examples 0046-1 and 0046-2.

| Example No. | | |
|---|---|---|
| 0088 | | |
| 0088-1 | 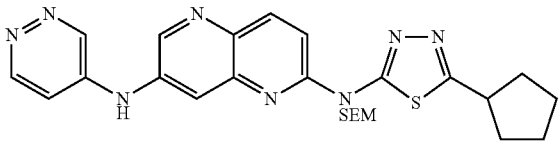 | MS m/z (M + H): 521. |
| 0088-2 |  | ¹H-NMR (CDCl₃/CD₃OD = 4/1) δ: 8.97 (1H, d, J = 2.7 Hz), 8.79 (1H, 6.6 Hz), 8.60 (1H, 2.7 Hz), 8.19 (1H, d, J = 9.3 Hz), 8.06 (1H, d, J = 1.8 Hz), 7.34-7.26 (2H, m), 3.54-3.44 (1H, m), 2.32-2.18 (2H, m), 1.94-1.70 (6H, m). MS m/z (M + H): 391. |
| 0089 | | |
| 0089-1 | 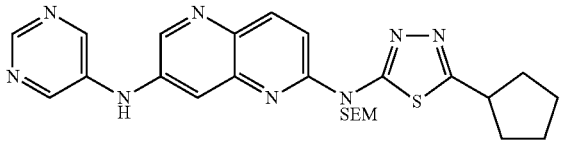 | MS m/z (M + H): 521. |
| 0089-2 | 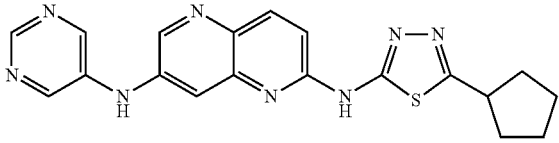 [SMILES: c1ncc(Nc2cnc3ccc(Nc4nnc(C5CCCC5)s4)nc3c2)cn1] | ¹H-NMR (CDCl₃/CD₃OD = 4/1) δ: 8.83 (1H, s), 8.77 (2H, s), 8.52 (1H, d, J = 2.7 Hz), 8.13 (1H, d, H = 8.4 Hz), 7.88 (1H, d, J = 2.7 Hz), 7.19 (1H, d, J = 8.4 Hz), 3.54-3.44 (1H, m), 2.32-2.18 (2H, m), 1.94-1.76 (6H, m). MS m/z (M + H): 391. |

Example 0090

0090-1

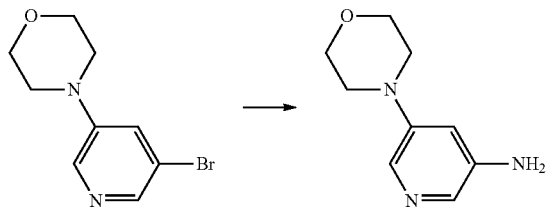 [SMILES: Brc1cncc(N2CCOCC2)c1 ; Nc1cncc(N2CCOCC2)c1]

A 25% ammonia aqueous solution (2 mL) was added to a mixture of 4-(5-bromopyridin-3-yl)morpholine (447 mg) and copper(I) oxide (130 mg) in N-methylpyrrolidone (2 mL), followed by stirring at 120° C. for 60 minutes using a microwave reaction apparatus. Dichloromethane and water were added to the reaction mixture. The organic layer was collected by separation, and dried over anhydrous sodium sulfate. The obtained solution was purified by silica gel column chromatography (methanol-ethyl acetate), thereby obtaining 5-morpholinopyridine-3-amine (34 mg).
MS m/z (M+H): 180.

0090-2 and 0090-3

The following compounds were obtained in the same manner as in Examples 0046-1 and 0046-2.

| Example No. | | |
|---|---|---|
| 0090 | | |
| 0090-2 | 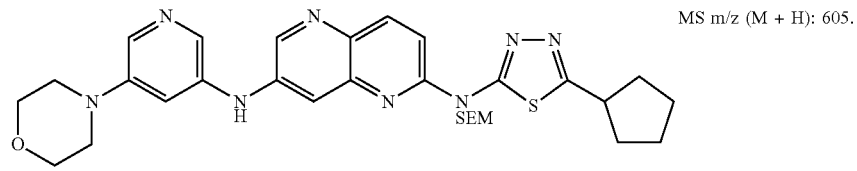 | MS m/z (M + H): 605. |
| 0090-3 | 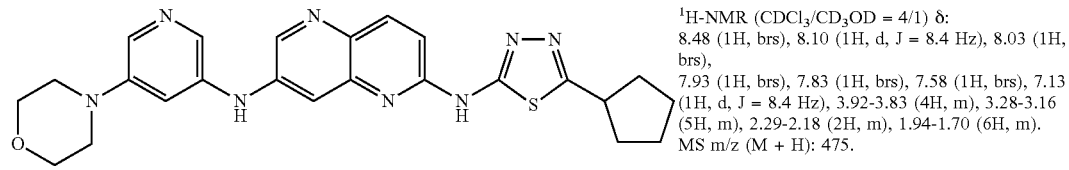 | $^1$H-NMR (CDCl$_3$/CD$_3$OD = 4/1) δ:<br>8.48 (1H, brs), 8.10 (1H, d, J = 8.4 Hz), 8.03 (1H, brs),<br>7.93 (1H, brs), 7.83 (1H, brs), 7.58 (1H, brs), 7.13 (1H, d, J = 8.4 Hz), 3.92-3.83 (4H, m), 3.28-3.16 (5H, m), 2.29-2.18 (2H, m), 1.94-1.70 (6H, m).<br>MS m/z (M + H): 475. |

Examples 0091 and 0092

The following compounds were obtained in the same manner as in Examples 0046-1 and 0046-2.

| Example No. | | |
|---|---|---|
| 0091 | | |
| 0091-1 | 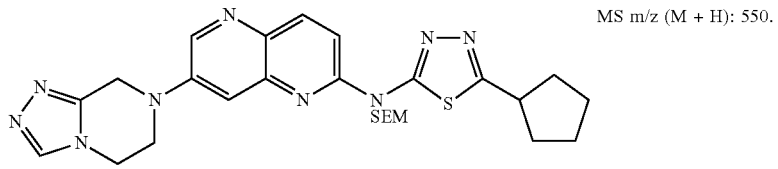 | MS m/z (M + H): 550. |
| 0091-2 | 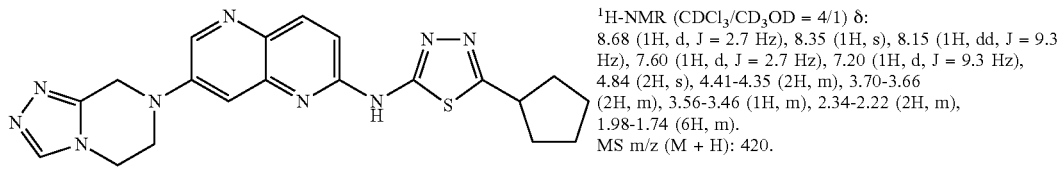 | $^1$H-NMR (CDCl$_3$/CD$_3$OD = 4/1) δ:<br>8.68 (1H, d, J = 2.7 Hz), 8.35 (1H, s), 8.15 (1H, dd, J = 9.3 Hz), 7.60 (1H, d, J = 2.7 Hz), 7.20 (1H, d, J = 9.3 Hz),<br>4.84 (2H, s), 4.41-4.35 (2H, m), 3.70-3.66 (2H, m), 3.56-3.46 (1H, m), 2.34-2.22 (2H, m),<br>1.98-1.74 (6H, m).<br>MS m/z (M + H): 420. |

| Example No. | | |
|---|---|---|
| 0092 | | |
| 0092-1 | 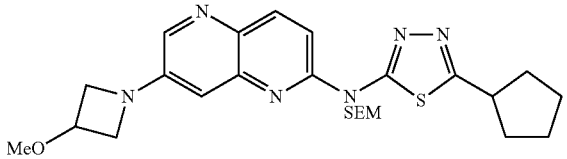 | MS m/z (M + H): 513. |
| 0092-2 | 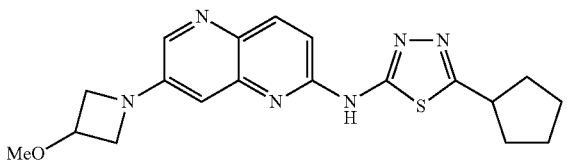 [SMILES: COC1CN(c2cnc3ccc(Nc4nnc(C5CCCC5)s4)nc3c2)C1] | $^1$H-NMR (CDCl$_3$/CD$_3$OD = 4/1) δ: 8.11 (1H, d, J = 2.4 Hz), 8.08 (1H, d, J = 8.7 Hz), 7.07 (1H, d, J = 8.7 Hz), 7.03 (1H, d, J = 2.4 Hz), 4.54-4.45 (1H, m), 4.40-4.33 (2H, m), 4.03-3.96 (2H, m), 3.52-3.43 (1H, m), 3.36 (3H, s), 2.34-2.20 (2H, m), 1.98-1.74 (6H, m). MS m/z (M + H): 383. |

Example 0093

0093-1

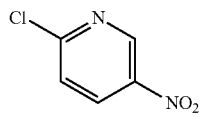 → 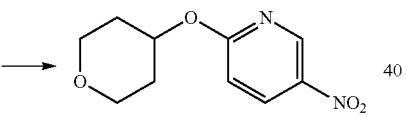

60% sodium hydride (189 mg) was added to a solution of 2-chloro-5-nitropyridine (500 mg) and tetrahydro-2H-pyran-4-ol (386 mg) in tetrahydrofuran (6 mL) under ice-cooling, followed by stirring at the same temperature for 1 hour. A 1 mol/L potassium hydrogen sulfate solution and ethyl acetate were added to the reaction mixture. The organic layer was collected by separation, washed with a saturated sodium chloride aqueous solution, and dried over anhydrous sodium sulfate, and the solvent was distilled off under reduced pressure, thereby obtaining 5-nitro-2-((tetrahydro-2H-pyran-4-yl)oxy)pyridine (838 mg).

MSm/z(M+H):225.

0093-2

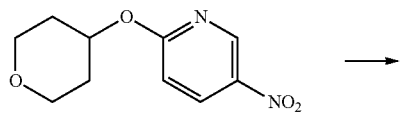 →

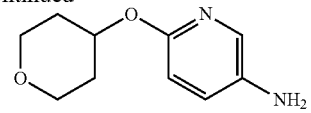

5-Nitro-2-((tetrahydro-2H-pyran-4-yl)oxy)pyridine (838 mg) and ammonium formate (1.98 g) were added to a mixture of 10% palladium-carbon (100 mg) in methanol (15 mL), followed by stirring at room temperature for 6 hours. The insolubles were filtered off using celite, and the solvent was distilled off under reduced pressure. The obtained residue was purified by silica gel column chromatography (ethyl acetate-hexane), thereby obtaining 6-((tetrahydro-2H-pyran-4-yl)oxy)pyridine-3-amine (349 mg).

$^1$H-NMR(CDCl$_3$)δ:7.63(1H,d,J=2.7 Hz),7.03(1H,dd,J=9.2 Hz,2.7 Hz),6.60(1H,d,J=9.0 Hz),5.13-5.03(1H,m),4.02-3.93(2H,m),3.64-3.54(2H,m),2.09-1.98(2H,m),1.81-1.68(2H,m).

0093-3 and 0093-4

The following compounds were obtained in the same manner as in Examples 0046-1 and 0046-2.

| Example No. | | |
|---|---|---|
| 0093 | | |
| 0093-3 | 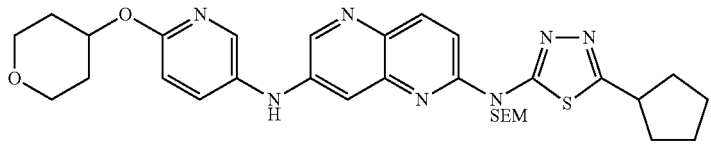 | MS m/z (M + H): 620. |
| 0093-4 | 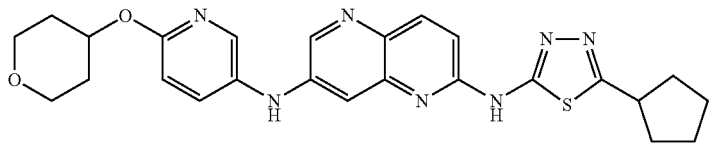 [SMILES: c1cc(OC2CCOCC2)ncc1Nc1cnc2ccc(Nc3nnc(C4CCCC4)s3)nc2c1] | ¹H-NMR (CDCl₃/CD₃OD = 4/1) δ: 8.41 (1H, d, J = 2.7 Hz), 8.15 (1H, d, J = 2.7 Hz), 8.06 (1H, d, J = 8.4 Hz), 7.65 (1H, dd, J = 8.4 Hz, 2.7 Hz), 7.49 (1H, brs), 7.08 (1H, d, J = 8.4 Hz), 6.86 (1H, d, J = 8.4 Hz), 5.26-5.15 (1H, m), 3.72-3.62 (4H, m), 3.53-3.42 (1H, m), 2.29-2.04 (4H, m), 1.93-1.68 (8H, m).<br>MS m/z (M + H): 490. |

Examples 0094 to 0096

The following compounds were obtained in the same manner as in Examples 0046-1 and 0046-2.

| Example No. | | |
|---|---|---|
| 0094 | | |
| 0094-1 | 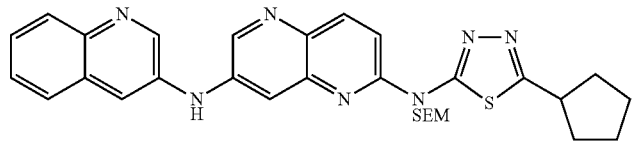 | MS m/z (M + H): 570. |
| 0094-2 | 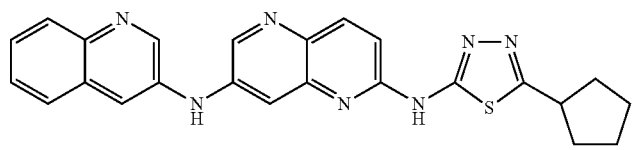 [SMILES: c1ccc2ncc(Nc3cnc4ccc(Nc5nnc(C6CCCC6)s5)nc4c3)cc2c1] | ¹H-NMR (CDCl₃/CD₃OD = 4/1) δ: 8.82 (1H, d, J = 2.7 Hz), 8.60 (1H, d, J = 1.8 Hz), 8.14 (1H, d, J = 9.3 Hz), 8.12 (1H, d, J = 2.7 Hz), 8.05 (1H, d, J = 4.8 Hz), 7.95 (1H, d, J = 2.7 Hz), 7.83-7.54 (3H, m), 7.17 (1H, d, J = 9.3 Hz), 3.46 (1H, m), 2.34-2.22 (2H, m), 1.98-1.74 (6H, m).<br>MS m/z (M + H): 440. |
| 0095 | | |
| 0095-1 | 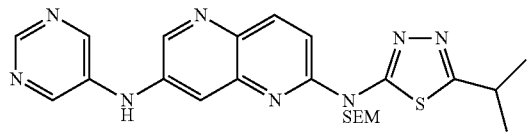 | MS m/z (M + H): 495. |
| 0095-2 | 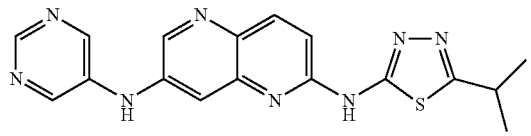 [SMILES: CC(C)c1nnc(Nc2ccc3ncc(Nc4cncnc4)cc3n2)s1] | ¹H-NMR (CDCl₃/CD₃OD = 4/1) δ: 8.83 (1H, s), 8.77 (2H, s), 8.53 (1H, d, J = 2.7 Hz), 8.14 (1H, d, J = 9.3 Hz), 7.88 (1H, d, J = 2.7 Hz), 7.20 (1H, d, J = 9.3 Hz), 3.47-3.35 (1H, m), 1.47 (6H, d, J = 6.6 Hz).<br>MS m/z (M + H): 365. |

| Example No. | | |
|---|---|---|
| 0096 | | |
| 0096-1 | 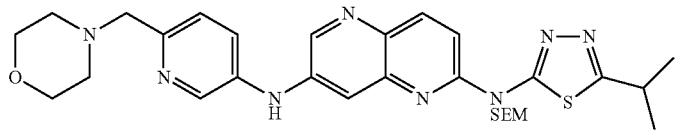 | MS m/z (M + H): 593. |
| 0096-2 | 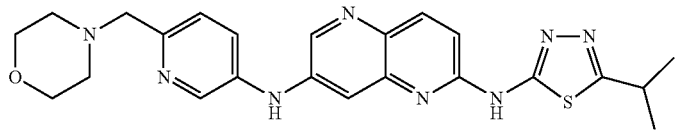 [SMILES: CC(C)c1nnc(Nc2ccc3ncc(Nc4ccc(CN5CCOCC5)nc4)cc3n2)s1] | $^1$H-NMR (CDCl$_3$/CD$_3$OD = 4/1) δ: 8.49 (2H, d, J = 2.7 Hz), 8.11 (1H, d, J = 9.0 Hz), 7.81 (1H, d, J = 2.7 Hz), 7.72 (1H, dd, J = 8.7 Hz, 2.7 Hz), 7.48 (1H, d, J = 8.7 Hz), 7.17 (1H, d, J = 9.0 Hz), 3.80-3.75 (4H, m), 3.67 (2H, s), 3.48-3.36 (1H, m), 2.60-2.56 (4H, m), 1.47 (6H, d, J = 6.6 Hz). MS m/z (M + H): 463. |

Example 0097

0097-1

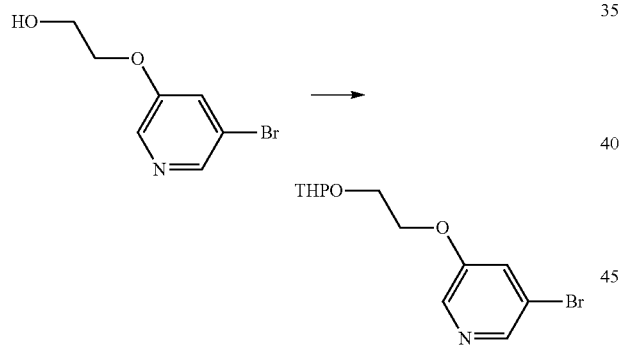

Dihydropyran (0.262 mL) and camphorsulfonic acid (505 mg) were added sequentially to a solution of 2-((5-bromopyridin-3-yl)oxy)ethanol (318 mg) in dichloromethane (7 mL) at room temperature, followed by stirring at the same temperature for 26 hours. A saturated sodium hydrogen carbonate aqueous solution and ethyl acetate were added to the reaction mixture. The organic layer was collected by separation, washed with a saturated sodium chloride aqueous solution, and dried over anhydrous sodium sulfate, and the solvent was distilled off under reduced pressure, thereby obtaining 3-bromo-5-(2-((tetrahydro-2H-pyran-2-yl)oxy)ethoxy)pyridine (779 mg).

MSm/z(M+H):302.

0097-2

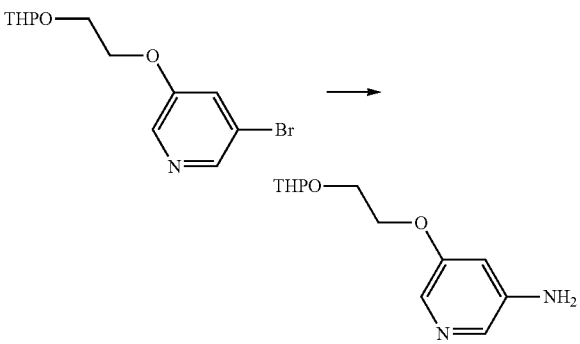

A 25% ammonia aqueous solution (2 mL) was added to a mixture of 3-bromo-5-(2-((tetrahydro-2H-pyran-2-yl)oxy)ethoxy)pyridine (779 mg) and copper(I) oxide (103 mg) in N-methylpyrrolidone (2 mL), followed by stirring at 120° C. for 60 minutes using a microwave reaction apparatus. Dichloromethane and water were added to the reaction mixture. The organic layer was collected by separation, and dried over anhydrous sodium sulfate. The obtained solution was purified by silica gel column chromatography (methanol-ethyl acetate), thereby obtaining 5-(2-((tetrahydro-2H-pyran-2-yl)oxy)ethoxy)pyridine-3-amine (456 mg).

MSm/z(M+H):239.

0097-3 and 0097-4

The following compounds were obtained in the same manner as in Examples 0046-1 and 0046-2.

| Example No. | | |
|---|---|---|
| 0097 | | |
| 0097-3 | 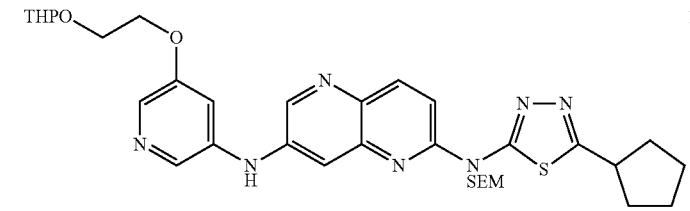 | MS m/z (M + H): 664. |
| 0097-4 | 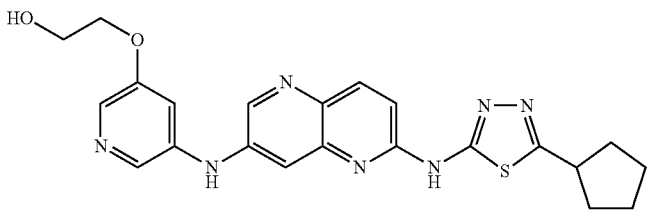 [SMILES: OCCOc1cncc(Nc2cnc3ccc(Nc4nnc(C5CCCC5)s4)nc3c2)c1] | $^1$H-NMR (CDCl$_3$/CD$_3$OD = 4/1) δ:<br>8.51 (1H, d, J = 2.7 Hz), 8.18 (1H, d, J = 2.1 Hz), 8.11 (1H, d, J = 9.0 Hz), 7.95 (1H, d, J = 1.8 Hz), 7.85 (1H, d,<br>J = 2.1 Hz), 7.25 (1H, dd, J = 2.7 Hz, 1.8 Hz), 7.16 (1H,<br>d, J = 9.0 Hz), 4.18-4.09 (2H, m), 3.98-3.90 (2H, m), 3.46 (1H, m), 2.34-2.22 (2H, m), 1.98-1.74 (6H, m).<br>MS m/z (M + H): 450. |

Example 0098

The following compounds were obtained in the same manner as in Examples 0046-1 and 0046-2.

3-Isopropyl-5-nitropyridine (103 mg) and ammonium formate (390 mg) were added to a mixture of 10% palladium-carbon (20 mg) in methanol (6 mL), followed by stirring at room temperature for 1 day. The insolubles were filtered off

| Example No. | | |
|---|---|---|
| 0098 | | |
| 0098-1 | 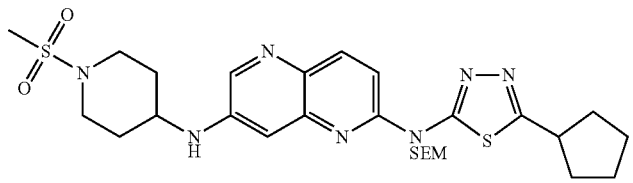 | MS m/z (M + H): 604. |
| 0098-2 | 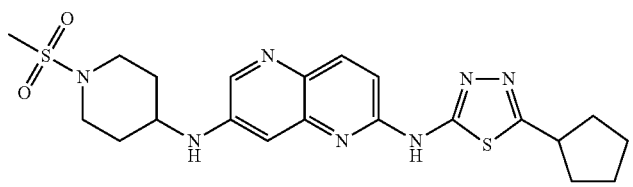 [SMILES: CS(=O)(=O)N1CCC(Nc2cnc3ccc(Nc4nnc(C5CCCC5)s4)nc3c2)CC1] | $^1$H-NMR (DMSO-d$_6$) δ:<br>8.35 (1H, d, J = 2.7 Hz), 8.05 (1H, d, J = 9.3 Hz), 7.11 (1H, d, J = 2.7 Hz), 7.09 (1H, d, J = 9.3 Hz), 3.74-3.44 (4H, m), 3.07-2.96 (2H, m),<br>2.91 (3H, s), 2.20-2.01 (4H, m), 1.93-1.62 (6H, m), 1.59-1.44 (2H, m).<br>MS m/z (M + H): 474. |

Example 0099

0099-1

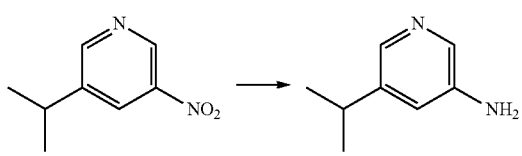

using celite, the solvent was distilled off under reduced pressure, and the obtained residue was purified by silica gel column chromatography (methanol-ethyl acetate-hexane), thereby obtaining 5-isopropylpyridine-3-amine (18 mg).

MSm/z(M+H):137.

0099-2 and 0099-3

The following compounds were obtained in the same manner as in Examples 0046-1 and 0046-2.

| Example No. | | |
|---|---|---|
| 0099 | | |
| 0099-2 | 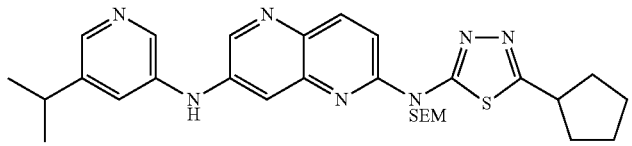 | MS m/z (M + H): 562. |
| 0099-3 | 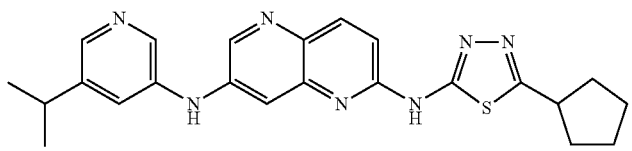 [SMILES: CC(C)c1cncc(Nc2cnc3ccc(Nc4nnc(C5CCCC5)s4)nc3c2)c1] | $^1$H-NMR (CDCl$_3$/CD$_3$OD = 4/1) δ:<br>8.51 (1H, d, J = 2.7 Hz), 8.34 (1H, d, J = 2.7 Hz), 8.12 (1H, d, J = 2.7 Hz), 8.11 (1H, d, J = 9.0 Hz), 7.94 (1H, d, J = 2.7 Hz), 7.86 (1H, d, J = 2.7 Hz), 7.17 (1H, d, J = 9.0 Hz), 3.54-3.40 (1H, m), 3.10-2.90 (1H, m), 2.28-2.17 (2H, m), 1.90-1.72 (6H, m),<br>1.30 (6H, d, J = 4.2 Hz).<br>MS m/z (M + H): 432. |

Example 0100

0100-1

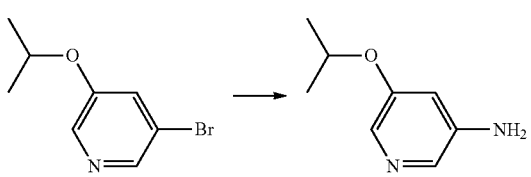

A 25% ammonia aqueous solution (2 mL) was added to a mixture of 3-bromo-5-isopropyloxypyridine (590 mg) and copper(I) oxide (195 mg) in N-methylpyrrolidone (2 mL), followed by stirring at 120° C. for 60 minutes using a microwave reaction apparatus. Ethyl acetate and water were added to the reaction mixture. The organic layer was collected by separation, and dried over anhydrous sodium sulfate. The obtained residue was purified by silica gel column chromatography (methanol-ethyl acetate), thereby obtaining 5-isopropyloxypyridine-3-amine (302 mg).

MSm/z(M+H):153.

0100-2 and 0100-3

The following compounds were obtained in the same manner as in Examples 0046-1 and 0046-2.

| Example No. | | |
|---|---|---|
| 0100 | | |
| 0100-2 | 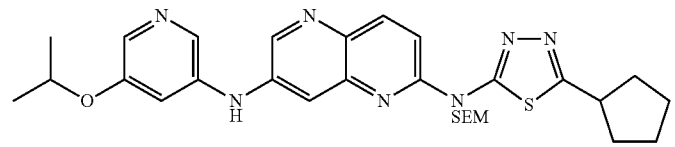 | MS m/z (M + H): 578. |
| 0100-3 |  | $^1$H-NMR (CDCl$_3$/CD$_3$OD = 4/1) δ:<br>8.52 (1H, d, J = 2.7 Hz), 8.13 (1H, d, J = 9.0 Hz), 8.10 (1H, d, J = 2.1 Hz), 7.91 (1H, d, J = 2.7 Hz), 7.88 (1H, d,<br>J = 2.1 Hz), 7.84 (1H, dd, J = 2.7 Hz, 2.1 Hz), 7.19 (1H,<br>d, J = 9.0 Hz), 4.74-4.57 (1H, m), 3.54-3.42 (1H, m), 2.30-2.18 (2H, m), 1.94-1.72 (6H, m),<br>1.42 (6H, d, J = 8.7 Hz).<br>MS m/z (M + H): 448. |

Example 0101

0101-1

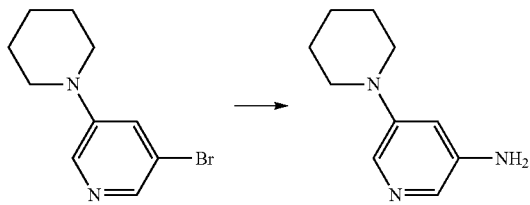 [SMILES: Brc1cncc(N2CCCCC2)c1 ; Nc1cncc(N2CCCCC2)c1]

A 25% ammonia aqueous solution (2 mL) was added to a mixture of 3-bromo-5-(piperidin-1-yl)pyridine (119 mg), and copper(I) oxide (36 mg) in N-methylpyrrolidone (2 mL), followed by stirring at 120° C. for 60 minutes using a microwave reaction apparatus. Ethyl acetate and water were added to the reaction mixture. The organic layer was collected by separation, and dried over anhydrous sodium sulfate. The obtained residue was purified by silica gel column chromatography (methanol-ethyl acetate), thereby obtaining 5-(piperidin-1-yl)pyridine-3-amine (28 mg).
MSm/z(M+H):178.

0101-2 and 0101-3

The following compounds were obtained in the same manner as in Examples 0046-1 and 0046-2.

| Example No. | | |
|---|---|---|
| 0101 | | |
| 0101-2 | 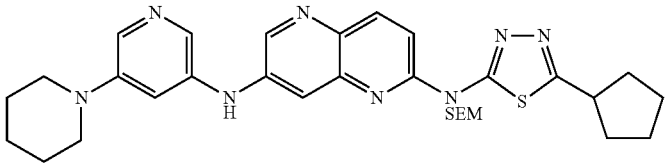 | MS m/z (M + H): 603. |
| 0101-3 |  | $^1$H-NMR (CDCl$_3$/CD$_3$OD = 4/1) δ: 6.49 (1H, d, J = 2.7 Hz), 8.11 (1H, d, J = 8.7 Hz), 7.95-7.91 (2H, m), 7.86-7.83 (1H, m), 7.28-7.25 (1H, m), 7.14 (1H, d, J = 8.7 Hz), 3.51-3.42 (1H, m), 3.31-3.25 (4H, m), 2.30-2.18 (2H, m), 1.94-1.60 (12H, m). MS m/z (M + H): 473. |

Example 0102

0102-1

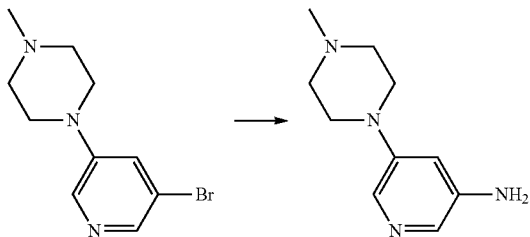

A 25% ammonia aqueous solution (1 mL) was added to a mixture of 1-(5-bromopyridin-3-yl)-4-methylpiperazine (28 mg), and copper(I) oxide (8 mg) in N-methylpyrrolidone (1 mL), followed by stirring at 120° C. for 2.5 hours using a microwave reaction apparatus. Dichloromethane and water were added to the reaction mixture. The organic layer was collected by separation, and dried over anhydrous sodium sulfate. The obtained residue was purified by silica gel column chromatography (methanol-ethyl acetate), thereby obtaining 5-(4-methylpiperazin-1-yl)pyridine-3-amine (11 mg).

MSm/z(M+H):193.

0102-2 and 0102-3

The following compounds were obtained in the same manner as in Examples 0046-1 and 0046-2.

Example 0103

0103-1

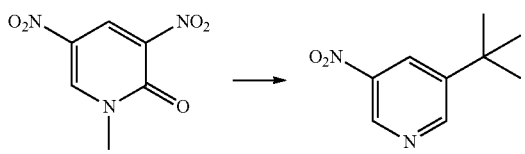

3,3-Dimethylbutanal (200 mg) was added to a solution of 1-methyl-3,5-dinitropyridin-2(1H)-one (200 mg) and ammonium acetate (790 mg) in methanol (18 mL) and 7 mol/L ammonia/methanol (2 mL), followed by stirring at 100° C. for 1 hour using a microwave reaction apparatus. The reaction mixture was cooled to room temperature, the solvent was distilled off under reduced pressure, and ethyl acetate and water were added thereto. The organic layer was collected by separation, washed with a saturated sodium chloride aqueous solution, and dried over anhydrous sodium hydrogen sulfate. The obtained residue was purified by silica gel column chromatography (ethyl acetate-hexane), thereby obtaining 3-(tert-butyl)-5-nitropyridine (72 mg).

$^1$H-NMR(CDCl$_3$)δ:9.28(1H,d,J=2.7 Hz),8.96(1H,d,J=2.1 Hz),8.47-8.44(1H,m),1.43(9H,s).

| Example No. | | |
|---|---|---|
| 0102 | | |
| 0102-2 | 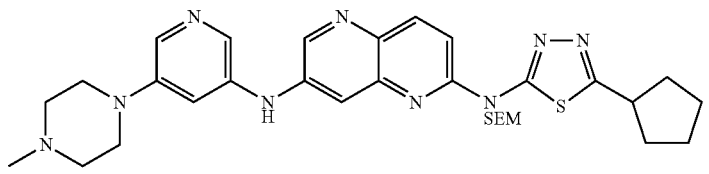 | MS m/z (M + H): 618. |
| 0102-3 | 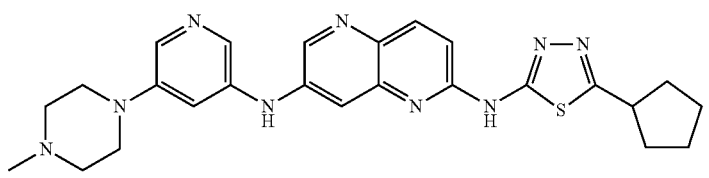 [SMILES: CN1CCN(c2cncc(Nc3cnc4ccc(Nc5nnc(C6CCCC6)s5)nc4c3)c2)CC1] | $^1$H-NMR (CDCl$_3$/CD$_3$OD = 4/1) δ: 8.49 (1H, d, J = 2.7 Hz), 8.11 (1H, d, J = 9.0 Hz), 8.04 (1H, d, J = 1.8 Hz), 7.94 (1H, d, J = 2.7 Hz), 7.82 (1H, d, J = 2.4 Hz), 7.16 (1H, dd, J = 2.4 Hz, 1.8 Hz), 7.14 (1H, d, J = 9.0 Hz), 3.54-3.42 (1H, m), 3.33-3.27 (4H, m), 2.67-2.61 (4H, m), 2.38 (3H, s), 2.30-2.18 (2H, m), 1.94-1.76 (6H, m). MS m/z (M + H): 486. |

0103-2

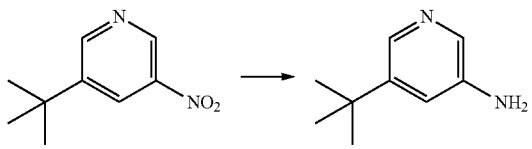

3-(tert-Butyl)-5-nitropyridine (72 mg) and ammonium formate (503 mg) were added to a mixture of 10% palladium-carbon (20 mg) in methanol (4 mL), followed by stirring at room temperature for 6 hours, and for 1.5 hours under heating to reflux. The insolubles were filtered off using celite, and the solvent was distilled off under reduced pressure. The obtained residue was purified by silica gel column chromatography (methanol-ethyl acetate-hexane), thereby obtaining 5-(tert-butyl)pyridine-3-amine (48 mg).

MSm/z(M+H):151.

0103-3 and 0103-4

The following compounds were obtained in the same manner as in Examples 0046-1 and 0046-2.

| Example No. | | |
|---|---|---|
| 0103 | | |
| 0103-3 | 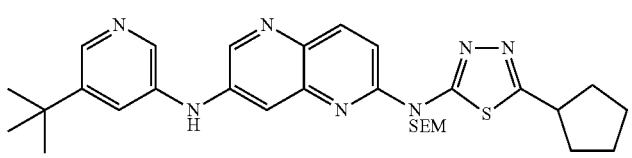 | MS m/z (M + H): 576. |
| 0103-4 | 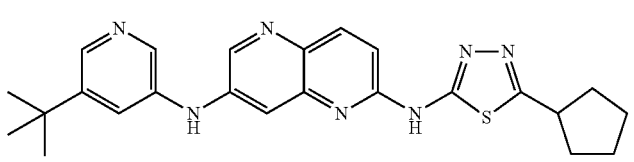 [SMILES: CC(C)(C)c1cncc(Nc2cnc3ccc(Nc4nnc(C5CCCC5)s4)nc3c2)c1] | $^1$H-NMR (CDCl$_3$/CD$_3$OD = 4/1) δ: 8.49 (1H, brs), 8.32 (1H, brs), 8.28 (1H, brs), 8.12 (1H, d, J = 8.7 Hz), 7.94-7.83 (2H, m), 7.17 (1H, d, J = 8.7 Hz), 3.54-3.42 (1H, m), 2.30-2.18 (2H, m), 1.94-1.76 (6H, m), 1.42 (9H, s). MS m/z (M + H): 446. |

Examples 0104 to 0109

The following compounds were obtained in the same manner as in Examples 0046-1 and 0046-2.

| Example No. | | |
|---|---|---|
| 0104 | | |
| 0104-1 | 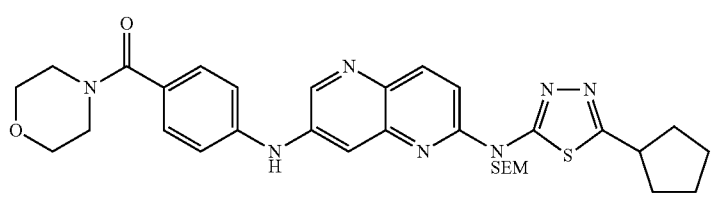 | MS m/z (M + H): 632. |
| 0104-2 | 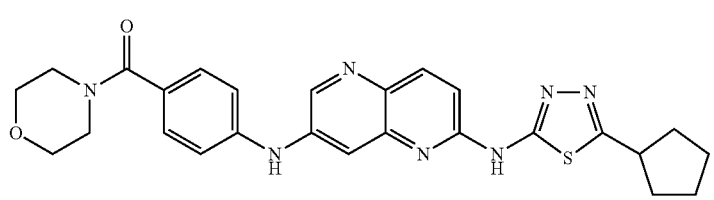 [SMILES: O=C(c1ccc(Nc2cnc3ccc(Nc4nnc(C5CCCC5)s4)nc3c2)cc1)N1CCOCC1] | $^1$H-NMR (CDCl$_3$/CD$_3$OD = 4/1) δ: 8.52 (1H, brs), 8.12 (1H, d, J = 8.7 Hz), 7.89 (1H, brs), 7.46 (2H, d, J = 8.7 Hz), 7.32 (2H, d, J = 8.7 Hz), 7.16 (1H, d, J = 8.7 Hz), 3.82-3.69 (9H, m), 3.54-3.42 (1H, m), 2.30-2.18 (2H, m), 1.94-1.76 (6H, m). MS m/z (M + H): 502. |

| Example No. | | |
|---|---|---|
| 0105 | | |
| 0105-1 | 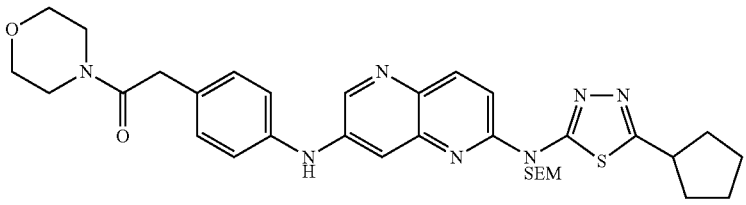 | MS m/z (M + H): 646. |
| 0105-2 |  | $^1$H-NMR (CDCl$_3$/CD$_3$OD = 4/1) δ: 8.49 (1H, brs), 8.11 (1H, d, J = 8.7 Hz), 7.87 (1H, brs), 7.28 (2H, d, J = 8.1 Hz), 7.25 (2H, d, J = 8.1 Hz), 7.13 (1H, d, J = 8.7 Hz), 3.75 (2H, brs), 3.72-3.42 (9H, m), 2.30-2.16 (2H, m), 1.94-1.76 (6H, m). MS m/z (M + H): 516. |
| 0106 | | |
| 0106-1 | 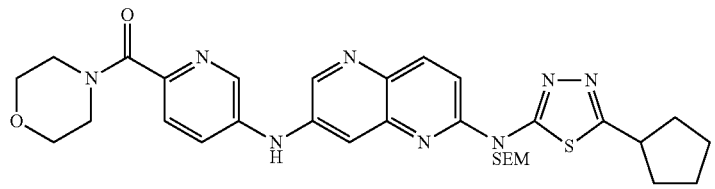 | MS m/z (M + H): 633. |
| 0106-2 | 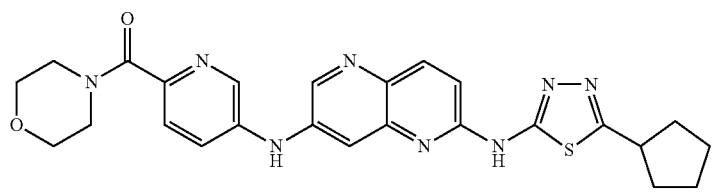 [SMILES: O=C(c1ccc(Nc2cnc3ccc(Nc4nnc(C5CCCC5)s4)nc3c2)cn1)N1CCOCC1] | $^1$H-NMR (CDCl$_3$/CD$_3$OD = 4/1) δ: 8.53 (1H, d, J = 2.7 Hz), 8.50 (1H, brs), 8.13 (1H, d, J = 9.0 Hz), 7.93 (1H, d, J = 2.7 Hz), 7.76-7.73 (2H, m), 7.18 (1H, d, J = 9.0 Hz), 3.86-3.64 (8H, m), 3.54-3.42 (1H, m), 2.30-2.18 (2H, m), 1.94-1.72 (6H, m). MS m/z (M + H): 503. |
| 0107 | | |
| 0107-1 | 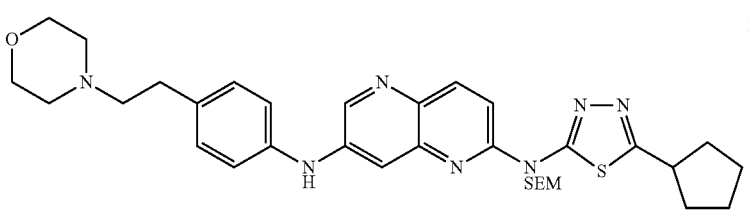 | MS m/z (M + H): 632. |
| 0107-2 | 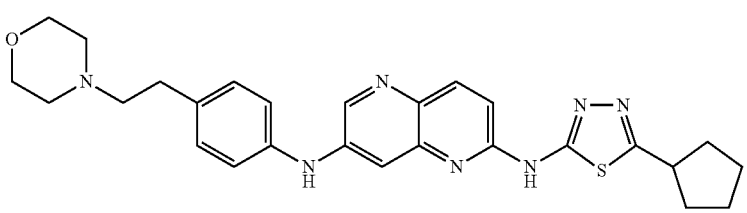 [SMILES: c1cc(Nc2cnc3ccc(Nc4nnc(C5CCCC5)s4)nc3c2)ccc1CCN1CCOCC1] | $^1$H-NMR (CDCl$_3$/CD$_3$OD = 4/1) δ: 8.44 (1H, brs), 8.07 (1H, d, J = 9.0 Hz), 7.77 (1H, brs), 7.41-7.87 (2H, brs), 7.27-7.23 (2H, brs), 7.08 (1H, d, J = 9.0 Hz), 3.83-3.75 (4H, m), 3.54-3.42 (1H, m), 2.90-2.81 (2H, m), 2.73-2.56 (6H, m), 2.18 (2H, m), 1.94-1.76 (6H, m). MS m/z (M + H): 502. |
| 0108 | | |
| 0108-1 | 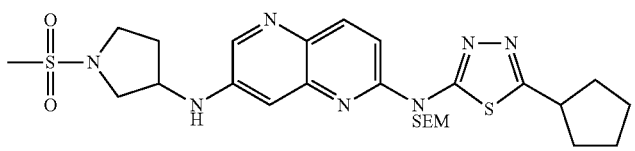 | MS m/z (M + H): 590. |

| Example No. | | |
|---|---|---|
| 0108-2 | 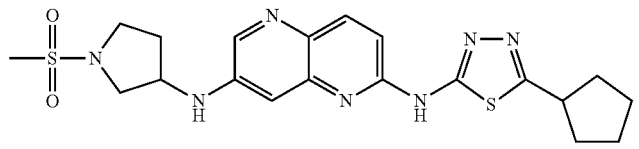 [SMILES: CS(=O)(=O)N1CCC(Nc2cnc3ccc(Nc4nnc(C5CCCC5)s4)nc3c2)C1] | $^1$H-NMR (DMSO-$d_6$) δ: 8.35 (1H, d, J = 2.7 Hz), 8.06 (1H, d, J = 8.7 Hz), 7.10 (1H, d, J = 8.7 Hz), 7.07 (1H, d, J = 2.7 Hz), 3.70-3.14 (6H, m), 2.93 (3H, s), 2.36-2.25 (2H, m), 2.21-2.08 (2H, m), 2.00-1.64 (6H, m). MS m/z (M + H): 460. |
| 0109 | | |
| 0109-1 | 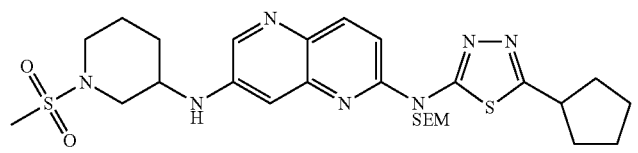 | MS m/z (M + H): 604. |
| 0109-2 | 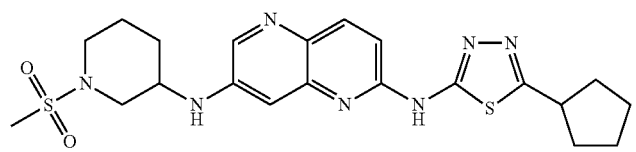 [SMILES: CS(=O)(=O)N1CCCC(Nc2cnc3ccc(Nc4nnc(C5CCCC5)s4)nc3c2)C1] | $^1$H-NMR (DMSO-$d_6$) δ: 8.37 (1H, d, J = 2.1 Hz), 8.04 (1H, d, J = 8.4 Hz), 7.10 (1H, d, J = 2.1 Hz), 7.08 (1H, d, J = 8.4 Hz), 3.77-3.24 (6H, m), 2.90 (3H, s), 2.19-1.43 (12H, m). MS m/z (M + H): 474. |

Example 0110

0110-1

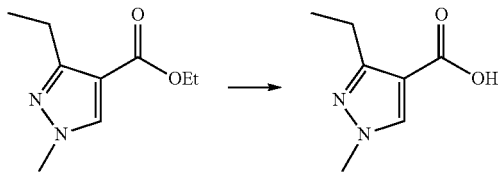

A 4 mol/L sodium hydroxide aqueous solution (2 mL) was added to a solution of ethyl 3-ethyl-1-methyl-1H-pyrazole-4-carboxylate (100 mg) in ethanol (2 mL), followed by stirring at room temperature for 3 hours, and stirring at 70° C. for 2 hours. After the reaction mixture was cooled to room temperature, the solvent was distilled off under reduced pressure, the resultant product was adjusted to pH 2 by the addition of 2 mol/L hydrochloric acid, and ethyl acetate was added thereto. The organic layer was collected by separation, washed with a saturated sodium chloride aqueous solution, and dried over anhydrous sodium sulfate. The solvent was distilled off under reduced pressure, thereby obtaining 3-ethyl-1-methyl-1H-pyrazole-4-carboxylic acid (71 mg).

MSm/z(M+H):155.

0110-2

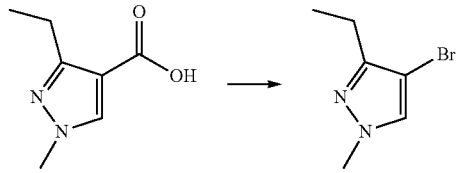

N-bromosuccinimide (90 mg) was added to a mixture of 3-ethyl-1-methyl-1H-pyrazole-4-carboxylic acid (71 mg), and sodium hydrogen carbonate (132 mg) in N,N-dimethylformamide (2.3 mL), followed by stirring at room temperature for 16 hours. Ethyl acetate and water were added to the reaction mixture. The organic layer was collected by separation, washed with a saturated sodium chloride aqueous solution, and dried over anhydrous sodium sulfate, and the solvent was distilled off under reduced pressure, thereby obtaining 4-bromo-3-ethyl-1-methyl-1H-pyrazole (74 mg).

MSm/z(M+H):189.

0110-3

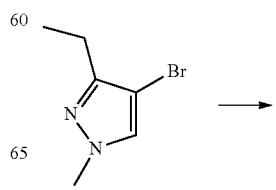

167

-continued

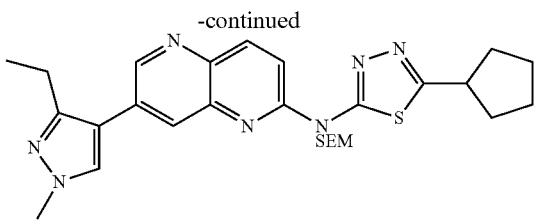

A mixture of N-(7-bromo-1,5-naphthyridin-2-yl)-5-cyclopentyl-N-((2-(trimethylsilyl)ethoxy)methyl)-1,3,4-thiadiazole-2-amine) (20 mg), bis(pinacolato)diboron (15 mg), (1,1'-bis(diphenylphosphino)ferrocene)palladium(II) dichloride (3 mg), and potassium acetate (8 mg) in 1,4-dioxane (0.8 mL) was stirred at 100° C. for 2 hours in a nitrogen atmosphere. 4-Bromo-3-ethyl-1-methyl-1H-pyrazole (14 mg), sodium carbonate (8 mg), and bis(di-tert-butyl (4-dimethylaminophenyl)phosphine)dichloropalladium(II) (5 mg) were added to the reaction mixture, followed by reacting at 100° C. for 5 hours. The reaction mixture was cooled to room temperature, and ethyl acetate and water were added thereto. The organic layer was collected by separation, washed with a saturated sodium chloride aqueous solution, and dried over anhydrous sodium sulfate, and the solvent was distilled off under reduced pressure, thereby obtaining 5-cyclopentyl-N-(7-(3-ethyl-1-methyl-1H-pyrazol-4-yl)-1,5-naphthyridin-2-yl)-N-((2-(trimethylsilyl)ethoxy)methyl)-1,3,4-thiadiazole-2-amine (33 mg).
MSm/z(M+H):536.

0110-4

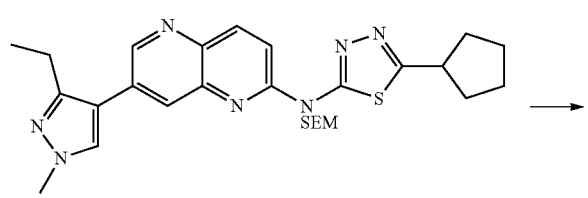

168

-continued

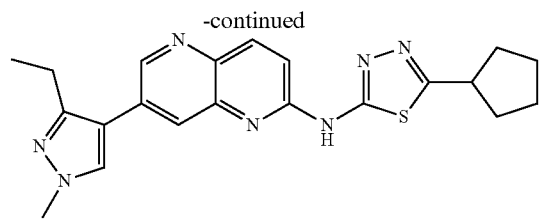

Water (0.1 mL) and trifluoroacetic acid (2 mL) were added to 5-cyclopentyl-N-(7-(3-ethyl-1-methyl-1H-pyrazol-4-yl)-1,5-naphthyridin-2-yl)-N-((2-(trimethylsilyl)ethoxy) methyl)-1,3,4-thiadiazole-2-amine (33 mg), followed by stirring at room temperature for 4 hours. The solvent was distilled off under reduced pressure, and the obtained residue was purified by silica gel column chromatography (methanol-ethyl acetate, NH silica), thereby obtaining 5-cyclopentyl-N-(7-(3-ethyl-1-methyl-1H-pyrazol-4-yl)-1,5-naphthyridin-2-yl)-1,3,4-thiadiazole-2-amine (10 mg).
¹H-NMR(CDCl₃/CD₃OD=4/1)δ:8.78(1H,d,J=2.1 Hz), 8.24(1H,d,J=9.0 Hz),8.18(1H,d,J=2.1 Hz),7.70(1H,s),7.36 (1H,d,J=9.0 Hz),3.54-3.42(1H,m),3.37(3H,s),2.89(2H,q,7.8 Hz),2.30-2.18(2H,m),1.94-1.72(6H,m). 1.31(3H,t,J=7.8 Hz).
MSm/z(M+H):406.

Example 0111

The following compounds were obtained in the same manner as in Examples 0110-3 and 0110-4.

| Example No. | | |
|---|---|---|
| 0111 | | |
| 0111-1 | 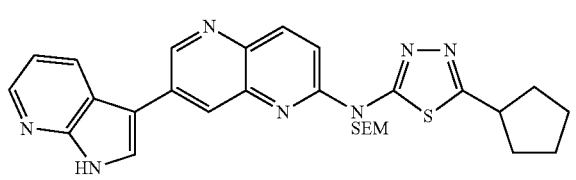 | MS m/z (M + H): 544. |
| 0111-2 | 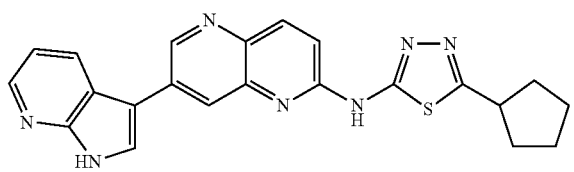 [SMILES: c1cnc2[nH]cc(-c3cnc4ccc(Nc5nnc(C6CCCC6)s5)nc4c3)c2c1] | ¹H-NMR (CDCl₃/CD₃OD = 4/1) δ: 9.07 (1H, d, J = 2.1 Hz), 8.46-8.34 (3H, m), 8.26 (1H, d, J = 9.0 Hz), 7.84 (1H, s), 7.35 (1H, d, J = 9.0 Hz), 7.33-7.27 (1H, m), 3.54-3.42 (1H, m), 2.30-2.18 (2H, m), 1.94-1.72 (6H, m). MS m/z (M + H): 414. |

Example 0112

0112-1 and 0112-2

The following compounds were obtained in the same manner as in Examples 0110-1 and 0110-2.

| Example No. | | |
|---|---|---|
| 0112 | | |
| 0112-1 | 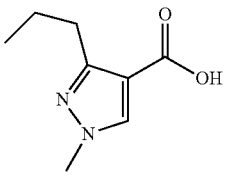 | MS m/z (M + H): 169. |

-continued

| Example No. | | |
|---|---|---|
| 0112-2 | 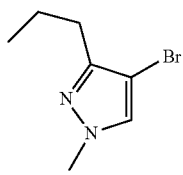 | MS m/z (M + H): 203. |

0112-3 and 0112-4

The following compounds were obtained in the same manner as in Examples 0110-3 and 0110-4.

| Example No. | | |
|---|---|---|
| 0112 | | |
| 0112-3 | 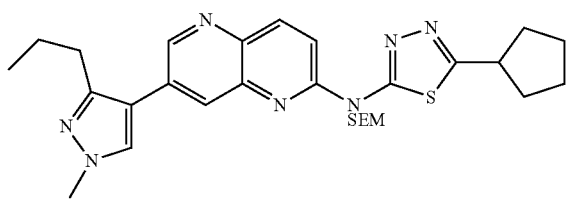 [SMILES: CCCc1nn(C)cc1-c1cnc2ccc(N(COCC[Si](C)(C)C)c3nnc(C4CCCC4)s3)nc2c1] | MS m/z (M + H): 550. |
| 0112-4 | 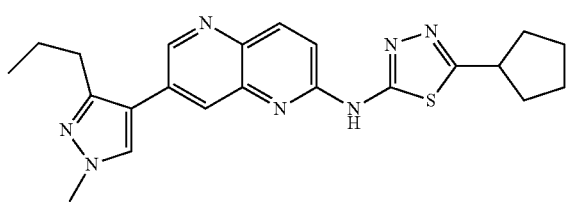 [SMILES: CCCc1nn(C)cc1-c1cnc2ccc(Nc3nnc(C4CCCC4)s3)nc2c1] | ¹H-NMR (CDCl₃/CD₃OD = 4/1) δ: 8.78 (1H, d, J = 2.1 Hz), 8.23 (1H, d, J = 8.7 Hz), 8.19 (1H, d, J = 2.1 Hz), 7.73 (1H, s), 7.35 (1H, d, J = 8.7 Hz), 3.95 (3H, s), 3.56-3.46 (1H, m), 2.87-2.80 (2H, m), 2.33-2.22 (4H, m), 1.98-1.66 (9H, m). MS m/z (M + H): 420. |

Example 0113

The following compounds were obtained in the same manner as in Examples 0110-3 and 0110-4.

| Example No. | | |
|---|---|---|
| 0113 | | |
| 0113-1 | 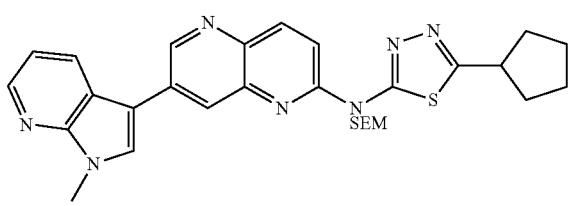 [SMILES: Cn1cc(-c2cnc3ccc(N(COCC[Si](C)(C)C)c4nnc(C5CCCC5)s4)nc3c2)c2cccnc21] | MS m/z (M + H): 558. |
| 0113-2 | 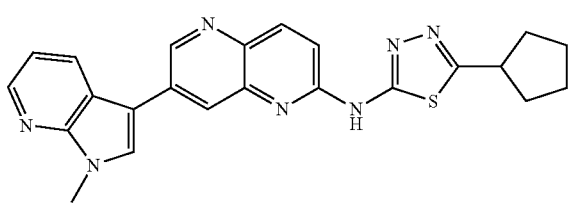 [SMILES: Cn1cc(-c2cnc3ccc(Nc4nnc(C5CCCC5)s4)nc3c2)c2cccnc21] | ¹H-NMR (CDCl₃/CD₃OD = 4/1) δ: 9.05 (1H, d, J = 2.1 Hz), 8.45-8.23 (4H, m), 7.76 (1H, s), 7.37-7.22 (2H, m), 4.03 (1H, s), 3.54-3.42 (1H, m), 2.30-2.18 (2H, m), 1.94-1.72 (6H, m). MS m/z (M + H): 428. |

Example 0114

The following compounds were obtained in the same manner as in Examples 0110-1 to 0110-4.

| Example No. | | |
|---|---|---|
| 0114 | | |
| 0114-1 | 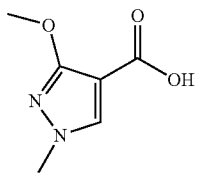 | MS m/z (M + H): 157. |
| 0114-2 | 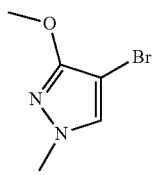 | MS m/z (M + H): 191. |
| 0114-3 | 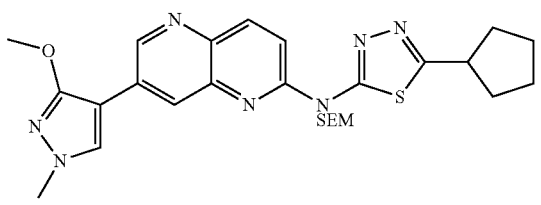 [SMILES: COc1nn(C)cc1-c1cnc2ccc(N(COCC[Si](C)(C)C)c3nnc(C4CCCC4)s3)nc2c1] | MS m/z (M + H): 538. |
| 0114-4 | 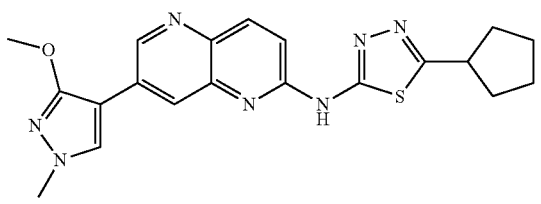 [SMILES: COc1nn(C)cc1-c1cnc2ccc(Nc3nnc(C4CCCC4)s3)nc2c1] | $^1$H-NMR (CDCl$_3$/CD$_3$OD = 4/1) δ: 8.60 (1H, brs), 8.40 (1H, brs), 8.33 (1H, d, J = 9.0 Hz), 7.81 (1H, s), 7.27 (1H, d, J = 9.0 Hz), 4.16 (3H, s), 3.87 (3H, s), 3.54-3.42 (1H, m), 2.30-2.18 (2H, m), 1.94-1.72 (6H, m). MS m/z (M + H): 408. |

Example 0115

0115-1

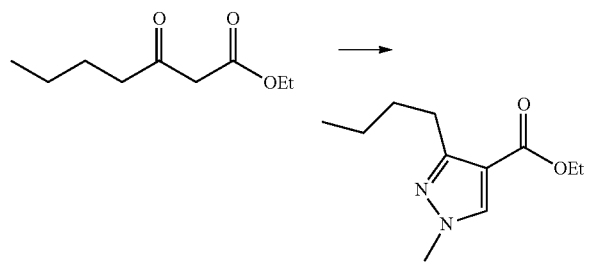

A solution of methylhydrazine (0.37 mL) and ethyl formate (0.90 mL) in ethanol (3.5 mL) was stirred for 4 hours under heating to reflux, and ethyl 3-oxoheptanoate (2.4 mL) was added thereto, followed by stirring at the same temperature for 4 hours. The reaction mixture was cooled to room temperature, and a 20% sodium ethoxide-ethanol solution (3.5 mL) was added thereto, followed by stirring for 1.5 hours under heating to reflux. The reaction mixture was cooled to room temperature, and ethyl acetate and a 3 mol/L potassium hydrogen sulfate aqueous solution were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining ethyl 3-butyl-1-methyl-1H-pyrazole-4-carboxylate (669 mg).

MS m/z(M+H):211.

0115-2 to 0115-5

The following compounds were obtained in the same manner as in Examples 0110-1 to 0110-4.

| Example No. | | |
|---|---|---|
| 0115 | | |
| 0115-2 | 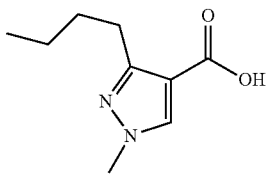 | MS m/z (M + H): 183. |
| 0115-3 | 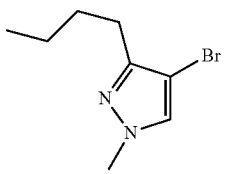 | MS m/z (M + H): 217. |
| 0115-4 | 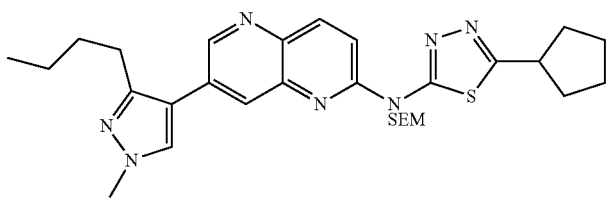 [SMILES: CCCCc1nn(C)cc1-c1cnc2ccc(N(COCC[Si](C)(C)C)c3nnc(C4CCCC4)s3)nc2c1] | MS m/z (M + H): 564. |
| 0115-5 | 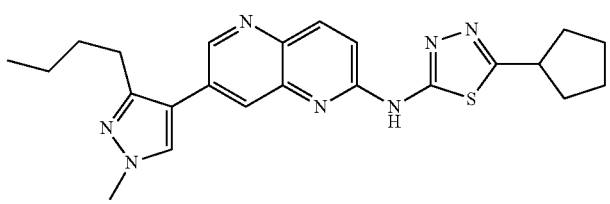 [SMILES: CCCCc1nn(C)cc1-c1cnc2ccc(Nc3nnc(C4CCCC4)s3)nc2c1] | $^1$H-NMR (CDCl$_3$/CD$_3$OD = 4/1) δ: 8.78 (1H, brs), 8.24 (1H, d, J = 9.0 Hz), 8.20 (1H, brs), 7.73 (1H, s), 7.35 (1H, d, J = 9.0 Hz), 3.95 (3H, s), 3.57-3.42 (1H, m), 2.90-2.82 (2H, m), 2.33-2.21 (2H, m), 1.96-1.63 (8H, m), 1.52-1.48 (2H, m), 0.95 (3H, t, J = 7.2 Hz). MS m/z (M + H): 434. |

Example 0116

0116-1

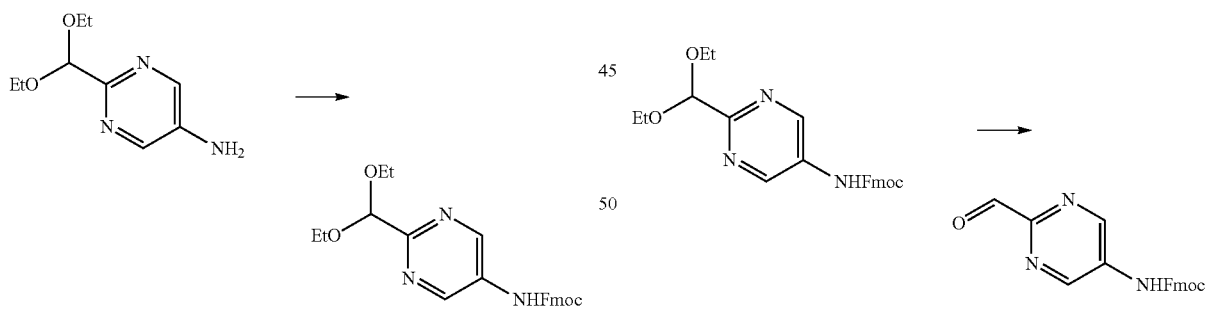

A solution of (9H-fluoren-9-ylmethoxy)carbonyl chloride (826 mg) in 1,4-dioxane (4 mL) was added to a mixture of 2-(diethoxymethyl)pyrimidine-5-amine (629 mg), and sodium hydrogen carbonate (800 mg) in 1,4-dioxane (4 mL), and water (4 mL) at room temperature, followed by stirring at the same temperature for 3 hours. Ethyl acetate and water were added to the reaction mixture. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 9H-fluoren-9-yl)methyl (2-(diethoxymethyl)pyrimidin-5-yl)carbamate (810 mg).
MSm/z(M+H):420.

0116-2

1 mol/L hydrochloric acid was added to a solution of (9H-fluoren-9-yl)methyl (2-(diethoxymethyl)pyrimidin-5-yl)carbamate (810 mg) in acetone (2.4 mL), followed by stirring at room temperature for 2 hours, and (+)-10-camphorsulfonic acid (66 mg) was added thereto, followed by stirring at the same temperature for 1 hour. Ethyl acetate and water were added to the reaction mixture. The organic layer was collected by separation, washed with a saturated sodium chloride aqueous solution, and dried over anhydrous sodium sulfate, and the solvent was distilled off under reduced pressure, thereby obtaining (9H-fluoren-9-yl)methyl (2-formylpyrimidin-5-yl)carbamate (99 mg).
MSm/z(M+H):346.

0116-3

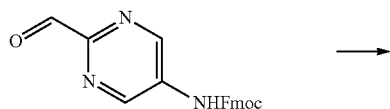 

carbamate (89 mg) in dichloromethane (2 mL), followed by stirring at room temperature for 14 hours. The solvent was distilled off under reduced pressure, and the obtained residue was purified by silica gel column chromatography (methanol-ethyl acetate, NH silica), thereby obtaining 2-(morpholinomethyl)pyrimidine-5-amine (30 mg).

MSm/z(M+H):195.

0116-5 and 0116-6

The following compounds were obtained in the same manner as in Examples 0046-1 and 0046-2.

| Example No. | | |
|---|---|---|
| 0116 | | |
| 0116-5 | 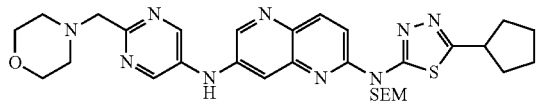 [SMILES: C[Si](C)(C)CCOCN(c1ccc2ncc(Nc3cnc(CN4CCOCC4)nc3)cc2n1)c1nnc(C2CCCC2)s1] | MS m/z (M + H): 620. |
| 0116-6 | 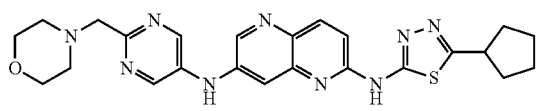 [SMILES: c1nc(CN2CCOCC2)ncc1Nc1cnc2ccc(Nc3nnc(C4CCCC4)s3)nc2c1] | $^1$H-NMR (CDCl$_3$/CD$_3$OD = 4/1) δ: 8.77 (2H, s), 8.49 (1H, brs), 8.12 (1H, d, J = 9.0 Hz), 7.85 (1H, m), 7.19 (1H, d, J = 9.0 Hz), 3.84-3.78 (4H, m) 3.39-3.34 (2H, s), 2.69-2.63 (4H, m) 3.54-3.42 (1H, m), 2.30-2.18 (2H, m) 1.94-1.72 (6H, m). MS m/z (M + H): 490. |

-continued

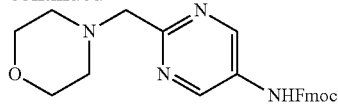

Morpholine (0.037 mL), sodium triacetoxyborohydride (150 mg), and acetic acid (0.024 mL) were added to a solution of (9H-fluoren-9-yl)methyl (2-formylpyrimidin-5-yl)carbamate (99 mg) in dichloromethane (2.8 mL), followed by stirring at room temperature for 1 hour. Ethyl acetate and a saturated sodium hydrogen carbonate aqueous solution were added to the reaction mixture. The organic layer was collected by separation, washed with a saturated sodium chloride aqueous solution, and dried over anhydrous sodium sulfate, and the solvent was distilled off under reduced pressure. The obtained residue was purified by silica gel column chromatography (methanol-ethyl acetate), thereby obtaining (9H-fluoren-9-yl)methyl (2-(morpholinomethyl)pyrimidin-5-yl)carbamate (89 mg).

MSm/z(M+H):417.

0116-4

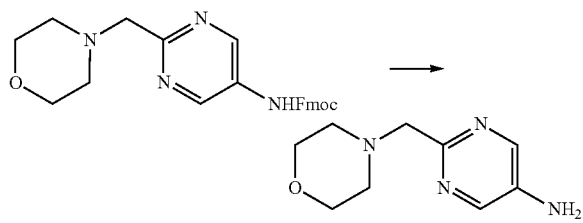

Diethylamine (1 mL) was added to a solution of (9H-fluoren-9-yl)methyl (2-(morpholinomethyl)pyrimidin-5-yl)

Example 0117

0117-1

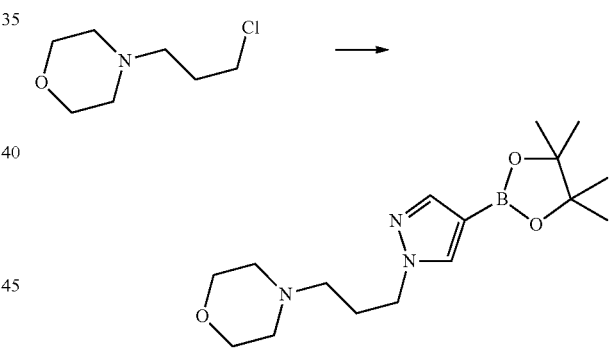

A mixture of 4-(3-chloropropyl)morpholine (648 mg), 4-(4,4,5,5-tetramethyl-1,3,2-dioxaborolan-2-yl)-1H-pyrazole (500 mg), cesium carbonate (837 mg), and sodium iodide (77 mg) in acetonitrile (3 mL) and tetrahydrofuran (1 mL) was stirred at 80° C. for 18 hours. The reaction mixture was cooled to room temperature, and the solvent was distilled off under reduced pressure. The obtained residue was purified by silica gel column chromatography (methanol-ethyl acetate, NH silica), thereby obtaining 4-(3-(4-(4,4,5,5-tetramethyl-1,3,2-dioxaborolan-2-yl)-1H-pyrazol-1-yl)propyl)morpholine (485 mg).

$^1$H-NMR(CDCl$_3$)δ:7.78(1H,s),7.68(1H,s),4.19(2H,t,J=6.6 Hz),3.76-3.66(4H,m),3.70(2H,t,J=4.8 Hz),2.45-2.35 (4H,m),2.10-1.98(2H,m),1.31(12H,s).

0117-2 and 0117-3

The following compounds were obtained in the same manner as in Examples 0001-4 and 0001-5.

| Example No. | | |
|---|---|---|
| 0117 | | |
| 0117-2 | 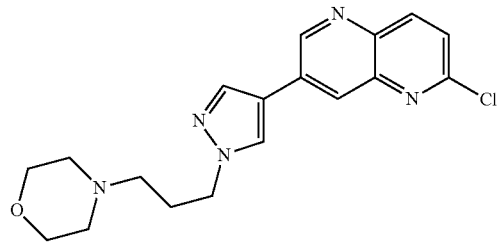 [SMILES: Clc1ccc2ncc(-c3cnn(CCCN4CCOCC4)c3)cc2n1] | MS m/z (M + H): 358. |
| 0117-3 | 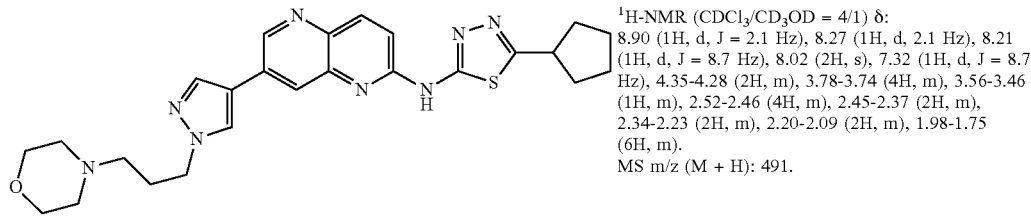 | ¹H-NMR (CDCl₃/CD₃OD = 4/1) δ: 8.90 (1H, d, J = 2.1 Hz), 8.27 (1H, d, 2.1 Hz), 8.21 (1H, d, J = 8.7 Hz), 8.02 (2H, s), 7.32 (1H, d, J = 8.7 Hz), 4.35-4.28 (2H, m), 3.78-3.74 (4H, m), 3.56-3.46 (1H, m), 2.52-2.46 (4H, m), 2.45-2.37 (2H, m), 2.34-2.23 (2H, m), 2.20-2.09 (2H, m), 1.98-1.75 (6H, m). MS m/z (M + H): 491. |

Examples 0118 and 0119

The following compounds were obtained in the same manner as in Example 0001-5.

| Example No. | | |
|---|---|---|
| 0118 | | |
| 0118-1 | 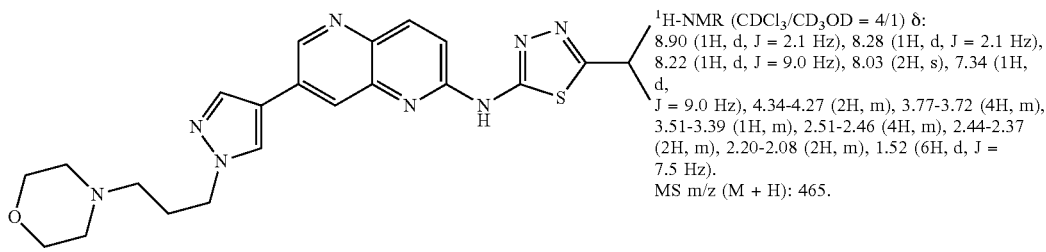 | ¹H-NMR (CDCl₃/CD₃OD = 4/1) δ: 8.90 (1H, d, J = 2.1 Hz), 8.28 (1H, d, J = 2.1 Hz), 8.22 (1H, d, J = 9.0 Hz), 8.03 (2H, s), 7.34 (1H, d, J = 9.0 Hz), 4.34-4.27 (2H, m), 3.77-3.72 (4H, m), 3.51-3.39 (1H, m), 2.51-2.46 (4H, m), 2.44-2.37 (2H, m), 2.20-2.08 (2H, m), 1.52 (6H, d, J = 7.5 Hz). MS m/z (M + H): 465. |
| 0119 | | |
| 0119-1 | 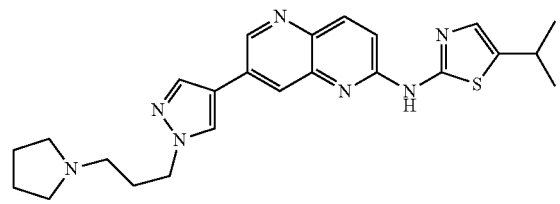 [SMILES: CC(C)c1cnc(Nc2ccc3ncc(-c4cnn(CCCN5CCCC5)c4)cc3n2)s1] | ¹H-NMR (CDCl₃/CD₃OD = 4/1): 8.86 (1H, brs), 8.29 (1H, brs), 8.15 (1H, d, J = 9.0 Hz), 8.04 (1H, s), 8.01 (1H, s), 7.26 (1H, d, J = 9.0 Hz), 7.09 (1H, s), 4.33-4.26 (2H, m), 3.27-3.15 (1H, m), 2.60-2.47 (4H, m), 2.23-2.11 (2H, m), 1.91-1.78 (6H, m), 1.42 (6H, d, J = 6.3 Hz). MS m/z (M + H): 448. |

Example 0120

0120-1

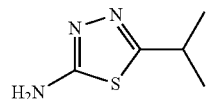 

-continued

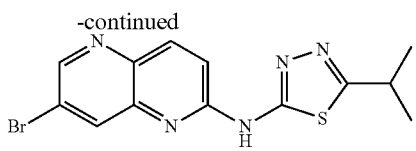

A mixture of 7-bromo-2-chloro-1,5-naphthyridine (2.01 g), 5-isopropyl-1,3,4-thiadiazole-2-amine (1.18 g), and potassium carbonate (1.71 g) in dimethylsulfoxide (16 mL) was stirred at 130° C. for 2 hours. After the obtained reaction mixture was cooled to room temperature, the solid matter was collected by filtration, thereby obtaining N-(7-bromo-1,5-naphthyridin-2-yl)-5-isopropyl-1,3,4-thiadiazole-2-amine (2.21 g).

MSm/z(M+H):351.

0120-2

(2-(Trimethylsilyl)ethoxy)methyl chloride (1.66 mL) was added to a solution of N-(7-bromo-1,5-naphthyridin-2-yl)-5-isopropyl-1,3,4-thiadiazole-2-amine (2.21 g) in N-methylpyrrolidone (60 mL), followed by stirring for 15 minutes under ice-cooling, and 60% sodium hydride (505 mg) was added thereto, followed by stirring at the same temperature for 2 hours. Ethyl acetate and water were added to the reaction mixture. The organic layer was collected by separation, washed sequentially with water and a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining N-(7-bromo-1,5-naphthyridin-2-yl)-5-isopropyl-N-((2-(trimethylsilyl)ethoxy)methyl)-1,3,4-thiadiazole-2-amine (1.71 g).

MSm/z(M+H):480.

0120-3 and 0120-4

The following compounds were obtained in the same manner as in Examples 0110-3 and 0110-4.

Example No.

0120

0120-3  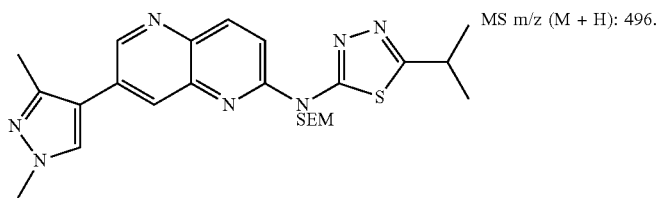  MS m/z (M + H): 496.

0120-4  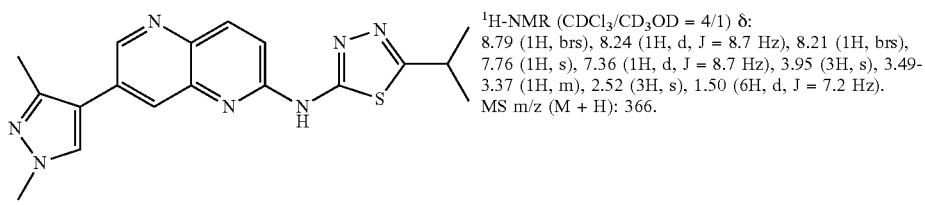  ¹H-NMR (CDCl₃/CD₃OD = 4/1) δ:
8.79 (1H, brs), 8.24 (1H, d, J = 8.7 Hz), 8.21 (1H, brs), 7.76 (1H, s), 7.36 (1H, d, J = 8.7 Hz), 3.95 (3H, s), 3.49-3.37 (1H, m), 2.52 (3H, s), 1.50 (6H, d, J = 7.2 Hz).
MS m/z (M + H): 366.

Examples 0121 and 0122

The following compounds were obtained in the same manner as in Examples 0110-3 and 0110-4.

Example No.

0121

0121-1  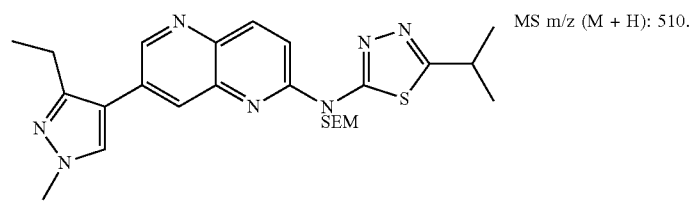  MS m/z (M + H): 510.

| Example No. | | |
|---|---|---|
| 0121-2 | 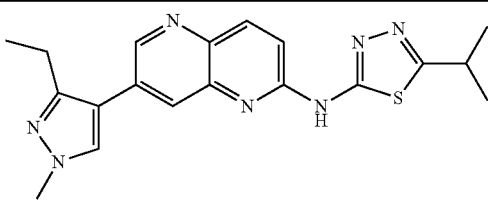 | ¹H-NMR (CDCl₃/CD₃OD = 4/1):<br>8.78 (1H, d, J = 2.1 Hz), 8.24 (1H, d, J = 8.7 Hz), 8.20 (1H, d, J = 2.1 Hz), 7.71 (1H, s), 7.37 (1H, d, J = 8.7 Hz), 3.96 (3H, s), 3.49-336 (1H, m), 2.90 (2H, d, J = 7.8 Hz), 1.50 (6H, d, J = 6.6 Hz), 1.31 (3H, t, J = 7.8 Hz).<br>MS m/z (M + H): 380. |
| 0122 | | |
| 0122-1 | 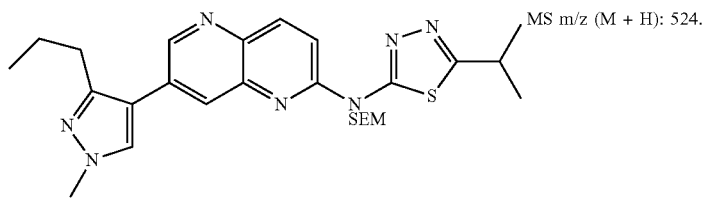 | MS m/z (M + H): 524. |
| 0122-2 | 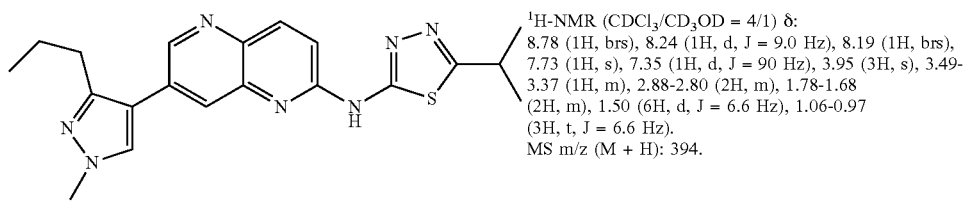 | ¹H-NMR (CDCl₃/CD₃OD = 4/1) δ:<br>8.78 (1H, brs), 8.24 (1H, d, J = 9.0 Hz), 8.19 (1H, brs), 7.73 (1H, s), 7.35 (1H, d, J = 90 Hz), 3.95 (3H, s), 3.49-3.37 (1H, m), 2.88-2.80 (2H, m), 1.78-1.68 (2H, m), 1.50 (6H, d, J = 6.6 Hz), 1.06-0.97 (3H, t, J = 6.6 Hz).<br>MS m/z (M + H): 394. |

Example 0123

0123-1

¹H-NMR(CDCl₃/CD₃OD=4/1)δ:8.85(1H,brs),8.29(1H,brs),8.14(1H,d,J=8.7 Hz),8.00(1H,s),7.98(1H,s),7.26(1H,d,J=8.7 Hz),7.08(1H,s),3.36(3H,s),3.25-3.15(1H,m),1.42(6H,d,J=6.6 Hz).

MSm/z(M+H):351.

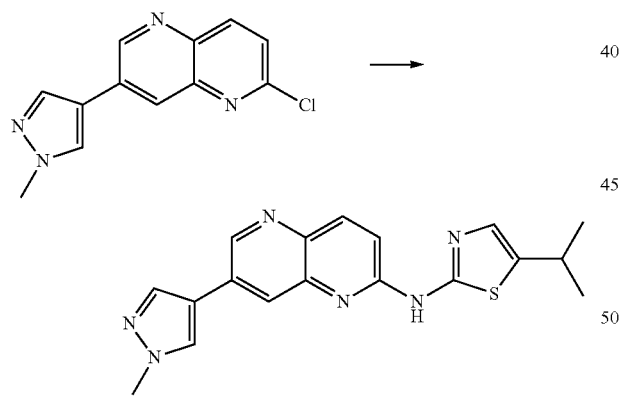

A mixture of 2-chloro-7-(1-methyl-1H-pyrazol-4-yl)-1,5-naphthyridine (14 mg), 5-isopropylthiazole-2-amine (10 mg), tris(dibenzylideneacetone)dipalladium(0) (5 mg), 4,5-bis(diphenylphosphino)-9,9-dimethylxanthene (7 mg), and cesium carbonate (48 mg) in 1,4-dioxane (1 mL) was stirred at 150° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining 5-isopropyl-N-(7-(1-methyl-1H-pyrazol-4-yl)-1,5-naphthyridin-2-yl)thiazole-2-amine (3.8 mg).

Example 0124

0124-1

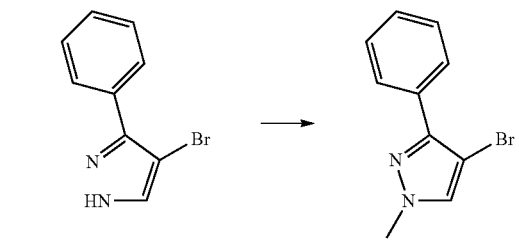

60% sodium hydride (516 mg) was added to a solution of 4-bromo-3-phenyl-1H-pyrazole (1.44 g) and iodomethane (0.80 mL) in N-methylpyrrolidone (13 mL) under ice-cooling, followed by stirring at the same temperature for 1.5 hours. Ethyl acetate and water were added to the reaction mixture at the same temperature. The organic layer was collected by separation, washed with a saturated sodium chloride aqueous solution, and dried over anhydrous sodium sulfate, and the solvent was distilled off under reduced pressure, thereby obtaining 4-bromo-1-methyl-3-phenyl-1H-pyrazole (811 mg).

MSm/z(M+H):237,239.

0124-2

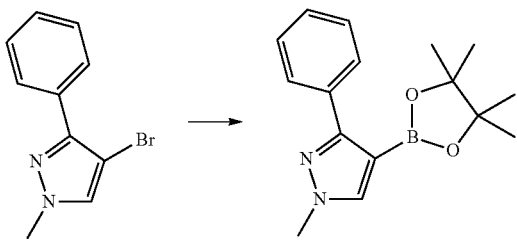 [SMILES: Cn1cc(Br)c(-c2ccccc2)n1 ; Cn1cc(B2OC(C)(C)C(C)(C)O2)c(-c2ccccc2)n1]

A 1.6 mol/L n-butyllithium-hexane solution (1.2 mL) was added to a solution of 4-bromo-1-methyl-3-phenyl-1H-pyrazole (300 mg) in tetrahydrofuran (6 mL) at −80° C., followed by stirring at the same temperature for 30 minutes, and 2-isopropyloxy-4,4,5,5-tetramethyl-1,3,2-dioxaborolane (470 mg) was added thereto at the same temperature, followed by stirring while heating to room temperature over a period of 4 hours. A saturated ammonium chloride aqueous solution and ethyl acetate were added to the reaction mixture. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 1-methyl-3-phenyl-4-(4,4,5,5-tetramethyl-1,3,2-dioxaborolan-2-yl)-1H-pyrazole (184 mg).

MSm/z(M+H):285.

0124-3

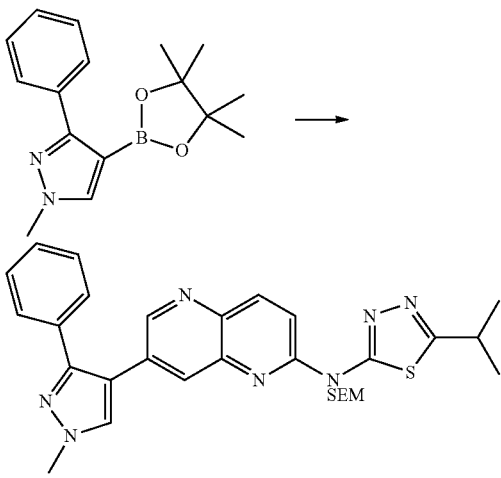

A mixture of N-(7-bromo-1,5-naphthyridin-2-yl)-5-isopropyl-N-((2-(trimethylsilyl)ethoxy)methyl)-1,3,4-thiadiazole-2-amine (20 mg), 1-methyl-3-phenyl-4-(4,4,5,5-tetramethyl-1,3,2-dioxaborolan-2-yl)-1H-pyrazole (15 mg), sodium carbonate (8 mg), bis(di-tert-butyl(4-dimethylaminophenyl)phosphine)dichloropalladium (II) (5 mg), and water (0.1 mL) in 1,4-dioxane (1 mL) was stirred at 100° C. for 2 hours. The reaction mixture was cooled to room temperature, and ethyl acetate and water were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (methanol-ethyl acetate-hexane), thereby obtaining 5-isopropyl-N-(7-(1-methyl-3-phenyl-1H-pyrazol-4-yl)-1,5-naphthyridin-2-yl)-N-((2-(trimethylsilyl)ethoxy)methyl)-1,3,4-thiadiazole-2-amine (11 mg).

MSm/z(M+H):558.

0124-4

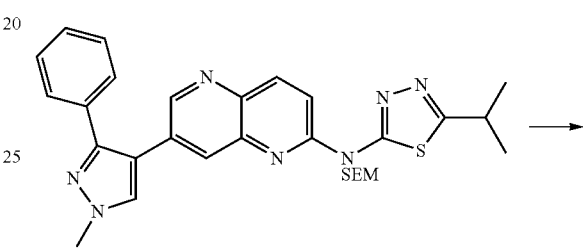

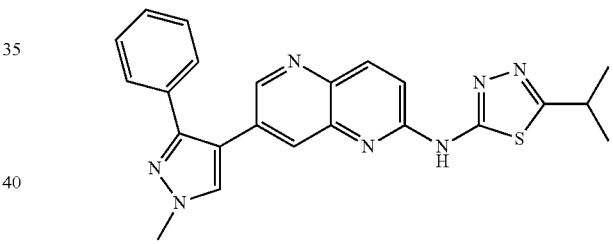

Water (0.1 mL) and trifluoroacetic acid (2 mL) were added to 5-isopropyl-N-(7-(1-methyl-3-phenyl-1H-pyrazol-4-yl)-1,5-naphthyridin-2-yl)-N-((2-(trimethylsilyl)ethoxy)methyl)-1,3,4-thiadiazole-2-amine (11 mg), followed by stirring at room temperature for 1 hour. The solvent was distilled off under reduced pressure, and the obtained residue was purified by silica gel column chromatography (methanol-ethyl acetate, NH silica), thereby obtaining 5-isopropyl-N-(7-(1-methyl-3-phenyl-1H-pyrazol-4-yl)-1,5-naphthyridin-2-yl)-1,3,4-thiadiazole-2-amine (5.2 mg).

$^1$H-NMR(CDCl$_3$/CD$_3$OD=4/1)δ:8.59(1H,brs),8.18(1H,d,J=8.7 Hz),8.13(1H,brs),7.84(1H,s),7.56-7.24(6H,m),3.47-3.34(1H,m),3.36(3H,s),1.48(6H,d,J=7.2 Hz).

MSm/z(M+H):428.

Example 0125

The following compounds were obtained in the same manner as in Examples 0110-1 to 0110-4.

| Example No. | | |
|---|---|---|
| 0125 | | |
| 0125-1 | 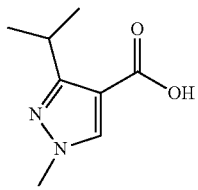 | MS m/z (M + H): 169. |
| 0125-2 | 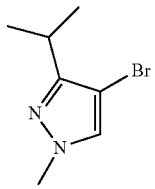 | MS m/z (M + H): 203, 205. |
| 0125-3 | 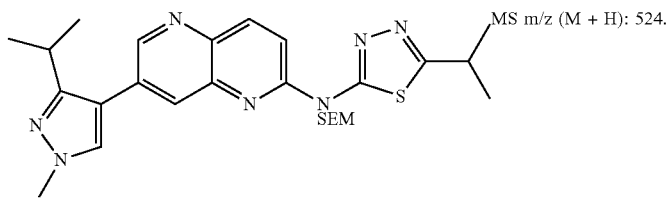 | MS m/z (M + H): 524. |
| 0125-4 | 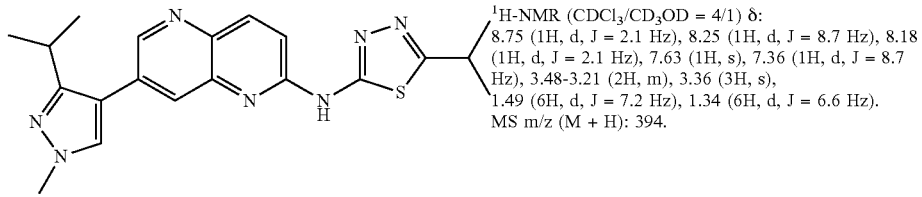 | $^1$H-NMR (CDCl$_3$/CD$_3$OD = 4/1) δ: 8.75 (1H, d, J = 2.1 Hz), 8.25 (1H, d, J = 8.7 Hz), 8.18 (1H, d, J = 2.1 Hz), 7.63 (1H, s), 7.36 (1H, d, J = 8.7 Hz), 3.48-3.21 (2H, m), 3.36 (3H, s), 1.49 (6H, d, J = 7.2 Hz), 1.34 (6H, d, J = 6.6 Hz). MS m/z (M + H): 394. |

Example 0126

0126-1

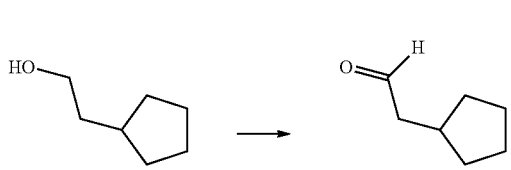 [SMILES: OCCC1CCCC1 ; O=CCC1CCCC1]

A 6% sodium hypochlorite aqueous solution (7 mL) was added to a mixture of 2-cyclopentylethanol (1.4 g), sodium hydrogen carbonate (3.1 g), and 4-hydroxy-2,2,6,6-tetramethylpiperidine-1-oxyl free radical (19 mg) in toluene (20 mL), ethyl acetate (20 mL) and water (3.5 mL) under ice-cooling, followed by stirring at the same temperature for 10 minutes. A 3 mol/L potassium hydrogen sulfate aqueous solution (10 mL), potassium iodide (120 mg), and ethyl acetate were added to the reaction mixture. The organic layer was collected by separation, washed with a saturated sodium chloride aqueous solution, and dried over anhydrous sodium sulfate, and the solvent was distilled off under reduced pressure, thereby obtaining 2-cyclopentyl acetaldehyde (2.5 g).

$^1$H-NMR(CDCl$_3$)δ:9.75(1H,t,J=1.8 Hz),2.44(2H,dd, J=7.2 Hz,1.8 Hz),2.34-2.19(1H,m),1.92-1.46(6H,m),1.22-1.05(2H,m).

0126-2

Trimethylphenylammonium tribromide (4.7 g) was added to a solution of 2-cyclopentyl acetaldehyde (2.5 g) in tetrahydrofuran (60 mL) under ice-cooling, followed by stirring while slowly heating to room temperature for 1 day. Ethyl acetate and water were added to the reaction mixture. The organic layer was collected by separation, washed sequentially with a 10% sodium hydrogen sulfite aqueous solution and a saturated sodium chloride aqueous solution, and dried over anhydrous sodium sulfate, and the solvent was distilled off under reduced pressure, thereby obtaining 2-bromo-2-cyclopentyl acetaldehyde (2.4 g).

$^1$H-NMR(CDCl$_3$):9.39(1H,d,J=3.9 Hz),3.73-3.64(1H,m), 2.03-1.46(7H,m),1.22-1.05(2H,m).

0126-3

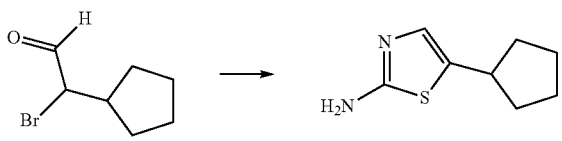 [SMILES: O=CC(Br)C1CCCC1 ; Nc1ncc(C2CCCC2)s1]

Thiourea (936 mg) was added to a solution of 2-bromo-2-cyclopentyl acetaldehyde (2.4 g) in ethanol (12 mL), followed by stirring for 4 hours under heating to reflux. The reaction mixture was cooled to room temperature, and ethyl acetate and water were added thereto. The organic layer was collected by separation, washed sequentially with a 4 mol/L sodium hydroxide aqueous solution and a saturated sodium chloride aqueous solution, and dried over anhydrous sodium sulfate, and the solvent was distilled off under reduced pressure. The obtained residue was purified by silica gel column chromatography (methanol-ethyl acetate), thereby obtaining 5-cyclopentylthiazole-2-amine (412 mg)

MS m/z (M+H): 169.

0126-4

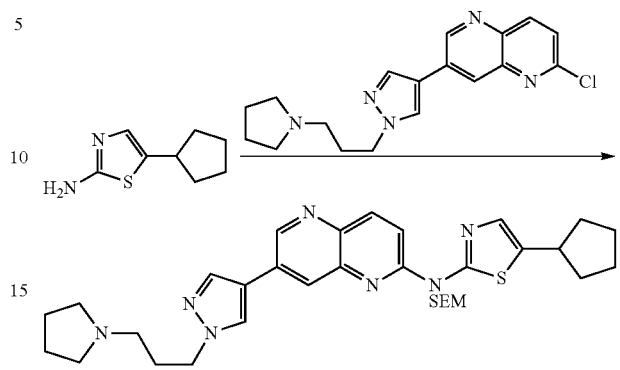

5-cyclopentyl-N-(7-(1-(3-(pyrrolidin-1-yl)propyl)-1H-pyrazol-4-yl)-1,5-naphthyridin-2-yl)thiazole-2-amine was obtained in the same manner as in Example 0001-5.

$^1$H-NMR(CDCl$_3$/CD$_3$OD=4/1)δ:8.86(1H,brs),8.28(1H,brs),8.14(1H,d,J=9.0 Hz),8.04(1H,s),8.01(1H,s),7.25(1H,d,J=9.0 Hz),7.09(1H,s),4.33-4.25(2H,m),3.30-3.19(1H,m),2.61-2.46(6H,m),2.24-2.11(4H,m),1.94-1.67(10H,m).

MS m/z (M+H): 474.

Examples 0127 and 0128

The following compounds were obtained in the same manner as in Example 0015-4.

| Example No. | | |
|---|---|---|
| 0127 | | |
| 0127-1 | 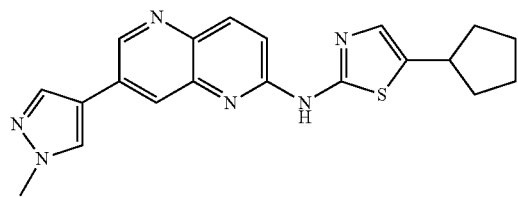 [SMILES: Cn1cc(-c2cnc3ccc(Nc4ncc(C5CCCC5)s4)nc3c2)cn1] | $^1$H-NMR (DMSO-d$_6$) δ: 11.57 (1H, brs), 9.02 (1H, d, J = 2.1 Hz), 8.52 (1H, s), 8.25 (1H, d, J = 2.1 Hz), 8.20 (1H, s), 8.17 (1H, d, J = 8.7 Hz), 7.35 (1H, d, J = 8.7 Hz), 7.18 (1H, s), 3.92 (3H, s), 3.44-3.35 (1H, m), 2.16-2.05 (2H, m), 1.84-1.58 (6H, m). MS m/z (M + H): 377. |
| 0128 | | |
| 0128-1 | 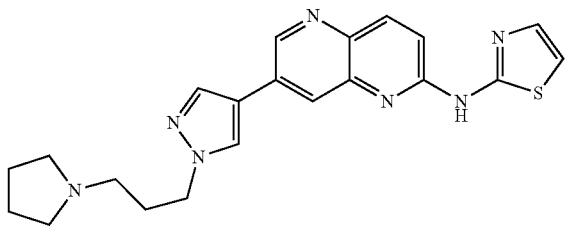 [SMILES: c1csc(Nc2ccc3ncc(-c4cnn(CCCN5CCCC5)c4)cc3n2)n1] | $^1$H-NMR (CDCl$_3$/CD$_3$OD = 4/1) δ: 8.88 (1H, brs), 8.31 (1H, brs), 8.17 (1H, d, J = 9.0 Hz), 8.04 (1H, s), 8.00 (1H, s), 7.45 (1H, d, J = 3.9 Hz), 7.30 (1H, d, J = 9.0 Hz), 6.97 (1H, d, J = 3.9 Hz), 4.33-4.26 (2H, m), 2.60-2.47 (6H, m), 2.23-2.11 (2H, m), 1.88-1.78 (4H, m). MS m/z (M + H): 406. |

Example 0129

0129-1

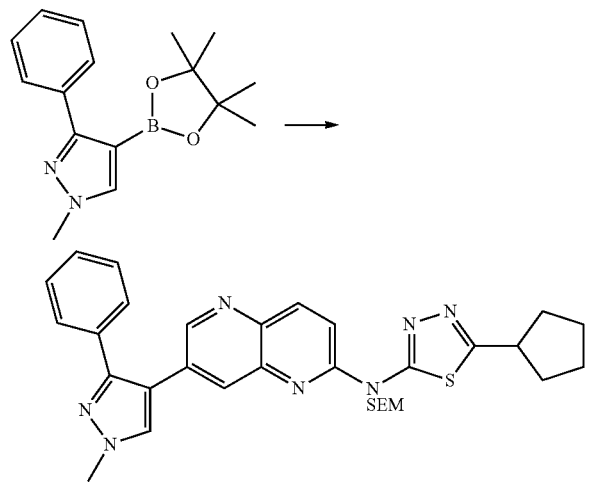

A mixture of N-(7-bromo-1,5-naphthyridin-2-yl)-5-cyclopentyl-N-((2-(trimethylsilyl)ethoxy)methyl)-1,3,4-thiadiazole-2-amine (10 mg), 1-methyl-3-phenyl-4-(4,4,5,5-tetramethyl-1,3,2-dioxaborolan-2-yl)-1H-pyrazole (8 mg), sodium carbonate (5 mg), bis(di-tert-butyl(4-dimethylaminophenyl)phosphine)dichloropalladium(II) (2 mg), and water (0.07 mL) in 1,4-dioxane (0.7 mL) was stirred at 100° C. for 6 hours. The reaction mixture was cooled to room temperature, the insolubles were filtered off using celite, and the solvent was distilled off under reduced pressure. The obtained residue was purified by silica gel column chromatography (ethyl acetate-hexane), thereby obtaining 5-cyclopentyl-N-(7-(1-methyl-3-phenyl-1H-pyrazol-4-yl)-1,5-naphthyridin-2-yl)-N-((2-(trimethylsilyl)ethoxy)methyl)-1,3,4-thiadiazole-2-amine (4.7 mg).

MSm/z(M+H):584.

0129-2

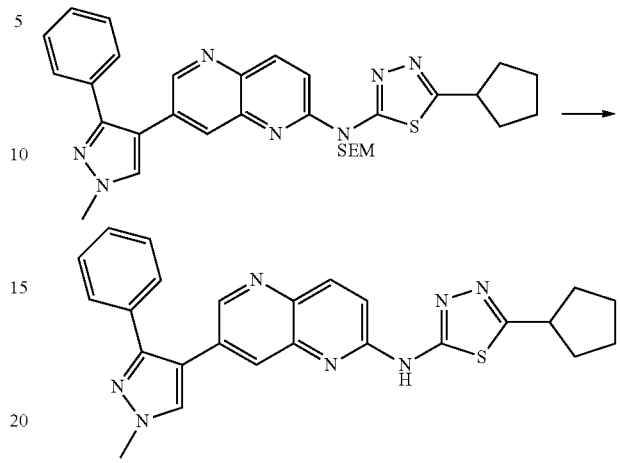

Water (0.1 mL) and trifluoroacetic acid (2 mL) were added to 5-cyclopentyl-N-(7-(1-methyl-3-phenyl-1H-pyrazol-4-yl)-1,5-naphthyridin-2-yl)-N-((2-(trimethylsilyl)ethoxy)methyl)-1,3,4-thiadiazole-2-amine (4.7 mg), followed by stirring at room temperature for 30 minutes. The solvent was distilled off under reduced pressure, and the obtained residue was purified by silica gel column chromatography (methanol-ethyl acetate, NH silica), thereby obtaining 5-cyclopentyl-N-(7-(1-methyl-3-phenyl-1H-pyrazol-4-yl)-1,5-naphthyridin-2-yl)-1,3,4-thiadiazole-2-amine (2.6 mg).

$^1$H-NMR(CDCl$_3$/CD$_3$OD=4/1)δ:8.59(1H,brs),8.18(1H,d, J=8.7 Hz),8.13(1H,brs),7.84(1H,s),7.56-7.24(6H,m),3.56-3.3.43(1H,m),3.36(3H,s),2.32-2.20(2H,m),1.96-1.74(6H, m).

MSm/z(M+H):454.

Examples 0130 and 0131

The following compounds were obtained in the same manner as in Examples 0110-3 and 0110-4.

| Example No. | | |
|---|---|---|
| 0130 | | |
| 0130-1 | 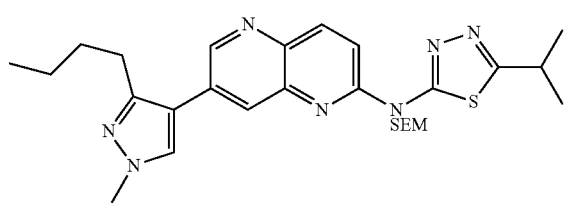 [SMILES: CCCCc1nn(C)cc1-c1cnc2ccc(N(COCC[Si](C)(C)C)c3nnc(C(C)C)s3)nc2c1] | MS m/z (M + H): 538. |
| 0130-2 | 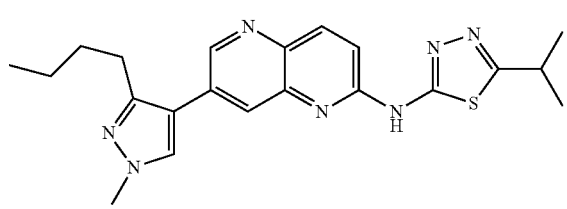 [SMILES: CCCCc1nn(C)cc1-c1cnc2ccc(Nc3nnc(C(C)C)s3)nc2c1] | $^1$H-NMR (CDCl$_3$/CD$_3$OD = 4/1) δ: 8.78 (1H, brs), 8.24 (1H, d, J = 9.0 Hz), 8.21 (1H, brs), 7.73 (1H, s), 7.36 (1H, d, J = 9.0 Hz), 3.47-3.38 (1H, m), 3.36 (3H, s), 2.91-2.84 (2H, m), 1.76-1.63 (2H, m), 1.51-1.40 (2H, m), 1.49 (6H, d, J = 6.6 Hz), 0.96 (3H, t, J = 7.2 Hz). MS m/z (M + H): 408. |

| Example No. | | |
|---|---|---|
| 0131 | | |
| 0131-1 | 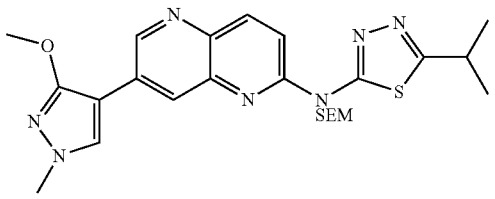 [SMILES: COc1nn(C)cc1-c1cnc2ccc(N(COCC[Si](C)(C)C)c3nnc(C(C)C)s3)nc2c1] | MS m/z (M + H): 512. |
| 0131-2 | 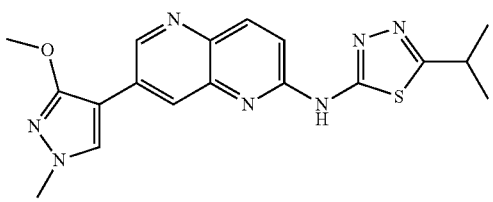 [SMILES: COc1nn(C)cc1-c1cnc2ccc(Nc3nnc(C(C)C)s3)nc2c1] | ¹H-NMR (CDCl₃/CD₃OD = 4/1) δ:<br>9.01 (1H, d, J = 1.8 Hz), 8.40 (1H, d, J = 1.8 Hz), 8.19 (1H, d, J = 9.0 Hz), 7.80 (1H, s), 7.30 (1H, d, J = 9.0 Hz),<br>4.09 (3H, s), 3.87 (3H, s), 3.50-3.38 (1H, m), 1.51 (6H, d, J = 6.6 Hz).<br>MS m/z (M + H): 382. |

Example 0132

0132-1

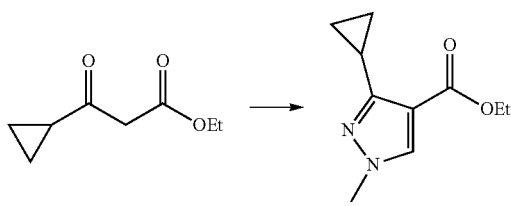

A solution of methylhydrazine (0.18 mL) and ethyl formate (0.45 mL) in ethanol (2 mL) was stirred for 4 hours under heating to reflux, and ethyl 3-cyclopropyl-3-oxopropanoate (1.0 g) was added thereto, followed by stirring at the same temperature for 4 hours. The reaction mixture was cooled to room temperature, and a 20% sodium ethoxide-ethanol solution (2 mL) was added thereto, followed by stirring for 1.5 hours under heating to reflux. The reaction mixture was cooled to room temperature, and ethyl acetate and a 3 mol/L potassium hydrogen sulfate aqueous solution were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining ethyl 3-cyclopropyl-1-methyl-1H-pyrazole-4-carboxylate (167 mg).

¹H-NMR(CDCl₃/CD₃OD=4/1):7.74(1H,s),4.29(2H,q,J=6.6 Hz),3.79(3H,s),2.56-2.46(1H,m),1.34(3H,t,J=6.6 Hz),1.00-0.87(4H,m).

0132-2 to 0132-5

The following compounds were obtained in the same manner as in Examples 0110-1 to 0110-4.

| Example No. | | |
|---|---|---|
| 0132 | | |
| 0132-2 | 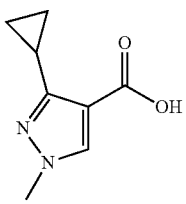 | MS m/z (M + H): 167. |
| 0132-3 | 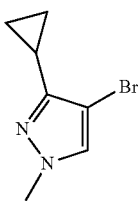 | MS m/z (M + H): 201, 203. |

| Example No. | | |
|---|---|---|
| 0132-4 | 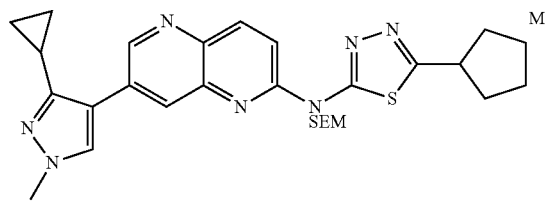 | MS m/z (M + H): 548. |
| 0132-5 | 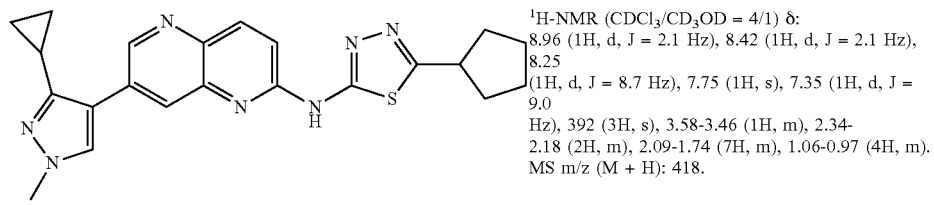 | ¹H-NMR (CDCl₃/CD₃OD = 4/1) δ: 8.96 (1H, d, J = 2.1 Hz), 8.42 (1H, d, J = 2.1 Hz), 8.25 (1H, d, J = 8.7 Hz), 7.75 (1H, s), 7.35 (1H, d, J = 9.0 Hz), 392 (3H, s), 3.58-3.46 (1H, m), 2.34-2.18 (2H, m), 2.09-1.74 (7H, m), 1.06-0.97 (4H, m). MS m/z (M + H): 418. |

Example 0133

The following compounds were obtained in the same manner as in Examples 0110-3 and 0110-4.

| Example No. | | |
|---|---|---|
| 0133 | | |
| 0133-1 | 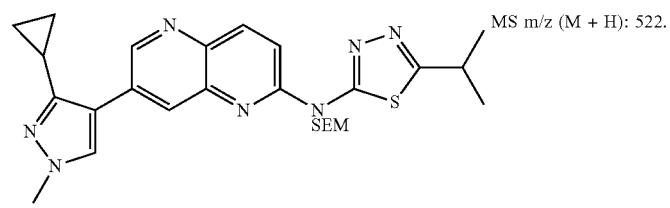 | MS m/z (M + H): 522. |
| 0133-2 | 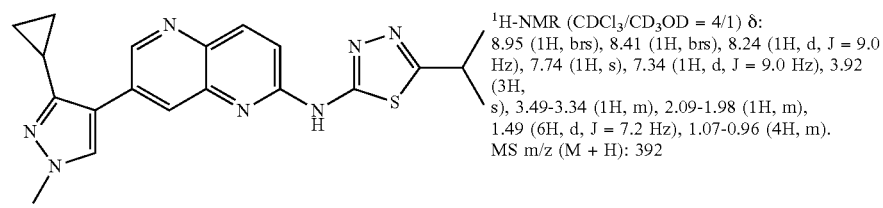 | ¹H-NMR (CDCl₃/CD₃OD = 4/1) δ: 8.95 (1H, brs), 8.41 (1H, brs), 8.24 (1H, d, J = 9.0 Hz), 7.74 (1H, s), 7.34 (1H, d, J = 9.0 Hz), 3.92 (3H, s), 3.49-3.34 (1H, m), 2.09-1.98 (1H, m), 1.49 (6H, d, J = 7.2 Hz), 1.07-0.96 (4H, m). MS m/z (M + H): 392 |

Example 0134

0134-1

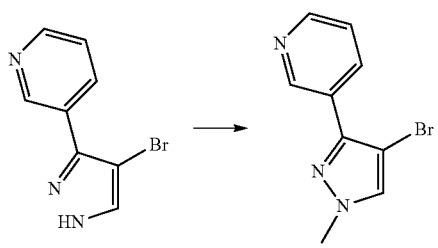

60% sodium hydride (412 mg) was added to a solution of 3-(4-bromo-1H-pyrazol-3-yl)pyridine (1.90 g) in N-methyl-pyrrolidone (7 mL) under ice-cooling, followed by stirring at the same temperature for 10 minutes, and iodomethane (0.64 mL) was added thereto, followed by stirring at the same temperature for 1 hour. Ethyl acetate and water were added to the reaction mixture. The organic layer was collected by separation, washed with a saturated sodium chloride aqueous solution, and dried over anhydrous sodium sulfate, and the solvent was distilled off under reduced pressure, thereby obtaining 3-(4-bromo-1-methyl-1H-pyrazol-3-yl)pyridine (284 mg).

MSm/z(M+H):238,240.

0134-2 and 0134-3

The following compounds were obtained in the same manner as in Examples 0110-3 and 0110-4.

| Example No. | | |
|---|---|---|
| 0134 | | |
| 0134-2 | 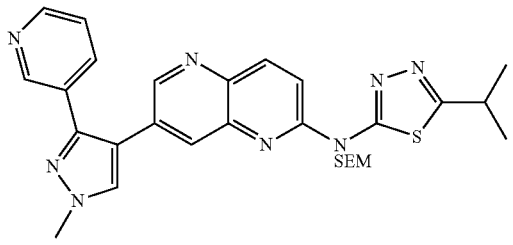 [SMILES: CC(C)c1nnc(N(COCC[Si](C)(C)C)c2ccc3ncc(-c4cn(C)nc4-c4cccnc4)cc3n2)s1] | MS m/z (M + H): 559. |
| 0134-3 | 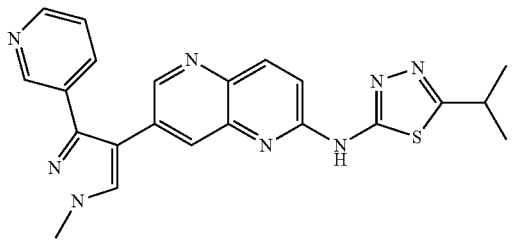 [SMILES: CN/C=C(\C(=N)c1cccnc1)c1cnc2ccc(Nc3nnc(C(C)C)s3)nc2c1] | ¹H-NMR (CDCl₃/CD₃OD = 4/1) δ: 8.73 (1H, d, J = 1.8 Hz), 8.57 (1H, d, J = 1.8 Hz), 8.55-8.52 (1H, m), 8.23 (1H, d, J = 9.0 Hz), 8.14 (1H, d, J = 2.1 hz), 7.86 (1H, s), 7.89-7.83 (1H, m), 7.41 (1H, d, J = 9.0 Hz), 7.40-7.34 (1H, m), 3.50-3.36 (1H, m), 3.37 (3H, s), 1.48 (6H, d, J = 7.2 Hz). MS m/z (M + H): 429. |

Example 0135

0135-1

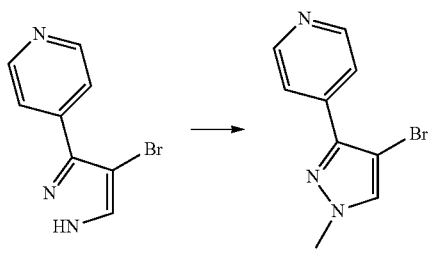

60% sodium hydride (412 mg) was added to a solution of 4-(4-bromo-1H-pyrazol-3-yl)pyridine (2.77 g) in N-methylpyrrolidone (7 mL) under ice-cooling, followed by stirring at the same temperature for 10 minutes, and iodomethane (0.64 mL) was added thereto, followed by stirring at the same temperature for 1 hour. Ethyl acetate and water were added to the reaction mixture. The organic layer was collected by separation, washed with a saturated sodium chloride aqueous solution, and dried over anhydrous sodium sulfate, and the solvent was distilled off under reduced pressure, thereby obtaining 4-(4-bromo-1-methyl-1H-pyrazol-3-yl)pyridine (177 mg).

MSm/z(M+H):238,240.

0135-2 and 0135-3

The following compounds were obtained in the same manner as in Examples 0110-3 and 0110-4.

| Example No. | | |
|---|---|---|
| 0135 | | |
| 0135-2 | 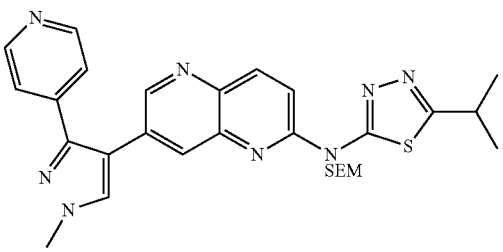 [SMILES: CN/C=C(\C(=N)c1ccncc1)c1cnc2ccc(N(COCC[Si](C)(C)C)c3nnc(C(C)C)s3)nc2c1] | MS m/z (M + H): 559. |

| Example No. | | |
|---|---|---|
| 0135-3 | 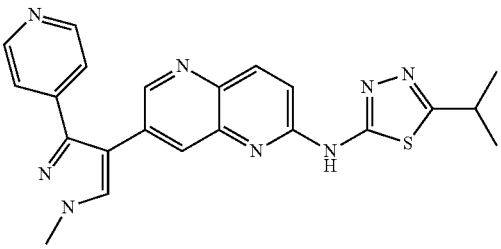 [SMILES: CN/C=C(\C(=N)c1ccncc1)c1cnc2ccc(Nc3nnc(C(C)C)s3)nc2c1] | $^1$H-NMR (CDCl$_3$/CD$_3$OD = 4/1) δ: 8.59 (1H, d, J = 2.1 Hz), 8.50 (2H, d, J = 6.0 Hz), 8.25 (1H, d, J = 9.0 Hz), 8.19 (1H, d, J = 2.1 Hz), 7.82 (1H, s), 7.49 (2H, d, J = 6.0 Hz), 7.38 (1H, d, J = 9.0 Hz), 3.47-3.36 (1H, m), 3.36 (3H, s), 1.47 (6H, d, J = 7.2 Hz). MS m/z (M + H): 429. |

Example 0136

0136-1

60% sodium hydride (412 mg) was added to a solution of 2-(4-bromo-1H-pyrazol-3-yl)pyridine (1.59 g) in N-methylpyrrolidone (7 mL) under ice-cooling, followed by stirring at the same temperature for 10 minutes, and iodomethane (0.64 mL) was added thereto, followed by stirring at the same temperature for 1 hour. Ethyl acetate and water were added to the reaction mixture. The organic layer was collected by separation, washed with a saturated sodium chloride aqueous solution, and dried over anhydrous sodium sulfate, and the solvent was distilled off under reduced pressure, thereby obtaining 2-(4-bromo-1-methyl-1H-pyrazol-3-yl)pyridine (770 mg).

MSm/z(M+H):238,240.

0136-2

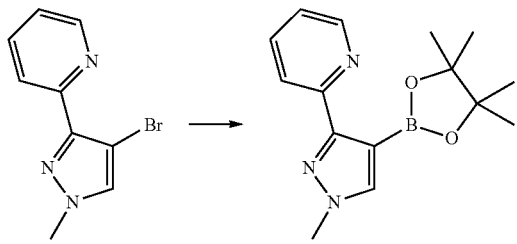 [SMILES: Cn1cc(Br)c(-c2ccccn2)n1 ; Cn1cc(B2OC(C)(C)C(C)(C)O2)c(-c2ccccn2)n1]

A 1.6 mol/L n-butyllithium-hexane solution (1.45 mL) was added to a solution of 2-(4-bromo-1-methyl-1H-pyrazol-3-yl)pyridine (370 mg) in tetrahydrofuran (8 mL) at −80° C., followed by stirring at the same temperature for 30 minutes, and 2-isopropyloxy-4,4,5,5-tetramethyl-1,3,2-dioxaborolane (576 mg) was added thereto at the same temperature, followed by stirring while slowly heating to room temperature over a period of 2.5 hours. A saturated ammonium chloride aqueous solution and ethyl acetate were added to the reaction mixture. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 2-(1-methyl-4-(4,4,5,5-tetramethyl-1,3,2-dioxaborolan-2-yl)-1H-pyrazol-3-yl)pyridine (20 mg).

$^1$H-NMR(CDCl$_3$/CD$_3$OD=4/1):8.54-8.51(1H,m),8.34-8.23(1H,m),7.84-7.78(1H,m),7.79(1H,s),7.30-7.25(1H,m),3.97(3H,s),1.56(12H,s).

0136-3

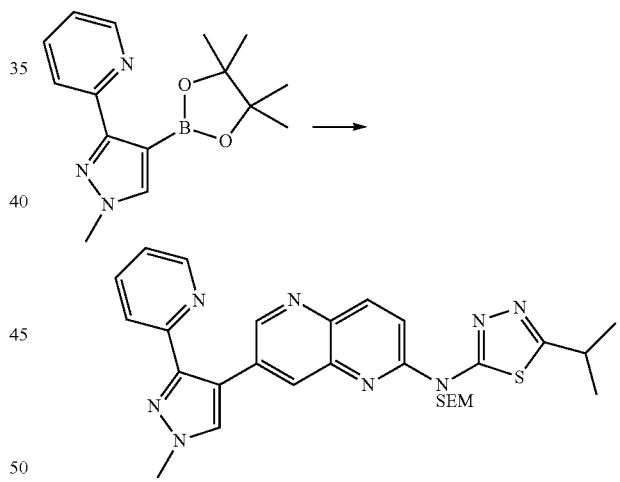

A mixture of N-(7-bromo-1,5-naphthyridin-2-yl)-5-isopropyl-N-((2-(trimethylsilyl)ethoxy)methyl)-1,3,4-thiadiazole-2-amine (20 mg), 2-(1-methyl-4-(4,4,5,5-tetramethyl-1,3,2-dioxaborolan-2-yl)-1H-pyrazol-3-yl)pyridine (15 mg), sodium carbonate (8 mg), bis(di-tert-butyl(4-dimethylaminophenyl)phosphine)dichloropalladium (II) (5 mg), and water (0.1 mL) in 1,4-dioxane (1 mL) was stirred at 100° C. for 2 hours. The reaction mixture was cooled to room temperature, the insolubles were filtered off using celite, and the solvent was distilled off under reduced pressure. The obtained residue was purified by silica gel column chromatography (methanol-ethyl acetate-hexane), thereby obtaining 5-isopropyl-N-(7-(1-methyl-3-(pyridin-2-yl)-1H-pyrazol-4-yl)-1,5-naphthyridin-2-yl)-N-((2-(trimethylsilyl)ethoxy)methyl)-1,3,4-thiadiazole-2-amine (12 mg).

MSm/z(M+H):559.

0136-4

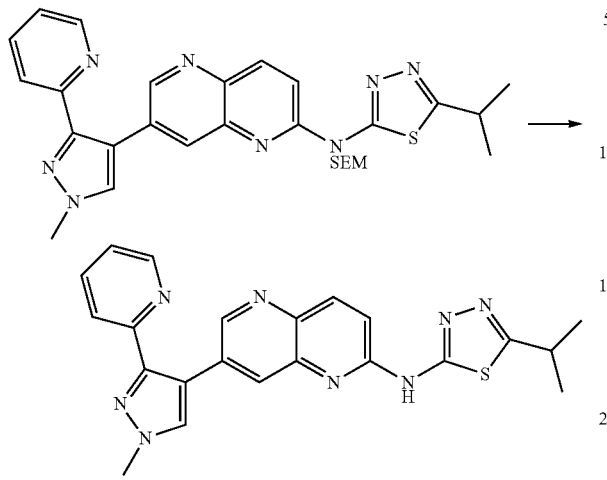

Water (0.1 mL) and trifluoroacetic acid (2 mL) were added to 5-isopropyl-N-(7-(1-methyl-3-(pyridin-2-yl)-1H-pyrazol-4-yl)-1,5-naphthyridin-2-yl)-N-((2-(trimethylsilyl)ethoxy)methyl)-1,3,4-thiadiazole-2-amine (12 mg), followed by stirring at room temperature for 12 hours. The solvent was distilled off under reduced pressure, and the obtained residue was purified by silica gel column chromatography (methanol-ethyl acetate, NH silica), thereby obtaining 5-isopropyl-N-(7-(1-methyl-3-(pyridin-2-yl)-1H-pyrazol-4-yl)-1,5-naphthyridin-2-yl)-1,3,4-thiadiazole-2-amine (6.4 mg).

$^1$H-NMR(CDCl$_3$/CD$_3$OD=4/1)δ:8.67(1H,brs),8.54(1H,d,J=3.9 Hz),8.24(1H,brs),8.21(1H,d,J=8.7 Hz),7.85(1H,s),7.82-7.69(2H,m),7.35-7.27(1H,m),7.33(1H,d,J=8.7 Hz),3.47-3.36(1H,m),3.37(3H,s),1.47(6H,d,J=6.6 Hz).

MSm/z(M+H):429.

Example 0137

0137-1

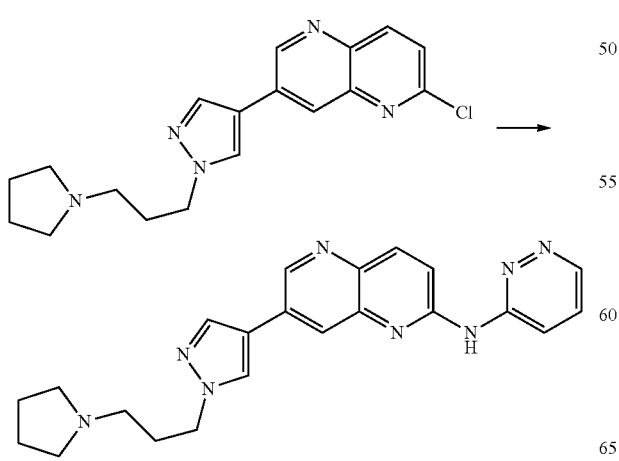

N-(pyridazin-3-yl)-7-(1-(3-(pyrrolidin-1-yl)propyl)-1H-pyrazol-4-yl)-1,5-naphthyridine-2-amine was obtained in the same manner as in Example 0001-5.

$^1$H-NMR(CDCl$_3$/CD$_3$OD=4/1)δ:9.12(1H,d,J=9.0 Hz),8.89(1H,s),8.81(1H,d,J=1.8 Hz),8.22(1H,s),8.21(1H,d,J=9.0 Hz),8.02(1H,s),7.98(1H,s),7.61(1H,dd,J=9.0 Hz,1.8 Hz),7.47(1H,d,J=9.0 Hz),4.33-4.25(2H,m),2.61-2.46(6H,m),2.23-2.15(2H,m),1.86-1.77(4H,m).

MSm/z(M+H):401.

Example 0138

0138-1

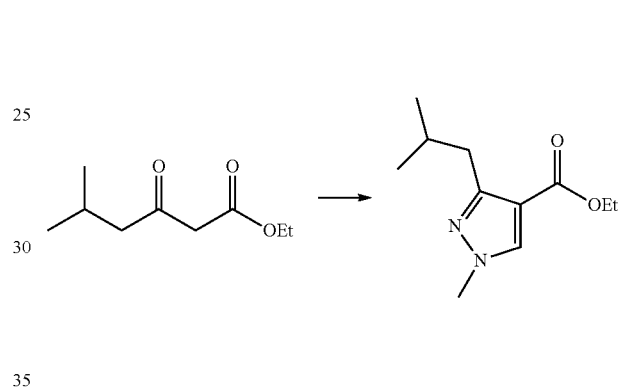

A solution of methylhydrazine (0.29 mL) and ethyl formate (0.65 mL) in ethanol (3 mL) was stirred for 4 hours under heating to reflux, and ethyl 5-methyl-3-oxohexanoate (1.91 g) was added thereto, followed by stirring at the same temperature for 4 hours. The reaction mixture was cooled to room temperature, and a 20% sodium ethoxide-ethanol solution (3 mL) was added thereto, followed by stirring for 1.5 hours under heating to reflux. The reaction mixture was cooled to room temperature, and ethyl acetate and a 3 mol/L potassium hydrogen sulfate aqueous solution were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining ethyl 3-isobutyl-1-methyl-1H-pyrazole-4-carboxylate (280 mg).

MSm/z(M+H):211.

0138-2 to 0138-5

The following compounds were obtained in the same manner as in Examples 0110-1 to 0110-4.

| Example No. | | |
|---|---|---|
| 0138 | | |
| 0138-2 | 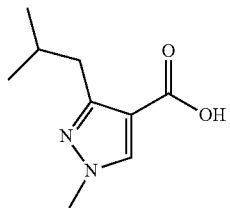 | MS m/z (M + H): 183. |
| 0138-3 | 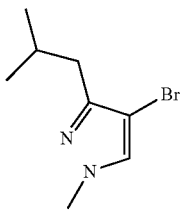 | MS m/z (M + H): 217, 219. |
| 0138-4 | 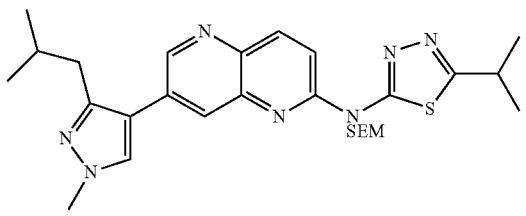 [SMILES: CC(C)Cc1nn(C)cc1-c1cnc2ccc(N(COCC[Si](C)(C)C)c3nnc(C(C)C)s3)nc2c1] | MS m/z (M + H): 538. |
| 0138-5 | 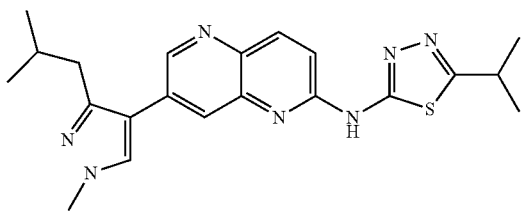 [SMILES: CN/C=C(\C(=N)CC(C)C)c1cnc2ccc(Nc3nnc(C(C)C)s3)nc2c1] | $^1$H-NMR (CDCl$_3$/CD$_3$OD = 4/1) δ: 8.79 (1H, d, J = 2.1 Hz), 8.24 (1H, d, J = 9.0 Hz), 8.22 (1H, d, J = 2.1 Hz), 7.74 (1H, s), 7.37 (1H, d, J = 9.0 Hz), 3.96 (3H, s), 3.49-3.36 (1H, m), 2.75 (2H, d, J = 7.2 Hz), 2.07-1.92 (1H, m), 1.49 (6H, d, J = 7.2 Hz), 0.97 (6H, d, J = 7.2 Hz). MS m/z (M + H): 408. |

Example 0139 to 0141

The following compounds were obtained in the same manner as in Example 0015-4.

| Example No. | | |
|---|---|---|
| 0139 | | |
| 0139-1 | 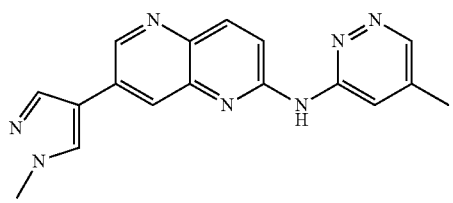 [SMILES: CN/C=C(\C=N)c1cnc2ccc(Nc3cc(C)cnn3)nc2c1] | $^1$H-NMR (DMSO-d$_6$) δ: 10.69 (1H, brs), 9.03 (1H, d, J = 2.7 Hz), 8.76 (2H, brs), 8.47 (1H, brs), 8.31 (1H, d, J = 2.7 Hz), 8.21 (1H, d, J = 9.0 Hz), 8.18 (1H, s), 7.66 (1H, d, J = 9.0 Hz), 3.92 (3H, s), 2.42 (3H, s). MS m/z (M + H): 318. |
| 0140-1 | 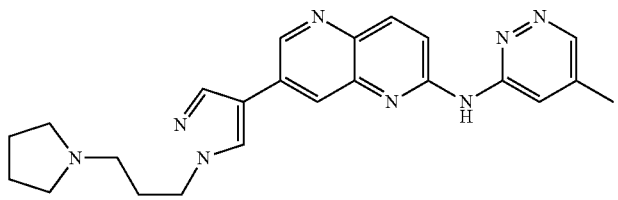 [SMILES: Cc1cnnc(Nc2ccc3ncc(/C(C=N)=C/NCCCN4CCCC4)cc3n2)c1] | $^1$H-NMR (CDCl$_3$/CD$_3$OD = 4/1) δ: 8.89 (1H, brs), 8.66 (1H, brs), 8.20 (1H, d, J = 9.0 Hz), 8.04 (1H, s), 7.99 (1H, s), 7.46 (1H, d, J = 9.0 Hz), 7.35 (1H, brs), 4.34-4.25 (2H, m), 3.73-3.66 (2H, m), 2.61-2.49 (4H, m), 2.50 (3H, s), 2.23-2.10 (2H, m), 1.88-1.78 (4H, m). MS m/z (M + H): 415. |

| Example No. | | |
|---|---|---|
| 0141-1 | 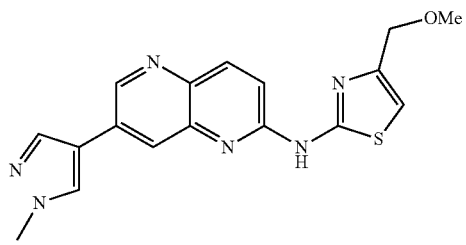 [SMILES: CN/C=C(\C=N)c1cnc2ccc(Nc3nc(COC)cs3)nc2c1] | $^1$H-NMR (CDCl$_3$/CD$_3$OD = 4/1) δ: 8.86 (1H, brs), 8.28 (1H, brs), 8.17 (1H, d, J = 9.0 Hz), 7.98 (1H, s), 7.96 (1H, s), 7.27 (1H, d, J = 9.0 Hz), 6.85 (1H, s), 4.48 (2H, s), 4.02 (3H, s), 3.46 (3H, s). MS m/z (M + H): 353. |

Example 0142

0142-1

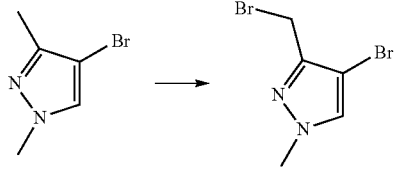

2,2'-Azobis(isobutyronitrile) (27 mg) was added to a solution of 4-bromo-1,3-dimethyl-1H-pyrazole (286 mg) and N-bromosuccinimide (320 mg) in chlorobenzene (6 mL), followed by stirring at 80° C. for 7 hours. The reaction mixture was cooled to room temperature, and ethyl acetate and a saturated sodium hydrogen carbonate aqueous solution were added thereto. The organic layer was collected by separation, washed with a saturated sodium chloride aqueous solution, and dried over anhydrous sodium sulfate, and the solvent was distilled off under reduced pressure, thereby obtaining 4-bromo-3-(bromomethyl)-1-methyl-1H-pyrazole (465 mg) as a white solid.

MSm/z(M+H):253.

0142-2

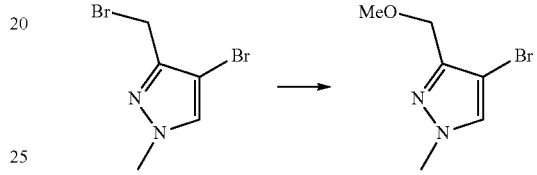

A 28% sodium methoxide-methanol solution (2 mL) was added to a solution of 4-bromo-3-(bromomethyl)-1-methyl-1H-pyrazole (84 mg) in methanol (2 mL), followed by stirring at room temperature for 3 hours. The solvent was distilled off under reduced pressure, and ethyl acetate and water were added thereto. The organic layer was collected by separation, washed with a saturated sodium chloride aqueous solution, and dried over anhydrous sodium sulfate, and the solvent was distilled off under reduced pressure, thereby obtaining 4-bromo-3-(methoxymethyl)-1-methyl-1H-pyrazole (42 mg).

MSm/z(M+H):205.

0142-3 and 0142-4

The following compounds were obtained in the same manner as in Examples 0110-3 and 0110-4

| Example No. | | |
|---|---|---|
| 0142 | | |
| 0142-3 | 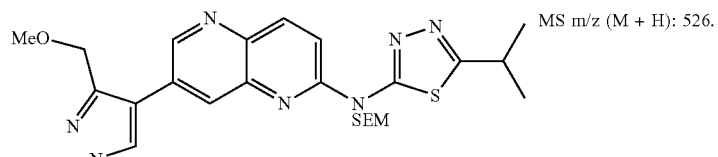 | MS m/z (M + H): 526. |
| 0142-4 | 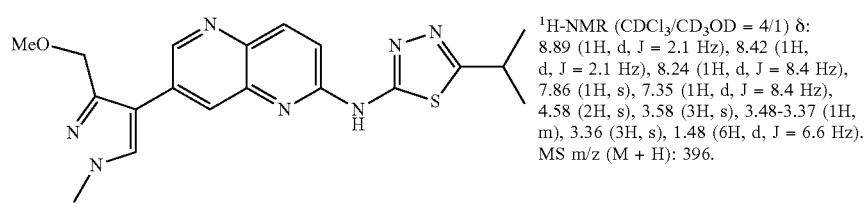 | $^1$H-NMR (CDCl$_3$/CD$_3$OD = 4/1) δ: 8.89 (1H, d, J = 2.1 Hz), 8.42 (1H, d, J = 2.1 Hz), 8.24 (1H, d, J = 8.4 Hz), 7.86 (1H, s), 7.35 (1H, d, J = 8.4 Hz), 4.58 (2H, s), 3.58 (3H, s), 3.48-3.37 (1H, m), 3.36 (3H, s), 1.48 (6H, d, J = 6.6 Hz). MS m/z (M + H): 396. |

Example 0143

0143-1

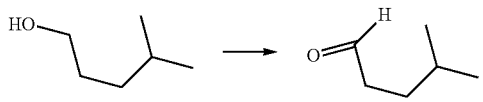

Tetrapropylammonium perruthenate (171 mg) was added to a mixture of 4-methylpentan-1-ol (1.0 g), molecular sieve 4A (1.0 g), and N-methylmorpholine-N-oxide (1.26 g) in dichloromethane (30 mL) under ice-cooling, followed by stirring at the same temperature for 5 minutes. The reaction mixture was purified by silica gel column chromatography (dichloromethane), thereby obtaining 4-methylpentanal (2.79 g).

$^1$H-NMR(CDCl$_3$)δ:9.77(1H,t,J=2.1 Hz),2.43(2H,td,J=5.1 Hz,2.1 Hz),1.66-1.48(1H,m),1.28-1.18(2H,m),0.91(6H,d,J=6.0 Hz).

0143-2

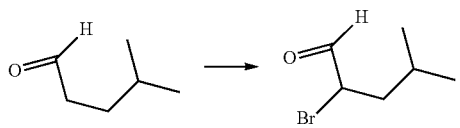

Trimethylphenylammonium tribromide (4.0 g) was added to a solution of 4-methylpentanal (2.79 g) in tetrahydrofuran (30 mL) under ice-cooling, followed by stirring while slowly heating to room temperature for 1 day. Ethyl acetate and water were added to the reaction mixture. The organic layer was collected by separation, washed sequentially with a 10% sodium hydrogen sulfite aqueous solution and a saturated sodium chloride aqueous solution, and dried over anhydrous sodium sulfate, and the solvent was distilled off under reduced pressure, thereby obtaining 2-bromo-4-methylpentanal (2.84 g).

$^1$H-NMR(CDCl$_3$)δ:9.13(1H,s),3.46(1H,t,J=6.6 Hz),1.80-1.46(3H,m),1.04(6H,d,J=6.6 Hz).

0143-3

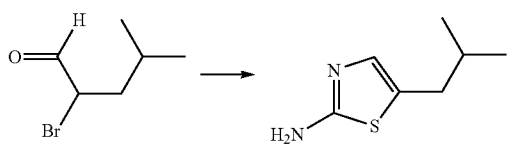

Thiourea (744 mg) was added to a solution of 2-bromo-4-methylpentanal (2.84 g) in ethanol (10 mL), followed by stirring for 3 hours under heating to reflux. The reaction mixture was cooled to room temperature, and ethyl acetate and water were added thereto. The organic layer was collected by separation, washed sequentially with a saturated sodium hydrogen carbonate aqueous solution and a saturated sodium chloride aqueous solution, and dried over anhydrous sodium sulfate, and the solvent was distilled off under reduced pressure. The obtained residue was purified by silica gel column chromatography (methanol-ethyl acetate), thereby obtaining 5-isobutylthiazole-2-amine (449 mg).

MSm/z(M+H):157.

0143-4

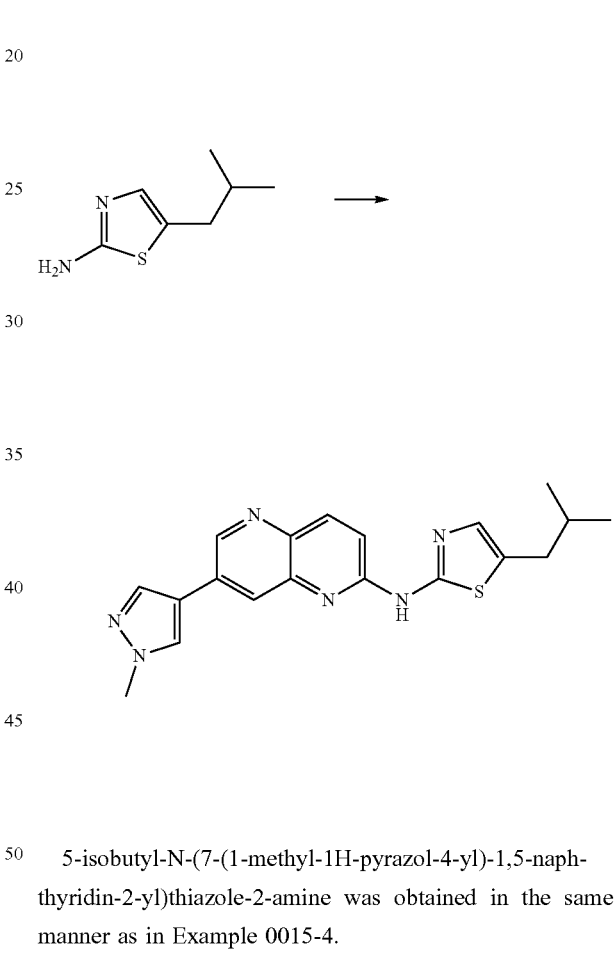

5-isobutyl-N-(7-(1-methyl-1H-pyrazol-4-yl)-1,5-naphthyridin-2-yl)thiazole-2-amine was obtained in the same manner as in Example 0015-4.

$^1$H-NMR(CDCl$_3$/CD$_3$OD=4/1)δ:8.85(1H,brs),8.26(1H,brs),8.15(1H,d,J=9.0 Hz),7.99(1H,s),7.93(1H,s),7.24(1H,d,J=9.0 Hz),7.07(1H,s),4.02(3H,s),2.68(2H,d,J=7.5 Hz),2.02-1.90(1H,m),1.01(6H,d,J=6.36 Hz).

MSm/z(M+H):365.

Examples 0144 and 0145

The following compounds were obtained in the same manner as in Example 0015-4.

| Example No. | | |
|---|---|---|
| 0144 | | |
| 0144-1 | 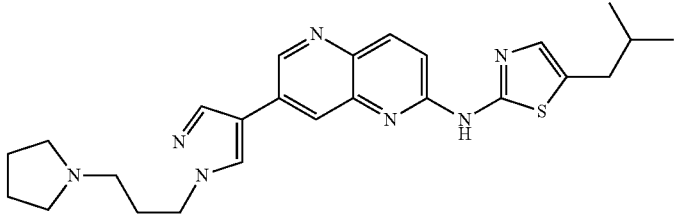 [SMILES: CC(C)Cc1cnc(Nc2ccc3ncc(/C(C=N)=C/NCCCN4CCCC4)cc3n2)s1] | $^1$H-NMR (CDCl$_3$/CD$_3$OD = 4/1) δ: 8.86 (1H, brs), 8.27 (1H, brs), 8.15 (1H, d, J = 8.4 Hz), 8.00 (2H, s), 7.24 (1H, d, J = 8.4 Hz), 7.07 (1H, s), 4.29 (2H, t, J = 6.6 Hz), 2.68 (2H, d, J = 6.6 Hz), 2.59-2.47 (6H, m), 2.22-2.11 (2H, m), 2.02-1.91 (1H, m), 1.86-1.78 (4H, m), 1.01 (6H, d, J = 6.6 Hz).<br>MS m/z (M + H): 462. |
| 0145 | | |
| 0145-1 | 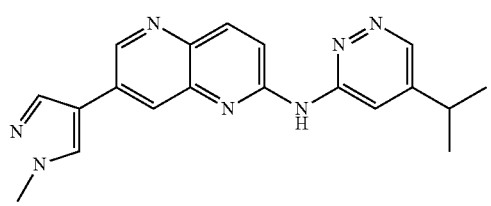 [SMILES: CN/C=C(\C=N)c1cnc2ccc(Nc3cc(C(C)C)cnn3)nc2c1] | $^1$H-NMR (DMSO-d$_6$) δ: 10.72 (1H, brs), 9.04 (1H, d, J = 1.8 Hz), 8.87 (1H, d, J = 1.8 Hz), 8.72 (1H, brs), 8.46 (1H, s), 8.23-8.19 (2H, m), 8.17 (1H, s), 7.70 (1H, d, J = 9.0 Hz), 3.92 (3H, s), 3.11-2.98 (1H, m), 1.33 (6H, d, J = 6.6 Hz).<br>MS m/z (M + H): 346. |

Example 0146

0146-1

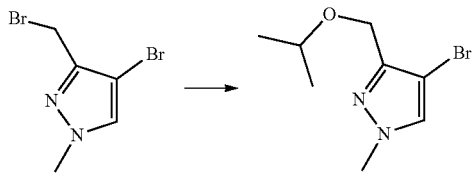

60% sodium hydride (23 mg) was added to a mixture solution of 4-bromo-3-(bromomethyl)-1-methyl-1H-pyrazole (72 mg) in 1,4-dioxane (0.5 mL) and 2-propanol (0.5 mL), followed by stirring at 120° C. for 5 hours. The reaction mixture was cooled to room temperature, and ethyl acetate and water were added thereto. The organic layer was collected by separation, washed sequentially with a saturated sodium hydrogen carbonate aqueous solution and a saturated sodium chloride aqueous solution, and dried over anhydrous sodium sulfate, and the solvent was distilled off under reduced pressure, thereby obtaining 4-bromo-3-(isopropyloxymethyl)-1-methyl-1H-pyrazole (57 mg).
$^1$H-NMR(CDCl$_3$)δ:7.34(1H,s),4.46(2H,s),3.85(3H,s), 3.78-3.68(1H,m),1.22(6H,d,J=6.6 Hz).

0146-2 and 0146-3

The following compounds were obtained in the same manner as in Examples 0110-3 and 0110-4.

| Example No. | | |
|---|---|---|
| 0146 | | |
| 0146-2 | 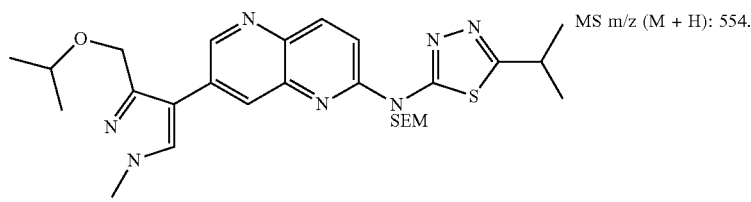 | MS m/z (M + H): 554. |
| 0146-3 | 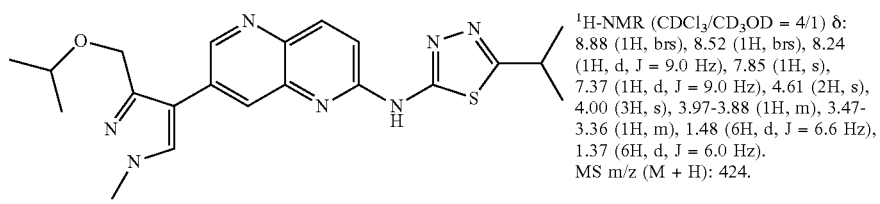 | $^1$H-NMR (CDCl$_3$/CD$_3$OD = 4/1) δ: 8.88 (1H, brs), 8.52 (1H, brs), 8.24 (1H, d, J = 9.0 Hz), 7.85 (1H, s), 7.37 (1H, d, J = 9.0 Hz), 4.61 (2H, s), 4.00 (3H, s), 3.97-3.88 (1H, m), 3.47-3.36 (1H, m), 1.48 (6H, d, J = 6.6 Hz), 1.37 (6H, d, J = 6.0 Hz).<br>MS m/z (M + H): 424. |

Example 0147

0147-1

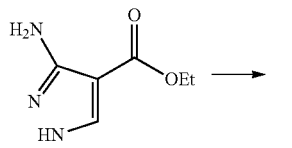

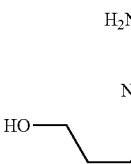

After a mixture of ethyl 3-amino-1H-pyrazole-4-carboxylate (2.00 g), trioctylmethylammonium chloride (0.31 mg), and potassium carbonate (3.25 g) in toluene (25 mL) was stirred for 15 minutes under heating to reflux, 3-bromopropanol (1.45 mL) was added to the mixture, followed by stirring at the same temperature for 7 hours. The reaction mixture was cooled to room temperature, and ethyl acetate and water were added thereto. The organic layer was collected by separation, washed sequentially with a saturated sodium hydrogen carbonate aqueous solution and a saturated sodium chloride aqueous solution, and dried over anhydrous sodium sulfate, and the solvent was distilled off under reduced pressure, thereby obtaining ethyl 3-amino-1-(3-hydroxypropyl)-1H-pyrazole-4-carboxylate (3.01 g).

MSm/z(M+H):214.

0147-2

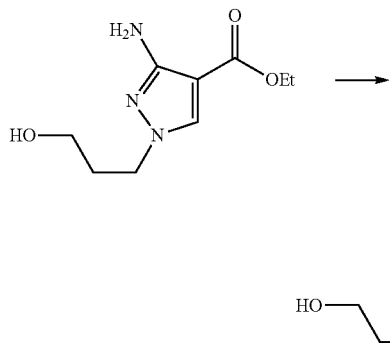

tert-Butyl nitrite (2.12 mL) was added to a mixture of copper(II) bromide (3.71 g) in acetonitrile (30 mL) under ice-cooling, followed by stirring at the same temperature for 5 minutes, and ethyl 3-amino-1-(3-hydroxypropyl)-1H-pyrazole-4-carboxylate (3.01 g) was added thereto, followed by stirring at room temperature for 5 hours. Ethyl acetate and water were added to the reaction mixture. The organic layer was collected by separation, washed sequentially with a saturated sodium hydrogen carbonate aqueous solution and a saturated sodium chloride aqueous solution, and dried over anhydrous sodium sulfate, and the solvent was distilled off under reduced pressure. The obtained residue was purified by silica gel column chromatography (methanol-ethyl acetate), thereby obtaining ethyl 3-bromo-1-(3-hydroxypropyl)-1H-pyrazole-4-carboxylate (1.58 g).

MSm/z(M+H):277.

0147-3

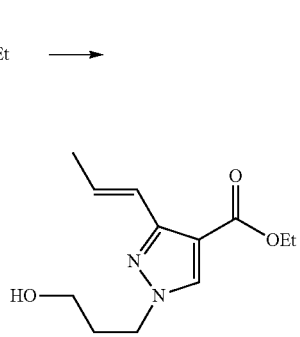

A mixture of ethyl 3-bromo-1-(3-hydroxypropyl)-1H-pyrazole-4-carboxylate (383 mg), (E)-4,4,5,5-tetramethyl-2-(prop-1-en-1-yl)-1,3,2-dioxaborolane (278 mg), sodium carbonate (366 mg), bis(di-tert-butyl(4-dimethylaminophenyl)phosphine)dichloropalladium(II) (97 mg), and water (1 mL) in 1,4-dioxane (10 mL) was stirred for 2 hours under heating to reflux. The reaction mixture was cooled to room temperature, the insolubles were filtered off using celite, and the solvent was distilled off under reduced pressure. The obtained residue was purified by silica gel column chromatography (ethyl acetate-hexane), thereby obtaining (E)-ethyl 1-(3-hydroxypropyl)-3-(prop-1-en-1-yl)-1H-pyrazole-4-carboxylate (236 mg).

MSm/z(M+H):239.

0147-4

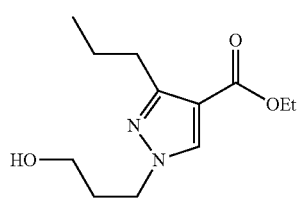

(E)-ethyl 1-(3-hydroxypropyl)-3-(prop-1-en-1-yl)-1H-pyrazole-4-carboxylate (236 mg) was added to a mixture of 10% palladium-carbon (50 mg) in methanol (10 mL), followed by stirring for 1.5 hours in a hydrogen atmosphere. The insolubles were filtered off using celite, and the solvent was distilled off under reduced pressure, thereby obtaining ethyl 1-(3-hydroxypropyl)-3-propyl-1H-pyrazole-4-carboxylate (206 mg).

MSm/z(M+H):241.

0147-5

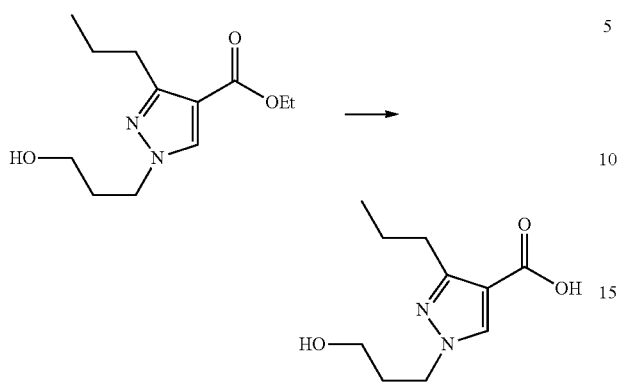

A 4 mol/L sodium hydroxide aqueous solution (2 mL) was added to a solution of ethyl 1-(3-hydroxypropyl)-3-propyl-1H-pyrazole-4-carboxylate (206 mg) in ethanol (2 mL), followed by stirring at 70° C. for 1 hour. After the reaction mixture was cooled to room temperature, the solvent was distilled off under reduced pressure, the resultant product was adjusted to pH 2 by the addition of a 3 mol/L potassium hydrogen sulfate aqueous solution, and ethyl acetate was added thereto. The organic layer was collected by separation, washed with a saturated sodium chloride aqueous solution, and dried over anhydrous sodium sulfate, and the solvent was distilled off under reduced pressure, thereby obtaining 1-(3-hydroxypropyl)-3-propyl-1H-pyrazole-4-carboxylic acid (171 mg).
MS m/z(M+H):213.

0147-6

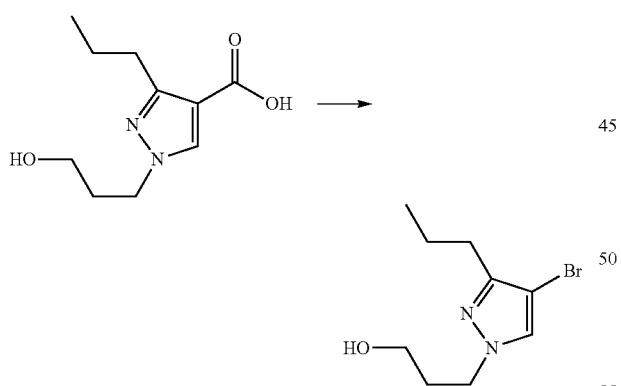

N-bromosuccinimide (158 mg) was added to a mixture of 1-(3-hydroxypropyl)-3-propyl-1H-pyrazole-4-carboxylic acid (206 mg), and sodium hydrogen carbonate (291 mg) in N,N-dimethylformamide (4 mL), followed by stirring at room temperature for 2.5 hours. Ethyl acetate and water were added to the reaction mixture. The organic layer was collected by separation, washed with a saturated sodium chloride aqueous solution, and dried over anhydrous sodium sulfate, and the solvent was distilled off under reduced pressure, thereby obtaining 3-(4-bromo-3-propyl-1H-pyrazol-1-yl)propan-1-ol (146 mg).

$^1$H-NMR(CDCl$_3$)δ:7.34(1H,s),4.20(2H,t,J=6.6 Hz),2.56 (2H,t,J=6.6 Hz),3.67-3.56(2H,m),2.06-1.96(2H,m),1.75-1.61(2H,m),0.95(3H,t,J=7.2 Hz).

0147-7

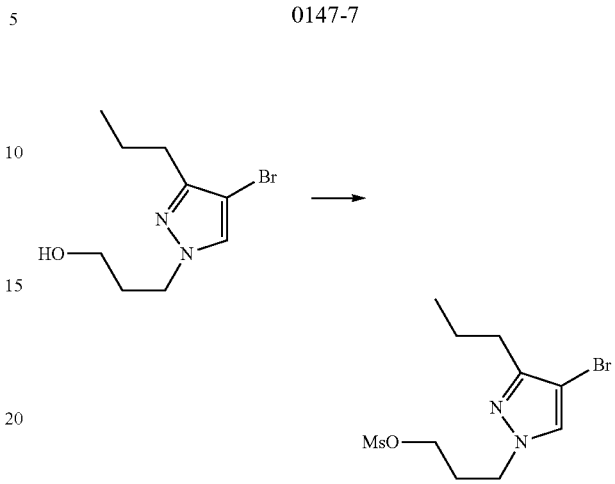

Methanesulfonyl chloride (0.043 mL) was added to a solution of 3-(4-bromo-3-propyl-1H-pyrazol-1-yl)propan-1-ol (90 mg) and triethylamine (0.10 mL) in dichloromethane (3 mL) under ice-cooling, followed by stirring at the same temperature for 30 minutes. Ethyl acetate and water were added to the reaction mixture. The organic layer was collected by separation, washed with a saturated sodium chloride aqueous solution, and dried over anhydrous sodium sulfate, and the solvent was distilled off under reduced pressure, thereby obtaining 3-(4-bromo-3-propyl-1H-pyrazol-1-yl)propyl methanesulfonate (136 mg).
$^1$H-NMR(CDCl$_3$)δ:7.35(1H,s),4.27-4.08(4H,m),3.03(3H,s),2.56(2H,t,J=7.2 Hz),2.34-2.23(2H,m),1.74-1.59(2H,m), 0.95(3H,t,J=7.2 Hz).

0147-8

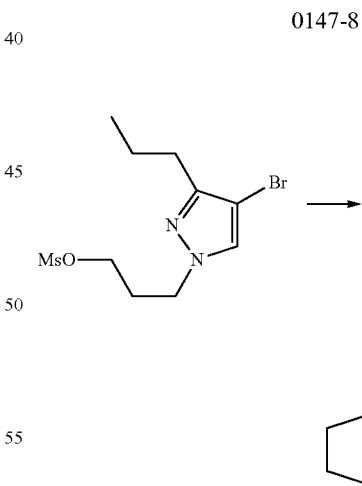

Pyrrolidine (0.037 mL) was added to a mixture of 3-(4-bromo-3-propyl-1H-pyrazol-1-yl)propyl methanesulfonate (136 mg), and potassium carbonate (127 mg) in acetonitrile (2 mL), followed by stirring at 50° C. for 10 hours. The reaction mixture was cooled to room temperature, and ethyl acetate and water were added thereto. The organic layer was collected by separation, washed with a saturated sodium chloride aqueous solution, and dried over anhydrous sodium sulfate, and the solvent was distilled off under reduced pressure, thereby obtaining 4-bromo-3-propyl-1-(3-(pyrrolidin-1-yl)propyl)-1H-pyrazole (63 mg).

$^1$H-NMR(CDCl$_3$)δ:7.33(1H,s),4.10(2H,t,J=6.6 Hz),2.56 (2H,t,J=7.2 Hz),2.50-2.43(4H,m),2.40(2H,t,J=7.5 Hz),2.06-1.96(2H,m),1.82-1.73(4H,m),1.72-1.60(2H,m),0.95(3H,t,J=7.2 Hz).

0147-9 and 0147-10

The following compounds were obtained in the same manner as in Examples 0110-3 and 0110-4.

| Example No. | | |
|---|---|---|
| 0147 | | |
| 0147-9 | 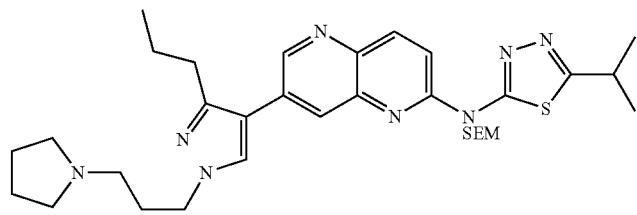 [SMILES: CCCC(=N)/C(=C\NCCCN1CCCC1)c1cnc2ccc(N(COCC[Si](C)(C)C)c3nnc(C(C)C)s3)nc2c1] | MS m/z (M + H): 621. |
| 0147-10 | 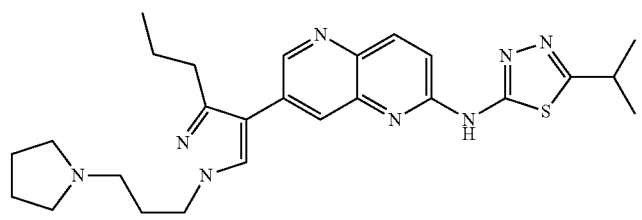 [SMILES: CCCC(=N)/C(=C\NCCCN1CCCC1)c1cnc2ccc(Nc3nnc(C(C)C)s3)nc2c1] | $^1$H-NMR (CDCl$_3$/CD$_3$OD = 4/1) δ: 8.80 (1H, brs), 8.24 (1H, J = 9.0 Hz), 8.21 (1H, brs), 7.80 (1H, s), 7.36 (1H, d, J = 9.0 Hz), 4.27-4.18 (2H, m), 3.78-3.64 (2H, m), 3.49-3.36 (1H, m), 2.92-2.81 (2H, m), 2.63-2.48 (4H, m), 2.22-2.08 (2H, m), 1.87-1.66 (6H, m), 1.49 (6H, d, J = 6.0 Hz), 1.10-0.96 (3H, m). MS m/z (M + H): 491. |

Examples 0148 and 0149

The following compounds were obtained in the same manner as in Example 0001-5.

| 実施例 番号 | | |
|---|---|---|
| 0148 | | |
| 0148-1 | 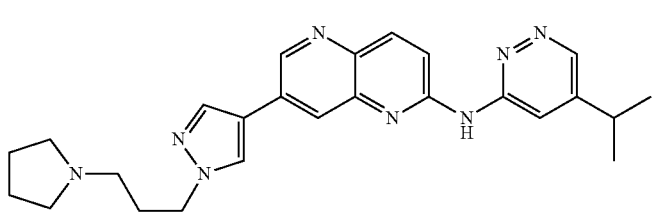 [SMILES: CC(C)c1cnnc(Nc2ccc3ncc(-c4cnn(CCCN5CCCC5)c4)cc3n2)c1] | $^1$H-NMR (CDCl$_3$/CD$_3$OD = 4/1) δ: 8.89 (2H, brs), 8.72 (1H, brs), 8.20 (1H, d, J = 9.0 Hz), 8.15 (1H, brs), 8.02 (1H, s), 7.98 (1H, s), 7.51 (1H.d.J = 9.0 Hz), 4.33-4.26 (2H, m), 3.14-3.00 (1H, m), 2.60-2.48 (6H, m), 2.24-2.10 (2H, m), 1.86-1.78 (4H, m), 1.42 (6H, d, J = 6.6 Hz). MS m/z (M + H): 443. |
| 0149 | | |
| 0149-1 | 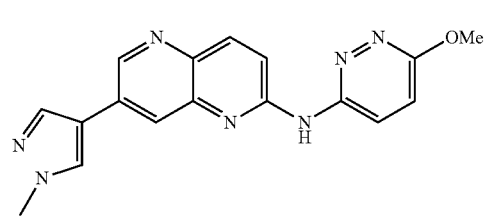 [SMILES: CN/C=C(\C=N)c1cnc2ccc(Nc3ccc(OC)nn3)nc2c1] | $^1$H-NMR (CDCl$_3$/CD$_3$OD = 4/1) δ: 8.84 (1H, d, J = 2.1 Hz), 8.17 (1H, d, J = 2.1 Hz), 8.16 (1H, d, J = 8.7 Hz), 7.96 (1H, s), 7.94 (1H, s), 7.48 (1H, d, J = 8.7 Hz), 7.38 (1H, d, J = 9.3 Hz), 7.14 (1H, d, J = 9.3 Hz), 6.86 (3H, s), 3.97 (3H, s). MS m/z (M + H): 334. |

Example 0150

The following compounds were obtained in the same manner as in Examples 0110-1 to 0110-4.

| Example No. | | |
|---|---|---|
| 0150 | | |
| 0150-1 | 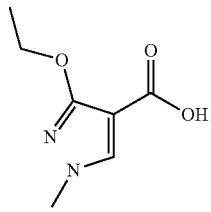 | MS m/z (M + H): 171. |
| 0150-2 | 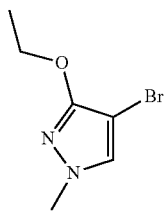 | MS m/z (M + H): 205. |
| 0150-3 | 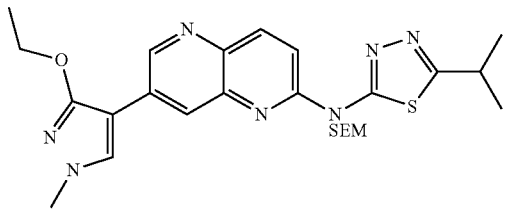 [SMILES: CCOC(=N)/C(=C\NC)c1cnc2ccc(N(COCC[Si](C)(C)C)c3nnc(C(C)C)s3)nc2c1] | MS m/z (M + H): 526. |
| 0150-4 | 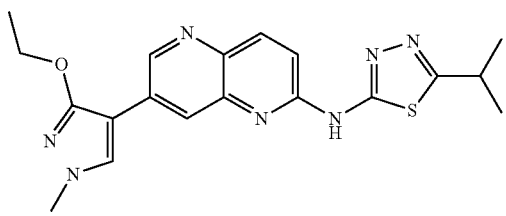 [SMILES: CCOC(=N)/C(=C\NC)c1cnc2ccc(Nc3nnc(C(C)C)s3)nc2c1] | $^1$H-NMR (CDCl$_3$/CD$_3$OD = 4/1) δ: 8.97 (1H, d, J = 2.1 Hz), 8.35 (1H, d, J = 2.1 Hz), 8.23 (1H, d, J = 9.0 Hz), 7.84 (1H, s), 7.33 (1H, d, J9.0 Hz), 4.13 (2H, q, 6.6 Hz), 3.82 (3H, s), 3.49-3.37 (1H, m), 1.50 (6H, d, J = 6.6 Hz), 1.47 (3H, t, J = 6.6 Hz). MS m/z (M + H): 396. |

Examples 0151 and 0152

The following compounds were obtained in the same manner as in Example 0001-5.

| Example No. | | |
|---|---|---|
| 0151 | | |
| 0151-1 | 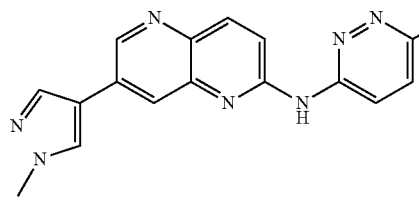 | $^1$H-NMR (CDCl$_3$/CD$_3$OD = 4/1) δ: 8.86 (1H, d, J = 1.8 Hz), 8.19 (1H, d, J = 1.8 Hz), 8.17 (1H, d, J = 9.0 Hz), 7.96 (1H, s), 7.95 (1H, s), 7.47 (1H, d, J = 9.0 Hz), 7.15 (1H, d, J = 9.0 Hz), 6.83 (1H, d, J = 9.0 Hz), 4.06 (3H, s), 2.49 (3H, s). MS m/z (M + H): 318. |

-continued

| Example No. | | |
|---|---|---|
| 0152 | | |
| 0152-1 | 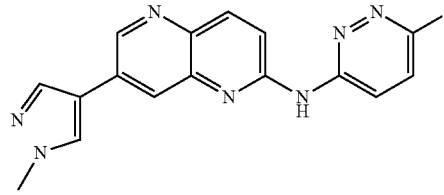 | $^1$H-NMR (CDCl$_3$/CD$_3$OD = 4/1) δ: 9.15 (1H, d, J = 9.0 Hz), 8.89 (1H, d, J = 2.1 Hz), 8.22 (1H, d, J = 2.1 Hz), 8.21 (1H, d, J = 9.0 Hz), 7.97 (1H, s), 7.96 (1H, s), 7.60 (1H, d, J = 9.0 Hz), 7.44 (1H, d, J = 9.0 Hz), 3.63 (3H, s). MS m/z (M + H): 338. |

Example 0153

The following compounds were obtained in the same manner as in Examples 0001-4 and 0001-5.

| Example No. | | |
|---|---|---|
| 0153 | | |
| 0153-1 | 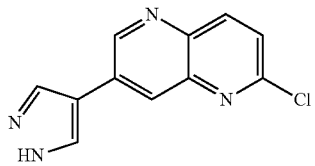 [SMILES: N=C/C(=C\N)c1cnc2ccc(Cl)nc2c1] | MS m/z (M + H): 231. |
| 0153-2 | 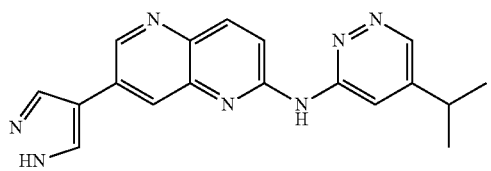 [SMILES: CC(C)c1cnnc(Nc2ccc3ncc(/C(C=N)=C/N)cc3n2)c1] | $^1$H-NMR (DMSO-d$_6$) δ: 8.86 (1H, brs), 8.72 (1H, brs), 8.24 (1H, d, J = 8.7 Hz), 8.20 (1H, brs), 7.39 (2H, s), 7.35 (1H, d, J = 8.7 Hz), 7.46 (1H, brs), 3.31-3.23 (1H, m), 1.33 (6H, d, J = 6.6 Hz). MS m/z (M + H): 332. |

Example 0154

The following compounds were obtained in the same manner as in Example 0001-5.

| Example No. | | |
|---|---|---|
| 0154 | | |
| 0154-1 | 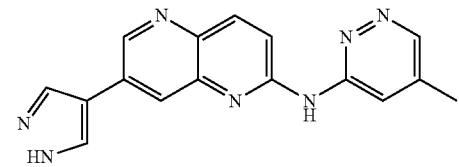 [SMILES: Cc1cnnc(Nc2ccc3ncc(/C(C=N)=C/N)cc3n2)c1] | $^1$H-NMR (DMSO-d$_6$) δ: 8.86 (1H, brs), 8.72 (1H, brs), 8.24 (1H, d, J = 8.7 Hz), 8.20 (1H, brs), 7.39 (2H, s), 7.35 (1H, d, J = 8.7 Hz), 7.46 (1H, brs), 4.06 (3H, s). MS m/z (M + H): 304. |

Example 0155

0155-1

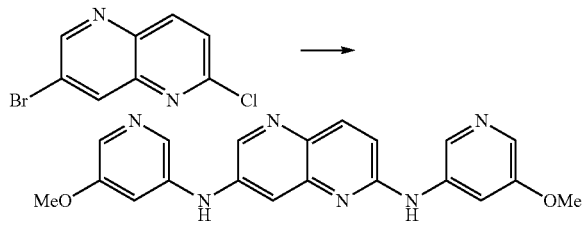

A mixture of 7-bromo-2-chloro-1,5-naphthyridine (50 mg), 5-methoxypyridine-3-amine (25 mg), tris(dibenzylideneacetone)dipalladium(0) (19 mg), 4,5-bis(diphenylphosphino)-9,9-dimethylxanthene (24 mg), and cesium carbonate (33 mg) in 1,4-dioxane (1 mL) was stirred at 140° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining $N^2,N^7$-bis(5-methoxypyridin-3-yl)-1,5-naphthyridine-2,7-diamine (15 mg).

$^1$H-NMR(CDCl$_3$/CD$_3$OD=4/1)δ:8.44(1H,d,J=2.7 Hz), 8.37(2H,brs),8.07(1H,d,J=2.7 Hz),7.99(1H,d,J=9.0 Hz), 7.88(2H,brs),7.21(2H,brs),7.02(1H,d,J=9.0 Hz),3.91(3H,s), 3.89(3H,s).

MSm/z(M+H):375.

Example 0156

0156-1

A solution of ((3-bromopropyloxy)methyl)benzene (5.0 g) in ethanol (5 mL) was added to hydrazine monohydrate (6.4 mL) at 65° C., followed by stirring at the same temperature for 1 hour. The reaction mixture was cooled to room temperature, and filtered through DOWEX MONOSPHERE 550A (OH) (product name, manufactured by Wako Pure Chemical Industries, Ltd.). The solvent was distilled off under reduced pressure, thereby obtaining (3-(benzyloxy)propyl)hydrazine (3.7 g).

MSm/z(M+H):181.

0156-2

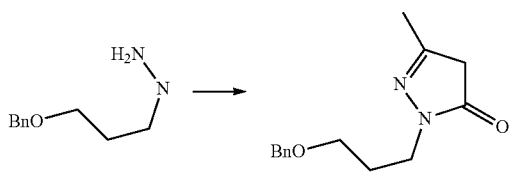 [SMILES: NNCCCOCc1ccccc1 ; CC1=NN(CCCOCc2ccccc2)C(=O)C1]

Ethyl 3-oxobutanoate (0.254 mL) was added to a solution of (3-(benzyloxy)propyl)hydrazine (500 mg) in ethanol (5 mL), followed by stirring for 3 hours under heating to reflux. The reaction mixture was cooled to room temperature, and the solvent was distilled off under reduced pressure. The obtained residue was purified by silica gel column chromatography (ethyl acetate-hexane), thereby obtaining 1-(3-(benzyloxy)propyl)-3-methyl-1H-pyrazol-5(4H)-one (261 mg).

MSm/z(M+H):247.

0156-3

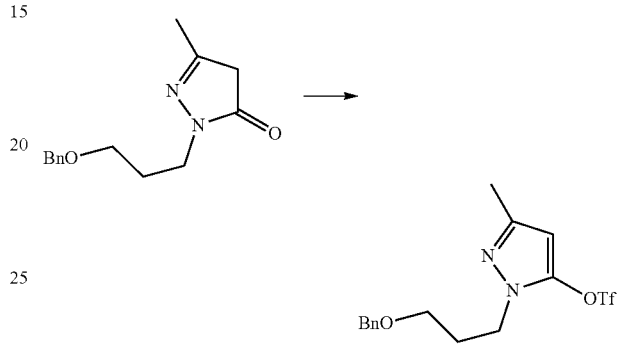

Trifluoromethanesulfonic acid anhydride (0.260 mL) was added to a solution of 1-(3-(benzyloxy)propyl)-3-methyl-1H-pyrazol-5(4H)-one (261 mg) and pyridine (0.154 mL) in dichloromethane (10 mL) under ice-cooling, followed by stirring at the same temperature for 30 minutes. A saturated sodium hydrogen carbonate aqueous solution and ethyl acetate were added to the reaction mixture. The organic layer was collected by separation, washed with a saturated sodium chloride aqueous solution, and dried over anhydrous sodium sulfate, and the solvent was distilled off under reduced pressure. The obtained residue was purified by silica gel column chromatography (methanol-ethyl acetate-hexane), thereby obtaining (1-(3-(benzyloxy)propyl)-3-methyl-1H-pyrazol-5-yl) trifluoromethanesulfonate (237 mg).

MSm/z(M+H):379.

0156-4

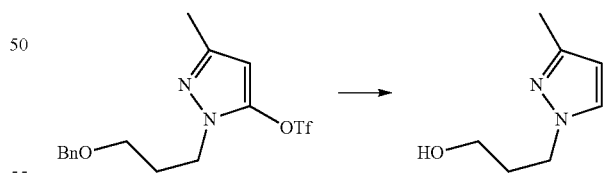

(1-(3-(Benzyloxy)propyl)-3-methyl-1H-pyrazol-5-yl) trifluoromethanesulfonate (237 mg) was added to a mixture of 20%-palladium hydroxide-carbon (50 mg) in methanol (10 mL), followed by stirring for 5 hours in a hydrogen atmosphere. The insolubles were filtered off using celite, and the solvent was distilled off under reduced pressure, thereby obtaining 3-(3-methyl-1H-pyrazol-1-yl)propan-1-ol (177 mg).

$^1$H-NMR(CDCl$_3$)δ:7.73(1H,d,J=2.7 Hz),6.40(1H,d,J=2.7 Hz),4.58(2H,t,J=6.6 Hz),3.73(2H,5.1 Hz),2.52(3H,s),2.26-2.15(2H,m).

0156-5

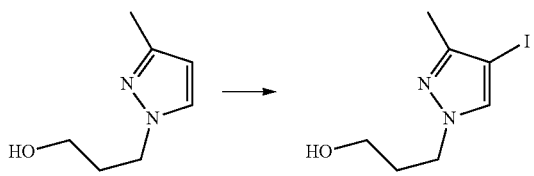

Iodine (95 mg) and ammonium cerium nitrate (206 mg) were added to a solution of 3-(3-methyl-1H-pyrazol-1-yl)propan-1-ol (177 mg) in acetonitrile (6 mL), followed by stirring at room temperature for 9 hours. Ethyl acetate and water were added to the reaction mixture. The organic layer was collected by separation, washed sequentially with a 10% sodium hydrogen sulfite aqueous solution and a saturated sodium chloride aqueous solution, and dried over anhydrous sodium sulfate, and the solvent was distilled off under reduced pressure, thereby obtaining 3-(4-iodo-3-methyl-1H-pyrazol-1-yl)propan-1-ol (134 mg).

MSm/z(M+H):267.

0156-6

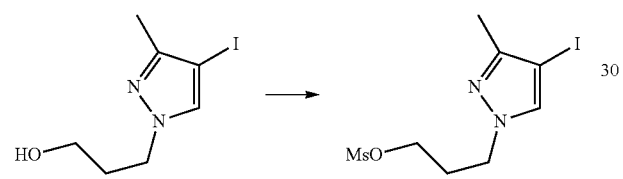

Methanesulfonyl chloride (0.059 mL) was added to a solution of 3-(4-iodo-3-methyl-1H-pyrazol-1-yl)propan-1-ol (134 mg) and triethylamine (0.14 mL) in dichloromethane (5 mL) under ice-cooling, followed by stirring at the same temperature for 30 minutes. Ethyl acetate and water were added to the reaction mixture. The organic layer was collected by separation, washed with a saturated sodium chloride aqueous solution, and dried over anhydrous sodium sulfate, and the solvent was distilled off under reduced pressure, thereby obtaining 3-(4-iodo-3-methyl-1H-pyrazol-1-yl)propyl methanesulfonate (165 mg).

MSm/z(M+H):345.

0156-7

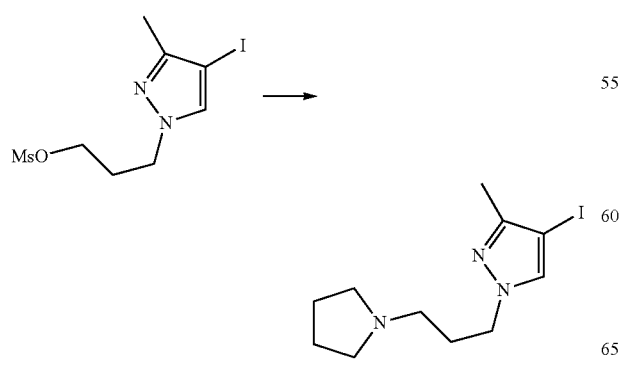

Pyrrolidine (0.048 mL) was added to a mixture of 3-(4-iodo-3-methyl-1H-pyrazol-1-yl)propyl methanesulfonate (165 mg), and potassium carbonate (100 mg) in acetonitrile (2.4 mL), followed by stirring at 50° C. for 10 hours. The reaction mixture was cooled to room temperature, and ethyl acetate and water were added thereto. The organic layer was collected by separation, washed with a saturated sodium chloride aqueous solution, and dried over anhydrous sodium sulfate, and the solvent was distilled off under reduced pressure, thereby obtaining 4-iodo-3-methyl-1-(3-(pyrrolidin-1-yl)propyl)-1H-pyrazole (73 mg).

MSm/z(M+H):320.

0156-8

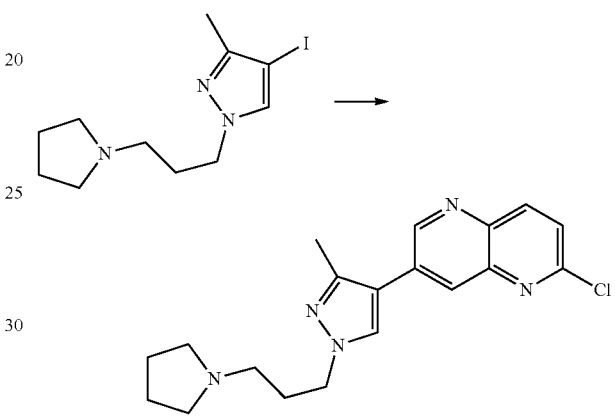

A mixture of 7-bromo-2-chloro-1,5-naphthyridine (56 mg), bis(pinacolato)diboron (87 mg), (1,1'-bis(diphenylphosphino)ferrocene)palladium(II) dichloride (19 mg), and potassium acetate (45 mg) in 1,4-dioxane (2 mL) was stirred at 100° C. for 2 hours in a nitrogen atmosphere. 4-Iodo-3-methyl-1-(3-(pyrrolidin-1-yl)propyl)-1H-pyrazole (73 mg), sodium carbonate (49 mg), and bis(di-tert-butyl(4-dimethylaminophenyl)phosphine)dichloropalladium(II) (16 mg) were added to the reaction mixture, followed by stirring at 100° C. for 2 hours. The reaction mixture was cooled to room temperature, the insolubles were filtered off using celite, and the solvent was distilled off under reduced pressure. The obtained residue was purified by silica gel column chromatography (methanol-ethyl acetate, NH silica), thereby obtaining 2-chloro-7-(3-methyl-1-(3-(pyrrolidin-1-yl)-1H-pyrazol-4-yl)-1,5-naphthyridine (13 mg).

MSm/z(M+H):356.

0156-9

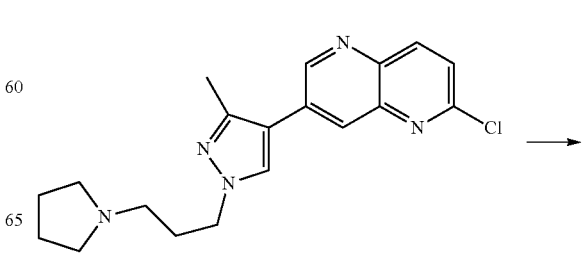

-continued

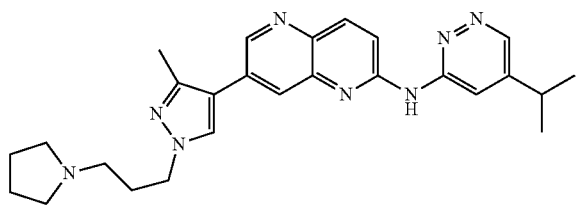

A mixture of 2-chloro-7-(3-methyl-1-(3-(pyrrolidin-1-yl)-1H-pyrazol-4-yl)-1,5-naphthyridine (13 mg), 5-isopropylpyridazine-3-amine (8 mg), tris(dibenzylideneacetone)dipalladium(0) (4 mg), 4,5-bis(diphenylphosphino)-9,9-dimethylxanthene (5 mg), and cesium carbonate (30 mg) in 1,4-dioxane (1 mL) was stirred at 140° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining N-(5-isopropylpyridazin-3-yl)-7-(3-methyl-1-(3-(pyrrolidin-1-yl)propyl)-1H-pyrazol-4-yl)-1,5-naphthyridine-2-amine (4.4 mg).

$^1$H-NMR(CDCl$_3$/CD$_3$OD=4/1)δ:8.92(1H,brs),8.79(1H,d,J=1.8 Hz),8.72(1H,brs),8.22(1H,d,J=9.0 Hz),8.10(1H,d,J=1.8 Hz),7.81(1H,s),7.52(1H,d,J=9.0 Hz),4.25-4.18(2H,m),3.38-3.35(2H,m),3.10-2.99(1H,m),2.61-2.49(4H,m),2.50(3H,s),2.20-2.07(2H,m),1.89-1.79(4H,m),1.40(6H,d,J=6.6 Hz).

MSm/z(M+H):457.

Example 0157

0157-1

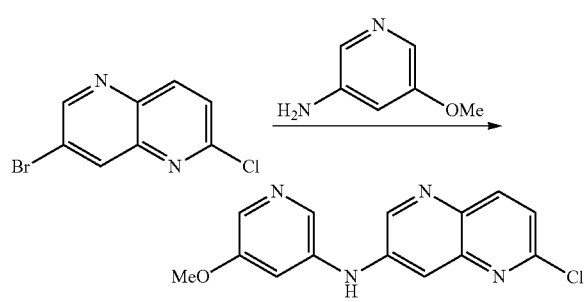

A mixture of 7-bromo-2-chloro-1,5-naphthyridine (50 mg), 5-methoxypyridine-3-amine (25 mg), tris(dibenzylideneacetone)dipalladium(0) (19 mg), 4,5-bis(diphenylphosphino)-9,9-dimethylxanthene (24 mg), and cesium carbonate (33 mg) in 1,4-dioxane (1 mL) was stirred at 140° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining 6-chloro-N-(5-methoxypyridin-3-yl)-1,5-naphthyridine-3-amine (5.4 mg).

MSm/z(M+H):287.

0157-2

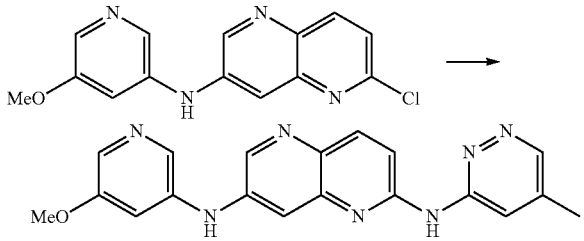

A mixture of 6-chloro-N-(5-methoxypyridin-3-yl)-1,5-naphthyridine-3-amine (5 mg), 5-methylpyrazine-3-amine (3 mg), tris(dibenzylideneacetone)dipalladium(0) (5 mg), 4,5-bis(diphenylphosphino)-9,9-dimethylxanthene (10 mg), and cesium carbonate (20 mg) in 1,4-dioxane (1 mL) was stirred at 140° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining $N^7$-(5-methoxypyridin-3-yl)-$N^2$-(5-methylpyridazin-3-yl)-1,5-naphthyridine-2,7-diamine (15 mg).

$^1$H-NMR(CDCl$_3$/CD$_3$OD=4/1)δ:8.69(1H,brs),8.63(1H,brs),8.50(1H,d,J=2.7 Hz),8.13(1H,d,J=2.7 Hz),8.10(1H,d,J=9.3 Hz),7.92(1H,d,J=2.7 Hz),7.78(1H,brs),7.35(1H,d,J=9.0 Hz),7.22(1H,d,J=2.7 Hz),3.90(3H,s),2.43(3H,s).

MSm/z(M+H):360.

Example 0158

0158-1

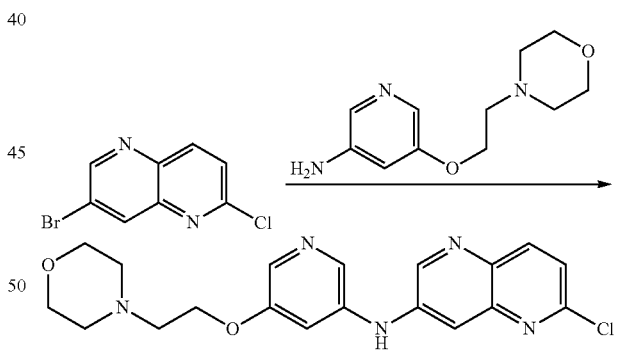

A mixture of 7-bromo-2-chloro-1,5-naphthyridine (100 mg), 5-(2-morpholinoethoxyl)pyridine-3-amine (92 mg), tris(dibenzylideneacetone)dipalladium(0) (37 mg), 4,5-bis(diphenylphosphino)-9,9-dimethylxanthene (47 mg), and cesium carbonate (267 mg) in 1,4-dioxane (2 mL) was stirred at 140° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining 6-chloro-N-(5-(2-morpholinoethoxyl)pyridin-3-yl)-1,5-naphthyridine-3-amine (5.4 mg).

MSm/z(M+H):386.

0158-2

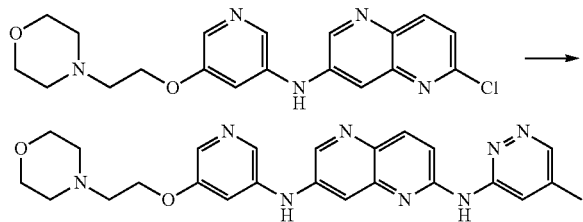

A mixture of 6-chloro-N-(5-(2-morpholinoethoxy)pyridin-3-yl)-1,5-naphthyridine-3-amine (10 mg), 5-methylpyridazine-3-amine (4 mg), tris(dibenzylideneacetone)dipalladium(0) (5 mg), 4,5-bis(diphenylphosphino)-9,9-dimethylxanthene (10 mg), and cesium carbonate (20 mg) in 1,4-dioxane (1 mL) was stirred at 140° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining $N^2$-(5-methylpyridazin-3-yl)-$N^7$-(5-(2-morpholinoethoxy)pyridin-3-yl)-1,5-naphthyridine-2,7-diamine (1.9 mg).

$^1$H-NMR(CDCl$_3$/CD$_3$OD=4/1)δ:8.67(1H,brs),8.63(1H,brs),8.50(1H,brs),8.14(1H,brs),8.11(1H,d,J=9.0 Hz),7.91(1H,brs),7.78(1H,brs),7.24(1H,d,J=9.0 Hz),7.21(1H,brs),4.20(2H,t,J=5.4 Hz),3.79-3.71(4H,m),2.85(2H,t,J=5.4 Hz),2.66-2.56(4H,m),2.43(3H,s).

MSm/z(M+H):459.

Example 0159

0159-1

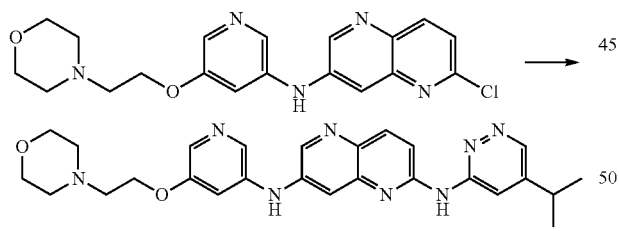

A mixture of 6-chloro-N-(5-(2-morpholinoethoxy)pyridin-3-yl)-1,5-naphthyridine-3-amine (10 mg), 5-isopropylpyridazine-3-amine (5 mg), tris(dibenzylideneacetone)dipalladium(0) (5 mg), 4,5-bis(diphenylphosphino)-9,9-dimethylxanthene (10 mg), and cesium carbonate (20 mg) in 1,4-dioxane (1 mL) was stirred at 140° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining $N^2$-(5-isopropylpyridazin-3-yl)-$N^7$-(5-(2-morpholinoethoxy)pyridin-3-yl)-1,5-naphthyridine-2,7-diamine (3.8 mg).

$^1$H-NMR(CDCl$_3$/CD$_3$OD=4/1)δ:8.75(1H,brs),8.69(1H,brs),8.52(1H,d,J=2.7 Hz),8.12(1H,brs),8.11(1H,d,J=8.7 Hz),7.91(1H,brs),7.73(1H,brs),7.40(1H,d,J=8.7 Hz),7.22(1H,brs),4.18(2H,t,J=5.4 Hz),3.77-3.72(4H,m),3.06-2.95(1H,m),2.84(2H,t,J=5.4 Hz),2.63-2.57(4H,m),1.37(6H,d,J=7.4 Hz).

MSm/z(M+H):487.

Example 0160

0160-1

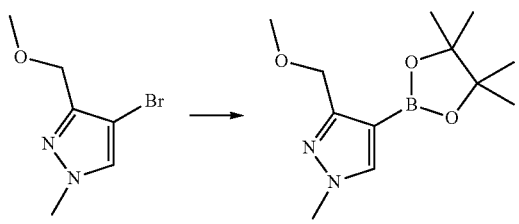

A 2.6 mol/L n-butyllithium-hexane solution (0.52 mL) was added to a solution of 4-bromo-3-(methoxymethyl)-1-methyl-1H-pyrazole (185 mg) in tetrahydrofuran (4.5 mL) at −80° C., followed by stirring at the same temperature for 30 minutes, and 2-isopropyloxy-4,4,5,5-tetramethyl-1,3,2-dioxaborolane (369 mg) was added thereto at the same temperature, followed by stirring while slowly heating to room temperature over a period of 2.5 hours. A saturated ammonium chloride aqueous solution and ethyl acetate were added to the reaction mixture. The organic layer was collected by separation, washed with a saturated sodium chloride aqueous solution, and dried over anhydrous sodium sulfate, and the solvent was distilled off under reduced pressure, thereby obtaining 3-(methoxymethyl)-1-methyl-4-(4,4,5,5-tetramethyl-1,3,2-dioxaborolan-2-yl)-1H-pyrazole (304 mg).

$^1$H-NMR(CDCl$_3$)δ:7.59(1H,s),4.60(2H,s),3.87(3H,s),3.43(3H,s),1.24(12H,s).

0160-2 and 0160-3

The following compounds were obtained in the same manner as in Examples 0001-4 and 0001-5.

| Example No. | | |
|---|---|---|
| 0160 | | |
| 0160-2 | 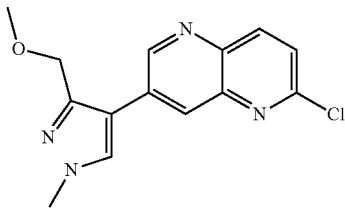 [SMILES: CN/C=C(\C(=N)COC)c1cnc2ccc(Cl)nc2c1] | MS m/z (M + H): 289. |
| 0160-3 | 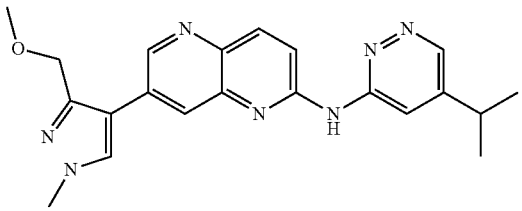 [SMILES: CN/C=C(\C(=N)COC)c1cnc2ccc(Nc3cc(C(C)C)cnn3)nc2c1] | ¹H-NMR (CDCl₃/CD₃OD = 4/1) δ: 8.98 (1H, brs), 8.85 (1H, d, J = 1.8 Hz), 8.70 (1H, brs), 8.37 (1H, d, J = 1.8 Hz), 8.22 (1H, d, J = 9.3 Hz), 7.84 (1H, s), 7.50 (1H, d, J = 9.3 Hz), 4.57 (2H, s), 3.97 (3H, s), 3.51 (3H, s), 3.08-2.98 (1H, m), 1.41 (6H, d, J = 7.2 Hz). MS m/z (M + H): 390. |

Examples 0161 to 0164

The following compounds were obtained in the same manner as in Example 0001-5.

| Example No. | | |
|---|---|---|
| 0161 | | |
| 0161-1 | 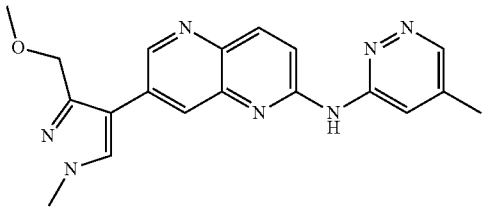 | ¹H-NMR (CDCl₃/CD₃OD = 4/1) δ: 8.98 (1H, brs), 8.87 (1H, brs), 8.66 (1H, brs), 8.32 (1H, brs), 8.22 (1H, d, J = 9.3 Hz), 7.85 (1H, s), 7.51 (1H, d, J = 9.3 Hz), 4.58 (2H, s), 4.00 (3H, s), 3.54 (3H, s), 2.46 (3H, s). MS m/z (M + H): 362. |
| 0162 | | |
| 0162-1 | 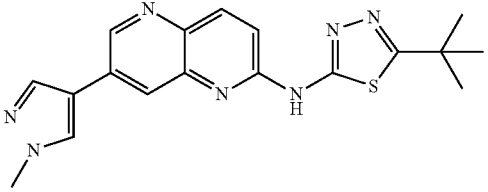 [SMILES: CN/C=C(\C=N)c1cnc2ccc(Nc3nnc(C(C)(C)C)s3)nc2c1] | ¹H-NMR (DMSO-d₆) δ: 12.03 (1H, s), 9.07 (1H, d, J = 2.0 Hz), 8.53 (1H, s), 8.33 (1H, d, J = 1.3 Hz), 8.26-8.23 (2H, m), 7.39 (1H, d, J = 8.9 Hz), 3.93 (3H, s), 1.48 (9H, s). MS m/z (M + H): 366. |
| 0163 | | |
| 0163-1 | 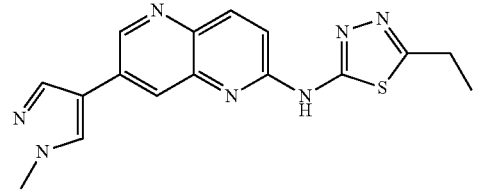 [SMILES: CCc1nnc(Nc2ccc3ncc(/C(C=N)=C/NC)cc3n2)s1] | ¹H-NMR (DMSO-d₆) δ: 12.04 (1H, s), 9.07 (1H, d, J = 2.0 Hz), 8.52 (1H, s), 8.32 (1H, d, J = 1.3 Hz), 8.25 (1H, d, J = 8.9 Hz), 8.21 (1H, s), 7.39 (1H, d, J = 8.9 Hz), 3.93 (3H, s), 3.03 (2H, q, J = 7.5 Hz), 1.38 (3H, t, J = 7.4 Hz). MS m/z (M + H): 338. |

| Example No. | | |
|---|---|---|
| 0164 | | |
| 0164-1 | 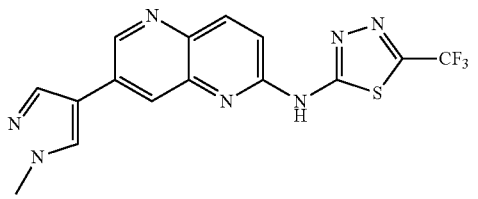 [SMILES: CN/C=C(\C=N)c1cnc2ccc(Nc3nnc(C(F)(F)F)s3)nc2c1] | ¹H-NMR (DMSO-d₆) δ: 12.94 (1H, s), 9.15 (1H, d, J = 2.0 Hz), 8.57 (1H, s), 8.53 (1H, s), 8.37 (1H, d, J = 8.9 Hz), 8.26 (1H, s), 7.50 (1H, d, J = 9.2 Hz), 3.93 (3H, s). MS m/z (M + H): 378. |

Example 0165

0165-1

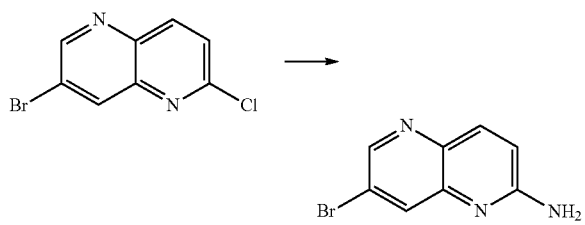

A mixture solution of 7-bromo-2-chloro-1,5-naphthyridine (100 mg) in 1,4-dioxane (2 mL) and a 25% ammonia aqueous solution was stirred at 120° C. for 3 hours using a microwave reaction apparatus. The reaction mixture was cooled to room temperature, and a saturated sodium chloride aqueous solution and ethyl acetate were added thereto. The organic layer was collected by separation, and dried over anhydrous sodium sulfate, and the solvent was distilled off under reduced pressure, thereby obtaining 7-bromo-1,5-naphthyridine-2-amine (90 mg) as a white solid.
MSm/z(M+H):224,226.

0165-2

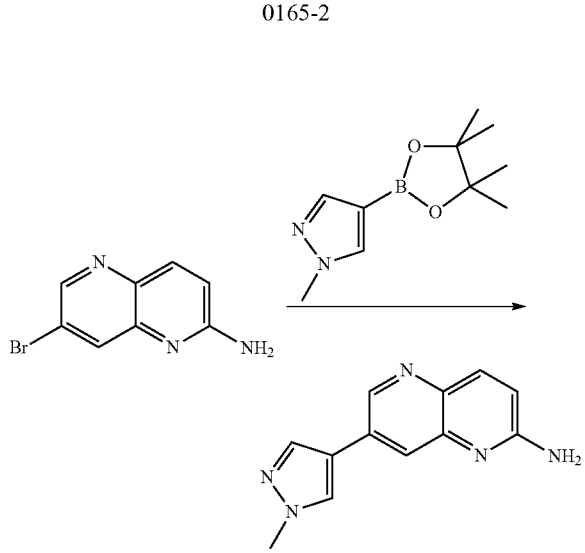

1-Methylpyrazole-4-boronic acid pinacol ester (460 mg), bis(di-tert-butyl(4-dimethylaminophenyl)phosphine)dichloropalladium(II) (70 mg), sodium carbonate (440 mg), 1,4-dioxane (1 mL), and water (200 μL) were added to a solution of 7-bromo-1,5-naphthyridine-2-amine (500 mg) in 1,4-dioxane (2 mL), followed by stirring at 100° C. for 2 hours in a nitrogen atmosphere. The reaction liquid was cooled to room temperature, a solution of chloroform-methanol was added thereto, and the resultant product was purified by silica gel column chromatography (chloroform-methanol, NH silica), thereby obtaining 7-(1-methyl-1H-pyrazol-4-yl)-1,5-naphthyridine-2-amine (180 mg).

MSm/z(M+H):226.

0165-3

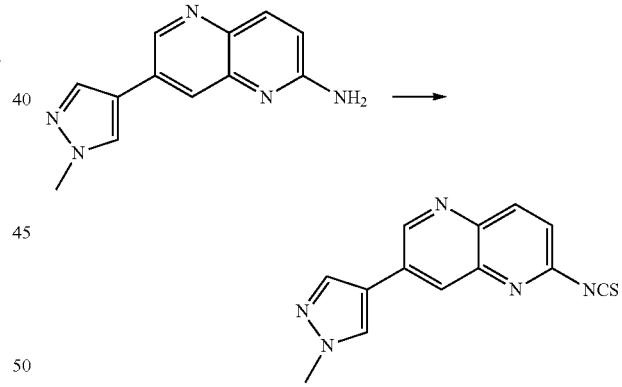

Pyridine (5 mL) was added to a mixture of 7-(1-methyl-1H-pyrazol-4-yl)-1,5-naphthyridine-2-amine (100 mg) and phenyl chlorothioformate (200 mg), followed by stirring at room temperature for 1 hour. The solvent was distilled off at 60° C. under reduced pressure, and the obtained residue was purified by silica gel column chromatography (hexane-ethyl acetate), thereby obtaining 2-isothiocyanate-7-(1-methyl-1H-pyrazol-4-yl)-1,5-naphthyridine (105 mg).

¹H-NMR(CDCl₃)δ:9.11(1H,d,J=2.3 Hz),8.37(1H,d,J=8.6 Hz),8.26(1H,t,J=1.0 Hz),7.96(1H,s),7.84(1H,s),7.38(1H,d,J=8.9 Hz),4.02(3H,s).

0165-4

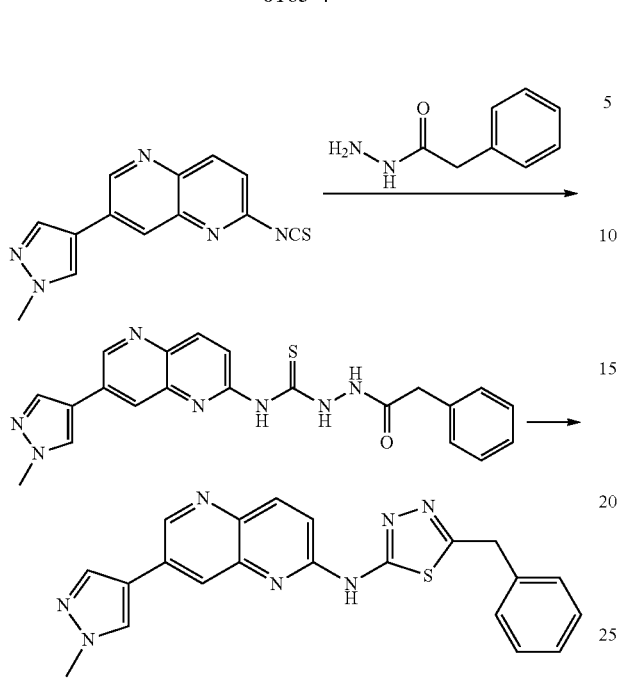

A solution of 2-isothiocyanate-7-(1-methyl-1H-pyrazol-4-yl)-1,5-naphthyridine (10 mg) and benzeneacetic acid hydrazide (10 mg) in 1,4-dioxane (1 mL) was stirred at 120° C. for 30 minutes using a microwave reaction apparatus. The solvent was distilled off under reduced pressure, and sulfuric acid (0.6 mL) was added thereto under ice-coolong, followed by stirring at room temperature for 30 minutes. The reaction mixture was added dropwise to ice water, and the resultant product was neutralized with a sodium hydroxide aqueous solution. The solid matter was collected by filtration, thereby obtaining 5-benzyl-N-(7-(1-methyl-1H-pyrazol-4-yl)-1,5-naphthyridin-2-yl)-1,3,4-thiadiazole-2-amine (10 mg) as a yellow solid.

$^1$H-NMR(DMSO-$d_6$)δ:12.10(1H,s),9.06(1H,d,J=2.0 Hz),8.49(1H,s),8.27-8.23(2H,m),8.18(1H,s),7.42-7.34(5H,m),7.31-7.25(1H,m),4.40(2H,s),3.92(3H,s).

MSm/z(M+H):400.

Example 0166

0166-1

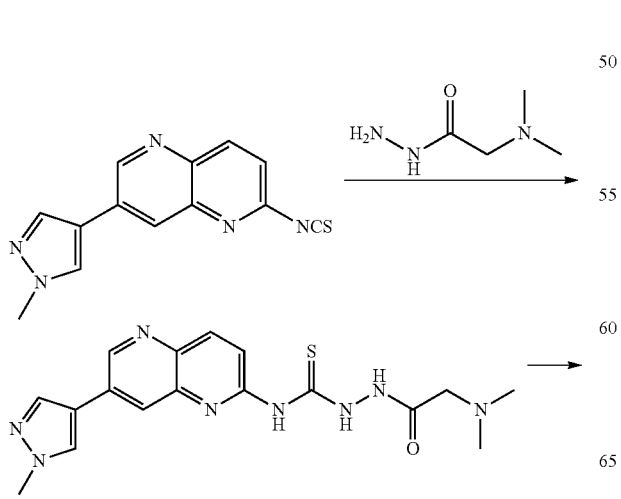

-continued

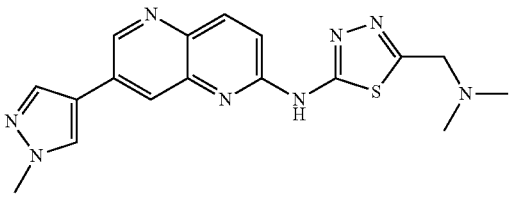

5-((Dimethylamino)methyl)-N-(7-(1-methyl-1H-pyrazol-4-yl)-1,5-naphthyridin-2-yl)-1,3,4-thiadiazole-2-amine was obtained as a yellow solid in the same manner as in Example 0165-4.

$^1$H-NMR(CDCl$_3$)δ:8.96(1H,s),8.36-8.28(2H,m),8.02(1H,s),7.90(1H,s),7.63-7.59(1H,m),4.04(3H,s),3.96(2H,s),2.45(6H,s).

MSm/z(M+H):367.

Example 0167

0167-1

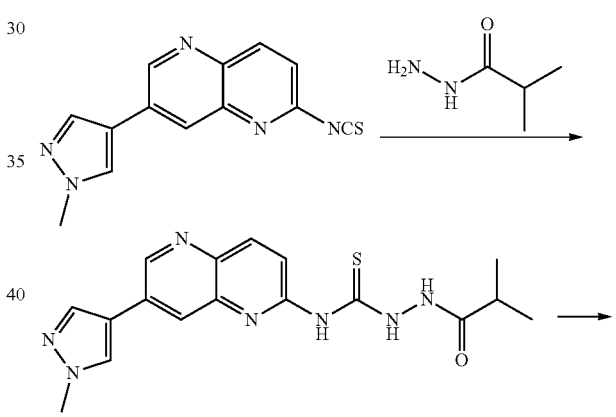

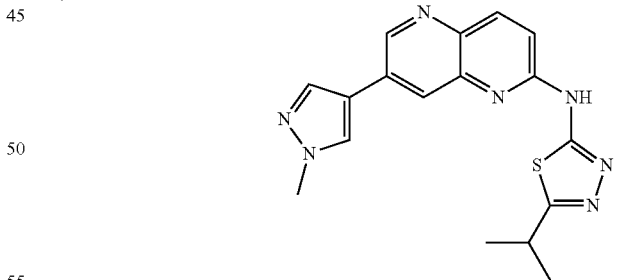

5-Isopropyl-N-(7-(1-methyl-1H-pyrazol-4-yl)-1,5-naphthyridin-2-yl)-1,3,4-thiadiazole-2-amine was obtained as a white solid in the same manner as in Example 0165-4.

$^1$H-NMR(DMSO-$d_6$)δ:12.04(1H,s),9.05(1H,d,J=2.0 Hz),8.52(1H,s),8.31(1H,d,J=1.7 Hz),8.24-8.21(2H,m),7.38(1H,d,J=9.2 Hz),3.93(3H,s),3.41-3.35(1H,m),1.42(6H,d,J=6.9 Hz).

MSm/z(M+H):352.

Example 0168

0168-1

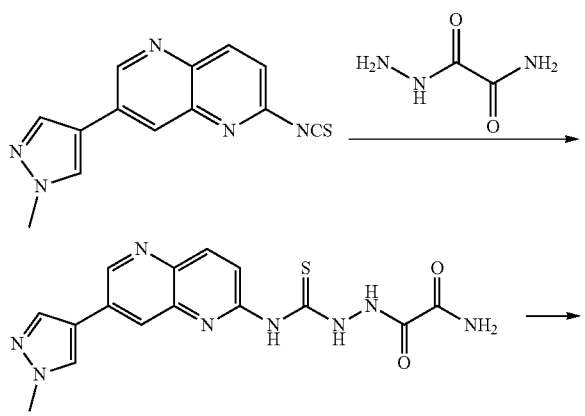

5-((7-(1-Methyl-1H-pyrazol-4-yl)-1,5-naphthyridin-2-yl)amino)-1,3,4-thiadiazole-2-carboxamide was obtained as a pale yellow solid in the same manner as in Example 0165-4.

$^1$H-NMR(DMSO-d$_6$)δ:12.56(1H,s),9.12(1H,d,J=2.3 Hz), 8.59(1H,s),8.37-8.35(2H,m),8.32(1H,d,J=9.2 Hz),8.25(1H,s),7.91(1H,s),7.45(1H,d,J=8.9 Hz),3.92(3H,s).

MSm/z(M+H):353.

Example 0169

0169-1

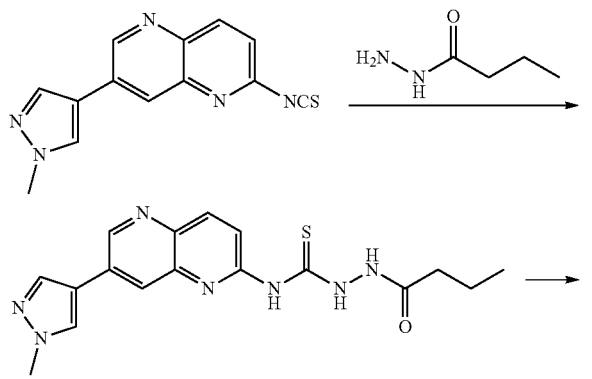

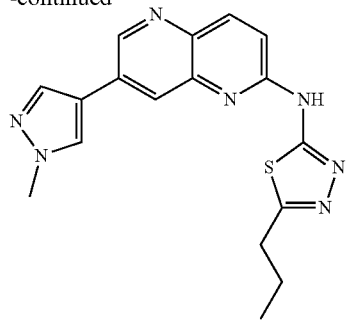

N-(7-(1-methyl-1H-pyrazol-4-yl)-1,5-naphthyridin-2-yl)-5-propyl-1,3,4-thiadiazol-2-amine was obtained as a white solid in the same manner as in Example 0165-4.

$^1$H-NMR(CDCl$_3$)δ:12.04(1H,s),9.07(1H,d,J=2.0 Hz), 8.53(1H,s),8.32(1H,d,J=1.7 Hz),8.25(1H,d,J=8.9 Hz),8.21 (1H,s),7.39(1H,d,J=8.9 Hz),3.93(3H,s),2.99(2H,t,J=7.4 Hz), 1.87-1.75(2H,m),1.00(3H,t,J=7.4 Hz).

MSm/z(M+H):352.

Example 0170

0170-1

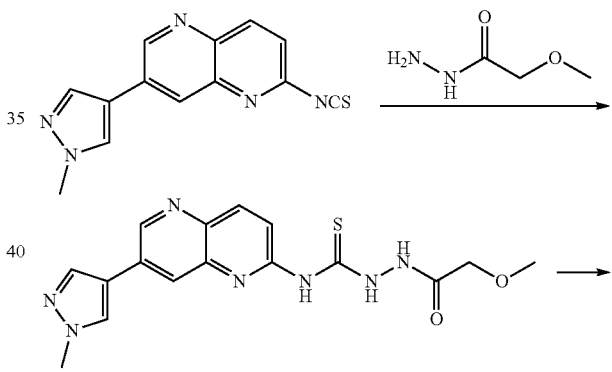

5-(Methoxymethyl)-N-(7-(1-methyl-1H-pyrazol-4-yl)-1,5-naphthyridin-2-yl)-1,3,4-thiadiazole-2-amine) was obtained as a white solid in the same manner as in Example 0165-4.

$^1$H-NMR(CDCl$_3$)δ:12.20(1H,s),9.09(1H,d,J=2.3 Hz), 8.55(1H,s),8.34(1H,d,J=1.7 Hz),8.28(1H,d,J=8.9 Hz),8.23 (1H,s),7.42(1H,d,J=8.9 Hz),4.79(2H,s),3.92(3H,s),3.39(3H,s).

MSm/z(M+H):354.

Example 0171

171-1

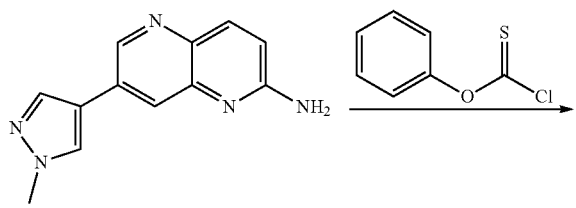

Pyridine (5 mL) was added to a mixture of 7-(1-methyl-1H-pyrazol-4-yl)-1,5-naphthyridine-2-amine (150 mg) and phenyl chlorothioformate (200 μL), followed by stirring at room temperature for 1 hour. Phenyl chlorothioformate (200 μL) was added thereto, followed by stirring at room temperature for 1 hour. The solvent was distilled off at 40° C. under reduced pressure. A solution of ethanol-chloroform was added to the obtained residue, and the resultant product was purified by silica gel column chromatography (hexane-ethyl acetate), thereby obtaining (7-(1-methyl-1H-pyrazol-4-yl)-1,5-naphthyridin-2-yl)thiocarbamic acid phenyl (100 mg).

MSm/z(M+H):362.

0171-2

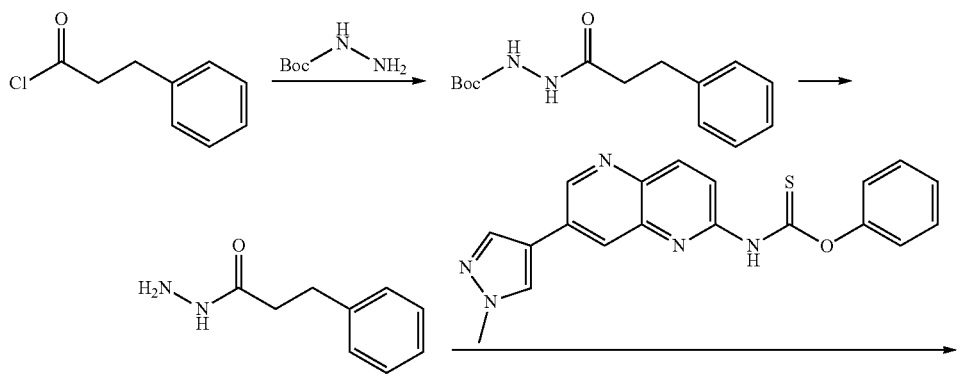

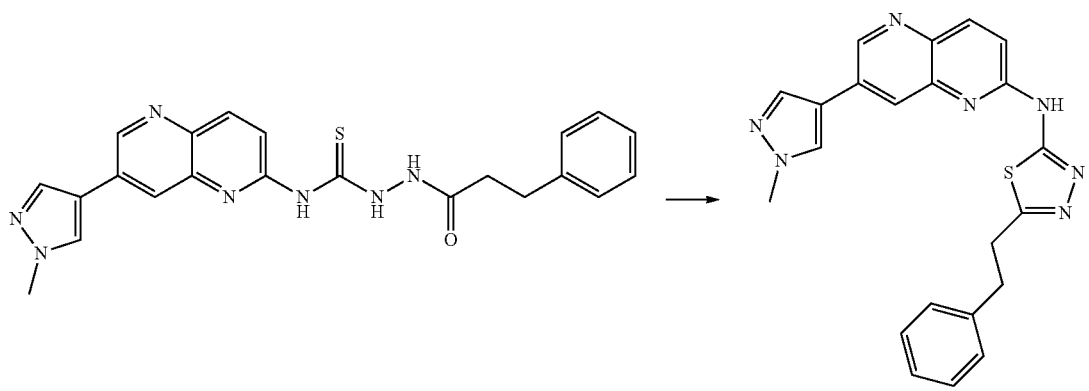

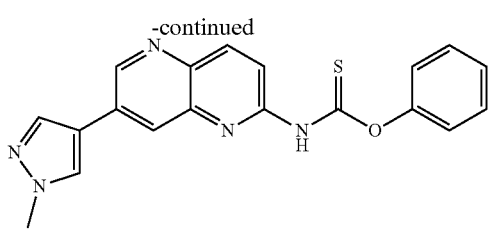

N,N-diisopropylethylamine (400 μL) was added to a solution of 3-phenylpropionyl chloride (170 mg) and tert-butyl carbazate (150 mg) in 1,4-dioxane (2 mL), followed by stirring at room temperature for 2 hours. A 4 mol/L hydrogen chloride/1,4-dioxane solution (2 mL) was added to the reaction mixture, followed by allowing to stand at room temperature overnight. The solvent was distilled off under reduced pressure, and ethyl acetate and water were added to the obtained residue. The organic layer was collected by separation, washed with a saturated sodium chloride aqueous solution, and dried over anhydrous sodium sulfate, and the solvent was distilled off under reduced pressure. The obtained residue was purified by silica gel column chromatography (chloroform-methanol, NH silica), thereby obtaining 3-phenylpropanoic acid hydrazide.

(7-(1-Methyl-1H-pyrazol-4-yl)-1,5-naphthyridin-2-yl)thiocarbamic acid phenyl (10 mg) and 1,4-dioxane (1 mL) were added to 3-phenylpropanoic acid hydrazide, followed by stirring at room temperature for 30 minutes. The solvent was distilled off under reduced pressure, and the obtained residue was washed with ethyl acetate, thereby obtaining N-(7-(1-methyl-1H-pyrazol-4-yl)-1,5-naphthyridin-2-yl)-2-(3-phenylpropanoyl)hydrazine carbothioamide.

Sulfuric acid (0.6 mL) was added to N-(7-(1-methyl-1H-pyrazol-4-yl)-1,5-naphthyridin-2-yl)-2-(3-phenylpropanoyl)hydrazine carbothioamide under ice-cooling, followed by stirring at room temperature for 30 minutes. The reaction mixture was added dropwise to ice water, and the resultant product was neutralized with a sodium hydroxide aqueous solution. The solid matter was collected by filtration, and washed with a solution of chloroform-methanol, thereby obtaining N-(7-(1-methyl-1H-pyrazol-4-yl)-1,5-naphthyridin-2-yl)-5-phenethyl-1,3,4-thiadiazole-2-amine (6 mg) as a white solid.

$^1$H-NMR(DMSO-$d_6$)δ:12.05(1H,s),9.07(1H,d,J=2.0 Hz),8.51(1H,s),8.27-8.23(2H,m),8.20(1H,s),7.39(1H,d,J=9.2 Hz),7.34-7.32(4H,m),7.26-7.19(1H,m),3.94(3H,s),3.38-3.34(2H,m),3.12(2H,t,J=7.8 Hz).

MSm/z(M+H):414.

Example 0172

0172-1

A solution of cyclopentanecarboxylic acid methyl (20 μL) and hydrazine monohydrate (20 μL) in methanol (1 mL) was stirred at 100° C. for 1 hour using a microwave reaction apparatus. The solvent was distilled off under reduced pressure, and (7-(1-methyl-1H-pyrazol-4-yl)-1,5-naphthyridin-2-yl)thiocarbamic acid phenyl (10 mg) and 1,4-dioxane (1 mL) were added to the obtained residue, followed by stirring at 140° C. for 30 minutes using a microwave reaction apparatus. The solvent was distilled off under reduced pressure, and ethanol (1 mL) and sulfuric acid (10 μL) were added to the obtained residue, followed by stirring at 100° C. for 30 minutes using a microwave reaction apparatus. Water was added to the reaction mixture, and the resultant product was neutralized with a sodium hydroxide aqueous solution. The solid matter was collected by filtration, and washed with a solution of chloroform-methanol, thereby obtaining 5-cyclopentyl-N-(7-(1-methyl-1H-pyrazol-4-yl)-1,5-naphthyridin-2-yl)-1,3,4-thiadiazole-2-amine (2 mg) as a yellow solid.

$^1$H-NMR(DMSO-$d_6$)δ:12.03(1H,s),9.06(1H,d,J=2.0 Hz),8.53(1H,s),8.31(1H,d,J=1.7 Hz),8.26-8.20(2H,m),7.38(1H,d,J=8.9 Hz),3.93(3H,s),3.52-3.43(1H,m),2.21-2.13(2H,m),1.93-1.65(6H,m).

MSm/z(M+H):378.

Example 0173

0173-1

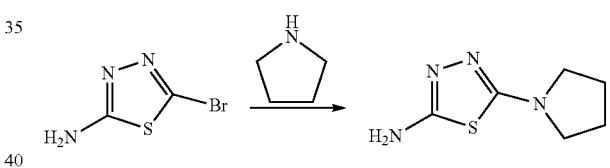

A solution of 5-bromo-1,3,4-thiadiazole-2-amine (20 mg), potassium carbonate (20 mg), and pyrrolidine (20 μL) in 1,4-dioxane (1 mL) was stirred at 100° C. for 30 minutes using a microwave reaction apparatus. Water was added to the reaction mixture, the solid matter was collected by filtration, and the obtained residue was purified by silica gel column chromatography (chloroform-methanol, NH silica), thereby obtaining 2-amino-5-(1-pyrrolidinyl)-1,3,4-thiadiazole (10 mg).

$^1$H-NMR(DMSO-$d_6$)δ:6.27(2H,s),3.30-3.23(4H,m),1.93-1.88(4H,m).

0173-2

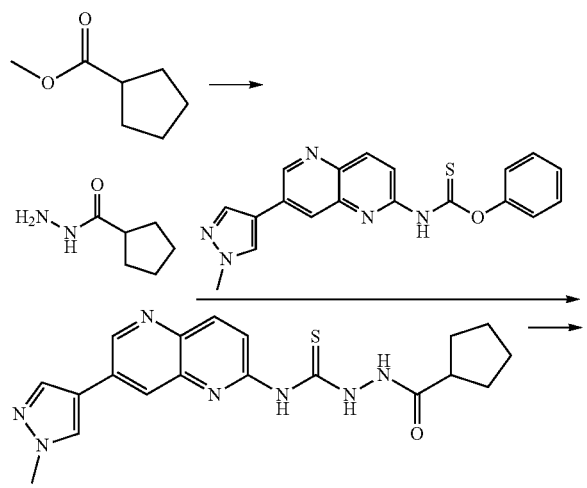

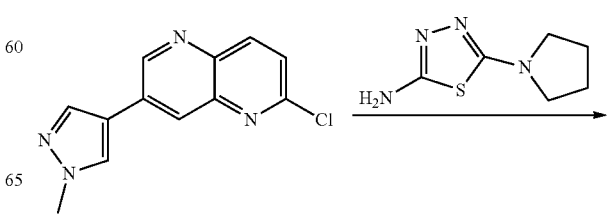

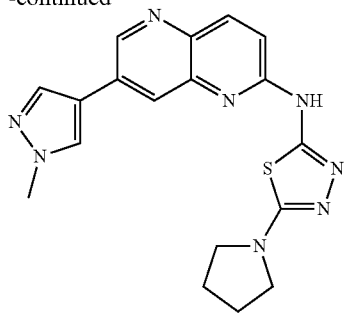

N-(7-(1-methyl-1H-pyrazol-4-yl)-1,5-naphthyridin-2-yl)-5-(pyrrolidin-1-yl)-1,3,4-thiadiazole-2-amine was obtained as a yellow solid in the same manner as in Example 0001-5.

$^1$H-NMR(DMSO-d$_6$)δ:11.55(1H,s),9.01(1H,d,J=2.3 Hz), 8.50(1H,s),8.22(1H,d,J=1.3 Hz),8.20(1H,s),8.16(1H,d, J=8.9 Hz),7.29(1H,d,J=9.2 Hz),3.92(3H,s),3.47(4H,t,J=6.6 Hz),2.01(4H,t,J=6.4 Hz).

MSm/z(M+H):379.

Example 0174

0174-1

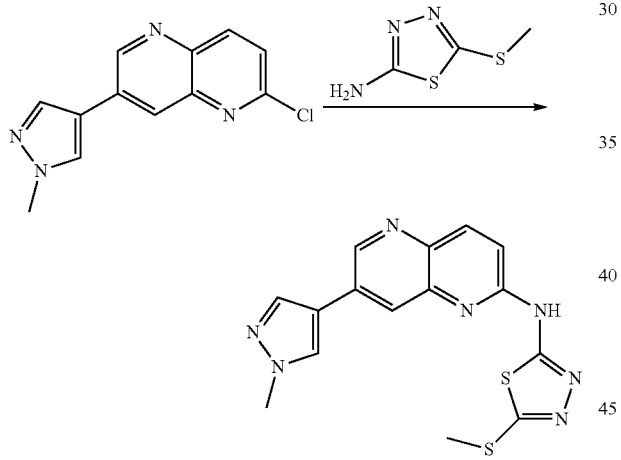

N-(7-(1-methyl-1H-pyrazol-4-yl)-1,5-naphthyridin-2-yl)-5-(methylthio)-1,3,4-thiadiazole-2-amine was obtained as a yellow solid in the same manner as in Example 0001-5.

$^1$H-NMR(DMSO-d$_6$)δ:9.08(1H,d,J=2.3 Hz),8.54(1H,s), 8.39(1H,d,J=1.7 Hz),8.26(1H,d,J=9.2 Hz),8.23(1H,s),7.38 (1H,d,J=8.9 Hz),3.92(3H,s),2.76(3H,s).

MSm/z(M+H):356.

Example 0175

0175-1

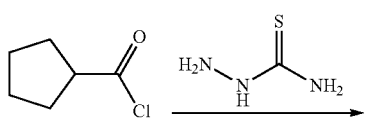

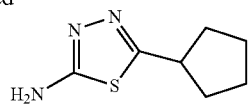

Cyclopentanecarbonyl chloride (3 mL) was added to a solution of thiosemicarbazide (2.0 g) in hydrochloric acid (10 mL), followed by stirring for 60 hours under heating to reflux. The reaction mixture was cooled to room temperature, and neutralized by the addition of a sodium hydroxide aqueous solution under ice-cooling. The solid matter was collected by filtration, and dissolved by the addition of ethyl acetate and methanol. The resultant product was dried over anhydrous sodium sulfate, and passed through silica gel column chromatography (NH silica). The solvent was distilled off under reduced pressure, and the obtained residue was washed with a solution of ethyl acetate-hexane, thereby obtaining 2-amino-5-cyclopentyl-1,3,4-thiadiazole (2.83 g).

$^1$H-NMR(DMSO-d$_6$)δ:6.98(2H,s),3.30-3.20(1H,m),2.07-1.95(2H,m),1.69-1.59(6H,m).

0175-2

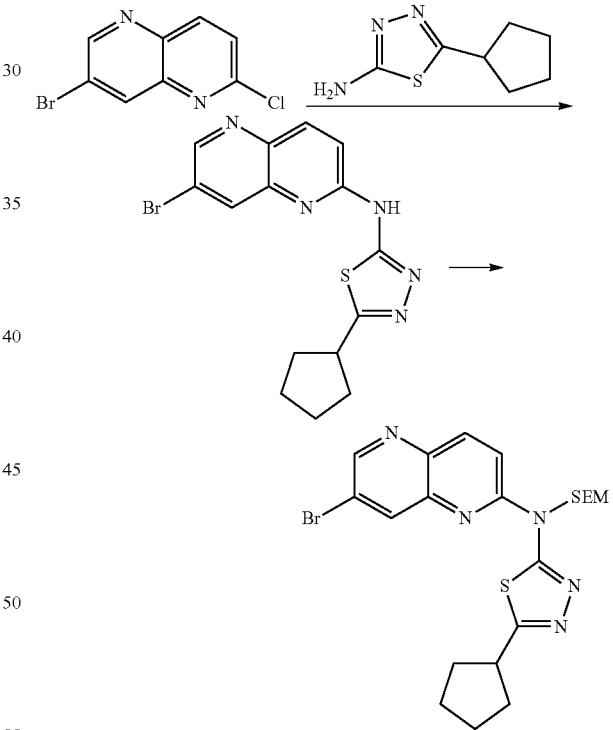

A mixture of 2-amino-5-cyclopentyl-1,3,4-thiadiazole (1.73 g), 7-bromo-2-chloro-1,5-naphthyridine (2.40 g), and potassium carbonate (1.99 g) in dimethylsulfoxide (20 mL) was stirred at 150° C. for 1.5 hours. The reaction mixture was cooled to room temperature, and water (300 mL) was added thereto. The solid matter was collected by filtration, thereby obtaining N-(7-bromo-1,5-naphthyridin-2-yl)-5-cyclopentyl-1,3,4-thiadiazole-2-amine (1.55 g).

60% sodium hydride (150 mg) was added to a solution of the obtained N-(7-bromo-1,5-naphthyridin-2-yl)-5-cyclopentyl-1,3,4-thiadiazole-2-amine in N,N-dimethylformamide (25 mL) under ice-cooling, followed by stirring at 0° C. for 15 minutes. 2-(Chloromethoxy)ethyltrimethylsilane (700 µL) was added to the reaction mixture, followed by stirring at room temperature for 30 minutes. Methanol (2 mL) was added to the reaction mixture at 0° C., and a saturated sodium chloride aqueous solution and ethyl acetate were added thereto. The organic layer was collected by separation, and dried over anhydrous sodium sulfate, and the solvent was distilled off under reduced pressure. The obtained residue was purified by silica gel column chromatography (hexane-ethyl acetate, NH silica), thereby obtaining N-(7-bromo-1,5-naphthyridin-2-yl)-5-cyclopentyl-N-((2-(trimethylsilyl)ethoxy)methyl)-1,3,4-thiadiazole-2-amine (1.82 g) as brown oily substance.

$^1$H-NMR(DMSO-d$_6$)δ:8.92(1H,d,J=2.0 Hz),8.70(1H,d,J=2.0 Hz),8.34(1H,d,J=8.9 Hz),7.55(1H,d,J=9.2 Hz),5.73 (2H,s),3.81(2H,td,J=7.9,3.2 Hz),3.58(1H,t,J=7.9 Hz),2.28-2.16(2H,m),2.01-1.76(8H,m),0.03(9H,s).

0175-3

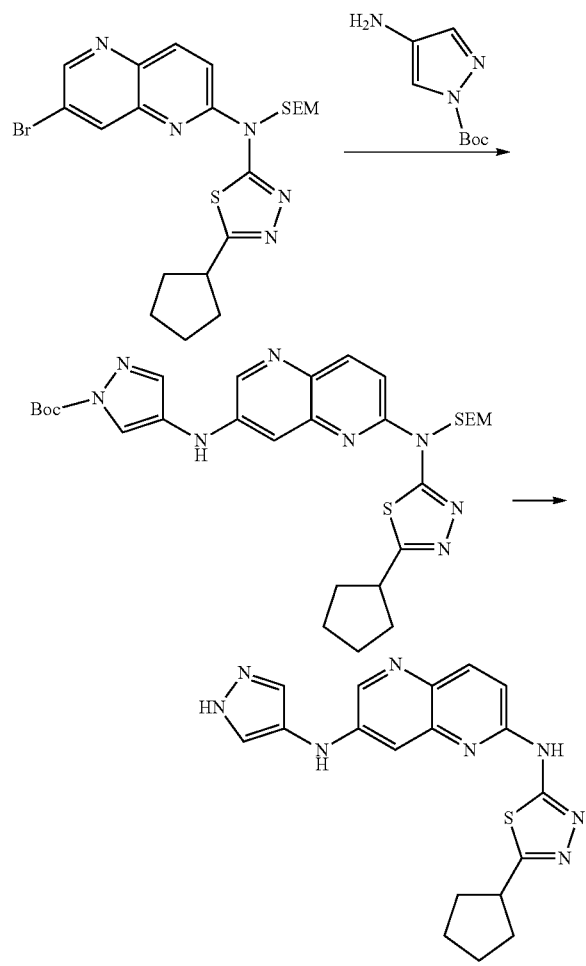

tert-Butyl=4-amino-1H-pyrazole-1-carboxylate (25 mg), 4,5-bis(diphenylphosphino)-9,9-dimethylxanthene (7 mg), cesium carbonate (65 mg), and tris(dibenzylideneacetone) dipalladium(0) (6 mg) were added to a solution of N-(7-bromo-1,5-naphthyridin-2-yl)-5-cyclopentyl-N-((2-(trimethylsilyl)ethoxy)methyl)-1,3,4-thiadiazole-2-amine (50 mg) in 1,4-dioxane (1 mL), followed by stirring at 100° C. for 8 hours in a nitrogen atmosphere. 4,5-Bis(diphenylphosphino)-9,9-dimethylxanthene (5 mg) and tris(dibenzylideneacetone)dipalladium(0) (5 mg) were added thereto, followed by stirring at 100° C. for 3 hours in a nitrogen atmosphere. The reaction mixture was cooled to room temperature, and water was added thereto. The solid matter was collected by filtration, thereby obtaining tert-butyl 4-((6-((5-cyclopentyl-1,3,4-thiadiazol-2-yl)((2-(trimethylsilyl)ethoxy)methyl)amino)-1,5-naphthyridin-3-yl)amino)-1H-pyrazole-1-carboxylate.

Hydrochloric acid (1 mL) was added to the obtained tert-butyl 4-((6-((5-cyclopentyl-1,3,4-thiadiazol-2-yl)((2-(trimethylsilyl)ethoxy)methyl)amino)-1,5-naphthyridin-3-yl)amino)-1H-pyrazole-1-carboxylate, followed by stirring at 90° C. for 1 hour. The reaction mixture was cooled to room temperature, and the resultant product was neutralized with a sodium hydroxide aqueous solution. The solid matter was collected by filtration, and purified by preparative reversed phase HPLC (a 0.1% formic acid aqueous solution-a 0.1% formic acid acetonitrile solution), thereby obtaining N$^2$-(5-cyclopentyl-1,3,4-thiadiazol-2-yl)-N$^7$-(1H-pyrazol-4-yl)-1,5-naphthyridine-2,7-diamine (4.5 mg) as a yellow solid.

$^1$H-NMR(DMSO-d$_6$)δ:12.82(1H,s),11.79(1H,s),8.42(1H,d,J=2.6 Hz),8.36(1H,s),8.05(1H,d,J=8.9 Hz),7.90(1H,s),7.56(1H,s),7.12(1H,d,J=2.3 Hz),7.09(1H,d,J=8.9 Hz),3.52-3.40(1H,m),2.16-2.07(2H,m),1.88-1.62(6H,m).

MSm/z(M+H):379.

Example 0176

0176-1

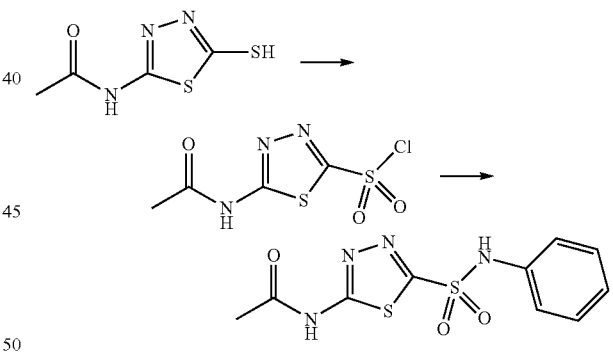

A sodium hypochlorite solution (13 mL) was added dropwise to a mixture solution of dichloromethane (25 mL) and 2 mol/L hydrochloric acid (15 mL) at −10° C., and a solution of 5-acetamide-2-mercapto-1,3,4-thiadiazole (300 mg) in dichloromethane (5 mL) was added dropwise thereto. Then, sodium hydrogen sulfite aqueous solution was added thereto until potassium iodide starch paper was decolorized. The organic layer was collected by separation, washed with a saturated sodium chloride aqueous solution, and dried over anhydrous sodium sulfate, and aniline (400 µL) was added thereto under ice-cooling. A saturated ammonium chloride aqueous solution was added to the reaction mixture. The organic layer was collected by separation, and dried over anhydrous sodium sulfate, and the solvent was distilled off under reduced pressure. The obtained residue was purified by silica gel column chromatography (chloroform-methanol), thereby obtaining N-(5-(N-phenylsulfamoyl)-1,3,4-thiadiazol-2-yl)acetamide (161 mg).

¹H-NMR(DMSO-d₆)δ:13.10(1H,s),11.16(1H,s),7.35-7.29(2H,m),7.20-7.12(3H,m),2.21(3H,s).

0176-2

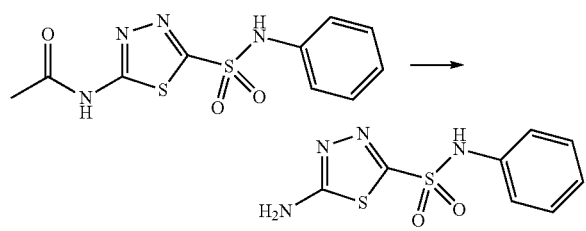

Hydrochloric acid (2 mL) was added to a solution of N-(5-(N-phenylsulfamoyl)-1,3,4-thiadiazol-2-yl)acetamide (155 mg) in ethanol (2 mL), followed by stirring at 90° C. for 30 minutes. The reaction mixture was cooled to room temperature, and neutralized with a sodium hydroxide aqueous solution under ice-cooling. Liquid-liquid separation was performed by the addition of chloroform thereto, and the water of the aqueous layer was distilled off under reduced pressure. A solution of chloroform-methanol was added to the residue, the solid was separated by filtration, and the filtrate was purified by silica gel column chromatography (ethyl acetate, NH silica), thereby obtaining 5-amino-N-phenyl-1,3,4-thiadiazole-2-sulfonamide (98 mg).

¹H-NMR(DMSO-d₆)δ:10.91(1H,s),7.95(2H,s),7.35-7.28(2H,m),7.19-7.10(3H,m).

0176-3

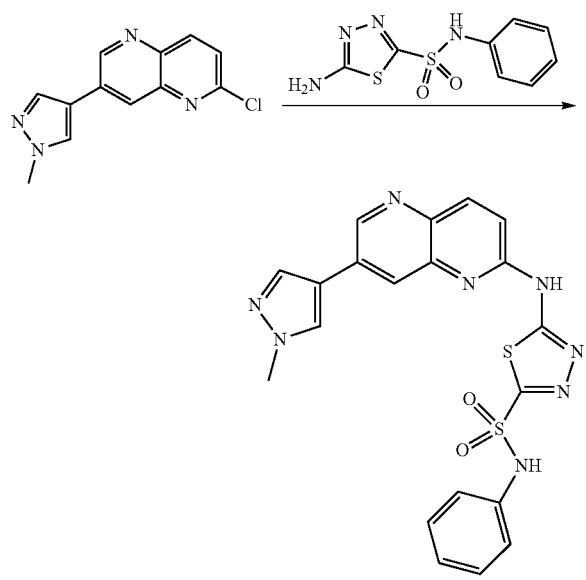

5-((7-(1-methyl-1H-pyrazol-4-yl)-1,5-naphthyridin-2-yl)amino)-N-phenyl-1,3,4-thiadiazole-2-sulfonamide was obtained as a pale yellow solid in the same manner as in Example 0015-4.

¹H-NMR(DMSO-d₆)δ:12.81(1H,s),11.15(1H,s),9.14(1H,d,J=2.3 Hz),8.56(1H,s),8.33-8.32(2H,m),8.24(1H,s),7.46(1H,d,J=8.9 Hz),7.36-7.29(2H,m),7.27-7.23(2H,m),7.11(1H,t,J=7.1 Hz),3.94(3H,s).

MSm/z(M+H):465.

Example 0177

0177-1

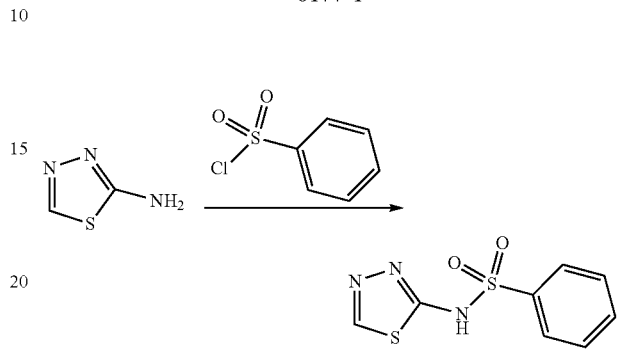

Benzenesulfonyl chloride (300 μL) was added dropwise to a solution of 2-amino-1,3,4-thiadiazole (202 mg) in pyridine (4 mL) over a period of 5 minutes under ice-cooling, followed by stirring at 0° C. for 30 minutes. Benzenesulfonyl chloride (150 μL) was added dropwise thereto over a period of 5 minutes, followed by stirring at 80° C. for 30 minutes. The solvent was distilled off under reduced pressure, and the resultant product was neutralized by the addition of hydrochloric acid. The organic layer was collected by separation, and dried over anhydrous sodium sulfate, and the solvent was distilled off under reduced pressure. The obtained residue was purified by silica gel column chromatography (hexane-ethyl acetate), thereby obtaining N-(1,3,4-thiadiazol-2-yl)benzene sulfonamide (240 mg).

¹H-NMR(DMSO-d₆)δ:8.76(1H,s),7.83-7.77(2H,m),7.63-7.53(3H,m).

0177-2

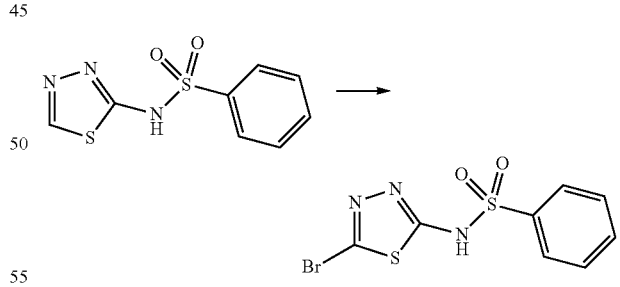

A mixture of N-(1,3,4-thiadiazol-2-yl)benzene sulfonamide (120 mg), and sodium acetate (80 mg) in acetic acid (3 mL) was stirred at 80° C. for 5 minutes. Bromine (30 μL) was added dropwise thereto, followed by stirring at 80° C. for 30 minutes. Bromine (10 μL) was added dropwise thereto, followed by stirring at 80° C. for 30 minutes. After the reaction mixture was cooled to room temperature, a sodium hydrogen sulfite aqueous solution was added thereto until potassium iodide starch paper was decolorized, and the resultant product was neutralized by the addition of a sodium hydroxide aqueous solution. The solid matter was collected by filtration, thereby obtaining N-(5-bromo-1,3,4-thiadiazol-2-yl)benzene sulfonamide (190 mg).

¹H-NMR(DMSO-d₆)δ:7.84-7.77(2H,m),7.67-7.54(3H,m).

0177-3

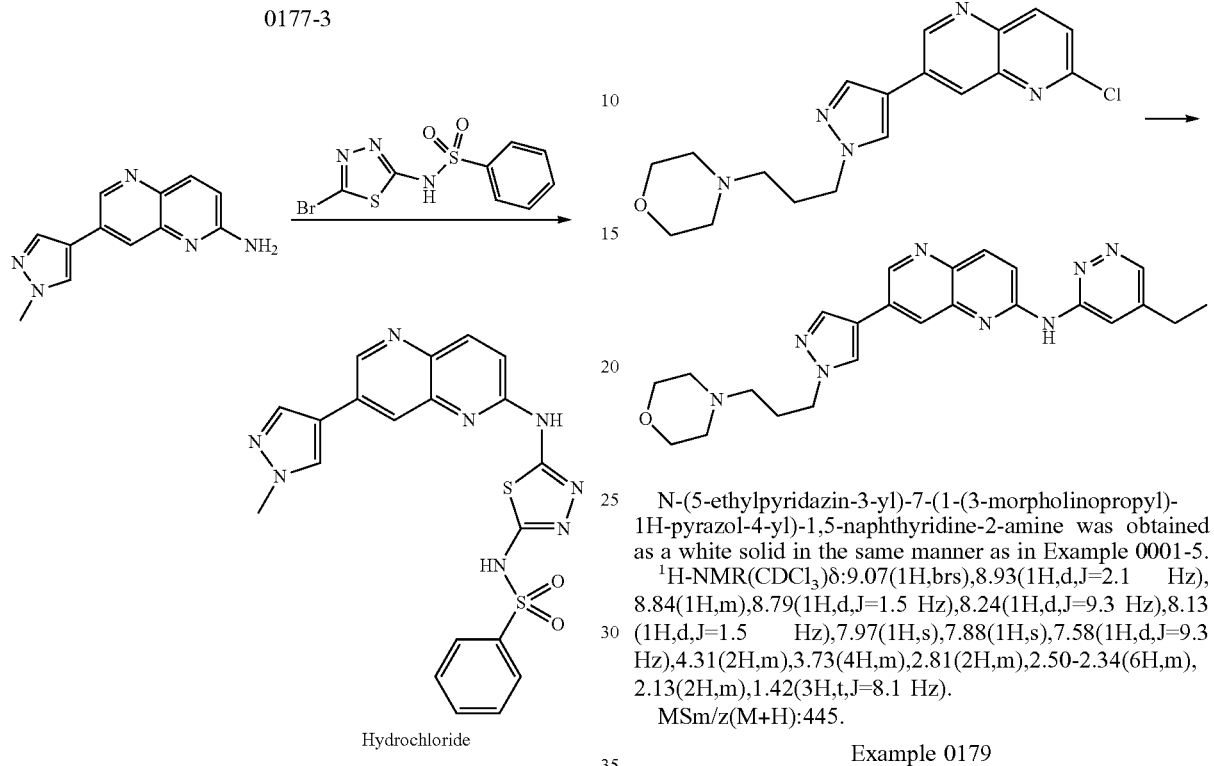

Hydrochloride 4,5-Bis(diphenylphosphino)-9,9-dimethylxanthene (10 mg), potassium tert-butoxide (60 mg), and tris(dibenzylideneacetone)dipalladium(0) (10 mg) were added to a solution of 7-(1-methyl-1H-pyrazol-4-yl)-1,5-naphthyridine-2-amine (20 mg) and N-(5-bromo-1,3,4-thiadiazol-2-yl)benzene sulfonamide (30 mg) in 1,4-dioxane (1 mL), followed by stirring at 170° C. for 2 hours using a microwave reaction apparatus. The reaction mixture was cooled to room temperature, and ethyl acetate and water were added thereto. Liquid-liquid separation was performed, and the water of the aqueous layer was distilled off under reduced pressure. The obtained residue was purified by preparative reversed phase HPLC (a 0.1% formic acid aqueous solution-a 0.1% formic acid acetonitrile solution), thereby obtaining N-(5-((7-(1-methyl-1H-pyrazol-4-yl)-1,5-naphthyridin-2-yl)amino)-1,3,4-thiadiazol-2-yl)benzene sulfonamide (5 mg).

A solution (1 mL) of 4 mol/L hydrogen chloride/1,4-dioxane was added to the obtained N-(5-((7-(1-methyl-1H-pyrazol-4-yl)-1,5-naphthyridin-2-yl)amino)-1,3,4-thiadiazol-2-yl)benzene sulfonamide, and the solvent was distilled off under reduced pressure, thereby obtaining N-(5-((7-(1-methyl-1H-pyrazol-4-yl)-1,5-naphthyridin-2-yl)amino)-1,3,4-thiadiazol-2-yl)benzene sulfonamide hydrochloride (3 mg) as a white solid.

¹H-NMR(DMSO-d₆)δ:9.09(1H,d,J=2.0 Hz),8.51(1H,s),8.28(1H,d,J=9.6 Hz),8.18(1H,s),8.09(1H,d,J=1.7 Hz),7.90-7.87(2H,m),7.79-7.42(4H,m),7.32(1H,d,J=8.9 Hz),3.94(3H,s).

MSm/z(M+H):465.

Example 0178

0178-1

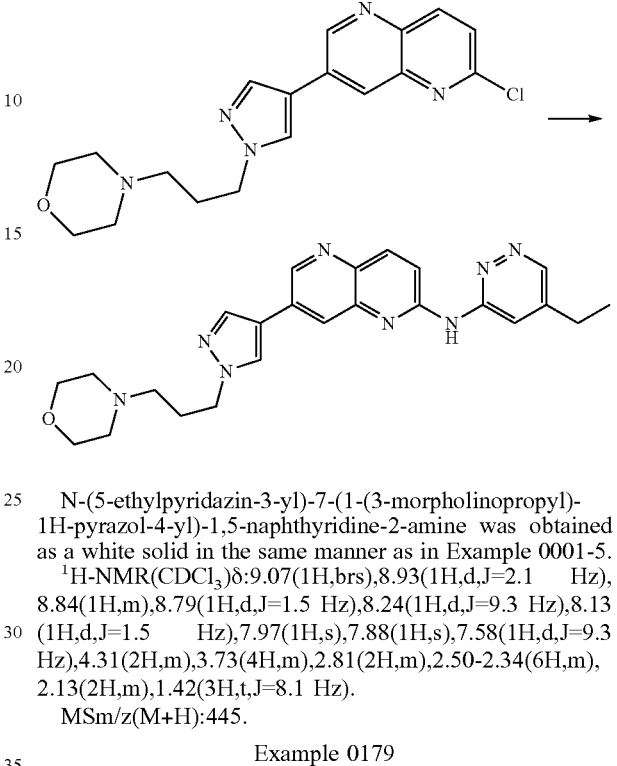

N-(5-ethylpyridazin-3-yl)-7-(1-(3-morpholinopropyl)-1H-pyrazol-4-yl)-1,5-naphthyridine-2-amine was obtained as a white solid in the same manner as in Example 0001-5.

¹H-NMR(CDCl₃)δ:9.07(1H,brs),8.93(1H,d,J=2.1 Hz),8.84(1H,m),8.79(1H,d,J=1.5 Hz),8.24(1H,d,J=9.3 Hz),8.13(1H,d,J=1.5 Hz),7.97(1H,s),7.88(1H,s),7.58(1H,d,J=9.3 Hz),4.31(2H,m),3.73(4H,m),2.81(2H,m),2.50-2.34(6H,m),2.13(2H,m),1.42(3H,t,J=8.1 Hz).

MSm/z(M+H):445.

Example 0179

0179-1

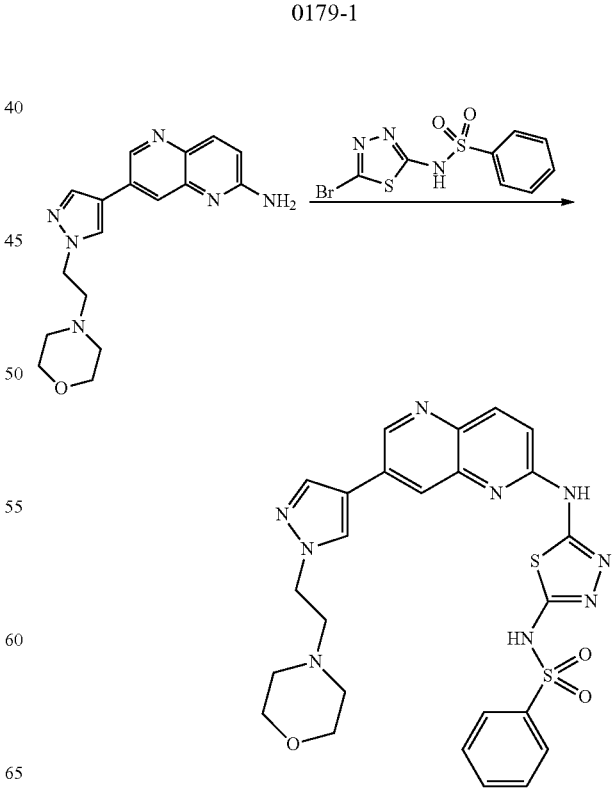

N-(5-((7-(1-(2-morpholinoethyl)-1H-pyrazol-4-yl)-1,5-naphthyridin-2-yl)amino)-1,3,4-thiadiazol-2-yl)benzene sulfonamide was obtained as a yellow solid in the same manner as in Example 0177-3.

$^1$H-NMR(DMSO-d$_6$)δ:11.86(1H,s),9.09(1H,d,J=2.0 Hz), 8.55(1H,s),8.27(1H,d,J=9.2 Hz),8.18(1H,s),8.08(1H,d, J=1.7 Hz),7.90-7.87(2H,m),7.79-7.42(4H,m),7.32(1H,d, J=8.9 Hz),4.33(2H,t,J=6.4 Hz),3.56(4H,t,J=4.6 Hz),2.80 (2H,t,J=6.6 Hz),2.50-2.42(4H,m).

MSm/z(M+H):564.

Example 0180

0180-1

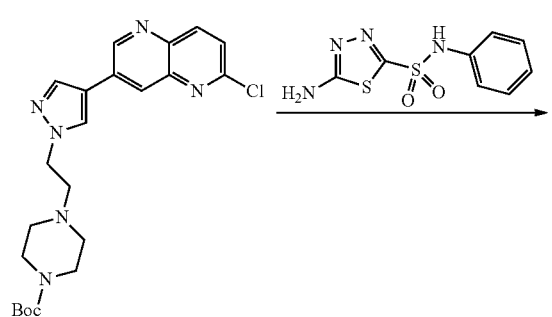

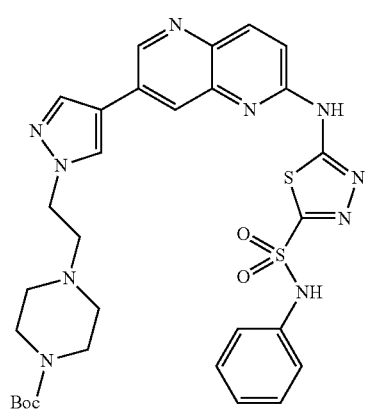

tert-Butyl 4-(2-(4-(6-((5-(N-phenyl sulfamoyl)-1,3,4-thiadiazol-2-yl)amino)-1,5-naphthyridin-3-yl)-1H-pyrazol-1-yl)ethyl)piperazine-1-carboxylate was obtained as a pale yellow solid in the same manner as in Example 0015-4.

$^1$H-NMR(DMSO-d$_6$)δ:9.06(1H,d,J=2.0 Hz),8.62(1H,s), 8.37-8.32(2H,m),8.24(1H,s),7.37(1H,d,J=9.2 Hz),7.03-6.94 (5H,m),4.34-4.27(2H,m),3.33-3.25(4H,m),2.86-2.78(2H, m),2.44-2.38(4H,m)1.38(9H,s).

MSm/z(M+H):663.

Example 0181

0181-1

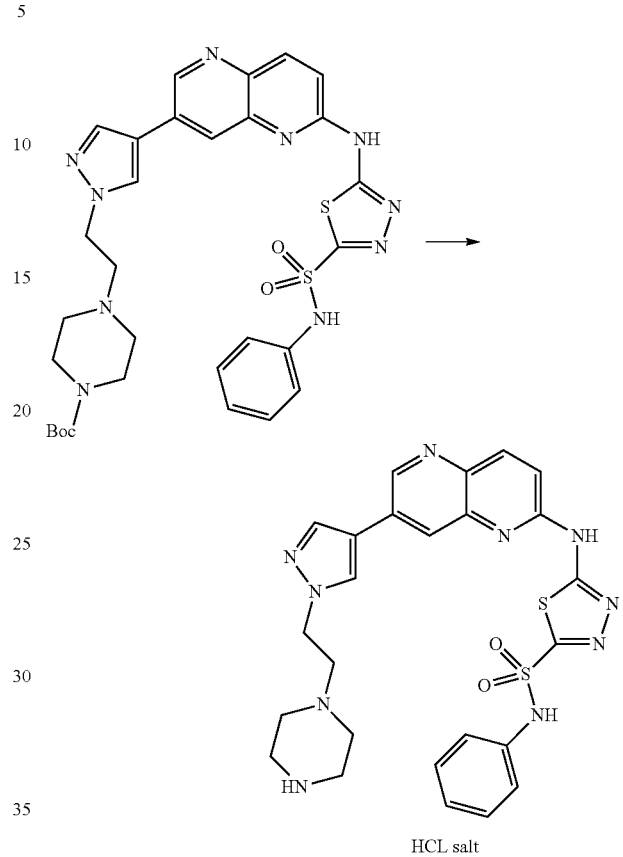

HCL salt

A solution (2 mL) of 4 mol/L hydrogen chloride/1,4-dioxane was added to tert-butyl 4-(2-(4-(6-((5-(N-phenyl-sulfamoyl)-1,3,4-thiadiazol-2-yl)amino)-1,5-naphthyridin-3-yl)-1H-pyrazol-1-yl)ethyl)piperazine-1-carboxylate (52 mg), followed by stirring at room temperature for 30 minutes. The solvent was distilled off under reduced pressure, and the obtained residue was washed with a solution of ethyl acetate-methanol-chloroform, thereby obtaining N-phenyl-5-((7-(1-(2-(piperazin-1-yl)ethyl)-1H-pyrazol-4-yl)-1,5-naphthyridin-2-yl)amino)-1,3,4-thiadiazole-2-sulfonamide hydrochloride (41 mg) as a pale yellow solid.

$^1$H-NMR(DMSO-d$_6$)δ:12.90(1H,s),11.21(1H,s),9.17(1H, d,J=2.0 Hz),8.69(1H,s),8.37-8.32(2H,m),8.24(1H,s),7.52 (1H,d,J=8.9 Hz),7.36-7.29(2H,m),7.27-7.23(2H,m),7.11 (1H,t,J=7.1 Hz),4.66-4.56(2H,m),3.57-3.56(4H,m),3.39-3.27(6H,m).

MSm/z(M+H):563.

Example 0182

0182-1

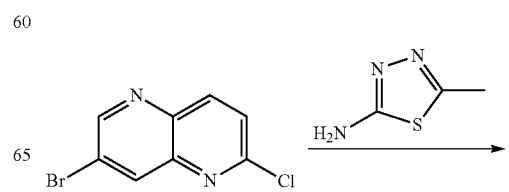

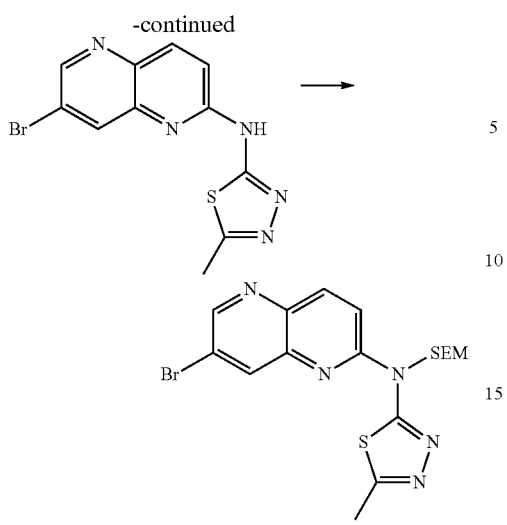
N-(7-bromo-1,5-naphthyridin-2-yl)-5-methyl-N-((2-(trimethylsilyl)ethoxy)methyl)-1,3,4-thiadiazole-2-amine was obtained as brown oily substance in the same manner as in Example 0175-2.
MSm/z(M+H):452.
0182-2 and 0182-3
The following compounds were obtained in the same manner as in Example 0175-3.
| Example No. |
| --- |
| 0182 |
0182-2
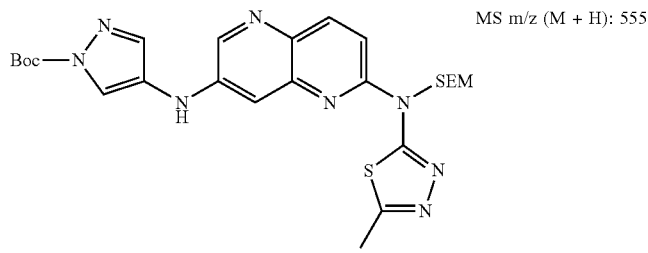
MS m/z (M + H): 555
0182-3
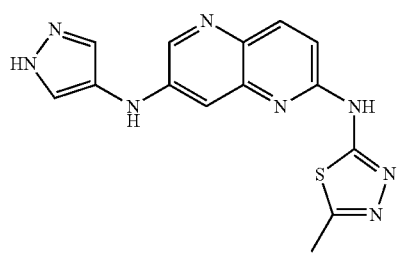 [SMILES: Cc1nnc(Nc2ccc3ncc(Nc4cn[nH]c4)cc3n2)s1]
$^1$H-NMR (DMSO-d$_6$) δ:
12.32(1H, s), 11.82 (1H, s), 9.27 (1H, s), 8.56 (1H, d, J = 2.6 Hz),
8.34 (1H, s), 8.06 (1H, d, J = 8.9 Hz), 7.68 (1H, d, J =2.3 Hz), 7.12
(1H, d, J = 8.9 Hz), 5.95 (1H, d, J = 2.3 Hz), 2.64 (3H, s).
MS m/z (M + H): 325.

Example 0183

0183-1

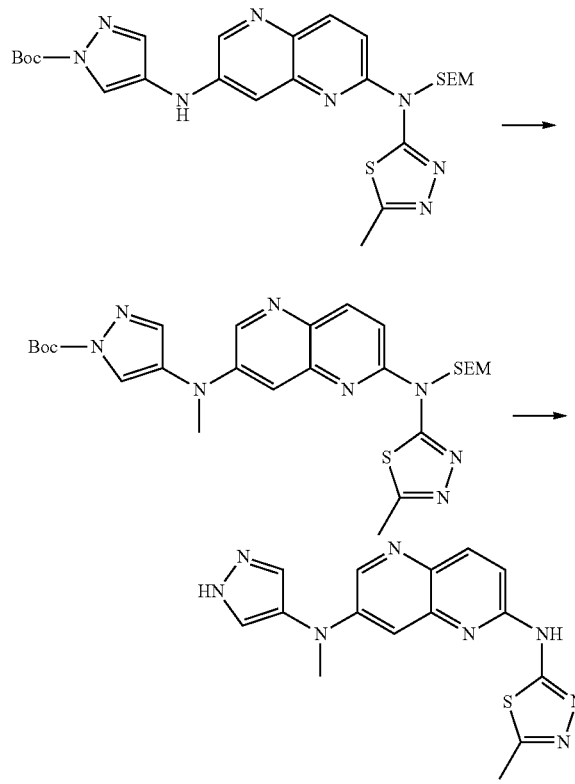

60% sodium hydride (3 mg) was added to a solution of tert-butyl 4-((6-((5-methyl-1,3,4-thiadiazol-2-yl)((2-(trimethylsilyl)ethoxy)methyl)amino)-1,5-naphthyridin-3-yl) amino)-1H-pyrazole-1-carboxylate (10 mg) in N,N-dimethylformamide (1 mL) under ice-cooling, and iodomethane (10 μL) was added thereto, followed by stirring at room temperature for 30 minutes. Methanol (1 drop) was added to the reaction mixture, and water and ethyl acetate were added thereto. The organic layer was collected by separation, and dried over anhydrous sodium sulfate, the solvent was distilled off under reduced pressure, and the obtained residue was purified by silica gel column chromatography (hexane-ethyl acetate, NH silica), thereby obtaining tert-butyl 4-(methyl (6-((5-methyl-1,3,4-thiadiazol-2-yl)((2-(trimethylsilyl)ethoxy)methyl)amino)-1,5-naphthyridin-3-yl) amino)-1H-pyrazole-1-carboxylate.

Methanol (500 μL) and a 4 mol/L hydrogen chloride/1,4-dioxane solution (1 mL) were added to the obtained tert-butyl 4-(methyl (6-((5-methyl-1,3,4-thiadiazol-2-yl)((2-(trimethylsilyl)ethoxy)methyl)amino)-1,5-naphthyridin-3-yl)amino)-1H-pyrazole-1-carboxylate, followed by stirring at 60° C. for 1.5 hours. The solvent was distilled off under reduced pressure, the obtained residue was neutralized by the addition of a saturated sodium hydrogen carbonate aqueous solution, and a solution of methanol-chloroform was added thereto. The organic layer was collected by separation, and dried over anhydrous sodium sulfate, and the solvent was distilled off under reduced pressure. The obtained residue was purified by silica gel column chromatography (hexane-ethyl acetate, NH silica), thereby obtaining $N^7$-methyl-$N^2$-(5-methyl-1,3,4-thiadiazol-2-yl)-$N^7$-(1H-pyrazol-4-yl)-1,5-naphthyridine-2,7-diamine (8.5 mg) as a yellow solid.

$^1$H-NMR(DMSO-$d_6$)δ:12.54(1H,s),11.86(1H,s),8.66(1H,d,J=2.6 Hz),8.12(1H,d,J=8.9 Hz),7.77(1H,d,J=2.3 Hz),7.52 (1H,d,J=2.3 Hz),7.19(1H,d,J=8.9 Hz),6.19(1H,d,J=2.3 Hz), 3.43(3H,s),2.64(3H,s).

MS m/z(M+H):339.

Example 0184

The following compounds were obtained in the same manner as in Example 0175-3.

| Example No | | |
|---|---|---|
| 0184 | | |
| 0184-1 | 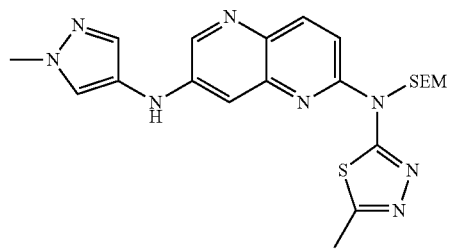 [SMILES: Cc1nnc(N(COCC[Si](C)(C)C)c2ccc3ncc(Nc4cnn(C)c4)cc3n2)s1] | MS m/z (M + H): 469 |
| 0184-2 | 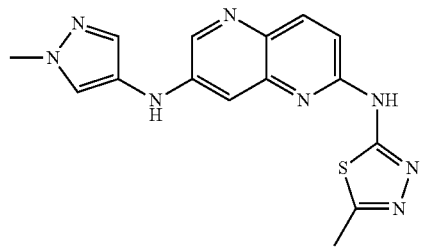 [SMILES: Cc1nnc(Nc2ccc3ncc(Nc4cnn(C)c4)cc3n2)s1] | $^1$H-NMR (DMSO-$d_6$) δ: 11.77 (1H, s), 9.21 (1H, s), 8.58 (1H, d, J = 2.6 Hz), 8.17 (1H, d, J = 2.3 Hz), 8.04 (1H, d , J = 8.9 Hz), 7.63 (1H, d, J = 2.3 Hz), 7.11 (1 H, d, J = 8.9 Hz), 5.93 (1H, d, J = 2.0 Hz), 3.85 (3H, s), 2.64 (3H, s). MS m/z (M + H): 339. |

Example 0185

0185-1

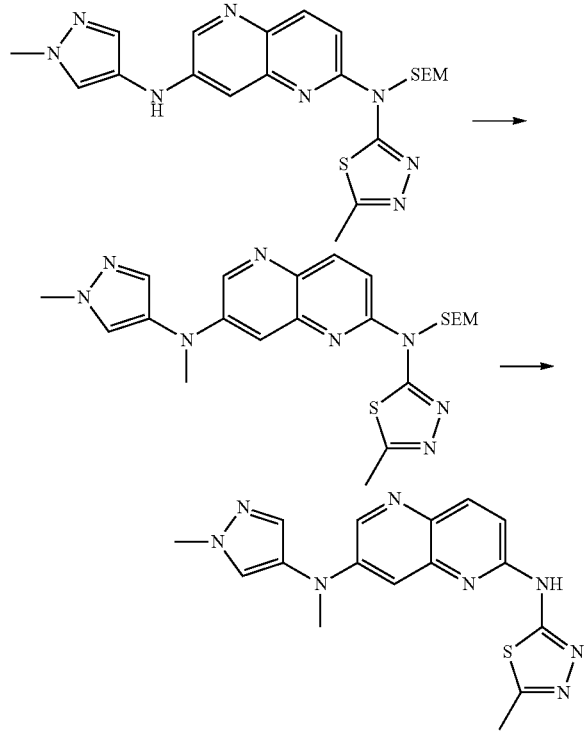

$N^7$-methyl-$N^2$-(5-methyl-1,3,4-thiadiazol-2-yl)-$N^7$-(1-methyl-1H-pyrazol-4-yl)-1,5-naphthyridine-2,7-diamine was obtained as a yellow solid in the same manner as in Example 0183.

$^1$H-NMR(DMSO-$d_6$)δ:11.87(1H,s),8.68(1H,d,J=2.6 Hz), 8.12(1H,d,J=8.9 Hz),7.71(1H,d,J=2.0 Hz),7.49(1H,d,J=2.6 Hz),7.20(1H,d,J=8.9 Hz),6.14(1H,d,J=2.3 Hz),3.81(3H,s), 3.41(3H,s),2.64(3H,s).
MSm/z(M+H):353.

Example 0186

0186-1

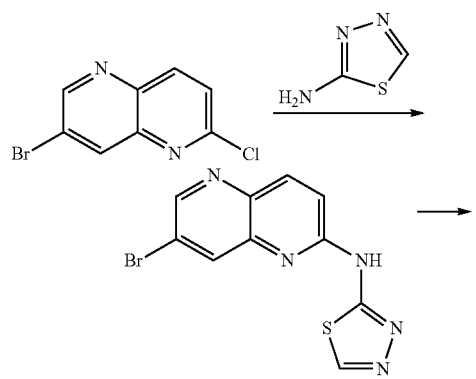

-continued

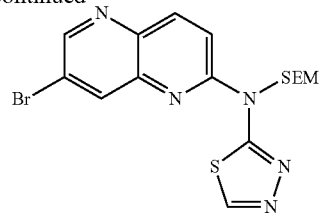

N-(7-bromo-1,5-naphthyridin-2-yl)-N-((2-(trimethylsilyl)ethoxy)methyl)-1,3,4-thiadiazole-2-amine was obtained in the same manner as in Example 0175-2.
MSm/z(M+H):438,440.

0186-2

$N^7$-(1H-pyrazol-4-yl)-$N^2$-(1,3,4-thiadiazol-2-yl)-1,5-naphthyridine-2,7-diamine was obtained as a yellow solid in the same manner as in Example 0175-3.
$^1$H-NMR(DMSO-$d_6$)δ:12.32(1H,s),12.03(1H,s),9.32(1H, s),9.10(1H,s),8.60(1H,d,J=2.6 Hz),8.40(1H,d,J=2.3 Hz), 8.12(1H,d,J=8.9 Hz),7.69(1H,t,J=2.0 Hz),7.19(1H,d,J=8.9 Hz),5.96(1H,t,J=2.1 Hz).
MSm/z(M+H):311.

Example 0187

0187-1

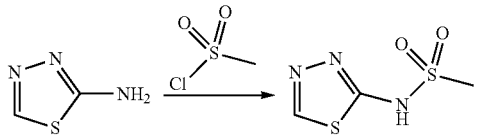

N-(1,3,4-thiadiazol-2-yl)methane sulfonamide was obtained in the same manner as in Example 0177-1.

MSm/z(M+H):180.

0187-2

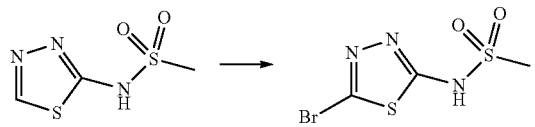

N-(5-bromo-1,3,4-thiadiazol-2-yl)methane sulfonamide was obtained in the same manner as in Example 0177-2.

MSm/z(M+H):258,260.

0187-3

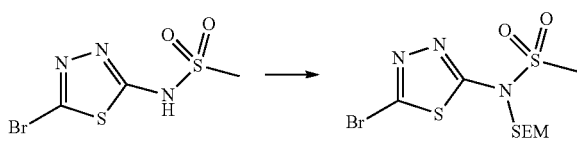 [SMILES: CS(=O)(=O)Nc1nnc(Br)s1 ; C[Si](C)(C)CCOCN(c1nnc(Br)s1)S(C)(=O)=O]

60% sodium hydride (15 mg) was added to a solution of N-(5-bromo-1,3,4-thiadiazol-2-yl)methane sulfonamide (100 mg) in N,N-dimethylformamide (10 mL) under ice-cooling, followed by stirring at 0° C. for 15 minutes. 2-(Chloromethoxy)ethyltrimethylsilane (60 μL) was added to the reaction mixture, followed by stirring at room temperature for 30 minutes. After the reaction mixture was cooled to 0° C., methanol (2 drops) was added thereto, and a saturated sodium chloride aqueous solution and ethyl acetate were added thereto. The organic layer was collected by separation, and dried over anhydrous sodium sulfate, and the solvent was distilled off under reduced pressure. The obtained residue was purified by silica gel column chromatography (hexane-ethyl acetate), thereby obtaining N-(5-bromo-1,3,4-thiadiazol-2-yl)-N-((2-(trimethylsilyl)ethoxy)methyl)methane sulfonamide (100 mg) as oily substance.

MSm/z(M+H):388,390.

187-4

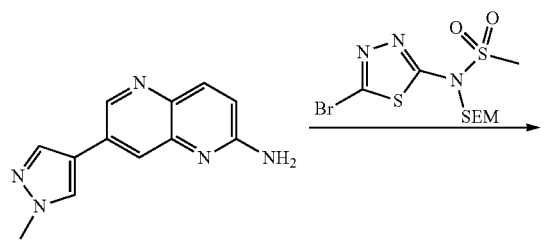

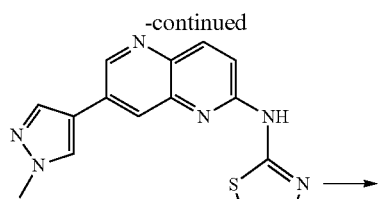

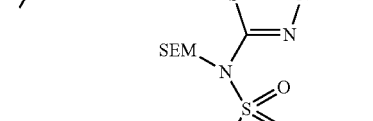

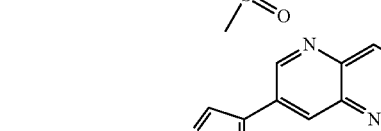


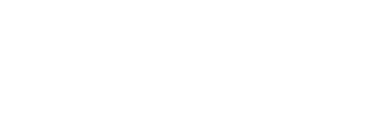

4,5-Bis(diphenylphosphino)-9,9-dimethylxanthene (10 mg), potassium tert-butoxide (20 mg), and tris(dibenzylideneacetone)dipalladium(0) (10 mg) were added to a solution of 7-(1-methyl-1H-pyrazol-4-yl)-1,5-naphthyridine-2-amine (25 mg) and N-(5-bromo-1,3,4-thiadiazol-2-yl)-N-((2-(trimethylsilyl)ethoxy)methyl)methane sulfonamide (45 mg) in 1,4-dioxane (1 mL), followed by stirring at 150° C. for 2 hour using a microwave reaction apparatus. The reaction mixture was cooled to room temperature, and chloroform and water were added thereto. The organic layer was collected by separation, and the solvent was distilled off under reduced pressure. The obtained residue was purified by silica gel column chromatography (ethyl acetate-methanol), thereby obtaining N-(5-((7-(1-methyl-1H-pyrazol-4-yl)-1,5-naphthyridin-2-yl)amino)-1,3,4-thiadiazol-2-yl)-N-((2-(trimethylsilyl)ethoxy)methyl)methane sulfonamide (20 mg).

A 4 mol/L hydrogen chloride/1,4-dioxane solution (1 mL) was added to a solution of the obtained N-(5-((7-(1-methyl-1H-pyrazol-4-yl)-1,5-naphthyridin-2-yl)amino)-1,3,4-thiadiazol-2-yl)-N-((2-(trimethylsilyl)ethoxy)methyl)methane sulfonamide in ethanol (1 mL), followed by stirring at 65° C. for 2 hours. The reaction mixture was cooled to room temperature, and the solvent was distilled off under reduced pressure. A saturated sodium hydrogen carbonate aqueous solution was added to the obtained residue, and the solvent was distilled off under reduced pressure. The obtained residue was purified by preparative reversed phase HPLC (a 0.1% formic acid aqueous solution-a 0.1% formic acid acetonitrile solution), thereby obtaining N-(5-((7-(1-methyl-1H-pyrazol-4-yl)-1,5-naphthyridin-2-yl)amino)-1,3,4-thiadiazol-2-yl)methane sulfonamide (0.5 mg) as a pale yellow solid.

$^1$H-NMR(DMSO-d$_6$)δ:11.10(1H,s),8.96(1H,d,J=2.3 Hz), 8.47(1H,s),8.13-8.09(2H,m),8.02(1H,d,J=1.7 Hz),7.30(1H,d,J=9.2 Hz),3.92(3H,s),2.74(3H,s).

MSm/z(M+H):403.

Example 0188

0188-1

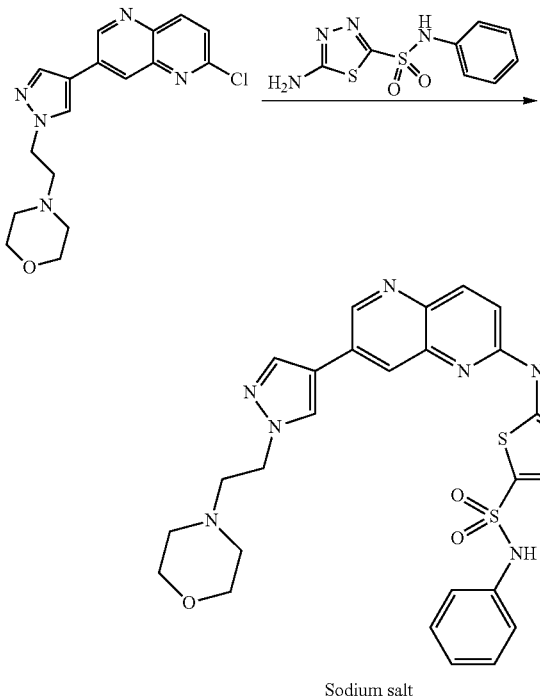

Sodium salt

A 5-((7-(1-(2-morpholinoethyl)-1H-pyrazol-4-yl)-1,5-naphthyridin-2-yl)amino)-N-phenyl-1,3,4-thiadiazole-2-sulfonamide sodium salt was obtained as a pale yellow solid in the same manner as in Example 0015-4.

$^1$H-NMR(DMSO-d$_6$)δ:12.18(1H,s),9.07(1H,d,J=1.7 Hz), 8.61(1H,s),8.25-8.20(3H,m),7.38(1H,d,J=8.9 Hz),7.07-6.98 (4H,m),6.70-6.63(1H,m),4.30(2H,t,J=6.6 Hz),3.57(4H,t, J=4.5 Hz),2.80(2H,t,J=6.6 Hz),2.45(4H,t,J=4.6 Hz).

MSm/z(M+H):564.

Example 0189

0189-1

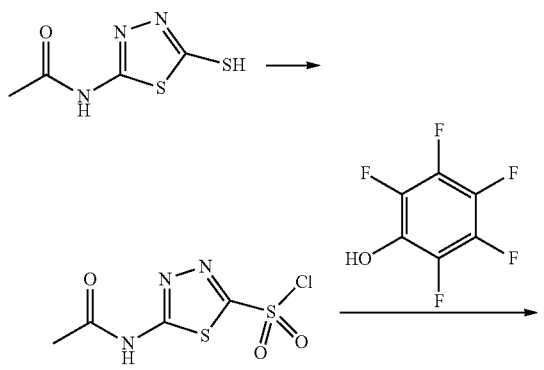

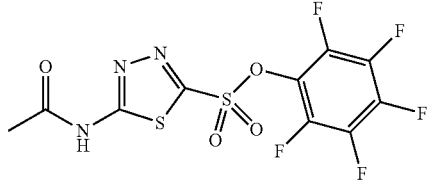

A solution of 5-acetamide-2-mercapto-1,3,4-thiadiazole (1.0 g) in dichloromethane (20 mL) was added dropwise to a mixture of dichloromethane (15 mL),2 mol/L hydrochloric acid (15 mL), and a sodium hypochlorite solution (10 mL) at −10° C. A sodium hydrogen sulfite aqueous solution was added thereto until potassium iodide starch paper was decolorized. The organic layer was collected by separation, washed with a saturated sodium chloride aqueous solution, and dried over anhydrous sodium sulfate, then, pentafluorophenol (1.0 g) and triethylamine (2.0 mL) were added thereto under ice-cooling, followed by stirring for 5 minutes, and the solvent was distilled off under reduced pressure. The obtained residue was purified by silica gel column chromatography (hexane-ethyl acetate), thereby obtaining pentafluorophenyl 5-acetamide-1,3,4-thiadiazole-2-sulfonate (210 mg).

$^1$H-NMR(CDCl$_3$)δ:11.61(1H,s),2.52(3H,s).

0189-2

Methylamine hydrochloride (20 mg) and triethylamine (100 μL) were added to a solution of pentafluorophenyl 5-acetamide-1,3,4-thiadiazole-2-sulfonate (70 mg) in acetonitrile (1 mL), followed by stirring at room temperature for 30 minutes. The solvent was distilled off under reduced pressure, and the obtained residue was purified by silica gel column chromatography (chloroform-methanol), thereby obtaining N-(5-(N-methylsulfamoyl)-1,3,4-thiadiazol-2-yl) acetamide.

Hydrochloric acid (1 mL) was added to the obtained N-(5-(N-methylsulfamoyl)-1,3,4-thiadiazol-2-yl)acetamide, followed by stirring at 60° C. for 1 hour. The reaction mixture was cooled to room temperature, and neutralized with a sodium hydroxide aqueous solution, and the solvent was distilled off under reduced pressure. The obtained residue was purified by silica gel column chromatography (chloroform-methanol), thereby obtaining 5-amino-N-methyl-1,3,4-thiadiazole-2-sulfonamide (37 mg).

$^1$H-NMR(CDCl$_3$)δ:1.25(3H,s).

MSm/z(M+H):195.

0189-3

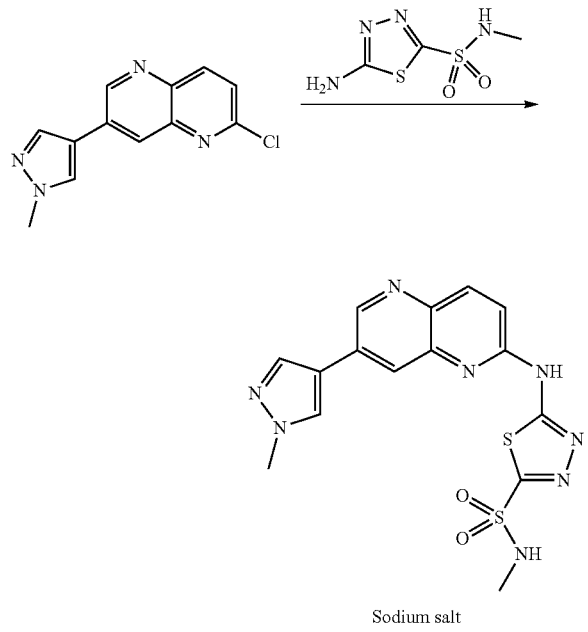

Sodium salt 4,5-Bis(diphenylphosphino)-9,9-dimethylxanthene (7 mg), potassium tert-butoxide (30 mg), and tris(dibenzylideneacetone)dipalladium(0) (7 mg) were added to a solution of 2-chloro-7-(1-methyl-1H-pyrazol-4-yl)-1,5-naphthyridine (35 mg) and 5-amino-N-methyl-1,3,4-thiadiazole-2-sulfonamide (35 mg) in 1,4-dioxane (1 mL), followed by stirring at 150° C. for 1 hour using a microwave reaction apparatus. The reaction mixture was cooled to room temperature, and chloroform and water were added thereto. Liquid-liquid separation was performed, and the water of the aqueous layer was distilled off under reduced pressure. The obtained residue was purified by preparative reversed phase HPLC (a 0.1% formic acid aqueous solution-a 0.1% formic acid acetonitrile solution), and purified by reversed silica gel chromatography (methanol-sodium hydrogen carbonate aqueous solution), thereby obtaining methyl ((5-((7-(1-methyl-1H-pyrazol-4-yl)-1,5-naphthyridin-2-yl)amino)-1,3,4-thiadiazol-2-yl)sulfonyl)amide sodium salt (3.2 mg) as a yellow solid.

$^1$H-NMR(DMSO-d$_6$)δ:8.83(1H,d,J=1.7 Hz),8.46(1H,s), 8.12(1H,s),8.06(1H,s),7.92(1H,d,J=8.9 Hz),7.81(1H,s),7.15 (1H,d,J=8.9 Hz),3.91(3H,s),2.62(3H,s).

MSm/z(M+H):403.

Example 0190

The following compounds were obtained in the same manner as in Examples 0177-1 to 0177-3.

| Example No. | | |
|---|---|---|
| 0190 | | |
| 0190-1 | 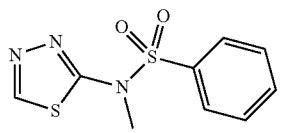 [SMILES: CN(c1nncs1)S(=O)(=O)c1ccccc1] | $^1$H-NMR (DMSO-d$_6$) δ:<br>9.28 (1H, s), 7.88-7.78 (3H, m), 7.71-7.64 (2H, m), 3.44 (3H, s). |
| 0190-2 | 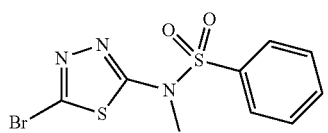 [SMILES: CN(c1nnc(Br)s1)S(=O)(=O)c1ccccc1] | $^1$H-NMR (DMSO-d$_6$) δ:<br>7.92-7.81 (3H, m), 7.72-7.63 (2H, m), 3.38 (3H, s). |
| 0190-3 | 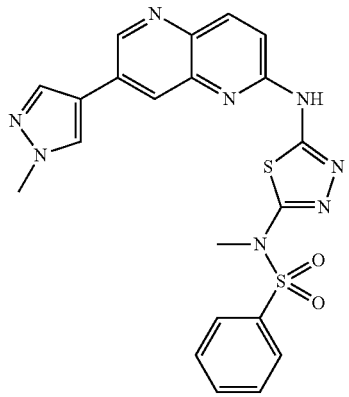 [SMILES: CN(c1nnc(Nc2ccc3ncc(-c4cnn(C)c4)cc3n2)s1)S(=O)(=O)c1ccccc1] | $^1$H-NMR (DMSO-d$_6$) δ:<br>12.15 (1H, s), 9.10 (1H, d, J = 2.0 Hz), 8.54 (1H, s), 8.29 (1H, d, J = 9.2 Hz), 8.24 (1H, d, J = 2.0 Hz), 8.21 (1H, s),<br>7.84-7.76 (3H, m), 7.70-7.63 (2H, m), 7.40 (1H, d, J = 9.2 Hz), 3.93 (3H, s), 3.34 (3H, s).<br>MS m/z (M + H): 479. |

Example 0191

0191-1

A ((5-((7-(1-methyl-1H-pyrazol-4-yl)-1,5-naphthyridin-2-yl)amino)-1,3,4-thiadiazol-2-yl)sulfonyl)amide sodium salt was obtained as a white solid in the same manner as in Example 0189-3.

$^1$H-NMR(DMSO-d$_6$)δ:8.73(1H,d,J=2.0 Hz),8.42(1H,s), 8.07(1H,s),7.96(1H,d,J=1.7 Hz),7.80(1H,d,J=8.9 Hz),7.53 (2H,s),7.05(1H,d,J=8.9 Hz),3.91(3H,s).

MSm/z(M+H):389.

Example 0192

0192-1

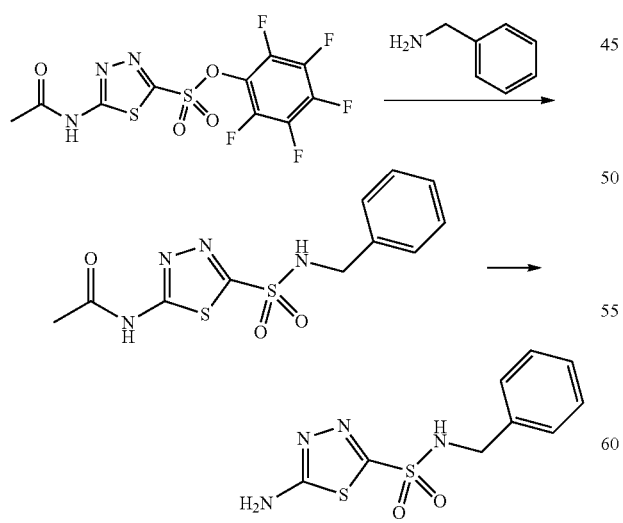

5-Amino-N-benzyl-1,3,4-thiadiazole-2-sulfonamide was obtained in the same manner as in Example 0189-2.
MSm/z(M+H):271.

0192-2

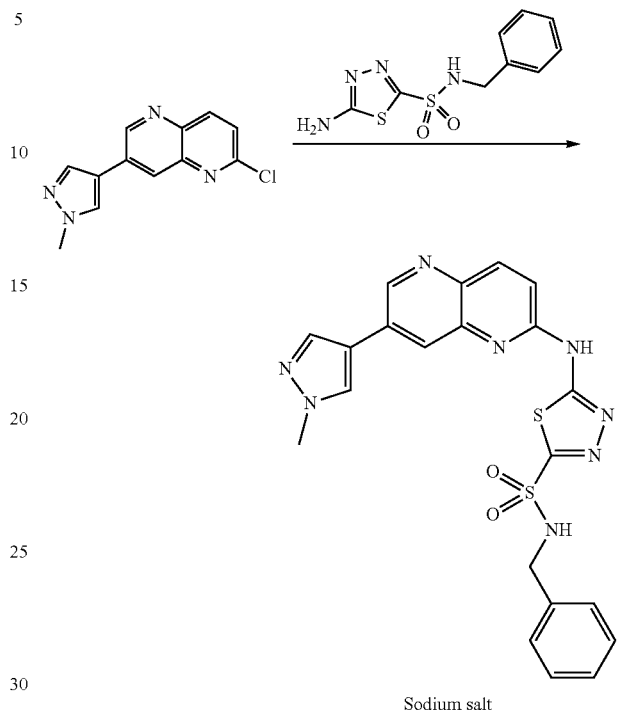

An N-benzyl-5-((7-(1-methyl-1H-pyrazol-4-yl)-1,5-naphthyridin-2-yl)amino)-1,3,4-thiadiazole-2-sulfonamide sodium salt was obtained as a yellow solid in the same manner as in Example 0189-3.

$^1$H-NMR(DMSO-d$_6$)δ:8.75(1H,d,J=2.3 Hz),8.43(1H,s), 8.08(1H,d,J=4.6 Hz),7.99(1H,d,J=1.7 Hz),7.82(1H,d,J=8.9 Hz),7.36-7.23(5H,m),7.08(1H,d,J=8.9 Hz),4.19(2H,s),3.90 (3H,s).

MSm/z(M+H):479.

Example 0193

0193-1

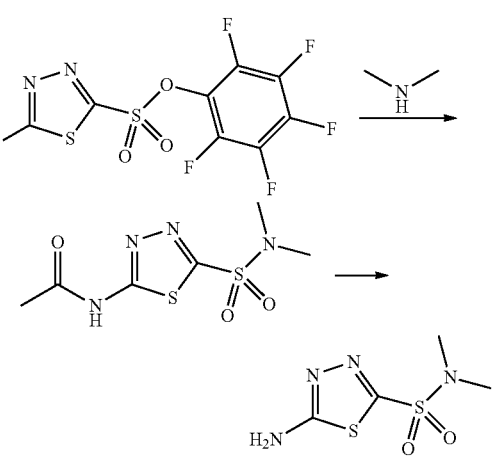

5-Amino-N,N-dimethyl-1,3,4-thiadiazole-2-sulfonamide was obtained in the same manner as in Example 0189-2.

¹H-NMR(DMSO-d₆)δ:8.03(2H,s),2.83(6H,s).

0193-2

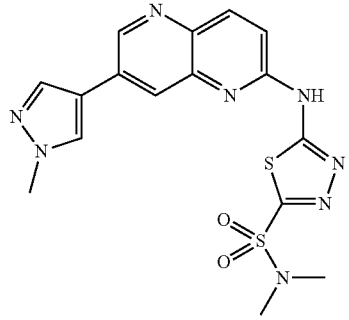

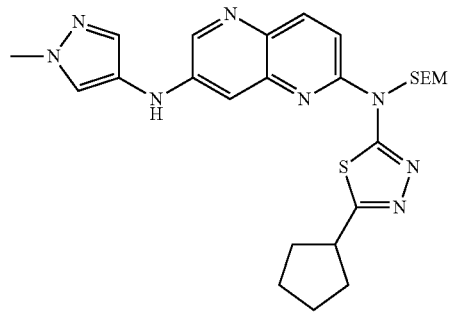 [SMILES: Cn1cc(Nc2cnc3ccc(N(COCC[Si](C)(C)C)c4nnc(C5CCCC5)s4)nc3c2)cn1]

N,N-dimethyl-5-((7-(1-methyl-1H-pyrazol-4-yl)-1,5-naphthyridin-2-yl)amino)-1,3,4-thiadiazole-2-sulfonamide was obtained as a pale yellow solid in the same manner as in Example 0015-4.

¹H-NMR(DMSO-d₆)δ:12.88(1H,s),9.14(1H,d,J=2.3 Hz), 8.58(1H,s),8.42(1H,d,J=1.3 Hz),8.36(1H,d,J=8.9 Hz),8.26 (1H,s),7.49(1H,d,J=8.9 Hz),3.93(3H,s),2.93(6H,s).
MSm/z(M+H):417.

Example 0194

The following compounds were obtained in the same manner as in Example 0175-3.

| Example No. | | |
|---|---|---|
| 0194 | | |
| 0194-1 | (structure) | MS m/z (M + H): 523 |
| 0194-2 | 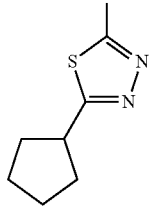 | ¹H-NMR (DMSO-d₆) δ: 12.54 (1H, s), 11.88 (1H, s), 8.67 (1H, d, J = 2.0 Hz), 8.12 (1H, d, J = 8.9 Hz), 7.77 (1H, s), 7.53 (1H, d, J = 2.3 Hz), 7.20 (1H, d, J = 8.9 Hz), 6.19 (1H, s), 3.44 (3H, s), 2.20-2.08 (2H, m), 1.92-1.62 (7H, m). MS m/z (M + H): 393. |

Example 0195

0195-1

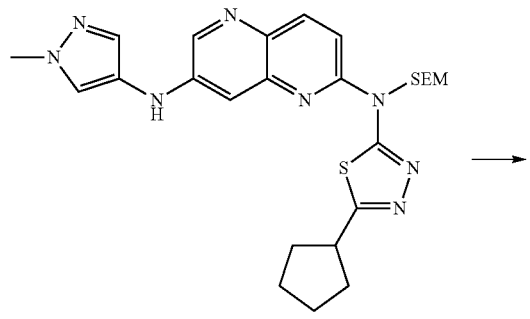

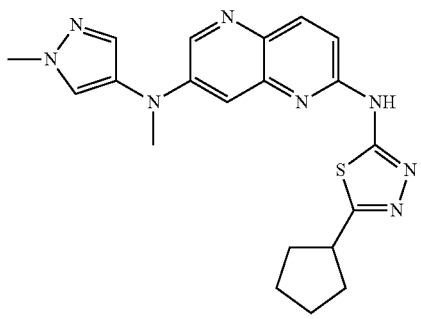 [SMILES: Cn1cc(Nc2cnc3ccc(Nc4nnc(C5CCCC5)s4)nc3c2)cn1]

$N^2$-(5-cyclopentyl-1,3,4-thiadiazol-2-yl)-$N^7$-methyl-$N^7$-(1-methyl-1H-pyrazol-4-yl)-1,5-naphthyridine-2,7-diamine was obtained as a yellow solid in the same manner as in Example 0183-1.

$^1$H-NMR(DMSO-$d_6$)δ:11.89(1H,s),8.68(1H,d,J=2.6 Hz), 8.12(1H,d,J=8.9 Hz),7.70(1H,d,J=2.3 Hz),7.55(1H,d,J=2.3 Hz),7.20(1H,d,J=8.9 Hz),6.14(1H,d,J=2.3 Hz),3.81(3H,s), 3.42(3H,s),2.21-2.06(2H,m),1.92-1.62(7H,m).
MSm/z(M+H):407.

Example 0196

0196-1

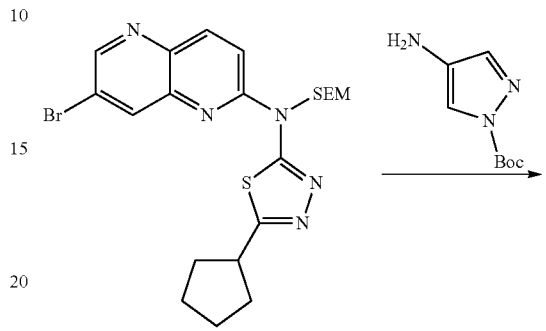

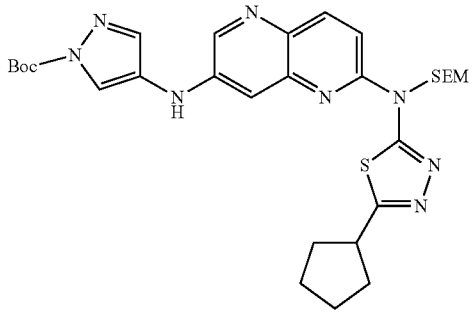

tert-Butyl 4-amino-1H-pyrazole-1-carboxylate (25 mg), 4,5-bis(diphenylphosphino)-9,9-dimethylxanthene (5 mg), cesium carbonate (45 mg), and tris(dibenzylideneacetone) dipalladium(0) (5 mg) were added to a solution of N-(7-bromo-1,5-naphthyridin-2-yl)-5-cyclopentyl-N-((2-(trimethylsilyl)ethoxy)methyl)-1,3,4-thiadiazole-2-amine (40 mg) in 1,4-dioxane (1 mL), followed by stirring at 100° C. for 8 hours in a nitrogen atmosphere. 4,5-Bis(diphenylphosphino)-9,9-dimethylxanthene (5 mg) and tris(dibenzylideneacetone)dipalladium(0) (5 mg) were added thereto, followed by stirring at 100° C. for 3 hours in a nitrogen atmosphere. The reaction mixture was cooled to room temperature, and ethyl acetate and water were added thereto. The organic layer was collected by separation, and the solvent was distilled off under reduced pressure. The obtained residue was purified by silica gel column chromatography (hexane-ethyl acetate, NH silica), thereby obtaining tert-butyl 4-((6-((5-cyclopentyl-1,3,4-thiadiazol-2-yl) ((2-(trimethylsilyl)ethoxy)methyl)amino)-1,5-naphthyridin-3-yl)amino)-1H-pyrazole-1-carboxylate (40 mg).
MSm/z(M+H):609.

267
0196-2
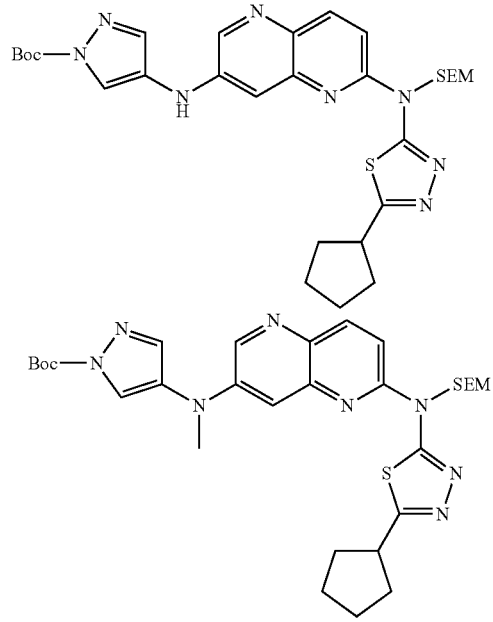
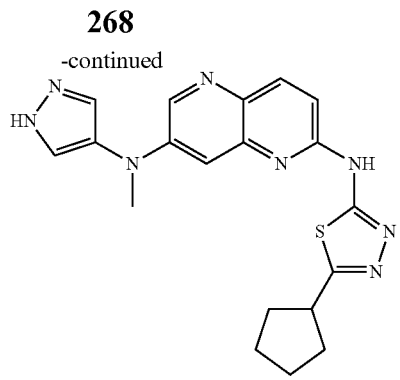
N²-(5-cyclopentyl-1,3,4-thiadiazol-2-yl)-N⁷-methyl-N⁷-(1H-pyrazol-4-yl)-1,5-naphthyridine-2,7-diamine was obtained as a yellow solid in the same manner as in Example 0183-1.
$^1$H-NMR(DMSO-$d_6$)δ:12.04(1H,s),9.08(1H,d,J=2.0 Hz), 8.56(1H,s),8.32(1H,d,J=1.7 Hz),8.24(2H,d,J=10.9 Hz),7.39 (1H,d,J=8.9 Hz),2.14(3H,s),2.04-1.68(9H,m).
MS m/z(M+H):393.
Example 0197
0197-1
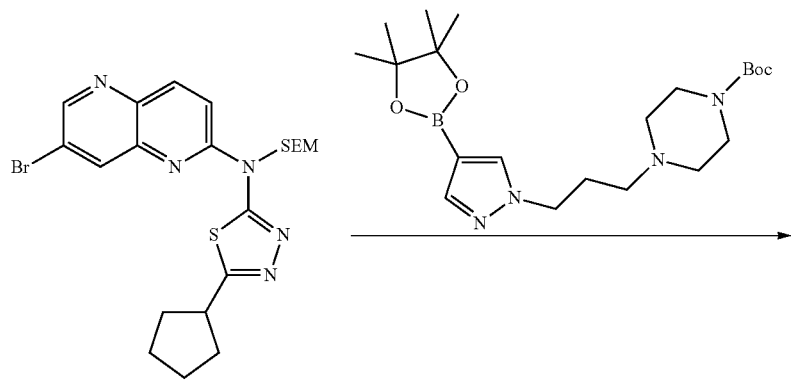
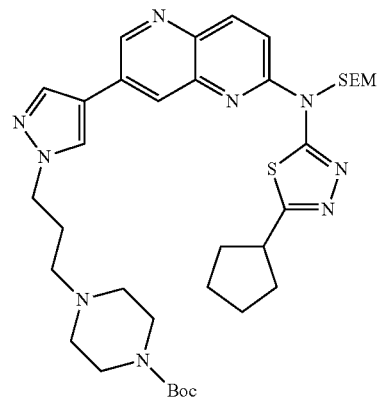

tert-Butyl 4-(3-(4-(4,4,5,5-tetramethyl-1,3,2-dioxaborolan-2-yl)-1H-pyrazol-1-yl)propyl)piperazine-1-carboxylate (30 mg), bis(di-tert-butyl(4-dimethylaminophenyl)phosphine)dichloropalladium(II) (5 mg), sodium carbonate (12 mg), and water (100 μL) were added to a solution of N-(7-bromo-1,5-naphthyridin-2-yl)-5-cyclopentyl-N-((2-(trimethylsilyl)ethoxy)methyl)-1,3,4-thiadiazole-2-amine (50 mg) in 1,4-dioxane (1 mL), followed by stirring at 80° C. for 2 hours in a nitrogen atmosphere. The reaction mixture was cooled to room temperature, and water and ethyl acetate were added thereto. The organic layer was collected by separation, and dried over anhydrous sodium sulfate, and the solvent was distilled off under reduced pressure. The solid matter was collected by filtration, and hydrochloric acid (1 mL) was added thereto, followed by stirring at 90° C. for 1 hour. The reaction mixture was cooled to room temperature, and the resultant product was neutralized with a sodium hydroxide aqueous solution. The solid matter was collected by filtration, and purified by silica gel column chromatography (chloroform-methanol, NH silica), thereby obtaining tert-butyl 4-(3-(4-(6-((5-cyclopentyl-1,3,4-thiadiazol-2-yl)((2-(trimethylsilyl)ethoxy)methyl)amino)-1,5-naphthyridin-3-yl)-1H-pyrazol-1-yl)propyl)piperazine-1-carboxylate (27 mg) as a yellow solid.

MSm/z(M+H):720.

0197-2

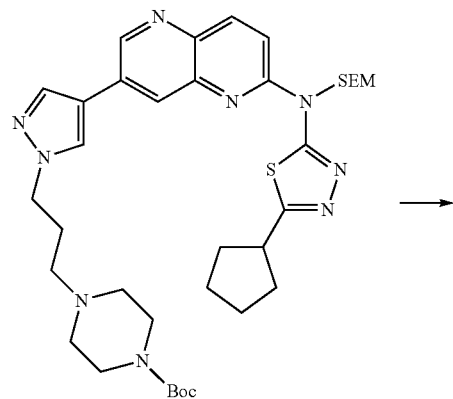

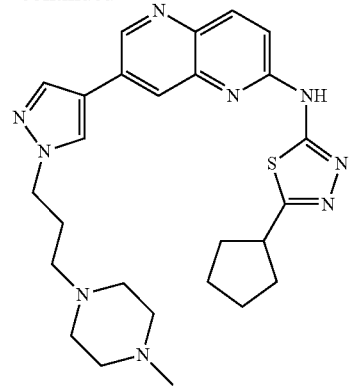

Methanol (1 mL) and hydrochloric acid (1 mL) were added to tert-butyl 4-(3-(4-(6-((5-cyclopentyl-1,3,4-thiadiazol-2-yl)((2-(trimethylsilyl)ethoxy)methyl)amino)-1,5-naphthyridin-3-yl)-1H-pyrazol-1-yl)propyl)piperazine-1-carboxylate (27 mg), followed by stirring at 60° C. for 1 hour. The solvent was distilled off under reduced pressure, the resultant product was neutralized with a saturated sodium hydrogen carbonate aqueous solution, and a solution of methanol-chloroform was added thereto.

The organic layer was collected by separation, and dried over anhydrous sodium sulfate, and the solvent was distilled off under reduced pressure, thereby obtaining 5-cyclopentyl-N-(7-(1-(3-(piperazin-1-yl)propyl)-1H-pyrazol-4-yl)-1,5-naphthyridin-2-yl)-1,3,4-thiadiazole-2-amine.

A 20% formaldehyde solution (5 μL) and sodium triacetoxyborohydride (12 mg) were added to a solution of the obtained 5-cyclopentyl-N-(7-(1-(3-(piperazin-1-yl)propyl)-1H-pyrazol-4-yl)-1,5-naphthyridin-2-yl)-1,3,4-thiadiazole-2-amine in methanol (600 μL) and chloroform (600 μL), followed by stirring at room temperature for 2 hours. A saturated sodium chloride aqueous solution and chloroform were added to the reaction mixture. The organic layer was collected by separation, and dried over anhydrous sodium sulfate, and the solvent was distilled off under reduced pressure. The obtained residue was purified by silica gel column chromatography (chloroform-methanol, NH silica), thereby obtaining 5-cyclopentyl-N-(7-(1-(3-(4-methylpiperazin-1-yl)propyl)-1H-pyrazol-4-yl)-1,5-naphthyridin-2-yl)-1,3,4-thiadiazole-2-amine (4 mg) as a yellow solid.

¹H-NMR(DMSO-d₆)δ:12.04(1H,s),9.07(1H,d,J=2.0 Hz), 8.56(1H,s),8.32(1H,d,J=1.3 Hz),8.26-8.22(2H,m),7.39(1H, d,J=8.9 Hz),4.19(2H,t,J=7.1 Hz),3.51-3.44(1H,m),2.74-2.71 (1H,m),2.42-2.24(11H,m),2.14(3H,s),2.02-1.72(8H,m).

MSm/z(M+H):504.

Example 0198

0198-1

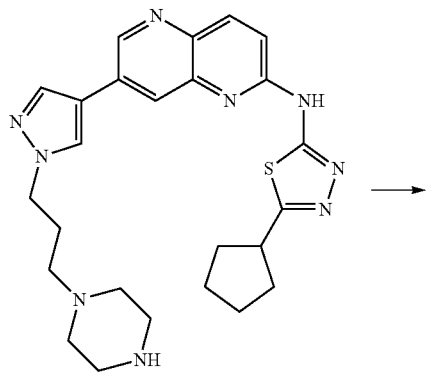

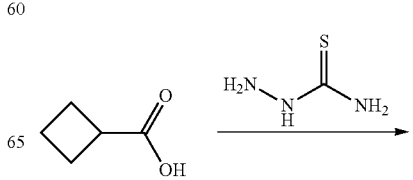

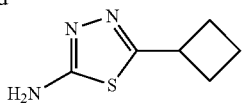

Cyclobutanecarboxylic acid (600 µL) was added to a solution of thiosemicarbazide (500 mg) in hydrochloric acid (2 mL), followed by stirring for 60 hours under heating to reflux. The reaction mixture was cooled to room temperature, and neutralized by the addition of a sodium hydroxide aqueous solution under ice-cooling. The solid matter was collected by filtration, thereby obtaining 2-amino-5-cyclobutyl-1,3,4-thiadiazole (650 mg).

MSm/z(M+H):156.

0198-2

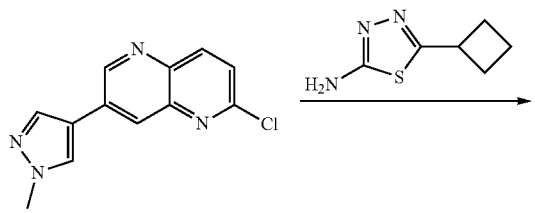

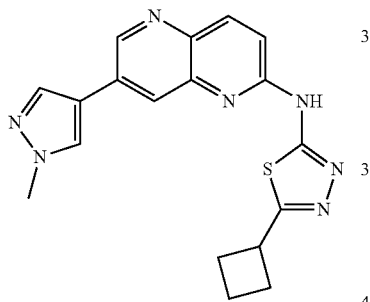

5-Cyclobutyl-N-(7-(1-methyl-1H-pyrazol-4-yl)-1,5-naphthyridin-2-yl)-1,3,4-thiadiazole-2-amine was obtained as a pale yellow solid in the same manner as in Example 0001-5.

$^1$H-NMR(DMSO-$d_6$)δ:12.06(1H,s),9.07(1H,d,J=2.0 Hz), 8.53(1H,s),8.34(1H,d,J=1.7 Hz),8.25(1H,d,J=9.2 Hz),8.22 (1H,s),7.39(1H,d,J=8.9 Hz),3.93(3H,s),2.45-2.27(5H,m), 2.17-1.92(2H,m).

MSm/z(M+H):364.

Example 0199

0199-1

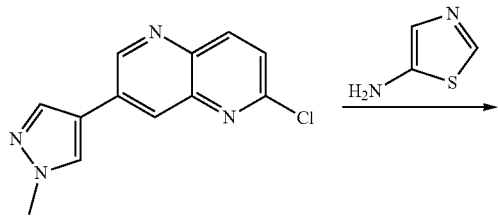

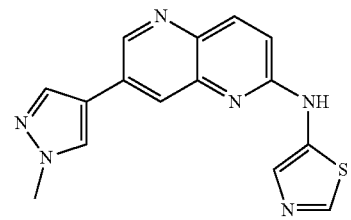

5-Aminothiazole (15 mg), 4,5-bis(diphenylphosphino)-9,9-dimethylxanthene (5 mg), cesium carbonate (45 mg), and tris(dibenzylideneacetone)dipalladium(0) (5 mg) were added to a solution of 2-chloro-7-(1-methyl-1H-pyrazol-4-yl)-1,5-naphthyridine (25 mg) in 1,4-dioxane (2 mL), followed by stirring at 100° C. in a nitrogen atmosphere overnight. The reaction mixture was cooled to room temperature, and a mixed solvent of chloroform-methanol was added thereto. The obtained solution was purified by silica gel column chromatography (chloroform-methanol, NH silica), thereby obtaining N-(7-(1-methyl-1H-pyrazol-4-yl)-1,5-naphthyridin-2-yl)thiazole-5-amine (2 mg) as a brown solid.

$^1$H-NMR(DMSO-$d_6$)δ:10.99(1H,s),8.97(1H,d,J=2.3 Hz), 8.56(1H,s),8.49(1H,s),8.21-8.11(3H,m),7.74(1H,d,J=0.7 Hz),7.21(1H,d,J=8.9 Hz),3.91(3H,d,J=6.3 Hz).

MSm/z(M+H):309.

Example 0200

0200-1

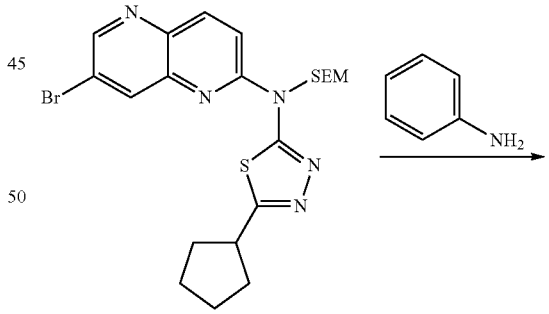

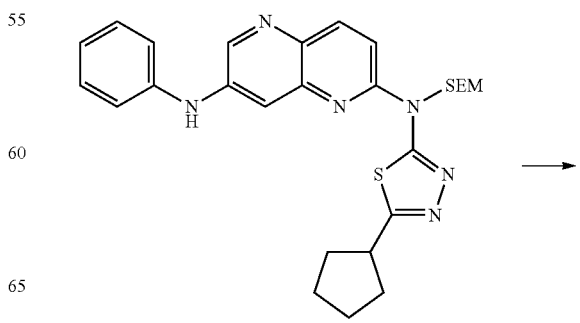

-continued

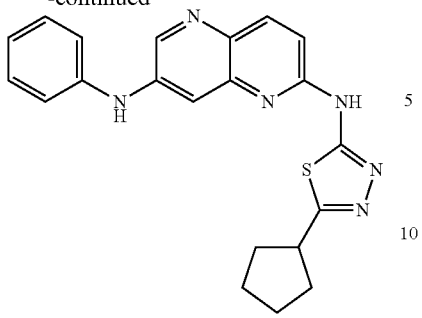

N²-(5-cyclopentyl-1,3,4-thiadiazol-2-yl)-N⁷-phenyl-1,5-naphthyridine-2,7-diamine was obtained as a yellow solid in the same manner as in Example 0175-3.

¹H-NMR(DMSO-d₆)δ:11.88(1H,s),8.90(1H,s),8.56(1H,d,J=2.6 Hz),8.11(1H,d,J=8.9 Hz),7.59(1H,d,J=2.3 Hz),7.39(2H,t,J=7.9 Hz),7.28(2H,dd,J=8.4,1.2 Hz),7.18(1H,d,J=9.2 Hz),7.03(1H,t,J=7.3 Hz),3.52-3.41(1H,m),2.17-2.05(2H,m),1.87-1.60(6H,m).

MS m/z(M+H):389.

Examples 0201 to 0204

The following compounds were obtained in the same manner as in Examples 0197-1 and 0197-2.

| Example No. | | |
|---|---|---|
| 0201 | | |
| 0201-1 | 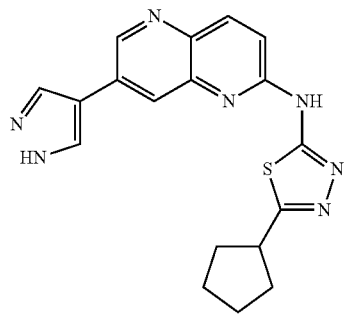 [SMILES: N=C/C(=C\N)c1cnc2ccc(Nc3nnc(C4CCCC4)s3)nc2c1] | ¹H-NMR (DMSO-d₆) δ: 13.21 (1H, s), 12.03 (1H, s), 9.12 (1H, d, J = 2.0 Hz), 8.59 (1H, s), 8.36 (1H, d, J = 1.7 Hz), 8.29-8.22 (2H, m), 7.39 (1H, d, J = 9.2 Hz), 3.55-3.43 (1H, m), 2.29-2.12 (2H, m), 1.92-1.68 (6H, m). MS m/z (M + H): 364 |
| 0202 | | |
| 0202-1 | 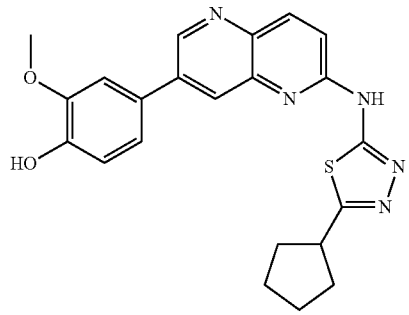 [SMILES: COc1cc(-c2cnc3ccc(Nc4nnc(C5CCCC5)s4)nc3c2)ccc1O] | ¹H-NMR (DMSO-d₆) δ: 12.06 (1H, s), 9.36 (1H, s), 9.09 (1H, d, J = 2.3 Hz), 8.34-8.27 (2H, m), 7.47-7.33 (3H, m), 6.95 (1H, d, J = 8.3 Hz), 3.93 (3H, s), 3.53-3.43 (1H, m), 2.20-2.09 (2H, m), 1.92-1.63 (6H, m). MS m/z (M + H): 420. |
| 0203 | | |
| 0203-1 | 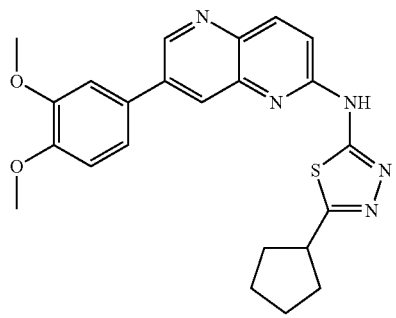 [SMILES: COc1ccc(-c2cnc3ccc(Nc4nnc(C5CCCC5)s4)nc3c2)cc1OC] | ¹H-NMR (DMSO-d₆) δ: 12.07 (1H, s), 9.12 (1H, d, J = 2.0 Hz), 8.39 (1H, d, J = 1.7 Hz), 8.31 (1H, d, J = 8.9 Hz), 7.51-7.43 (3H, m), 7.13 (1H, d, J = 8.6 Hz), 3.92 (3H, s), 3.84 (3H, s), 3.54-3.44 (1H, m), 2.22-2.10 (2H, m), 1.91-1.67 (6H, m). MS m/z (M + H): 434. |

-continued
| Example No. | | |
|---|---|---|
| 0204 | | |
| 0204-1 | 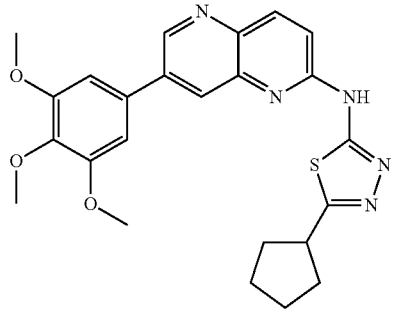 [SMILES: COc1cc(-c2cnc3ccc(Nc4nnc(C5CCCC5)s4)nc3c2)cc(OC)c1OC] | ¹H-NMR (DMSO-d₆) δ: 12.07 (1H, s), 9.12 (1H, d, J = 2.0 Hz), 8.39 (1H, d, J = 1.7 Hz), 8.31 (1H, d, J = 8.9 Hz), 7.51-7.43 (3H, m), 7.13 (1H, d, J = 8.6 Hz), 3.92 (3H, s), 3.84 (3H, s), 3.54-3.44 (1H, m), 2.22-2.10 (2H, m), 1.91-1.67 (6H, m). MS m/z (M + H): 464. |
Examples 0205 to 0210
The following compounds were obtained in the same manner as in Example 0175-3.
| Example No. | | |
|---|---|---|
| 0205 | | |
| 0205-1 | 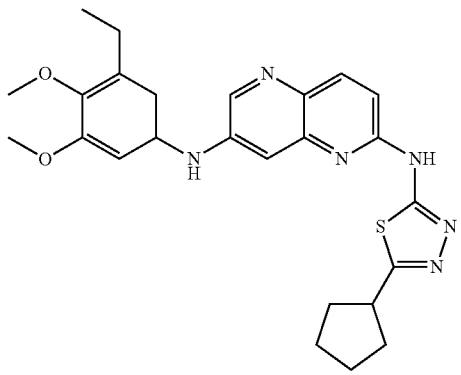 [SMILES: CCC1=C(OC)C(OC)=CC(Nc2cnc3ccc(Nc4nnc(C5CCCC5)s4)nc3c2)C1] | ¹H-NMR (DMSO-d₆) δ: 11.88 (1H, s), 8.87 (1H, s), 8.53 (1H, d, J = 2.6 Hz), 8.10 (1H, d, J = 8.9 Hz), 7.68 (1H, d, J = 2.3 Hz), 7.15 (1H, d, J = 8.9 Hz), 6.60 (2 H, s), 3.80 (6H, s), 3.66 (3H, s), 3.51-3.40 (1H, m), 2.16-2.08 (2H, m), 1.81-1.68 (6H, m). MS m/z (M + H): 479. |
| 0206 | | |
| 0206-1 | 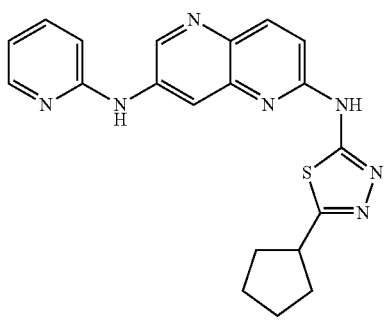 [SMILES: c1ccc(Nc2cnc3ccc(Nc4nnc(C5CCCC5)s4)nc3c2)nc1] | ¹H-NMR (DMSO-d₆) δ: 11.92 (1H, s), 9.72 (1H, s), 8.91 (1H, d), 8.76 (1H, d), 8.33 (1H, dd,) 8.15 (1H, d), 7.73-7.67 (1H, m), 7.24 (1H, d), 6.98 (1H, d), 6.91 (1H, dd), 3.56-3.46 (1H, m), 2.21-2.09 (2H, m), 1.91-1.68 (6H, m). MS m/z (M + H): 390. |

-continued

| Example No. | | |
|---|---|---|
| 0207 | | |
| 0207-1 | 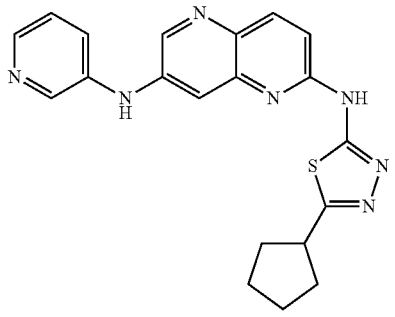 [SMILES: c1cncc(Nc2cnc3ccc(Nc4nnc(C5CCCC5)s4)nc3c2)c1] | ¹H-NMR (DMSO-d₆) δ:<br>11.92 (1H, s), 9.06 (1H, s), 8.59 (1H, d, J = 2.6 Hz), 8.54 (1H, d, J = 2.3 Hz), 8.23 (1H, dd, J = 4.6, 1.3 Hz), 8.14 (1H, d, J = 8.9 Hz), 7.72 (1H, dq, J = 8.3, 1.3 Hz), 7.62 (1H, d, J = 2.3 Hz), 7.40 (1H, dd, J = 8.3, 4.6 Hz), 7.22 (1H, d, J = 8.9 Hz), 3.52-3.41 (1H, m), 2.17-2.09 (2H, m), 1.90-1.61 (6H, m).<br>MS m/z (M + H): 390. |
| 0208 | | |
| 0208-1 | 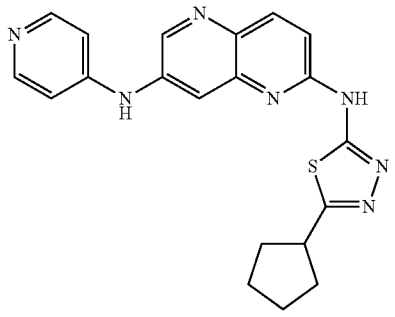 [SMILES: c1cc(Nc2cnc3ccc(Nc4nnc(C5CCCC5)s4)nc3c2)ccn1] | ¹H-NMR (DMSO-d₆) δ:<br>12.00 (1H, s), 9.38 (1H, s), 8.67 (1H, d, J = 2.6 Hz), 8.35 (2H, dd, J = 5.01, 1.3 Hz), 8.20 (1H, d, J = 8.9 Hz), 7.85 (1H, d, J = 2.3 Hz), 7.31 (1H, d, J = 8.9 Hz), 7.14-7.11 (2H, m), 3.57-3.39 (1H, m), 2.20-2.05 (2H, m), 1.91-1.62 (6H, m).<br>MS m/z (M + H): 390. |
| 0209 | | |
| 0209-1 | 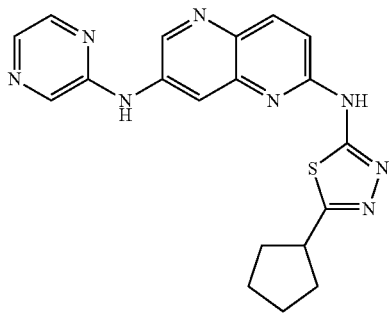 [SMILES: c1cnc(Nc2cnc3ccc(Nc4nnc(C5CCCC5)s4)nc3c2)cn1] | ¹H-NMR (DMSO-d₆) δ:<br>11.98 (1H, s), 10.16 (1H, s), 8.91 (1H, d, J = 2.6 Hz), 8.71 (1H, d, J = 2.0 Hz), 8.38 (1H, d, J = 1.3 Hz), 8.32 (1H, dd, J = 2.8, 1.5 Hz), 8.17 (1H, d, J = 8.9 Hz), 8.09 (1H, d, J = 2.6 Hz), 7.28 (1H, d, J = 8.9 Hz), 3.56-3.45 (1H, m), 2.21-2.09 (2H, m), 1.91-1.68 (6H, m).<br>MS m/z (M + H): 391. |
| 0210 | | |
| 0210-1 | 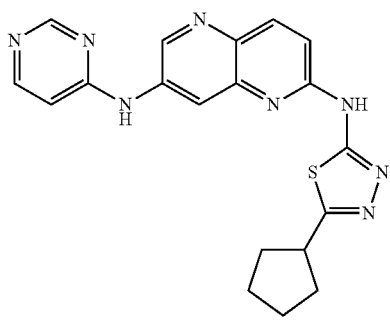 [SMILES: c1cc(Nc2cnc3ccc(Nc4nnc(C5CCCC5)s4)nc3c2)ncn1] | ¹H-NMR (DMSO-d₆) δ:<br>11.94 (1H, s), 10.20 (1H, s), 8.97 (1H, d, 2.6 Hz), 8.82-8.70 (2H, m), 8.42 (1H, d, J = 5.6 Hz), 8.21 (1H, d, J = 8.9 Hz), 7.33 (1H, d, J = 8.9 Hz), 6.96 (1H, dd, J = 5.9, 1.0 Hz), 3.55-3.43 (1H, m), 2.28-2.09 (2H, m), 1.90-1.68 (6H, m).<br>MS m/z (M + H) 391. |

Examples 0211 to 0216

The following compounds were obtained in the same manner as in Examples 0197-1 and 0197-2.

| Example No. | | |
|---|---|---|
| 0211 | | |
| 0211-1 | 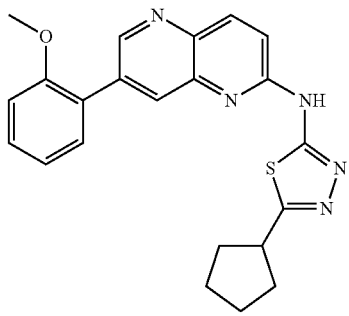 [SMILES: COc1ccccc1-c1cnc2ccc(Nc3nnc(C4CCCC4)s3)nc2c1] | ¹H-NMR (DMSO-d₆) δ:<br>12.07 (1H, s), 8.88 (1H, d, J = 2.3 Hz), 8.32 (1H, d, J = 92 Hz), 8.22 (1H, d, J = 1.7 Hz), 7.55-7.45 (3H, m), 7.22 (1H, d, J = 7.6 Hz), 7.13 (1H, t, J = 7.4 Hz), 3.83 (3H, s), 3.52-3.42 (1H, m), 2.17-2.09 (2H, m), 1.90-1.62 (6H, m).<br>MS m/z (M + H): 404. |
| 0212 | | |
| 0212-1 | 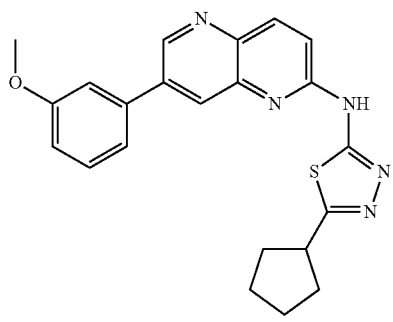 [SMILES: COc1cccc(-c2cnc3ccc(Nc4nnc(C5CCCC5)s4)nc3c2)c1] | ¹H-NMR (DMSO-d₆) δ:<br>12.10 (1H, s), 9.11 (1H, d, J = 2.0 Hz), 8.44-8.43 (1H, m), 8.33 (1H, d, J = 9.2 Hz), 7.50-7.46 (4H, m), 7.10-7.04 (1H, m), 3.89 (3H, s), 3.54-3.43 (1H, m), 2.20-2.10 (2H, m), 1.92-1.66 (6H, m).<br>MS m/z (M + H): 404 |
| 0213 | | |
| 0213-1 |  | ¹H-NMR (DMSO-d₆) δ:<br>12.07 (1H, s), 9.10 (1H, d, J = 2.3 Hz), 8.37 (1H, t, J = 1.2 Hz), 8.30 (1H, d, J = 8.9 Hz), 7.91 (2H, dd, J = 6.9, 2.0 Hz), 7.45 (1H, d, J = 8.9 Hz), 7.13 (2H, d, J = 8.9 Hz), 3.85 (3H, s), 3.52-3.44 (1H, m), 2.21-2.13 (2H, m), 1.90-1.67 (6H, m).<br>MS m/z (M + H): 404. |
| 0214 | | |
| 0214-1 | 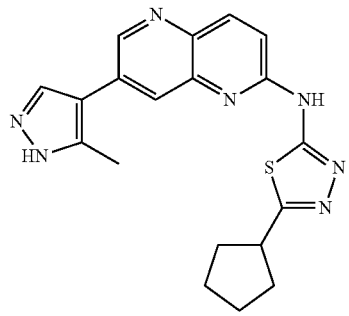 [SMILES: Cc1[nH]ncc1-c1cnc2ccc(Nc3nnc(C4CCCC4)s3)nc2c1] | ¹H-NMR (DMSO-d₆) δ:<br>12.92 (1H, s), 12.04 (1H, s), 8.94 (1H, d, J = 1.7 Hz), 8.33-8.00 (3H, m), 7.41 (1H, d, J = 9.2 Hz), 3.54-3.43 (1H, m), 2.53 (3H, s), 2.20-2.12 (2H, m), 1.90-1.67 (6H, m).<br>MS m/z (M + H): 378. |

| Example No. | | |
|---|---|---|
| 0215 | | |
| 0215-1 | 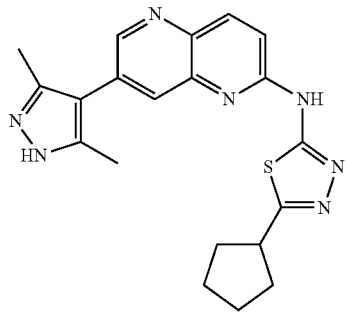 [SMILES: Cc1n[nH]c(C)c1-c1cnc2ccc(Nc3nnc(C4CCCC4)s3)nc2c1] | ¹H-NMR (DMSO-d₆) δ:<br>12.52 (1H, s), 12.04 (1H, s), 8.67 (1H, s), 8.21 (1H, d, J = 8.6 Hz),<br>7.99 (1H, s), 7.38 (1H, d, J = 8.9 Hz), 3.47-3.40 (1H, m), 2.29 (6H, s), 2.18-2.07 (2H, m), 1.87-1.66 (6H, m).<br>MS m/z (M + H): 392. |
| 0216 | | |
| 0216-1 | 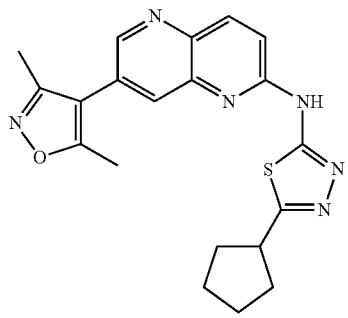 [SMILES: Cc1noc(C)c1-c1cnc2ccc(Nc3nnc(C4CCCC4)s3)nc2c1] | ¹H-NMR (CD₃OD) δ: 8.73 (1H, d, J = 2.0 Hz), 8.32-8.28 (2H, m), 7.47 (1H, d, J = 9.2 Hz), 3.54-3.49 (1H, m), 2.53 (3H, s), 2.36 (3H, s), 2.29-2.21 (2H, m), 1.95-1.75 (6H, m).<br>MS m/z (M + H): 393. |

Example 0217

0217-1

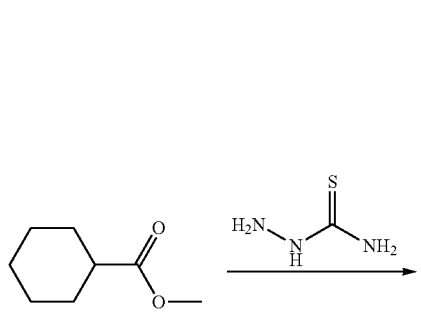

2-Amino-5-cyclohexyl-1,3,4-thiadiazole was obtained in the same manner as in Example 0198-1.

MS m/z (M+H): 184.

0217-2

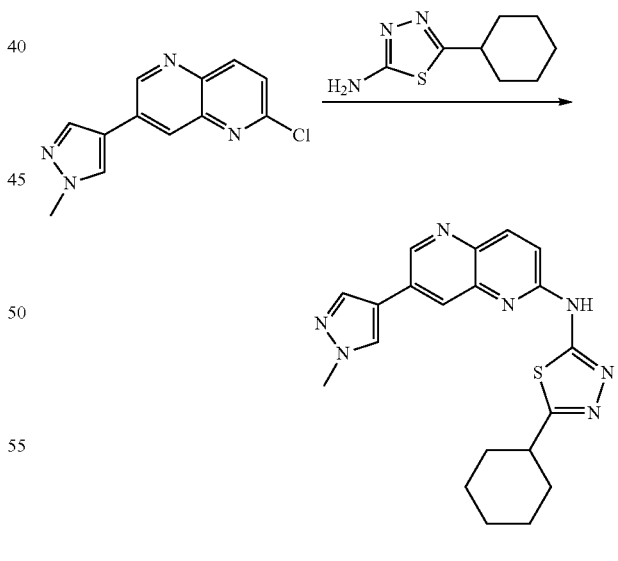

5-Cyclohexyl-N-(7-(1-methyl-1H-pyrazol-4-yl)-1,5-naphthyridin-2-yl)-1,3,4-thiadiazole-2-amine was obtained as a yellow solid in the same manner as in Example 0001-5.

¹H-NMR(DMSO-d₆)δ:12.03(1H,s),9.07(1H,d,J=2.3 Hz), 8.53(1H,s),8.33(1H,d,J=1.7 Hz),8.26-8.22(2H,m),7.39(1H, d,J=9.2 Hz),3.93(3H,s),3.13-3.02(1H,m),2.17-2.08(2H,m), 1.85-1.15(8H,m).

MS m/z(M+H):392.

Example 0218

0218-1

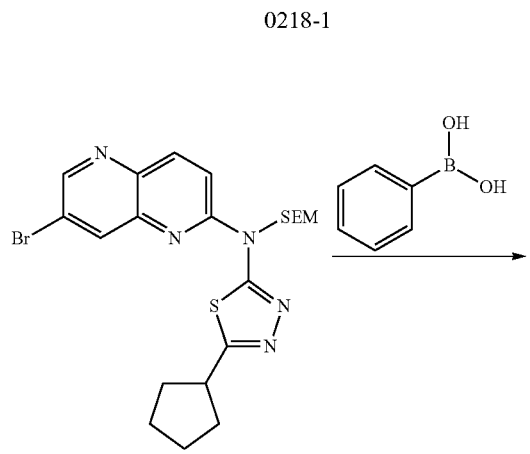

5-Cyclopentyl-N-(7-phenyl-1,5-naphthyridin-2-yl)-1,3,4-thiadiazole-2-amine was obtained as a pale yellow solid in the same manner as in Examples 0197-1 and 0197-2.

$^1$H-NMR(DMSO-$d_6$)δ:12.10(1H,s),9.12(1H,d,J=2.0 Hz),8.44(1H,d,J=1.7 Hz),8.33(1H,d,J=9.2 Hz),7.97-7.92(2H,m),7.61-7.55(2H,m),7.53-7.47(2H,m),3.57-3.44(1H,m),2.21-2.08(2H,m),1.92-1.64(6H,m).

MSm/z(M+H):374.

Example 0219

0219-1

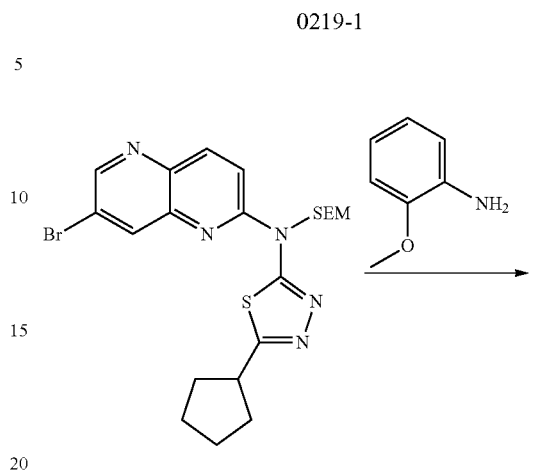

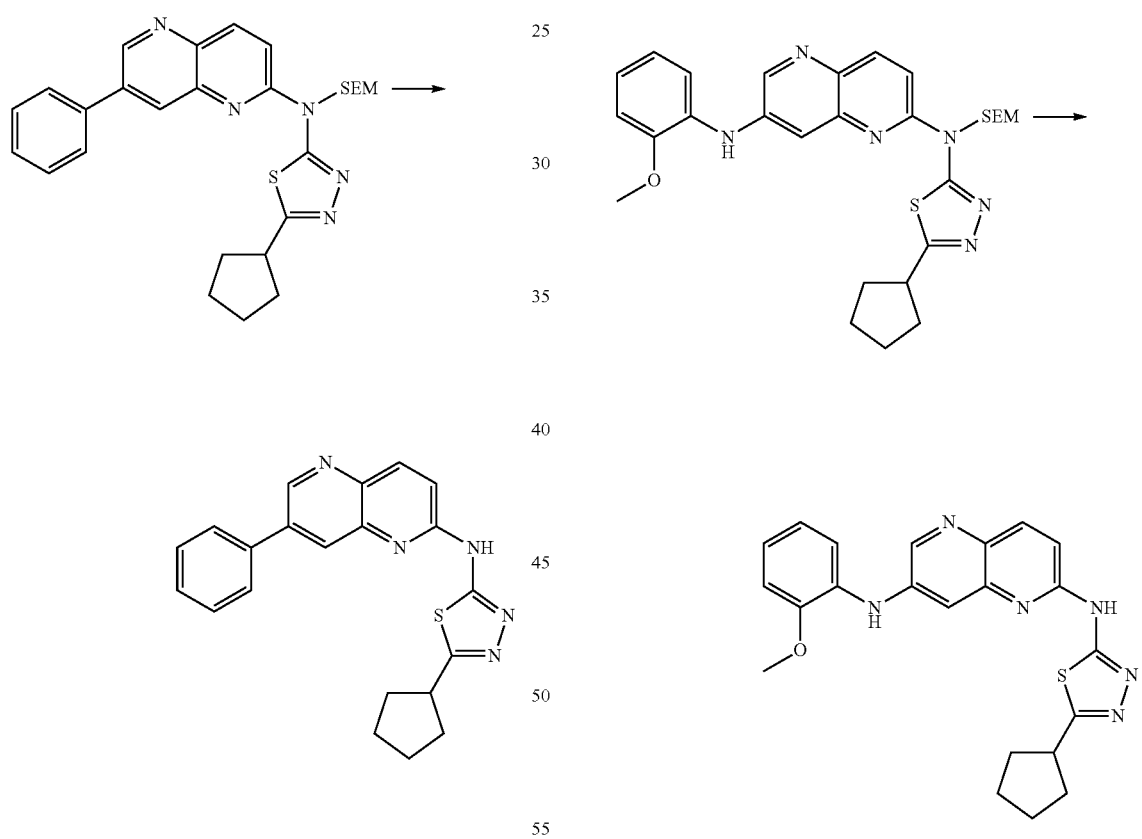

$N^2$-(5-cyclopentyl-1,3,4-thiadiazol-2-yl)-$N^7$-(2-methoxyphenyl)-1,5-naphthyridine-2,7-diamine was obtained as a yellow solid in the same manner as in Example 0175-3.

$^1$H-NMR(DMSO-$d_6$)δ:11.84(1H,s),8.57(1H,d,J=2.3 Hz),8.29(1H,s),8.09(1H,d,J=8.6 Hz),7.38(1H,t,J=4.3 Hz),7.33(1H,d,J=2.3 Hz),7.16-7.09(3H,m),7.03-6.97(1H,m),3.84(3H,s),3.51-3.40(1H,m),2.16-2.07(2H,m),1.85-1.67(6H,m).

MSm/z(M+H):419.

Example 0220

220-1

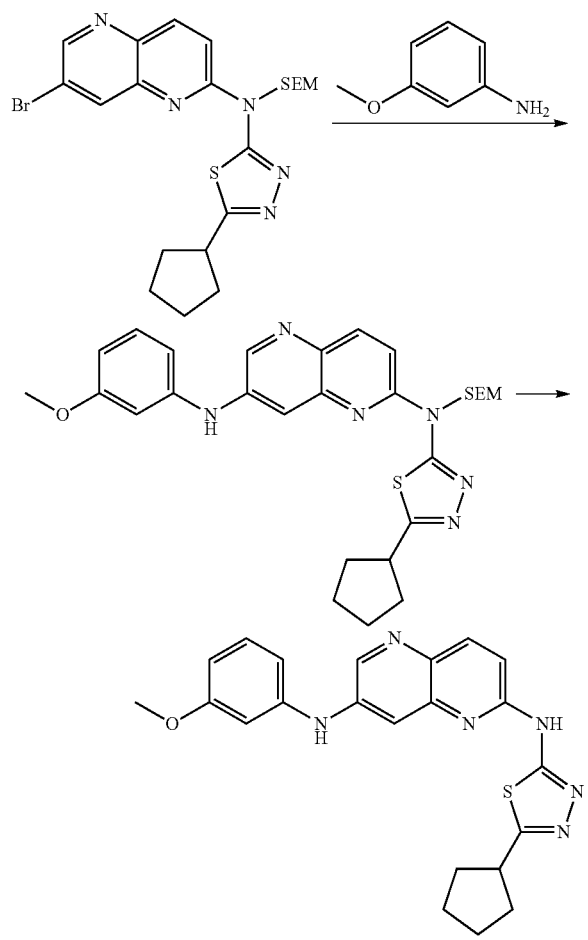

N²-(5-cyclopentyl-1,3,4-thiadiazol-2-yl)-N⁷-(3-methoxyphenyl)-1,5-naphthyridine-2,7-diamine was obtained as a yellow solid in the same manner as in Example 0175-3.

¹H-NMR(DMSO-d₆)δ:11.89(1H,s),8.91(1H,s),8.55(1H, d,J=2.6 Hz),8.11(1H,d,J=8.9 Hz),7.64(1H,d,J=2.3 Hz),7.29 (1H,t,J=8.1 Hz),7.18(1H,d,J=8.9 Hz),6.84(2H,dt,J=12.1,3.4 Hz),6.61(1H,dd,J=8.1,2.1 Hz),3.78(3H,s),3.54-3.42(1H,m), 2.17-2.08(2H,m),1.86-1.66(6H,m).

MSm/z(M+H):419.

Example 0221

0221-1

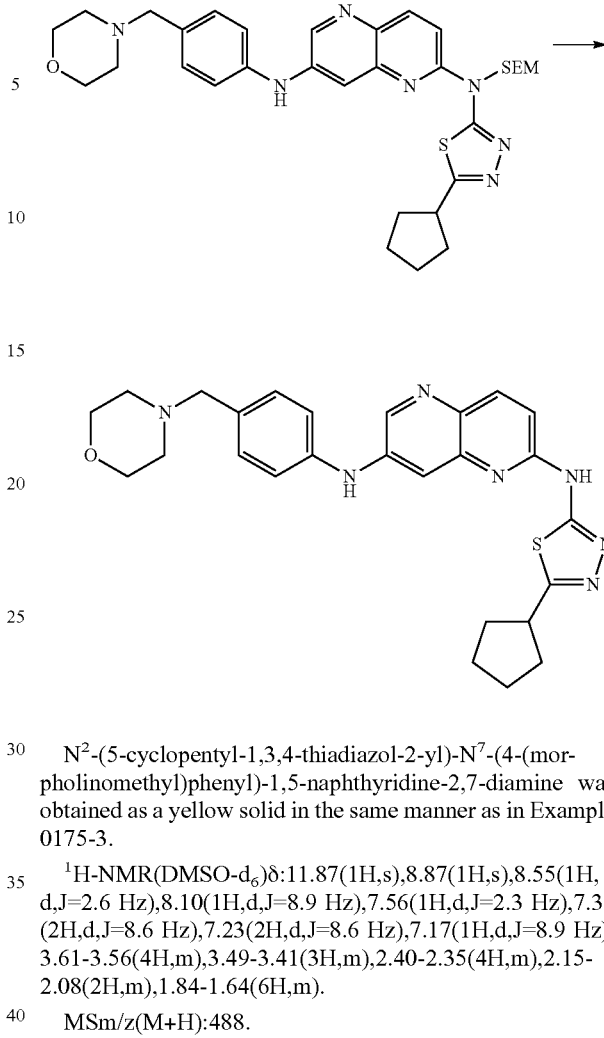

N²-(5-cyclopentyl-1,3,4-thiadiazol-2-yl)-N⁷-(4-(morpholinomethyl)phenyl)-1,5-naphthyridine-2,7-diamine was obtained as a yellow solid in the same manner as in Example 0175-3.

¹H-NMR(DMSO-d₆)δ:11.87(1H,s),8.87(1H,s),8.55(1H, d,J=2.6 Hz),8.10(1H,d,J=8.9 Hz),7.56(1H,d,J=2.3 Hz),7.31 (2H,d,J=8.6 Hz),7.23(2H,d,J=8.6 Hz),7.17(1H,d,J=8.9 Hz), 3.61-3.56(4H,m),3.49-3.41(3H,m),2.40-2.35(4H,m),2.15-2.08(2H,m),1.84-1.64(6H,m).

MSm/z(M+H):488.

Example 0222

0222-1

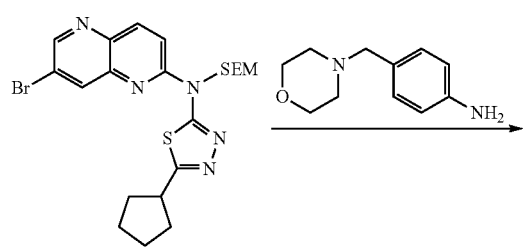

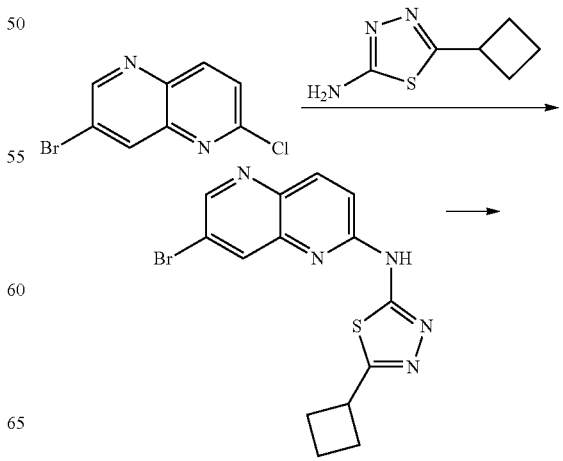

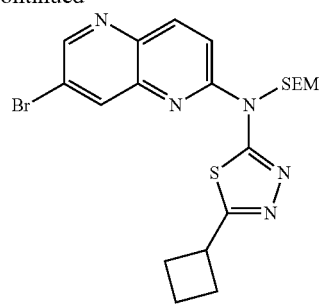

N-(7-bromo-1,5-naphthyridin-2-yl)-5-cyclobutyl-N-((2-(trimethylsilyl)ethoxy)methyl)-1,3,4-thiadiazole-2-amine was obtained as brown oily substance in the same manner as in Example 0175-2.

MSm/z(M+H):492,494.

0222-2

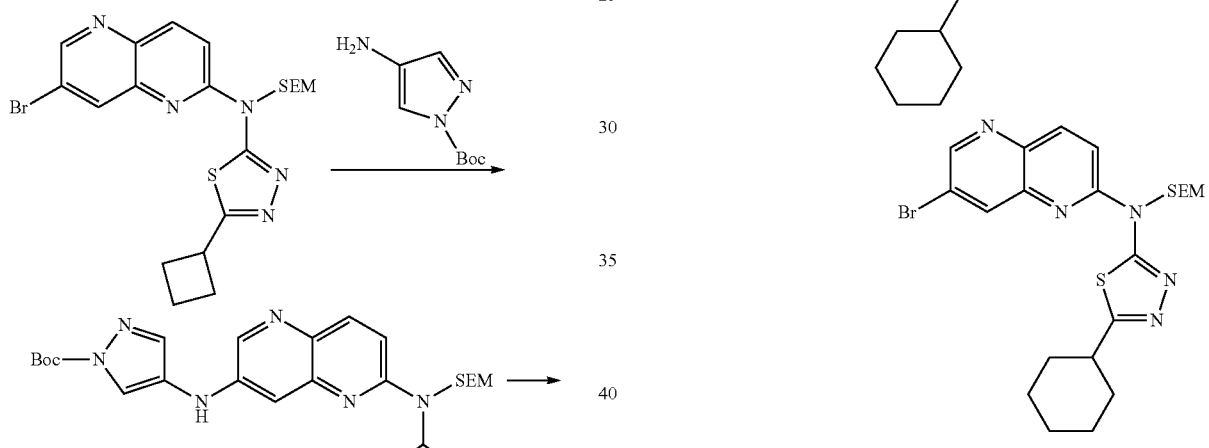

$N^2$-(5-cyclobutyl-1,3,4-thiadiazol-2-yl)-$N^7$-(1H-pyrazol-4-yl)-1,5-naphthyridine-2,7-diamine was obtained as a yellow solid in the same manner as in Example 0175-3.

$^1$H-NMR(DMSO-$d_6$)δ:12.30(1H,s),11.85(1H,s),9.28(1H,s),8.62(1H,d,J=2.3 Hz),8.32(1H,d,J=2.0 Hz),8.09(1H,d,J=8.9 Hz),7.69(1H,t,J=2.0 Hz),7.15(1H,d,J=8.9 Hz),5.95 (1H,t,J=2.1 Hz),4.04-3.87(1H,m),2.45-2.27(4H,m),2.16-1.90(2H,m).

MSm/z(M+H):365.

Example 0223

0223-1

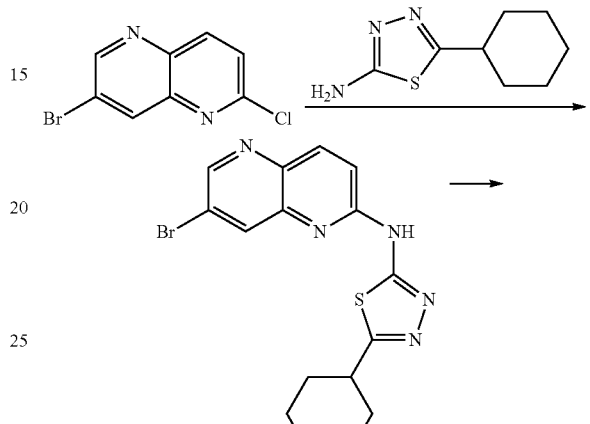

N-(7-bromo-1,5-naphthyridin-2-yl)-5-cyclohexyl-N-((2-(trimethylsilyl)ethoxy)methyl)-1,3,4-thiadiazole-2-amine was obtained as brown oily substance in the same manner as in Example 0175-2.

MSm/z(M+H):520,522.

0223-2

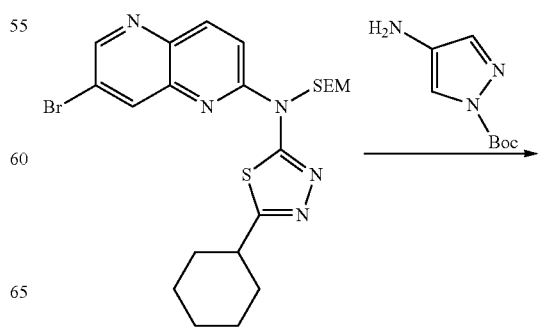

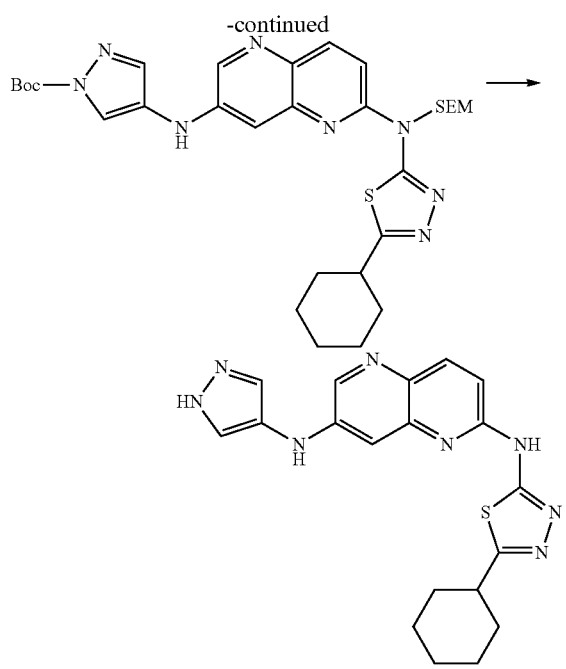

N²-(5-cyclohexyl-1,3,4-thiadiazol-2-yl)-N⁷-((1H-pyrazol-4-yl)-1,5-naphthyridine-2,7-diamine was obtained as a yellow solid in the same manner as in Example 0175-3.
¹H-NMR(DMSO-d₆)δ:12.29(1H,s),11.83(1H,s),9.27(1H,s),8.62(1H,d,J=2.6 Hz),8.31(1H,d,J=2.0 Hz),8.08(1H,d,J=8.9 Hz),7.69(1H,t,J=2.0 Hz),7.15(1H,d,J=8.9 Hz),5.94 (1H,t,J=2.3 Hz),3.11-3.03(1H,m),2.16-2.04(2H,m),1.84-1.27(8H,m).
MSm/z(M+H):393.

Example 0224

0224-1

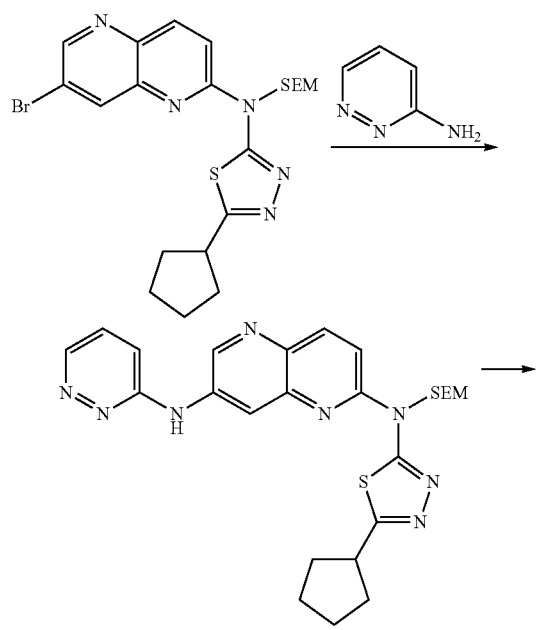

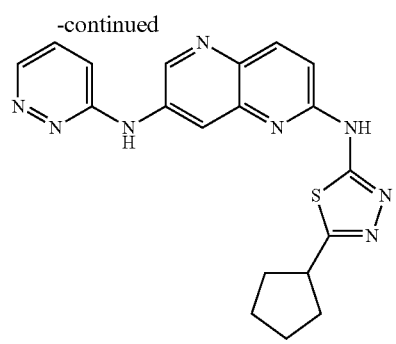

N²-(5-cyclopentyl-1,3,4-thiadiazol-2-yl)-N⁷-(pyridazin-3-yl)-1,5-naphthyridine-2,7-diamine was obtained as a yellow solid in the same manner as in Example 0175-3.
¹H-NMR(DMSO-d₆)δ:11.70(1H,s),9.02(1H,d,J=2.0 Hz),8.49(1H,s),8.29(1H,d,J=1.7 Hz),8.19(2H,dd,J=4.8,4.1 Hz),7.31(1H,d,J=8.9 Hz),3.92(3H,s),3.80-3.76(4H,m),3.48-3.42 (4H,m).
MSm/z(M+H):391.

Example 0225

0225-1

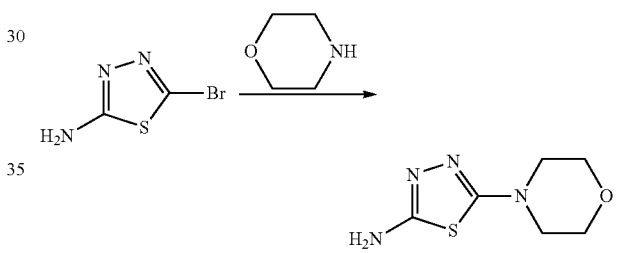

5-Morpholino-1,3,4-thiadiazole-2-amine was obtained in the same manner as in Example 0173-1.
¹H-NMR(DMSO-d₆)δ:6.52(2H,s),3.67(4H,t,J=5.0 Hz),3.20(4H,t,J=4.8 Hz).

0225-2

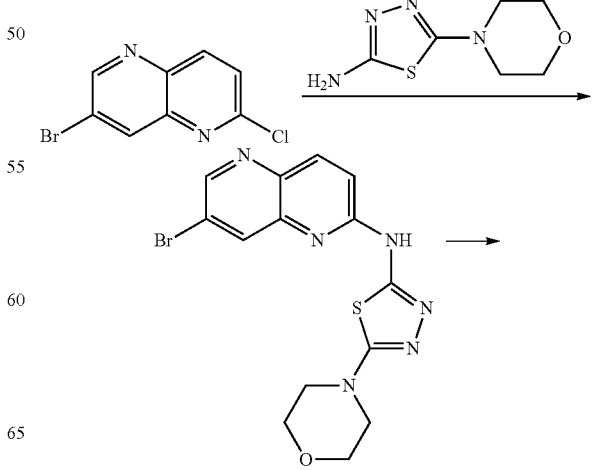

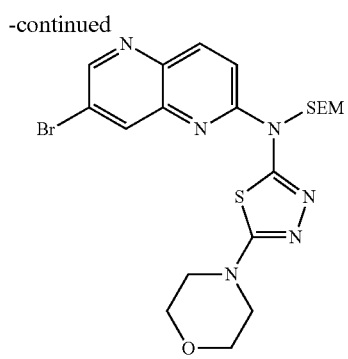

N-(7-bromo-1,5-naphthyridin-2-yl)-5-morpholino-N-((2-(trimethylsilyl)ethoxy)methyl)-1,3,4-thiadiazole-2-amine was obtained as brown oily substance in the same manner as in Example 0175-2.

MSm/z(M+H):523,525.

0225-3

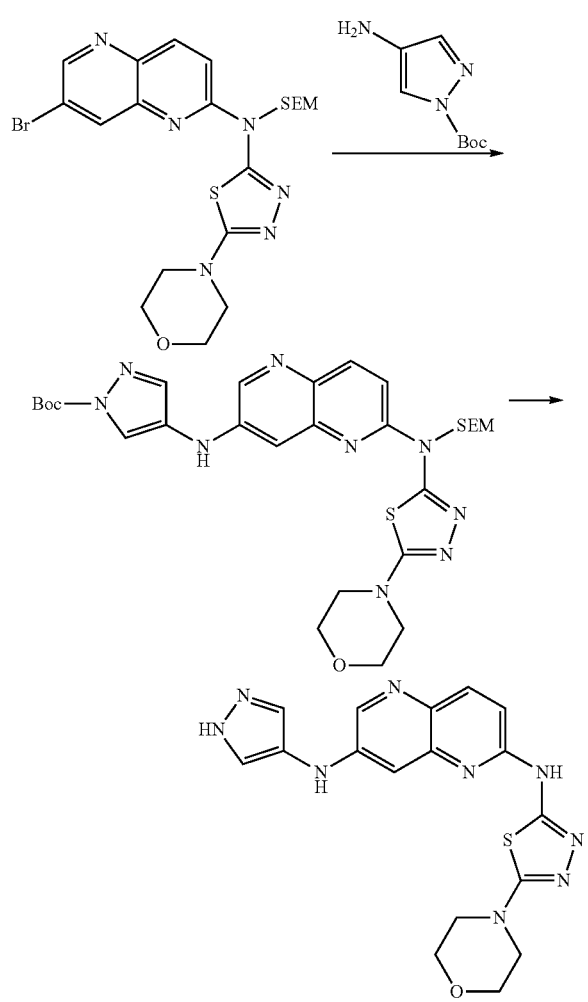

$N^2$-(5-morpholino-1,3,4-thiadiazol-2-yl)-$N^7$-(1H-pyrazol-4-yl)-1,5-naphthyridine-2,7-diamine was obtained as a yellow solid in the same manner as in Example 0175-3.

$^1$H-NMR(DMSO-d$_6$)δ:12.25(1H,s),11.48(1H,s),9.22(1H,s),8.61(1H,d,J=2.3 Hz),8.22(1H,s),8.03(1H,d,J=8.9 Hz),7.67(1H,s),7.07(1H,d,J=8.9 Hz),5.94(1H,s),3.79-3.75(4H,m),3.43-3.39(4H,m).

MSm/z(M+H):396.

Example 0226

0226-1

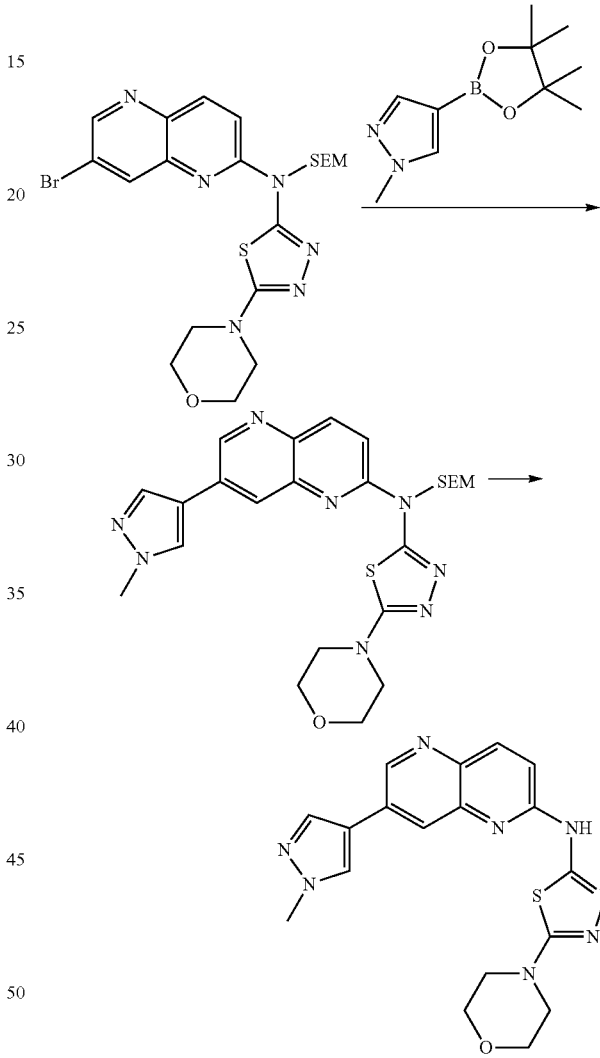

1-Methylpyrazole-4-boronic acid pinacol ester (10 mg), bis(di-tert-butyl(4-dimethylaminophenyl)phosphine)dichloropalladium(II) (5 mg), and 2 mol/L sodium carbonate aqueous solution (50 μL) were added to a solution of N-(7-bromo-1,5-naphthyridin-2-yl)-5-morpholino-N-((2-(trimethylsilyl)ethoxy)methyl)-1,3,4-thiadiazole-2-amine (20 mg) in 1,4-dioxane (1 mL), followed by stirring at 130° C. for 0.5 hours using a microwave reaction apparatus. The reaction mixture was cooled to room temperature, and water and ethyl acetate were added thereto. The organic layer was collected by separation, and dried over anhydrous sodium sulfate, and the solvent was distilled off under reduced pressure. The solid matter was collected by filtration, thereby obtaining N-(7-(1-methyl-1H-pyrazol-4-yl)-1,5-naphthyridin-2-yl)-5-morpholino-N-((2-(trimethylsilyl)ethoxy)methyl)-1,3,4-thiadiazole-2-amine.

A 4 mol/L hydrogen chloride/1,4-dioxane solution (1 mL) was added to the obtained N-(7-(1-methyl-1H-pyrazol-4-yl)-1,5-naphthyridin-2-yl)-5-morpholino-N-((2-(trimethylsilyl)ethoxy)methyl)-1,3,4-thiadiazole-2-amine, followed by allowing to stand at room temperature overnight. The solvent was distilled off under reduced pressure, and the obtained residue was purified by preparative thin layer silica gel chromatography (chloroform-methanol, NH silica), thereby obtaining N-(7-(1-methyl-1H-pyrazol-4-yl)-1,5-naphthyridin-2-yl)-5-morpholino-1,3,4-thiadiazole-2-amine (9 mg) as a yellow solid.

$^1$H-NMR(DMSO-d$_6$)δ:11.70(1H,s),9.02(1H,d,J=2.0 Hz), 8.49(1H,s),8.29(1H,d,J=1.7 Hz),8.19(2H,dd,J=4.8,4.1 Hz), 7.31(1H,d,J=8.9 Hz),3.92(3H,s),3.80-3.76(4H,m),3.48-3.42 (4H,m).

MSm/z(M+H):395.

Example 0227

The following compounds were obtained in the same manner as in Examples 0198-1 and 0001-5.

| Example No. | | |
|---|---|---|
| 0227 | | |
| 0227-1 | 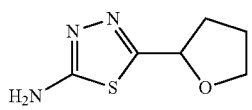 | $^1$H-NMR (DMSO-d$_6$) δ: 7.13 (2H, s), 5.03-4.95 (1H, m), 3.88-3.73 (2H, m), 2.32-2.21 (1H, m), 2.06-1.87 (3H, m). |
| 0227-2 | 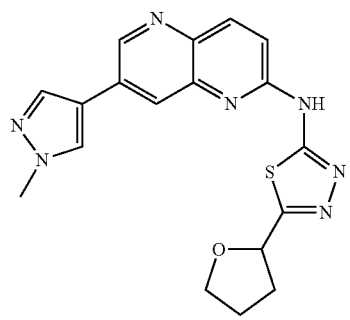 [SMILES: Cn1cc(-c2cnc3ccc(Nc4nnc(C5CCCO5)s4)nc3c2)cn1] | $^1$H-NMR (DMSO-d$_6$) δ: 12.12 (1H, s), 9.08 (1H, d, J = 2.0 Hz), 8.54 (1H, d, J = 4.0 Hz), 8.31 (1H, d, J = 2.0 Hz), 8.26 (1H, d, J = 9.2 Hz), 8.23 (1H, d, J = 0.7 Hz), 7.41 (1H, d, J = 8.9 Hz), 5.24 (1H, dd, J = 7.1, 6.1 Hz), 4.06-3.98 (1H, m), 3.92 (3H, s), 3.90-3.85 (1H, m), 2.43-2.34 (1H, m), 2.26-2.17 (1H, m), 2.07-1.99 (2H, m). MS m/z (M + H): 380. |

Example 0228

The following compounds were obtained in the same manner as in Examples 0175-2 and 0175-3.

| Example No. | | |
|---|---|---|
| 0228 | | |
| 0228-1 | 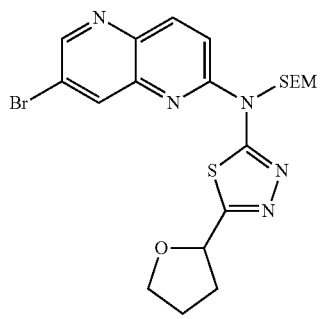 [SMILES: C[Si](C)(C)CCOCN(c1ccc2ncc(Br)cc2n1)c1nnc(C2CCCO2)s1] | MS m/z (M + H): 508, 510. |

-continued

| Example No. | | |
|---|---|---|
| 0228-2 | 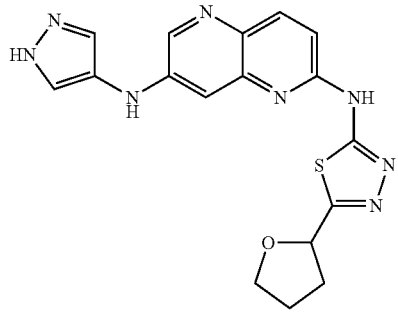 [SMILES: c1n[nH]cc1Nc1cnc2ccc(Nc3nnc(C4CCCO4)s3)nc2c1] | ¹H-NMR (DMSO-d₆) δ:<br>12.35 (1H, s), 11.93 (1H, s), 9.32 (1H, s), 8.62 (1H, d, J = 2.3 Hz), 8.37 (1H, s), 8.10 (1H, d, J = 8.9 Hz), 7.69 (1H, d, J = 2.0 Hz), 7.16 (1H, d, J = 8.9 Hz), 5.94 (1H, s), 5.24 (1H, dd, J = 7.3, 5.9 Hz), 4.05-3.84 (2H, m), 2.43-2.17 (2H, m), 2.05-1.96 (2H, m).<br>MS m/z (M + H): 381. |

Examples 0229 to 0238

Example 0198-1, The following compounds were obtained in the same manner as in Examples 0001-4 and 0001-5

| Example No. | | |
|---|---|---|
| 0229 | | |
| 0229-1 | 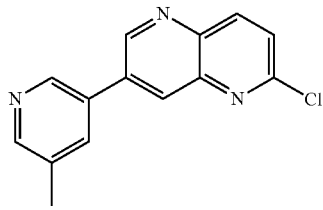 [SMILES: Cc1cncc(-c2cnc3ccc(Cl)nc3c2)c1] | 1H-NMR (DMSO-d₆) δ:<br>9.48 (1H, d, J = 2.0 Hz), 8.82 (1H, d, J = 2.0 Hz), 8.62 (1H, d, J = 5.3 Hz), 8.56 (1H, d, J = 8.6 Hz), 7.96-7.87 (2H, m), 7.82 (1H, d, J = 5.3 Hz), 2.59 (3H, s). |
| 0229-2 | 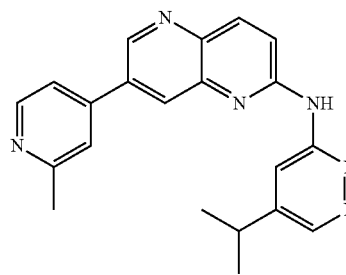 | ¹H-NMR (DMSO-d₆) δ:<br>10.83 (1H, s), 9.17 (1H, d, J = 2.0 Hz), 8.89 (1H, d, J = 1.3 Hz), 8.77 (1H, d, J = 2.0 Hz), 8.61 (1H, d, J = 5.3 Hz), 8.48 (1H, d, J = 2.0 Hz) 8.32 (1H, d, J = 9.2 Hz), 7.87-7.78 (2H, m), 7.76 (1H, d, J = 5.3 Hz), 3.13-2.98 (1H, m), 2.60 (3H, s), 1.33 (6H, d, J = 7.3 Hz).<br>MS m/z (M + H): 357. |
| 0230 | | |
| 0230-1 | 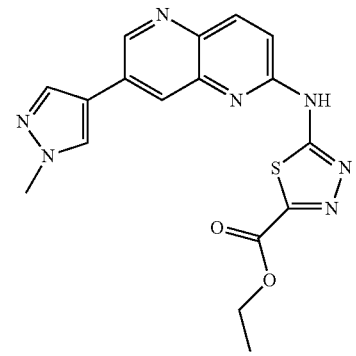 [SMILES: CCOC(=O)c1nnc(Nc2ccc3ncc(-c4cnn(C)c4)cc3n2)s1] | 1H-NMR (DMSO-d₆) δ:<br>12.76 (1H, s), 9.13 (1H, d, J = 2.0 Hz), 8.57 (1H, s), 8.39 (1H, d, J = 1.7 Hz), 8.34 (1H, d, J = 8.9 Hz), 8.25 (1H, s), 7.48 (1H, d, J = 8.9 Hz), 4.45 (2H, d, J = 7.0 Hz), 3.93 (3H, s), 1.39 (3H, t, J = 7.1 Hz).<br>MS m/z (M + H): 382. |

| Example No. | | |
|---|---|---|
| 0231 | | |
| 0231-1 | 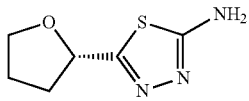 [SMILES: Nc1nnc([C@@H]2CCCO2)s1] | 1H-NMR (DMSO-d$_6$) δ:<br>7.13 (2H, s), 5.02-4.95 (1H, m), 3.88-3.73 (2H, m), 2.31-2.20 (1H, m), 2.04-1.89 (3H, m). |
| 0231-2 | 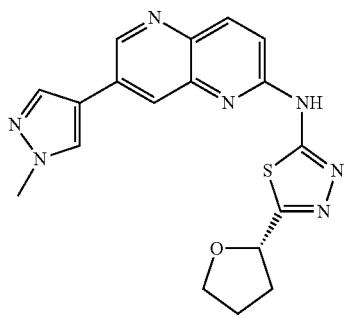 [SMILES: Cn1cc(-c2cnc3ccc(Nc4nnc([C@@H]5CCCO5)s4)nc3c2)cn1] | 1H-NMR (DMSO-d$_6$) δ:<br>12.13 (1H, s), 9.08 (1H, d, J = 2.3 Hz), 8.55 (1H, s), 8.31 (1H, d, J = 1.7 Hz), 827 (1H, d, J = 9.2 Hz), 8.23 (1H, d, J = 0.7 Hz), 7.41 (1H, d, J = 9.2 Hz), 5.24 (1H, dd, J = 7.3, 5.9 Hz), 4.06-3.85 (5H, m), 2.45-2.34 (1H, m), 2.28-214 (1H, m), 2.07-1.98 (2H, m). |
| 0232 | | |
| 0232-1 | 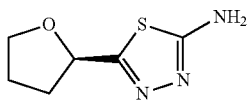 [SMILES: Nc1nnc([C@H]2CCCO2)s1] | 1H-NMR (DMSO-d$_6$) δ:<br>7.13 (2H, s), 5.02-4.95 (1H, m), 3.88-3.73 (2H, m), 2.29-2.21 (1H, m), 2.06-1.88 (3H, m). |
| 0232-2 | 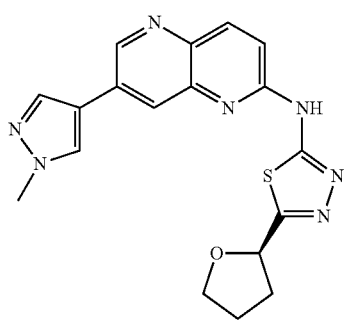 [SMILES: Cn1cc(-c2cnc3ccc(Nc4nnc([C@H]5CCCO5)s4)nc3c2)cn1] | 1H-NMR (DMSO-d$_6$) δ:<br>12.12 (1H, s), 9.07 (1H, d, J = 2.0 Hz), 8.55 (1H, s), 8.30 (1H, d, J = 1.7 Hz), 8.25 (1H, d, J = 8.9 Hz), 8.23 (1H, s), 7.40 (1H, d, J =8.9 Hz), 5.24 (1H, dd, J = 7.1, 6.1 Hz), 4.05-3.85 (5H, m), 2.45-2.34 (1H, m), 2.28-2.15 (1H, m), 2.07-1.96 (2H, m).<br>MS m/z (M + H): 380. |
| 0233 | | |
| 0233-1 | 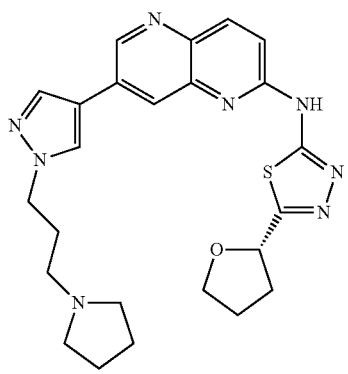 [SMILES: c1nc2ccc(Nc3nnc([C@@H]4CCCO4)s3)nc2cc1-c1cnn(CCCN2CCCC2)c1] | 1H-NMR (DMSO-d$_6$) δ:<br>12.14 (1H, s), 9.07 (1H, d, J = 2.3 Hz), 8.59 (1H, s), 8.32-821 (3H, m), 7.39 (1H, d, J = 92 Hz), 5.23 (1H, dd, J = 7.1, 6.1 Hz),<br>4.21 (2H, t, J = 7.1 Hz), 4.05-3.84 (2H, m), 2.46-2.36 (7H, m), 2.27-2.14 (1H, m), 2.09-1.96 (4H, m), 1.74-1.64 (4H, m).<br>MS m/z (M + H): 477. |
| 0234 | | |
| 0234-1 | 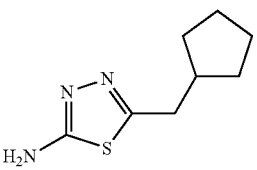 [SMILES: Nc1nnc(CC2CCCC2)s1] | MS m/z (M + H): 184. |

| Example No. | | |
|---|---|---|
| 0234-2 | 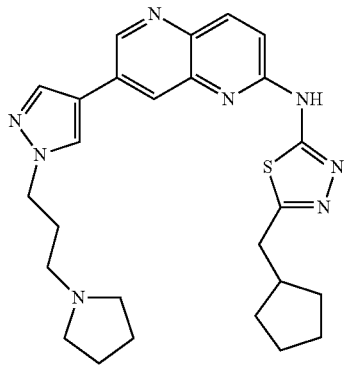 [SMILES: c1nc2ccc(Nc3nnc(CC4CCCC4)s3)nc2cc1-c1cnn(CCCN2CCCC2)c1] | 1H-NMR (DMSO-d<sub>6</sub>) δ:
12.05 (1H, s), 9.07 (1H, d, J = 2.0 Hz), 8.57 (1H, s), 8.31 (1H, d, J = 1.7 Hz), 8.26 (1H, s), 8.22 (1H, d, J = 2.0 Hz), 7.39 (1H, d, J = 8.9 Hz), 4.21 (2H, t, J = 7.1 Hz), 3.00 (2H, d, J = 7.6 Hz), 2.45-2.37 (5H, m), 2.36-2.26 (1H, m), 2.07-1.96 (2H, m), 1.86-1.49 (10H, m), 1.35-1.21 (3H, m).
MS m/z (M + H): 489. |
| 0235 | | |
| 0235-1 | 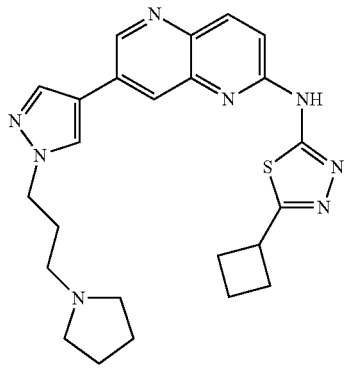 [SMILES: c1nc2ccc(Nc3nnc(C4CCC4)s3)nc2cc1-c1cnn(CCCN2CCCC2)c1] | 1H-NMR (DMSO-d<sub>6</sub>) δ:
12.02 (1H, s), 9.03 (1H, d, J = 1.7 Hz), 8.56 (1H, s), 8.29 (1H, s), 8.21 (1H, s), 8.18 (1H, d, J = 8.9 Hz), 7.34 (1H, d, J = 8.9 Hz), 4.21 (2H, t, J = 6.9 Hz), 3.96-3.85 (1H, m), 2.46-2.19 (10H, m), 2.16-1.91 (4H, m), 1.71-1.67 (4H, m).
MS m/z (M + H): 461. |
| 0236 | | |
| 0236-1 | 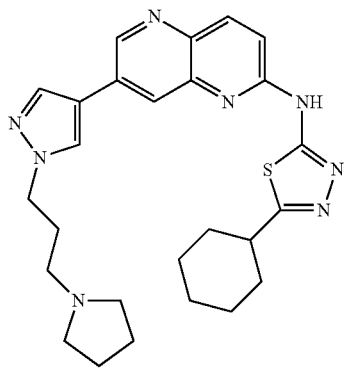 [SMILES: c1nc2ccc(Nc3nnc(C4CCCCC4)s3)nc2cc1-c1cnn(CCCN2CCCC2)c1] | 1H-NMR (DMSO-d<sub>6</sub>) δ:
12.05 (1H, s), 9.02 (1H, d, J = 1.7 Hz), 8.56 (1H, s), 8.32-8.16 (3H, m), 7.33 (1H, d, J = 9.2 Hz), 4.21 (2H, t, J = 7.1 Hz), 3.09-3.01 (1H, m), 2.44-2.38 (6H, m), 2.12-1.23 (16H, m).
MS m/z (M + H): 489. |

| Example No. | | |
|---|---|---|
| 0237 | | |
| 0237-1 | 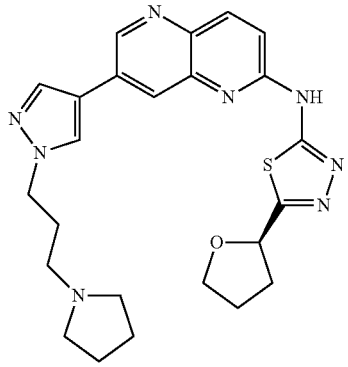 [SMILES: c1nc2ccc(Nc3nnc([C@H]4CCCO4)s3)nc2cc1-c1cnn(CCCN2CCCC2)c1] | 1H-NMR (DMSO-d$_6$) δ:<br>12.13 (1H, s), 9.09 (1H, d, J = 2.0 Hz), 8.60 (1H, s), 8.32 (1H, d, J =<br>1.7 Hz), 8.27 (1H, d, J = 9.6 Hz), 8.24 (1H, s), 7.41 (1H, d, J = 8.9 Hz), 5.24 (1H, dd, J = 7.3, 5.9 Hz), 422 (2H, t, J = 6.9 Hz), 4.05-3.85 (2H, m), 2.44-2.15 (8H, m), 2.07-1.87 (4H, m), 1.69 (4H, s).<br>MS m/z (M + H): 477. |
| 0238 | | |
| 0238-1 | 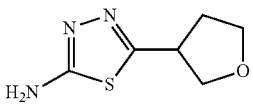 | MS m/z (M + H): 172. |
| 0238-2 | 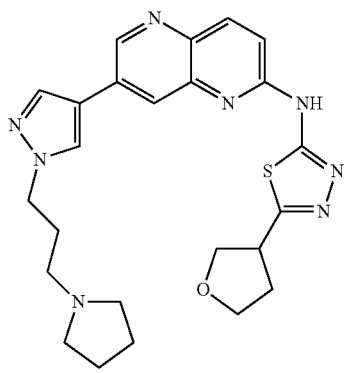 [SMILES: c1nc2ccc(Nc3nnc(C4CCOC4)s3)nc2cc1-c1cnn(CCCN2CCCC2)c1] | 1H-NMR (DMSO-d$_6$) δ:<br>12.13 (1H, s), 9.09 (1H, d, J = 2.3 Hz), 8.57 (1H, s), 8.33 (1H, d, J =<br>1.7 Hz), 8.26 (1H, d, J = 9.2 Hz), 8.23 (1H, s), 7.40 (1H, d, J = 8.9 Hz), 4.22 (2H, t, J = 6.9 Hz), 4.15-4.08 (1H, m), 4.02-3.82 (4H, m), 2.46-2.39 (6H, m), 2.35-2.19 (2H, m), 2.07-1.98 (2H, m), 1.74-1.66 (4H, m).<br>MS m/z (M + H): 477. |

Example 0239

0239-1

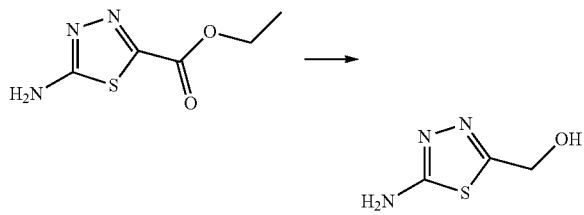

A solution of ethyl 5-amino-1,3,4-thiadiazole-2-carboxylate (340 mg) in tetrahydrofuran (10 mL) was cooled by ice, and lithium aluminum hydride (a 10% tetrahydrofuran solution, about 2.5 mol/L, 1 mL) was added dropwise thereto, followed by stirring at room temperature for 1 hour. After the reaction mixture was cooled by ice, ethyl acetate (2 mL) was added thereto, followed by stirring for 15 minutes under ice-cooling, and methanol (1 mL) was added thereto, followed by stirring for 5 minutes under ice-cooling. Anhydrous sodium sulfate aqueous solution (anhydrous sodium sulfate: 100 mg, water: 2 mL) was added to the reaction mixture, followed by neutralizing with 2 mol/L hydrochloric acid. The solid matter was separated by filtration, ethyl acetate was added thereto, and liquid-liquid separation was performed. The organic layer was collected by separation, and dried over anhydrous sodium sulfate, and the solvent was distilled off under reduced pressure. The obtained residue was purified by silica gel column chromatography (chloroform-methanol), thereby obtaining (5-amino-1,3,4-thiadiazol-2-yl)methanol (75 mg).

$^1$H-NMR(DMSO-d$_6$)δ:7.07(2H,s),5.74(1H,t,J=6.1 Hz), 4.55(2H,d,J=5.9 Hz).

0239-2

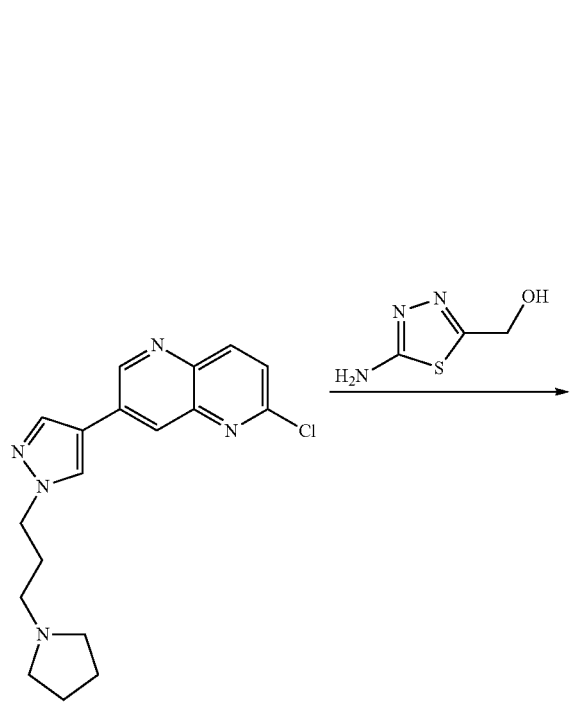

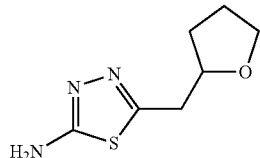

(5-((7-(1-(3-(Pyrrolidin-1-yl)propyl)-1H-pyrazol-4-yl)-1,5-naphthyridin-2-yl)amino)-1,3,4-thiadiazol-2-yl)methanol was obtained as a yellow solid in the same manner as in Example 0001-5.

1H-NMR(DMSO-$d_6$)δ:12.09(1H,s),9.09(1H,d,J=2.0 Hz),8.60(1H,s),8.32-8.25(2H,m),8.23(1H,s),7.41(1H,d,J=8.9 Hz),5.98(1H,t,J=5.8 Hz),4.82(2H,d,J=5.9 Hz),4.21(2H,t,J=6.9 Hz),2.47-2.40(6H,m),2.09-1.99(2H,m),1.70(4H,s).
MSm/z(M+H):437.

Examples 0240 and 0241

The following compounds were obtained in the same manner as in Examples 0198-1, 0001-4 and 0001-5.

| Example No. | | |
|---|---|---|
| 0240 | | |
| 0240-1 | 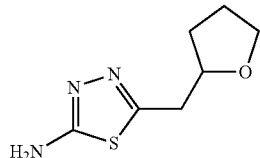 | 1H-NMR (DMSO-$d_6$) δ: 6.98 (2H, s), 4.06-3.97 (1H, m), 3.80-3.73 (1H, m), 3.67-3.60 (1H, m), 3.04-2.89 (2H, m), 2.01-1.89 (1H, m), 1.85-1.76 (2H, m), 1.55-1.43 (1H, m). |
| 0240-2 | 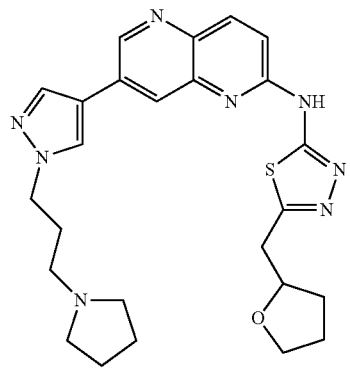 [SMILES: c1nc2ccc(Nc3nnc(CC4CCCO4)s3)nc2cc1-c1cnn(CCCN2CCCC2)c1] | 1H-NMR (DMSO-$d_6$) δ: 12.06 (1H, s), 9.01 (1H, s), 8.55 (1H, s), 8.19 (3H, t, J = 9.6 Hz), 7.33 (1H, d, J = 8.9 Hz), 4.23-4.15 (3H, m), 3.88-3.80 (1H, m), 3.71-3.63 (1H, m), 3.19-3.15 (2H, m), 2.45-2.37 (6H, m), 2.06-1.96 (2H, m), 1.88-1.80 (2H, m), 1.70-1.54 (6H, m). |

| Example No. | | |
|---|---|---|
| 0241 | | |
| 0241-1 | 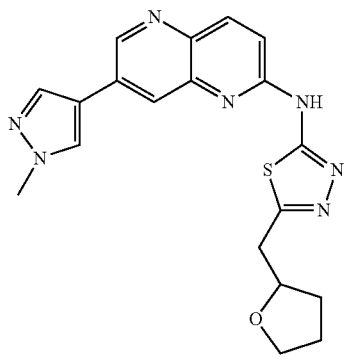 [SMILES: Cn1cc(-c2cnc3ccc(Nc4nnc(CC5CCCO5)s4)nc3c2)cn1] | 1H-NMR (DMSO-d$_6$) δ:<br>12.04 (1H, s), 9.07 (1H, d, J = 2.3 Hz), 8.52 (1H, s), 8.29-8.23 (2H, m), 820 (1H, s), 7.40 (1H, d, J = 9.2 Hz), 4.24-4.15 (1H, m), 3.93 (3H, s), 3.88-3.80 (1H, m), 3.72-3.65 (1H, m), 3.20 (2H, t, J = 5.8 Hz), 2.07-1.97 (1H, m), 1.90-1.80 (2H, m), 1.66-1.57 (1H, m). |

Example 0242

0242-1

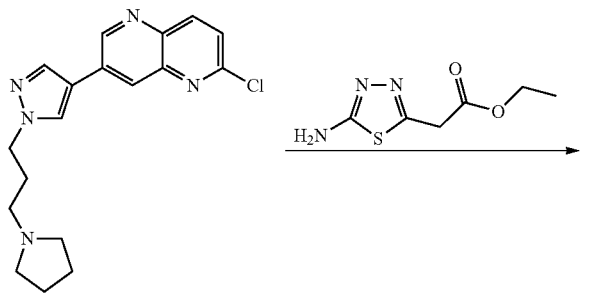

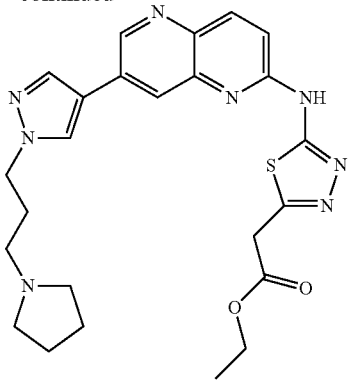

Ethyl (5-amino-1,3,4-thiadiazol-2-yl)acetate (15 mg), 2-dicyclohexylphosphino-2',4',6'-triisopropylbiphenyl (10 mg), cesium carbonate (90 mg), and tris(dibenzylideneacetone)dipalladium(0) (10 mg) were added to a solution of 2-chloro-7-(1-(3-(pyrrolidin-1-yl)propyl)-1H-pyrazol-4-yl)-1,5-naphthyridine (25 mg) in 1,4-dioxane (1 mL), followed by stirring at 150° C. for 1 hour using a microwave reaction apparatus. After the reaction mixture was cooled to room temperature, a mixed solvent of chloroform-methanol was added thereto, and the resultant product was purified by silica gel column chromatography (chloroform-methanol, NH silica), and purified by preparative thin layer silica gel chromatography (chloroform-methanol, NH silica), thereby obtaining ethyl (5-((7-(1-(3-(pyrrolidin-1-yl)propyl)-1H-pyrazol-4-yl)-1,5-naphthyridin-2-yl)amino)-1,3,4-thiadiazol-2-yl)acetate (17 mg) as a yellow solid.

$^1$H-NMR(DMSO-d$_6$)δ:12.17(1H,s),9.09(1H,d,J=2.3 Hz), 8.58(1H,s),8.32-8.26(2H,m),8.21(1H,s),7.42(1H,d,J=8.9 Hz),4.25-4.15(4H,m),3.71(3H,s),2.46-2.37(6H,m),2.06-1.96(2H,m),1.71-1.67(4H,m).

MSm/z(M+H):479.

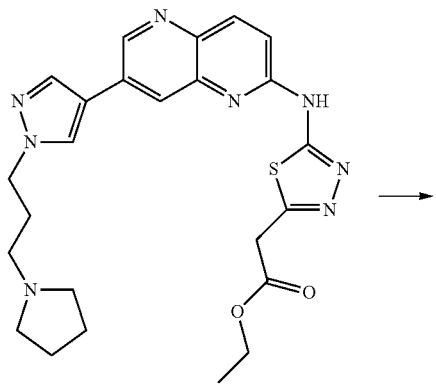

Example 0243

0243-1

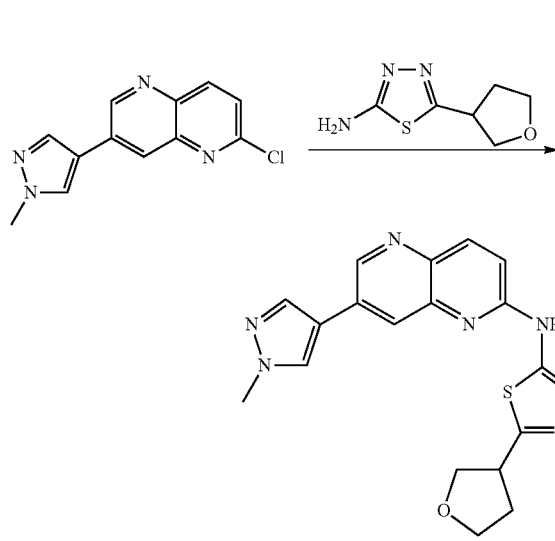

N-(7-(1-methyl-1H-pyrazol-4-yl)-1,5-naphthyridin-2-yl)-5-(tetrahydrofuran-3-yl)-1,3,4-thiadiazole-2-amine was obtained as a white solid in the same manner as in Example 0001-5.

$^1$H-NMR(DMSO-d$_6$)δ:12.12(1H,s),9.07(1H,d,J=2.0 Hz), 8.52(1H,s),8.32(1H,d,J=1.3 Hz),8.26(1H,d,J=8.9 Hz),8.21(1H,s),7.40(1H,d,J=8.9 Hz),4.15-4.08(1H,m),4.02-3.82(7H,m),2.48-2.39(1H,m),2.31-2.19(1H,m).
MSm/z(M+H):380.

Example 0244

0244-1

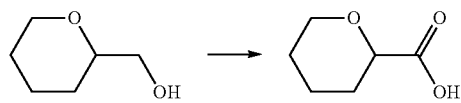

0.5 mol/L sodium hydroxide aqueous solution (20 mL) was added to tetrahydropyran-2-methanol (1.16 g), followed by stirring at room temperature for 5 minutes. Potassium permanganate (3.30 g) was added to the reaction mixture, followed by stirring at 90° C. for 1 hour. Potassium permanganate (1.58 g) was added thereto, followed by stirring at 90° C. for 30 minutes. After the reaction mixture was cooled to room temperature, the insolubles were filtered off using celite, and ethyl acetate was added thereto. After the aqueous layer was collected by separation, the aqueous layer was neutralized by the addition of hydrochloric acid under ice-cooling, and the water was distilled off under reduced pressure. The obtained residue was purified by silica gel column chromatography (chloroform-methanol), thereby obtaining tetrahydro-2H-pyran-2-carboxylic acid (150 mg) as colorless oily substance.

$^1$H-NMR(CDCl$_3$)δ:4.16-4.08(1H,m),4.02-3.94(1H,m), 3.60-3.42(2H,m),2.11-2.04(1H,m),1.97-1.90(1H,m),1.61-1.54(3H,m).

0244-2

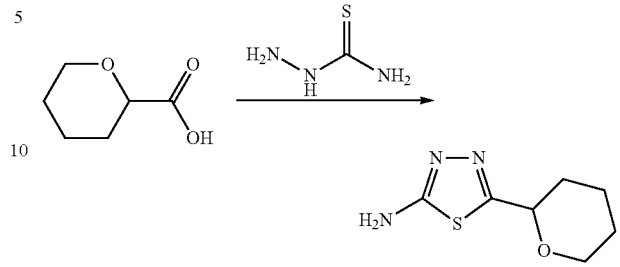

5-(Tetrahydro-2H-pyran-2-yl)-1,3,4-thiadiazole-2-amine was obtained as a white solid in the same manner as in Example 0198-1.
MSm/z(M+H):186.

0244-3

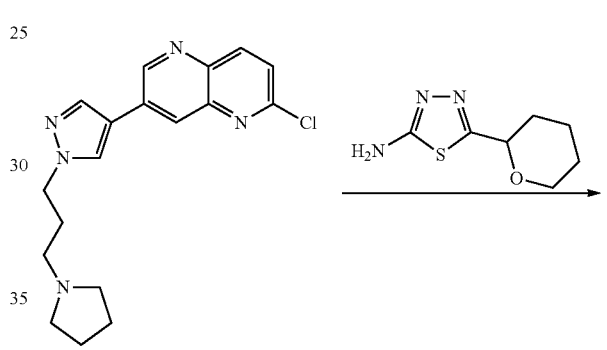

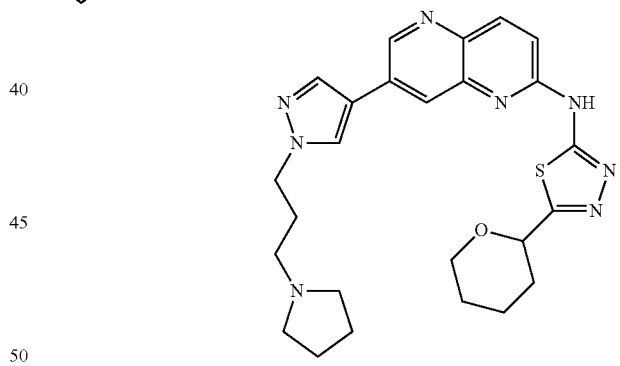

N-(7-(1-(3-(pyrrolidin-1-yl)propyl)-1H-pyrazol-4-yl)-1,5-naphthyridin-2-yl)-5-(tetrahydro-2H-pyran-2-yl)-1,3,4-thiadiazole-2-amine was obtained as a yellow solid in the same manner as in Example 0001-5.

$^1$H-NMR(DMSO-d$_6$)δ:12.09(1H,s),9.02(1H,s),8.58(1H,s),8.29-8.15(3H,m),7.34(1H,d,J=8.9 Hz),4.77(1H,t,J=5.0 Hz),4.21(2H,t,J=6.9 Hz),4.04(1H,d,J=11.6 Hz),3.64(1H,dd,J=14.4,10.4 Hz),2.40(6H,t,J=7.1 Hz),2.18-1.82(4H,m),1.81-1.55(8H,m).
MSm/z(M+H):491.

Example 0245

The following compounds were obtained in the same manner as in Examples 0198-1, 0001-4 and 0001-5.

| Example No. | | |
|---|---|---|
| 0245 | | |
| 0245-1 | 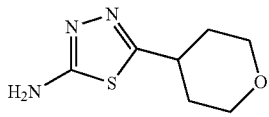 [SMILES: Nc1nnc(C2CCOCC2)s1] | MS m/z (M + H): 186. |
| 0245-2 | 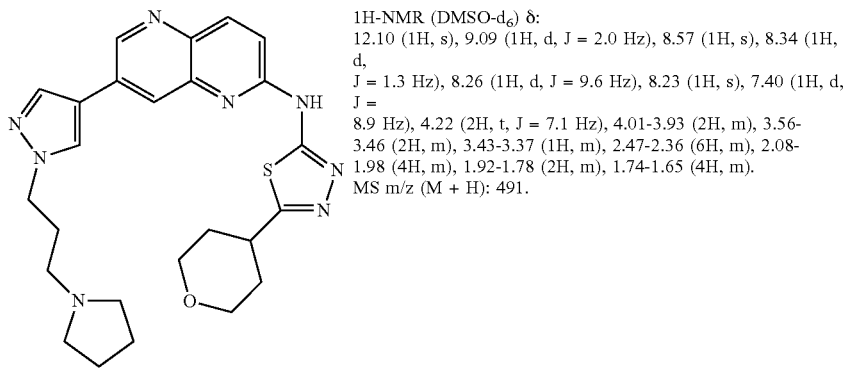 | 1H-NMR (DMSO-d$_6$) δ:<br>12.10 (1H, s), 9.09 (1H, d, J = 2.0 Hz), 8.57 (1H, s), 8.34 (1H, d,<br>J = 1.3 Hz), 8.26 (1H, d, J = 9.6 Hz), 8.23 (1H, s), 7.40 (1H, d,<br>J =<br>8.9 Hz), 4.22 (2H, t, J = 7.1 Hz), 4.01-3.93 (2H, m), 3.56-<br>3.46 (2H, m), 3.43-3.37 (1H, m), 2.47-2.36 (6H, m), 2.08-<br>1.98 (4H, m), 1.92-1.78 (2H, m), 1.74-1.65 (4H, m).<br>MS m/z (M + H): 491. |

Example 0246

0246-1

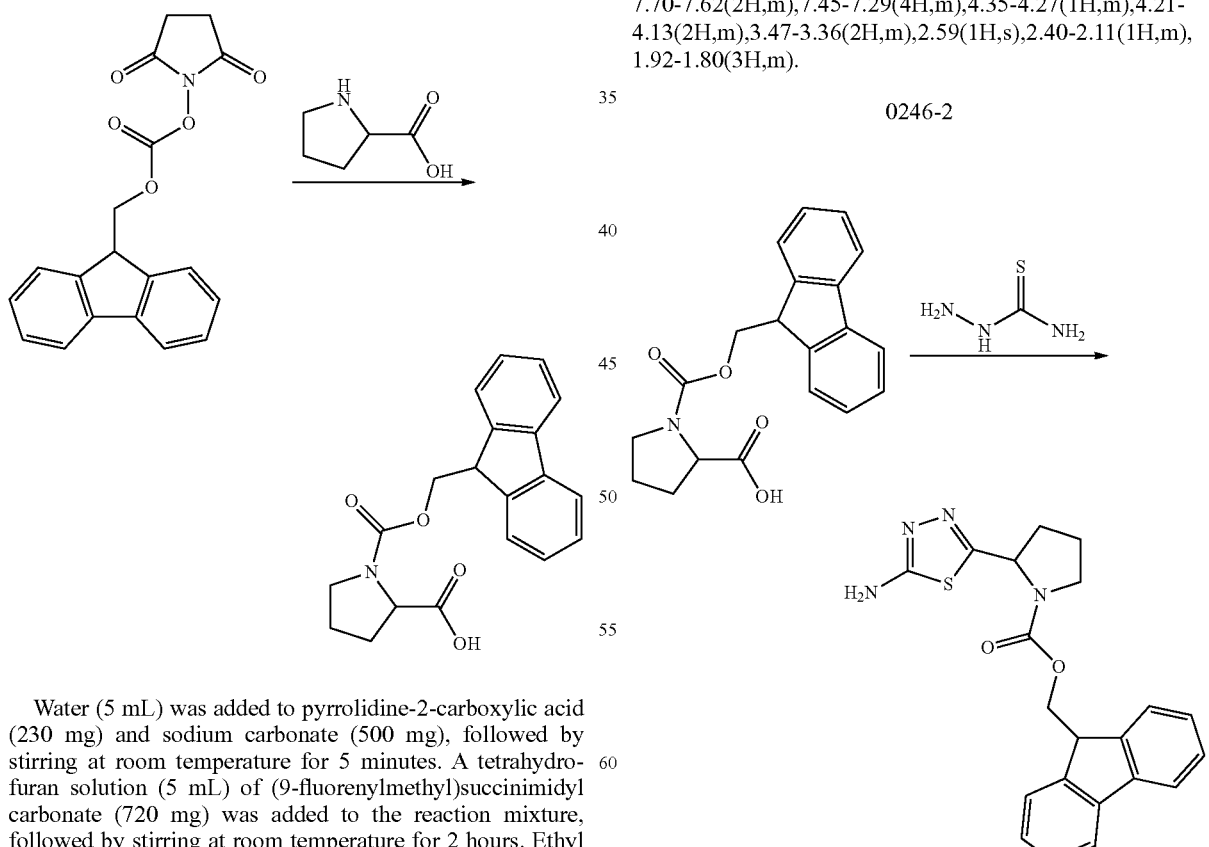

Water (5 mL) was added to pyrrolidine-2-carboxylic acid (230 mg) and sodium carbonate (500 mg), followed by stirring at room temperature for 5 minutes. A tetrahydrofuran solution (5 mL) of (9-fluorenylmethyl)succinimidyl carbonate (720 mg) was added to the reaction mixture, followed by stirring at room temperature for 2 hours. Ethyl acetate was added to the reaction mixture. The aqueous layer was neutralized by the addition of hydrochloric acid, extracted three times with ethyl acetate, and the organic layer was washed with a saturated sodium chloride aqueous solution. The organic layer was dried over anhydrous sodium sulfate, and the solvent was distilled off under reduced pressure, thereby obtaining 1-(((9H-fluoren-9-yl)methoxy)carbonyl)pyrrolidine-2-carboxylic acid (620 mg).

$^1$H-NMR(DMSO-d$_6$)δ:12.62(1H,s),7.93-7.87(2H,m), 7.70-7.62(2H,m),7.45-7.29(4H,m),4.35-4.27(1H,m),4.21-4.13(2H,m),3.47-3.36(2H,m),2.59(1H,s),2.40-2.11(1H,m), 1.92-1.80(3H,m).

0246-2

Phosphorus oxychloride (5 mL) was added to 1-(((9H-fluoren-9-yl)methoxy)carbonyl)pyrrolidine-2-carboxylic acid (505 mg) and thiosemicarbazide (175 mg), followed by stirring at 80° C. for 2 hours. The reaction mixture was cooled to room temperature, and added dropwise to water. The resultant product was neutralized by the addition of a sodium hydroxide aqueous solution under ice-cooling, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate, NH silica), thereby obtaining (9H-fluoren-9-yl)methyl 2-(5-amino-1,3,4-thiadiazol-2-yl)pyrrolidine-1-carboxylate (238 mg).

MSm/z(M+H):393.

0246-3

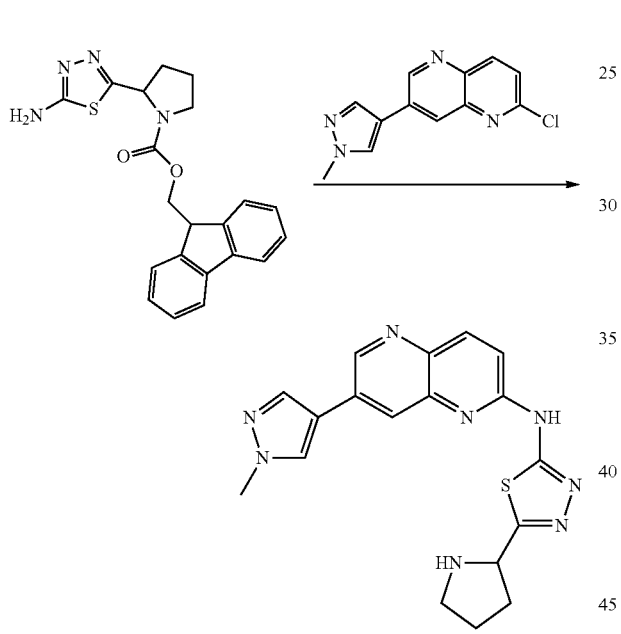

(9H-fluoren-9-yl)methyl 2-(5-amino-1,3,4-thiadiazol-2-yl)pyrrolidine-1-carboxylate (115 mg), 2-dicyclohexylphosphino-2',4',6'-triisopropylbiphenyl (20 mg), cesium carbonate (150 mg), and tris(dibenzylideneacetone)dipalladium(0) (20 mg) were added to a solution of 2-chloro-7-(1-methyl-1H-pyrazol-4-yl)-1,5-naphthyridine (75 mg) in 1,4-dioxane (1 mL), followed by stirring at 100° C. for 3 hours in a nitrogen atmosphere. The reaction mixture was cooled to room temperature, and chloroform and methanol were added thereto. The obtained solution was purified by silica gel column chromatography (chloroform-methanol, NH silica), thereby obtaining N-(7-(1-methyl-1H-pyrazol-4-yl)-1,5-naphthyridin-2-yl)-5-(pyrrolidin-2-yl)-1,3,4-thiadiazole-2-amine (64 mg) as a yellow solid.

$^1$H-NMR(DMSO-d$_6$)δ:11.93(1H,s),9.06(1H,d,J=2.0 Hz), 8.54(1H,s),8.23(3H,dd,J=8.3,5.9 Hz),7.40(1H,d,J=8.9 Hz), 4.54-4.47(1H,m),3.92(3H,s),3.02-2.90(2H,m),2.28-2.13 (1H,m),2.01-1.90(1H,m),1.86-1.72(2H,m).

MSm/z(M+H):379.

Example 0247

0247-1

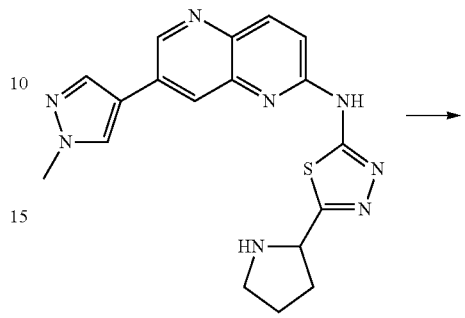

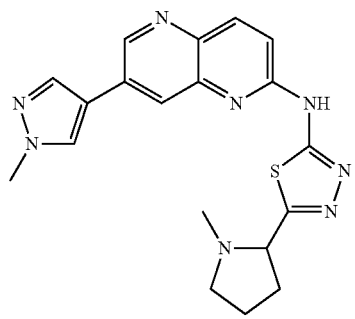

A 20% formaldehyde solution (10 μL) and sodium triacetoxyborohydride (10 mg) were added to a solution of N-(7-(1-methyl-1H-pyrazol-4-yl)-1,5-naphthyridin-2-yl)-5-(pyrrolidin-2-yl)-1,3,4-thiadiazole-2-amine (17 mg) in methanol (1 mL), followed by stirring at room temperature for 30 minutes. A 20% formaldehyde solution (10 μL) and sodium triacetoxyborohydride (5 mg) were added thereto, followed by stirring at room temperature for 30 minutes. The solvent was distilled off under reduced pressure, and water and ethyl acetate were added thereto. The organic layer was collected by separation, and dried over anhydrous sodium sulfate, and the solvent was distilled off under reduced pressure. The obtained residue was purified by silica gel column chromatography (chloroform-methanol, NH silica), thereby obtaining N-(7-(1-methyl-1H-pyrazol-4-yl)-1,5-naphthyridin-2-yl)-5-(1-methylpyrrolidin-2-yl)-1,3,4-thiadiazole-2-amine (5 mg) as a yellow solid.

$^1$H-NMR(DMSO-d$_6$)δ:12.06(1H,s),9.07(1H,d,J=2.0 Hz), 8.56(1H,s),8.25(3H,t,J=5.8 Hz),7.41(1H,d,J=8.9 Hz),3.93 (3H,s),3.67(1H,t,J=7.6 Hz),2.38-2.25(5H,m),1.99-1.81(4H, m).

MSm/z(M+H):393.

Example 0248

0248-1

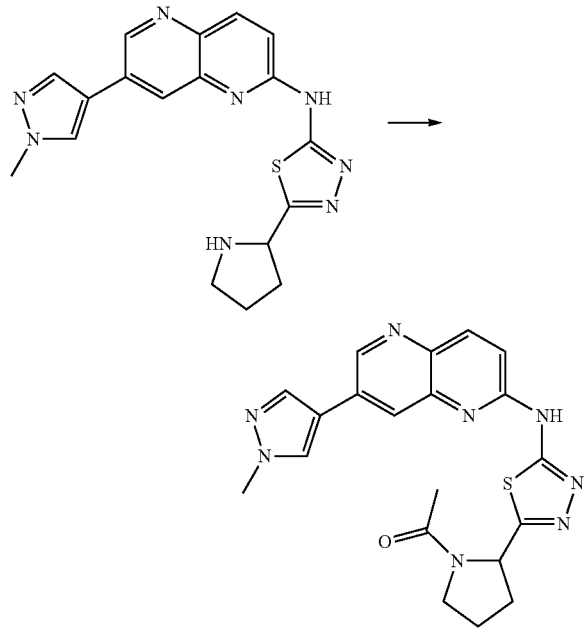

Pyridine (40 μL) and acetyl chloride (7 μL) were added to a solution of N-(7-(1-methyl-1H-pyrazol-4-yl)-1,5-naphthyridin-2-yl)-5-(pyrrolidin-2-yl)-1,3,4-thiadiazole-2-amine (15 mg) in dichloromethane (3 mL), followed by stirring at room temperature for 5 minutes. The reaction mixture was purified by silica gel column chromatography (chloroform-methanol, NH silica), thereby obtaining 1-(2-(5-((7-(1-methyl-1H-pyrazol-4-yl)-1,5-naphthyridin-2-yl)amino)-1,3,4-thiadiazol-2-yl)pyrrolidin-1-yl)ethanone (10 mg) as a yellow solid.

$^1$H-NMR(DMSO-d$_6$)δ:12.11(1H,s),9.06(1H,d,J=2.0 Hz), 8.50(1H,s),8.26-8.19(3H,m),7.40(1H,d,J=8.9 Hz),5.50-5.31 (1H,m),3.93(3H,s),3.78-3.46(2H,m),2.32-1.95(7H,m).

MSm/z(M+H):421.

Example 0249

0249-1

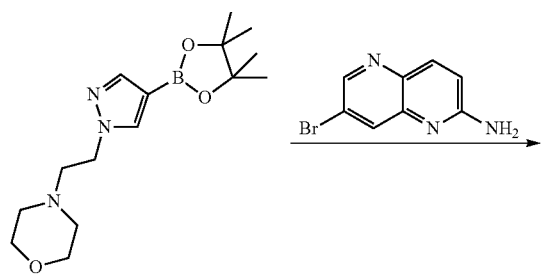 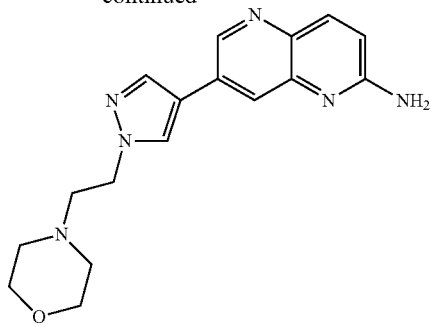

A mixture of 7-bromo-1,5-naphthyridine-2-amine (50 mg), sodium carbonate (47 mg), 1-(2-morpholinoethyl)-1H-pyrazole-4-boronic acid pinacol ester (137 mg), bis(tri-tert-butylphosphine)palladium(0) (11 mg), 1,4-dioxane (1 mL), and water (0.1 mL) was stirred at 140° C. for 1 hour using a microwave reaction apparatus. The reaction mixture was cooled to room temperature, and purified by silica gel column chromatography (chloroform-methanol, NH silica), thereby obtaining 7-(1-(2-morpholinoethyl)-1H-pyrazol-4-yl)-1,5-naphthyridine-2-amine (49 mg) as a white solid.

$^1$H-NMR(DMSO-d$_6$)δ:8.78(1H,d,J=2.0 Hz),8.41(1H,s), 8.08(1H,s),7.89(2H,dd,J=7.1,5.8 Hz),6.90(1H,d,J=8.9 Hz), 6.65(2H,s),4.27(2H,t,J=6.6 Hz),3.59-3.51(4H,m),2.75(2H,t, J=6.6 Hz),2.43(4H,t,J=4.5 Hz).

0249-2

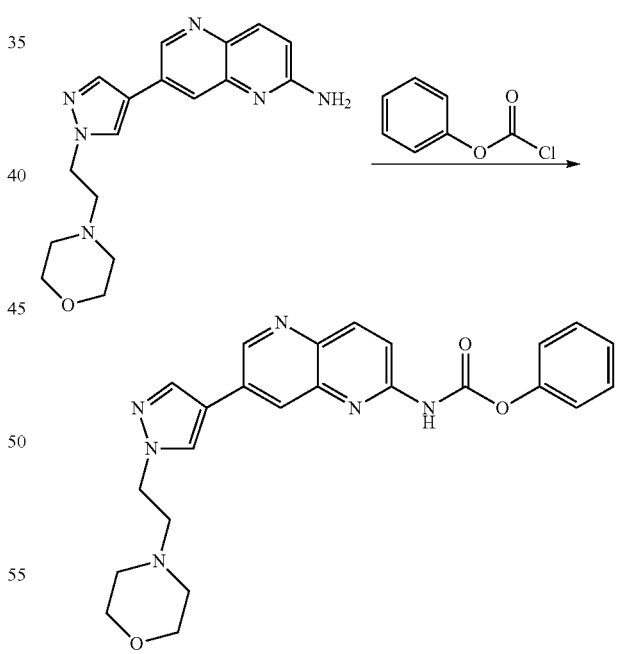

Phenyl chlorocarbonate (60 μL) was added to a solution of 7-(1-(2-morpholinoethyl)-1H-pyrazol-4-yl)-1,5-naphthyridine-2-amine (168 mg) in pyridine (10 mL), and candy-like lumps were dissolved using an ultrasonic cleaning machine. The reaction liquid was stirred at room temperature for 1 hour, and phenyl chlorocarbonate (20 μL) was added thereto, followed by stirring at room temperature for 1 hour. The solvent was distilled off under reduced pressure, and the obtained residue was purified by silica gel column chromatography (chloroform-methanol), thereby obtaining phenyl (7-(1-(2-morpholinoethyl)-1H-pyrazol-4-yl)-1,5-naphthyridin-2-yl)carbamate (84 mg).
$^1$H-NMR(DMSO-$d_6$)δ:11.21(1H,s),9.18(1H,d,J=2.0 Hz),8.57(1H,s),8.38(1H,d,J=9.2 Hz),8.27(1H,d,J=1.7 Hz),8.23-8.18(2H,m),7.49-7.42(2H,m),7.33-7.25(3H,m),4.30(2H,t,J=6.4 Hz),3.56(4H,t,J=4.6 Hz),2.78(2H,t,J=6.6 Hz),2.44(4H,t,J=4.5 Hz).
0249-3
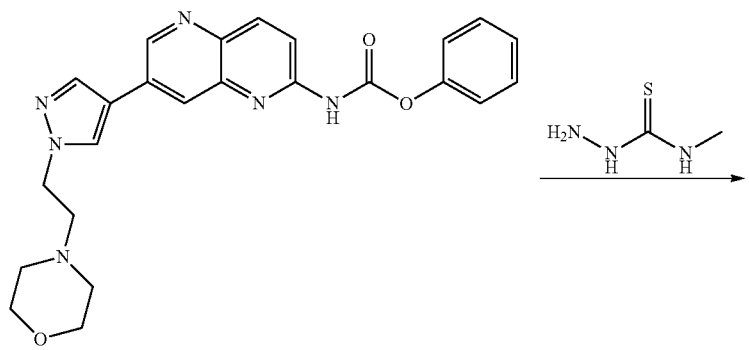
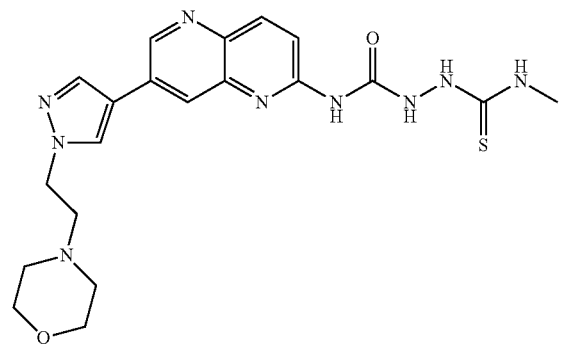

317

4-Methylthiosemicarbazide (7 mg) was added to a solution of phenyl (7-(1-(2-morpholinoethyl)-1H-pyrazol-4-yl)-1,5-naphthyridin-2-yl)carbamate (20 mg) in 1,4-dioxane (1.2 mL), followed by stirring at 70° C. for 1 hour. The reaction mixture was cooled to room temperature, and the solvent was distilled off under reduced pressure. The obtained residue was washed with ethyl acetate, thereby obtaining 2-(methylcarbamothioyl)-N-(7-(1-(2-morpholinoethyl)-1H-pyrazol-4-yl)-1,5-naphthyridin-2-yl)hydrazinecarboxamide (20 mg).

MSm/z(M+H):456.

0249-4

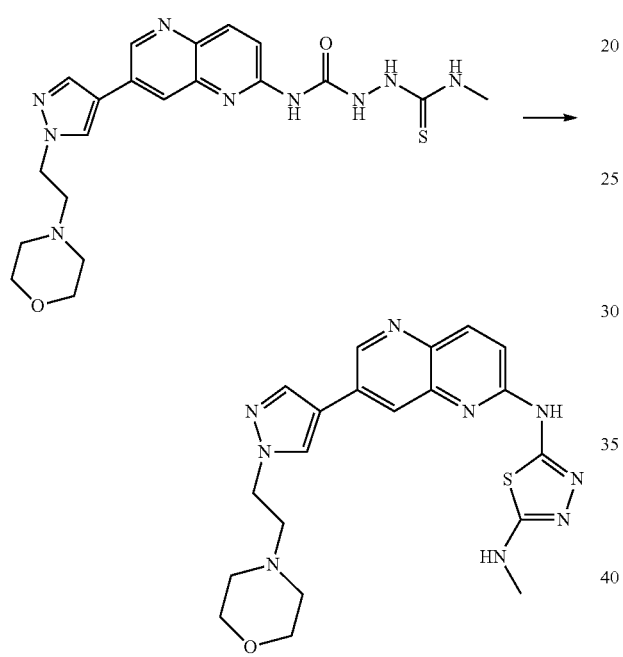

Phosphorus oxychloride (500 μL) was added to 2-(methylcarbamothioyl)-N-(7-(1-(2-morpholinoethyl)-1H-pyrazol-4-yl)-1,5-naphthyridin-2-yl)hydrazinecarboxamide (7 mg), followed by stirring at 80° C. for 1 hour. The reaction mixture was cooled to room temperature, and added dropwise to water. The resultant product was neutralized by the addition of a sodium hydroxide aqueous solution under ice-cooling, and chloroform was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (chloroform-methanol, NH silica), thereby obtaining $N^2$-methyl-$N^5$-(7-(1-(2-morpholinoethyl)-1H-pyrazol-4-yl)-1,5-naphthyridin-2-yl)-1,3,4-thiadiazole-2,5-diamine (1.4 mg) as a yellow solid.

$^1$H-NMR(DMSO-$d_6$)δ:11.52(1H,s),8.97(1H,s),8.51(1H,s),8.11(3H,t,J=7.3 Hz),7.26(1H,d,J=9.2 Hz),7.06(1H,s),4.29(2H,t,J=6.6 Hz),3.56(4H,t,J=4.6 Hz),2.87(3H,d,J=4.6 Hz),2.78(2H,t,J=6.6 Hz),2.44(4H,t,J=4.5 Hz).

MSm/z(M+H):438.

318

Example 0250

0250-1

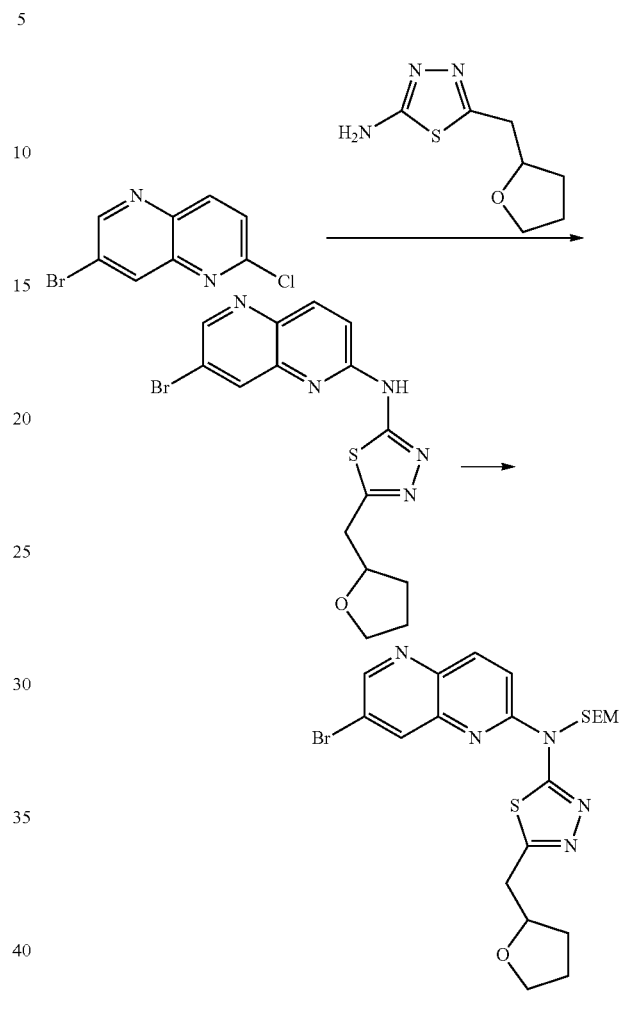

N-(7-bromo-1,5-naphthyridin-2-yl)-5-((tetrahydrofuran-2-yl)methyl)-N-((2-(trimethylsilyl)methoxy)methyl)-1,3,4-thiadiazole-2-amine was obtained as brown oily substance in the same manner as in Example 0175-2.

MSm/z(M+H):522,524.

0250-2

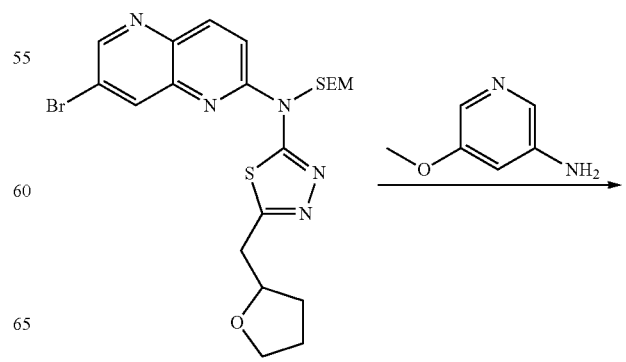

-continued

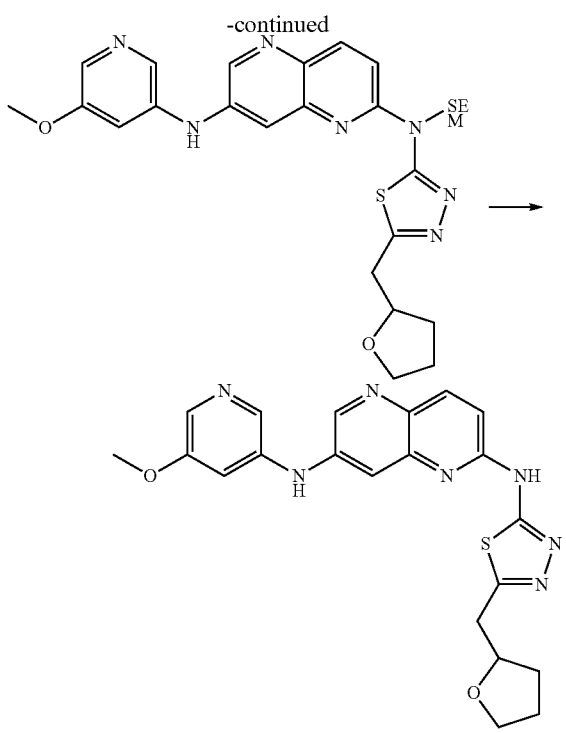

3-Amino-5-methoxypyridine (14 mg), 2-dicyclohexylphosphino-2',4',6'-triisopropylbiphenyl (5 mg), cesium carbonate (45 mg), and tris(dibenzylideneacetone)dipalladium (0) (5 mg) were added to a solution of N-(7-bromo-1,5-naphthyridin-2-yl)-5-((tetrahydrofuran-2-yl)methyl)-N-((2-(trimethylsilyl)methoxy)methyl)-1,3,4-thiadiazole-2-amine (58 mg) in 1,4-dioxane (2 mL), followed by stirring at 100° C. in a nitrogen atmosphere overnight. The reaction mixture was cooled to room temperature, and the solvent was distilled off under reduced pressure, thereby obtaining $N^7$-(5-methoxypyridin-3-yl)-$N^2$-(5-((tetrahydrofuran-2-yl)methyl)-1,3,4-thiadiazol-2-yl)-$N^2$-((2-(trimethylsilyl)ethoxy)methyl)-1,5-naphthyridine-2,7-diamine.

A 4 mol/L hydrogen chloride/1,4-dioxane solution (2 mL) was added to the obtained $N^7$-(5-methoxypyridin-3-yl)-$N^2$-(5-((tetrahydrofuran-2-yl)methyl)-1,3,4-thiadiazol-2-yl)-$N^2$-((2-(trimethylsilyl)ethoxy)methyl)-1,5-naphthyridine-2,7-diamine, followed by stirring at room temperature for 1 hour. The solvent was distilled off under reduced pressure, the resultant product was neutralized with a saturated sodium hydrogen carbonate aqueous solution, and a chloroform-methanol solution was added thereto. The organic layer was collected by separation, the solvent was distilled off under reduced pressure, and the obtained residue was purified by silica gel column chromatography (ethyl acetate-methanol), thereby obtaining $N^7$-(5-methoxypyridin-3-yl)-$N^2$-(5-((tetrahydrofuran-2-yl)methyl)-1,3,4-thiadiazol-2-yl)-1,5-naphthyridine-2,7-diamine (7 mg) as a yellow solid.

$^1$H-NMR(DMSO-$d_6$)δ:11.92(1H,s),11.92-1.49(1H,m),9.11(1H,s),8.59(1H,d,J=2.6 Hz),8.17-8.13(2H,m),7.98(1H,d,J=2.6 Hz),7.64(1H,d,J=2.3 Hz),7.27(1H,t,J=2.3 Hz),7.22(1H,d,J=8.9 Hz),4.18-4.10(1H,m),3.85(3H,s),3.84-3.78(1H,m),3.72-3.64(1H,m),3.22-3.13(1H,m),2.06-1.94(1H,m),1.90-1.78(2H,m),1.62-1.49(1H,m).
MSm/z(M+H):436.

Example 0251

The following compounds were obtained in the same manner as in Examples 0246-1 to 0246-3.

| Example No. | | |
|---|---|---|
| 0251 | | |
| 0251-1 | 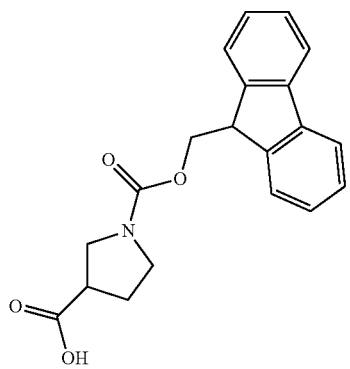 [SMILES: O=C(O)C1CCN(C(=O)OCC2c3ccccc3-c3ccccc32)C1] | 1H-NMR (DMSO-$d_6$) δ: 12.52 (1H, s), 7.96-7.87 (2H, m), 7.67-7.60 (2H, m), 7.47-7.27 (4H, m), 4.44-4.28 (3H, m), 3.51-3.43 (2H, m), 3.13-2.99 (1H, m), 2.59 (2H, s), 2.18-1.91 (2H, m). |
| 0251-2 | 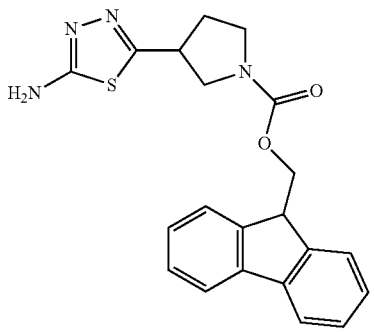 [SMILES: Nc1nnc(C2CCN(C(=O)OCC3c4ccccc4-c4ccccc43)C2)s1] | MS m/z (M + H): 393. |

| Example No. | | |
|---|---|---|
| 0251-3 | 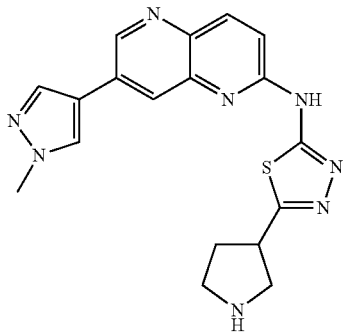 [SMILES: Cn1cc(-c2cnc3ccc(Nc4nnc(C5CCNC5)s4)nc3c2)cn1] | 1H-NMR (DMSO-d$_6$) δ:<br>9.08 (1H, d, J = 2.0 Hz), 8.52 (1H, s), 8.33 (1H, d, J = 1.7 Hz), 8.26 (2H, d, J = 7.9 Hz), 8.17 (1H, t, J = 12.4 Hz), 7.40 (1H, d, J = 8.9 Hz),<br>3.93 (3H, s), 3.84-3.75 (1H, m), 3.51-3.42 (1H, m), 3.27-3.08 (3H, m), 2.36 (1H, td, J = 13.3, 7.6 Hz), 2.12 (1H, m).<br>MS m/z (M + H): 379. |

Example 0252

0252-1

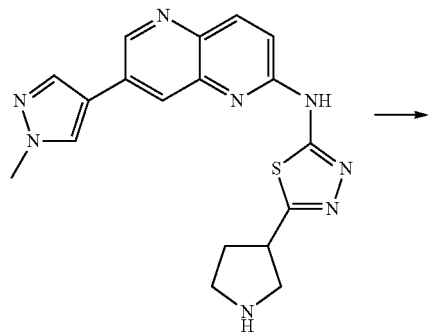 →

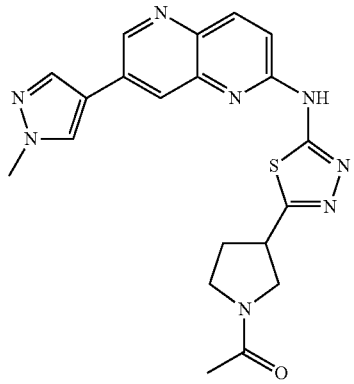

N-(7-(1-methyl-1H-pyrazol-4-yl)-1,5-naphthyridin-2-yl)-5-(1-methylpyrrolidin-3-yl)-1,3,4-thiadiazole-2-amine was obtained as a yellow solid in the same manner as in Example 0247-1.

$^1$H-NMR(DMSO-d$_6$)δ:12.01(1H,s),9.07(1H,d,J=2.0 Hz), 8.52(1H,s),8.29-8.21(3H,m),7.40(1H,d,J=9.2 Hz),3.93(3H, s),3.86-3.76(2H,m),3.01-2.93(1H,m),2.81-2.58(2H,m), 2.43-2.24(4H,m),2.23-2.09(1H,m).

MS m/z(M+H):393.

Example 0253

0253-1

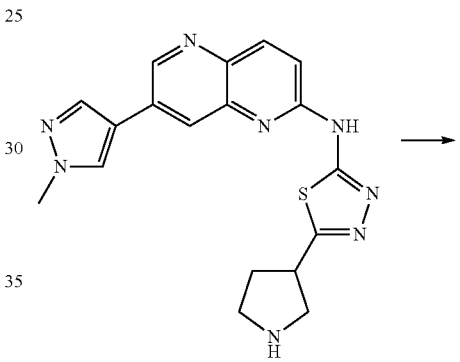 →

1-(3-(5-((7-(1-Methyl-1H-pyrazol-4-yl)-1,5-naphthyridin-2-yl)amino)-1,3,4-thiadiazol-2-yl)pyrrolidin-1-yl)ethanone was obtained as a yellow solid in the same manner as in Example 0247-1.

$^1$H-NMR(DMSO-d$_6$)δ:9.09-9.06(1H,m),8.52(1H,s),8.33-8.31(1H,m),8.26(1H,d,J=9.2 Hz),8.21(1H,s),7.40(1H, J=8.9 Hz),4.01-3.95(1H,m),3.93(3H,s),3.89-3.75(2H,m), 3.73-3.50(2H,m),3.06-2.92(1H,m),2.47-2.09(2H,m),2.01 (2H,d,J=5.0 Hz).

MS m/z(M+H):421.

Example 0254

0254-1

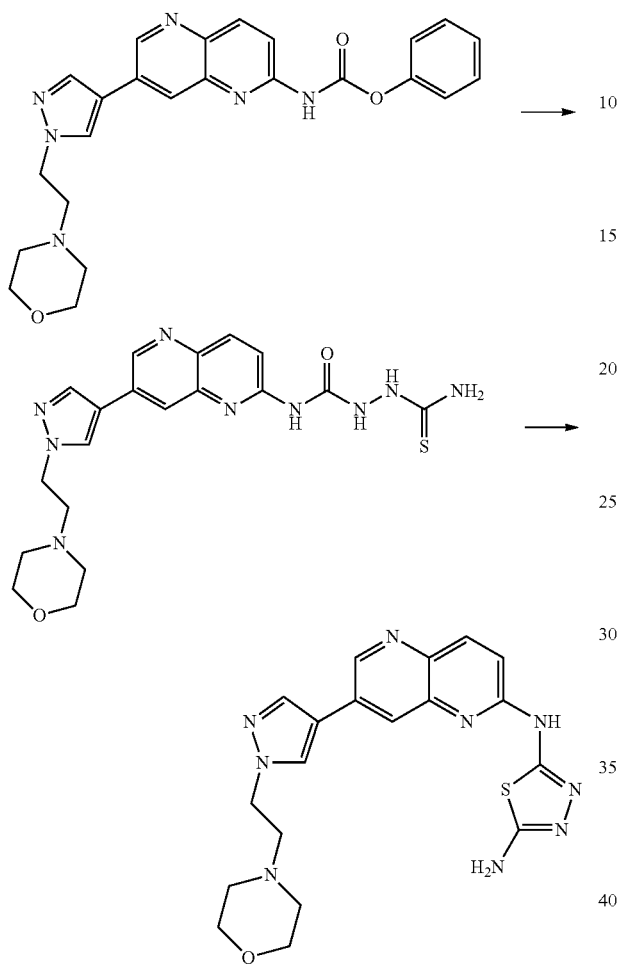

Thiosemicarbazide (7 mg) was added to a solution of phenyl ((7-(1-(2-morpholinoethyl)-1H-pyrazol-4-yl)-1,5-naphthyridin-2-yl)carbamate (43 mg) in 1,4-dioxane (1 mL), followed by stirring at 90° C. for 3 hours. The reaction mixture was cooled to room temperature, and the solvent was distilled off under reduced pressure. The obtained residue was washed with ethyl acetate, thereby obtaining 2-carbamothioyl-N-(7-(1-(2-morpholinoethyl)-1H-pyrazol-4-yl)-1,5-naphthyridin-2-yl)hydrazinecarboxamide. Phosphorus oxychloride (1 mL) was added to the obtained 2-carbamothioyl-N-(7-(1-(2-morpholinoethyl)-1H-pyrazol-4-yl)-1,5-naphthyridin-2-yl)hydrazinecarboxamide, followed by stirring at 80° C. for 1 hour. The reaction mixture was cooled to room temperature, and added dropwise to water. The resultant product was neutralized by the addition of a sodium hydroxide aqueous solution under ice-cooling, and chloroform was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (chloroform-methanol, NH silica), thereby obtaining N²-(7-(1-(2-morpholinoethyl)-1H-pyrazol-4-yl)-1,5-naphthyridin-2-yl)-1,3,4-thiadiazole-2,5-diamine (2 mg) as a yellow solid.

$^1$H-NMR(DMSO-$d_6$)δ:11.42(1H,s),9.00(1H,d,J=1.7 Hz), 8.51(1H,s),8.18-8.09(3H,m),7.31(1H,d,J=9.2 Hz),6.61(2H, s),4.33-4.26(2H,m),3.59-3.53(4H,m),2.82-2.75(2H,m), 2.47-2.41(4H,m).
MS m/z(M+H):424.

Example 0255

0255-1

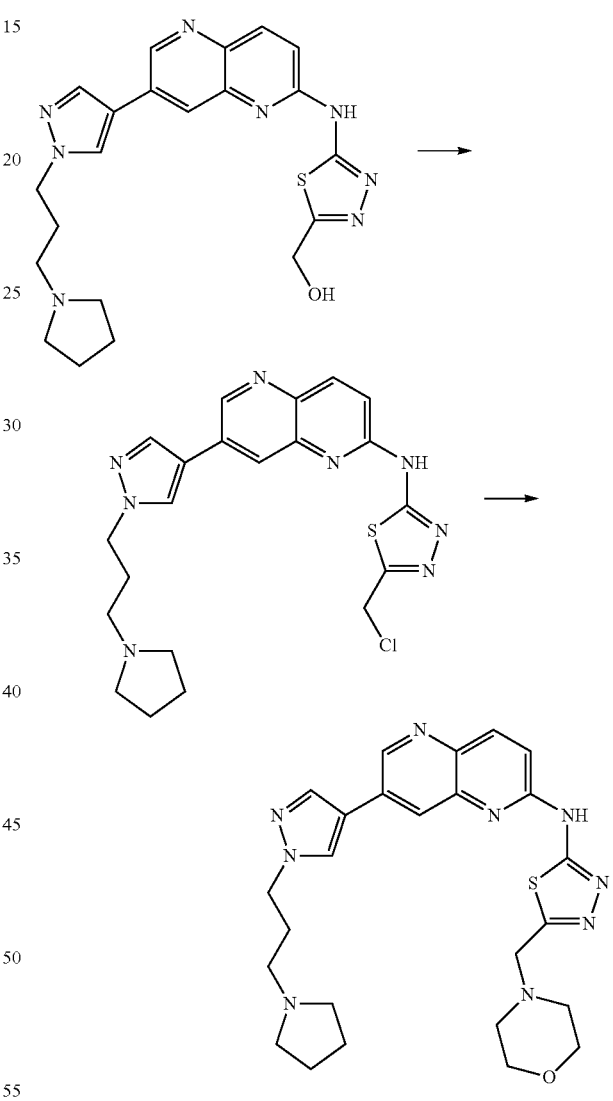

Methanesulfonyl chloride (20 μL) was added to a solution of (5-((7-(1-(3-(pyrrolidin-1-yl)propyl)-1H-pyrazol-4-yl)-1,5-naphthyridin-2-yl)amino)-1,3,4-thiadiazol-2-yl)methanol and pyridine (200 μL) in N,N-dimethylformamide (500 μL) under ice-cooling, followed by stirring at 0° C. for 30 minutes. Morpholine (50 μL) was added to the reaction mixture, followed by stirring at 0° C. for 1 hour. Morpholine (50 μL) was added thereto, followed by stirring at room temperature for 30 minutes. Ethyl acetate and water were added to the reaction mixture, and the solvent was distilled off under reduced pressure. The obtained residue was purified by silica gel column chromatography (chloroform-methanol, NH silica), thereby obtaining 5-(morpholinomethyl)-N-(7-(1-(3-(pyrrolidin-1-yl)propyl)-1H-pyrazol-4-yl)-1,5-naphthyridin-2-yl)-1,3,4-thiadiazole-2-amine (4.5 mg) as a yellow solid.

$^1$H-NMR(DMSO-d$_6$)δ:12.12(1H,s),9.09(1H,d,J=2.0 Hz), 8.59(1H,s),8.31(1H,d,J=2.0 Hz),8.27(1H,d,J=9.2 Hz),8.23 (1H,s),7.41(1H,d,J=8.9 Hz),4.22(2H,t,J=6.9 Hz),3.89(2H,s), 3.66-3.58(4H,m),3.44-3.38(2H,m),2.46-2.39(8H,m),2.07-1.98(2H,m),1.70(4H,s).

MSm/z(M+H):506.

Example 0256

0256-1

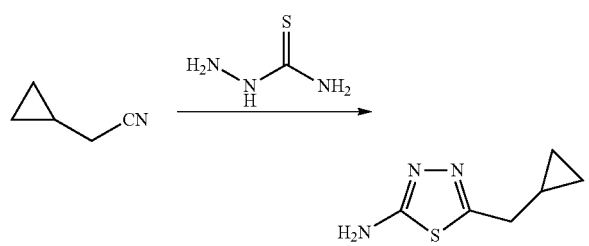

A solution of cyclopropylacetonitrile (486 mg) and thiosemicarbazide (455 mg) in trifluoroacetic acid (5 mL) was stirred at 65° C. for 2 hours. The reaction mixture was cooled to room temperature, neutralized by the addition of a sodium hydroxide aqueous solution, and ethyl acetate was added thereto. The organic layer was collected by separation, washed with a saturated sodium chloride aqueous solution, and dried over anhydrous sodium sulfate, and the solvent was distilled off under reduced pressure. The obtained residue was washed with a hexane-ethyl acetate solution, thereby obtaining 5-(cyclopropylmethyl)-1,3,4-thiadiazole-2-amine (536 mg).

MSm/z(M+H):156.

0256-2

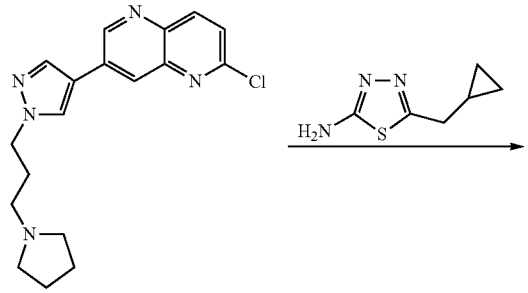

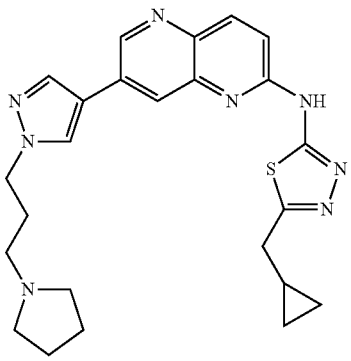

5-(Cyclopropylmethyl)-N-(7-(1-(3-(pyrrolidin-1-yl)propyl)-1H-pyrazol-4-yl)-1,5-naphthyridin-2-yl)-1,3,4-thiadiazole-2-amine was obtained as a yellow solid in the same manner as in Example 0001-5.

$^1$H-NMR(DMSO-d$_6$)δ:12.07(1H,s),9.08(1H,d,J=2.0 Hz), 8.56(1H,s),8.30(1H,d,J=1.7 Hz),8.26(1H,d,J=9.2 Hz),8.22 (1H,s),7.40(1H,d,J=8.9 Hz),4.22(2H,t,J=6.9 Hz),2.93(2H,d, J=6.9 Hz),2.48-2.40(5H,m),2.09-1.97(2H,m),1.75-1.66(4H, m),1.25-1.12(1H,m),1.24-1.12(1H,m),0.64-0.59(2H,m), 0.40-0.33(2H,m).

MSm/z(M+H):461.

Example 0257

0257-1

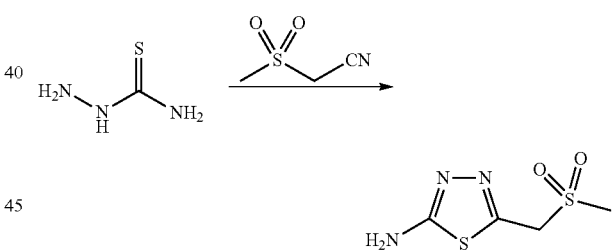

5-((Methylsulfonyl)methyl)-1,3,4-thiadiazole-2-amine was obtained in the same manner as in Example 0256-1.

MSm/z(M+H):194.

0257-2

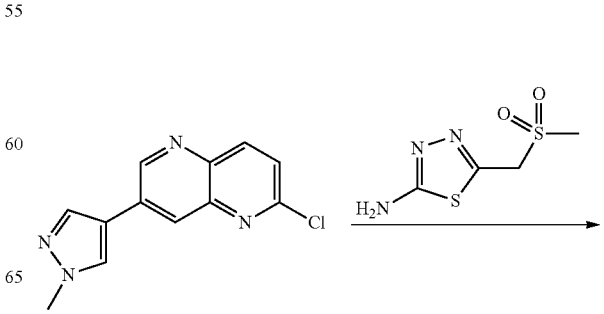

-continued

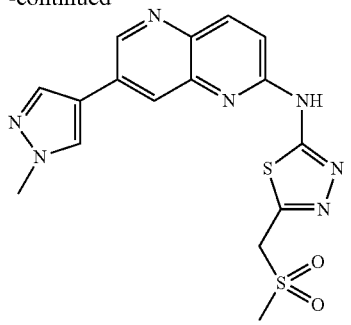

N-(7-(1-methyl-1H-pyrazol-4-yl)-1,5-naphthyridin-2-yl)-5-((methylsulfonyl)methyl)-1,3,4-thiadiazole-2-amine was obtained as a yellow solid in the same manner as in Example 0246-3.

$^{1}$H-NMR(DMSO-d$_{6}$)δ:9.09(1H,d,J=2.0 Hz),8.51(1H,s), 8.37(1H,s),8.30(1H,d,J=8.9 Hz),8.25(1H,d,J=1.7 Hz),8.18 (1H,s),7.45(1H,d,J=8.9 Hz),5.08(2H,s),3.93(3H,s),3.13(3H, s).

MS m/z(M+H):402.

Examples 0258 to 0263

The following compounds were obtained in the same manner as in Examples 0256-1 and 0001-5.

| Example No. | | |
|---|---|---|
| 0258 | | |
| 0258-1 | 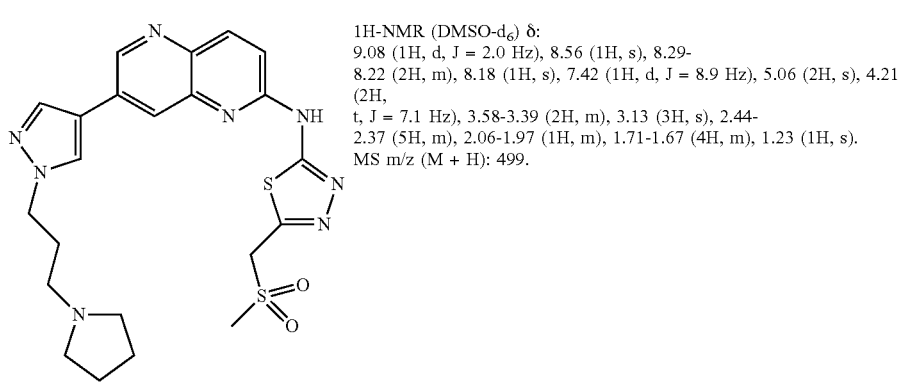 | 1H-NMR (DMSO-d$_{6}$) δ:<br>9.08 (1H, d, J = 2.0 Hz), 8.56 (1H, s), 8.29-<br>8.22 (2H, m), 8.18 (1H, s), 7.42 (1H, d, J = 8.9 Hz), 5.06 (2H, s), 4.21 (2H,<br>t, J = 7.1 Hz), 3.58-3.39 (2H, m), 3.13 (3H, s), 2.44-<br>2.37 (5H, m), 2.06-1.97 (1H, m), 1.71-1.67 (4H, m), 1.23 (1H, s).<br>MS m/z (M + H): 499. |
| 0259 | | |
| 0259-1 | 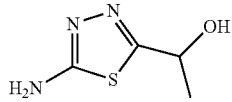 | MS m/z (M + H): 146. |
| 0259-2 | 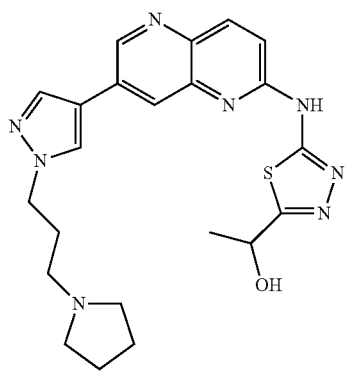 [SMILES: CC(O)c1nnc(Nc2ccc3ncc(-c4cnn(CCCN5CCCC5)c4)cc3n2)s1] | 1H-NMR (DMSO-d$_{6}$) δ:<br>12.04 (1H, s), 9.09 (1H, d, J = 2.0 Hz), 8.60 (1H, s), 8.25 (3H, dd, J = 12.2,<br>3.3 Hz), 7.41 (1H, d, J = 8.9 Hz), 6.14 (1H, d, J = 5.0 Hz), 5.12-<br>5.04 (1H, m), 425-4.16 (2H, m), 2.46-2.37 (6H, m), 2.06-<br>1.96 (2H, m), 1.71-1.67 (4H, m), 1.55 (3H, d, J = 6.6 Hz).<br>MS m/z (M + H): 451. |
| 0260 | | |
| 0260-1 | 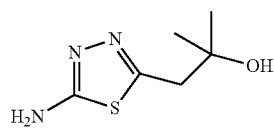 | MS m/z (M + H): 174. |

| Example No. | | |
|---|---|---|
| 0260-2 | 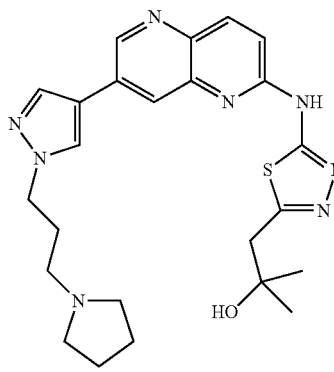 | 1H-NMR (DMSO-d$_6$) δ:<br>11.98 (1H, s), 9.07 (1H, d, J = 2.3 Hz), 8.55 (1H, s), 8.25 (1H, d, J = 9.2 Hz),<br>8.19 (1H, d, J = 1.7 Hz), 8.17 (1H, s), 7.41 (1H, d, J = 8.9 Hz), 4.91 (1H, s),<br>4.21 (2H, t, J = 6.9 Hz), 3.08 (2H, s), 2.45-2.37 (6H, m), 2.06-1.96 (2H, m), 1.71-1.67 (4H, m), 1.20 (6H, s).<br>MS m/z (M + H): 479. |
| 0261 | | |
| 0261-1 | 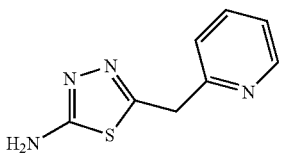 [SMILES: Nc1nnc(Cc2ccccn2)s1] | MS m/z (M + H): 193. |
| 0261-2 | 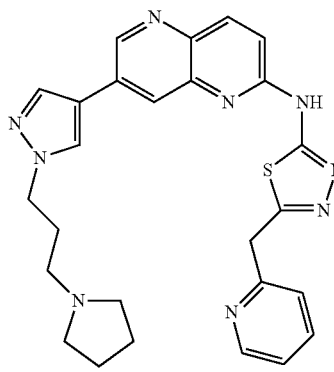 | 1H-NMR (DMSO-d$_6$) δ:<br>12.09 (1H, s), 9.08 (1H, d, J = 2.0 Hz), 8.57 (2H, s), 8.27 (1H, s), 8.25 (1H,<br>d, J = 6.9 Hz), 8.21 (1H, s), 7.80 (1H, td, J = 7.7, 1.9 Hz), 7.44 (1H, d, J =<br>7.6 Hz), 7.40 (1H, d, J = 8.9 Hz), 7.34-7.27 (1H, m), 4.54 (2H, s), 4.21 (2H, t, J = 6.9 Hz), 2.45-2.37 (6H, m), 2.05-1.96 (2H, m), 1.73-1.64 (4H, m).<br>MS m/z (M + H): 498. |
| 0262 | | |
| 0262-1 | 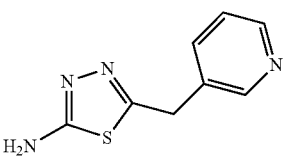 [SMILES: Nc1nnc(Cc2cccnc2)s1] | MS m/z (M + H): 193. |
| 0262-2 | 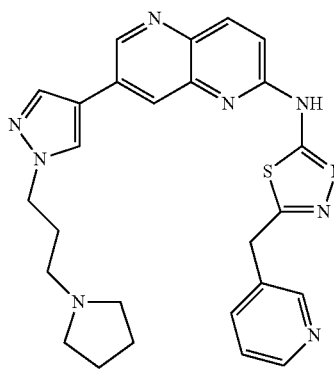 | 1H-NMR (DMSO-d$_6$) δ:<br>12.14 (1H, s), 9.08 (1H, d, J = 2.0 Hz), 8.62 (1H, d, J = 1.7 Hz), 8.55 (1H, s),<br>8.50 (1H, dd, J = 5.0, 1.7 Hz), 8.26 (2H, t, J = 5.3 Hz), 8.19 (1H, s), 7.77 (1H, dt, J = 7.9, 2.0 Hz), 7.41-7.38 (2H, m), 4.45 (2H, s), 4.21 (2H, t, J = 7.1 Hz), 2.46-2.37 (6H, m), 2.05-1.96 (2H, m), 1.74-1.64 (4H, m).<br>MS m/z (M + H): 498. |

| Example No. |
|---|

0263

0263-1

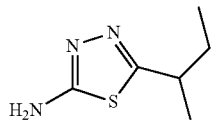

0263-2

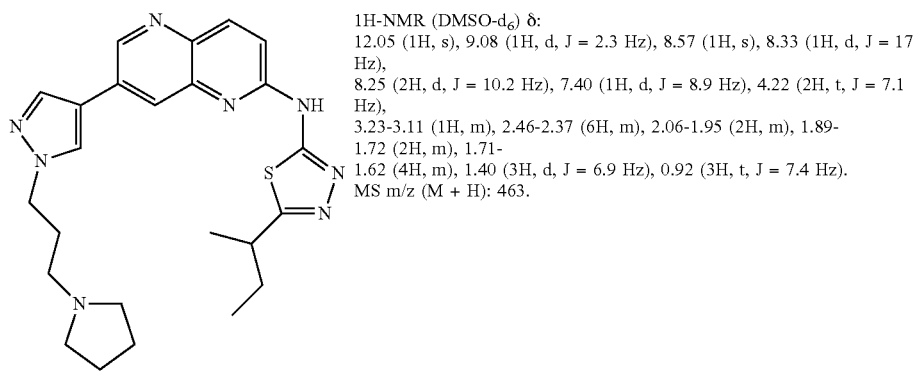

1H-NMR (DMSO-d$_6$) δ:
12.05 (1H, s), 9.08 (1H, d, J = 2.3 Hz), 8.57 (1H, s), 8.33 (1H, d, J = 17 Hz),
8.25 (2H, d, J = 10.2 Hz), 7.40 (1H, d, J = 8.9 Hz), 4.22 (2H, t, J = 7.1 Hz),
3.23-3.11 (1H, m), 2.46-2.37 (6H, m), 2.06-1.95 (2H, m), 1.89-1.72 (2H, m), 1.71-1.62 (4H, m), 1.40 (3H, d, J = 6.9 Hz), 0.92 (3H, t, J = 7.4 Hz).
MS m/z (M + H): 463.

Example 0264

0264-1

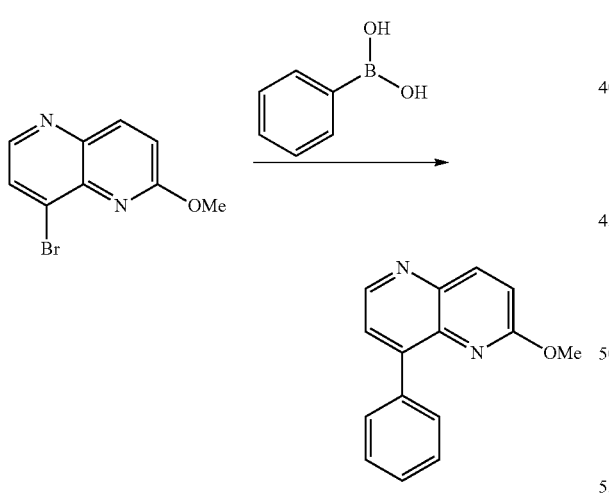

Phenylboronic acid (40 mg), bis(di-tert-butyl(4-dimethylaminophenyl)phosphine)dichloropalladium(II) (10 mg), sodium carbonate (45 mg), and water (200 μL) were added to a solution of 8-bromo-2-methoxy-1,5-naphthyridine (60 mg) in 1,4-dioxane (1 mL), followed by stirring at 120° C. for 1 hour using a microwave reaction apparatus. The reaction mixture was cooled to room temperature, and ethyl acetate and a saturated sodium chloride aqueous solution were added thereto. The organic layer was collected by separation, and dried over anhydrous sodium sulfate, and the solvent was distilled off under reduced pressure. The obtained residue was purified by silica gel column chromatography (hexane-ethyl acetate), thereby obtaining 2-methoxy-8-phenyl-1,5-naphthyridine (50 mg).

$^1$H-NMR(DMSO-d$_6$)δ:8.85(1H,d,J=4.3 Hz),8.33(1H,d,J=9.2 Hz),7.94-7.91(2H,m),7.75(1H,d,J=4.6 Hz),7.57-7.48 (3H,m),7.30(1H,d,J=9.2 Hz),3.91(3H,s).

0264-2

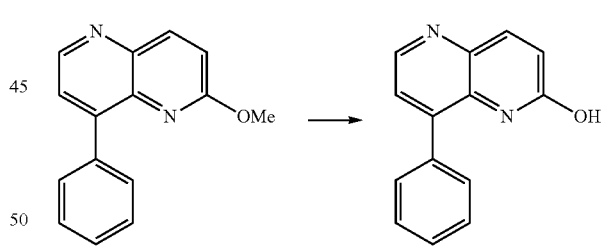

Hydrochloric acid (2 mL) was added to 2-methoxy-8-phenyl-1,5-naphthyridine (49 mg), followed by stirring at 80° C. for 1 hour. The reaction mixture was cooled to room temperature, neutralized with a sodium hydroxide aqueous solution, and ethyl acetate was added thereto. The organic layer was collected by separation, and dried over anhydrous sodium sulfate, and the solvent was distilled off under reduced pressure, thereby obtaining 8-phenyl-1,5-naphthyridin-2-ol (45 mg).

$^1$H-NMR(DMSO-d$_6$)δ:10.40(1H,s),8.54(1H,d,J=4.6 Hz), 8.02(1H,d,J=9.9 Hz),7.57-7.51(5H,m),7.43(1H,d,J=5.0 Hz), 6.81(1H,d,J=9.6 Hz).

0264-3

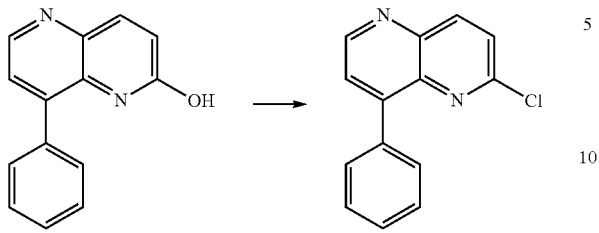

Phosphorus oxychloride (500 μL) and N,N-dimethylformamide (2 mL) were added to 8-phenyl-1,5-naphthyridin-2-ol (39 mg), followed by stirring at 80° C. for 30 minutes. Phosphorus oxychloride (400 μL) was added thereto, followed by stirring at 80° C. for 3 hours. The reaction mixture was cooled to room temperature, and added dropwise to water. The resultant product was neutralized by the addition of a sodium hydroxide aqueous solution, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate), thereby obtaining 2-chloro-8-phenyl-1,5-naphthyridine (25 mg).

$^1$H-NMR(DMSO-$d_6$)δ:9.08(1H,d,J=4.6 Hz),8.55(1H,d,J=8.9 Hz),7.92-7.86(2H,m),7.80-7.75(2H,m),7.60-7.52(3H,m).

0264-4

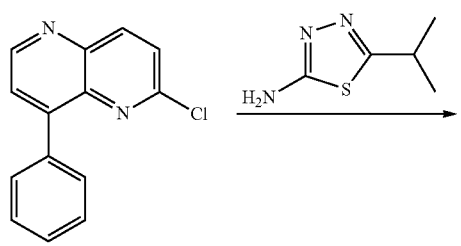

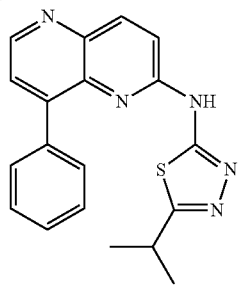

2-Amino-5-isopropyl-1,3,4-thiadiazole (8 mg), 2-dicyclohexylphosphino-2',4',6'-triisopropylbiphenyl (5 mg), cesium carbonate (15 mg), and tris(dibenzylideneacetone)dipalladium(0) (5 mg) were added to a solution of 2-chloro-8-phenyl-1,5-naphthyridine (10 mg) in 1,4-dioxane (1 mL), followed by stirring at 150° C. for 45 minutes using a microwave reaction apparatus. After the reaction mixture was cooled to room temperature, a mixed solvent of chloroform-methanol was added thereto, and the obtained solution was purified by silica gel column chromatography (chloroform-methanol, NH silica), thereby obtaining 5-isopropyl-N-(8-phenyl-1,5-naphthyridin-2-yl)-1,3,4-thiadiazole-2-amine (3 mg) as a pale yellow solid.

$^1$H-NMR(DMSO-$d_6$)δ:11.99(1H,s),8.80(1H,d,J=4.6 Hz),8.35(1H,d,J=8.9 Hz),7.66-7.48(7H,m),3.21-3.10(1H,m),1.21(6H,d,J=7.2 Hz).

MSm/z(M+H):348.

Examples 0265 and 0266

The following compounds were obtained in the same manner as in Examples 0256-1 and 0001-5.

| Example No. |
| --- |

| 0265 | | |
| --- | --- | --- |
| 0265-1 | 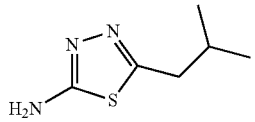 | MS m/z (M + H): 158. |

-continued

| Example No. | | |
|---|---|---|
| 0265-2 | 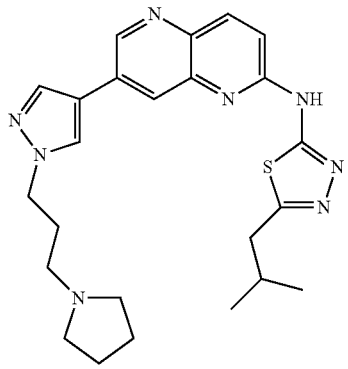 [SMILES: CC(C)Cc1nnc(Nc2ccc3ncc(-c4cnn(CCCN5CCCC5)c4)cc3n2)s1] | 1H-NMR (DMSO-d$_6$) δ:<br>12.06 (1H, s), 9.08 (1H, d, J = 2.0 Hz), 8.58 (1H, s), 8.32 (1H, d, J = 1.7 Hz),<br>8.25 (1H, d, J = 8.9 Hz), 8.23 (1H, s), 7.40 (1H, d, J = 8.9 Hz), 4.22 (2H, t,<br>J = 6.9 Hz), 2.89 (2H, d, J = 7.3 Hz), 2.20-1.97 (9H, m), 1.77-<br>1.66 (4H, m), 0.99 (6H, d, J = 7.2 Hz).<br>MS m/z (M + H): 463. |
| 0266 | | |
| 0266-1 | 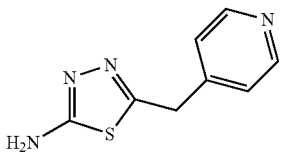 [SMILES: Nc1nnc(Cc2ccncc2)s1] | MS m/z (M + H): 193. |
| 0266-2 | 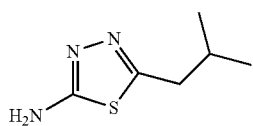 | 1H-NMR (DMSO-d$_6$) δ:<br>12.19 (1H, s), 9.08 (1H, d, J = 2.3 Hz), 8.56-8.53 (3H, m), 8.29-<br>8.21 (3H, m), 7.44-<br>7.35 (4H, m), 4.46 (2H, s), 4.24 (2H, t, J = 6.8 Hz), 2.87-<br>2.61 (5H, m), 2.13-2.04 (2H, m), 1.89-1.68 (4H, m).<br>MS m/z (M + H): 498. |
| | 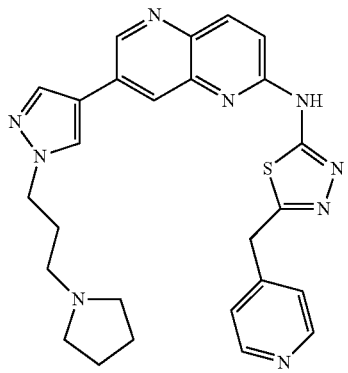 | |

Example 0267

0267-1

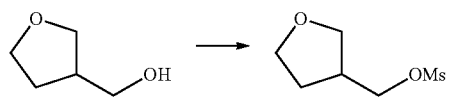 [SMILES: OCC1CCOC1 ; CS(=O)(=O)OCC1CCOC1]

Triethylamine (800 μL) was added to a solution of (tetrahydrofuran-3-yl)methanol (410 mg) in dichloromethane (4 mL), and methanesulfonyl chloride (350 μL) was added dropwise thereto under ice-cooling, followed by stirring at 0° C. for 30 minutes. Methanesulfonyl chloride (50 μL) was added thereto, followed by stirring at 0° C. for 30 minutes. The reaction mixture was purified by silica gel column chromatography (hexane-ethyl acetate), thereby obtaining (tetrahydrofuran-3-yl)methyl methanesulfonate (540 mg).
$^1$H-NMR(CDCl$_3$)δ:4.21-4.10(2H,m),3.88-3.63(4H,m),3.05(3H,s),2.75-2.64(1H,m),2.18-2.04(1H,m),1.76-1.62 (1H,m).

0267-2

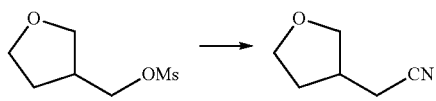 [SMILES: CS(=O)(=O)OCC1CCOC1 ; N#CCC1CCOC1]

Sodium cyanide (70 mg) was added to a solution of (tetrahydrofuran-3-yl)methyl methanesulfonate (200 mg) in dimethylsulfoxide (3 mL), followed by stirring at 80° C.

overnight. The reaction mixture was cooled to room temperature, and ethyl acetate and a saturated sodium chloride aqueous solution were added thereto. The organic layer was collected by separation, and dried over anhydrous sodium sulfate, and the solvent was distilled off under reduced pressure. The obtained residue was purified by silica gel column chromatography (hexane-ethyl acetate), thereby obtaining 2-(tetrahydrofuran-3-yl)acetonitrile (80 mg).

$^1$H-NMR(CDCl$_3$)δ:3.98-3.87(2H,m),3.84-3.77(1H,m), 3.60-3.52(1H,m),2.65-2.56(1H,m),2.50-2.37(2H,m),2.25-2.14(1H,m),1.78-1.66(1H,m).

0267-3 and 0267-4

The following compounds were obtained in the same manner as in Examples 0256-1 and 0001-5.

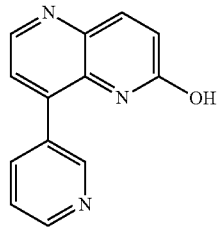

3-Pyridylboronic acid (35 mg), bis(di-tert-butyl(4-dimethylaminophenyl)phosphine)dichloropalladium(II) (5 mg),

| Example No. | | |
|---|---|---|
| 0267 | | |
| 0267-3 | 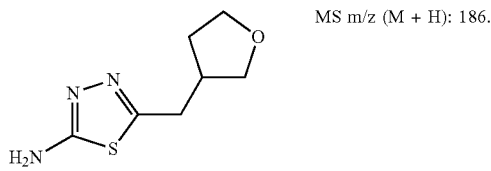 | MS m/z (M + H): 186. |
| 0267-4 | 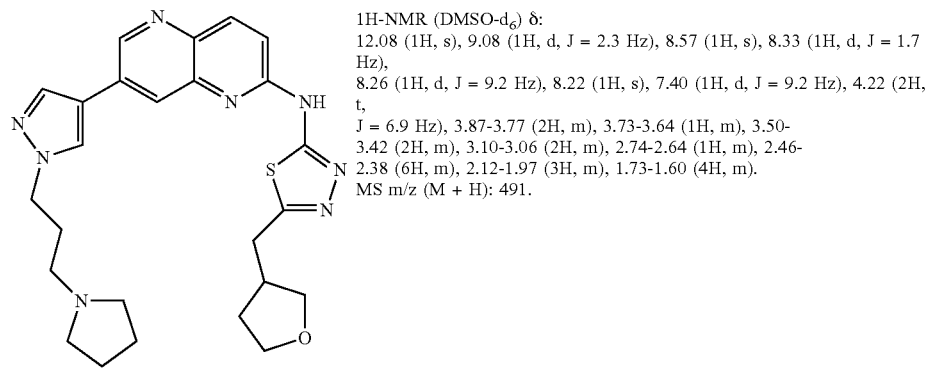 | 1H-NMR (DMSO-d$_6$) δ: 12.08 (1H, s), 9.08 (1H, d, J = 2.3 Hz), 8.57 (1H, s), 8.33 (1H, d, J = 1.7 Hz), 8.26 (1H, d, J = 9.2 Hz), 8.22 (1H, s), 7.40 (1H, d, J = 9.2 Hz), 4.22 (2H, t, J = 6.9 Hz), 3.87-3.77 (2H, m), 3.73-3.64 (1H, m), 3.50-3.42 (2H, m), 3.10-3.06 (2H, m), 2.74-2.64 (1H, m), 2.46-2.38 (6H, m), 2.12-1.97 (3H, m), 1.73-1.60 (4H, m). MS m/z (M + H): 491. |

Example 0268

0268-1

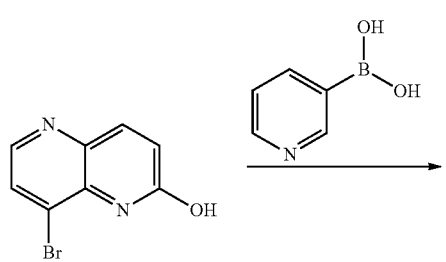

and a 2 mol/L sodium carbonate aqueous solution (100 μL) were added to a solution of 8-bromo-1,5-naphthyridin-2-ol (50 mg) in 1,4-dioxane (1.5 mL), followed by stirring at 130° C. for 1 hour using a microwave reaction apparatus. The reaction mixture was cooled to room temperature, and ethyl acetate was added thereto. The obtained solution was purified by silica gel column chromatography (ethyl acetate-methanol, NH silica), thereby obtaining 8-(pyridin-3-yl)-1,5-naphthyridin-2-ol (33 mg).

$^1$H-NMR(DMSO-d$_6$)δ:11.12(1H,s),8.68(2H,dd,J=5.0,1.7 Hz),8.55(1H,d,J=4.3 Hz),8.02(1H,d,J=10.2 Hz),7.93(1H,d, J=7.6 Hz),7.55(1H,ddd,J=7.8,4.9,0.7 Hz),7.46(1H,d,J=4.3 Hz),6.81(1H,d,J=9.2 Hz).

0268-2

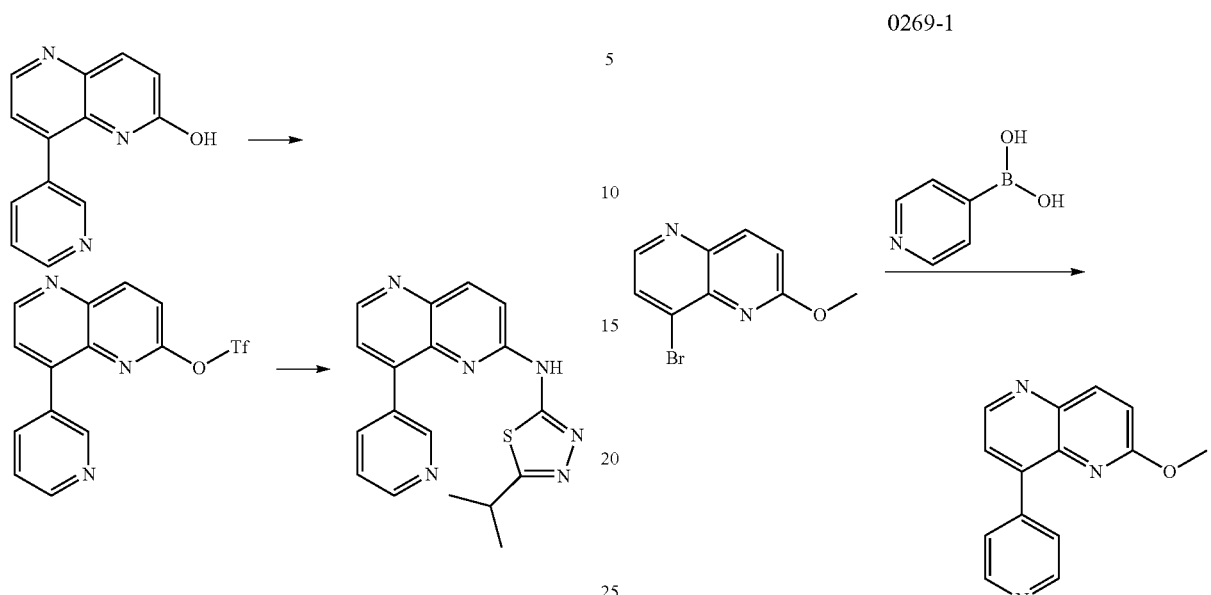

Triethylamine (50 μL) was added to a solution of 8-(pyridin-3-yl)-1,5-naphthyridin-2-ol (25 mg) in dichloromethane (2 mL), and trifluoromethanesulfonic acid anhydride (20 μL) was added dropwise thereto under ice-cooling, followed by stirring at room temperature for 30 minutes. The reaction mixture was purified by silica gel column chromatography (hexane-ethyl acetate, NH silica), thereby obtaining (8-(pyridin-3-yl)-1,5-naphthyridin-2-yl) trifluoromethanesulfonate.

2-Amino-5-isopropyl-1,3,4-thiadiazole (14 mg), 2-dicyclohexylphosphino-2',4',6'-triisopropylbiphenyl (5 mg), cesium carbonate (20 mg), and tris(dibenzylideneacetone)dipalladium(0) (5 mg) were added to a solution of the obtained (8-(pyridin-3-yl)-1,5-naphthyridin-2-yl) trifluoromethanesulfonate in 1,4-dioxane (1.5 mL), followed by stirring at 150° C. for 45 minutes using a microwave reaction apparatus. The reaction mixture was cooled to room temperature, and a mixed solvent of chloroform-methanol was added thereto. The obtained solution was purified by silica gel column chromatography (chloroform-methanol, NH silica), thereby obtaining 5-isopropyl-N-(8-(pyridin-3-yl)-1,5-naphthyridin-2-yl)-1,3,4-thiadiazole-2-amine (6 mg) as a pale yellow solid.

$^1$H-NMR(DMSO-d$_6$)δ:12.06(1H,s),8.87(1H,d,J=1.3 Hz), 8.84(1H,d,J=4.3 Hz),8.73(1H,dd,J=5.0,1.7 Hz),8.38(1H,d, J=8.9 Hz),8.10-8.04(1H,m),7.71(1H,d,J=4.6 Hz),7.65-7.58 (1H,m),7.52(1H,d,J=9.2 Hz),3.22-3.12(1H,m),1.24(6H,d, J=7.2 Hz).

MSm/z(M+H):349.

Example 0269

0269-1

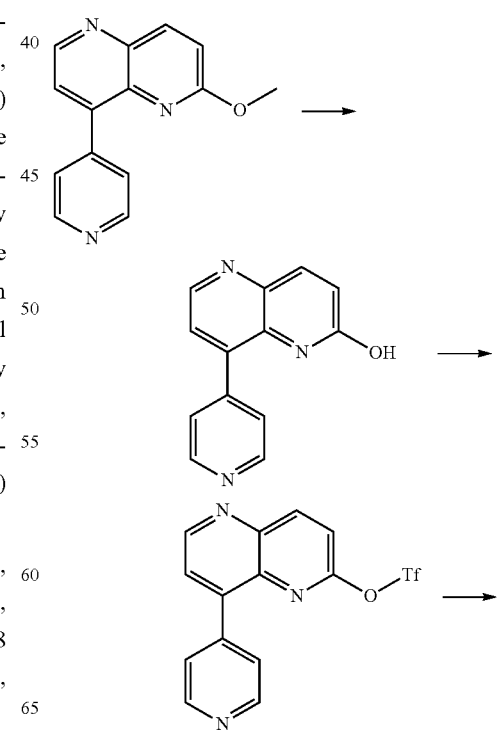

2-Methoxy-8-(pyridin-4-yl)-1,5-naphthyridine was obtained in the same manner as in Example 0264-1.

$^1$H-NMR(DMSO-d$_6$)δ:8.91(1H,d,J=4.3 Hz),8.75-8.72 (2H,m),8.37(1H,d,J=8.9 Hz),7.93-7.91(2H,m),7.86-7.83 (1H,m),7.34(1H,d,J=8.9 Hz),3.93(3H,s).

0269-2

-continued

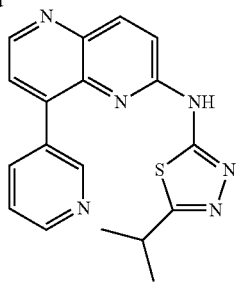

Hydrochloric acid (3 mL) was added to 2-methoxy-8-(pyridin-4-yl)-1,5-naphthyridine (90 mg), followed by stirring at 80° C. for 3 hours. The reaction mixture was cooled to room temperature, neutralized with a sodium hydroxide aqueous solution, and the solvent was distilled off under reduced pressure, thereby obtaining 8-(pyridin-4-yl)-1,5-naphthyridine-2-ol. Triethylamine (300 µL) was added to a solution of the obtained 8-(pyridin-4-yl)-1,5-naphthyridin-2-ol in dichloromethane (3 mL), and trifluoromethanesulfonic acid anhydride (150 µL) was added dropwise thereto under ice-cooling, followed by stirring at room temperature for 30 minutes. Water was added to the reaction mixture. The organic layer was collected by separation, and dried over anhydrous sodium sulfate, then, the solvent was distilled off under reduced pressure, and the resultant product was purified by silica gel column chromatography (hexane-ethyl acetate, NH silica), thereby obtaining (8-(pyridin-4-yl)-1,5-naphthyridin-2-yl) trifluoromethanesulfonate. 2-Amino-5-isopropyl-1,3,4-thiadiazole (30 mg), 2-dicyclohexylphosphino-2',4',6'-triisopropylbiphenyl (10 mg), cesium carbonate (70 mg), and tris(dibenzylideneacetone)dipalladium(0) (10 mg) were added to a solution of the obtained (8-(pyridin-4-yl)-1,5-naphthyridin-2-yl) trifluoromethanesulfonate in 1,4-dioxane (2 mL), followed by stirring at 150° C. for 30 minutes using a microwave reaction apparatus. The reaction mixture was cooled to room temperature, and purified by silica gel column chromatography (ethyl acetate-methanol, NH silica), thereby obtaining 5-isopropyl-N-(8-(pyridin-4-yl)-1,5-naphthyridin-2-yl)-1,3,4-thiadiazol-2-amine (23 mg) as a pale yellow solid.

$^1$H-NMR(DMSO-$d_6$)δ:12.07(1H,s),8.84(1H,d,J=4.6 Hz), 8.77(2H,dd,J=4.5,1.5 Hz),8.38(1H,d,J=8.9 Hz),7.68-7.65 (3H,m),7.51(1H,d,J=9.2 Hz),3.24-3.09(1H,m),1.22(6H,d, J=7.2 Hz).

MS m/z(M+H):349.

Examples 0270 to 0276

The following compounds were obtained in the same manner as in Examples 0268-1 and 0268-2.

| Example No. | | |
|---|---|---|
| 0270 | | |
| 0270-1 | 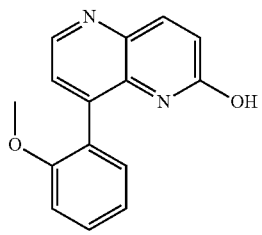 [SMILES: COc1ccccc1-c1ccnc2ccc(O)nc12] | 1H-NMR (DMSO-$d_6$) δ:<br>10.33 (1H, s), 8.49 (1H, d, J = 5.0 Hz), 7.99 (1H, d, J = 9.9 Hz), 7.53-7.47 (1H, m), 7.34 (1H, d, J = 4.6 Hz), 7.26 (1H, dd, J = 7.6, 1.7 Hz), 7.18 (1H, d, J = 8.3 Hz), 7.09 (1H, dd, J = 7.9, 6.9 Hz), 6.76 (1H, d, J = 9.6 Hz), 3.74 (3H, s). |
| 0270-2 | 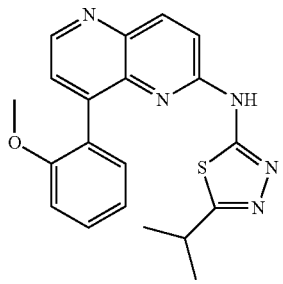 [SMILES: COc1ccccc1-c1ccnc2ccc(Nc3nnc(C(C)C)s3)nc12] | 1H-NMR (DMSO-$d_6$) δ:<br>12.00 (1H, s), 8.79 (1H, d, J = 4.3 Hz), 8.35 (1H, d, J = 8.9 Hz), 7.61 (1H, d,<br>J = 4.3 Hz), 7.51-7.45 (2H, m), 7.23-7.20 (1H, m), 7.18-7.14 (1H, m), 7.12-7.06 (1H, m), 3.77 (3H, s), 3.20-3.08 (1H, m), 1.22 (6H, d, J = 7.2 Hz).<br>MS m/z (M + H): 378. |
| 0271 | | |
| 0271-1 | 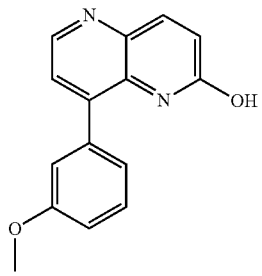 [SMILES: COc1cccc(-c2ccnc3ccc(O)nc23)c1] | 1H-NMR (DMSO-$d_6$) δ:<br>11.95 (1H, s), 8.77 (1H, d, J = 4.3 Hz), 8.33 (1H, d, J = 9.2 Hz), 7.55-7.49 (2H, m), 7.45 (1H, d, J = 9.2 Hz), 7.29 (1H, dd, J = 7.4, 1.8 Hz), 7.21 (1H, d, J = 7.9 Hz), 7.13 (1H, td, J = 7.3, 0.8 Hz), 3.59 (3H, s). |

| Example No. | | |
|---|---|---|
| 0271-2 | 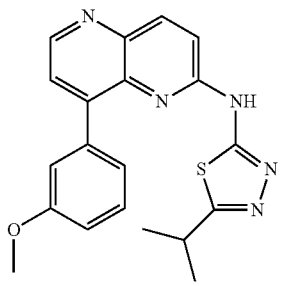 [SMILES: COc1cccc(-c2ccnc3ccc(Nc4nnc(C(C)C)s4)nc23)c1] | 1H-NMR (DMSO-d$_6$) δ:<br>11.95 (1H, s), 8.77 (1H, d, J = 4.3 Hz), 8.33 (1H, d, J = 9.2 Hz), 7.55-7.49 (2H, m), 7.45 (1H, d, J = 9.2 Hz), 7.29 (1H, dd, J = 7.4, 1.8 Hz), 7.21 (1H, d, J = 7.9 Hz), 7.13 (1H, td, J = 7.3, 0.8 Hz), 3.59 (3H, s), 3.20-3.07 (1H, m), 1.23 (6H, d, J = 7.2 Hz).<br>MS m/z (M + H): 378. |
| 0272 | | |
| 0272-1 | 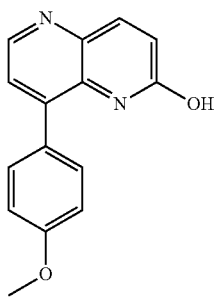 [SMILES: COc1ccc(-c2ccnc3ccc(O)nc23)cc1] | 1H-NMR (DMSO-d$_6$) δ:<br>11.97 (1H, s), 8.76 (1H, d, J = 4.6 Hz), 8.33 (1H, d, J = 8.9 Hz), 7.61-7.57 (3H, m), 7.48 (1H, d, J = 9.2 Hz), 7.12 (2H, d, J = 8.9 Hz), 3.85 (3H, s). |
| 0272-2 | 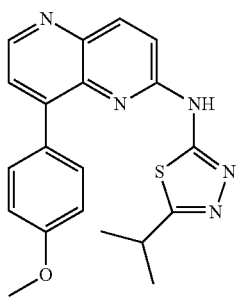 [SMILES: COc1ccc(-c2ccnc3ccc(Nc4nnc(C(C)C)s4)nc23)cc1] | 1H-NMR (DMSO-d$_6$) δ:<br>11.97 (1H, s), 8.76 (1H, d, J = 4.6 Hz), 8.33 (1H, d, J = 8.9 Hz), 7.62-7.57 (3H, m), 7.48 (1H, d, J = 9.2 Hz), 7.15-7.09 (2H, m), 3.85 (3H, s), 3.24-3.12 (1H, m), 1.22 (6H, d, J = 7.2 Hz).<br>MS m/z (M + H): 378. |
| 0273 | | |
| 0273-1 | 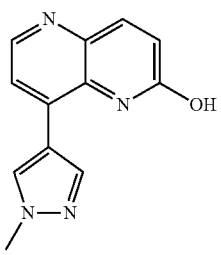 [SMILES: Cn1cc(-c2ccnc3ccc(O)nc23)cn1] | 1H-NMR (DMSO-d$_6$) δ:<br>10.36 (1H, s), 8.50 (2H, d, J = 4.0 Hz), 8.03 (2H, d, J = 9.9 Hz), 7.59 (1H, s),<br>6.88 (1H, s), 3.93 (3H, s). |
| 0273-2 | 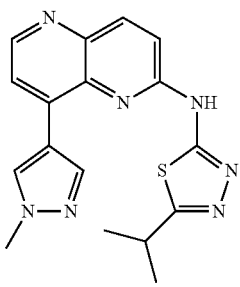 [SMILES: CC(C)c1nnc(Nc2ccc3nccc(-c4cnn(C)c4)c3n2)s1] | 1H-NMR (DMSO-d$_6$) δ:<br>11.90 (1H, s), 8.68 (1H, d, J = 4.6 Hz), 8.50 (1H, s), 8.29 (1H, d, J = 8.9 Hz),<br>8.10 (1H, s), 7.70 (1H, d, J = 4.6 Hz), 7.53 (1H, d, J = 9.2 Hz), 3.96 (3H, s), 3.54-3.39 (1H, m), 1.34 (6H, d, J = 7.2 Hz)<br>MS m/z (M + H): 352. |

-continued

| Example No. | | |
|---|---|---|
| 0274 | | |
| 0274-1 | 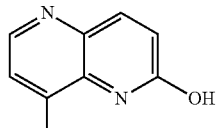 | 1H-NMR (DMSO-d$_6$) δ:<br>10.23 (1H, s), 8.50 (2H, d, J = 4.6 Hz), 8.04 (2H, d, J = 9.6 Hz), 7.60 (1H, s),<br>6.90 (1H, d, J = 7.6 Hz), 4.31 (2H, t, J = 6.8 Hz), 3.57 (4H, t, J = 4.6 Hz), 2.79<br>(2H, t, J = 6.8 Hz), 2.45 (4H, t, J = 4.5 Hz). |
| 0274-2 | 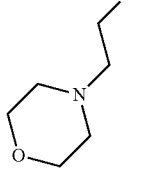 | 11.90 (1H, s), 8.69 (1H, d, J = 4.6 Hz), 8.55 (1H, s), 8.29 (1H, d, J = 8.9 Hz),<br>8.17 (1H, s), 7.70 (1H, d, J = 4.6 Hz), 7.53 (1H, d, J = 9.2 Hz), 4.34 (2H, t, J = 6.8 Hz), 3.60-3.50 (4H, m), 3.30-3.20 (1H, m), 2.79 (2H, t, J = 6.8 Hz), 2.46-2.39 (4H, m), 1.34 (6H, d, J = 7.2 Hz).<br>MS m/z (M + H): 451. |
| 0275 | | |
| 0275-1 | 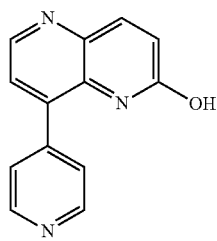 [SMILES: Oc1ccc2nccc(-c3ccncc3)c2n1] | 1H-NMR (DMSO-d$_6$) δ:<br>10.98 (1H, s), 8.72 (2H, dd, J = 4.3, 1.7 Hz), 8.57 (1H, d, J = 4.6 Hz), 8.03 (1H,<br>d, J = 9.6 Hz), 7.54 (2H, d, J = 5.9 Hz), 7.46 (1H, d, J = 4.6 Hz), 6.82 (1H, d,<br>J = 9.6 Hz). |
| 0275-2 | 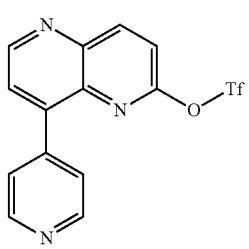 | 1H-NMR (DMSO-d$_6$) δ:<br>9.24 (1H, d, J = 4.3 Hz), 8.88 (1H, d, J = 8.9 Hz), 8.76 (2H, dd, J = 4.3, 1.7 Hz),<br>8.07 (1H, d, J = 4.6 Hz), 8.02 (1H, d, J = 8.9 Hz), 7.77 (2H, dd, J = 4.3, 1.7 Hz). |
| 0275-3 | 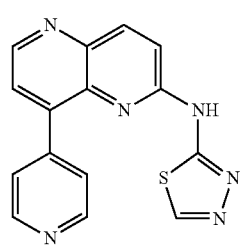 [SMILES: c1cc(-c2ccnc3ccc(Nc4nncs4)nc23)ccn1] | 1H-NMR (DMSO-d$_6$) δ:<br>12.26 (1H, s), 9.00 (1H, s), 8.86 (1H, d, J = 4.3 Hz), 8.77 (2H, dd, J = 4.3, 1.7<br>Hz), 8.41 (1H, d, J = 9.2 Hz), 7.70 (3H, t, J = 3.0 Hz), 7.57 (1H, d, J = 9.2 Hz).<br>MS m/z (M + H): 307. |

-continued

Example No.

0276

0276-1

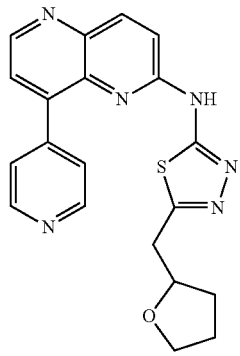 [SMILES: c1cc(-c2ccnc3ccc(Nc4nnc(CC5CCCO5)s4)nc23)ccn1]

1H-NMR (DMSO-d$_6$) δ:
12.07 (1H, s), 8.85 (1H, d, J = 4.3 Hz), 8.76 (2H, dd, J = 4.5, 1.5 Hz), 8.38 (1H,
d, J = 9.2 Hz), 7.68 (3H, dd, J = 4.0, 2.0 Hz), 7.53 (1H, d, J = 8.9 Hz), 4.04-
3.92 (1H, m), 3.80-3.63 (2H, m), 3.02-2.97 (2H, m), 2.01-1.79 (3H, m), 1.53-
1.43 (1H, m).
MS m/z (M + H): 391.

Example 0277

0277-1

Example 0278

0278-1

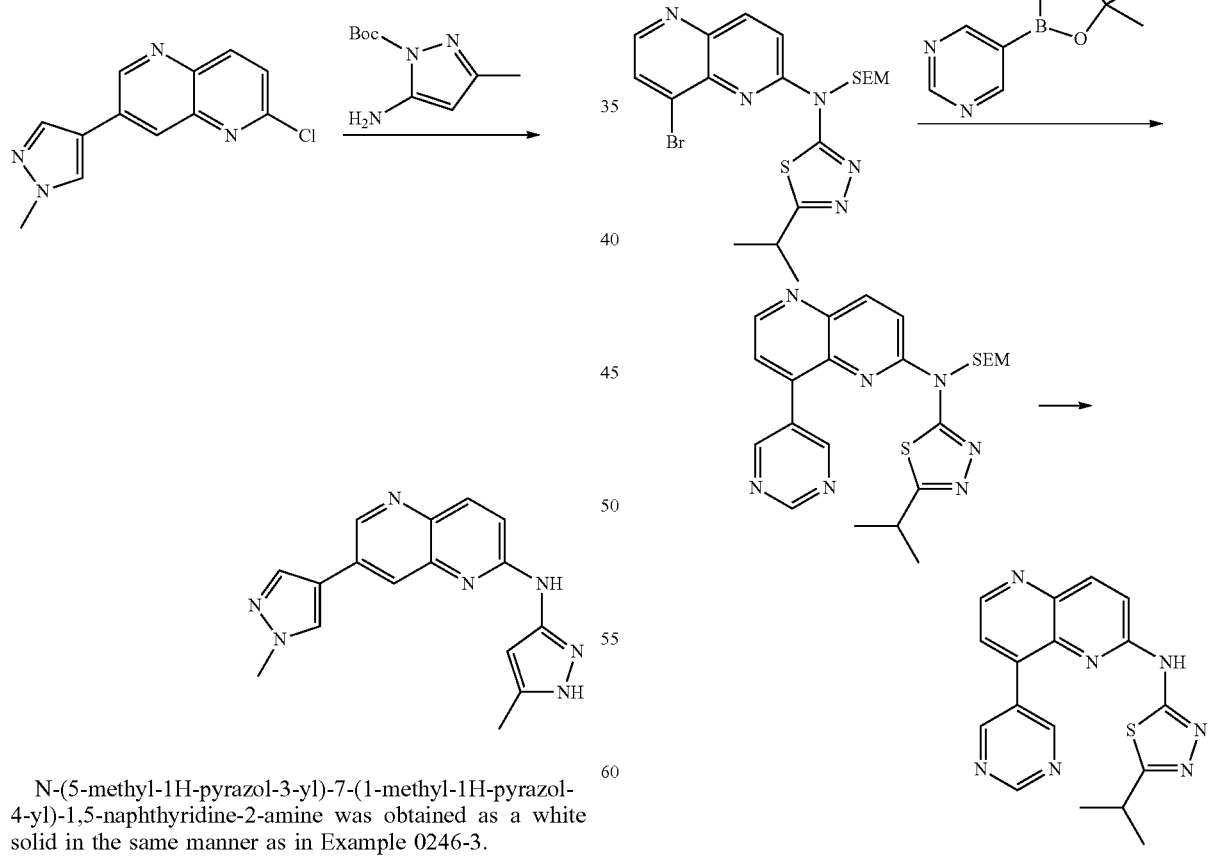

N-(5-methyl-1H-pyrazol-3-yl)-7-(1-methyl-1H-pyrazol-4-yl)-1,5-naphthyridine-2-amine was obtained as a white solid in the same manner as in Example 0246-3.

$^1$H-NMR(CD$_3$OD)δ:7.62(1H,d,J=1.7 Hz),7.03(1H,s), 6.91(1H,d,J=9.6 Hz),6.84(1H,s),6.62(1H,s),5.90(1H,d, J=9.2 Hz),4.57(1H,s),2.48(3H,s),0.88(3H,s).
MSm/z(M+H):306.

5-(4,4,5,5-Tetramethyl-1,3,2-dioxaborolan-2-yl)pyrimidine (5 mg), bis(di-tert-butyl (4-dimethylaminophenyl) phosphine)dichloropalladium(II) (3 mg), and a 2 mol/L sodium carbonate aqueous solution (50 μL) were added to a solution of N-(8-bromo-1,5-naphthyridin-2-yl)-5-isopropyl-N-((2-trimethylsilyl)ethoxy)methyl)-1,3,4-thiadiazole-2-amine (10 mg) in 1,4-dioxane (1 mL), followed by stirring at 130° C. for 45 minutes using a microwave reaction apparatus. The reaction mixture was cooled to room temperature, and ethyl acetate and water were added thereto. The organic layer was collected by separation, and dried over anhydrous sodium sulfate, and the solvent was distilled off under reduced pressure. The obtained solution was purified by silica gel column chromatography (hexane-ethyl acetate, NH silica), thereby obtaining 5-isopropyl-N-(8-(pyrimidin-5-yl)-1,5-naphthyridin-2-yl)-N-((2-(trimethylsilyl)ethoxy)methyl)-1,3,4-thiadiazole-2-amine.

Trifluoroacetic acid (1 mL) and water (50 μL) were added to the obtained 5-isopropyl-N-(8-(pyrimidin-5-yl)-1,5-naphthyridin-2-yl)-N-((2-(trimethylsilyl)ethoxy)methyl)-1,3,4-thiadiazole-2-amine, followed by stirring at room temperature for 1 hour. After the solvent was distilled off under reduced pressure, triethylamine (2 drops) was added thereto, and the resultant product was purified by silica gel column chromatography (ethyl acetate-methanol, NH silica), thereby obtaining 5-isopropyl-N-(8-(pyrimidin-5-yl)-1,5-naphthyridin-2-yl)-1,3,4-thiadiazole-2-amine (0.58 mg).

$^1$H-NMR(DMSO-$d_6$)δ:12.14(1H,s),9.37(1H,s),9.15(2H,s),8.88(1H,d,J=4.6 Hz),8.40(1H,d,J=8.9 Hz),7.82(1H,d,J=4.3 Hz),7.54(1H,d,J=9.2 Hz),3.26-3.15(1H,m),1.27(6H,d,J=6.9 Hz).

MS m/z(M+H):350.

Examples 0279 and 0280

The following compounds were obtained in the same manner as in Example 0278-1.

| Example No. | | |
|---|---|---|
| 0279 | | |
| 0279-1 | 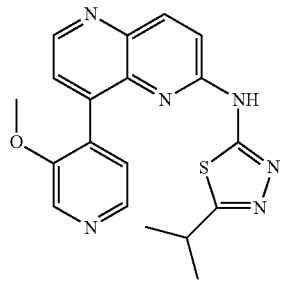 [SMILES: COc1cnccc1-c1ccnc2ccc(Nc3nnc(C(C)C)s3)nc12] | 1H-NMR (DMSO-$d_6$) δ:<br>12.09 (1H, s), 8.83 (1H, d, J = 4.3 Hz), 8.39-8.33 (2H, m), 7.65 (1H, d, J = 4.3 Hz), 7.51 (1H, d, J = 9.2 Hz), 7.20 (1H, dd, J = 5.3, 1.7 Hz), 7.10 (1H, d, J = 1.3 Hz), 3.93 (3H, d, J = 1.7 Hz), 3.25-3.12 (1H, m), 1.23 (6H, d, J = 7.2 Hz).<br>MS m/z (M + H): 379. |
| 0280 | | |
| 0280-1 | 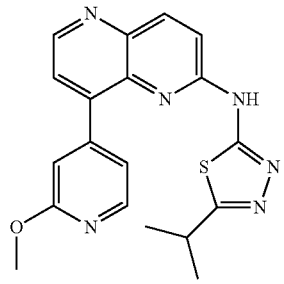 | 1H-NMR (DMSO-$d_6$) δ:<br>12.08 (1H, s), 8.82 (1H, d, J = 4.3 Hz), 8.61 (1H, s), 8.43 (1H, d, J = 4.6 Hz), 8.36 (1H, d, J = 8.9 Hz), 7.61 (1H, d, J = 4.3 Hz), 7.48 (1H, d, J = 9.2 Hz), 7.42 (1H, d, J = 5.0 Hz), 3.73 (3H, s), 3.20-3.11 (1H, m), 1.23 (6H, d, J = 6.9 Hz).<br>MS m/z (M + H): 379. |

Example 0281

0281-1

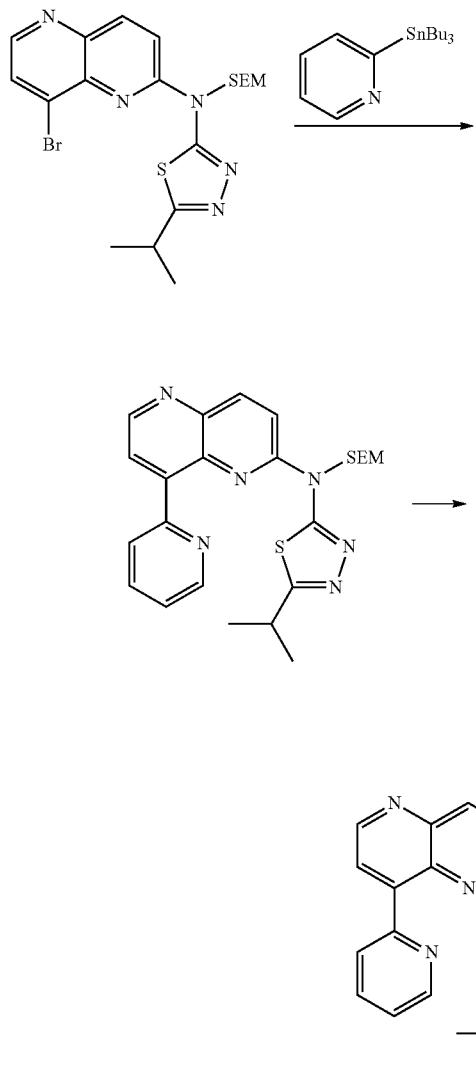

2-(Tributyltin)pyridine (15 μL), tetrakis(triphenylphosphine)palladium(0) (5 mg), and cesium carbonate (20 mg) were added to a solution of N-(8-bromo-1,5-naphthyridin-2-yl)-5-isopropyl-N-((2-trimethylsilyl)ethoxy)methyl)-1,3,4-thiadiazole-2-amine (10 mg) in 1,4-dioxane (1 mL), followed by stirring at 100° C. for 30 minutes using a microwave reaction apparatus. The reaction mixture was cooled to room temperature, and ethyl acetate and water were added thereto. The organic layer was collected by separation, and dried over anhydrous sodium sulfate, and the solvent was distilled off under reduced pressure, thereby obtaining 5-isopropyl-N-(8-(pyridin-2-yl)-1,5-naphthyridin-2-yl)-N-((2-(trimethylsilyl)ethoxy)methyl)-1,3,4-thiadiazole-2-amine.

Trifluoroacetic acid (1 mL) and water (50 μL) were added to the obtained 5-isopropyl-N-(8-(pyridin-2-yl)-1,5-naphthyridin-2-yl)-N-((2-(trimethylsilyl)ethoxy)methyl)-1,3,4-thiadiazole-2-amine, followed by allowing to stand at room temperature overnight. The solvent was distilled off under reduced pressure, and ethyl acetate and a saturated sodium hydrogen carbonate aqueous solution were added thereto. The organic layer was collected by separation, and dried over anhydrous sodium sulfate, and the solvent was distilled off under reduced pressure. The obtained residue was purified by silica gel column chromatography (ethyl acetate-methanol, NH silica), thereby obtaining 5-isopropyl-N-(8-(pyridin-2-yl)-1,5-naphthyridin-2-yl)-1,3,4-thiadiazole-2-amine (2.5 mg).

$^1$H-NMR(DMSO-d$_6$)δ:12.05(1H,s),8.85(1H,d,J=4.3 Hz),8.81(1H,d,J=5.0 Hz),8.38(1H,d,J=8.9 Hz),8.03-7.93(2H,m),7.77(1H,d,J=4.6 Hz),7.58-7.55(1H,m),7.52(1H,d,J=9.2 Hz),3.24-3.16(1H,m),1.23(6H,d,J=6.9 Hz).
MS m/z(M+H):349.

Examples 0282 and 0283

The following compounds were obtained in the same manner as in Example 0278-1.

| Example No. | | |
|---|---|---|
| 0828 | | |
| 0828-1 | 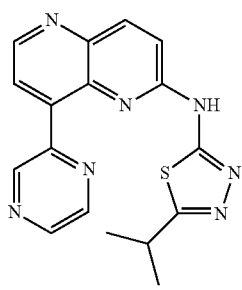 [SMILES: CC(C)c1nnc(Nc2ccc3nccc(-c4cnccn4)c3n2)s1] | 1H-NMR (DMSO-d$_6$) δ:<br>12.13 (1H, s), 9.24 (1H, d, J = 1.7 Hz), 8.92-8.89 (2H, m), 8.82 (1H, s), 8.41 (1H, d, J = 9.2 Hz), 7.86 (1H, d, J = 4.6 Hz),<br>7.55 (1H, d, J = 8.9 Hz), 3.24-3.13 (1H, m), 1.26 (6H, d, J = 6.9 Hz).<br>MS m/z (M + H): 350. |

| Example No. | | |
|---|---|---|
| 0283 | | |
| 0283-1 | 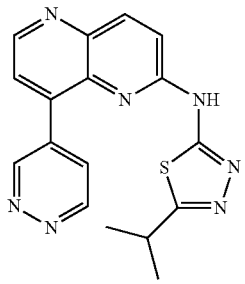 [SMILES: CC(C)c1nnc(Nc2ccc3nccc(-c4ccnnc4)c3n2)s1] | 1H-NMR (DMSO-$d_6$) δ:<br>12.15 (1H, s), 9.60-9.55 (1H, m), 9.49-<br>9.45 (1H, m), 8.89 (1H, d, J = 4.3 Hz), 8.41 (1H, d, J = 8.9 Hz), 8.02-<br>7.99 (1H, m), 7.80 (1H, d, J = 4.3 Hz), 7.54 (1H, d, J = 9.2 Hz), 3.21-<br>3.12 (1H, m), 123 (6H, d, J = 69 Hz).<br>MS m/z (M + H): 350. |

Examples 0284 and 0285

The following compounds were obtained in the same manner as in Example 0278-1.

| Example No. | | |
|---|---|---|
| 0284 | | |
| 0284-1 | 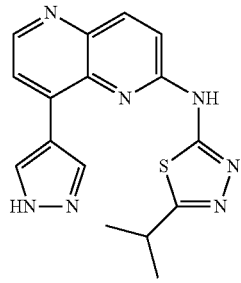 [SMILES: CC(C)c1nnc(Nc2ccc3nccc(-c4cn[nH]c4)c3n2)s1] | 1H-NMR (DMSO-$d_6$) δ:<br>11.91 (1H, s), 8.70 (1H, dd, J = 4.5, 3.1 Hz), 8.63 (1H, s), 8.30 (1H, d,<br>J =<br>8.9 Hz), 7.76-7.69 (2H, m), 7.54 (1H, dd, J = 8.9, 2.3 Hz), 3.32-<br>3.21 (1H, m), 1.33 (6H, d, J = 6.9 Hz).<br>MS m/z (M + H): 338. |
| 0285 | | |
| 0285-1 | 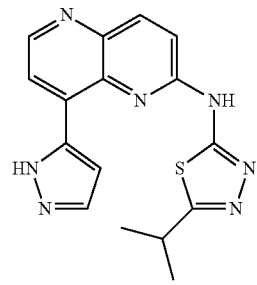 [SMILES: CC(C)c1nnc(Nc2ccc3nccc(-c4ccn[nH]4)c3n2)s1] | 1H-NMR (DMSO-$d_6$) δ:<br>11.97 (1H, s), 8.76 (1H, d, J = 4.6 Hz), 8.36-<br>8.31 (1H, m), 8.00 (1H, d, J = 2.3 Hz), 7.86 (1H, d, J = 4.3 Hz), 7.57-<br>7.50 (1H, m), 7.13 (1H, d, J = 2.3 Hz), 3.25-<br>3.20 (1H, m), 1.23 (6H, d, J = 6.9 Hz).<br>MS m/z (M + H): 338. |

Example 0286

0286-1

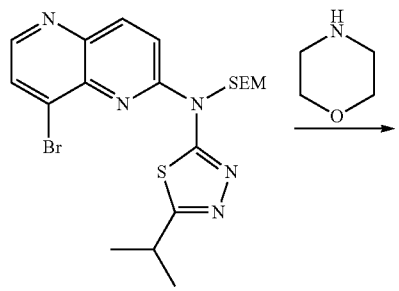

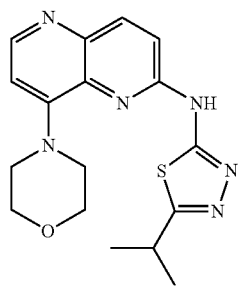

Morpholine (50 μL), tris(dibenzylideneacetone)palladium (0) (3.1 mg), 2-(dicyclohexylphosphino)-2',4',6'-triisopropylbiphenyl (5 mg), and cesium carbonate (30 mg) were added to a solution of N-(8-bromo-1,5-naphthyridin-2-yl)-5-isopropyl-N-((2-(trimethylsilyl)ethoxy)methyl)-1,3,4-thiadiazole-2-amine (15 mg) in 1,4-dioxane (1 mL), followed by stirring at 150° C. for 30 minutes using a microwave reaction apparatus. Ethyl acetate and water were added to the reaction mixture. The organic layer was collected by separation, washed with a saturated sodium chloride aqueous solution, and dried over anhydrous sodium sulfate, and the solvent was distilled off under reduced pressure, thereby obtaining 5-isopropyl-N-(8-morpholino-1,5-naphthyridin-2-yl)-N-((2-(trimethylsilyl)ethoxy)methyl)-1,3,4-thiadiazole-2-amine.

Trifluoroacetic acid (1 mL) was added to the obtained 5-isopropyl-N-(8-morpholino-1,5-naphthyridin-2-yl)-N-((2-(trimethylsilyl)ethoxy)methyl)-1,3,4-thiadiazole-2-amine, followed by stirring at room temperature for 30 minutes. The solvent was distilled off under reduced pressure, and the obtained residue was purified by silica gel column chromatography (methanol-ethyl acetate, NH silica), thereby obtaining 5-isopropyl-N-(8-morpholino-1,5-naphthyridin-2-yl)-1,3,4-thiadiazole-2-amine (10 mg) as a yellow solid.

$^1$H-NMR(DMSO-$d_6$)δ:8.54(1H,d,J=5.0 Hz),8.22(1H,d,J=8.9 Hz),7.45(1H,d,J=9.2 Hz),7.09(1H,d,J=5.3 Hz),4.01-3.92(4H,m),3.47-3.38(5H,m),1.41(6H,d,J=6.9 Hz).

MSm/z(M+H):357.

Examples 0287 and 0288

The following compounds were obtained in the same manner as in Example 0278-1.

| Example No. | | |
|---|---|---|
| 0287 | | |
| 0287-1 | 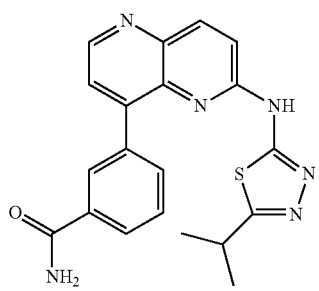 [SMILES: CC(C)c1nnc(Nc2ccc3nccc(-c4cccc(C(N)=O)c4)c3n2)s1] | 1H-NMR (DMSO-$d_6$) δ: 12.02 (1H, s), 8.82 (1H, d, J = 4.3 Hz), 8.37 (1H, d, J = 8.9 Hz), 8.19 (1H, s), 8.10-8.01 (2H, m), 7.79 (1H, d, J = 7.9 Hz), 7.69-7.63 (2H, m), 7.51 (1H, d, J = 9.2 Hz), 7.41 (1H, s), 3.15-3.08 (1H, m), 1.17 (6H, d, J = 6.9 Hz). MS m/z (M + H): 391. |

-continued

| Example No. | | |
|---|---|---|
| 0288 | | |
| 0288-1 | 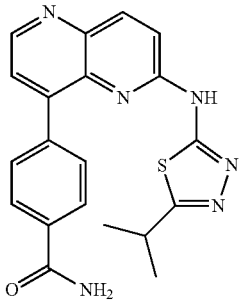 [SMILES: CC(C)c1nnc(Nc2ccc3nccc(-c4ccc(C(N)=O)cc4)c3n2)s1] | 1H-NMR (DMSO-$d_6$) δ:<br>12.03 (1H, s), 8.82 (1H, d, J = 4.6 Hz), 8.36 (1H, d, J = 8.9 Hz), 8.10 (2H, d,<br>J = 8.6 Hz), 7.70 (2H, d, J = 8.3 Hz), 7.64 (1H, d, J = 4.3 Hz), 7.50 (1H, d,<br>J = 9.2 Hz), 7.46 (2H, s), 3.30-3.29 (1H, m), 1.17 (6H, d, J = 6.9 Hz).<br>MS m/z (M + H): 391. |

Example 0289

0289-1

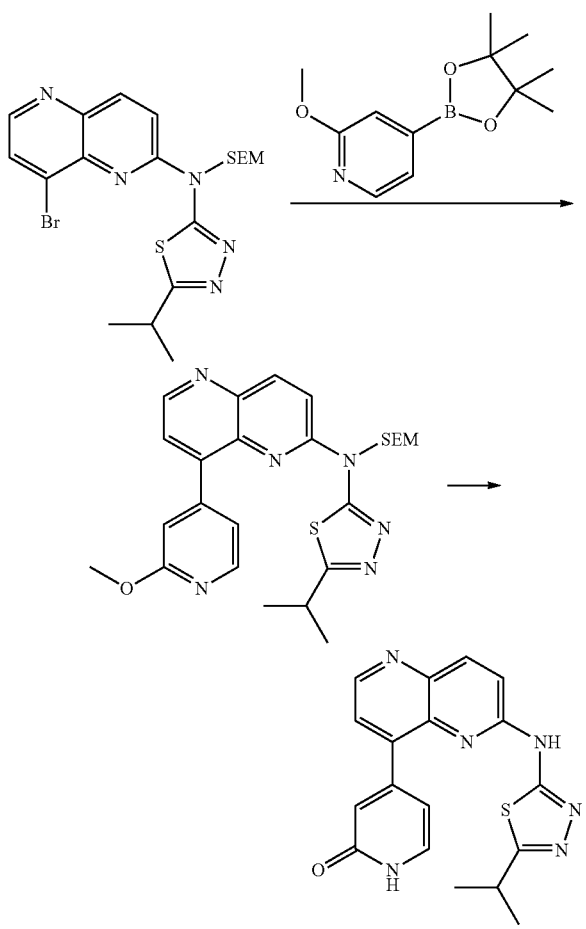

2-Methoxy-4-(4,4,5,5-tetramethyl-1,3,2-dioxaborolan-2-yl)pyridine (6 mg), bis(di-tert-butyl(4-dimethylaminophenyl)phosphine)dichloropalladium(II) (5 mg), and a 2 mol/L sodium carbonate aqueous solution (100 μL) were added to a solution of N-(8-bromo-1,5-naphthyridin-2-yl)-5-isopropyl-N-((2-trimethylsilyl)ethoxy)methyl)-1,3,4-thiadiazole-2-amine (10 mg) in 1,4-dioxane (1 mL), followed by stirring at 130° C. for 45 minutes using a microwave reaction apparatus. The reaction mixture was cooled to room temperature, and ethyl acetate and water were added thereto. The organic layer was collected by separation, and dried over anhydrous sodium sulfate, and the solvent was distilled off under reduced pressure, thereby obtaining 5-isopropyl-N-(8-(2-methoxypyridin-4-yl)-1,5-naphthyridin-2-yl)-N-((2-(trimethylsilyl)ethoxy)methyl)-1,3,4-thiadiazole-2-amine.

Hydrobromic acid (1 mL) was added to the obtained 5-isopropyl-N-(8-(2-methoxypyridin-4-yl)-1,5-naphthyridin-2-yl)-N-((2-(trimethylsilyl)ethoxy)methyl)-1,3,4-thiadiazole-2-amine, followed by stirring at 80° C. for 3 hours. The solvent was distilled off under reduced pressure, the resultant product was neutralized by the addition of a saturated sodium hydrogen carbonate aqueous solution, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-methanol, NH silica), thereby obtaining 4-(6-((5-isopropyl-1,3,4-thiadiazol-2-yl)amino)-1,5-naphthyridin-4-yl)pyridin-2(1H)-one (0.7 mg) as a pale yellow solid.

$^1$H-NMR(DMSO-$d_6$)δ:12.08(1H,s),8.81(1H,d,J=4.3 Hz), 8.36(1H,dd,J=9.2,2.0 Hz),7.84(1H,d,J=6.9 Hz),7.65(1H,d, J=4.6 Hz),7.51(2H,dd,J=9.2,2.3 Hz),6.67(1H,d,J=1.3 Hz), 6.46(1H,dd,J=6.9,2.0 Hz),3.25-3.19(1H,m),1.26(6H,d,J=6.9 Hz).
MSm/z(M+H):365.

Examples 0290 to 0294

The following compounds were obtained in the same manner as in Examples 0015-1 to 0015-4.

| Example No. | | |
|---|---|---|
| 0290 | | |
| 0290-1 | 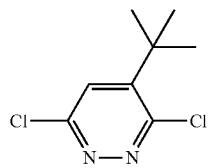 | 1H-NMR(CDCl₃)δ:<br>7.47(1 H, s), 1.49(9H, s). |
| 0290-2 | 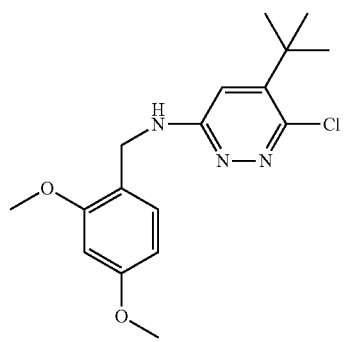 [SMILES: COc1ccc(CNc2cc(C(C)(C)C)c(Cl)nn2)c(OC)c1] | MSm/z(M + H): 336. |
| 0290-3 | 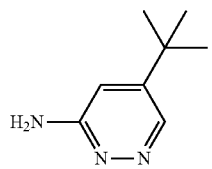 | MSm/z(M + H): 152. |
| 0290-4 | 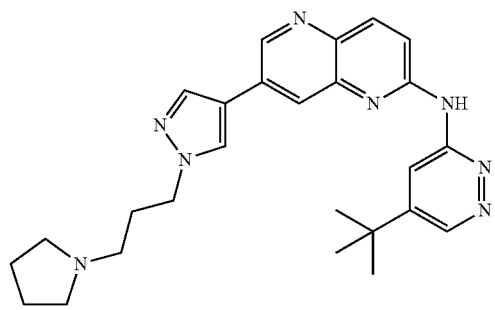 [SMILES: CC(C)(C)c1cnnc(Nc2ccc3ncc(-c4cnn(CCCN5CCCC5)c4)cc3n2)c1] | 1H-NMR(DMSO-d₆)δ:<br>10.68(1 H, s), 9.03(2H, dd, J = 7.3, 2.0 Hz), 8.76(1 H, d, J = 2.0 Hz),<br>8.49(1 H, s), 8.22(1 H, d, J = 9.2 Hz), 8.17(1 H, s), 8.11(1 H, d, J =<br>2.3 Hz), 7.75(1 H, d, J = 8.9 Hz), 4.22(2H, t, J = 6.9 Hz), 2.46-2.35<br>(6H, m), 2.06-1.96(2H, m), 1.73-1.65(4H, m), 1.40(9H, s).<br>MSm/z(M + H): 457. |
| 0291 | | |
| 0291-1 | 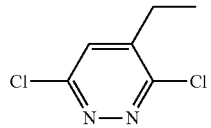 | 1H-NMR(CDCl₃)δ:<br>7.38(1 H, s), 2.77(2H, q, J = 7.2 Hz), 1.32(3H, t, J = 7.2 Hz). |
| 0291-2 | 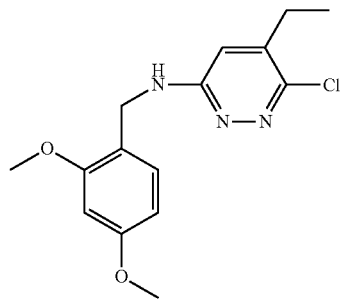 [SMILES: CCc1cc(NCc2ccc(OC)cc2OC)nnc1Cl] | MSm/z(M + H): 308. |

-continued
| Example No. | | |
|---|---|---|
| 0291-3 | 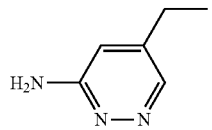 | MS m/z(M + H): 124. |
| 0291-4 | 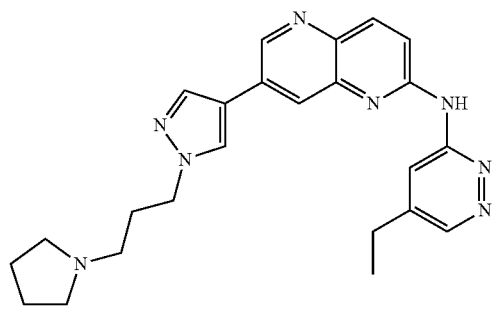 [SMILES: CCc1cnnc(Nc2ccc3ncc(-c4cnn(CCCN5CCCC5)c4)cc3n2)c1] | 1H-NMR(DMSO-d$_6$)δ: 10.70(1 H, s), 9.04(1 H, d, J = 2.0 Hz), 8.81(1 H, d, J = 2.0 Hz), 8.74 (1 H, s), 8.51(1 H, s), 8.26(1 H, d, J = 1.7 Hz), 8.23- 8.17(2H, m), 7.68(1 H, d, J = 9.2 Hz), 4.21(2H, t, J = 6.9 Hz), 2.74 (2H, q, J = 7.7 Hz), 2.46-2.36(6H, m), 2.05-1.96(2H, m), 1.71- 1.67(4H, m), 1.31(3H, t, J = 7.6 Hz). MS m/z(M + H): 429. |
| 0292 | | |
| 0292-1 | 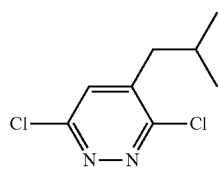 | 1H-NMR(CDCl$_3$)δ: 7.32(1 H, s), 2.60(2H, d, J = 7.3 Hz), 2.12-1.98(1 H, m), 0.99(6H, d, J = 6.6 Hz). |
| 0292-2 | 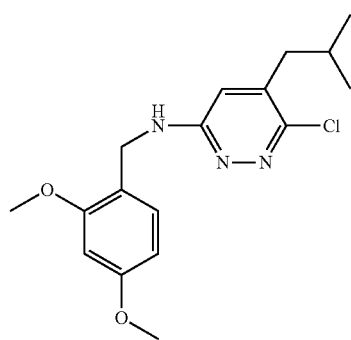 [SMILES: COc1ccc(CNc2cc(CC(C)C)c(Cl)nn2)c(OC)c1] | MS m/z(M + H): 336. |
| 0292-3 | 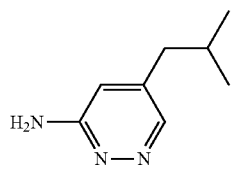 | MS m/z(M + H): 152. |
| 0292-4 | 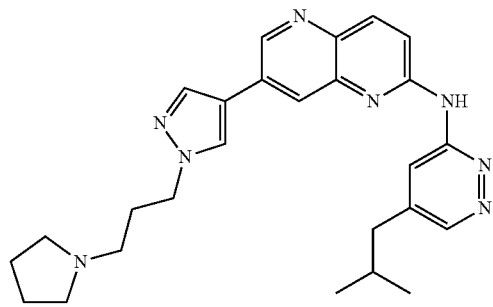 [SMILES: CC(C)Cc1cnnc(Nc2ccc3ncc(-c4cnn(CCCN5CCCC5)c4)cc3n2)c1] | 1H-NMR(DMSO-d$_6$)δ: 10.69(1 H, s), 9.04(1 H, d, J = 2.0 Hz), 8.76(1 H, d, J = 2.0 Hz), 8.64 (1 H, s), 8.49(1 H, s), 8.21(2H, dd, J = 5.4, 3.5 Hz), 8.17(1 H, s), 7.69 (1 H, d, J = 9.2 Hz), 4.22(2H, t, J = 6.9 Hz), 2.60(2H, d, J = 7.3 Hz), 2.44-2.36(6H, m), 2.04-1.98(3H, m), 1.72- 1.65(4H, m), 0.99(6H, d, J = 6.6 Hz). MS m/z(M + H): 457. |

-continued
| Example No. | | |
|---|---|---|
| 0293 | | |
| 0293-1 | 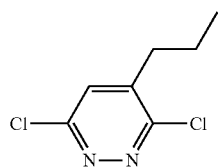 | 1H-NMR(CDCl₃)δ:<br>7.36(1 H, s), 2.70(2H, t, J = 7.8 Hz), 1.79-1.65(2H, m), 1.04(3H, t, J = 7.2 Hz). |
| 0293-2 | 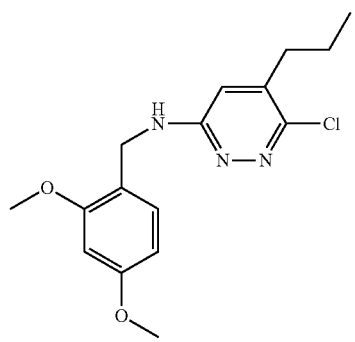 [SMILES: CCCc1cc(NCc2ccc(OC)cc2OC)nnc1Cl] | MSm/z(M + H): 322. |
| 0293-3 | 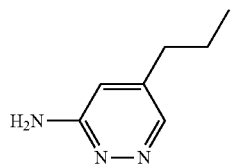 | MSm/z(M + H): 138. |
| 0293-4 | 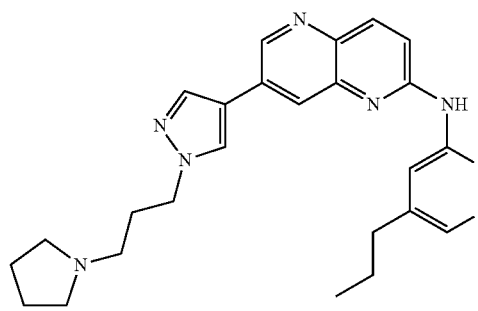 | 1H-NMR(DMSO-d₆)δ:<br>10.69(1 H, s), 9.04(1 H, d, J = 2.0 Hz), 8.79(1 H, d, J = 2.0 Hz), 8.69<br>(1 H, s), 8.51(1 H, s), 8.25(1 H, d, J = 1.3 Hz), 8.21(1 H, d, J = 9.2<br>Hz), 8.19(1 H, s), 7.68(1 H, d, J = 9.2 Hz), 4.22(2H, t, J = 6.9 Hz),<br>2.69(2H, t, J = 7.6 Hz), 2.40(6H, t, J = 7.1 Hz), 2.00(2H, dd, J = 9.1,<br>5.1 Hz), 1.76-1.67(6H, m), 0.99(3H, t, J = 7.4 Hz).<br>MSm/z(M + H): 443. |
| 0294 | | |
| 0294-1 | 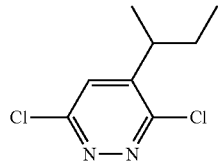 | 1H-NMR(CDCl₃)δ:<br>7.34(1 H, s), 3.07(1 H, td, J = 13.7, 6.9 Hz), 1.78-<br>1.54(2H, m), 1.28(3H, d, J = 6.9 Hz), 0.94(3H, t, J = 7.4 Hz). |

-continued
| Example No. | | |
|---|---|---|
| 0294-2 | 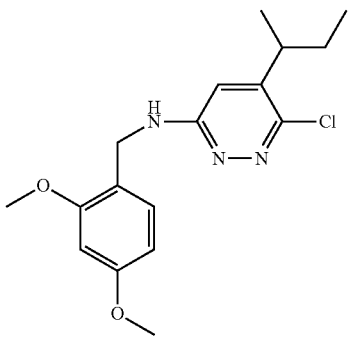 [SMILES: CCC(C)c1cc(NCc2ccc(OC)cc2OC)nnc1Cl] | MS m/z(M + H): 336. |
| 0294-3 | 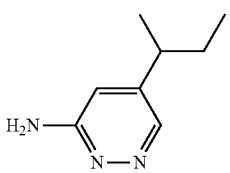 | MS m/z(M + H): 152. |
| 0294-4 | 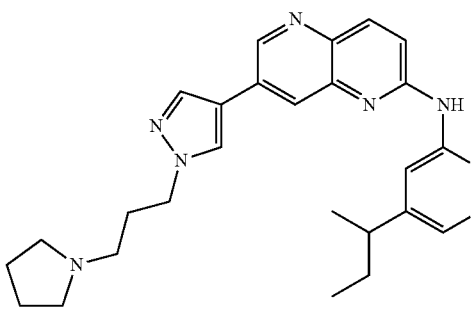 | 1H-NMR(DMSO-d$_6$)δ:<br>10.69(1 H, s), 9.04(1 H, d, J = 2.0 Hz), 8.82(1 H, d, J = 2.0 Hz), 8.68<br>(1 H, d, J = 1.7 Hz), 8.50(1 H, s), 8.21(3H, dd, J = 8.1, 5.8 Hz), 7.70<br>(1 H, d, J = 9.2 Hz), 4.22(2H, t, J = 6.9 Hz), 2.81-2.73(1 H, m), 2.46-<br>2.37(6H, m), 2.04-1.96(2H, m), 1.74-<br>1.65(6H, m), 1.32(3H, d, J = 6.9 Hz), 0.88(3H, t, J = 7.3 Hz).<br>MS m/z(M + H): 457. |
Example 0295
0295-1 and 0295-2
The following compounds were obtained in the same manner as in Examples 0015-1 and 0015-2.
| Example No. | | |
|---|---|---|
| 0295 | | |
| 0295-1 | 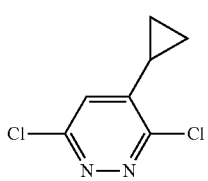 [SMILES: Clc1cc(C2CC2)c(Cl)nn1] | 1H-NMR(CDCl$_3$)δ:<br>6.94(1 H, s), 2.25-2.17(1 H, m), 1.34-1.27(2H, m), 0.90-0.83(2H, m). |

| Example No. | | |
|---|---|---|
| 0295-2 | 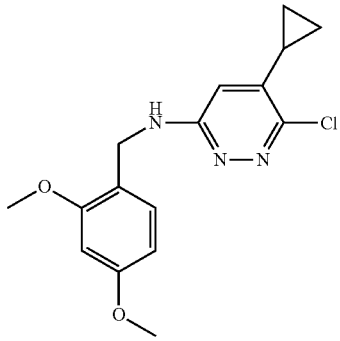 [SMILES: COc1ccc(CNc2cc(C3CC3)c(Cl)nn2)c(OC)c1] | MSm/z(M + H): 320. |

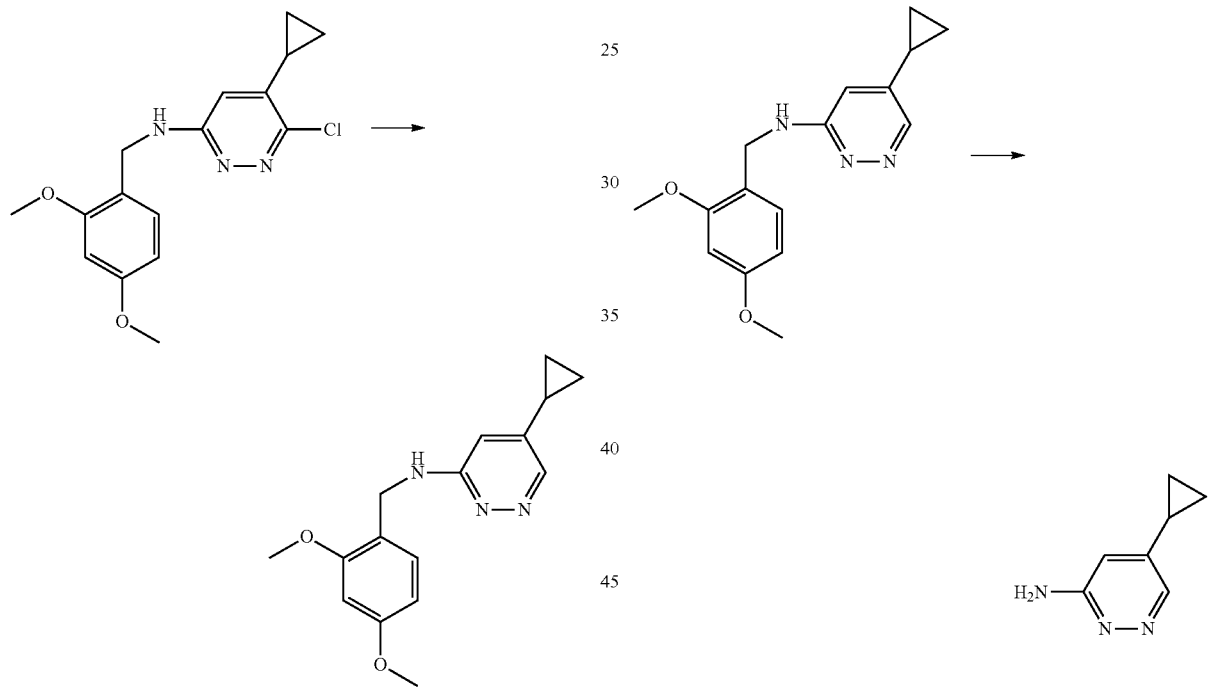

0295-3

0295-4

Ammonium formate (120 mg), triethylamine (200 μL), and tetrakis(triphenylphosphine)palladium(0) (50 mg) were added to a solution of 6-chloro-5-cyclopropyl-N-(2,4-dimethoxybenzyl)pyridazine-3-amine (300 mg) in 1,4-dioxane (1.2 mL), followed by stirring at 100° C. for 3 hours in a nitrogen atmosphere. The reaction mixture was cooled to room temperature, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-methanol, NH silica), thereby obtaining 5-cyclopropyl-N-(2,4-dimethoxybenzyl)pyridazine-3-amine (235 mg).

MSm/z(M+H):286.

Trifluoroacetic acid (3 mL) was added to 5-cyclopropyl-N-(2,4-dimethoxybenzyl)pyridazine-3-amine (235 mg), followed by stirring at room temperature for 30 minutes. The solvent was distilled off under reduced pressure, the resultant product was neutralized with a saturated sodium hydrogen carbonate aqueous solution, and chloroform was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (chloroform-methanol, NH silica), thereby obtaining 5-cyclopropylpyridazine-3-amine (105 mg).

MSm/z(M+H):136.

0295-5

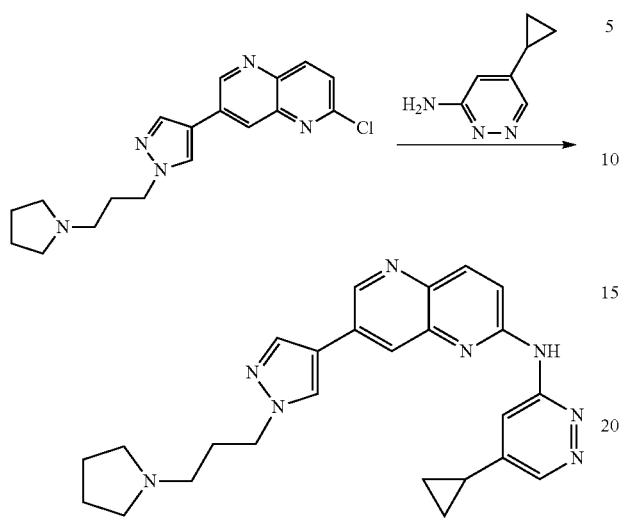

N-(5-cyclopropylpyridazin-3-yl)-7-(1-(3-(pyrrolidin-1-yl)propyl)-1H-pyrazol-4-yl)-1,5-naphthyridine-2-amine was obtained in the same manner as in Examples 0015-1 and 0015-2.

$^1$H-NMR(DMSO-d$_6$)δ:10.63(1H,s),9.04(1H,d,J=2.3 Hz), 8.64(1H,d,J=2.0 Hz),8.60(1H,d,J=2.0 Hz),8.51(1H,s),8.25 (1H,d,J=1.7 Hz),8.20(2H,d,J=9.2 Hz),7.66(1H,d,J=9.2 Hz), 4.22(2H,t,J=6.9 Hz),2.47-2.38(6H,m),2.13-1.97(3H,m), 1.73-1.64(4H,m),1.23-1.17(2H,m),1.04-0.96(2H,m).

MSm/z(M+H):441.

Example 0296

The following compounds were obtained in the same manner as in Examples 0015-1 to 0015-4.

| Example No. | | |
|---|---|---|
| 0296 | | |
| 0296-1 | 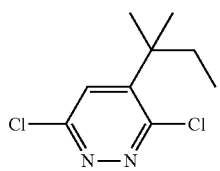 | 1H-NMR(CDCl$_3$)δ: 7.42(1 H, s), 2.06-1.97(2H, m), 1.45(6H, d, J = 3.3 Hz), 0.74-0.66 (3H, m). |
| 0296-2 | 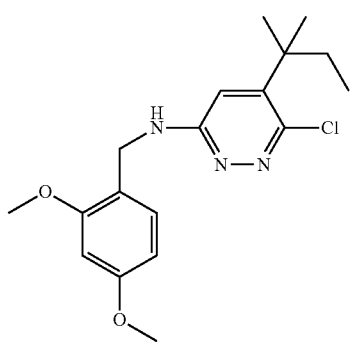 [SMILES: CCC(C)(C)c1cc(NCc2ccc(OC)cc2OC)nnc1Cl] | MSm/z(M + H): 350. |
| 0296-3 | 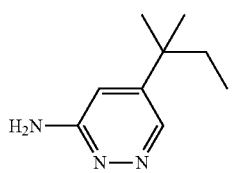 | MSm/z(M + H): 166. |

| Example No. | | |
|---|---|---|
| 0296-4 | 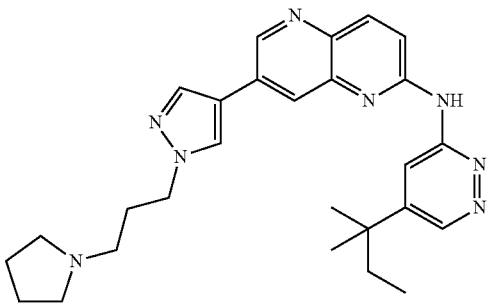 [SMILES: CCC(C)(C)c1cnnc(Nc2ccc3ncc(-c4cnn(CCCN5CCCC5)c4)cc3n2)c1] | 1H-NMR(DMSO-d$_6$)δ:<br>10.68(1 H, s), 9.04(1 H, d, J = 2.0 Hz), 8.95(1 H, d, J = 2.0 Hz), 8.72(1 H, d, J = 2.0 Hz), 8.49(1 H, s), 8.23(1 H, d, J = 9.2 Hz), 8.16(1 H, s), 8.09(1 H, d, J = 1.3 Hz), 7.76(1 H, d, J = 9.2 Hz), 4.22(2H, t, J = 7.1 Hz), 2.45-2.37(6H, m), 2.04-1.97(2H, m), 1.79-1.68(6H, m), 1.37(6H, s), 0.74(3H, t, J = 7.4 Hz).<br>MSm/z(M + H): 471. |

Example 0297

0297-1

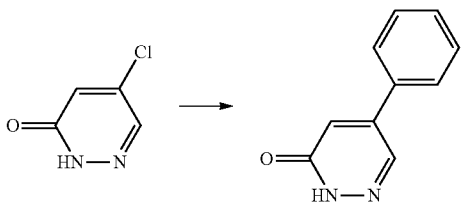 [SMILES: O=c1cc(Cl)cn[nH]1 ; O=c1cc(-c2ccccc2)cn[nH]1]

Phenylboronic acid (60 mg), bis(di-tert-butyl(4-dimethylaminophenyl)phosphine)dichloropalladium(II) (5 mg), and a 2 mol/L sodium carbonate aqueous solution (50 µL) were added to a solution of 5-chloropyridazin-3(2H)-one (50 mg) in 1,4-dioxane (1 mL), followed by stirring at 130° C. for 30 minutes using a microwave reaction apparatus. The reaction mixture was cooled to room temperature, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-methanol, NH silica), thereby obtaining 5-phenylpyridazin-3(2H)-one (25 mg).

$^1$H-NMR(DMSO-d$_6$)δ:13.12(1H,s),8.31(1H,d,J=2.3 Hz), 7.85-7.79(2H,m),7.56-7.51(3H,m),7.14(1H,s).

0297-2

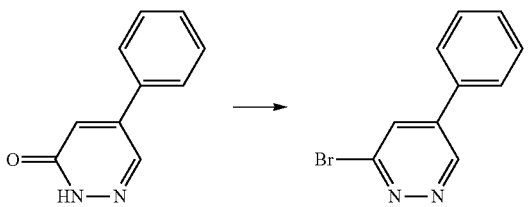 [SMILES: O=c1cc(-c2ccccc2)cn[nH]1 ; Brc1cc(-c2ccccc2)cnn1]

A mixture of 5-phenylpyridazin-3(2H)-one (25 mg) and phosphorous oxybromide (1 g) was stirred at 120° C. for 30 minutes. The reaction mixture was added dropwise to a mixture solution of methanol-water (1:10), the resultant product was neutralized by the addition of a sodium hydroxide aqueous solution, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate), thereby obtaining 3-bromo-5-phenylpyridazine (25 mg).

$^1$H-NMR(CDCl$_3$)δ:9.40(1H,d,J=2.0 Hz),7.85(1H,d,J=2.0 Hz),7.69-7.64(2H,m),7.61-7.53(3H,m).

0297-3

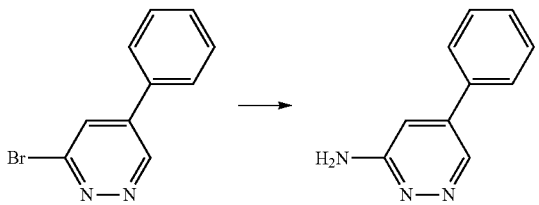 [SMILES: Brc1cc(-c2ccccc2)cnn1 ; Nc1cc(-c2ccccc2)cnn1]

25% ammonia water (1 mL) and copper(I) oxide (10 mg) were added to a solution of 3-bromo-5-phenylpyridazine (60 mg) in ethylene glycol (1 mL), followed by stirring at 150° C. for 45 minutes using a microwave reaction apparatus. The reaction mixture was cooled to room temperature, neutralized with 2 mol/L hydrochloric acid, and the resultant product was extracted three times with ethyl acetate. The organic layers were combined, washed with a saturated sodium chloride aqueous solution, and dried over anhydrous sodium sulfate, and the solvent was distilled off under reduced pressure. The obtained residue was purified by silica gel column chromatography (ethyl acetate-methanol, NH silica), thereby obtaining 5-phenylpyridazine-3-amine (45 mg).

MSm/z(M+H):172.

s),7.87(1H,s),7.51(1H,d,J=9.3 Hz),4.31(2H,m),3.73(4H,m), 2.50-2.34(6H,m),2.13(2H,m),2.01(1H,m),1.27(2H,m),1.03 (2H,m).

MSm/z(M+H):457.

Example 0299

0299-1

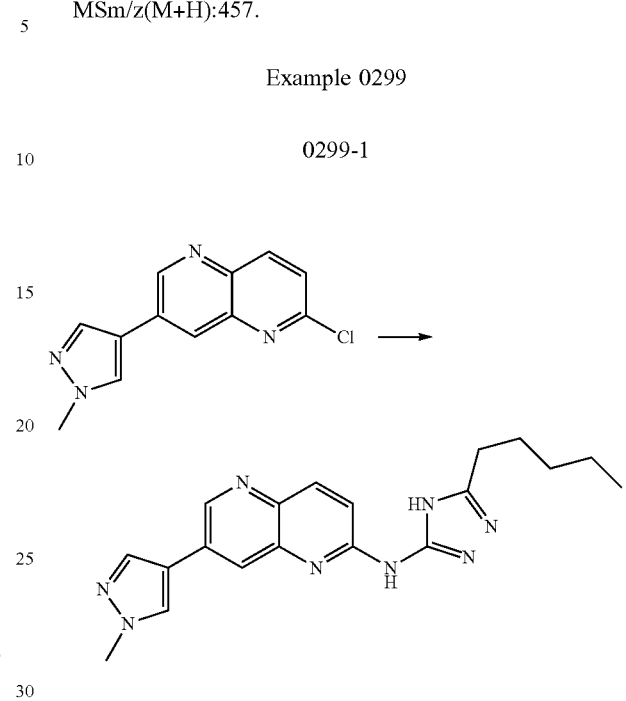

A mixture of 2-chloro-7-(1-methyl-1H-pyrazol-4-yl)-1,5-naphthyridine (45 mg), 5-pentyl-4H-1,2,4-triazole-3-amine (56.7 mg), tris(dibenzylideneacetone)dipalladium(0) (21.2 mg), 2-dicyclohexylphosphino-2',4',6'-triisopropylbiphenyl (35.1 mg), cesium carbonate (120 mg), and 1,4-dioxane (1 mL) was stirred at 100° C. for 2 hours in a nitrogen atmosphere in a sealed tube. The reaction mixture was cooled to room temperature, purified by silica gel column chromatography (chloroform-methanol, NH silica), and purified by preparative thin layer silica gel chromatography (chloroform-methanol), thereby obtaining 7-(1-methyl-1H-pyrazol-4-yl)-N-(5-pentyl-4H-1,2,4-triazol-3-yl)-1,5-naphthyridine-2-amine (4.5 mg) as a yellow solid.

$^1$H-NMR(DMSO-d$_6$)δ:13.16(1H,s),11.19(1H,s),9.00(1H, d,J=1.7 Hz),8.79(1H,d,J=1.7 Hz),8.36(1H,s),8.18(1H,d, J=9.2 Hz),8.04(1H,s),7.28(1H,d,J=9.2 Hz),3.94(3H,s),2.58 (2H,t,J=7.6 Hz),1.78-1.60(2H,m),1.42-1.25(4H,m),0.97-0.80(3H,m).

MSm/z(M+H):363.

Example 0300

0300-1

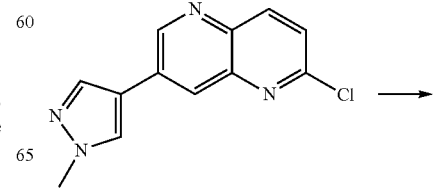

0297-4

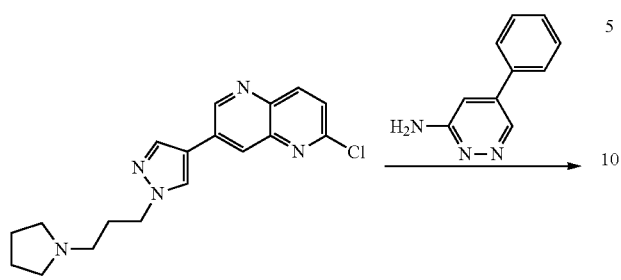

N-(5-phenylpyridazin-3-yl)-7-(1-(3-(pyrrolidin-1-yl)propyl)-1H-pyrazol-4-yl)-1,5-naphthyridine-2-amine was obtained in the same manner as in Example 0015-4.

$^1$H-NMR(DMSO-d$_6$)δ:10.87(1H,s),9.28(1H,d,J=2.0 Hz), 9.06(2H,d,J=2.0 Hz),8.52(1H,s),8.24(3H,dd,J=9.9,8.3 Hz), 7.97(2H,dd,J=8.3,1.3 Hz),7.74(1H,d,J=9.2 Hz),7.68-7.58 (3H,m),4.21(2H,t,J=6.9 Hz),2.45-2.36(6H,m),2.05-1.95 (2H,m),1.70-1.66(4H,m).

MSm/z(M+H):477.

Example 0298

0298-1

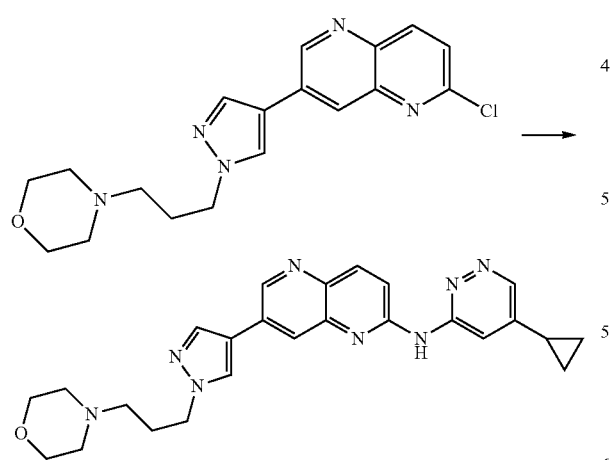

N-(5-cyclopropylpyridazin-3-yl)-7-(1-(3-morpholinopropyl)-1H-pyrazol-4-yl)-1,5-naphthyridine-2-amine was obtained as a white solid in the same manner as in Example 0015-4.

$^1$H-NMR(CDCl$_3$)δ:8.93(1H,d,J=1.8 Hz),8.88(1H,brs), 8.68-8.62(2H,m),8.23(1H,d,J=9.3 Hz),8.09(1H,m),7.97(1H,

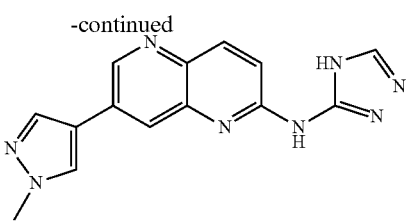

7-(1-Methyl-1H-pyrazol-4-yl)-N-(4H-1,2,4-triazol-3-yl)-1,5-naphthyridine-2-amine was obtained as a yellow solid in the same manner as in Example 0299-1.

$^1$H-NMR(DMSO-d$_6$)δ:13.56(1H,s),11.28(1H,s),9.02(1H,d,J=2.0 Hz),8.83(1H,d,J=2.0 Hz),8.36(1H,s),8.20(1H,d,J=8.6 Hz),8.05(1H,s),7.78(1H,d,J=1.3 Hz),7.32(1H,d,J=8.6 Hz),3.94(3H,s).

MSm/z(M+H):293.

Examples 0301 and 0302

The following compounds were obtained in the same manner as in Examples 0001-4 and 0001-5.

| Example No. | | |
|---|---|---|
| 0301 | | |
| 0301-1 | 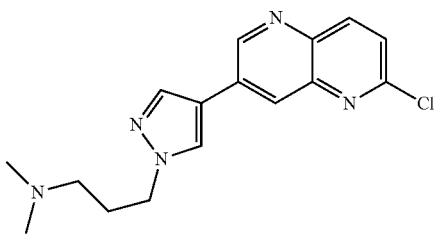 [SMILES: CN(C)CCCn1cc(-c2cnc3ccc(Cl)nc3c2)cn1] | 1H-NMR(DMSO-d$_6$)δ:<br>9.35(1 H, d, J = 2.0 Hz), 8.59(1 H, s), 8.54(1 H, d, J = 2.0 Hz), 8.43(1 H, d, J = 8.9 Hz), 8.26(1 H, s), 7.75(1 H, d, J = 8.9 Hz), 4.19(2H, t, J = 6.9 Hz), 2.22(2H, t, J = 6.9 Hz), 2.14(6H, s), 2.05-1.87(2H, m). |
| 0301-2 | 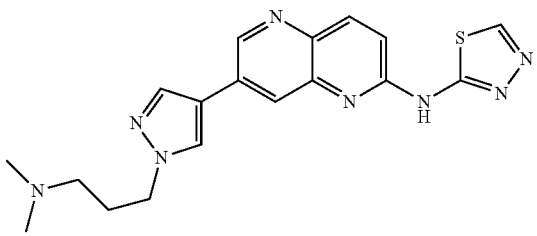 [SMILES: CN(C)CCCn1cc(-c2cnc3ccc(Nc4nncs4)nc3c2)cn1] | 1H-NMR(DMSO-d$_6$)δ:<br>12.23(1 H, brs), 9.17(1 H, s), 9.10(1 H, d, J = 2.0 Hz), 8.57(1 H, s), 8.34(1 H, d, J = 2.0 Hz), 8.28(1 H, d, J = 8.6 Hz), 8.21(1 H, s),<br>7.44(1 H, d, J = 8.6 Hz), 4.19(2H, t, J = 6.9 Hz), 2.22(2H, t, J = 6.9 Hz), 2.14(6H, s), 2.05-1.89(2H, m).<br>MSm/z(M + H): 381. |
| 0302 | | |
| 0302-1 | 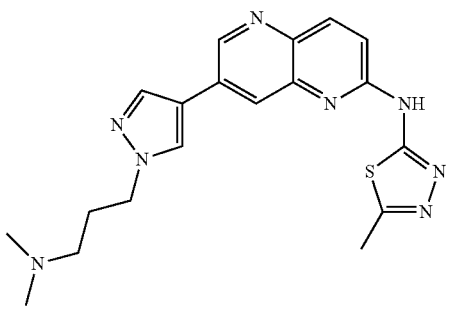 [SMILES: Cc1nnc(Nc2ccc3ncc(-c4cnn(CCCN(C)C)c4)cc3n2)s1] | 1H-NMR(DMSO-d$_6$)δ:<br>12.03(1 H, brs), 9.08(1 H, d, J = 2.0 Hz), 8.58(1 H, s), 8.33(1 H, d, J = 2.0 Hz), 8.25(1 H, d, J = 8.9 Hz), 8.22(1 H, s), 7.39(1 H, d,<br>J = 8.9 Hz), 4.19 (2H, t, J = 6.9 Hz), 2.66(3H, s), 2.22(2H, t, J = 6.9 Hz), 2.15(6H, s), 2.05-1.89(2H, m).<br>MSm/z(M + H): 395. |

Example 0303

0303-1

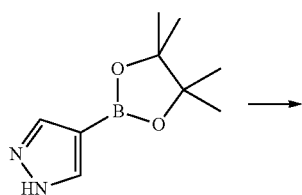

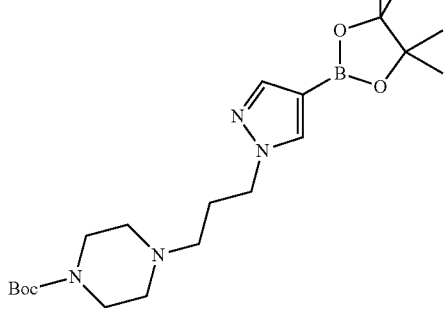

A mixture of 4-(4,4,5,5-tetramethyl-1,3,2-dioxaborolan-2-yl)-1H-pyrazole (0.473 g), tert-butyl 4-(3-bromopropyl)piperazine-1-carboxylate (0.818 g), potassium carbonate (0.61 g), and N,N-dimethylformamide (5 mL) was stirred at 80° C. for 3 hours in a nitrogen atmosphere. After the reaction mixture was cooled to room temperature, diisopropyl ether was added thereto, the solid matter was filtered off, and the solvent was distilled off under reduced pressure. The obtained residue was purified by silica gel column chromatography (chloroform-methanol), thereby obtaining tert-butyl 4-(3-(4-(4,4,5,5-tetramethyl-1,3,2-dioxaborolan-2-yl)-1H-pyrazol-1-yl)propyl)piperazine-1-carboxylate (0.78 g) as yellow oily substance.

$^1$H-NMR(CDCl$_3$)δ:7.56(1H,s),7.45(1H,s),4.19(2H,t,J=6.9 Hz),3.49-3.33(4H,m),2.44-2.26(6H,m),2.13-1.93(2H,m),1.51-1.37(21H,m).

0303-2

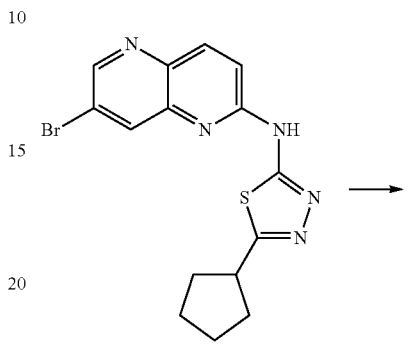

60% sodium hydride (40 mg) was added to a solution of N-(7-bromo-1,5-naphthyridin-2-yl)-5-cyclopentyl-1,3,4-thiadiazole-2-amine (0.25 g) and 2-(chloromethoxy)ethyltrimethylsilane (125 mg) in N-methylpyrrolidone (32 mL) under ice-cooling, followed by stirring at the same temperature for 1 hour, and stirring at room temperature for 1 hour. Ethyl acetate and water were added to the reaction mixture. The organic layer was collected by separation, washed with a saturated sodium chloride aqueous solution, and dried over anhydrous sodium sulfate. The obtained solution was purified by silica gel column chromatography (ethyl acetate-hexane), thereby obtaining N-(7-bromo-1,5-naphthyridin-2-yl)-5-cyclopentyl-N-((2-(trimethylsilyl)ethoxy)methyl)-1,3,4-thiadiazole-2-amine (601 mg) and (Z)-7-bromo-N-(5-cyclopentyl-3-((2-(trimethylsilyl)ethoxy)methyl)-1,3,4-thiadiazol-2(3H)-ylidene)-1,5-naphthyridine-2-amine (255 mg).

MS m/z(M+H):506,508, 506,508.

0303-3

A mixture of a mixture (30 mg) of N-(7-bromo-1,5-naphthyridin-2-yl)-5-cyclopentyl-N-((2-(trimethylsilyl)ethoxy)methyl)-1,3,4-thiadiazole-2-amine and (Z)-7-bromo-N-(5-cyclopentyl-3-((2-(trimethylsilyl)ethoxy)methyl)-1,3,4-thiadiazol-2(3H)-ylidene)-1,5-naphthyridine-2-amine, tert-butyl 4-(3-(4-(4,4,5,5-tetramethyl-1,3,2-dioxaborolan-2-yl)-1H-pyrazol-1-yl)propyl)piperazine-1-carboxylate (29.9 mg), bis(di-tert-butyl(4-dimethylaminophenyl)phosphine)dichloropalladium (II) (4.2 mg), sodium carbonate (12.5 mg), 1,4-dioxane (1 mL), and water (0.1 mL) was stirred at 100° C. for 4 hours in a nitrogen atmosphere in a sealed tube. The reaction mixture was cooled to room temperature, and purified by silica gel column chromatography (chloroform-methanol, NH silica), thereby obtaining a mixture (29.8 mg) of tert-butyl 4-(3-(4-(6-((5-cyclopentyl-1,3,4-thiadiazol-2-yl)((2-(trimethylsilyl)ethoxy)methyl)amino)-1,5-naphthyridin-3-yl)-1H-pyrazol-1-yl)propyl)piperazine-1-carboxylate and (Z)-tert-butyl 4-(3-(4-(6-((5-cyclopentyl-3-((2-(trimethylsilyl)ethoxy)methyl)-1,3,4-thiadiazol-2(3H)-ylidene)amino)-1,5-naphthyridin-3-yl)-1H-pyrazol-1-yl)propyl)piperazine-1-carboxylate as yellow oily substance.

A 4 mol/L hydrogen chloride/1,4-dioxane solution (1 mL) was added to a solution of the obtained mixture (29.8 mg) in methanol (1 mL) at room temperature, followed by stirring for 2 hours. The solvent was distilled off under reduced pressure, methanol and a saturated sodium hydrogen carbonate aqueous solution were added to the obtained residue in order to neutralize, and the water was distilled off under reduced pressure. The obtained residue was purified by silica gel column chromatography (chloroform-methanol, NH silica), thereby obtaining 5-cyclopentyl-N-(7-(1-(3-(piperazin-1-yl)propyl)-1H-pyrazol-4-yl)-1,5-naphthyridin-2-yl)-1,3,4-thiadiazole-2-amine (5.9 mg) as a yellow solid.

$^1$H-NMR(DMSO-$d_6$)δ:9.07(1H,d,J=2.3 Hz),8.57(1H,s),8.32(1H,d,J=2.3 Hz),8.28-8.20(2H,m),7.39(1H,d,J=9.2 Hz),4.20(2H,t,J=6.9 Hz),3.60-3.35(1H,m),2.69(4H,t,J=4.6 Hz),2.38-1.61(16H,m).

MSm/z(M+H):490.

Example 0304
0304-1
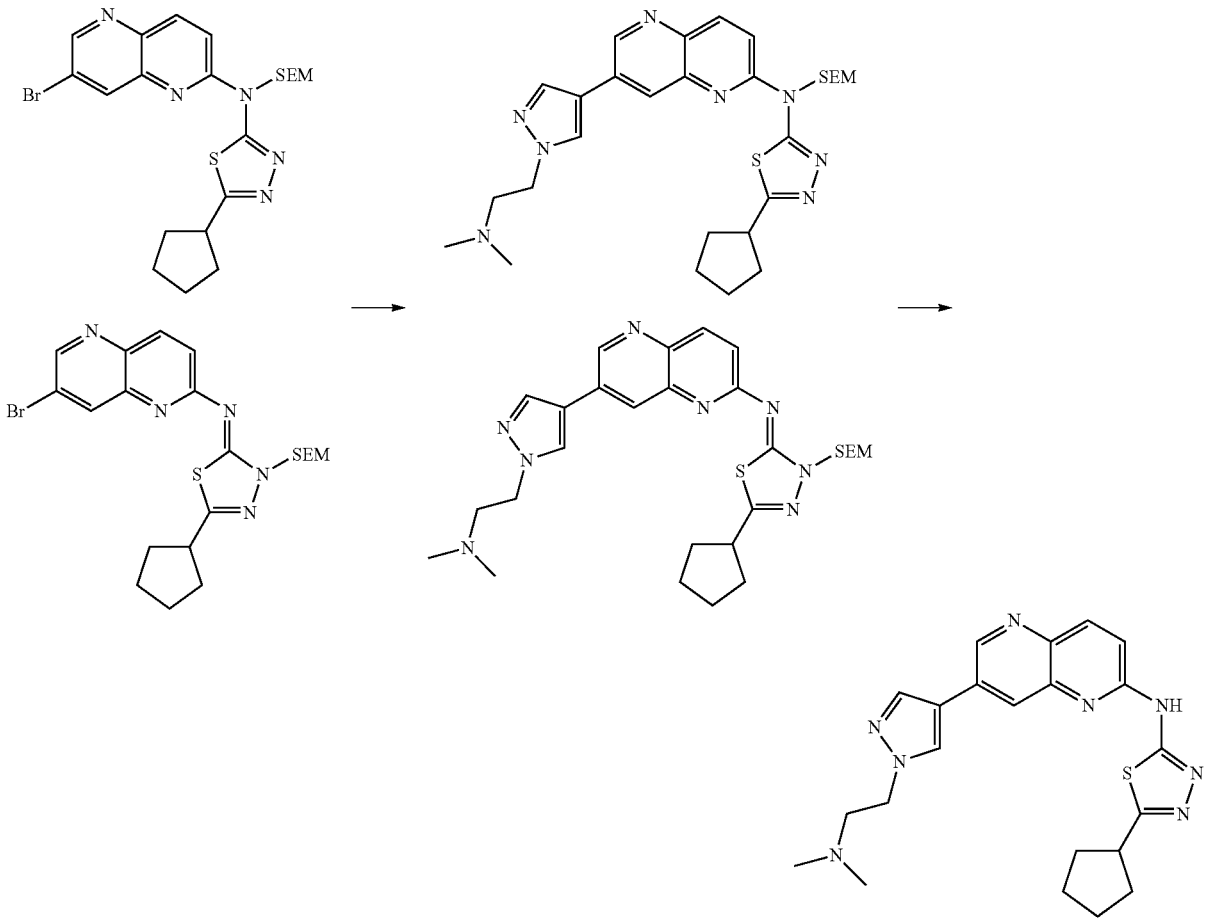
d,J=9.2 Hz),4.26(2H,t,J=6.3 Hz),3.55-3.40(1H,m),2.72(2H,
t,J=6.6 Hz),2.31-2.06(8H,m),1.98-1.59(6H,m).
MSm/z(M+H):435.
5-Cyclopentyl-N-(7-(1-(2-(dimethylamino)ethyl)-1H-pyrazol-4-yl)-1,5-naphthyridin-2-yl)-1,3,4-thiadiazole-2-amine was obtained as a yellow solid in the same manner as in Example 0303-3.
$^1$H-NMR(DMSO-d$_6$)δ:12.05(1H,s),9.07(1H,d,J=2.0 Hz), 8.57(1H,s),8.32(1H,d,J=2.0 Hz),8.29-8.19(2H,m),7.39(1H,
Example 0305 and 0305-2
The following compounds were obtained in the same manner as in Examples 0001-4 and 0001-5.
| Example No. | | |
|---|---|---|
| 0305 | | |
| 0305-1 | 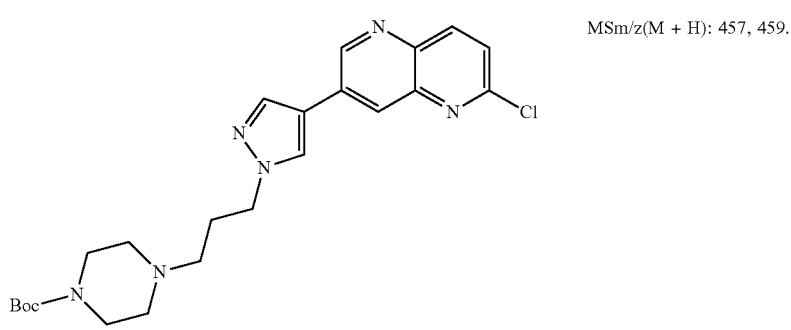 | MSm/z(M + H): 457, 459. |

| Example No. | |
|---|---|
| 0305-2 | MSm/z(M + H): 522. |

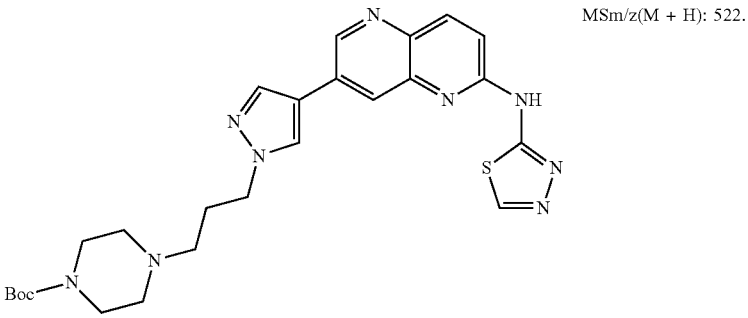

0305-3

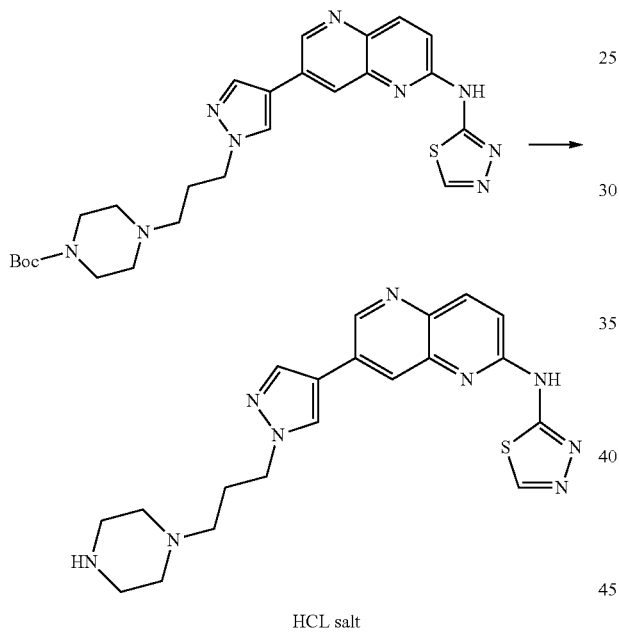

HCL salt

A 4 mol/L hydrogen chloride/1,4-dioxane solution (1 mL) was added to a solution of tert-butyl 4-(3-(4-(6-((1,3,4-thiadiazol-2-yl)amino)-1,5-naphthyridin-3-yl)-1H-pyrazol-1-yl)propyl)piperazine-1-carboxylate (59.8 mg) in methanol (1 mL) at room temperature, followed by stirring for 2 hours. The solid matter was collected by filtration, and washed with methanol, thereby obtaining N-(7-(1-(3-(piperazin-1-yl)propyl)-1H-pyrazol-4-yl)-1,5-naphthyridin-2-yl)-1,3,4-thiadiazole-2-amine hydrochloride (38.4 mg) as a yellow solid.

$^1$H-NMR(DMSO-$d_6$)δ:9.46(2H,brs),9.20(1H,s),9.14(1H,d,J=2.0 Hz),8.63(1H,s),8.40(1H,d,J=2.0 Hz),8.35-8.25(2H,m),7.48(1H,d,=8.6 Hz),4.32(2H,t,J=6.6 Hz),3.84-3.09(10H,m),2.43-2.22(2H,m).

MSm/z(M+H):422.

Example 0306

0306-1

70% meta-chloroperoxybenzoic acid (200 mg) was added to a solution of 2-chloro-7-(1-methyl-1H-pyrazol-4-yl)-1,5-naphthyridine (200 mg) in dichloromethane (4 mL) at room temperature, followed by stirring at room temperature for 30 minutes. 70% meta-chloroperoxybenzoic acid (200 mg) was added thereto, followed by stirring at room temperature for 30 minutes. 70% meta-chloroperoxybenzoic acid (200 mg) was added thereto, followed by stirring at room temperature for 30 minutes, and 70% meta-chloroperoxybenzoic acid (400 mg) was added thereto, followed by stirring at room temperature for 1 hour. A saturated sodium hydrogen carbonate aqueous solution and sodium sulfite were added to the reaction mixture, and ethyl acetate was added thereto. The organic layer was collected by separation, washed with a saturated sodium hydrogen carbonate aqueous solution and a saturated sodium chloride aqueous solution, and dried over anhydrous sodium sulfate, and the solvent was distilled off under reduced pressure, thereby obtaining 6-chloro-3-(1-methyl-1H-pyrazol-4-yl)-1,5-naphthyridine 1-oxide (240 mg) as a yellow solid.

MSm/z(M+H):261,263.

0306-2

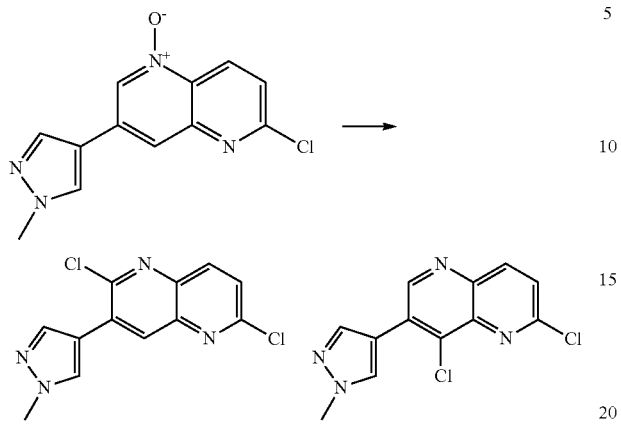

Phosphorus oxychloride (2 mL) was added to 6-chloro-3-(1-methyl-1H-pyrazol-4-yl)-1,5-naphthyridine 1-oxide (240 mg), followed by stirring at 100° C. for 30 minutes. The reaction mixture was cooled to room temperature, and added dropwise to water. The resultant product was neutralized by the addition of sodium carbonate, and ethyl acetate was added thereto. The organic layer was collected by separation, washed with a saturated sodium chloride aqueous solution, and dried over anhydrous sodium sulfate, and the solvent was distilled off under reduced pressure, thereby obtaining a mixture (210 mg) of 2,6-dichloro-3-(1-methyl-1H-pyrazol-4-yl)-1,5-naphthyridine and 2,8-dichloro-7-(1-methyl-1H-pyrazol-4-yl)-1,5-naphthyridine as a yellow solid.

MSm/z(M+H):279,281.

0306-3

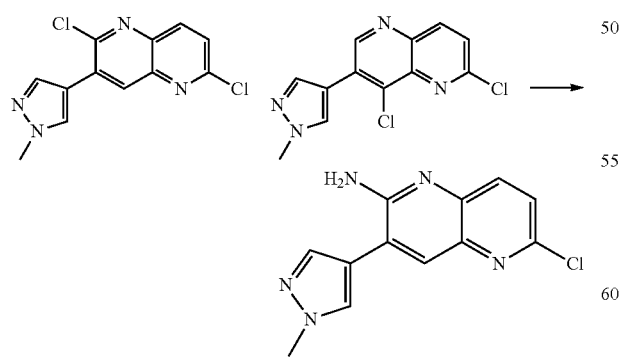

A mixture of a mixture (200 mg) of 2,6-dichloro-3-(1-methyl-1H-pyrazol-4-yl)-1,5-naphthyridine and 2,8-dichloro-7-(1-methyl-1H-pyrazol-4-yl)-1,5-naphthyridine,1, 4-dioxane (5 mL) and a 25% ammonia aqueous solution (5 mL) was stirred at 120° C. for 2 hours, and stirred at 140° C. for 2 hours using a microwave reaction apparatus. The reaction mixture was cooled to room temperature, and the solvent was distilled off under reduced pressure. The obtained residue was purified by silica gel column chromatography (chloroform-methanol, NH silica), thereby obtaining 6-chloro-3-(1-methyl-1H-pyrazol-4-yl)-1,5-naphthyridine-2-amine (46.9 mg) as a white solid.

MSm/z(M+H):260,262.

0306-4

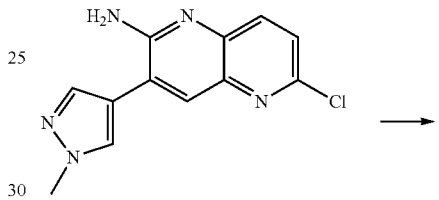

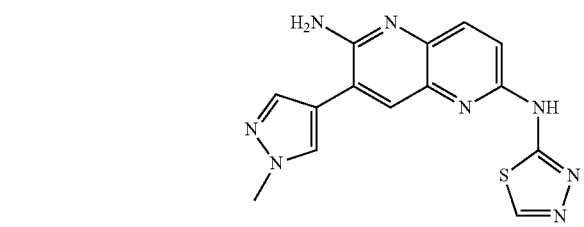

7-(1-methyl-1H-pyrazol-4-yl)-N²-(1,3,4-thiadiazol-2-yl)-1,5-naphthyridine-2,6-diamine was obtained as a yellow solid in the same manner as in Example 0001-5.

$^1$H-NMR(DMSO-d$_6$)δ:11.82(1H,s),9.03(1H,s),8.20(1H,s),7.94-7.79(3H,m),7.30(1H,d,J=9.2 Hz),6.13(2H,brs),3.92(3H,s).

MSm/z(M+H):325.

Examples 0307 to 0310

The following compounds were obtained in the same manner as in Examples 0053-1 and 0053-2.

| Example No. | | |
|---|---|---|
| 0307 | | |
| 0307-1 | 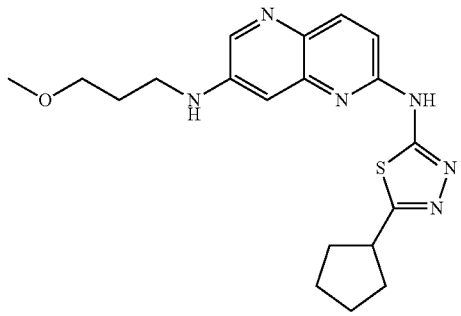 [SMILES: COCCCNc1cnc2ccc(Nc3nnc(C4CCCC4)s3)nc2c1] | 1H-NMR(DMSO-d$_6$)δ:<br>11.75(1 H, brs), 8.30(1 H, d, J = 2.6 Hz), 8.01(1 H, d, J = 8.9 Hz), 7.03 (1 H, d, J = 8.9 Hz), 6.92(1 H, d, J = 2.6 Hz), 6.61(1 H, d, J = 5.3 Hz),<br>3.54-3.39(3H, m), 3.29(3H, s), 3.27-3.15(2H, m), 2.22-2.04(2H, m), 1.94-1.60(8H, m).<br>MSm/z(M + H): 385. |
| 0308 | | |
| 0308-1 | 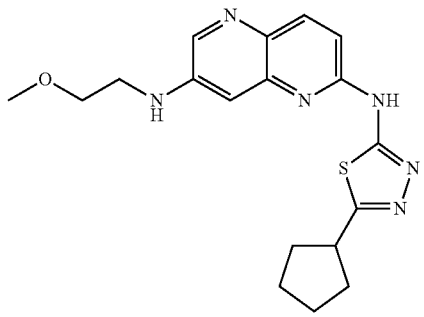 [SMILES: COCCNc1cnc2ccc(Nc3nnc(C4CCCC4)s3)nc2c1] | 1H-NMR(DMSO-d$_6$)δ:<br>11.75(1 H, brs), 8.36(1 H, d, J = 2.3 Hz), 8.01(1 H, d, J = 9.2 Hz), 7.03 (1 H, d, J = 9.2 Hz), 6.96(1 H, d, J = 2.3 Hz), 6.63(1 H, t, J = 5.3 Hz),<br>3.59(2H, t, J = 5.6 Hz), 3.53-3.41(1 H, m), 3.40-3.27(5H, m), 2.23-2.03(2H, m), 1.95-1.59(6H, m).<br>MSm/z(M + H): 371. |
| 0309 | | |
| 0309-1 | 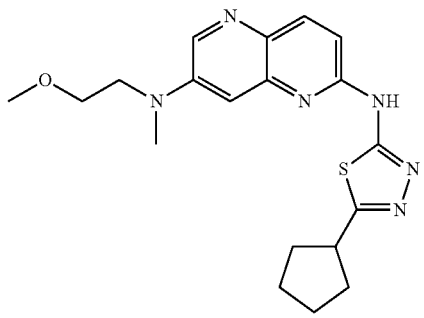 [SMILES: COCCN(C)c1cnc2ccc(Nc3nnc(C4CCCC4)s3)nc2c1] | 1H-NMR(DMSO-d$_6$)δ:<br>11.79(1 H, s), 8.55(1 H, d, J = 2.6 Hz), 8.05(1 H, d, J = 8.6 Hz), 7.13-7.05(2H, m), 3.73(2H, t, J = 5.3 Hz), 3.57(2H, t, J = 5.3 Hz), 3.53-3.39(1 H, m), 3.26(3H, s), 3.09(3H, s), 2.22-2.04(2H, m), 1.93-1.56(6H, m).<br>MSm/z(M + H): 385. |
| 0310 | | |
| 0310-1 | 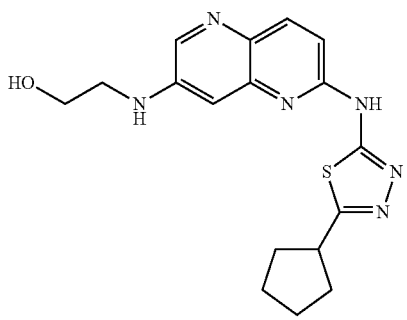 [SMILES: OCCNc1cnc2ccc(Nc3nnc(C4CCCC4)s3)nc2c1] | 1H-NMR(DMSO-d$_6$)δ:<br>11.73(1 H, brs), 8.34(1 H, d, J = 2.6 Hz), 8.00(1 H, d, J = 8.6 Hz), 7.03 (1 H, d, J = 8.6 Hz), 6.94(1 H, d, J = 2.6 Hz), 6.59(1 H, t, J = 5.6 Hz),<br>4.83(2H, t, J = 5.6 Hz), 3.65(2H, dt, J = 5.6, 5.6 Hz), 3.53-3.39(1 H, m), 2.24-2.03(2H, m), 1.96-1.54(6H, m).<br>MSm/z(M + H): 357. |

Example 0311

0311-1

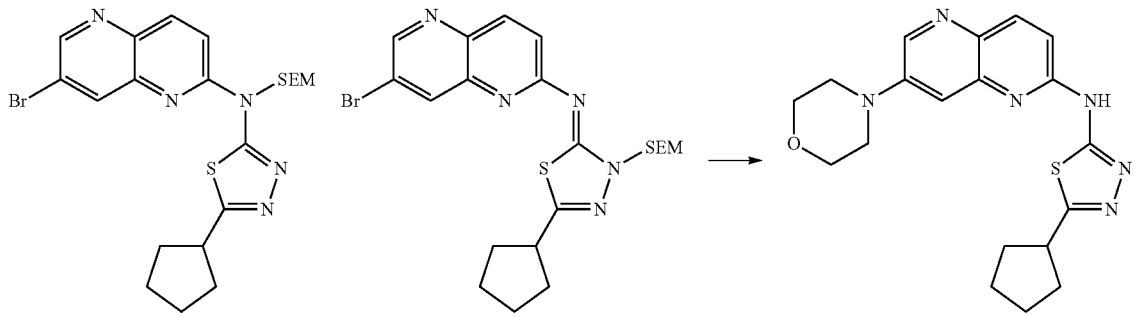 [SMILES: C[Si](C)(C)CCOCN(c1ccc2ncc(Br)cc2n1)c1nnc(C2CCCC2)s1 ; C[Si](C)(C)CCOCn1nc(C2CCCC2)s/c1=N\c1ccc2ncc(Br)cc2n1 ; c1nc2ccc(Nc3nnc(C4CCCC4)s3)nc2cc1N1CCOCC1]

A mixture of a mixture (20 mg) of N-(7-bromo-1,5-naphthyridin-2-yl)-5-cyclopentyl-N-((2-(trimethylsilyl)ethoxy)methyl)-1,3,4-thiadiazole-2-amine and (Z)-7-bromo-N-(5-cyclopentyl-3-((2-(trimethylsilyl)ethoxy)methyl)-1,3,4-thiadiazol-2(3H)-ylidene)-1,5-naphthyridine-2-amine, morpholine (6.9 μL), tris(dibenzylideneacetone)dipalladium(0) (2.3 mg), 2-dicyclohexylphosphino-2',4',6'-triisopropylbiphenyl (3.8 mg), sodium tert-butoxide (7.6 mg), and 1,4-dioxane (1 mL) was stirred at 100° C. for 4.5 hours in a nitrogen atmosphere in a sealed tube. The reaction mixture was cooled to room temperature, and methanol (1 mL) and a 4 mol/L hydrogen chloride/1,4-dioxane solution (1 mL) were added thereto, followed by stirring at 40° C. for 15 hours. The reaction mixture was cooled to room temperature, and the solvent was distilled off under reduced pressure. Methanol and triethylamine were added to the obtained residue, and the solvent was distilled off under reduced pressure. The obtained residue was purified by silica gel column chromatography (chloroform-methanol, NH silica), thereby obtaining 5-cyclopentyl-N-(7-morpholino-1,5-naphthyridin-2-yl)-1,3,4-thiadiazole-2-amine (9.0 mg) as a yellow solid.

$^1$H-NMR(DMSO-d$_6$)δ:11.88(1H,brs),8.72(1H,d,J=2.6 Hz),8.13(1H,d,J=9.2 Hz),7.38(1H,d,J=2.6 Hz),7.20(1H,d,J=9.2 Hz),3.87-3.75(4H,m),3.52-3.28(5H,m),2.22-2.06(2H,m),1.94-1.61(6H,m).

MS m/z(M+H):383.

Examples 0312 to 0314

The following compounds were obtained in the same manner as in Example 0311-1.

| Example No. | | |
|---|---|---|
| 0312 | | |
| 0312-1 | 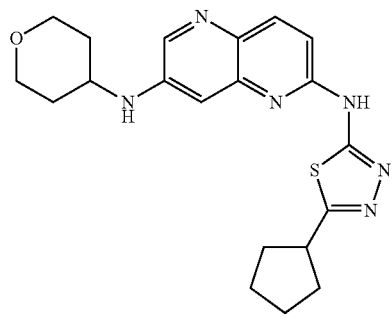 [SMILES: c1nc2ccc(Nc3nnc(C4CCCC4)s3)nc2cc1NC1CCOCC1] | 1H-NMR(DMSO-d$_6$)δ:<br>11.75(1 H, s), 8.32(1 H, d, J = 2.6 Hz), 8.00(1 H, d, J = 9.2 Hz), 7.08-6.99(2H, m), 6.54(1 H, d, J = 7.9 Hz), 3.96-3.83(2H, m), 3.80-3.61(1 H, m), 3.58-3.28 (3H, m), 2.21-2.06(2H, m), 2.03-1.60(8H, m), 1.55-1.36(2H, m).<br>MSm/z(M + H): 397. |
| 0313 | | |
| 0313-1 | 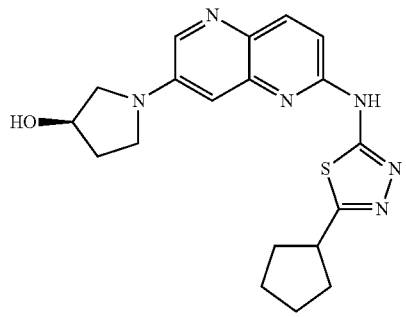 [SMILES: O[C@@H]1CCN(c2cnc3ccc(Nc4nnc(C5CCCC5)s4)nc3c2)C1] | 1H-NMR(DMSO-d$_6$)δ:<br>11.78(1 H, brs), 8.35(1 H, d, J = 2.6 Hz), 8.05(1 H, d, J = 8.6 Hz), 7.06(1 H,<br>d, J = 8.6 Hz), 6.94(1 H, d, J = 2.6 Hz), 5.06(1 H, d, J = 4.0 Hz), 4.52-4.42(1 H, m), 3.66-3.20(5H, m), 2.24-1.57(10H, m).<br>MSm/z(M + H): 383. |

| Example No. | | |
|---|---|---|
| 0314 | | |
| 0314-1 | 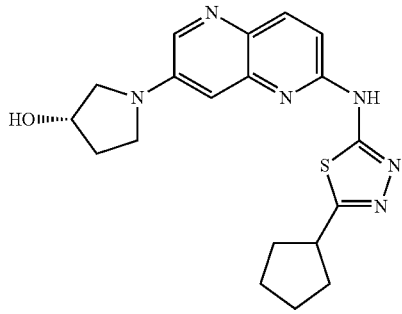 [SMILES: O[C@H]1CCN(c2cnc3ccc(Nc4nnc(C5CCCC5)s4)nc3c2)C1] | 1H-NMR(DMSO-d$_6$)δ:<br>11.78(1 H, brs), 8.35(1 H, d, J = 2.6 Hz), 6.05(1 H, d, J = 8.6 Hz), 7.06(1 H, d, J = 8.6 Hz), 6.94(1 H, d, J = 2.6 Hz), 5.06(1 H, d, J = 4.0 Hz), 4.52-4.42(1 H, m), 3.66-3.20(5H, m), 2.24-1.57(10H, m).<br>MSm/z(M + H): 383. |

Example 0315

0315-1

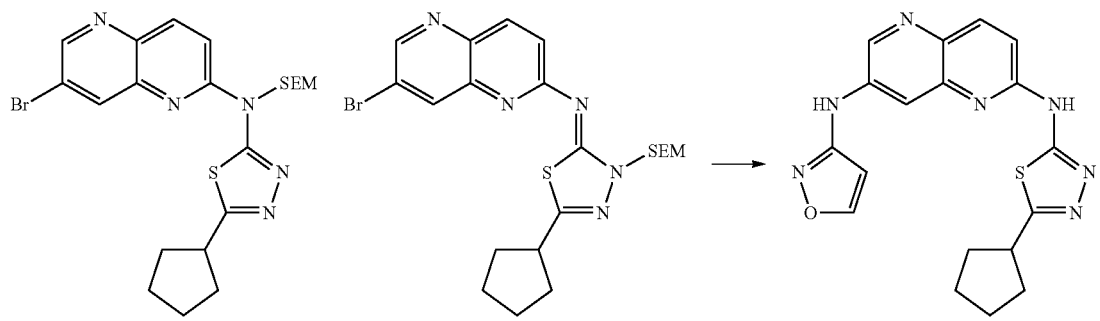 [SMILES: C[Si](C)(C)CCOCN(c1ccc2ncc(Br)cc2n1)c1nnc(C2CCCC2)s1 ; C[Si](C)(C)CCOCn1nc(C2CCCC2)s/c1=N\c1ccc2ncc(Br)cc2n1 ; c1cc(Nc2cnc3ccc(Nc4nnc(C5CCCC5)s4)nc3c2)no1]

$^1$H-NMR(DMSO-d$_6$)δ:11.95(1H,brs),10.00(1H,s),8.74(1H,d,J=1.3 Hz),8.69(1H,d,J=2.6 Hz),8.37(1H,d,J=2.6 Hz),8.18(1H,d,J=9.2 Hz),7.27(1H,d,J=9.2 Hz),6.36(1H,d,J=1.3 Hz),3.57-3.39(1H,m),2.24-2.06(2H,m),1.96-1.60(6H,m).
MSm/z(M+H):380.

A mixture of N-(7-bromo-1,5-naphthyridin-2-yl)-5-cyclopentyl-N-((2-(trimethylsilyl)ethoxy)methyl)-1,3,4-thiadiazole-2-amine (30 mg), isoxazole-3-amine (9.9 mg), tris(dibenzylideneacetone)dipalladium(0) (3.4 mg), 2-dicyclohexylphosphino-2',4',6'-triisopropylbiphenyl (5.6 mg), cesium carbonate (38.4 mg), and 1,4-dioxane (1 mL) was stirred at 100° C. for 14.5 hours in a nitrogen atmosphere in a sealed tube. The reaction mixture was cooled to room temperature, and methanol and a 4 mol/L hydrogen chloride/1,4-dioxane solution were added thereto, followed by stirring at room temperature for 2 hours, and stirring at 50° C. for 30 minutes. The reaction mixture was cooled to room temperature, and the solvent was distilled off under reduced pressure. Methanol and triethylamine were added to the obtained residue, and the solvent was distilled off under reduced pressure. The obtained residue was purified by silica gel column chromatography (chloroform-methanol, NH silica), thereby obtaining N$^2$-(5-cyclopentyl-1,3,4-thiadiazol-2-yl)-N$^7$-(isoxazol-3-yl)-1,5-naphthyridine-2,7-diamine (4.4 mg) as a white solid.

Example 0316

0316-1

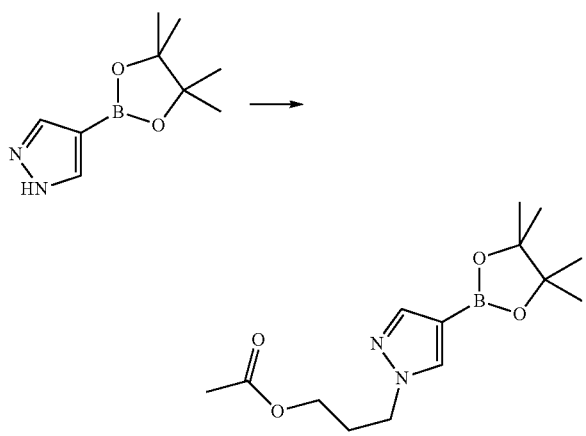

A mixture of 4-(4,4,5,5-tetramethyl-1,3,2-dioxaborolan-2-yl)-1H-pyrazole (0.867 g), 3-bromopropyl acetate (0.970 g), potassium carbonate (1.85 g), and acetonitrile (4 mL) was stirred at 65° C. for 16.5 hours in a nitrogen atmosphere.

The reaction mixture was cooled to room temperature, the solid matter was filtered off, and the solvent was distilled off under reduced pressure. The obtained residue was purified by silica gel column chromatography (chloroform-methanol), thereby obtaining 3-(4-(4,4,5,5-tetramethyl-1,3,2-dioxaborolan-2-yl)-1H-pyrazol-1-yl)propyl acetate (1.24 g) as yellow oily substance.

$^1$H-NMR(CDCl$_3$)δ:7.79(1H,s),7.69(1H,s),4.23(2H,t,J=6.6 Hz),4.05(2H,t,J=5.9 Hz),2.26-2.14(2H,m),2.05(3H,s),1.32(12H,s).

0316-2

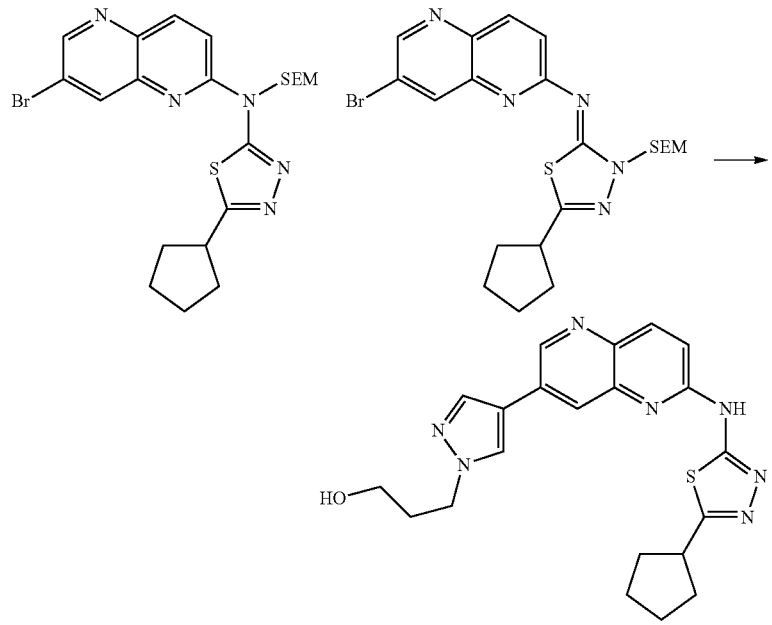

A mixture of a mixture (100 mg) of N-(7-bromo-1,5-naphthyridin-2-yl)-5-cyclopentyl-N-((2-(trimethylsilyl)ethoxy)methyl)-1,3,4-thiadiazole-2-amine and (Z)-7-bromo-N-(5-cyclopentyl-3-((2-(trimethylsilyl)ethoxy)methyl)-1,3,4-thiadiazol-2(3H)-ylidene)-1,5-naphthyridine-2-amine, 3-(4-(4,4,5,5-tetramethyl-1,3,2-dioxaborolan-2-yl)-1H-pyrazol-1-yl)propyl acetate (87.1 mg), bis(di-tert-butyl(4-dimethylaminophenyl)phosphine)dichloropalladium(II) (13.9 mg), sodium carbonate (41.8 mg), 1,4-dioxane (1 mL), and water (0.1 mL) was stirred at 150° C. for 30 minutes in a nitrogen atmosphere using a microwave reaction apparatus. The reaction mixture was cooled to room temperature, and methanol (1 mL) and a 4 mol/L hydrogen chloride/1,4-dioxane solution (1 mL) were added thereto, followed by stirring at room temperature for 2 hours. The solvent was distilled off under reduced pressure, methanol and triethylamine were added to the obtained residue, and the solvent was distilled off under reduced pressure. The obtained residue was purified by silica gel column chromatography (chloroform-methanol, NH silica), thereby obtaining 3-(4-(6-((5-cyclopentyl-1,3,4-thiadiazol-2-yl)amino)-1,5-naphthyridin-3-yl)-1H-pyrazol-1-yl)propan-1-ol (20.1 mg) as a white solid.

$^1$H-NMR(DMSO-d$_6$)δ:12.03(1H,s),9.08(1H,d,J=2.0 Hz),8.57(1H,s),8.33(1H,d,J=2.0 Hz),8.28-8.21(2H,m),7.39(1H,d,J=9.2 Hz),4.64(1H,t,J=5.0 Hz),4.24(2H,t,J=7.3 Hz),3.56-3.36(3H,m),2.25-1.62(10H,m).

MSm/z(M+H):422.

Example 0317

0317-1

Methanesulfonyl chloride (0.326 mL) was added to a solution of 3-(dimethylamino)-2,2-dimethylpropan-1-ol (0.50 g) in pyridine (3.8 mL) in an ice bath, followed by stirring at room temperature for 30 minutes. A saturated sodium hydrogen carbonate aqueous solution was added to the reaction mixture, followed by stirring at room temperature for 20 minutes, and after sodium chloride was added thereto, ethyl acetate was added thereto. The organic layer was collected by separation, washed with a saturated sodium chloride aqueous solution, and dried over anhydrous sodium sulfate. The obtained solid matter was washed with ethyl acetate, thereby obtaining 3-(dimethylamino)-2,2-dimethylpropyl methanesulfonate (0.327 g) as a white solid.

$^1$H-NMR(CDCl$_3$)δ:4.32(4H,s),3.49(6H,s),2.74(3H,s),1.46(6H,s).

0317-2

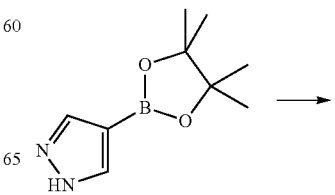

-continued

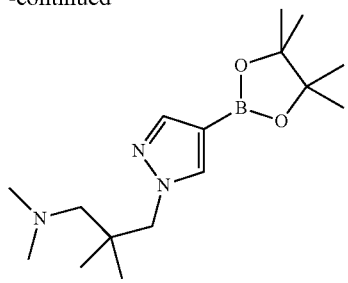

N,N,2,2-tetramethyl-3-(4-(4,4,5,5-tetramethyl-1,3,2-dioxaborolan-2-yl)-1H-pyrazol-1-yl)propane-1-amine was obtained as colorless oily substance in the same manner as in Example 0316-1.

$^{1}$H-NMR(CDCl$_{3}$)δ:7.76(1H,s),7.65(1H,s),4.02(2H,s), 2.31(6H,s),2.16(2H,s),1.32(12H,s),0.90(6H,s).

0317-3

5-Cyclopentyl-N-(7-(1-(3-(dimethylamino)-2,2-dimethylpropyl)-1H-pyrazol-4-yl)-1,5-naphthyridin-2-yl)-1,3,4-thiadiazole-2-amine was obtained as a white solid in the same manner as in Example 0303-3.

$^{1}$H-NMR(DMSO-d$_{6}$)δ:12.04(1H,brs),9.09(1H,d,J=1.7 Hz),8.52(1H,s),8.34(1H,d,J=1.7 Hz),8.28-8.20(2H,m),7.39 (1H,d,J=9.2 Hz),4.06(2H,s),3.54-3.37(1H,m),2.30(6H,s), 2.25-2.05(4H,m),1.98-1.63(6H,m),0.89(6H,s).

MSm/z(M+H):477.

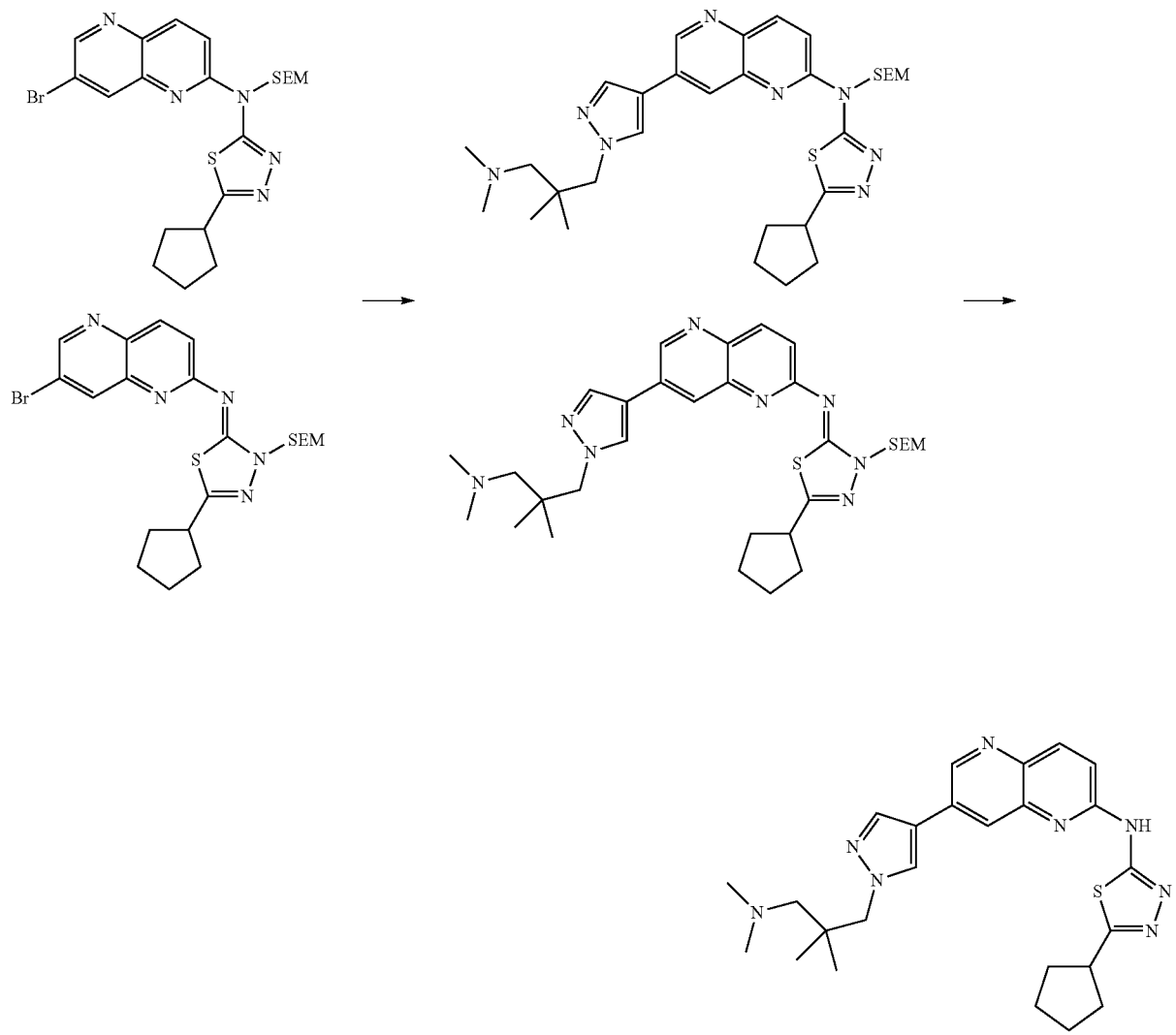

Example 0318

0318-1

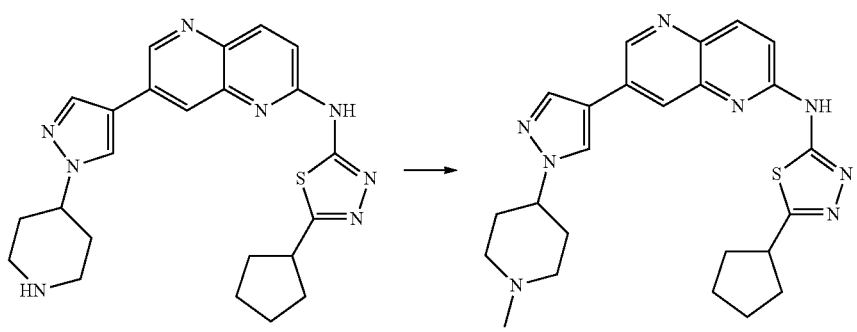

A mixture of a mixture (30 mg) of N-(7-bromo-1,5-naphthyridin-2-yl)-5-cyclopentyl-N-((2-(trimethylsilyl)ethoxy)methyl)-1,3,4-thiadiazole-2-amine and (Z)-7-bromo-N-(5-cyclopentyl-3-((2-(trimethylsilyl)ethoxy)methyl)-1,3,4-thiadiazol-2(3H)-ylidene)-1,5-naphthyridine-2-amine, bis(pinacolato)diboron (22.5 mg), (1,1'-bis(diphenylphosphino)ferrocene)palladium(II) dichloride (4.8 mg), potassium acetate (11.6 mg), and 1,4-dioxane (1 mL) was stirred at 80° C. for 6 hours in a nitrogen atmosphere in a sealed tube. Bis(pinacolato)diboron (22.5 mg), (1,1'-bis(diphenylphosphino)ferrocene)palladium(II) dichloride (4.8 mg), and potassium acetate (11.6 mg) were added to the reaction mixture, followed by stirring at 80° C. for 14 hours. The reaction mixture was cooled to room temperature, and sodium carbonate (31.4 mg), tert-butyl 4-(4-iodo-1H-pyrazol-1-yl)piperidine-1-carboxylate (33.5 mg), bis(di-tert-butyl(4-dimethylaminophenyl)phosphine)dichloropalladium(II) (4.2 mg), and water (0.1 mL) were added thereto, followed by stirring at 100° C. for 23 hours. The reaction mixture was cooled to room temperature, and methanol (1 mL) and a 4 mol/L hydrogen chloride/1,4-dioxane solution (1 mL) were added thereto, followed by stirring at room temperature for 2 hours, and stirring at 50° C. for 1 hour. The reaction mixture was cooled to room temperature, and the solvent was distilled off under reduced pressure. Methanol and triethylamine were added to the obtained residue, the solvent was distilled off under reduced pressure, and the obtained residue was purified by silica gel column chromatography (chloroform-methanol, NH silica), thereby obtaining 5-cyclopentyl-N-(7-(1-(piperidin-4-yl)-1H-pyrazol-4-yl)-1,5-naphthyridin-2-yl)-1,3,4-thiadiazole-2-amine.

The obtained 5-cyclopentyl-N-(7-(1-(piperidin-4-yl)-1H-pyrazol-4-yl)-1,5-naphthyridin-2-yl)-1,3,4-thiadiazole-2-amine was dissolved in a mixture of methanol (0.5 mL) and dichloromethane (0.5 mL), and a 36 to 38% formaldehyde aqueous solution (0.5 mL) and sodium triacetoxyborohydride (20 mg) were added thereto at room temperature, followed by stirring for 2 hours. The solvent was distilled off under reduced pressure, and the obtained residue was purified by silica gel column chromatography (chloroform-methanol, NH silica), thereby obtaining 5-cyclopentyl-N-(7-(1-(1-methylpiperidin-4-yl)-1H-pyrazol-4-yl)-1,5-naphthyridin-2-yl)-1,3,4-thiadiazole-2-amine (3.5 mg) as a yellow solid.

$^1$H-NMR(DMSO-$d_6$)δ:12.04(1H,brs),9.09(1H,d,J=1.7 Hz),8.65(1H,s),8.34(1H,d,J=1.7 Hz),8.28-8.18(2H,m),7.38 (1H,d,J=9.2 Hz),4.27-4.07(1H,m),3.57-3.38(1H,m),2.98-2.80(2H,m),2.31-1.60(17H,m).

MS m/z(M+H):461.

Example 0319

0319-1

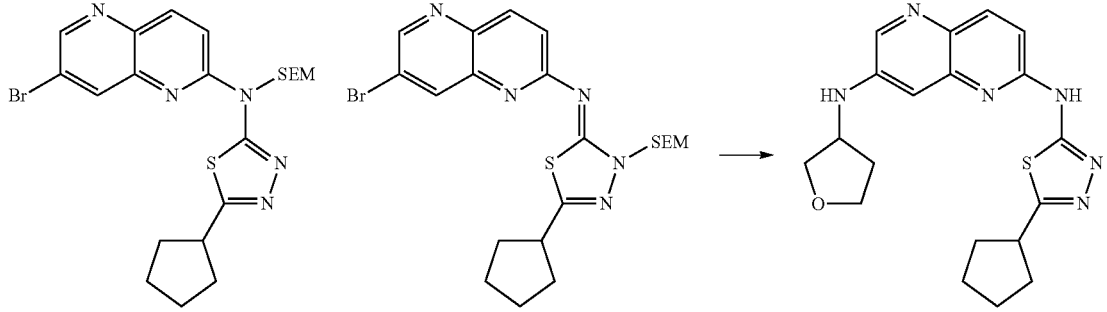 [SMILES: C[Si](C)(C)CCOCN(c1ccc2ncc(Br)cc2n1)c1nnc(C2CCCC2)s1 ; C[Si](C)(C)CCOCn1nc(C2CCCC2)s/c1=N\c1ccc2ncc(Br)cc2n1 ; c1nc2ccc(Nc3nnc(C4CCCC4)s3)nc2cc1NC1CCOC1]

A mixture of a mixture (20 mg) of N-(7-bromo-1,5-naphthyridin-2-yl)-5-cyclopentyl-N-((2-(trimethylsilyl)ethoxy)methyl)-1,3,4-thiadiazole-2-amine and (Z)-7-bromo-N-(5-cyclopentyl-3-((2-(trimethylsilyl)ethoxy)methyl)-1,3,4-thiadiazol-2(3H)-ylidene)-1,5-naphthyridine-2-amine, tetrahydrofuran-3-amine (6.9 mg), tris(dibenzylideneacetone)dipalladium(0) (3.6 mg), 2-dicyclohexylphosphino-2',4',6'-triisopropylbiphenyl (3.8 mg), cesium carbonate (25.7 mg), and 1,4-dioxane (1 mL) was stirred at 100° C. for 14 hours in a nitrogen atmosphere in a sealed tube. The reaction mixture was cooled to room temperature, and methanol (1 mL) and a 4 mol/L hydrogen chloride/1,4-dioxane solution (1 mL) were added thereto, followed by stirring at room temperature for 2 days. The solvent was distilled off under reduced pressure, triethylamine was added to the obtained residue, and the solvent was distilled off under reduced pressure. The obtained residue was purified by silica gel column chromatography (chloroform-methanol, NH silica), thereby obtaining $N^2$-(5-cyclopentyl-1,3,4-thiadiazol-2-yl)-$N^7$-(tetrahydrofuran-3-yl)-1,5-naphthyridine-2,7-diamine (2.0 mg) as a yellow solid.

$^1$H-NMR(DMSO-d$_6$)δ:11.76(1H,brs),8.31(1H,d,J=2.3 Hz),8.01(1H,d,J=8.9 Hz),7.05(1H,d,J=8.9 Hz),6.94(1H,d,J=2.3 Hz),6.84(1H,d,J=6.6 Hz),4.27-4.14(1H,m),3.96(1H,dd,J=8.9,5.6 Hz),3.92-3.83(1H,m),3.78(1H,td,J=8.3,5.5 Hz),3.63(1H,dd,J=8.9,3.6 Hz),3.52-3.38(1H,m),2.36-2.21(1H,m),2.20-2.04(2H,m),1.93-1.60(7H,m).
MSm/z(M+H):383.

Example 0320

0320-1

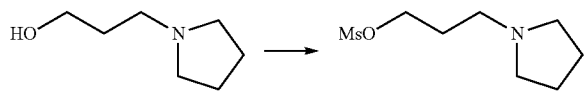 [SMILES: OCCCN1CCCC1 ; CS(=O)(=O)OCCCN1CCCC1]

Pyridine (2.1 mL) and methanesulfonyl chloride (1.0 mL) were added to a solution of 3-(pyrrolidin-1-yl)propan-1-ol (1.14 g) in dichloromethane (18 mL) in an ice bath, followed by stirring for 30 minutes in an ice bath. A saturated sodium hydrogen carbonate aqueous solution was added to the reaction mixture, followed by stirring at room temperature for 30 minutes. The solvent was distilled off under reduced pressure, and the obtained residue was purified by silica gel column chromatography (ethyl acetate-methanol, NH silica), thereby obtaining 3-(pyrrolidin-1-yl)propyl methanesulfonate (1.60 g) as yellow oily substance.

$^1$H-NMR(CDCl$_3$)δ:4.32(2H,t,J=6.6 Hz),3.02(3H,s),2.56(2H,t,J=7.3 Hz),2.53-2.44(4H,m),2.03-1.88(2H,m),1.86-1.71(4H,m).

0320-2 and 0320-3

The following compounds were obtained in the same manner as in Examples 0316-1 and 0303-3.

| Example No. | |
|---|---|
| 0320 | |
| 0320-2 | 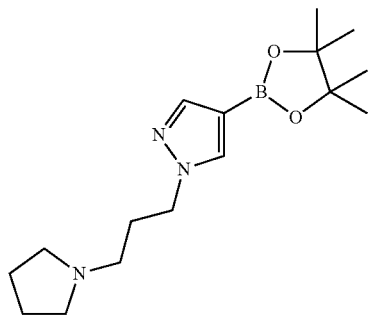 [SMILES: CC1(C)OB(c2cnn(CCCN3CCCC3)c2)OC1(C)C] | 1H-NMR(CDCl$_3$)δ: 7.78(1 H, s), 7.69(1 H, s), 4.20(2H, t, J = 6.9 Hz), 2.53-2.37(6H, m), 2.14-1.98(2H, m), 1.84-1.69(4H, m), 1.32(12H, s). |

| Example No. | | |
|---|---|---|
| 0320-3 | 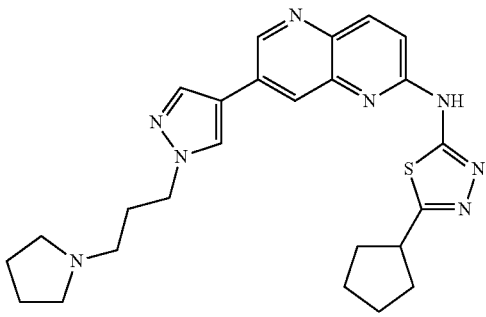 [SMILES: c1nc2ccc(Nc3nnc(C4CCCC4)s3)nc2cc1-c1cnn(CCCN2CCCC2)c1] | 1H-NMR(DMSO-d₆)δ: 12.04(1 H, brs), 9.08(1 H, d, J = 1.7 Hz), 8.57(1 H, s), 8.33(1 H, d, J = 1.7 Hz), 8.30-8.16(2H, m), 7.39(1 H, d, J = 8.6 Hz), 4.22(2H, t, J = 6.9 Hz), 3.57-3.34(1 H, m), 2.62-2.83(6H, m), 2.26-1.52(14H, m). MSm/z(M + H): 375. |

Example 0321

0321-1

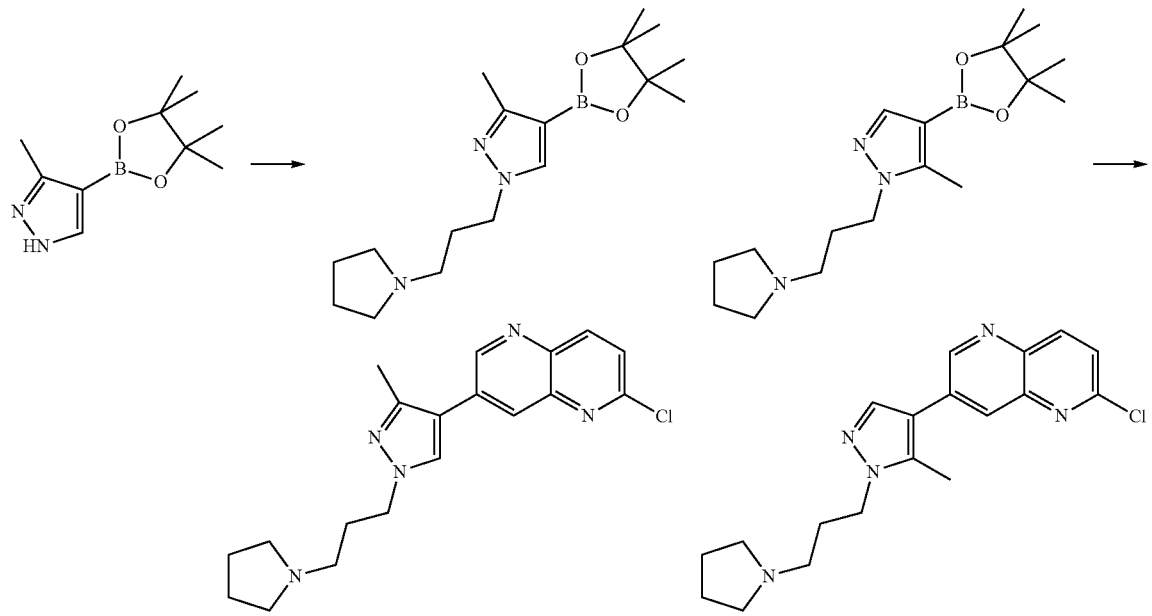

A mixture of 3-methyl-1-(3-(pyrrolidin-1-yl)propyl)-4-(4,4,5,5-tetramethyl-1,3,2-dioxaborolan-2-yl)-1H-pyrazole and 5-methyl-1-(3-(pyrrolidin-1-yl)propyl)-4-(4,4,5,5-tetramethyl-1,3,2-dioxaborolan-2-yl)-1H-pyrazole was obtained as colorless oily substance in the same manner as in Example 0316-1.

A mixture of the obtained mixture (59.8 mg) of 3-methyl-1-(3-(pyrrolidin-1-yl)propyl)-4-(4,4,5,5-tetramethyl-1,3,2-dioxaborolan-2-yl)-1H-pyrazole and 5-methyl-1-(3-(pyrrolidin-1-yl)propyl)-4-(4,4,5,5-tetramethyl-1,3,2-dioxaborolan-2-yl)-1H-pyrazole, 7-bromo-2-chloro-1,5-naphthyridine (38.0 mg), bis(di-tert-butyl(4-dimethylaminophenyl)phosphine)dichloropalladium(II) (11.1 mg), sodium carbonate (33.1 mg), 1,4-dioxane (1 mL), and water (0.1 mL) was stirred at 100° C. for 64 hours in a nitrogen atmosphere in a sealed tube. The reaction mixture was cooled to room temperature, and the solvent was distilled off under reduced pressure. After the obtained residue was purified by silica gel column chromatography (chloroform-methanol), the obtained residue was purified by preparative thin layer silica gel chromatography (chloroform-methanol, NH silica), thereby obtaining 2-chloro-7-(3-methyl-1-(3-(pyrrolidin-1-yl)propyl)-1H-pyrazol-4-yl)-1,5-naphthyridine (12.2 mg) as colorless oily substance and 2-chloro-7-(5-methyl-1-(3-(pyrrolidin-1-yl)propyl)-1H-pyrazol-4-yl)-1,5-naphthyridine (9.4 mg) as colorless oily substance.

2-Chloro-7-(3-methyl-1-(3-(pyrrolidin-1-yl)propyl)-1H-pyrazol-4-yl)-1,5-naphthyridine MSm/z(M+H):356,358.

2-Chloro-7-(5-methyl-1-(3-(pyrrolidin-1-yl)propyl)-1H-pyrazol-4-yl)-1,5-naphthyridine MSm/z(M+H):356,358.

0321-3

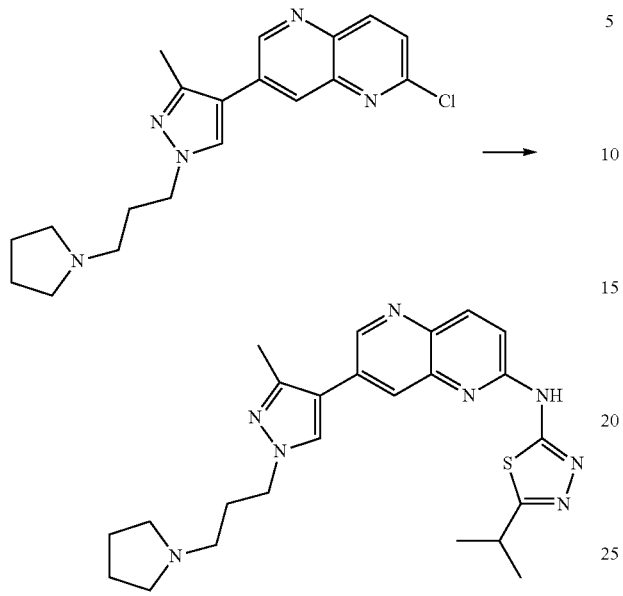

A mixture of 2-chloro-7-(3-methyl-1-(3-(pyrrolidin-1-yl)propyl)-1H-pyrazol-4-yl)-1,5-naphthyridine (12.2 mg), 5-isopropyl-1,3,4-thiadiazole-2-amine (9.8 mg), tris(dibenzylideneacetone)dipalladium(0) (3.1 mg), 2-dicyclohexylphosphino-2',4',6'-triisopropylbiphenyl (4.0 mg), cesium carbonate (22.4 mg), and 1,4-dioxane (0.5 mL) was stirred at 100° C. for 13 hours in a nitrogen atmosphere in a sealed tube. The reaction mixture was cooled to room temperature, and the solvent was distilled off under reduced pressure. The obtained residue was purified by preparative thin layer silica gel chromatography (chloroform-methanol, NH silica), thereby obtaining 5-isopropyl-N-(7-(3-methyl-1-(3-(pyrrolidin-1-yl)propyl)-1H-pyrazol-4-yl)-1,5-naphthyridin-2-yl)-1,3,4-thiadiazole-2-amine (9.0 mg) as a yellow solid.

$^1$H-NMR(DMSO-$d_6$)δ:12.06(1H,brs),8.92(1H,d,J=2.0 Hz),8.31(1H,s),8.27(1H,d,J=9.2 Hz),8.16(1H,d,J=2.0 Hz),7.42(1H,d,J=9.2 Hz),4.13(2H,t,J=6.9 Hz),3.42-3.30(1H,m),2.47-2.35(9H,m),2.05-1.91(2H,m),1.75-1.63(4H,m),1.40 (6H,d,J=7.3 Hz).

MSm/z(M+H):463.

Examples 0322 and 0323

The following compounds were obtained in the same manner as in Examples 0001-4 and 0001-5.

| Example No. | | |
|---|---|---|
| 0322 | | |
| 0322-1 | 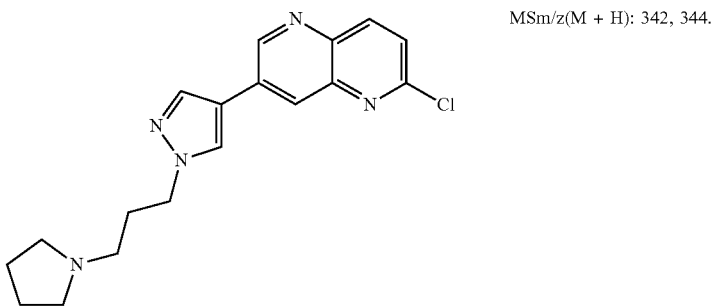 | MSm/z(M + H): 342, 344. |
| 0322-2 | 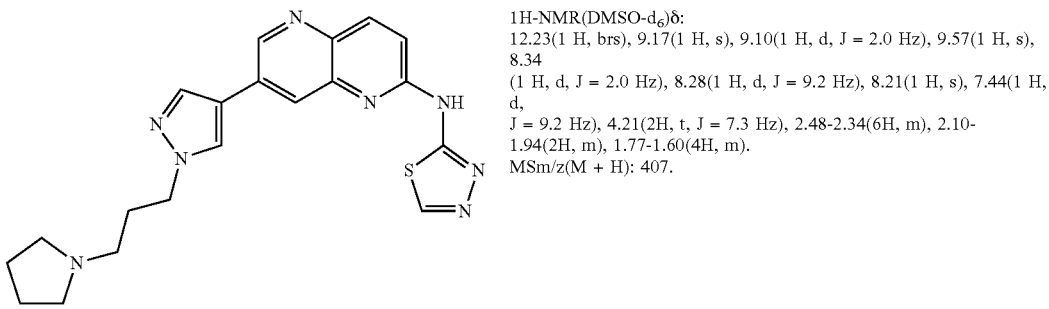 | 1H-NMR(DMSO-$d_6$)δ:<br>12.23(1 H, brs), 9.17(1 H, s), 9.10(1 H, d, J = 2.0 Hz), 9.57(1 H, s), 8.34<br>(1 H, d, J = 2.0 Hz), 8.28(1 H, d, J = 9.2 Hz), 8.21(1 H, s), 7.44(1 H, d,<br>J = 9.2 Hz), 4.21(2H, t, J = 7.3 Hz), 2.48-2.34(6H, m), 2.10-<br>1.94(2H, m), 1.77-1.60(4H, m).<br>MSm/z(M + H): 407. |

| Example No. | | |
|---|---|---|
| 0323 | | |
| 0323-1 | 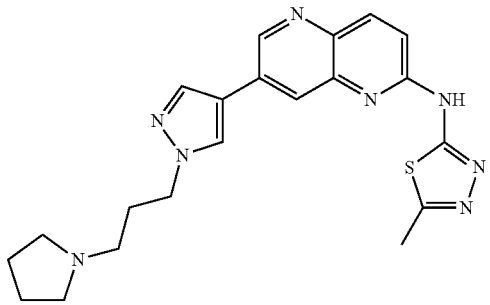 [SMILES: Cc1nnc(Nc2ccc3ncc(-c4cnn(CCCN5CCCC5)c4)cc3n2)s1] | 1H-NMR(DMSO-$d_6$)δ:<br>12.02(1 H, brs), 9.08(1 H, d, J = 1.7 Hz), 8.58(1 H, s), 8.33(1 H, d, J = 1.7 Hz), 6.25(1 H, d, J = 8.6 Hz), 8.22(1 H, s), 7.39(1 H, d, J = 8.6 Hz),<br>4.21(2H, t, J = 6.9 Hz), 2.66(3H, s), 2.49-2.34(6H, m), 2.10-1.94(2H, m), 1.77-1.60(4H, m).<br>MSm/z(M + H): 421. |

Example 0324

0324-1

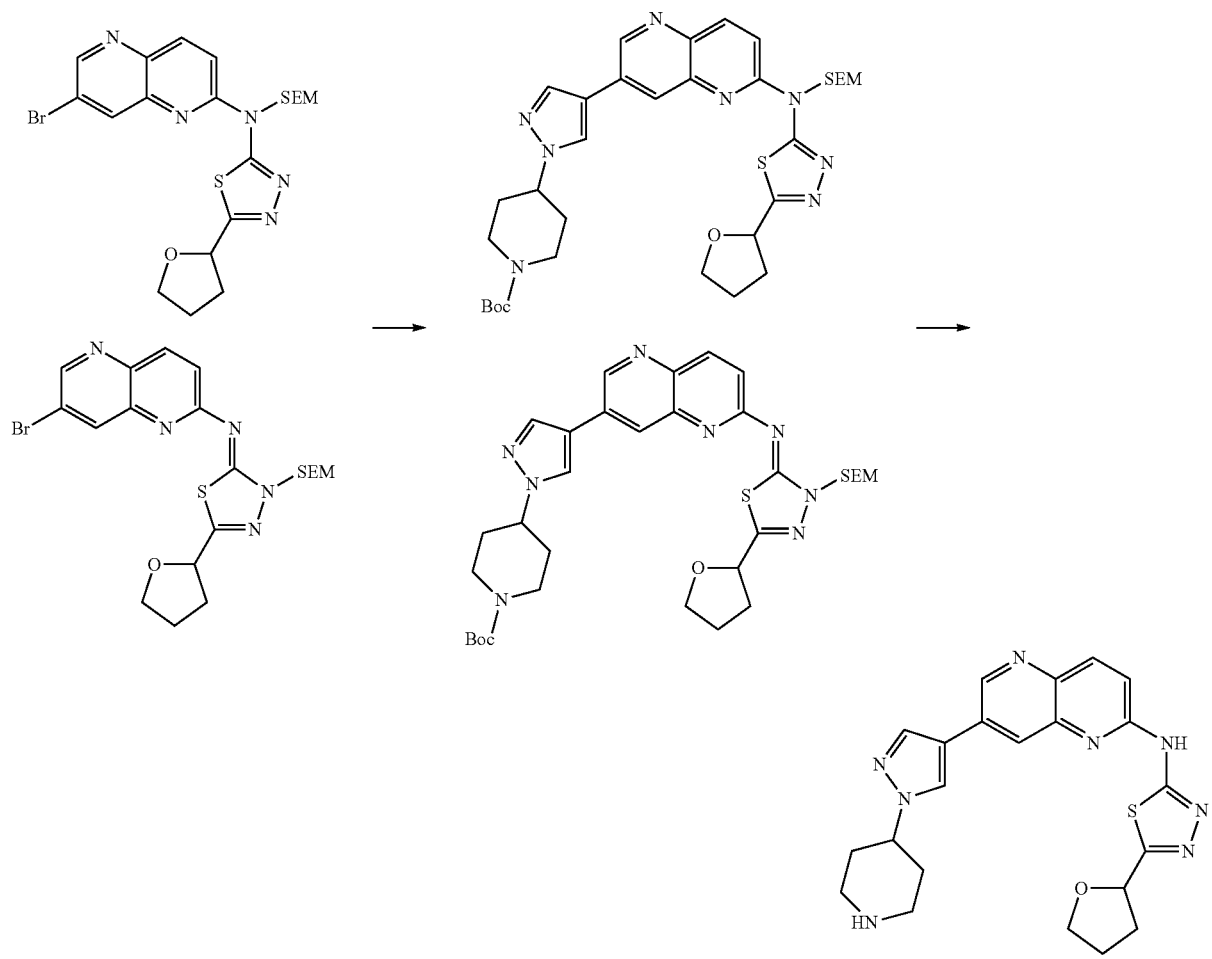

A solution of a mixture (30 mg) of N-(7-bromo-1,5-naphthyridin-2-yl)-5-(tetrahydrofuran-2-yl)-N-((2-(trimethylsilyl)ethoxy)methyl)-1,3,4-thiadiazole-2-amine and (Z)-7-bromo-N-(5-(tetrahydrofuran-2-yl)-3-((2-(trimethylsilyl)ethoxy)methyl)-1,3,4-thiadiazol-2(3H)-ylidene)-1,5-naphthyridine-2-amine, bis(pinacolato)diboron (22.5 mg), (1,1'-bis(diphenylphosphino)ferrocene)palladium(II) dichloride (4.8 mg), and potassium acetate (11.6 mg) in 1,4-dioxane (1 mL) was stirred at 100° C. for 12 hours in a nitrogen atmosphere in a sealed tube. The reaction mixture was cooled to room temperature, and tert-butyl 4-(4-iodo-1H-pyrazol-1-yl)piperidine-1-carboxylate (33.4 mg), bis(di-tert-butyl(4-dimethylaminophenyl)phosphine)dichloropalladium(II) (4.2 mg), sodium carbonate (31.3 mg), and water (0.1 mL) were added thereto, followed by stirring at 120° C. for 19 hours. The reaction mixture was cooled to room temperature, and purified by silica gel column chromatography (hexane-ethyl acetate, NH silica), thereby obtaining a mixture (61.2 mg) of tert-butyl 4-(4-(6-((5-(tetrahydrofuran-2-yl)-1,3,4-thiadiazol-2-yl)((2-(trimethylsilyl)ethoxy)methyl)amino)-1,5-naphthyridin-3-yl)-1H-pyrazol-1-yl)piperidine-1-carboxylate and (Z)-tert-butyl 4-(4-(6-((5-(tetrahydrofuran-2-yl)-3-((2-(trimethylsilyl)ethoxy)methyl)-1,3,4-thiadiazol-2(3H)-ylidene)amino)-1,5-naphthyridin-3-yl)-1H-pyrazol-1-yl)piperidine-1-carboxylate as brown oily substance.

A 4 mol/L hydrogen chloride/1,4-dioxane solution (1 mL) was added to a solution of the obtained mixture (20 mg) in ethanol (1 mL) at room temperature, followed by stirring for 2 hours. The solvent was distilled off under reduced pressure, triethylamine was added to the obtained residue, and the solvent was distilled off under reduced pressure. The obtained residue was purified by silica gel column chromatography (chloroform-methanol, NH silica), thereby obtaining N-(7-(1-(piperidin-4-yl)-1H-pyrazol-4-yl)-1,5-naphthyridin-2-yl)-5-(tetrahydrofuran-2-yl)-1,3,4-thiadiazole-2-amine (1.4 mg) as a yellow solid.

$^1$H-NMR(DMSO-$d_6$)δ:9.11(1H,d,J=2.0 Hz),8.65(1H,s), 8.34(1H,d,J=2.0 Hz),8.30-8.21(2H,m),7.41(1H,d,J=9.2 Hz), 5.24(1H,dd,J=7.3,5.9 Hz),4.36-4.20(1H,m),4.07-3.96(1H,m),3.95-3.83(1H,m),3.17-3.04(2H,m),2.75-2.60(2H,m), 2.46-2.32(1H,m),2.30-2.13(1H,m),2.11-1.96(4H,m),1.96-1.79(2H,m).

MSm/z(M+H):449.

Example 0325

0325-1

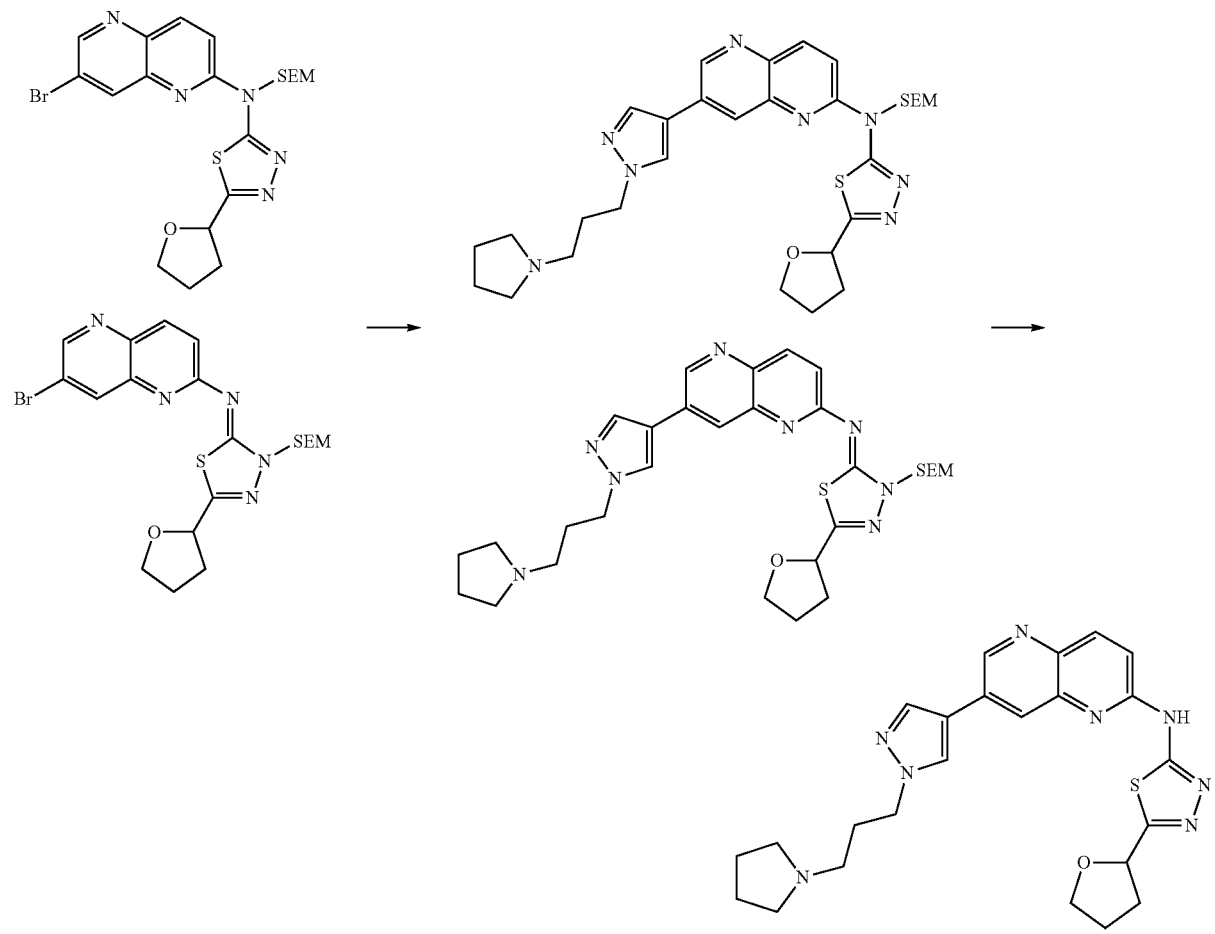

N-(7-(1-(3-(pyrrolidin-1-yl)propyl)-1H-pyrazol-4-yl)-1,5-naphthyridin-2-yl)-5-(tetrahydrofuran-2-yl)-1,3,4-thiadiazole-2-amine was obtained as a white solid in the same manner as in Example 0303-3.

$^1$H-NMR(DMSO-$d_6$)δ:12.12(1H,brs),9.09(1H,d,J=1.7 Hz),8.59(1H,s),8.32(1H,d,J=1.7 Hz),8.27(1H,d,J=8.9 Hz), 8.24(1H,s),7.41(1H,d,J=8.9 Hz),5.24(1H,dd,J=7.3,5.9 Hz), 4.22(2H,t,J=6.9 Hz),4.07-3.96(1H,m),3.94-3.83(1H,m), 2.61-2.32(7H,m),2.31-2.13(1H,m),2.12-1.95(4H,m),1.79-1.58(4H,m).

MSm/z(M+H):477.

Example 0326

0326-1

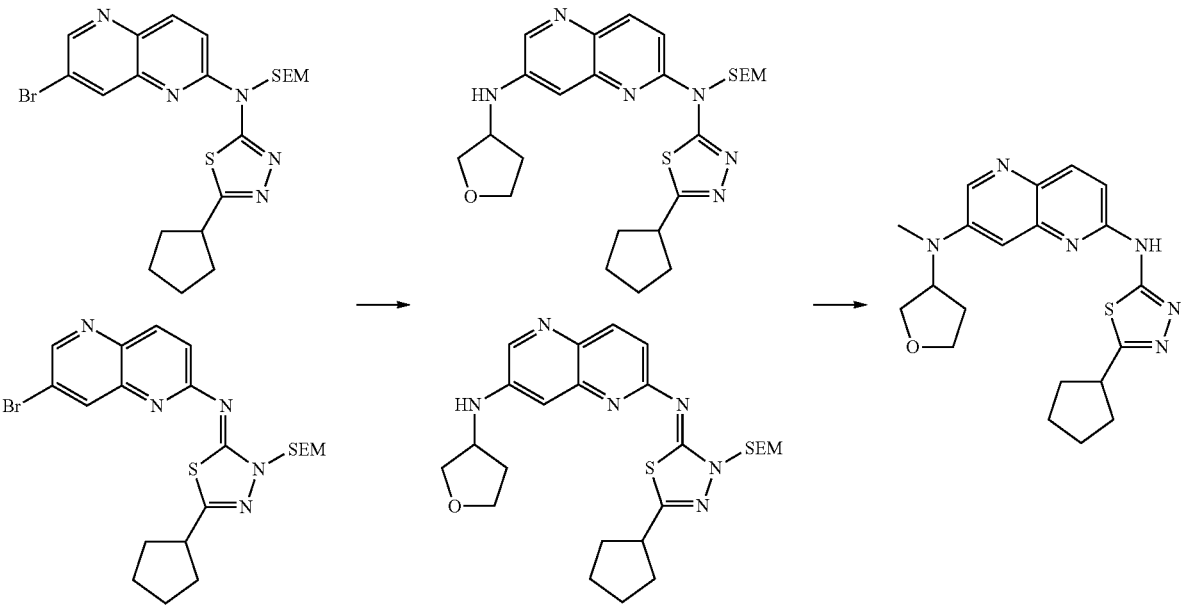

A mixture of a mixture (20 mg) of N-(7-bromo-1,5-naphthyridin-2-yl)-5-cyclopentyl-N-((2-(trimethylsilyl)ethoxy)methyl)-1,3,4-thiadiazole-2-amine and (Z)-7-bromo-N-(5-cyclopentyl-3-((2-(trimethylsilyl)ethoxy)methyl)-1,3,4-thiadiazol-2(3H)-ylidene)-1,5-naphthyridine-2-amine, tetrahydrofuran-3-amine (6.9 mg), tris(dibenzylideneacetone)dipalladium(0) (3.6 mg), 2-dicyclohexylphosphino-2',4',6'-triisopropylbiphenyl (3.8 mg), cesium carbonate (25.7 mg), and 1,4-dioxane (1 mL) was stirred at 100° C. for 12 hours in a sealed tube. The reaction mixture was cooled to room temperature, and purified by silica gel column chromatography (hexane-ethyl acetate, NH silica), thereby obtaining a mixture (13.7 mg) of $N^2$-(5-cyclopentyl-1,3,4-thiadiazol-2-yl)-$N^7$-(tetrahydrofuran-3-yl)-$N^2$-((2-(trimethylsilyl)ethoxy)methyl)-1,5-naphthyridine-2,7-diamine and (Z)-$N^2$-(5-cyclopentyl-3-((2-(trimethylsilyl)ethoxy)methyl)-1,3,4-thiadiazol-2(3H)-ylidene)-$N^7$-(tetrahydrofuran-3-yl)-1,5-naphthyridine-2,7-diamine as yellow oily substance.

60% sodium hydride (1.6 mg) was added to a solution of the obtained mixture in tetrahydrofuran (1 mL) in an ice bath, followed by stirring at room temperature for 5 minutes, and iodomethane (6.6 mL) was added thereto in an ice bath. The reaction mixture was stirred at room temperature for 1 hour, and heated to reflux for 1 hour. The reaction mixture was cooled to room temperature, and methanol (1 mL) and a 4 mol/L hydrogen chloride/1,4-dioxane solution (1 mL) were added thereto, followed by stirring at room temperature for 2 hours. The solvent was distilled off under reduced pressure, triethylamine was added to the obtained residue, and the solvent was distilled off under reduced pressure. The obtained residue was purified by silica gel column chromatography (chloroform-methanol, NH silica), thereby obtaining $N^2$-(5-cyclopentyl-1,3,4-thiadiazol-2-yl)-$N^7$-methyl-$N^7$-(tetrahydrofuran-3-yl)-1,5-naphthyridine-2,7-diamine (7.6 mg) as a white solid.

$^1$H-NMR(DMSO-$d_6$)δ:11.82(1H,s),8.66(1H,d,J=2.6 Hz), 8.08(1H,d,J=8.6 Hz),7.22(1H,d,J=2.6 Hz),7.12(1H,d,J=8.6 Hz),4.95-4.78(1H,m),4.07-3.92(1H,m),3.89-3.75(2H,m), 3.73-3.58(1H,m),3.55-3.38(1H,m),2.96(3H,s),2.39-2.23 (1H,m),2.22-2.03(2H,m),2.01-1.56(7H,m).

MSm/z(M+H):397.

Examples 0327 to 0329

The following compounds were obtained in the same manner as in Examples 0001-4 and 0001-5.

| Example No. |
| --- |
| 0327 |

0327-1 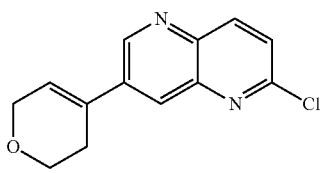 [SMILES: Clc1ccc2ncc(C3=CCOCC3)cc2n1]   MSm/z(M + H): 247.

| Example No. | | |
|---|---|---|
| 0327-2 | 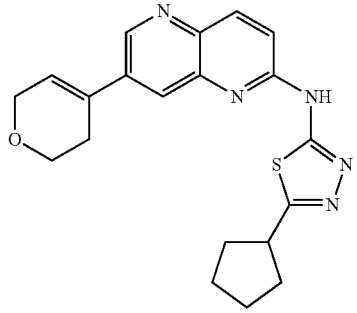 [SMILES: C1=C(c2cnc3ccc(Nc4nnc(C5CCCC5)s4)nc3c2)CCOC1] | 1H-NMR(DMSO-d₆)δ:<br>12.05(1 H, s), 8.98(1 H, d, J = 2.3 Hz), 8.27(1 H, d, J = 8.9 Hz), 8.10<br>(1 H, d, J = 2.3 Hz), 7.43(1 H, d, J = 8.9 Hz), 6.72-6.64(1 H, m),<br>4.36-4.27(2H, m), 3.90(2H, t, J = 5.6 Hz), 3.57-3.39(1 H, m), 2.70-<br>2.58(2H, m), 2.23-2.04(2H, m), 1.96-1.58(6H, m).<br>MSm/z(M + H): 380. |
| 0328 | | |
| 0328-1 | 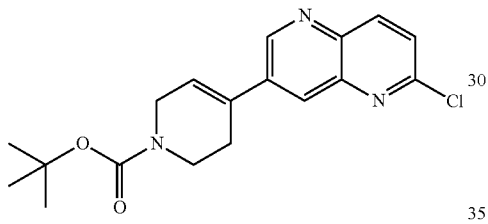 | MSm/z(M + H): 346. |
| 0328-2 | 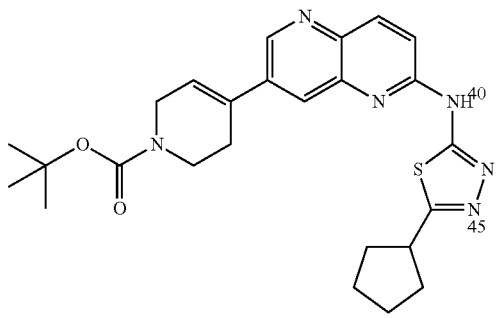 [SMILES: CC(C)(C)OC(=O)N1CC=C(c2cnc3ccc(Nc4nnc(C5CCCC5)s4)nc3c2)CC1] | 1H-NMR(DMSO-d₆)δ:<br>12.05(1 H, brs), 8.95(1 H, d, J = 2.0 Hz), 8.27(1 H, d, J = 9.2 Hz),<br>8.11(1 H, d, J = 2.0 Hz), 7.43(1 H, d, J = 9.2 Hz), 6.65-6.46(1 H,<br>m), 4.17-4.02(2H, m), 3.68-3.55(2H, m), 3.55-3.39(1 H, m), 2.71-<br>2.59(2H, m), 2.24-2.06(2H, m), 1.96-1.61(6H, m), 1.45(9H, s).<br>MSm/z(M + H): 479. |
| 0329 | | |
| 0329-1 | 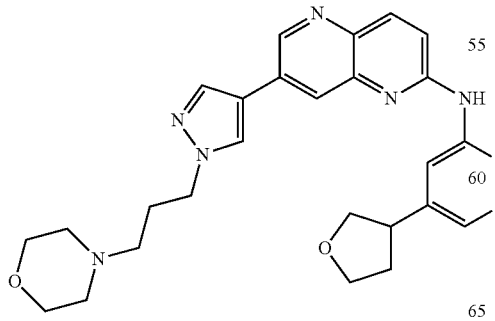 | 1H-NMR(CDCl₃)δ:<br>9.12(1 H, brs), 8.92(1 H, d, J = 1.8 Hz), 8.86(1 H, m), 8.82(1 H, d,<br>J = 2.1 Hz), 8.24(1 H, d, J = 9.3 Hz), 8.09(1 H, d, J = 2.1 Hz),<br>7.97<br>(1 H, s), 7.86(1 H, s), 7.58(1 H, d, J = 9.3 Hz), 4.31(2H, m), 3.73<br>(4H, m), 3.15(1 H, m), 2.50-2.34(6H, m), 2.25(2H, m), 2.13(2H,<br>m), 2.00-1.70(6H, m).<br>MSm/z(M + H): 485. |

Example 0330

0330-1

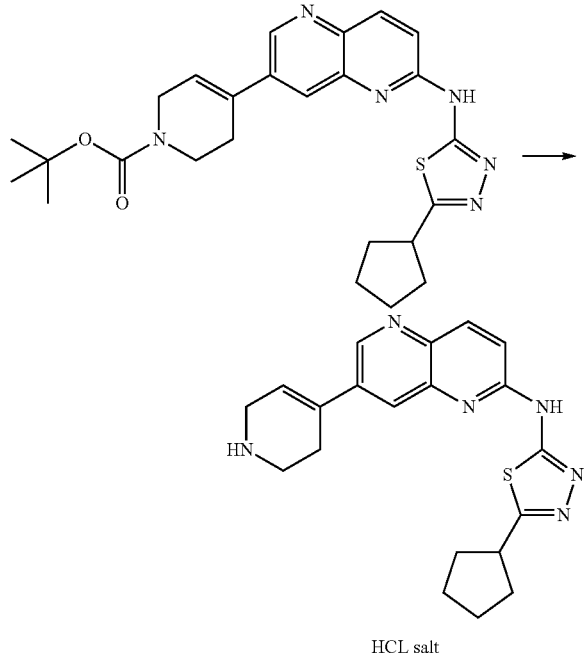

HCL salt

A 4 mol/L hydrogen chloride/1,4-dioxane solution (1 mL) was added to a solution of tert-butyl 4-(6-((5-cyclopentyl-1,3,4-thiadiazol-2-yl)amino)-1,5-naphthyridin-3-yl)-5,6-dihydropyridine-1(2H)-carboxylate (20 mg) in methanol (1 mL) at room temperature, followed by stirring for 1 hour. The solvent was distilled off under reduced pressure, and the obtained residue was washed with ethyl acetate, thereby obtaining 5-cyclopentyl-N-(7-(1,2,3,6-tetrahydropyridin-4-yl)-1,5-naphthyridin-2-yl)-1,3,4-thiadiazole-2-amine hydrochloride (12 mg) as a white solid.

$^1$H-NMR(DMSO-d$_6$)δ:9.13(2H,brs),9.00(1H,d,J=2.0 Hz),8.30(1H,d,J=9.2 Hz),8.18(1H,d,J=2.0 Hz),7.47(1H,d,J=9.2 Hz),6.65-6.58(1H,m),3.55-3.43(3H,m),2.94-2.82(2H,m),2.23-2.08(2H,m),1.94-1.59(8H,m).
MSm/z(M+H):379.

Example 0331

0331-1

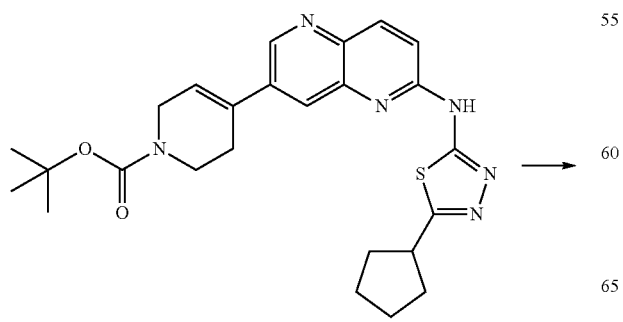

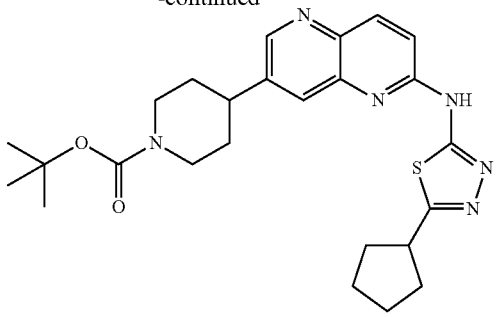

A mixture of tert-butyl 4-(6-((5-cyclopentyl-1,3,4-thiadiazol-2-yl)amino)-1,5-naphthyridin-3-yl)-5,6-dihydropyridine-1(2H)-carboxylate (30 mg), methanol (3 mL), and tetrahydrofuran (1 mL) was reacted using a flow-type hydrogenation reaction apparatus (atmospheric pressure, 1.0 mL/min, room temperature, 10% Pd/C). The solvent was distilled off under reduced pressure, and the obtained residue was washed with ethyl acetate, thereby obtaining tert-butyl 4-(6-((5-cyclopentyl-1,3,4-thiadiazol-2-yl)amino)-1,5-naphthyridin-3-yl)piperidine-1-carboxylate (8.3 mg) as a white solid.

$^1$H-NMR(DMSO-d$_6$)δ:12.02(1H,s),8.72(1H,d,J=2.3 Hz),8.26(1H,d,J=9.2 Hz),8.04(1H,d,J=2.3 Hz),7.42(1H,d,J=9.2 Hz),4.24-4.06(2H,m),3.56-3.38(1H,m),3.10-2.74(3H,m),2.22-2.01(2H,m),1.96-1.58(10H,m),1.44(9H,s).
MSm/z(M+H):481.

Example 0332

0332-1

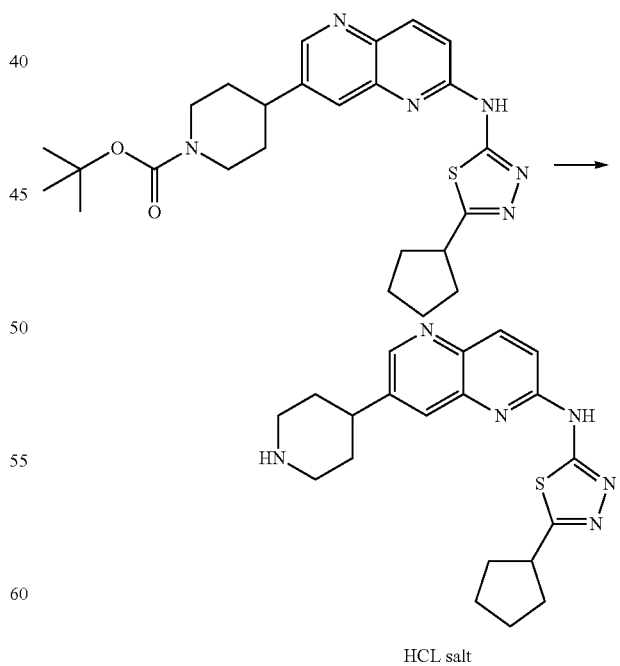

HCL salt

5-Cyclopentyl-N-(7-(piperidin-4-yl)-1,5-naphthyridin-2-yl)-1,3,4-thiadiazole-2-amine hydrochloride was obtained as a white solid in the same manner as in Example 0330-1.

¹H-NMR(DMSO-d₆)δ:12.11(1H,brs),8.85-8.40(3H,m), 8.29(1H,d,J=8.9 Hz),7.99(1H,d,J=2.0 Hz),7.46(1H,d,J=8.9 Hz),3.78-3.25(2H,m),3.24-2.96(3H,m),2.23-1.60(13H,m).

MSm/z(M+H):381.

Example 0333

0333-1

Example 0334

0334-1

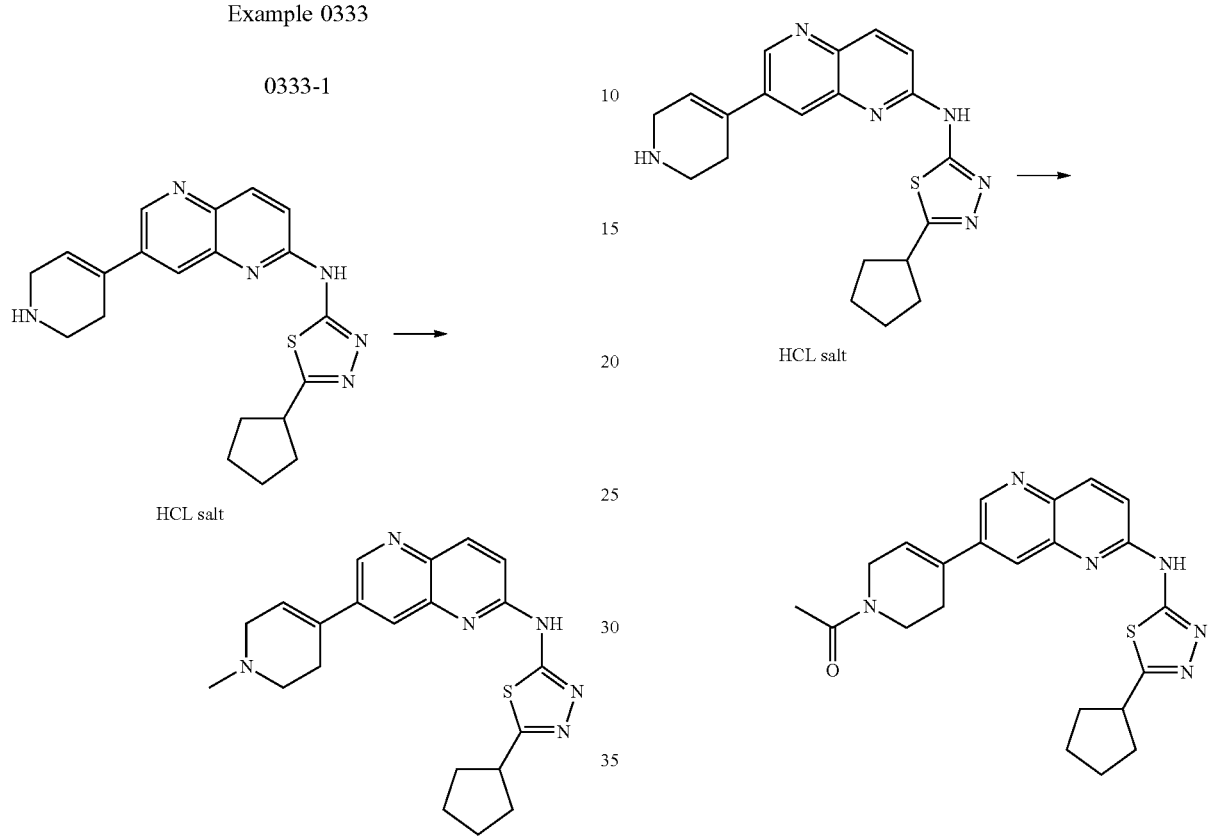

HCL salt

A 36 to 38% formaldehyde aqueous solution (0.2 mL) and sodium triacetoxyborohydride (15.3 mg) were added to a solution of 5-cyclopentyl-N-(7-(1,2,3,6-tetrahydropyridin-4-yl)-1,5-naphthyridin-2-yl)-1,3,4-thiadiazole-2-amine hydrochloride (3.0 mg) in methanol (0.5 mL) and dichloromethane (0.5 mL) at room temperature, followed by stirring for 2 hours. The solvent was distilled off under reduced pressure, and the obtained residue was purified by silica gel column chromatography (chloroform-methanol, NH silica), thereby obtaining 5-cyclopentyl-N-(7-(1-methyl-1,2,3,6-tetrahydropyridin-4-yl)-1,5-naphthyridin-2-yl)-1,3,4-thiadiazole-2-amine (1.7 mg) as a white solid.

¹H-NMR(DMSO-d₆)δ:12.04(1H,brs),8.96(1H,d,J=2.3 Hz),8.26(1H,d,J=9.2 Hz),8.08(1H,d,J=2.3 Hz),7.41(1H,d,J=9.2 Hz),6.57(1H,bt,J=3.3 Hz),3.56-3.39(1H,m),3.10(2H,bd,J=3.3 Hz),2.71-2.59(4H,m),2.32(3H,s),2.24-2.06(2H,m),1.97-1.59(6H,m).

MSm/z(M+H):393.

Acetyl chloride (2 μL) was added to a solution of 5-cyclopentyl-N-(7-(1,2,3,6-tetrahydropyridin-4-yl)-1,5-naphthyridin-2-yl)-1,3,4-thiadiazole-2-amine hydrochloride (4.0 mg) in pyridine (0.5 mL) in an ice bath, followed by stirring at room temperature for 1 hour. A saturated sodium hydrogen carbonate aqueous solution was added to the reaction mixture, and the solvent was distilled off under reduced pressure. The obtained residue was purified by silica gel column chromatography (chloroform-methanol, NH silica), thereby obtaining 1-(4-(6-((5-cyclopentyl-1,3,4-thiadiazol-2-yl)amino)-1,5-naphthyridin-3-yl)-5,6-dihydropyridine-1(2H)-yl)ethanone (1.4 mg) as a white solid.

¹H-NMR(DMSO-d₆)δ:12.06(1H,brs),8.99-8.93(1H,m), 8.27(1H,d,J=9.2 Hz),8.14-8.08(1H,m),7.43(1H,d,J=9.2 Hz),6.62-6.54(1H,m),4.27-4.15(2H,m),3.77-3.66(2H,m),3.57-3.40(1H,m),2.78-2.59(2H,m),2.22-2.04(5H,m),1.94-1.62 (6H,m).

MSm/z(M+H):421.

Example 0335

0335-1

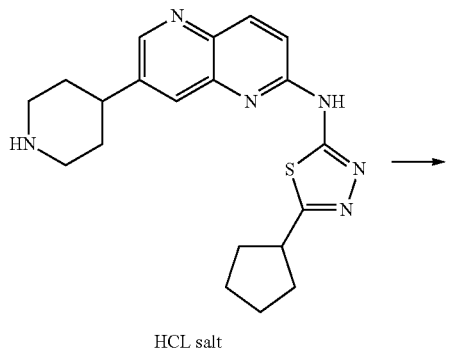

HCL salt

↓

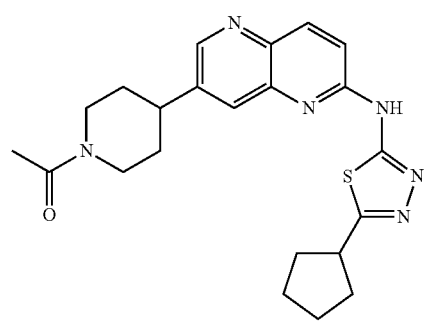

1-(4-(6-((5-Cyclopentyl-1,3,4-thiadiazol-2-yl)amino)-1,5-naphthyridin-3-yl)piperidin-1-yl)ethanone was obtained as a white solid in the same manner as in Example 0334-1.

¹H-NMR(DMSO-d₆)δ:12.03(1H,brs),8.73(1H,d,J=2.0 Hz),8.26(1H,d,J=8.9 Hz),8.03(1H,d,J=2.0 Hz),7.42(1H,d,J=8.9 Hz),4.66-4.53(1H,m),4.04-3.93(1H,m),3.55-3.39(1H,m),3.25-3.00(2H,m),2.71-2.56(1H,m),2.23-2.03(6H,m),1.97-1.51(9H,m).

MSm/z(M+H):423.

Example 0336

0336-1

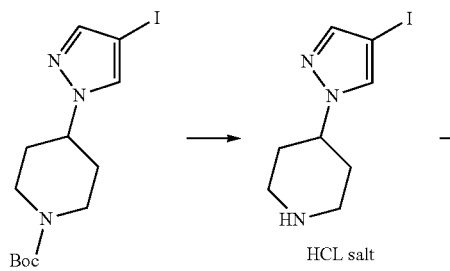

-continued

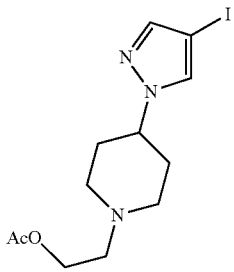

A 4 mol/L hydrogen chloride/1,4-dioxane solution (1.5 mL) was added to a solution of tert-butyl 4-(4-iodo-1H-pyrazol-1-yl)piperidine-1-carboxylate (300 mg) in methanol (1.5 mL) at room temperature, followed by stirring for 1 hour. The solvent was distilled off under reduced pressure, hexane was added to the obtained residue, and the solid matter was collected by filtration, thereby obtaining 4-(4-iodo-1H-pyrazol-1-yl)piperidine hydrochloride (0.283 g) as a white solid.

60% sodium hydride (30.6 mg) was added to a solution of the obtained hydrochloride (100 mg) in N,N-dimethylformamide (1 mL) in an ice bath, followed by stirring at room temperature for 30 minutes. 2-Bromoethyl acetate (70 μL) was added to the reaction mixture at room temperature, followed by stirring at room temperature for 1 hour, and stirring at 80° C. for 1 hour. The reaction mixture was cooled to room temperature, and water and ethyl acetate were added thereto. The organic layer was collected by separation, washed with water and a saturated sodium chloride aqueous solution, and dried over anhydrous sodium sulfate, and the solvent was distilled off under reduced pressure. The obtained residue was purified by silica gel column chromatography (hexane-ethyl acetate), thereby obtaining 2-(4-(4-iodo-1H-pyrazol-1-yl)piperidin-1-yl)ethyl acetate (62.1 mg) as colorless oily substance.

¹H-NMR(CDCl₃)δ:7.50(1H,s),7.46(1H,s),4.20(2H,t,J=5.9 Hz),3.11-2.99(2H,m),2.67(2H,t,J=5.9 Hz),2.23(2H,td,J=11.7,2.4 Hz),2.17-1.90(8H,m).

0336-2

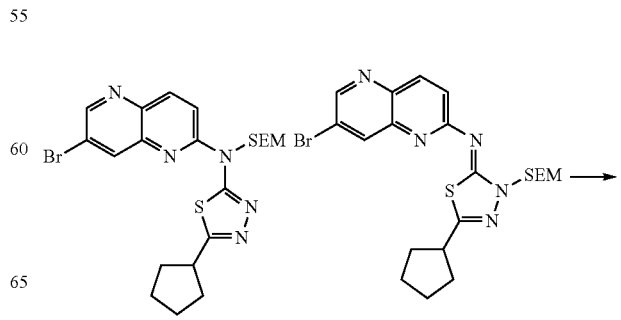

-continued

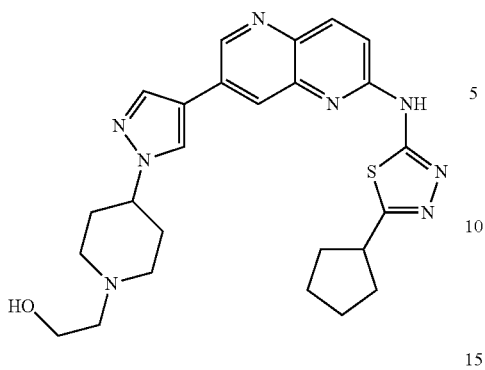

2-(4-(4-(6-((5-cyclopentyl-1,3,4-thiadiazol-2-yl)amino)-1,5-naphthyridin-3-yl)-1H-pyrazol-1-yl)piperidin-1-yl)ethanol (2.2 mg) was obtained as a white solid in the same manner as in Examples 0110-3 and 0110-4.

$^1$H-NMR(DMSO-d$_6$)δ:12.04(1H,s),9.09(1H,d,J=2.0 Hz), 8.66(1H,s),8.34(1H,d,J=2.0 Hz),8.28-8.20(2H,m),7.39(1H, d,J=8.6 Hz),4.43(1H,t,J=5.3 Hz),4.27-4.11(1H,m),3.61-3.21 (5H,m),3.07-2.93(2H,m),2.45(2H,t,J=6.3 Hz),2.30-1.62 (12H,m).

MSm/z(M+H):491.

Example 0337

0337-1

0337-2

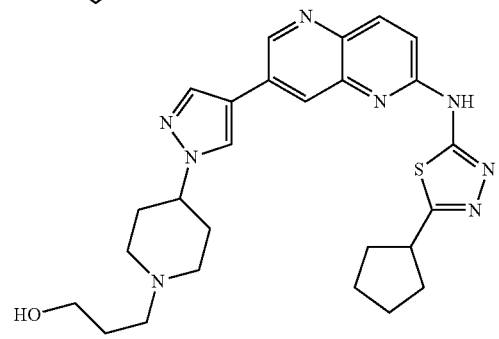

3-(4-(4-(6-((5-Cyclopentyl-1,3,4-thiadiazol-2-yl)amino)-1,5-naphthyridin-3-yl)-1H-pyrazol-1-yl)piperidin-1-yl)propan-1-ol was obtained as a white solid in the same manner as in Examples 0110-3 and 0110-4.

$^1$H-NMR(DMSO-d$_6$)δ:9.09-8.92(1H,m),8.68-8.59(1H, m),8.35-8.02(3H,m),7.41-7.19(1H,m),4.56-4.38(1H,m), 4.29-4.10(1H,m),3.55-3.11(5H,m),3.07-2.89(2H,m),2.39 (2H,t,J=7.3 Hz),2.23-1.51(14H,m).

MSm/z(M+H):505.

Example 0338

0338-1

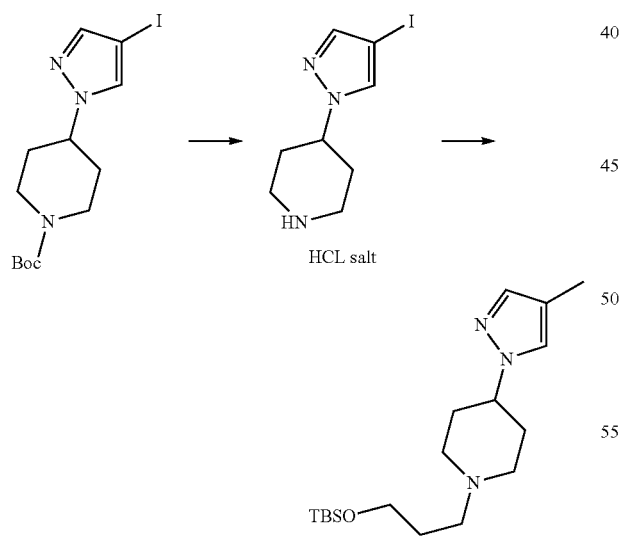

1-(3-((tert-Butyldimethylsilyl)oxy)propyl)-4-(4-iodo-1H-pyrazol-1-yl)piperidine was obtained as a white solid in the same manner as in Example 0336-1.

$^1$H-NMR(CDCl$_3$)δ:7.50(1H,s),7.47(1H,s),3.66(2H,t, J=6.3 Hz),3.08-2.96(2H,m),2.50-2.39(2H,m),2.19-1.88(5H, m),1.78-1.64(2H,m),0.95-0.78(11H,m),0.05(6H,s).

60% sodium hydride (74.4 mg) was added to a solution of 4-iodo-1H-pyrazole (300 mg) in N,N-dimethylformamide (2 mL) at room temperature, followed by stirring for 30 minutes. 4-(Chloromethyl)-2,2-dimethyl-1,3-dioxolane (0.439 mL) was added to the reaction mixture at room temperature, followed by stirring at room temperature for 1 hour, and stirring at 80° C. for 3 hours. The reaction mixture was cooled to room temperature, and a saturated ammonium chloride aqueous solution and ethyl acetate were added thereto. The organic layer was collected by separation, and dried over anhydrous sodium sulfate, and the solvent was distilled off under reduced pressure. The obtained residue was purified by silica gel column chromatography (hexane-ethyl acetate), thereby obtaining 1-((2,2-dimethyl-1,3-dioxolan-4-yl)methyl)-4-iodo-1H-pyrazole (304 mg) as a white solid.

$^1$H-NMR(CDCl$_3$)δ:7.54(1H,s),7.51(1H,s),4.48-4.37(1H, m),4.33-4.17(2H,m),4.07(1H,dd,J=8.6,6.6 Hz),3.75(1H,dd, J=8.6,5.9 Hz),1.38(3H,s),1.35(3H,s).

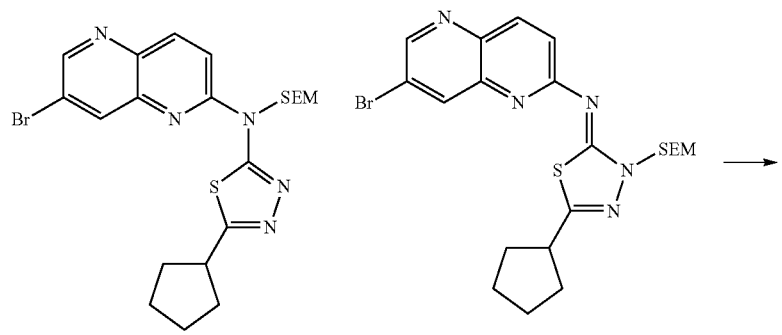

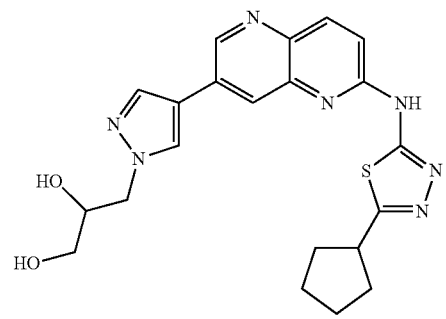

-continued 3-(4-(6-((5-Cyclopentyl-1,3,4-thiadiazol-2-yl)amino)-1,5-naphthyridin-3-yl)-1H-pyrazol-1-yl)propane-1,2-diol was obtained as a white solid in the same manner as in Examples 0110-3 and 0110-4.

$^1$H-NMR(DMSO-d$_6$)δ:12.03(1H,s),9.09(1H,d,J=2.0 Hz),8.52(1H,s),8.34(1H,d,J=2.0 Hz),8.28-8.20(2H,m),7.39(1H,d,J=9.2 Hz),5.07(1H,d,J=5.3 Hz),4.79(1H,t,J=5.6 Hz),4.30(1H,dd,J=13.9,4.0 Hz),4.05(1H,dd,J=13.9,7.9 Hz),3.95-3.82(1H,m),3.57-3.21(3H,m),2.24-2.09(2H,m),1.97-1.62(6H,m).

MSm/z(M+H):438.

Example 0339

0339-1

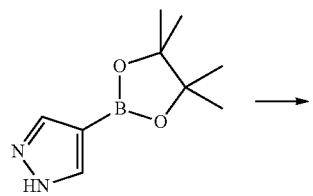

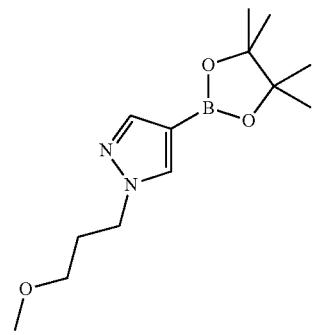

1-(3-Methoxypropyl)-4-(4,4,5,5-tetramethyl-1,3,2-dioxaborolan-2-yl)-1H-pyrazole was obtained as colorless oily substance in the same manner as in Example 0316-1.

$^1$H-NMR(CDCl$_3$)δ:7.84-7.76(1H,m),7.74-7.65(1H,m),4.30-4.19(2H,m),3.39-3.27(5H,m),2.20-2.06(2H,m),1.39-1.29(12H,m).

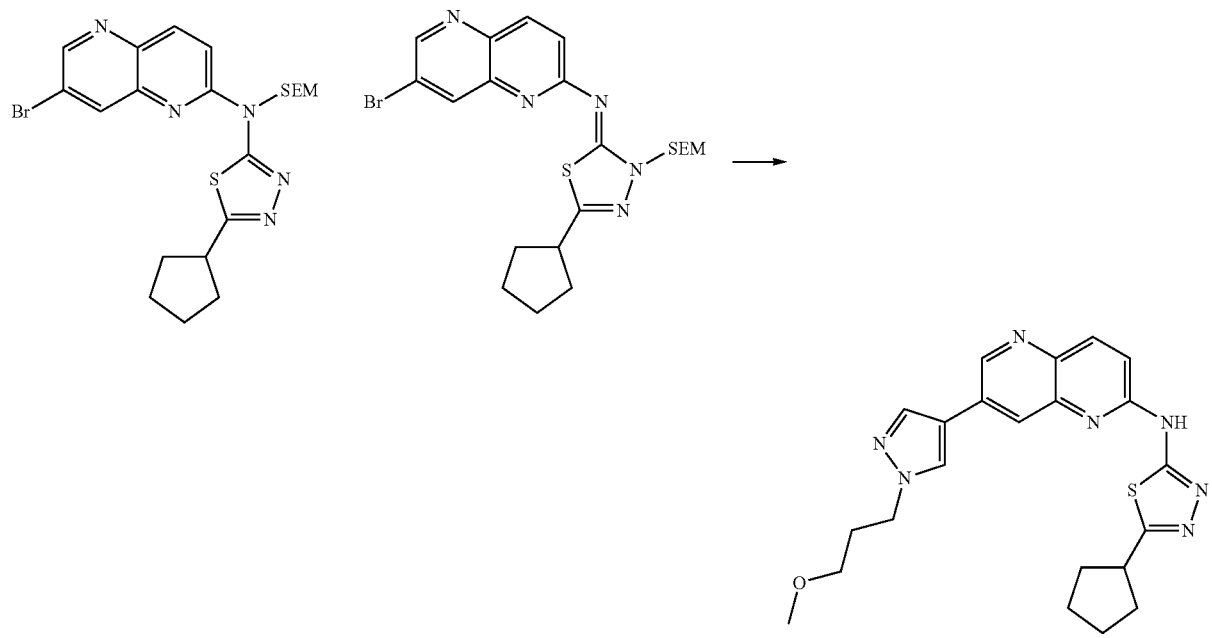

A mixture of a mixture (10 mg) of N-(7-bromo-1,5-naphthyridin-2-yl)-5-cyclopentyl-N-((2-(trimethylsilyl)ethoxy)methyl)-1,3,4-thiadiazole-2-amine and (Z)-7-bromo-N-(5-cyclopentyl-3-((2-(trimethylsilyl)ethoxy)methyl)-1,3,4-thiadiazol-2(3H)-ylidene)-1,5-naphthyridine-2-amine, 1-(3-methoxypropyl)-4-(4,4,5,5-tetramethyl-1,3,2-dioxaborolan-2-yl)-1H-pyrazole (7.9 mg), bis(di-tert-butyl(4-dimethylaminophenyl)phosphine)dichloropalladium(II) (1.4 mg), sodium carbonate (4.2 mg), 1,4-dioxane (1 mL), and water (0.1 mL) was stirred at 100° C. for 12.5 hours in a nitrogen atmosphere in a sealed tube. The reaction mixture was cooled to room temperature, and methanol (1 mL) and a 4 mol/L hydrogen chloride/1,4-dioxane solution (1 mL) were added thereto, followed by stirring at room temperature for 2 hours. The solvent was distilled off under reduced pressure, triethylamine was added to the obtained residue, and the solvent was distilled off under reduced pressure. The obtained residue was purified by silica gel column chromatography (hexane-ethyl acetate), thereby obtaining 5-cyclopentyl-N-(7-(1-(3-methoxypropyl)-1H-pyrazol-4-yl)-1,5-naphthyridin-2-yl)-1,3,4-thiadiazole-2-amine (2.5 mg) as a white solid.

$^1$H-NMR(DMSO-$d_6$)δ:12.02(1H,brs),9.06(1H,s),8.57(1H,s),8.31(1H,s),8.27-8.15(2H,m),7.37(1H,d,J=8.6 Hz),4.22(2H,t,J=6.9 Hz),3.57-3.12(6H,m),2.24-2.02(4H,m),1.96-1.62(6H,m).

MSm/z(M+H):436.

Example 0340

0340-1

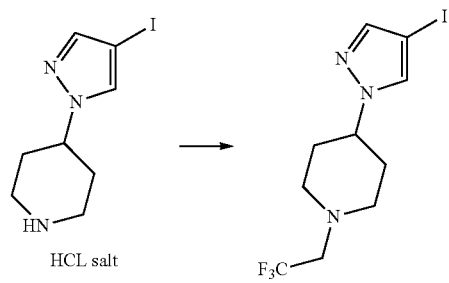 [SMILES: Ic1cnn(C2CCNCC2)c1 ; FC(F)(F)CN1CCC(n2cc(I)cn2)CC1]

Triethylamine (123 μL) and 2,2,2-trifluoroethyl trifluoromethanesulfonate (102 mg) were added to a solution of 4-(4-iodo-1H-pyrazol-1-yl)piperidine hydrochloride (69 mg) in tetrahydrofuran (1 mL) at room temperature, followed by stirring at 80° C. for 13.5 hours in a sealed tube. The reaction mixture was cooled to room temperature, and the solvent was distilled off under reduced pressure. The obtained residue was purified by silica gel column chromatography (hexane-ethyl acetate), thereby obtaining 4-(4-iodo-1H-pyrazol-1-yl)-1-(2,2,2-trifluoroethyl)piperidine (49.5 mg) as a white solid.

$^1$H-NMR(CDCl$_3$)δ:7.67-7.41(2H,m),4.32-4.05(1H,m),3.35-2.95(4H,m),2.82-2.49(2H,m),2.40-1.91(4H,m).

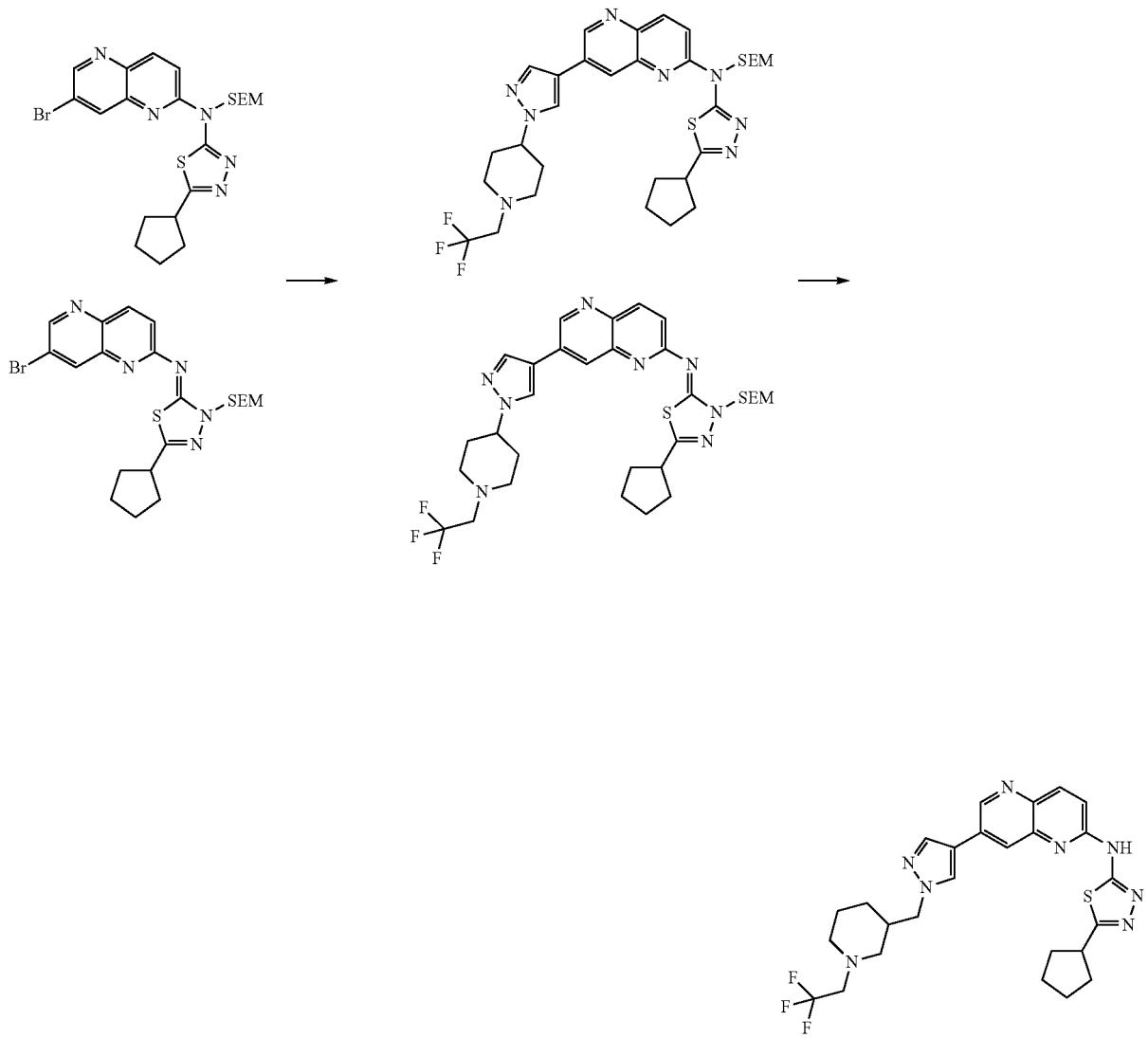

A mixture of a mixture (20 mg) of N-(7-bromo-1,5-naphthyridin-2-yl)-5-cyclopentyl-N-((2-(trimethylsilyl)ethoxy)methyl)-1,3,4-thiadiazole-2-amine and (Z)-7-bromo-N-(5-cyclopentyl-3-((2-(trimethylsilyl)ethoxy)methyl)-1,3,4-thiadiazol-2(3H)-ylidene)-1,5-naphthyridine-2-amine, bis(pinacolato)diboron (15.1 mg), (1,1'-bis(diphenylphosphino)ferrocene)palladium(II) dichloride (3.2 mg), potassium acetate (7.8 mg), and 1,4-dioxane (0.4 mL) was stirred at 80° C. for 4 hours in a nitrogen atmosphere in a sealed tube. The reaction mixture was cooled to room temperature, and sodium carbonate (21.0 mg), bis(di-tert-butyl(4-dimethylaminophenyl)phosphine)dichloropalladium(II) (2.8 mg), 4-(4-iodo-1H-pyrazol-1-yl)-1-(2,2,2-trifluoroethyl)piperidine (17.0 mg), 1,4-dioxane (1 mL), and water (0.14 mL) were added thereto, followed by stirring at 120° C. for 18 hours in a sealed tube. The reaction mixture was cooled to room temperature, and the solvent was distilled off under reduced pressure, thereby obtaining a mixture of 5-cyclopentyl-N-(7-(1-(1-(2,2,2-trifluoroethyl)piperidin-4-yl)-1H-pyrazol-4-yl)-1,5-naphthyridin-2-yl)-N-((2-(trimethylsilyl)ethoxy)methyl)-1,3,4-thiadiazole-2-amine and (Z)-N-(5-cyclopentyl-3-((2-(trimethylsilyl)ethoxy)methyl)-1,3,4-thiadiazol-2(3H)-ylidene)-7-(1-(1-(2,2,2-trifluoroethyl)piperidin-4-yl)-1H-pyrazol-4-yl)-1,5-naphthyridine-2-amine.

Methanol (1 mL) and a 4 mol/L hydrogen chloride/1,4-dioxane solution (1 mL) were added to the obtained mixture at room temperature, followed by stirring for 1 hour. The solvent was distilled off under reduced pressure, triethylamine was added to the obtained residue, and the solvent was distilled off under reduced pressure. The obtained residue was purified by silica gel column chromatography (chloroform-methanol, NH silica), thereby obtaining 5-cyclopentyl-N-(7-(1-(1-(2,2,2-trifluoroethyl)piperidin-4-yl)-1H-pyrazol-4-yl)-1,5-naphthyridin-2-yl)-1,3,4-thiadiazole-2-amine (5.6 mg) as a white solid.

$^1$H-NMR(DMSO-$d_6$)δ:12.04(1H,brs),9.09(1H,d,J=2.0 Hz),8.69(1H,s),8.35(1H,d,J=2.0 Hz),8.28-8.20(2H,m),7.39(1H,d,J=8.6 Hz),4.32-4.16(1H,m),3.57-3.18(3H,m),3.11-2.98(2H,m),2.67-2.45(2H,m),2.23-1.62(12H,m).

MS m/z(M+H):529.

Example 0341

0341-1

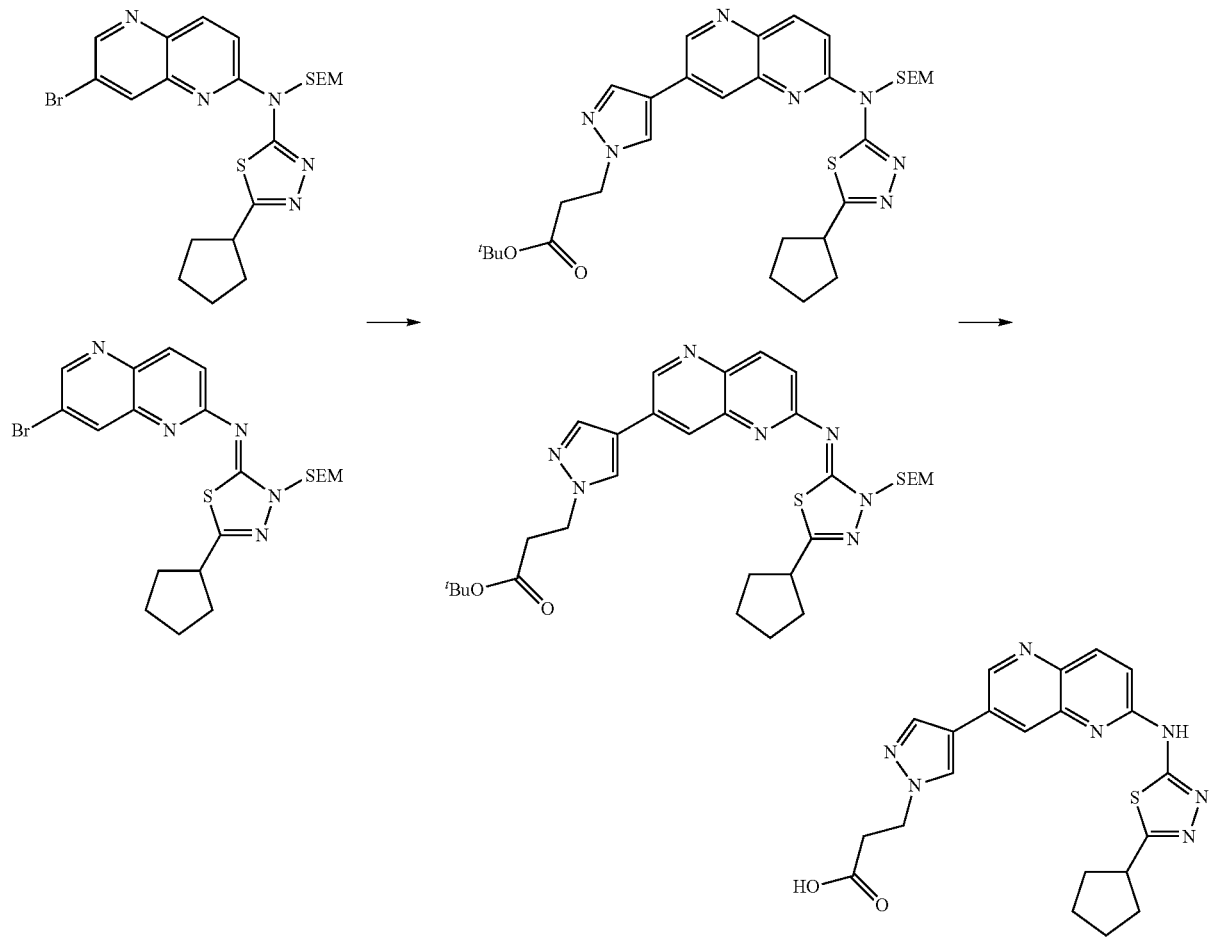

A mixture of a mixture (30 mg) of N-(7-bromo-1,5-naphthyridin-2-yl)-5-cyclopentyl-N-((2-(trimethylsilyl)ethoxy)methyl)-1,3,4-thiadiazole-2-amine and (Z)-7-bromo-N-(5-cyclopentyl-3-((2-(trimethylsilyl)ethoxy)methyl)-1,3,4-thiadiazol-2(3H)-ylidene)-1,5-naphthyridine-2-amine, tert-butyl 3-(4-(4,4,5,5-tetramethyl-1,3,2-dioxaborolan-2-yl)-1H-pyrazol-1-yl)propanoate (23.2 mg), bis(di-tert-butyl(4-dimethylaminophenyl)phosphine)dichloropalladium(II) (3.4 mg), sodium carbonate (10.2 mg), 1,4-dioxane (1 mL), and water (0.1 mL) was stirred at 120° C. for 18 hours in a nitrogen atmosphere in a sealed tube. The reaction mixture was cooled to room temperature, and the solvent was distilled off under reduced pressure, thereby obtaining a mixture of tert-butyl 3-(4-(6-((5-cyclopentyl-1,3,4-thiadiazol-2-yl)((2-(trimethylsilyl)ethoxy)methyl)amino)-1,5-naphthyridin-3-yl)-1H-pyrazol-1-yl)propanoate and (Z)-tert-butyl 3-(4-(6-((5-cyclopentyl-3-((2-(trimethylsilyl)ethoxy)methyl)-1,3,4-thiadiazol-2(3H)-ylidene)amino)-1,5-naphthyridin-3-yl)-1H-pyrazol-1-yl)propanoate.

Methanol (1 mL) and a 4 mol/L hydrogen chloride/1,4-dioxane solution (1 mL) were added to the obtained mixture at room temperature, followed by stirring for 1 hour. The solvent was distilled off under reduced pressure, ethanol was added to the obtained residue, and the resultant product was neutralized with a saturated sodium hydrogen carbonate aqueous solution. The solvent was distilled off under reduced pressure, thereby obtaining 3-(4-(6-((5-cyclopentyl-1,3,4-thiadiazol-2-yl)amino)-1,5-naphthyridin-3-yl)-1H-pyrazol-1-yl)propionic acid (48.3 mg) as a yellow solid.
MS m/z (M+H): 436.

0341-2

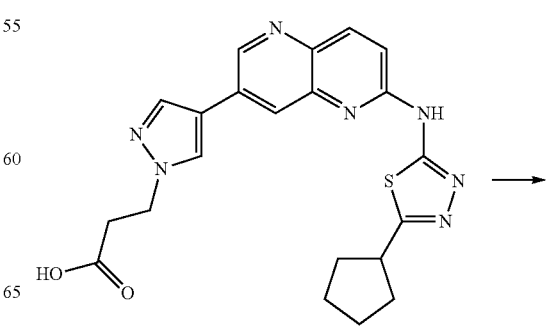

-continued

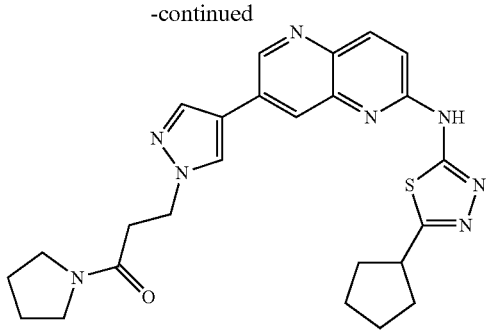

1,1'-Carbonyldiimidazole (29.8 mg) was added to a solution of 3-(4-(6-((5-cyclopentyl-1,3,4-thiadiazol-2-yl)amino)-1,5-naphthyridin-3-yl)-1H-pyrazol-1-yl)propionic acid (20 mg) in N,N-dimethylformamide (0.5 mL) at room temperature, followed by stirring for 1 hour. Pyrrolidine (38 µL) was added to the reaction mixture at room temperature, followed by stirring for 30 minutes, and after methanol was added thereto, the solvent was distilled off under reduced pressure. The obtained residue was purified by preparative thin layer silica gel chromatography (chloroform-methanol, NH silica), thereby obtaining 3-(4-(6-((5-cyclopentyl-1,3,4-thiadiazol-2-yl)amino)-1,5-naphthyridin-3-yl)-1H-pyrazol-1-yl)-1-(pyrrolidin-1-yl)propan-1-one (3.7 mg) as a white solid.

$^1$H-NMR(DMSO-$d_6$)δ:12.03(1H,brs),9.06(1H,d,J=2.0 Hz),8.56(1H,s),8.31(1H,d,J=2.0 Hz),8.27-8.19(2H,m),7.38 (1H,d,J=9.2 Hz),4.41(2H,t,J=6.9 Hz),3.58-3.23(5H,m),2.89 (2H,t,J=6.9 Hz),2.23-2.08(2H,m),1.96-1.62(10H,m).

MSm/z(M+H):489.

Examples 0342 and 0343

The following compounds were obtained in the same manner as in Example 0341-2.

| Example No. | | |
|---|---|---|
| 0342 | | |
| 0342-1 | 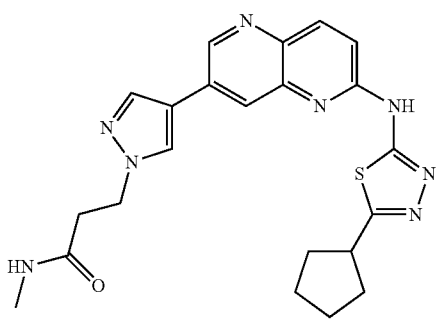 [SMILES: CNC(=O)CCn1cc(-c2cnc3ccc(Nc4nnc(C5CCCC5)s4)nc3c2)cn1] | 1H-NMR(DMSO-$d_6$)δ: 12.03(1 H, brs), 9.06(1 H, d, J = 2.6 Hz), 8.52(1 H, s), 8.32(1 H, d, J = 2.0 Hz), 8.27-8.21(2H, m), 7.91(1 H, brd, J = 4.6 Hz), 7.39(1 H, d, J = 9.2 Hz), 4.39(2H, t, J = 6.9 Hz), 3.58-3.27 (1 H, m), 2.71(2H, t, J = 6.9 Hz), 2.57(3H, d, J = 4.6 Hz), 2.24-2.09 (2H, m), 1.96-1.68(6H, m). MSm/z(M + H): 449. |
| 0343 | | |
| 0343-1 | 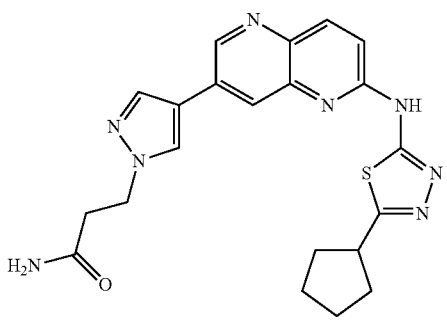 [SMILES: NC(=O)CCn1cc(-c2cnc3ccc(Nc4nnc(C5CCCC5)s4)nc3c2)cn1] | 1H-NMR(DMSO-$d_6$)δ: 9.02(1 H, brs), 8.51(1 H, s), 8.28(1 H, brs), 8.25-8.13(2H, m), 7.44(1 H, brs), 7.34(1 H, brd, J = 9.2 Hz), 7.00-6.86(1 H, m), 4.37(2H, t, J = 6.9 Hz), 3.60-3.18 (1 H, m), 2.71(2H, t, J = 6.9 Hz), 2.24-2.06(2H, m), 1.95-1.62(6H, m). MSm/z(M + H): 435. |

Example 0344

0344-1

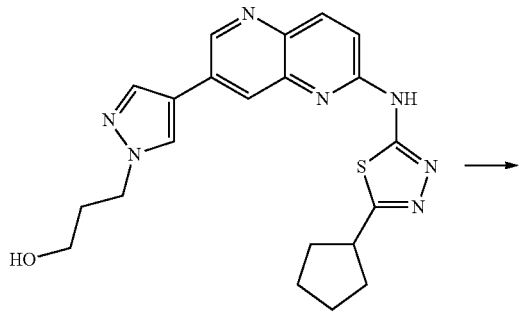

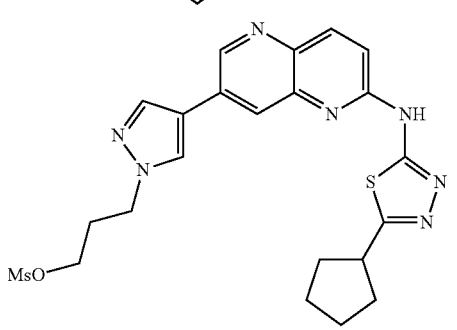

Methanesulfonyl chloride (110 µL) was added to a solution of 3-(4-(6-((5-cyclopentyl-1,3,4-thiadiazol-2-yl)amino)-1,5-naphthyridin-3-yl)-1H-pyrazol-1-yl)propan-1-ol (200 mg) in pyridine (2.4 mL) in an ice bath, followed by stirring at room temperature for 1.5 hours. A saturated sodium hydrogen carbonate aqueous solution was added to the reaction mixture, followed by stirring at room temperature for 30 minutes. The solvent was distilled off under reduced pressure, and the obtained residue was purified by silica gel column chromatography (chloroform-methanol), thereby obtaining 3-(4-(6-((5-cyclopentyl-1,3,4-thiadiazol-2-yl)amino)-1,5-naphthyridin-3-yl)-1H-pyrazol-1-yl)propyl methanesulfonate (173 mg) as a white solid.

MSm/z(M+H):500.

0344-2

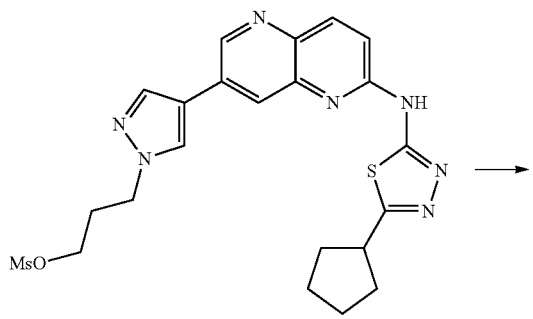

Piperidine (15.8 µL) was added to a mixture of 3-(4-(6-((5-cyclopentyl-1,3,4-thiadiazol-2-yl)amino)-1,5-naphthyridin-3-yl)-1H-pyrazol-1-yl)propyl methanesulfonate (30 mg), potassium carbonate (22.1 mg), and N,N-dimethylformamide (0.5 mL) at room temperature, followed by stirring at 80° C. for 18 hours. The reaction mixture was cooled to room temperature, and the solvent was distilled off under reduced pressure. The obtained residue was purified by silica gel column chromatography (chloroform-methanol, NH silica), and purified by preparative thin layer silica gel chromatography (chloroform-methanol, NH silica), thereby obtaining 5-cyclopentyl-N-(7-(1-(3-(piperidin-1-yl)propyl)-1H-pyrazol-4-yl)-1,5-naphthyridin-2-yl)-1,3,4-thiadiazole-2-amine (5.3 mg) as a white solid.

$^1$H-NMR(DMSO-d$_6$)δ:9.07(1H,d,J=2.0 Hz),8.56(1H,s), 8.31(1H,d,J=2.0 Hz),8.28-8.20(2H,m),7.39(1H,d,J=9.2 Hz), 4.19(2H,t,J=7.3 Hz),3.58-3.25(1H,m),2.39-2.08(8H,m), 2.07-1.63(8H,m),1.59-1.32(6H,m).

MSm/z(M+H):489.

Examples 0345 and 0346

The following compounds were obtained in the same manner as in Example 0342-2.

| Example No. | | |
|---|---|---|
| 0345 | | |
| 0345-1 | 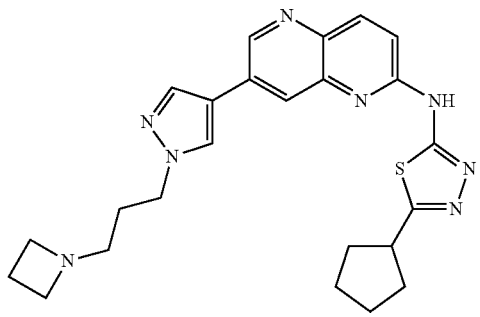 [SMILES: c1nc2ccc(Nc3nnc(C4CCCC4)s3)nc2cc1-c1cnn(CCCN2CCC2)c1] | 1H-NMR(DMSO-d₆)δ:<br>9.08(1 H, d, J = 2.0 Hz), 8.56(1 H, s), 8.33(1 H, d, J = 2.0 Hz), 8.28-8.20(2H, m), 7.39(1 H, d, J = 9.2 Hz), 4.17(2H, t, J = 7.3 Hz), 3.60-3.22(1 H, m), 3.08(4H, t, J = 6.9 Hz), 2.33(2H, t, J = 6.6 Hz), 2.24-2.09(2H, m), 2.01-1.63(10H, m).<br>MSm/z(M + H): 461. |
| 0346 | | |
| 0346-1 | 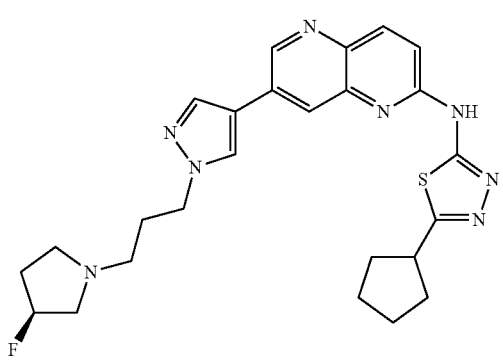 [SMILES: F[C@H]1CCN(CCCn2cc(-c3cnc4ccc(Nc5nnc(C6CCCC6)s5)nc4c3)cn2)C1] | 1H-NMR(DMSO-d₆)δ:<br>12.02(1 H, brs), 9.08(1 H, d, J = 2.0 Hz), 8.57(1 H, s), 8.32(1 H, d, J = 2.0 Hz), 8.29-8.19(2H, m), 7.39(1 H, d, J = 8.6 Hz), 5.33-5.05(1 H, m), 4.22(2H, t, J = 7.3 Hz), 3.62-3.27(1 H, m), 2.91-2.47(4H, m), 2.43(2H, t, J = 6.6 Hz), 2.36-1.63(12H, m).<br>MSm/z(M + H): 493. |

Examples 0347 and 0348
The following compounds were obtained in the same manner as in Examples 0110-3 and 0110-4.
| Example No. | | |
|---|---|---|
| 0347 | | |
| 0347-1 | 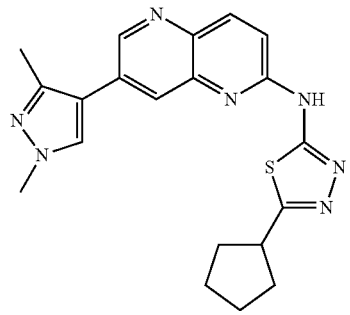 [SMILES: Cc1nn(C)cc1-c1cnc2ccc(Nc3nnc(C4CCCC4)s3)nc2c1] | 1H-NMR(DMSO-$d_6$)δ: 12.05(1 H, brs), 8.91(1 H, d, J = 2.0 Hz), 8.30-8.24(2H, m), 8.15(1 H, d, J = 2.0 Hz), 7.42(1 H, d, J = 8.6 Hz), 3.85(3H, s) 3.55-3.27(1 H, m), 2.43(3H, s), 2.23-2.07(2H, m), 1.95-1.62(6H, m). MSm/z(M + H): 392. |
| 0348 | | |
| 0348-1 | 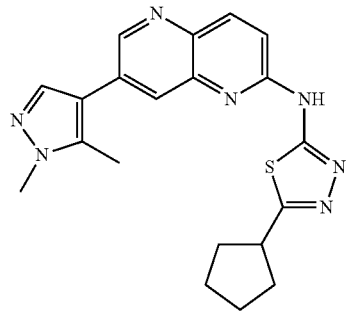 [SMILES: Cc1c(-c2cnc3ccc(Nc4nnc(C5CCCC5)s4)nc3c2)cnn1C] | 1H-NMR(DMSO-$d_6$)δ: 12.05(1 H, brs), 8.87(1 H, d, J = 2.0 Hz), 8.28(1 H, d, J = 8.6 Hz), 8.13(1 H, d, J = 2.0 Hz), 7.89(1 H, s), 7.43(1 H, d, J = 9.2 Hz), 3.85(3H, s), 3.59-3.24(4H, m), 2.23-2.07(2H, m), 1.94-1.61(6H, m). MSm/z(M + H): 392. |

Examples 0349 and 0350

0349-1 and 350-1

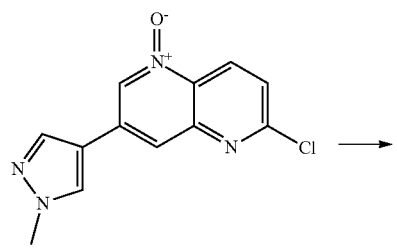

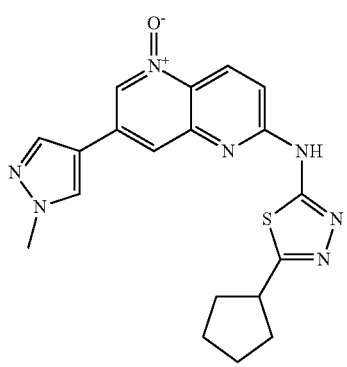

-continued

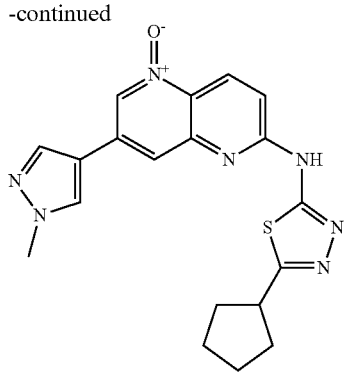

A mixture of 6-chloro-3-(1-methyl-1H-pyrazol-4-yl)-1,5-naphthyridine 1-oxide (230 mg), 5-cyclopentyl-1,3,4-thiadiazole-2-amine (223 mg), tris(dibenzylideneacetone)dipalladium(0) (80.8 mg), 2-dicyclohexylphosphino-2',4',6'-triisopropylbiphenyl (102 mg), cesium carbonate (573 mg), and 1,4-dioxane (3 mL) was stirred at 120° C. for 17 hours in a nitrogen atmosphere in a sealed tube. The reaction mixture was cooled to room temperature, and water was added thereto. The solid matter was collected by filtration, and washed with water and ethyl acetate, thereby obtaining 6-((5-cyclopentyl-1,3,4-thiadiazol-2-yl)amino)-3-(1-methyl-1H-pyrazol-4-yl)-1,5-naphthyridine 1-oxide (415 mg) as a black solid.

MS m/z(M+H):394.

0349-2 and 0350-2

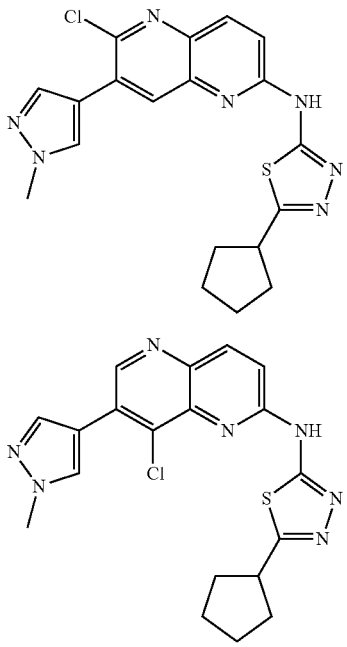

Phosphorus oxychloride (1 mL) was added to 6-((5-cyclopentyl-1,3,4-thiadiazol-2-yl)amino)-3-(1-methyl-1H-pyrazol-4-yl)-1,5-naphthyridine 1-oxide (415 mg), followed by stirring at 80° C. for 2 hours. The reaction mixture was cooled to room temperature, and added dropwise to water in an ice bath, followed by stirring at room temperature for 30 minutes. The resultant product was neutralized by the addition of sodium carbonate. The solid matter was collected by filtration, and washed with water and ethyl acetate, thereby obtaining a yellow solid (260 mg).

The obtained yellow solid (30 mg) was purified by preparative thin layer silica gel chromatography (chloroform-methanol), thereby obtaining N-(6-chloro-7-(1-methyl-1H-pyrazol-4-yl)-1,5-naphthyridin-2-yl)-5-cyclopentyl-1,3,4-thiadiazole-2-amine (9.7 mg) as a white solid and N-(8-chloro-7-(1-methyl-1H-pyrazol-4-yl)-1,5-naphthyridin-2-yl)-5-cyclopentyl-1,3,4-thiadiazole-2-amine (3.5 mg) as a white solid.

Example 0349

N-(6-chloro-7-(1-methyl-1H-pyrazol-4-yl)-1,5-naphthyridin-2-yl)-5-cyclopentyl-1,3,4-thiadiazole-2-amine $^1$H-NMR(DMSO-$d_6$)δ:12.14(1H,brs),8.42(1H,s),8.37(1H,s),8.23(1H,d,J=8.9 Hz),8.09(1H,s),7.47(1H,d,J=8.9 Hz),3.95(3H,s),3.53-3.31(1H,m),2.24-2.04(2H,m),1.95-1.58(6H,m).
MSm/z(M+H):412.

Example 0350

N-(8-chloro-7-(1-methyl-1H-pyrazol-4-yl)-1,5-naphthyridin-2-yl)-5-cyclopentyl-1,3,4-thiadiazole-2-amine $^1$H-NMR(DMSO-$d_6$)δ:12.30(1H,brs),9.02(1H,s),8.58(1H,s),8.34(1H,d,J=8.9 Hz),8.21(1H,s),7.50(1H,d,J=8.9 Hz),3.97(3H,s),3.63-3.24(1H,m),2.24-2.07(2H,m),1.94-1.62(6H,m).
MSm/z(M+H):412.

Example 0351

0351-1

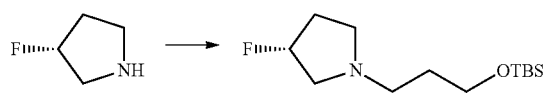 [SMILES: F[C@@H]1CCNC1 ; CC(C)(C)[Si](C)(C)OCCCN1CC[C@@H](F)C1]

60% sodium hydride (96 mg) was added to a solution of (R)-3-fluoropyrrolidine hydrochloride (126 mg) in tetrahydrofuran (2 mL) in an ice bath, followed by stirring at room temperature for 30 minutes. (3-Bromopropoxy) (tert-butyl) dimethylsilane (348 μL) was added to the reaction mixture in an ice bath, followed by stirring at room temperature for 62 hours. A saturated sodium hydrogen carbonate aqueous solution and ethyl acetate were added to the reaction mixture. The organic layer was collected by separation, and dried over anhydrous sodium sulfate, and the solvent was distilled off under reduced pressure. The obtained residue was purified by silica gel column chromatography (chloroform-methanol), thereby obtaining (R)-1-(3-((tert-butyldimethylsilyl)oxy)propyl)-3-fluoropyrrolidine (322 mg) as colorless oily substance.

$^1$H-NMR(CDCl$_3$)δ:5.29-5.03(1H,m),3.67(2H,t,J=6.3 Hz),2.94-2.61(3H,m),2.58-2.50(2H,m),2.46-2.36(1H,m),2.26-1.92(2H,m),1.79-1.68(2H,m),0.89(9H,s),0.05(6H,s).

0351-2

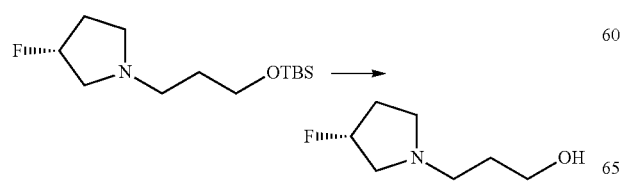

A 4 mol/L hydrogen chloride/1,4-dioxane solution (1 mL) was added to a solution of (R)-1-(3-((tert-butyldimethylsilyl)oxy)propyl)-3-fluoropyrrolidine (0.322 g) in methanol (1 mL) at room temperature, followed by stirring for 30 minutes. The solvent was distilled off under reduced pressure, methanol (1 mL) and a saturated sodium hydrogen carbonate aqueous solution (1 mL) were added to the obtained residue, and the solvent was distilled off under reduced pressure. The obtained residue was purified by silica gel column chromatography (chloroform-methanol), thereby obtaining (R)-3-(3-fluoropyrrolidin-1-yl)propan-1-ol (0.101 mg) as colorless oily substance.

$^1$H-NMR(CDCl$_3$)δ:5.29-5.02(1H,m),3.81(2H,t,J=5.3 Hz),3.02-2.69(5H,m),2.58-2.47(1H,m),2.23-1.93(2H,m),1.79-1.68(2H,m).

0351-3

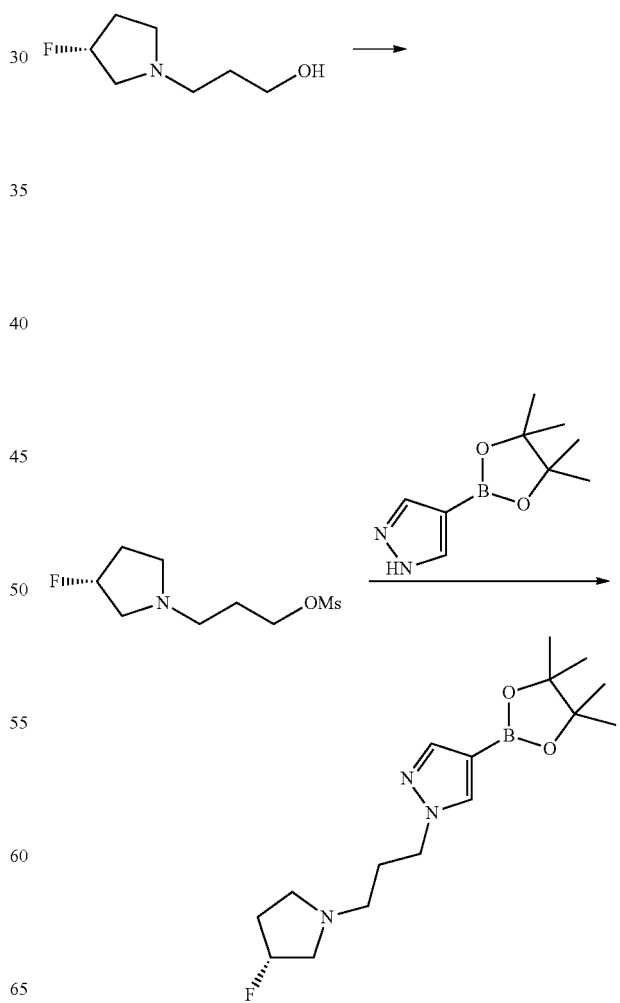

Pyridine (136 μL) and methanesulfonyl chloride (65.2 μL) were added to a solution of (R)-3-(3-fluoropyrrolidin-1-yl)propan-1-ol (80.1 mg) in dichloromethane (2 mL) in an ice bath, followed by stirring for 30 minutes. A saturated sodium hydrogen carbonate aqueous solution was added to the reaction mixture, followed by stirring at room temperature for 30 minutes, and ethyl acetate was added thereto. The organic layer was collected by separation, and dried over anhydrous sodium sulfate, and the solvent was distilled off under reduced pressure. The obtained residue was purified by silica gel column chromatography (ethyl acetate-methanol, NH silica), thereby obtaining (R)-3-(3-fluoropyrrolidin-1-yl)propyl methanesulfonate (106 mg) as yellow oily substance.

A mixture of 4-(4,4,5,5-tetramethyl-1,3,2-dioxaborolan-2-yl)-1H-pyrazole (60.9 mg), (R)-3-(3-fluoropyrrolidin-1-yl)propyl methanesulfonate (106 mg), potassium carbonate (86.8 mg), and acetonitrile (1 mL) was stirred at the external temperature of 80° C. for 14 hours in a nitrogen atmosphere. The reaction mixture was cooled to room temperature, the solid matter was filtered off, and the solvent was distilled off under reduced pressure. The obtained residue was purified by silica gel column chromatography (chloroform-methanol), thereby obtaining (R)-1-(3-(3-fluoropyrrolidin-1-yl)propyl)-4-(4,4,5,5-tetramethyl-1,3,2-dioxaborolan-2-yl)-1H-pyrazole (58.1 mg) as yellow oily substance.

$^1$H-NMR(CDCl$_3$)δ:7.78(1H,s),7.69(1H,s),5.28-5.02(1H,m),4.21(2H,t,J=6.9 Hz),2.93-2.56(3H,m),2.50-2.31(3H,m),2.25-1.89(4H,m),1.32(12H,s).

0351-4

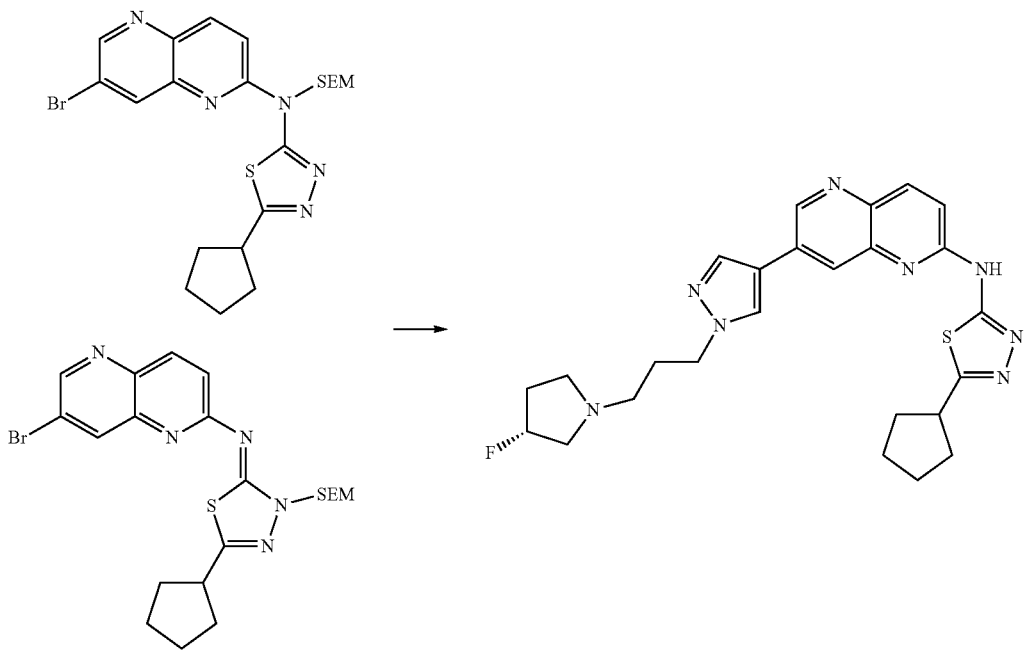 [SMILES: C[Si](C)(C)CCOCn1nc(C2CCCC2)s/c1=N\c1ccc2ncc(Br)cc2n1 ; C[Si](C)(C)CCOCN(c1ccc2ncc(Br)cc2n1)c1nnc(C2CCCC2)s1 ; F[C@@H]1CCN(CCCn2cc(-c3cnc4ccc(Nc5nnc(C6CCCC6)s5)nc4c3)cn2)C1]

(R)-5-cyclopentyl-N-(7-(1-(3-(3-fluoropyrrolidin-1-yl)propyl)-1H-pyrazol-4-yl)-1,5-naphthyridin-2-yl)-1,3,4-thiadiazole-2-amine was obtained as a white solid in the same manner as in Example 0339-2.

$^1$H-NMR(DMSO-d$_6$)δ:12.05(1H,brs),9.08(1H,d,J=2.0 Hz),8.58(1H,s),8.33(1H,d,J=2.0 Hz),8.28-8.21(2H,m),7.39 (1H,d,J=9.2 Hz),5.34-5.05(1H,m),4.22(2H,t,J=6.9 Hz), 3.57-3.40(1H,m),2.94-2.38(6H,m),2.35-1.61(12H,m).
MSm/z(M+H):493.

Examples 0352 to 0354

The following compounds were obtained in the same manner as in Examples 0351-1, 0351-2, 0351-3, and 0339-2.

| Example No. | | |
|---|---|---|
| 0352 | | |
| 0352-1 | 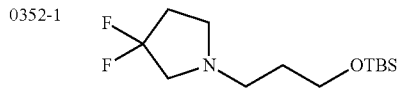 | 1H-NMR(CDCl$_3$)δ: 3.66(2H, t, J = 6.3 Hz), 2.88(2H, t, J = 13.2 Hz), 2.71(2H, t, J = 7.3 Hz), 2.52(2H, t, J = 7.3 Hz), 2.35-2.17(2H, m), 1.75-1.63(2H, m), 0.89(9H, s), 0.05(6H, s). |

| Example No. | | |
|---|---|---|
| 0352-2 | 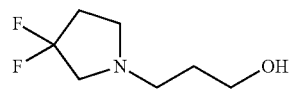 | 1H-NMR(CDCl$_3$)δ:<br>3.96(1 H, s), 3.79(2H, t, J = 5.6 Hz), 2.96(2H, t, J = 12.9 Hz), 2.80(2H, t, J = 6.4 Hz), 2.72(2H, t, J = 6.4 Hz), 2.37-2.18(2H, m), 1.79-1.66(2H, m). |
| 0352-3 | 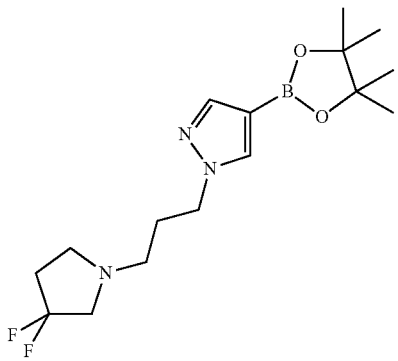 [SMILES: CC1(C)OB(c2cnn(CCCN3CCC(F)(F)C3)c2)OC1(C)C] | 1H-NMR(CDCl$_3$)δ:<br>7.78(1 H, s) 7.68(1 H, s), 4.20(2H, t, J = 6.6 Hz), 2.85(2H, t, J = 11.6 Hz), 2.68(2H, t, J = 6.9 Hz), 2.41(2H, t, J = 6.9 Hz), 2.35-2.17(2H, m), 2.08-1.96(2H, m), 1.32(12H, s). |
| 0352-4 | 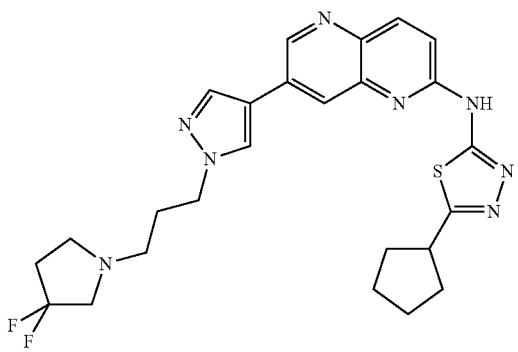 [SMILES: FC1(F)CCN(CCCn2cc(-c3cnc4ccc(Nc5nnc(C6CCCC6)s5)nc4c3)cn2)C1] | 1H-NMR(DMSO-d$_6$)δ:<br>12.04(1 H, s), 9.08(1 H, d, J = 2.0 Hz), 8.58(1 H, s), 8.32 (1 H, d, J = 2.0 Hz), 8.28-8.22(2H, m), 7.39(1 H, d, J = 9.2 Hz),<br>4.22(1 H, d, J = 6.9 Hz), 3.55-3.41(1 H, m), 2.89(2H, t, J = 13.2<br>Hz), 2.69(2H, t, J = 7.1 Hz), 2.45(2H, d, J = 7.1 Hz), 2.34-2.10 (4H, m), 2.07-1.63(8H, m).<br>MSm/z(M + H): 511. |
| 0353 | | |
| 0353-1 | 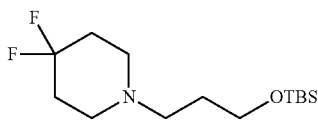 [SMILES: CC(C)(C)[Si](C)(C)OCCCN1CCC(F)(F)CC1] | 1H-NMR(CDCl$_3$)δ:<br>3.65(2H, t, J = 6.3 Hz), 2.59-2.42(6H, m), 2.07-1.91(4H, m), 1.76-1.63(2H, m), 0.89(9H, s), 0.05(6H, s). |
| 0353-2 | 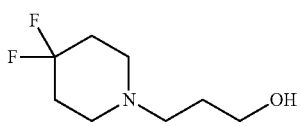 [SMILES: OCCCN1CCC(F)(F)CC1] | 1H-NMR(CDCl$_3$)δ:<br>4.77(1 H, brs), 3.81(2H, t, J = 5.3 Hz), 2.70-2.56(6H, m), 2.09-1.91(4H, m), 1.79-1.68(2H, m). |
| 0353-3 | 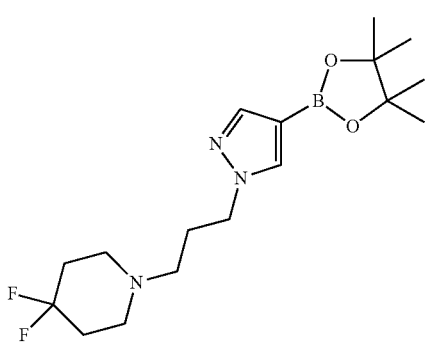 [SMILES: CC1(C)OB(c2cnn(CCCN3CCC(F)(F)CC3)c2)OC1(C)C] | 1H-NMR(CDCl$_3$)δ:<br>7.78(1 H, s) 7.68(1 H, s), 4.19(2H, t, J = 6.9 Hz), 2.58-2.43 (4H, m), 2.35(2H, t, J = 6.9 Hz), 2.10-1.89(6H, m), 1.32(12H, s). |

| Example No. | | |
|---|---|---|
| 0353-4 | 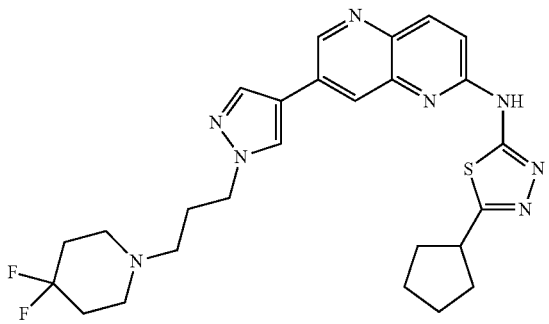 [SMILES: FC1(F)CCN(CCCn2cc(-c3cnc4ccc(Nc5nnc(C6CCCC6)s5)nc4c3)cn2)CC1] | 1H-NMR(DMSO-d$_6$)δ:<br>12.04(1 H, s), 9.08(1 H, d, J = 2.0 Hz), 8.58(1 H, s), 8.32 (1 H, d, J = 2.0 Hz), 8.28-8.21(2H, m), 7.39(1 H, d, J = 9.2 Hz),<br>4.21(2H, t, J = 6.6 Hz), 3.55-3.42(1H, m), 2.35(2H, d, J = 6.6 Hz), 2.23-1.62(18H, m).<br>MSm/z(M + H): 525. |
| 0354 | | |
| 0354-1 | 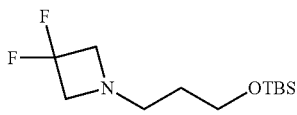 [SMILES: CC(C)(C)[Si](C)(C)OCCCN1CC(F)(F)C1] | 1H-NMR(CDCl$_3$)δ:<br>3.65(2H, t, J = 6.3 Hz), 3.54(4H, t, J = 11.9 Hz), 2.62(2H, t, J = 6.9 Hz), 1.65-1.51(2H, m), 0.89(9H, s), 0.05(6H, s). |
| 0354-2 | 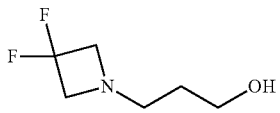 | 1H-NMR(CDCl$_3$)δ:<br>3.76(2H, t, J = 5.6 Hz), 3.61(4H, t, J = 12.2 Hz), 2.81(2H, t, J = 5.9 Hz), 1.68-1.58(2H, m). |
| 0354-3 | 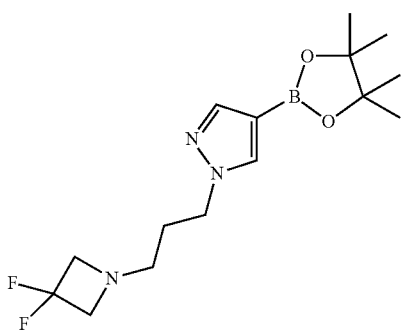 [SMILES: CC1(C)OB(c2cnn(CCCN3CC(F)(F)C3)c2)OC1(C)C] | 1H-NMR(CDCl$_3$)δ:<br>7.78(1 H, s) 7.68(1 H, s), 4.19(2H, t, J = 6.9 Hz), 3.53(4H, t, J = 12.2 Hz), 2.50(2H, t, J = 6.9 Hz), 1.92(2H, t, J = 6.9 Hz), 1.32 (12H, s). |
| 0354-4 | 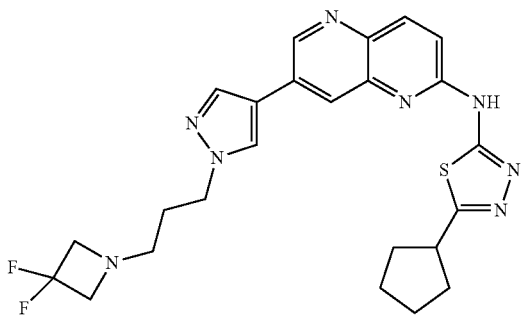 [SMILES: FC1(F)CN(CCCn2cc(-c3cnc4ccc(Nc5nnc(C6CCCC6)s5)nc4c3)cn2)C1] | 1H-NMR(DMSO-d$_6$)δ:<br>12.04(1 H, s), 9.08(1 H, d, J = 2.0 Hz), 8.57(1 H, s), 8.33(1 H, d, J = 2.0 Hz), 8.28-8.21(2H, m), 7.39(1 H, d, J = 9.2 Hz),<br>4.21 (2H, t, J = 6.9 Hz), 3.58(4H, t, J = 12.6 Hz), 3.52-3.25(1 H, m),<br>2.62-2.46(2H, m), 2.24-2.10(2H, m), 1.97-1.62(8H, m).<br>MSm/z(M + H): 497. |

Example 0355

0355-1

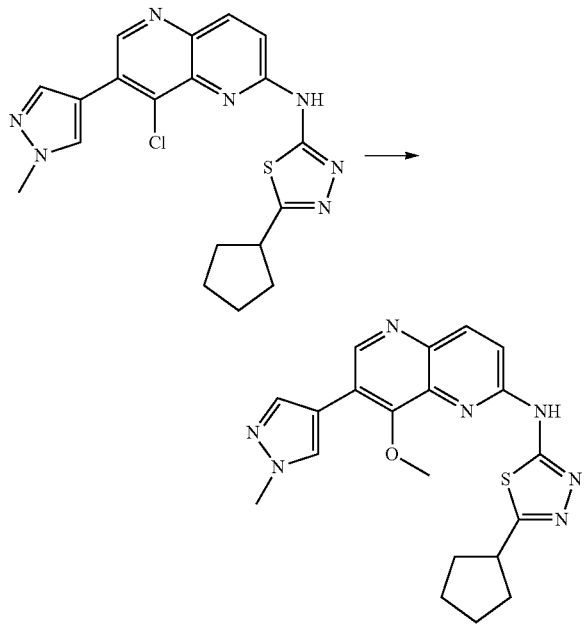

A 5 mol/L sodium methoxide/methanol solution (20 μL) was added to a solution of N-(8-chloro-7-(1-methyl-1H-pyrazol-4-yl)-1,5-naphthyridin-2-yl)-5-cyclopentyl-1,3,4-thiadiazole-2-amine (2.0 mg) in methanol (1 mL), followed by stirring at 150° C. for 30 minutes using a microwave reaction apparatus. The reaction mixture was cooled to room temperature, and a 5 mol/L sodium methoxide/methanol solution (50 μL) was added thereto, followed by stirring at 150° C. for 1 hour. The reaction mixture was cooled to room temperature, and a saturated ammonium chloride aqueous solution was added thereto. The solvent was distilled off under reduced pressure, and the obtained residue was purified by silica gel column chromatography (chloroform-methanol), thereby obtaining 5-cyclopentyl-N-(8-methoxy-7-(1-methyl-1H-pyrazol-4-yl)-1,5-naphthyridin-2-yl)-1,3,4-thiadiazole-2-amine (0.4 mg) as a yellow solid.

$^1$H-NMR(DMSO-$d_6$)δ:12.10(1H,brs),9.08(1H,s),8.47 (1H,s),8.27(1H,d,J=8.9 Hz),8.19(1H,s),7.42(1H,d,J=8.9 Hz),4.12(3H,s),3.95(3H,s),3.59-3.25(1H,m),2.26-2.10(2H, m),1.93-1.66(6H,m).

MSm/z(M+H):408.

Example 0356

0356-1

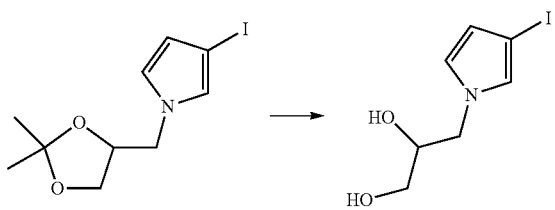

A 4 mol/L hydrogen chloride/1,4-dioxane solution (1 mL) was added to a solution of 1-((2,2-dimethyl-1,3-dioxolan-4-yl)methyl)-4-iodo-1H-pyrazole (0.2 g) in methanol (1 mL) at room temperature, followed by stirring for 30 minutes. The solvent was distilled off under reduced pressure, thereby obtaining 3-(4-iodo-1H-pyrazol-1-yl)propane-1,2-diol (184 mg) as a white solid.

MSm/z(M+H):269.

0356-2

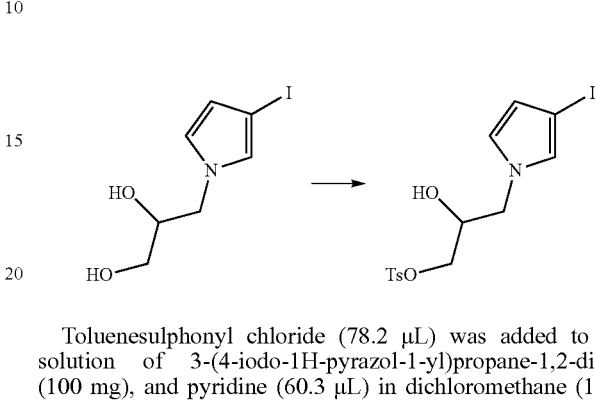

Toluenesulphonyl chloride (78.2 μL) was added to a solution of 3-(4-iodo-1H-pyrazol-1-yl)propane-1,2-diol (100 mg), and pyridine (60.3 μL) in dichloromethane (1.9 mL) in an ice bath, followed by stirring for 30 minutes, and stirring at room temperature for 30 minutes. Toluenesulphonyl chloride (78.2 μL) was added thereto, followed by stirring for 30 minutes. A saturated sodium hydrogen carbonate aqueous solution was added to the reaction mixture, followed by stirring at room temperature for 30 minutes, and ethyl acetate was added thereto. The organic layer was collected by separation, and dried over anhydrous sodium sulfate, then, the solvent was distilled off under reduced pressure, and the obtained residue was purified by silica gel column chromatography (chloroform-methanol), thereby obtaining 2-hydroxy-3-(4-iodo-1H-pyrazol-1-yl)propyl 4-methylbenzenesulfonate (120 mg) as yellow oily substance.

MSm/z(M+H):423.

0356-3

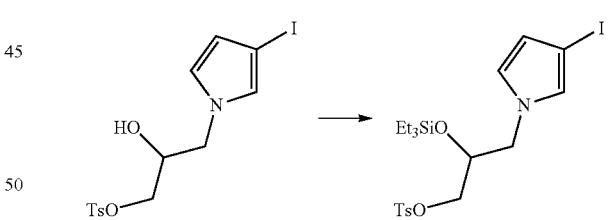

Triethylsilyl trifluoromethanesulfonate (127 μL) was added to a solution of 2-hydroxy-3-(4-iodo-1H-pyrazol-1-yl)propyl 4-methylbenzenesulfonate (120 mg) and 2,6-lutidine (130 μL) in dichloromethane (1.9 mL) at room temperature, followed by stirring for 30 minutes. A saturated sodium hydrogen carbonate aqueous solution and ethyl acetate were added to the reaction mixture. The organic layer was collected by separation, and dried over anhydrous sodium sulfate, and the solvent was distilled off under reduced pressure. The obtained residue was purified by silica gel column chromatography (hexane-ethyl acetate), thereby obtaining 3-(4-iodo-1H-pyrazol-1-yl)-2-((triethylsilyl)oxy) propyl 4-methylbenzenesulfonate (82.0 mg) as yellow oily substance.

MSm/z(M+H):537.

0356-4

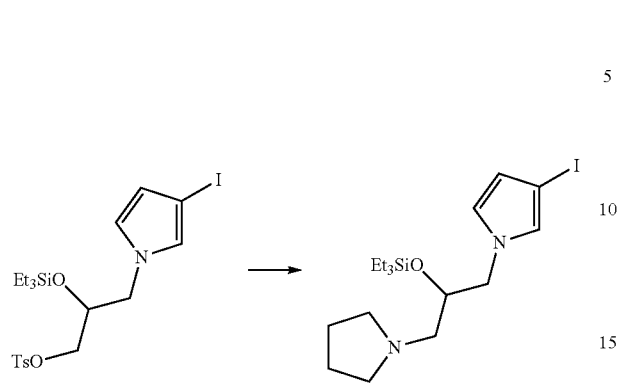

A mixture of 3-(4-iodo-1H-pyrazol-1-yl)-2-((triethylsilyl)oxy)propyl 4-methylbenzenesulfonate (82.0 mg), pyrrolidine (37.1 μL), triethylamine (64 μL), and tetrahydrofuran (1 mL) was stirred at 70° C. for 2 hours, and stirred at 80° C. for 16 hours. The reaction mixture was cooled to room temperature, and the solvent was distilled off under reduced pressure. The obtained residue was purified by silica gel column chromatography (chloroform-methanol), thereby obtaining 4-iodo-1-(3-(pyrrolidin-1-yl)-2-((triethylsilyl)oxy)propyl)-1H-pyrazole (27.7 mg) as brown oily substance.

MSm/z(M+H):436.

0356-5

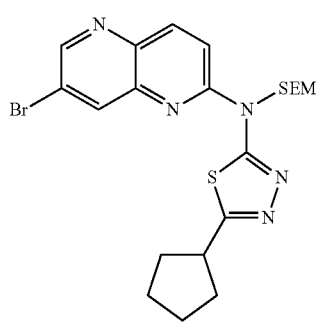

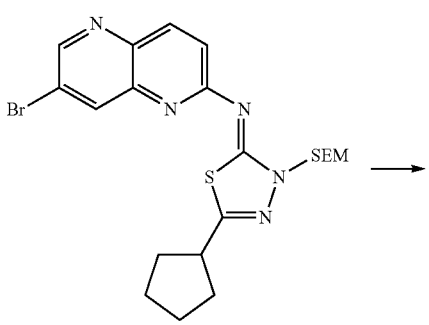

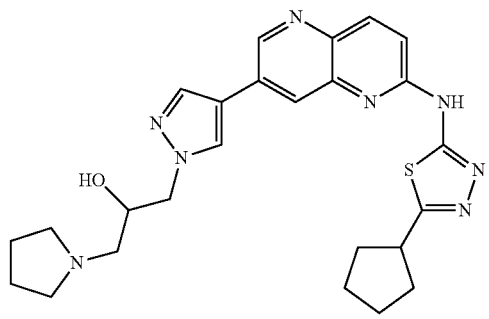

1-(4-(6-(((5-Cyclopentyl-1,3,4-thiadiazol-2-yl)amino)-1,5-naphthyridin-3-yl)-1H-pyrazol-1-yl)-3-(pyrrolidin-1-yl)propan-2-ol was obtained as a yellow solid in the same manner as in Examples 0110-3 and 0110-4.

$^1$H-NMR(DMSO-$d_6$)δ:12.03(1H,brs),9.09(1H,d,J=2.0 Hz),8.52(1H,s),8.34(1H,d,J=2.0 Hz),8.27-8.21(2H,m),7.39(1H,d,J=9.2 Hz),5.01(1H,d,J=4.6 Hz),4.30(1H,d,J=10.6 Hz),4.14-3.92(2H,m),3.56-3.42(1H,m),2.69-2.36(6H,m),2.24-2.09(2H,m),1.95-1.62(10H,m).

MSm/z(M+H):491.

Examples 0357 and 0358

0357-1 and 0358-1

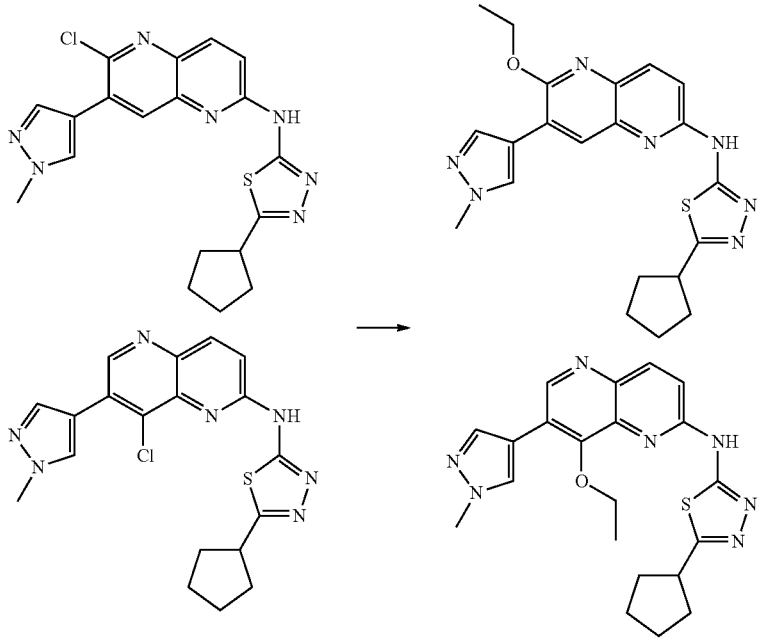

An ethanol solution (0.1 mL) of 20% sodium ethoxide was added to a solution of a mixture (30 mg) of N-(6-chloro-7-(1-methyl-1H-pyrazol-4-yl)-1,5-naphthyridin-2-yl)-5-cyclopentyl-1,3,4-thiadiazole-2-amine and N-(8-chloro-7-(1-methyl-1H-pyrazol-4-yl)-1,5-naphthyridin-2-yl)-5-cyclopentyl-1,3,4-thiadiazole-2-amine in ethanol (1 ml), followed by stirring at 150° C. for 1.5 hours using a microwave reaction apparatus. The reaction mixture was cooled to room temperature, and a saturated ammonium chloride aqueous solution was added thereto. The solvent was distilled off under reduced pressure, the obtained residue was purified by silica gel column chromatography (chloroform-methanol), and purified by preparative thin layer silica gel chromatography (chloroform-methanol), thereby obtaining 5-cyclopentyl-N-(6-ethoxy-7-(1-methyl-1H-pyrazol-4-yl)-1,5-naphthyridin-2-yl)-1,3,4-thiadiazole-2-amine (2.0 mg) as a white solid and 5-cyclopentyl-N-(8-ethoxy-7-(1-methyl-1H-pyrazol-4-yl)-1,5-naphthyridin-2-yl)-1,3,4-thiadiazole-2-amine (3.1 mg) as a white solid.

Example 0357

5-Cyclopentyl-N-(6-ethoxy-7-(1-methyl-1H-pyrazol-4-yl)-1,5-naphthyridin-2-yl)-1,3,4-thiadiazole-2-amine $^1$H-NMR(DMSO-$d_6$)δ:11.82(1H,s),8.39(1H,s),8.36(1H,s),8.22(1H,s),8.06(1H,d,J=8.6 Hz),7.33(1H,d,J=8.6 Hz), 4.55(2H,q,J=6.9 Hz),3.94(3H,s),3.53-3.26(1H,m),2.23-2.07(2H,m),1.95-1.64(6H,m),1.48(3H,t,J=6.9 Hz).

MSm/z(M+H):422.

Example 0358

5-Cyclopentyl-N-(8-ethoxy-7-(1-methyl-1H-pyrazol-4-yl)-1,5-naphthyridin-2-yl)-1,3,4-thiadiazole-2-amine $^1$H-NMR(DMSO-$d_6$)δ:12.10(1H,s),9.05(1H,s),8.43(1H,s),8.27(1H,d,J=8.9 Hz),8.17(1H,s),7.41(1H,d,J=8.9 Hz),4.34(2H,q,J=6.9 Hz),3.96(3H,s),3.59-3.44(1H,m),2.31-2.08(2H,m),1.96-1.63(6H,m),1.54(3H,t,J=6.9 Hz).

MSm/z(M+H):422.

Example 0359

0359-1

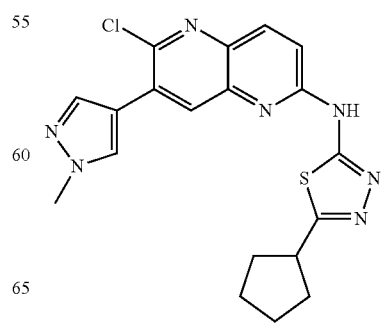

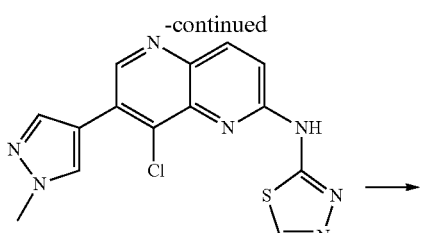

60% sodium hydride (29.1 mg) was added to 2-propanol (1 mL) at room temperature, and a mixture (30 mg) of N-(6-chloro-7-(1-methyl-1H-pyrazol-4-yl)-1,5-naphthyridin-2-yl)-5-cyclopentyl-1,3,4-thiadiazole-2-amine and N-(8-chloro-7-(1-methyl-1H-pyrazol-4-yl)-1,5-naphthyridin-2-yl)-5-cyclopentyl-1,3,4-thiadiazole-2-amine was added thereto at room temperature, followed by stirring at 150° C. for 1.5 hours using a microwave reaction apparatus. The reaction mixture was cooled to room temperature, and a saturated ammonium chloride aqueous solution was added thereto. The solvent was distilled off under reduced pressure, the obtained residue was purified by silica gel column chromatography (chloroform-methanol), and purified by preparative thin layer silica gel chromatography (chloroform-methanol), thereby obtaining 5-cyclopentyl-N-(8-isopropyloxy-7-(1-methyl-1H-pyrazol-4-yl)-1,5-naphthyridin-2-yl)-1,3,4-thiadiazole-2-amine (1.8 mg) as a white solid.

$^1$H-NMR(DMSO-$d_6$)δ:12.06(1H,s),9.02(1H,s),8.43(1H,s),8.26(1H,d,J=9.2 Hz),8.18(1H,s),7.41(1H,d,J=9.2 Hz),5.52-5.39(1H,m),3.95(3H,s),3.58-3.43(1H,m),2.30-2.11(2H,m),1.93-1.64(6H,m),1.26(6H,d,J=6.6 Hz).
MSm/z(M+H):436.

Example 0360

0360-1

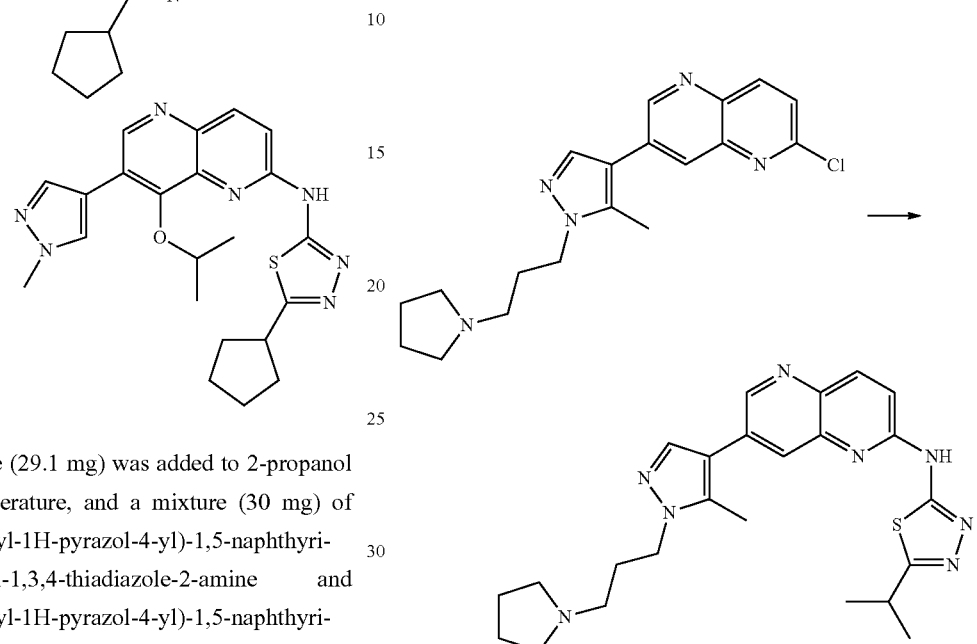

5-Isopropyl-N-(7-(5-methyl-1-(3-(pyrrolidin-1-yl)propyl)-1H-pyrazol-4-yl)-1,5-naphthyridin-2-yl)-1,3,4-thiadiazole-2-amine was obtained as a yellow solid in the same manner as in Example 0321-3.

$^1$H-NMR(DMSO-$d_6$)δ:12.07(1H,brs),8.88(1H,d,J=2.0 Hz),8.28(1H,d,J=8.9 Hz),8.15(1H,d,J=2.0 Hz),7.92(1H,s),7.43(1H,d,J=8.9 Hz),4.18(2H,t,J=6.9),3.42-3.27(1H,m),2.58-2.34(9H,m),2.03-1.88(2H,m),1.76-1.62(4H,m),1.40(6H,d,J=6.6 Hz).
MSm/z(M+H):463.

Examples 0361 to 0363

The following compounds were obtained in the same manner as in Examples 0001-4 and 0001-5.

| Example No. | | |
|---|---|---|
| 0361 | | |
| 0361-1 | 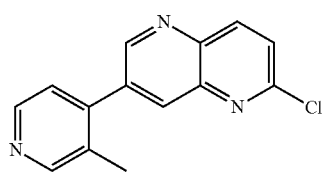 [SMILES: Cc1cnccc1-c1cnc2ccc(Cl)nc2c1] | 1H-NMR(DMSO-$d_6$)δ: 9.11(1 H, d, J = 2.0 Hz), 8.64-8.49(4H, m), 7.93(1 H, d, J = 8.6 Hz), 7.48(1 H, d, J = 5.3 Hz), 2.34 (3H, s). |

| Example No. | | |
|---|---|---|
| 0361-2 | 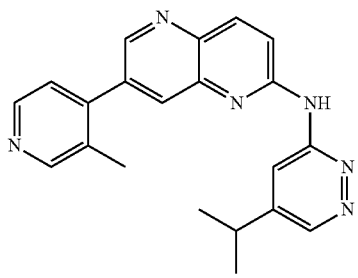 [SMILES: Cc1cnccc1-c1cnc2ccc(Nc3cc(C(C)C)cnn3)nc2c1] | 1H-NMR(DMSO-d$_6$)δ:<br>10.83(1 H, s), 8.86(1 H, d, J = 2.0 Hz), 8.79(1 H, d, J = 2.0 Hz), 8.76<br>(1 H, d, J = 2.0 Hz), 8.61(1 H, s), 8.55(1 H, d, J = 5.3 Hz), 8.33(1 H,<br>d, J = 9.2 Hz), 8.20(1 H, d, J = 2.0 Hz), 7.83(1 H, d, J = 9.2 Hz), 7.46<br>(1 H, d, J = 5.3 Hz), 3.09-2.94(1 H, m), 2.33(3H, s), 1.29(6H, d, J =<br>6.6 Hz).<br>MSm/z(M + H): 357. |
| 0362 | | |
| 0362-1 | 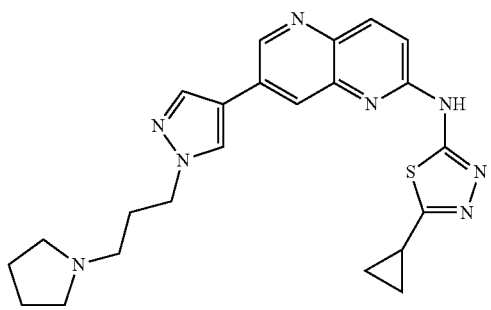 [SMILES: c1nc2ccc(Nc3nnc(C4CC4)s3)nc2cc1-c1cnn(CCCN2CCCC2)c1] | 1H-NMR(DMSO-d$_6$)δ:<br>12.04(1 H, brs), 9.08(1 H, d, J = 2.1 Hz), 8.58(1 H, s), 8.33(1 H, d,<br>J = 2.1 Hz), 8.27-<br>8.21(2H, m), 7.40(1 H, d, J = 9.3 Hz), 4.23(2H, t, J = 7.2 Hz), 2.44-<br>2.14(6H, m), 2.12-1.88(6H, m), 1.80-1.40(6H, m).<br>MSm/z(M + H): 447. |
| 0363 | | |
| 0363-1 | 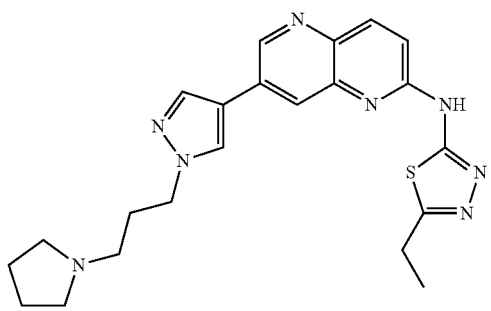 [SMILES: CCc1nnc(Nc2ccc3ncc(-c4cnn(CCCN5CCCC5)c4)cc3n2)s1] | 1H-NMR(DMSO-d$_6$)δ:<br>12.05(1 H, brs), 9.08(1 H, s), 8.58(1 H, s), 8.33(1 H, m), 8.28-<br>8.20(2H, m), 7.40(1 H, d, J = 9.3 Hz), 4.22(2H, t, J = 7.2 Hz), 3.03<br>(2H, m), 2.48-2.38(4H, m), 2.02(2H, m), 1.70(4H, m), 1.38(3H, t,<br>J = 8.1 Hz).<br>MSm/z(M + H): 435. |

Examples 0364 to 0369

The following compounds were obtained in the same manner as in Examples 0198-1 and 0001-5.

| Example No. | | |
|---|---|---|
| 0364 | | |
| 0364-1 | 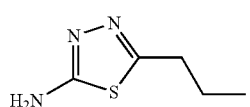 | $^1$H-NMR (DMSO-d$_6$) δ:<br>6.98 (2H, brs), 2.76 (2H, t,<br>J = 7.2 Hz), 1.62 (2H, m),<br>0.92 (3H, t, J = 7.5 Hz). |

| Example No. | | |
|---|---|---|
| 0364-2 | 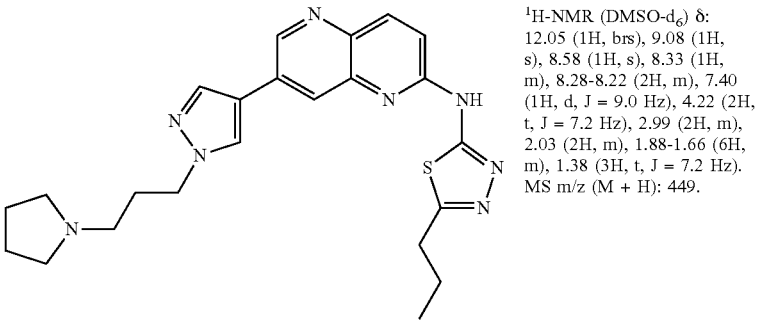 | ¹H-NMR (DMSO-d₆) δ: 12.05 (1H, brs), 9.08 (1H, s), 8.58 (1H, s), 8.33 (1H, m), 8.28-8.22 (2H, m), 7.40 (1H, d, J = 9.0 Hz), 4.22 (2H, t, J = 7.2 Hz), 2.99 (2H, m), 2.03 (2H, m), 1.88-1.66 (6H, m), 1.38 (3H, t, J = 7.2 Hz). MS m/z (M + H): 449. |
| 0365 | | |
| 0365-1 |  | ¹H-NMR (DMSO-d₆) δ: 6.99 (2H, brs), 3.12 (1H, m), 0.92 (6H, d, J = 6.9 Hz). |
| 0365-2 | 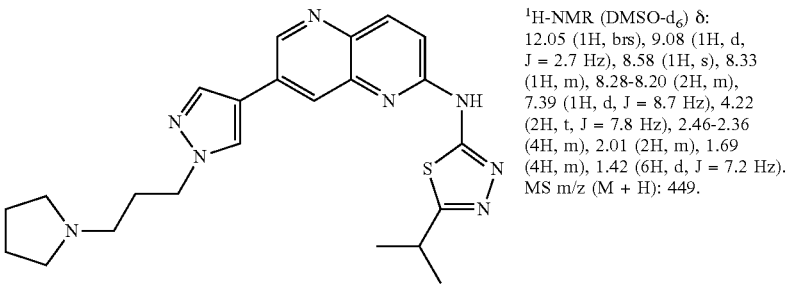 | ¹H-NMR (DMSO-d₆) δ: 12.05 (1H, brs), 9.08 (1H, d, J = 2.7 Hz), 8.58 (1H, s), 8.33 (1H, m), 8.28-8.20 (2H, m), 7.39 (1H, d, J = 8.7 Hz), 4.22 (2H, t, J = 7.8 Hz), 2.46-2.36 (4H, m), 2.01 (2H, m), 1.69 (4H, m), 1.42 (6H, d, J = 7.2 Hz). MS m/z (M + H): 449. |
| 0366 | | |
| 0366-1 | 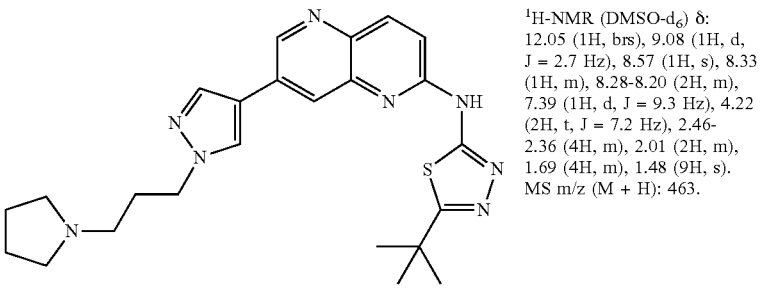 | ¹H-NMR (DMSO-d₆) δ: 12.05 (1H, brs), 9.08 (1H, d, J = 2.7 Hz), 8.57 (1H, s), 8.33 (1H, m), 8.28-8.20 (2H, m), 7.39 (1H, d, J = 9.3 Hz), 4.22 (2H, t, J = 7.2 Hz), 2.46-2.36 (4H, m), 2.01 (2H, m), 1.69 (4H, m), 1.48 (9H, s). MS m/z (M + H): 463. |
| 0367 | | |
| 0367-1 |  | ¹H-NMR (DMSO-d₆) δ: 7.33 (1H, brs), 7.08 (2H, brs), 3.18 (1H, t, J = 7.2 Hz). |
| 0367-2 | 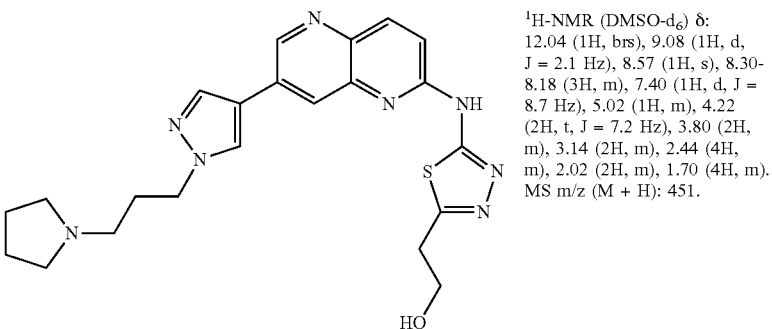 | ¹H-NMR (DMSO-d₆) δ: 12.04 (1H, brs), 9.08 (1H, d, J = 2.1 Hz), 8.57 (1H, s), 8.30-8.18 (3H, m), 7.40 (1H, d, J = 8.7 Hz), 5.02 (1H, m), 4.22 (2H, t, J = 7.2 Hz), 3.80 (2H, m), 3.14 (2H, m), 2.44 (4H, m), 2.02 (2H, m), 1.70 (4H, m). MS m/z (M + H): 451. |

| Example No. | | |
|---|---|---|
| 0368 | | |
| 0368-1 | 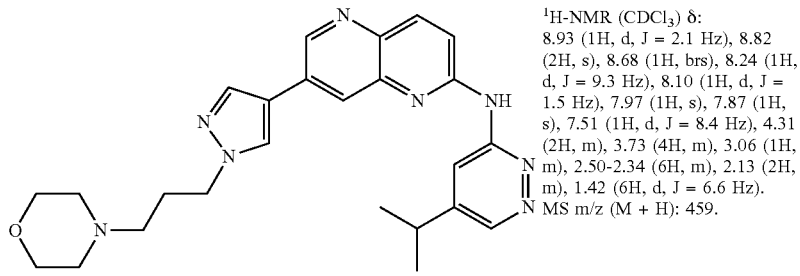 | ¹H-NMR (CDCl₃) δ: 8.93 (1H, d, J = 2.1 Hz), 8.82 (2H, s), 8.68 (1H, brs), 8.24 (1H, d, J = 9.3 Hz), 8.10 (1H, d, J = 1.5 Hz), 7.97 (1H, s), 7.87 (1H, s), 7.51 (1H, d, J = 8.4 Hz), 4.31 (2H, m), 3.73 (4H, m), 3.06 (1H, m), 2.50-2.34 (6H, m), 2.13 (2H, m), 1.42 (6H, d, J = 6.6 Hz). MS m/z (M + H): 459. |
| 0369 | | |
| 0369-1 | 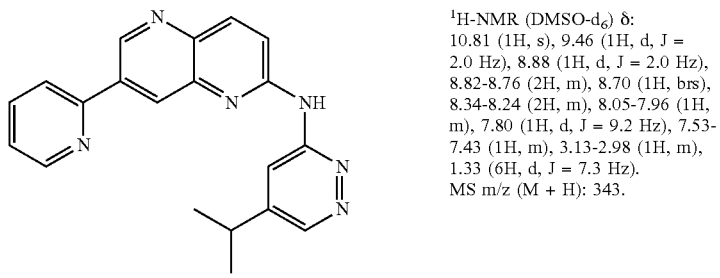 | ¹H-NMR (DMSO-d₆) δ: 10.81 (1H, s), 9.46 (1H, d, J = 2.0 Hz), 8.88 (1H, d, J = 2.0 Hz), 8.82-8.76 (2H, m), 8.70 (1H, brs), 8.34-8.24 (2H, m), 8.05-7.96 (1H, m), 7.80 (1H, d, J = 9.2 Hz), 7.53-7.43 (1H, m), 3.13-2.98 (1H, m), 1.33 (6H, d, J = 7.3 Hz). MS m/z (M + H): 343. |

Example 0370

0370-1

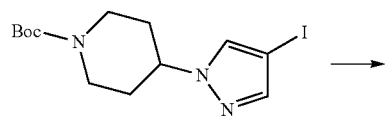

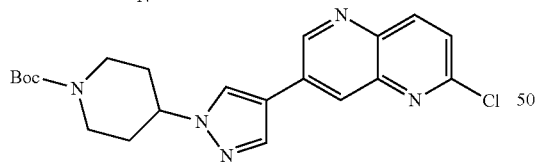

A mixture of 7-bromo-2-chloro-1,5-naphthyridine (300 mg), bis(pinacolato)diboron (469 mg), (1,1'-bis(diphenylphosphino)ferrocene)palladium(II) dichloride (100 mg), potassium acetate (241 mg), and 1,4-dioxane (12.3 mL) was stirred at 100° C. for 3 hours in a nitrogen atmosphere. The reaction mixture was cooled to room temperature, and tert-butyl 4-(4-iodo-1H-pyrazol-1-yl)piperidine-1-carboxylate (557 mg), sodium carbonate (261 mg), bis(di-tert-butyl (4-dimethylaminophenyl)phosphine)dichloropalladium(II) (87 mg), and water (1.2 mL) were added thereto, followed by stirring at 110° C. for 1 hour. The reaction mixture was cooled to room temperature, the solvent was distilled off under reduced pressure, and the obtained residue was purified by silica gel column chromatography (ethyl acetate-hexane, chloroform-methanol), thereby obtaining tert-butyl 4-(4-(6-chloro-1,5-naphthyridin-3-yl)-1H-pyrazol-1-yl)piperidine-1-carboxylate (149 mg) as a white solid.

MSm/z(M+H):414.

0370-2

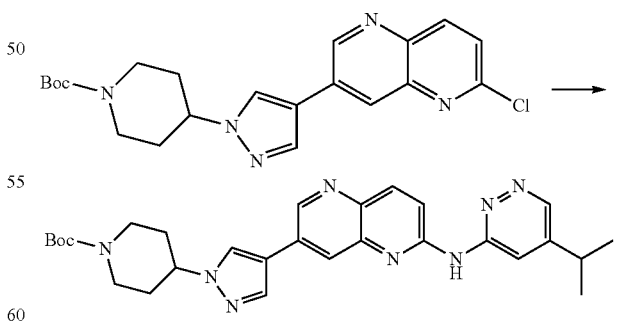

tert-Butyl 4-(4-(6-((5-isopropylpyridazin-3-yl)amino)-1,5-naphthyridin-3-yl)-1H-pyrazol-1-yl)piperidine-1-carboxylate (56 mg) was obtained as a white solid in the same manner as in Example 0001-5.

MSm/z(M+H):515.

0370-3

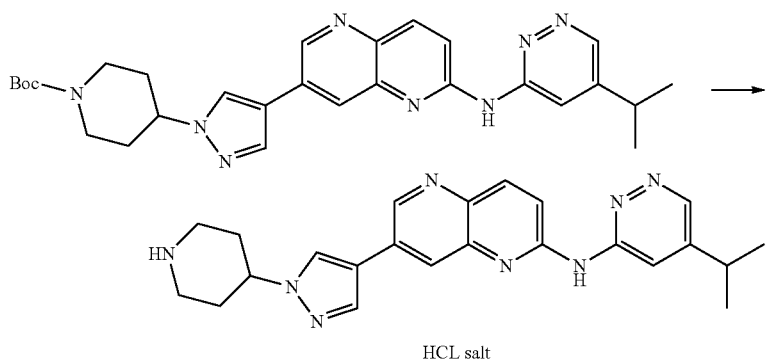

A 4 mol/L hydrogen chloride/1,4-dioxane solution (1 mL) was added to a solution of tert-butyl 4-(4-(6-((5-isopropylpyridazin-3-yl)amino)-1,5-naphthyridin-3-yl)-1H-pyrazol-1-yl)piperidine-1-carboxylate (50 mg) in methanol (1 mL) at room temperature, followed by stirring for 13 hours. The solvent was distilled off under reduced pressure, ethyl acetate was added to the obtained residue, and the solid matter was collected by filtration, thereby obtaining N-(5-isopropylpyridazin-3-yl)-7-(1-(piperidin-4-yl)-1H-pyrazol-4-yl)-1,5-naphthyridine-2-amine hydrochloride (44.9 mg) as a yellow solid.

MSm/z(M+H):415.

0370-4

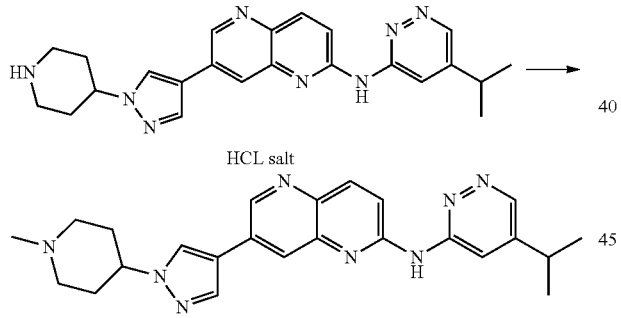

A 36 to 38% formaldehyde aqueous solution (0.33 mL) and sodium triacetoxyborohydride (103 mg) were added to a solution of N-(5-isopropylpyridazin-3-yl)-7-(1-(piperidin-4-yl)-1H-pyrazol-4-yl)-1,5-naphthyridine-2-amine hydrochloride (44.9 mg) in methanol (3.3 mL) and dichloromethane (3.3 mL) at room temperature, followed by stirring for 12 hours. Chloroform, a saturated sodium hydrogen carbonate aqueous solution, and a saturated sodium chloride aqueous solution were added to the reaction mixture. The organic layer was collected by separation, and dried over anhydrous sodium sulfate, and the solvent was distilled off under reduced pressure. The obtained residue was purified by silica gel column chromatography (chloroform-methanol, NH silica), thereby obtaining N-(5-isopropylpyridazin-3-yl)-7-(1-(1-methylpiperidin-4-yl)-1H-pyrazol-4-yl)-1,5-naphthyridine-2-amine (10.0 mg) as a white solid.

$^1$H-NMR(DMSO-d$_6$)δ:8.96(1H,d,J=2.7 Hz),8.85-8.78 (2H,m),8.69(1H,brs),8.24(1H,d,J=8.7 Hz),8.10(1H,m),7.97 (1H,s),7.89(1H,s),7.49(1H,d,J=9.3 Hz),4.23(1H,m),3.10-2.96(3H,m),2.37(3H,s),2.30-2.08(6H,m),1.42(6H,d,J=7.2 Hz).

MSm/z(M+H):429.

Example 0371

0371-1

3-(4-(4,4,5,5-Tetramethyl-1,3,2-dioxaborolan-2-yl)-1H-pyrazol-1-yl)propan-1-ol was obtained as brown oily substance in the same manner as in Example 0316-1.

MSm/z(M+H):253.

0371-2

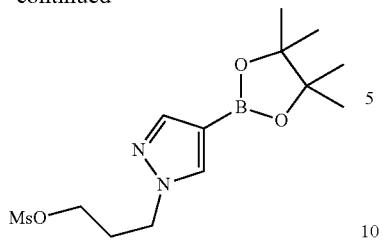

Triethylamine (550 μL) and methanesulfonyl chloride (168 μL) were added to a solution of 3-(4-(4,4,5,5-tetramethyl-1,3,2-dioxaborolan-2-yl)-1H-pyrazol-1-yl)propan-1-ol (500 mg) in dichloromethane (19.8 mL) in an ice bath, followed by stirring at room temperature for 15 minutes. A saturated sodium hydrogen carbonate aqueous solution and chloroform were added to the reaction mixture. The organic layer was collected by separation, washed with a saturated sodium chloride aqueous solution, and dried over anhydrous sodium sulfate, and the solvent was distilled off under reduced pressure. The obtained residue was purified by silica gel column chromatography (chloroform-methanol), thereby obtaining 3-(4-(4,4,5,5-tetramethyl-1,3,2-dioxaborolan-2-yl)-1H-pyrazol-1-yl)propyl methanesulfonate (667 mg) as brown oily substance.

MSm/z(M+H):331.

0371-3

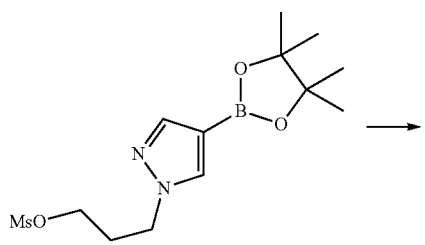

Azetidine (534 μL) was added to a mixture of 3-(4-(4,4,5,5-tetramethyl-1,3,2-dioxaborolan-2-yl)-1H-pyrazol-1-yl) propyl methanesulfonate (667 mg), cesium carbonate (1.29 g), sodium iodide (89 mg), and 1,4-dioxane (10 mL), followed by stirring at 80° C. for 11 hours. The reaction mixture was cooled to room temperature, and the solvent was distilled off under reduced pressure, thereby obtaining 1-(3-(azetidin-1-yl)propyl)-4-(4,4,5,5-tetramethyl-1,3,2-dioxaborolan-2-yl)-1H-pyrazole (188 mg) as brown oily substance.

MSm/z(M+H):292.

0371-4 and 0371-5

The following compounds were obtained in the same manner as in Examples 0001-4 and 0001-5.

| Example No. | | |
|---|---|---|
| 0371 | | |
| 0371-4 | 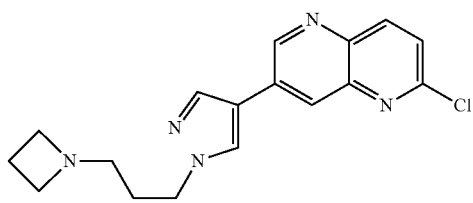 [SMILES: N=C/C(=C\NCCCN1CCC1)c1cnc2ccc(Cl)nc2c1] | MS m/z (M + H): 328. |
| 0371-5 | 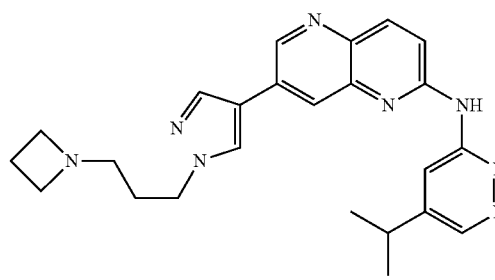 | $^1$H-NMR (CDCl$_3$) δ: 8.94-8.88 (2H, m), 8.86 (1H, d, J = 1.2 Hz), 8.82 (1H, d, J = 1.8 Hz), 8.24 (1H, d, J = 9.3 Hz), 8.10 (1H, d, J = 1.2 Hz), 7.96 (1H, s), 7.88 (1H, s), 7.54 (1H, d, J = 9.3 Hz), 4.27 (2H, t, J = 6.6 Hz), 3.19 (4H, m), 3.06 (1H, m), 2.42 (2H, m), 2.08 (2H, m), 1.96 (2H, m), 1.42 (6H, d, J = 7.2 Hz). MS m/z (M + H): 429. |

Example 0372

0372-1

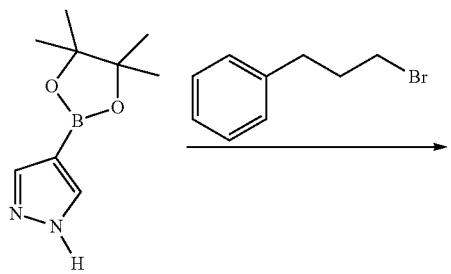

3-Phenylpropyl bromide (0.12 mL) was added to a suspension of 4-(4,4,5,5-tetramethyl-1,3,2-dioxaborolan-2-yl)-1H-pyrazole (100 mg) and potassium carbonate (144 mg) in acetonitrile (1 mL), followed by stirring at 80° C. overnight. The reaction mixture was cooled to room temperature, the insolubles were filtered off, and the solvent was distilled off under reduced pressure. The obtained residue was purified by silica gel column chromatography (ethyl acetate-hexane), thereby obtaining 1-(3-phenylpropyl)-4-(4,4,5,5-tetramethyl-1,3,2-dioxaborolan-2-yl)-1H-pyrazole (61 mg).

MSm/z(M+H):313.

0372-2 and 0372-3

The following compounds were obtained in the same manner as in Examples 0001-4 and 0001-5.

| Example No. | | |
|---|---|---|
| 0372 | | |
| 0372-2 | 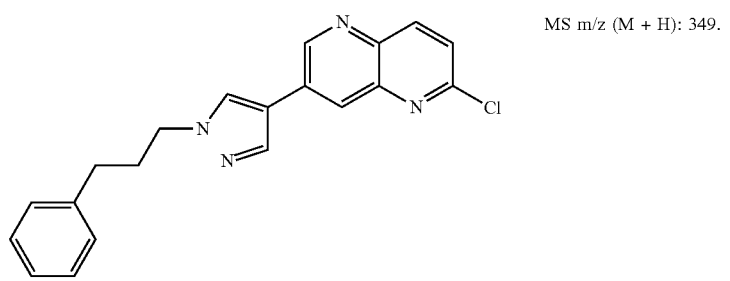 | MS m/z (M + H): 349. |
| 0372-3 | 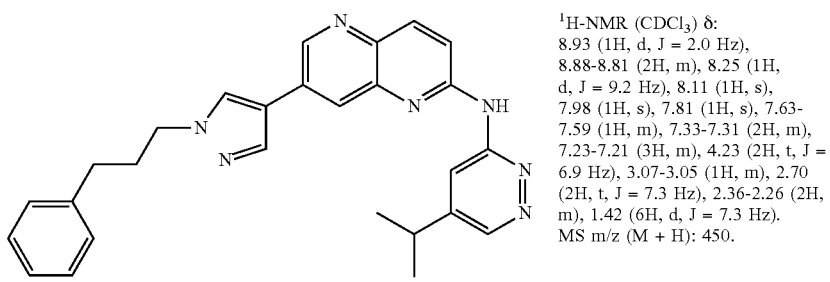 | $^1$H-NMR (CDCl$_3$) δ: 8.93 (1H, d, J = 2.0 Hz), 8.88-8.81 (2H, m), 8.25 (1H, d, J = 9.2 Hz), 8.11 (1H, s), 7.98 (1H, s), 7.81 (1H, s), 7.63-7.59 (1H, m), 7.33-7.31 (2H, m), 7.23-7.21 (3H, m), 4.23 (2H, t, J = 6.9 Hz), 3.07-3.05 (1H, m), 2.70 (2H, t, J = 7.3 Hz), 2.36-2.26 (2H, m), 1.42 (6H, d, J = 7.3 Hz). MS m/z (M + H): 450. |

-continued

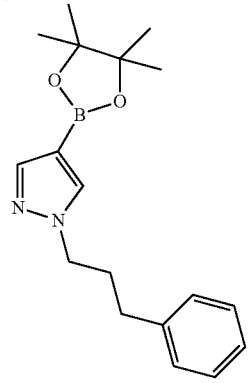

Example 0373

0373-1

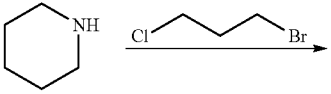

-continued

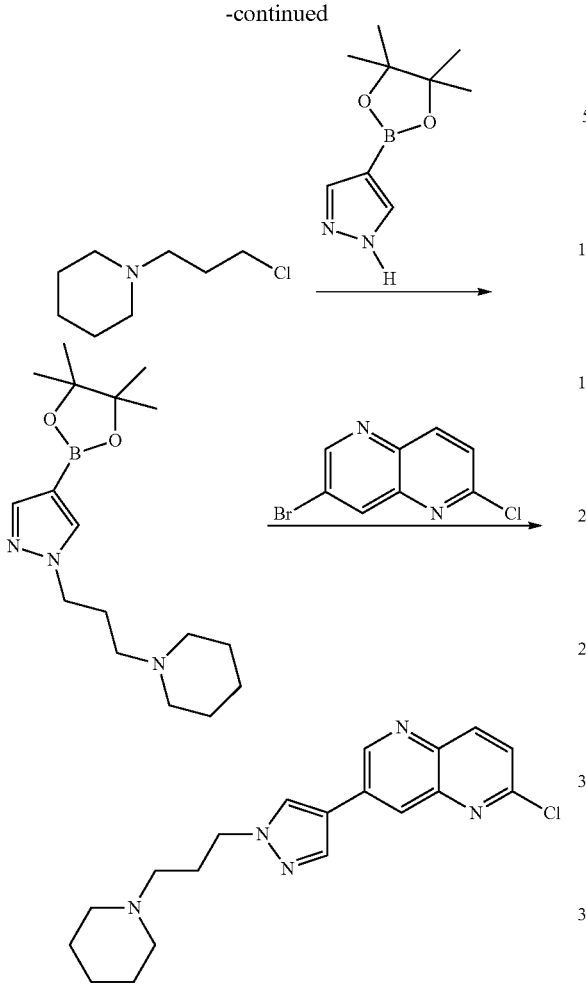

Piperidine (0.43 mL) was added to a solution of 1-bromo-3-chloropropane (0.32 mL) in toluene (1.6 mL), followed by stirring at 80° C. for 2.5 hours. The reaction mixture was cooled to room temperature, ethyl acetate and water were added thereto, and 2 mol/L hydrochloric acid was added thereto. The aqueous layer was collected by separation, adjusted to pH 12 by the addition of a 2 mol/L sodium hydroxide aqueous solution, and ethyl acetate was added thereto. The organic layer was collected by separation, washed with a saturated sodium chloride aqueous solution, and dried over anhydrous sodium sulfate, and the solvent was distilled off under reduced pressure, thereby obtaining 1-(3-chloropropyl)piperidine (451 mg) as pale yellow oily substance. A mixture of the obtained 1-(3-chloropropyl) piperidine (180 mg), 4-(4,4,5,5-tetramethyl-1,3,2-dioxaborolan-2-yl)-1H-pyrazole (180 mg), cesium carbonate (610 mg), sodium iodide (28 mg), and 1,4-dioxane (1.9 mL) was stirred at 80° C. overnight. The reaction mixture was cooled to room temperature, the insolubles were filtered off, and the solvent was distilled off under reduced pressure, thereby obtaining 1-(3-(4-(4,4,5,5-tetramethyl-1,3,2-dioxaborolan-2-yl)-1H-pyrazol-1-yl)propyl)piperidine.

7-Bromo-2-chloro-1,5-naphthyridine (50 mg), bis(di-tert-butyl(4-dimethylaminophenyl)phosphine)dichloropalladium(II) (14.7 mg), and sodium carbonate (44.1 mg) were added to a mixture solution of the obtained 1-(3-(4-(4,4,5,5-tetramethyl-1,3,2-dioxaborolan-2-yl)-1H-pyrazol-1-yl)propyl)piperidine (80 mg) in 1,4-dioxane (2 mL)/water (0.2 mL), followed by stirring at 100° C. for 2 hours. After the reaction mixture was cooled to room temperature, the insolubles were filtered off using celite, and the filter cake was washed with ethyl acetate. The filtrate and the washings were combined, and the solvent was distilled off under reduced pressure. The obtained residue was purified by silica gel column chromatography (ethyl acetate-hexane, methanol-ethyl acetate, NH silica), thereby obtaining 2-chloro-7-(1-(3-(piperidin-1-yl)propyl)-1H-pyrazol-4-yl)-1,5-naphthyridine (45 mg)

MSm/z(M+H):356.

0373-2

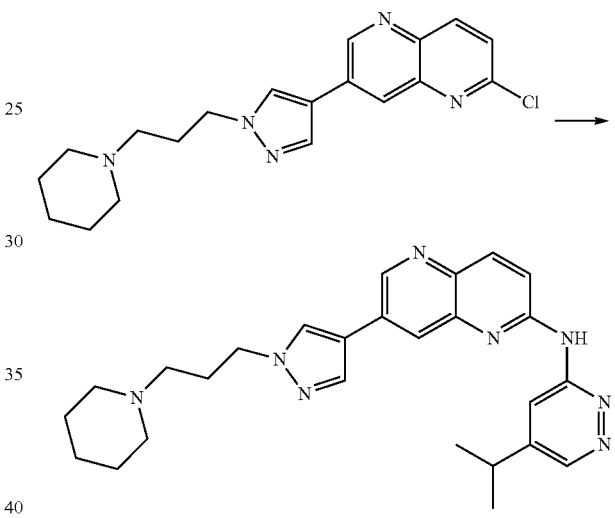

N-(5-isopropylpyridazin-3-yl)-7-(1-(3-(piperidin-1-yl)propyl)-1H-pyrazol-4-yl)-1,5-naphthyridine-2-amine was obtained as a pale yellow solid in the same manner as in Example 0001-5.

¹H-NMR(CDCl₃)δ:8.93(1H,d,J=2.0 Hz),8.89(1H,d,J=2.0 Hz),8.82(1H,d,J=2.0 Hz),8.24(1H,d,J=9.2 Hz),8.10(1H,d,J=2.0 Hz),7.96(1H,s),7.88(1H,s),7.58(1H,d,J=8.6 Hz),4.29 (2H,t,J=6.9 Hz),3.11-3.02(1H,m),2.36-2.31(6H,m),2.14-2.10(2H,m),1.62-1.60(6H,m),1.43(6H,d,J=7.3 Hz).

MSm/z(M+H):457.

Example 0374

0374-1

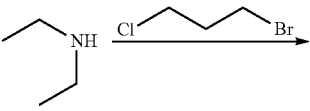

-continued

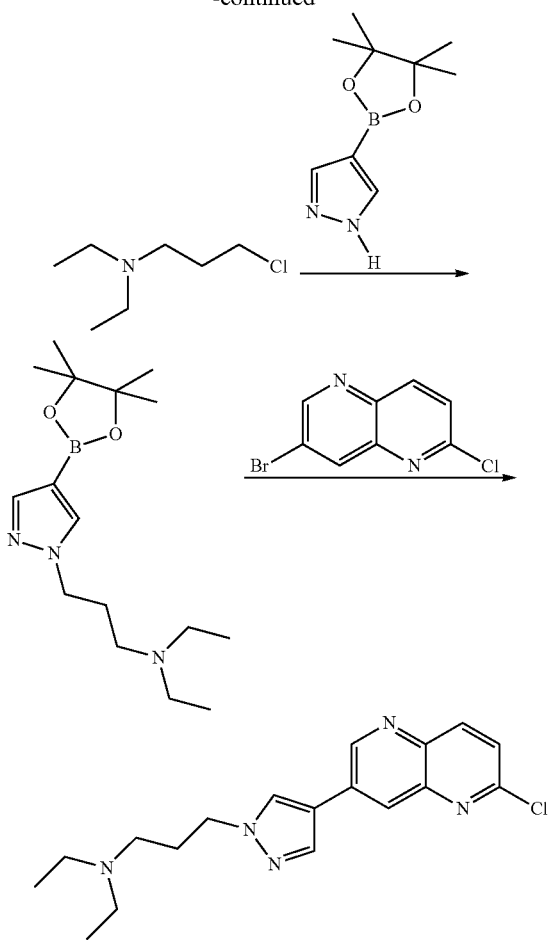

Diethylamine (0.62 mL) was added to a solution of 1-bromo-3-chloropropane (0.3 mL) in 1,4-dioxane (2 mL), followed by stirring at 50° C. for 4.5 hours. The reaction mixture was cooled to room temperature, the insolubles were filtered off, and 4-(4,4,5,5-tetramethyl-1,3,2-dioxaborolan-2-yl)-1H-pyrazole (194 mg), cesium carbonate (651 mg), and sodium iodide (30 mg) were added thereto, followed by stirring at 80° C. overnight. The reaction mixture was cooled to room temperature, the insolubles were filtered off, and the solvent was distilled off under reduced pressure, thereby obtaining N,N-diethyl-3-(4-(4,4,5,5-tetramethyl-1,3,2-dioxaborolan-2-yl)-1H-pyrazol-1-yl)propane-1-amine.

7-Bromo-2-chloro-1,5-naphthyridine (50 mg), bis(di-tert-butyl(4-dimethylaminophenyl)phosphine)dichloropalladium(II) (14.7 mg), and sodium carbonate (44.1 mg) were added to a mixture solution of the obtained N,N-diethyl-3-(4-(4,4,5,5-tetramethyl-1,3,2-dioxaborolan-2-yl)-1H-pyrazol-1-yl)propane-1-amine (80 mg) in 1,4-dioxane (2 mL)/water (0.2 mL), followed by stirring at 100° C. for 2 hours. After the reaction mixture was cooled to room temperature, the insolubles were filtered off using celite, and the filter cake was washed with ethyl acetate. The filtrate and the washings were combined, and the solvent was distilled off under reduced pressure. The obtained residue was purified by silica gel column chromatography (ethyl acetate-hexane, NH silica), thereby obtaining 3-(4-(6-chloro-1,5-naphthyridin-3-yl)-1H-pyrazol-1-yl)-N,N-diethylpropane-1-amine (15 mg).

MSm/z(M+H):344.

0374-2

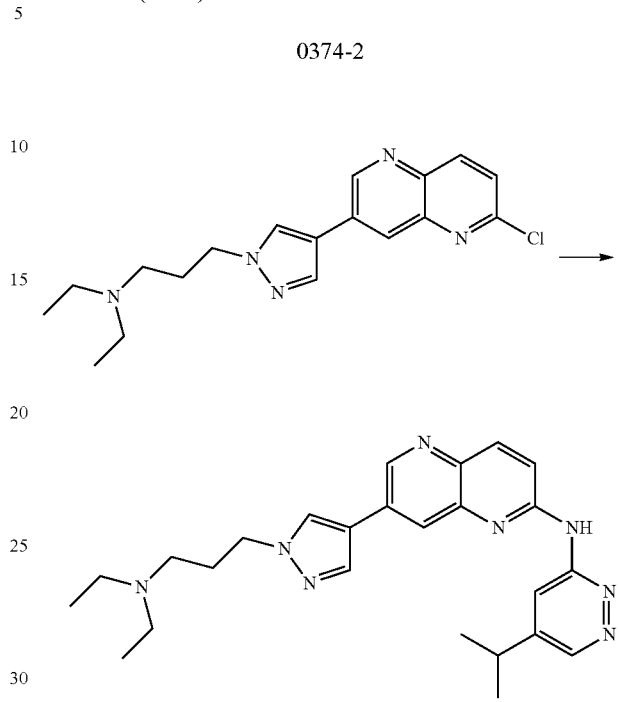

7-(1-(3-(Diethylamino)propyl)-1H-pyrazol-4-yl)-N-(5-isopropylpyridazin-3-yl)-1,5-naphthyridine-2-amine was obtained as a pale yellow solid in the same manner as in Example 0001-5.

$^1$H-NMR(CDCl$_3$)δ:8.93(1H,d,J=2.0 Hz),8.83-8.82(2H, m),8.24(1H,d,J=9.2 Hz),8.10(1H,d,J=1.3 Hz),7.97(1H,s), 7.89(1H,s),7.50(1H,d,J=9.2 Hz),4.29(2H,t,J=6.9 Hz),3.07-3.05(1H,m),2.58-2.55(6H,m),2.15(2H,m),1.43-1.41(6H,m), 1.04(6H,t,J=6.9 Hz).

MSm/z(M+H):445.

Example 0375

0375-1

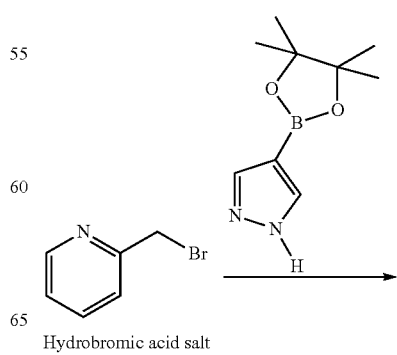

Hydrobromic acid salt

-continued

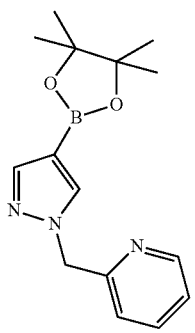

A suspension of 4-(4,4,5,5-tetramethyl-1,3,2-dioxaborolan-2-yl)-1H-pyrazole (195 mg), 2-(bromomethyl)pyridine hydrobromate (302 mg), and potassium carbonate (415 mg) in acetonitrile (2 mL) was stirred at 80° C. overnight. The reaction mixture was cooled to room temperature, the insolubles were filtered off, and the solvent was distilled off under reduced pressure, thereby obtaining 2-((4-(4,4,5,5-tetramethyl-1,3,2-dioxaborolan-2-yl)-1H-pyrazol-1-yl)methyl)pyridine (284 mg) as brown oily substance.

MSm/z(M+H):286.

0375-2

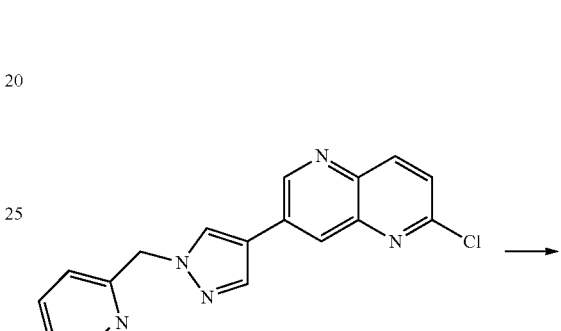

1,4-Dioxane (2 mL)/water (0.2 mL) was added to a mixture of 7-bromo-2-chloro-1,5-naphthyridine (75 mg), 2-((4-(4,4,5,5-tetramethyl-1,3,2-dioxaborolan-2-yl)-1H-pyrazol-1-yl)methyl)pyridine (105 mg), bis(di-tert-butyl(4-dimethylaminophenyl)phosphine)dichloropalladium(II) (21 mg), and sodium carbonate (65 mg), followed by stirring at 100° C. for 2 hours. After the reaction mixture was cooled to room temperature, the insolubles were filtered off using celite, and the filter cake was washed with ethyl acetate. The filtrate and the washings were combined, and the solvent was distilled off under reduced pressure. The obtained residue was purified by silica gel column chromatography (ethyl acetate-hexane, methanol-ethyl acetate, NH silica), thereby obtaining 2-chloro-7-(1-(pyridin-2-ylmethyl)-1H-pyrazol-4-yl)-1,5-naphthyridine (64 mg) as a yellow solid.

MSm/z(M+H):322.

0375-3

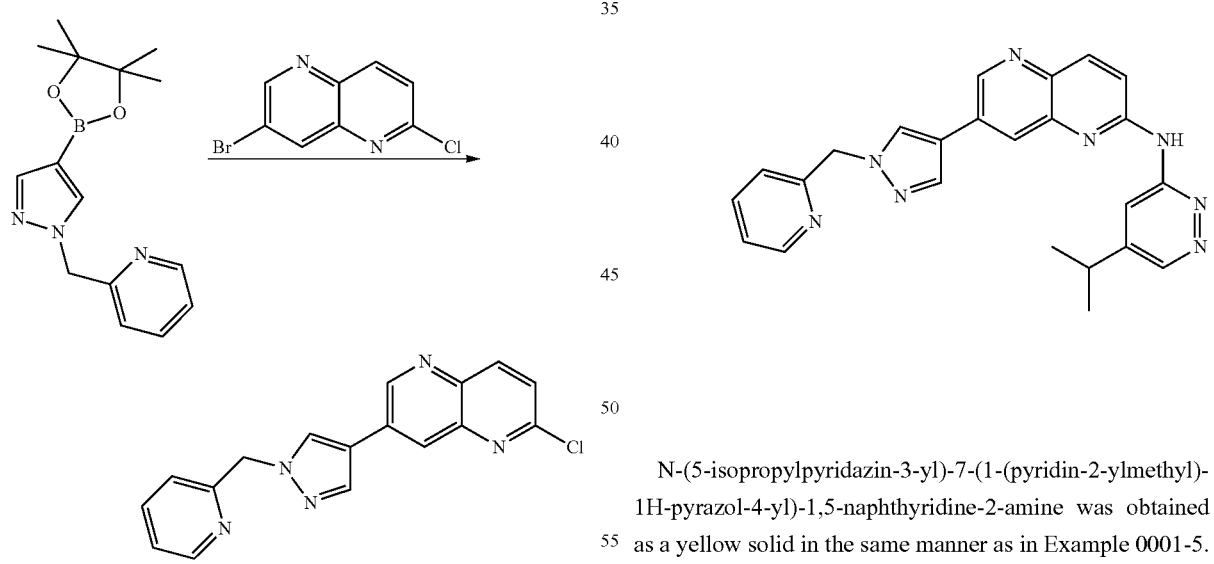

N-(5-isopropylpyridazin-3-yl)-7-(1-(pyridin-2-ylmethyl)-1H-pyrazol-4-yl)-1,5-naphthyridine-2-amine was obtained as a yellow solid in the same manner as in Example 0001-5.

$^1$H-NMR(CDCl$_3$)δ:8.94(1H,s),8.83-8.80(2H,m),8.63(2H, d,J=4.6 Hz),8.24(1H,d,J=9.9 Hz),8.13(1H,s),8.04(3H,m), 7.72-7.70(1H,m),7.22(1H,d,J=7.9 Hz),5.56-5.52(2H,m), 3.07-3.05(1H,m),1.42(6H,d,J=6.6 Hz).

MSm/z(M+H):423.

Example 0376

The following compounds were obtained in the same manner as in Examples 0375-1, 0375-2, and 0001-5.

| Example No. | | |
|---|---|---|
| 0376 | | |
| 0376-1 | 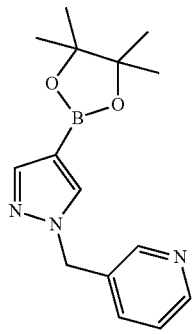 [SMILES: CC1(C)OB(c2cnn(Cc3cccnc3)c2)OC1(C)C] | MS m/z (M + H): 286. |
| 0376-2 | 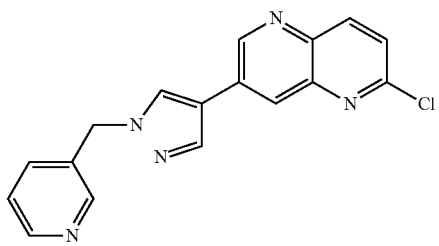 [SMILES: N=C/C(=C\NCc1cccnc1)c1cnc2ccc(Cl)nc2c1] | MS m/z (M + H): 322. |
| 0376-3 | 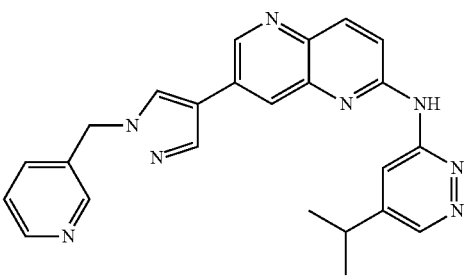 [SMILES: CC(C)c1cnnc(Nc2ccc3ncc(/C(C=N)=C/NCc4cccnc4)cc3n2)c1] | $^1$H-NMR (CDCl$_3$) δ: 8.91 (1H, d, J = 2.0 Hz), 8.79 (1H, s), 8.64-8.62 (2H, m), 8.53-8.52 (1H, m), 8.24 (1H, d, J = 9.2 Hz), 8.10 (1H, d, J = 2.0 Hz), 8.02 (1H, s), 7.88 (1H, s), 7.65-7.58 (2H, m), 7.35-7.32 (1H, m), 5.44 (2H, s), 3.06-3.04 (1H, m), 1.41 (6H, d, J = 6.6 Hz). MS m/z (M + H): 423. |

Example 0377

0377-1

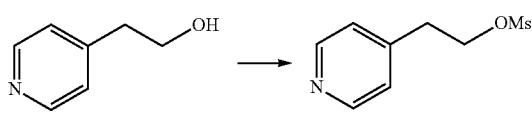 [SMILES: OCCc1ccncc1 ; CS(=O)(=O)OCCc1ccncc1]

Triethylamine (1 mL) was added to a solution of 4-pyridineethanol (0.28 mL) in tetrahydrofuran (5.8 mL), and methanesulfonyl chloride (0.28 mL) was added thereto at 0° C., followed by stirring at room temperature for 1.5 hours. The insolubles were filtered off using celite, and the filter cake was washed with tetrahydrofuran. The filtrate and the washings were combined, and the solvent was distilled off under reduced pressure, thereby obtaining 2-(pyridin-4-yl) ethyl methanesulfonate (517 mg) as an orange solid.

MSm/z(M+H):202.

0377-2 to 0377-4

The following compounds were obtained in the same manner as in Examples 0375-1, 0375-2, and 0001-5.

| Example No. | | |
|---|---|---|
| 0377 | | |
| 0377-2 | 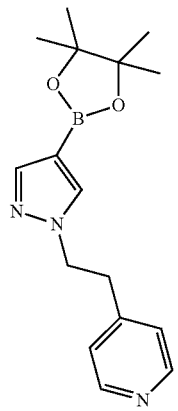 [SMILES: CC1(C)OB(c2cnn(CCc3ccncc3)c2)OC1(C)C] | MS m/z (M + H): 300. |
| 0377-3 | 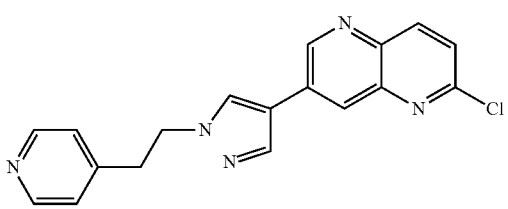 [SMILES: N=C/C(=C\NCCc1ccncc1)c1cnc2ccc(Cl)nc2c1] | MS m/z (M + H): 336. |
| 0377-4 | 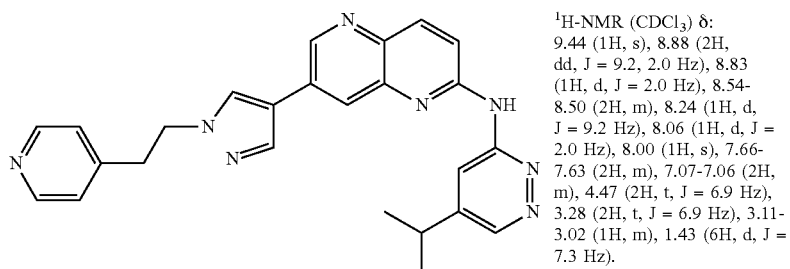 | $^1$H-NMR (CDCl$_3$) δ: 9.44 (1H, s), 8.88 (2H, dd, J = 9.2, 2.0 Hz), 8.83 (1H, d, J = 2.0 Hz), 8.54-8.50 (2H, m), 8.24 (1H, d, J = 9.2 Hz), 8.06 (1H, d, J = 2.0 Hz), 8.00 (1H, s), 7.66-7.63 (2H, m), 7.07-7.06 (2H, m), 4.47 (2H, t, J = 6.9 Hz), 3.28 (2H, t, J = 6.9 Hz), 3.11-3.02 (1H, m), 1.43 (6H, d, J = 7.3 Hz). MS m/z (M + H): 437. |
Example 0378
0378-1
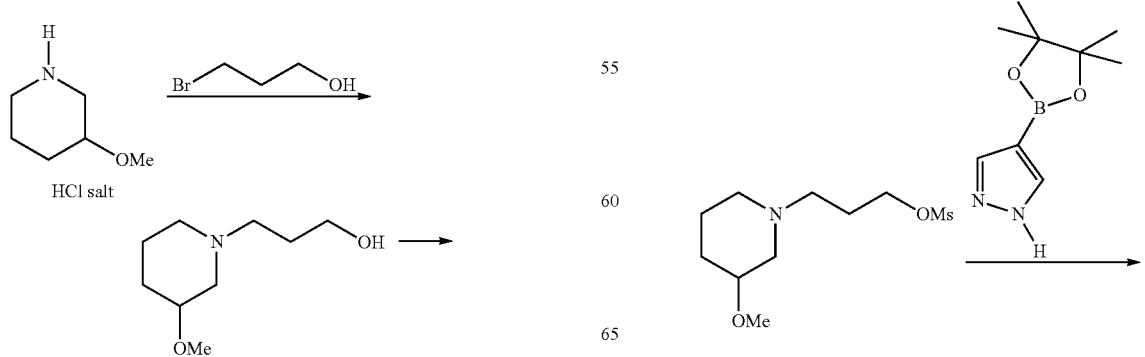

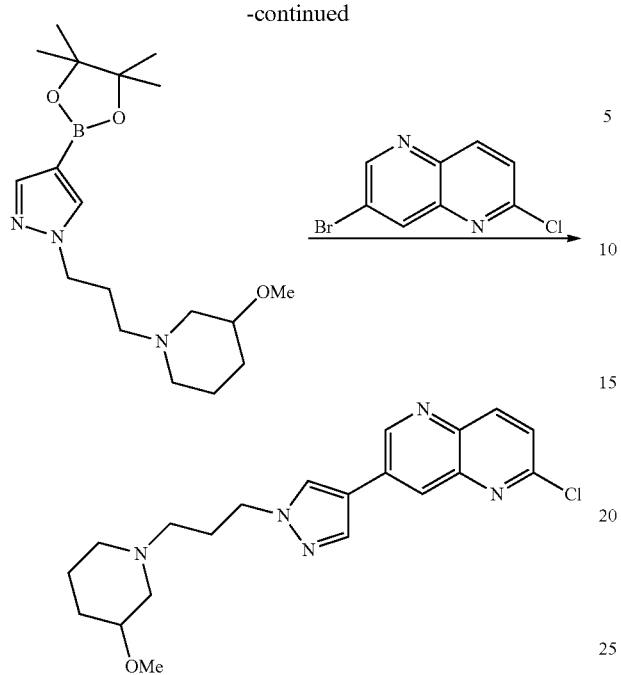

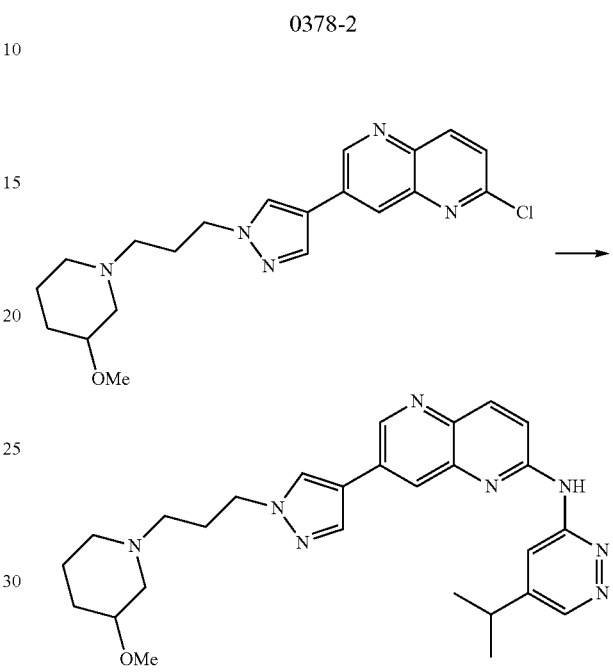

Potassium carbonate (0.82 g) and 3-bromo-1-propanol (0.27 mL) were added to a suspension of 3-methoxypiperidine hydrochloride in acetonitrile (4 mL), followed by stirring at 80° C. for 15 hours. The reaction mixture was cooled to room temperature, the insolubles were filtered off, and the solvent was distilled off under reduced pressure, thereby obtaining 3-(3-methoxypiperidin-1-yl)propan-1-ol (400 mg) as brown oily substance.

Triethylamine (0.97 mL) was added to a suspension of the obtained 3-(3-methoxypiperidin-1-yl)propan-1-ol (400 mg) in tetrahydrofuran (5.5 mL), and methanesulfonyl chloride (0.27 mL) was added thereto at 0° C., followed by stirring at room temperature for 2 hours. The insolubles were filtered off using celite, and the solvent was distilled off under reduced pressure, thereby obtaining 3-(3-methoxypiperidin-1-yl)propyl methanesulfonate (668 mg) as brown oily substance.

4-(4,4,5,5-Tetramethyl-1,3,2-dioxaborolan-2-yl)-1H-pyrazole (195 mg) and potassium carbonate (279 mg) were added to a solution of the obtained 3-(3-methoxypiperidin-1-yl)propyl methanesulfonate (375 mg) in acetonitrile (2 mL), followed by stirring at 80° C. for 17.5 hours. The reaction mixture was cooled to room temperature, the insolubles were filtered off, and the solvent was distilled off under reduced pressure, thereby obtaining 3-methoxy-1-(3-(4-(4,4,5,5-tetramethyl-1,3,2-dioxaborolan-2-yl)-1H-pyrazol-1-yl)propyl)piperidine (393 mg) as brown oily substance.

7-Bromo-2-chloro-1,5-naphthyridine (50 mg), bis(di-tert-butyl(4-dimethylaminophenyl)phosphine)dichloropalladium(II) (15 mg), and sodium carbonate (44 mg) were added to a mixture solution of the obtained 3-methoxy-1-(3-(4-(4,4,5,5-tetramethyl-1,3,2-dioxaborolan-2-yl)-1H-pyrazol-1-yl)propyl)piperidine (181 mg) in 1,4-dioxane (2.1 mL)/water (0.21 mL), followed by stirring at 100° C. for 2 hours. After the reaction mixture was cooled to room temperature, the insolubles were filtered off using celite, and the filter cake was washed with ethyl acetate. The filtrate and the washings were combined, and the solvent was distilled off under reduced pressure. The obtained residue was purified by silica gel column chromatography (ethyl acetate-hexane, methanol-ethyl acetate, NH silica), thereby obtaining 2-chloro-7-(1-(3-(3-methoxypiperidin-1-yl)propyl)-1H-pyrazol-4-yl)-1,5-naphthyridine (23 mg) as a white solid.

MSm/z(M+H):386.

0378-2

N-(5-isopropylpyridazin-3-yl)-7-(1-(3-(3-methoxypiperidin-1-yl)propyl)-1H-pyrazol-4-yl)-1,5-naphthyridine-2-amine was obtained as a pale yellow solid in the same manner as in Example 0001-5.

$^1$H-NMR(CDCl$_3$)δ:9.48(1H,s),8.93(2H,s),8.83-8.83(1H,m),8.25(1H,d,J=9.2 Hz),8.11-8.10(1H,m),7.93(2H,d,J=20.5 Hz),7.67(1H,d,J=9.2 Hz),4.29(2H,t,J=6.9 Hz),3.37(3H,s),3.35-3.29(1H,m),3.12-3.03(1H,m),2.86-2.82(1H,m),2.59-2.57(1H,m),2.38(2H,t,J=6.9 Hz),2.25-1.74(8H,m),1.43(6H,d,J=7.3 Hz).

MSm/z(M+H):487.

Example 0379

0379-1

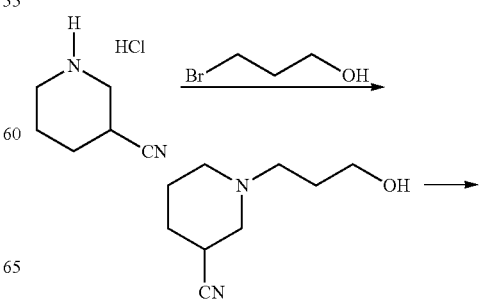

479

-continued

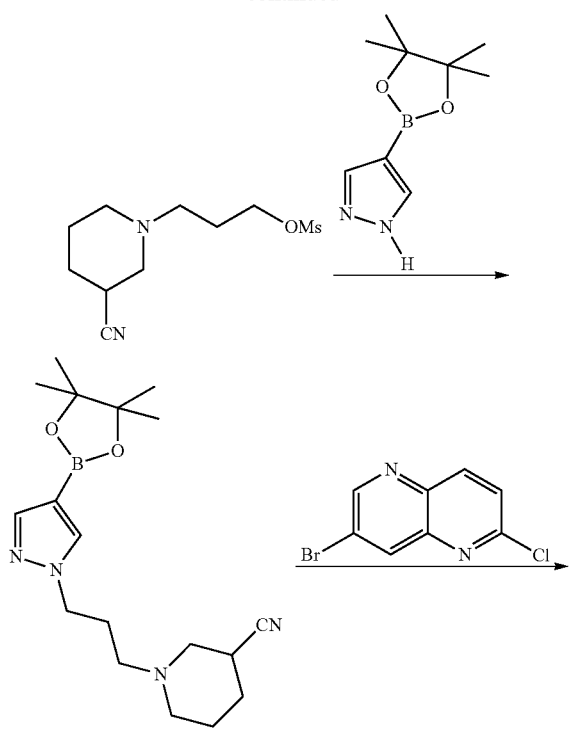

1-(3-(4-(6-Chloro-1,5-naphthyridin-3-yl)-1H-pyrazol-1-yl)propyl)piperidine-3-carbonitrile was obtained as colorless oily substance in the same manner as in Example 0378-1.

MSm/z(M+H):381.

0379-2

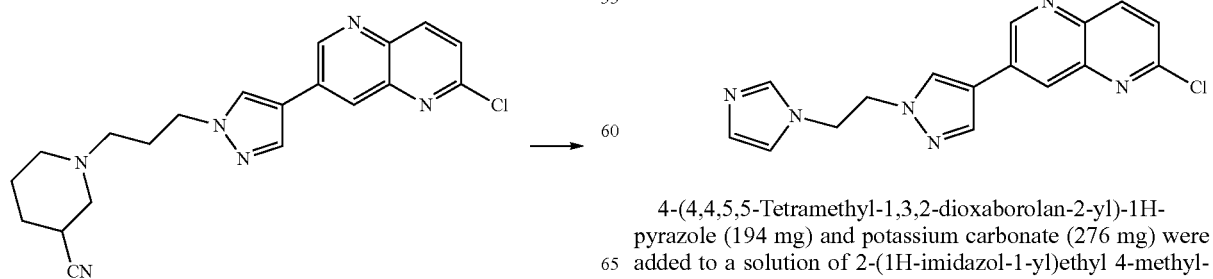

480

-continued

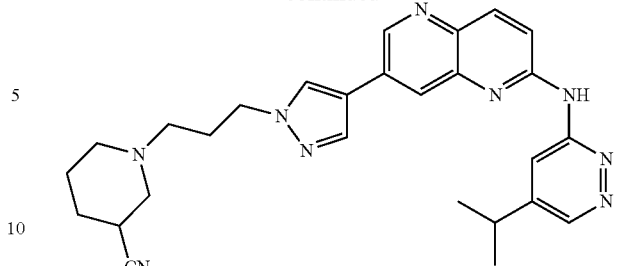

1-(3-(4-(6-(((5-Isopropylpyridazin-3-yl)amino)-1,5-naphthyridin-3-yl)-1H-pyrazol-1-yl)propyl)piperidine-3-carbonitrile was obtained as a pale yellow solid in the same manner as in Example 0001-5.

$^1$H-NMR(CDCl$_3$)δ:8.97(1H,s),8.83-8.81(2H,m),8.26-8.23(1H,m),8.15(1H,s),8.04(1H,s),7.99(1H,s),7.45-7.42(1H,m),4.36-4.32(2H,m),3.07-3.05(1H,m),2.87-2.83(1H,m),2.67-1.64(12H,m),1.42(6H,d,J=6.6 Hz).

MSm/z(M+H):482.

Example 0380

0380-1

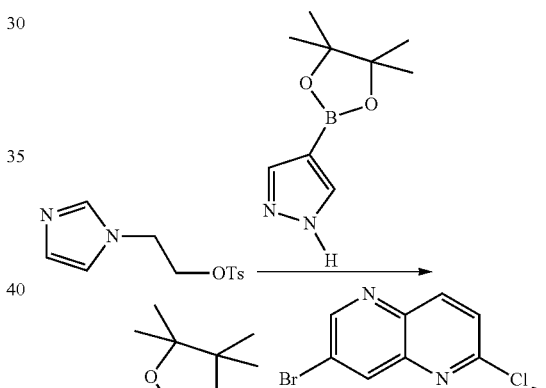

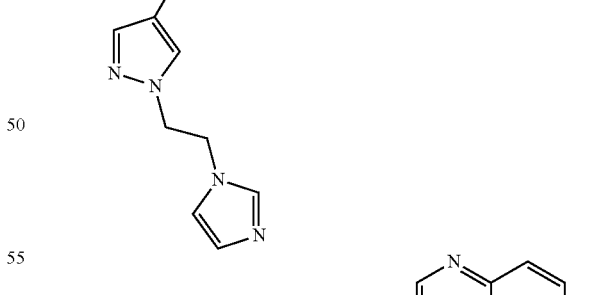

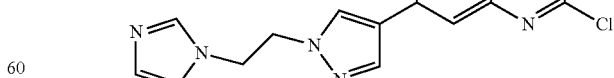

4-(4,4,5,5-Tetramethyl-1,3,2-dioxaborolan-2-yl)-1H-pyrazole (194 mg) and potassium carbonate (276 mg) were added to a solution of 2-(1H-imidazol-1-yl)ethyl 4-methylbenzenesulfonate (430 mg) in acetonitrile (2 mL), followed by stirring at 80° C. for 17.5 hours. The reaction mixture was cooled to room temperature, and the insolubles were filtered off. The filtrate and the washings were combined, and the solvent was distilled off under reduced pressure, thereby obtaining 1-(2-(1H-imidazol-1-yl)ethyl)-4-(4,4,5,5-tetramethyl-1,3,2-dioxaborolan-2-yl)-1H-pyrazole (341 mg) as brown oily substance.

7-Bromo-2-chloro-1,5-naphthyridine (50 mg), bis(di-tert-butyl(4-dimethylaminophenyl)phosphine)dichloropalladium(II) (14 mg) and sodium carbonate (45 mg) were added to a mixture solution of the obtained 1-(2-(1H-imidazol-1-yl)ethyl)-4-(4,4,5,5-tetramethyl-1,3,2-dioxaborolan-2-yl)-1H-pyrazole (152 mg) in 1,4-dioxane (2.1 mL)/water (0.21 mL), followed by stirring at 100° C. for 2 hours. After the reaction mixture was cooled to room temperature, the insolubles were filtered off using celite, and the filter cake was washed with ethyl acetate. The filtrate and the washings were combined, and the solvent was distilled off under reduced pressure. The obtained residue was purified by silica gel column chromatography (ethyl acetate-hexane, methanol-ethyl acetate, NH silica), thereby obtaining 7-(1-(2-(1H-imidazol-1-yl)ethyl)-1H-pyrazol-4-yl)-2-chloro-1,5-naphthyridine (20 mg) as a white solid.

MSm/z(M+H):325.

0380-2

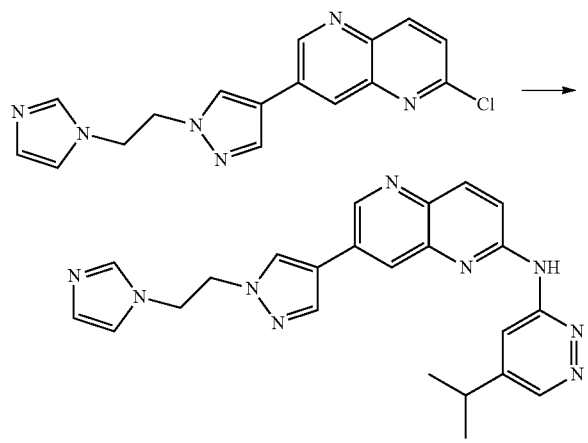

7-(1-(2-(1H-imidazol-1-yl)ethyl)-1H-pyrazol-4-yl)-N-(5-isopropylpyridazin-3-yl)-1,5-naphthyridine-2-amine was obtained as a brown solid in the same manner as in Example 0001-5.

$^1$H-NMR(CDCl$_3$)δ:8.84-8.82(3H,m),8.24(1H,d,J=8.6 Hz),8.05-8.04(2H,m),7.55(1H,d,J=9.2 Hz), 7.49(1H,s),7.29(1H,s),7.04(1H,s),6.73(1H,s),4.55-4.49(4H,m),3.08-3.06(1H,m),1.44-1.42(6H,d).

MSm/z(M+H):426.

Example 0381

0381-1

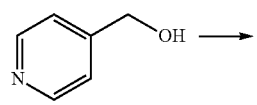

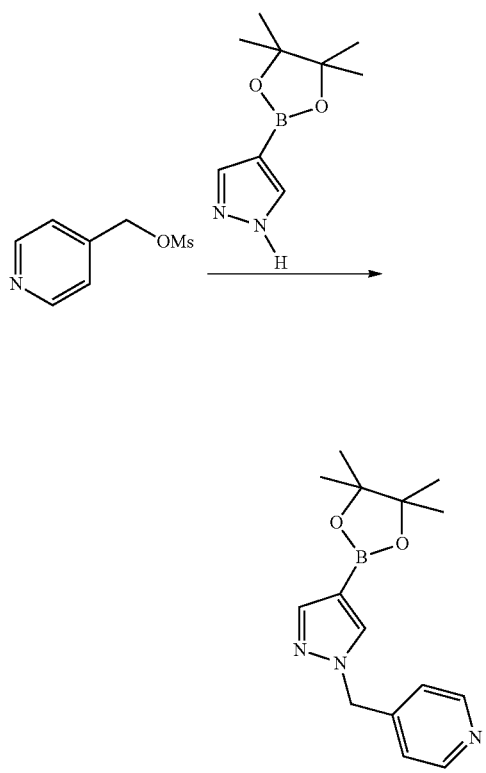

Triethylamine (0.15 mL) was added to a solution of 4-pyridinemethanol (102 mg) in tetrahydrofuran (2.2 mL), and methanesulfonyl chloride (0.08 mL) was added thereto at 0° C., followed by stirring at room temperature for 2 hours. The insolubles were filtered off using celite, and the filter cake was washed with tetrahydrofuran (5 mL). The filtrate and the washings were combined, thereby obtaining (pyridin-4-yl)methyl methanesulfonate as a yellow solution.

Acetonitrile (2 mL), 4-(4,4,5,5-tetramethyl-1,3,2-dioxaborolan-2-yl)-1H-pyrazole (148 mg), and potassium carbonate (211 mg) were added to the obtained yellow solution, followed by stirring at 80° C. overnight. The reaction mixture was cooled to room temperature, the insolubles were filtered off, and the solvent was distilled off under reduced pressure. The obtained residue was purified by silica gel column chromatography (ethyl acetate-hexane, methanol-ethyl acetate), thereby obtaining 4-((4,4,5,5-tetramethyl-1,3,2-dioxaborolan-2-yl)-1H-pyrazol-1-yl)methyl)pyridine (29 mg).

MSm/z(M+H):286.

0381-2 and 0381-3

The following compounds were obtained in the same manner as in Examples 0375-2 and 0001-5.

| Example No. | | |
|---|---|---|
| 0381 | | |
| 0381-2 | 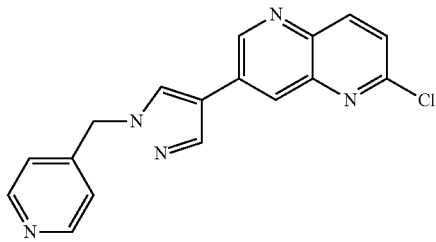 [SMILES: N=C/C(=C\NCc1ccncc1)c1cnc2ccc(Cl)nc2c1] | MS m/z (M + H): 322. |
| 0381-3 | 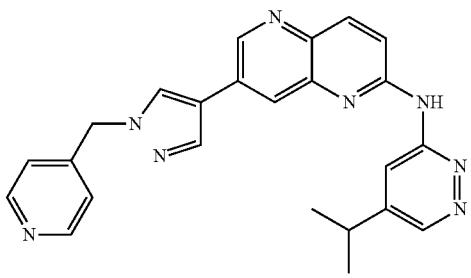 [SMILES: CC(C)c1cnnc(Nc2ccc3ncc(/C(C=N)=C/NCc4ccncc4)cc3n2)c1] | ¹H-NMR (CDCl₃) δ: 8.94 (1H, s), 8.83-8.80 (2H, m), 8.63 (2H, d, J = 5.3 Hz), 8.27-8.24 (1H, m), 8.09 (2H, d, J = 18.5 Hz), 7.92 (1H, s), 7.54 (1H, d, J = 8.6 Hz), 7.15 (2H, d, J = 5.3 Hz), 5.44 (2H, s), 3.06-3.04 (1H, m), 1.41 (6H, d, J = 7.3 Hz). MS m/z (M + H): 423. |

Example 0382

0382-1

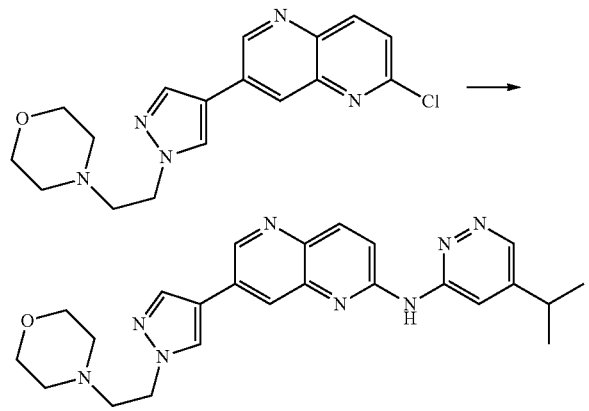

N-(5-isopropylpyridazin-3-yl)-7-(1-(2-morpholinoethyl)-1H-pyrazol-4-yl)-1,5-naphthyridine-2-amine was obtained as a white solid in the same manner as in Example 0001-5.

¹H-NMR(CDCl₃)δ:9.40(1H,brs),8.93(1H,d,J=2.1 Hz), 8.91(1H,d,J=2.1 Hz),8.83(1H,d,J=1.8 Hz),8.25(1H,d,J=8.7 Hz),8.11(1H,d,J=2.4 Hz),7.96(2H,s),7.66(1H,d,J=8.7 Hz), 4.35(2H,t,J=6.6 Hz),3.73(4H,m),3.07(1H,m),2.89(2H,t,J=6.6 Hz),2.54(4H,m),1.43(6H,d,J=6.6 Hz).

MSm/z(M+H):445.

Example 0383

0383-1

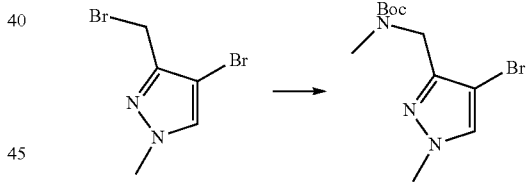

60% sodium hydride (47 mg) was added to a solution of 4-bromo-3-(bromomethyl)-1-methyl-1H-pyrazole (200 mg) and tert-butyl N-methylcarbamate (155 mg) in N-methyl-pyrrolidone (4 mL) under ice-cooling, followed by stirring at the same temperature for 1 hour, and stirring at room temperature for 2 hours. Ethyl acetate and water were added to the reaction mixture. The organic layer was collected by separation, washed with water and a saturated sodium chloride aqueous solution, and dried over anhydrous sodium sulfate, and the solvent was distilled off under reduced pressure. The obtained residue was purified by silica gel column chromatography (methanol-ethyl acetate-hexane), thereby obtaining tert-butyl ((4-bromo-1-methyl-1H-pyrazol-3-yl)methyl) (methyl)carbamate (60 mg).

MSm/z(M+H):304,306.

0383-2

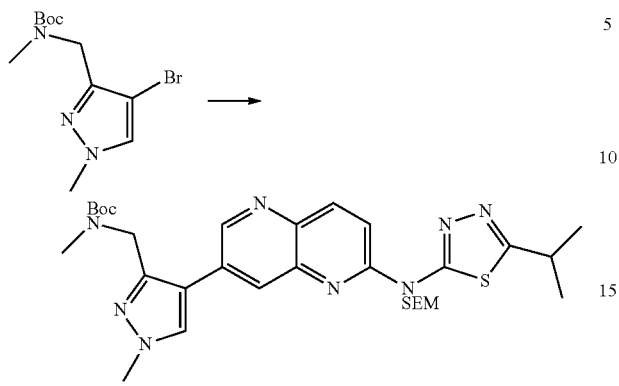

A mixture of N-(7-bromo-1,5-naphthyridin-2-yl)-5-isopropyl-N-((2-(trimethylsilyl)ethoxy)methyl)-1,3,4-thiadiazole-2-amine (20 mg), bis(pinacolato)diboron (157 mg), (1,1'-bis(diphenylphosphino)ferrocene)palladium(II) dichloride (3 mg), potassium acetate (8 mg), and 1,4-dioxane (1 mL) was stirred at 100° C. for 2 hours in a nitrogen atmosphere. tert-Butyl ((4-bromo-1-methyl-1H-pyrazol-3-yl)methyl) (methyl)carbamate (13 mg), sodium carbonate (8 mg), bis(di-tert-butyl(4-dimethylaminophenyl) phosphine)dichloropalladium(II) (5 mg), and water (0.1 mL) were added to the reaction mixture, followed by stirring at 100° C. for 4 hours. The reaction mixture was cooled to room temperature, the insolubles were filtered off using celite, and the solvent was distilled off under reduced pressure. The obtained residue was purified by silica gel column chromatography (methanol-ethyl acetate, NH silica), thereby obtaining tert-butyl ((4-(6-((5-isopropyl-1,3,4-thiadiazol-2-yl)((2-(trimethylsilyl)ethoxy)methyl)amino)-1,5-naphthyridin-3-yl)-1-methyl-1H-pyrazol-3-yl)methyl) (methyl)carbamate (4.3 mg).
MS m/z (M+H): 625.

0383-3

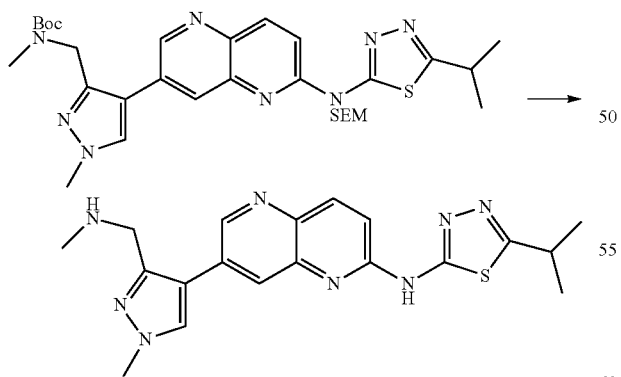

Water (0.2 mL) and trifluoroacetic acid (2 mL) were added to tert-butyl ((4-(6-((5-isopropyl-1,3,4-thiadiazol-2-yl)((2-(trimethylsilyl)ethoxy)methyl)amino)-1,5-naphthyridin-3-yl)-1-methyl-1H-pyrazol-3-yl)methyl) (methyl)carbamate (4.3 mg), followed by stirring at room temperature for 30 minutes. The solvent was distilled off under reduced pressure, and the obtained residue was purified by silica gel column chromatography (methanol-ethyl acetate, NH silica), thereby obtaining 5-isopropyl-N-(7-(1-methyl-3-((methylamino)methyl)-1H-pyrazol-4-yl)-1,5-naphthyridin-2-yl)-1,3,4-thiadiazole-2-amine (1.6 mg).
¹H-NMR(CDCl₃/CD₃OD=4/1)δ:8.83(1H,d,J=2.1 Hz), 8.33(1H,d,J=2.1 Hz),8.24(1H,d,J=8.4 Hz),7.80(1H,s),7.35 (1H,d,J=8.4 Hz),3.99(3H,s),3.94(2H,s),3.49-3.36(1H,m), 2.54(3H,s),1.49(6H,d,J=7.2 Hz).
MS m/z (M+H): 395.

Example 0384

0384-1

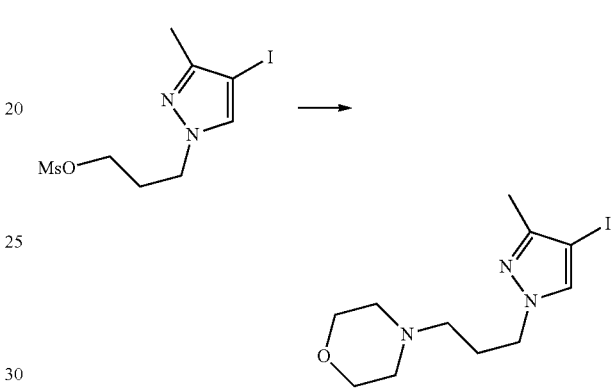

Morpholine (0.051 mL) was added to a mixture of 3-(4-iodo-3-methyl-1H-pyrazol-1-yl)propylmethanesulfonate (135 mg), potassium carbonate (108 mg), and acetonitrile (2 mL), followed by stirring at 50° C. for 5 hours. The reaction mixture was cooled to room temperature, and ethyl acetate and water were added thereto. The organic layer was collected by separation, washed with a saturated sodium chloride aqueous solution, and dried over anhydrous sodium sulfate, and the solvent was distilled off under reduced pressure, thereby obtaining 4-(3-(4-iodo-3-methyl-1H-pyrazol-1-yl)propyl)morpholine (44 mg).
MS m/z (M+H): 336.

0384-2

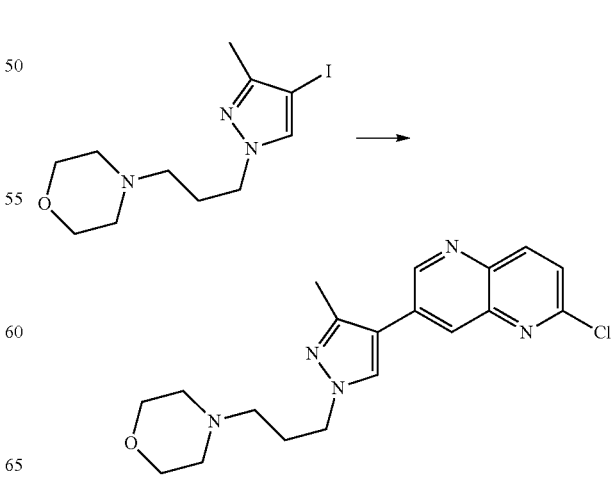

A mixture of 7-bromo-2-chloro-1,5-naphthyridine (32 mg), bis(pinacolato)diboron (50 mg), (1,1'-bis(diphenylphosphino)ferrocene)palladium(II) dichloride (11 mg), potassium acetate (26 mg), and 1,4-dioxane (1 mL) was stirred at 80° C. for 2 hours in a nitrogen atmosphere. The reaction mixture was cooled to room temperature, and 4-(3-(4-iodo-3-methyl-1H-pyrazol-1-yl)propyl)morpholine (44 mg), sodium carbonate (28 mg), bis(di-tert-butyl(4-dimethylaminophenyl)phosphine)dichloropalladium(II) (9 mg), and water (0.1 mL) were added thereto, followed by stirring at 80° C. for 2 hours. The reaction mixture was cooled to room temperature, the insolubles were filtered off using celite, and the solvent was distilled off under reduced pressure. The obtained residue was purified by silica gel column chromatography (methanol-ethyl acetate, NH silica), thereby obtaining 4-(3-(4-(6-chloro-1,5-naphthyridin-3-yl)-3-methyl-1H-pyrazol-1-yl)propyl)morpholine (10 mg).

MSm/z(M+H):372.

0384-3

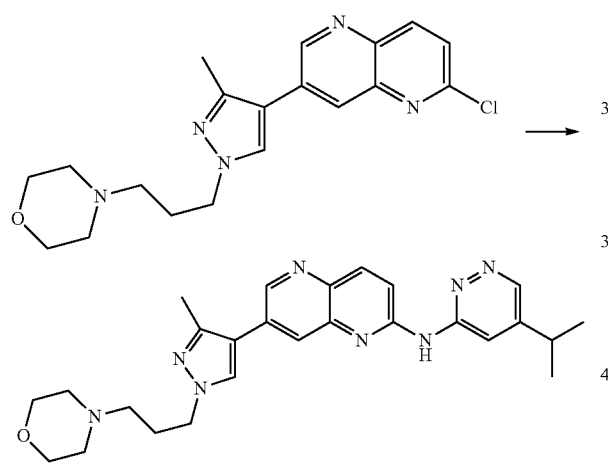

A mixture of 4-(3-(4-(6-chloro-1,5-naphthyridin-3-yl)-3-methyl-1H-pyrazol-1-yl)propyl)morpholine (10 mg), 5-isopropylpyridazine-3-amine (5.5 mg), tris(dibenzylideneacetone)dipalladium(0) (2.4 mg), 4,5-bis(diphenylphosphino)-9,9-dimethylxanthene (3.1 mg), cesium carbonate (22 mg), and 1,4-dioxane (1 mL) was stirred at 140° C. for 30 minutes using a microwave reaction apparatus. The reaction mixture was cooled to room temperature, the insolubles were filtered off using celite, and purified by silica gel column chromatography (methanol-ethyl acetate, NH silica), thereby obtaining N-(5-isopropylpyridazin-3-yl)-7-(3-methyl-1-(3-morpholinopropyl)-1H-pyrazol-4-yl)-1,5-naphthyridine-2-amine (2.8 mg).

$^1$H-NMR(CDCl$_3$/CD$_3$OD=4/1)δ:8.90(1H,brs),8.79(1H,d,J=1.8 Hz),8.71(1H,brs),8.22(1H,d,J=8.7 Hz),8.10(1H,d,J=1.8 Hz),7.78(1H,s),7.52(1H,d,J=8.7 Hz),4.22(2H,t,J=6.9 Hz),3.77-3.71(4H,m),3.10-2.99(1H,m),2.52-2.45(4H,m),2.51(3H,s),2.41(2H,t,J=7.2 Hz),2.17-2.05(2H,m),1.41(6H,d,J=7.5 Hz).

MSm/z(M+H):473.

Example 0385

385-1

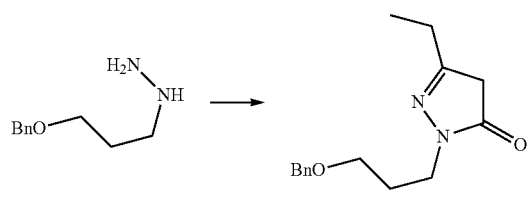 [SMILES: NNCCCOCc1ccccc1 ; CCC1=NN(CCCOCc2ccccc2)C(=O)C1]

Ethyl 3-oxopentanoate (2.15 mL) was added to a solution of (3-(benzyloxy)propyl)hydrazine (2.27 g) in ethanol (12 mL), followed by stirring for 5 hours under heating to reflux. The reaction mixture was cooled to room temperature, and the solvent was distilled off under reduced pressure. The obtained residue was purified by silica gel column chromatography (ethyl acetate-hexane), thereby obtaining 1-(3-(benzyloxy)propyl)-3-ethyl-1H-pyrazol-5(4H)-one (994 mg).

MSm/z(M+H):261.

0385-2

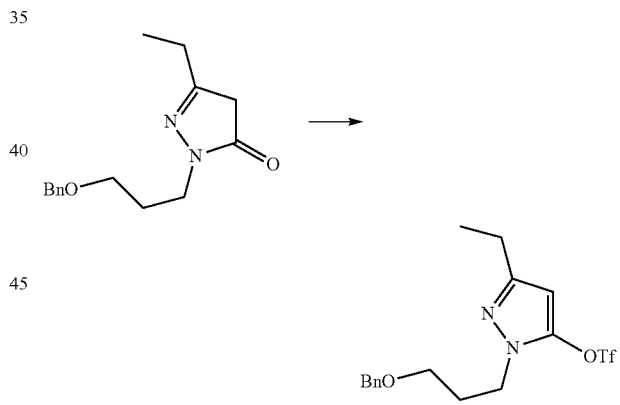

Trifluoromethanesulfonic acid anhydride (0.937 mL) was added to a solution of 1-(3-(benzyloxy)propyl)-3-ethyl-1H-pyrazol-5(4H)-one (994 mg) and pyridine (0.553 mL) in dichloromethane (19 mL) under ice-cooling, followed by stirring at the same temperature for 1 hour. A saturated sodium hydrogen carbonate aqueous solution and dichloromethane were added to the reaction mixture. The organic layer was collected by separation, and dried over anhydrous sodium sulfate, and the solvent was distilled off under reduced pressure, thereby obtaining (1-(3-(benzyloxy)propyl)-3-ethyl-1H-pyrazol-5-yl) trifluoromethanesulfonate (1.43 g).

$^1$H-NMR(CDCl$_3$) δ:7.372.50(5H,m),5.91(1H,s),4.49(2H,s),4.12(2H,t,J=7.2 Hz),3.46(2H,t,J=6.0 Hz),2.59(2H,q,J=7.2 Hz),2.19-2.08(2H,m),1.21(3H,t,J=7.2 Hz).

0385-3

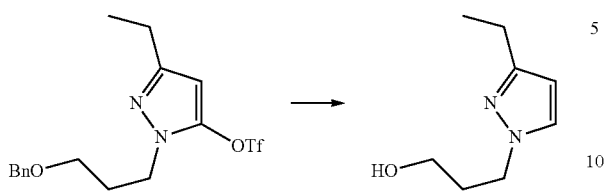

(1-(3-(Benzyloxy)propyl)-3-ethyl-1H-pyrazol-5-yl) trifluoromethanesulfonate (1.43 g) was added to a mixture of 20% palladium hydroxide-carbon (150 mg) and methanol (30 mL), followed by stirring for 5 hours in a hydrogen atmosphere. The insolubles were filtered off using celite, and the solvent was distilled off under reduced pressure, thereby obtaining 3-(3-ethyl-1H-pyrazol-1-yl)propan-1-ol (1.15 g).
$^1$H-NMR(CDCl$_3$)δ:7.79(1H,d,J=2.7 Hz),6.42(1H,d,J=2.7 Hz),4.60(2H,t,J=6.6 Hz),3.73(2H,t,J=5.4 Hz),2.88(2H,q,J=8.1 Hz),2.27-2.14(2H,m),1.26(3H,t,J=8.1 Hz).

0385-4

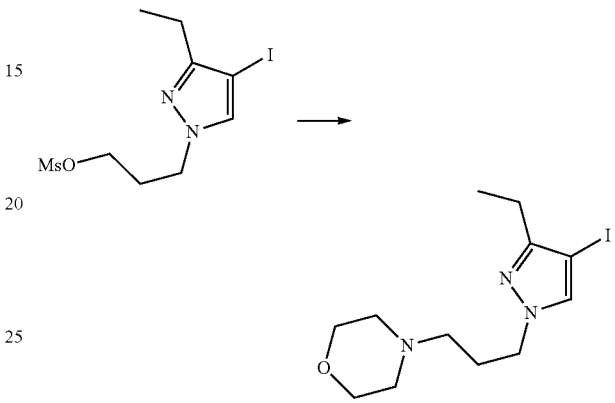

Iodine (557 mg) and ammonium cerium nitrate (1.20 g) were added to a solution of 3-(3-ethyl-1H-pyrazol-1-yl)propan-1-ol (1.15 g) in acetonitrile (8 mL), followed by stirring at room temperature for 16 hours. Ethyl acetate and water were added to the reaction mixture. The organic layer was collected by separation, washed sequentially with a 10% sodium hydrogen sulfite aqueous solution and a saturated sodium chloride aqueous solution, and dried over anhydrous sodium sulfate, and the solvent was distilled off under reduced pressure, thereby obtaining 3-(3-ethyl-4-iodo-1H-pyrazol-1-yl)propan-1-ol (821 mg).
MSm/z(M+H):281.

0385-5

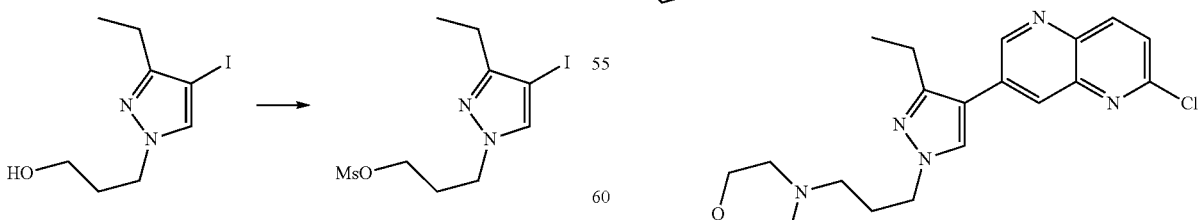

Methanesulfonyl chloride (0.342 mL) was added to a solution of 3-(3-ethyl-4-iodo-1H-pyrazol-1-yl)propan-1-ol (821 mg) and triethylamine (0.823 mL) in dichloromethane (15 mL) under ice-cooling, followed by stirring at the same temperature for 1 hour. Dichloromethane and water were added to the reaction mixture. The organic layer was collected by separation, and dried over anhydrous sodium sulfate, and the solvent was distilled off under reduced pressure, thereby obtaining 3-(3-ethyl-4-iodo-1H-pyrazol-1-yl)propyl methanesulfonate (1.00 g).
$^1$H-NMR(CDCl$_3$)δ:7.39(1H,s),4.20(2H,t,J=6.6 Hz),4.21(2H,t,J=6.6 Hz),3.03(3H,s),2.60(2H,q,J=7.8 Hz),2.33-2.22(2H,m),1.22(3H,t,J=7.8 Hz).

0385-6

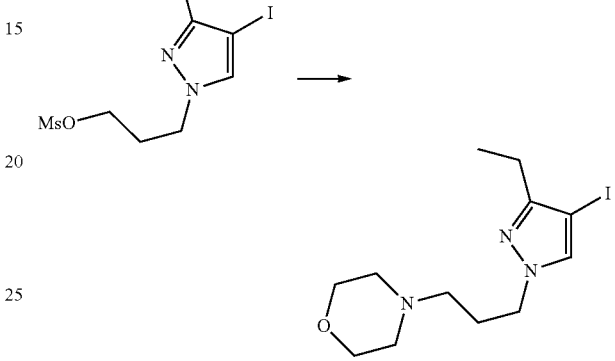

Morpholine (0.182 mL) was added to a mixture of 3-(3-ethyl-4-iodo-1H-pyrazol-1-yl)propyl methanesulfonate (500 mg), potassium carbonate (384 mg), and acetonitrile (7 mL), followed by stirring at 50° C. for 5 hours. Ethyl acetate and water were added to the reaction mixture. The organic layer was collected by separation, washed with a saturated sodium chloride aqueous solution, and dried over anhydrous sodium sulfate, and the solvent was distilled off under reduced pressure, thereby obtaining 4-(3-(3-ethyl-4-iodo-1H-pyrazol-1-yl)propyl)morpholine (204 mg).
MSm/z(M+H):350.

0385-7

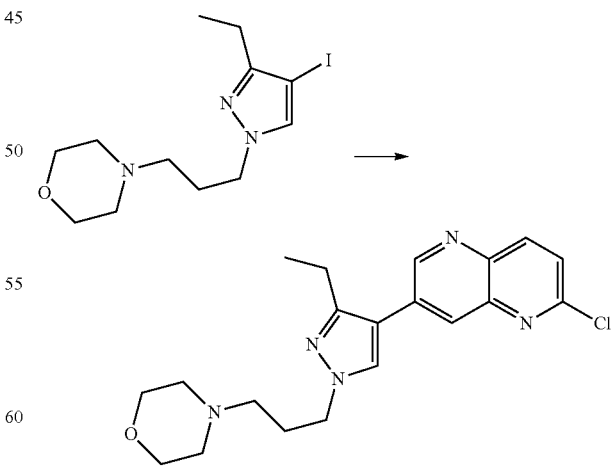

A mixture of 7-bromo-2-chloro-1,5-naphthyridine (142 mg), bis(pinacolato)diboron (223 mg), (1,1'-bis(diphenylphosphino)ferrocene)palladium(II) dichloride (47 mg), potassium acetate (115 mg), and 1,4-dioxane (3 mL) was stirred at 80° C. for 2 hours in a nitrogen atmosphere. 4-(3-(3-ethyl-4-iodo-1H-pyrazol-1-yl)propyl)morpholine (204 mg), sodium carbonate (124 mg), bis(di-tert-butyl(4-dimethylaminophenyl)phosphine)dichloropalladium(II) (41 mg), and water (0.3 mL) were added thereto, followed by stirring at 80° C. for 4 hours. The reaction mixture was cooled to room temperature, the insolubles were filtered off using celite, and the solvent was distilled off under reduced pressure. The obtained residue was purified by silica gel column chromatography (methanol-ethyl acetate, NH silica), thereby obtaining 4-(3-(4-(6-chloro-1,5-naphthyridin-3-yl)-3-ethyl-1H-pyrazol-1-yl)propyl)morpholine (18 mg).

MSm/z(M+H):386.

0385-8

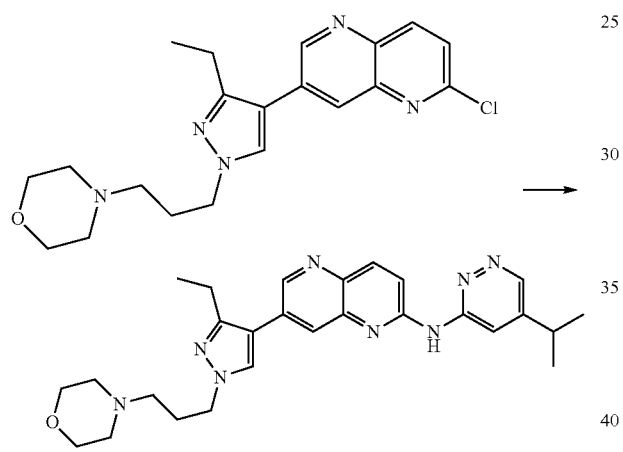

A mixture of 4-(3-(4-(6-chloro-1,5-naphthyridin-3-yl)-3-ethyl-1H-pyrazol-1-yl)propyl)morpholine (18 mg), 5-isopropylpyridazine-3-amine (9.6 mg), tris(dibenzylideneacetone)dipalladium(0) (4.2 mg), 4,5-bis(diphenylphosphino)-9,9-dimethylxanthene (5.4 mg), cesium carbonate (38 mg), and 1,4-dioxane (1 mL) was stirred at 140° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining 7-(3-ethyl-1-(3-morpholinopropyl)-1H-pyrazol-4-yl)-N-(5-isopropylpyridazin-3-yl)-1,5-naphthyridine-2-amine (6.9 mg).

$^1$H-NMR(CDCl$_3$/CD$_3$OD=4/1)δ:8.94(1H,brs),8.76(1H,brs),8.71(1H,brs),8.22(1H,d,J=9.0 Hz),8.08(1H,brs),7.74(1H,s),7.51(1H,d,J=9.0 Hz),4.23(2H,t,J=7.2 Hz),3.78-3.71(4H,m),3.10-2.98(1H,m),2.89(2H,q,J=7.2 Hz),2.53-2.45(4H,m),2.42(2H,t,J=6.6 Hz),2.19-2.05(2H,m),1.40(6H,d,J=6.6 Hz),1.31(3H,t,J=7.2 Hz).

MSm/z(M+H):487.

Example 0386

0386-1

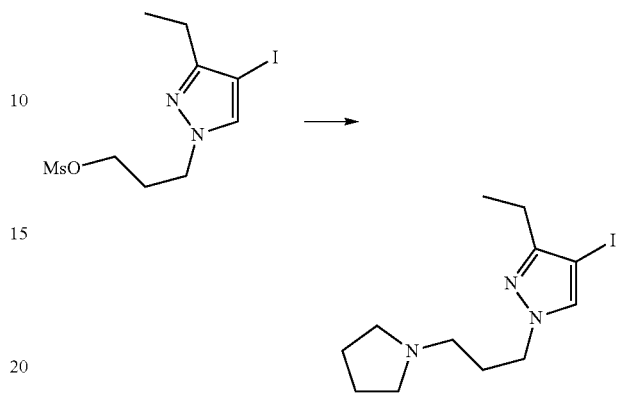

Pyrrolidine (0.172 mL) was added to a mixture of 3-(3-ethyl-4-iodo-1H-pyrazol-1-yl)propyl methanesulfonate (500 mg), potassium carbonate (384 mg), and acetonitrile (7 mL), followed by stirring at 50° C. for 5 hours. Ethyl acetate and water were added to the reaction mixture. The organic layer was collected by separation, washed with a saturated sodium chloride aqueous solution, and dried over anhydrous sodium sulfate, and the solvent was distilled off under reduced pressure, thereby obtaining 3-ethyl-4-iodo-1-(3-(pyrrolidin-1-yl)propyl)-1H-pyrazole (250 mg).

MSm/z(M+H):334.

0386-2

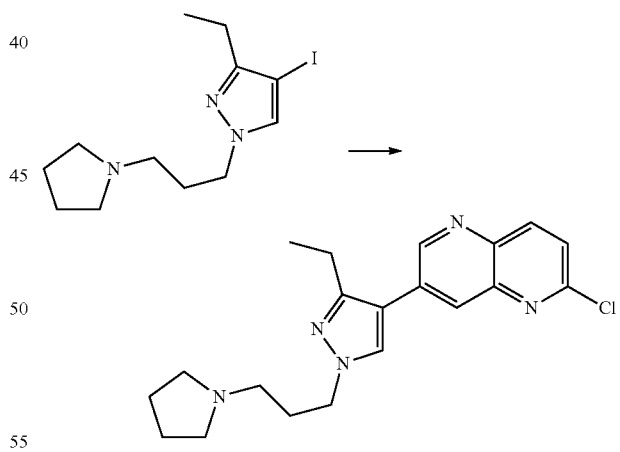

A mixture of 7-bromo-2-chloro-1,5-naphthyridine (182 mg), bis(pinacolato)diboron (286 mg), (1,1'-bis(diphenylphosphino)ferrocene)palladium(II) dichloride (61 mg), potassium acetate (147 mg), and 1,4-dioxane (4 mL) was stirred at 80° C. for 2 hours in a nitrogen atmosphere. 3-Ethyl-4-iodo-1-(3-(pyrrolidin-1-yl)propyl)-1H-pyrazole (250 mg), sodium carbonate (158 mg), bis(di-tert-butyl(4-dimethylaminophenyl)phosphine)dichloropalladium(II) (53 mg), and water (0.4 mL) were added thereto, followed by stirring at 80° C. for 3 hours. The reaction mixture was cooled to room temperature, the insolubles were filtered off using celite, and the solvent was distilled off under reduced pressure. The obtained residue was purified by silica gel column chromatography (methanol-ethyl acetate, NH silica), thereby obtaining 2-chloro-7-(3-ethyl-1-(3-(pyrrolidin-1-yl)propyl)-1H-pyrazol-4-yl)-1,5-naphthyridine (161 mg).

MSm/z(M+H):370.

0386-3

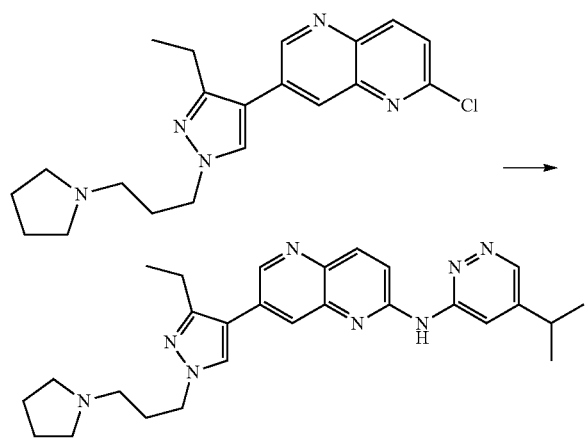

A mixture of 2-chloro-7-(3-ethyl-1-(3-(pyrrolidin-1-yl)propyl)-1H-pyrazol-4-yl)-1,5-naphthyridine (161 mg), 5-isopropylpyridazine-3-amine (9.6 mg), tris(dibenzylideneacetone)dipalladium(0) (4.2 mg), 4,5-bis(diphenylphosphino)-9,9-dimethylxanthene (5.4 mg), cesium carbonate (38 mg), and 1,4-dioxane (1 mL) was stirred at 140° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining 7-(3-ethyl-1-(3-(pyrrolidin-1-yl)propyl)-1H-pyrazol-4-yl)-N-(5-isopropylpyridazin-3-yl)-1,5-naphthyridine-2-amine (9.3 mg).

$^1$H-NMR(CDCl$_3$/CD$_3$OD=4/1)δ:8.95(1H,brs),8.78(1H,d,J=2.1 Hz),8.71(1H,m),8.22(1H,d,J=8.7 Hz),8.09(1H,d,J=2.1 Hz),7.77(1H,s),7.50(1H,d,J=8.7 Hz),4.22(2H,t,J=7.5 Hz),3.10-2.98(1H,m),2.89(2H,q,J=7.2 Hz),2.65-2.48(6H,m),2.21-2.07(2H,m),1.88-1.80(4H,m),1.41(6H,d,J=7.5 Hz),1.31(3H,t,J=7.2 Hz).

MSm/z(M+H):471.

Example 0387

0387-1

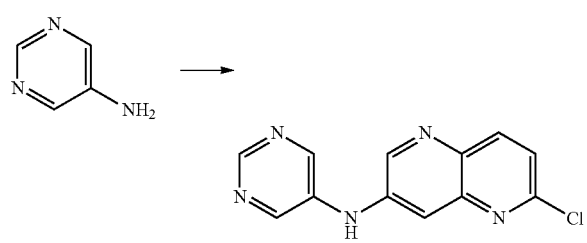

A mixture of 7-bromo-2-chloro-1,5-naphthyridine (100 mg), pyrimidine-5-amine (38 mg), tris(dibenzylideneacetone)dipalladium(0) (37 mg), 4,5-bis(diphenylphosphino)-9,9-dimethylxanthene (47 mg), cesium carbonate (267 mg), and 1,4-dioxane (2 mL) was stirred at 80° C. for 6 hours. The reaction mixture was cooled to room temperature, the insolubles were filtered off using celite, and the obtained solution was purified by silica gel column chromatography (methanol-ethyl acetate), thereby obtaining 6-chloro-N-(pyrimidin-5-yl)-1,5-naphthyridine-3-amine (32 mg).

MSm/z(M+H):258.

0387-2

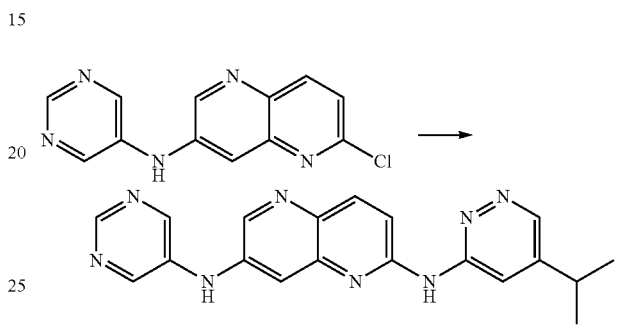

A mixture of 6-chloro-N-(pyrimidin-5-yl)-1,5-naphthyridine-3-amine (10 mg), 5-isopropylpyridazine-3-amine (8.0 mg), tris(dibenzylideneacetone)dipalladium(0) (3.5 mg), 4,5-bis(diphenylphosphino)-9,9-dimethylxanthene (4.5 mg), cesium carbonate (25 mg), and 1,4-dioxane (1 mL) was stirred at 140° C. for 30 minutes using a microwave reaction apparatus. The reaction mixture was cooled to room temperature, and the solid matter was collected by filtration, thereby obtaining N$^2$-(5-isopropylpyridazin-3-yl)-N$^7$-(pyrimidin-5-yl)-1,5-naphthyridine-2,7-diamine (4.5 mg).

$^1$H-NMR(DMSO-d$_6$)δ:10.63(1H,s),9.17(1H,s),8.83(1H,d,J=1.8 Hz),8.79(1H,s),8.77(2H,s),8.70(1H,d,J=1.8 Hz),8.62(1H,d,J=2.7 Hz),8.14(1H,d,J=9.0 Hz),7.67(1H,d,J=2.7 Hz),7.58(1H,d,J=9.0 Hz),3.07-2.93(1H,m),1.29(6H,d,J=7.2 Hz).

MSm/z(M+H):359.

Example 0388

0388-1

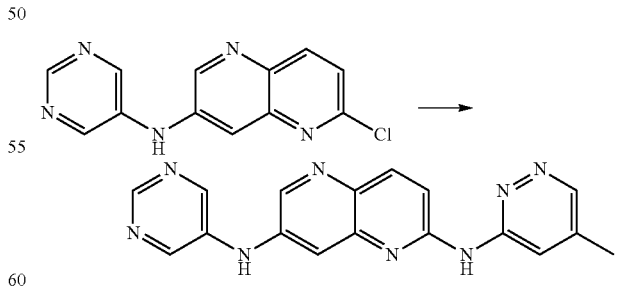

A mixture of 6-chloro-N-(pyrimidin-5-yl)-1,5-naphthyridine-3-amine (10 mg), 5-methylpyridazine-3-amine (6.4 mg), tris(dibenzylideneacetone)dipalladium(0) (3.5 mg), 4,5-bis(diphenylphosphino)-9,9-dimethylxanthene (4.5 mg), cesium carbonate (25 mg), and 1,4-dioxane (1 mL) was stirred at 140° C. for 30 minutes using a microwave reaction apparatus. The reaction mixture was cooled to room temperature, and the solid matter was collected by filtration, thereby obtaining N²-(5-methylpyridazin-3-yl)-N⁷-(pyrimidin-5-yl)-1,5-naphthyridine-2,7-diamine (1.6 mg).

¹H-NMR(CDCl₃/CD₃OD=4/1)δ:8.81(1H,s),8.75(2H,s), 8.73(1H,brs),8.64(1H,brs),8.51(1H,d,J=2.4 Hz),8.12(1H,d, J=9.0 Hz),7.83(1H,d,J=2.4 Hz),7.36(1H,d,J=9.0 Hz),2.45 (3H,s).

MSm/z(M+H):331.

Example 0389

0389-1

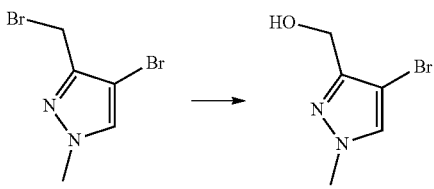

A solution of 4-bromo-3-(bromomethyl)-1-methyl-1H-pyrazole (521 mg) and potassium carbonate (850 mg) in 1,4-dioxane (3 mL) and water (6 mL) was stirred for 8 hours under heating to reflux. The reaction mixture was cooled to room temperature, and ethyl acetate and water were added thereto. The organic layer was collected by separation, washed with a saturated sodium chloride aqueous solution, and dried over anhydrous sodium sulfate, and the solvent was distilled off under reduced pressure, thereby obtaining (4-bromo-1-methyl-1H-pyrazol-3-yl)methanol (334 mg).

MSm/z(M+H):191,193.

0389-2

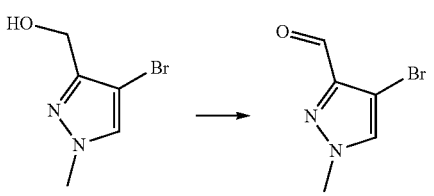

A mixture of (4-bromo-1-methyl-1H-pyrazol-3-yl)methanol (334 mg), manganese dioxide (756 mg), and dichloromethane (8 mL) was stirred at 50° C. for 24 hours. The reaction mixture was cooled to room temperature, the insolubles were filtered off using celite, and the solvent was distilled off under reduced pressure, thereby obtaining 4-bromo-1-methyl-1H-pyrazole-3-carbaldehyde (271 mg).

MSm/z(M+H):189,191.

0389-3

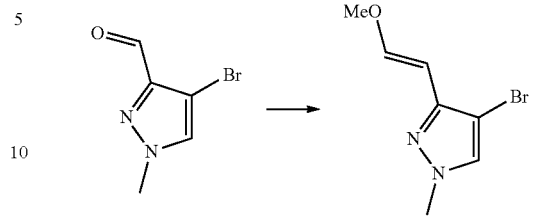

Potassium tert-butoxide (159 mg) was added to a solution of (methoxymethyl)triphenylphosphonium chloride (396 mg) in tetrahydrofuran (2 mL) under ice-cooling, followed by stirring at the same temperature for 30 minutes, and a solution of 4-bromo-1-methyl-1H-pyrazole-3-carbaldehyde (168 mg) in tetrahydrofuran (1 mL) was added to the reaction mixture, followed by stirring at room temperature for 4 hours. Water and ethyl acetate were added to the reaction mixture. The organic layer was collected by separation, washed with a saturated sodium chloride aqueous solution, and dried over anhydrous sodium sulfate, and the obtained solution was purified by silica gel column chromatography (ethyl acetate-hexane), thereby obtaining (E)-4-bromo-3-(2-methoxyvinyl)-1-methyl-1H-pyrazole (49 mg).

MSm/z(M+H):217.

0389-4

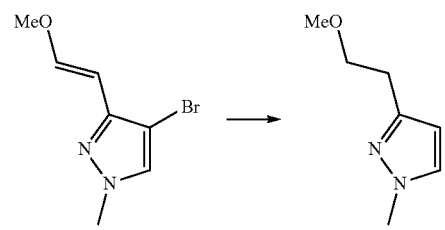

(E)-4-bromo-3-(2-methoxyvinyl)-1-methyl-1H-pyrazole (49 mg) was added to a mixture of 10% palladium-carbon (20 mg) and methanol (5 mL), followed by stirring for 4 hours in a hydrogen atmosphere. The insolubles were filtered off using celite, and the solvent was distilled off under reduced pressure, thereby obtaining 3-(2-methoxyethyl)-1-methyl-1H-pyrazole (46 mg).

¹H-NMR(CDCl₃)δ:7.53(1H,brs),6.46(1H,brs),4.28(3H, s),3.76(2H,t,J=6.0 Hz),3.38(3H,s),3.15(2H,t,J=6.0 Hz).

0389-5

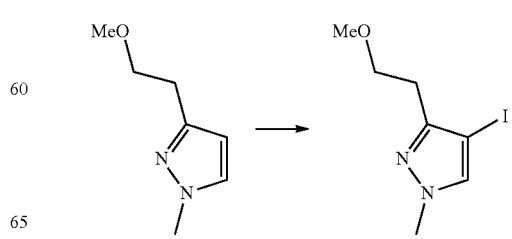

Iodine (34 mg) and ammonium cerium nitrate (74 mg) were added to a solution of 3-(2-methoxyethyl)-1-methyl-1H-pyrazole (46 mg) in acetonitrile (2 mL), followed by stirring at room temperature for 22 hours. Ethyl acetate and water were added to the reaction mixture. The organic layer was collected by separation, washed sequentially with a 10% sodium hydrogen sulfite aqueous solution and a saturated sodium chloride aqueous solution, and dried over anhydrous sodium sulfate, and the solvent was distilled off under reduced pressure, thereby obtaining 4-iodo-3-(2-methoxyethyl)-1-methyl-1H-pyrazole (35 mg).

MSm/z(M+H):267.

0389-6

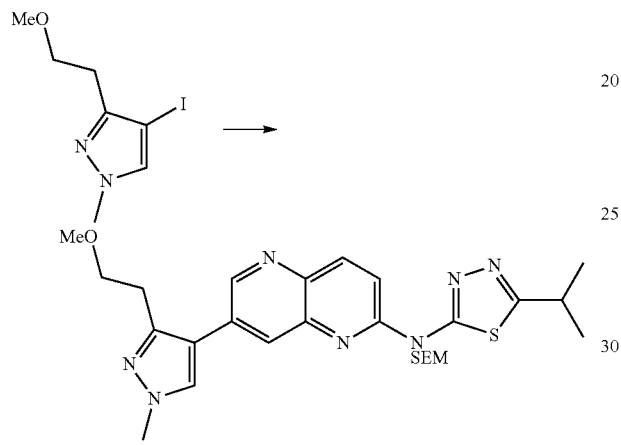

A mixture of N-(7-bromo-1,5-naphthyridin-2-yl)-5-isopropyl-N-((2-(trimethylsilyl)ethoxy)methyl)-1,3,4-thiadiazole-2-amine (20 mg), bis(pinacolato)diboron (13 mg), (1,1'-bis(diphenylphosphino)ferrocene)palladium(II) dichloride (3 mg), potassium acetate (8 mg), and 1,4-dioxane (1 mL) was stirred at 80° C. for 2 hours in a nitrogen atmosphere. 4-Iodo-3-(2-methoxyethyl)-1-methyl-1H-pyrazole (11 mg), sodium carbonate (8 mg), bis(di-tert-butyl(4-dimethylaminophenyl)phosphine)dichloropalladium(II) (5 mg), and water (0.1 mL) were added thereto, followed by stirring at 80° C. for 3 hours. The reaction mixture was cooled to room temperature, the insolubles were filtered off using celite, and the solvent was distilled off under reduced pressure. The obtained residue was purified by silica gel column chromatography (methanol-ethyl acetate-hexane), thereby obtaining 5-isopropyl-N-(7-(3-(2-methoxyethyl)-1-methyl-1H-pyrazol-4-yl)-1,5-naphthyridin-2-yl)-N-((2-(trimethylsilyl)ethoxy)methyl)-1,3,4-thiadiazole-2-amine (5.6 mg).

MSm/z(M+H):540.

0389-7

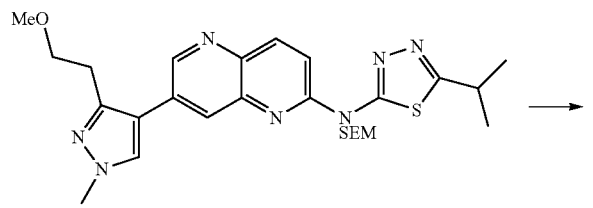

-continued

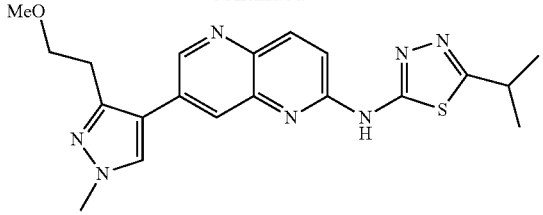

Water (0.2 mL) and trifluoroacetic acid (2 mL) were added to 5-isopropyl-N-(7-(3-(2-methoxyethyl)-1-methyl-1H-pyrazol-4-yl)-1,5-naphthyridin-2-yl)-N-((2-(trimethylsilyl)ethoxy)methyl)-1,3,4-thiadiazole-2-amine (5.6 mg), followed by stirring at room temperature for 30 minutes. The solvent was distilled off under reduced pressure, and the obtained residue was purified by silica gel column chromatography (methanol-ethyl acetate, NH silica), thereby obtaining 5-isopropyl-N-(7-(3-(2-methoxyethyl)-1-methyl-1H-pyrazol-4-yl)-1,5-naphthyridin-2-yl)-1,3,4-thiadiazol-2-amine (5.2 mg).

$^1$H-NMR(CDCl$_3$/CD$_3$OD=4/1)δ:8.80(1H,brs),8.31(1H,brs),8.24(1H,d,J=9.0 Hz),7.70(1H,s),7.35(1H,d,J=9.0 Hz),3.97(3H,s),3.75(2H,t,J=7.5 Hz),3.48-3.34(1H,m),3.40(3H,s),3.11(2H,t,J=7.5 Hz),1.48(6H,d,J=6.6 Hz).

MSm/z(M+H):410.

Example 0390

0390-1

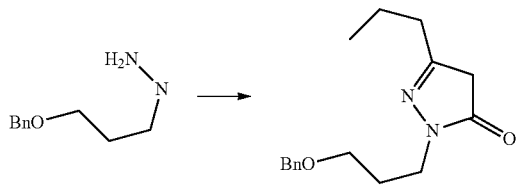 [SMILES: NNCCCOCc1ccccc1 ; CCCC1=NN(CCCOCc2ccccc2)C(=O)C1]

Ethyl 3-oxohexanoate (2.32 mL) was added to a solution of (3-(benzyloxy)propyl)hydrazine (2.19 g) in ethanol (12 mL), followed by stirring for 2 hours under heating to reflux. The reaction mixture was cooled to room temperature, and the solvent was distilled off under reduced pressure. The obtained residue was purified by silica gel column chromatography (ethyl acetate-hexane), thereby obtaining 1-(3-(benzyloxy)propyl)-3-propyl-1H-pyrazol-5(4H)-one (930 mg).

MSm/z(M+H):275.

0390-2

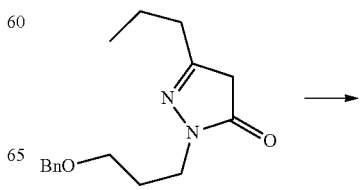

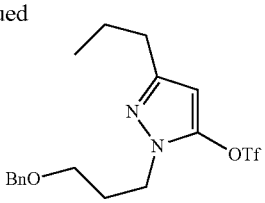

Trifluoromethanesulfonic acid anhydride (0.834 mL) was added to a solution of 1-(3-(benzyloxy)propyl)-3-propyl-1H-pyrazol-5(4H)-one (930 mg) and pyridine (0.492 mL) in dichloromethane (17 mL) under ice-cooling, followed by stirring at the same temperature for 1 hour. A saturated sodium hydrogen carbonate aqueous solution and dichloromethane were added to the reaction mixture. The organic layer was collected by separation, and dried over anhydrous sodium sulfate, and the solvent was distilled off under reduced pressure, thereby obtaining (1-(3-(benzyloxy)propyl)-3-propyl-1H-pyrazol-5-yl) trifluoromethanesulfonate (1.41 g).

$^1$H-NMR(CDCl$_3$)δ:7.367.24(5H,m),5.90(1H,s),4.48(2H,s),4.12(2H,t,J=6.6 Hz),3.45(2H,t,J=6.0 Hz),2.53(2H,t,J=8.1 Hz),2.19-2.08(2H,m),1.75-1.55(2H,m),0.94(3H,t,J=7.2 Hz).

390-3

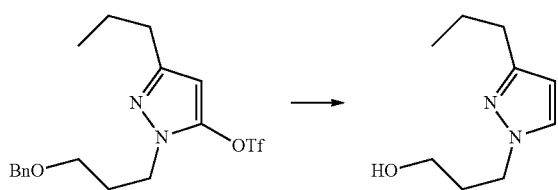 [SMILES: CCCc1cc(OS(=O)(=O)C(F)(F)F)n(CCCOCc2ccccc2)n1 ; CCCc1ccn(CCCO)n1]

(1-(3-(Benzyloxy)propyl)-3-propyl-1H-pyrazol-5-yl) trifluoromethanesulfonate (1.41 g) was added to a mixture of 20% palladium hydroxide-carbon (100 mg) and methanol (15 mL), followed by stirring for 2 hours in a hydrogen atmosphere. The insolubles were filtered off using celite, and the solvent was distilled off under reduced pressure, thereby obtaining 3-(3-propyl-1H-pyrazol-1-yl)propan-1-ol (1.08 g).

$^1$H-NMR(CDCl$_3$)δ:7.83(1H,d,J=2.7 Hz),6.41(1H,d,J=2.7 Hz),4.59(2H,t,J=6.6 Hz),3.73(2H,t,J=5.7 Hz),2.79(2H,t,J=8.1 Hz),2.25-2.14(2H,m),1.82-1.67(2H,m),1.00(3H,t,J=7.5 Hz).

0390-4

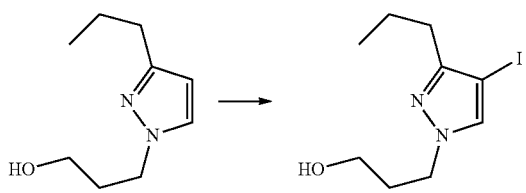

Iodine (516 mg) and ammonium cerium nitrate (1.12 g) were added to a solution of 3-(3-propyl-1H-pyrazol-1-yl)propan-1-ol (1.08 g) in acetonitrile (17 mL), followed by stirring at room temperature for 1 day. Ethyl acetate and water were added to the reaction mixture. The organic layer was collected by separation, washed sequentially with a 10% sodium hydrogen sulfite aqueous solution and a saturated sodium chloride aqueous solution, and dried over anhydrous sodium sulfate, and the solvent was distilled off under reduced pressure, thereby obtaining 3-(4-iodo-3-propyl-1H-pyrazol-1-yl)propan-1-ol (856 mg).

$^1$H-NMR(CDCl$_3$)δ:7.36(1H,s),4.23(2H,t,J=6.0 Hz),3.62(2H,t,J=6.0 Hz),2.55(2H,t,J=7.8 Hz),2.06-1.95(2H,m),1.76-1.59(2H,m),0.95(3H,t,J=7.5 Hz).

0390-5

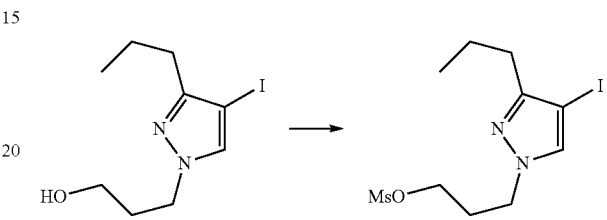

Methanesulfonyl chloride (0.192 mL) was added to a solution of 3-(4-iodo-3-propyl-1H-pyrazol-1-yl)propan-1-ol (856 mg) and triethylamine (0.460 mL) in dichloromethane (8 mL) under ice-cooling, followed by stirring at the same temperature for 1 hour. Dichloromethane and water were added to the reaction mixture. The organic layer was collected by separation, and dried over anhydrous sodium sulfate, and the solvent was distilled off under reduced pressure, thereby obtaining 3-(4-iodo-3-propyl-1H-pyrazol-1-yl)propyl methanesulfonate (539 mg).

$^1$H-NMR(CDCl$_3$)δ:7.39(1H,s),4.24-4.17(4H,m),3.03(3H,s),2.55(2H,t,J=7.5 Hz),2.33-2.22(2H,m),1.76-1.57(2H,m),0.96(3H,t,J=7.5 Hz).

0390-6

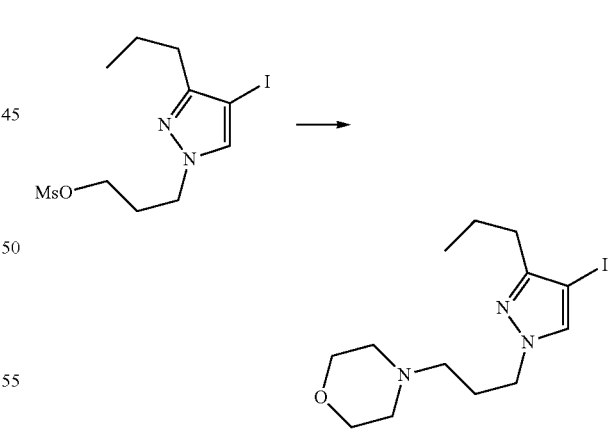

Morpholine (0.094 mL) was added to a mixture of 3-(4-iodo-3-propyl-1H-pyrazol-1-yl)propyl methanesulfonate (269 mg), potassium carbonate (199 mg), and acetonitrile (4 mL), followed by stirring at 50° C. for 8 hours. The reaction mixture was cooled to room temperature, and ethyl acetate and water were added thereto. The organic layer was collected by separation, washed with a saturated sodium chloride aqueous solution, and dried over anhydrous sodium sulfate, and the solvent was distilled off under reduced pressure, thereby obtaining 4-(3-(4-iodo-3-propyl-1H-pyrazol-1-yl)propyl)morpholine (43 mg).
MSm/z(M+H):364.

0390-7

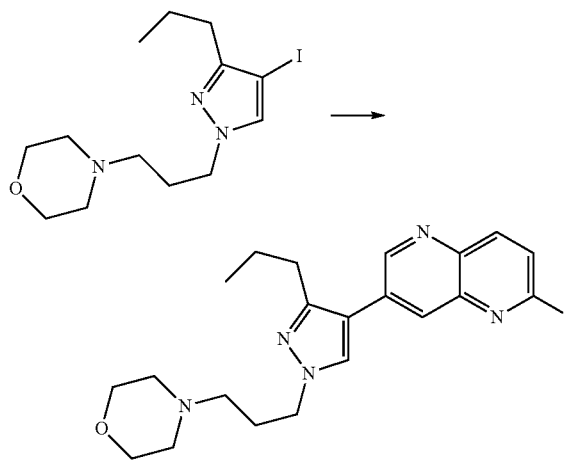

A mixture of 7-bromo-2-chloro-1,5-naphthyridine (29 mg), bis(pinacolato)diboron (36 mg), (1,1'-bis(diphenylphosphino)ferrocene)palladium(II) dichloride (10 mg), potassium acetate (23 mg), and 1,4-dioxane (1 mL) was stirred at 80° C. for 2 hours in a nitrogen atmosphere. 4-(3-(4-iodo-3-propyl-1H-pyrazol-1-yl)propyl)morpholine (43 mg), sodium carbonate (25 mg), bis(di-tert-butyl(4-dimethylaminophenyl)phosphine)dichloropalladium(II) (8 mg), and water (0.1 mL) were added thereto, followed by stirring at 80° C. for 3 hours. The reaction mixture was cooled to room temperature, the insolubles were filtered off using celite, and the solvent was distilled off under reduced pressure. The obtained residue was purified by silica gel column chromatography (methanol-ethyl acetate, NH silica), thereby obtaining 4-(3-(4-(6-chloro-1,5-naphthyridin-3-yl)-3-propyl-1H-pyrazol-1-yl)propyl)morpholine (11 mg).
MSm/z(M+H):400.

0390-8

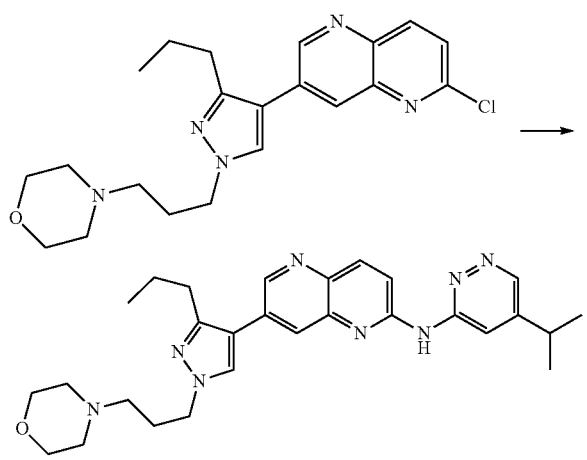

A mixture of 4-(3-(4-(6-chloro-1,5-naphthyridin-3-yl)-3-propyl-1H-pyrazol-1-yl)propyl)morpholine (11 mg), 5-isopropylpyridazine-3-amine (5.6 mg), tris (dibenzylideneacetone)dipalladium(0) (5 mg), 4,5-bis(diphenylphosphino)-9,9-dimethylxanthene (10 mg), cesium carbonate (22 mg), and 1,4-dioxane (1 mL) was stirred at 140° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining N-(5-isopropylpyridazin-3-yl)-7-(1-(3-morpholinopropyl)-3-propyl-1H-pyrazol-4-yl)-1,5-naphthyridine-2-amine (6.5 mg).
$^1$H-NMR(CDCl$_3$/CD$_3$OD=4/1)δ:8.95(1H,brs),8.76(1H,d,J=1.8 Hz),8.71(1H,brs),8.22(1H,d,J=9.0 Hz),8.08(1H,d,J=1.8 Hz),7.74(1H,s),7.50(1H,d,J=9.0 Hz),4.23(2H,t,J=6.6 Hz),3.78-3.70(4H,m),3.10-2.98(1H,m),2.83(2H,t,J=7.5 Hz),2.53-2.44(4H,m),2.41(2H,t,J=7.2 Hz),2.18-2.06(2H,m),1.79-1.66(2H,m),1.40(6H,d,J=6.6 Hz),0.99(3H,t,J=7.2 Hz).
MSm/z(M+H):501.

Example 0391

0391-1

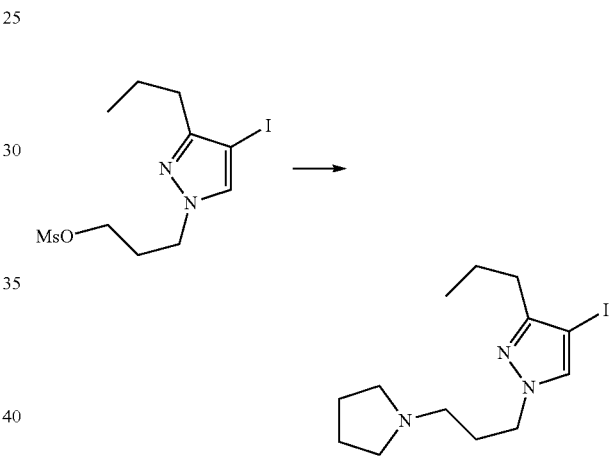

Pyrrolidine (0.089 mL) was added to a mixture of 3-(4-iodo-3-propyl-1H-pyrazol-1-yl)propyl methanesulfonate (269 mg), potassium carbonate (199 mg), and acetonitrile (4 mL), followed by stirring at 50° C. for 1 day. Ethyl acetate and water were added to the reaction mixture. The organic layer was collected by separation, washed with a saturated sodium chloride aqueous solution, and dried over anhydrous sodium sulfate, and the solvent was distilled off under reduced pressure, thereby obtaining 4-iodo-3-propyl-1-(3-(pyrrolidin-1-yl)propyl)-1H-pyrazole (113 mg).
MSm/z(M+H):348.

0391-2

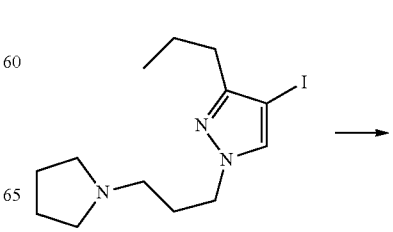

-continued

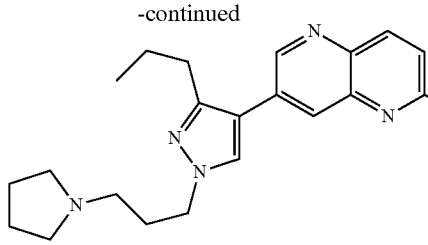

A mixture of 7-bromo-2-chloro-1,5-naphthyridine (79 mg), bis(pinacolato)diboron (99 mg), (1,1'-bis(diphenylphosphino)ferrocene)palladium(II) dichloride (26 mg), potassium acetate (64 mg), and 1,4-dioxane (2 mL) was stirred at 80° C. for 2 hours in a nitrogen atmosphere. 4-Iodo-3-propyl-1-(3-(pyrrolidin-1-yl)propyl)-1H-pyrazole (113 mg), sodium carbonate (69 mg), bis(di-tert-butyl(4-dimethylaminophenyl)phosphine)dichloropalladium(II) (23 mg), and water (0.2 mL) were added thereto, followed by stirring at 80° C. for 3 hours. The reaction mixture was cooled to room temperature, the insolubles were filtered off using celite, and the solvent was distilled off under reduced pressure. The obtained residue was purified by silica gel column chromatography (methanol-ethyl acetate, NH silica), thereby obtaining 2-chloro-7-(3-propyl-1-(3-(pyrrolidin-1-yl)propyl)-1H-pyrazol-4-yl)-1,5-naphthyridine (53 mg).

MSm/z(M+H):384.

0391-3

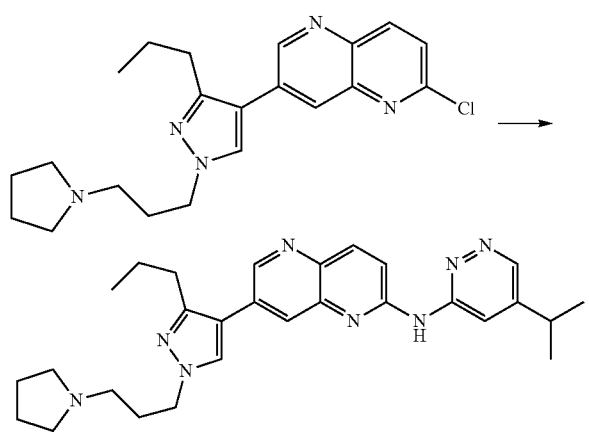

A mixture of 2-chloro-7-(3-propyl-1-(3-(pyrrolidin-1-yl)propyl)-1H-pyrazol-4-yl)-1,5-naphthyridine (27 mg), 5-isopropylpyridazine-3-amine (14 mg), tris(dibenzylideneacetone)dipalladium(0) (5 mg), 4,5-bis(diphenylphosphino)-9,9-dimethylxanthene (10 mg), cesium carbonate (57 mg), and 1,4-dioxane (1 mL) was stirred at 140° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining N-(5-isopropylpyridazin-3-yl)-7-(3-propyl-1-(3-(pyrrolidin-1-yl)propyl)-1H-pyrazol-4-yl)-1,5-naphthyridine-2-amine (6.5 mg).

$^1$H-NMR(CDCl$_3$/CD$_3$OD=4/1)δ:8.96(1H,brs),8.77(1H,brs),8.71(1H,brs),8.22(1H,d,J=9.3 Hz),8.08(1H,brs),7.77(1H,s),7.50(1H,d,J=9.3 Hz),4.22(2H,t,J=6.6 Hz),3.10-2.98(1H,m),2.83(2H,t,J=7.2 Hz),2.61-2.47(6H,m),2.20-2.08(2H,m),1.88-1.68(6H,m),1.41(6H,d,J=6.6 Hz),0.99(3H,t,J=7.2 Hz).

MSm/z(M+H):485.

Example 0392

0392-1

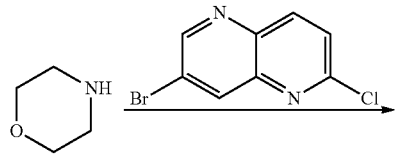

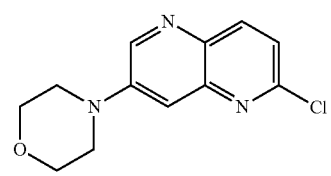

A mixture of 7-bromo-2-chloro-1,5-naphthyridine (50 mg), morpholine (18 mL), tris(dibenzylideneacetone)dipalladium(0) (18 mg), 4,5-bis(diphenylphosphino)-9,9-dimethylxanthene (24 mg), sodium tert-butoxide (39 mg), and 1,4-dioxane (2 mL) was stirred at 80° C. for 3 hours. The reaction mixture was cooled to room temperature, the insolubles were filtered off using celite, and the obtained solution was purified by silica gel column chromatography (methanol-ethyl acetate), thereby obtaining 4-(6-chloro-1,5-naphthyridin-3-yl)morpholine (5.5 mg).

MSm/z(M+H):250.

0392-2

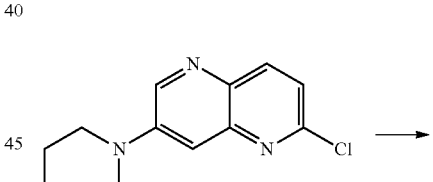

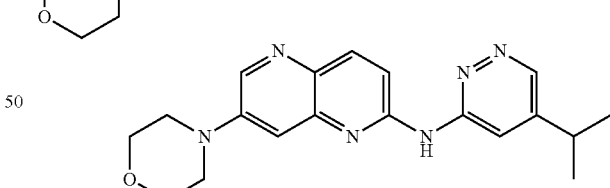

A mixture of 4-(6-chloro-1,5-naphthyridin-3-yl)morpholine (5.5 mg), 5-isopropylpyridazine-3-amine (4.5 mg), tris (dibenzylideneacetone)dipalladium(0) (5 mg), 4,5-bis(diphenylphosphino)-9,9-dimethylxanthene (10 mg), cesium carbonate (20 mg), and 1,4-dioxane (1 mL) was stirred at 140° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining N-(5-isopropylpyridazin-3-yl)-7-morpholino-1,5-naphthyridine-2-amine (5.4 mg).

¹H-NMR(CDCl₃/CD₃OD=4/1)δ:8.78(1H,brs),8.69(1H,brs),8.56(1H,brs),8.11(1H,d,J=8.4 Hz),7.35(1H,brs),7.34(1H,d,J=8.4 Hz),3.99-3.93(4H,m),3.42-3.36(4H,m),3.10-2.97(1H,m),1.40(6H,d,J=6.6 Hz).

MSm/z(M+H):351.

Example 0393

0393-1

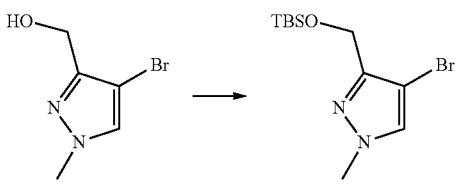

A solution of (4-bromo-1-methyl-1H-pyrazol-3-yl)methanol (325 mg), tert-butyldimethylsilyl chloride (307 mg), and imidazole (289 mg) in N,N-dimethylformamide (6 mL) was stirred at room temperature for 3 days. Ethyl acetate and water were added to the reaction mixture. The organic layer was collected by separation, washed with a saturated sodium chloride aqueous solution, and dried over anhydrous sodium sulfate. The obtained solution was purified by silica gel column chromatography (ethyl acetate-hexane), thereby obtaining 4-bromo-3-(((tert-butyldimethylsilyl)oxy)methyl)-1-methyl-1H-pyrazole (446 mg).

¹H-NMR(CDCl₃)δ:7.32(1H,s),4.65(2H,s),3.85(3H,s),0.91(9H,s),0.11(6H,s).

0393-2

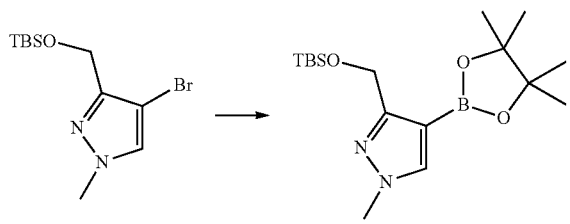 [SMILES: Cn1cc(Br)c(CO[Si](C)(C)C(C)(C)C)n1 ; Cn1cc(B2OC(C)(C)C(C)(C)O2)c(CO[Si](C)(C)C(C)(C)C)n1]

A 1.6 mol/L n-butyllithium-hexane solution (1.36 mL) was added to a solution of 4-bromo-3-(((tert-butyldimethylsilyl)oxy)methyl)-1-methyl-1H-pyrazole (446 mg) in tetrahydrofuran (7 mL) at −80° C., followed by stirring at the same temperature for 30 minutes, and 2-isopropyloxy-4,4,5,5-tetramethyl-1,3,2-dioxaborolane (0.595 mL) was added thereto at the same temperature, followed by stirring while slowly heating to room temperature over a period of 2.5 hours. A saturated ammonium chloride aqueous solution and ethyl acetate were added to the reaction mixture. The organic layer was collected by separation, washed with a saturated sodium chloride aqueous solution, and dried over anhydrous sodium sulfate, and the solvent was distilled off under reduced pressure, thereby obtaining 3-(((tert-butyldimethylsilyl)oxy)methyl)-1-methyl-4-(4,4,5,5-tetramethyl-1,3,2-dioxaborolan-2-yl)-1H-pyrazole (687 mg).

¹H-NMR(CDCl₃)δ:7.57(1H,s),4.79(2H,s),3.85(3H,s),1.24(12H,s),0.92(9H,s),0.11(6H,s).

0393-3

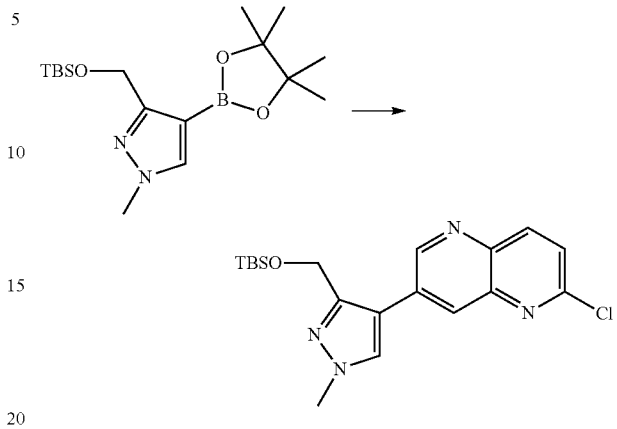

A mixture of 7-bromo-2-chloro-1,5-naphthyridine (80 mg), 3-(((tert-butyldimethylsilyl)oxy)methyl)-1-methyl-4-(4,4,5,5-tetramethyl-1,3,2-dioxaborolan-2-yl)-1H-pyrazole (231 mg), sodium carbonate (87 mg), bis(di-tert-butyl(4-dimethylaminophenyl)phosphine)dichloropalladium(II) (23 mg), water (0.3 mL), and 1,4-dioxane (3 mL) was stirred at 80° C. for 2 hours. The reaction mixture was cooled to room temperature, the insolubles were filtered off using celite, and the solvent was distilled off under reduced pressure. The obtained residue was purified by silica gel column chromatography (methanol-ethyl acetate-hexane), thereby obtaining 7-(3-(((tert-butyldimethylsilyl)oxy)methyl)-1-methyl-1H-pyrazol-4-yl)-2-chloro-1,5-naphthyridine (76 mg).

MSm/z(M+H):389.

0393-4

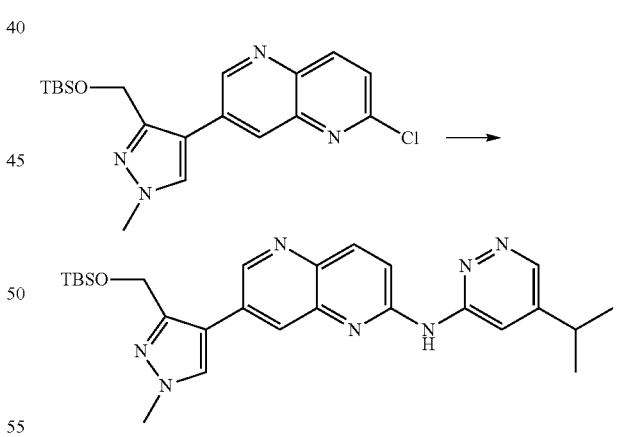

A mixture of 7-(3-(((tert-butyldimethylsilyl)oxy)methyl)-1-methyl-1H-pyrazol-4-yl)-2-chloro-1,5-naphthyridine (25 mg), 5-isopropylpyridazine-3-amine (13 mg), tris (dibenzylideneacetone)dipalladium(0) (5 mg), 4,5-bis(diphenylphosphino)-9,9-dimethylxanthene (10 mg), cesium carbonate (20 mg), and 1,4-dioxane (1 mL) was stirred at 140° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining 7-(3-

(((tert-butyldimethylsilyl)oxy)methyl)-1-methyl-1H-pyrazol-4-yl)-N-(5-isopropylpyridazin-3-yl)-1,5-naphthyridine-2-amine (20 mg).

$^1$H-NMR(CDCl$_3$)δ:8.95(1H,brs),8.86(1H,brs),8.71(1H,brs),8.27(1H,s),8.23(1H,d,J=9.0 Hz),7.79(1H,s),7.51(1H,d,J=9.0 Hz),4.85(2H,s),3.98(3H,s),3.10-2.98(1H,m),1.40(6H,d,J=6.6 Hz),0.83(9H,s),0.08(6H,s).

MSm/z(M+H):490.

Example 0394

0394-1

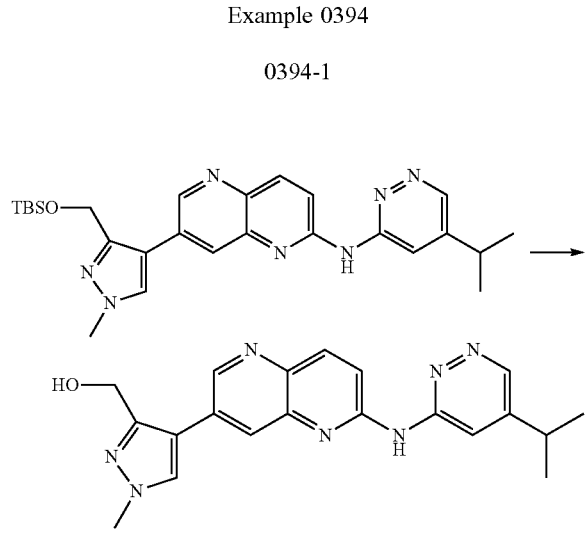

Water (0.1 mL) and trifluoroacetic acid (2 mL) were added to 7-(3-(((tert-butyldimethylsilyl)oxy)methyl)-1-methyl-1H-pyrazol-4-yl)-N-(5-isopropylpyridazin-3-yl)-1,5-naphthyridine-2-amine (20 mg), followed by stirring at room temperature for 1 hour. The solvent was distilled off under reduced pressure, and the obtained residue was purified by silica gel column chromatography (methanol-ethyl acetate, NH silica), thereby obtaining (4-(6-((5-isopropylpyridazin-3-yl)amino)-1,5-naphthyridin-3-yl)-1-methyl-1H-pyrazol-3-yl)methanol (5.9 mg).

$^1$H-NMR(CDCl$_3$/CD$_3$OD=4/1)δ:8.90(1H,d,J=2.1 Hz),8.87(1H,brs),8.71(1H,brs),8.36(1H,d,J=2.1 Hz),8.22(1H,d,J=9.3 Hz),7.81(1H,s),7.55(1H,d,J=9.3 Hz),4.76(2H,s),3.99(3H,s),3.10-2.97(1H,m),1.40(6H,d,J=6.6 Hz).

MSm/z(M+H):376.

Example 0395

0395-1

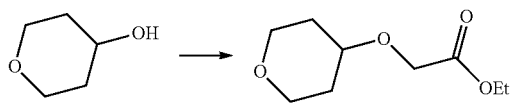 [SMILES: OC1CCOCC1 ; CCOC(=O)COC1CCOCC1]

60% sodium hydride (318 mg) was added to a solution of tetrahydro-2H-pyran-4-ol (542 mg), ethyl bromoacetate (0.590 mL), and tetrahydrofuran (25 mL), under ice-cooling, followed by stirring at room temperature for 2.5 hours. A saturated ammonium chloride aqueous solution and ethyl acetate were added to the reaction mixture. The organic layer was collected by separation, washed sequentially with water and a saturated sodium chloride aqueous solution, and dried over anhydrous sodium sulfate. The obtained solution was purified by silica gel column chromatography (ethyl acetate-hexane), thereby obtaining ethyl 2-((tetrahydro-2H-pyran-4-yl)oxy)acetate (184 mg).

MSm/z(M+H):189.

0395-2

A solution of ethyl 2-((tetrahydro-2H-pyran-4-yl)oxy)acetate (184 mg) in tetrahydrofuran (10 mL) was added to a mixture of lithium aluminium hydride (185 mg) and tetrahydrofuran (10 mL) under ice-cooling, followed by stirring at room temperature for 1 hour, and a 3 mol/L potassium sodium tartrate aqueous solution (10 mL) was added thereto under ice-cooling, followed by stirring at room temperature for 1 day. Ethyl acetate was added to the reaction mixture, and the insolubles were filtered off using celite. The organic layer was collected by separation, washed with a saturated sodium chloride aqueous solution, and dried over anhydrous sodium sulfate, and the solvent was distilled off under reduced pressure, thereby obtaining 2-((tetrahydro-2H-pyran-4-yl)oxy)ethanol (95 mg).

MSm/z(M+H):147.

0395-3

Methanesulfonyl chloride (0.076 mL) was added to a solution of 2-((tetrahydro-2H-pyran-4-yl)oxy)ethanol (95 mg) and triethylamine (0.183 mL) in dichloromethane (6 mL) under ice-cooling, followed by stirring at the same temperature for 30 minutes. Dichloromethane and water were added to the reaction mixture. The organic layer was collected by separation, and dried over anhydrous sodium sulfate, and the solvent was distilled off under reduced pressure, thereby obtaining 2-((tetrahydro-2H-pyran-4-yl)oxy)ethyl methanesulfonate (242 mg).

$^1$H-NMR(CDCl$_3$)δ:3.75(2H,t,J=4.5 Hz),3.99-3.90(2H,m),3.74(2H,t,J=4.5 Hz),3.60-3.39(3H,m),3.06(3H,s),1.96-1.82(2H,m),1.66-1.52(2H,m).

0395-4

-continued

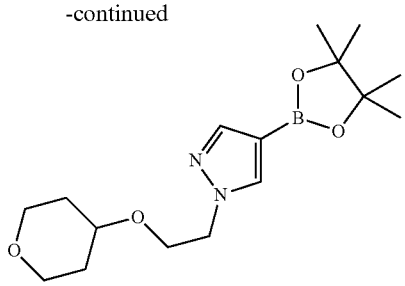

A mixture of 2-((tetrahydro-2H-pyran-4-yl)oxy)ethyl methanesulfonate (242 mg), 4-(4,4,5,5-tetramethyl-1,3,2-dioxaborolan-2-yl)-1H-pyrazole (80 mg), cesium carbonate (425 mg), acetonitrile (1 mL), and 1,4-dioxane (2 mL) was stirred at 80° C. for 5 hours. The reaction mixture was cooled to room temperature, and ethyl acetate and water were added thereto. The organic layer was collected by separation, washed with a saturated sodium chloride aqueous solution, and dried over anhydrous sodium sulfate. The obtained solution was purified by silica gel column chromatography (methanol-ethyl acetate-hexane), thereby obtaining 1-(2-((tetrahydro-2H-pyran-4-yl)oxy)ethyl)-4-(4,4,5,5-tetramethyl-1,3,2-dioxaborolan-2-yl)-1H-pyrazole (108 mg).

MSm/z(M+H):323.

0395-5 and 0395-6

The following compounds were obtained in the same manner as in Examples 0001-4 and 0001-5.

| Example No. | | |
|---|---|---|
| 0395 | | |
| 0395-5 | 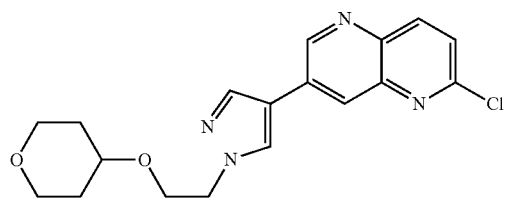 [SMILES: N=C/C(=C\NCCOC1CCOCC1)c1cnc2ccc(Cl)nc2c1] | MS m/z (M + H): 359. |
| 0395-6 | 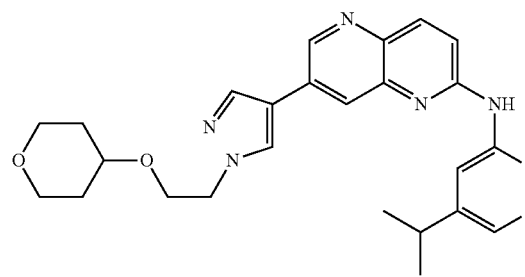 | $^1$H-NMR (CDCl$_3$/CD$_3$OD = 4/1) δ: 8.88 (2H, brs), 8.72 (1H, brs), 8.20 (1H, d, J = 8.7 Hz), 8.14 (1H, brs), 8.05 (1H, s), 7.99 (1H, s), 7.50 (1H, d, J = 8.7 Hz), 4.45-4.36 (2H, m), 3.94-3.81 (4H, m), 3.56-3.34 (3H, m), 3.16-2.98 (1H, m), 1.93-1.81 (2H, m), 1.64-1.46 (2H, m), 1.42 (6H, d, J = 7.2 Hz). MS m/z (M + H): 460. |

Example 0396

0396-1

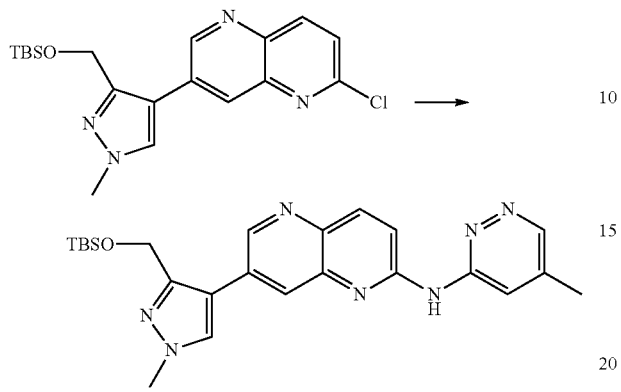

A mixture of 7-(3-(((tert-butyldimethylsilyl)oxy)methyl)-1-methyl-1H-pyrazol-4-yl)-2-chloro-1,5-naphthyridine (25 mg), 5-methylpyridazine-3-amine (11 mg), tris (dibenzylideneacetone)dipalladium(0) (5 mg), 4,5-bis(diphenylphosphino)-9,9-dimethylxanthene (10 mg), cesium carbonate (20 mg), and 1,4-dioxane (1 mL) was stirred at 140° C. for 30 minutes using a microwave reaction apparatus. The reaction mixture was cooled to room temperature, the insolubles were filtered off using celite, and the obtained solution was purified by silica gel column chromatography (methanol-ethyl acetate, NH silica), thereby obtaining 7-(3-(((tert-butyldimethylsilyl)oxy)methyl)-1-methyl-1H-pyrazol-4-yl)-N-(5-methylpyridazin-3-yl)-1,5-naphthyridine-2-amine (12 mg).

$^1$H-NMR(CDCl$_3$)δ:8.97(1H,brs),8.78(1H,brs),8.73(1H,brs),8.37(1H,s),8.26(1H,d,J=8.4 Hz),7.71(1H,s),7.44(1H,d,J=8.4 Hz),4.84(2H,s),3.98(3H,s),2.45(3H,s),0.87(9H,s),0.11(6H,s).
MSm/z(M+H):462.

Example 0397

0397-1

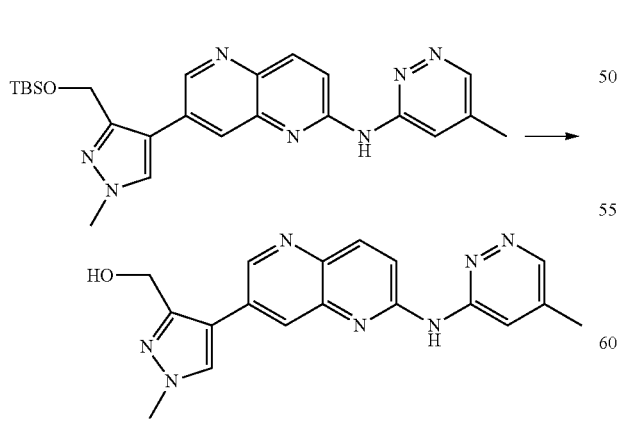

Water (0.1 mL) and trifluoroacetic acid (2 mL) were added to 7-(3-(((tert-butyldimethylsilyl)oxy)methyl)-1-methyl-1H-pyrazol-4-yl)-N-(5-methylpyridazin-3-yl)-1,5-naphthyridine-2-amine (12 mg), followed by stirring at room temperature for 3 hours. The solvent was distilled off under reduced pressure, and the obtained residue was purified by silica gel column chromatography (methanol-ethyl acetate, NH silica), thereby obtaining (1-methyl-4-(6-((5-methylpyridazin-3-yl)amino)-1,5-naphthyridin-3-yl)-1H-pyrazol-3-yl)methanol (9.6 mg).

$^1$H-NMR(CDCl$_3$/CD$_3$OD=4/1)δ:8.90(1H,brs),8.79(1H,brs),8.64(1H,brs),8.35(1H,brs),8.20(1H,d,J=8.1 Hz),7.80(1H,s),7.53(1H,d,J=8.1 Hz),4.77(2H,s),3.36(3H,s),2.46(3H,s).
MSm/z(M+H):348.

Example 0398

0398-1

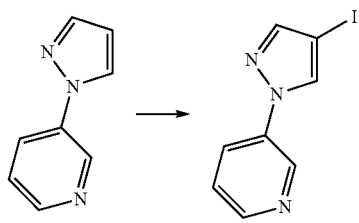 [SMILES: c1cncc(-n2cccn2)c1 ; Ic1cnn(-c2cccnc2)c1]

Iodine (208 mg) and ammonium cerium nitrate (450 mg) were added to a solution of 3-(1H-pyrazol-1-yl)pyridine (200 mg) in acetonitrile (3 mL), followed by stirring at room temperature for 13 hours, and stirring for 8 hours under heating to reflux. After the reaction mixture was cooled to room temperature, ethyl acetate and water were added thereto. The organic layer was collected by separation, washed sequentially with a 10% sodium hydrogen sulfite aqueous solution and a saturated sodium chloride aqueous solution, and dried over anhydrous sodium sulfate, and the solvent was distilled off under reduced pressure, thereby obtaining 3-(4-iodo-1H-pyrazol-1-yl)pyridine (333 mg).
MSm/z(M+H):272.

0398-2

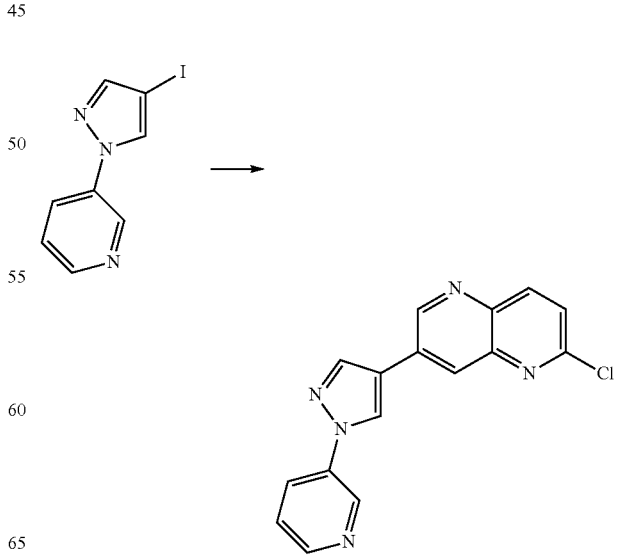

513

A mixture of 7-bromo-2-chloro-1,5-naphthyridine (50 mg), bis(pinacolato)diboron (62 mg), (1,1'-bis(diphenylphosphino)ferrocene)palladium(II) dichloride (16 mg), potassium acetate (40 mg), and 1,4-dioxane (2 mL) was stirred at 80° C. for 2 hours in a nitrogen atmosphere. 3-(4-Iodo-1H-pyrazol-1-yl)pyridine (61 mg), sodium carbonate (43 mg), bis(di-tert-butyl(4-dimethylaminophenyl)phosphine)dichloropalladium(II) (17 mg), and water (0.2 mL) were added thereto, followed by stirring at 80° C. for 8 hours. The reaction mixture was cooled to room temperature, the insolubles were filtered off using celite, and the solvent was distilled off under reduced pressure. The obtained residue was purified by silica gel column chromatography (methanol-ethyl acetate-hexane), thereby obtaining 2-chloro-7-(1-(pyridin-3-yl)-1H-pyrazol-4-yl)-1,5-naphthyridine (27 mg).

MSm/z(M+H):308.

0398-3

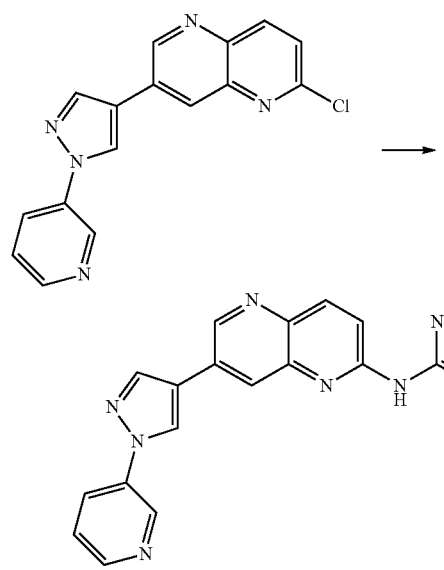

A mixture of 2-chloro-7-(1-(pyridin-3-yl)-1H-pyrazol-4-yl)-1,5-naphthyridine (13 mg), 5-isopropylpyridazine-3-amine (7.4 mg), tris (dibenzylideneacetone)dipalladium(0) (5 mg), 4,5-bis(diphenylphosphino)-9,9-dimethylxanthene (10 mg), cesium carbonate (20 mg), and 1,4-dioxane (1 mL) was stirred at 140° C. for 30 minutes using a microwave reaction apparatus. The reaction mixture was cooled to room temperature, and the solid matter was collected by filtration, thereby obtaining N-(5-isopropylpyridazin-3-yl)-7-(1-(pyridin-3-yl)-1H-pyrazol-4-yl)-1,5-naphthyridine-2-amine (12 mg).

¹H-NMR(DMSO-d₆)δ:10.74(1H,s),9.41(1H,s),9.21(1H,brs),9.19(1H,brs),8.88(1H,brs),8.72(1H,brs),8.63(1H,s),8.59(1H,d,J=4.2 Hz),8.39(1H,brs),8.38-8.29(1H,m),8.27(1H,d,J=8.7 Hz),7.75(1H,d,J=8.7 Hz),7.66-7.58(1H,m),3.07-2.93(1H,m),1.35(6H,d,J=6.6 Hz).

MSm/z(M+H):409.

514

Example 0399

0399-1

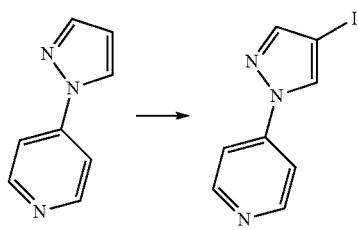 [SMILES: c1cnn(-c2ccncc2)c1 ; Ic1cnn(-c2ccncc2)c1]

Iodine (569 mg) and ammonium cerium nitrate (1.22 g) were added to a solution of 4-(1H-pyrazol-1-yl)pyridine (544 mg) in acetonitrile (8 mL), followed by stirring for 3 hours under heating to reflux. The reaction mixture was cooled to room temperature, and ethyl acetate and water were added thereto. The organic layer was collected by separation, washed sequentially with a 10% sodium hydrogen sulfite aqueous solution and a saturated sodium chloride aqueous solution, and dried over anhydrous sodium sulfate. The obtained solution was purified by silica gel column chromatography (methanol-ethyl acetate-hexane), thereby obtaining 4-(4-iodo-1H-pyrazol-1-yl)pyridine (75 mg).

MSm/z(M+H):272.

0399-2

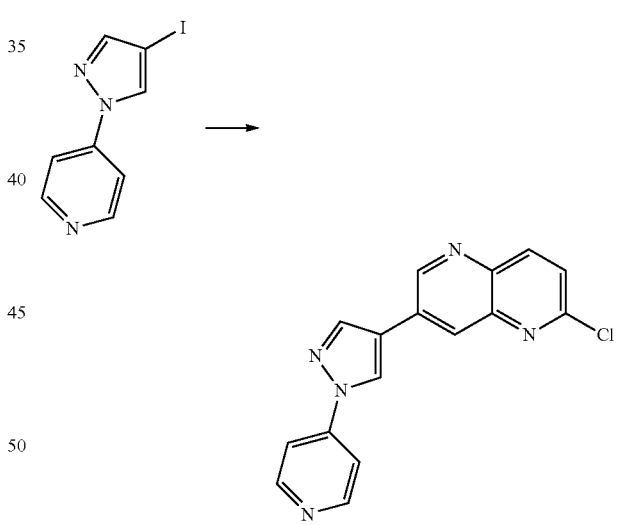

A mixture of 7-bromo-2-chloro-1,5-naphthyridine (48 mg), bis(pinacolato)diboron (60 mg), (1,1'-bis(diphenylphosphino)ferrocene)palladium(II) dichloride (16 mg), potassium acetate (39 mg), and 1,4-dioxane (2 mL) was stirred at 80° C. for 2 hours in a nitrogen atmosphere. 4-(4-Iodo-1H-pyrazol-1-yl)pyridine (75 mg), sodium carbonate (42 mg), bis(di-tert-butyl(4-dimethylaminophenyl)phosphine)dichloropalladium(II) (14 mg), and water (0.2 mL) were added thereto, followed by stirring at 80° C. for 8 hours. The reaction mixture was cooled to room temperature, the insolubles were filtered off using celite, and the solvent was distilled off under reduced pressure. The obtained residue was purified by silica gel column chromatography (methanol-ethyl acetate-hexane), thereby obtaining 2-chloro-7-(1-(pyridin-4-yl)-1H-pyrazol-4-yl)-1,5-naphthyridine (29 mg).
MSm/z(M+H):308.

0399-3

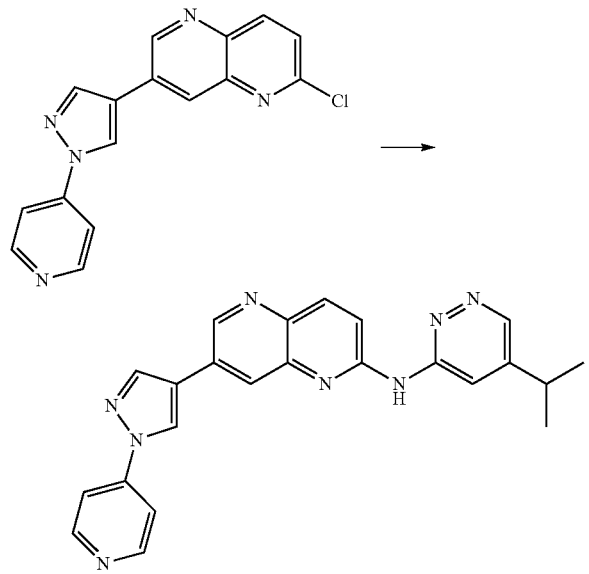

A mixture of 2-chloro-7-(1-(pyridin-4-yl)-1H-pyrazol-4-yl)-1,5-naphthyridine (14 mg), 5-isopropylpyridazine-3-amine (7.8 mg), tris(dibenzylideneacetone)dipalladium(0) (4.3 mg), 4,5-bis(diphenylphosphino)-9,9-dimethylxanthene (5.5 mg), cesium carbonate (39 mg), and 1,4-dioxane (1 mL) was stirred at 140° C. for 30 minutes using a microwave reaction apparatus. The reaction mixture was cooled to room temperature, and the solid matter was collected by filtration, thereby obtaining N-(5-isopropylpyridazin-3-yl)-7-(1-(pyridin-4-yl)-1H-pyrazol-4-yl)-1,5-naphthyridine-2-amine (2.2 mg).
$^1$H-NMR(DMSO-$d_6$)δ:10.74(1H,s),9.52(1H,s),9.19(1H,brs),8.88(1H,brs),8.72(2H,brs),8.67(1H,brs),8.42(1H,brs), 8.27(1H,d,J=7.8 Hz),7.96(2H,brs),7.75(1H,d,J=7.8 Hz), 7.50-7.32(1H,m),3.07-2.93(1H,m),1.35(6H,d,J=6.0 Hz).
MSm/z(M+H):409.

Example 0400

0400-1

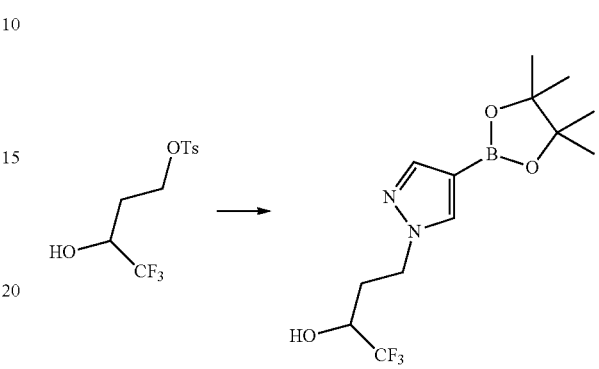

A mixture of (4,4,4-trifluoro-3-hydroxybutyl) 4-methylbenzenesulfonate (267 mg), 4-(4,4,5,5-tetramethyl-1,3,2-dioxaborolan-2-yl)-1H-pyrazole (100 mg), cesium carbonate (317 mg), acetonitrile (0.5 mL), and 1,4-dioxane (1 mL) was stirred at 80° C. for 4 hours. After the reaction mixture was cooled to room temperature, ethyl acetate and water were added thereto. The organic layer was collected by separation, washed with a saturated sodium chloride aqueous solution, and dried over anhydrous sodium sulfate. The obtained solution was purified by silica gel column chromatography (methanol-ethyl acetate-hexane), thereby obtaining 1,1,1-trifluoro-4-(4-(4,4,5,5-tetramethyl-1,3,2-dioxaborolan-2-yl)-1H-pyrazol-1-yl)butan-2-ol (203 mg).
$^1$H-NMR(CDCl$_3$)δ:7.79(1H,s),7.71(1H,s),4.51-4.25(2H,m),3.99-3.87(1H,m),2.32-1.82(2H,m),1.32(12H,s).

0400-2 and 0400-3

The following compounds were obtained in the same manner as in Examples 0001-4 and 0001-5.

| Example No. | | |
|---|---|---|
| 0400 | | |
| 0400-2 | 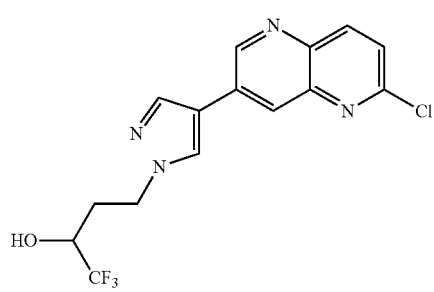 [SMILES: N=C/C(=C\NCCC(O)C(F)(F)F)c1cnc2ccc(Cl)nc2c1] | MS m/z (M + H): 357. |

-continued

| Example No. | | |
|---|---|---|
| 0400-3 | 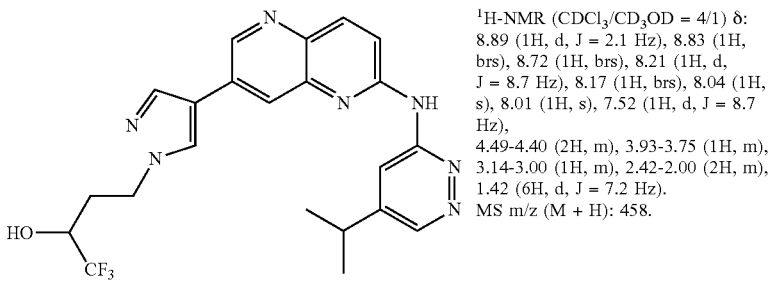 | ¹H-NMR (CDCl₃/CD₃OD = 4/1) δ: 8.89 (1H, d, J = 2.1 Hz), 8.83 (1H, brs), 8.72 (1H, brs), 8.21 (1H, d, J = 8.7 Hz), 8.17 (1H, brs), 8.04 (1H, s), 8.01 (1H, s), 7.52 (1H, d, J = 8.7 Hz), 4.49-4.40 (2H, m), 3.93-3.75 (1H, m), 3.14-3.00 (1H, m), 2.42-2.00 (2H, m), 1.42 (6H, d, J = 7.2 Hz). MS m/z (M + H): 458. |

Example 0401

0401-1

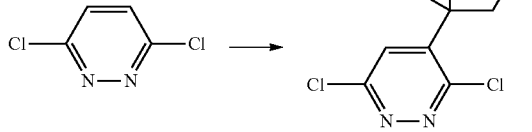

2-(3,6-Dichloropyridazin-4-yl)-2-methylpropan-1-ol was obtained as a white solid in the same manner as in Example 0014 except that 2,2-dimethyl-3-hydroxypropionic acid was used instead of the isobutyric acid used in Example 0014.

¹H-NMR(CDCl₃)δ:7.58(1H,s),4.00(2H,s),1.48(6H,s).

0401-2

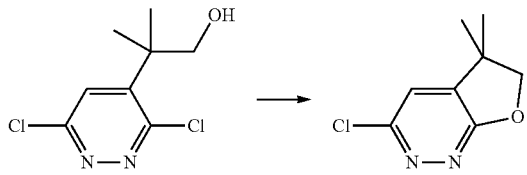

2,4-dimethoxybenzylamine (650 μL) and 1,8-diazabicyclo[5.4.0]undeca-7-ene (850 μL) were added to a solution of 2-(3,6-dichloropyridazin-4-yl)-2-methylpropan-1-ol (497 mg) in 1,4-dioxane (7 mL), followed by stirring at 150° C. for 30 minutes using a microwave reaction apparatus. The reaction mixture was cooled to room temperature, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane, NH silica), thereby obtaining 3-chloro-5,5-dimethyl-5,6-dihydrofuro[2,3-c]pyridazine (165 mg) as a white solid.

¹H-NMR(CDCl₃)δ:7.19(1H,s),4.41(2H,s),1.43(6H,s).

0401-3

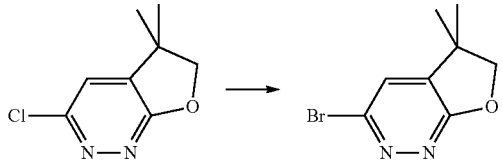

Phosphorous oxybromide (1.0 g) was added to 3-chloro-5,5-dimethyl-5,6-dihydrofuro[2,3-c]pyridazine (50 mg), followed by stirring at 100° C. for 30 minutes. The reaction mixture was cooled to room temperature, added dropwise to a mixture solution of methanol-water (1:10), the resultant product was neutralized by the addition of a sodium hydroxide aqueous solution, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 3-bromo-5,5-dimethyl-5,6-dihydrofuro[2,3-c]pyridazine (45 mg).

MSm/z(M+H):229,231.

0401-3

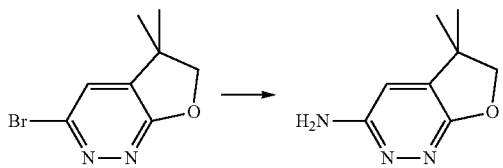

25% ammonia water (1 mL) and copper(I) oxide (5 mg) were added to a solution of 3-bromo-5,5-dimethyl-5,6-dihydrofuro[2,3-c]pyridazine (30 mg) in ethylene glycol (1 mL), followed by stirring at 150° C. for 30 minutes using a microwave reaction apparatus. The reaction mixture was cooled to room temperature, and the solvent was distilled off under reduced pressure. The obtained residue was purified by silica gel column chromatography (ethyl acetate-methanol), thereby obtaining 5,5-dimethyl-5,6-dihydrofuro[2,3-c]pyridazine-3-amine (20 mg).

MSm/z(M+H):166.

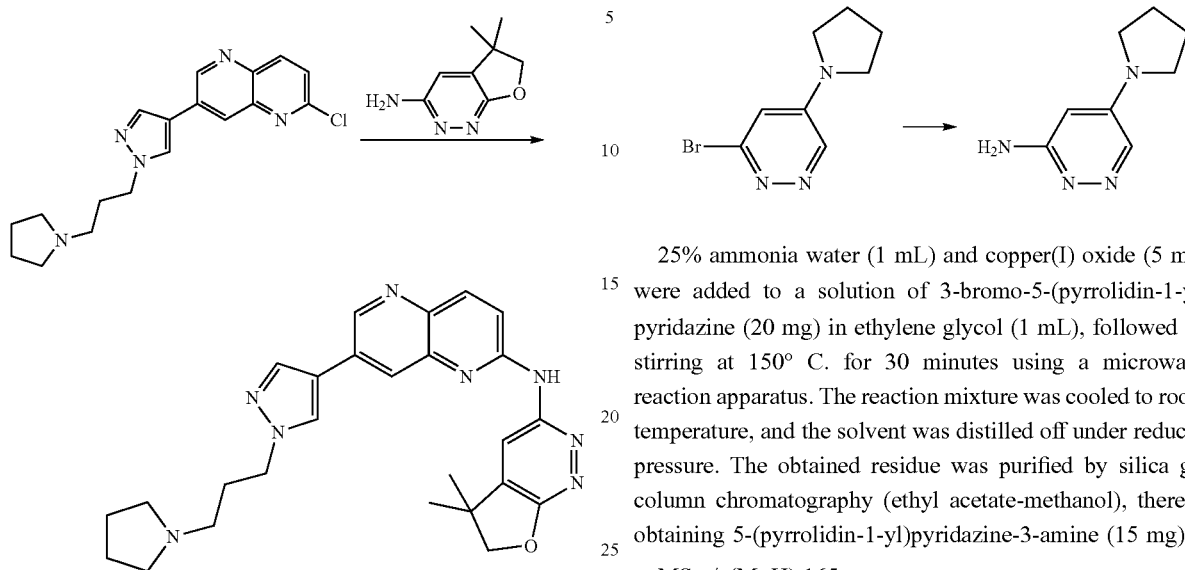

5,5-Dimethyl-N-(7-(1-(3-(pyrrolidin-1-yl)propyl)-1H-pyrazol-4-yl)-1,5-naphthyridin-2-yl)-5,6-dihydrofuro[2,3-c]pyridazine-3-amine was obtained as a pale yellow solid in the same manner as in Example 0001-5.

$^1$H-NMR(DMSO-d$_6$)δ:10.50(1H,s),9.01(1H,d,J=2.0 Hz),8.63(1H,s),8.49(1H,s),8.20-8.15(3H,m),7.60(1H,d,J=8.9 Hz),4.37(2H,s),4.23(2H,t,J=6.9 Hz),3.62-3.45(6H,m),2.08-2.02(2H,m),1.77-1.71(4H,m),1.45(6H,s).

MSm/z(M+H):471.

Example 0402

0402-1

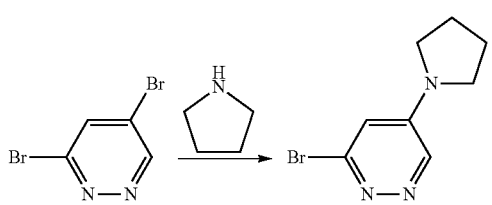

Pyrrolidine (100 μL) was added to a solution of 3,5-dibromopyridazine (30 mg) in tetrahydrofuran (1 mL), followed by stirring at room temperature overnight. The solvent was distilled off under reduced pressure, and the obtained residue was purified by silica gel column chromatography (ethyl acetate-methanol), thereby obtaining 3-bromo-5-(pyrrolidin-1-yl)pyridazine (20 mg).

MSm/z(M+H):228,230.

0402-2

25% ammonia water (1 mL) and copper(I) oxide (5 mg) were added to a solution of 3-bromo-5-(pyrrolidin-1-yl)pyridazine (20 mg) in ethylene glycol (1 mL), followed by stirring at 150° C. for 30 minutes using a microwave reaction apparatus. The reaction mixture was cooled to room temperature, and the solvent was distilled off under reduced pressure. The obtained residue was purified by silica gel column chromatography (ethyl acetate-methanol), thereby obtaining 5-(pyrrolidin-1-yl)pyridazine-3-amine (15 mg).

MSm/z(M+H):165.

0402-3

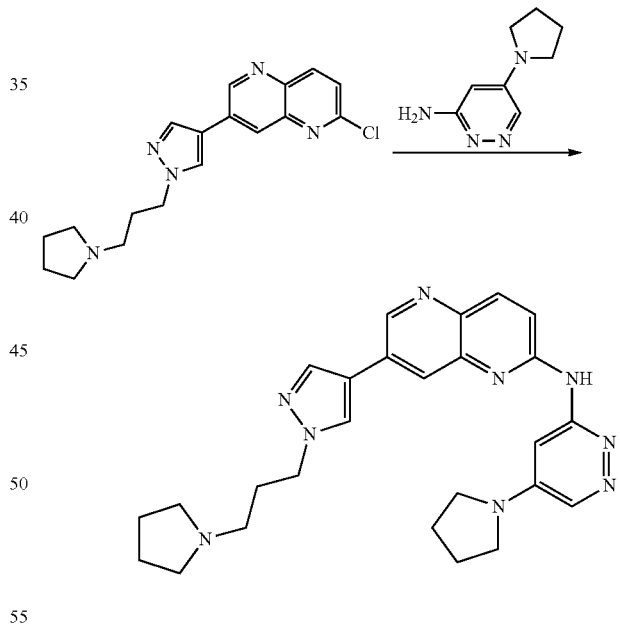

7-(1-(3-(Pyrrolidin-1-yl)propyl)-1H-pyrazol-4-yl)-N-(5-(pyrrolidin-1-yl)pyridazin-3-yl)-1,5-naphthyridine-2-amine was obtained as a pale yellow solid in the same manner as in Example 0001-5.

$^1$H-NMR(DMSO-d$_6$)δ:10.25(1H,s),9.00(1H,d,J=2.3 Hz),8.49(1H,s),8.36(1H,d,J=2.6 Hz),8.19-8.13(3H,m),7.90(1H,d,J=2.6 Hz),7.64(1H,d,J=9.2 Hz),4.21(2H,t,J=6.9 Hz),3.50-3.41(4H,m),2.46-2.37(6H,m),2.05-1.98(6H,m),1.71-1.66(4H,m).

MSm/z(M+H):470.

Example 0403

0403-1

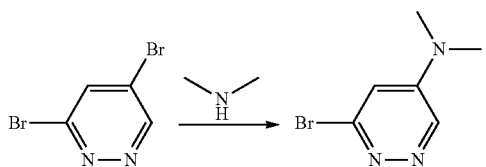

A 2.0 mol/L dimethylamine-tetrahydrofuran solution (200 μL) was added to a solution of 3,5-dibromopyridazine (30 mg) in tetrahydrofuran (1 mL), followed by stirring at room temperature overnight. The solvent was distilled off under reduced pressure, and the obtained residue was purified by silica gel column chromatography (ethyl acetate-methanol), thereby obtaining 6-bromo-N,N-dimethylpyridazine-4-amine (23 mg).

MSm/z(M+H):202,204.

403-2

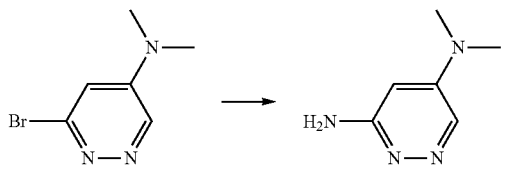

25% ammonia water (1 mL) and copper(I) oxide (5 mg) were added to a solution of 6-bromo-N,N-dimethyl-pyridazine-4-amine (23 mg) in ethylene glycol (1 mL), followed by stirring at 150° C. for 30 minutes using a microwave reaction apparatus. The reaction mixture was cooled to room temperature, and the solvent was distilled off under reduced pressure. The obtained residue was purified by silica gel column chromatography (chloroform-methanol), thereby obtaining $N^5,N^5$-dimethylpyridazine-3,5-diamine (18 mg).

MSm/z(M+H):139.

0403-3

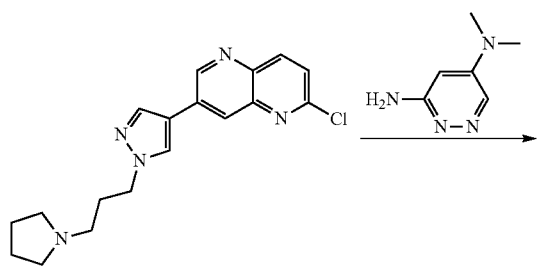

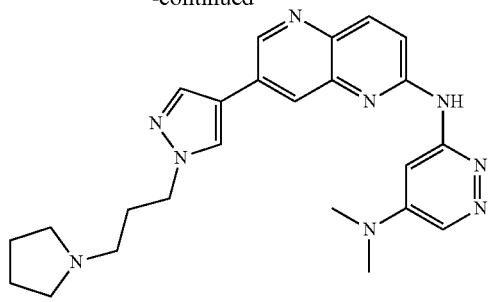

$N^5,N^5$-dimethyl-$N^3$-(7-(1-(3-(pyrrolidin-1-yl)propyl)-1H-pyrazol-4-yl)-1,5-naphthyridin-2-yl)pyridazine-3,5-diamine was obtained as a pale yellow solid in the same manner as in Example 0001-5.

$^1$H-NMR(DMSO-d$_6$)δ:10.29(1H,s),9.00(1H,d,J=2.0 Hz), 8.52(1H,d,J=2.6 Hz),8.49(1H,s),8.18-8.14(3H,m),8.08(1H, d,J=2.6 Hz),7.65(1H,d,J=9.2 Hz),4.21(2H,t,J=6.9 Hz),3.12 (6H,s),2.44-2.37(6H,m),2.04-1.95(2H,m),1.72-1.65(4H,m).

MSm/z(M+H):444.

Example 0404

0404-1

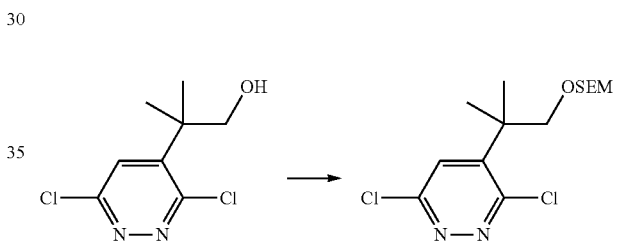

N,N-diisopropylethylamine (300 μL) was added to a solution of 2-(3,6-dichloropyridazin-4-yl)-2-methylpropan-1-ol (150 mg) in dichloromethane (3 mL), and 2-(chloromethoxy)ethyltrimethylsilane (150 μL) was added thereto under ice-cooling, followed by stirring at room temperature for 30 minutes. Water was added to the reaction mixture. The organic layer was collected by separation, and dried over anhydrous sodium sulfate, and the solvent was distilled off under reduced pressure. The obtained residue was purified by silica gel column chromatography (hexane-ethyl acetate), thereby obtaining 3,6-dichloro-4-(2-methyl-1-((2-(trimethylsilyl)ethoxy)methoxy)propan-2-yl)pyridazine (170 mg) as brown oily substance.

MSm/z(M+H):351,353.

0404-2

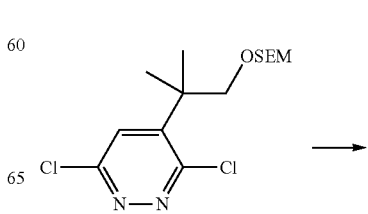

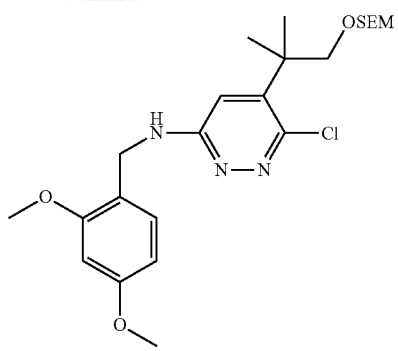

2,4-Dimethoxybenzylamine (200 µL) and 1,8-diazabicyclo[5.4.0]undeca-7-ene (400 µL) were added to a solution of 3,6-dichloro-4-(2-methyl-1-((2-(trimethylsilyl)ethoxy)methoxy)propan-2-yl)pyridazine (170 mg) in 1,4-dioxane (3 mL), followed by stirring at 150° C. for 30 minutes using a microwave reaction apparatus. The reaction mixture was cooled to room temperature, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 6-chloro-N-(2,4-dimethoxybenzyl)-5-(2-methyl-1-((2-(trimethylsilyl)ethoxy)methoxy)propan-2-yl)pyridazine-3-amine (110 mg) as brown oily substance.

MSm/z(M+H):482.

0404-3

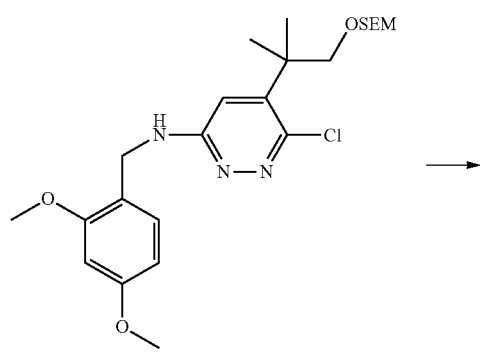

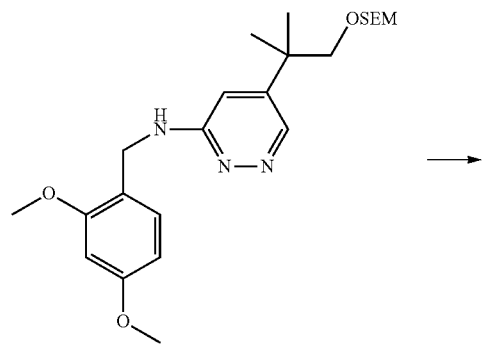

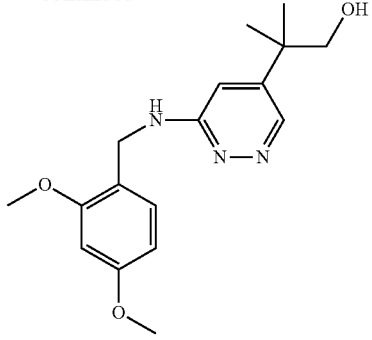

A mixture solution of 6-chloro-N-(2,4-dimethoxybenzyl)-5-(2-methyl-1-((2-(trimethylsilyl)ethoxy)methoxy)propan-2-yl)pyridazine-3-amine (110 mg) in methanol (10 mL)/acetic acid (1 mL) was reacted using a flow-type hydrogenation reaction apparatus (20 bar, 1.0 mL/min, 50° C., 10% Pd/C). The solvent was distilled off under reduced pressure, thereby obtaining N-(2,4-dimethoxybenzyl)-5-(2-methyl-1-((2-(trimethylsilyl)ethoxy)methoxy)propan-2-yl) pyridazine-3-amine as pale yellow oily substance.

A 4 mol/L hydrogen chloride/1,4-dioxane solution (5 mL) was added to the obtained N-(2,4-dimethoxybenzyl)-5-(2-methyl-1-((2-(trimethylsilyl)ethoxy)methoxy)propan-2-yl) pyridazine-3-amine, followed by stirring at room temperature for 30 minutes. The solvent was distilled off under reduced pressure, the obtained residue was neutralized by the addition of a saturated sodium hydrogen carbonate aqueous solution, and ethyl acetate was added thereto. The organic layer was collected by separation, washed with a saturated sodium chloride aqueous solution, and dried over anhydrous sodium sulfate. The obtained solution was purified by silica gel column chromatography (hexane-ethyl acetate), thereby obtaining 2-(6-((2,4-dimethoxybenzyl)amino)pyridazin-4-yl)-2-methylpropan-1-ol (65 mg).

MSm/z(M+H):318.

0404-4

525
-continued

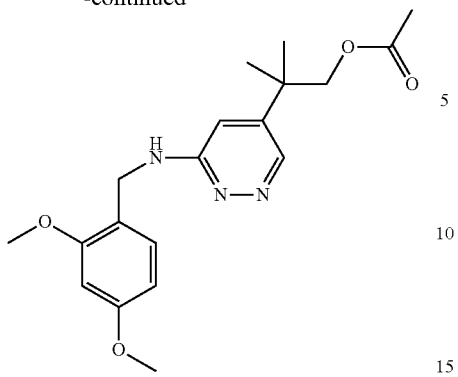

Acetic anhydride (100 μL) was added to a solution of 2-(6-((2,4-dimethoxybenzyl)amino)pyridazin-4-yl)-2-methylpropan-1-ol in acetic acid (500 μL), followed by stirring at room temperature for 30 minutes. The solvent was distilled off under reduced pressure, the obtained residue was neutralized by the addition of a saturated sodium hydrogen carbonate aqueous solution, and ethyl acetate was added thereto. The organic layer was collected by separation, washed with a saturated sodium chloride aqueous solution, and dried over anhydrous sodium sulfate. The obtained solution was purified by silica gel column chromatography (hexane-ethyl acetate), thereby obtaining 2-(6-((2,4-dimethoxybenzyl)amino)pyridazin-4-yl)-2-methylpropyl acetate (60 mg).

MSm/z(M+H):360.

526

0404-5

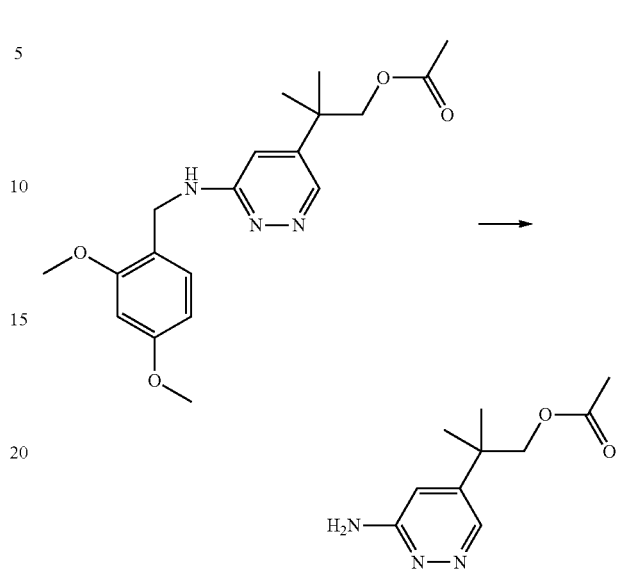

A solution of 2-(6-((2,4-dimethoxybenzyl)amino)pyridazin-4-yl)-2-methylpropyl acetate (60 mg) in trifluoroacetic acid (1 mL) was stirred at room temperature for 30 minutes. The solvent was distilled off under reduced pressure, triethylamine was added to the resultant product, and the solvent was distilled off under reduced pressure. The obtained residue was purified by silica gel column chromatography (hexane-ethyl acetate, NH silica), thereby obtaining 2-(6-aminopyridazin-4-yl)-2-methylpropyl acetate (30 mg).

MSm/z(M+H):210.

0404-6

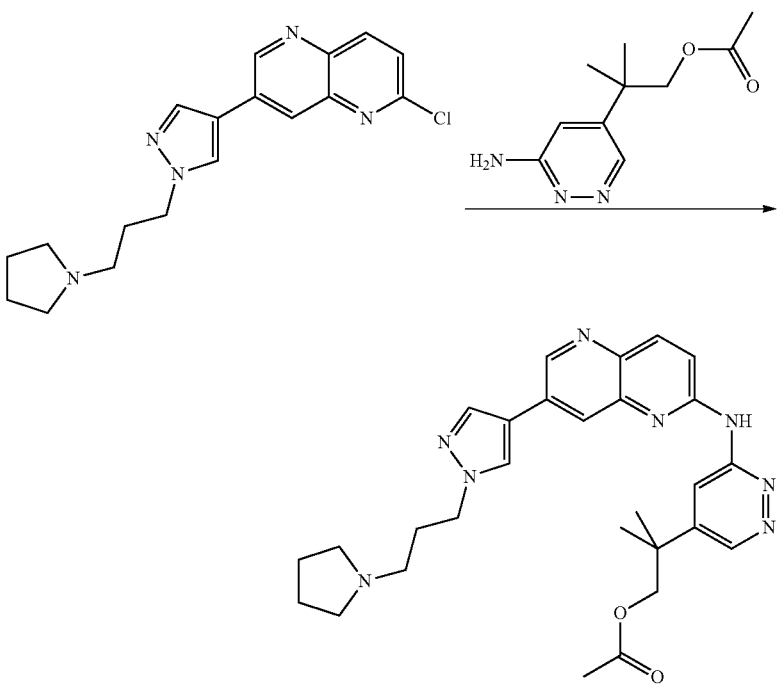

2-Methyl-2-(6-((7-(1-(3-(pyrrolidin-1-yl)propyl)-1H-pyrazol-4-yl)-1,5-naphthyridin-2-yl)amino)pyridazin-4-yl)propyl acetate was obtained as a pale yellow solid in the same manner as in Example 0001-5.

$^1$H-NMR(DMSO-$d_6$)δ:10.75(1H,s),9.05(1H,d,J=2.3 Hz), 9.02(1H,d,J=2.3 Hz),8.89(1H,d,J=2.0 Hz),8.50(1H,s),8.22 (1H,d,J=9.2 Hz),8.19(1H,s),8.12(1H,d,J=1.7 Hz),7.70(1H,d, J=9.2 Hz),4.29(2H,s),4.22(2H,t,J=6.9 Hz),2.45-2.38(6H,m), 2.04-1.96(5H,m),1.72-1.66(4H,m),1.42(6H,s).

MS m/z(M+H):515.

Example 0405

0405-1

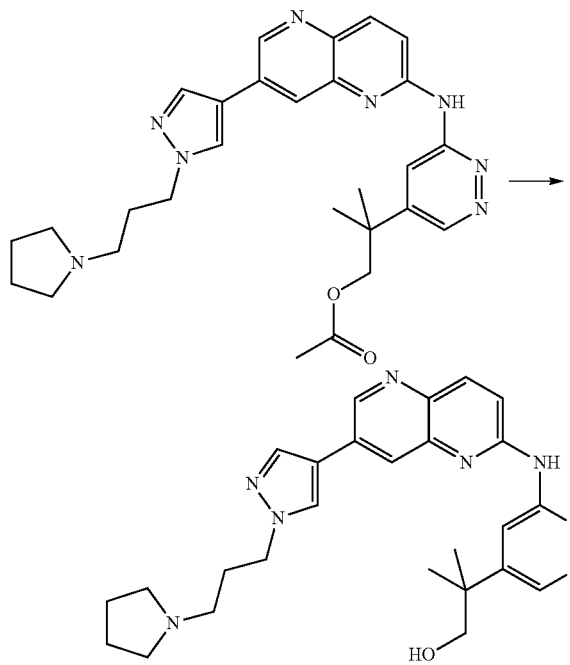

A 2 mol/L sodium hydroxide aqueous solution (500 μL) wa added to a solution of 2-methyl-2-(6-((7-(1-(3-(pyrrolidin-1-yl)propyl)-1H-pyrazol-4-yl)-1,5-naphthyridin-2-yl)amino)pyridazin-4-yl)propyl acetate (8 mg) in methanol (500 μL), followed by stirring at room temperature for 30 minutes. The solvent was distilled off under reduced pressure, the obtained residue was neutralized by the addition of 2 mol/L hydrochloric acid, and ethyl acetate was added thereto. The organic layer was collected by separation, washed with a saturated sodium chloride aqueous solution, and dried over anhydrous sodium sulfate. The obtained solution was purified by silica gel column chromatography (ethyl acetate-methanol, NH silica), thereby obtaining 2-methyl-2-(6-((7-(1-(3-(pyrrolidin-1-yl)propyl)-1H-pyrazol-4-yl)-1,5-naphthyridin-2-yl)amino)pyridazin-4-yl)propan-1-ol (4.7 mg).

$^1$H-NMR(DMSO-$d_6$)δ:10.65(1H,s),9.04(1H,d,J=2.0 Hz), 8.95(1H,d,J=2.0 Hz),8.76(1H,d,J=2.0 Hz),8.49(1H,s),8.22 (1H,d,J=9.2 Hz),8.16(1H,s),8.10(1H,d,J=1.7 Hz),7.76(1H,d, J=9.2 Hz),4.93(1H,t,J=5.3 Hz),4.22(2H,t,J=6.9 Hz),3.56 (2H,d,J=5.3 Hz),2.45-2.38(6H,m),2.04-1.95(2H,m),1.71-1.67(4H,m),1.34(6H,s).

MS m/z(M+H):473.

Examples 0406 to 0408

The following compounds were obtained in the same manner as in Examples 0001-4 and 0001-5.

| Example No. | | |
|---|---|---|
| 0406 | | |
| 0406-1 | 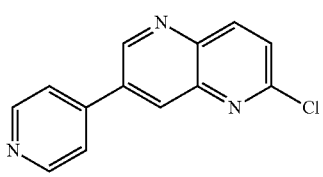 [SMILES: Clc1ccc2ncc(-c3ccncc3)cc2n1] | $^1$H-NMR (DMSO-$d_6$) δ: 9.50 (1H, d, J = 2.0 Hz), 8.86 (1H, d, J = 2.0 Hz), 8.77 (2H, d, J = 5.9 Hz), 8.57 (1H, d, J = 8.6 Hz), 8.03 (2H, d, J = 5.9 Hz), 7.92 (1H, d, J = 8.6 Hz). |
| 0406-2 | 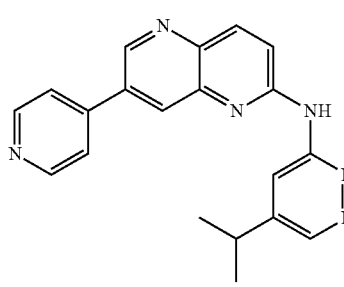 | $^1$H-NMR (DMSO-$d_6$) δ: 10.84 (1H, s), 9.17 (1H, d, J = 2.0 Hz), 8.88 (1H, d, J = 2.0 Hz), 8.79 (1H, s), 8.75 (2H, d, J = 5.9 Hz), 8.50 (1H, s), 8.33 (1H, d, J = 9.2 Hz), 7.98 (2H, d, J = 5.9 Hz), 7.82 (1H, d, J = 9.2 Hz), 3.13-2.98 (1H, m), 1.33 (6H, d, J = 6.6 Hz). MS m/z (M + H): 343. |

-continued

| Example No. | | |
|---|---|---|
| 0407 | | |
| 0407-1 | 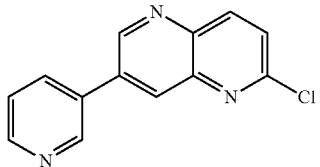 [SMILES: Clc1ccc2ncc(-c3cccnc3)cc2n1] | $^1$H-NMR (DMSO-$d_6$) δ: 9.46 (1H, d, J = 2.6 Hz), 9.19 (1H, d, J = 1.3 Hz), 8.79 (1H, d, J = 2.6 Hz), 8.73-8.69 (1H, m), 8.55 (1H, d, J = 8.6 Hz), 8.43-8.38 (1H, m), 7.89 (1H, d, J = 8.6 Hz), 7.65-7.58 (1H, m). |
| 0407-2 | 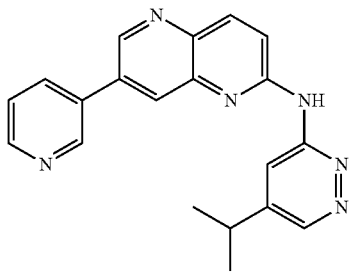 [SMILES: CC(C)c1cnnc(Nc2ccc3ncc(-c4cccnc4)cc3n2)c1] | $^1$H-NMR (DMSO-$d_6$) δ: 10.82 (1H, s), 9.16-9.11 (2H, m), 8.88 (1H, d, J = 2.0 Hz), 8.79 (1H, d, J = 2.0 Hz), 8.71-8.67 (1H, m), 8.46 (1H, d, J = 2.0 Hz), 8.38-8.29 (2H, m), 7.80 (1H, d, J = 9.2 Hz), 7.63-7.57 (1H, m), 3.12-2.97 (1H, m), 1.32 (6H, d, J = 6.6 Hz). MS m/z (M + H): 343. |
| 0408 | | |
| 0408-1 | 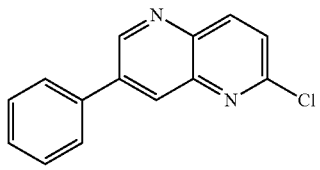 [SMILES: Clc1ccc2ncc(-c3ccccc3)cc2n1] | $^1$H-NMR (DMSO-$d_6$) δ: 9.42 (1H, d, J = 2.0 Hz), 8.65 (1H, d, J = 2.0 Hz), 8.53 (1H, d, J = 9.2 Hz), 8.00-7.95 (2H, m), 7.86 (1H, d, J = 9.2 Hz), 7.63-7.48 (3H, m). |
| 0408-2 | 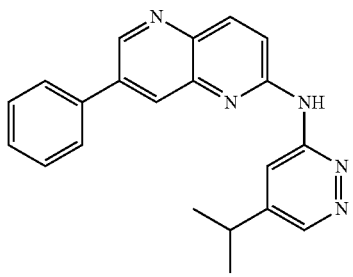 [SMILES: CC(C)c1cnnc(Nc2ccc3ncc(-c4ccccc4)cc3n2)c1] | $^1$H-NMR (DMSO-$d_6$) δ: 12.80 (1H, s), 11.10 (1H, d, J = 2.6 Hz), 10.89 (1H, d, J = 2.0 Hz), 10.81 (1H, d, J = 2.0 Hz), 10.37-10.29 (2H, m), 9.96-9.90 (2H, m), 9.80 (1H, d, J = 9.2 Hz), 9.64-9.47 (3H, m), 5.12-4.99 (1H, m), 3.34 (6H, d, J = 6.6 Hz). MS m/z (M + H): 342. |

Example 0409

0409-1

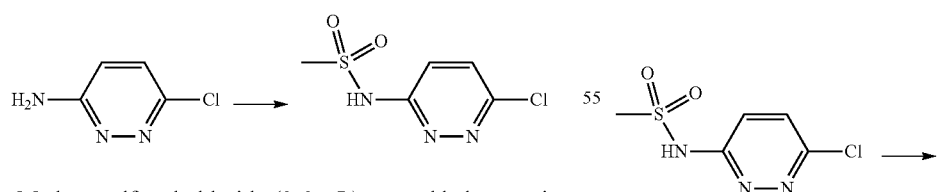

Methanesulfonyl chloride (0.6 mL) was added to a mixture of 6-chloropyridazine-3-amine (500 mg) and pyridine (5 mL) at a temperature of from 0° C. to 5° C., followed by stirring at a temperature of from 0° C. to 5° C. for 15 minutes, and stirring at 40° C. for 30 minutes. Methanesulfonyl chloride (0.1 mL) was added to the reaction mixture, followed by stirring at 40° C. for 30 minutes. The solvent was distilled off under reduced pressure, and the obtained residue was purified by silica gel column chromatography (methanol-chloroform), thereby obtaining N-(6-chloropyridazin-3-yl)methane sulfonamide (257 mg).

MSm/z(M+H):208.

0409-2

A mixture of N-(6-chloropyridazin-3-yl)methane sulfonamide (150 mg) and 48% hydrobromic acid (5 mL) was stirred at 80° C. for 8.5 hours. The reaction mixture was cooled to room temperature, followed by allowing to stand overnight, and stirring at 100° C. for 1 hour. The reaction mixture was cooled to room temperature, and the solvent was distilled off under reduced pressure. After the obtained residue was neutralized by the addition of a 1 mol/L sodium hydroxide aqueous solution, chloroform and methanol were added thereto, the insolubles were filtered off, and the solvent was distilled off under reduced pressure. The obtained residue was purified by silica gel column chromatography (hexane-ethyl acetate), thereby obtaining N-(6-bromopyridazin-3-yl)methane sulfonamide (95 mg).

MSm/z(M+H):254.

0409-3 and 0409-4

The following compounds were obtained in the same manner as in Examples 0403-2 and 0015-4.

| Example No. | | |
|---|---|---|
| 0409 | | |
| 0409-3 | 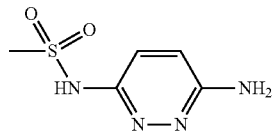 | MS m/z (M + H): 189. |
| 0409-4 | 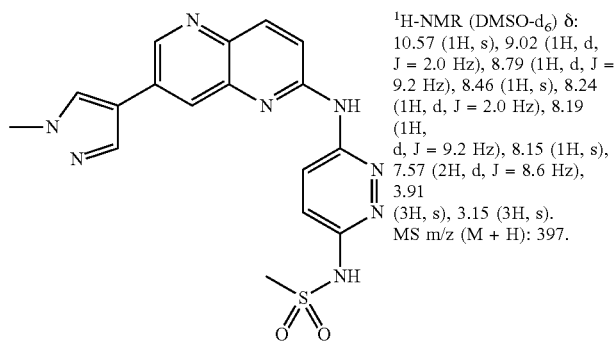 | ¹H-NMR (DMSO-d₆) δ: 10.57 (1H, s), 9.02 (1H, d, J = 2.0 Hz), 8.79 (1H, d, J = 9.2 Hz), 8.46 (1H, s), 8.24 (1H, d, J = 2.0 Hz), 8.19 (1H, d, J = 9.2 Hz), 8.15 (1H, s), 7.57 (2H, d, J = 8.6 Hz), 3.91 (3H, s), 3.15 (3H, s). MS m/z (M + H): 397. |

Example 0410

The following compounds were obtained in the same manner as in Examples 0004-3 and 0015-4.

| Example No. | | |
|---|---|---|
| 0410 | | |
| 0410-1 | 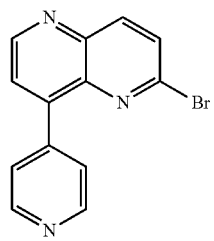 [SMILES: Brc1ccc2nccc(-c3ccncc3)c2n1] | MS m/z (M + H): 286. |
| 0410-2 | 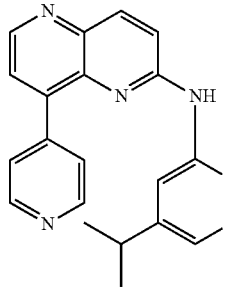 | ¹H-NMR (DMSO-d₆) δ: 10.80 (1H, s), 8.82 (1H, d, J = 4.6 Hz), 8.79 (1H, d, J = 2.0 Hz), 8.74-8.73 (2H, m), 8.34 (1H, d, J = 8.6 Hz), 8.25 (1H, d, J = 2.0 Hz), 7.74-7.71 (3H, m), 7.66 (1H, d, J = 4.6 Hz), 1.01 (6H, d, J = 7.3 Hz). MS m/z (M + H): 343. |

Example 0411

0411-1

Triethylamine (1 mL) was added to a solution of (6-methylpyridin-2-yl)methanol (302 mg) in tetrahydrofuran (5.8 mL) at room temperature, and methanesulfonyl chloride (0.28 mL) was added thereto at a temperature of from 0° C. to 5° C., followed by stirring at room temperature for 2 hours. The insolubles were filtered off using celite, and the solvent was distilled off under reduced pressure, thereby obtaining (6-methylpyridin-2-yl)methyl methanesulfonate (555 mg) as brown oily substance.

MSm/z(M+H):202.

0411-2

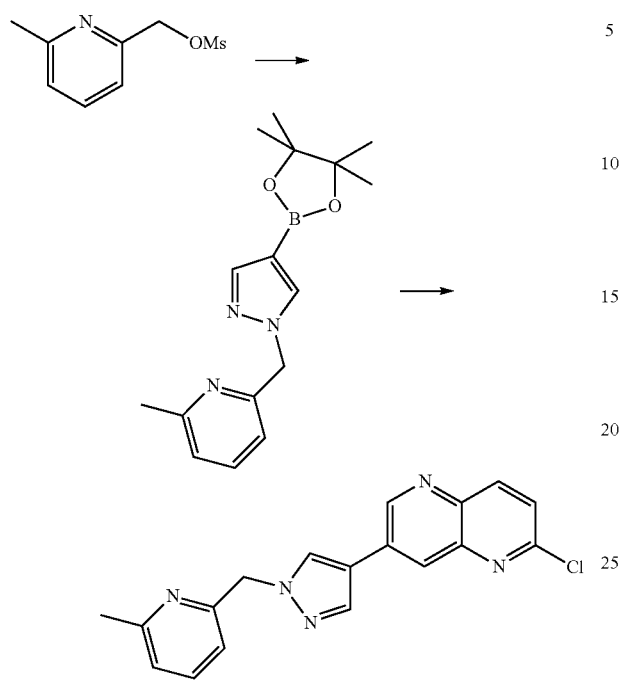

4-(4,4,5,5-Tetramethyl-1,3,2-dioxaborolan-2-yl)-1H-pyrazole (195 mg) and potassium carbonate (275 mg) were added to a solution of (6-methylpyridin-2-yl)methyl methanesulfonate (408 mg) in acetonitrile (2 mL), followed by stirring at 80° C. for 4.5 hours. The resultant product was allowed to stand for 16 hours, followed by stirring at 80° C. for 6 hours. The reaction mixture was cooled to room temperature, the insolubles were filtered off, and the solvent was distilled off under reduced pressure, thereby obtaining brown oily substance (385 mg). A mixture of the obtained brown oily substance (167 mg), 7-bromo-2-chloro-1,5-naphthyridine (50 mg), sodium carbonate (43 mg), bis(di-tert-butyl(4-dimethylaminophenyl)phosphine)dichloropalladium(II) (14 mg), 1,4-dioxane (2.1 mL), and water (0.21 mL) was stirred at 100° C. for 1 hour in a nitrogen atmosphere. The reaction mixture was cooled to room temperature, the insolubles were filtered off, and the solvent was distilled off under reduced pressure. The obtained residue was purified by silica gel column chromatography (ethyl acetate-hexane), thereby obtaining 2-chloro-7-(1-((6-methylpyridin-2-yl)methyl)-1H-pyrazol-4-yl)-1,5-naphthyridine (73 mg) as a pale yellow solid.
MSm/z(M+H):336.

0411-3

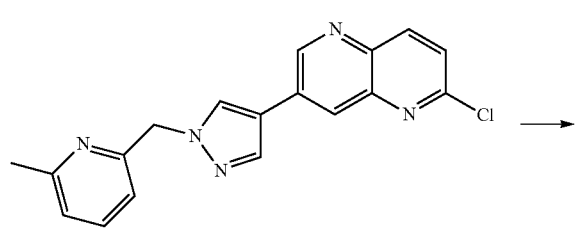

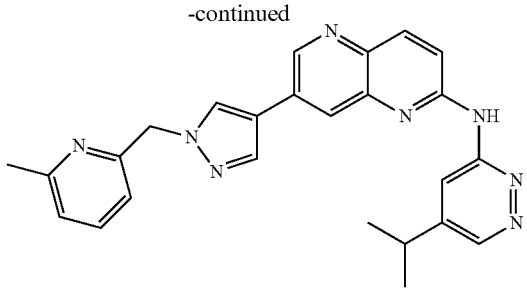

N-(5-isopropylpyridazin-3-yl)-7-(1-((6-methylpyridin-2-yl)methyl)-1H-pyrazol-4-yl)-1,5-naphthyridine-2-amine (12.1 mg) was obtained as a yellow solid in the same manner as in Example 0015-4.
$^1$H-NMR(CDCl$_3$)δ:8.94(1H,d,J=2.0 Hz),8.81(2H,s),8.24(1H,d,J=9.2 Hz),8.12(1H,d,J=2.0 Hz),8.03(2H,d,J=1.3 Hz),7.60(1H,d,J=2.0 Hz),7.56(1H,d,J=7.9 Hz),7.43(1H,d,J=8.6 Hz),7.11(1H,d,J=7.9 Hz),6.95(1H,d,J=7.9 Hz),5.50(2H,s),3.06-3.02(1H,m),2.58(3H,s),1.41(6H,d,J=7.3 Hz).
MSm/z(M+H):437.

Example 0412

0412-1

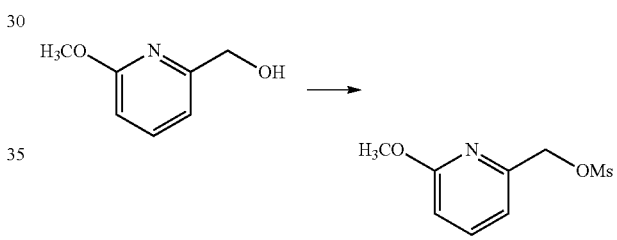

(6-Methoxypyridin-2-yl)methyl methanesulfonate was obtained as brown oily substance in the same manner as in Example 0411-1.
MSm/z(M+H):218.

0412-2

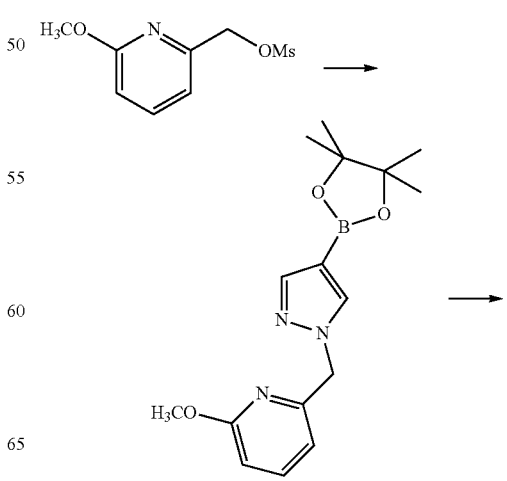

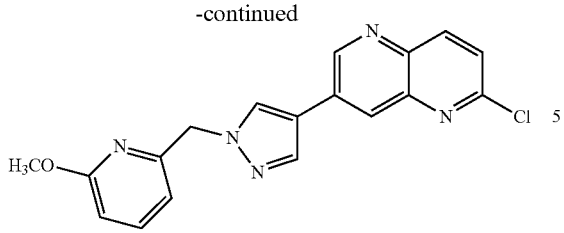

4-(4,4,5,5-Tetramethyl-1,3,2-dioxaborolan-2-yl)-1H-pyrazole (194 mg) and potassium carbonate (275 mg) were added to a solution of (6-methoxypyridin-2-yl)methyl methanesulfonate (432 mg) in acetonitrile (4 mL), followed by stirring at 80° C. for 17.5 hours. The reaction mixture was cooled to room temperature, the insolubles were filtered off, and the solvent was distilled off under reduced pressure, thereby obtaining brown oily substance (366 mg).

A mixture of the obtained brown oily substance (157 mg), 7-bromo-2-chloro-1,5-naphthyridine (50 mg), sodium carbonate (44 mg), bis(di-tert-butyl(4-dimethylaminophenyl)phosphine)dichloropalladium(II) (16 mg), 1,4-dioxane (2.1 mL), and water (0.21 mL) was stirred at 100° C. for 1 hour in a nitrogen atmosphere. The reaction mixture was cooled to room temperature, the insolubles were filtered off, and the solvent was distilled off under reduced pressure. The obtained solid matter was suspended in methanol-ethyl acetate-hexane, and the solid matter was collected by filtration, thereby obtaining 2-chloro-7-(1-(((6-methoxypyridin-2-yl)methyl)-1H-pyrazol-4-yl)-1,5-naphthyridine (43 mg) as a pale yellow solid.

MSm/z(M+H):352.

0412-3

N-(5-isopropylpyridazin-3-yl)-7-(1-(((6-methoxypyridin-2-yl)methyl)-1H-pyrazol-4-yl)-1,5-naphthyridine-2-amine was obtained as a yellow solid in the same manner as in Example 0015-4.

$^1$H-NMR(CDCl$_3$)δ:8.95(1H,d,J=2.0 Hz),8.81-8.80(2H,m),8.24(1H,d,J=9.2 Hz),8.12(1H,d,J=2.0 Hz),8.04(2H,d,J=13.2 Hz),7.61-7.43(1H,m),6.73-6.69(3H,m),5.42(2H,s),3.93(3H,s),3.06-3.04(1H,m),1.41(6H,d,J=7.3 Hz).

MSm/z(M+H):453.

Example 0413

0413-1

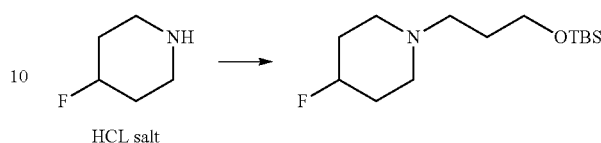

60% sodium hydride (211 mg) was added to a mixture of 4-fluoropiperidine hydrochloride (281 mg) and tetrahydrofuran (4 mL) under ice-cooling, followed by stirring at room temperature for 30 minutes. The reaction mixture was cooled by ice, and (3-bromopropoxy)(tert-butyl)dimethylsilane (0.7 mL) was added thereto, followed by stirring at room temperature for 42 hours. After the reaction mixture was cooled by ice, a saturated sodium hydrogen carbonate aqueous solution, water, and ethyl acetate were added thereto, and the organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate, NH silica), thereby obtaining 1-(3-((tert-butyldimethylsilyl)oxy)propyl)-4-fluoropiperidine (473 mg) as colorless oily substance.

$^1$H-NMR(CDCl$_3$)δ:3.69(2H,t,J=5.6 Hz),3.60(1H,t,J=6.3 Hz),3.47(2H,t,J=6.3 Hz),2.53-2.51(2H,m),2.37-2.31(2H,m),1.99(2H,t,J=5.9 Hz),1.82-1.80(2H,m),1.70-1.61(2H,m),0.85(9H,s),0.02(6H,s).

0413-2

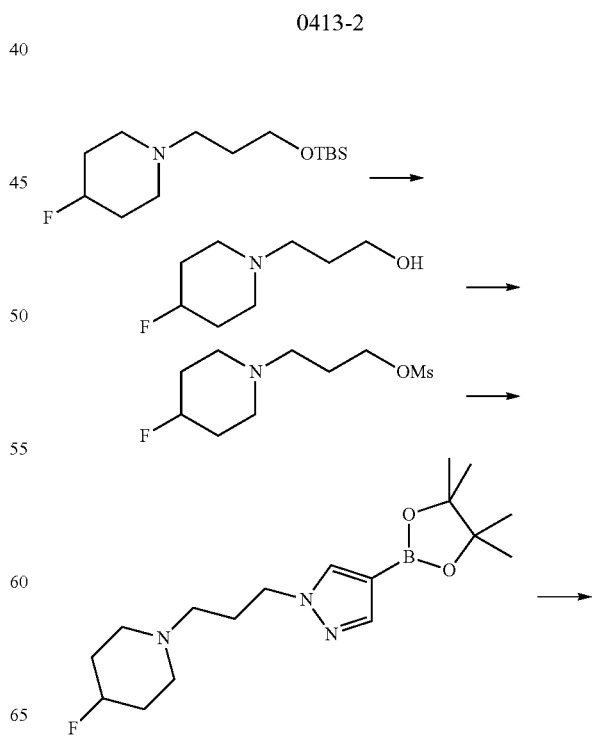

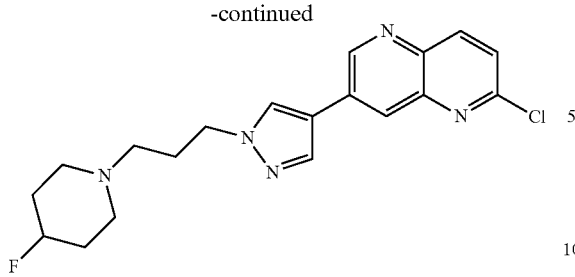

A 4 mol/L hydrogen chloride/1,4-dioxane solution (1 mL) was added to a mixture of 1-(3-((tert-butyldimethylsilyl)oxy)propyl)-4-fluoropiperidine (473 mg), and methanol (1 mL) at 0° C. The reaction mixture was heated to room temperature, followed by stirring for 30 minutes. The solvent was distilled off under reduced pressure, and methanol and a saturated sodium hydrogen carbonate aqueous solution were added to the obtained oily substance, followed by stirring at room temperature for 5 minutes. The solvent was distilled off under reduced pressure, methanesulfonyl chloride (0.2 mL) was added to a mixture of the obtained residue, tetrahydrofuran (4.1 mL), and triethylamine (0.72 mL), followed by stirring at room temperature for 3.5 hours. The insolubles were filtered off, and the solvent was distilled off under reduced pressure. 4-(4,4,5,5-tetramethyl-1,3,2-dioxaborolan-2-yl)-1H-pyrazole (196 mg) and potassium carbonate (281 mg) were added to a solution of the obtained residue in acetonitrile (4 mL), followed by stirring at 80° C. for 17.5 hours. The reaction mixture was cooled to room temperature, the insolubles were filtered off, and the solvent was distilled off under reduced pressure. A mixture of the obtained residue, 7-bromo-2-chloro-1,5-naphthyridine (74.5 mg), sodium carbonate (65.7 mg), bis(di-tert-butyl(4-dimethylaminophenyl)phosphine)dichloropalladium(II) (22.8 mg), 1,4-dioxane (3 mL), and water (0.3 mL) was stirred at 80° C. for 1 hour in a nitrogen atmosphere. The reaction mixture was cooled to room temperature, the insolubles were filtered off, and the solvent was distilled off under reduced pressure. The obtained residue was purified by silica gel column chromatography (hexane-ethyl acetate, NH silica), thereby obtaining 2-chloro-7-(1-(3-(4-fluoropiperidin-1-yl)propyl)-1H-pyrazol-4-yl)-1,5-naphthyridine (72 mg) as yellow oily substance.

MSm/z(M+H):374.

0413-3

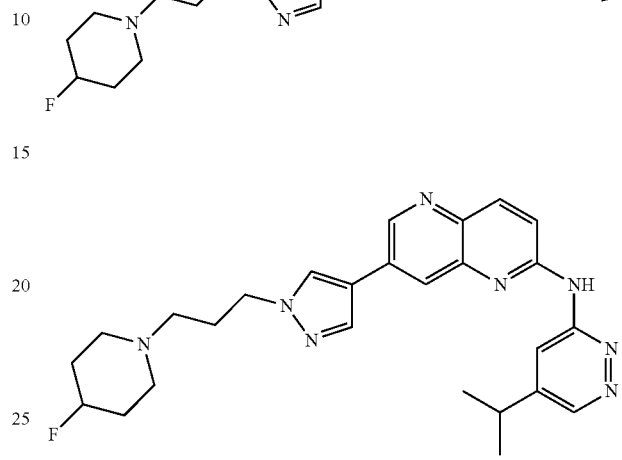

7-(1-(3-(4-Fluoropiperidin-1-yl)propyl)-1H-pyrazol-4-yl)-N-(5-isopropylpyridazin-3-yl)-1,5-naphthyridine-2-amine was obtained as a pale yellow solid in the same manner as in Example 0015-4.

$^1$H-NMR(CDCl$_3$)δ:8.93(1H,d,J=2.0 Hz),8.84-8.81(2H,m),8.24(1H,d,J=8.6 Hz),8.10(1H,d,J=2.0 Hz),7.97(1H,s),7.86(1H,s),7.67-7.38(1H,m),4.76-4.60(1H,m),4.29(2H,t,J=6.9 Hz),3.07-3.05(1H,m),2.58-2.56(2H,m),2.38-2.36(4H,m),2.14-2.12(2H,m),1.93-1.87(4H,m),1.42(6H,d,J=6.6 Hz).

MSm/z(M+H):475.

Example 0414

The following compounds were obtained in the same manner as in Examples 0411-1, 0412-2, and 0015-4

| Example No. | | |
|---|---|---|
| 0414 | | |
| 0414-1 | 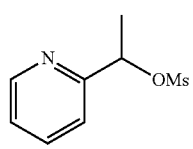 | MS m/z (M + H): 202. |

| Example No. | | |
|---|---|---|
| 0414-2 | 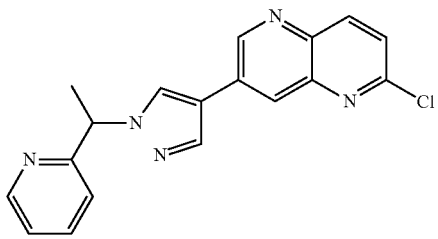 [SMILES: CC(N/C=C(\C=N)c1cnc2ccc(Cl)nc2c1)c1ccccn1] | MS m/z (M + H): 336. |
| 0414-3 | | ¹H-NMR (CDCl₃) δ: 8.94 (1H, d, J = 2.0 Hz), 8.81 (2H, s), 8.63-8.61 (1H, m), 8.24 (1H, d, J = 9.2 Hz), 8.12 (1H, d, J = 1.3 Hz), 8.08 (1H, s), 8.01 (1H, s), 7.70-7.68 (1H, m), 7.46 (1H, d, J = 8.6 Hz), 7.21-7.18 (2H, m), 5.73-5.71 (1H, m), 3.07-3.05 (1H, m), 2.05 (3H, d, J = 3.6 Hz), 1.42 (6H, d, J = 6.6 Hz). MS m/z (M + H): 437. |

Example 0415

0415-1

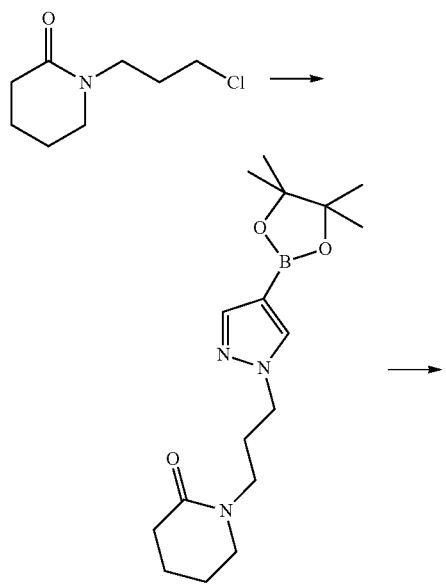

Sodium iodide (33 mg), cesium carbonate (701 mg), and 4-(4,4,5,5-tetramethyl-1,3,2-dioxaborolan-2-yl)-1H-pyrazole (231 mg) were added to a solution of 1-(3-chloropropyl)piperidin-2-one (189 mg) in 1,4-dioxane (3.6 mL), followed by stirring at 80° C. for 16 hours. The reaction mixture was cooled to room temperature, the insolubles were filtered off, and the solvent was distilled off under reduced pressure, thereby obtaining brown oily substance (376 mg).

A mixture of the obtained brown oily substance (155 mg), 7-bromo-2-chloro-1,5-naphthyridine (76 mg), sodium carbonate (65 mg), bis(di-tert-butyl(4-dimethylaminophenyl)phosphine)dichloropalladium(II) (23 mg), 1,4-dioxane (3.1 mL), and water (0.31 mL) was stirred at 100° C. for 1.5 hours in a nitrogen atmosphere. The reaction mixture was cooled to room temperature, the insolubles were filtered off, and the solvent was distilled off under reduced pressure. The obtained residue was purified by silica gel column chromatography (hexane-ethyl acetate-methanol, NH silica), thereby obtaining 1-(3-(4-(6-chloro-1,5-naphthyridin-3-yl)-1H-pyrazol-1-yl)propyl)piperidin-2-one (24 mg) as a pale yellow solid.

MSm/z(M+H):370.

0415-2

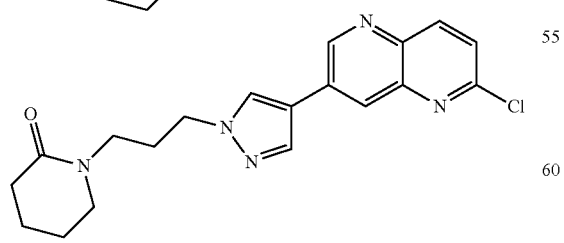

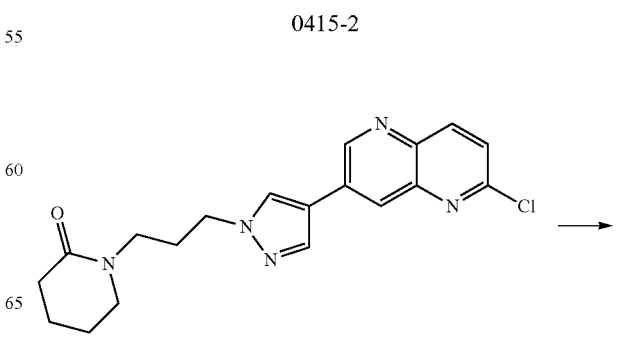

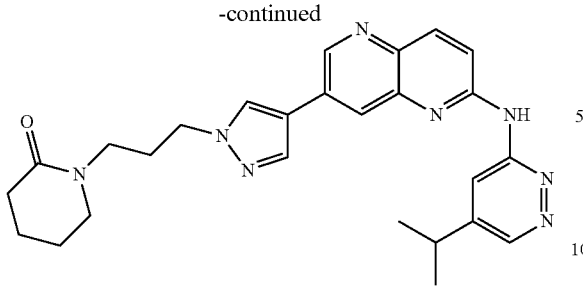

1-(3-(4-(6-((5-Isopropylpyridazin-3-yl)amino)-1,5-naphthyridin-3-yl)-1H-pyrazol-1-yl)propyl)piperidin-2-one was obtained as a yellow solid in the same manner as in Example 0015-4.

$^1$H-NMR(CDCl$_3$)δ:9.05(1H,brs),8.94(1H,d,J=1.3 Hz), 8.85(2H,d,J=17.2 Hz),8.24(1H,d,J=9.2 Hz),8.11(1H,d,J=1.3 Hz),7.97(2H,d,J=1.3 Hz),7.57(1H,d,J=9.2 Hz),4.27(2H,t, J=6.6 Hz),3.49(2H,t,J=6.6 Hz),3.27(2H,t,J=5.3 Hz),3.08-3.04(1H,m),2.35(2H,t,J=5.9 Hz),2.25-2.21(2H,m),1.78-1.74 (4H,m),1.43(6H,d,J=6.6 Hz).

MSm/z(M+H):471.

Example 0416

The following compounds were obtained in the same manner as in Examples 0415-1 and 0015-4.

Example 0417

0417-1

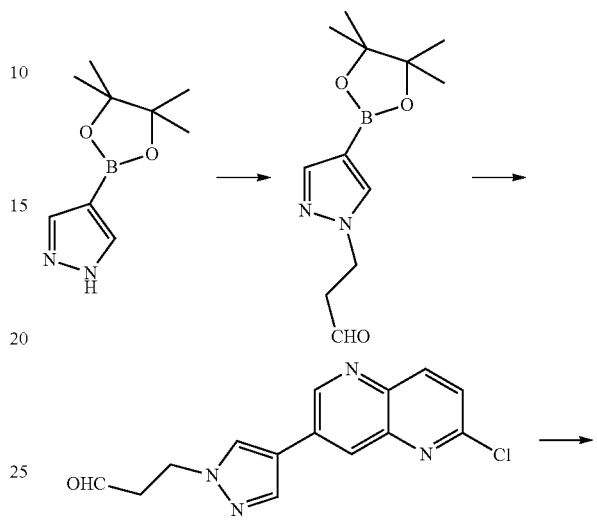

| Example No. | | |
|---|---|---|
| 0416 | | |
| 0416-1 | 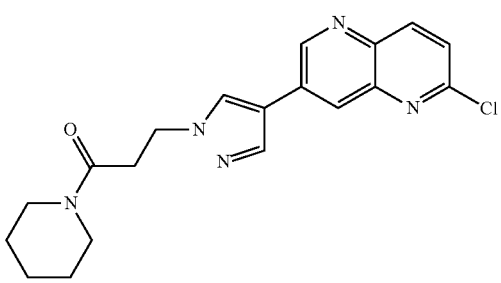 [SMILES: N=C/C(=C\NCCC(=O)N1CCCCC1)c1cnc2ccc(Cl)nc2c1] | MS m/z (M + H): 370. |
| 0416-2 | 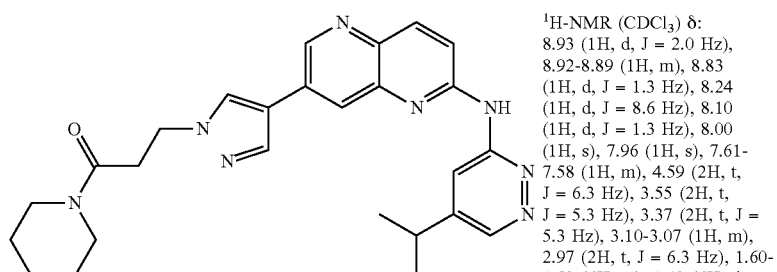 | $^1$H-NMR (CDCl$_3$) δ: 8.93 (1H, d, J = 2.0 Hz), 8.92-8.89 (1H, m), 8.83 (1H, d, J = 1.3 Hz), 8.24 (1H, d, J = 8.6 Hz), 8.10 (1H, d, J = 1.3 Hz), 8.00 (1H, s), 7.96 (1H, s), 7.61-7.58 (1H, m), 4.59 (2H, t, J = 6.3 Hz), 3.55 (2H, t, J = 5.3 Hz), 3.37 (2H, t, J = 5.3 Hz), 3.10-3.07 (1H, m), 2.97 (2H, t, J = 6.3 Hz), 1.60-1.53 (6H, m), 1.43 (6H, d, J = 7.3 Hz). MS m/z (M + H): 471. |

543
-continued

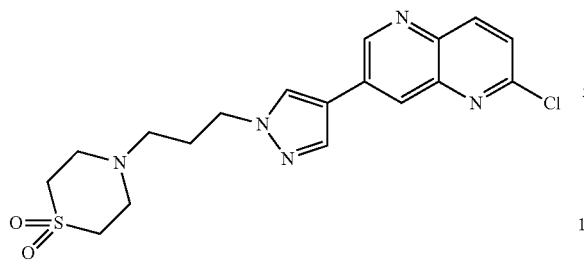

Hafnium chloride (IV) (82 mg) and acrolein (0.41 mL) were added to a solution of 4-(4,4,5,5-tetramethyl-1,3,2-dioxaborolan-2-yl)-1H-pyrazole (500 mg) in dichloromethane (13 mL), followed by stirring at room temperature for 5 hours. After water and ethyl acetate were added to the reaction mixture, the organic layer was collected by separation, washed with a saturated sodium chloride aqueous solution, and dried over anhydrous sodium sulfate, and the solvent was distilled off under reduced pressure, thereby obtaining pale yellow oily substance (359 mg).

A mixture of the obtained pale yellow oily substance (77 mg), 7-bromo-2-chloro-1,5-naphthyridine (51 mg), sodium carbonate (43 mg), bis(di-tert-butyl(4-dimethylaminophenyl)phosphine)dichloropalladium(II) (15 mg), 1,4-dioxane (2.1 mL), and water (0.21 mL) was stirred at 100° C. for 1.5 hours in a nitrogen atmosphere. The reaction mixture was cooled to room temperature, the insolubles were filtered off, and the solvent was distilled off under reduced pressure, thereby obtaining a yellow solid (117 mg).

Thiomorpholine 1,1-dioxide (47 mg) and acetic acid (0.5 mL) were added to a solution of the obtained yellow solid (58 mg) in dichloromethane (1.5 mL), followed by stirring at room temperature for 1 hour in a nitrogen atmosphere. Sodium triacetoxyborohydride (218 mg) was added to the reaction mixture, followed by stirring at room temperature for 1 hour. After water and ethyl acetate were added to the reaction mixture, the organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-methanol, NH silica), thereby obtaining 4-(3-(4-(6-chloro-1,5-naphthyridin-3-yl)-1H-pyrazol-1-yl)propyl)thiomorpholine 1,1-dioxide (13 mg).

MSm/z(M+H):406.

0417-2

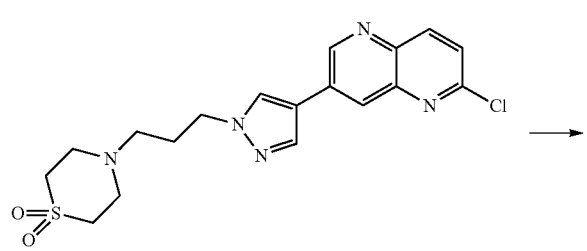

544
-continued

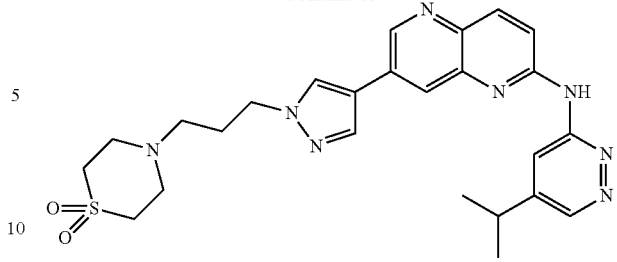

4-(3-(4-(6-((5-isopropylpyridazin-3-yl)amino)-1,5-naphthyridin-3-yl)-1H-pyrazol-1-yl)propyl)thiomorpholine 1,1-dioxide was obtained as a white solid in the same manner as in Example 0015-4.

$^1$H-NMR(DMSO-d$_6$)δ:10.70(1H,s),9.05(1H,d,J=2.0 Hz), 8.86(1H,d,J=2.0 Hz),8.72(1H,s),8.53(1H,s),8.22-8.21(3H, m),7.70(1H,d,J=9.2 Hz),4.23(2H,t,J=6.6 Hz),3.11-3.09(4H, m),3.03(1H,t,J=6.9 Hz),2.88-2.87(4H,m),2.46-2.44(2H,m), 2.01-1.99(2H,m),1.33(6H,d,J=7.3 Hz).

MSm/z(M+H):507.

Example 0418

0418-1

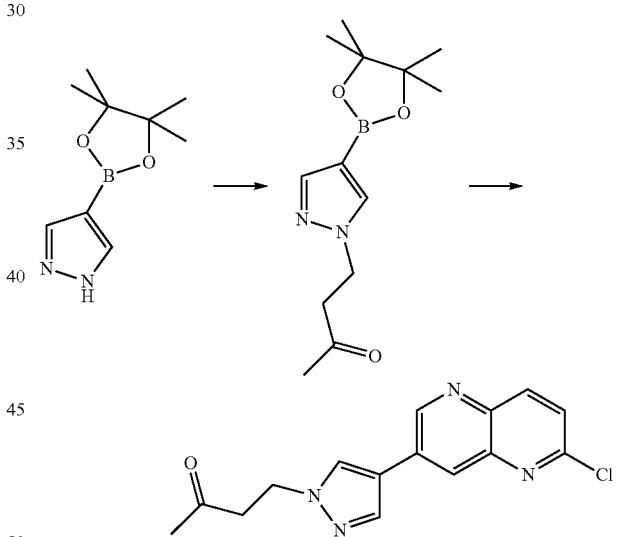

Hafnium chloride (IV) (49 mg) and methyl vinyl ketone (0.29 mL) were added to a solution of 4-(4,4,5,5-tetramethyl-1,3,2-dioxaborolan-2-yl)-1H-pyrazole (290 mg) in dichloromethane (7.5 mL), followed by stirring at room temperature for 5 hours. After water and ethyl acetate were added to the reaction mixture, the organic layer was collected by separation, washed with a saturated sodium chloride aqueous solution, and dried over anhydrous sodium sulfate, and the solvent was distilled off under reduced pressure, thereby obtaining brown oily substance (316 mg).

A mixture of the obtained brown oily substance (84 mg), 7-bromo-2-chloro-1,5-naphthyridine (51 mg), sodium carbonate (44 mg), bis(di-tert-butyl(4-dimethylaminophenyl) phosphine)dichloropalladium(II) (15 mg), 1,4-dioxane (2.1 mL), and water (0.21 mL) was stirred at 100° C. for 4 hours in a nitrogen atmosphere. The reaction mixture was cooled to room temperature, and purified by silica gel column chromatography (hexane-ethyl acetate-methanol, NH silica), thereby obtaining 4-(4-(6-chloro-1,5-naphthyridin-3-yl)-1H-pyrazol-1-yl)butan-2-one (48 mg) as a pale yellow solid.

MSm/z(M+H):301.

0418-2

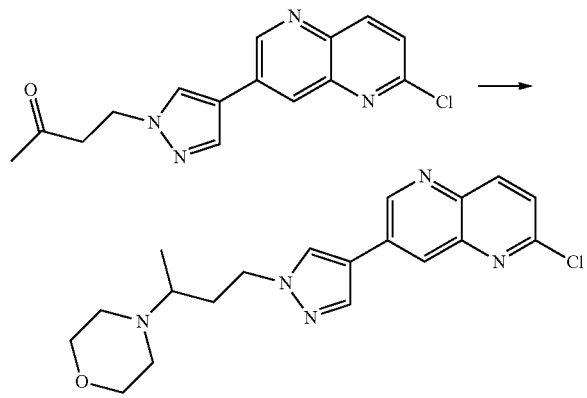

Morpholine (0.02 mL) and acetic acid (0.1 mL) were added to a solution of 4-(4-(6-chloro-1,5-naphthyridin-3-yl)-1H-pyrazol-1-yl)butan-2-one (24 mg) in dichloromethane (1 mL), followed by stirring at room temperature for 1 hour in a nitrogen atmosphere. Sodium triacetoxyborohydride (168 mg) was added to the reaction mixture, followed by stirring at room temperature for 1 hour. Morpholine (0.1 mL) was added to the reaction mixture, followed by stirring at room temperature for 1 hour. Morpholine (0.2 mL) was added to the reaction mixture, followed by stirring at room temperature for 1.5 hours. Morpholine (0.2 mL), sodium triacetoxyborohydride (89 mg), and acetic acid (0.5 mL) were added to the reaction mixture, followed by stirring at room temperature for 30 minutes. After water and ethyl acetate were added to the reaction mixture, the organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate-methanol, NH silica), thereby obtaining 4-(4-(4-(6-chloro-1,5-naphthyridin-3-yl)-1H-pyrazol-1-yl)butan-2-yl)morpholine (12 mg) as colorless oily substance.

MSm/z(M+H):372.

0418-3

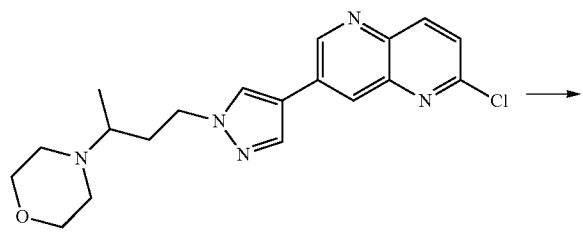

-continued

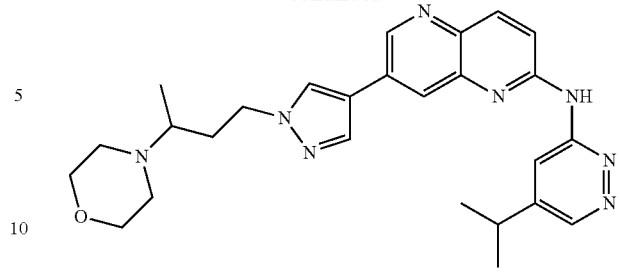

N-(5-isopropylpyridazin-3-yl)-7-(1-(3-morpholinobutyl)-1H-pyrazol-4-yl)-1,5-naphthyridine-2-amine was obtained as a yellow solid in the same manner as in Example 0015-4.

$^1$H-NMR(DMSO-$d_6$)δ:10.70(1H,s),9.04(1H,d,J=2.0 Hz), 8.87(1H,d,J=2.0 Hz),8.73(1H,d,J=2.0 Hz),8.50(1H,s),8.22-8.19(3H,m),7.70(1H,d,J=9.2 Hz),4.24-4.21(2H,m),3.62-3.57(4H,m),3.03(1H,t,J=6.9 Hz),2.75-2.72(1H,m),2.33-2.30 (2H,m),2.00-1.99(1H,m),1.86-1.83(1H,m),1.33(6H,d,J=7.3 Hz),1.23(2H,s),1.17(3H,d,J=7.3 Hz).

MSm/z(M+H):473.

Example 0419

0419-1

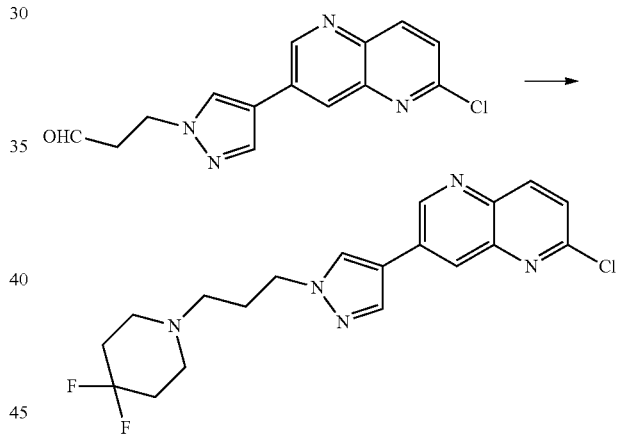

Triethylamine (0.07 mL) was added to a mixture of 4,4-difluoropiperidine hydrochloride (133 mg) and dichloromethane (0.5 mL), followed by stirring at room temperature for 10 minutes. 3-(4-(6-Chloro-1,5-naphthyridin-3-yl)-1H-pyrazol-1-yl)propanal (50 mg), dichloromethane (2 mL), and acetic acid (0.5 mL) were added to the reaction mixture, followed by stirring at room temperature for 30 minutes. Sodium triacetoxyborohydride (370 mg) was added to the reaction mixture, followed by stirring at room temperature for 1 hour. Methanol and acetone were added to the reaction mixture, and the solvent was distilled off under reduced pressure. Ethyl acetate and hexane were added to the obtained residue, the insolubles were filtered off, and the solvent was distilled off under reduced pressure. The obtained residue was purified by silica gel column chromatography (hexane-ethyl acetate-methanol, NH silica), thereby obtaining 2-chloro-7-(1-(3-(4,4-difluoropiperidin-1-yl)propyl)-1H-pyrazol-4-yl)-1,5-naphthyridine (14 mg) as a pale yellow solid.

MSm/z(M+H):392.

0419-2

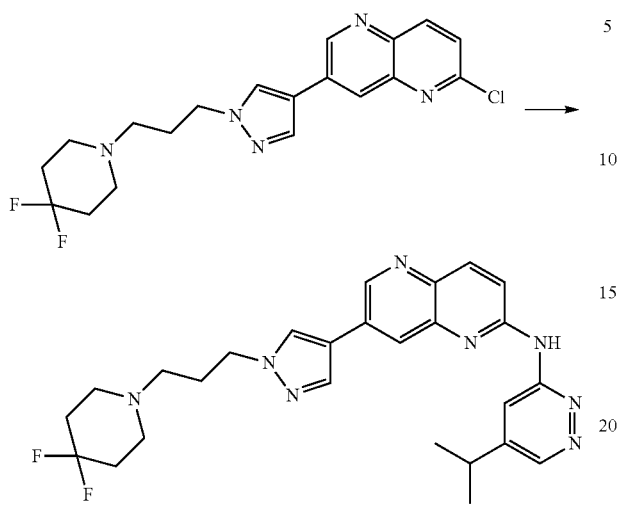

7-(1-(3-(4,4-Difluoropiperidin-1-yl)propyl)-1H-pyrazol-4-yl)-N-(5-isopropylpyridazin-3-yl)-1,5-naphthyridine-2-amine was obtained as a pale yellow solid in the same manner as in Example 0015-4.

$^1$H-NMR(CDCl$_3$)δ:8.93(1H,d,J=2.0 Hz),8.84-8.82(2H,m),8.25(1H,d,J=9.2 Hz),8.11-8.08(1H,m),7.97(1H,s),7.85(1H,s),7.56-7.54(1H,m),4.30(2H,t,J=6.6 Hz),3.49(2H,s),3.06(1H,t,J=6.6 Hz),2.56(4H,t,J=5.3 Hz),2.43(2H,t,J=6.6 Hz),2.14-2.05(4H,m),1.42(6H,d,J=6.6 Hz).

MS m/z(M+H):493.

Example 0420

The following compounds were obtained in the same manner as in Examples 0419-1 and 0015-4.

| Example No. | | |
|---|---|---|
| 0420 | | |
| 0420-1 | 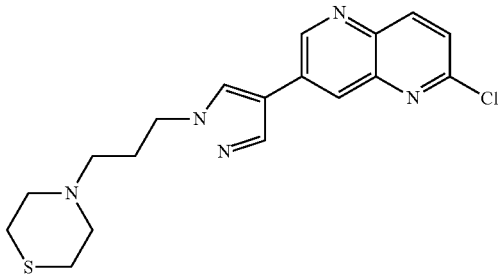 [SMILES: N=C/C(=C\NCCCN1CCSCC1)c1cnc2ccc(Cl)nc2c1] | MS m/z (M + H): 374. |
| 0420-2 | 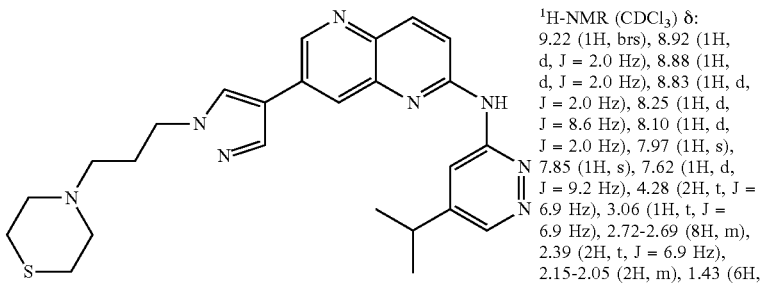 | $^1$H-NMR (CDCl$_3$) δ: 9.22 (1H, brs), 8.92 (1H, d, J = 2.0 Hz), 8.88 (1H, d, J = 2.0 Hz), 8.83 (1H, d, J = 2.0 Hz), 8.25 (1H, d, J = 8.6 Hz), 8.10 (1H, d, J = 2.0 Hz), 7.97 (1H, s), 7.85 (1H, s), 7.62 (1H, d, J = 9.2 Hz), 4.28 (2H, t, J = 6.9 Hz), 3.06 (1H, t, J = 6.9 Hz), 2.72-2.69 (8H, m), 2.39 (2H, t, J = 6.9 Hz), 2.15-2.05 (2H, m), 1.43 (6H, d, J = 7.3 Hz). MS m/z (M + H): 475. |

Example 0421

0421-1

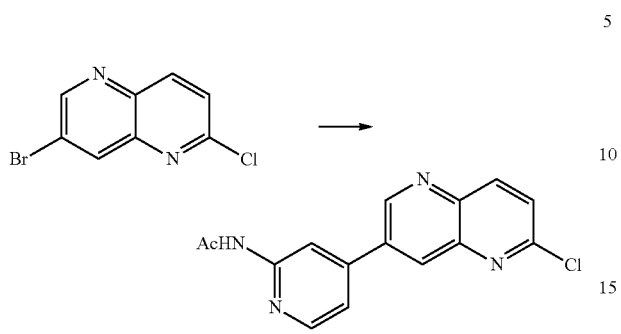

A mixture of 7-bromo-2-chloro-1,5-naphthyridine (48 mg), bis(pinacolato)diboron (58 mg), a 1,1'-bis(diphenylphosphino)ferrocenepalladium(II) dichloride-dichloromethane complex (16 mg), potassium acetate (42 mg), and 1,4-dioxane (1.9 mL) was stirred at 100° C. for 2 hours. N-(4-bromopyridin-2-yl)acetamide (42 mg), sodium carbonate (45 mg), a bis(di-tert-butyl(4-dimethylaminophenyl)phosphine)dichloropalladium(II) (14 mg), 1,4-dioxane (0.3 mL), and water (0.19 mL)) were added to the reaction mixture, followed by stirring at 100° C. for 2 hours. The reaction mixture was cooled to room temperature, and purified by silica gel column chromatography (hexane-ethyl acetate-methanol), thereby obtaining N-(4-(6-chloro-1,5-naphthyridin-3-yl)pyridin-2-yl)acetamide (12.6 mg) as a pale brown solid.

MSm/z(M+H):299.

0421-2

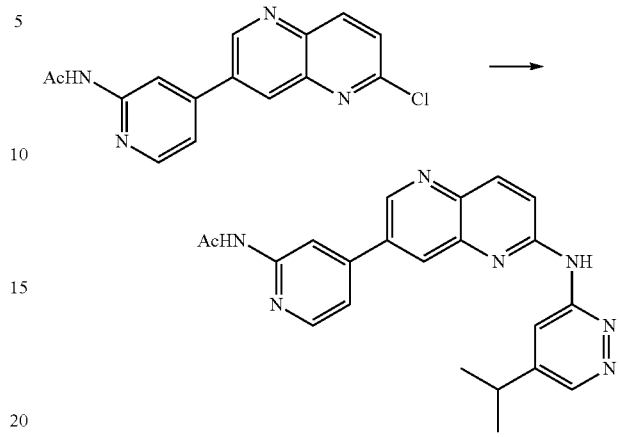

N-(4-(6-((5-isopropylpyridazin-3-yl)amino)-1,5-naphthyridin-3-yl)pyridin-2-yl)acetamide was obtained in the same manner as in Example 0015-4.

$^1$H-NMR(CDCl$_3$)δ:9.05(1H,d,J=2.0 Hz),8.83(2H,s),8.63(1H,s),8.42(1H,d,J=5.3 Hz),8.32(2H,d,J=8.6 Hz),8.06(1H,s),7.62(1H,t,J=4.6 Hz),7.40(1H,dd,J=5.3,2.0 Hz),3.08-3.05(1H,m),2.28(3H,s),1.42(6H,d,J=7.3 Hz).

MSm/z(M+H):400.

Example 0422

The following compounds were obtained in the same manner as in Examples 0415-1 and 0015-4.

| Example No. | | |
|---|---|---|
| 0422 | | |
| 0422-1 | 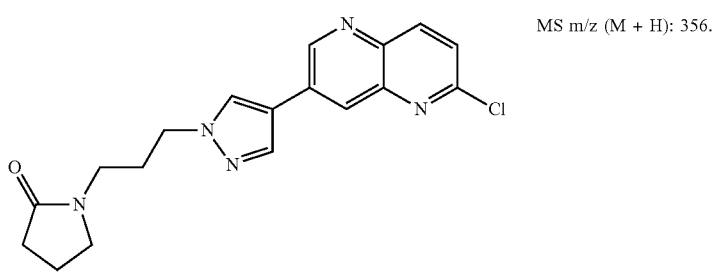 | MS m/z (M + H): 356. |
| 0422-2 | 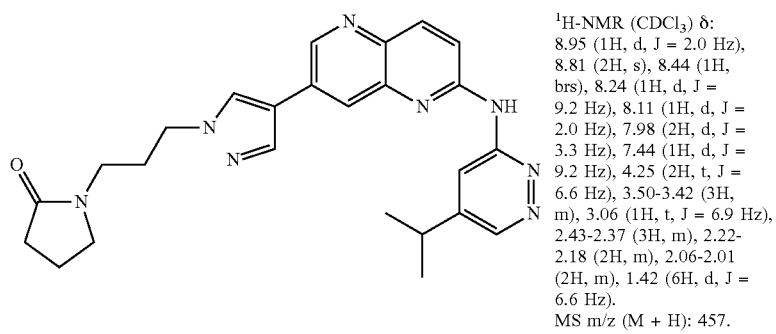 | $^1$H-NMR (CDCl$_3$) δ: 8.95 (1H, d, J = 2.0 Hz), 8.81 (2H, s), 8.44 (1H, brs), 8.24 (1H, d, J = 9.2 Hz), 8.11 (1H, d, J = 2.0 Hz), 7.98 (2H, d, J = 3.3 Hz), 7.44 (1H, d, J = 9.2 Hz), 4.25 (2H, t, J = 6.6 Hz), 3.50-3.42 (3H, m), 3.06 (1H, t, J = 6.9 Hz), 2.43-2.37 (3H, m), 2.22-2.18 (2H, m), 2.06-2.01 (2H, m), 1.42 (6H, d, J = 6.6 Hz). MS m/z (M + H): 457. |

Example 0423

The following compounds were obtained in the same manner as in Examples 0421-1 and 0015-4.

| Example No. | | |
|---|---|---|
| 0423 | | |
| 0423-1 | 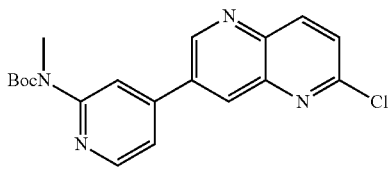 [SMILES: CN(C(=O)OC(C)(C)C)c1cc(-c2cnc3ccc(Cl)nc3c2)ccn1] | MS m/z (M + H): 371. |
| 0423-2 | 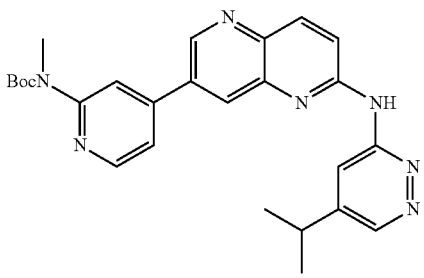 [SMILES: CC(C)c1cnnc(Nc2ccc3ncc(-c4ccnc(N(C)C(=O)OC(C)(C)C)c4)cc3n2)c1] | MS m/z (M + H): 472. |

0423-3

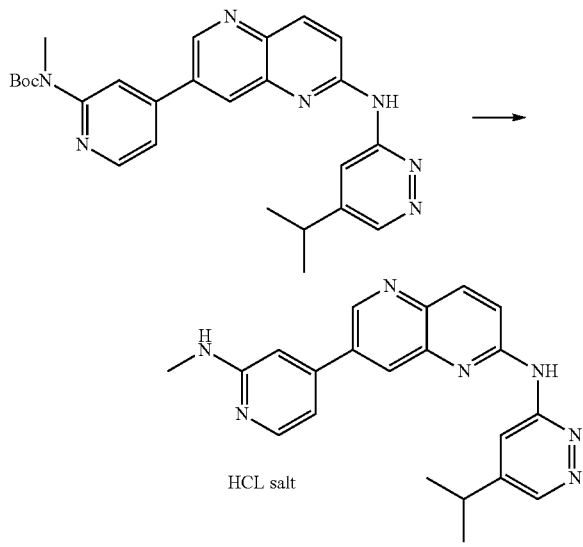

HCL salt

A 4.0 mol/L hydrogen chloride/1,4-dioxane solution (3 mL) was added to tert-butyl (4-(6-((5-isopropylpyridazin-3-yl)amino)-1,5-naphthyridin-3-yl)pyridin-2-yl) (methyl)carbamate (7.8 mg), followed by stirring at room temperature for 1 hour, and stirring at 50° C. for 6 hours. The reaction mixture was cooled to room temperature, and hexane was added thereto. The solid matter was collected by filtration, thereby obtaining N-(5-isopropylpyridazin-3-yl)-7-(2-(methylamino)pyridin-4-yl)-1,5-naphthyridine-2-amine hydrochloride (5.2 mg) as a yellow solid.

$^1$H-NMR(CD$_3$OD)δ:9.33-9.32(1H,m),9.15(1H,s),8.99-8.98(1H,m),8.64(1H,d,J=9.2 Hz),8.05(1H,d,J=6.6 Hz),7.84(1H,s),7.74(1H,d,J=9.2 Hz),7.49-7.44(3H,m),3.15(3H,s),3.07-3.07(1H,m),1.43(6H,d,J=6.6 Hz).

MSm/z(M+H):372.

Example 0424

0424-1

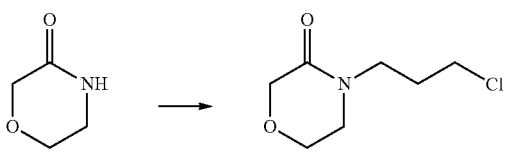 [SMILES: O=C1COCCN1 ; O=C1COCCN1CCCCl]

60% sodium hydride (105 mg) was added to a solution of morpholin-3-one (262 mg) in tetrahydrofuran (9.6 mL), followed by stirring at room temperature for 20 minutes in a nitrogen atmosphere. The reaction mixture was cooled by ice, and 1-bromo-3-chloropropane (0.31 mL) was added thereto, followed by stirring at room temperature for 15 hours. After water and ethyl acetate were added to the reaction mixture, the organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate-methanol), thereby obtaining 4-(3-chloropropyl)morpholin-3-one (50 mg) as pale yellow oily substance.

MSm/z(M+H):178.

0424-2 and 0424-3

The following compounds were obtained in the same manner as in Examples 0415-1 and 0015-4.

| Example No. | | |
|---|---|---|
| 0424 | | |
| 0424-2 | 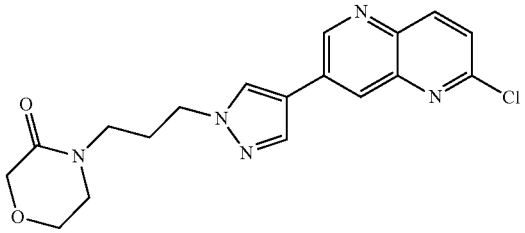 [SMILES: O=C1COCCN1CCCn1cc(-c2cnc3ccc(Cl)nc3c2)cn1] | MS m/z (M + H): 372. |
| 0424-3 | 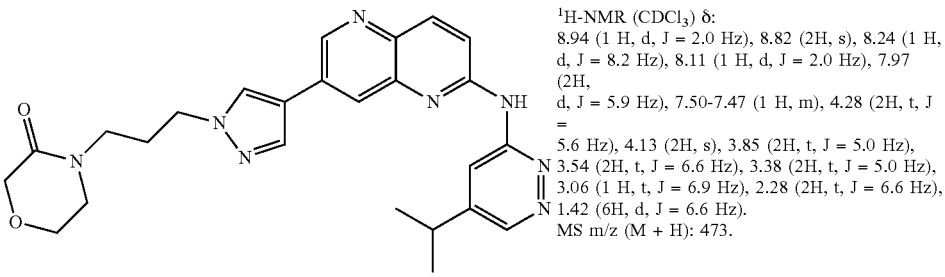 | $^1$H-NMR (CDCl$_3$) δ:<br>8.94 (1 H, d, J = 2.0 Hz), 8.82 (2H, s), 8.24 (1 H, d, J = 8.2 Hz), 8.11 (1 H, d, J = 2.0 Hz), 7.97 (2H, d, J = 5.9 Hz), 7.50-7.47 (1 H, m), 4.28 (2H, t, J = 5.6 Hz), 4.13 (2H, s), 3.85 (2H, t, J = 5.0 Hz), 3.54 (2H, t, J = 6.6 Hz), 3.38 (2H, t, J = 5.0 Hz), 3.06 (1 H, t, J = 6.9 Hz), 2.28 (2H, t, J = 6.6 Hz), 1.42 (6H, d, J = 6.6 Hz).<br>MS m/z (M + H): 473. |

Example 0425

The following compounds were obtained in the same manner as in Examples 0424-1, 0415-1, and 0015-4.

| Example No. | | |
|---|---|---|
| 0425 | | |
| 0425-1 | 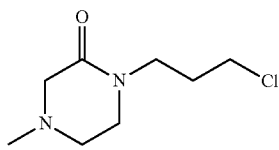 | MS m/z (M + H): 191. |
| 0425-2 | 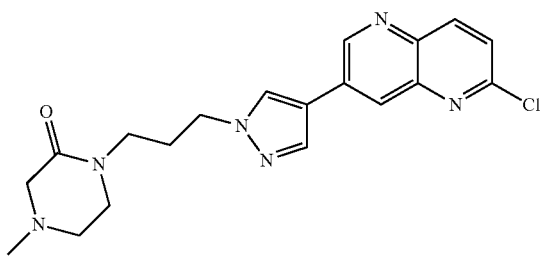 [SMILES: CN1CCN(CCCn2cc(-c3cnc4ccc(Cl)nc4c3)cn2)C(=O)C1] | MS m/z (M + H): 385. |
| 0425-3 | 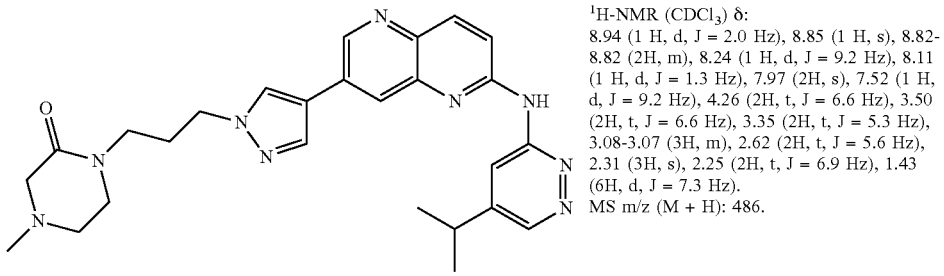 | $^1$H-NMR (CDCl$_3$) δ:<br>8.94 (1 H, d, J = 2.0 Hz), 8.85 (1 H, s), 8.82-8.82 (2H, m), 8.24 (1 H, d, J = 9.2 Hz), 8.11 (1 H, d, J = 1.3 Hz), 7.97 (2H, s), 7.52 (1 H, d, J = 9.2 Hz), 4.26 (2H, t, J = 6.6 Hz), 3.35 (2H, t, J = 5.3 Hz), 3.08-3.07 (3H, m), 2.62 (2H, t, J = 5.6 Hz), 2.31 (3H, s), 2.25 (2H, t, J = 6.9 Hz), 1.43 (6H, d, J = 7.3 Hz).<br>MS m/z (M + H): 486. |

Example 0426

0426-1

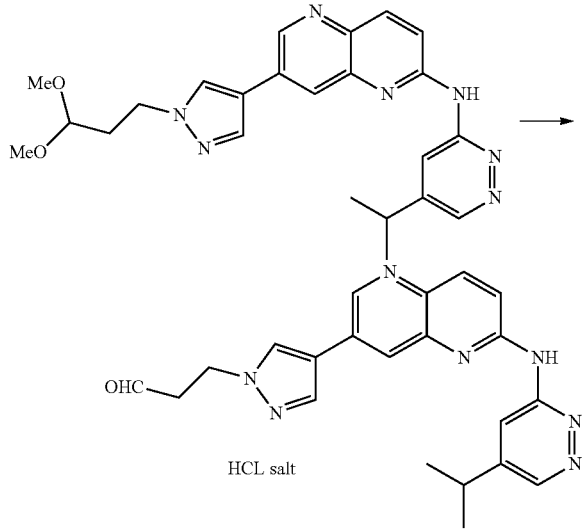

1 mol/L hydrochloric acid (15 mL) was added to a mixture of 7-(1-(3,3-dimethoxypropyl)-1H-pyrazol-4-yl)-N-(5-isopropylpyridazin-3-yl)-1,5-naphthyridine-2-amine (1.66 g) and 1,4-dioxane (30 mL), followed by stirring at 70° C. for 1 hour. The solvent was distilled off under reduced pressure, thereby obtaining 3-(4-(6-((5-isopropylpyridazin-3-yl)amino)-1,5-naphthyridin-3-yl)-1H-pyrazol-1-yl)propanal hydrochloride (1.9 g) as a yellow solid.

MSm/z(M+H):388.

0426-2

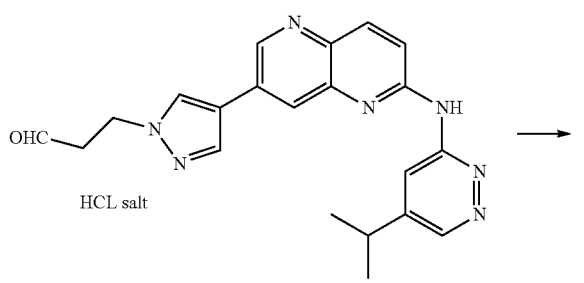

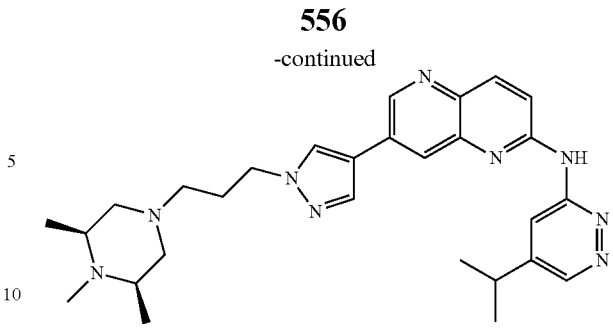

Triethylamine (6.7 μL) was added to a mixture of (2S,6R)-1,2,6-trimethylpiperazine trifluoroacetate (11.6 mg) and dichloromethane (0.5 mL), followed by stirring at room temperature for 15 minutes in a nitrogen atmosphere. 3-(4-(6-((5-Isopropylpyridazin-3-yl)amino)-1,5-naphthyridin-3-yl)-1H-pyrazol-1-yl)propanal hydrochloride (6.2 mg) and dichloromethane (2.0 mL) were added to the reaction mixture, followed by stirring at room temperature for 30 minutes. Sodium triacetoxyborohydride (35 mg) and acetic acid (0.5 mL) were added to the reaction mixture, followed by stirring at room temperature for 3 hours. The reaction mixture was purified by silica gel column chromatography (ethyl acetate-methanol, NH silica), thereby obtaining N-(5-isopropylpyridazin-3-yl)-7-(1-(3-((3S,5R)-3,4,5-trimethyl-piperazin-1-yl)propyl)-1H-pyrazol-4-yl)-1,5-naphthyridine-2-amine (2.0 mg) as a yellow solid.

$^1$H-NMR(CDCl$_3$)δ:8.91(2H,d,J=8.6 Hz),8.80(1H,s),8.25(1H,d,J=8.6 Hz),8.10(1H,d,J=1.3 Hz),7.96(1H,s),7.86(1H,s),7.60(1H,d,J=9.2 Hz),4.28(2H,t,J=6.6 Hz),3.06(1H,t,J=6.6 Hz),2.74(2H,d,J=9.9 Hz),2.35-2.30(9H,m),2.17-2.10(2H,m),1.42(6H,d,J=7.3 Hz),1.10(6H,d,J=6.6 Hz).

MSm/z(M+H):500.

Examples 0427 to 0430

The following compounds were obtained in the same manner as in Example 0426-2.

| Example No. | | $^1$H-NMR (CDCl$_3$) δ: |
|---|---|---|
| 0427 | 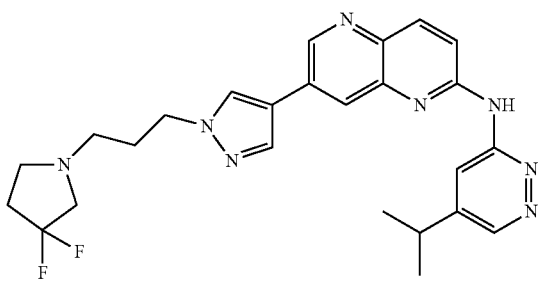 [SMILES: CC(C)c1cnnc(Nc2ccc3ncc(-c4cnn(CCCN5CCC(F)(F)C5)c4)cc3n2)c1] | 8.93 (1 H, d, J = 2.0 Hz), 8.89 (1 H, brs), 8.74 (1 H, s), 8.27-8.23 (1 H, m), 8.10 (1 H, d, J = 2.0 Hz), 8.08 (1 H, s), 7.97 (1 H, d, J = 4.6 Hz), 7.87 (1 H, d, J = 2.0 Hz), 7.61-7.53 (1 H, m), 4.31 (2H, t, J = 6.9 Hz), 3.20-2.86 (8H, m), 2.74-2.72 (1 H, m), 2.43-2.26 (2H, m), 1.41 (6H, d, J = 6.6 Hz). MS m/z (M + H): 479. |

| Example No. | | |
|---|---|---|
| 0428 | 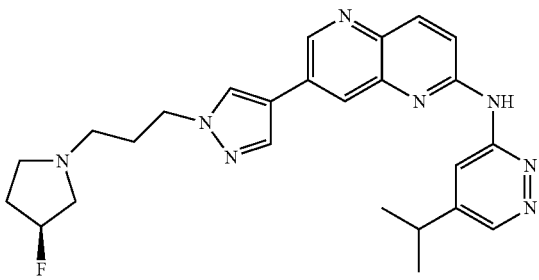 [SMILES: CC(C)c1cnnc(Nc2ccc3ncc(-c4cnn(CCCN5CC[C@H](F)C5)c4)cc3n2)c1] | $^1$H-NMR (CDCl$_3$) δ: 8.94-8.93 (2H, m), 8.75 (1 H, s), 8.24 (1 H, d, J = 9.2 Hz), 8.10-8.09 (1 H, m), 7.97 (1 H, s), 7.89 (1 H, s), 7.58-7.55 (1 H, m), 4.32 (2 H, t, J = 6.9 Hz), 3.08-2.46 (6 H, m), 2.18-2.16 (6H, m), 1.42 (6H, d, J = 7.3 Hz). MS m/z (M + H): 461. |
| 0429 | | $^1$H-NMR (CDCl$_3$) δ: 8.90-8.83 (3H, m), 8.26-8.23 (1 H, m), 8.10-8.08 (2H, m), 7.97 (1 H, s), 7.91-7.87 (1 H, m), 7.54 (1 H, d, J = 9.2 Hz), 4.32 (2H, t, J = 6.6 Hz), 3.08-2.04 (12H, m), 1.42 (6H, d, J = 6.6 Hz). MS m/z (M + H): 461 |
| 0430 | | $^1$H-NMR (CDCl$_3$) δ: 8.93 (2H, d, J = 2.0 Hz), 8.75 (1 H, s), 8.24 (1 H, d, J = 9.2 Hz), 8.10 (1 H, d, J = 2.0 Hz), 7.97 (1 H, s), 7.89 (1 H, s), 7.58 (1 H, d, J = 9.2 Hz), 4.29 (2H, t, J = 6.6 Hz), 3.78 (1 H, t, J = 4.0 Hz), 3.07-3.02 (1 H, m), 2.87-2.74 (2H, m), 2.47 (2H, t, J = 7.3 Hz), 2.33-2.30 (2H, m), 2.18-2.16 (2H, m), 1.94-1.89 (2H, m), 1.71-1.65 (2H, m), 1.42 (6H, d, J = 6.6 Hz). MS m/z (M + H): 473. |
Example 0431
0431-1

-continued

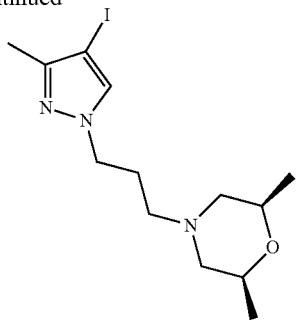

A solution of ((3-bromopropoxy)methyl)benzene (7.7 mL) in ethanol (10 mL) was added dropwise to hydrazine monohydrate (17 mL) at 65° C. over a period of 1 hour, followed by stirring at 65° C. for 3.5 hours. The reaction mixture was cooled to room temperature, passed through DOWEX™ MONOSPHERE™ 550A (OH) (product name, manufactured by Wako Pure Chemical Industries, Ltd.), and the solvent was distilled off under reduced pressure, thereby obtaining pale yellow oily substance (7.27 g).

Ethyl acetoacetate (2.8 mL) was added to a solution of the obtained pale yellow oily substance (7.27 g) in ethanol (22.4 mL), followed by stirring at room temperature for 1 hour. The solvent was distilled off under reduced pressure, tert-butyl methyl ether and a 2.0 mol/L sodium hydroxide aqueous solution were added to the obtained residue, and the aqueous layer was collected by separation. After a 3.0 mol/L potassium hydrogen sulfate aqueous solution and ethyl acetate were added to the aqueous layer, the organic layer was collected by separation, washed with a saturated sodium chloride aqueous solution, and dried over anhydrous sodium sulfate, and the solvent was distilled off under reduced pressure, thereby obtaining brown oily substance (3.5 g).

A solution of the obtained brown oily substance (3.5 g) in dichloromethane (71 mL) was cooled by ice, and pyridine (2.1 mL) and trifluoromethanesulfonic acid anhydride (3.5 mL) were added thereto, followed by stirring at 0° C. for 2 hours. After water and dichloromethane were added to the reaction mixture, the organic layer was collected by separation, washed with a saturated sodium chloride aqueous solution, and dried over anhydrous sodium sulfate, and the solvent was distilled off under reduced pressure, thereby obtaining brown oily substance (3.5 g). The obtained brown oily substance was purified by silica gel column chromatography (hexane-ethyl acetate), thereby obtaining brown oily substance (3.85 g).

A mixture of the obtained brown oily substance (3.85 g), 20% palladium hydroxide/carbon (0.20 g), and methanol (40 mL) was stirred at 50° C. for 1 hour in a hydrogen (0.8 MPa) atmosphere. The insolubles were filtered off, and the solvent was distilled off under reduced pressure, thereby obtaining pale brown oily substance (2.2 g).

Iodine (1.55 g) and ammonium cerium(IV) nitrate (3.36 g) were added to a solution of the obtained brown oily substance (2.2 g) in acetonitrile (20 mL), followed by stirring at room temperature for 4 hours. The reaction mixture was allowed to stand for 14.5 hours, and stirred at room temperature for 2 hours. After water and ethyl acetate were added to the reaction mixture, the organic layer was collected by separation, washed with a saturated sodium chloride aqueous solution and a 10% sodium hydrogen sulfite aqueous solution, and dried over anhydrous sodium sulfate, and the solvent was distilled off under reduced pressure, thereby obtaining brown oily substance (1.66 g).

Triethylamine (1.74 mL) was added to a solution of the obtained brown oily substance (1.66 g) in dichloromethane (31 mL), followed by stirring for 10 minutes under ice-cooling. Methanesulfonyl chloride (0.73 mL) was added to the reaction mixture, followed by stirring at 0° C. for 1 hour. After water was added to the reaction mixture, the organic layer was collected by separation, washed with a saturated sodium chloride aqueous solution, and dried over anhydrous sodium sulfate, and the solvent was distilled off under reduced pressure, thereby obtaining brown oily substance (2.24 g).

A mixture of the obtained brown oily substance (288 mg), potassium carbonate (230 mg), (2S,6R)-2,6-dimethylmorpholine (156 μL), and acetonitrile (4.2 mL) was stirred at 80° C. for 16 hours. After the reaction mixture was cooled to room temperature, water and ethyl acetate were added thereto, the organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate, NH silica), thereby obtaining (2S,6R)-4-(3-(4-iodo-3-methyl-1H-pyrazol-1-yl)propyl)-2,6-dimethylmorpholine (29.8 mg) as pale yellow oily substance.

MS m/z(M+H):364.

0431-2 and 0431-3

The following compounds were obtained in the same manner as in Examples 0421-1 and 0015-4.

| 実施例<br>番号 | | |
|---|---|---|
| 0431 | | |
| 0431-2 | 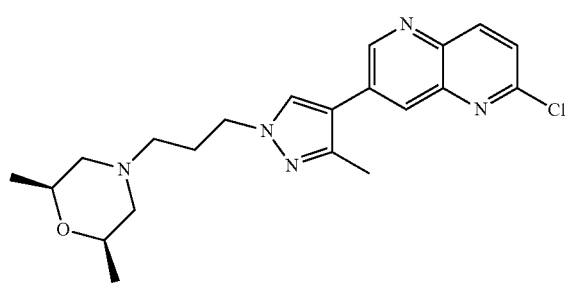 [SMILES: Cc1nn(CCCN2C[C@@H](C)O[C@@H](C)C2)cc1-c1cnc2ccc(Cl)nc2c1] | MS m/z (M + H): 400. |

| 0431-3 | 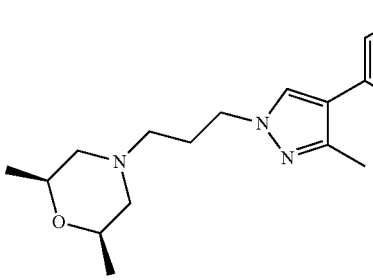 | ¹H-NMR (CDCl₃) δ:<br>8.85-8.80 (3H, m), 8.26 (1 H, d, J = 8.6 Hz), 8.06 (1 H, s), 7.69 (1 H, s), 7.50 (1 H, d, J = 9.2 Hz), 4.22 (2H, t, J = 6.6 Hz), 3.73-3.71 (2H, m), 3.03 (1 H, t, J = 6.3 Hz), 2.76-2.73 (2H, m), 2.51 (3H, s), 2.39-2.36 (2H, m), 2.17-2.13 (2H, m), 1.40 (6H, d, J = 7.3 Hz), 1.17 (6H, d, J = 6.6 Hz).<br>MS m/z (M + H): 501. |
|---|---|---|

Example 0432

0432-1

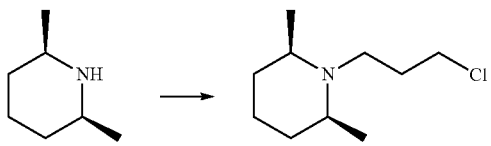

A mixture of (2S,6R)-2,6-dimethylpiperidine (0.27 mL), cesium carbonate (979 mg), 1-bromo-3-chloropropane (0.24 mL), and 1,4-dioxane (4 mL) was stirred at 80° C. for 16 hours. The reaction mixture was cooled to room temperature, the insolubles were filtered off, and the solvent was distilled off under reduced pressure, thereby obtaining (2S, 6R)-1-(3-chloropropyl)-2,6-dimethylpiperidine (56 mg) as pale yellow oily substance.

MSm/z(M+H):190.

0432-2 and 0432-3

The following compounds were obtained in the same manner as in Examples 0415-1 and 0015-4.

| Example No. | | |
|---|---|---|
| 0432 | | |
| 0432-2 | 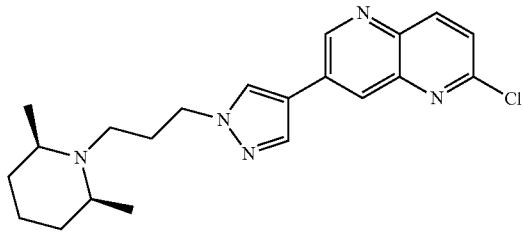 [SMILES: C[C@@H]1CCC[C@H](C)N1CCCn1cc(-c2cnc3ccc(Cl)nc3c2)cn1] | MS m/z (M + H): 384. |
| 0432-3 | 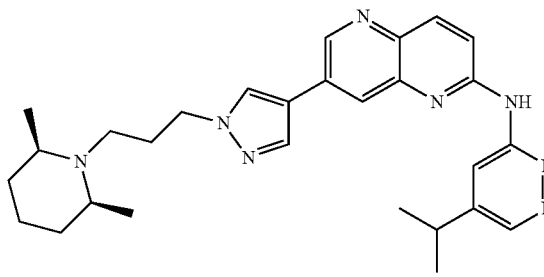 | ¹H-NMR (CDCl₃) δ:<br>8.93 (1 H, d, J = 2.0 Hz), 8.82 (2H, s), 8.24 (1 H, d, J = 9.2 Hz), 8.10 (1 H, d, J = 2.0 Hz), 7.97 (1 H, s), 7.85 (1 H, s), 7.50 (1 H, d, J = 9.2 Hz), 6.55 (1 H, s), 4.18 (2H, t, J = 6.9 Hz), 3.06 (1 H, t, J = 6.9 Hz), 2.82-2.80 (2H, m), 2.46-2.43 (2H, m), 2.08-2.05 (2H, m), 1.42 (6H, d, J = 6.6 Hz), 1.29-1.26 (4H, m), 1.07 (6H, d, J = 6.6 Hz).<br>MS m/z (M + H): 485. |

Examples 0433 to 0435

The following compounds were obtained in the same manner as in Example 0426-2.

| Example No. | | |
|---|---|---|
| 0433 | 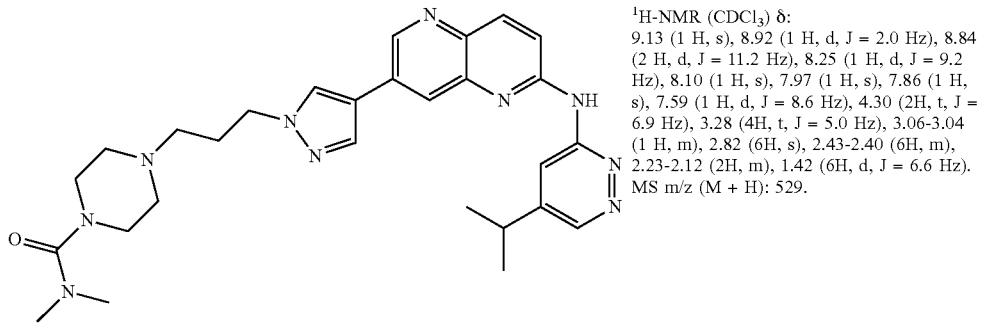 | ¹H-NMR (CDCl₃) δ: 9.13 (1 H, s), 8.92 (1 H, d, J = 2.0 Hz), 8.84 (2 H, d, J = 11.2 Hz), 8.25 (1 H, d, J = 9.2 Hz), 8.10 (1 H, s), 7.97 (1 H, s), 7.86 (1 H, s), 7.59 (1 H, d, J = 8.6 Hz), 4.30 (2H, t, J = 6.9 Hz), 3.28 (4H, t, J = 5.0 Hz), 3.06-3.04 (1 H, m), 2.82 (6H, s), 2.43-2.40 (6H, m), 2.23-2.12 (2H, m), 1.42 (6H, d, J = 6.6 Hz). MS m/z (M + H): 529. |
| 0434 | 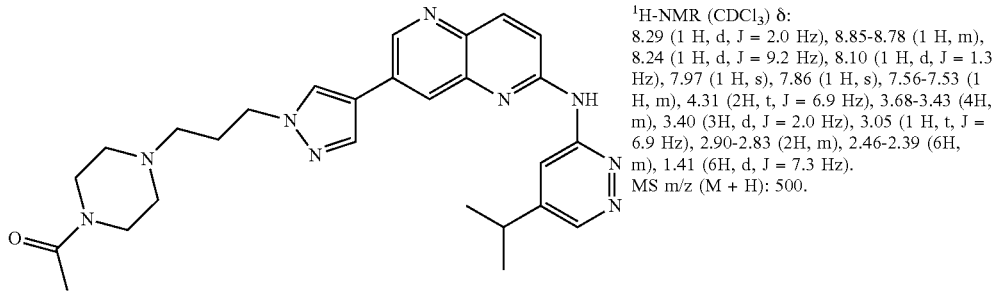 | ¹H-NMR (CDCl₃) δ: 8.29 (1 H, d, J = 2.0 Hz), 8.85-8.78 (1 H, m), 8.24 (1 H, d, J = 9.2 Hz), 8.10 (1 H, d, J = 1.3 Hz), 7.97 (1 H, s), 7.86 (1 H, s), 7.56-7.53 (1 H, m), 4.31 (2H, t, J = 6.9 Hz), 3.68-3.43 (4H, m), 3.40 (3H, d, J = 2.0 Hz), 3.05 (1 H, t, J = 6.9 Hz), 2.90-2.83 (2H, m), 2.46-2.39 (6H, m), 1.41 (6H, d, J = 7.3 Hz). MS m/z (M + H): 500. |
| 0435 | 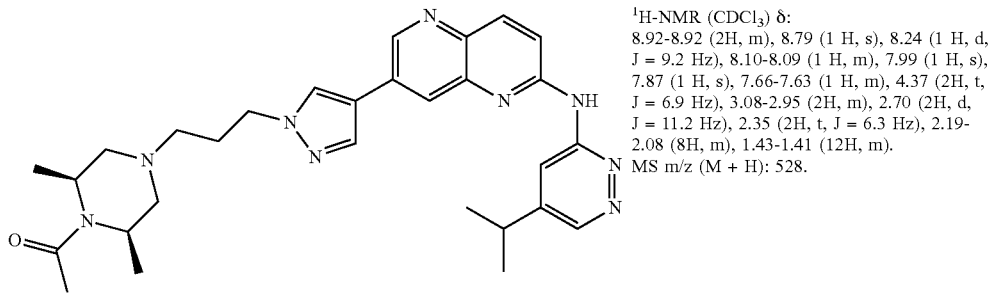 | ¹H-NMR (CDCl₃) δ: 8.92-8.92 (2H, m), 8.79 (1 H, s), 8.24 (1 H, d, J = 9.2 Hz), 8.10-8.09 (1 H, m), 7.99 (1 H, s), 7.87 (1 H, s), 7.66-7.63 (1 H, m), 4.37 (2H, t, J = 6.9 Hz), 3.08-2.95 (2H, m), 2.70 (2H, d, J = 11.2 Hz), 2.35 (2H, t, J = 6.3 Hz), 2.19-2.08 (8H, m), 1.43-1.41 (12H, m). MS m/z (M + H): 528. |

Example 0436

Example 0432-1, The following compounds were obtained in the same manner as in Examples 0415-1 and 0015-4.

| Example No. | | |
|---|---|---|
| 0436 | | |
| 0436-1 | 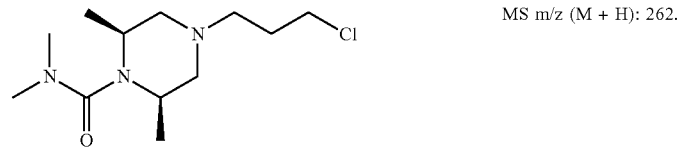 | MS m/z (M + H): 262. |

| Example No. | | |
|---|---|---|
| 0436-2 | 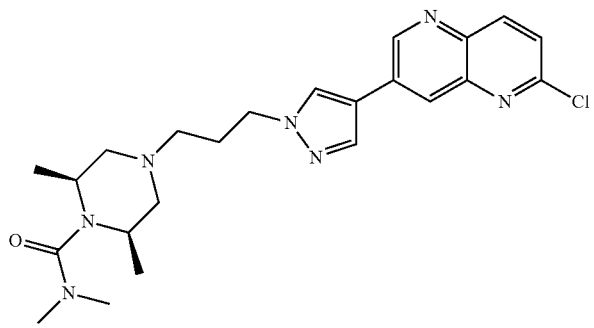 [SMILES: C[C@@H]1CN(CCCn2cc(-c3cnc4ccc(Cl)nc4c3)cn2)C[C@H](C)N1C(=O)N(C)C] | MS m/z (M + H): 456. |
| 0436-3 | 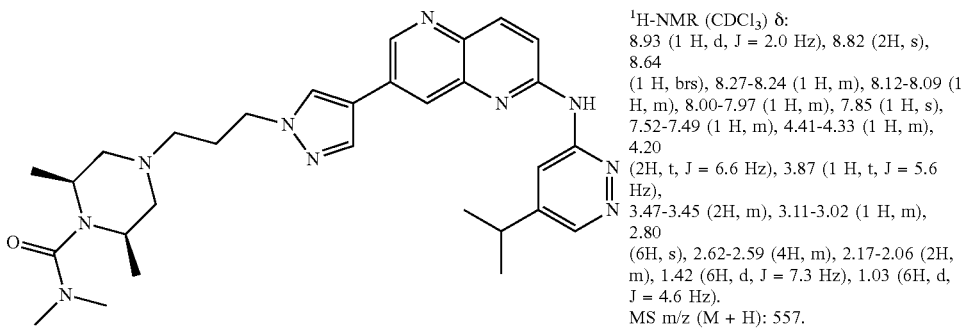 | ¹H-NMR (CDCl₃) δ:<br>8.93 (1 H, d, J = 2.0 Hz), 8.82 (2H, s), 8.64<br>(1 H, brs), 8.27-8.24 (1 H, m), 8.12-8.09 (1 H, m), 8.00-7.97 (1 H, m), 7.85 (1 H, s), 7.52-7.49 (1 H, m), 4.41-4.33 (1 H, m), 4.20<br>(2H, t, J = 6.6 Hz), 3.87 (1 H, t, J = 5.6 Hz),<br>3.47-3.45 (2H, m), 3.11-3.02 (1 H, m), 2.80<br>(6H, s), 2.62-2.59 (4H, m), 2.17-2.06 (2H, m), 1.42 (6H, d, J = 7.3 Hz), 1.03 (6H, d, J = 4.6 Hz).<br>MS m/z (M + H): 557. |

Example 0437

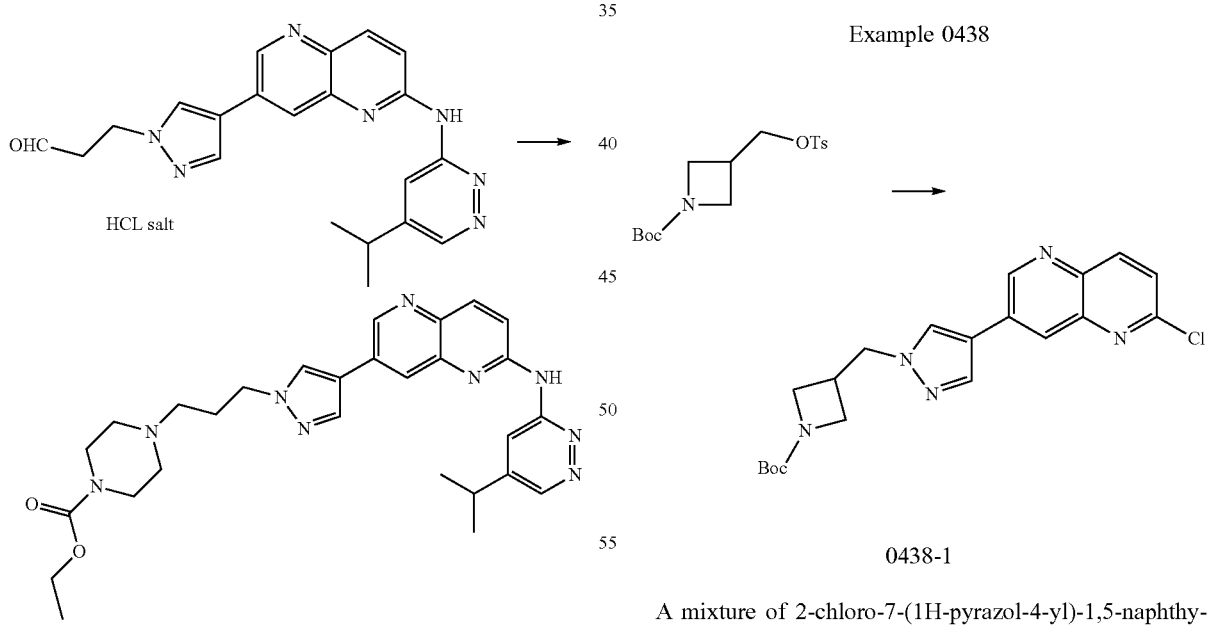

Ethyl 4-(3-(4-(6-((5-isopropylpyridazin-3-yl)amino)-1,5-naphthyridin-3-yl)-1H-pyrazol-1-yl)propyl)piperazine-1-carboxylate was obtained as a yellow solid in the same manner as in Example 0426-2.

¹H-NMR(CDCl₃)δ:8.93-8.92(1H,m),8.80(2H,s),8.26-8.23(1H,m),8.09-8.08(1H,m),7.87(1H,s),7.86(1H,s),7.48-7.45(1H,m),4.30(2H,t,J=6.6 Hz),4.14(2H,q,J=7.0 Hz),3.50 (4H,t,J=5.0 Hz),3.06(1H,t,J=6.6 Hz),2.41-2.38(6H,m),2.15-2.13(2H,m),1.42(6H,d,J=6.6 Hz),1.26(3H,t,J=12.2 Hz). MSm/z(M+H):530.

Example 0438

0438-1

A mixture of 2-chloro-7-(1H-pyrazol-4-yl)-1,5-naphthyridine (146 mg), tert-butyl 3-((paratoluenesulfonyloxy)methyl)azetidine-1-carboxylate (259 mg), potassium carbonate (174 mg), and N,N-dimethylformamide (2 mL) was stirred at 100° C. for 1 hour. After the reaction mixture was cooled to room temperature, water and ethyl acetate were added thereto, the organic layer was collected by separation, washed with a saturated sodium chloride aqueous solution, and dried over anhydrous sodium sulfate, and the solvent was distilled off under reduced pressure, thereby obtaining tert-butyl 3-((4-(6-chloro-1,5-naphthyridin-3-yl)-1H-pyrazol-1-yl)methyl)azetidine-1-carboxylate (273 mg) as a pale brown solid.

MSm/z(M+H):400.

0438-2

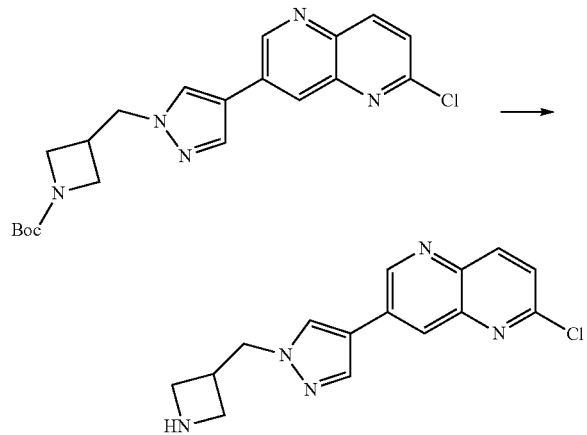

Trifluoroacetic acid (1.5 mL) was added to a mixture of tert-butyl 3-((4-(6-chloro-1,5-naphthyridin-3-yl)-1H-pyrazol-1-yl)methyl)azetidine-1-carboxylate (273 mg), and dichloromethane (3 mL), followed by stirring at room temperature for 30 minutes. The solvent was distilled off under reduced pressure, and the obtained residue was purified by silica gel column chromatography (ethyl acetate-methanol, NH silica), thereby obtaining 7-(1-(azetidin-3-ylmethyl)-1H-pyrazol-4-yl)-2-chloro-1,5-naphthyridine (104 mg) as a yellow solid.

MSm/z(M+H):300.

0438-3

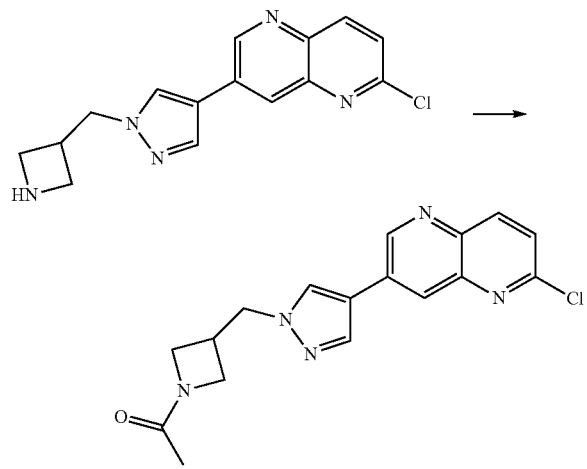

Acetyl chloride (13 µL) was added to a mixture of 7-(1-(azetidin-3-ylmethyl)-1H-pyrazol-4-yl)-2-chloro-1,5-naphthyridine (36 mg), triethylamine (33 µL), and dichloromethane (2.6 mL) under ice-cooling, followed by stirring for 1.5 hours. The reaction mixture was purified by silica gel column chromatography (hexane-ethyl acetate-methanol, NH silica), thereby obtaining 1-(3-((4-(6-chloro-1,5-naphthyridin-3-yl)-1H-pyrazol-1-yl)methyl)azetidin-1-yl)ethanone (9.7 mg) as a yellow solid.

MSm/z(M+H):342.

0438-4

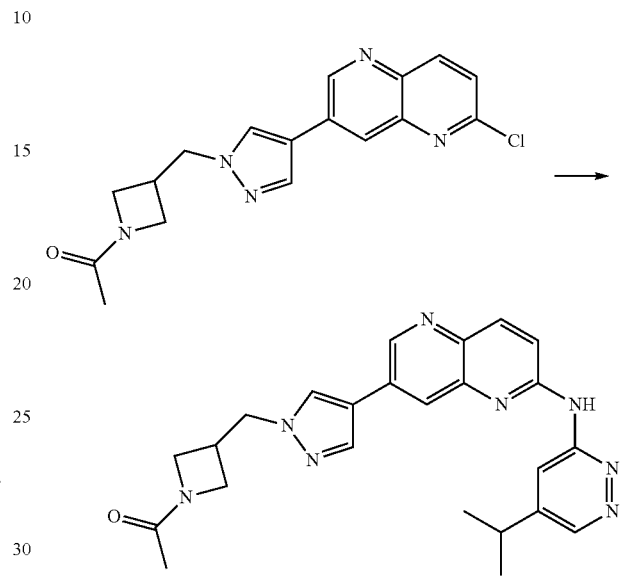

A mixture of 1-(3-((4-(6-chloro-1,5-naphthyridin-3-yl)-1H-pyrazol-1-yl)methyl)azetidin-1-yl)ethanone (9.7 mg), 5-isopropylpyridazine-3-amine (5 mg), potassium tert-butoxide (10.4 mg), and 1,4-dioxane (1 mL) was stirred at 110° C. for 1 hour. The reaction mixture was cooled to room temperature, and purified by silica gel column chromatography (ethyl acetate-methanol, NH silica), thereby obtaining 1-(3-((4-(6-((5-isopropylpyridazin-3-yl)amino)-1,5-naphthyridin-3-yl)-1H-pyrazol-1-yl)methyl)azetidin-1-yl)ethanone (1.8 mg) as a pale yellow solid.

$^1$H-NMR(CDCl$_3$)δ:8.94-8.91(2H,m),8.84-8.83(1H,m), 8.26-8.23(1H,m),8.12-8.08(1H,m),7.97-7.96(1H,m),7.85-7.84(1H,m),7.71-7.69(1H,m),4.27-4.08(6H,m),3.07(1H,t, J=6.9 Hz),2.05-2.01(1H,m),1.89(3H,s),1.43(6H,d,J=6.6 Hz).

MSm/z(M+H):443.

Example 0439

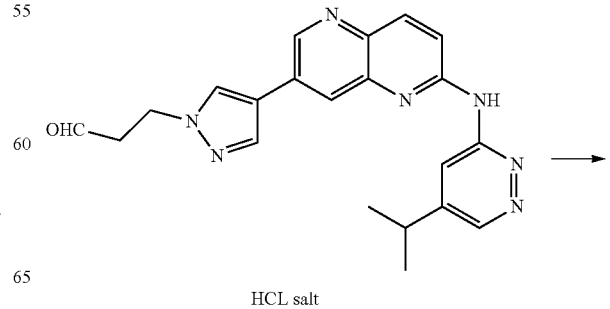

HCL salt

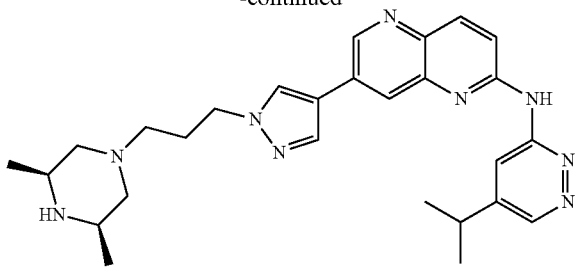

7-(1-(3-((3S,5R)-3,5-dimethylpiperazin-1-yl)propyl)-1H-pyrazol-4-yl)-N-(5-isopropylpyridazin-3-yl)-1,5-naphthyridine-2-amine was obtained as a yellow solid in the same manner as in Example 0426-2.

¹H-NMR(CDCl₃)δ:8.92(1H,d,J=2.6 Hz),8.75(1H,s),8.24(1H,d,J=9.2 Hz),8.10(1H,d,J=1.3 Hz),7.97(1H,s),7.86(1H,s),7.57(1H,d,J=9.2 Hz),4.28(2H,t,J=6.9 Hz),3.08-2.99(3H,m),2.84-2.82(2H,m),2.42(2H,q,J=6.8 Hz),2.15(2H,t,J=6.9 Hz),1.73(2H,t,J=10.9 Hz),1.41(6H,d,J=7.3 Hz),1.11-1.09 (6H,m).

MSm/z(M+H):486.

Example 0440

0440-1

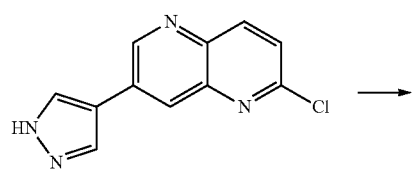

A mixture of 2-chloro-7-(1H-pyrazol-4-yl)-1,5-naphthyridine (49 mg), bromoethane (49 μL), cesium carbonate (91 mg), and N,N-dimethylformamide (1 mL) was stirred at 80° C. for 2 hours. After the reaction mixture was cooled to room temperature, water and ethyl acetate were added thereto, the organic layer was collected by separation, washed with a saturated sodium chloride aqueous solution, and dried over anhydrous sodium sulfate, and the solvent was distilled off under reduced pressure, thereby obtaining 2-chloro-7-(1-ethyl-1H-pyrazol-4-yl)-1,5-naphthyridine (58 mg) as a brown solid.

MSm/z(M+H):259.

0440-2

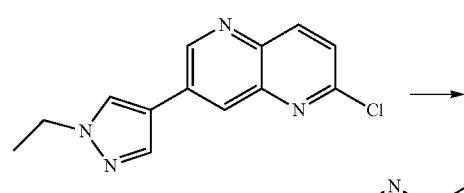

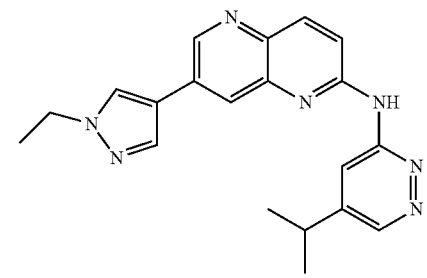

7-(1-Ethyl-1H-pyrazol-4-yl)-N-(5-isopropylpyridazin-3-yl)-1,5-naphthyridine-2-amine was obtained as a pale yellow solid in the same manner as in Example 0438-4.

¹H-NMR(CD₃OD)δ:8.97(1H,d,J=2.0 Hz),8.85(1H,s),8.77(1H,d,J=2.0 Hz),8.34(1H,s),8.29(1H,d,J=1.3 Hz),8.18(1H,d,J=9.2 Hz),8.10(1H,s),7.60(1H,d,J=9.2 Hz),4.28(2H,q,J=7.3 Hz),3.09(1H,t,J=6.6 Hz),1.53(3H,t,J=7.3 Hz),1.41 (6H,d,J=7.3 Hz).

MSm/z(M+H):360.

Examples 0441 and 0442

The following compounds were obtained in the same manner as in Examples 0440-1 and 0438-4.

| Example No. | | |
|---|---|---|
| 0441 | | |
| 0441-1 | 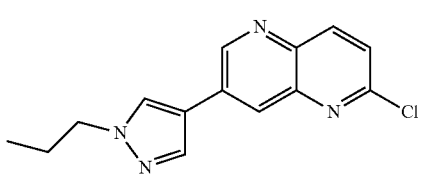 [SMILES: CCCn1cc(-c2cnc3ccc(Cl)nc3c2)cn1] | MS m/z (M + H): 273. |

| Example No. | | |
|---|---|---|
| 0441-2 | 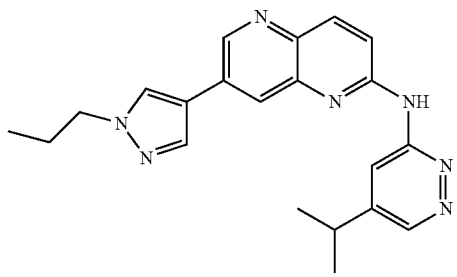 [SMILES: CCCn1cc(-c2cnc3ccc(Nc4cc(C(C)C)cnn4)nc3c2)cn1] | $^1$H-NMR (CD$_3$OD) δ: 8.97 (1 H, d, J = 2.0 Hz), 8.85 (1 H, s), 8.78 (1 H, d, J = 2.0 Hz), 8.34 (1 H, s), 8.30 (1 H, d, J = 2.0 Hz), 8.19 (1 H, d, J = 9.2 Hz), 8.11 (1 H, s), 7.61 (1 H, d, J = 9.2 Hz), 4.21 (2H, t, J = 7.3 Hz), 3.09 (1 H, t, J = 6.9 Hz), 2.01-1.92 (2H, m), 1.42 (6H, d, J = 6.6 Hz), 0.96 (3H, t, J = 7.3 Hz). MS m/z (M + H): 374. |
| 0442 | | |
| 0442-1 | 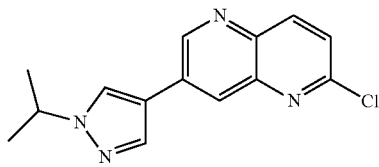 [SMILES: CC(C)n1cc(-c2cnc3ccc(Cl)nc3c2)cn1] | MS m/z (M + H): 273. |
| 0442-2 | 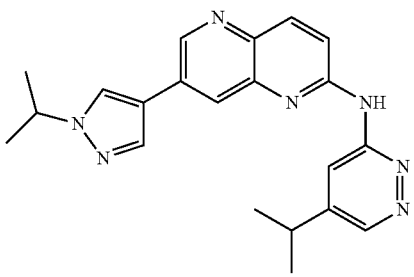 [SMILES: CC(C)c1cnnc(Nc2ccc3ncc(-c4cnn(C(C)C)c4)cc3n2)c1] | $^1$H-NMR (CD$_3$OD) δ: 8.99 (1 H, d, J = 2.0 Hz), 8.85 (1 H, s), 8.78 (1 H, d, J = 1.3 Hz), 8.39 (1 H, s), 8.30 (1 H, d, J = 1.3 Hz), 8.19 (1 H, d, J = 9.2 Hz), 8.10 (1 H, s), 7.61 (1 H, d, J = 8.6 Hz), 4.63 (1 H, t, J = 6.6 Hz), 3.10-3.04 (1 H, m), 1.58 (6H, d, J = 6.6 Hz), 1.42 (6H, d, J = 7.3 Hz). MS m/z (M + H): 374. |
Example 0443
The following compounds were obtained in the same manner as in Examples 0421-1, 0438-2, 0438-3, and 0015-4.
| Example No. | | |
|---|---|---|
| 0443 | | |
| 0443-1 | 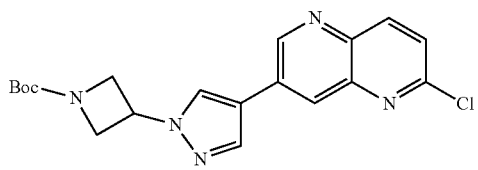 [SMILES: CC(C)(C)OC(=O)N1CC(n2cc(-c3cnc4ccc(Cl)nc4c3)cn2)C1] | MS m/z (M + H): 386. |
| 0443-2 | 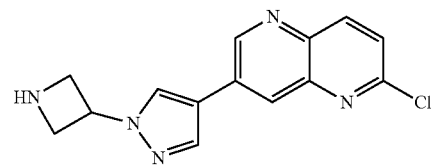 [SMILES: Clc1ccc2ncc(-c3cnn(C4CNC4)c3)cc2n1] | MS m/z (M + H): 286. |
| 0443-3 | 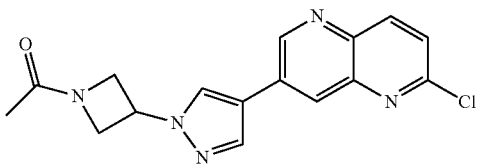 [SMILES: CC(=O)N1CC(n2cc(-c3cnc4ccc(Cl)nc4c3)cn2)C1] | MS m/z (M + H): 328. |

-continued

| Example No. | | |
|---|---|---|
| 0443-4 | 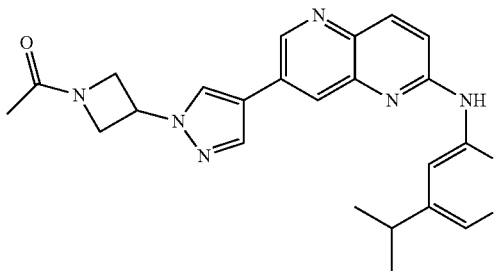 | ¹H-NMR (CDCl₃) δ:<br>9.10 (1 H, brs), 8.93 (1 H, d, J = 2.6 Hz), 8.85-8.83 (2H, m), 8.26 (1 H, d, J = 9.2 H), 8.12 (1 H, d, J = 1.3 Hz), 8.07 (1 H, s), 7.96 (1 H, s),<br>7.62 (1 H, d, J = 9.2 Hz), 5.24-5.19 (1 H, m), 4.64-4.55 (4H, m), 3.07 (1 H, t, J = 6.9 Hz), 1.99 (3H, s), 1.43 (6H, d, J = 6.6 Hz).<br>MS m/z (M + H): 429. |

Examples 0444 to 0446

The following compounds were obtained in the same manner as in Example 0426-2.

| Example No. | | |
|---|---|---|
| 0444 | 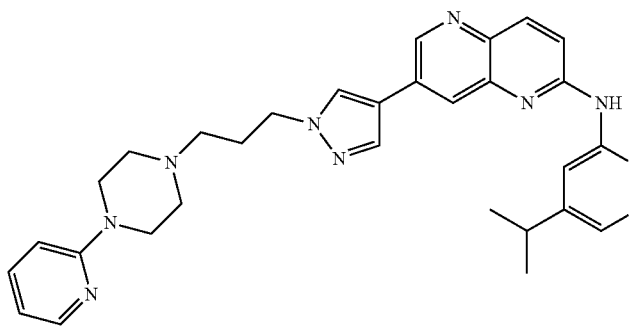 | ¹H-NMR (CDCl₃) δ:<br>8.93 (1 H, d, J = 2.6 Hz), 8.81 (2H, s), 8.24 (1 H, d, J = 9.2 Hz), 8.20-8.19 (1 H, m), 8.10 (1 H, d, J = 2.0 Hz), 7.98 (1 H, s), 7.89 (1 H, s), 7.50-7.46 (2H, m), 6.66-6.61 (2H, m), 4.33 (2H, t, J = 6.9 Hz), 3.57 (4H, t, J = 5.0 Hz), 3.05 (1 H, t, J = 6.9 Hz), 2.57 (4H, t, J = 5.0 Hz), 2.44 (2H, t, J = 6.9 Hz), 2.18 (2H, t, J = 6.9 Hz), 1.41 (6H, d, J = 6.6 Hz).<br>MS m/z (M + H): 535. |
| 0445 | 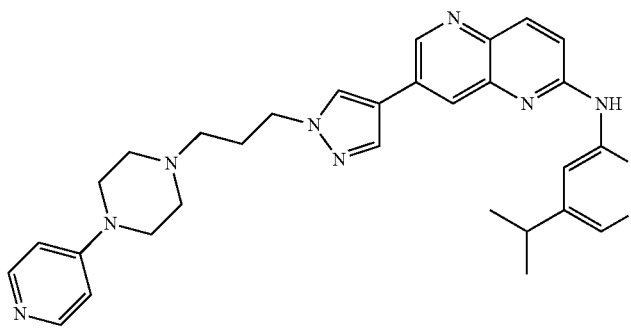 | ¹H-NMR (CDCl₃) δ:<br>8.94-8.91 (2H, m), 8.82 (2H, s), 8.27-8.25 (3H, m), 8.10 (1 H, s), 7.98 (1 H, s), 7.88 (1 H, s), 7.59-7.56 (1 H, m), 6.66 (2H, t, J = 3.3 Hz), 4.33 (2H, t, J = 6.9 Hz), 3.36 (4H, t, J = 5.0 Hz), 3.05 (1 H, t, J = 6.6 Hz), 2.58 (4H, t, J = 5.0 Hz), 2.44 (2H, t, J = 6.9 Hz), 2.21-2.13 (2H, m), 1.42 (6H, d, J = 6.6 Hz).<br>MS m/z (M + H): 535. |
| 0446 |  | ¹H-NMR (CDCl₃) δ:<br>8.93 (1 H, s), 8.79-8.77 (1 H, m), 8.32 (1 H, s), 8.25 (1 H, d, J = 8.6 Hz), 8.10-8.09 (2H, m), 7.98 (1 H, s), 7.89 (1 H, s), 7.50-7.47 (1 H, m), 7.20-7.18 (2H, m), 4.33 (2H, t, J = 6.6 Hz), 3.27<br>(4H, t, J = 4.6 Hz), 3.03 (1 H, t, J = 6.6 Hz), 2.66-2.63 (4H, m), 2.48-2.46 (2H, m), 2.21-2.17 (2H, m), 1.40 (6H, d, J = 6.6 Hz).<br>MS m/z (M + H): 535. |

Example 0447

0447-1

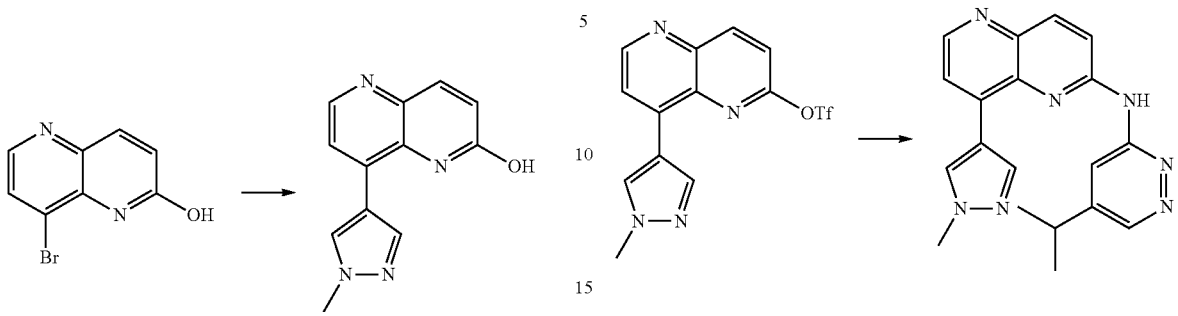

A mixture of 8-bromo-1,5-naphthyridin-2-ol (199 mg), 1-methyl-4-(4,4,5,5-tetramethyl-1,3,2-dioxaborolan-2-yl)-1H-pyrazole (202 mg), sodium carbonate (191 mg), bis(di-tert-butyl(4-dimethylaminophenyl)phosphine)dichloropalladium(II) (32 mg), 1,4-dioxane (3 mL), and water (0.3 mL) was stirred at 100° C. for 1 hour in a nitrogen atmosphere. The reaction mixture was cooled to room temperature, water and ethyl acetate were added thereto, and the organic layer was collected by separation. The organic layer was purified by silica gel column chromatography (hexane-ethyl acetate-methanol), thereby obtaining 8-(1-methyl-1H-pyrazol-4-yl)-1,5-naphthyridin-2-ol (24.7 mg) as a white solid.

MSm/z(M+H):227.

0447-2

Triethylamine (0.1 mL) was added to a mixture of 8-(1-methyl-1H-pyrazol-4-yl)-1,5-naphthyridin-2-ol (24.7 mg) and dichloromethane (2 mL) at room temperature, and trifluoromethanesulfonic acid anhydride (0.05 mL) was added thereto at a temperature of from 0° C. to 5° C., followed by stirring at 0° C. for 1.5 hours. The reaction mixture was purified by silica gel column chromatography (hexane-ethyl acetate-methanol), thereby obtaining 8-(1-methyl-1H-pyrazol-4-yl)-1,5-naphthyridin-2-yl trifluoromethanesulfonate (11.6 mg) as a yellowish green solid.

MSm/z(M+H):359.

0447-3

N-(5-isopropylpyridazin-3-yl)-8-(1-methyl-1H-pyrazol-4-yl)-1,5-naphthyridine-2-amine was obtained as a white solid in the same manner as in Example 0015-4.

$^1$H-NMR(DMSO-d$_6$)δ:10.49(1H,s),8.91(1H,s),8.87(1H,d,J=2.0 Hz),8.66(1H,d,J=4.6 Hz),8.35(1H,s),8.27(1H,d,J=9.2 Hz),8.00(1H,s),7.95(1H,d,J=8.6 Hz),7.83(1H,d,J=4.6 Hz),3.95(3H,s),1.20(6H,d,J=7.3 Hz).

MSm/z(M+H):346.

Example 0448

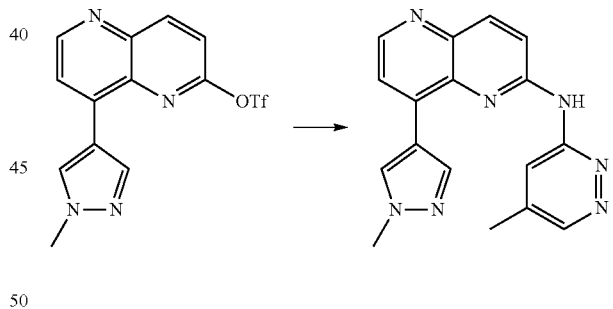

8-(1-Methyl-1H-pyrazol-4-yl)-N-(5-methylpyridazin-3-yl)-1,5-naphthyridine-2-amine was obtained as a yellow solid in the same manner as in Example 0015-4.

$^1$H-NMR(DMSO-d$_6$)δ:10.56(1H,s),8.79-8.78(2H,m),8.65(1H,d,J=4.6 Hz),8.33(1H,s),8.26-8.25(2H,m),7.82(2H,t,J=4.6 Hz),3.96(3H,s),2.31(3H,s).

MSm/z(M+H):318.

Examples 0449 and 0450

The following compounds were obtained in the same manner as in Examples 0440-1 and 0015-4.

| Example No. | | |
|---|---|---|
| 0449 | | |
| 0449-1 | 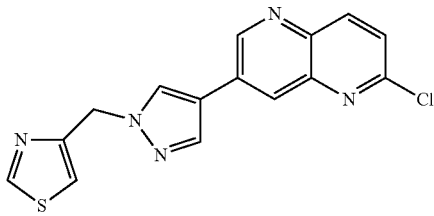 [SMILES: Clc1ccc2ncc(-c3cnn(Cc4cscn4)c3)cc2n1] | MS m/z (M + H): 328. |
| 0449-2 | 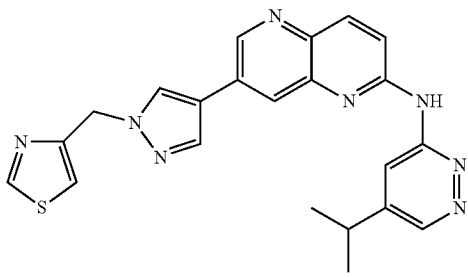 [SMILES: CC(C)c1cnnc(Nc2ccc3ncc(-c4cnn(Cc5cscn5)c4)cc3n2)c1] | ¹H-NMR (CD₃OD) δ: 9.02 (1 H, d, J = 2.0 Hz), 8.98 (1 H, d, J = 2.6 Hz), 8.85 (1 H, s), 8.77 (1 H, d, J = 2.0 Hz), 8.44 (1 H, s), 8.31-8.30 (1 H, m), 8.19-8.16 (2H, m), 7.61 (1 H, d, J = 9.2 Hz), 7.55-7.55 (1 H, m), 4.60 (2H, s), 3.08 (1 H, t, J = 3.0 Hz), 1.41 (6H, d, J = 6.6 Hz). MS m/z (M + H): 429. |
| 0450 | | |
| 0450-1 | 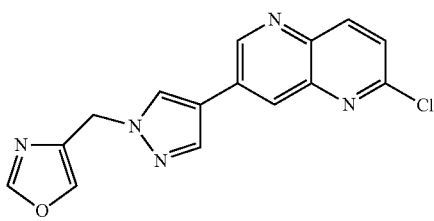 [SMILES: Clc1ccc2ncc(-c3cnn(Cc4cocn4)c3)cc2n1] | MS m/z (M + H): 312. |
| 0450-2 | 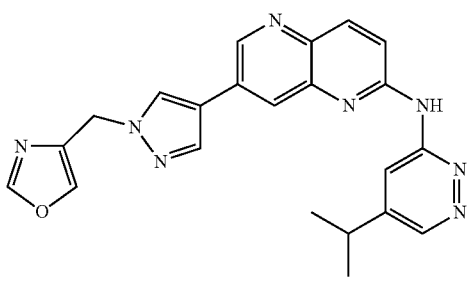 [SMILES: CC(C)c1cnnc(Nc2ccc3ncc(-c4cnn(Cc5cocn5)c4)cc3n2)c1] | ¹H-NMR (DMSO-d₆) δ: 10.70 (1 H, s), 9.05 (1 H, d, J = 2.0 Hz), 8.87 (1 H, d, J = 2.0 Hz), 8.74 (1 H, d, J = 1.3 Hz), 8.56 (1 H, s), 8.40 (1 H, s), 8.24-8.18 (4H, m), 7.70 (1 H, d, J = 9.2 Hz), 5.34 (2H, s), 3.04 (1 H, t, J = 6.9 Hz), 1.33 (6H, d, J = 7.3 Hz). MS m/z (M + H): 413. |

Example 0451

0451-1

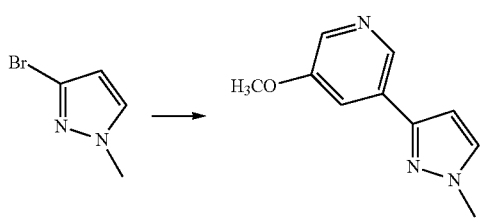

A mixture of 3-bromo-1-methyl-1H-pyrazole (112 mg), 3-methoxy-5-(4,4,5,5-tetramethyl-1,3,2-dioxaborolan-2-yl)pyridine (175 mg), sodium carbonate (133 mg), bis(di-tert-butyl(4-dimethylaminophenyl)phosphine)dichloropalladium(II) (21 mg), 1,4-dioxane (2.1 mL), and water (0.21 mL) was stirred at 100° C. for 1 hour in a nitrogen atmosphere. The reaction mixture was cooled to room temperature, and purified by silica gel column chromatography (hexane-ethyl acetate-methanol), thereby obtaining 3-methoxy-5-(1-methyl-1H-pyrazol-3-yl)pyridine (45 mg) as a pale yellow solid.

MS m/z(M+H):190.

0451-2

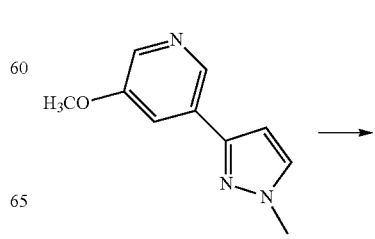

-continued

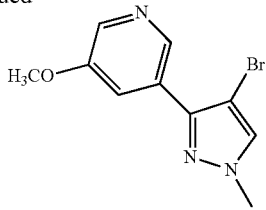

N-bromosuccinimide (23.4 mg) was added to a solution of 3-methoxy-5-(1-methyl-1H-pyrazol-3-yl)pyridine (22.3 mg) in N,N-dimethylformamide (1.2 mL), followed by stirring at room temperature for 1 hour. After a 10% sodium carbonate aqueous solution, a 10% sodium hydrogen sulfite aqueous solution, and ethyl acetate were added to the reaction mixture, the organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate), thereby obtaining 3-(4-bromo-1-methyl-1H-pyrazol-3-yl)-5-methoxypyridine (19 mg) as pale yellow oily substance.

MSm/z(M+H):268.

0451-3 and 0451-4

The following compounds were obtained in the same manner as in Examples 0421-1 and 0015-4.

| Example No. | | |
|---|---|---|
| 0451 | | |
| 0451-3 | 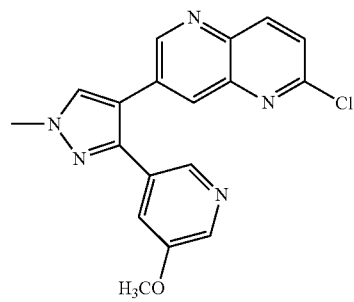 | MS m/z (M + H): 352. |
| 0451-4 | (structure) | $^1$H-NMR (CD$_3$OD) δ: 8.80 (1 H, s), 8.74 (1 H, d, J = 1.3 Hz), 8.69 (1 H, d, J = 2.0 Hz), 8.22-8.19 (4H, m), 7.98 (1 H, d, J = 1.3 Hz), 7.60 (1 H, d, J = 9.2 Hz), 7.55 (1 H, t, J = 2.3 Hz), 4.06 (3H, s), 3.81 (3H, s), 3.01 (1 H, t, J = 6.9 Hz), 1.31 (6H, d, J = 7.3 Hz). MS m/z (M + H): 453. |

Example 0452

The following compounds were obtained in the same manner as in Examples 0451-1, 0451-2, 0421-1 and 0015-4.

| Example No. | | |
|---|---|---|
| 0452 | | |
| 0452-1 | 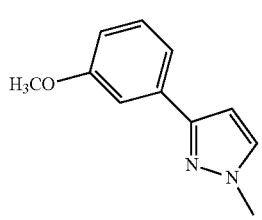 | MS m/z (M + H): 189. |

-continued

| Example No. | | |
|---|---|---|
| 0452-2 | 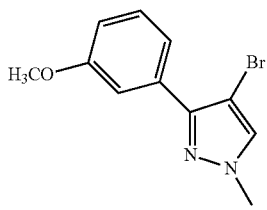 | MS m/z (M + H): 269. |
| 0452-3 | | MS m/z (M + H): 351. |
| 0452-4 | 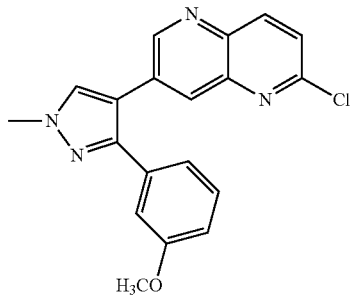 | ¹H-NMR (CDCl₃) δ: 9.37 (1 H, brs), 8.86 (1 H, d, J = 1.3 Hz), 8.79 (1 H, d, J = 2.0 Hz), 8.70 (1 H, d, J = 2.0 Hz), 8.23 (1 H, d, J = 8.6 Hz), 7.97 (1 H, d, J = 2.0 Hz), 7.70 (1 H, s), 7.62 (1 H, t, J = 4.6 Hz), 7.22 (1 H, d, J = 8.6 Hz), 7.08-7.06 (2H, m), 6.88-6.86 (1 H, m), 4.05 (3H, s), 3.73 (3H, s), 2.99 (1 H, t, J = 6.9 Hz), 1.34 (6H, d, J = 6.6 Hz). MS m/z (M + H): 452. |

Example 0453

0453-1

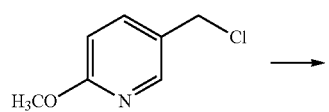

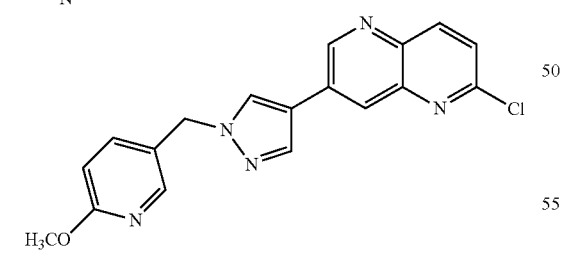

A mixture of 2-chloro-7-(1H-pyrazol-4-yl)-1,5-naphthyridine (100 mg), 5-(chloromethyl)-2-methoxypyridine (82 mg), cesium carbonate (227 mg), sodium iodide (21 mg), 1,4-dioxane (1.5 mL), and N,N-dimethylformamide (1.5 mL) was stirred at 100° C. for 1.5 hours. After the reaction mixture was cooled to room temperature, water and ethyl acetate were added thereto, the organic layer was collected by separation, washed with a saturated sodium chloride aqueous solution, and dried over anhydrous sodium sulfate, and the solvent was distilled off under reduced pressure. Ethyl acetate was added to the obtained residue, and the solid matter was collected by filtration, thereby obtaining 2-chloro-7-(1-(((6-methoxypyridin-3-yl)methyl)-1H-pyrazol-4-yl)-1,5-naphthyridine (70 mg) as a pale brown solid.

MSm/z(M+H):352.

0453-2

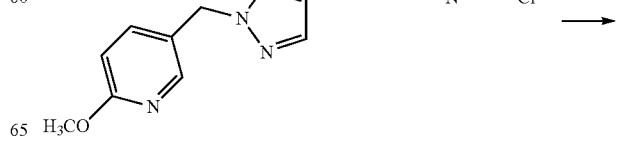

-continued

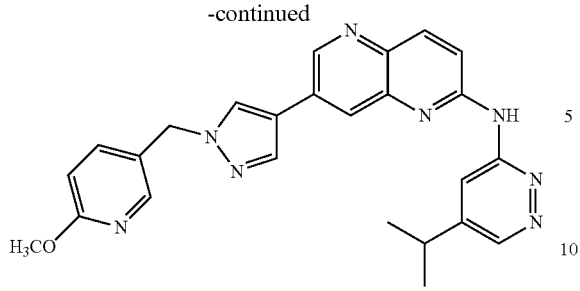

N-(5-isopropylpyridazin-3-yl)-7-(1-((6-methoxypyridin-3-yl)methyl)-1H-pyrazol-4-yl)-1,5-naphthyridine-2-amine was obtained as a pale yellow solid in the same manner as in Example 0015-4.

$^1$H-NMR(CDCl$_3$)δ:8.89(1H,d,J=2.0 Hz),8.82-8.79(3H, m),8.24-8.20(2H,m),8.09-8.06(1H,m),7.99(1H,s),7.83(1H, s),7.60-7.51(2H,m),6.79-6.78(1H,m),5.34(2H,s),3.95(3H, s),1.41(6H,d,J=7.3 Hz).

MS m/z(M+H):453.

Example 0454

The following compounds were obtained in the same manner as in Examples 0453-1 and 0015-4.

| Example No. | | |
|---|---|---|
| 0454 | | |
| 0454-1 | 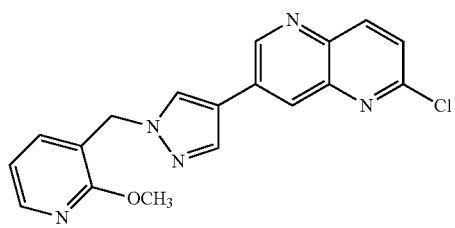 [SMILES: COc1ncccc1Cn1cc(-c2cnc3ccc(Cl)nc3c2)cn1] | MS m/z (M + H): 352. |
| 0454-2 | | $^1$H-NMR (CDCl$_3$) δ: 8.93(1 H, d, J = 2.0 Hz), 8.81 (2H, s), 8.73 (1 H, brs), 8.26-8.23 (1 H, m), 8.16-8.15 (1 H, m),8.12-8.09 (1 H, m), 8.00 (1 H, s), 7.94 (1 H, s) 7.53-7.50 (1 H, m), 7.41-7.39 (1 H, m), 6.92-6.88 (1 H, m), 5.38 (2H, s), 4.04 (3H, s), 3.04 (1 H, t, J = 7.3 Hz), 1.41 (6H, d, J = 6.6 Hz). MS m/z (M + H): 453. |

Examples 0455 and 0456

The following compounds were obtained in the same manner as in Examples 0451-1, 0451-2, 0421-1 and 0015-4.

| Example No. | | |
|---|---|---|
| 0455 | | |
| 0455-1 | 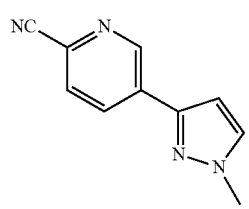 | MS m/z (M + H): 185. |

| Example No. | | |
|---|---|---|
| 0455-2 | 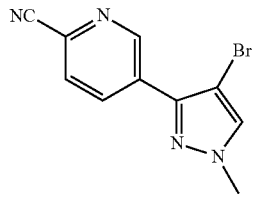 | MS m/z (M + H): 263. |
| 0455-3 | 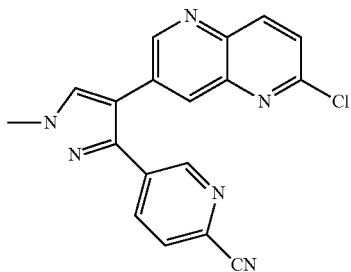 [SMILES: CN/C=C(\C(=N)c1ccc(C#N)nc1)c1cnc2ccc(Cl)nc2c1] | MS m/z (M + H): 347. |
| 0455-4 | 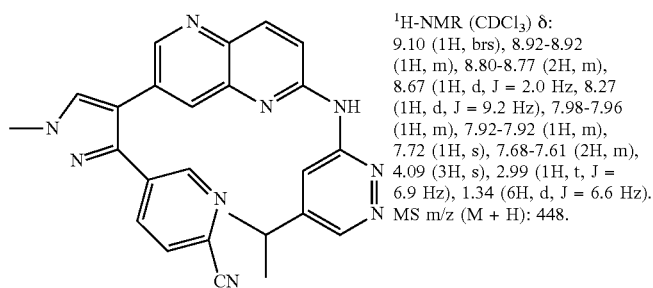 | ¹H-NMR (CDCl₃) δ: 9.10 (1H, brs), 8.92-8.92 (1H, m), 8.80-8.77 (2H, m), 8.67 (1H, d, J = 2.0 Hz, 8.27 (1H, d, J = 9.2 Hz), 7.98-7.96 (1H, m), 7.92-7.92 (1H, m), 7.72 (1H, s), 7.68-7.61 (2H, m), 4.09 (3H, s), 2.99 (1H, t, J = 6.9 Hz), 1.34 (6H, d, J = 6.6 Hz). MS m/z (M + H): 448. |
| 0456 | | |
| 0456-1 | 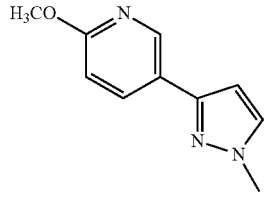 | MS m/z (M + H): 190. |
| 0456-2 | 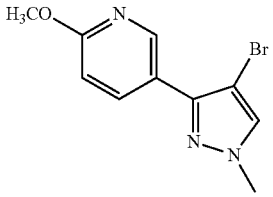 | MS m/z (M + H): 268. |
| 0456-3 | 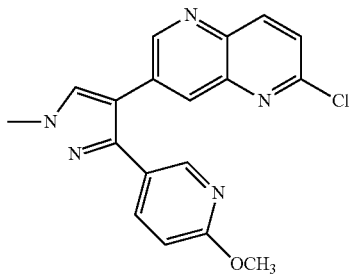 [SMILES: CN/C=C(\C(=N)c1ccc(OC)nc1)c1cnc2ccc(Cl)nc2c1] | MS m/z (M + H): 352. |

| Example No. | | |
|---|---|---|
| 0456-4 | 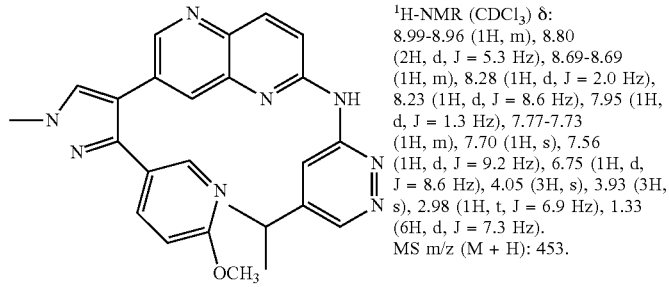 | ¹H-NMR (CDCl₃) δ: 8.99-8.96 (1H, m), 8.80 (2H, d, J = 5.3 Hz), 8.69-8.69 (1H, m), 8.28 (1H, d, J = 2.0 Hz), 8.23 (1H, d, J = 8.6 Hz), 7.95 (1H, d, J = 1.3 Hz), 7.77-7.73 (1H, m), 7.70 (1H, s), 7.56 (1H, d, J = 9.2 Hz), 6.75 (1H, d, J = 8.6 Hz), 4.05 (3H, s), 3.93 (3H, s), 2.98 (1H, t, J = 6.9 Hz), 1.33 (6H, d, J = 7.3 Hz). MS m/z (M + H): 453. |

Examples 0457 and 0458

The following compounds were obtained in the same manner as in Example 0015-4.

| Example No. | | |
|---|---|---|
| 0457 |  | ¹H-NMR (CDCl₃) δ: 8.90 (1H, d, J = 1.3 Hz), 8.74 (1H, s), 8.62 (2H, d, J = 19.2 Hz), 8.28-8.26 (1H, m), 8.01 (1H, s), 7.96 (1H, dd, J = 8.3, 2.3 Hz), 7.71 (1H, s), 7.63 (1H, t, J = 8.3 Hz), 4.09 (3H, s), 2.43 (3H, s). MS m/z (M + H): 420. |
| 0458 | 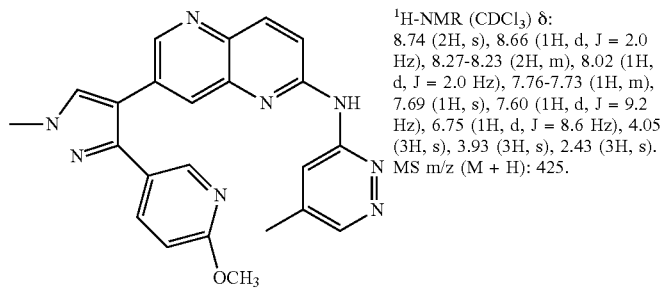 | ¹H-NMR (CDCl₃) δ: 8.74 (2H, s), 8.66 (1H, d, J = 2.0 Hz), 8.27-8.23 (2H, m), 8.02 (1H, d, J = 2.0 Hz), 7.76-7.73 (1H, m), 7.69 (1H, s), 7.60 (1H, d, J = 9.2 Hz), 6.75 (1H, d, J = 8.6 Hz), 4.05 (3H, s), 3.93 (3H, s), 2.43 (3H, s). MS m/z (M + H): 425. |

Example 0459

The following compounds were obtained in the same manner as in Examples 0451-1, 0451-2, 0421-1 and 0015-4.

| Example No. | | |
|---|---|---|
| 0459 | | |
| 0459-1 | 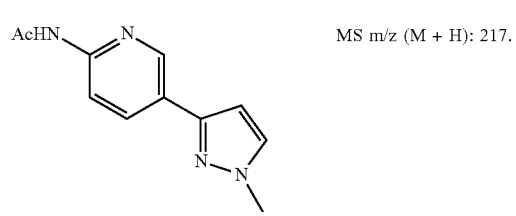 | MS m/z (M + H): 217. |

-continued
| Example No. | | |
|---|---|---|
| 0459-2 | 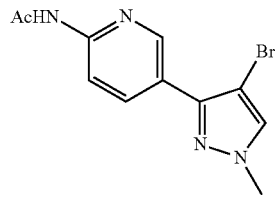 | MS m/z (M + H): 295. |
| 0459-3 | 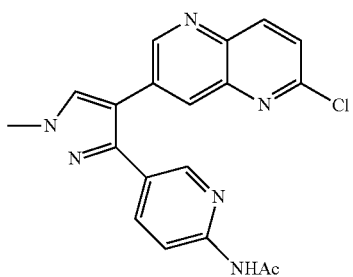 [SMILES: CN/C=C(\C(=N)c1ccc(NC(C)=O)nc1)c1cnc2ccc(Cl)nc2c1] | MS m/z (M + H): 379. |
| 0459-4 | 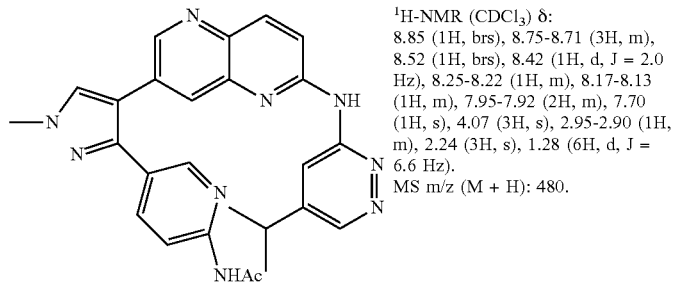 | $^1$H-NMR (CDCl$_3$) δ: 8.85 (1H, brs), 8.75-8.71 (3H, m), 8.52 (1H, brs), 8.42 (1H, d, J = 2.0 Hz), 8.25-8.22 (1H, m), 8.17-8.13 (1H, m), 7.95-7.92 (2H, m), 7.70 (1H, s), 4.07 (3H, s), 2.95-2.90 (1H, m), 2.24 (3H, s), 1.28 (6H, d, J = 6.6 Hz). MS m/z (M + H): 480. |
Example 0460
The following compounds were obtained in the same manner as in Examples 0440-1 and 0438-4.
| Example No. | | |
|---|---|---|
| 0460 | | |
| 0460-1 | 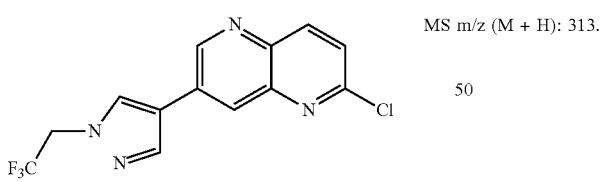 | MS m/z (M + H): 313. |
| 0460-2 | 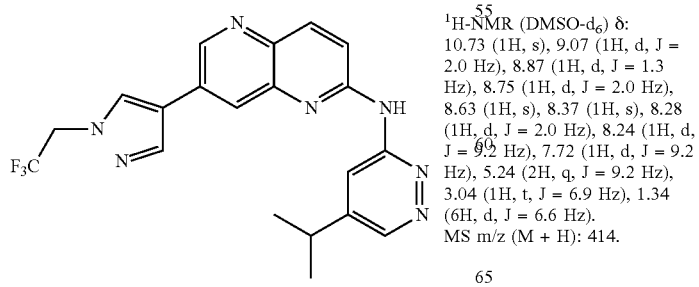 | $^1$H-NMR (DMSO-d$_6$) δ: 10.73 (1H, s), 9.07 (1H, d, J = 2.0 Hz), 8.87 (1H, d, J = 1.3 Hz), 8.75 (1H, d, J = 2.0 Hz), 8.63 (1H, s), 8.37 (1H, s), 8.28 (1H, d, J = 2.0 Hz), 8.24 (1H, d, J = 9.2 Hz), 7.72 (1H, d, J = 9.2 Hz), 5.24 (2H, q, J = 9.2 Hz), 3.04 (1H, t, J = 6.9 Hz), 1.34 (6H, d, J = 6.6 Hz). MS m/z (M + H): 414. |

Example 0461

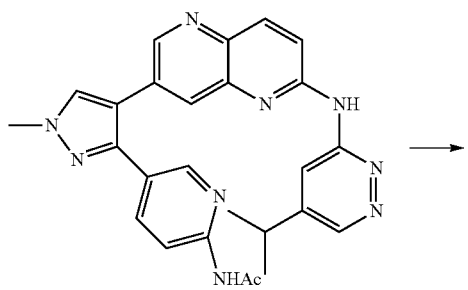

A 3 mol/L sodium hydroxide aqueous solution (1 mL) was added to a solution of N-(5-(4-(6-((5-isopropylpyridazin-3-yl)amino)-1,5-naphthyridin-3-yl)-1-methyl-1H-pyrazol-3-yl)pyridin-2-yl)acetamide (1 mg) in 1,4-dioxane (1 mL), followed by stirring at 110° C. for 3 hours. After the reaction mixture was cooled to room temperature, water and ethyl acetate were added thereto, the organic layer was collected by separation, washed with a saturated sodium chloride aqueous solution, and dried over anhydrous sodium sulfate, and the solvent was distilled off under reduced pressure, thereby obtaining 7-(3-(6-aminopyridin-3-yl)-1-methyl-1H-pyrazol-4-yl)-N-(5-isopropylpyridazin-3-yl)-1,5-naphthyridine-2-amine (1.1 mg) as a pale yellow solid.

$^1$H-NMR(CDCl$_3$)δ:8.85(1H,brs),8.75-8.71(3H,m),8.52 (1H,brs),8.42(1H,d,J=2.0 Hz),8.25-8.22(1H,m),8.17-8.13 (1H,m),7.95-7.92(2H,m),7.70(1H,s),4.07(3H,s),2.95-2.90 (1H,m),2.24(3H,s),1.28(6H,d,J=6.6 Hz).

MSm/z(M+H):438.

Example 0462

0462-1

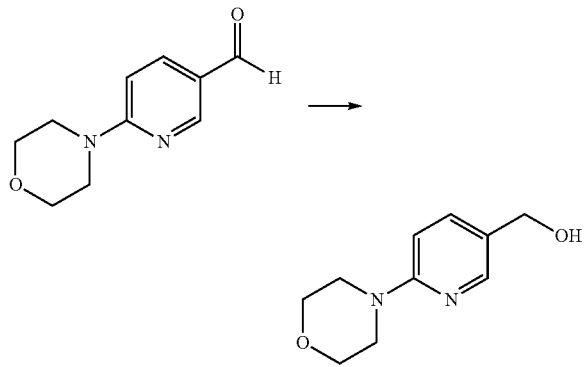

A mixture of 6-morpholinonicotinaldehyde (101.9 mg) and methanol (1.6 mL) was cooled to a temperature of from 0° C. to 5° C., and, sodium borohydride (31 mg) was added thereto, followed by stirring at room temperature for 1 minutes in a nitrogen atmosphere. Acetone was added to the reaction mixture, and the solvent was distilled off under reduced pressure. After water and ethyl acetate were added to the obtained residue, the organic layer was collected by separation, washed with a saturated sodium chloride aqueous solution, and dried over anhydrous sodium sulfate, and the solvent was distilled off under reduced pressure, thereby obtaining (6-morpholinopyridin-3-yl)methanol (88 mg) as a white solid.

MSm/z(M+H):195.

0462-2

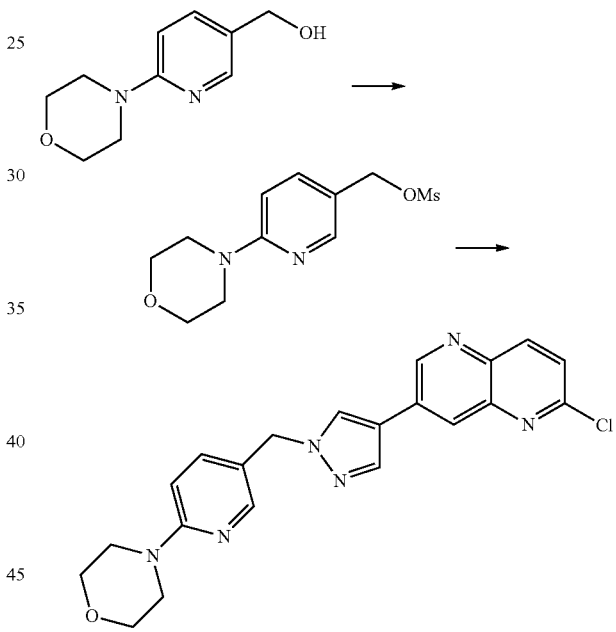

Methanesulfonyl chloride (42 μL) was added to a mixture of (6-morpholinopyridin-3-yl)methanol (88 mg), dichloromethane (2.3 mL), and triethylamine (95 μL) at a temperature of from 0° C. to 5° C., followed by stirring for 1 hour. N,N-dimethylformamide (1.1 mL) was added to the reaction mixture, and the solvent was distilled off under reduced pressure.

1,4-Dioxane (1.1 mL), 2-chloro-7-(1H-pyrazol-4-yl)-1,5-naphthyridine (50 mg) and cesium carbonate (114 mg) were added to the obtained residue, followed by stirring at 100° C. for 1 hour. After the reaction mixture was cooled to room temperature, water and ethyl acetate were added thereto, and the solid matter was collected by filtration, thereby obtaining 4-(5-((4-(6-chloro-1,5-naphthyridin-3-yl)-1H-pyrazol-1-yl)methyl)pyridin-2-yl)morpholine (53 mg) as a pale brown solid.

MSm/z(M+H):407.

0462-3

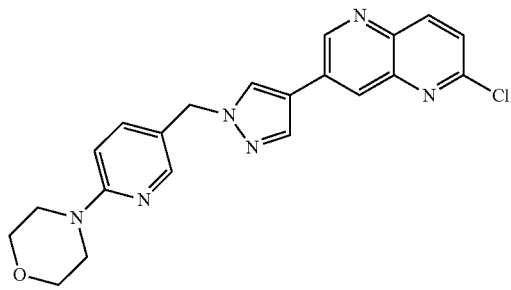

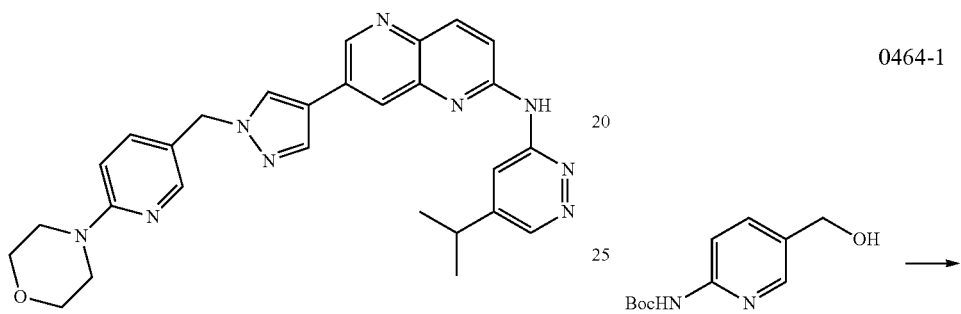

N-(5-isopropylpyridazin-3-yl)-7-(1-((6-morpholinopyridin-3-yl)methyl)-1H-pyrazol-4-yl)-1,5-naphthyridine-2-amine was obtained as a pale yellow solid in the same manner as in Example 0015-4.

¹H-NMR(DMSO-d₆)δ:10.69(1H,s),9.03(1H,d,J=2.0 Hz),8.86(1H,d,J=2.0 Hz),8.72(1H,d,J=2.0 Hz),8.58(1H,s),8.21-8.20(4H,m),7.69(1H,d,J=9.2 Hz),7.58(1H,dd,J=8.6,2.6 Hz),6.84(1H,d,J=8.6 Hz),5.28(2H,s),3.68(4H,t,J=4.6 Hz),3.42(4H,t,J=5.0 Hz),3.04(1H,t,J=10.0 Hz),1.33(6H,d,J=7.3 Hz).

MSm/z(M+H):508.

Example 0463

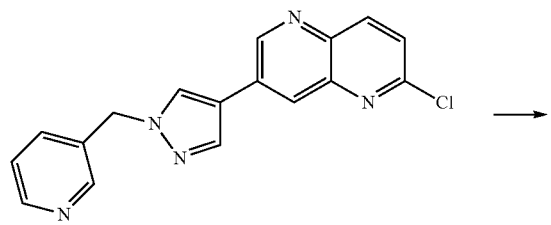

N-(5-cyclopropylpyridazin-3-yl)-7-(1-(pyridin-3-ylmethyl)-1H-pyrazol-4-yl)-1,5-naphthyridine-2-amine was obtained as a pale yellow solid in the same manner as in Example 0001-5.

¹H-NMR(CDCl₃)δ:8.97-8.93(1H,m),8.64-8.54(3H,m),8.25-8.23(1H,m),8.11-8.09(1H,m),8.03(1H,s),7.91-7.88(1H,m),7.67-7.65(1H,m),7.61(1H,s),7.39-7.32(1H,m),5.44(2H,s),2.05-2.04(1H,m),1.28-0.86(4H,m).

MSm/z(M+H):421.

Example 0464

0464-1

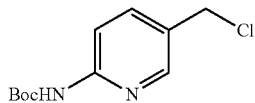

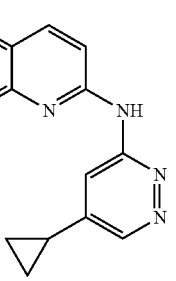

Methanesulfonyl chloride (0.14 mL) was added to a mixture of (tert-butyl (5-(hydroxymethyl)pyridin-2-yl)carbamate (133 mg), N,N-diisopropylethylamine (0.62 mL), and tetrahydrofuran (1.3 mL) at a temperature of from 0° C. to 5° C., followed by stirring at room temperature for 6 hours. After water and ethyl acetate were added to the reaction mixture, the organic layer was collected by separation, washed with a saturated sodium chloride aqueous solution, and dried over anhydrous sodium sulfate, and the solvent was distilled off under reduced pressure, thereby obtaining tert-butyl (5-(chloromethyl)pyridin-2-yl)carbamate (158 mg) as a pale brown solid.

MSm/z(M+H):243.

0464-2 and 0464-3

The following compounds were obtained in the same manner as in Examples 0453-1 and 0015-4.

| Example No. | | |
|---|---|---|
| 0464 | | |
| 0464-2 | 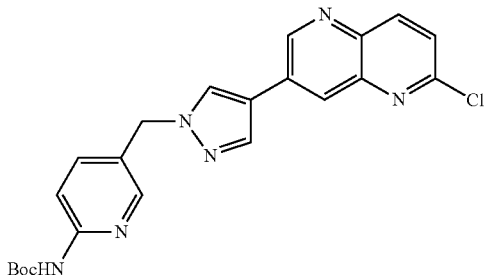 [SMILES: CC(C)(C)OC(=O)Nc1ccc(Cn2cc(-c3cnc4ccc(Cl)nc4c3)cn2)cn1] | MS m/z (M + H): 437. |
| 0464-3 | 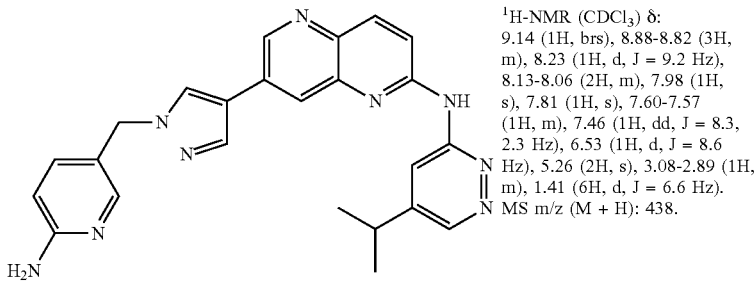 | $^1$H-NMR (CDCl$_3$) δ: 9.14 (1H, brs), 8.88-8.82 (3H, m), 8.23 (1H, d, J = 9.2 Hz), 8.13-8.06 (2H, m), 7.98 (1H, s), 7.81 (1H, s), 7.60-7.57 (1H, m), 7.46 (1H, dd, J = 8.3, 2.3 Hz), 6.53 (1H, d, J = 8.6 Hz), 5.26 (2H, s), 3.08-2.89 (1H, m), 1.41 (6H, d, J = 6.6 Hz). MS m/z (M + H): 438. |

Example 0465

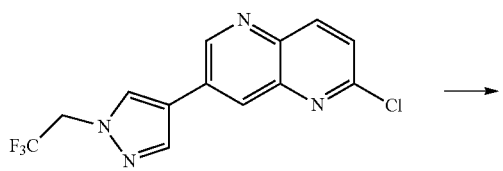

→

N-(5-cyclopropylpyridazin-3-yl)-7-(1-(2,2,2-trifluoroethyl)-1H-pyrazol-4-yl)-1,5-naphthyridine-2-amine was obtained as a pale yellow solid in the same manner as in Example 0438-4.

$^1$H-NMR(DMSO-d$_6$)δ:10.66(1H,s),9.07(1H,d,J=2.0 Hz), 8.65-8.61(3H,m),8.37(1H,s),8.32(1H,d,J=2.0 Hz),8.22(1H, d,J=9.2 Hz),7.68(1H,d,J=9.2 Hz),5.24(2H,q,J=9.0 Hz),2.09 (1H,s),1.23-1.00(4H,m).

MSm/z(M+H):412.

Examples 0466 to 0468

The following compounds were obtained in the same manner as in Examples 0440-1 and 0438-4.

| Example No. | | |
|---|---|---|
| 0466 | | |
| 0466-1 | 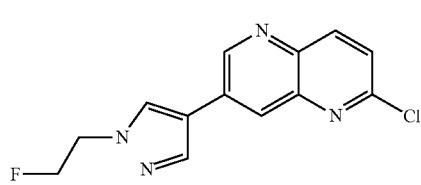 [SMILES: N=C/C(=C\NCCF)c1cnc2ccc(Cl)nc2c1] | MS m/z (M + H): 277. |

| Example No. | | |
|---|---|---|
| 0466-2 | 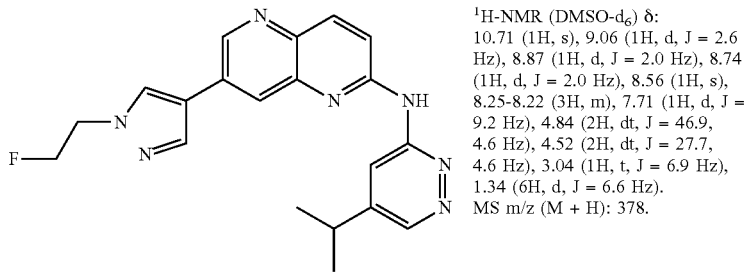 | ¹H-NMR (DMSO-d₆) δ: 10.71 (1H, s), 9.06 (1H, d, J = 2.6 Hz), 8.87 (1H, d, J = 2.0 Hz), 8.74 (1H, d, J = 2.0 Hz), 8.56 (1H, s), 8.25-8.22 (3H, m), 7.71 (1H, d, J = 9.2 Hz), 4.84 (2H, dt, J = 46.9, 4.6 Hz), 4.52 (2H, dt, J = 27.7, 4.6 Hz), 3.04 (1H, t, J = 6.9 Hz), 1.34 (6H, d, J = 6.6 Hz). MS m/z (M + H): 378. |
| 0467 | | |
| 0467-1 | 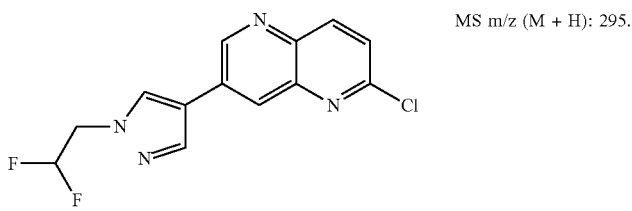 | MS m/z (M + H): 295. |
| 0467-2 | 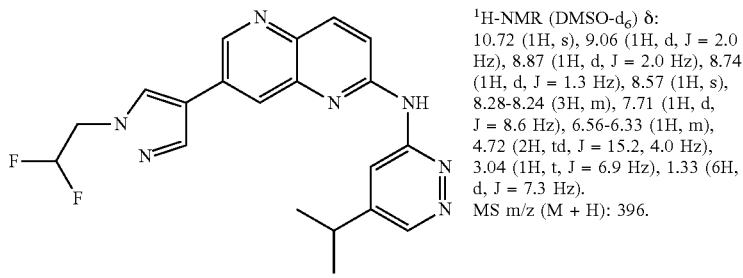 | ¹H-NMR (DMSO-d₆) δ: 10.72 (1H, s), 9.06 (1H, d, J = 2.0 Hz), 8.87 (1H, d, J = 2.0 Hz), 8.74 (1H, d, J = 1.3 Hz), 8.57 (1H, s), 8.28-8.24 (3H, m), 7.71 (1H, d, J = 8.6 Hz), 6.56-6.33 (1H, m), 4.72 (2H, td, J = 15.2, 4.0 Hz), 3.04 (1H, t, J = 6.9 Hz), 1.33 (6H, d, J = 7.3 Hz). MS m/z (M + H): 396. |
| 0468 | | |
| 0468-1 | 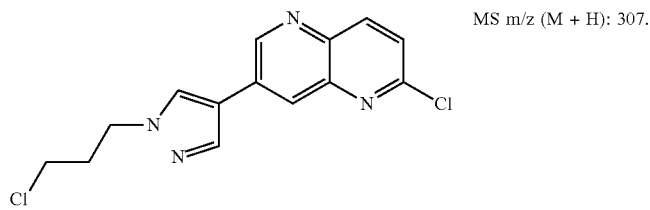 | MS m/z (M + H): 307. |
| 0468-2 | 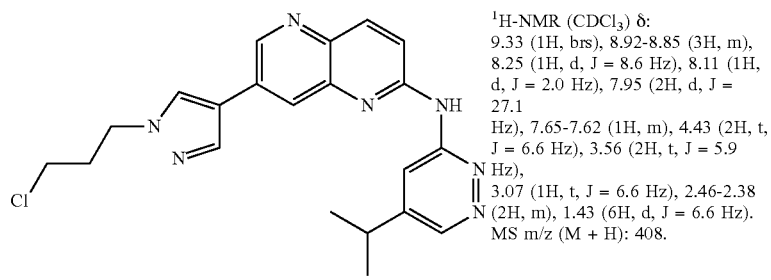 | ¹H-NMR (CDCl₃) δ: 9.33 (1H, brs), 8.92-8.85 (3H, m), 8.25 (1H, d, J = 8.6 Hz), 8.11 (1H, d, J = 2.0 Hz), 7.95 (2H, d, J = 27.1 Hz), 7.65-7.62 (1H, m), 4.43 (2H, t, J = 6.6 Hz), 3.56 (2H, t, J = 5.9 Hz), 3.07 (1H, t, J = 6.6 Hz), 2.46-2.38 (2H, m), 1.43 (6H, d, J = 6.6 Hz). MS m/z (M + H): 408. |

Example 0469

0469-1

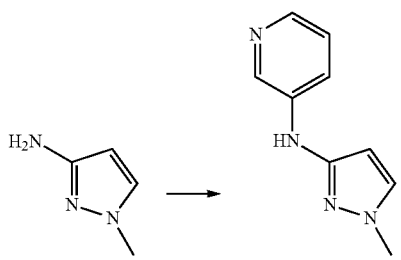

A mixture of 3-amino-1-methylpyrazole (46 µL), 3-bromopyridine (61 µL), tris(dibenzylideneacetone)dipalladium (0) (29.6 mg), 4,5-bis(diphenylphosphino)-9,9-dimethylxanthene (36.9 mg), cesium carbonate (408.5 mg), and 1,4-dioxane (3.2 mL) was stirred at 150° C. for 30 minutes using a microwave reaction apparatus. The reaction mixture was cooled to room temperature, and purified by silica gel column chromatography (hexane-ethyl acetate, NH silica), thereby obtaining N-(1-methyl-1H-pyrazol-3-yl)pyridine-3-amine (106 mg) as a pale brown solid.

MS m/z (M+H): 175.

0469-2 to 0469-4

The following compounds were obtained in the same manner as in Examples 0451-2, 0421-1, and 0015-4.

| Example No. | | |
|---|---|---|
| 0469 | | |
| 0469-2 | 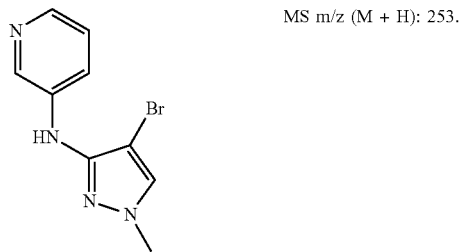 | MS m/z (M + H): 253. |
| 0469-3 | 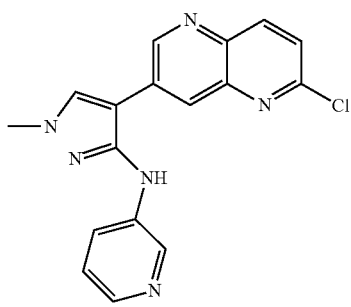 [SMILES: CN/C=C(\C(=N)Nc1cccnc1)c1cnc2ccc(Cl)nc2c1] | MS m/z (M + H): 337. |
| 0469-4 | 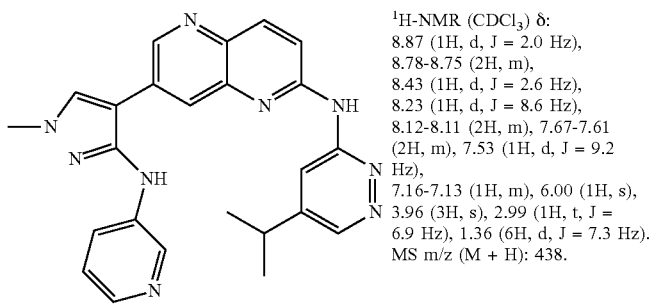 | $^1$H-NMR (CDCl$_3$) δ: 8.87 (1H, d, J = 2.0 Hz), 8.78-8.75 (2H, m), 8.43 (1H, d, J = 2.6 Hz), 8.23 (1H, d, J = 8.6 Hz), 8.12-8.11 (2H, m), 7.67-7.61 (2H, m), 7.53 (1H, d, J = 9.2 Hz), 7.16-7.13 (1H, m), 6.00 (1H, s), 3.96 (3H, s), 2.99 (1H, t, J = 6.9 Hz), 1.36 (6H, d, J = 7.3 Hz). MS m/z (M + H): 438. |

Example 0470

0470-1

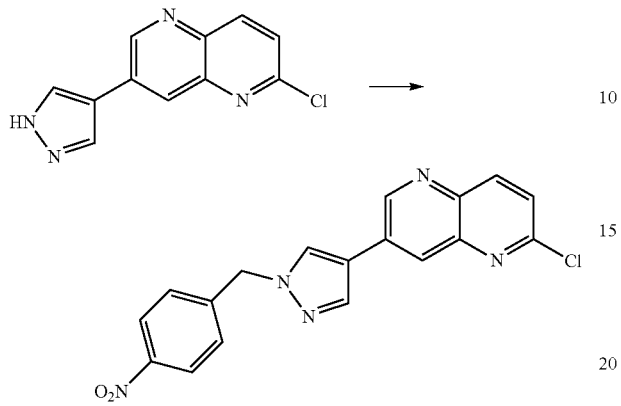

A mixture of 2-chloro-7-(1H-pyrazol-4-yl)-1,5-naphthyridine (101.6 mg), 1-(bromomethyl)-4-nitrobenzene (105.1 mg), potassium carbonate (119.2 mg), and N,N-dimethylformamide (2.2 mL) was stirred at 80° C. for 1 hour. The reaction mixture was cooled to room temperature, water and ethyl acetate were added thereto, and the solid matter was collected by filtration, thereby obtaining 2-chloro-7-(1-(4-nitrobenzyl)-1H-pyrazol-4-yl)-1,5-naphthyridine (41 mg) as a pale yellow solid.

MSm/z(M+H):366.

0470-2

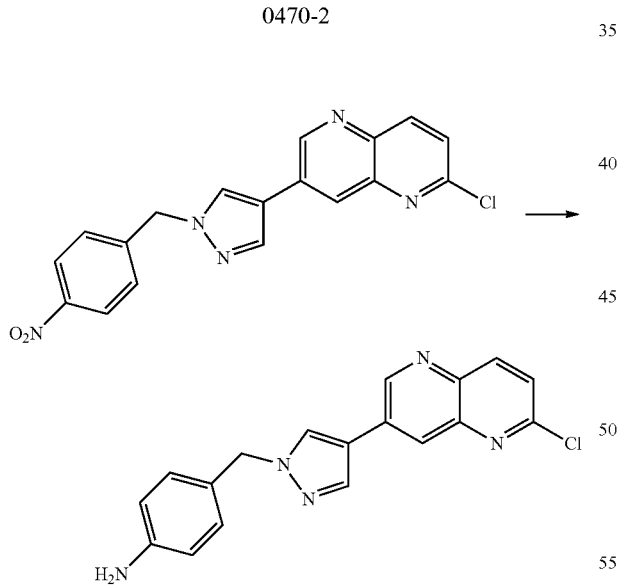

A mixture of reduced iron (21 mg), ammonium chloride (8.5 mg), 2-propanol (1.1 mL), and water (0.5 mL) was stirred at 50° C. for 30 minutes. A mixture of 2-chloro-7-(1-(4-nitrobenzyl)-1H-pyrazol-4-yl)-1,5-naphthyridine and 2-propanol (3 mL) was added to the reaction mixture, followed by stirring at 50° C. for 1.5 hours, and stirring at 70° C. for 3.5 hours. The reaction mixture was cooled to room temperature, the insolubles were filtered off, and the solvent was distilled off under reduced pressure. The obtained residue was purified by silica gel column chromatography (hexane-ethyl acetate, NH silica), thereby obtaining 4-((4-(6-chloro-1,5-naphthyridin-3-yl)-1H-pyrazol-1-yl)methyl)aniline (16.2 mg) as a pale yellow solid.

MSm/z(M+H):336.

0470-3

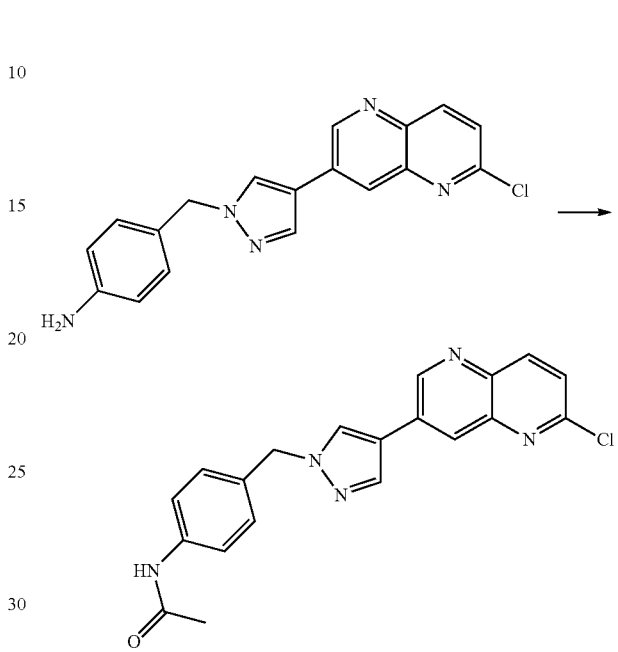

Acetic anhydride (5.5 μL) was added to a mixture of 4-((4-(6-chloro-1,5-naphthyridin-3-yl)-1H-pyrazol-1-yl)methyl)aniline (16.2 mg), and dichloromethane (1 mL), followed by stirring at room temperature for 1 hour in a nitrogen atmosphere. After water and dichloromethane were added to the reaction mixture, the organic layer was collected by separation, washed with a saturated sodium carbonate aqueous solution, and dried over anhydrous sodium sulfate, and the solvent was distilled off under reduced pressure, thereby obtaining N-(4-((4-(6-chloro-1,5-naphthyridin-3-yl)-1H-pyrazol-1-yl)methyl)phenyl)acetamide (19.2 mg) as a pale yellow solid.

MSm/z(M+H):378.

0470-4

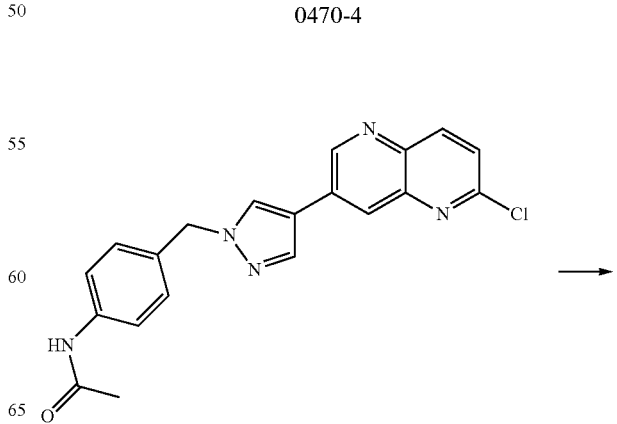

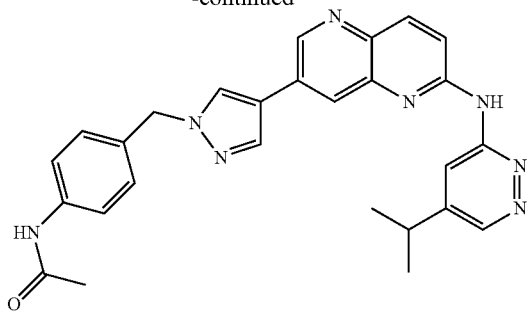

N-(4-((4-(6-((5-isopropylpyridazin-3-yl)amino)-1,5-naphthyridin-3-yl)-1H-pyrazol-1-yl)methyl)phenyl)acetamide was obtained as a yellow solid in the same manner as in Example 0015-4.

$^1$H-NMR(CDCl$_3$)δ:8.90(1H,s),8.78(2H,d,J=11.2 Hz),8.35(1H,s),8.23(1H,d,J=9.2 Hz),8.08(1H,s),8.00(1H,s),7.82(1H,s),7.55-7.52(2H,m),7.43-7.41(1H,m),7.31-7.28(2H,m),7.17(1H,s),5.37(2H,s),3.04(1H,t,J=6.9 Hz),2.19(3H,s),1.41(6H,d,J=7.3 Hz).

MSm/z(M+H):479.

Example 0471

0471-1

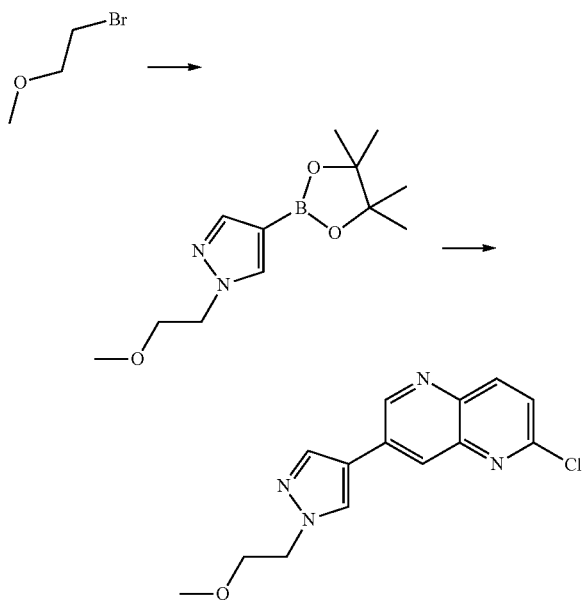

A suspension of 1-bromo-2-methoxyethane (0.064 mL), 4-(4,4,5,5-tetramethyl-1,3,2-dioxaborolan-2-yl)-1H-pyrazole (100 mg), and potassium carbonate (168 mg) in acetonitrile (2 mL) was stirred at 80° C. for 7 hours. After the reaction mixture was cooled to room temperature, ethyl acetate and water were added thereto. The organic layer was collected by separation, and dried over anhydrous sodium sulfate, and the solvent was distilled off under reduced pressure, thereby obtaining 1-(2-methoxyethyl)-4-(4,4,5,5-tetramethyl-1,3,2-dioxaborolan-2-yl)-1H-pyrazole (60 mg).

A mixture of the obtained 1-(2-methoxyethyl)-4-(4,4,5,5-tetramethyl-1,3,2-dioxaborolan-2-yl)-1H-pyrazole (31 mg), 7-bromo-2-chloro-1,5-naphthyridine (20 mg), sodium carbonate (22 mg), bis(di-tert-butyl(4-dimethylaminophenyl)phosphine)dichloropalladium(II) (6 mg), water (0.2 mL), and 1,4-dioxane (2 mL) was stirred at 100° C. for 2 hours. The reaction mixture was cooled to room temperature, the insolubles were filtered off, and the solvent was distilled off under reduced pressure. The obtained residue was purified by silica gel column chromatography (methanol-ethyl acetate), thereby obtaining 2-chloro-7-(1-(2-methoxyethyl)-1H-pyrazol-4-yl)-1,5-naphthyridine (8.1 mg).

MSm/z(M+H):289.

0471-2

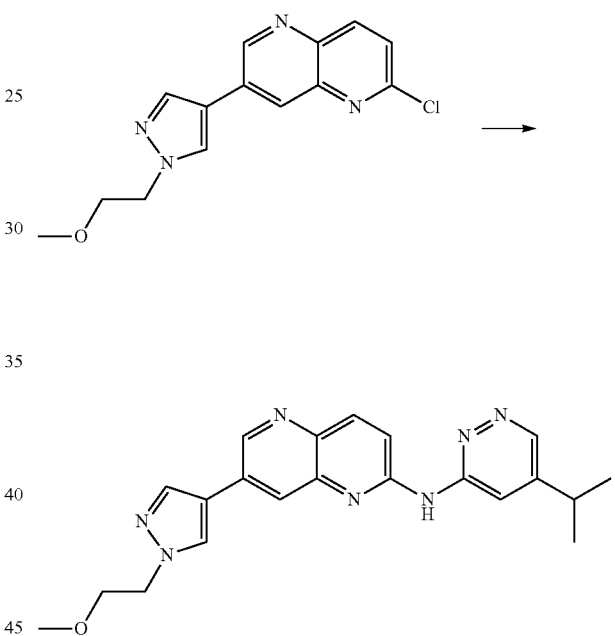

N-(5-isopropylpyridazin-3-yl)-7-(1-(2-methoxyethyl)-1H-pyrazol-4-yl)-1,5-naphthyridine-2-amine was obtained in the same manner as in Example 0015-4.

$^1$H-NMR(CDCl$_3$/CD$_3$OD=4/1)δ:8.89(2H,brs),8.72(1H,brs),8.20(1H,d,J=8.7 Hz),8.16(1H,d,J=2.1 Hz),8.04(1H,s),8.00(1H,s),7.49(1H,d,J=8.7 Hz),4.40(2H,t,J=4.5 Hz),3.83(2H,t,J=4.5 Hz),3.40(3H,s),3.15-3.00(1H,m),1.42(6H,d,J=6.6 Hz).

MSm/z(M+H):390.

Examples 0472 to 0474

The following compounds were obtained in the same manner as in Examples 0471-1 and 0015-4.

| Example No. | | |
|---|---|---|
| 0472 | | |
| 0472-1 | 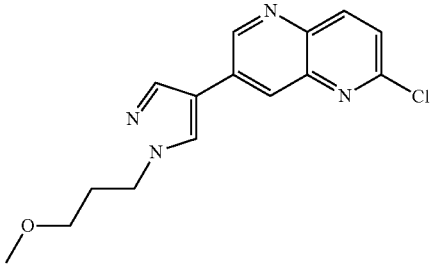 [SMILES: COCCCN/C=C(\C=N)c1cnc2ccc(Cl)nc2c1] | MS m/z (M + H): 303. |
| 0472-2 | 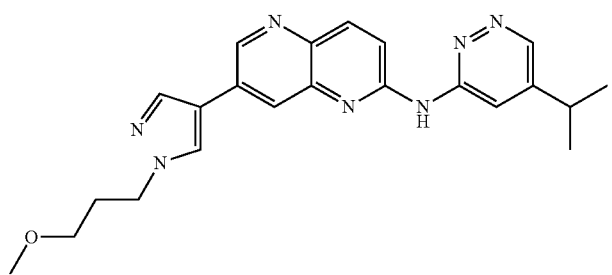 [SMILES: COCCCN/C=C(\C=N)c1cnc2ccc(Nc3cc(C(C)C)cnn3)nc2c1] | $^1$H-NMR (CDCl$_3$/CD$_3$OD = 4/1) δ: 8.90 (1H, brs), 8.89 (1H, d, J = 2.1 Hz), 8.73 (1H, m), 8.21 (1H, d, J = 9.0 Hz), 8.15 (1H, d, J = 2.1 Hz), 7.99 (1H, s), 7.98 (1H, s), 7.52 (1H, d, J = 9.0 Hz), 4.34 (2H, t, J = 7.5 Hz), 3.41 (2H, t, J = 6.0 Hz), 3.37 (3H, s), 3.15-3.00 (1H, m), 2.25-2.14 (2H, m), 1.42 (6H, d, J = 6.6 Hz). MS m/z (M + H): 404. |
| 0473 | | |
| 0473-1 | 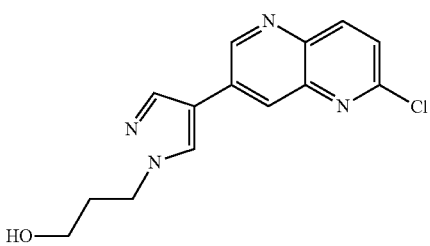 [SMILES: N=C/C(=C\NCCCO)c1cnc2ccc(Cl)nc2c1] | MS m/z (M + H): 289. |
| 0473-2 | 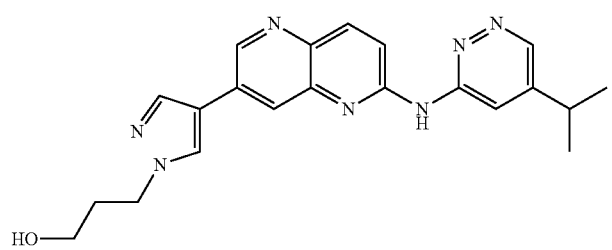 [SMILES: CC(C)c1cnnc(Nc2ccc3ncc(/C(C=N)=C/NCCCO)cc3n2)c1] | $^1$H-NMR (CDCl$_3$/CD$_3$OD = 4/1) δ: 8.88 (2H, brs), 8.72 (1H, brs), 8.20 (1H, d, J = 9.0 Hz), 8.15 (1H, brs), 8.04 (1H, s), 7.98 (1H, s), 7.50 (1H, d, J = 9.0 Hz), 4.37 (2H, t, J = 6.6 Hz), 3.63 (2H, t, J = 6.0 Hz), 3.14-3.00 (1H, m), 2.20-2.07 (2H, m), 1.42 (6H, d, J = 7.2 Hz). MS m/z (M + H): 390. |
| 0474 | | |
| 0474-1 | 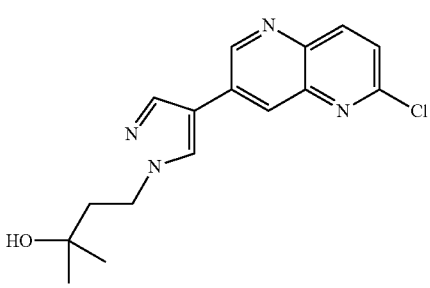 [SMILES: CC(C)(O)CCN/C=C(\C=N)c1cnc2ccc(Cl)nc2c1] | MS m/z (M + H): 317. |

| Example No. | | |
|---|---|---|
| 0474-2 | 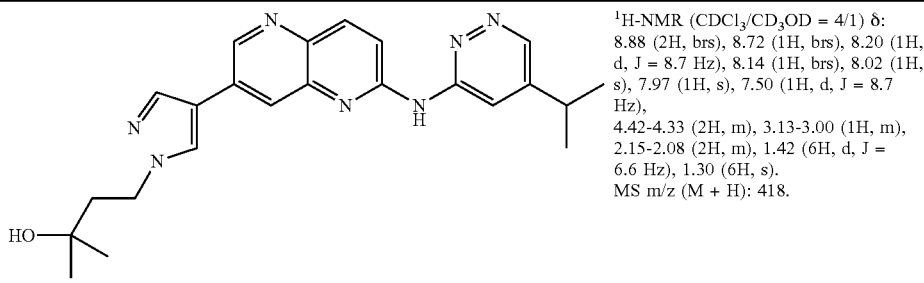 | ¹H-NMR (CDCl₃/CD₃OD = 4/1) δ: 8.88 (2H, brs), 8.72 (1H, brs), 8.20 (1H, d, J = 8.7 Hz), 8.14 (1H, brs), 8.02 (1H, s), 7.97 (1H, s), 7.50 (1H, d, J = 8.7 Hz), 4.42-4.33 (2H, m), 3.13-3.00 (1H, m), 2.15-2.08 (2H, m), 1.42 (6H, d, J = 6.6 Hz), 1.30 (6H, s). MS m/z (M + H): 418. |

Example 0475

475-1

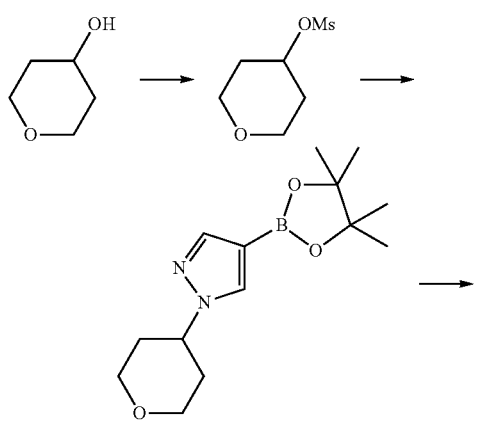

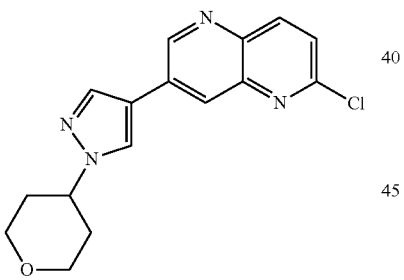

Methanesulfonyl chloride (0.138 mL) was added to a mixture of tetrahydro-2H-pyran-4-ol (166 mg), triethylamine (0.273 mL), and dichloromethane (8 mL) under ice-cooling, followed by stirring at the same temperature for 30 minutes. After water and dichloromethane were added to the reaction mixture, the organic layer was collected by separation, and dried over anhydrous sodium sulfate, and the solvent was distilled off under reduced pressure, thereby obtaining (tetrahydro-2H-pyran-4-yl) methanesulfonate (303 mg).

A suspension of the obtained (tetrahydro-2H-pyran-4-yl) methanesulfonate (303 mg), 4-(4,4,5,5-tetramethyl-1,3,2-dioxaborolan-2-yl)-1H-pyrazole (200 mg), and cesium carbonate (632 mg) in N-methylpyrrolidone (2 mL) was stirred at 100° C. for 14 hours. After the reaction mixture was cooled to room temperature, ethyl acetate and water were added thereto. The organic layer was collected by separation, washed sequentially with water and a saturated sodium chloride aqueous solution, and dried over anhydrous sodium sulfate, and the solvent was distilled off under reduced pressure, thereby obtaining 1-(tetrahydro-2H-pyran-4-yl)-4-(4,4,5,5-tetramethyl-1,3,2-dioxaborolan-2-yl)-1H-pyrazole (118 mg).

A mixture of the obtained 1-(tetrahydro-2H-pyran-4-yl)-4-(4,4,5,5-tetramethyl-1,3,2-dioxaborolan-2-yl)-1H-pyrazole (34 mg), 7-bromo-2-chloro-1,5-naphthyridine (20 mg), sodium carbonate (22 mg), bis(di-tert-butyl(4-dimethylaminophenyl)phosphine)dichloropalladium(II) (6 mg), water (0.2 mL), and 1,4-dioxane (2 mL) was stirred at 100° C. for 2 hours. The reaction mixture was cooled to room temperature, the insolubles were filtered off, and the solvent was distilled off under reduced pressure. The obtained residue was purified by silica gel column chromatography (methanol-ethyl acetate), thereby obtaining 2-chloro-7-(1-(tetrahydro-2H-pyran-4-yl)-1H-pyrazol-4-yl)-1,5-naphthyridine (15 mg).

MSm/z(M+H):315.

0475-2

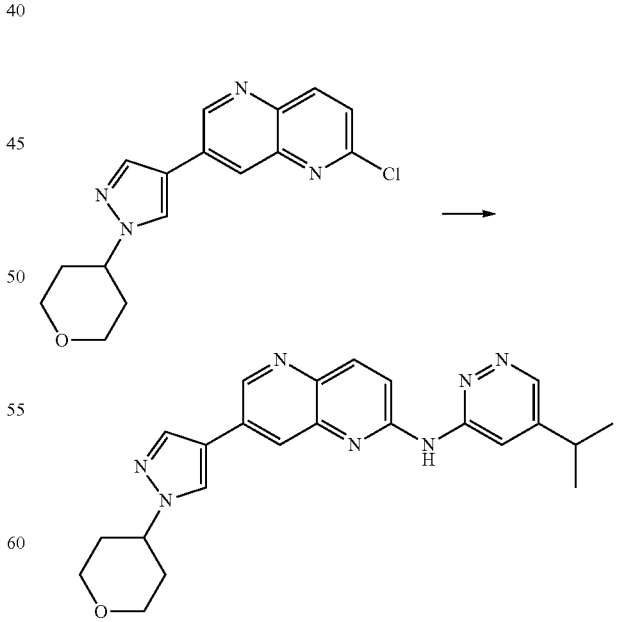

N-(5-isopropylpyridazin-3-yl)-7-(1-(tetrahydro-2H-pyran-4-yl)-1H-pyrazol-4-yl)-1,5-naphthyridine-2-amine was obtained in the same manner as in Example 0015-4.

¹H-NMR(CDCl₃/CD₃OD=4/1)δ:8.88(2H,brs),8.72(1H, brs),8.20(1H,d,J=9.0 Hz),8.15(1H,brs),8.04(1H,s),8.00(1H, s),7.51(1H,d,J=9.0 Hz),4.54-4.40(1H,m),4.22-4.12(2H,m), 3.70-3.56(2H,m),3.14-2.99(1H,m),2.25-2.13(4H,m),1.42 (6H,d,J=7.2 Hz).

MSm/z(M+H):416.

Example 0476

0476-1

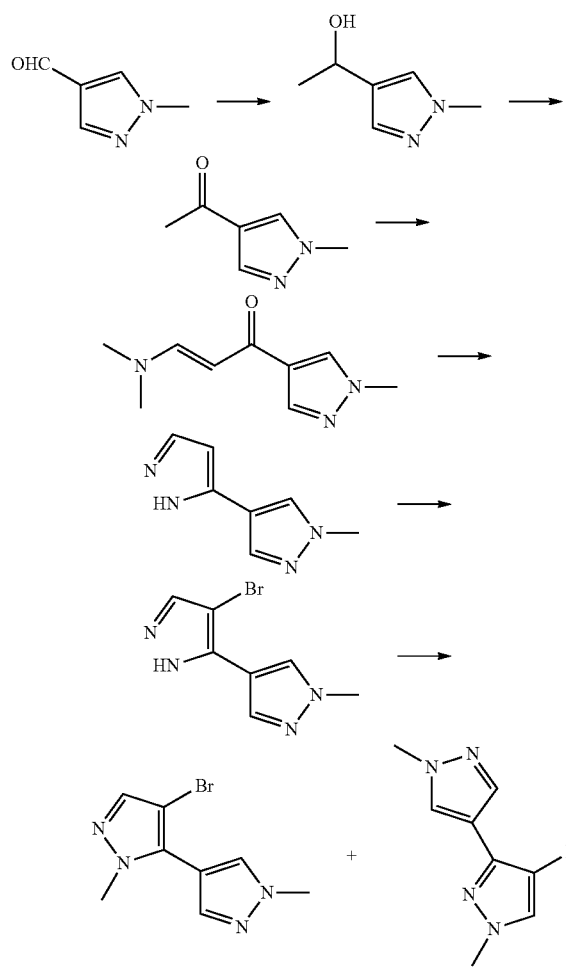

A 1 mol/L methyllithium/tetrahydrofuran solution (21 mL) was added to a mixture of 1-methyl-1H-pyrazole-4-carbaldehyde (465 mg) and tetrahydrofuran (20 mL) under ice-cooling, followed by stirring at the same temperature for 1 hour. After water and ethyl acetate were added to the reaction mixture, the organic layer was collected by separation, washed with a saturated sodium chloride aqueous solution, and dried over anhydrous sodium sulfate, and the solvent was distilled off under reduced pressure, thereby obtaining 1-(1-methyl-1H-pyrazol-4-yl)ethanol (377 mg).

A mixture of the obtained 1-(1-methyl-1H-pyrazol-4-yl) ethanol (377 mg), manganese dioxide (1.29 g), and dichloromethane (15 mL) was stirred for 12 hours under heating to reflux. The reaction mixture was cooled to room temperature, the insolubles were filtered off, and the solvent was distilled off under reduced pressure, thereby obtaining 1-(1-methyl-1H-pyrazol-4-yl)ethanone (365 mg).

A mixture of the obtained 1-(1-methyl-1H-pyrazol-4-yl) ethanone (365 mg) and N,N-dimethylformamide dimethyl acetal (2 mL) was stirred for 4 hours under heating to reflux. The reaction mixture was cooled to room temperature, and the solvent was distilled off under reduced pressure, thereby obtaining (E)-3-(dimethylamino)-1-(1-methyl-1H-pyrazol-4-yl)-2-propen-1-one (1.15 g).

Hydrazine monohydrate (0.172 mL) was added to a mixture of the obtained (E)-3-(dimethylamino)-1-(1-methyl-1H-pyrazol-4-yl)-2-propen-1-one (1.15 g) and ethanol (3 mL), followed by stirring at room temperature for 14 hours. The solvent of the reaction mixture was distilled off under reduced pressure, thereby obtaining 1'-methyl-1'H, 2H-3,4'-bipyrazole (868 mg).

N-bromosuccinimide (575 mg) was added to a solution of the obtained 1'-methyl-1'H,2H-3,4'-bipyrazole (868 mg) in N,N-dimethylformamide (6 mL) under ice-cooling, followed by stirring at the same temperature for 1 hour, and iodomethane (0.732 mL) and 60% sodium hydride (505 mg) were added thereto under ice-cooling, followed by stirring at room temperature for 1.5 hours. Ethyl acetate and water were added to the reaction mixture. The organic layer was collected by separation, washed sequentially with water and a saturated sodium chloride aqueous solution, and dried over anhydrous sodium sulfate, and the solvent was distilled off under reduced pressure. The obtained residue was purified by silica gel column chromatography (ethyl acetate-hexane, NH silica), thereby obtaining 4-bromo-1',2-dimethyl-1'H, 2H-3,4'-bipyrazole (142 mg) and 4-bromo-1,1'-dimethyl-1H,1'H-3,4'-bipyrazole (120 mg).

4-Bromo-1',2-dimethyl-1'H,2H-3,4'-bipyrazole

MSm/z(M+H):241.

4-Bromo-1,1'-dimethyl-1H,1'H-3,4'-bipyrazole

MSm/z(M+H):241.

0476-2

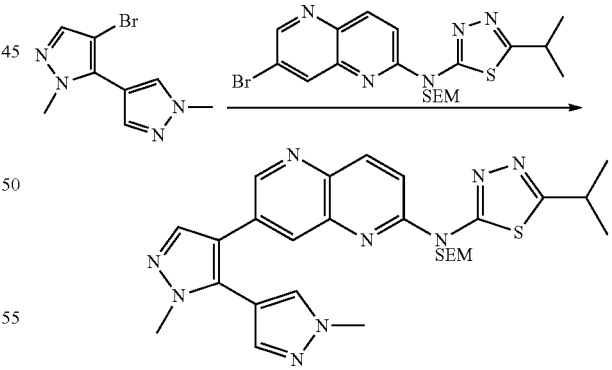

A suspension of N-(7-bromo-1,5-naphthyridin-2-yl)-5-isopropyl-N-((2-(trimethylsilyl)ethoxy)methyl)-1,3,4-thiadiazole-2-amine (20 mg), bis(pinacolato)diboron (15 mg), (1,1'-bis(diphenylphosphino)ferrocene)palladium(II) dichloride (3 mg), and potassium acetate (8 mg) in 1,4-dioxane (0.8 mL) was stirred at 100° C. for 2 hours in a nitrogen atmosphere. 4-Bromo-1',2-dimethyl-1'H,2H-3,4'-bipyrazole (15 mg), water (0.1 mL), sodium carbonate (8 mg), and bis(di-tert-butyl(4-dimethylaminophenyl)phosphine)dichloropalladium(II) (5 mg) were added to the reaction mixture, followed by stirring at 100° C. for 3 hours. The reaction mixture was cooled to room temperature, the insolubles were filtered off, and the obtained residue was purified by silica gel column chromatography (methanol-ethyl acetate), thereby obtaining N-(7-(1',2-dimethyl-1'H,2H[3,4'-bipyrazole]-4-yl)-1,5-naphthyridin-2-yl)-5-isopropyl-N-((2-(trimethylsilyl)ethoxy)methyl)-1,3,4-thiadiazole-2-amine (13 mg).

MSm/z(M+H):562.

0476-3

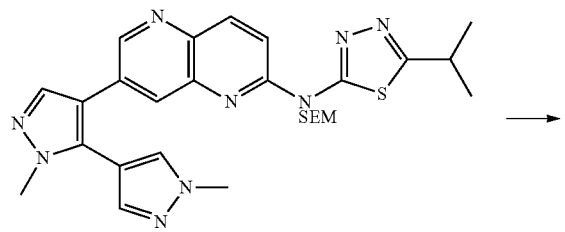

yl)-1,5-naphthyridin-2-yl)-5-isopropyl-N-((2-(trimethylsilyl)ethoxy)methyl)-1,3,4-thiadiazole-2-amine (10 mg), followed by stirring at room temperature for 30 minutes. The solvent was distilled off under reduced pressure, and the obtained residue was purified by silica gel column chromatography (methanol-ethyl acetate, NH silica), thereby obtaining N-(7-(1',2-dimethyl-1'H,2H-[3,4'-bipyrazole]-4-yl)-1,5-naphthyridin-2-yl)-5-isopropyl-1,3,4-thiadiazole-2-amine (8.7 mg).

$^{1}$H-NMR(CDCl$_{3}$/CD$_{3}$OD=4/1)δ:8.58(1H,brs),8.19(1H,d,J=9.0 Hz),8.17(1H,brs),7.89(1H,s),7.57(1H,s),7.53(1H,s),7.35(1H,d,J=9.0 Hz),3.97(3H,s),3.89(3H,s),3.51-3.37(1H,m),1.50(6H,d,J=7.5 Hz).

MSm/z(M+H):432.

Example 0477

The following compounds were obtained in the same manner as in Examples 0476-2 and 0476-3.

| Example No. | | |
|---|---|---|
| 0477 | | |
| 0477-1 | 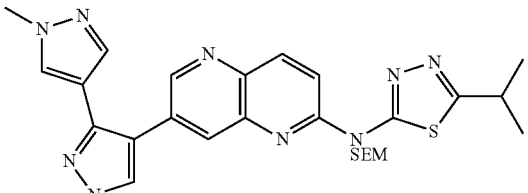 | MS m/z (M + H): 562. |
| 0477-2 | 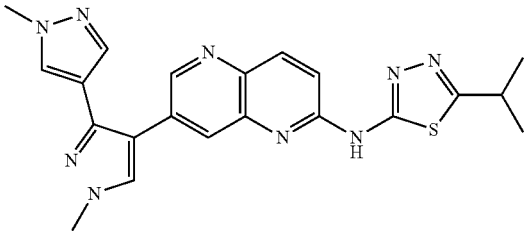 [SMILES: CN/C=C(\C(=N)c1cnn(C)c1)c1cnc2ccc(Nc3nnc(C(C)C)s3)nc2c1] | $^{1}$H-NMR (CDCl$_{3}$/CD$_{3}$OD = 4/1) δ: 8.70 (1H, d, J = 2.1 Hz), 8.25 (1H, d, J = 9.0 Hz), 8.24 (1H, d, J = 2.1 Hz), 7.72 (1H, s), 7.56 (1H, s), 7.53 (1H, s), 7.39 (1H, d, J = 9.0 Hz), 4.01 (3H, s), 3.88 (3H, s), 3.48-3.37 (1H, m), 1.48 (6H, d, J = 7.2 Hz). MS m/z (M + H): 432. |

-continued

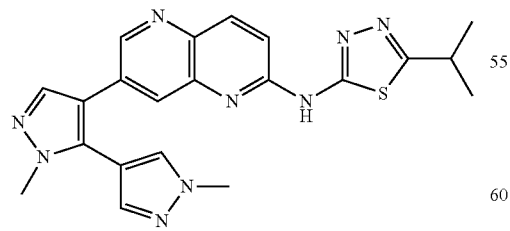

Example 0478

0478-1

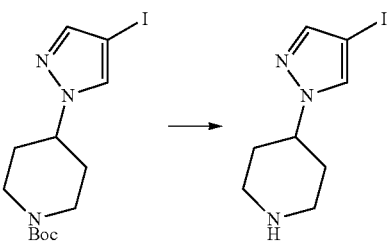 [SMILES: CC(C)(C)OC(=O)N1CCC(n2cc(I)cn2)CC1 ; Ic1cnn(C2CCNCC2)c1]

Water (0.1 mL) and trifluoroacetic acid (2 mL) were added to N-(7-(1',2-dimethyl-1'H,2H-[3,4'-bipyrazole]-4-

Water (1 mL) and trifluoroacetic acid (10 mL) were added to tert-butyl 4-(4-iodo-1H-pyrazol-1-yl)piperidine-1-carboxylate (745 mg), followed by stirring at room temperature for 1.5 hours. The solvent was distilled off under reduced pressure, and the obtained residue was purified by silica gel column chromatography (methanol-ethyl acetate, NH silica), thereby obtaining 4-(4-iodo-1H-pyrazol-1-yl)piperidine (411 mg).

MSm/z(M+H):278.

0478-2

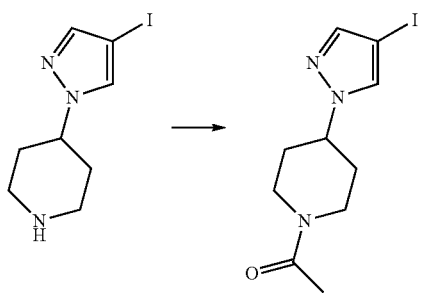

Acetyl chloride (0.051 mL) was added to a solution of 4-(4-iodo-1H-pyrazol-1-yl)piperidine (132 mg) and triethylamine (0.133 mL) in tetrahydrofuran (5 mL) under ice-cooling, followed by stirring at the same temperature for 2 hours. After water and ethyl acetate were added to the reaction mixture, the organic layer was collected by separation, washed with a saturated sodium chloride aqueous solution, and dried over anhydrous sodium sulfate, and the solvent was distilled off under reduced pressure, thereby obtaining 1-(4-(4-iodo-1H-pyrazol-1-yl)piperidin-1-yl)ethanone (150 mg).

MSm/z(M+H):320.

0478-3

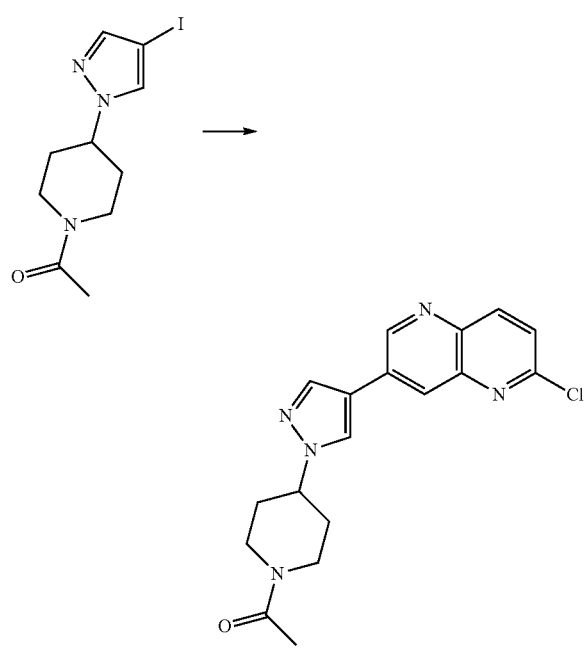

A suspension of 7-bromo-2-chloro-1,5-naphthyridine (48 mg), bis(pinacolato)diboron (60 mg), (1,1'-bis(diphenylphosphino)ferrocene)palladium(II) dichloride (16 mg), and potassium acetate (39 mg) in 1,4-dioxane (2 mL) was stirred at 80° C. for 2 hours in a nitrogen atmosphere. 1-(4-(4-Iodo-1H-pyrazol-1-yl)piperidin-1-yl)ethanone (75 mg), sodium carbonate (42 mg) and bis(di-tert-butyl(4-dimethylaminophenyl)phosphine)dichloropalladium(II) (14 mg) were added to the reaction mixture, followed by stirring at 80° C. for 3 hours. The reaction mixture was cooled to room temperature, the insolubles were filtered off, and the solvent was distilled off under reduced pressure. The obtained residue was purified by silica gel column chromatography (methanol-ethyl acetate), thereby obtaining 1-(4-(4-(6-chloro-1,5-naphthyridin-3-yl)-1H-pyrazol-1-yl)piperidin-1-yl)ethanone (35 mg).

MSm/z(M+H):356.

0478-4

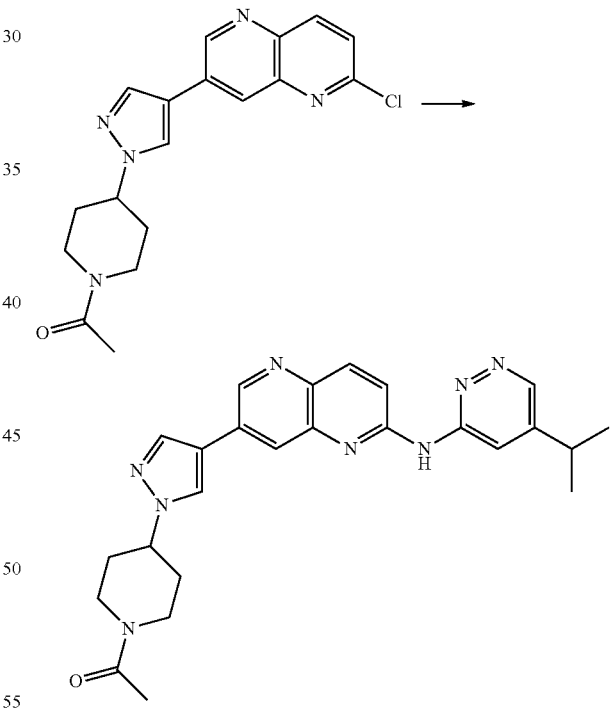

1-(4-(4-(6-((5-Isopropylpyridazin-3-yl)amino)-1,5-naphthyridin-3-yl)-1H-pyrazol-1-yl)piperidin-1-yl)ethanone was obtained in the same manner as in Example 0015-4.

$^1$H-NMR(CDCl$_3$/CD$_3$OD=4/1):8.88,(2H,brs),8.73(1H,brs),8.10(1H,d,J=9.3 Hz),8.15(1H,brs),8.04(1H,s),8.00(1H,s),7.52(1H,d,J=9.3 Hz),4.79-4.71(1H,m),4.54-4.43(1H,m),4.15-4.02(1H,m),3.38-3.28(3H,m),3.12-3.02(1H,m),2.90-2.79(1H,m),2.38-2.22(1H,m),2.19(3H,s),2.15-1.98(1H,m),1.42(6H,d,J=7.4 Hz).

MSm/z(M+H):457.

Example 0479

0479-1

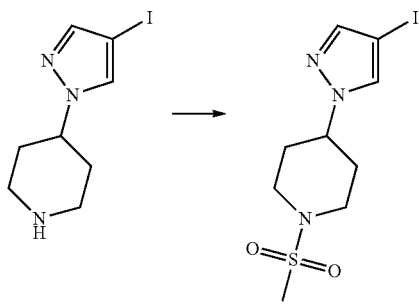 [SMILES: Ic1cnn(C2CCNCC2)c1 ; CS(=O)(=O)N1CCC(n2cc(I)cn2)CC1]

Methanesulfonyl chloride (0.057 mL) was added to a solution of 4-(4-iodo-1H-pyrazol-1-yl)piperidine (132 mg) and triethylamine (0.133 mL) in tetrahydrofuran (5 mL) under ice-cooling, followed by stirring at the same temperature for 2 hours. After water and ethyl acetate were added to the reaction mixture, the organic layer was collected by separation, washed with a saturated sodium chloride aqueous solution, and dried over anhydrous sodium sulfate, and the solvent was distilled off under reduced pressure, thereby obtaining 4-(4-iodo-1H-pyrazol-1-yl)-1-(methylsulfonyl)piperidine (151 mg).

MSm/z(M+H):356.

0479-2 and 0479-3

The following compounds were obtained in the same manner as in Examples 0478-3 and 0015-4.

| Example No. | | |
|---|---|---|
| 0479 | | |
| 0479-2 | 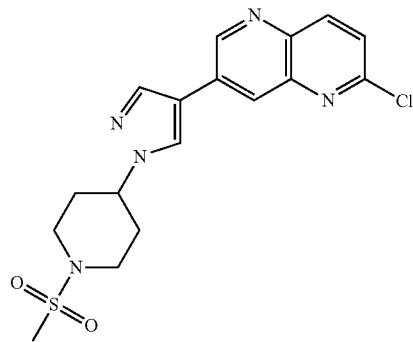 [SMILES: CS(=O)(=O)N1CCC(N/C=C(\C=N)c2cnc3ccc(Cl)nc3c2)CC1] | MS m/z (M + H): 392. |
| 0479-3 | 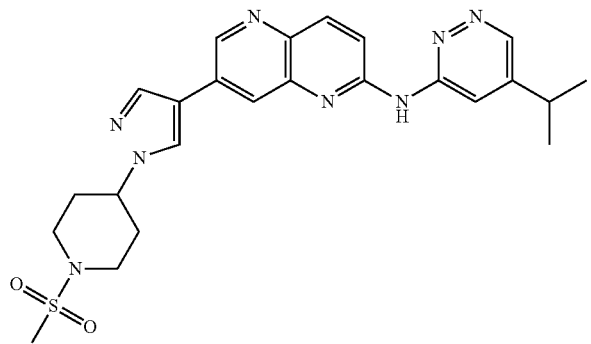 [SMILES: CC(C)c1cnnc(Nc2ccc3ncc(/C(C=N)=C/NC4CCN(S(C)(=O)=O)CC4)cc3n2)c1] | $^1$H-NMR (CDCl$_3$/CD$_3$OD = 4/1) δ: 8.88 (2H, brs), 8.73 (1H, brs), 8.21 (1H, d, J = 9.3 Hz), 8.16 (1H, brs), 8.06 (1H, s), 8.00 (1H, s), 7.51 (1H, d, J = 9.3 Hz), 4.48-4.33 (1H, m), 4.03-3.93 (2H, m), 3.14-2.94 (3H, m), 2.91 (3H, s), 2.42-2.15 (4H, m), 1.42 (6H, d, J = 7.2 Hz). MS m/z (M + H): 493. |

Example 0480

0480-1

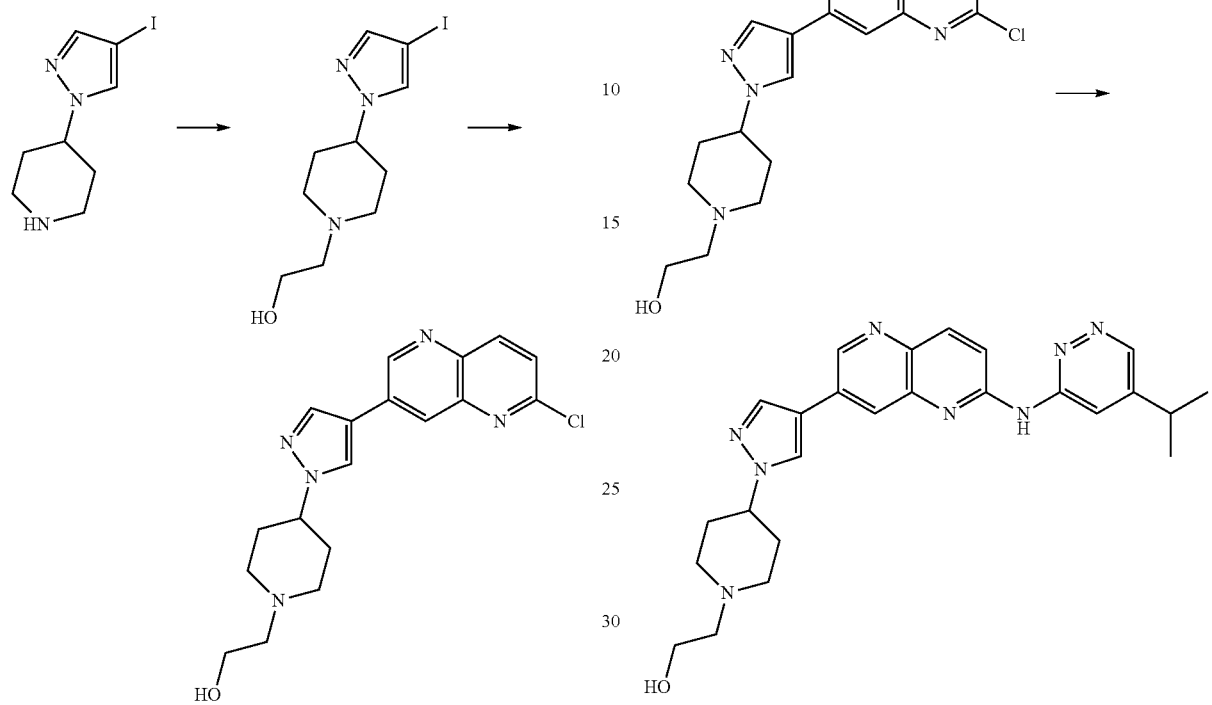

0480-2

A mixture of 4-(4-iodo-1H-pyrazol-1-yl)piperidine (147 mg), 2-bromoethanol (0.042 mL), potassium carbonate (146 mg), tetrahydrofuran (5 mL), and 1,4-dioxane (0.5 mL) was stirred at 80° C. for 2 hours. The reaction mixture was cooled to room temperature, the insolubles were filtered off, and the solvent was distilled off under reduced pressure, thereby obtaining 2-(4-(4-iodo-1H-pyrazol-1-yl)piperidin-1-yl)ethanol (250 mg).

MSm/z(M+H):322.

A suspension of 7-bromo-2-chloro-1,5-naphthyridine (48 mg), bis(pinacolato)diboron (60 mg), (1,1'-bis(diphenylphosphino)ferrocene)palladium(II) dichloride (16 mg), and potassium acetate (39 mg) in 1,4-dioxane (2 mL) was stirred at 80° C. for 2 hours in a nitrogen atmosphere. 2-(4-(4-Iodo-1H-pyrazol-1-yl)piperidin-1-yl)ethanol (75 mg), sodium carbonate (42 mg) and bis(di-tert-butyl(4-dimethylaminophenyl)phosphine)dichloropalladium(II) (14 mg) were added to the reaction mixture, followed by stirring at 80° C. for 3 hours. The reaction mixture was cooled to room temperature, the insolubles were filtered off, and the solvent was distilled off under reduced pressure. The obtained residue was purified by silica gel column chromatography (methanol-ethyl acetate), thereby obtaining 2-(4-(4-(6-chloro-1,5-naphthyridin-3-yl)-1H-pyrazol-1-yl)piperidin-1-yl)ethanol (30 mg).

MSm/z(M+H):358.

2-(4-(4-(6-((5-Isopropylpyridazin-3-yl)amino)-1,5-naphthyridin-3-yl)-1H-pyrazol-1-yl)piperidin-1-yl)ethanol was obtained in the same manner as in Example 0015-4.

$^1$H-NMR(CDCl$_3$/CD$_3$OD=4/1):8.89(2H,brs),8.72(1H,brs),8.20(1H,d,J=9.3 Hz),8.16(1H,brs),8.06(1H,s),7.99(1H,s),7.50(1H,d,J=9.3 Hz),4.33-4.20(1H,m),3.71(2H,t,J=6.0 Hz),3.20-3.00(3H,m),2.64(2H,t,J=6.0 Hz),2.40-2.07(6H,m),1.42(6H,d,J=7.2 Hz).

MSm/z(M+H):459.

Example 0481

0481-1

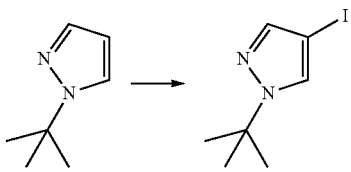

Iodine (1.59 g) and ammonium cerium nitrate (3.45 g) were added to a solution of 1-(tert-butyl)-1H-pyrazole (1.30 g) in acetonitrile (6 mL), followed by stirring at room temperature for 2 hours. After ethyl acetate and water were added to the reaction mixture, the organic layer was collected by separation, washed sequentially with a 10% sodium hydrogen sulfite aqueous solution and a saturated sodium chloride aqueous solution, and dried over anhydrous sodium sulfate, and the solvent was distilled off under reduced pressure, thereby obtaining 1-(tert-butyl)-4-iodo-1H-pyrazole (487 mg).
MSm/z(M+H):251.

0481-2 and 0481-3

The following compounds were obtained in the same manner as in Examples 0478-3 and 0015-4.

| Example No. | | |
|---|---|---|
| 0481 | | |
| 0481-2 | 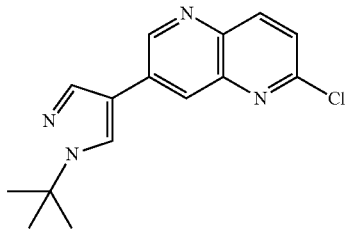 [SMILES: CC(C)(C)N/C=C(\C=N)c1cnc2ccc(Cl)nc2c1] | MS m/z (M + H): 287. |
| 0481-3 | 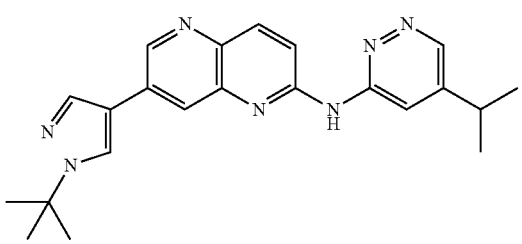 [SMILES: CC(C)c1cnnc(Nc2ccc3ncc(/C(C=N)=C/NC(C)(C)C)cc3n2)c1] | ¹H-NMR (CDCl₃/CD₃OD = 4/1) δ: 8.90 (1H, d, J = 1.8 Hz), 8.87 (1H, brs), 8.73 (1H, brs), 8.20 (1H, d, J = 9.3 Hz), 8.16 (1H, d, J = 1.8 Hz), 8.07 (1H, s), 8.00 (1H, s), 7.50 (1H, d, J = 9.3 Hz), 3.15-2.98 (1H, m), 1.69 (9H, s), 1.42 (6H, d, J = 6.6 Hz). MS m/z (M + H): 388. |

Examples 0482 to 0484

The following compounds were obtained in the same manner as in Examples 0475-1 and 0015-4.

| Example No. | | |
|---|---|---|
| 0482 | | |
| 0482-1 | 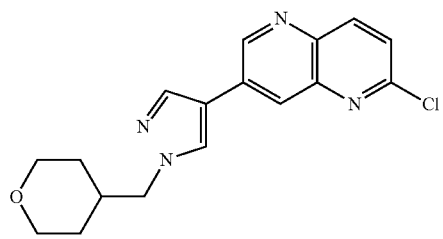 [SMILES: N=C/C(=C\NCC1CCOCC1)c1cnc2ccc(Cl)nc2c1] | MS m/z (M + H): 329. |
| 0482-2 | 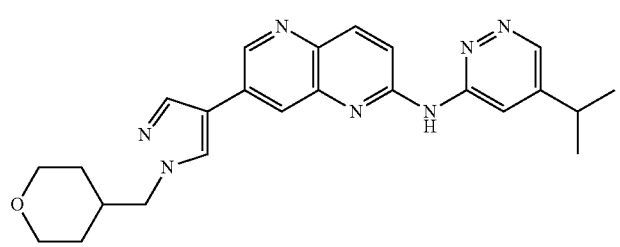 [SMILES: CC(C)c1cnnc(Nc2ccc3ncc(/C(C=N)=C/NCC4CCOCC4)cc3n2)c1] | ¹H-NMR (CDCl₃/CD₃OD = 4/1): 8.88 (2H, brs), 8.73 (1H, brs), 8.21 (1H, d, J = 9.3 Hz), 8.15 (1H, d, J = 1.8 Hz), 8.00 (1H, s), 7.96 (1H, s), 7.52 (1H, d, J = 9.3 Hz), 4.12 (2H, d, J = 6.6 Hz), 3.48-3.35 (4H, m), 3.12-3.02 (1H, m), 2.30-2.20 (1H, m), 1.64-1.54 (2H, m), 1.52-1.37 (2H, m), 1.42 (6H, d, J = 7.2 Hz). MS m/z (M + H): 430. |

| Example No. | | |
|---|---|---|
| 0483 | | |
| 0483-1 | 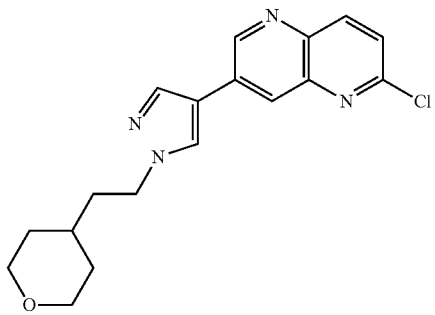 [SMILES: N=C/C(=C\NCCC1CCOCC1)c1cnc2ccc(Cl)nc2c1] | MS m/z (M + H): 343. |
| 0483-2 | 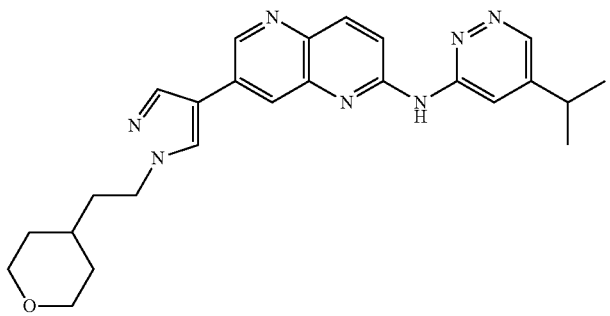 [SMILES: CC(C)c1cnnc(Nc2ccc3ncc(/C(C=N)=C/NCCC4CCOCC4)cc3n2)c1] | $^1$H-NMR (CDCl$_3$/CD$_3$OD = 4/1): 8.88 (2H, brs), 8.72 (1H, brs), 8.20 (1H, d, J = 9.3 Hz), 8.15 (1H, brs), 7.98 (1H, s), 7.97 (1H, s), 7.51 (1H, d, J = 9.3 Hz), 4.29 (2H, t, J = 7.5 Hz), 3.47-3.34 (4H, m), 3.12-3.01 (1H, m), 1.98-1.88 (2H, m), 1.74-1.65 (2H, m), 1.65-1.52 (1H, m), 1.47-1.32 (2H, m), 1.42 (6H, d, J = 7.2 Hz). MS m/z (M + H): 444. |
| 0484 | | |
| 0484-1 | 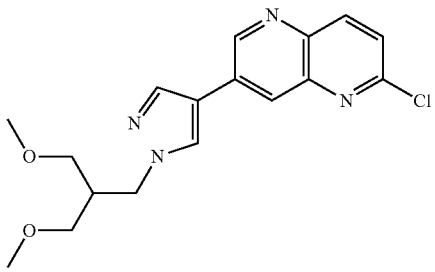 [SMILES: COCC(CN/C=C(\C=N)c1cnc2ccc(Cl)nc2c1)COC] | MS m/z (M + H): 347. |
| 0484-2 | 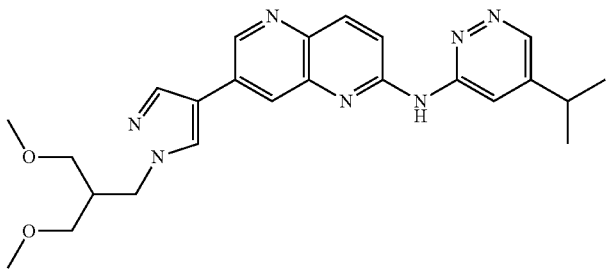 [SMILES: COCC(CN/C=C(\C=N)c1cnc2ccc(Nc3cc(C(C)C)cnn3)nc2c1)COC] | $^1$H-NMR (CDCl$_3$/CD$_3$OD = 4/1): 8.90 (1H, brs), 8.89 (1H, d, J = 2.1 Hz), 8.72 (1H, brs), 8.20 (1H, d, J = 9.3 Hz), 8.14 (1H, brs), 7.98 (1H, s), 7.95 (1H, s), 7.50 (1H, d, J = 9.3 Hz), 4.32 (2H, d, J = 7.2 Hz), 4.01 (6H, s), 3.39 (4H, d, J = 5.4 Hz), 3.15-3.01 (1H, m), 2.59-2.44 (1H, m), 1.42 (6H, d, J = 6.6 Hz). MS m/z (M + H): 448. |

Example 0485

0485-1

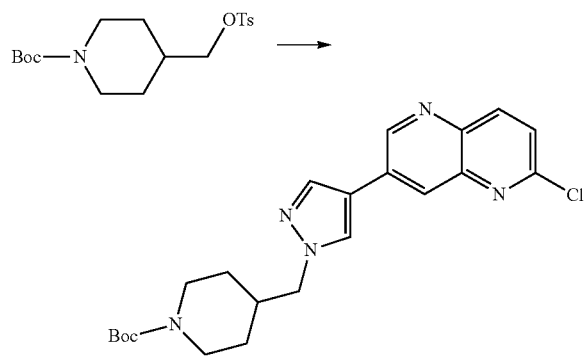

A suspension of tert-butyl 4-((paratoluenesulfonyloxy)methyl)piperidine-1-carboxylate (185 mg), 2-chloro-7-(1H-pyrazol-4-yl)-1,5-naphthyridine (115 mg), and cesium carbonate (326 mg) in N,N-dimethylformamide (1.5 mL) was stirred at 110° C. for 1.5 hours. After the reaction mixture was cooled to room temperature, ethyl acetate and water were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining tert-butyl 4-((4-(6-chloro-1,5-naphthyridin-3-yl)-1H-pyrazol-1-yl)methyl)piperidine-1-carboxylate (142 mg) as a white solid.

MS m/z(M+H):428.

0485-2

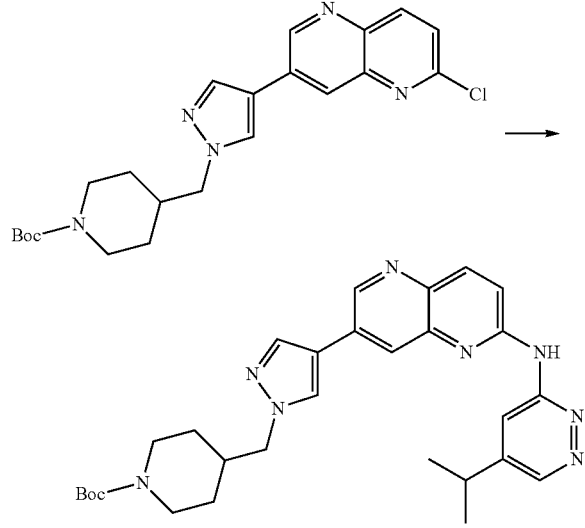

A suspension of tert-butyl 4-((4-(6-chloro-1,5-naphthyridin-3-yl)-1H-pyrazol-1-yl)methyl)piperidine-1-carboxylate (86 mg), 5-isopropylpyridazine-3-amine (30 mg), ((2-dicyclohexylphosphino-3,6-dimethoxy-2',4',6'-triisopropyl-1,1'-biphenyl)-2-(2'-amino-1,1'-biphenyl))palladium(II) methanesulfonate (BRETTPHOS PD G3 (product name, manufactured by Sigma-Aldrich Co. LLC.)) (4.5 mg), and cesium carbonate (130 mg) in 1,4-dioxane (1 mL) was stirred at 110° C. for 1 hour in a nitrogen atmosphere in a sealed tube. After the reaction mixture was cooled to room temperature, ethyl acetate and water were added thereto. The organic layer was collected by separation, washed with a saturated sodium chloride aqueous solution, and dried over anhydrous sodium sulfate, and the solvent was distilled off under reduced pressure. Ethyl acetate was added to the obtained residue, and the solid matter was collected by filtration, thereby obtaining tert-butyl 4-((4-(6-((5-isopropylpyridazin-3-yl)amino)-1,5-naphthyridin-3-yl)-1H-pyrazol-1-yl)methyl)piperidine-1-carboxylate (55 mg) as a white solid.

MS m/z(M+H):529.

0485-3

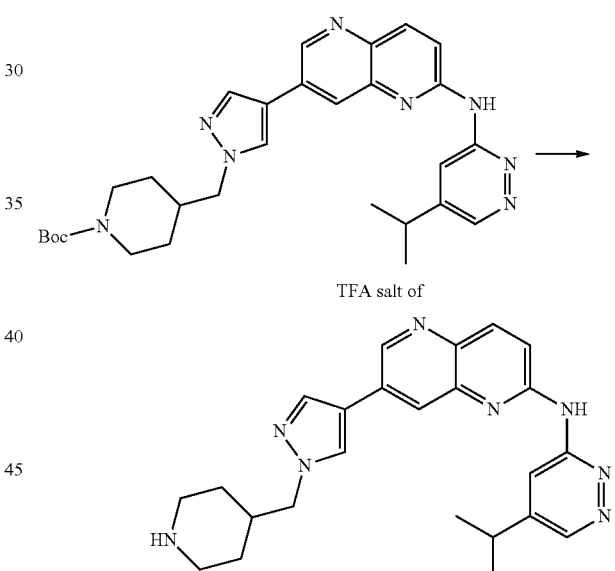

Trifluoroacetic acid (1 mL) was added to tert-butyl 4-((4-(6-((5-isopropylpyridazin-3-yl)amino)-1,5-naphthyridin-3-yl)-1H-pyrazol-1-yl)methyl)piperidine-1-carboxylate (50 mg), followed by stirring at room temperature for 30 minutes. The solvent was distilled off under reduced pressure, thereby obtaining trifluoroacetic acid salt of N-(5-isopropylpyridazin-3-yl)-7-(1-(piperidin-4-ylmethyl)-1H-pyrazol-4-yl)-1,5-naphthyridine-2-amine (39 mg) as a pale yellow solid.

$^1$H-NMR(DMSO-$d_6$)δ:9.16(1H,d,J=1.8 Hz),9.02(1H,d,J=2.1 Hz),8.65-8.54(3H,m),8.45-8.36(2H,m),8.25(1H,s),7.67(1H,d,J=9.0 Hz),4.15(2H,d,J=6.6 Hz),3.33-3.12(2H,m),3.17-3.09(1H,m),2.95-2.82(2H,m),2.25-2.15(1H,m),1.76-1.68(2H,m),1.49-1.32(8H,m).

MS m/z(M+H):429.

Example 0486

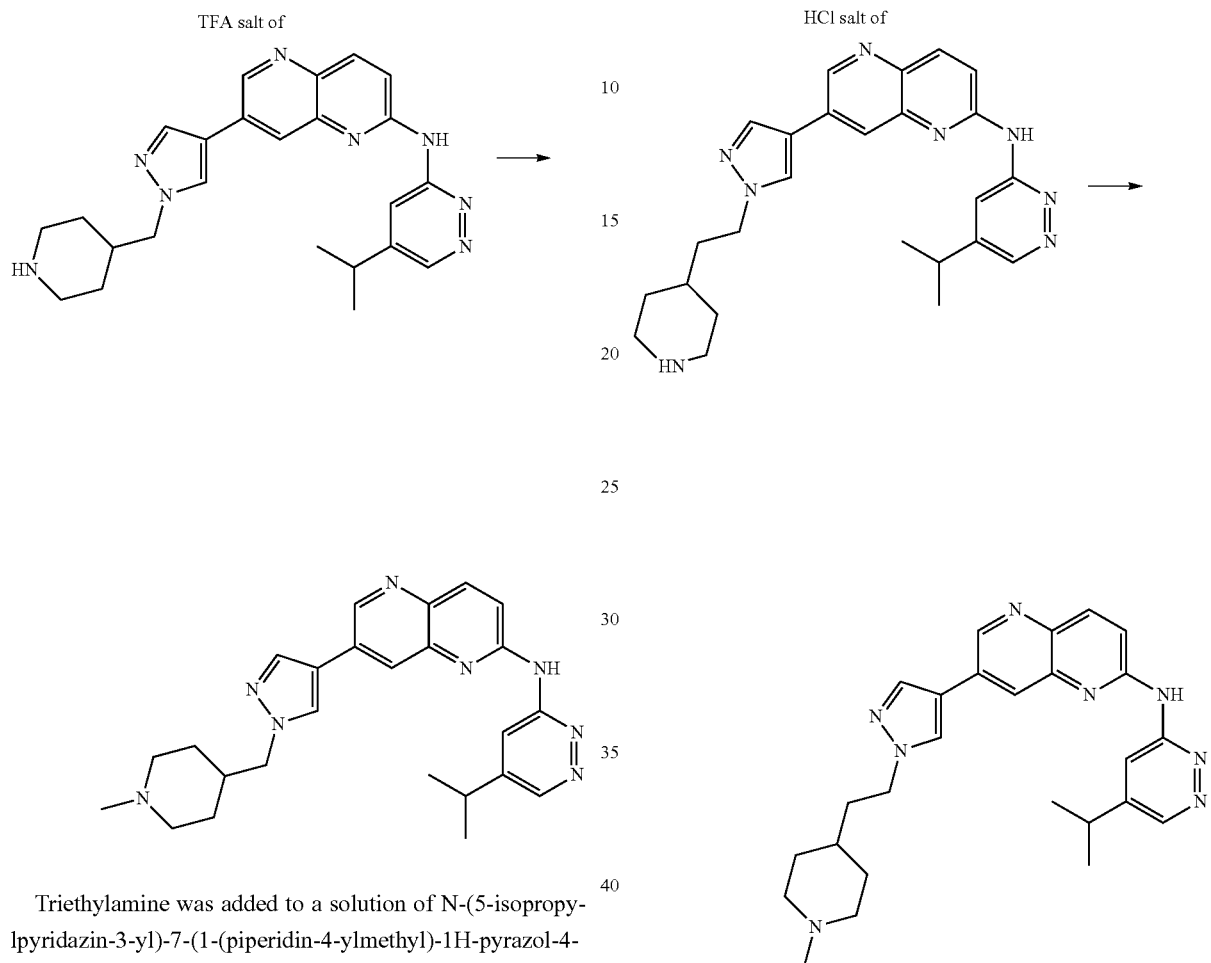

Example 0487

Triethylamine was added to a solution of N-(5-isopropylpyridazin-3-yl)-7-(1-(piperidin-4-ylmethyl)-1H-pyrazol-4-yl)-1,5-naphthyridine-2-amine, and trifluoroacetate (20 mg) in dichloromethane (0.25 mL) and methanol (0.25 mL), followed by adjusting to pH 8. A 37% (w/w) formaldehyde aqueous solution (0.1 mL) and sodium triacetoxyborohydride (40 mg) were added thereto, followed by stirring at room temperature for 30 minutes. The solvent was distilled off under reduced pressure, and the obtained residue was purified by silica gel column chromatography (ethyl acetate-methanol, NH silica), thereby obtaining N-(5-isopropylpyridazin-3-yl)-7-(1-((1-methylpiperidin-4-yl)methyl)-1H-pyrazol-4-yl)-1,5-naphthyridine-2-amine (13 mg) as a pale yellow solid.

$^1$H-NMR(DMSO-d$_6$)δ:10.70(1H,s),9.04(1H,d,J=1.8 Hz), 8.87(1H,d,J=2.1 Hz),8.73(1H,s),8.50(1H,s),8.22-8.18(3H, m),7.71(1H,d,J=9.3 Hz),4.07(2H,d,J=6.3 Hz),3.09-3.00(1H, m),2.78-2.72(2H,m),2.14(3H,s),1.87-1.78(3H,m),1.53-1.47 (2H,m),1.33(6H,d,J=5.7 Hz),1.29-1.22(2H,m).

MSm/z(M+H):443.

N-(5-isopropylpyridazin-3-yl)-7-(1-(2-(1-methylpiperidin-4-yl)ethyl)-1H-pyrazol-4-yl)-1,5-naphthyridine-2-amine was obtained as a white solid in the same manner as in Example 0486.

$^1$H-NMR(DMSO-d$_6$)δ:10.71(1H,s),9.04(1H,d,J=1.8 Hz), 8.87(1H,d,J=2.1 Hz),8.73(1H,s),8.53(1H,s),8.22-8.17(3H, m),7.72(1H,d,J=9.3 Hz),4.22-4.17(2H,m),3.09-2.99(1H,m), 2.75-2.69(2H,m),2.11(3H,s),1.81-1.73(4H,m),1.70-1.64 (2H,m),1.34(6H,d,J=5.7 Hz),1.24-1.15(3H,m).

MSm/z(M+H):457.

Example 0488

0488-1 and 0488-2

The following compounds were obtained in the same manner as in Examples 0485-1 and 0485-2.

| Example No. | | |
|---|---|---|
| 0488 | | |
| 0488-1 | 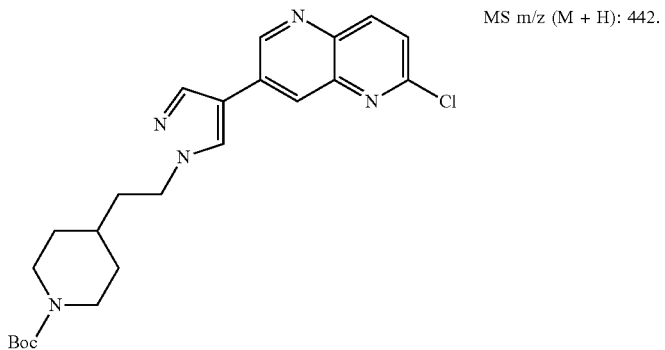 | MS m/z (M + H): 442. |
| 0488-2 | 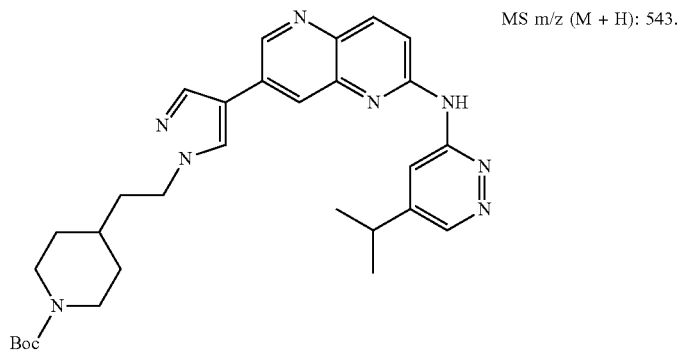 | MS m/z (M + H): 543. |
0488-3
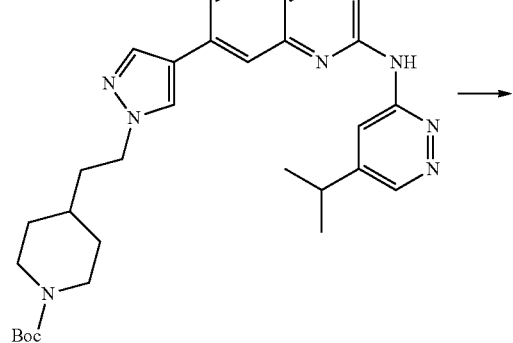
→
-continued
HCl salt of
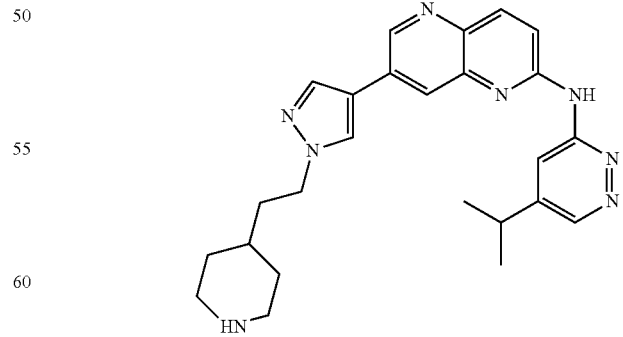
A 4 mol/L hydrogen chloride/1,4-dioxane solution (1 mL) was added to tert-butyl 4-(2-(4-(6-((5-isopropylpyridazin-3-yl)amino)-1,5-naphthyridin-3-yl)-1H-pyrazol-1-yl)ethyl)piperidine-1-carboxylate (54 mg), followed by stirring at room temperature for 1 hour. The solvent was distilled off under reduced pressure, thereby obtaining hydrochloric acid salt of N-(5-isopropylpyridazin-3-yl)-7-(1-(2-(piperidin-4-yl)ethyl)-1H-pyrazol-4-yl)-1,5-naphthyridine-2-amine (31 mg) as a white solid.

$^1$H-NMR(DMSO-d$_6$)δ:9.29(1H,d,J=1.8 Hz),9.13(1H,d,J=2.1 Hz),9.00-8.95(2H,m),8.63(1H,s),8.55(1H,d,J=9.3 Hz),8.39(1H,s),8.23(1H,s),7.88(1H,d,J=9.3 Hz),4.30-4.22 (2H,m),3.23-3.16(2H,m),2.88-2.73(2H,m),1.89-1.78(4H,m),1.56-1.32(10H,m).

MSm/z(M+H):443.

Example 0489

The following compounds were obtained in the same manner as in Examples 0014-2, 0295-3, 0295-4, and 0015-4.

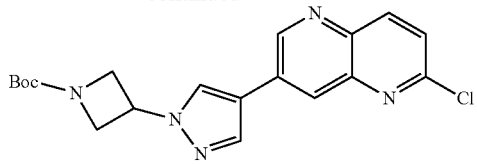

A suspension of 7-bromo-2-chloro-1,5-naphthyridine (183 mg), bis(pinacolato)diboron (190 mg), (1,1'-bis(diphenylphosphino)ferrocene)palladium(II) dichloride (46 mg), and potassium acetate (147 mg) in 1,4-dioxane (2 mL) was stirred at 100° C. for 1 hour in a nitrogen atmosphere. tert-Butyl 3-(4-bromo-1H-pyrazol-1-yl)azetidine-1-carboxylate (151 mg), sodium carbonate (106 mg) and bis(di-

| Example No. | | |
|---|---|---|
| 0489 | | |
| 0489-1 | 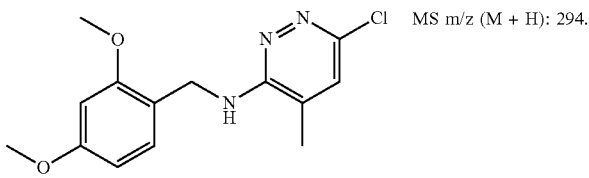 | MS m/z (M + H): 294. |
| 0489-2 | 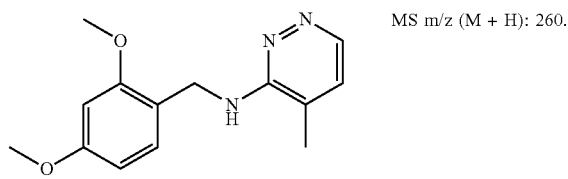 | MS m/z (M + H): 260. |
| 0489-3 | 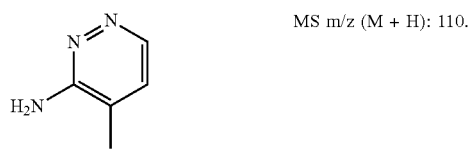 | MS m/z (M + H): 110. |
| 0489-4 | 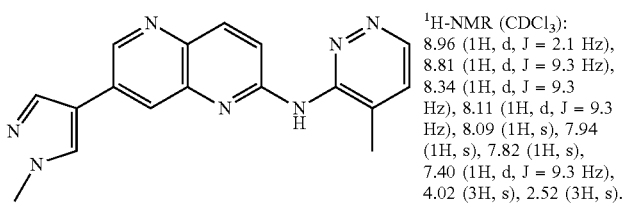 | $^1$H-NMR (CDCl$_3$): 8.96 (1H, d, J = 2.1 Hz), 8.81 (1H, d, J = 9.3 Hz), 8.34 (1H, d, J = 9.3 Hz), 8.11 (1H, d, J = 9.3 Hz), 8.09 (1H, s), 7.94 (1H, s), 7.82 (1H, s), 7.40 (1H, d, J = 9.3 Hz), 4.02 (3H, s), 2.52 (3H, s). MS m/z (M + H): 318. |

Example 0490

0490-1

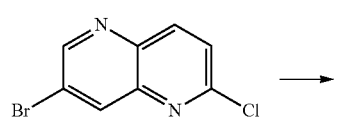

tert-butyl(4-dimethylaminophenyl)phosphine)dichloropalladium(II) (18 mg) were added to the reaction mixture, followed by stirring at 110° C. for 1 hour. After the reaction mixture was cooled to room temperature, ethyl acetate and water were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining tert-butyl 3-(4-(6-chloro-1,5-naphthyridin-3-yl)-1H-pyrazol-1-yl)azetidine-1-carboxylate (63 mg) as a white solid.

MSm/z(M+H):386.

0490-2 to 0490-4

The following compounds were obtained in the same manner as in Examples 0485-2, 0488-3, and 0486.

A suspension of 2-chloro-7-(1H-pyrazol-4-yl)-1,5-naphthyridine (115 mg), tert-butyl 3-((paratoluenesulfonyloxy)methyl)azetidine-1-carboxylate (205 mg), and potassium carbonate (138 mg) in N,N-dimethylformamide (2 mL) was

| Example No. | | |
|---|---|---|
| 0490 | | |
| 0490-2 | 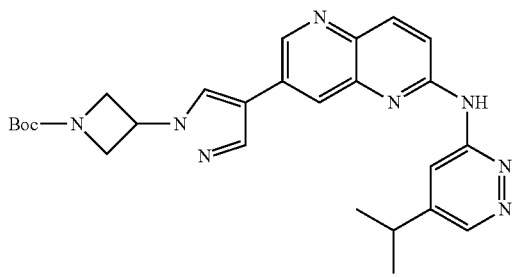 [SMILES: CC(C)c1cnnc(Nc2ccc3ncc(/C(C=N)=C/NC4CN(C(=O)OC(C)(C)C)C4)cc3n2)c1] | MS m/z (M + H): 487. |
| 0490-3 | 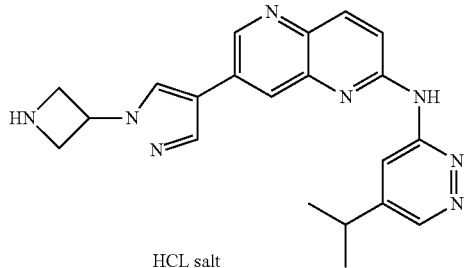 [SMILES: CC(C)c1cnnc(Nc2ccc3ncc(/C(C=N)=C/NC4CNC4)cc3n2)c1 ; "HCL salt"] HCL salt | MS m/z (M + H): 387. |
| 0490-4 | 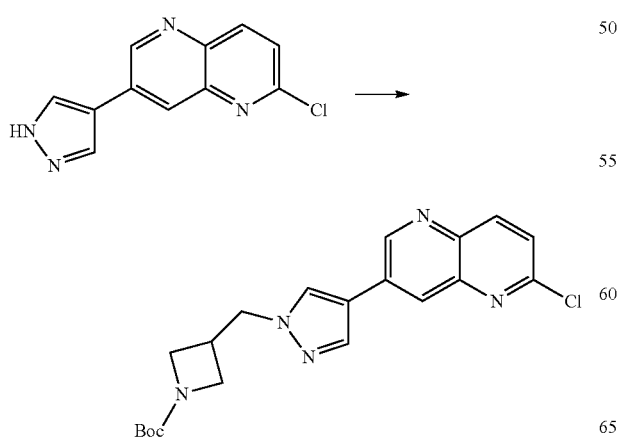 | $^1$H-NMR (DMSO-d$_6$) δ: 10.70 (1H, s), 9.06 (1H, d, J = 1.8 Hz), 8.87 (1H, d, J = 2.1 Hz), 8.72 (1H, s), 8.67 (1H, s), 8.27-8.19 (3H, m), 7.71 (1H, d, J = 9.3 Hz), 5.06-4.95 (1H, m), 3.77-3.71(2H, m), 3.47-3.40 (2H, m), 3.08-2.90 (1H, m), 2.35 (3H, s), 1.34 (6H, d, J = 6.6 Hz). MS m/z (M + H): 401. |

Example 0491

0491-1 stirred at 100° C. for 1.5 hours. After the reaction mixture was cooled to room temperature, ethyl acetate and water were added thereto. The organic layer was collected by separation, washed with a saturated sodium chloride aqueous solution, and dried over anhydrous sodium sulfate, and the solvent was distilled off under reduced pressure. Ethyl acetate was added to the obtained residue, and the solid matter was collected by filtration, thereby obtaining tert-butyl 3-((4-(6-chloro-1,5-naphthyridin-3-yl)-1H-pyrazol-1-yl)methyl)azetidine-1-carboxylate (72 mg) as a white solid.

MSm/z(M+H):400.

0491-2 to 0491-4

The following compounds were obtained in the same manner as in Examples 0485-2, 0488-3, and 0486.

| Example No. | | |
|---|---|---|
| 0491 | | |
| 0491-2 | 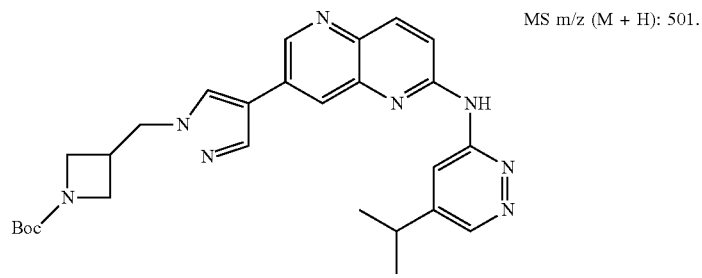 | MS m/z (M + H): 501. |
| 0491-3 | 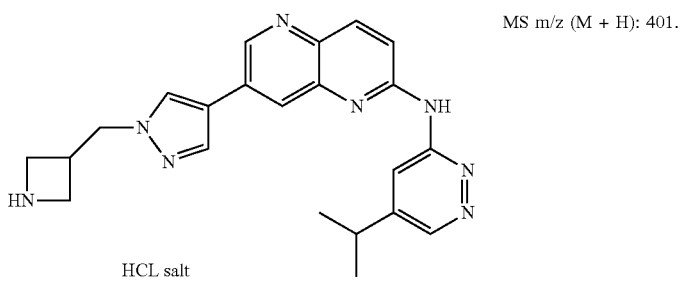  HCL salt | MS m/z (M + H): 401. |
| 0491-4 |  | $^1$H-NMR (DMSO-$d_6$) δ: 10.71 (1H, s), 9.04 (1H, d, J = 1.8 Hz), 8.87 (1H, d, J = 2.1 Hz), 8.72 (1H, s), 8.53 (1H, s), 8.22-8.17 (3H, m), 7.71 (1H, d, J = 9.3 Hz), 4.36 (2H, d, J = 7.2 Hz), 3.25-3.18 (2H, m), 3.09-2.93 (3H, m), 2.85-2.76 (1H, m), 2.19 (3H, s), 1.34 (6H, d, J = 7.2 Hz). MS m/z (M + H): 415. |
Examples 0492 and 0493
The following compounds were obtained in the same manner as in Examples 0491-1, 0485-2, 0488-3, and 0486.
| Example No. | | |
|---|---|---|
| 0492 | | |
| 0492-1 | 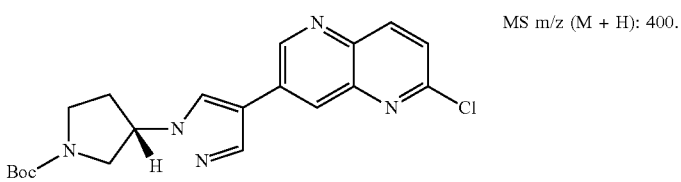 | MS m/z (M + H): 400. |
| 0492-2 | 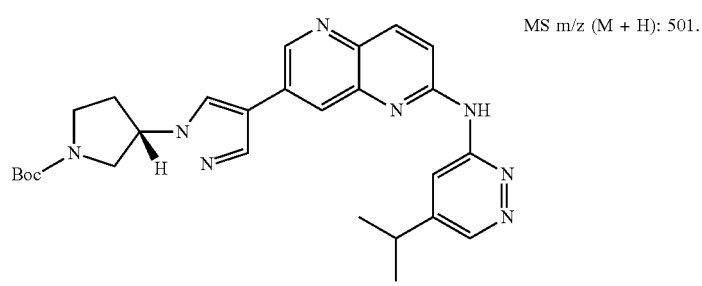 | MS m/z (M + H): 501. |

| Example No. | | |
|---|---|---|
| 0492-3 | 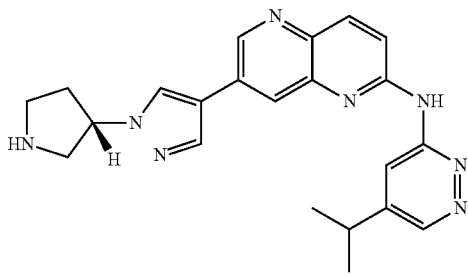 [SMILES: CC(C)c1cnnc(Nc2ccc3ncc(/C(C=N)=C/N[C@H]4CCNC4)cc3n2)c1] | MS m/z (M + H): 401. |
| 0492-4 | 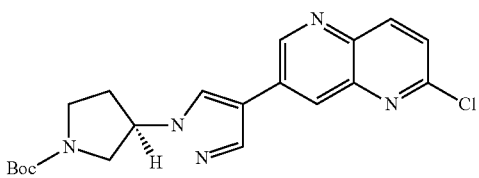 [SMILES: CC(C)(C)OC(=O)N1CC[C@@H](N/C=C(\C=N)c2cnc3ccc(Cl)nc3c2)C1] | ¹H-NMR (DMSO-d₆) δ: 10.70 (1H, s), 9.06 (1H, d, J = 1.8 Hz), 8.87 (1H, d, J = 2.1 Hz), 8.73 (1H, s), 8.57 (1H, s), 8.29-8.18 (3H, m), 7.71 (1H, d, J = 9.3 Hz), 5.01-4.93 (1H, m), 3.09-2.98 (1H, m), 2.97-2.87 (1H, m), 2.85-2.76 (2H, m), 2.59-2.51 (1H, m), 2.44-2.35 (1H, m), 2.32 (3H, s), 2.24-2.12 (1H, m), 1.34 (6H, d, J = 6.6 Hz). MS m/z (M + H): 415. |
| 0493 | | |
| 0493-1 | 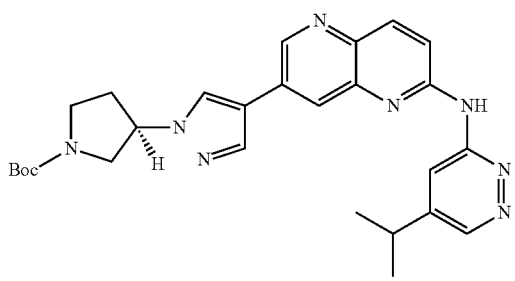 [SMILES: CC(C)c1cnnc(Nc2ccc3ncc(/C(C=N)=C/N[C@@H]4CCN(C(=O)OC(C)(C)C)C4)cc3n2)c1] | MS m/z (M + H): 400. |
| 0493-2 | | MS m/z (M + H): 501. |
| 0493-3 | 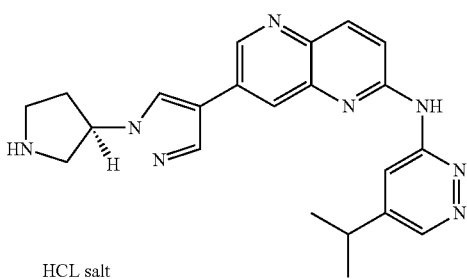 [SMILES: CC(C)c1cnnc(Nc2ccc3ncc(/C(C=N)=C/N[C@@H]4CCNC4)cc3n2)c1 ; "HCL salt"] HCL salt | MS m/z (M + H): 401. |

| Example No. | | |
|---|---|---|
| 0493-4 | 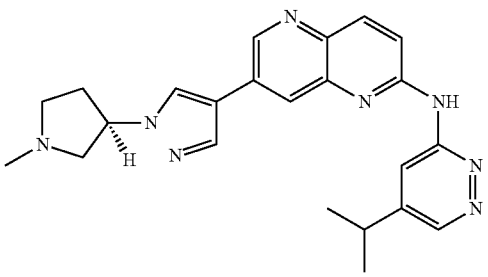 [SMILES: CC(C)c1cnnc(Nc2ccc3ncc(/C(C=N)=C/N[C@@H]4CCN(C)C4)cc3n2)c1] | ¹H-NMR (DMSO-d₆) δ: 10.70 (1H, s), 9.06 (1H, d, J = 1.8 Hz), 8.87 (1H, d, J = 2.1 Hz), 8.73 (1H, s), 8.57 (1H, s), 8.29-8.18 (3H, m), 7.71 (1H, d, J = 9.3 Hz), 5.01-4.93 (1H, m), 3.10-2.98 (1H, m), 2.97-2.87 (1H, m), 2.85-2.76 (2H, m), 2.58-2.51 (1H, m), 2.44-2.35 (1H, m), 2.32 (3H, s), 2.24-2.14 (1H, m), 1.34 (6H, d, J = 6.6 Hz). MS m/z (M + H): 415. |

Example 0494

0494-1

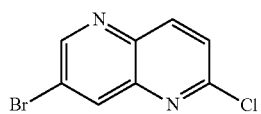 

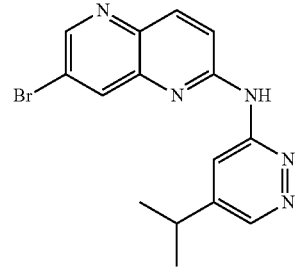

A suspension of 7-bromo-2-chloro-1,5-naphthyridine (1.22 g), 5-isopropylpyridazine-3-amine (755 mg), and potassium tert-butoxide (1.23 g) in N,N-dimethylformamide (10 mL) was stirred at room temperature for 1 hour. After ethyl acetate and water were added to the reaction mixture, the organic layer was collected by separation, washed with a saturated sodium chloride aqueous solution, and dried over anhydrous sodium sulfate, and the solvent was distilled off under reduced pressure. Toluene was added to the obtained residue, and the solid matter was collected by filtration, thereby obtaining 7-bromo-N-(5-isopropylpyridazin-3-yl)-1,5-naphthyridine-2-amine (0.92 g) as a white solid.
MSm/z(M+H):346.

0494-2

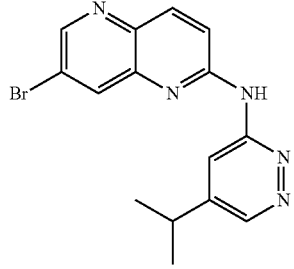 

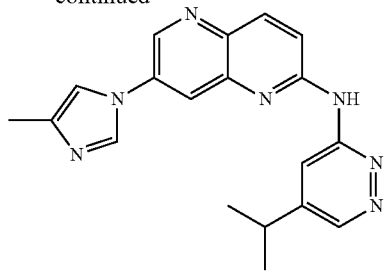

A suspension of tris(dibenzylideneacetone)dipalladium (0) (4.5 mg), 2-(di-tert-butylphosphino)-3,4,5,6-tetramethyl-2',4',6'-triisopropyl-1,1'-biphenyl (4.8 mg), and potassium phosphate (63 mg) in toluene (1 mL) was stirred at 120° C. for 3 minutes in a nitrogen atmosphere. 7-Bromo-N-(5-isopropylpyridazin-3-yl)-1,5-naphthyridine-2-amine (10 mg) and 4-methyl-1H-imidazole (7 mg) were added to the reaction mixture, followed by stirring at 120° C. for 4 hours. The insolubles were filtered off, and the solvent was distilled off under reduced pressure. The obtained residue was purified by silica gel column chromatography (ethyl acetate-methanol), thereby obtaining N-(5-isopropylpyridazin-3-yl)-7-(4-methyl-1H-imidazol-1-yl)-1,5-naphthyridine-2-amine (0.9 mg) as a white solid.
¹H-NMR(CDCl₃)δ:9.65(1H,s),8.90-8.83(3H,m),8.34(1H,d,J=9.3 Hz),8.01(1H,d,J=1.8 Hz),8.95(1H,d,J=1.2 Hz),7.80 (1H,d,J=9.3 Hz),7.18(1H,s),3.12-3.01(1H,m),2.37(3H,s), 1.42(6H,d,J=7.2 Hz).
MSm/z(M+H):346.

Example 0495

0495-1

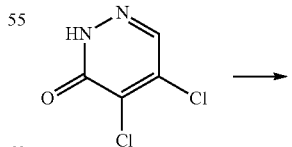

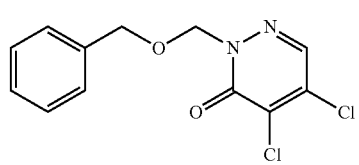

((Chloromethoxy)methyl)benzene (2.17 mL) was added to a mixture of 4,5-dichloropyridazin-3(2H)-one (2.00 g), 1,8-diazabicyclo[5.4.0]undeca-7-ene (1.85 mL), and N-methylpyrrolidone (24 mL) under ice-cooling, followed by stirring at room temperature for 1 hour. After water and ethyl acetate were added to the reaction mixture, the organic layer was collected by separation, washed sequentially with water and a saturated sodium chloride aqueous solution, and dried over anhydrous sodium sulfate, and the solvent was distilled off under reduced pressure, thereby obtaining 2-((benzyloxy)methyl)-4,5-dichloropyridazin-3(2H)-one (2.82 g).

MSm/z(M+H):285.

0495-2

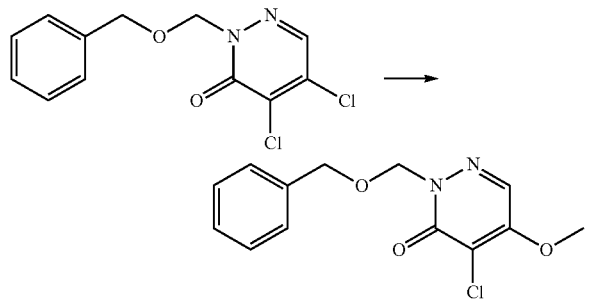

A mixture of 2-((benzyloxy)methyl)-4,5-dichloropyridazin-3(2H)-one (1.82 g), potassium carbonate (4.41 g), and methanol (13 mL) was stirred for 1 hour under heating to reflux. After the reaction mixture was cooled to room temperature, the insolubles were filtered off, and the solvent was distilled off under reduced pressure. The obtained solid matter was washed with water and ethyl acetate, thereby obtaining 2-((benzyloxy)methyl)-4-chloro-5-methoxypyridazin-3(2H)-one (942 mg).

MSm/z(M+H):281.

0495-3

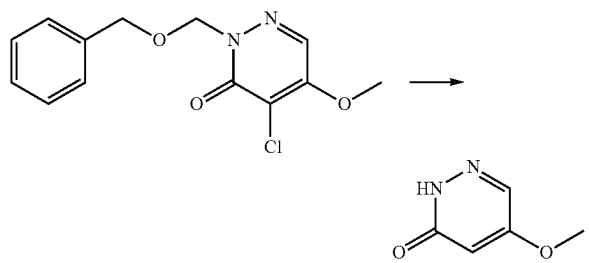

A mixture of 10% palladium/carbon (100 mg), 2-((benzyloxy)methyl)-4-chloro-5-methoxypyridazin-3(2H)-one (1.34 g), acetic acid (10 mL), and methanol (30 mL) was stirred at 50° C. for 10 hours in a hydrogen atmosphere (0.8 MPa). The insolubles were filtered off, and the solvent was distilled off under reduced pressure, thereby obtaining 5-methoxypyridazin-3(2H)-one (611 mg).

MSm/z(M+H):127.

0495-4

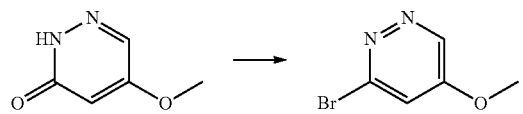

A mixture of 5-methoxypyridazin-3(2H)-one (703 mg), phosphoryl bromide (4.79 g), and acetonitrile (55 mL) was stirred for 1 hour under heating to reflux. The reaction mixture was added dropwise to a sodium carbonate aqueous solution under ice-cooling, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel chromatography (ethyl acetate-hexane), thereby obtaining 3-bromo-5-methoxypyridazine (175 mg).

MSm/z(M+H):189.

0495-5

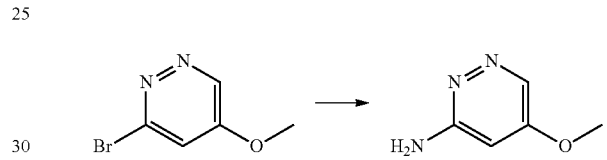

25% ammonia water (2 mL) and copper(I) oxide (61 mg) were added to a solution of 3-bromo-5-methoxypyridazine (81 mg) in 1,4-dioxane (2 mL), followed by stirring at 120° C. for 30 minutes using a microwave reaction apparatus. After the reaction mixture was cooled to room temperature, the insolubles were filtered off, and the solvent was distilled off under reduced pressure. The obtained residue was purified by silica gel column chromatography (ethyl acetate-methanol, NH silica), thereby obtaining 5-methoxypyridazine-3-amine (16 mg).

MSm/z(M+H):126.

0495-6

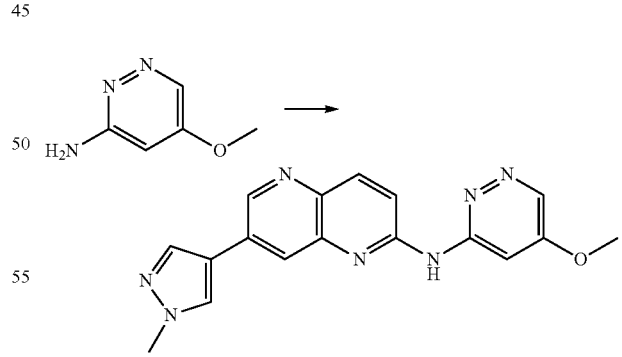

N-(5-methoxypyridazin-3-yl)-7-(1-methyl-1H-pyrazol-4-yl)-1,5-naphthyridine-2-amine was obtained in the same manner as in Example 0015-4.

$^1$H-NMR(CDCl$_3$/CD$_3$OD=4/1)δ:8.92(1H,d,J=2.4 Hz), 8.73(1H,brs),8.65(1H,brs),8.24(1H,d,J=9.3 Hz),8.08(1H,d,J=2.4 Hz),7.95(1H,s),7.86(1H,s),7.60(1H,d,J=9.3 Hz),4.08 (3H,s),4.02(3H,s).

MSm/z(M+H):334.

Example 0496

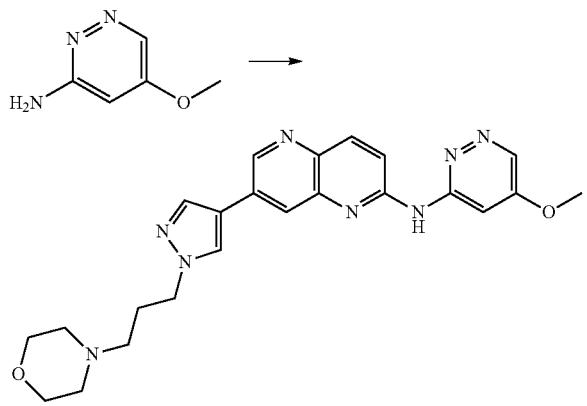

N-(5-methoxypyridazin-3-yl)-7-(1-(3-morpholinopropyl)-1H-pyrazol-4-yl)-1,5-naphthyridine-2-amine was obtained in the same manner as in Example 0495.

$^1$H-NMR(CDCl$_3$/CD$_3$OD=4/1)δ:8.92(1H,d,J=2.4 Hz), 8.73(1H,brs),8.65(1H,brs),8.24(1H,d,J=9.3 Hz),8.08(1H,d,J=2.4 Hz),7.95(1H,s),7.86(1H,s),7.60(1H,d,J=9.3 Hz),4.30 (2H,t,J=6.9 Hz),4.07(3H,s),3.76-3.70(4H,m),2.49-2.42(4H,m),2.38(2H,t,J=6.9 Hz),2.19-2.09(2H,m).

MSm/z(M+H):447.

Example 0497

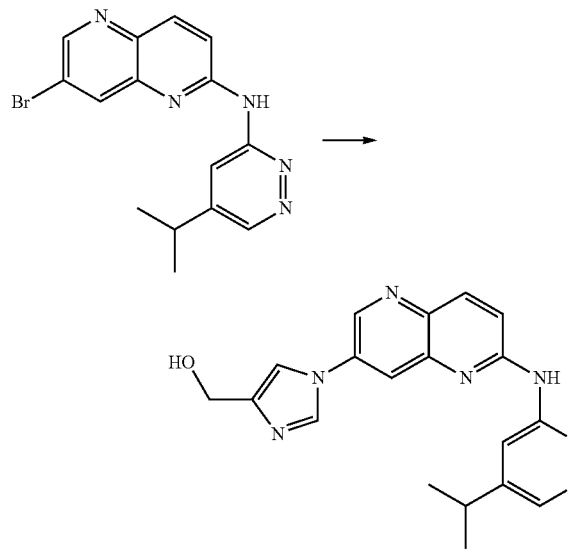

A suspension of 7-bromo-N-(5-isopropylpyridazin-3-yl)-1,5-naphthyridine-2-amine (17 mg), (1H-imidazol-4-yl)methanol (20 mg), copper iodide (3.1 mg), quinolin-8-ol (2.4 mg), and cesium carbonate (98 mg) in N,N-dimethylformamide (1 mL) was stirred at 120° C. for 7 hours in a nitrogen atmosphere. The insolubles were filtered off, and the solvent was distilled off under reduced pressure. The obtained residue was purified by silica gel column chromatography (ethyl acetate-methanol, NH silica), thereby obtaining (1-(6-((5-isopropylpyridazin-3-yl)amino)-1,5-naphthyridin-3-yl)-1H-imidazol-4-yl)methanol (3.6 mg) as a white solid.

$^1$H-NMR(DMSO-d$_6$)δ:10.76(1H,s),9.19(1H,d,J=2.1 Hz), 8.96(1H,d,J=2.7 Hz),8.91-8.83(2H,m),8.46(1H,s),8.44-8.42 (1H,m),7.78-7.69(1H,m),7.45(1H,d,J=9.3 Hz),5.87(2H,s), 3.27(1H,s),3.10-3.03(1H,m),1.48(6H,d,J=7.2 Hz).

MSm/z(M+H):362.

Example 0498

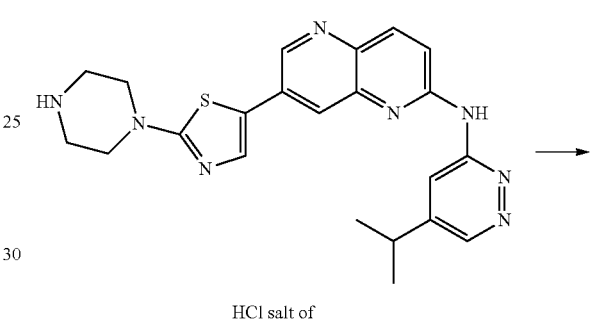

HCl salt of

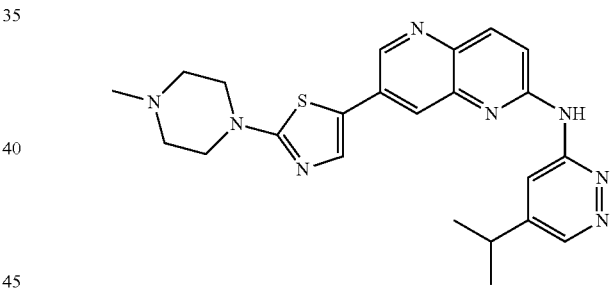

N-(5-isopropylpyridazin-3-yl)-7-(2-(4-methylpiperazin-1-yl)thiazol-5-yl)-1,5-naphthyridine-2-amine was obtained as a pale yellow solid in the same manner as in Example 0486.

$^1$H-NMR(DMSO-d$_6$)δ:10.73(1H,s),9.01(1H,d,J=1.8 Hz), 8.87(1H,d,J=2.1 Hz),8.72(1H,s),8.21(1H,d,J=8.7 Hz),8.00 (1H,s),7.94(1H,d,J=1.8 Hz),7.69(1H,d,J=9.0 Hz),3.54-3.50 (4H,m),3.08-2.98(1H,m),2.47-2.41(4H,m),2.25(3H,s),1.33 (6H,d,J=7.2 Hz).

MSm/z(M+H):447.

Example 0499

The following compounds were obtained in the same manner as in Examples 0495-2, 0495-3, 0495-4, 0495-5, and 0015-4.

| Example No. | | |
|---|---|---|
| 0499 | | |
| 0499-1 | 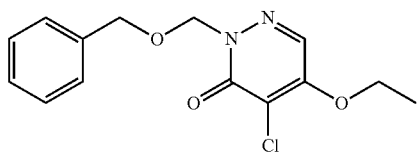 [SMILES: CCOc1cnn(COCc2ccccc2)c(=O)c1Cl] | MS m/z (M + H): 295. |
| 0499-2 | 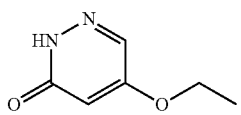 | MS m/z (M + H): 141. |
| 0499-3 | 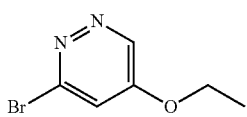 | MS m/z (M + H): 203. |
| 0499-4 | 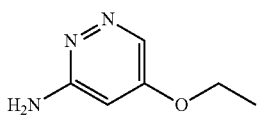 | MS m/z (M + H): 140. |
| 0499-5 | 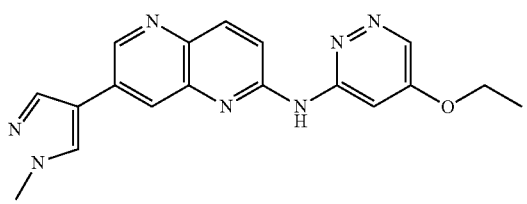 [SMILES: CCOc1cnnc(Nc2ccc3ncc(/C(C=N)=C/NC)cc3n2)c1] | $^1$H-NMR (DMSO-$d_6$) δ: 10.71 (1H, brs), 9.04 (1H, d, J = 2.1 Hz), 8.65 (1H, d, J = 2.7 Hz), 8.50 (1H, d, J = 2.7 Hz), 8.47 (1H, d), 6.22 (1H, d, J = 2.1 Hz), 8.21 (1H, d, J = 9.3 Hz), 8.19 (1H, s), 7.66 (1H, d, J = 9.3 Hz), 4.33 (2H, q, J = 6.9 Hz), 3.92 (3H, s), 1.46 (3H, t, J = 6.9 Hz). MS m/z (M + H): 348. |

Example 0500

0500-1

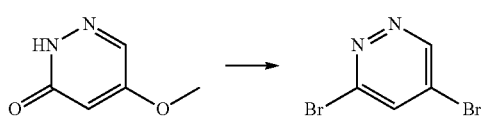

A mixture of 5-methoxypyridazin-3(2H)-one (2.35 g), phosphoryl bromide (16.0 g), and acetonitrile (90 mL) was stirred for 6 hour under reflux. The reaction mixture was added dropwise to a sodium carbonate aqueous solution under ice-cooling, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel chromatography (ethyl acetate-hexane), thereby obtaining 3,5-dibromopyridazine (1.67 g).

MSm/z(M+H):237.

0500-2

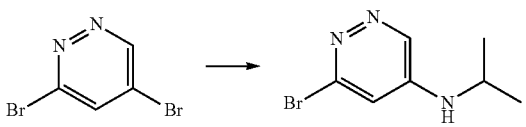

Isopropylamine (6 mL) was added to 3,5-dibromopyridazine (148 mg), followed by stirring at room temperature for 16 hours. After the solvent was distilled off under reduced pressure, water and ethyl acetate were added thereto, the organic layer was collected by separation, washed with a saturated sodium chloride aqueous solution, and dried over anhydrous sodium sulfate, and the solvent was distilled off under reduced pressure, thereby obtaining 6-bromo-N-isopropylpyridazine-4-amine (137 mg).

MSm/z(M+H):216.

0500-3

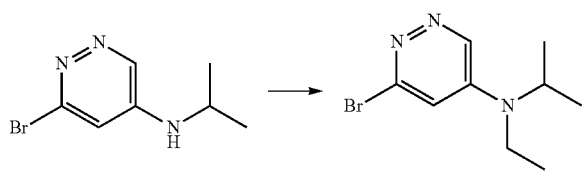

60% sodium hydride (19 mg) was added to a mixture of 6-bromo-N-isopropylpyridazine-4-amine (77 mg), iodoethane (0.050 mL), and N-methylpyrrolidone (2 mL) under ice-cooling, followed by stirring at the same temperature for 1 hour. After water and ethyl acetate were added to the reaction mixture, the organic layer was collected by separation, washed sequentially with water and a saturated sodium chloride aqueous solution, and dried over anhydrous sodium sulfate, and the solvent was distilled off under reduced pressure. The obtained residue was purified by silica gel chromatography (ethyl acetate-hexane), thereby obtaining 6-bromo-N-ethyl-N-isopropylpyridazine-4-amine (22 mg).

MSm/z(M+H):244.

0500-4 and 0500-5

The following compounds were obtained in the same manner as in Examples 0495-5 and 0015-4.

| Example No. | | |
|---|---|---|
| 0500 | | |
| 0500-4 | 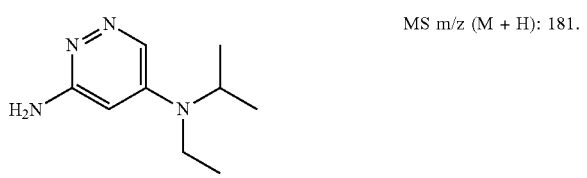 | MS m/z (M + H): 181. |
| 0500-5 | 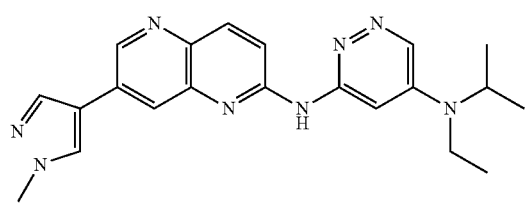 | $^1$H-NMR (CDCl$_3$) δ: 10.12 (1H, brs), 8.86 (1H, d, J = 1.8 Hz), 8.53 (1H, brs), 8.48 (1H, brs), 8.19 (1H, d, J = 9.3 Hz), 8.01 (1H, d, J = 1.8 Hz), 7.89 (1H, s), 7.78 (1H, s), 7.43 (1H, d, J = 9.3 Hz), 4.36-4.20 (1H, m), 4.02 (3H, s), 3.48 (2H, q, J = 7.2 Hz), 1.41 (3H, t, J = 7.2 Hz), 1.37 (6H, d, J = 6.6 Hz). MS m/z (M + H): 389. |

Example 0501

0501-1

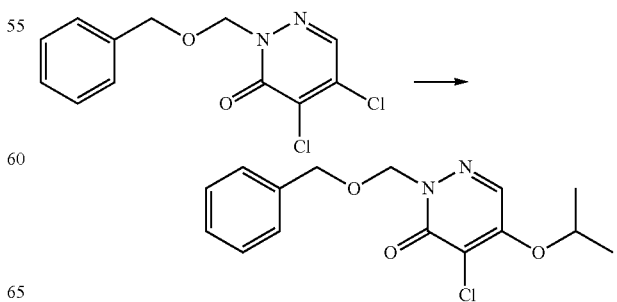

60% sodium hydride (141 mg) was added to a mixture of 2-((benzyloxy)methyl)-4,5-dichloropyridazin-3(2H)-one (506 mg), 2-propanol (0.678 mL), and tetrahydrofuran (8 mL) under ice-cooling, followed by stirring at the same temperature for 5 hours. After water and ethyl acetate were added to the reaction mixture, the organic layer was collected by separation, washed sequentially with water and a saturated sodium chloride aqueous solution, and dried over anhydrous sodium sulfate, and the solvent was distilled off under reduced pressure. The obtained residue was purified by silica gel chromatography (ethyl acetate-hexane), thereby obtaining 2-((benzyloxy)methyl)-4-chloro-5-isopropoxy-pyridazin-3(2H)-one (140 mg).

MS m/z (M+H):309.

0501-2 to 0501-5

The following compounds were obtained in the same manner as in Examples 0495-3, 0495-4, 0495-5, and 0015-4.

| Example No. | | |
|---|---|---|
| 0501 | | |
| 0501-2 | 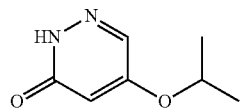 | MS m/z (M + H): 155. |
| 0501-3 | 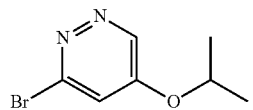 | MS m/z (M + H): 217. |
| 0501-4 | 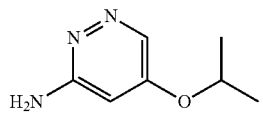 | MS m/z (M + H): 154. |
| 0501-5 | 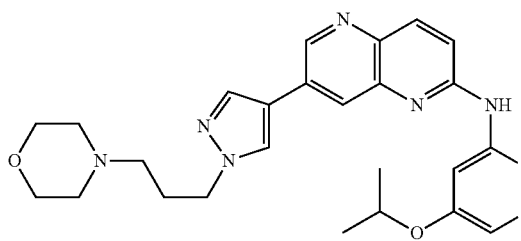 | $^1$H-NMR (CDCl$_3$/CD$_3$OD = 4/1) δ: 9.16 (1H, d, J = 9.3 Hz), 8.96 (1H, d, J = 2.1 Hz), 8.68 (1H, J = 6.0 Hz), 8.36 (1H, d, J = 9.3 Hz), 8.13 (1H, d, J = 2.1 Hz), 7.96 (1H, s), 7.85 (1H, s), 6.75 (1H, d, J = 6.0 Hz), 4.84-4.72 (1H, m), 4.30 (2H, t, J = 6.6 Hz), 3.76-3.69 (4H, m), 2.48-2.41 (4H, m), 2.37 (2H, t, J = 6.6 Hz), 2.11 (2H, t, J = 6.6 Hz), 1.51 (6H, d, J = 6.0 Hz). MS m/z (M + H): 475. |

Example 0502

The following compounds were obtained in the same manner as in Examples 0490-1, 0485-2, and 0488-3.

| Example No. | | |
|---|---|---|
| 0502 | | |
| 0502-1 | 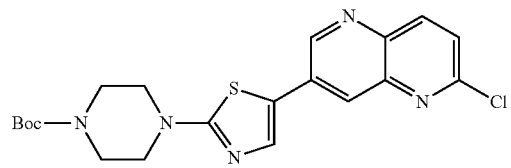 [SMILES: CC(C)(C)OC(=O)N1CCN(c2ncc(-c3cnc4ccc(Cl)nc4c3)s2)CC1] | MS m/z (M + H): 432. |

| Example No. | | |
|---|---|---|
| 0502-2 | 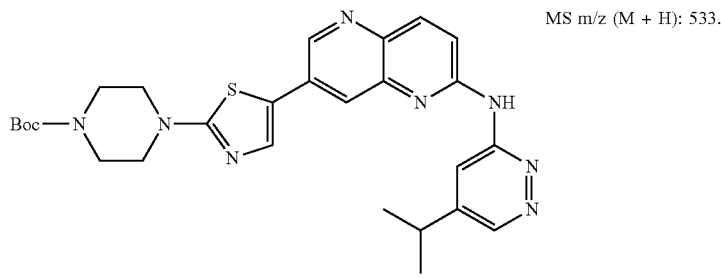 | MS m/z (M + H): 533. |
| 0502-3 | 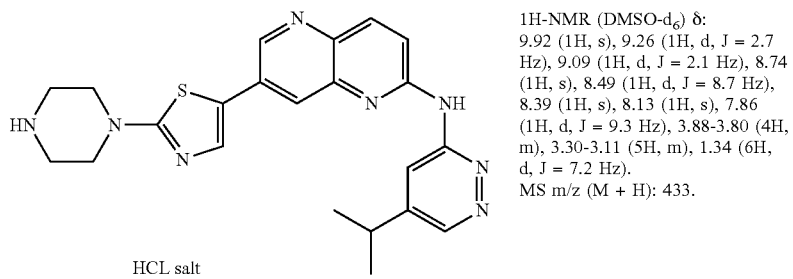 HCL salt | 1H-NMR (DMSO-d$_6$) δ: 9.92 (1H, s), 9.26 (1H, d, J = 2.7 Hz), 9.09 (1H, d, J = 2.1 Hz), 8.74 (1H, s), 8.49 (1H, d, J = 8.7 Hz), 8.39 (1H, s), 8.13 (1H, s), 7.86 (1H, d, J = 9.3 Hz), 3.88-3.80 (4H, m), 3.30-3.11 (5H, m), 1.34 (6H, d, J = 7.2 Hz). MS m/z (M + H): 433. |

Example 0503

Example 0504

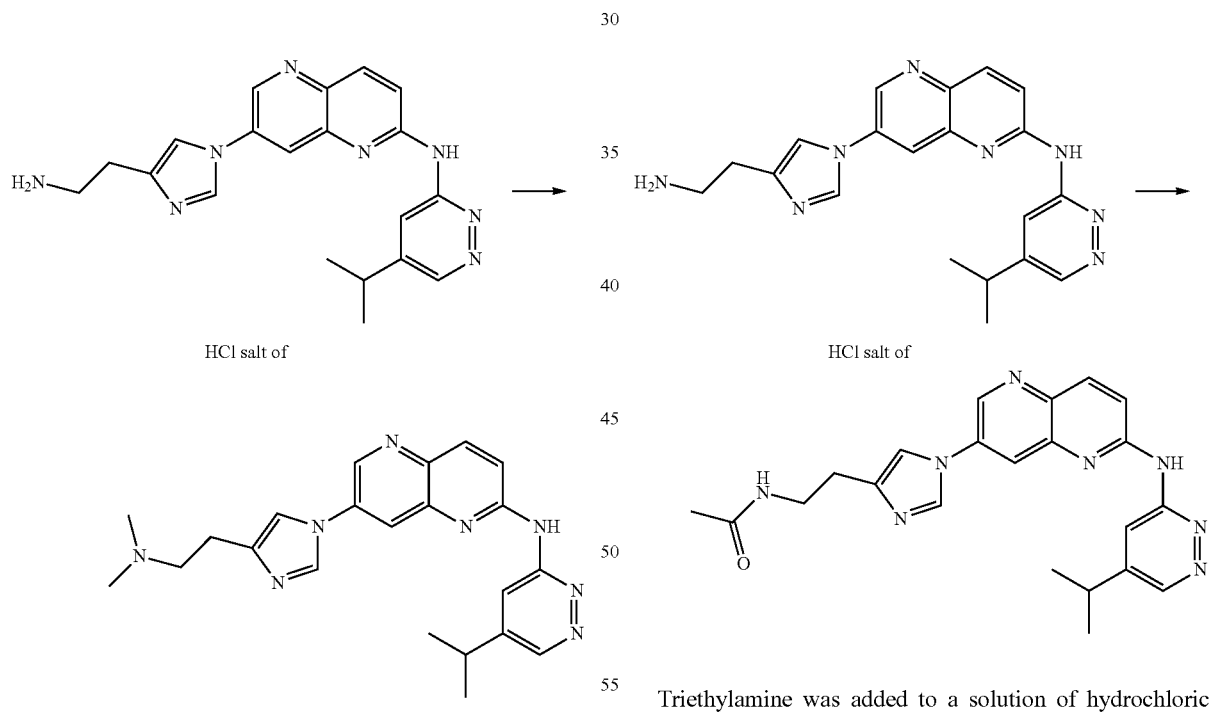

7-(4-(2-(Dimethylamino)ethyl)-1H-imidazol-1-yl)-N-(5-isopropylpyridazin-3-yl)-1,5-naphthyridine-2-amine was obtained as a white solid in the same manner as in Example 0486.

$^1$H-NMR(DMSO-d$_6$)δ:10.83(1H,s),9.11(1H,d,J=2.1 Hz), 8.88(1H,d,J=2.1 Hz),8.74(1H,d,J=1.8 Hz),8.46(1H,s),8.33-8.27(2H,m),7.80-7.74(2H,m),3.09-2.97(1H,m),2.74-2.66 (2H,m),2.60-2.54(2H,m),2.21(6H,s),1.33(6H,d,J=7.2 Hz).

MSm/z(M+H):403.

Triethylamine was added to a solution of hydrochloric acid salt of 7-(4-(2-aminoethyl)-1H-imidazol-1-yl)-N-(5-isopropylpyridazin-3-yl)-1,5-naphthyridine-2-amine (10 mg) in acetonitrile (0.8 mL) and methanol (0.2 mL), followed by adjusting to pH 8. Acetic anhydride (0.02 mL) was added thereto, followed by stirring at room temperature for 30 minutes. The solvent was distilled off under reduced pressure, and the obtained residue was purified by silica gel column chromatography (ethyl acetate-methanol, NH silica), thereby obtaining N-(2-(1-(6-((5-isopropylpyridazin-3-yl)amino)-1,5-naphthyridin-3-yl)-1H-imidazol-4-yl)ethyl)acetamide (3.7 mg) as a white solid.

651

¹H-NMR(DMSO-d₆)δ:10.84(1H,s),9.11(1H,d,J=2.7 Hz), 8.88(1H,d,J=2.1 Hz),8.74(1H,d,J=1.8 Hz),8.49(1H,s),8.33-8.27(2H,m),7.99-7.92(1H,m),7.82-7.74(2H,m),3.90-3.35 (2H,m),3.10-2.98(1H,m),2.74-2.65(2H,m),1.82(3H,s),1.33 (6H,d,J=6.6 Hz).

MSm/z(M+H):417.

Example 0505

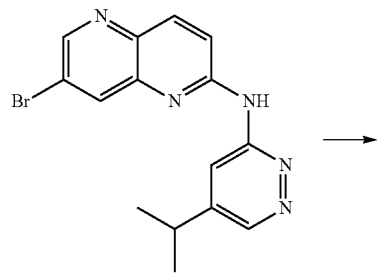

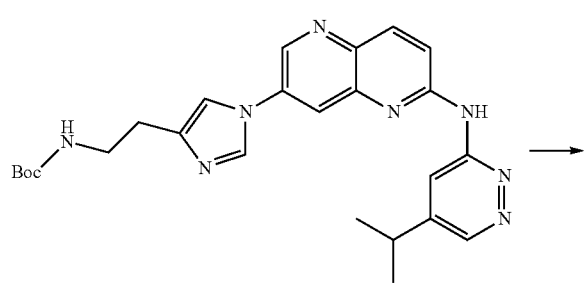

tert-Butyl (2-(1-(6-((5-isopropylpyridazin-3-yl)amino)-1, 5-naphthyridin-3-yl)-1H-imidazol-4-yl)ethyl)carbamate was obtained as a white solid in the same manner as in Example 0494 except that tert-butyl (2-(1H-imidazol-4-yl) ethyl)carbamate was used instead of the 4-methyl-1H-imidazole used in Example 0494-2.

¹H-NMR(DMSO-d₆)δ:10.84(1H,s),9.11(1H,d,J=2.7 Hz), 8.88(1H,d,J=2.1 Hz),8.74(1H,d,J=1.8 Hz),8.49(1H,s),8.33-8.27(2H,m),7.81-7.72(2H,m),6.96-6.88(1H,m),3.30-3.23 (2H,m),3.10-2.98(1H,m),2.73-2.65(2H,m),1.39(9H,s),1.33 (6H,d,J=7.2 Hz).

MSm/z(M+H):475.

Example 0506

652

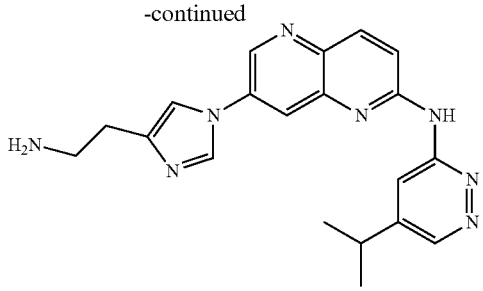

HCl salt of

Hydrochloric acid salt of 7-(4-(2-aminoethyl)-1H-imidazol-1-yl)-N-(5-isopropylpyridazin-3-yl)-1,5-naphthyridine-2-amine was obtained as a white solid in the same manner as in Example 0488-3.

¹H-NMR(DMSO-d₆)δ:9.95(1H,s),9.33(1H,d,J=2.7 Hz), 9.15-9.09(2H,m),8.61-8.55(2H,m),8.51-8.47(1H,m),8.40 (1H,s),8.00(1H,d,J=9.0 Hz),3.33-3.13(5H,m),1.34(6H,d, J=7.2 Hz).

MSm/z(M+H):375.

Example 0507

0507-1

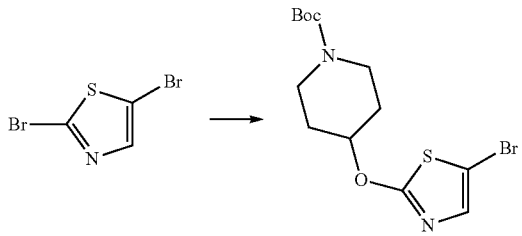 [SMILES: Brc1cnc(Br)s1 ; CC(C)(C)OC(=O)N1CCC(Oc2ncc(Br)s2)CC1]

60% sodium hydride (200 mg) was added to a solution of 2,5-dibromothiazole (0.97 g) in N,N-dimethylformamide (10 mL), followed by stirring at room temperature for 5 minutes. tert-Butyl 4-hydroxypiperidine-1-carboxylate (1.01 g) was added thereto, followed by stirring at 70° C. for 1 hour. After the reaction mixture was cooled to room temperature, ethyl acetate and water were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining tert-butyl 4-((5-bromothiazol-2-yl)oxy) piperidine-1-carboxylate (1.16 g) as a white solid.

MSm/z(M+H):365.

0507-2 to 0507-5

The following compounds were obtained in the same manner as in Examples 0490-1, 0485-2, 0488-3, and 0486.

| Example No. | | |
|---|---|---|
| 0507 | | |
| 0507-2 | 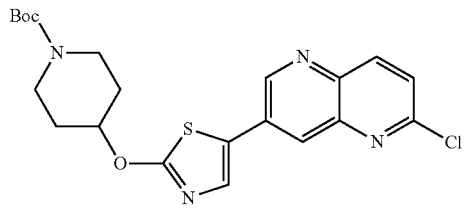 [SMILES: CC(C)(C)OC(=O)N1CCC(Oc2ncc(-c3cnc4ccc(Cl)nc4c3)s2)CC1] | MS m/z (M + H): 447. |
| 0507-3 | 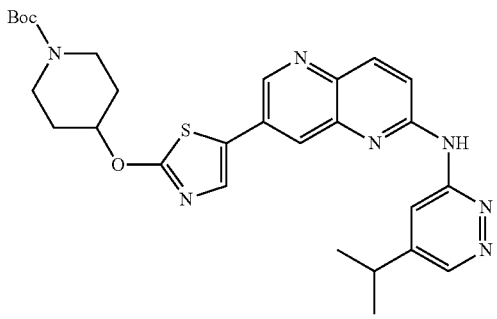 [SMILES: CC(C)c1cnnc(Nc2ccc3ncc(-c4cnc(OC5CCN(C(=O)OC(C)(C)C)CC5)s4)cc3n2)c1] | MS m/z (M + H): 548. |
| 0507-4 | 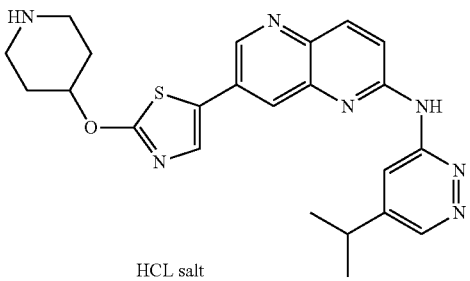 [SMILES: CC(C)c1cnnc(Nc2ccc3ncc(-c4cnc(OC5CCNCC5)s4)cc3n2)c1 ; "HCL salt"] HCL salt | MS m/z (M + H): 448. |
| 0507-5 | 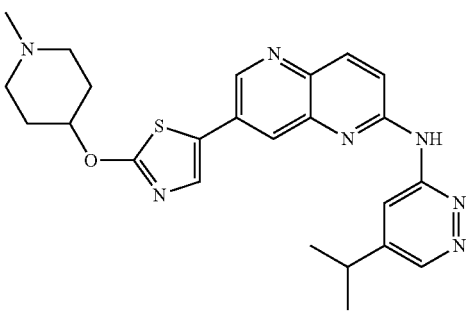 [SMILES: CC(C)c1cnnc(Nc2ccc3ncc(-c4cnc(OC5CCN(C)CC5)s4)cc3n2)c1] | $^1$H-NMR (DMSO-d$_6$) δ: 10.78 (1H, s), 9.02 (1H, d, J = 1.8 Hz), 8.88 (1H, d, J = 2.1 Hz), 8.72 (1H, s), 8.24 (1H, d, J = 9.3 Hz), 8.10 (1H, s), 7.99 (1H, s), 7.74 (1H, d, J = 9.3 Hz), 5.09-5.03 (1H, m), 3.08-3.00 (1H, m), 2.80-2.81 (2H, m), 2.62-2.56 (2H, m), 2.34 (3H, s), 2.10-2.00 (2H, m), 1.99-1.85 (2H, m), 1.33 (6H, d, J = 7.2 Hz). MS m/z (M + H): 462. |
Example 0508
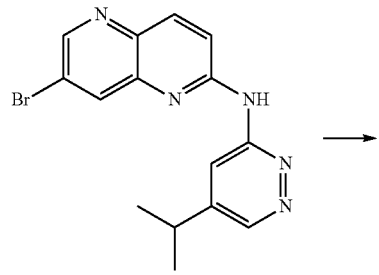 → 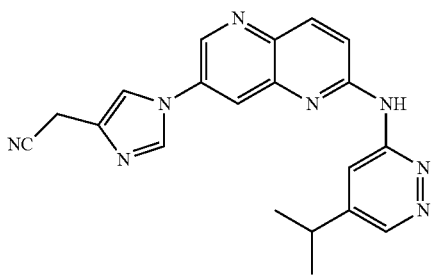
2-(1-(6-((5-Isopropylpyridazin-3-yl)amino)-1,5-naphthyridin-3-yl)-1H-imidazol-4-yl)acetonitrile was obtained as a white solid in the same manner as in Example 0494-2.

¹H-NMR(DMSO-d₆)δ:10.87(1H,s),9.12(1H,d,J=2.7 Hz), 8.89(1H,d,J=2.1 Hz),8.75(1H,d,J=2.1 Hz),8.38(1H,d,J=1.8 Hz),8.31(1H,d,J=9.3 Hz),7.99(1H,s),7.79(1H,d,J=9.3 Hz),7.06(1H,s),3.83(2H,s),3.09-2.99(1H,m),1.33(6H,d,J=7.2 Hz).
MSm/z(M+H):371.

Example 0509

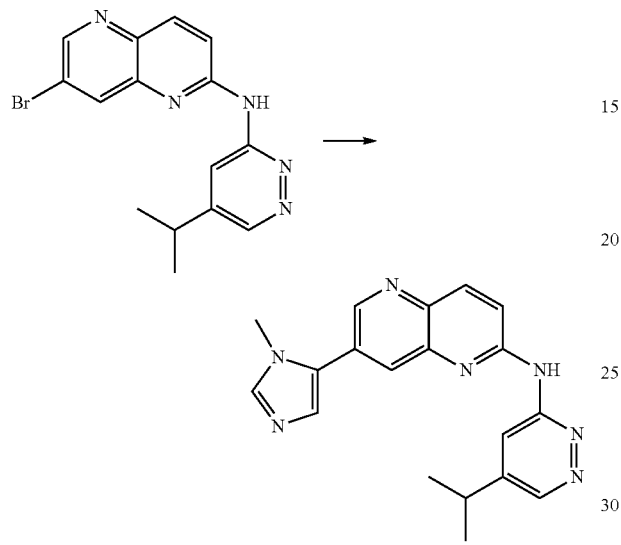

N-(5-isopropylpyridazin-3-yl)-7-(1-methyl-1H-imidazol-5-yl)-1,5-naphthyridine-2-amine was obtained as a white solid in the same manner as in Example 0490-1.
¹H-NMR(DMSO-d₆)δ:10.79(1H,s),8.91(1H,d,J=1.8 Hz), 8.86(1H,s),8.73(1H,s),8.29(1H,d,J=9.3 Hz),8.22(1H,d,J=1.2 Hz),7.86(1H,s),7.80(1H,d,J=9.3 Hz),7.39(1H,s),3.84 (3H,s),3.08-2.97(1H,m),1.31(6H,d,J=7.2 Hz).
MSm/z(M+H):346.

Example 0510

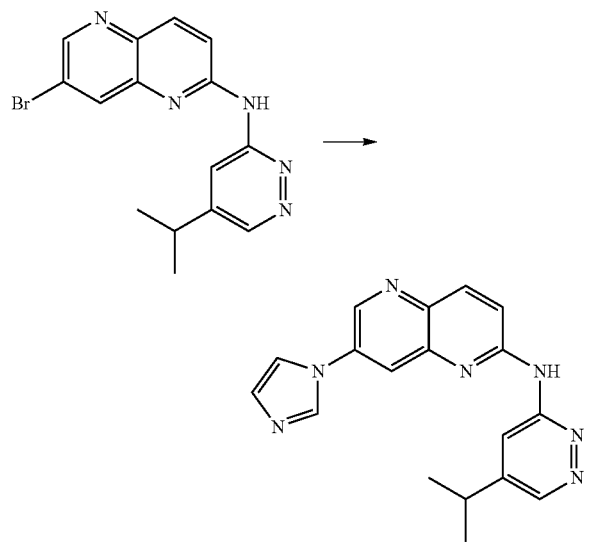

7-(1H-imidazol-1-yl)-N-(5-isopropylpyridazin-3-yl)-1,5-naphthyridine-2-amine was obtained as a white solid in the same manner as in Example 0494-2.
¹H-NMR(DMSO-d₆)δ:10.85(1H,s),9.14(1H,d,J=2.7 Hz), 8.89(1H,d,J=2.1 Hz),8.75(1H,d,J=2.1 Hz),8.57(1H,s),8.38 (1H,d,J=2.1 Hz),8.31(1H,d,J=8.7 Hz),8.06(1H,s),7.78(1H,d, J=9.0 Hz),7.21(1H,s),3.09-2.99(1H,m),1.33(6H,d,J=7.5 Hz).
MSm/z(M+H):332.

Example 0511

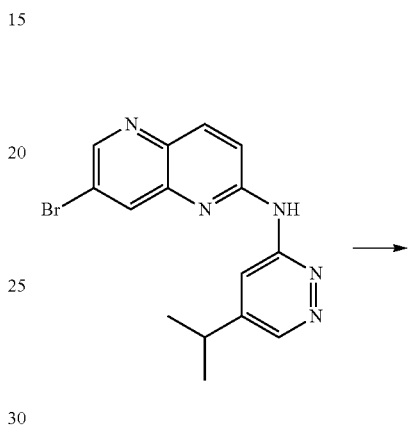

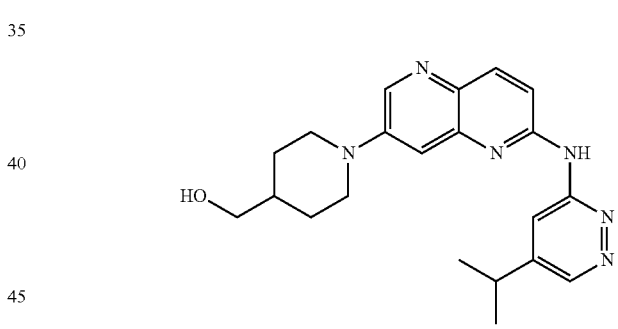

(1-(6-((5-Isopropylpyridazin-3-yl)amino)-1,5-naphthyridin-3-yl)piperidin-4-yl)methanol was obtained as a yellow solid in the same manner as in Example 0846.
¹H-NMR(CDCl₃)δ:8.80-8.75(1H,m),8.75-8.71(1H,m), 8.66-8.63(1H,m),8.53-8.47(1H,m),8.13(1H,d,J=8.6 Hz), 7.33-7.30(1H,m),7.27-7.25(1H,m),3.98-3.91(2H,m),3.62-3.55(2H,m),3.06-2.94(1H,m),3.00-2.89(2H,m),1.98-1.91 (2H,m),1.82-1.72(1H,m),1.57-1.38(2H,m),1.51-1.40(1H, m),1.39(6H,d,J=7.3 Hz).
MSm/z(M+H):379.

Examples 0512 to 0514

The following compounds were obtained in the same manner as in Example 0494-2.

| Example No. | | |
|---|---|---|
| 0512 | 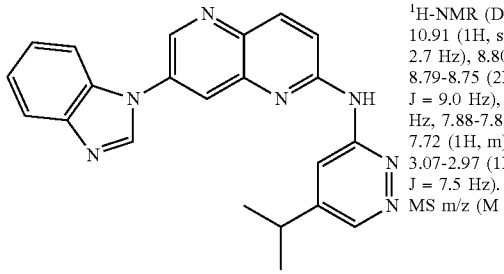 | ¹H-NMR (DMSO-d₆) δ: 10.91 (1H, s), 9.10 (1H, d, J = 2.7 Hz), 8.80 (1H, d, J = 2.1 Hz), 8.79-8.75 (2H, m), 8.48 (1H, d, J = 9.0 Hz), 8.39 (1H, d, J = 9.0 Hz), 7.88-7.81 (2H, m), 7.78-7.72 (1H, m), 7.41-7.35 (2H, m), 3.07-2.97 (1H, m), 1.30 (6H, d, J = 7.5 Hz). MS m/z (M + H): 382. |
| 0513 | 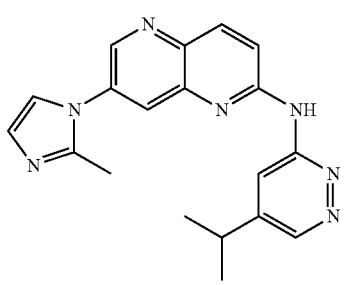 [SMILES: Cc1nccn1-c1cnc2ccc(Nc3cc(C(C)C)cnn3)nc2c1] | ¹H-NMR (DMSO-d₆) δ: 10.90 (1H, s), 8.88-8.83 (2H, m), 8.75 (1H, d, J = 1.8 Hz), 8.35 (1H, d, J = 9.6 Hz), 8.29 (1H, d, J = 2.7 Hz), 7.84 (1H, d, J = 9.3 Hz), 7.54 (1H, s), 7.02 (1H, s), 3.08-2.95 (1H, m), 2.39 (3H, s), 1.31 (6H, d, J = 6.6 Hz). MS m/z (M + H): 346. |
| 0514 | 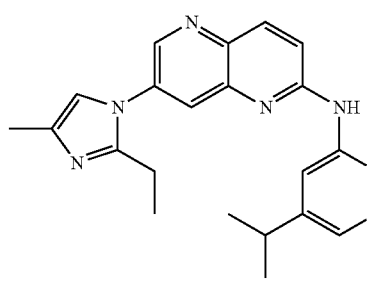 | ¹H-NMR (DMSO-d₆) δ: 10.89 (1H, s), 8.87 (1H, d, J = 1.8 Hz), 8.80-8.75 (2H, m), 8.34 (1H, d, J = 9.3 Hz), 8.21 (1H, d, J = 2.1 Hz), 7.82 (1H, d, J = 9.0 Hz), 7.19 (1H, s), 3.07-2.96 (1H, m), 2.67 (2H, q, J = 7.2 Hz), 2.16 (3H, s), 1.30 (6H, d, J = 6.6 Hz), 1.18 (3H, t, J = 7.2 Hz). MS m/z (M + H): 374. |

Example 0515

The following compounds were obtained in the same manner as in Examples 0478-3 and 0015-4.

| Example No. | | |
|---|---|---|
| 0515 | | |
| 0515-1 | 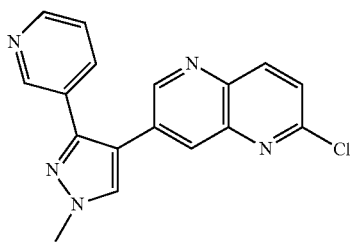 [SMILES: Cn1cc(-c2cnc3ccc(Cl)nc3c2)c(-c2cccnc2)n1] | MS m/z (M + H): 322. |
| 0515-2 | 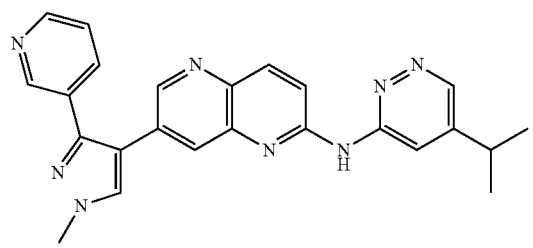 [SMILES: CN/C=C(\C(=N)c1cccnc1)c1cnc2ccc(Nc3cc(C(C)C)cnn3)nc2c1] | ¹H-NMR (CDCl₃) δ: 10.14 (1H, brs), 8.91 (1H, d, J = 1.4 Hz), 8.80 (1H, s), 8.79 (1H, s), 8.67 (1H, d, J = 2.7 Hz), 8.59-8.52 (2H, m), 8.24 (1H, d, J = 9.3 Hz), 7.86-7.79 (2H, m), 7.72 (1H, s), 7.27 (1H, d, J = 9.3 Hz), 4.08 (3H, s), 3.04-2.92 (1H, m), 1.34 (6H, d, J = 6.6 Hz). MS m/z (M + H): 423. |

Example 0516


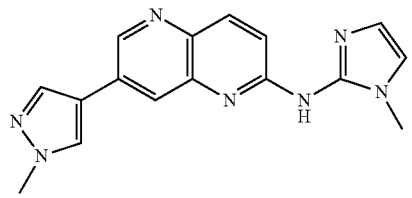

N-(1-methyl-1H-imidazol-2-yl)-7-(1-methyl-1H-pyrazol-4-yl)-1,5-naphthyridine-2-amine was obtained in the same manner as in Example 0015-4.

¹H-NMR(CDCl₃)δ:8.60(1H,brs),7.89(1H,s),7.78(1H,s),7.71(1H,d,J=9.3 Hz),7.61(1H,brs),7.00(1H,brs),6.94(1H,brs),6.74(1H,brs),4.00(3H,s),3.68(3H,s).
MSm/z(M+H):306.

Example 0517

0517-1

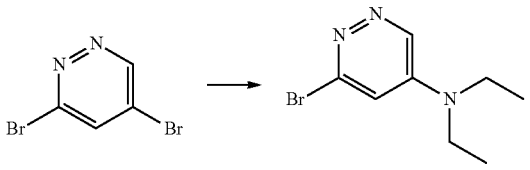

A mixture of 3,5-dibromopyridazine (150 mg), diethylamine (2 mL), and tetrahydrofuran (1 mL) was stirred at room temperature for 6 hours. The solvent was distilled off under reduced pressure, and the obtained residue was purified by silica gel chromatography (ethyl acetate-hexane), thereby obtaining 6-bromo-N,N-diethylpyridazine-4-amine (60 mg).
MSm/z(M+H):230.

0517-2 and 0517-3

The following compounds were obtained in the same manner as in Examples 0495-5 and 0015-4.

| Example No. | | |
|---|---|---|
| 0517 | | |
| 0517-2 | 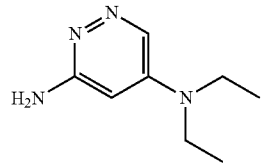 | MS m/z (M + H): 167. |
| 0517-3 | 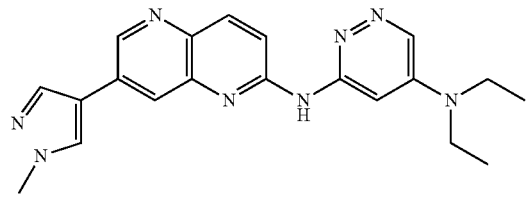 [SMILES: CCN(CC)c1cnnc(Nc2ccc3ncc(/C(C=N)=C/NC)cc3n2)c1] | ¹H-NMR (CDCl₃) δ: 9.66 (1H, brs), 8.86 (1H, d, J = 1.8 Hz), 8.46 (1H, brs), 8.37 (1H, brs), 8.18 (1H, d, J = 9.3 Hz), 8.01 (1H, d, J = 1.8 Hz), 7.90 (1H, s), 7.79 (1H, s), 7.63 (1H, d, J = 9.3 Hz), 4.02 (3H, s), 3.54 (4H, q, J = 6.6 Hz), 1.36 (6H, t, J = 6.6 Hz). MS m/z (M + H): 375. |

Example 0518

The following compounds were obtained in the same manner as in Examples 0517-1, 0495-5, and 0015-4.

| Example No. | | |
|---|---|---|
| 0518 | | |
| 0518-1 | 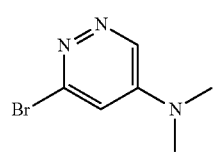 | MS m/z (M + H): 202. |

-continued

| Example No. | | |
|---|---|---|
| 0518-2 | 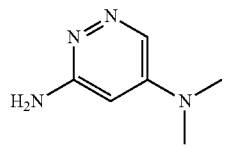 | MS m/z (M + H): 139. |
| 0518-3 | 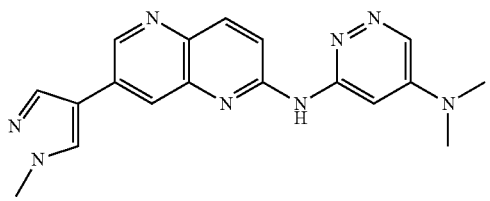 [SMILES: CN/C=C(\C=N)c1cnc2ccc(Nc3cc(N(C)C)cnn3)nc2c1] | $^1$H-NMR (CDCl$_3$/CD$_3$OD = 4/1) δ: 8.84 (1H, d, J = 2.1 Hz), 8.38 (1H, d, J = 2.1 Hz), 8.16 (1H, d, J = 9.3 Hz), 8.06 (1H, d, J = 2.1 Hz), 7.92 (1H, s), 7.90 (1H, s), 7.89 (1H, s), 7.42 (1H, d, J = 9.3 Hz), 4.02 (3H, s), 3.20 (6H, s). MS m/z (M + H): 347. |

Example 0519

0519-1

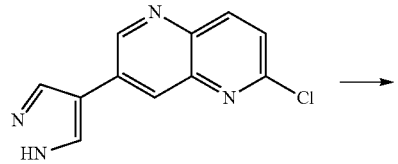

A mixture of 2-chloro-7-(1H-pyrazol-4-yl)-1,5-naphthyridine (20 mg), (bromomethyl)cyclohexane (0.024 mL), cesium carbonate (56 mg), and N,N-dimethylformamide was stirred for 2 hours under heating to reflux. After water and ethyl acetate were added to the reaction mixture, the organic layer was collected by separation, washed sequentially with water and a saturated sodium aqueous solution, and dried over anhydrous sodium sulfate, and the solvent was distilled off under reduced pressure, thereby obtaining 2-chloro-7-(1-(cyclohexylmethyl)-1H-pyrazol-4-yl)-1,5-naphthyridine (31 mg).

MSm/z(M+H):327.

0519-2

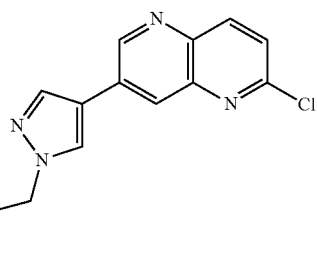

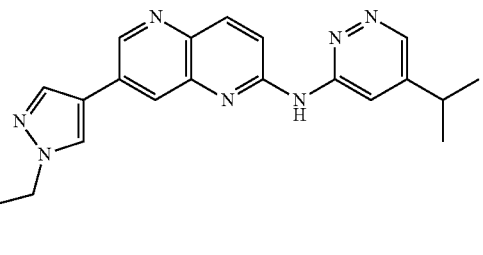

7-(1-(Cyclohexylmethyl)-1H-pyrazol-4-yl)-N-(5-isopropylpyridazin-3-yl)-1,5-naphthyridine-2-amine was obtained in the same manner as in Example 0015-4.

$^1$H-NMR(CDCl$_3$)δ:8.93(1H,d,J=2.1 Hz),8.82(2H,s),8.24 (1H,d,J=9.0 Hz),8.10(1H,d,J=2.1 Hz),7.96(1H,s),7.80(1H, s),7.49(1H,d,J=9.0 Hz),4.04(2H,d,J=7.2 Hz),3.16-2.95(1H, m),2.05-1.88(1H,m),1.82-1.63(4H,m),1.42(6H,d,J=7.5 Hz), 1.36-1.15(4H,m),1.11-0.93(2H,m).

MSm/z(M+H):428.

Example 0520

The following compounds were obtained in the same manner as in Examples 0517-1, 0495-5, and 0015-4.

| Example No. | | |
|---|---|---|
| 0520 | | |
| 0520-1 | 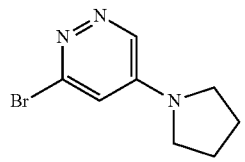 [SMILES: Brc1cc(N2CCCC2)cnn1] | MS m/z (M + H): 228. |
| 0520-2 | 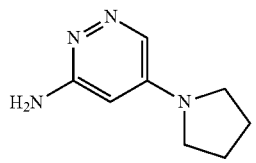 [SMILES: Nc1cc(N2CCCC2)cnn1] | MS m/z (M + H): 165. |
| 0520-3 | 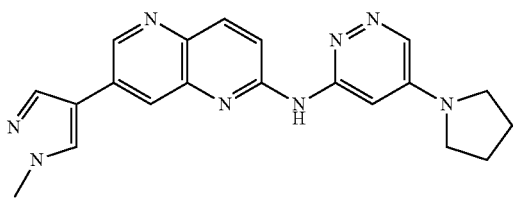 [SMILES: CN/C=C(\C=N)c1cnc2ccc(Nc3cc(N4CCCC4)cnn3)nc2c1] | $^1$H-NMR (DMSO-$d_6$) δ: 10.26 (1H, brs), 8.99 (1H, d, J = 2.1 Hz), 8.45 (1H, s), 8.35 (1H, d, J = 2.7 Hz), 8.18 (1H, s), 8.15 (1H, d, J = 9.3 Hz), 8.14 (1H, d, J = 2.7 Hz), 7.90 (1H, d, J = 2.1 Hz), 7.65 (1H, d, J = 9.3 Hz), 3.92 (3H, s), 3.49-3.38 (4H, m), 2.06-1.98 (4H, m). MS m/z (M + H): 373. |
Example 0521
The following compounds were obtained in the same manner as in Examples 0519-1 and 0015-4.
| Example No. | | |
|---|---|---|
| 0521 | | |
| 0521-1 | 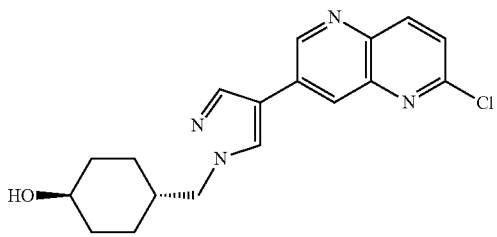 [SMILES: N=C/C(=C\NC[C@H]1CC[C@H](O)CC1)c1cnc2ccc(Cl)nc2c1] | MS m/z (M + H): 343. |
| 0521-2 | 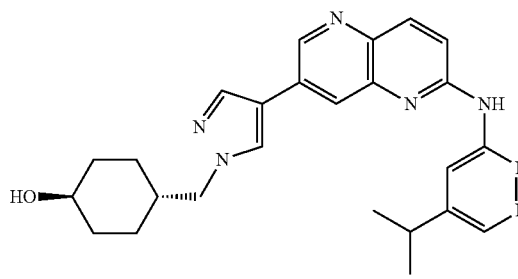 | $^1$H-NMR (CDCl$_3$) δ: 8.93 (1H, d, J = 2.1 Hz), 8.85 (1H, brs), 8.81 (1H, brs), 8.25 (1H, d, J = 9.3 Hz), 8.10 (1H, brs), 7.97 (1H, s), 7.81 (1H, s), 7.54 (1H, d, J = 9.3 Hz), 4.06 (2H, d, J = 7.2 Hz), 3.68 (1H, m), 3.54 (1H, m), 3.13-2.99 (1H, m), 2.08-1.54 (5H, m), 1.42 (6H, d, J = 6.6 Hz), 1.38-1.04 (4H, m). MS m/z (M + H): 444. |

Example 0522

0522-1

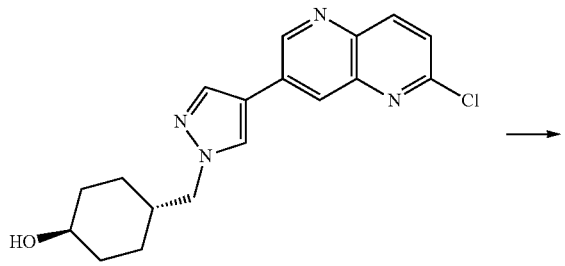

60% sodium hydride (6 mg) was added to a mixture of (1r,4r)-4-((4-(6-chloro-1,5-naphthyridin-3-yl)-1H-pyrazol-1-yl)methyl)cyclohexanol (10 mg), iodomethane (0.008 mL), and N,N-dimethylformamide (1 mL) under ice-cooling, followed by stirring at the same temperature for 2 hours. After water and ethyl acetate were added to the reaction mixture, the organic layer was collected by separation, washed sequentially with water and a saturated sodium aqueous solution, and dried over anhydrous sodium sulfate, and the solvent was distilled off under reduced pressure, thereby obtaining 2-chloro-7-(1-(((1r,4r)-4-methoxycyclohexyl)methyl)-1H-pyrazol-4-yl)-1,5-naphthyridine (17 mg).

MSm/z(M+H):357.

0522-2

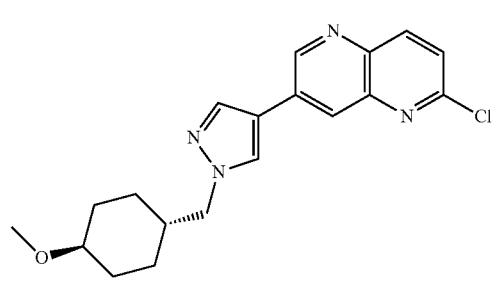

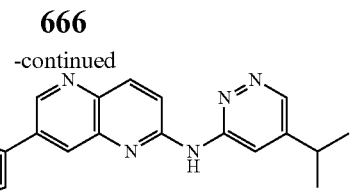

N-(5-isopropylpyridazin-3-yl)-7-(1-(((1r,4r)-4-methoxycyclohexyl)methyl)-1H-pyrazol-4-yl)-1,5-naphthyridine-2-amine was obtained in the same manner as in Example 0015-4.

$^1$H-NMR(CDCl$_3$)δ:8.93(1H,d,J=2.1 Hz),8.81(2H,brs),8.24(1H,d,J=9.3 Hz),8.11(1H,d,J=2.1 Hz),7.97(1H,s,),7.81(1H,s),7.48(1H,d,J=9.3 Hz),4.78(2H,brs),4.06(2H,d,J=7.2 Hz),3.35(3H,s),3.19-3.00(1H,m),2.15-2.07(2H,m),1.82-1.73(2H,m),1.42(6H,d,J=6.6 Hz),1.35-1.03(5H,m).

MSm/z(M+H):458.

Example 0523

0523-1

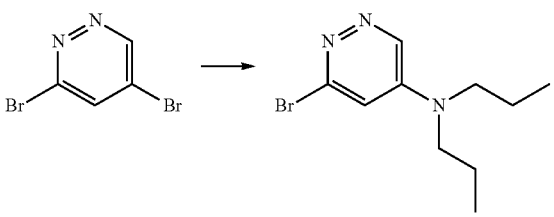

Dipropylamine (0.5 mL) was added to 3,5-dibromopyridazine (50 mg), followed by stirring at 80° C. for 3 hours. The reaction mixture was purified by silica gel chromatography (methanol-ethyl acetate-hexane), thereby obtaining 6-bromo-N,N-dipropylpyridazine-4-amine (42 mg).

MSm/z(M+H):258.

0523-2 and 0523-3

The following compounds were obtained in the same manner as in Examples 0495-5 and 0015-4.

| Example No. | | |
|---|---|---|
| 0523 | | |
| 0523-2 | 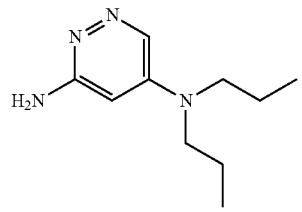 | MS m/z (M + H): 195. |
| 0523-3 | 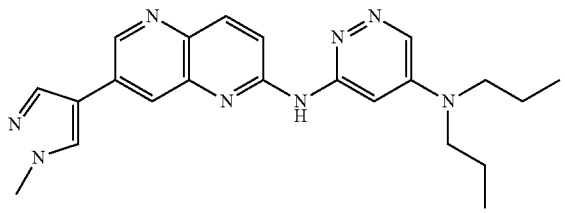 [SMILES: CCCN(CCC)c1cnnc(Nc2ccc3ncc(/C(C=N)=C/NC)cc3n2)c1] | ¹H-NMR (CDCl₃) δ: 8.87 (1H, brs), 8.43 (1H, brs), 8.39 (1H, brs), 8.18 (1H, d, J = 9.3 Hz), 8.03 (1H, d, J = brs), 7.89 (1H, s), 7.78 (1H, s), 7.54 (1H, d, J = 9.3 Hz), 4.02 (3H, s), 3.43 (4H, t, J = 7.8 Hz), 1.88-1.72 (4H, m), 1.26 (6H, t, J = 7.5 Hz). MS m/z (M + H): 403. |

Example 0524

The following compounds were obtained in the same manner as in Examples 0517-1, 0495-5, and 0015-4.

| Example No. | | |
|---|---|---|
| 0524 | | |
| 0524-1 | 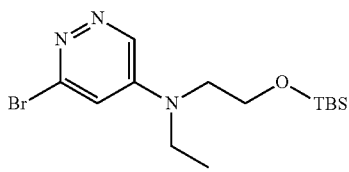 | MS m/z (M + H): 360. |
| 0524-2 | 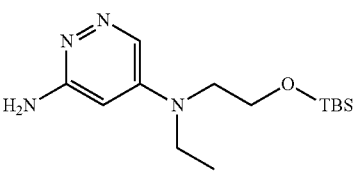 | MS m/z (M + H): 297. |
| 0524-3 | 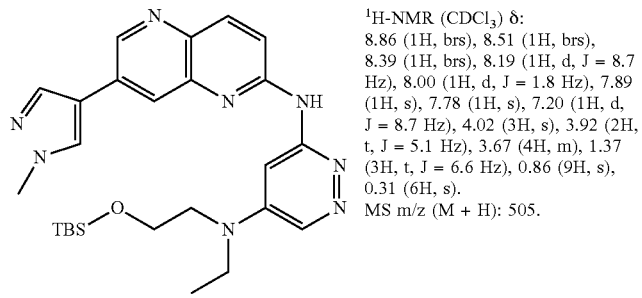 | ¹H-NMR (CDCl₃) δ: 8.86 (1H, brs), 8.51 (1H, brs), 8.39 (1H, brs), 8.19 (1H, d, J = 8.7 Hz), 8.00 (1H, d, J = 1.8 Hz), 7.89 (1H, s), 7.78 (1H, s), 7.20 (1H, d, J = 8.7 Hz), 4.02 (3H, s), 3.92 (2H, t, J = 5.1 Hz), 3.67 (4H, m), 1.37 (3H, t, J = 6.6 Hz), 0.86 (9H, s), 0.31 (6H, s). MS m/z (M + H): 505. |

Examples 0525 to 0527

The following compounds were obtained in the same manner as in Example 0015-4.

| Example No. | | |
|---|---|---|
| 0525 | 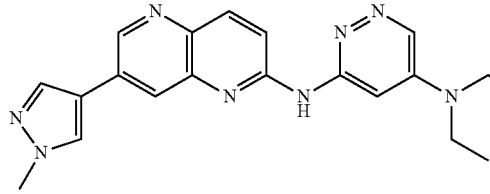 | ¹H-NMR (DMSO-d₆) δ:<br>9.18 (1H, d, J = 2.4 Hz), 8.83 (1H, m), 8.76 (1H, d, J = 2.4 Hz),<br>8.47 (1H, s), 8.43 (1H, s), 8.41 (1H, d, J = 9.0 Hz), 8.16 (1H, s),<br>7.46 (1H, d, J = 9.0 Hz), 3.94 (3H, s), 3.86-3.26 (6H, m),<br>1.23 (3H, t, J = 6.6 Hz).<br>MS m/z (M + H): 391. |
| 0526 | 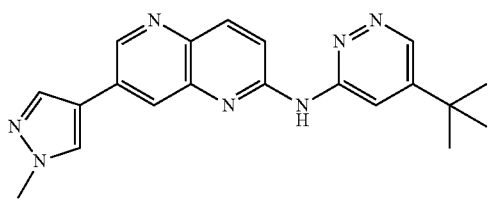 [SMILES: Cn1cc(-c2cnc3ccc(Nc4cc(C(C)(C)C)cnn4)nc3c2)cn1] | ¹H-NMR (DMSO-d₆) δ:<br>10.68 (1H, s), 9.03 (1H, d, J = 2.1 Hz), 9.02 (1H, J = 2.1 Hz),<br>8.76 (1H, d, J = 2.1 Hz), 8.45 (1H, s), 8.22 (1H, d, J = 9.3 Hz),<br>8.16 (1H, s), 8.10 (d, J = 2.1 Hz), 7.75 (1H, d, J = 9.3 Hz),<br>3.93 (3H, s), 1.40 (9H, s).<br>MS m/z (M + H): 360. |
| 0527 | 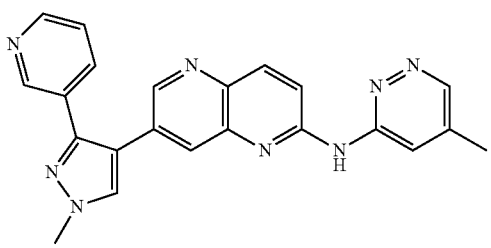 [SMILES: Cc1cnnc(Nc2ccc3ncc(-c4cn(C)nc4-c4cccnc4)cc3n2)c1] | ¹H-NMR (CDCl₃) δ:<br>8.80 (1H, d, J = 2.1 Hz), 8.72 (1H, brs), 8.64 (1H, d, J = 2.7 Hz),<br>8.57 (1H, dd, J = 5.1, 2.7 Hz), 8.47 (2H, brs), 8.23 (1H, d, J = 9.0 Hz), 8.00 (1H, d, J = 2.1 Hz), 7.81 (1H, dt, J = 5.1, 2.1 Hz),<br>7.71 (1H, d, J = 9.0 Hz), 7.71 (1H, s), 4.07 (3H, s), 2.42 (3H, s).<br>MS m/z (M + H): 395. |

Example 0528

0528-1

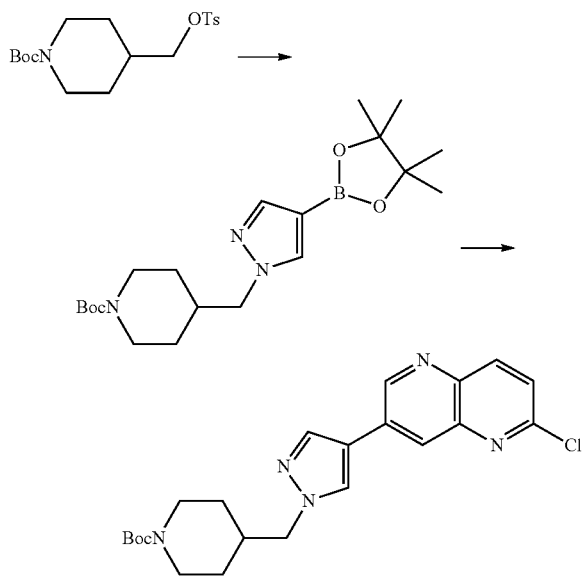

tert-Butyl 4-((4-(6-chloro-1,5-naphthyridin-3-yl)-1H-pyrazol-1-yl)methyl)piperidine-1-carboxylate was obtained in the same manner as in Example 0471-1 except that tert-butyl 4-((tosyloxy)methyl)piperidine-1-carboxylate was used instead of the 1-bromo-2-methoxyethane used in Example 0471-1.

MSm/z(M+H):428.

0528-2

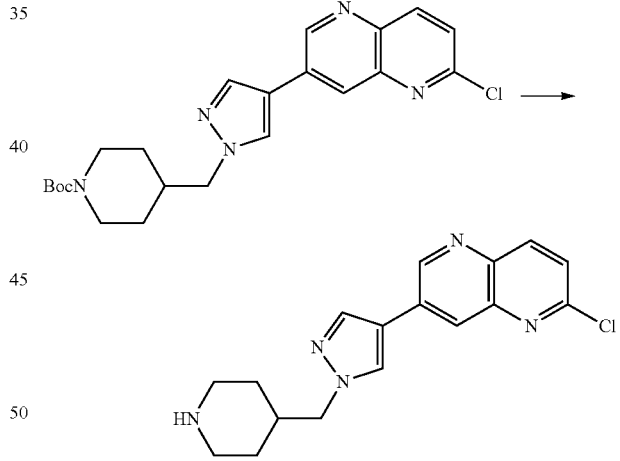

Trifluoroacetic acid (2 mL) was added to a mixture of tert-butyl 4-((4-(6-chloro-1,5-naphthyridin-3-yl)-1H-pyrazol-1-yl)methyl)piperidine-1-carboxylate (1.51 g), water (0.1 mL), and dichloromethane (1 mL), followed by stirring at room temperature for 2 hours. The solvent was distilled off under reduced pressure, the obtained residue was purified by silica gel column chromatography (methanol-ethyl acetate, NH silica), thereby obtaining 2-chloro-7-(1-(piperidin-4-ylmethyl)-1H-pyrazol-4-yl)-1,5-naphthyridine (540 mg).

MSm/z(M+H):328.

671
0528-3

672
0528-4

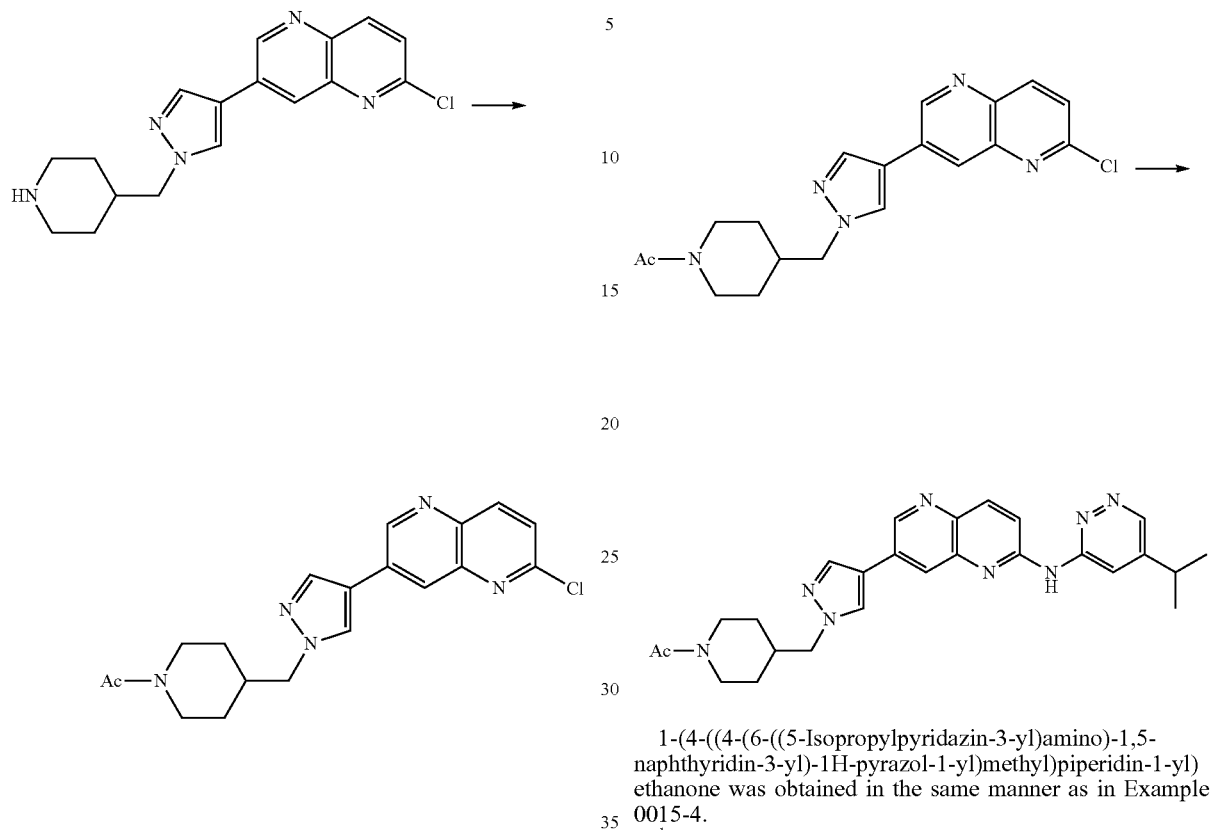

Acetyl chloride (0.008 mL) was added to a solution of 2-chloro-7-(1-(piperidin-4-ylmethyl)-1H-pyrazol-4-yl)-1,5-naphthyridine (23 mg), and triethylamine (0.020 mL) in dichloromethane (1 mL) under ice-cooling, followed by stirring at the same temperature for 2 hours. The reaction mixture was purified by silica gel column chromatography (methanol-ethyl acetate, NH silica), thereby obtaining 1-(4-((4-(6-chloro-1,5-naphthyridin-3-yl)-1H-pyrazol-1-yl)methyl)piperidin-1-yl)ethanone (8.5 mg).
MSm/z(M+H):370.

1-(4-((4-(6-((5-Isopropylpyridazin-3-yl)amino)-1,5-naphthyridin-3-yl)-1H-pyrazol-1-yl)methyl)piperidin-1-yl)ethanone was obtained in the same manner as in Example 0015-4.
$^1$H-NMR(CDCl$_3$)δ:9.72(1H,brs),8.94-8.91(2H,m),8.84 (1H,d,J=1.8 Hz),8.25(1H,d,J=9.3 Hz),8.11(1H,d,J=2.1 Hz), 7.98(1H,s,),7.81(1H,s),7.74(1H,J=9.3 Hz),4.74-4.64(1H, m),4.15-4.06(2H,m),3.91-3.80(1H,m),3.13-2.99(2H,m), 2.62-2.49(1H,m),2.35-2.18(1H,m),2.09(3H,s),1.77-1.60 (2H,m),1.43(6H,d,J=6.6 Hz),1.36-1.18(2H,m).
MSm/z(M+H):471.

Examples 0529 to 0539

The following compounds were obtained in the same manner as in Examples 0528-3 and 0015-4.

Example No.

0529

0529-1

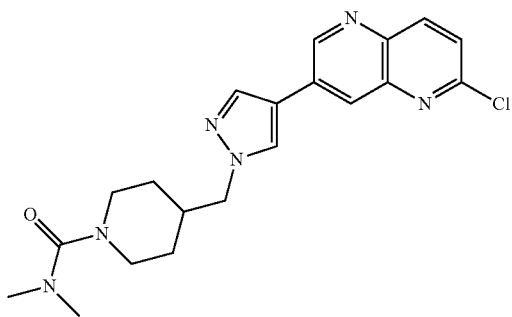 [SMILES: CN(C)C(=O)N1CCC(Cn2cc(-c3cnc4ccc(Cl)nc4c3)cn2)CC1]

MS m/z (M + H): 399.

| Example No. | | |
|---|---|---|
| 0529-2 | 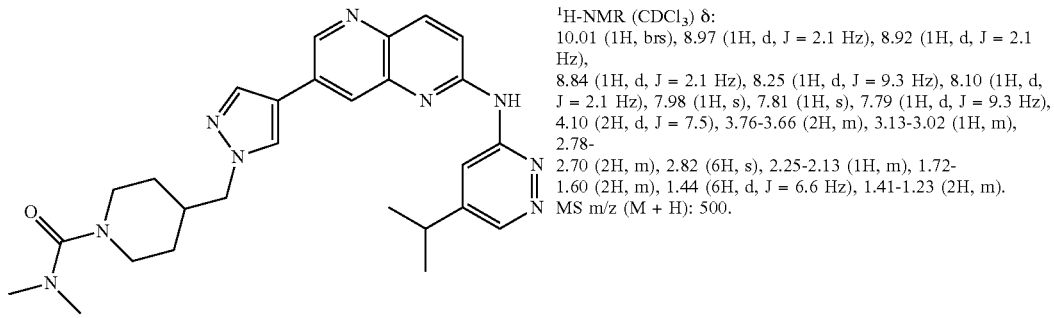 | ¹H-NMR (CDCl₃) δ:<br>10.01 (1H, brs), 8.97 (1H, d, J = 2.1 Hz), 8.92 (1H, d, J = 2.1 Hz),<br>8.84 (1H, d, J = 2.1 Hz), 8.25 (1H, d, J = 9.3 Hz), 8.10 (1H, d, J = 2.1 Hz), 7.98 (1H, s), 7.81 (1H, s), 7.79 (1H, d, J = 9.3 Hz), 4.10 (2H, d, J = 7.5), 3.76-3.66 (2H, m), 3.13-3.02 (1H, m), 2.78-2.70 (2H, m), 2.82 (6H, s), 2.25-2.13 (1H, m), 1.72-1.60 (2H, m), 1.44 (6H, d, J = 6.6 Hz), 1.41-1.23 (2H, m).<br>MS m/z (M + H): 500. |
| 0530 | | |
| 0530-1 | 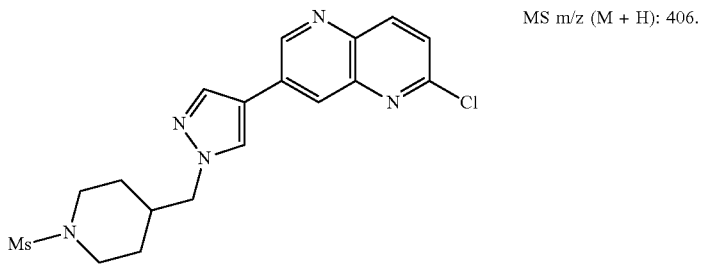 | MS m/z (M + H): 406. |
| 0530-2 | 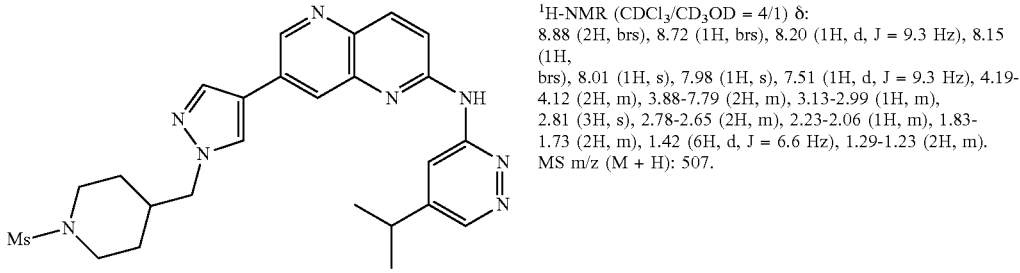 | ¹H-NMR (CDCl₃/CD₃OD = 4/1) δ:<br>8.88 (2H, brs), 8.72 (1H, brs), 8.20 (1H, d, J = 9.3 Hz), 8.15 (1H, brs), 8.01 (1H, s), 7.98 (1H, s), 7.51 (1H, d, J = 9.3 Hz), 4.19-4.12 (2H, m), 3.88-7.79 (2H, m), 3.13-2.99 (1H, m), 2.81 (3H, s), 2.78-2.65 (2H, m), 2.23-2.06 (1H, m), 1.83-1.73 (2H, m), 1.42 (6H, d, J = 6.6 Hz), 1.29-1.23 (2H, m).<br>MS m/z (M + H): 507. |
| 0531 | | |
| 0531-1 | 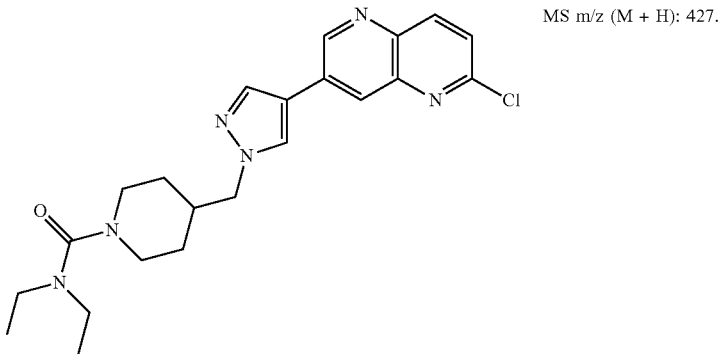 | MS m/z (M + H): 427. |

-continued
| Example No. | | |
|---|---|---|
| 0531-2 | 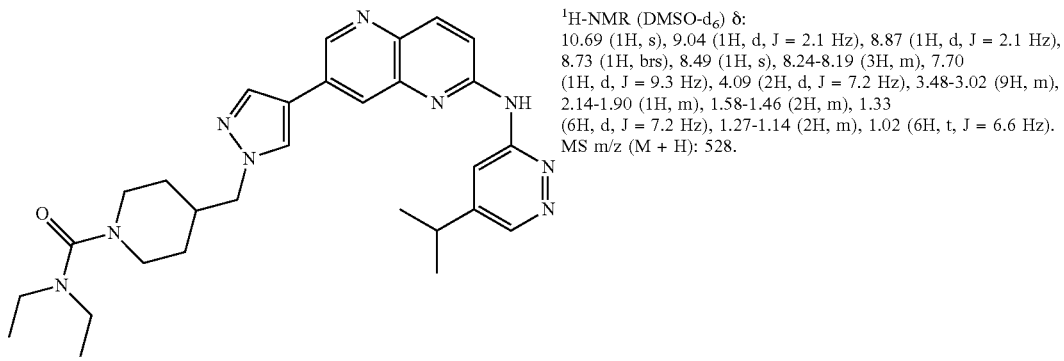 | ¹H-NMR (DMSO-d₆) δ: 10.69 (1H, s), 9.04 (1H, d, J = 2.1 Hz), 8.87 (1H, d, J = 2.1 Hz), 8.73 (1H, brs), 8.49 (1H, s), 8.24-8.19 (3H, m), 7.70 (1H, d, J = 9.3 Hz), 4.09 (2H, d, J = 7.2 Hz), 3.48-3.02 (9H, m), 2.14-1.90 (1H, m), 1.58-1.46 (2H, m), 1.33 (6H, d, J = 7.2 Hz), 1.27-1.14 (2H, m), 1.02 (6H, t, J = 6.6 Hz). MS m/z (M + H): 528. |
| 0532 | | |
| 0532-1 | 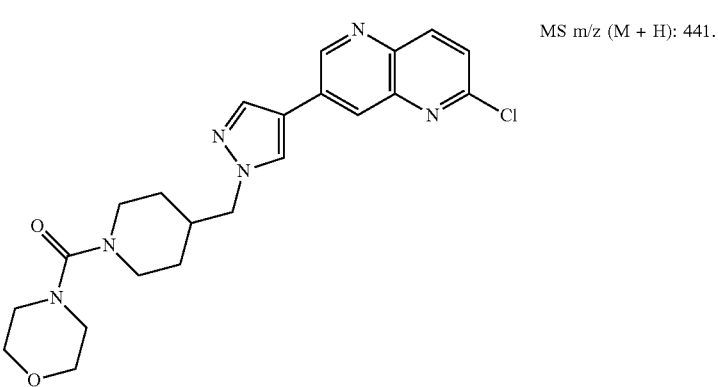 | MS m/z (M + H): 441. |
| 0532-2 | 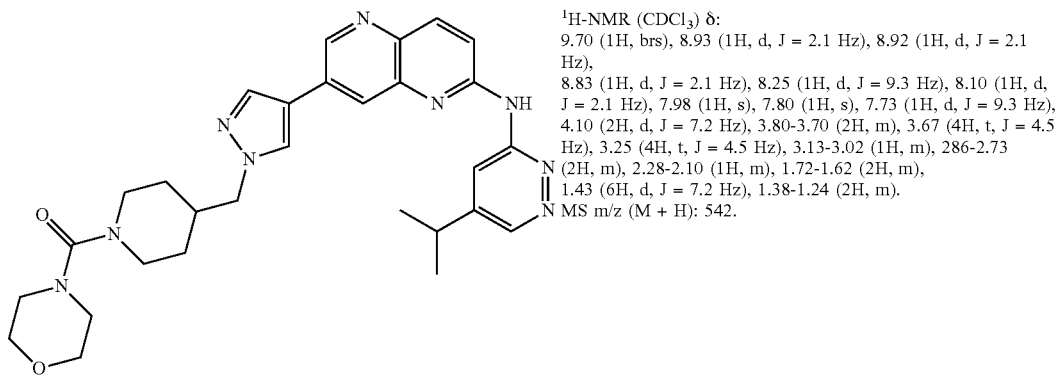 | ¹H-NMR (CDCl₃) δ: 9.70 (1H, brs), 8.93 (1H, d, J = 2.1 Hz), 8.92 (1H, d, J = 2.1 Hz), 8.83 (1H, d, J = 2.1 Hz), 8.25 (1H, d, J = 9.3 Hz), 8.10 (1H, d, J = 2.1 Hz), 7.98 (1H, s), 7.80 (1H, s), 7.73 (1H, d, J = 9.3 Hz), 4.10 (2H, d, J = 7.2 Hz), 3.80-3.70 (2H, m), 3.67 (4H, t, J = 4.5 Hz), 3.25 (4H, t, J = 4.5 Hz), 3.13-3.02 (1H, m), 286-2.73 (2H, m), 2.28-2.10 (1H, m), 1.72-1.62 (2H, m), 1.43 (6H, d, J = 7.2 Hz), 1.38-1.24 (2H, m). MS m/z (M + H): 542. |
| 0533 | | |
| 0533-1 | 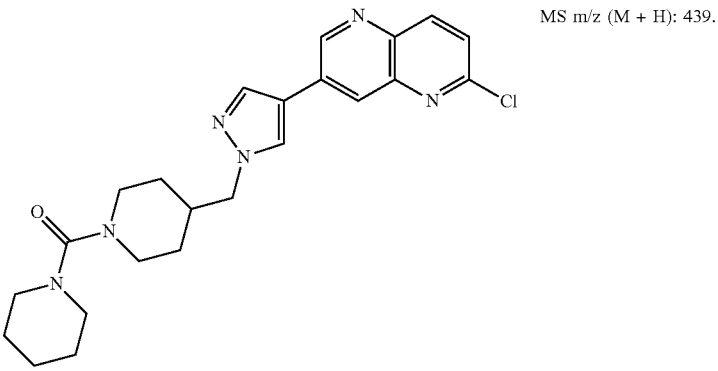 | MS m/z (M + H): 439. |

| Example No. | | |
|---|---|---|
| 0533-2 | 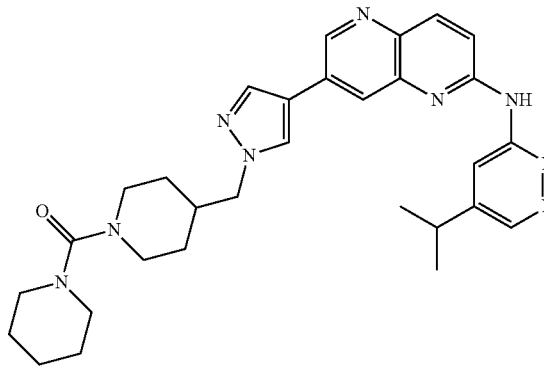 | $^1$H-NMR (CDCl$_3$) δ: 9.98 (1H, brs), 8.96 (1H, d, J = 2.1 Hz), 8.92 (1H, d, J = 2.1 Hz), 8.83 (1H, d, J = 2.1 Hz), 8.25 (1H, d, J = 93 Hz), 8.10 (1H, d, J = 2.1 Hz), 7.97 (1H, s), 7.81 (1H, s), 7.79 (1H, d, J = 93 Hz), 4.10 (2H, d, J = 6.6 Hz), 3.75-3.66 (2H, m), 3.22-3.14 (4H, m), 3.13-3.02 (1H, m), 2.82-2.70 (2H, m), 2.26-2.09 (1H, m), 1.72-1.58 (2H, m), 1.43 (6H, d, J = 6.6 Hz), 1.40-1.23 (4H, m). MS m/z (M + H): 540. |
| 0534 | | |
| 0534-1 | 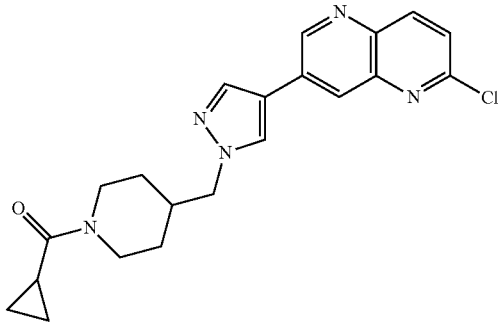 [SMILES: O=C(C1CC1)N1CCC(Cn2cc(-c3cnc4ccc(Cl)nc4c3)cn2)CC1] | MS m/z (M + H): 396. |
| 0534-2 | 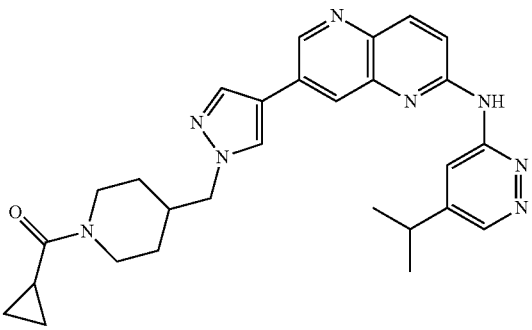 [SMILES: CC(C)c1cnnc(Nc2ccc3ncc(-c4cnn(CC5CCN(C(=O)C6CC6)CC5)c4)cc3n2)c1] | $^1$H-NMR (CDCl$_3$) δ: 9.38 (1H, brs), 8.92 (1H, d, J = 2.1 Hz), 8.88 (1H, brs), 8.83 (1H, d, J = 2.1 Hz), 8.25 (1H, d, J = 9.0 Hz), 8.11 (1H, d, J = 2.1 Hz), 7.98 (1H, s), 7.81 (1H, s), 7.67 (1H, d, J = 9.0 Hz), 4.78-4.60 (2H, m), 4.33-4.06 (4H, m), 3.13-3.01 (1H, m), 2.68-2.52 (1H, m), 2.37-2.20 (1H, m), 1.80-1.66 (2H, m), 1.43 (6H, d, J = 6.6 Hz), 1.36-1.23 (2H, m), 1.01-0.94 (2H, m), 0.79-0.71 (2H, m). MS m/z (M + H): 497. |
| 0535 | | |
| 0535-1 | 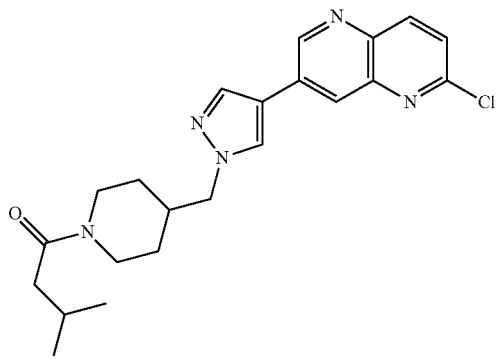 [SMILES: CC(C)CC(=O)N1CCC(Cn2cc(-c3cnc4ccc(Cl)nc4c3)cn2)CC1] | MS m/z (M + H): 412. |

| Example No. | | |
|---|---|---|
| 0535-2 | 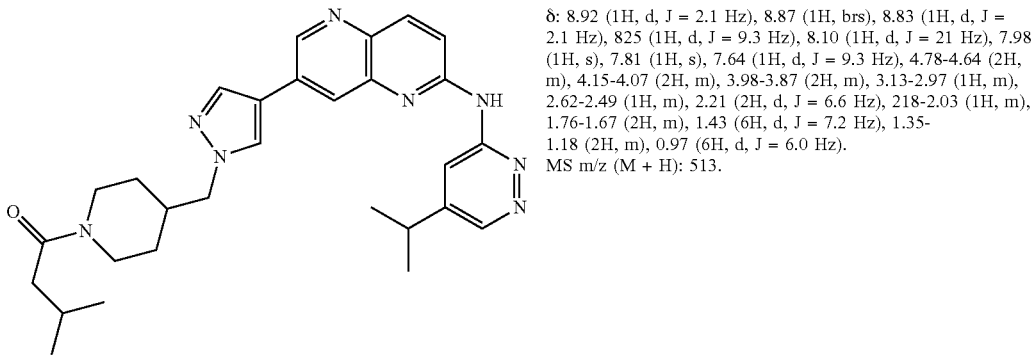 | δ: 8.92 (1H, d, J = 2.1 Hz), 8.87 (1H, brs), 8.83 (1H, d, J = 2.1 Hz), 825 (1H, d, J = 9.3 Hz), 8.10 (1H, d, J = 21 Hz), 7.98 (1H, s), 7.81 (1H, s), 7.64 (1H, d, J = 9.3 Hz), 4.78-4.64 (2H, m), 4.15-4.07 (2H, m), 3.98-3.87 (2H, m), 3.13-2.97 (1H, m), 2.62-2.49 (1H, m), 2.21 (2H, d, J = 6.6 Hz), 218-2.03 (1H, m), 1.76-1.67 (2H, m), 1.43 (6H, d, J = 7.2 Hz), 1.35-1.18 (2H, m), 0.97 (6H, d, J = 6.0 Hz).<br>MS m/z (M + H): 513. |
| 0536 | | |
| 0536-1 | 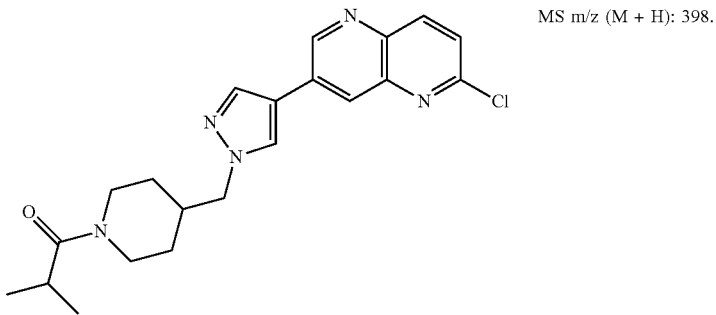 | MS m/z (M + H): 398. |
| 0536-2 | 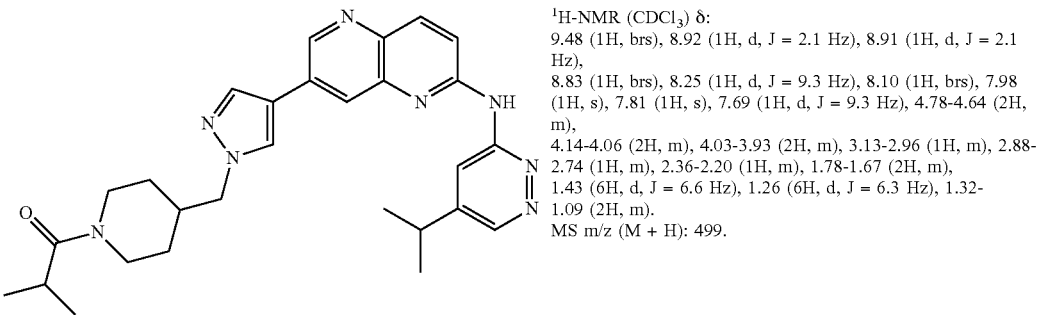 | $^1$H-NMR (CDCl$_3$) δ:<br>9.48 (1H, brs), 8.92 (1H, d, J = 2.1 Hz), 8.91 (1H, d, J = 2.1 Hz),<br>8.83 (1H, brs), 8.25 (1H, d, J = 9.3 Hz), 8.10 (1H, brs), 7.98 (1H, s), 7.81 (1H, s), 7.69 (1H, d, J = 9.3 Hz), 4.78-4.64 (2H, m),<br>4.14-4.06 (2H, m), 4.03-3.93 (2H, m), 3.13-2.96 (1H, m), 2.88-2.74 (1H, m), 2.36-2.20 (1H, m), 1.78-1.67 (2H, m),<br>1.43 (6H, d, J = 6.6 Hz), 1.26 (6H, d, J = 6.3 Hz), 1.32-1.09 (2H, m).<br>MS m/z (M + H): 499. |
| 0537 | | |
| 0537-1 | 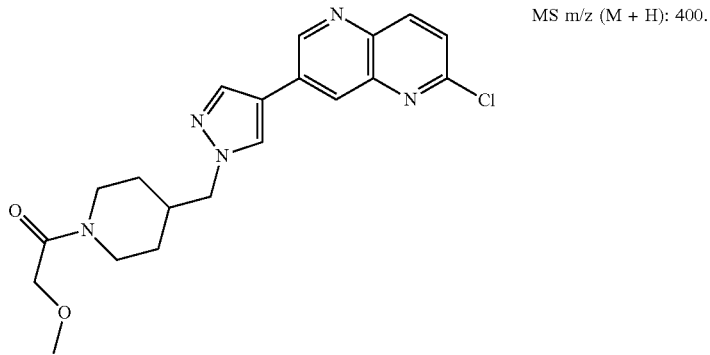 | MS m/z (M + H): 400. |

| Example No. | | |
|---|---|---|
| 0537-2 | 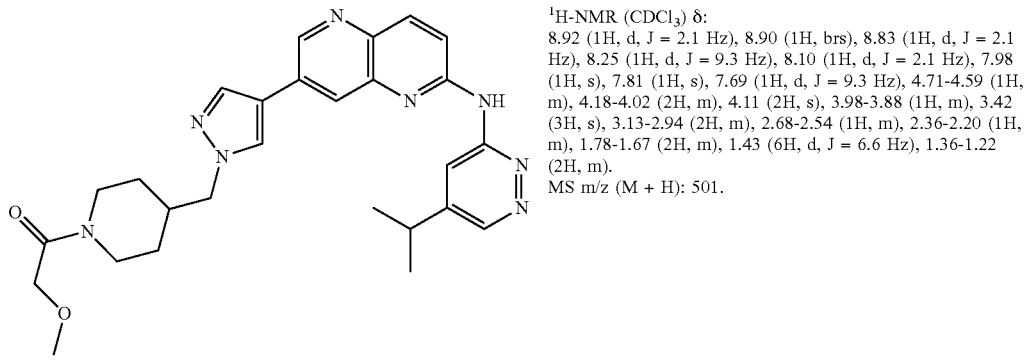 | ¹H-NMR (CDCl₃) δ:<br>8.92 (1H, d, J = 2.1 Hz), 8.90 (1H, brs), 8.83 (1H, d, J = 2.1 Hz), 8.25 (1H, d, J = 9.3 Hz), 8.10 (1H, d, J = 2.1 Hz), 7.98 (1H, s), 7.81 (1H, s), 7.69 (1H, d, J = 9.3 Hz), 4.71-4.59 (1H, m), 4.18-4.02 (2H, m), 4.11 (2H, s), 3.98-3.88 (1H, m), 3.42 (3H, s), 3.13-2.94 (2H, m), 2.68-2.54 (1H, m), 2.36-2.20 (1H, m), 1.78-1.67 (2H, m), 1.43 (6H, d, J = 6.6 Hz), 1.36-1.22 (2H, m).<br>MS m/z (M + H): 501. |
| 0538 | | |
| 0538-1 | 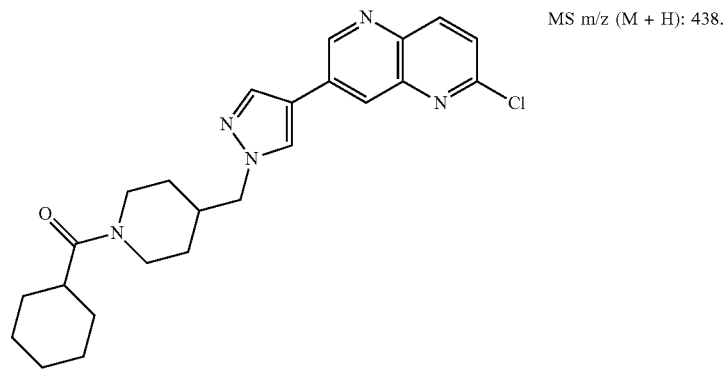 | MS m/z (M + H): 438. |
| 0538-2 | 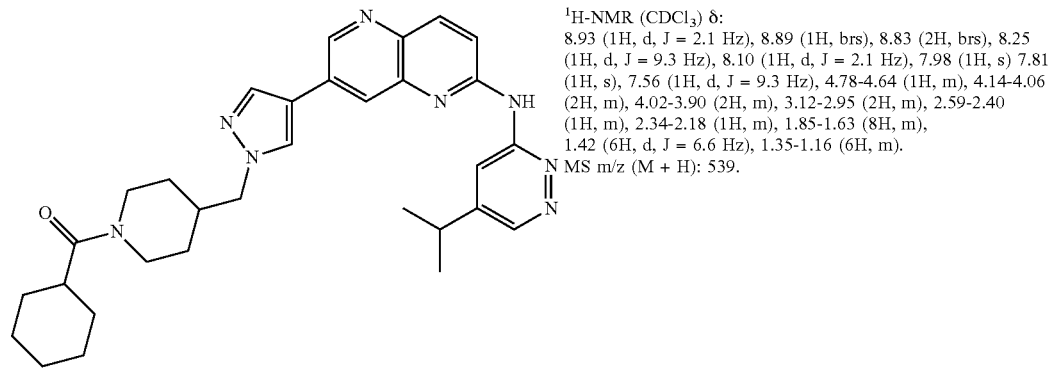 | ¹H-NMR (CDCl₃) δ:<br>8.93 (1H, d, J = 2.1 Hz), 8.89 (1H, brs), 8.83 (2H, brs), 8.25 (1H, d, J = 9.3 Hz), 8.10 (1H, d, J = 2.1 Hz), 7.98 (1H, s) 7.81 (1H, s), 7.56 (1H, d, J = 9.3 Hz), 4.78-4.64 (1H, m), 4.14-4.06 (2H, m), 4.02-3.90 (2H, m), 3.12-2.95 (2H, m), 2.59-2.40 (1H, m), 2.34-2.18 (1H, m), 1.85-1.63 (8H, m), 1.42 (6H, d, J = 6.6 Hz), 1.35-1.16 (6H, m).<br>MS m/z (M + H): 539. |
| 0539 | | |
| 0539-1 | 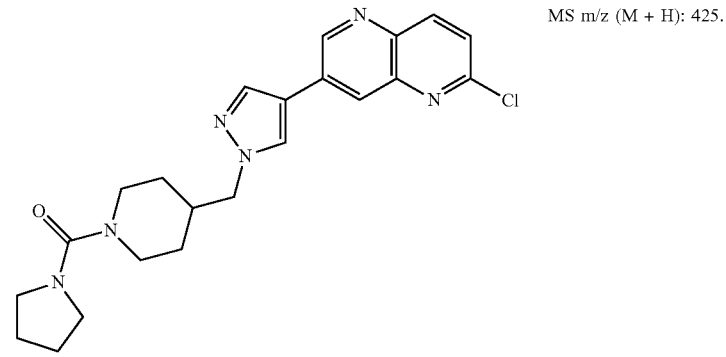 | MS m/z (M + H): 425. |

| Example No. | | |
|---|---|---|
| 0539-2 | 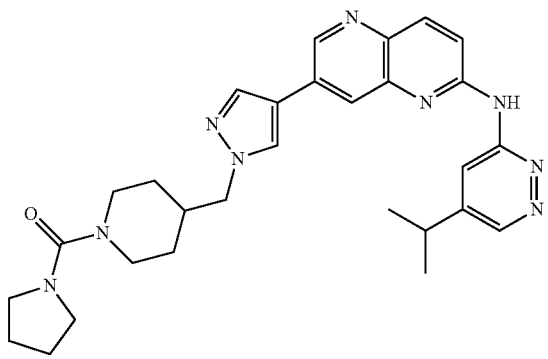 [SMILES: CC(C)c1cnnc(Nc2ccc3ncc(-c4cnn(CC5CCN(C(=O)N6CCCC6)CC5)c4)cc3n2)c1] | ¹H-NMR (CDCl₃) δ:<br>10.07 (1H, brs), 8.96 (1H, brs), 8.92 (1H, brs), 8.83 (1H, d, J = 2.1 Hz), 8.25 (1H, d, J = 8.4 Hz), 8.10 (1H, d, J = 2.1 Hz), 7.97 (1H, s), 7.81 (1H, s), 7.79 (1H, d, J = 8.4 Hz), 4.10 (2H, d, J = 7.2 Hz), 3.86-3.76 (2H, m), 3.39-3.31 (4H, m), 3.13-3.02 (1H, m), 2.88-2.69 (2H, m), 2.27-2.10 (1H, m), 1.86-1.60 (6H, m), 1.43 (6H, d, J = 7.2 Hz), 1.41-1.23 (2H, m).<br>MS m/z (M + H): 526. |

Example 0540

0540-1

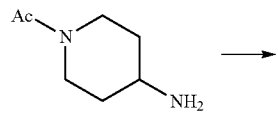

A suspension of 7-bromo-2-chloro-1,5-naphthyridine (44 mg), 1-(4-aminopiperidin-1-yl)ethanone (26 mg), tris(dibenzylideneacetone)dipalladium(0) (15 mg), 4,5-bis(diphenylphosphino)-9,9-dimethylxanthene (30 mg), and sodium tert-butoxide (50 mg) in 1,4-dioxane (2 mL) was stirred at 80° C. for 4 hours. The reaction mixture was cooled to room temperature, and purified by silica gel column chromatography (methanol-ethyl acetate), thereby obtaining 1-(4-((6-chloro-1,5-naphthyridin-3-yl)amino)piperidin-1-yl)ethanone (8.1 mg).

MSm/z(M+H):305.

0540-2

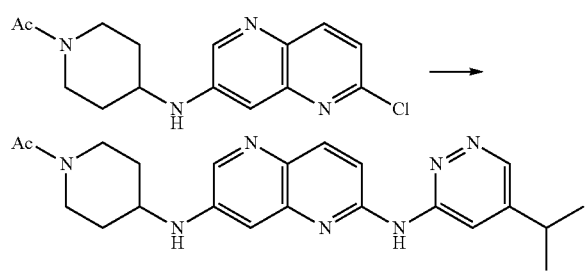

1-(4-((6-((5-Isopropylpyridazin-3-yl)amino)-1,5-naphthyridin-3-yl)amino)piperidin-1-yl)ethanone was obtained in the same manner as in Example 0015-4.

¹H-NMR(CDCl₃)δ:8.83(1H,brs),8.78(1H,d,J=2.1 Hz), 8.64(1H,d,J=2.1 Hz),8.27(1H,d,J=2.7 Hz),8.10(1H,d,J=9.3 Hz),7.37(1H,d,J=9.3 Hz),7.03(1H,d,J=2.7 Hz),4.61-4.50 (1H,m),3.94-3.82(1H,m),3.74-3.60(1H,m),3.35-3.21(1H, m),3.07-2.81(2H,m),2.28-2.13(2H,m),2.14(3H,s),1.55-1.41 (2H,m),1.40(6H,d,J=6.6 Hz).

MSm/z(M+H):406.

Example 0541

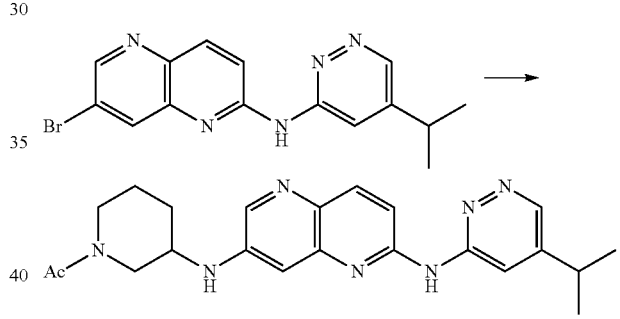

A suspension of 7-bromo-N-(5-isopropylpyridazin-3-yl)-1,5-naphthyridine-2-amine (10 mg), 1-(3-aminopiperidin-1-yl)ethanone (6.2 mg), tris(dibenzylideneacetone)dipalladium(0) (5 mg), 2-(dicyclohexylphosphino)-2',4',6'-triisopropylbiphenyl (10 mg), and sodium tert-butoxide (30 mg) in 1,4-dioxane (1 mL) was stirred at 140° C. for 30 minutes using a microwave reaction apparatus. The reaction mixture was cooled to room temperature, and purified by silica gel column chromatography (methanol-ethyl acetate, NH silica), thereby obtaining 1-(3-((6-(5-isopropylpyridazin-3-yl)amino)-1,5-naphthyridin-3-yl)amino)piperidin-1-yl)ethanone (3.9 mg).

¹H-NMR(CDCl₃)δ:8.77(1H,brs),8.70(1H,s),8.29-8.24 (1H,m),8.13-8.05(1H,m),7.26-7.19(1H,m),7.11-7.02(1H, m),4.28-4.23(1H,m),3.93-3.85(1H,m),3.71-3.21(3H,m), 3.07-2.94(1H,m),2.17(3H,s),1.91-1.58(2H,m),1.39(6H,d, J=6.6 Hz),1.38-1.24(2H,m).

MSm/z(M+H):406.

Example 0542

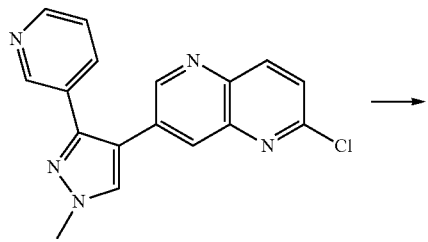

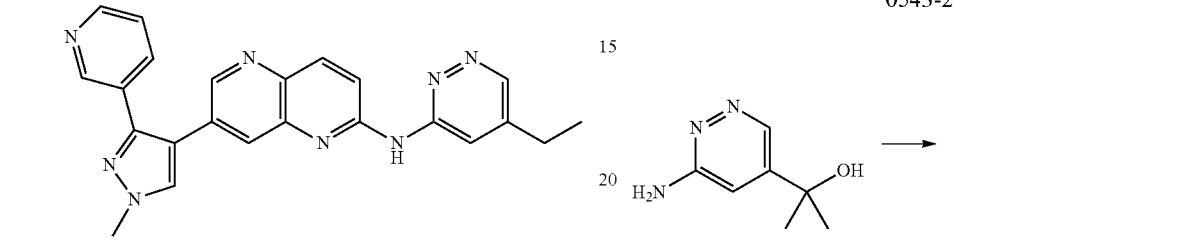

N-(5-ethylpyridazin-3-yl)-7-(1-methyl-3-(pyridin-3-yl)-1H-pyrazol-4-yl)-1,5-naphthyridine-2-amine was obtained in the same manner as in Example 0015-4.

$^1$H-NMR(CDCl$_3$)δ:9.65(1H,brs),8.80(2H,brs),8.76(1H,d,J=2.1 Hz),8.66(1H,d,J=2.1 Hz),8.57(1H,dd,J=5.4,2.1 Hz),8.24(1H,d,J=9.3 Hz),7.95(1H,d,J=2.1 Hz),7.81(1H,dt,J=7.8,2.1 Hz),7.73(1H,d,J=9.3 Hz),7.71(1H,s),7.31-7.24(1H,m),4.07(3H,s),2.73(2H,q,J=7.2 Hz),1.33(3H,t,J=7.2 Hz).

MSm/z(M+H):409.

Example 0543

0543-1

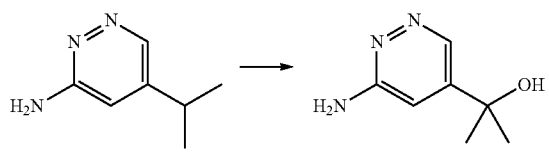

A mixture of 5-isopropylpyridazine-3-amine (300 mg), potassium permanganate (1.38 g), water (2 mL), and tert-butyl alcohol (10 mL) was stirred at 50° C. for 10 hours. The reaction mixture was cooled to room temperature, the insolubles were filtered off, and the solvent was distilled off under reduced pressure. The obtained residue was purified by silica gel column chromatography (methanol-ethyl acetate, NH silica), thereby obtaining 2-(6-aminopyridazin-4-yl)propan-2-ol (96 mg).

MSm/z(M+H):154.

0543-2

2-(6-((7-(1-Methyl-1H-pyrazol-4-yl)-1,5-naphthyridin-2-yl)amino)pyridazin-4-yl)propan-2-ol was obtained in the same manner as in Example 0015-4.

$^1$H-NMR(CDCl$_3$/CD$_3$OD=4/1)δ:9.06(1H,brs),8.91(1H,brs),8.88(1H,d,J=2.1 Hz),8.22(1H,d,J=2.1 Hz),8.19(1H,d,J=9.3 Hz),7.98(1H,s),7.97(1H,s),7.54(1H,d,J=9.3 Hz),4.02(3H,s),1.66(6H,s).

MSm/z(M+H):362.

Example 0544

The following compounds were obtained in the same manner as in Examples 0528-3 and 0438-4.

| Example No. | | |
|---|---|---|
| 0544 | | |
| 0544-1 | 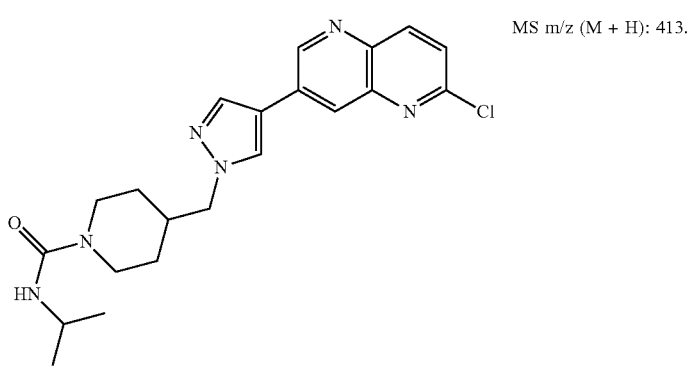 | MS m/z (M + H): 413. |

| Example No. | | |
|---|---|---|
| 0544-2 | 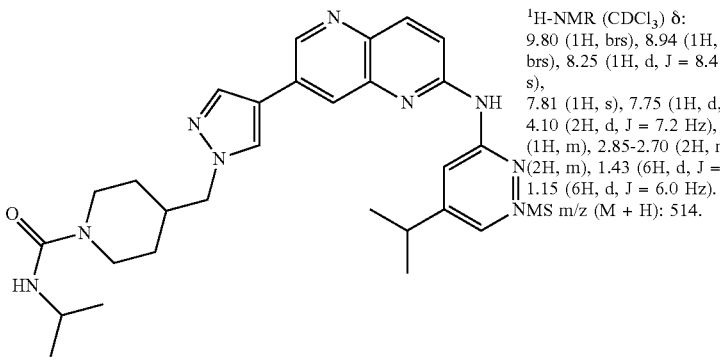 | ¹H-NMR (CDCl₃) δ:<br>9.80 (1H, brs), 8.94 (1H, brs), 8.92 (1H, d, J = 2.1 Hz), 8.83 (1H, brs), 8.25 (1H, d, J = 8.4 Hz), 8.10 (1H, d, J = 2.1 Hz), 7.97 (1H, s),<br>7.81 (1H, s), 7.75 (1H, d, J = 8.4 Hz), 4.23-4.18 (1H, m),<br>4.10 (2H, d, J = 7.2 Hz), 4.01-3.90 (3H, m), 3.13-2.99 (1H, m), 2.85-2.70 (2H, m), 2.27-2.10 (1H, m), 1.73-1.56 (2H, m), 1.43 (6H, d, J = 6.6 Hz), 1.39-1.18 (2H, m), 1.15 (6H, d, J = 6.0 Hz).<br>MS m/z (M + H): 514. |

Example 0545

0545-1

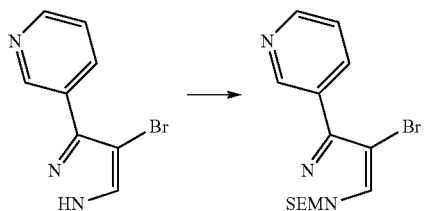

(2-(Chloromethoxy)ethyl)trimethylsilane (0.188 mL) was added to a mixture of 3-(4-bromo-1H-pyrazol-3-yl)pyridine (200 mg), N,N-diisopropylethylamine (0.200 mL), and dichloromethane (9 mL), followed by stirring at room temperature for 3 hours. After water and ethyl acetate were added to the reaction mixture, the organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 3-(4-bromo-1-((2-(trimethylsilyl)ethoxy)methyl)-1H-pyrazol-3-yl)pyridine (141 mg).
MSm/z(M+H):354.

0545-2 to 0545-4

The following compounds were obtained in the same manner as in Examples 0478-3, 0438-4, and 0015-4

| Example No. | | |
|---|---|---|
| 0545 | | |
| 0545-2 | 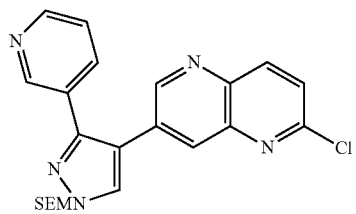 [SMILES: C[Si](C)(C)CCOCn1cc(-c2cnc3ccc(Cl)nc3c2)c(-c2cccnc2)n1] | MS m/z (M + H): 438. |
| 0545-3 | 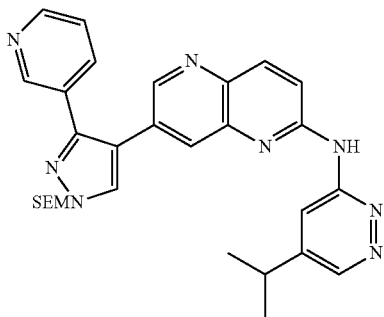 [SMILES: CC(C)c1cnnc(Nc2ccc3ncc(-c4cn(COCC[Si](C)(C)C)nc4-c4cccnc4)cc3n2)c1] | MS m/z (M + H): 539. |

| Example No. | | |
|---|---|---|
| 0545-4 | 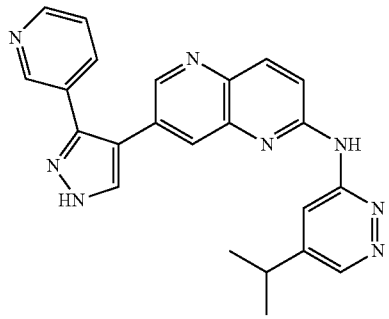 [SMILES: CC(C)c1cnnc(Nc2ccc3ncc(-c4c[nH]nc4-c4cccnc4)cc3n2)c1] | $^1$H-NMR (DMSO-$d_6$) δ:<br>8.97 (1H, brs), 8.88-8.65 (2H, m), 8.79 (1H, d, J = 2.1 Hz), 8.44 (1H, brs), 8.38 (1H, s), 8.37 (1H, d, J = 7.5 Hz), 8.27 (1H, brs), 8.15 (1H, d, J = 7.5 Hz), 7.74 (1H, d, J = 7.5 Hz), 7.73-7.63 (1H, m), 3.15-2.97 (1H, m), 1.27 (6H, d, J = 6.6 Hz).<br>MS m/z (M + H): 409. |

Examples 0546 and 0547

The following compounds were obtained in the same manner as in Example 0015-4.

| Example No. | | |
|---|---|---|
| 0546 | 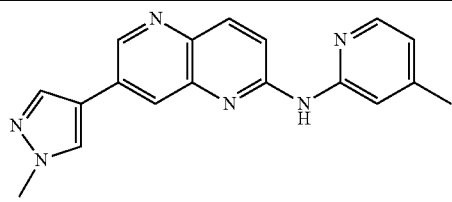 | $^1$H-NMR (CDCl$_3$) δ:<br>8.89 (1H, d, J = 2.1 Hz), 8.15 (1H, d, J = 5.4 Hz), 8.13 (1H, d, J = 9.3 Hz), 8.14 (1H, d, J = 2.1 Hz), 8.11 (1H, brs), 7.95 (1H, s),<br>7.83 (1H, s), 7.48 (1H, d, J = 9.3 Hz), 6.81 (1H, d, J = 5.4 Hz), 4.02 (3H, s), 2.44 (3H, s).<br>MS m/z (M + H): 317. |
| 0547 | 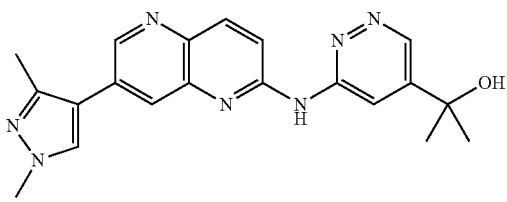 [SMILES: Cc1nn(C)cc1-c1cnc2ccc(Nc3cc(C(C)(C)O)cnn3)nc2c1] | $^1$H-NMR (CDCl$_3$/CD$_3$OD = 4/1) δ:<br>9.02 (1H, brs), 8.93 (1H, brs), 8.78 (1H, d, J = 1.8 Hz), 8.23 (1H, d, J = 9.3 Hz), 8.13 (1H, brs), 7.76 (1H, s), 7.58 (1H, d, J = 9.3 Hz), 3.94 (3H, s), 2.49 (3H, s), 1.64 (6H, s).<br>MS m/z (M + H): 376. |

Example 0548

The following compounds were obtained in the same manner as in Examples 0475-1, 0528-2, 0528-3, and 0438-4.

| Example No. | | |
|---|---|---|
| 0548 | | |
| 0548-1 | 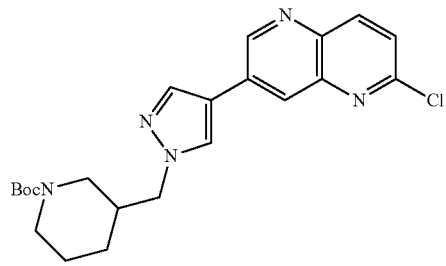 [SMILES: CC(C)(C)OC(=O)N1CCCC(Cn2cc(-c3cnc4ccc(Cl)nc4c3)cn2)C1] | MS m/z (M + H): 428. |

| Example No. | | |
|---|---|---|
| 0548-2 | 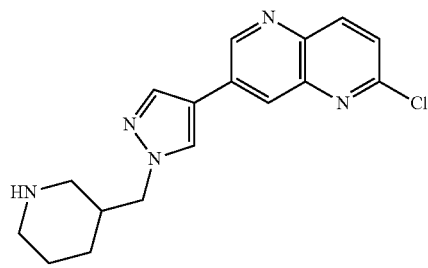 [SMILES: Clc1ccc2ncc(-c3cnn(CC4CCCNC4)c3)cc2n1] | MS m/z (M + H): 328. |
| 0548-3 | 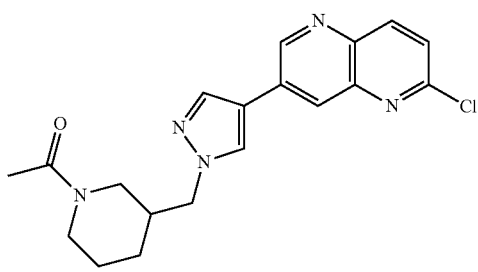 [SMILES: CC(=O)N1CCCC(Cn2cc(-c3cnc4ccc(Cl)nc4c3)cn2)C1] | MS m/z (M + H): 370. |
| 0548-4 | 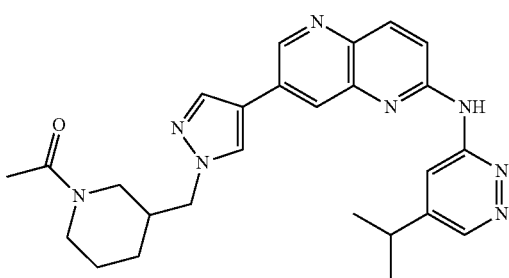 [SMILES: CC(=O)N1CCCC(Cn2cc(-c3cnc4ccc(Nc5cc(C(C)C)cnn5)nc4c3)cn2)C1] | ¹H-NMR (CDCl₃) δ:<br>8.92 (1H, d, J = 2.1 Hz), 8.90 (1H, brs), 8.82 (1H, brs), 8.24 (1H, d,<br>J = 3.1 Hz), 8.10 (1H, brs), 7.98 (1H, d, J = 11.1 Hz), 7.86 (1H, d,<br>J = 11.1 Hz), 7.75-7.55 (1H, m), 4.33-4.03 (3H, m), 3.75-3.58<br>(1H, m), 3.24-2.74 (3H, m), 2.29-2.14 (1H, m),<br>2.12 (3H, s), 1.94-1.70 (2H, m), 1.43 (6H, d, J = 6.6 Hz), 1.40-<br>1.25 (2H, m).<br>MS m/z (M + H): 471. |

Example 0549

0549-1

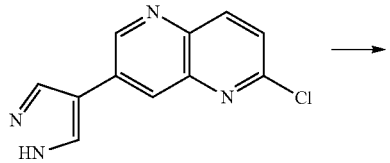

A suspension of 2-chloro-7-(1H-pyrazol-4-yl)-1,5-naphthyridine (20 mg), 2-chloro-N,N-dimethylacetamide (0.013 mL), and cesium carbonate (56 mg) in 1,4-dioxane (1 mL) was stirred at 80° C. for 4 hours. The reaction mixture was cooled to room temperature, and purified by silica gel column chromatography (methanol-ethyl acetate), thereby obtaining 2-(4-(6-chloro-1,5-naphthyridin-3-yl)-1H-pyrazol-1-yl)-N,N-dimethylacetamide (20 mg).

MSm/z(M+H):316.

0549-2

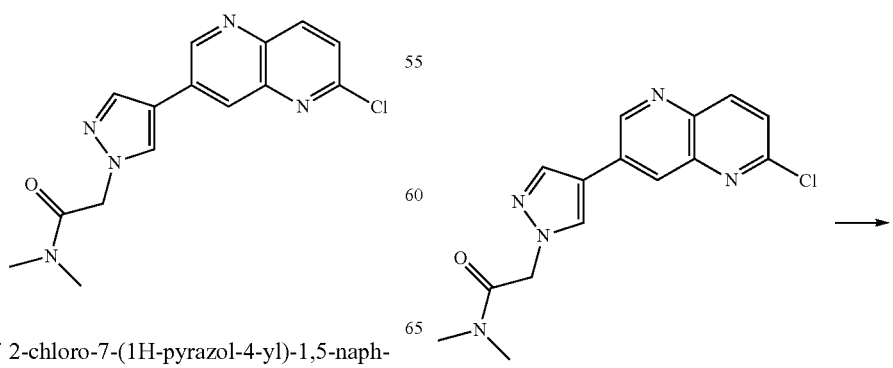

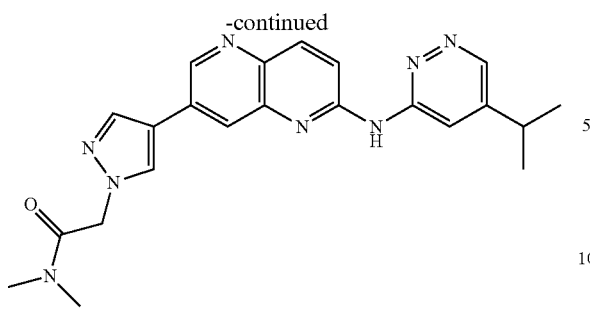

2-(4-(6-((5-Isopropylpyridazin-3-yl)amino)-1,5-naphthyridin-3-yl)-1H-pyrazol-1-yl)-N,N-dimethylacetamide was obtained in the same manner as in Example 0438-4.

¹H-NMR(CDCl₃)δ:8.94(1H,d,J=2.1 Hz),8.88(1H,brs),8.81(1H,brs),8.24(1H,d,J=9.3 Hz),8.11(1H,brs),8.02(1H,s),7.99(1H,s),7.52(1H,d,J=9.3 Hz),5.09(2H,s),3.16(3H,s),3.14-3.01(1H,m),3.04(3H,s),1.42(6H,d,J=7.5 Hz).

MSm/z(M+H):417.

Example 0550

The following compounds were obtained in the same manner as in Examples 0549-1 and 0438-4.

Example 0551

0551-1

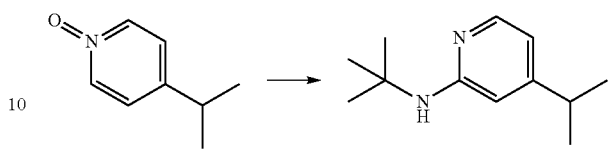

Paratoluenesulfonyl chloride (2.66 g) was added to a mixture of 4-isopropylpyridine 1-oxide (0.96 g), tert-butylamine (7.3 mL), and chloroform (35 mL) under ice-cooling, followed by stirring at room temperature for 4 hours. A 4 mol/L sodium hydroxide aqueous solution was added to the reaction mixture, the organic layer was collected by separation, and dried over anhydrous sodium sulfate, and the solvent was distilled off under reduced pressure. The obtained residue was purified by silica gel column chromatography (methanol-ethyl acetate-hexane), thereby obtaining N-(tert-butyl)-4-isopropylpyridine-2-amine (931 mg).

MSm/z(M+H):193.

| Example No. | | |
|---|---|---|
| 0550 | | |
| 0550-1 | 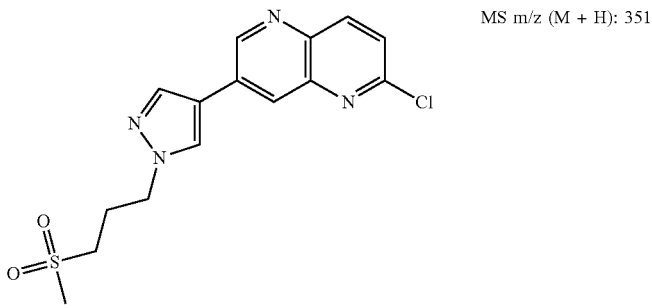 | MS m/z (M + H): 351 |
| 0550-2 |  | ¹H-NMR (DMSO-d₆) δ:<br>10.71 (1H, brs), 9.05 (1H, d, J = 2.1 Hz), 8.87 (1H, d, J = 2.1 Hz),<br>8.74 (1H, brs), 8.54 (1H, s), 8.24 (1H, d, J = 2.1 Hz), 8.22 (1H, d, J = 9.0 Hz), 7.70 (1H, d, J = 9.0 Hz), 4.32 (2H, t, J = 6.9 Hz), 3.23-3.13 (1H, m), 3.00 (3H, s), 2.78-2.70 (2H, m), 2.33-2.22 (2H, m), 1.33 (6H, d, J = 7.2 Hz).<br>MS m/z (M + H): 452. |

0551-2

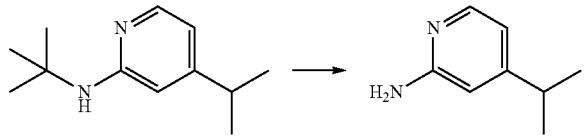

Trifluoroacetic acid (5 mL) was added to a mixture of N-(tert-butyl)-4-isopropylpyridine-2-amine (931 mg) and water (0.25 mL), followed by stirring at room temperature for 2 hours. The solvent was distilled off under reduced pressure, and the obtained residue was purified by silica gel column chromatography (methanol-ethyl acetate), thereby obtaining 4-isopropylpyridine-2-amine (475 mg).
MSm/z(M+H):137.

0551-3

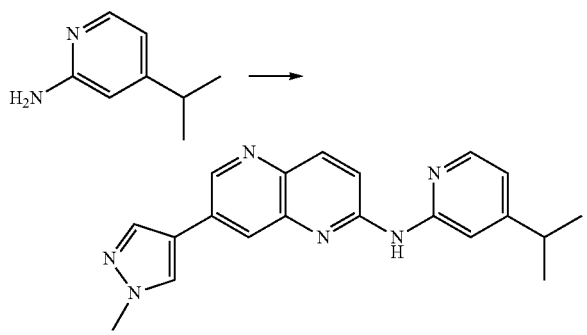

N-(4-isopropylpyridin-2-yl)-7-(1-methyl-1H-pyrazol-4-yl)-1,5-naphthyridine-2-amine was obtained in the same manner as in Example 0015-4.
¹H-NMR(CDCl₃)δ:8.89(1H,d,J=1.8 Hz),8.22-8.09(4H, m),7.94(1H,s),7.82(1H,s),7.52(1H,d,J=8.7 Hz),6.86(1H,dd, J=5.1,1.8 Hz),4.02(3H,s),3.07-2.92(1H,m),1.34(6H,d,J=7.2 Hz).
MSm/z(M+H):345.

Example 0552

The following compounds were obtained in the same manner as in Examples 0478-3 and 0438-4.

| Example No. | | |
|---|---|---|
| 0552 | | |
| 0552-1 | 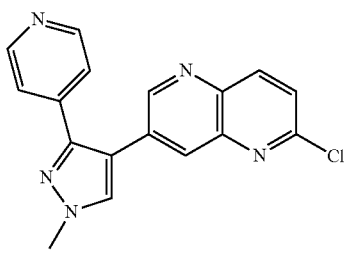 [SMILES: Cn1cc(-c2cnc3ccc(Cl)nc3c2)c(-c2ccncc2)n1] | MS m/z (M + H): 322. |
| 0552-2 | 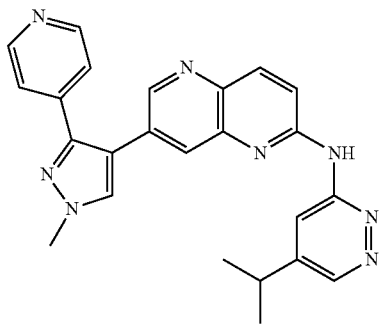 [SMILES: CC(C)c1cnnc(Nc2ccc3ncc(-c4cn(C)nc4-c4ccncc4)cc3n2)c1] | ¹H-NMR (CDCl₃) δ: 9.86 (1H, brs), 8.89 (1H, brs), 8.81 (1H, d, J = 2.1 Hz), 8.68 (1H, d, J = 2.1 Hz), 8.57 (2H, dd, J = 4.5, 1.8 Hz), 8.27 (1H, d, J = 9.3 Hz), 7.97 (1H, d, J = 2.1 Hz), 7.81 (1H, d, J = 9.3 Hz), 7.69 (1H, s), 7.45 (2H, d,, J = 4.5, 1.8 Hz), 4.07 (3H, s), 3.08-2.92 (1H, m), 1.34 (6H, d, J = 7.2 Hz). MS m/z (M + H): 423. |

Example 0553

553-1

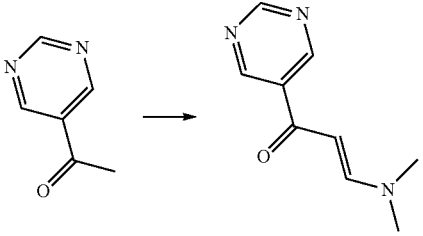

A mixture of 1-(pyrimidin-5-yl)ethanone (525 mg) and N,N-dimethylformamide dimethyl acetal (3 mL) was stirred for 2 hours under heating to reflux. The reaction mixture was cooled to room temperature, and the solvent was distilled off under reduced pressure. tert-Butyl methyl ether was added to the obtained residue, and the solid matter was collected by filtration, thereby obtaining (E)-3-(dimethylamino)-1-(pyrimidin-5-yl)prop-2-en-1-one (657 mg).
MSm/z(M+H):178.

0553-2

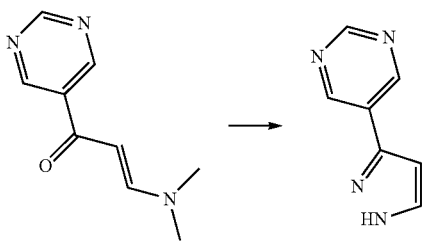

Hydrazine monohydrate (0.198 mL) was added to a mixture of (E)-3-(dimethylamino)-1-(pyrimidin-5-yl)prop-2-en-1-one (657 mg) and ethanol (4 mL), followed by stirring at room temperature for 1 hour. The reaction mixture was distilled off under reduced pressure, thereby obtaining 5-(1H-pyrazol-3-yl)pyrimidine (711 mg).
MSm/z(M+H):147.

0553-3

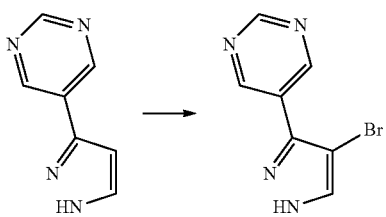 [SMILES: N=C(/C=C\N)c1cncnc1 ; N=C(/C(Br)=C\N)c1cncnc1]

N-bromosuccinimide (724 mg) was added to a solution of 5-(1H-pyrazol-3-yl)pyrimidine (711 mg) in N,N-dimethylformamide (7 mL) under ice-cooling, followed by stirring at the same temperature for 1 hour. After ethyl acetate and water were added to the reaction mixture, the organic layer was collected by separation, washed sequentially with water and a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 5-(4-bromo-1H-pyrazol-3-yl)pyrimidine (63 mg).
MSm/z(M+H):225.

0553-4

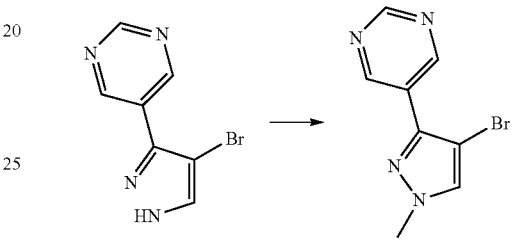

60% sodium hydride (34 mg) was added to a solution of 5-(4-bromo-1H-pyrazol-3-yl)pyrimidine (63 mg) and iodomethane (0.035 mL) in N,N-dimethylformamide (2 mL) under ice-cooling, followed by stirring at room temperature for 1 hour. After ethyl acetate and water were added to the reaction mixture, the organic layer was collected by separation, washed sequentially with water and a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 5-(4-bromo-1-methyl-1H-pyrazol-3-yl)pyrimidine (34 mg).
MSm/z(M+H):239.

0553-5 and 0553-6

The following compounds were obtained in the same manner as in Examples 0478-3 and 0438-4.

| Example No. | | |
|---|---|---|
| 0553 | | |
| 0553-5 | 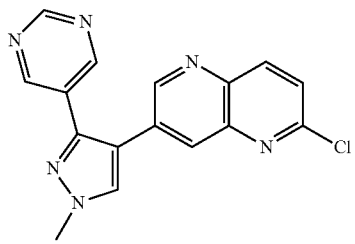 [SMILES: Cn1cc(-c2cnc3ccc(Cl)nc3c2)c(-c2cncnc2)n1] | MS m/z (M + H): 323. |

| Example No. | | |
|---|---|---|
| 0553-6 | 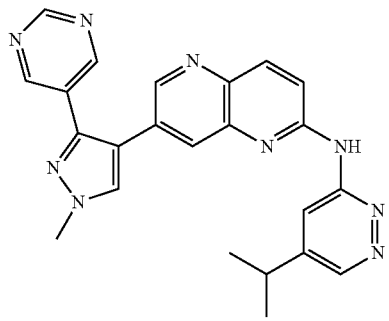 [SMILES: CC(C)c1cnnc(Nc2ccc3ncc(-c4cn(C)nc4-c4cncnc4)cc3n2)c1] | ¹H-NMR (DMSO-d₆) δ:<br>10.76 (1H, brs), 9.18 (1H, s), 8.87 (2H, s), 8.83 (1H, d, J = 1.8 Hz),<br>8.71 (1H, d, J = 1.8 Hz), 8.64 (1H, d, J = 1.8 Hz), 8.41 (1H, s),<br>8.25 (1H, d, J = 9.3 Hz), 7.85 (1H, d, J = 1.8 Hz), 7.74 (1H, d, J = 9.3 Hz),<br>4.02 (3H, s), 3.04-2.88 (1H, m), 1.23 (6H, d, J = 7.2 Hz).<br>MS m/z (M + H): 424. |

Example 0554

0554-1 and 0554-2

The following compounds were obtained in the same manner as in Examples 0517-1 and 0495-5.

| Example No. | | |
|---|---|---|
| 0554 | | |
| 0554-1 | 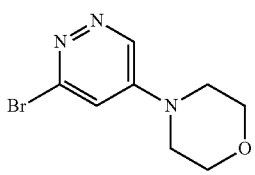 | MS m/z (M + H): 244. |
| 0554-2 | 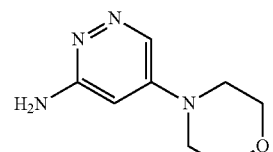 | MS m/z (M + H): 181. |

0554-3

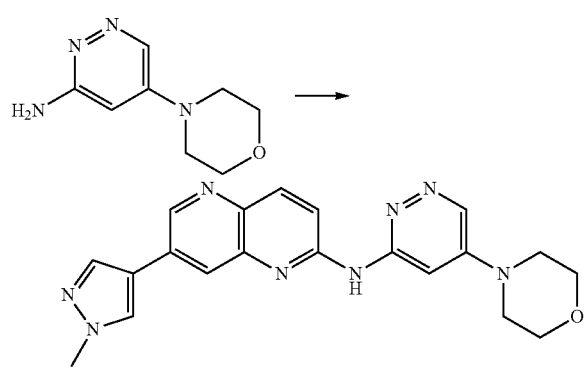

A suspension of 2-chloro-7-(1-methyl-1H-pyrazol-4-yl)-1,5-naphthyridine (13 mg), 5-morpholinopyridazine-3-amine (5.6 mg), sodiumtert-amyl oxide (10 mg), and anhydrous sodium sulfate (50 mg) in 1,4-dioxane (1 mL) was stirred at 110° C. for 2 hours. The reaction mixture was cooled to room temperature, and purified by silica gel column chromatography (methanol-ethyl acetate, NH silica), thereby obtaining 7-(1-methyl-1H-pyrazol-4-yl)-N-(5-morpholinopyridazin-3-yl)-1,5-naphthyridine-2-amine (6.6 mg).

¹H-NMR(CDCl₃/CD₃OD=4/1)δ:8.86(1H,d,J=2.1 Hz), 8.52(1H,d,J=2.1 Hz),8.31(1H,brs),8.18(1H,d,J=8.7 Hz), 8.08(1H,d,J=2.1 Hz),7.94(2H,s),7.47(1H,d,J=8.7 Hz),4.03 (3H,s),3.95(4H,t,J=5.1 Hz),3.52(4H,t,J=5.1 Hz).

MSm/z(M+H):389.

Example 0555

0555-1

A mixture of 1-methyl-1H-pyrazole-3-amine (200 mg), bis(pinacolato)diboron (575 mg), tert-butyl nitrite (0.364 mL), and acetonitrile (5 mL) was stirred for 2 hours under heating to reflux. After the reaction mixture was cooled to room temperature, a 10% sodium hydrogen sulfite aqueous solution was added thereto, the organic layer was collected by separation, washed with a saturated sodium chloride aqueous solution, and dried over anhydrous sodium sulfate, and the solvent was distilled off under reduced pressure, thereby obtaining 1-methyl-3-(4,4,5,5-tetramethyl-1,3,2-dioxaborolan-2-yl)-1H-pyrazole (834 mg).

A mixture of the obtained 1-methyl-3-(4,4,5,5-tetramethyl-1,3,2-dioxaborolan-2-yl)-1H-pyrazole (834 mg), 3-bromo-5-methylpyridine (0.238 mL), sodium carbonate (543 mg), bis(di-tert-butyl(4-dimethylaminophenyl)phosphine)dichloropalladium(II) (72 mg), water (1 mL), and 1,4-dioxane (10 mL) was stirred at 100° C. for 3 hours. The reaction mixture was cooled to room temperature, the insolubles were filtered off, and the obtained residue was purified by silica gel column chromatography (methanol-ethyl acetate), thereby obtaining 3-methyl-5-(1-methyl-1H-pyrazol-3-yl)pyridine (53 mg).

MSm/z(M+H):174.

0555-2

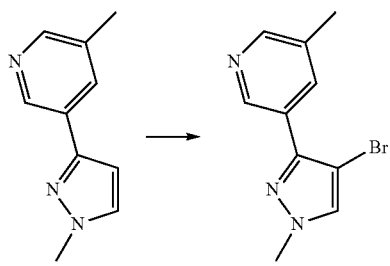

N-bromosuccinimide (60 mg) was added to a solution of 3-methyl-5-(1-methyl-1H-pyrazol-3-yl)pyridine (53 mg) in N,N-dimethylformamide (1.5 mL), followed by stirring at room temperature for 1 hour. Ethyl acetate and a 10% sodium hydrogen sulfite aqueous solution were added to the reaction mixture. The organic layer was collected by separation, washed sequentially with water and a saturated sodium chloride aqueous solution, and dried over anhydrous sodium sulfate, and the solvent was distilled off under reduced pressure. The obtained residue was purified by silica gel column chromatography (methanol-ethyl acetate), thereby obtaining 3-(4-bromo-1-methyl-1H-pyrazol-3-yl)-5-methylpyridine (35 mg).

MSm/z(M+H):252.

0555-3 and 0555-4

The following compounds were obtained in the same manner as in Examples 0478-3 and 0554-3.

| Example No. | | |
|---|---|---|
| 0555 | | |
| 0555-3 | 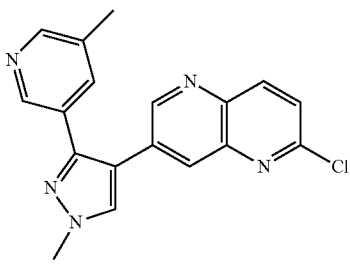 [SMILES: Cc1cncc(-c2nn(C)cc2-c2cnc3ccc(Cl)nc3c2)c1] | MS m/z (M + H): 336. |
| 0555-4 | 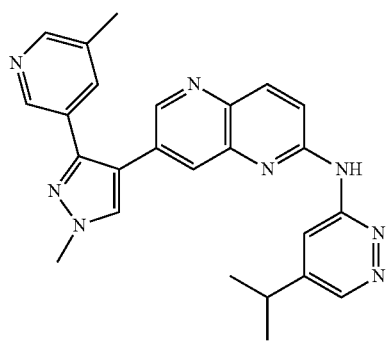 [SMILES: Cc1cncc(-c2nn(C)cc2-c2cnc3ccc(Nc4cc(C(C)C)cnn4)nc3c2)c1] | $^1$H-NMR (CDCl$_3$) δ:<br>10.35 (1H, brs), 8.94 (1H, brs), 8.80 (1H, brs), 8.66 (1H, d, J = 2.1 Hz), 8.52 (1H, d, J = 2.1 Hz), 8.40 (1H, d, J = 2.1 Hz), 8.24 (1H, d, J = 9.0 Hz), 7.92 (1H, d, J = 2.1 Hz), 7.88 (1H, d, J = 9.0 Hz), 7.71 (2H, brs), 4.06 (3H, s), 3.06-2.92 (1H, m), 2.31 (3H, s), 1.34 (6H, d, J = 72 Hz).<br>MS m/z (M + H): 437. |

Example 0556

The following compounds were obtained in the same manner as in Examples 0549-1 and 0554-3.

| Example No. | | |
|---|---|---|
| 0556 | | |
| 0556-1 | 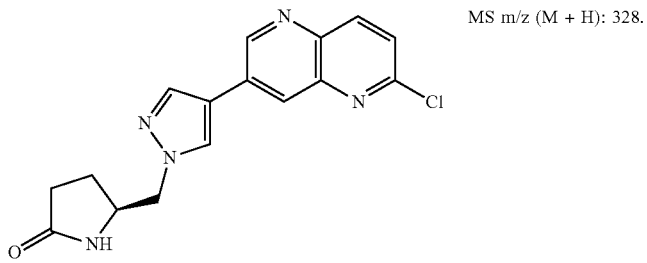 | MS m/z (M + H): 328. |
| 0556-2 | 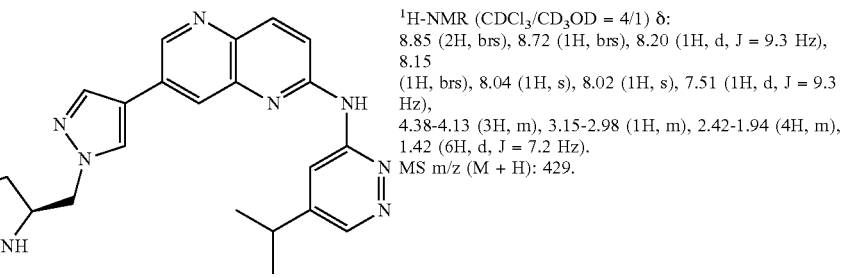 | $^1$H-NMR (CDCl$_3$/CD$_3$OD = 4/1) δ:<br>8.85 (2H, brs), 8.72 (1H, brs), 8.20 (1H, d, J = 9.3 Hz), 8.15<br>(1H, brs), 8.04 (1H, s), 8.02 (1H, s), 7.51 (1H, d, J = 9.3 Hz),<br>4.38-4.13 (3H, m), 3.15-2.98 (1H, m), 2.42-1.94 (4H, m),<br>1.42 (6H, d, J = 7.2 Hz).<br>MS m/z (M + H): 429. |

Example 0557

0557-1

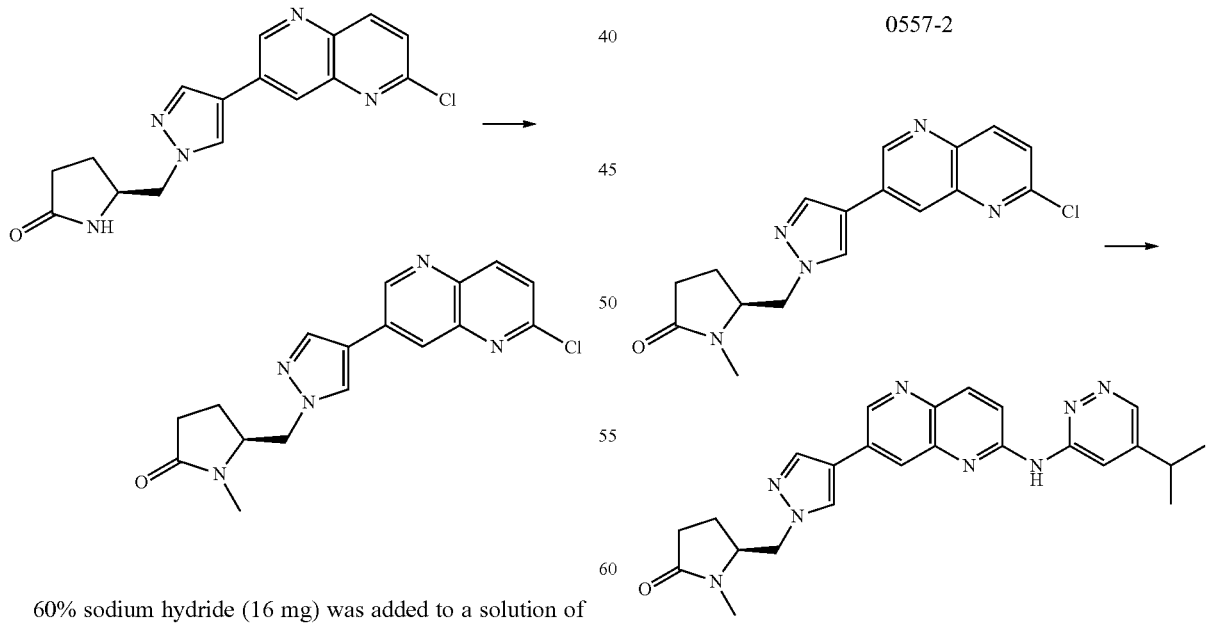

60% sodium hydride (16 mg) was added to a solution of (S)-5-((4-(6-chloro-1,5-naphthyridin-3-yl)-1H-pyrazol-1-yl)methyl)pyrrolidin-2-one (31 mg) and iodomethane (0.012 mL) in N,N-dimethylformamide (1 mL) under ice-cooling, followed by stirring at the same temperature for 1 hour. After ethyl acetate and water were added to the reaction mixture, the organic layer was collected by separation, washed sequentially with water and a saturated sodium chloride aqueous solution, and dried over anhydrous sodium sulfate, and the solvent was distilled off under reduced pressure. The obtained residue was purified by silica gel column chromatography (ethyl acetate-hexane, NH silica), thereby obtaining (S)-5-((4-(6-chloro-1,5-naphthyridin-3-yl)-1H-pyrazol-1-yl)methyl)-1-methylpyrrolidin-2-one (25 mg).

MS m/z(M+H):342.

0557-2

(S)-5-((4-(6-((5-isopropylpyridazin-3-yl)amino)-1,5-naphthyridin-3-yl)-1H-pyrazol-1-yl)methyl)-1-methylpyrrolidin-2-one was obtained in the same manner as in Example 0554-3.

1H-NMR(CDCl3/CD3OD=4/1)δ:8.88(2H,brs),8.73(1H, brs),8.21(1H,d,J=9.3 Hz),8.16(1H,d,J=1.8 Hz),8.03(1H,s), 7.99(1H,s),7.52(1H,d,J=9.3 Hz),4.41(2H,d,J=4.5 Hz),4.17-4.06(1H,m),3.16-3.00(1H,m),2.89(3H,s),2.35-1.96(4H,m), 1.42(6H,d,J=6.6 Hz).

MSm/z(M+H):443.

Example 0558

The following compounds were obtained in the same manner as in Examples 0549-1 and 0015-4.

were added to the reaction mixture, the organic layer was collected by separation, washed sequentially with water and a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 4-(1-((tert-butyldimethylsilyl)oxy)-2-methylpropan-2-yl)-3,6-dichloropyridazine (981 mg).

MSm/z(M+H):335.

| Example No. | | |
|---|---|---|
| 0558 | | |
| 0558-1 | 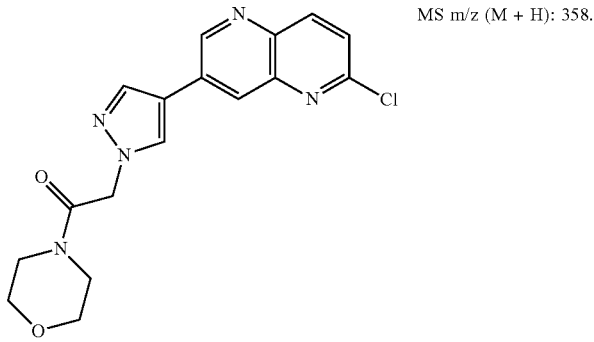 | MS m/z (M + H): 358. |
| 0558-2 | 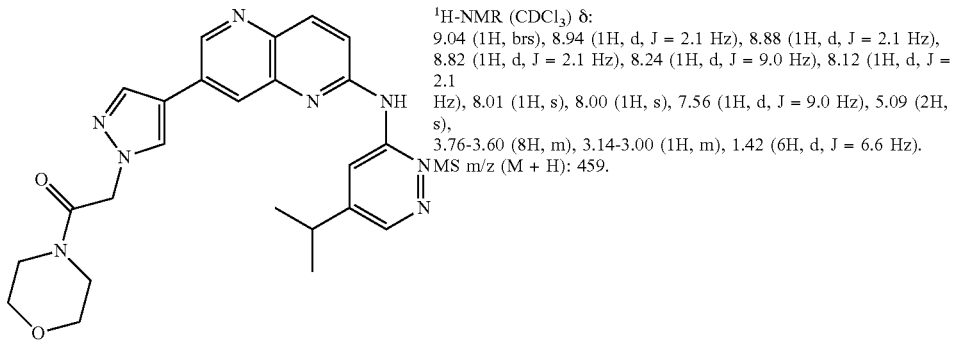 | 1H-NMR (CDCl3) δ: 9.04 (1H, brs), 8.94 (1H, d, J = 2.1 Hz), 8.88 (1H, d, J = 2.1 Hz), 8.82 (1H, d, J = 2.1 Hz), 8.24 (1H, d, J = 9.0 Hz), 8.12 (1H, d, J = 2.1 Hz), 8.01 (1H, s), 8.00 (1H, s), 7.56 (1H, d, J = 9.0 Hz), 5.09 (2H, s), 3.76-3.60 (8H, m), 3.14-3.00 (1H, m), 1.42 (6H, d, J = 6.6 Hz). MS m/z (M + H): 459. |

Example 0559

0559-1

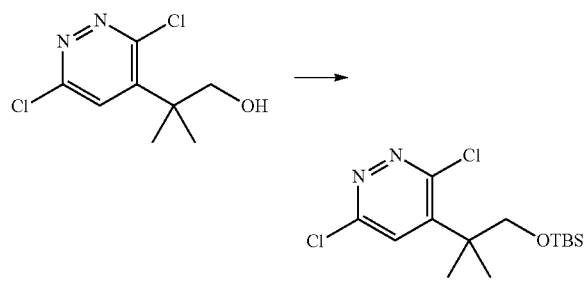

A mixture of 2-(3,6-dichloropyridazin-4-yl)-2-methylpropan-1-ol (969 mg), tert-butyldimethylchlorosilane (726 mg), imidazole (745 mg), N,N-dimethylpyridine-4-amine (53 mg), and N,N-dimethylformamide (8 mL) was stirred at room temperature for 16 hours. After ethyl acetate and water 0559-2

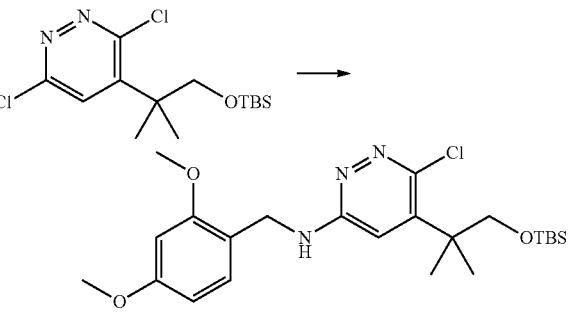

A mixture of 4-(1-((tert-butyldimethylsilyl)oxy)-2-methylpropan-2-yl)-3,6-dichloropyridazine (981 mg), 2,4-dimethoxybenzylamine (0.526 mL), 1,8-diazabicyclo[5.4.0]undeca-7-ene (0.654 mL), and toluene (3 mL) was stirred for 12 hours under heating to reflux. The reaction mixture was cooled to room temperature, ethyl acetate and a saturated sodium chloride aqueous solution were added thereto, and the organic layer was collected by separation. The organic layer was dried over anhydrous sodium sulfate, and the solvent was distilled off under reduced pressure. The obtained residue was purified by silica gel column chromatography (ethyl acetate-hexane), thereby obtaining 5-(1-((tert-butyldimethylsilyl)oxy)-2-methylpropan-2-yl)-6-chloro-N-(2,4-dimethoxybenzyl)pyridazine-3-amine (380 mg).

MSm/z(M+H):466.

0559-3

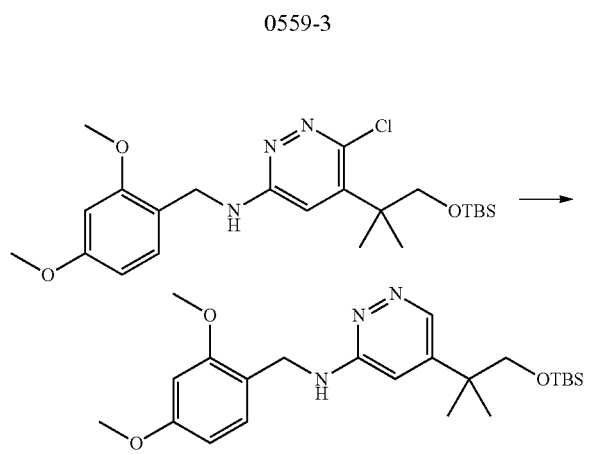

A mixture of 5-(1-((tert-butyldimethylsilyl)oxy)-2-methylpropan-2-yl)-6-chloro-N-(2,4-dimethoxybenzyl) pyridazine-3-amine (380 mg), 10% palladium/carbon (50 mg), ammonium formate (256 mg), ammonium chloride (217 mg), and methanol (4 mL) was stirred for 3 hours under heating to reflux. After the reaction mixture was cooled to room temperature, ethyl acetate was added thereto, the insolubles were filtered off, and the solvent was distilled off under reduced pressure. The obtained residue was purified by silica gel column chromatography (ethyl acetate-hexane), thereby obtaining 5-(1-((tert-butyldimethylsilyl)oxy)-2-methylpropan-2-yl)-N-(2,4-dimethoxybenzyl)pyridazine-3-amine (204 mg).

MSm/z(M+H):432.

0559-4

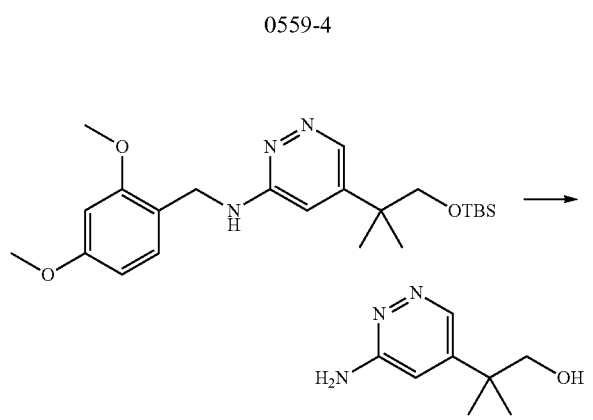

Trifluoroacetic acid (2 mL) was added to a mixture of 5-(1-((tert-butyldimethylsilyl)oxy)-2-methylpropan-2-yl)-N-(2,4-dimethoxybenzyl)pyridazine-3-amine (90 mg), and water (0.2 mL), followed by stirring at room temperature for 1 hour. The solvent was distilled off under reduced pressure, and the obtained residue was purified by silica gel column chromatography (methanol-ethyl acetate-hexane, NH silica), thereby obtaining 2-(6-aminopyridazin-4-yl)-2-methylpropan-1-ol (30 mg).

MSm/z(M+H):168.

0559-5

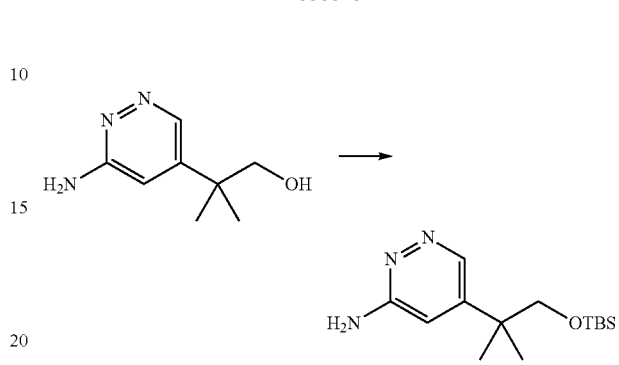

A mixture of 2-(6-aminopyridazin-4-yl)-2-methylpropan-1-ol (23 mg), tert-butyldimethylchlorosilane (11 mg), imidazole (23 mg), and N,N-dimethylformamide (2 mL) was stirred at room temperature for 15 hours. After ethyl acetate and water were added to the reaction mixture, the organic layer was collected by separation, washed sequentially with water and a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 5-(1-((tert-butyldimethylsilyl)oxy)-2-methylpropan-2-yl)pyridazine-3-amine (34 mg).

MSm/z(M+H):282.

0559-6

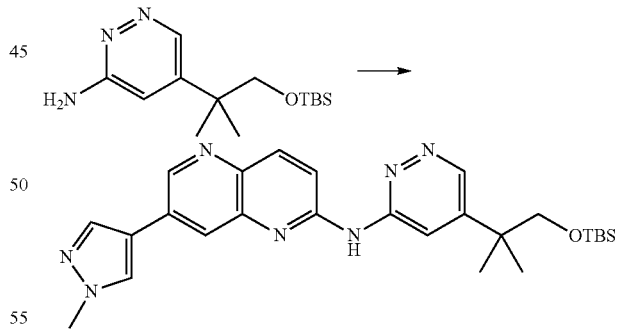

N-(5-(1-((tert-butyldimethylsilyl)oxy)-2-methylpropan-2-yl)pyridazin-3-yl)-7-(1-methyl-1H-pyrazol-4-yl)-1,5-naphthyridine-2-amine was obtained in the same manner as in Example 0554-3.

$^1$H-NMR(CDCl$_3$)δ:9.11(1H,brs),8.98(1H,brs),8.96(1H,brs),8.92(1H,d,J=2.1 Hz),8.24(1H,d,J=9.3 Hz),8.06(1H,d,J=2.1 Hz),7.93(1H,s),7.81(1H,s),7.60(1H,d,J=9.3 Hz),4.02(3H,s),3.68(2H,s),1.45(6H,s),0.82(9H,s),0.01(6H,s).

MSm/z(M+H):490.

Example 0560

0560-1

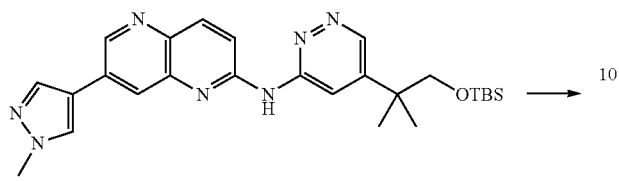

reduced pressure, the solid matter was collected by filtration, and washed with ethyl acetate, thereby obtaining 2-methyl-2-(6-((7-(1-methyl-1H-pyrazol-4-yl)-1,5-naphthyridin-2-yl)amino)pyridazin-4-yl)propan-1-ol (15 mg).

$^1$H-NMR(DMSO-d$_6$)δ:9.17(1H,d,J=2.1 Hz),9.13(1H,brs),8.59(1H,brs),8.48(1H,s),8.41(1H,d,J=9.0 Hz),8.38(1H,s),8.17(1H,s),7.69(1H,d,J=9.0 Hz),3.94(3H,s),3.58(2H,s),4.35(6H,s).

MS m/z(M+H):376.

Example 0561

The following compounds were obtained in the same manner as in Examples 0549-1 and 0015-4.

| Example No. | | |
|---|---|---|
| 0561 | | |
| 0561-1 | 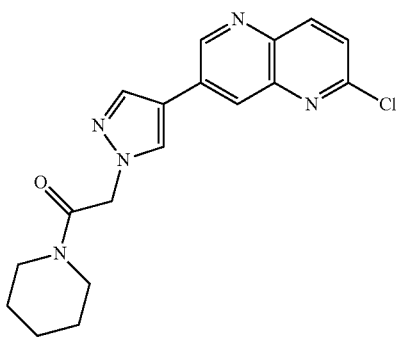 [SMILES: O=C(Cn1cc(-c2cnc3ccc(Cl)nc3c2)cn1)N1CCCCC1] | MS m/z (M + H): 356. |
| 0561-2 | 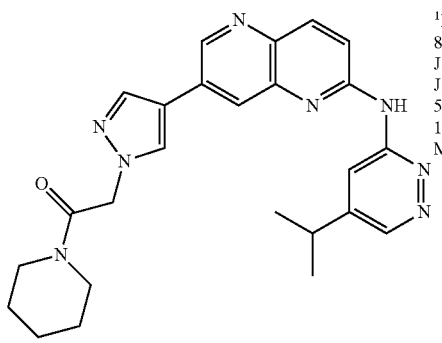 | $^1$H-NMR (CDCl$_3$) δ:<br>8.95 (1H, d, J = 1.8 Hz), 8.84 (1H, brs), 8.81 (1H, brs), 8.24 (1H, d, J = 9.0 Hz), 8.12 (1H, brs), 8.02 (1H, s), 8.00 (1H, s), 7.45 (1H, d, J = 9.0 Hz), 5.09 (2H, s), 3.61 (2H, t, J = 5.4 Hz), 3.52 (2H, t, J = 5.4 Hz), 3.14-2.98 (1H, m), 1.74-1.54 (6H, m), 1.42 (6H, d, J = 7.2 Hz).<br>MS m/z (M + H): 457. |

-continued

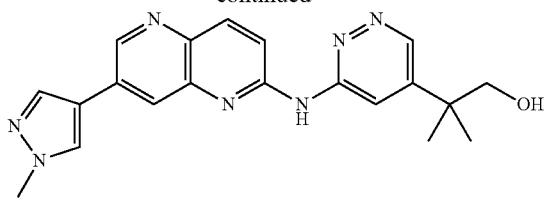

Concentrated hydrochloric acid (0.4 mL) was added to a mixture of N-(5-(1-(((tert-butyldimethylsilyl)oxy)-2-methyl-propan-2-yl)pyridazin-3-yl)-7-(1-methyl-1H-pyrazol-4-yl)-1,5-naphthyridine-2-amine (18 mg) and methanol (2.8 mL), followed by stirring at room temperature for 1 hour. The solvent of the reaction mixture was distilled off under

Example 0562

0562-1

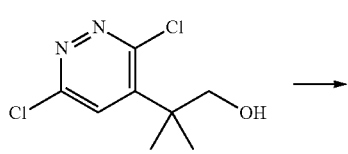 → 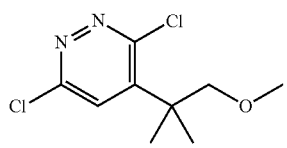

60% sodium hydride (72 mg) was added to a solution of 2-(3,6-dichloropyridazin-4-yl)-2-methylpropan-1-ol (200 mg) and iodomethane (0.112 mL) in N,N-dimethylformamide (5 mL) under ice-cooling, followed by stirring at the same temperature for 2 hours. After ethyl acetate and water were added to the reaction mixture, the organic layer was collected by separation, washed sequentially with water and a saturated sodium chloride aqueous solution, and dried over anhydrous sodium sulfate, and the solvent was distilled off under reduced pressure. The obtained residue was purified by silica gel column chromatography (ethyl acetate-hexane, NH silica), thereby obtaining 3,6-dichloro-4-(1-methoxy-2-methylpropan-2-yl)pyridazine (42 mg).

MSm/z(M+H):235.

0562-2 to 0562-5

Example 0559-2

The following compounds were obtained in the same manner as in Examples 0559-3, 0559-4, and 0554-3.

| Example No. | | |
|---|---|---|
| 0562 | | |
| 0562-2 | 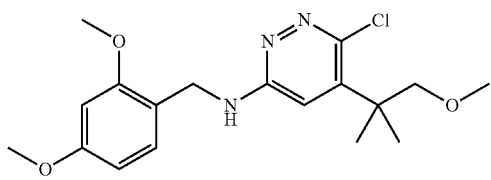 | MS m/z (M + H): 366. |
| 0562-3 | 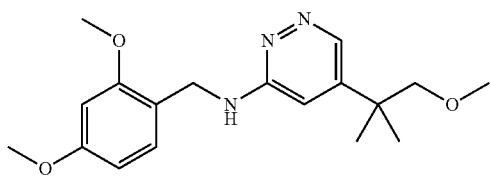 | MS m/z (M + H): 332. |
| 0562-4 | 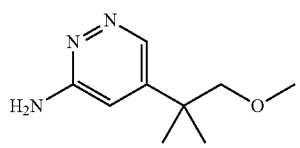 | MS m/z (M + H): 182. |
| 0562-5 | 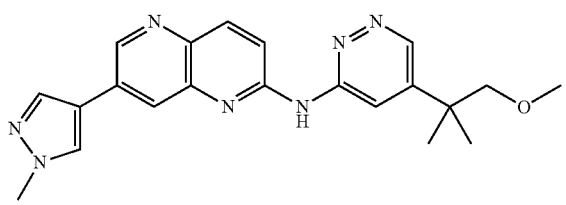 [SMILES: COCC(C)(C)c1cnnc(Nc2ccc3ncc(-c4cnn(C)c4)cc3n2)c1] | $^1$H-NMR (CDCl$_3$/CD$_3$OD = 4/1) δ: 9.00 (1H, brs), 8.87 (2H, brs), 8.20 (1H, d, J = 9.0 Hz), 8.11 (1H, brs), 7.94 (2H, brs), 7.54 (1H, d, J = 9.0 Hz), 4.03 (3H, d), 3.54 (2H, s), 3.37 (3H, s), 1.46 (6H, s). MS m/z (M + H): 390. |

Example 0563

0563-1

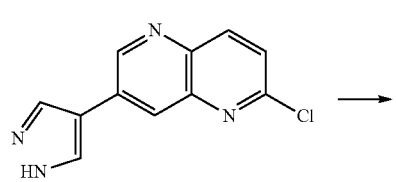

→

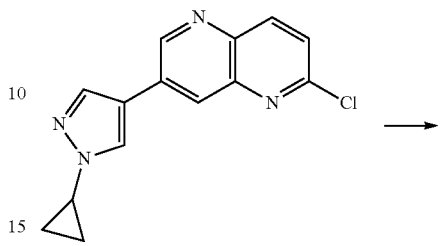

→

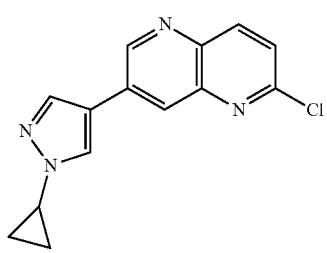

A mixture of 2-chloro-7-(1H-pyrazol-4-yl)-1,5-naphthyridine (20 mg), cyclopropylboronic acid monohydrate (18 mg), copper(II) acetate (47 mg), N,N-dimethylpyridine-4-amine (42 mg), pyridine (0.028 mL), triethylamine (0.061 mL), and 1,4-dioxane (1 mL) was stirred at 120° C. for 30 minutes using a microwave reaction apparatus. The reaction mixture was cooled to room temperature, the insolubles were filtered off, and the obtained solution was purified by silica gel column chromatography (methanol-ethyl acetate-hexane), thereby obtaining 2-chloro-7-(1-cyclopropyl-1H-pyrazol-4-yl)-1,5-naphthyridine (2.2 mg).

MSm/z(M+H):271.

0563-2

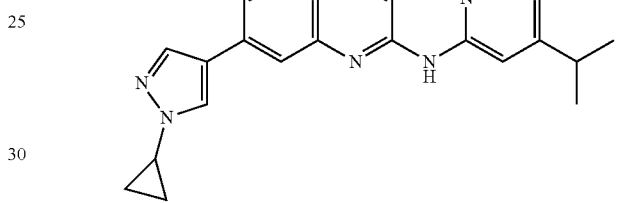

7-(1-Cyclopropyl-1H-pyrazol-4-yl)-N-(5-isopropylpyridazin-3-yl)-1,5-naphthyridine-2-amine was obtained in the same manner as in Example 0555-4 except that 2-chloro-7-(1-cyclopropyl-1H-pyrazol-4-yl)-1,5-naphthyridine was used instead of the 2-chloro-7-(1-methyl-3-(5-methylpyridin-3-yl)-1H-pyrazol-4-yl)-1,5-naphthyridine used in Example 0555-4.

$^1$H-NMR(CDCl$_3$/CD$_3$OD=4/1)δ:8.87(2H,brs),8.72(1H,brs),8.20(1H,d,J=9.0 Hz),8.13(1H,d,J=2.1 Hz),8.01(1H,s),7.95(1H,s),7.49(1H,d,J=9.0 Hz),3.75-3.67(1H,m),3.15-2.98(1H,m),1.42(6H,d,J=7.2 Hz),1.31-1.10(4H,m).

MSm/z(M+H):372.

Examples 0564 and 0565

The following compounds were obtained in the same manner as in Example 0554-3.

| Example No. | | |
|---|---|---|
| 0564 | 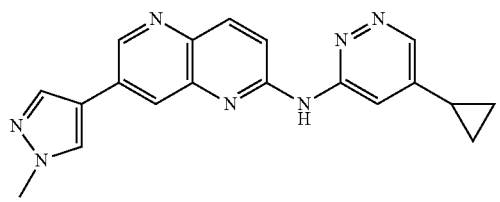 [SMILES: Cn1cc(-c2cnc3ccc(Nc4cc(C5CC5)cnn4)nc3c2)cn1] | $^1$H-NMR(CDCD$_3$/OD$_3$OD = 4/1)δ: 8.87(1H, d, J = 2.1 Hz), 8.69(1H, brs), 8.55(1H, brs), 8.19(1H, d, J = 9.0 Hz), 8.15(1H, d, J = 2.1 Hz), 7.97(2H, brs), 7.47(1H, d, J = 9.0 Hz), 4.03(3H, s), 2.10-1.96(1H, m), 1.36-1.21(2H, m), 1.07-0.98(2H, m). MS m/z(M + H): 344. |

-continued

| Example No. | Structure | Data |
|---|---|---|
| 0565 | | ¹H-NMR(CDCl₃/CD₃OD = 4/1)δ: 8.77(1H, d, J = 1.8 Hz), 8.66(1H, brs), 8.57(1H, brs), 8.21(1H, d, J = 9.0 Hz), 8.09(1H, d, J = 1.8 Hz), 7.75(1H, s), 7.49(1H, d, J = 9.0 Hz), 3.95(3H, s), 2.50(3H, s), 2.05-1.94(1H, m), 1.36-1.23(2H, m), 1.05-0.97(2H, m). MS m/z(M + H): 358. |

Example 0566

The following compounds were obtained in the same manner as in Examples 0549-1 and 0554-3.

| Example No. | Structure | Data |
|---|---|---|
| 0566 | | |
| 0566-1 | | MS m/z(M + H): 328. |
| 0566-2 | | ¹H-NMR(CDCl₃/CD₃OD = 4/1)δ: 8.88(1H, d, J = 1.8 Hz), 8.85(1H, brs), 8.71(1H, brs), 8.20(1H, d, J = 9.0 Hz), 8.16(1H, brs), 8.04(1H, s), 8.02(1H, s), 7.51(1H, d, J = 9.0 Hz), 4.36-4.13(3H, m), 3.15-2.98(1H, m), 2.42-1.94(4H, m), 1.42(6H, d, J = 6.6 Hz). MS m/z(M + H): 429. |

Example 0567

The following compounds were obtained in the same manner as in Examples 0478-3 and 0554-3.

| Example No. | Structure | Data |
|---|---|---|
| 0567 | | |
| 0567-1 | | MS m/z(M + H): 285. |

-continued

| Example No. | | |
|---|---|---|
| 0567-2 | 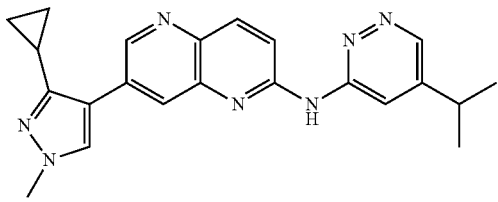 [SMILES: CC(C)c1cnnc(Nc2ccc3ncc(-c4cn(C)nc4C4CC4)cc3n2)c1] | ¹H-NMR(CDCl₃)δ: 9.13(1H, brs), 8.97(1H, d, J = 2.1 Hz), 8.94(1H, brs), 8.81(1H, brs), 8.29(1H, brs), 8.26(1H, d, J = 9.0 Hz), 7.63(1H, s), 7.60(1H, s), 3.91(3H, s), 3.11-2.95(1H, m), 2.09-1.94(1H, m), 1.41(6H, d, J = 7.2 Hz), 1.05-0.96(4H, m), MS m/z(M + H): 386. |

Example 0568

The following compounds were obtained in the same manner as in Examples 0557-1 and 0554-3.

| Example No. | | |
|---|---|---|
| 0568 | | |
| 0568-1 | 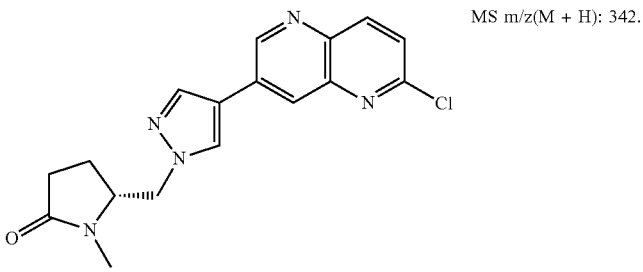 | MS m/z(M + H): 342. |
| 0568-2 | 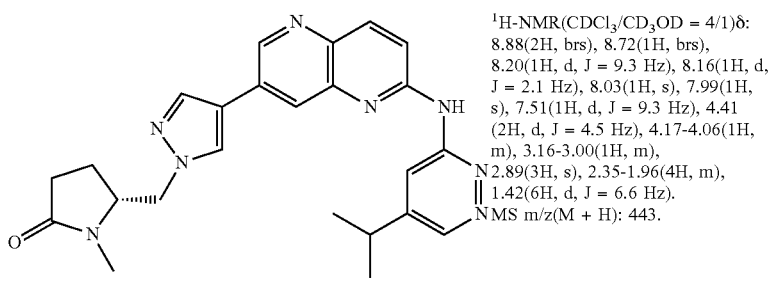 | ¹H-NMR(CDCl₃/CD₃OD = 4/1)δ: 8.88(2H, brs), 8.72(1H, brs), 8.20(1H, d, J = 9.3 Hz), 8.16(1H, d, J = 2.1 Hz), 8.03(1H, s), 7.99(1H, s), 7.51(1H, d, J = 9.3 Hz), 4.41 (2H, d, J = 4.5 Hz), 4.17-4.06(1H, m), 3.16-3.00(1H, m), 2.89(3H, s), 2.35-1.96(4H, m), 1.42(6H, d, J = 6.6 Hz). MS m/z(M + H): 443. |

Examples 0569 to 0571

The following compounds were obtained in the same manner as in Example 0554-3.

| Example No. | | |
|---|---|---|
| 0569 | 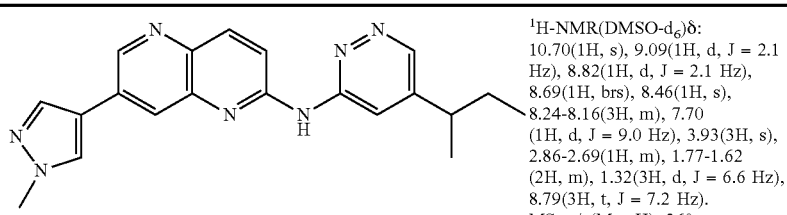 | ¹H-NMR(DMSO-d₆)δ: 10.70(1H, s), 9.09(1H, d, J = 2.1 Hz), 8.82(1H, d, J = 2.1 Hz), 8.69(1H, brs), 8.46(1H, s), 8.24-8.16(3H, m), 7.70 (1H, d, J = 9.0 Hz), 3.93(3H, s), 2.86-2.69(1H, m), 1.77-1.62 (2H, m), 1.32(3H, d, J = 6.6 Hz), 8.79(3H, t, J = 7.2 Hz). MS m/z(M + H): 360. |

-continued

| Example No. | | |
|---|---|---|
| 0570 | 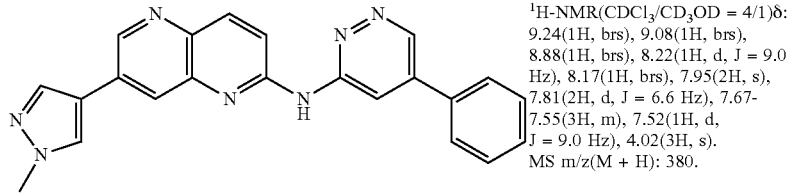 | ¹H-NMR(CDCl₃/CD₃OD = 4/1)δ: 9.24(1H, brs), 9.08(1H, brs), 8.88(1H, brs), 8.22(1H, d, J = 9.0 Hz), 8.17(1H, brs), 7.95(2H, s), 7.81(2H, d, J = 6.6 Hz), 7.67-7.55(3H, m), 7.52(1H, d, J = 9.0 Hz), 4.02(3H, s). MS m/z(M + H): 380. |
| 0571 | 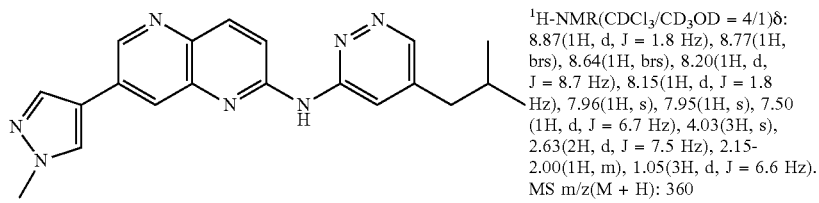 | ¹H-NMR(CDCl₃/CD₃OD = 4/1)δ: 8.87(1H, d, J = 1.8 Hz), 8.77(1H, brs), 8.64(1H, brs), 8.20(1H, d, J = 8.7 Hz), 8.15(1H, d, J = 1.8 Hz), 7.96(1H, s), 7.95(1H, s), 7.50 (1H, d, J = 6.7 Hz), 4.03(3H, s), 2.63(2H, d, J = 7.5 Hz), 2.15-2.00(1H, m), 1.05(3H, d, J = 6.6 Hz). MS m/z(M + H): 360 |

Example 0572

0572-1

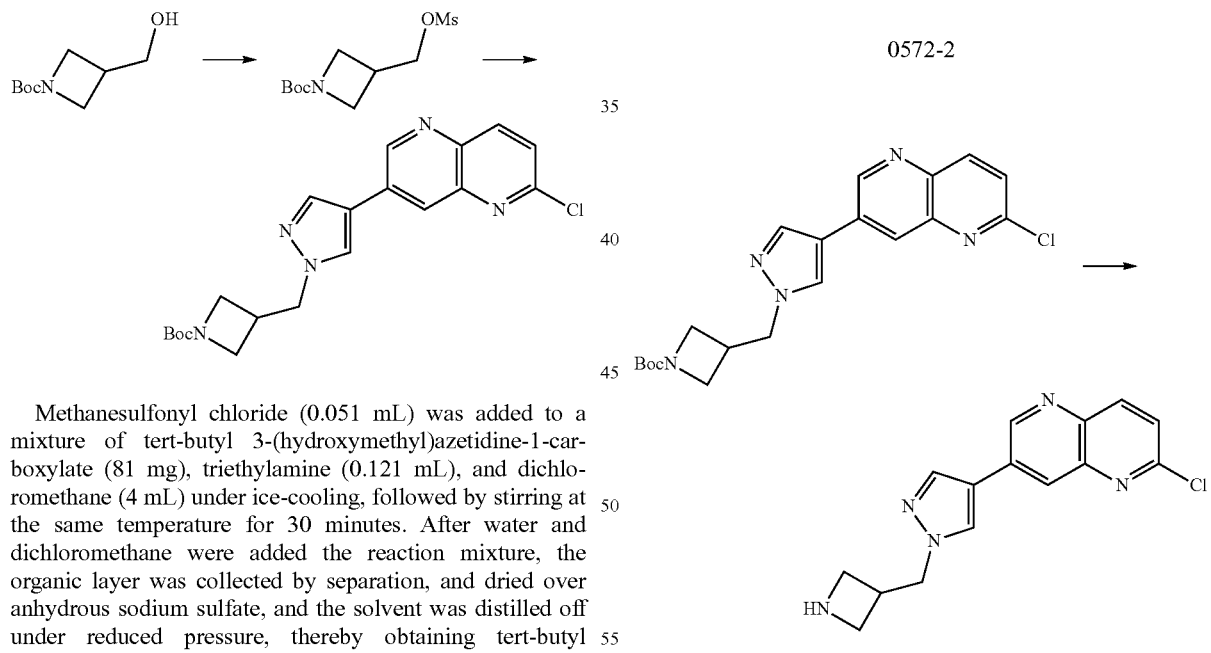

Methanesulfonyl chloride (0.051 mL) was added to a mixture of tert-butyl 3-(hydroxymethyl)azetidine-1-carboxylate (81 mg), triethylamine (0.121 mL), and dichloromethane (4 mL) under ice-cooling, followed by stirring at the same temperature for 30 minutes. After water and dichloromethane were added the reaction mixture, the organic layer was collected by separation, and dried over anhydrous sodium sulfate, and the solvent was distilled off under reduced pressure, thereby obtaining tert-butyl 3-(((methylsulfonyl)oxy)methyl)azetidine-1-carboxylate (159 mg).

A suspension of tert-butyl 3-(((methylsulfonyl)oxy)methyl)azetidine-1-carboxylate (115 mg), 2-chloro-7-(1H-pyrazol-4-yl)-1,5-naphthyridine (50 mg), and cesium carbonate (211 mg) in N,N-dimethylformamide (1 mL) was stirred at 80° C. for 1 hour. After the reaction mixture was cooled to room temperature, ethyl acetate and water were added thereto. The organic layer was collected by separation, washed sequentially with water and a saturated sodium chloride aqueous solution, and dried over anhydrous sodium sulfate, the solvent was distilled off under reduced pressure, and the obtained residue was purified by silica gel column chromatography (methanol-ethyl acetate-hexane), thereby obtaining tert-butyl 3-((4-(6-chloro-1,5-naphthyridin-3-yl)-1H-pyrazol-1-yl)methyl)azetidine-1-carboxylate (45 mg).

MSm/z(M+H):400.

0572-2

Trifluoroacetic acid (2 mL) was added to a mixture of tert-butyl 3-((4-(6-chloro-1,5-naphthyridin-3-yl)-1H-pyrazol-1-yl)methyl)azetidine-1-carboxylate (45 mg), and water (0.1 mL), followed by stirring at room temperature for 2 hours. The solvent was distilled off under reduced pressure, the obtained residue was purified by silica gel column chromatography (methanol-ethyl acetate, NH silica), thereby obtaining 7-(1-(azetidin-3-ylmethyl)-1H-pyrazol-4-yl)-2-chloro-1,5-naphthyridine (55 mg).

MSm/z(M+H):300.

0572-3

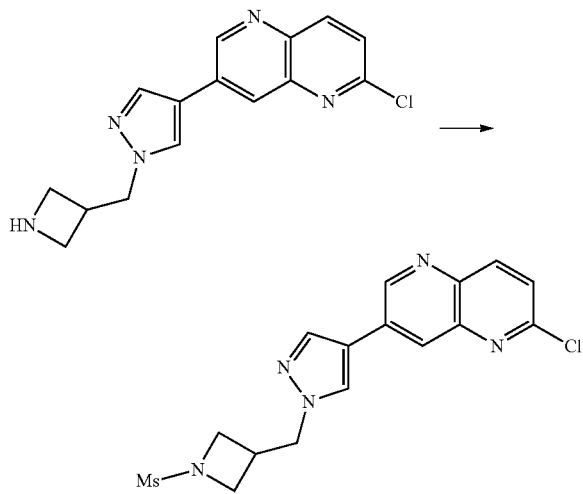

Methanesulfonyl chloride (0.018 mL) was added to a mixture of 7-(1-(azetidin-3-ylmethyl)-1H-pyrazol-4-yl)-2-chloro-1,5-naphthyridine (55 mg), triethylamine (0.048 mL), and dichloromethane (1 mL) under ice-cooling, followed by stirring at room temperature for 1 hour. The reaction mixture was purified by silica gel column chromatography (methanol-ethyl acetate-hexane), thereby obtaining 2-chloro-7-(1-((1-(methylsulfonyl)azetidin-3-yl)methyl)-1H-pyrazol-4-yl)-1,5-naphthyridine (5.4 mg).

MSm/z(M+H):378.

0572-4

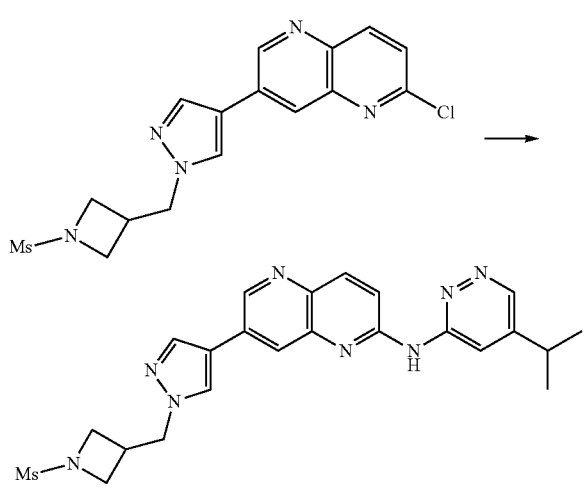

N-(5-isopropylpyridazin-3-yl)-7-(1-((1-(methylsulfonyl)azetidin-3-yl)methyl)-1H-pyrazol-4-yl)-1,5-naphthyridine-2-amine was obtained in the same manner as in Example 0554-3.

¹H-NMR(CDCl₃/CD₃OD=4/1)δ:8.87(2H,brs),8.72(1H,brs),8.20(1H,d,J=9.0 Hz),8.15(1H,brs),8.04(1H,s),8.00(1H,s),7.51(1H,d,J=9.0 Hz),4.98(2H,d,J=6.6 Hz),4.13-4.04(2H,m),3.90-3.82(2H,m),3.32-3.15(1H,m),3.14-2.98(1H,m),2.89(3H,s),1.42(6H,d,J=6.6 Hz).

MSm/z(M+H):479.

Example 0573

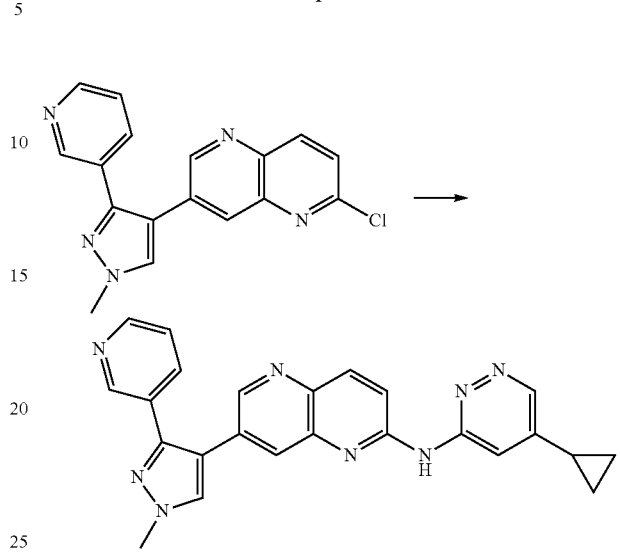

N-(5-cyclopropylpyridazin-3-yl)-7-(1-methyl-3-(pyridin-3-yl)-1H-pyrazol-4-yl)-1,5-naphthyridine-2-amine was obtained in the same manner as in Example 0554-3.

¹H-NMR(CDCl₃/CD₃OD=4/1)δ:8.73(1H,d,J=1.8 Hz), 8.62-8.52(4H,m),8.19(1H,d,J=9.0 Hz),7.93(1H,d,J=1.8 Hz), 7.92-7.83(3H,m),7.48(1H,d,J=9.0 Hz),4.09(3H,s),1.99-1.88(1H,m),1.28-1.20(2H,m),0.31-0.82(2H,m).

MSm/z(M+H):421.

Example 0574

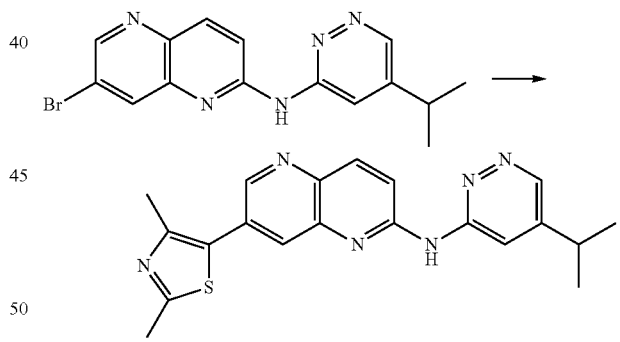

A mixture of 7-bromo-N-(5-isopropylpyridazin-3-yl)-1,5-naphthyridine-2-amine (20 mg), (2,4-dimethylthiazol-5-yl)boronic acid (20 mg), sodium carbonate (18 mg), bis(di-tert-butyl(4-dimethylaminophenyl)phosphine)dichloropalladium(II) (2 mg), water (0.1 mL), and 1,4-dioxane (1 mL) was stirred at 100° C. for 2 hours. The reaction mixture was cooled to room temperature, the insolubles were filtered off, and the solvent was distilled off under reduced pressure. The obtained residue was purified by silica gel column chromatography (methanol-ethyl acetate), thereby obtaining 7-(2,4-dimethylthiazol-5-yl)-N-(5-isopropylpyridazin-3-yl)-1,5-naphthyridine-2-amine (5.9 mg).

¹H-NMR(CDCl₃)δ:10.31(1H,brs),9.01(1H,brs),8.84(1H,brs),8.83(1H,d,J=1.8 Hz),8.29(1H,d,J=9.3 Hz),8.10(1H,d, J=1.8 Hz),7.93(1H,d,J=9.3 Hz),3.12-3.00(1H,m),2.75(3H,s),2.57(3H,s),1.41(6H,d,J=6.6 Hz).
MSm/z(M+H):377.

Example 0575

0575-1

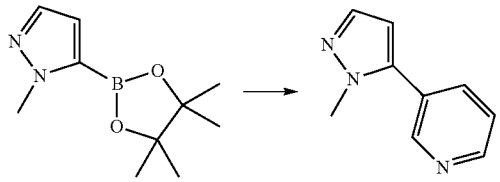

A mixture of 1-methyl-5-(4,4,5,5-tetramethyl-1,3,2-dioxaborolan-2-yl)-1H-pyrazole (500 mg), 3-bromopyridine (0.254 mL), sodium carbonate (635 mg), bis(di-tert-butyl (4-dimethylaminophenyl)phosphine)dichloropalladium(II) (85 mg), water (1.2 mL), and 1,4-dioxane (12 mL) was stirred at 100° C. for 2 hours. The reaction mixture was cooled to room temperature, the insolubles were filtered off, and the solvent was distilled off under reduced pressure. The obtained residue was purified by silica gel column chromatography (methanol-ethyl acetate), thereby obtaining 3-(1-methyl-1H-pyrazol-5-yl)pyridine (277 mg).
MSm/z(M+H):160.

0575-2 to 0575-4

The following compounds were obtained in the same manner as in Examples 0555-2, 0478-3, and 0554-3.

| Example No. | | |
|---|---|---|
| 0575 | | |
| 0575-2 | 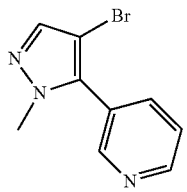 | MS m/z(M + H): 238. |
| 0575-3 | 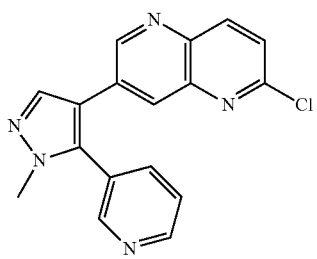 [SMILES: Cn1ncc(-c2cnc3ccc(Cl)nc3c2)c1-c1cccnc1] | MS m/z(M + H): 322. |
| 0575-4 | 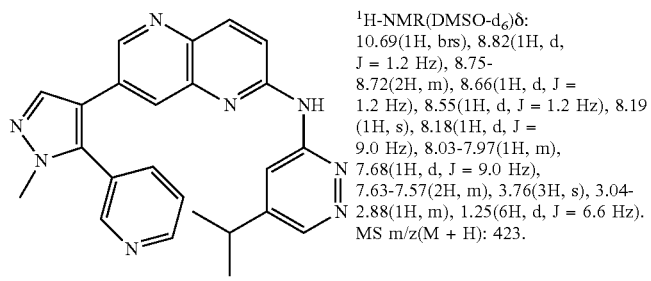 | $^1$H-NMR(DMSO-d$_6$)δ: 10.69(1H, brs), 8.82(1H, d, J = 1.2 Hz), 8.75-8.72(2H, m), 8.66(1H, d, J = 1.2 Hz), 8.55(1H, d, J = 1.2 Hz), 8.19 (1H, s), 8.18(1H, d, J = 9.0 Hz), 8.03-7.97(1H, m), 7.68(1H, d, J = 9.0 Hz), 7.63-7.57(2H, m), 3.76(3H, s), 3.04-2.88(1H, m), 1.25(6H, d, J = 6.6 Hz). MS m/z(M + H): 423. |

Example 0576

0576-1

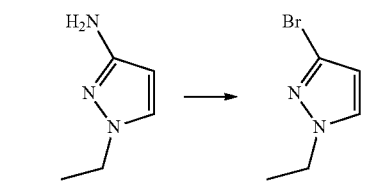

A solution of sodium nitrite (315 mg) in water (0.4 mL) and copper(II) bromide (1.48 g) were added to 1-ethyl-1H-pyrazole-3-amine (461 mg) in 48% hydrobromic acid under ice cooling, followed by stirring at room temperature for 3 hours. Sodium carbonate (4.0 g) was added to the reaction mixture, and the insolubles were filtered off. Ethyl acetate and a saturated sodium chloride aqueous solution were added to the filtrate, the organic layer was collected by separation, and dried over anhydrous sodium sulfate. The solvent was distilled off under reduced pressure, and the obtained residue was purified by silica gel column chromatography (ethyl acetate-hexane), thereby obtaining 3-bromo-1-ethyl-1H-pyrazole (530 mg).

MSm/z(M+H):175.

0576-2

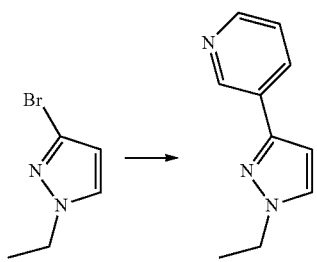

A mixture of 3-bromo-1-ethyl-1H-pyrazole (220 mg), 3-pyridineboronic acid (170 mg), sodium carbonate (331 mg), bis(di-tert-butyl(4-dimethylaminophenyl)phosphine)dichloropalladium(II) (44 mg), water (0.6 mL), and 1,4-dioxane (6 mL) was stirred at 100° C. for 5 hours. The reaction mixture was cooled to room temperature, the insolubles were filtered off, and the solvent was distilled off under reduced pressure. The obtained residue was purified by silica gel column chromatography (methanol-ethyl acetate-hexane), thereby obtaining 3-(1-ethyl-1H-pyrazol-3-yl)pyridine (53 mg).

MSm/z(M+H):174.

0576-3 to 0576-5

The following compounds were obtained in the same manner as in Examples 0555-2, 0478-3, and 0554-3.

| Example No. | | |
|---|---|---|
| 0576 | | |
| 0576-3 | 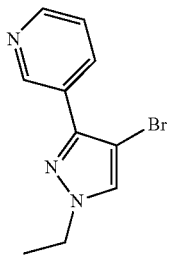 | MS m/z(M + H): 252. |
| 0576-4 | 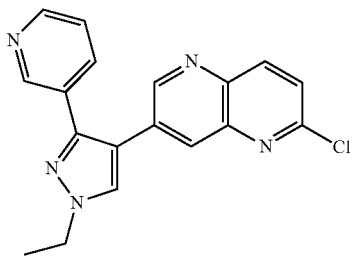 [SMILES: CCn1cc(-c2cnc3ccc(Cl)nc3c2)c(-c2cccnc2)n1] | MS m/z(M + H): 336. |

| Example No. | | |
|---|---|---|
| 0576-5 | 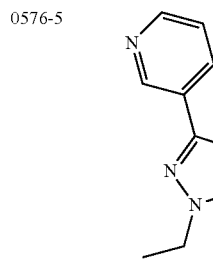 | ¹H-NMR(DMSO-d₆)δ: 10.72(1H, s) 8.63(1H, d, J = 2.1 Hz), 8.70(1H, d, J = 2.1 Hz), 8.63 (1H, brs), 8.62(1H, brs), 8.56(1H, dd, J = 4.5, 2.1 Hz), 8.42(1H, s), 8.23(1H, d, J = 9.0 Hz), 7.88-7.81(2H, m), 7.72(1H, d, J = 9.0 Hz), 7.43 (1H, dd, J = 7.8, 4.2 Hz), 4.29(2H, q, J = 4.2 Hz), 3.02-2.66(1H, m), 1.51(3H, t, J = 4.2 Hz), 1.22(6H, d, J = 6.6 Hz). MS m/z (M + H): 437. |

Example 0577

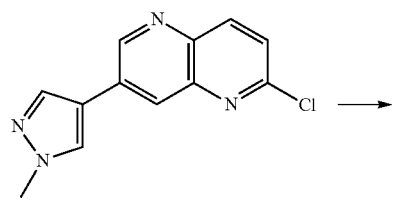

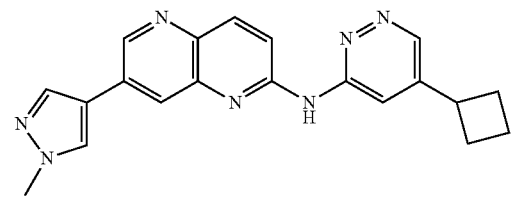

N-(5-cyclobutylpyridazin-3-yl)-7-(1-methyl-1H-pyrazol-4-yl)-1,5-naphthyridine-2-amine was obtained in the same manner as in Example 0554-3.

¹H-NMR(DMSO-d₆)δ:10.70(1H,s),9.03(1H,d,J=2.1 Hz),8.82(1H,d,J=2.1 Hz),8.68(1H,brs),8.46(1H,s),8.22(1H,d,J=9.0 Hz),8.19(1H,d,J=2.1 Hz),8.17(1H,s),7.70(1H,d,J=9.0 Hz),3.92(3H,s),3.75-3.59(1H,m),2.47-2.38(2H,m),2.32-1.88(4H,m).

MSm/z(M+H):358.

Example 0578

0578-1

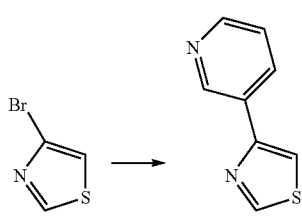 [SMILES: Brc1cscn1 ; c1cncc(-c2cscn2)c1]

4-(Pyridin-3-yl)thiazole was obtained in the same manner as in Example 0576-2.

MSm/z(M+H):163.

0578-2

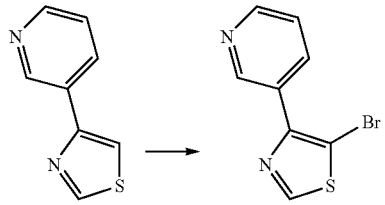 [SMILES: c1cncc(-c2cscn2)c1 ; Brc1scnc1-c1cccnc1]

Bromine (0.097 mL) was added to a solution of 4-(pyridin-3-yl)thiazole (254 mg) in acetic acid (1.6 mL) under ice cooling, followed by stirring at 60° C. for 4 hours. After a 4 mol/L sodium hydroxide aqueous solution, sodium hydrogen sulfite, sodium carbonate, and ethyl acetate were added to the reaction mixture, the organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 5-bromo-4-(pyridin-3-yl)thiazole (180 mg).

MSm/z(M+H):241.

0578-3 and 0578-4

The following compounds were obtained in the same manner as in Examples 0478-3 and 0554-3.

| Example No. | | |
|---|---|---|
| 0578 | | |
| 0578-3 | 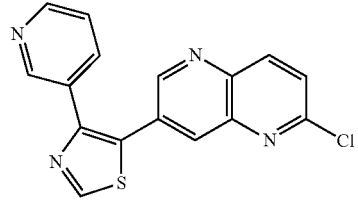 [SMILES: Clc1ccc2ncc(-c3scnc3-c3cccnc3)cc2n1] | MS m/z(M + H): 325. |
| 0578-4 | 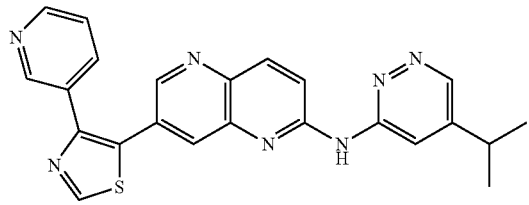 [SMILES: CC(C)c1cnnc(Nc2ccc3ncc(-c4scnc4-c4cccnc4)cc3n2)c1] | ¹H-NMR(DMSO-d₆)δ:<br>10.83(1H, s), 9.39(1H, s),<br>8.85(1H, d, J = 2.1 Hz), 8.69-8.63<br>(3H, m), 8.57(1H, d, J = 4.5, 2.1 Hz),<br>8.28(1H, d, J = 9.0 Hz), 8.11<br>(1H, brs), 7.91(1H, dt, J = 7.8, 2.1<br>Hz),<br>7.80(1H, d, J = 9.0 Hz), 7.47-<br>7.36(1H, m), 3.08-2.88(1H, m),<br>1.25(6H, d, J = 6.6 Hz).<br>MS m/z(M + H): 426 |

Examples 0579 and 0580

The following compounds were obtained in the same manner as in Example 0574.

| Example No. | | |
|---|---|---|
| 0579 | 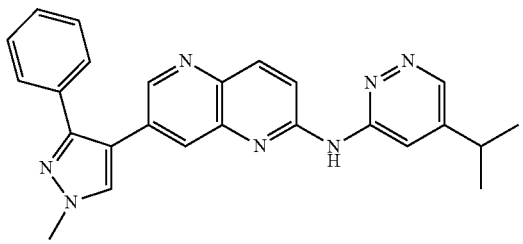 [SMILES: CC(C)c1cnnc(Nc2ccc3ncc(-c4cn(C)nc4-c4ccccc4)cc3n2)c1] | ¹H-NMR(CDCl₃)δ:<br>10.02(1H, brs), 8.92(1H, brs),<br>8.80(1H, brs), 8.69(1H, d, J = 2.1<br>Hz), 8.23(1H, d, J = 9.0 Hz),<br>7.95(1H, d, J = 2.1 Hz), 7.77(1H, d,<br>J = 9.0 Hz), 7.69(1H, s), 7.55-<br>7.49(2H, m), 7.39-7.30<br>(3H, m), 4.05(3H, s), 3.06-2.91<br>(1H, m), 1.34(6H, d, J = 7.2 Hz).<br>MS m/z(M + H): 422. |
| 0580 | 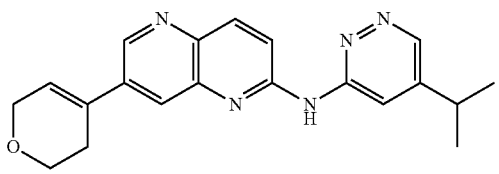 [SMILES: CC(C)c1cnnc(Nc2ccc3ncc(C4=CCOCC4)cc3n2)c1] | ¹H-NMR(DMSO-d₆)δ:<br>10.71(1H, s), 8.95(1H, d, J = 2.1 Hz),<br>8.86(1H, d, J = 2.1 Hz), 8.72<br>(1H, d, J = 2.1 Hz), 8.23(1H, d, J =<br>9.0 Hz), 8.01(1H, brs), 7.74<br>(1H, d, J = 9.0 Hz), 6.64(1H, brs),<br>4.31(2H, brs), 3.89(2H, t, J =<br>5.7 Hz), 3.12-2.95(1H, m), 2.61(2H,<br>brs), 1.31(6H, d, J = 6.6 Hz).<br>MS m/z(M + H): 348. |

Example 0581

The following compounds were obtained in the same manner as in Examples 0549-1 and 0554-3.

| Example No. | | |
|---|---|---|
| 0581 | | |
| 0581-1 | 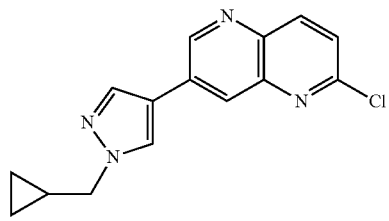 [SMILES: Clc1ccc2ncc(-c3cnn(CC4CC4)c3)cc2n1] | MS m/z(M + H): 285. |
| 0581-2 | 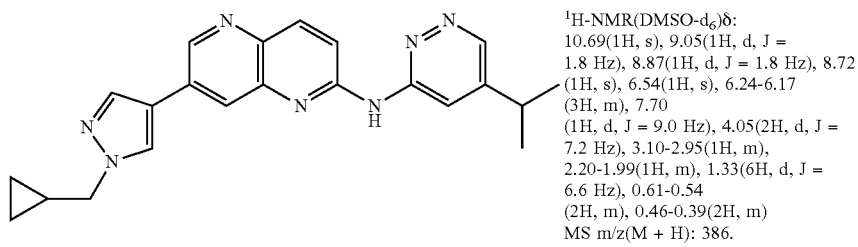 | ¹H-NMR(DMSO-d₆)δ: 10.69(1H, s), 9.05(1H, d, J = 1.8 Hz), 8.87(1H, d, J = 1.8 Hz), 8.72 (1H, s), 6.54(1H, s), 6.24-6.17 (3H, m), 7.70 (1H, d, J = 9.0 Hz), 4.05(2H, d, J = 7.2 Hz), 3.10-2.95(1H, m), 2.20-1.99(1H, m), 1.33(6H, d, J = 6.6 Hz), 0.61-0.54 (2H, m), 0.46-0.39(2H, m) MS m/z(M + H): 386. |

Example 0582

The following compounds were obtained in the same manner as in Examples 0478-3 and 0554-3.

| Example No. | | |
|---|---|---|
| 0582 | | |
| 0582-1 | 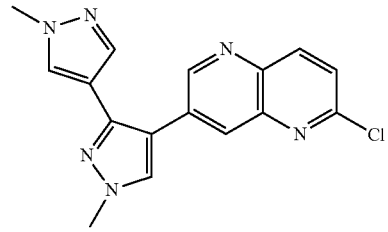 [SMILES: Cn1cc(-c2nn(C)cc2-c2cnc3ccc(Cl)nc3c2)cn1] | MS m/z(M + H): 325. |
| 0582-2 | 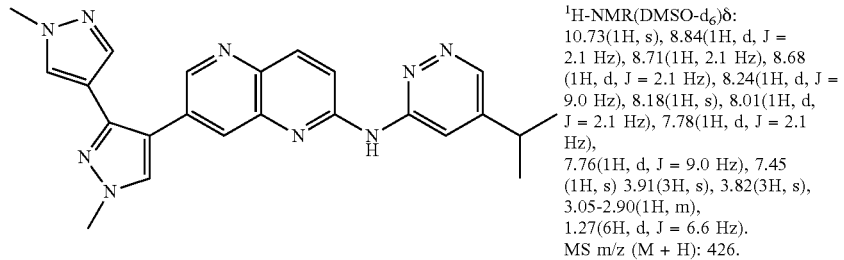 | ¹H-NMR(DMSO-d₆)δ: 10.73(1H, s), 8.84(1H, d, J = 2.1 Hz), 8.71(1H, 2.1 Hz), 8.68 (1H, d, J = 2.1 Hz), 8.24(1H, d, J = 9.0 Hz), 8.18(1H, s), 8.01(1H, d, J = 2.1 Hz), 7.78(1H, d, J = 2.1 Hz), 7.76(1H, d, J = 9.0 Hz), 7.45 (1H, s) 3.91(3H, s), 3.82(3H, s), 3.05-2.90(1H, m), 1.27(6H, d, J = 6.6 Hz). MS m/z (M + H): 426. |

Example 0583

0583-1

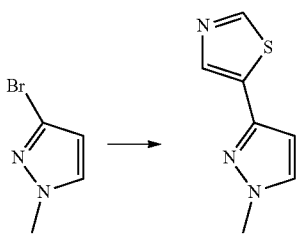

A suspension of 5-bromothiazole (200 mg), bis(pinacolato)diboron (371 mg), (1,1'-bis(diphenylphosphino)ferrocene)palladium(II) dichloride (98 mg) and potassium acetate (296 mg) in 1,4-dioxane (6 mL) was stirred at 100° C. for 2 hours in a nitrogen atmosphere. 3-Bromo-1-methyl-1H-pyrazole (194 mg), water (0.6 mL), sodium carbonate (320 mg), and bis(di-tert-butyl(4-dimethylaminophenyl)phosphine)dichloropalladium(II) (42 mg) were added to the reaction mixture, followed by stirring at 100° C. for 2 hours. The reaction mixture was cooled to room temperature, the insolubles were filtered off, and the obtained residue was purified by silica gel column chromatography (methanol-ethyl acetate), thereby obtaining 5-(1-methyl-1H-pyrazol-3-yl)thiazole (16 mg).

MS m/z(M+H):166.

0583-2 to 0583-4

The following compounds were obtained in the same manner as in Examples 0555-2, 0478-3, and 0554-3.

| Example No. | | |
|---|---|---|
| 0583 | | |
| 0583-2 | 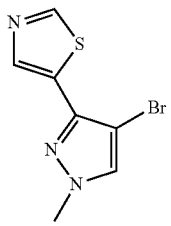 | MS m/z(M + H): 244. |
| 0583-3 | 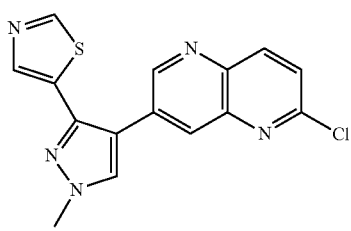 [SMILES: Cn1cc(-c2cnc3ccc(Cl)nc3c2)c(-c2cncs2)n1] | MS m/z(M + H): 328. |
| 0583-4 | 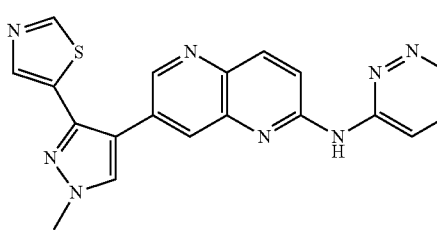 | $^1$H-NMR(DMSO-$d_6$)δ: 10.76(1H, s), 9.07(1H, s), 8.84(1H, d, J = 2.1 Hz), 8.72(1H, d, J = 2.1 Hz), 8.68(1H, d, J = 2.1 Hz), 8.29(1H, s), 8.27(1H, d, J = 9.0 Hz), 8.00(1H, d, J = 2.1 Hz), 7.62 (1H, s), 7.77(1H, d, J = 9.0 Hz), 3.97(3H, s), 3.06-2.90(1H, m), 1.26(6H, d, J = 6.6 Hz). MS m/z(M + H): 429. |

Example 0584

0584-1

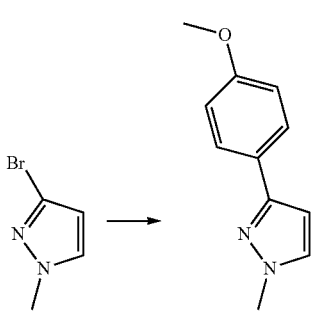

A mixture of 3-bromo-1-methyl-1H-pyrazole (200 mg), 4-methoxyphenylboronic acid (188 mg), sodium carbonate (328 mg), bis(di-tert-butyl(4-dimethylaminophenyl)phosphine)dichloropalladium(II) (43 mg), water (0.6 mL), and 1,4-dioxane (6 mL) was stirred at 100° C. for 4 hours. The reaction mixture was cooled to room temperature, the insolubles were filtered off, and the solvent was distilled off under reduced pressure. The obtained residue was purified by silica gel column chromatography (methanol-ethyl acetate-hexane), thereby obtaining 3-(4-methoxyphenyl)-1-methyl-1H-pyrazole (200 mg).

MS m/z(M+H):189.

0584-2 to 0584-4

The following compounds were obtained in the same manner as in Examples 0555-2, 0478-3, and 0554-3.

| Example No. | | |
|---|---|---|
| 0584 | | |
| 0584-2 | 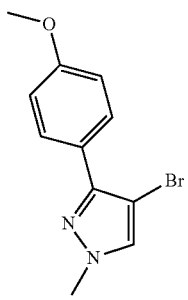 | MS m/z(M + H): 267. |
| 0584-3 | 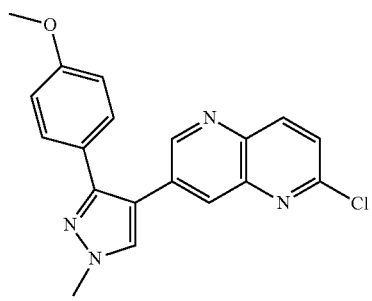 [SMILES: COc1ccc(-c2nn(C)cc2-c2cnc3ccc(Cl)nc3c2)cc1] | MS m/z(M + H): 351. |
| 0584-4 | 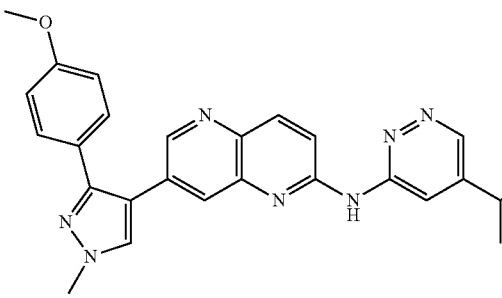 | $^1$H-NMR(CDCl$_3$)δ: 8.74(2h, brs), 8.70(1H, d, J = 1.8 Hz), 8.29(1H, d, J = 8.4 Hz), 7.97(1H, brs), 7.67(1H, s), 7.50 (1H, d, J = 8.4 Hz), 7.43(2H, d, J = 8.7 Jz), 6.88(2H, d, J = 8.7 Hz), 4.09(3H, s), 3.80(3H, s), 3.07-2.89(1H, m), 1.33(6H, d, J = 6.6 Hz). MS m/z(M + H): 452. |

Example 0585

0585-1

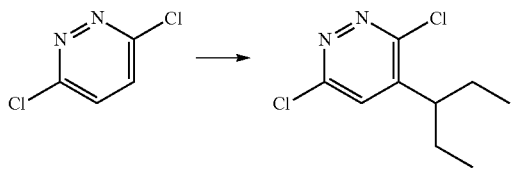

Potassium peroxodisulfate (1.81 g) was added to a mixture of 3,6-dichloropyridazine (1 g), sulfuric acid (1.4 mL), 2-ethylbutanoic acid (1.10 mL), silver nitrate (228 mg), and water (33 mL) at 70° C., followed by stirring at the same temperature for 30 minutes. After the reaction mixture was cooled by ice, sodium carbonate (10 g) and sodium chloride (1 g) were added thereto, followed by stirring at room temperature for 30 minutes. The insolubles were filtered off, and ethyl acetate was added thereto. The organic layer was collected by separation, washed with a saturated sodium chloride aqueous solution, and dried over anhydrous sodium sulfate, and the solvent was distilled off under reduced pressure, thereby obtaining 3,6-dichloro-4-(pentan-3-yl) pyridazine (1.07 g).
MSm/z(M+H):219.

0585-2 to 0585-5

The following compounds were obtained in the same manner as in Examples 0559-2, 0559-3, 0559-4, and 0554-3.

| Example No. | | |
|---|---|---|
| 0585 | | |
| 0585-2 | 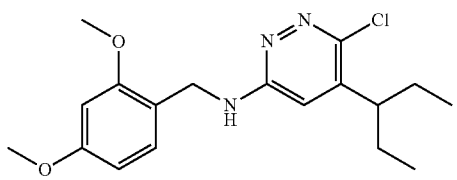 [SMILES: CCC(CC)c1cc(NCc2ccc(OC)cc2OC)nnc1Cl] | MS m/z(M + H): 350. |
| 0585-3 | 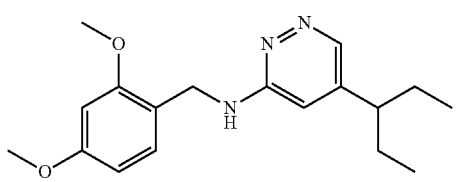 [SMILES: CCC(CC)c1cnnc(NCc2ccc(OC)cc2OC)c1] | MS m/z(M + H): 316. |
| 0585-4 | 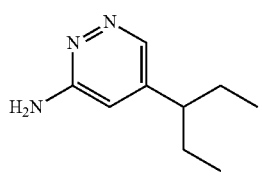 | MS m/z(M + H): 166. |
| 0585-5 | 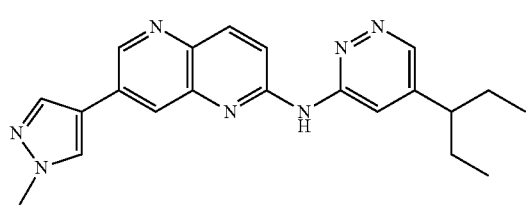 [SMILES: CCC(CC)c1cnnc(Nc2ccc3ncc(-c4cnn(C)c4)cc3n2)c1] | $^1$H-NMR(DMSO-d$_6$)δ: 10.68(1H, s), 9.03(1H, d, J = 1.8 Hz), 8.78(1H, d, J = 1.8 Hz), 8.63 (1H, d, J = 1.8 Hz), 8.45(1H, s), 8.22(1H, d, J = 9.0 Hz), 8.16(2 H, brs), 7.72(1H, d, J = 9.0 Hz), 3.93(3H, s), 3.52-3.30 (1H, m), 1.94-1.54(4H, m), 0.83(6H, t, J = 7.2 Hz). MS m/z(M + H): 374. |

Example 0586
The following compounds were obtained in the same manner as in Examples 0585-1, 0559-2, 0559-3, 0559-4, and 0554-3.
| Example No. | | |
|---|---|---|
| 0586 | | |
| 0586-1 | 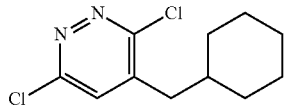 [SMILES: Clc1cc(CC2CCCCC2)c(Cl)nn1] | MS m/z(M + H): 245. |
| 0586-2 | 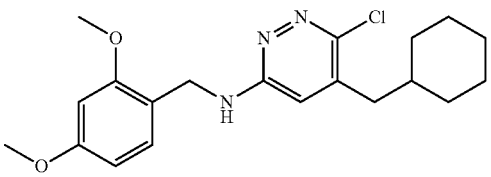 [SMILES: COc1ccc(CNc2cc(CC3CCCCC3)c(Cl)nn2)c(OC)c1] | MS m/z(M + H): 376. |
| 0586-3 | 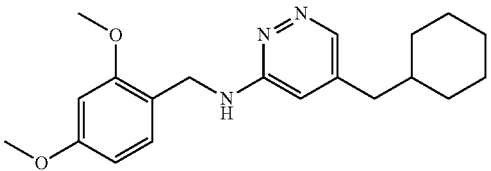 [SMILES: COc1ccc(CNc2cc(CC3CCCCC3)cnn2)c(OC)c1] | MS m/z(M + H): 342. |
| 0586-4 | 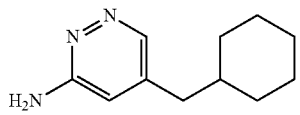 [SMILES: Nc1cc(CC2CCCCC2)cnn1] | MS m/z(M + H): 192. |
| 0586-5 | 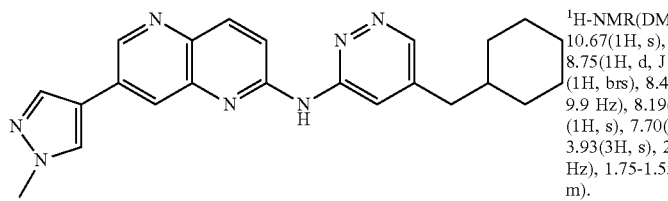 | $^1$H-NMR(DMSO-$d_6$)δ: 10.67(1H, s), 9.03(1H, d, J = 2.1 Hz), 8.75(1H, d, J = 2.1 Hz), 8.61 (1H, brs), 8.44(1H, s), 8.21(1H, d, J = 9.9 Hz), 8.19(1H, s), 8.13 (1H, s), 7.70(1H, d, J = 9.3 Hz), 3.93(3H, s), 2.60(2H, d, J = 6.6 Hz), 1.75-1.55(6H, m), 1.34-0.91(5H, m). MS m/z(M + H): 4.00. |
Example 0587
The following compounds were obtained in the same manner as in Examples 0583-1, 0555-2, 0478-3, and 0554-3.
| Example No. | | |
|---|---|---|
| 0587 | | |
| 0587-1 | 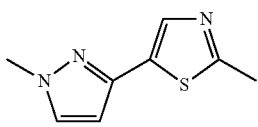 | MS m/z (M + H): 180. |
| 0587-2 | 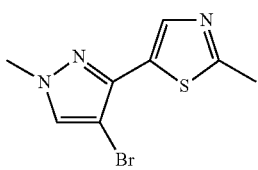 | MS m/z (M + H): 258. |

-continued
| Example No. | | |
|---|---|---|
| 0587-3 | 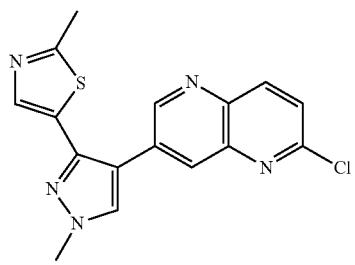 [SMILES: Cc1ncc(-c2nn(C)cc2-c2cnc3ccc(Cl)nc3c2)s1] | MS m/z (M + H): 342. |
| 0587-4 | 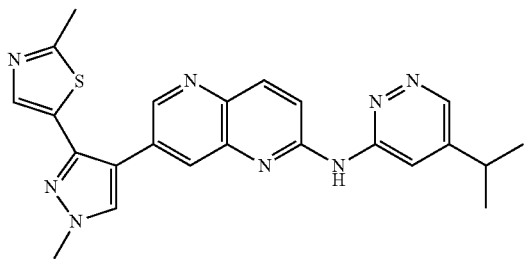 [SMILES: Cc1ncc(-c2nn(C)cc2-c2cnc3ccc(Nc4cc(C(C)C)cnn4)nc3c2)s1] | ¹H-NMR (CDCl₃) δ: 8.85 (1 H, brs), 8.77 (1 H, brs), 8.75 (1 H, d, J = 2.1 Hz), 8.28 (1 H, d, J = 9.0 Hz), 8.07 (1 H, d, J = 2.1 Hz), 7.67 (1 H, d, J = 9.0 Hz), 7.61 (1 H, s), 7.58 (1 H, s), 4.02 (3H, s), 3.07-2.94 (1 H, m), 2.67 (3H, s), 1.37 (6 H, d, J = 7.2 Hz). MS m/z (M + H): 443. |
Example 0588
The following compounds were obtained in the same manner as in Examples 0646-1 and 0015-4.
| Example No. | | |
|---|---|---|
| 0588 | | |
| 0588-1 | 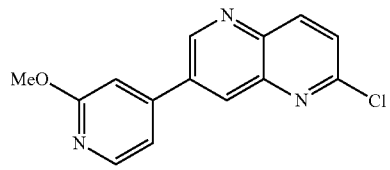 [SMILES: COc1cc(-c2cnc3ccc(Cl)nc3c2)ccn1] | MS m/z (M + H): 272. |
| 0588-2 | 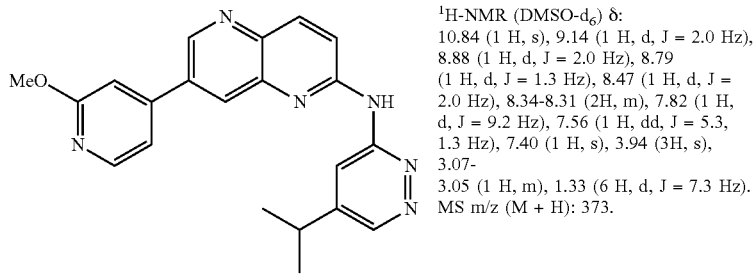 | ¹H-NMR (DMSO-d₆) δ: 10.84 (1 H, s), 9.14 (1 H, d, J = 2.0 Hz), 8.88 (1 H, d, J = 2.0 Hz), 8.79 (1 H, d, J = 1.3 Hz), 8.47 (1 H, d, J = 2.0 Hz), 8.34-8.31 (2H, m), 7.82 (1 H, d, J = 9.2 Hz), 7.56 (1 H, dd, J = 5.3, 1.3 Hz), 7.40 (1 H, s), 3.94 (3H, s), 3.07-3.05 (1 H, m), 1.33 (6 H, d, J = 7.3 Hz). MS m/z (M + H): 373. |

Example 0589

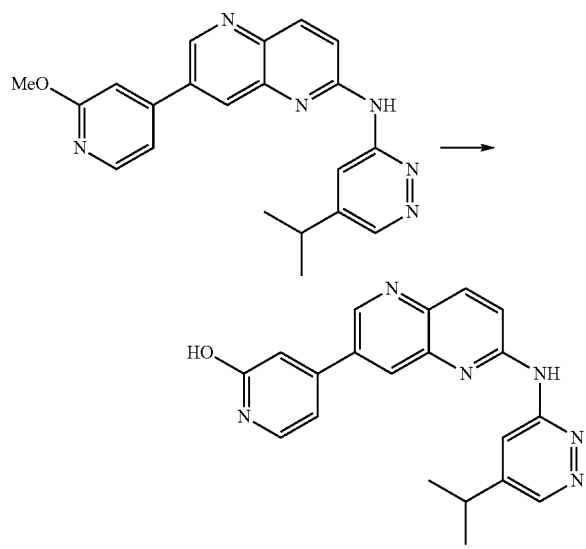

A mixture of N-(5-isopropylpyridazin-3-yl)-7-(2-methoxypyridin-4-yl)-1,5-naphthyridine-2-amine (29 mg), and 48% hydrobromic acid (2 mL) was stirred at 80° C. for 9 hours. A saturated sodium hydrogen carbonate aqueous solution was added to the reaction mixture, and the solvent was distilled off under reduced pressure. The obtained residue was purified by silica gel column chromatography (hexane-ethyl acetate, methanol-chloroform), thereby obtaining 4-(6-((5-isopropylpyridazin-3-yl)amino)-1,5-naphthyridin-3-yl)pyridin-2-ol (7 mg) as a white solid.

$^1$H-NMR(DMSO-d$_6$)δ:11.77(1H,s),10.83(1H,s),9.05(1H,d,J=2.0 Hz),8.88(1H,d,J=2.0 Hz),8.79(1H,d,J=1.3 Hz),8.38(1H,d,J=2.0 Hz),8.30(1H,d,J=9.2 Hz),7.80(1H,d,J=9.2 Hz),7.55(1H,d,J=7.3 Hz),6.87(1H,d,J=1.3 Hz),6.73(1H,d,J=7.3 Hz),3.07-3.04(1H,m),1.33(6H,d,J=7.3 Hz).

MS m/z(M+H):359.

Examples 0590 and 0591

The following compounds were obtained in the same manner as in Examples 0646-1 and 0015-4.

| Example No. | | |
|---|---|---|
| 0590 | | |
| 0590-1 | 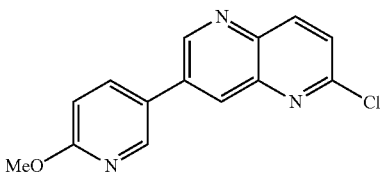 [SMILES: COc1ccc(-c2cnc3ccc(Cl)nc3c2)cn1] | MS m/z (M + H): 272. |
| 0590-2 | 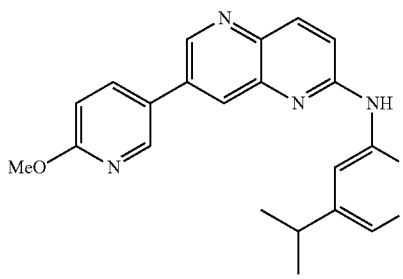 | $^1$H-NMR (DMSO-d$_6$) δ: 10.78 (1 H, s), 9.09 (1 H, d, J = 2.0 Hz), 8.87 (1 H, d, J = 2.0 Hz), 8.78 (1 H, d, J = 2.0 Hz), 8.76 (1 H, d, J = 2.6 Hz), 8.36 (1 H, d, J = 2.0 Hz), 8.30 (1 H, d, J = 2.6 Hz), 8.27 (1 H, d, J = 2.0 Hz), 7.77 (1 H, d, J = 8.9 Hz), 7.02 (1 H, d, J = 8.9 Hz), 3.94 (3 H, s), 3.09-2.98 (1 H, m), 1.32 (6 H, d, J = 6.6 Hz). MS m/z (M + H): 373. |
| 0591 | | |
| 0591-1 | 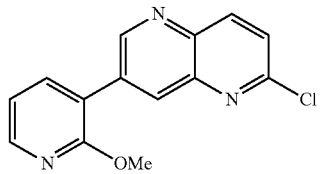 [SMILES: COc1ncccc1-c1cnc2ccc(Cl)nc2c1] | MS m/z (M + H): 272. |

-continued

| Example No. | | |
|---|---|---|
| 0591-2 | 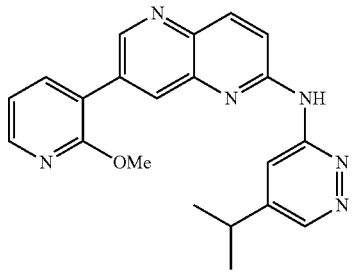 [SMILES: COc1ncccc1-c1cnc2ccc(Nc3cc(C(C)C)cnn3)nc2c1] | ¹H-NMR (DMSO-d₆) δ: 10.78 (1 H, s), 8.93 (1 H, d, J = 2.0 Hz), 8.86 (1 H, d, J = 2.0 Hz), 8.74 (1 H, d, J = 1.3 Hz), 8.31-8.28 (3H, m), 8.03 (1 H, dd, J = 7.3, 2.0 Hz), 7.80 (1 H, d, J = 9.2 Hz), 7.20 (1 H, dd, J = 7.3, 4.6 Hz), 3.94 (3H, s), 3.06-2.97 (1 H, m), 1.30 (6H, d, J = 7.3 Hz). MS m/z (M + H): 373. |

Examples 0592 and 0593

The following compounds were obtained in the same manner as in Example 0589.

| Example No. | | |
|---|---|---|
| 0592 | 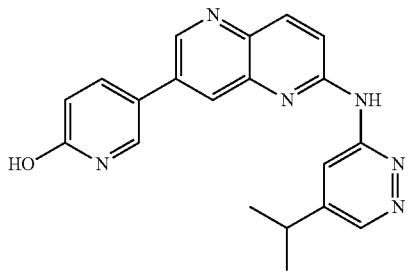 [SMILES: CC(C)c1cnnc(Nc2ccc3ncc(-c4ccc(O)nc4)cc3n2)c1] | ¹H-NMR (DMSO-d₆) δ: 12.03 (1 H, s), 10.74 (1 H, s), 9.01 (1 H, d, J = 2.6 Hz), 8.87 (1 H, d, J = 1.3 Hz), 8.77 (1 H, d, J = 1.3 Hz), 8.26-8.23 (2 H, m), 8.11-8.05 (2H, m), 7.73 (1 H, d, J = 9.2 Hz), 6.52 (1 H, d, J = 10.6 Hz), 3.08-2.98 (1 H, m), 1.32 (6H, d, J = 6.6 Hz). MS m/z (M + H): 359. |
| 0593 | 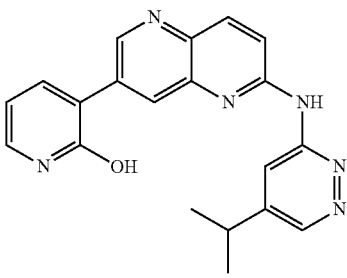 [SMILES: CC(C)c1cnnc(Nc2ccc3ncc(-c4cccnc4O)cc3n2)c1] | ¹H-NMR (DMSO-d₆) δ: 11.99 (1 H, s), 10.73 (1 H, s), 9.06 (1 H, d, J = 2.0 Hz), 8.86 (1 H, d, J = 2.0 Hz), 8.76 (1 H, d, J = 1.3 Hz), 8.51 (1 H, d, J = 1.3 Hz), 8.26 (1 H, d, J = 9.2 Hz), 7.98 (1 H, dd, J = 6.9, 2.2 Hz), 7.76 (1 H, d, J = 9.2 Hz), 7.52 (1 H, dd, J = 5.9, 2.2 Hz), 6.40 (1 H, dd, J = 6.9, 5.9 Hz), 3.06-2.97 (1 H, m), 1.31 (6H, d, J = 6.6 Hz). MS m/z (M + H): 359. |

Example 0594

 → 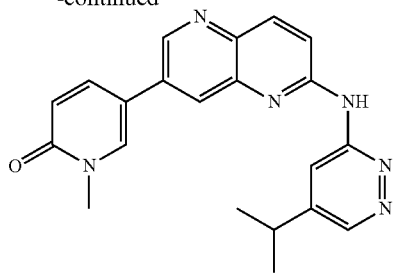

A mixture of 5-(6-((5-isopropylpyridazin-3-yl)amino)-1,5-naphthyridin-3-yl)pyridin-2-ol (10 mg), acetone (5 mL), iodomethane (3 µL), and potassium carbonate (12 mg) was stirred at room temperature for 5.5 hours. Methanol (1 mL)

was added to the reaction mixture, followed by stirring at room temperature for 18 hours. The solvent was distilled off under reduced pressure, and the obtained residue was purified by silica gel column chromatography (chloroform-methanol), thereby obtaining 5-(6-((5-isopropylpyridazin-3-yl)amino)-1,5-naphthyridin-3-yl)-1-methylpyridin-2(1H)-one (7 mg) as a pale yellow solid.

$^1$H-NMR(DMSO-d$_6$)δ:10.75(1H,s),9.02(1H,d,J=2.0 Hz),8.87(1H,d,J=2.0 Hz),8.75(1H,d,J=2.0 Hz),8.48(1H,d,J=2.6 Hz),8.28-8.24(2H,m),8.08(1H,dd,J=9.6,2.6 Hz),7.74(1H,d,J=9.2 Hz),6.58(1H,d,J=9.2 Hz),3.57(3H,s),3.08-2.99(1H,m),1.33(6H,d,J=6.6 Hz).

MSm/z(M+H):373.

Example 0595

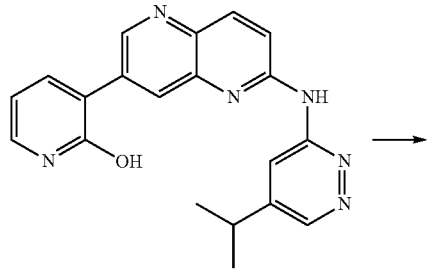

3-(6-((5-Isopropylpyridazin-3-yl)amino)-1,5-naphthyridin-3-yl)-1-methylpyridin-2(1H)-one was obtained as a pale yellow solid in the same manner as in Example 0594.

$^1$H-NMR(DMSO-d$_6$)δ:10.74(1H,s),9.03(1H,d,J=2.0 Hz),8.86(1H,d,J=2.0 Hz),8.74(1H,d,J=2.0 Hz),8.46(1H,d,J=2.0 Hz),8.26(1H,d,J=9.2 Hz),7.94(1H,dd,J=6.9,2.3 Hz),7.87(1H,dd,J=6.6,2.3 Hz),7.77(1H,d,J=9.2 Hz),6.43(1H,dd,J=6.9,6.6 Hz),3.57(3H,s),3.06-2.97(1H,m),1.31(6H,d,J=6.6 Hz).

MSm/z(M+H):373.

Example 0596

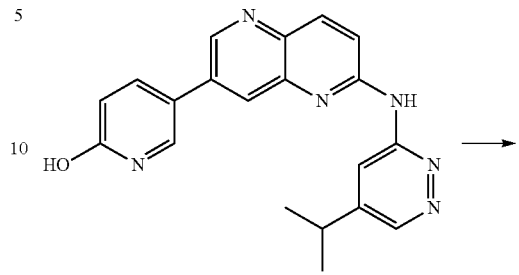

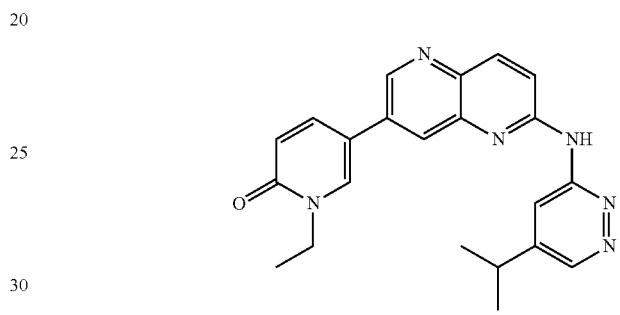

A mixture of 5-(6-((5-isopropylpyridazin-3-yl)amino)-1,5-naphthyridin-3-yl)pyridin-2-ol (20 mg), acetone (2 mL), methanol (2 mL), potassium carbonate (25 mg), and iodoethane (7 μL) was stirred at room temperature for 17.5 hours, and stirred for 5 hours under heating to reflux. Iodoethane (7 μL) was added to the reaction mixture, followed by stirring for 3 hours under heating to reflux. The reaction mixture was cooled to room temperature, and the solvent was distilled off under reduced pressure. The obtained residue was purified by silica gel column chromatography (hexane-ethyl acetate-methanol), and purified by silica gel column chromatography (chloroform-methanol, NH silica), thereby obtaining 1-ethyl-5-(6-((5-isopropylpyridazin-3-yl)amino)-1,5-naphthyridin-3-yl)pyridin-2(1H)-one (7 mg) as a pale yellow solid.

$^1$H-NMR(DMSO-d$_6$)δ:10.74(1H,s),9.04(1H,d,J=2.0 Hz),8.87(1H,d,J=2.0 Hz),8.74(1H,d,J=2.0 Hz),8.46(1H,d,J=2.6 Hz),8.28-8.24(2H,m),8.06(1H,dd,J=9.2,2.6 Hz),7.74(1H,d,J=9.2 Hz),6.57(1H,d,J=9.2 Hz),4.05(2H,q,J=7.3 Hz),3.09-2.99(1H,m),1.34-1.27(9H,m).

MSm/z(M+H):387.

Examples 0597 to 0600

The following compounds were obtained in the same manner as in Examples 0421-1 and 0015-4.

| Example No. | | |
|---|---|---|
| 0597 | | |
| 0597-1 | 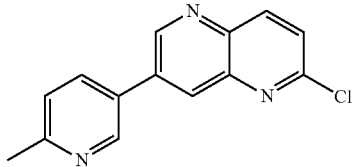 [SMILES: Cc1ccc(-c2cnc3ccc(Cl)nc3c2)cn1] | MS m/z (M + H): 256. |
| 0597-2 | 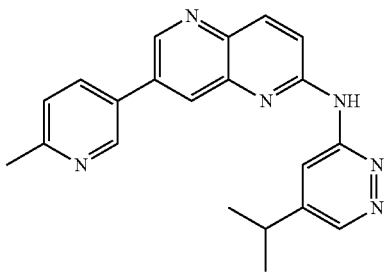 [SMILES: Cc1ccc(-c2cnc3ccc(Nc4cc(C(C)C)cnn4)nc3c2)cn1] | ¹H-NMR (DMSO-d$_6$) δ:<br>10.80 (1 H, s), 9.10 (1 H, d, J = 2.0 Hz), 9.00 (1 H, d, J = 2.0 Hz), 8.87 (1 H, d, J = 2.0 Hz), 8.78 (1 H, d, J = 2.0 Hz), 8.41 (1 H, d, J = 2.0 Hz), 8.31 (1 H, d, J = 9.2 Hz), 8.23 (1 H, dd, J = 7.9, 2.0 Hz), 7.79 (1 H, d, J = 9.2 Hz), 7.45 (1 H, d, J = 7.9 Hz), 3.06-3.03 (1 H, m), 2.57 (3H, s), 1.32 (6H, d, J = 7.3 Hz).<br>MS m/z (M + H): 357. |
| 0598 | | |
| 0598-1 | 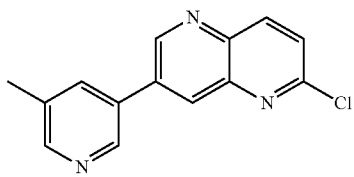 [SMILES: Cc1cncc(-c2cnc3ccc(Cl)nc3c2)c1] | MS m/z (M + H): 256. |
| 0598-2 | 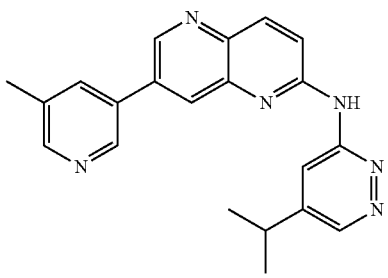 [SMILES: Cc1cncc(-c2cnc3ccc(Nc4cc(C(C)C)cnn4)nc3c2)c1] | ¹H-NMR (DMSO-d$_6$) δ:<br>10.80 (1 H, s), 9.11 (1 H, d, J = 2.0 Hz), 8.93 (1 H, d, J = 2.0 Hz), 8.88 (1 H, d, J = 2.0 Hz), 8.78 (1 H, d, J = 2.0 Hz), 8.53 (1 H, d, J = 1.3 Hz), 8.44 (1 H, d, J = 1.3 Hz), 8.31 (1 H, d, J = 9.2 Hz), 8.17 (1 H, s), 7.80 (1 H, d, J = 9.2 Hz), 3.10-3.01 (1 H, m), 2.43 (3H, s), 1.32 (6H, d, J = 6.6 Hz).<br>MS m/z (M + H): 357. |
| 0599 | | |
| 0599-1 | 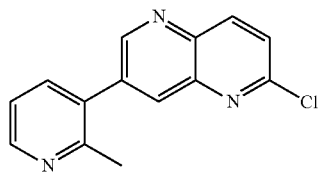 [SMILES: Cc1ncccc1-c1cnc2ccc(Cl)nc2c1] | MS m/z (M + H): 256. |
| 0599-2 |  | ¹H-NMR (DMSO-d$_6$) δ:<br>10.81 (1 H, s), 8.86 (1 H, d, J = 2.0 Hz), 8.78 (1 H, d, J = 2.0 Hz), 8.76 (1 H, d, J = 1.3 Hz), 8.57 (1 H, dd, J = 4.8, 1.3 Hz), 8.32 (1 H, d, J = 9.2 Hz), 8.18 (1 H, d, J = 2.0 Hz), 7.85-7.80 (2H, m), 7.40 (1 H, dd, J = 7.6, 4.8 Hz), 3.06-2.95 (1 H, m), 2.50 (3H, s), 1.29 (6H, d, J = 6.6 Hz).<br>MS m/z (M + H): 357. |

-continued

| Example No. | | |
|---|---|---|
| 0600 | | |
| 0600-1 | 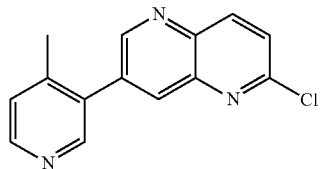 [SMILES: Cc1ccncc1-c1cnc2ccc(Cl)nc2c1] | MS m/z (M + H): 256. |
| 0600-2 | 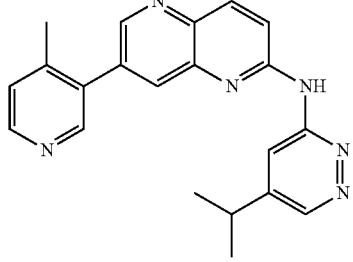 | ¹H-NMR (DMSO-d₆) δ: 10.82 (1 H, s), 8.86 (1 H, d, J = 2.0 Hz), 8.79 (1 H, d, J = 2.0 Hz), 8.77 (1 H, d, J = 2.0 Hz), 8.56 (1 H, s), 8.54 (1 H, d, J = 5.3 Hz), 8.33 (1 H, d, J = 9.2 Hz), 8.20 (1 H, d, J = 2.0 Hz), 7.82 (1 H, d, J = 9.2 Hz), 7.44 (1 H, d, J = 5.3 Hz), 3.06-2.95 (1 H, m), 2.35 (3H, s), 1.29 (6H, d, J = 7.3 Hz). MS m/z (M + H): 357. |

Example 0601

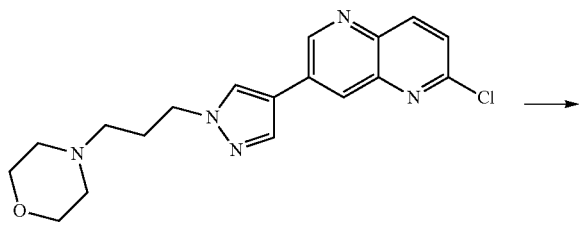

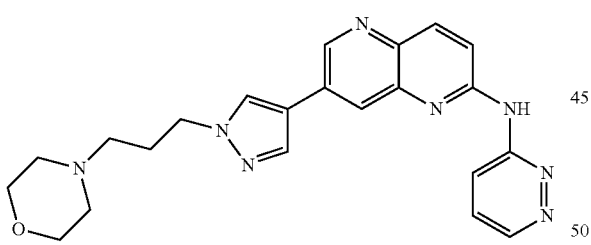

7-(1-(3-Morpholinopropyl)-1H-pyrazol-4-yl)-N-(pyridazin-3-yl)-1,5-naphthyridine-2-amine was obtained as a pale yellow solid in the same manner as in Example 0001-5.

¹H-NMR(DMSO-d₆)δ:10.81(1H,s),9.05(1H,d,J=2.0 Hz), 8.94(1H,dd,J=9.2,1.3 Hz),8.88(1H,dd,J=4.6,1.3 Hz),8.53 (1H,s),8.29(1H,d,J=2.0 Hz),8.22(1H,d,J=9.2 Hz),8.18(1H, s),7.70-7.63(2H,m),4.20(2H,t,J=6.9 Hz),3.58(4H,t,J=4.6 Hz),2.36-2.27(6H,m),2.05-1.96(2H,m).

MSm/z(M+H):417.

Example 0602

0602-1 and 0602-2

The following compounds were obtained in the same manner as in Examples 0421-1 and 0015-4.

| Example No. | | |
|---|---|---|
| 0602 | | |
| 0602-1 | 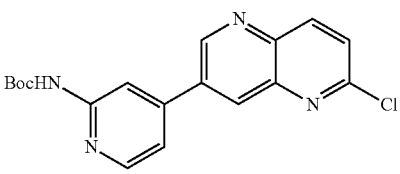 [SMILES: CC(C)(C)OC(=O)Nc1cc(-c2cnc3ccc(Cl)nc3c2)ccn1] | MS m/z (M + H): 301. |

| Example No. | | |
|---|---|---|
| 0602-2 | 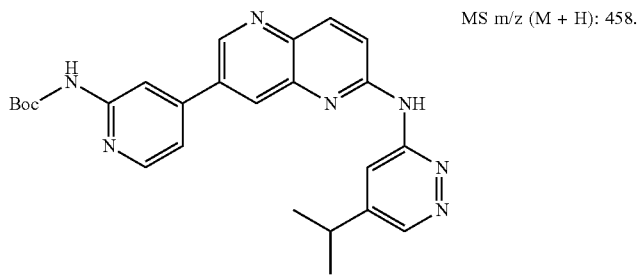 | MS m/z (M + H): 458. |

0602-3

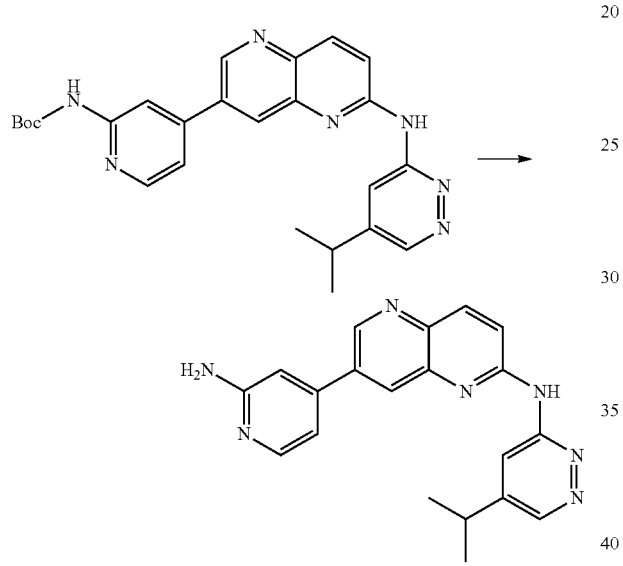

Example 0603

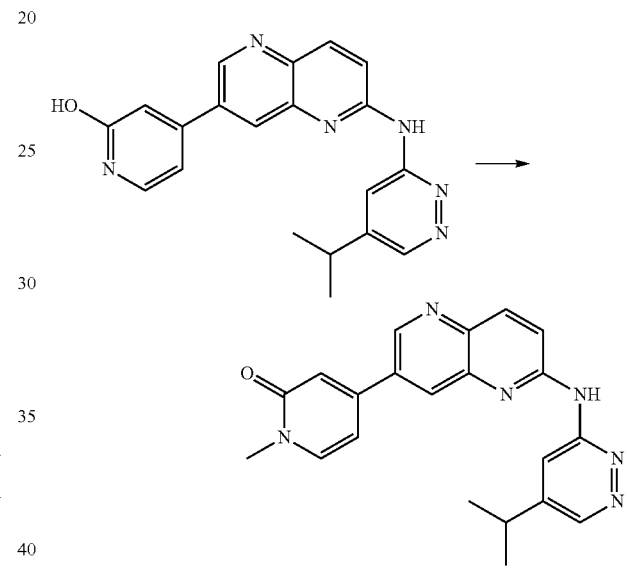

A mixture of tert-butyl (4-(6-(((5-isopropylpyridazin-3-yl)amino)-1,5-naphthyridin-3-yl)pyridin-2-yl)carbamate (19 mg), 1,4-dioxane (2 mL), and 2 mol/L hydrochloric acid (1 mL) was stirred at 80° C. for 1 hour. A saturated sodium hydrogen carbonate aqueous solution and water were added to the reaction mixture, and the solid matter was collected by filtration. The obtained solid matter was purified by preparative thin layer silica gel column chromatography (chloroform-methanol, NH silica), thereby obtaining 7-(2-aminopyridin-4-yl)-N-(5-isopropylpyridazin-3-yl)-1,5-naphthyridine-2-amine (7 mg) as a pale yellow solid.

$^1$H-NMR(DMSO-d$_6$)δ:10.82(1H,s),9.00(1H,d,J=2.0 Hz), 8.88(1H,d,J=2.0 Hz),8.78(1H,d,J=2.0 Hz),8.33-8.28(2H,m), 8.07(1H,d,J=5.3 Hz),7.80(1H,d,J=9.2 Hz),7.00(1H,dd, J=5.3,2.0 Hz),6.88(1H,s),6.12(2H,s),3.10-3.01(1H,m),1.32 (6H,d,J=6.6 Hz).

MSm/z(M+H):358.

A mixture of 4-(6-((5-isopropylpyridazin-3-yl)amino)-1,5-naphthyridin-3-yl)pyridin-2-ol (10 mg), acetone (1 mL), methanol (1 mL), potassium carbonate (12 mg), and iodomethane (3 μL) was stirred at room temperature for 3.5 hours. The solvent was distilled off under reduced pressure, and the obtained residue was purified by preparative thin layer silica gel column chromatography (chloroform-methanol, NH silica), thereby obtaining 4-(6-((5-isopropylpyridazin-3-yl)amino-1,5-naphthyridin-3-yl)-1-methyl-pyridin-2(1H)-one (6 mg) as a pale yellow solid.

$^1$H-NMR(DMSO-d$_6$)δ:10.83(1H,s),9.07(1H,d,J=2.0 Hz), 8.88(1H,d,J=2.0 Hz),8.79(1H,d,J=2.0 Hz),8.40(1H,d,J=2.0 Hz),8.30(1H,d,J=8.9 Hz),7.88(1H,d,J=7.3 Hz),7.81(1H,d, J=8.9 Hz),6.97(1H,d,J=2.0 Hz),6.81(1H,dd,J=7.3,2.0 Hz), 3.50(3H,s),3.11-3.01(1H,m),1.33(6H,d,J=6.6 Hz).

MSm/z(M+H):373.

Examples 0604 to 0606

The following compounds were obtained in the same manner as in Examples 0421-1 and 0015-4.

| Example No. | | |
|---|---|---|
| 0604 | | |
| 0604-1 | 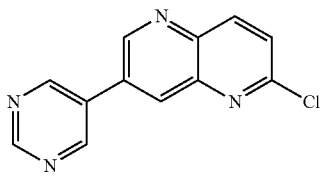 [SMILES: Clc1ccc2ncc(-c3cncnc3)cc2n1] | MS m/z (M + H): 243. |
| 0604-2 | 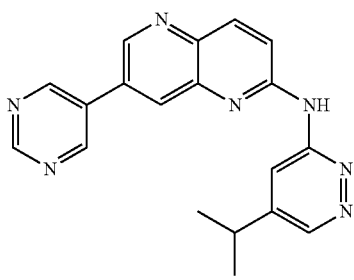 [SMILES: CC(C)c1cnnc(Nc2ccc3ncc(-c4cncnc4)cc3n2)c1] | ¹H-NMR (DMSO-d₆) δ: 10.84 (1 H, s), 9.40 (2H, s), 9.30 (1 H, s), 9.18 (1 H, d, J = 2.0 Hz), 8.88 (1 H, d, J = 2.0 Hz), 8.79 (1 H, d, J = 2.0 Hz), 8.58 (1 H, d, J = 2.0 Hz), 8.33 (1 H, d, J = 9.2 Hz), 7.82 (1 H, d, J = 9.2 Hz), 3.09-3.00 (1 H, m), 1.33 (6H, d, J = 7.3 Hz). MS m/z (M + H): 344. |
| 0605 | | |
| 0605-1 | 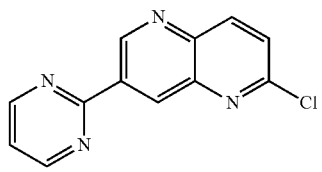 [SMILES: Clc1ccc2ncc(-c3ncccn3)cc2n1] | MS m/z (M + H): 243. |
| 0605-2 | 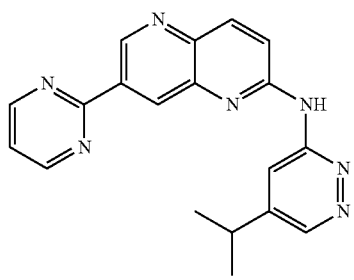 [SMILES: CC(C)c1cnnc(Nc2ccc3ncc(-c4ncccn4)cc3n2)c1] | ¹H-NMR (DMSO-d₆) δ: 10.86 (1 H, s), 9.67 (1 H, d, J = 2.0 Hz), 9.05 (2 H, d, J = 5.3 Hz), 8.95 (1 H, d, J = 2.0 Hz), 8.89 (1 H, d, J = 2.0 Hz), 8.81 (1 H, d, J = 2.0 Hz), 8.34 (1 H, d, J = 9.2 Hz), 7.84 (1 H, d, J = 9.2 Hz), 7.59 (1 H, dd, J = 5.3, 5.3 Hz), 3.11-3.01 (1 H, m), 1.34 (6H, d, J = 7.3 Hz). MS m/z (M + H): 344. |
| 0606 | | |
| 0606-1 | 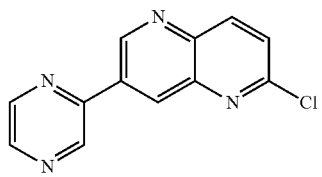 [SMILES: Clc1ccc2ncc(-c3cnccn3)cc2n1] | MS m/z (M + H): 243. |
| 0606-2 | 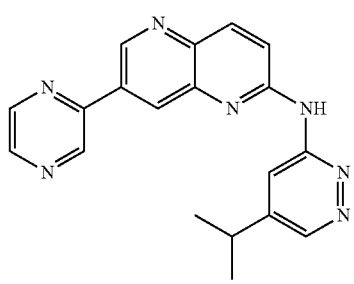 [SMILES: CC(C)c1cnnc(Nc2ccc3ncc(-c4cnccn4)cc3n2)c1] | ¹H-NMR (DMSO-d₆) δ: 10.85 (1 H, s), 9.56 (1 H, d, J = 2.0 Hz), 9.47 (1 H, d, J = 2.0 Hz), 8.89 (1 H, d, J = 2.0 Hz), 8.87-8.84 (1 H, m), 8.80 (2H, s), 8.75 (1 H, d, J = 2.0 Hz), 8.33 (1 H, d, J = 9.2 Hz), 7.83 (1 H, d, J = 9.2 Hz), 3.10-3.01 (1 H, m), 1.34 (6H, d, J = 6.6 Hz). MS m/z (M + H): 344. |

Example 0607

0607-1

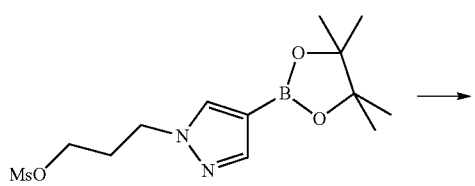

A mixture of 3-(4-(4,4,5,5-tetramethyl-1,3,2-dioxaborolan-2-yl)-1H-pyrazol-1-yl)propyl methanesulfonate (200 mg), 1,4-dioxane (5 mL), 3-methylmorpholine (247 mg), cesium carbonate (398 mg), and sodium iodide (27 mg) was stirred at 80° C. for 5 hours. After the reaction mixture was cooled to room temperature, water and ethyl acetate were added thereto, the organic layer was collected by separation, washed with a saturated sodium chloride aqueous solution, and dried over anhydrous sodium sulfate, and the solvent was distilled off under reduced pressure, thereby obtaining 3-methyl-4-(3-(4-(4,4,5,5-tetramethyl-1,3,2-dioxaborolan-2-yl)-1H-pyrazol-1-yl)propyl)morpholine (64 mg).

MSm/z(M+H):336.

0607-2

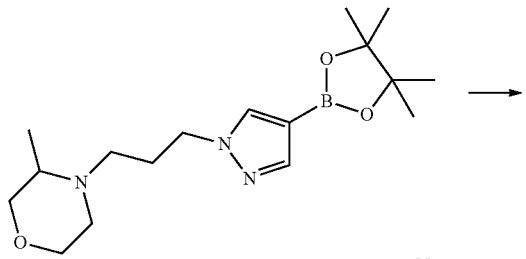

A mixture of 7-bromo-2-chloro-1,5-naphthyridine (46 mg), 3-methyl-4-(3-(4-(4,4,5,5-tetramethyl-1,3,2-dioxaborolan-2-yl)-1H-pyrazol-1-yl)propyl)morpholine (64 mg), sodium carbonate (40 mg), bis(di-tert-butyl(4-dimethylaminophenyl)phosphine)dichloropalladium(II) (7 mg), 1,4-dioxane (5 mL), and water (1 mL) was stirred at 80° C. for 5 hour in a nitrogen atmosphere. The reaction mixture was cooled to room temperature, and the solvent was distilled off under reduced pressure. The obtained residue was purified by silica gel column chromatography (hexane-ethyl acetate-methanol), thereby obtaining 4-(3-(4-(6-chloro-1,5-naphthyridin-3-yl)-1H-pyrazol-1-yl)propyl)-3-methylmorpholine (77 mg).

MSm/z(M+H):372.

0607-3

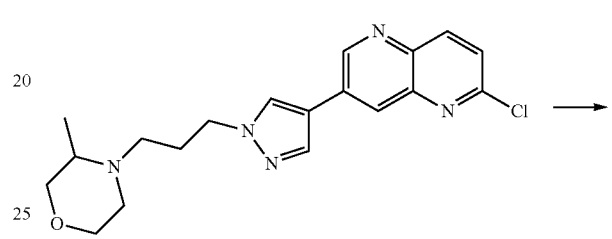

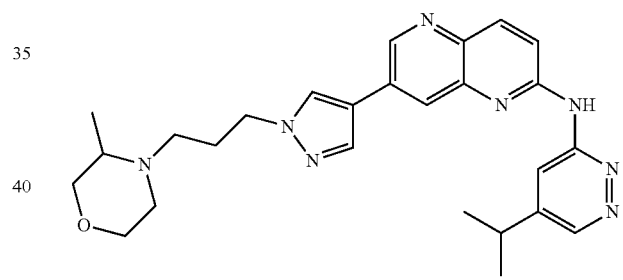

N-(5-isopropylpyridazin-3-yl)-7-(1-(3-(3-methylmorpholino)propyl)-1H-pyrazol-4-yl)-1,5-naphthyridine-2-amine was obtained as a yellow solid in the same manner as in Example 0015-4.

$^1$H-NMR(DMSO-d$_6$)δ:10.70(1H,s),9.04(1H,d,J=2.0 Hz), 8.86(1H,d,J=2.0 Hz),8.73(1H,d,J=2.0 Hz),8.52(1H,s),8.23-8.18(3H,m),7.69(1H,d,J=9.2 Hz),4.20(2H,t,J=6.9 Hz),3.70-3.46(3H,m),3.13-2.99(2H,m),2.74-2.64(2H,m),2.31-2.26(1H,m),2.20-2.11(2H,m),2.02-1.97(2H,m),1.33(6H,d,J=7.3 Hz),0.85(3H,d,J=6.3 Hz).

MSm/z(M+H):473.

Example 0608

The following compounds were obtained in the same manner as in Examples 0607-1, 0607-2, and 0015-4.

| Example No. | | |
|---|---|---|
| 0608 | | |
| 0608-1 | 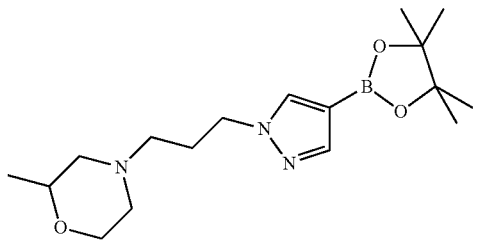 | MS m/z (M + H): 336. |
| 0608-2 | 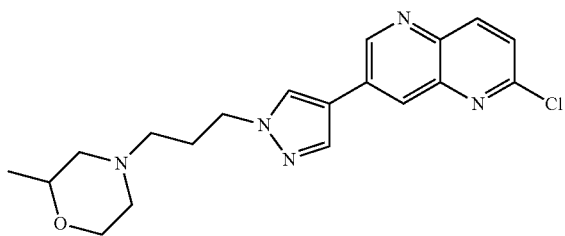 | MS m/z (M + H): 336. |
| 0608-3 | 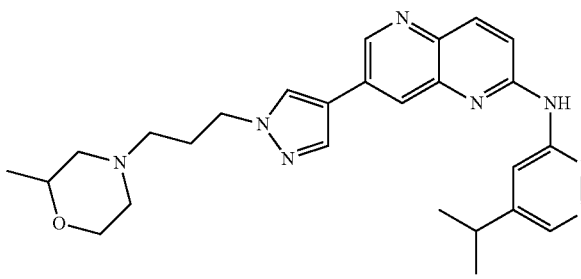 | ¹H-NMR (DMSO-d₆) δ:<br>10.70 (1 H, s), 9.04 (1 H, d, J = 2.0 Hz), 8.87<br>(1 H, d, J = 2.0 Hz), 8.73 (1 H, d, J = 2.0 Hz),<br>8.51 (1 H, s), 8.23-8.19 (3H, m), 7.70 (1 H, d, J = 9.2 Hz), 4.21 (2H, t, J = 6.9 Hz), 3.73 (1 H, d, J = 9.9 Hz), 3.54-3.45 (2H, m), 3.08-2.99 (1 H, m), 2.76-2.63 (2H, m), 2.28 (2H, t, J = 6.9 Hz), 2.05-1.89 (3H, m), 1.64 (1 H, t, J = 10.2 Hz), 1.33 (6H, d, J = 7.3 Hz), 1.03 (3H, d, J = 5.9 Hz).<br>MS m/z (M + H): 473. |

Examples 0609 and 0610

0609-1 and 0610-1

0609-2 and 0610-2

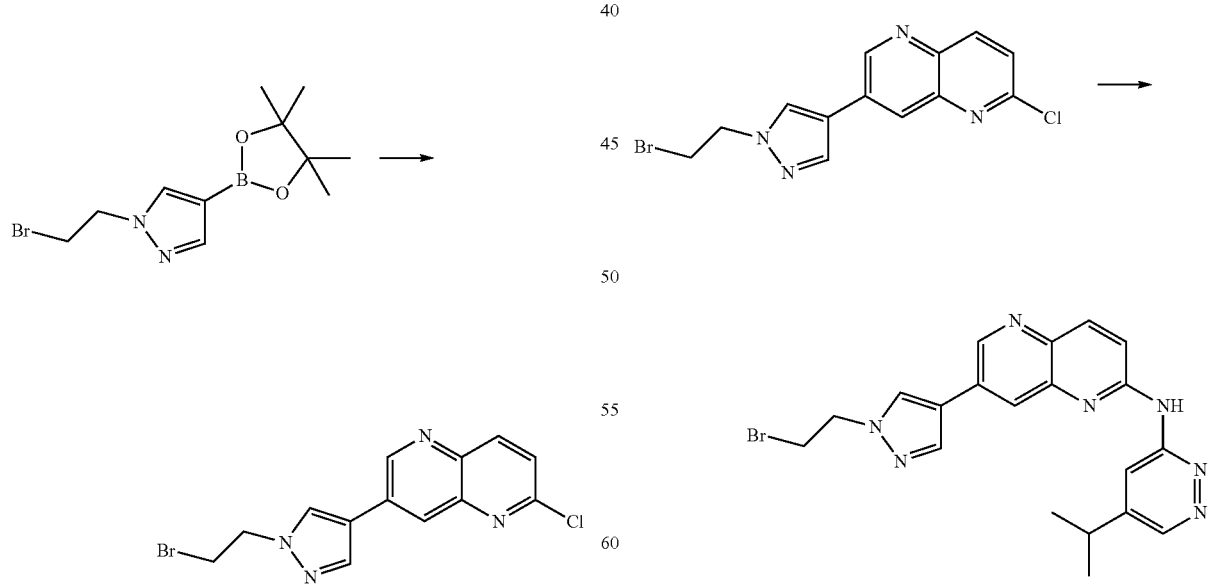

7-(1-(2-Bromoethyl)-1H-pyrazol-4-yl)-2-chloro-1,5-naphthyridine was obtained in the same manner as in Example 0607-2.

MSm/z(M+H):339.

7-(1-(2-Bromoethyl)-1H-pyrazol-4-yl)-N-(5-isopropylpyridazin-3-yl)-1,5-naphthyridine-2-amine was obtained in the same manner as in Example 0015-4.

MSm/z(M+H):438.

0609-3 and 0610-3

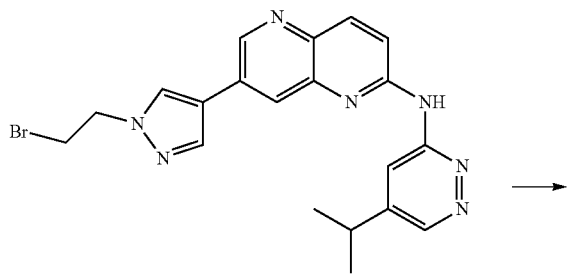

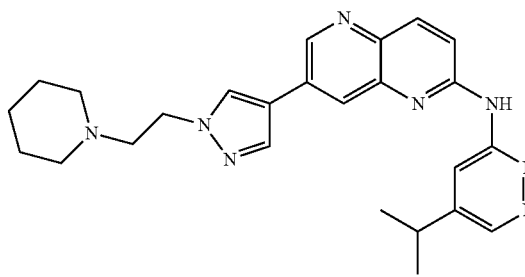

A mixture of 7-(1-(2-bromoethyl)-1H-pyrazol-4-yl)-N-(5-isopropylpyridazin-3-yl)-1,5-naphthyridine-2-amine (20 mg), 1,4-dioxane (5 mL), piperidine (10 μL), and cesium carbonate (33 mg) was stirred at 80° C. for 2.5 hours. Sodium iodide (2.2 mg) was added to the reaction mixture, followed by stirring at 100° C. for 3 hours. Piperidine (10 μL) was added to the reaction mixture, followed by stirring at 100° C. for 1 hour. The reaction mixture was allowed to stand overnight, and piperidine (10 μL) was added thereto, followed by stirring at 120° C. for 30 minutes using a microwave reaction apparatus. The reaction mixture was purified by silica gel column chromatography (hexane-ethyl acetate-methanol, NH silica), thereby obtaining N-(5-isopropylpyridazin-3-yl)-7-(1-(2-(piperidin-1-yl)ethyl)-1H-pyrazol-4-yl)-1,5-naphthyridine-2-amine (2 mg) as a pale yellow solid, and N-(5-isopropylpyridazin-3-yl)-7-(1-vinyl-1H-pyrazol-4-yl)-1,5-naphthyridine-2-amine (2 mg) as a pale yellow solid.

Example 0609

N-(5-isopropylpyridazin-3-yl)-7-(1-(2-(piperidin-1-yl)ethyl)-1H-pyrazol-4-yl)-1,5-naphthyridine-2-amine $^1$H-NMR(DMSO-$d_6$)δ:10.71(1H,s),9.03(1H,d,J=2.0 Hz), 8.86(1H,d,J=2.0 Hz),8.75(1H,d,J=2.0 Hz),8.50(1H,s),8.23-8.17(3H,m),7.69(1H,d,J=9.2 Hz),4.27(2H,t,J=6.6 Hz),3.08-2.98(1H,m),2.72(2H,t,J=6.6 Hz),2.41(4H,t,J=5.3 Hz),1.49 (4H,t,J=5.3 Hz),1.43-1.36(2H,m),1.33(6H,d,J=7.3 Hz). MSm/z(M+H):443.

Example 0610

N-(5-isopropylpyridazin-3-yl)-7-(1-vinyl-1H-pyrazol-4-yl)-1,5-naphthyridine-2-amine $^1$H-NMR(DMSO-$d_6$)δ:10.72(1H,s),9.10(1H,d,J=2.0 Hz), 8.88(1H,s),8.88(1H,d,J=2.0 Hz),8.73(1H,d,J=1.3 Hz),8.42 (1H,s),8.31(1H,d,J=1.3 Hz),8.24(1H,d,J=9.2 Hz),7.73(1H,d,J=9.2 Hz),7.30(1H,dd,J=15.3,8.7 Hz),5.69(1H,d,J=15.3 Hz),4.97(1H,d,J=8.7 Hz),3.09-2.99(1H,m),1.34(6H,d,J=6.6 Hz). MSm/z(M+H):358.

Examples 0611 and 0612

The following compounds were obtained in the same manner as in Example 0609-3.

| Example No. | | $^1$H-NMR (DMSO-$d_6$) δ: |
|---|---|---|
| 0611 | 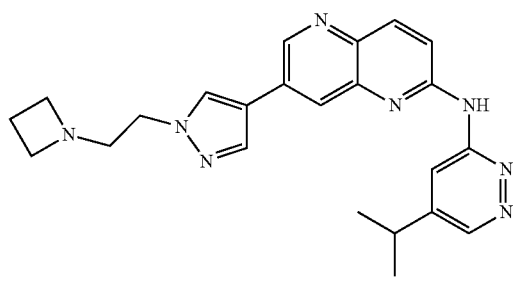 [SMILES: CC(C)c1cnnc(Nc2ccc3ncc(-c4cnn(CCN5CCC5)c4)cc3n2)c1] | 10.70 (1 H, s), 9.04 (1 H, d, J = 2.0 Hz), 8.87 (1 H, d, J = 2.0 Hz), 8.73 (1 H, d, J = 2.0 Hz), 8.49 (1 H, s), 8.24-8.19 (2H, m), 8.18 (1 H, s), 7.70 (1 H, d, J = 9.2 Hz), 4.10 (2H, t, J = 6.3 Hz), 3.12-2.99 (5H, m), 2.79 (2H, t, J = 6.3 Hz), 1.98-1.88 (2H, m), 1.34 (6H, d, J = 6.6 Hz). MS m/z (M + H): 415. |

| Example No. | | |
|---|---|---|
| 0612 | 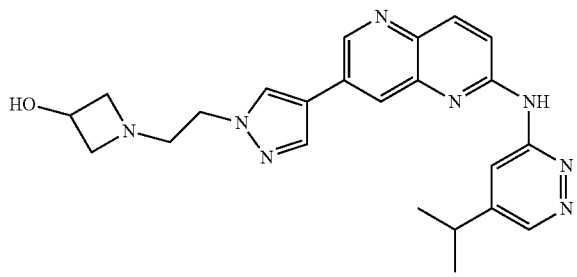 [SMILES: CC(C)c1cnnc(Nc2ccc3ncc(-c4cnn(CCN5CC(O)C5)c4)cc3n2)c1] | ¹H-NMR (DMSO-d₆) δ:<br>10.70 (1 H, s), 9.04 (1 H, d, J = 2.0 Hz), 8.87 (1 H, d, J = 2.0 Hz), 8.73 (1 H, d, J = 2.0 Hz), 8.49 (1 H, s), 8.23-8.17 (3H, m),<br>7.70 (1 H, d, J = 9.2 Hz), 5.27 (1 H, brs), 4.12 (2H, t, J = 6.1 Hz), 3.51-3.45 (2H, m), 3.39-3.26 (1 H, m), 3.09-2.99 (1 H, m), 2.83 (2H, t, J = 6.1 Hz), 2.76-2.72 (2H, m), 1.34 (6H, d, J = 6.6 Hz).<br>MS m/z (M + H): 431. |

Examples 0613 to 0615

The following compounds were obtained in the same manner as in Example 0426-2.

| Example No. | | |
|---|---|---|
| 0613 | 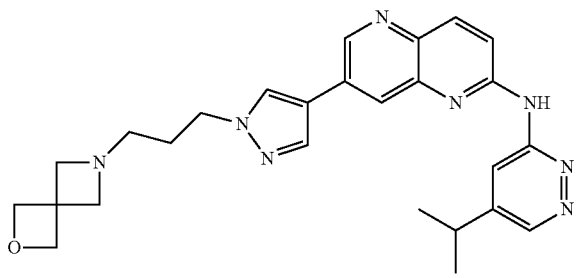 [SMILES: CC(C)c1cnnc(Nc2ccc3ncc(-c4cnn(CCCN5CC6(COC6)C5)c4)cc3n2)c1] | ¹H-NMR (DMSO-d₆) δ:<br>10.70 (1 H, s), 9.04 (1 H, d, J = 2.0 Hz), 8.87 (1 H, d, J = 2.0 Hz), 8.73 (1 H, d, J = 2.0 Hz), 8.49 (1 H, s), 8.23-8.17 (3H, m), 7.70 (1 H, d, J = 9.2 Hz), 4.59 (4H, s), 4.16 (2H, t, J = 6.9 Hz), 3.24 (4H, s), 3.09-2.99 (1 H, m), 2.30 (2H, t, J = 6.9 Hz), 1.85-1.75 (2H, m), 1.34 (6H, d, J = 6.6 Hz).<br>MS m/z (M + H): 471 |
| 0614 |  | ¹H-NMR (DMSO-d₆) δ:<br>10.70 (1 H, s), 9.04 (1 H, d, J = 2.0 Hz), 8.87 (1 H, d, J = 2.0 Hz), 8.73 (1 H, d, J = 2.0 Hz), 8.49 (1 H, s), 8.23-8.19 (3H, m), 7.70 (1 H, d, J = 9.2 Hz), 4.22 (2H, t, J = 6.9 Hz), 3.95-3.86 (2H, m), 3.09-2.98 (1 H, m), 2.40-2.35 (2H, m), 2.21 (2H, t, J = 5.9 Hz), 2.09-1.97 (4H, m), 1.33 (6H, d, J = 7.2 Hz), 1.14 (6H, d, J = 6.6 Hz).<br>MS m/z (M + H): 487. |
| 0615 | 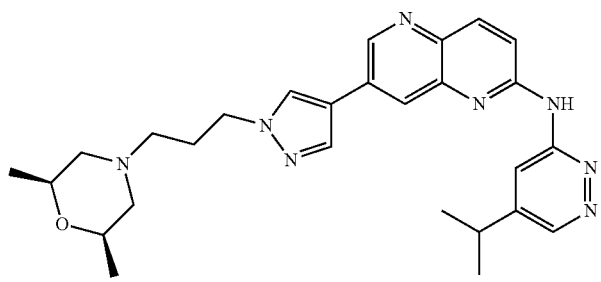 [SMILES: CC(C)c1cnnc(Nc2ccc3ncc(-c4cnn(CCCN5C[C@@H](C)O[C@@H](C)C5)c4)cc3n2)c1] | ¹H-NMR (DMSO-d₆) δ:<br>10.70 (1 H, s), 9.04 (1 H, d, J = 2.0 Hz), 8.87 (1 H, d, J = 2.0 Hz), 8.73 (1 H, d, J = 2.0 Hz), 8.51 (1 H, s), 8.23-8.18 (3H, m), 7.70 (1 H, d, J = 9.2 Hz), 4.20 (2H, t, J = 6.9 Hz), 3.60-3.51 (2H, m), 3.08-2.99 (1 H, m), 2.72 (2H, d, J = 9.9 Hz), 2.27 (2H, t, J = 6.9 Hz), 2.05-1.97 (2H, m), 1.55 (2H, t, J = 10.6 Hz), 1.33 (6H, d, J = 7.3 Hz), 1.03 (6H, d, J = 6.6 Hz).<br>MS m/z (M + H): 487. |

Examples 0616 and 0617

0616-1 and 0617-1

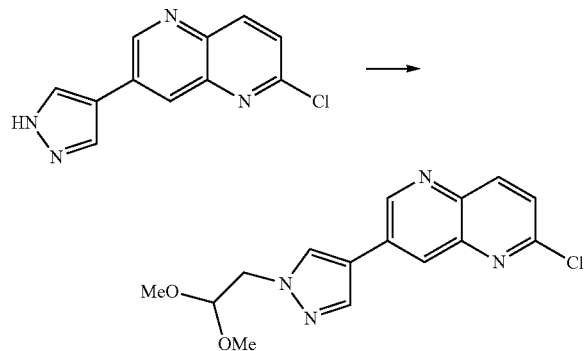

2-Chloro-7-(1-(2,2-dimethoxyethyl)-1H-pyrazol-4-yl)-1,5-naphthyridine was obtained in the same manner as in Example 0646-2.

0616-2 and 0617-2

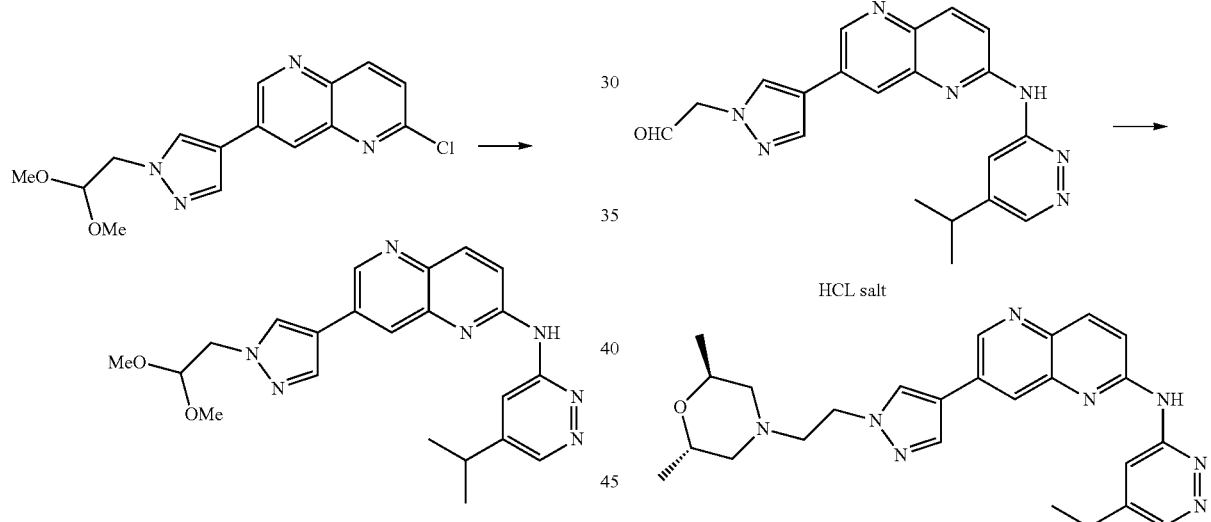

7-(1-(2,2-Dimethoxyethyl)-1H-pyrazol-4-yl)-N-(5-isopropylpyridazin-3-yl)-1,5-naphthyridine-2-amine was obtained in the same manner as in Example 0646-3. MSm/z(M+H):420.

0616-3 and 0617-3

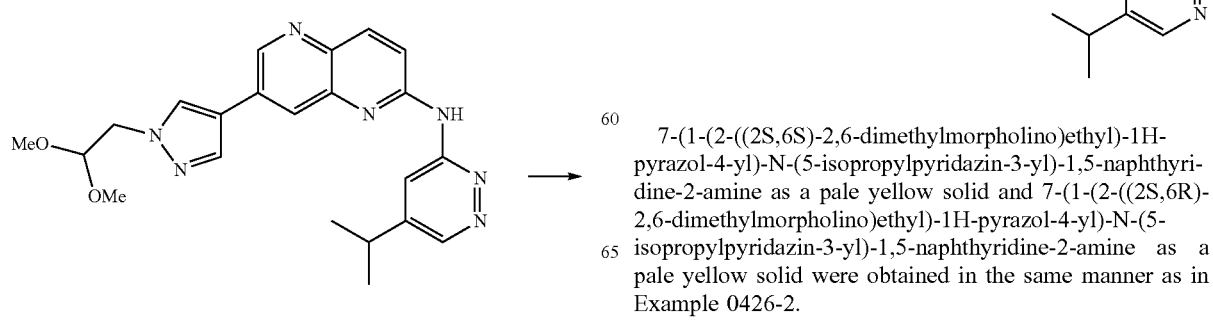

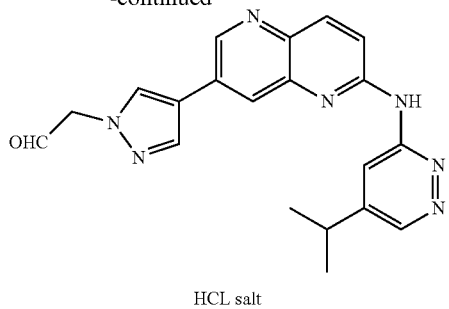

HCL salt 2-(4-(6-((5-Isopropylpyridazin-3-yl)amino)-1,5-naphthyridin-3-yl)-1H-pyrazol-1-yl)acetaldehyde hydrochloride was obtained in the same manner as in Example 0426-1.

$^1$H-NMR(DMSO-d$_6$)δ:10.73(1H,d,J=15.9 Hz),9.30(1H,dd,J=14.9,2.3 Hz),8.88(1H,dd,J=8.6,2.0 Hz),8.77-8.75(2H,m),8.62-8.20(4H,m),7.76-7.70(1H,m),6.54(1H,s),4.18-4.15 (2H,m),3.09-3.06(1H,m),1.35(6H,d,J=2.0 Hz).

0616-4 and 0617-4

7-(1-(2-((2S,6S)-2,6-dimethylmorpholino)ethyl)-1H-pyrazol-4-yl)-N-(5-isopropylpyridazin-3-yl)-1,5-naphthyridine-2-amine as a pale yellow solid and 7-(1-(2-((2S,6R)-2,6-dimethylmorpholino)ethyl)-1H-pyrazol-4-yl)-N-(5-isopropylpyridazin-3-yl)-1,5-naphthyridine-2-amine as a pale yellow solid were obtained in the same manner as in Example 0426-2.

Example 0616

7-(1-(2-((2S,6S)-2,6-dimethylmorpholino)ethyl)-1H-pyrazol-4-yl)-N-(5-isopropylpyridazin-3-yl)-1,5-naphthyridine-2-amine $^1$H-NMR(CDCl$_3$)δ:9.51(1H,s),8.93(2H,d,J=2.0 Hz),8.83(1H,s),8.25(1H,d,J=8.9 Hz),8.10(1H,d,J=2.0 Hz),7.98(1H,s),7.96(1H,s),7.67(1H,d,J=8.9 Hz),4.32(2H,t,J=5.9 Hz),4.07-3.98(2H,m),3.11-3.02(1H,m),2.88-2.71(2H,m),2.58-2.52(2H,m),2.25-2.17(2H,m),1.43(6H,d,J=6.6 Hz),1.24(6H,d,J=6.6 Hz).
MSm/z(M+H):473.

Example 0617

7-(1-(2-((2S,6R)-2,6-dimethylmorpholino)ethyl)-1H-pyrazol-4-yl)-N-(5-isopropylpyridazin-3-yl)-1,5-naphthyridine-2-amine $^1$H-NMR(CDCl$_3$)δ:9.78(1H,s),8.95(1H,s),8.92(1H,d,J=2.0 Hz),8.83(1H,s),8.25(1H,d,J=9.2 Hz),8.10(1H,d,J=2.0 Hz),7.96(2H,s),7.73(1H,d,J=9.2 Hz),4.34(2H,t,J=6.3 Hz),3.73-3.64(2H,m),3.12-3.02(1H,m),2.86(2H,t,J=6.3 Hz),2.74(2H,d,J=10.6 Hz),1.89(2H,t,J=10.6 Hz),1.43(6H,d,J=6.6 Hz),1.17(6H,d,J=6.6 Hz).
MSm/z(M+H):473.

Example 0618

0618-1

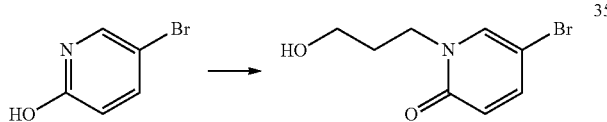

3-Bromopropan-1-ol (151 μL) and potassium carbonate (477 mg) were added to a solution of 5-bromopyridin-2-ol (200 mg) in methanol (5 mL), followed by stirring for 1.5 hours under reflux. Sodium iodide (17 mg) and 3-bromopropan-1-ol (100 μL) were added to the reaction mixture, followed by stirring for 11 hours under reflux. The reaction mixture was cooled to room temperature, and the solvent was distilled off under reduced pressure. The obtained residue was purified by silica gel column chromatography (hexane-ethyl acetate-methanol), thereby obtaining 5-bromo-1-(3-hydroxypropyl)pyridin-2(1H)-one (250 mg).
MSm/z(M+H):232.

0618-2

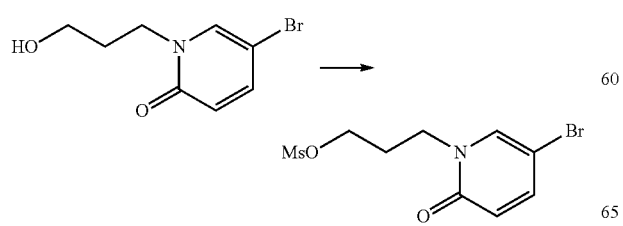

Methanesulfonyl chloride (91 μL) was added to a mixture of 5-bromo-1-(3-hydroxypropyl)pyridin-2(1H)-one (180 mg), dichloromethane (5 mL), and triethylamine (324 μL) at a temperature of from 0° C. to 5° C., followed by stirring for 1.5 hours. After water was added to the reaction mixture, the organic layer was collected by separation, washed with a saturated sodium chloride aqueous solution, and dried over anhydrous sodium sulfate, and the solvent was distilled off under reduced pressure, thereby obtaining 3-(5-bromo-2-oxopyridine-1(2H)-yl)propyl methanesulfonate (259 mg).
MSm/z(M+H):312.

0618-3

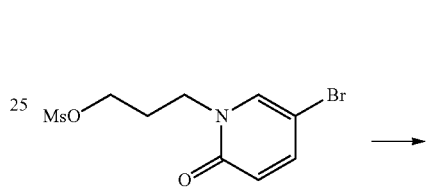

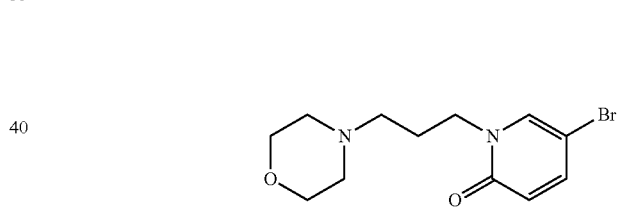

A mixture of 3-(5-bromo-2-oxopyridin-1(2H)-yl)propyl methanesulfonate (259 mg), 1,4-dioxane (5 mL), morpholine (295 μL), cesium carbonate (547 mg), and sodium iodide (37 mg) was stirred at 80° C. for 3 hours. Ethyl acetate was added to the reaction mixture, the insolubles were filtered off, and the solvent was distilled off under reduced pressure, thereby obtaining 5-bromo-1-(3-morpholinopropyl)pyridin-2(1H)-one (258 mg).
MSm/z(M+H):303.

0618-4 and 0618-5

The following compounds were obtained in the same manner as in Examples 0421-1 and 0015-4.

| Example No. | | |
|---|---|---|
| 0618 | | |
| 0618-4 | 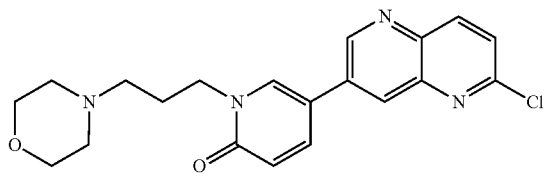 [SMILES: O=c1ccc(-c2cnc3ccc(Cl)nc3c2)cn1CCCN1CCOCC1] | MS m/z (M + H): 385. |
| 0618-5 | 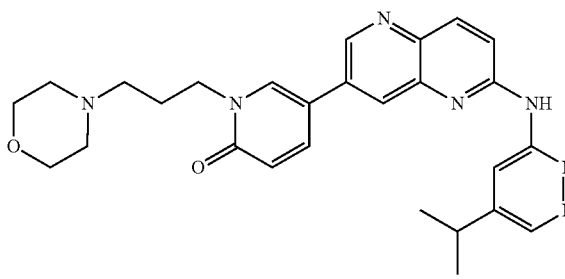 | ¹H-NMR (DMSO-d₆) δ: 10.75 (1 H, s), 9.04 (1 H, d, J = 2.0 Hz), 8.87 (1 H, d, J = 2.0 Hz), 8.75 (1 H, d, J = 2.0 Hz), 8.46 (1 H, d, J = 2.0 Hz), 8.28-8.24 (2H, m), 8.07 (1 H, dd, J = 9.2, 2.0 Hz), 7.73 (1 H, d, J = 9.2 Hz), 6.56 (1 H, d, J = 9.2 Hz), 4.05 (2H, t, J = 6.9 Hz), 3.54 (4 H, t, J = 4.3 Hz), 3.08-2.99 (1 H, m), 2.36-2.27 (6H, m), 1.90 (2H, t, J = 6.9 Hz), 1.32 (6H, d, J = 7.3 Hz). MS m/z (M + H): 486. |

Example 0619

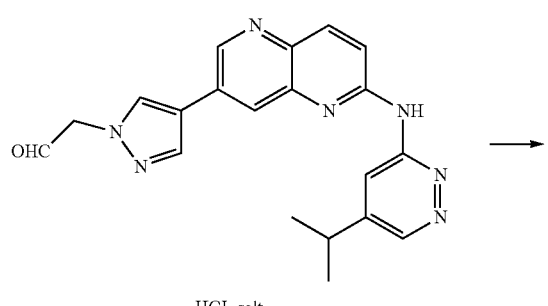

HCL salt

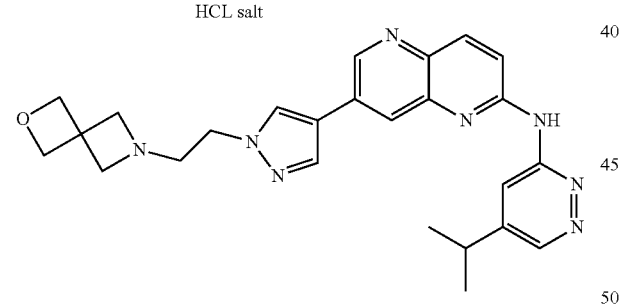

7-(1-(2-(2-Oxa-6-azaspiro[3.3]heptan-6-yl)ethyl)-1H-pyrazol-4-yl)-N-(5-isopropylpyridazin-3-yl)-1,5-naphthyridine-2-amine was obtained as a pale yellow solid in the same manner as in Example 0426-2.

¹H-NMR(CDCl₃)δ:9.23(1H,s),8.93(1H,d,J=2.0 Hz),8.86-8.76(2H,m),8.25(1H,d,J=8.9 Hz),8.11(1H,d,J=2.0 Hz),7.98 (1H,s),7.89(1H,s),7.52(1H,d,J=8.9 Hz),4.71(4H,s),4.23-4.16(2H,m),3.36(4H,s),3.11-3.03(1H,m),2.96-2.90(2H,m), 1.43(6H,d,J=7.3 Hz).

MSm/z(M+H):457.

Example 0620

The following compounds were obtained in the same manner as in Examples 0421-1 and 0015-4.

| Example No. | | |
|---|---|---|
| 0620 | | |
| 0620-1 | 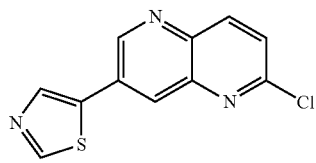 [SMILES: Clc1ccc2ncc(-c3cncs3)cc2n1] | MS m/z (M + H): 248. |

| Example No. | | |
|---|---|---|
| 0620-2 | 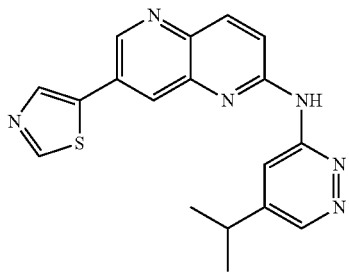 [SMILES: CC(C)c1cnnc(Nc2ccc3ncc(-c4cncs4)cc3n2)c1] | ¹H-NMR (DMSO-d₆) δ: 10.82 (1H, s), 9.25 (1 H, s), 9.12 (1 H, d, J = 2.6 Hz), 8.88 (1 H, d, J = 2.0 Hz), 8.75 (1 H, d, J = 2.0 Hz), 8.67 (1 H, s), 8.34 (1 H, d, J = 2.6 Hz), 8.28 (1 H, d, J = 9.2 Hz), 7.78 (1 H, d, J = 9.2 Hz), 3.11-3.01 (1 H, m), 1.33 (6H, d, J = 7.3 Hz). MS m/z (M + H): 349. |

Example 0621

The following compounds were obtained in the same manner as in Examples 0607-2 and 0015-4.

| Example No. | | |
|---|---|---|
| 0621 | | |
| 0621-1 | 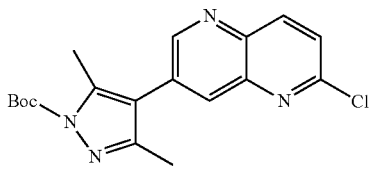 [SMILES: Cc1nn(C(=O)OC(C)(C)C)c(C)c1-c1cnc2ccc(Cl)nc2c1] | MS m/z (M + H): 359. |
| 0621-2 | 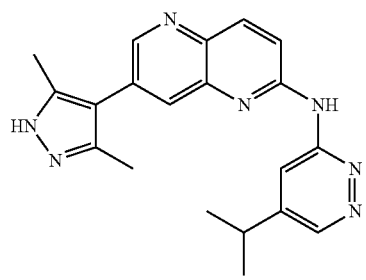 [SMILES: Cc1n[nH]c(C)c1-c1cnc2ccc(Nc3cc(C(C)C)cnn3)nc2c1] | ¹H-NMR (DMSO-d₆) δ: 12.54 (1 H, s), 10.73 (1 H, s), 8.84 (1 H, d, J = 2.0 Hz), 8.73 (1 H, d, J = 2.0 Hz), 8.70 (1 H, d, J = 2.0 Hz) 8.26 (1 H, d, J = 9.2 Hz), 7.95 (1 H, d, J = 2.0 Hz), 7.78 (1 H, d, J = 9.2 Hz), 3.03-2.97 (1 H, m), 2.33 (3H, s), 2.27 (3H, s), 1.30 (6H, d, J = 7.3 Hz). MS m/z (M + H): 360. |

Example 0622

0622-1 and 0622-2

The following compounds were obtained in the same manner as in Examples 0607-2 and 0015-4.

| Example No. | | |
|---|---|---|
| 0622 | | |
| 0622-1 | 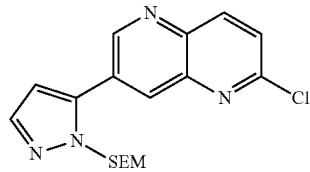 [SMILES: C[Si](C)(C)CCOCn1nccc1-c1cnc2ccc(Cl)nc2c1] | MS m/z (M + H): 361. |
| 0622-2 | 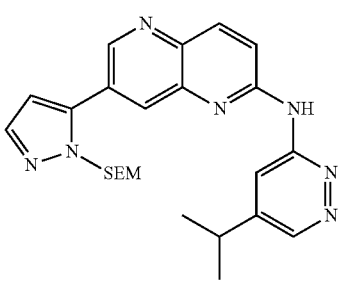 [SMILES: CC(C)c1cnnc(Nc2ccc3ncc(-c4ccnn4COCC[Si](C)(C)C)cc3n2)c1] | MS m/z (M + H): 462. |

0622-3

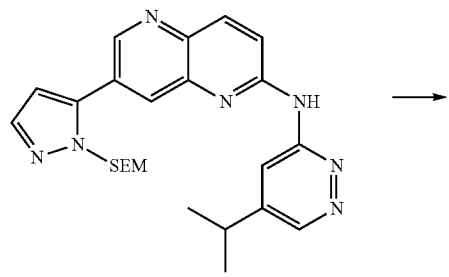

A mixture of N-(5-isopropylpyridazin-3-yl)-7-(1-((2-(trimethylsilyl)ethoxy)methyl)-1H-pyrazol-5-yl)-1,5-naphthyridine-2-amine (75 mg), 1,4-dioxane (2 mL), and 2 mol/L hydrochloric acid (1 mL) was stirred at 80° C. for 3.5 hours. After the reaction mixture was cooled to room temperature, a saturated sodium hydrogen carbonate aqueous solution and ethyl acetate were added thereto, and the organic layer was collected by separation, washed with a saturated sodium chloride aqueous solution, and dried over anhydrous sodium sulfate, and the solvent was distilled off under reduced pressure. The obtained residue was purified by silica gel column chromatography (chloroform-methanol, NH silica), thereby obtaining N-(5-isopropylpyridazin-3-yl)-7-(1H-pyrazol-5-yl)-1,5-naphthyridine-2-amine (21 mg)) as a yellow solid.

$^1$H-NMR(DMSO-d$_6$)δ:13.19(1H,s),10.74(1H,s),9.25(1H,d,J=2.0 Hz),8.87(1H,d,J=2.0 Hz),8.77(1H,d,J=2.0 Hz),8.42(1H,s),8.26(1H,d,J=9.2 Hz),7.92(1H,s),7.74(1H,d,J=9.2 Hz),7.05(1H,s),3.09-3.00(1H,m),1.33(6H,d,J=6.6 Hz).
MSm/z(M+H):332.

Example 0623

0623-1

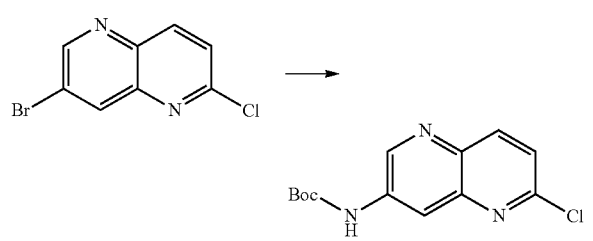

A mixture of 7-bromo-2-chloro-1,5-naphthyridine (50 mg), tert-butyl carbamate (32 mg), tris(dibenzylideneacetone)dipalladium(0) (18 mg), 4,5-bis(diphenylphosphino)-9,9-dimethylxanthene (23 mg), cesium carbonate (187 mg), and 1,4-dioxane (4 mL) was stirred at 120° C. for 9 hours in a nitrogen atmosphere. The reaction mixture was cooled to room temperature, and the solvent was distilled off under reduced pressure. The obtained residue was purified by silica gel column chromatography (hexane-ethyl acetate-methanol), thereby obtaining tert-butyl (6-chloro-1,5-naphthyridin-3-yl)carbamate (47 mg).
MSm/z(M+H):280.

0623-2

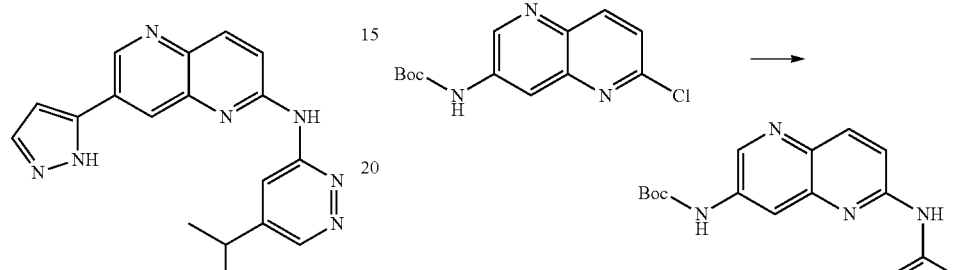

tert-Butyl (6-((5-isopropylpyridazin-3-yl)amino)-1,5-naphthyridin-3-yl)carbamate was obtained in the same manner as in Example 0646-3.
MSm/z(M+H):381.

0623-3

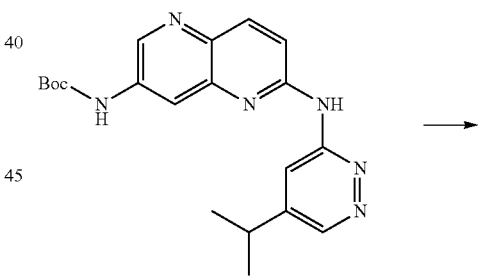

A mixture of tert-butyl (6-((5-isopropylpyridazin-3-yl)amino)-1,5-naphthyridin-3-yl)carbamate (16 mg), 1,4-dioxane (1 mL), and 2 mol/L hydrochloric acid (0.5 mL) was stirred at 80° C. for 1 hour. After the reaction mixture was cooled to room temperature, a saturated sodium hydrogen carbonate aqueous solution and ethyl acetate were added thereto, the organic layer was collected by separation, washed with a saturated sodium chloride aqueous solution, and dried over anhydrous sodium sulfate, and the solvent was distilled off under reduced pressure, thereby obtaining $N^2$-(5-isopropylpyridazin-3-yl)-1,5-naphthyridine-2,7-diamine (8 mg) as a yellow solid.

$^1$H-NMR(DMSO-$d_6$)δ:10.44(1H,s),8.79(1H,d,J=2.0 Hz), 8.74(1H,d,J=2.0 Hz),8.24(1H,d,J=2.0 Hz),7.97(1H,d,J=9.2 Hz),7.34(1H,d,J=9.2 Hz),7.02(1H,d,J=2.0 Hz),5.91(2H,s), 3.02-2.92(1H,m),1.30(6H,d,J=7.6 Hz).

MSm/z(M+H):281.

Example 0624

0624-1

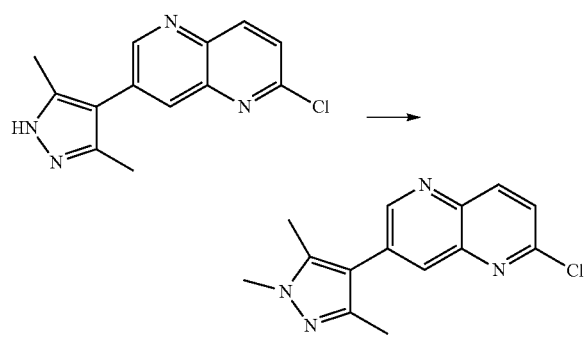

A mixture of 2-chloro-7-(3,5-dimethyl-1H-pyrazol-4-yl)-1,5-naphthyridine (34 mg), 1,4-dioxane (2 mL), potassium carbonate (54 mg), and iodomethane (16 μL) was stirred at room temperature for 1 hour. Iodomethane (16 μL) and N,N-dimethylformamide (1 mL) were added to the reaction mixture, followed by stirring at 80° C. for 6 hours. The reaction mixture was cooled to room temperature, and the solvent was distilled off under reduced pressure. The obtained residue was purified by silica gel column chromatography (chloroform-methanol), thereby obtaining 2-chloro-7-(1,3,5-trimethyl-1H-pyrazol-4-yl)-1,5-naphthyridine (20 mg).

MSm/z(M+H):273.

0624-2

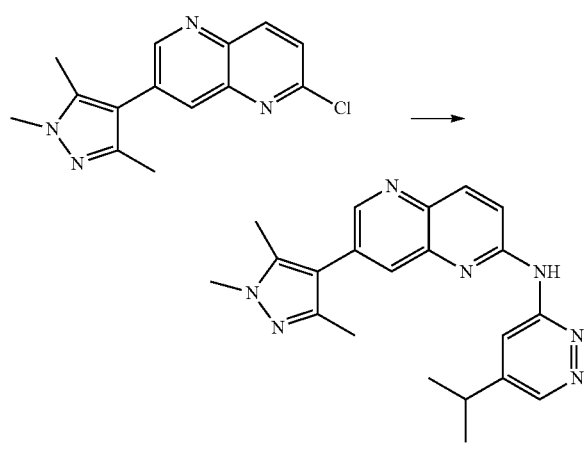

N-(5-isopropylpyridazin-3-yl)-7-(1,3,5-trimethyl-1H-pyrazol-4-yl)-1,5-naphthyridine-2-amine was obtained as a yellow solid in the same manner as in Example 0646-3.

$^1$H-NMR(DMSO-$d_6$)δ:10.74(1H,s),8.85(1H,d,J=2.0 Hz), 8.70(1H,d,J=2.0 Hz),8.68(1H,d,J=2.0 Hz),8.27(1H,d,J=9.2 Hz),7.92(1H,d,J=2.0 Hz),7.78(1H,d,J=9.2 Hz),3.76(3H,s), 3.02-2.99(1H,m),2.31(3H,s),2.22(3H,s),1.29(6H,d,J=7.3 Hz).

MSm/z(M+H):374.

Example 0625

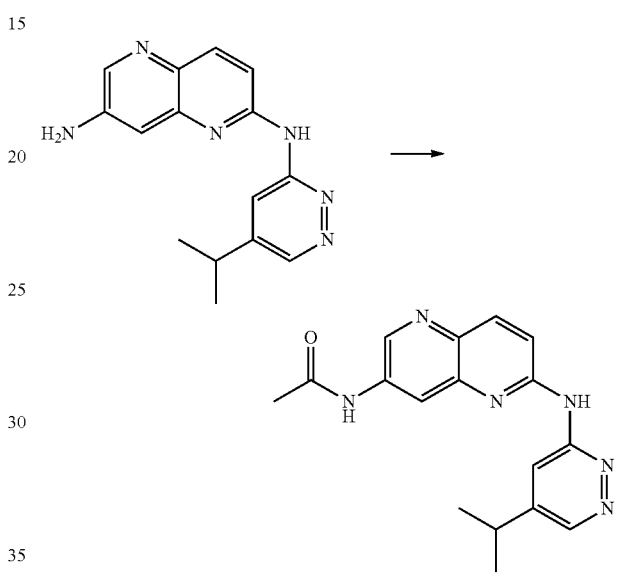

A mixture of $N^2$-(5-isopropylpyridazin-3-yl)-1,5-naphthyridine-2,7-diamine (5 mg), pyridine (1 mL), acetic anhydride (6 μL), and N,N-dimethylpyridine-4-amine (0.2 mg) was stirred at room temperature for 1 hour. The solvent was distilled off under reduced pressure, and the obtained residue was purified by preparative thin layer silica gel column chromatography (chloroform-methanol, NH silica), thereby obtaining N-(6-((5-isopropylpyridazin-3-yl)amino)-1,5-naphthyridin-3-yl)acetamide (6 mg) as a pale yellow solid.

$^1$H-NMR(DMSO-$d_6$)δ:10.69(1H,s),10.47(1H,s),8.84(1H, d,J=2.0 Hz),8.81(1H,d,J=2.0 Hz),8.72(1H,d,J=2.0 Hz),8.46 (1H,d,J=2.0 Hz),8.17(1H,d,J=9.2 Hz),7.65(1H,d,J=9.2 Hz), 3.05-2.95(1H,m),2.15(3H,s),1.31(6H,d,J=6.6 Hz).

MSm/z(M+H):323.

Example 0626

0626-1

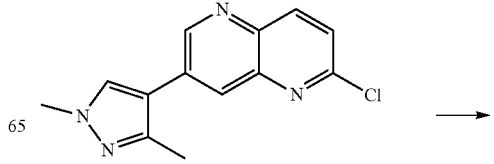

-continued

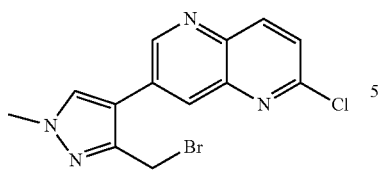

A mixture of 2-chloro-7-(1,3-dimethyl-1H-pyrazol-4-yl)-1,5-naphthyridine (50 mg), chlorobenzene (2 mL), N-bromosuccinimide (37 mg), and azobisisobutyronitrile (3 mg) was stirred at 80° C. for 2.5 hours. Azobisisobutyronitrile (19 mg) was added to the reaction mixture, followed by stirring at 80° C. for 7 hours. After the reaction mixture was cooled to room temperature, ethyl acetate and a saturated sodium hydrogen carbonate aqueous solution were added thereto, and the organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate-methanol), thereby obtaining 7-(3-(bromomethyl)-1-methyl-1H-pyrazol-4-yl)-2-chloro-1,5-naphthyridine (45 mg).

MSm/z(M+H):339.

0626-2

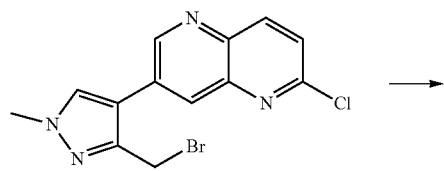

A mixture of 7-(3-(bromomethyl)-1-methyl-1H-pyrazol-4-yl)-2-chloro-1,5-naphthyridine (218 mg), 1,4-dioxane (10 mL), water (5 mL), and potassium carbonate (270 mg) was stirred at 70° C. for 1 hour, stirred at 80° C. for 2.5 hours, and stirred at 90° C. for 30 minutes. After the reaction mixture was cooled to room temperature, ethyl acetate and water were added thereto, the organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate-methanol), thereby obtaining (4-(6-chloro-1,5-naphthyridin-3-yl)-1-methyl-1H-pyrazol-3-yl)methanol (48 mg).

$^1$H-NMR(DMSO-d$_6$)δ:9.30(1H,d,J=2.0 Hz),8.62(1H,d,J=2.0 Hz),8.45(1H,d,J=8.6 Hz),8.42(1H,s),7.78-7.75(1H,m),5.44(1H,t,J=5.0 Hz),4.59(2H,d,J=4.6 Hz),3.89(3H,s).

0626-3

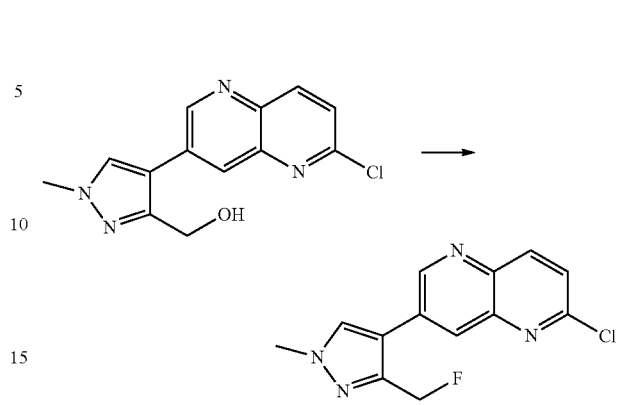

Bis(2-methoxyethyl)aminosulfur trifluoride (37 µL) was added to a mixture of (4-(6-chloro-1,5-naphthyridin-3-yl)-1-methyl-1H-pyrazol-3-yl)methanol (50 mg), and dichloromethane (4 mL) at a temperature of from 0° C. to 5° C., followed by stirring at 0° C. for 2.5 hours. After ethyl acetate and a saturated sodium hydrogen carbonate aqueous solution were added to the reaction mixture, the organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate-methanol), thereby obtaining 2-chloro-7-(3-(fluoromethyl)-1-methyl-1H-pyrazol-4-yl)-1,5-naphthyridine (44 mg).

MSm/z(M+H):277.

0626-4

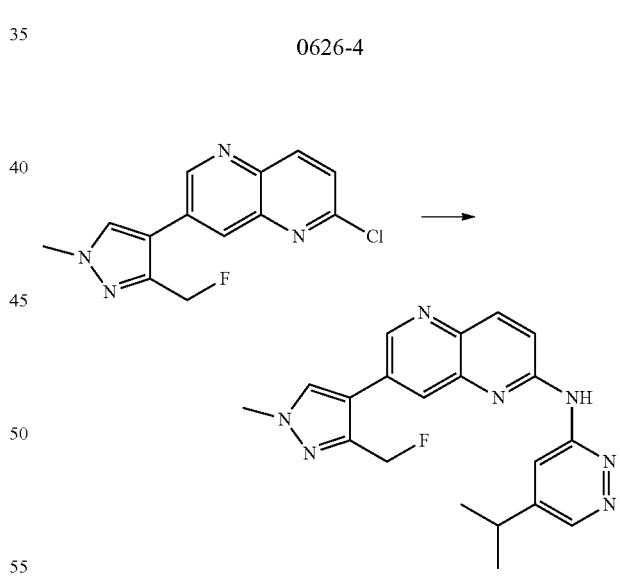

7-(3-(Fluoromethyl)-1-methyl-1H-pyrazol-4-yl)-N-(5-isopropylpyridazin-3-yl)-1,5-naphthyridine-2-amine was obtained as a white solid in the same manner as in Example 0646-3.

$^1$H-NMR(DMSO-d$_6$)δ:10.77(1H,s),8.92(1H,d,J=2.0 Hz),8.85(1H,d,J=2.0 Hz),8.77(1H,d,J=2.0 Hz),8.42(1H,s),8.27(1H,d,J=9.2 Hz),8.17(1H,d,J=2.0 Hz),7.76(1H,d,J=9.2 Hz),5.53(2H,d,J=49.5 Hz),3.95(3H,d,J=1.3 Hz),3.05-2.95(1H,m),1.31(6H,d,J=7.3 Hz).

MSm/z(M+H):378.

Examples 0627 and 0628

0627-1 and 0628-1

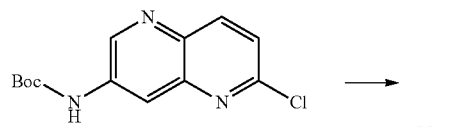

6-Chloro-1,5-naphthyridine-3-amine was obtained in the same manner as in Example 0623-3.
$^1$H-NMR(DMSO-d$_6$)δ:8.51(1H,d,J=2.6 Hz),8.15(1H,d,J=8.6 Hz),7.33(1H,d,J=8.6 Hz),7.08(1H,d,J=2.6 Hz),6.31 (2H,s).

0627-2 and 0628-2


N-(6-chloro-1,5-naphthyridin-3-yl)acetamide was obtained in the same manner as in Example 0625-1.
MSm/z(M+H):222.

0627-3 and 0628-3

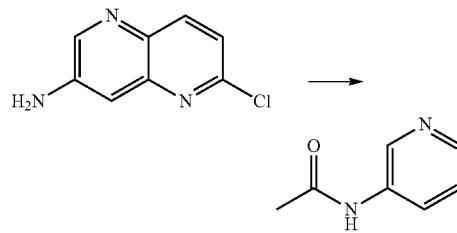

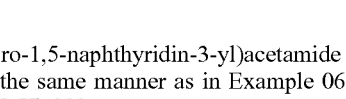

A mixture of N-(6-chloro-1,5-naphthyridin-3-yl)acetamide (16 mg), N,N-dimethylformamide (1 mL), iodomethane (7 μL), and 60% sodium hydride (3 mg) was stirred at room temperature for 1 hour. Iodomethane (7 μL) and 60% sodium hydride (3 mg) were added to the reaction mixture, followed by stirring at room temperature for 3 hours. The solvent was distilled off under reduced pressure, and the obtained residue was purified by silica gel column chromatography (hexane-ethyl acetate-methanol), thereby obtaining 6-chloro-N,N-dimethyl-1,5-naphthyridine-3-amine (10 mg) and N-(6-chloro-1,5-naphthyridin-3-yl)-N-methylacetamide (7 mg).

6-Chloro-N,N-dimethyl-1,5-naphthyridine-3-amine

MSm/z(M+H):208.

N-(6-chloro-1,5-naphthyridin-3-yl)-N-methylacetamide

MSm/z(M+H):236.

0627-4

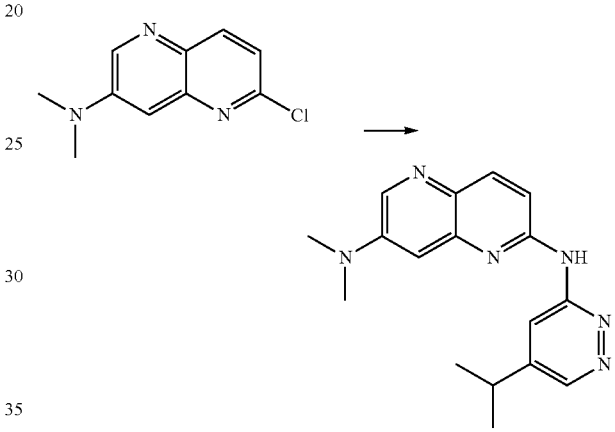

N$^2$-(5-isopropylpyridazin-3-yl)-N$^7$,N$^7$-dimethyl-1,5-naphthyridine-2,7-diamine was obtained as a yellow solid in the same manner as in Example 0646-3.
$^1$H-NMR(DMSO-d$_6$)δ:10.48(1H,s),8.82(1H,d,J=2.0 Hz),8.70(1H,d,J=2.0 Hz),8.53(1H,d,J=2.6 Hz),8.05(1H,d,J=9.2 Hz),7.43(1H,d,J=9.2 Hz),7.05(1H,d,J=2.6 Hz),3.09(6H,s),3.05-2.96(1H,m),1.30(6H,d,J=6.6 Hz).
MSm/z(M+H):309.

0628-4

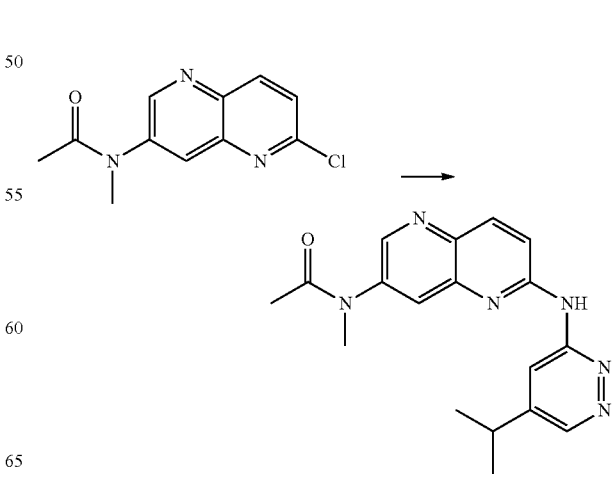

N-(6-((5-isopropylpyridazin-3-yl)amino)-1,5-naphthyridin-3-yl)-N-methylacetamide was obtained as a pale yellow solid in the same manner as in Example 0646-3.

$^1$H-NMR(DMSO-d$_6$)δ:10.81(1H,s),8.87(1H,d,J=2.0 Hz), 8.74(2H,s),8.28(1H,d,J=9.2 Hz),8.16(1H,s),7.77(1H,d, J=9.2 Hz),3.33(3H,s),3.06-2.97(1H,m),2.50(3H,s),1.31(6H, d,J=6.6 Hz).

MSm/z(M+H):337.

Examples 0629 and 0630

The following compounds were obtained in the same manner as in Example 0426-2.

N-(5-cyclopentylpyridazin-3-yl)-7-(3-(fluoromethyl)-1-methyl-1H-pyrazol-4-yl)-1,5-naphthyridine-2-amine was obtained as a pale yellow solid in the same manner as in Example 0646-3.

$^1$H-NMR(DMSO-d$_6$)δ:10.76(1H,s),8.91(1H,d,J=2.0 Hz), 8.82(1H,d,J=2.0 Hz),8.79(1H,d,J=2.0 Hz),8.42(1H,s),8.26 (1H,d,J=9.2 Hz),8.15(1H,d,J=2.0 Hz),7.75(1H,d,J=9.2 Hz), 5.52(2H,d,J=49.5 Hz),3.95(3H,d,J=1.3 Hz),3.14-3.06(1H, m),2.18-2.08(2H,m),1.88-1.80(2H,m),1.78-1.64(4H,m).

MSm/z(M+H):404.

| Example No. | | |
|---|---|---|
| 0629 | 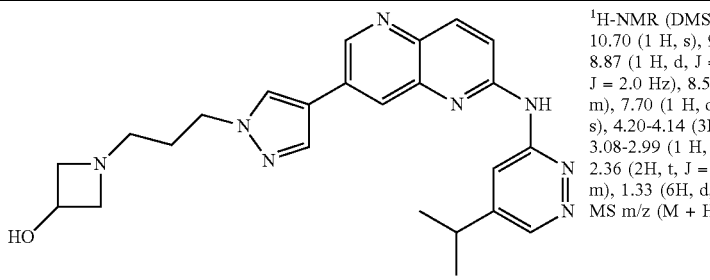 | $^1$H-NMR (DMSO-d$_6$) δ: 10.70 (1 H, s), 9.04 (1 H, d, J = 2.0 Hz), 8.87 (1 H, d, J = 2.0 Hz), 8.73 (1 H, d, J = 2.0 Hz), 8.50 (1 H, s), 8.23-8.17 (3H, m), 7.70 (1 H, d, J = 9.2 Hz), 5.26 (1 H, s), 4.20-4.14 (3H, m), 3.54-3.48 (2H, m), 3.08-2.99 (1 H, m), 2.67-2.61 (2H, m), 2.36 (2H, t, J = 6.6 Hz), 1.87-1.78 (2H, m), 1.33 (6H, d, J = 7.3 Hz). MS m/z (M + H): 445. |
| 0630 | 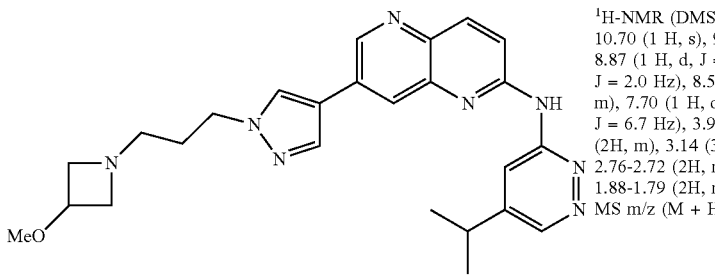 | $^1$H-NMR (DMSO-d$_6$) δ: 10.70 (1 H, s), 9.04 (1 H, d, J = 2.0 Hz), 8.87 (1 H, d, J = 2.0 Hz), 8.73 (1 H, d, J = 2.0 Hz), 8.50 (1 H, s), 8.23-8.18 (3 H, m), 7.70 (1 H, d, J = 9.2 Hz), 4.18 (2H, t, J = 6.7 Hz), 3.98-3.91 (1 H, m), 3.52-3.46 (2H, m), 3.14 (3H, s), 3.08-2.99 (1 H, m), 2.76-2.72 (2H, m), 2.39 (2H, t, J = 6.7 Hz), 1.88-1.79 (2H, m), 1.33 (6H, d, J = 6.6 Hz). MS m/z (M + H): 459. |

Example 0631

Example 0632

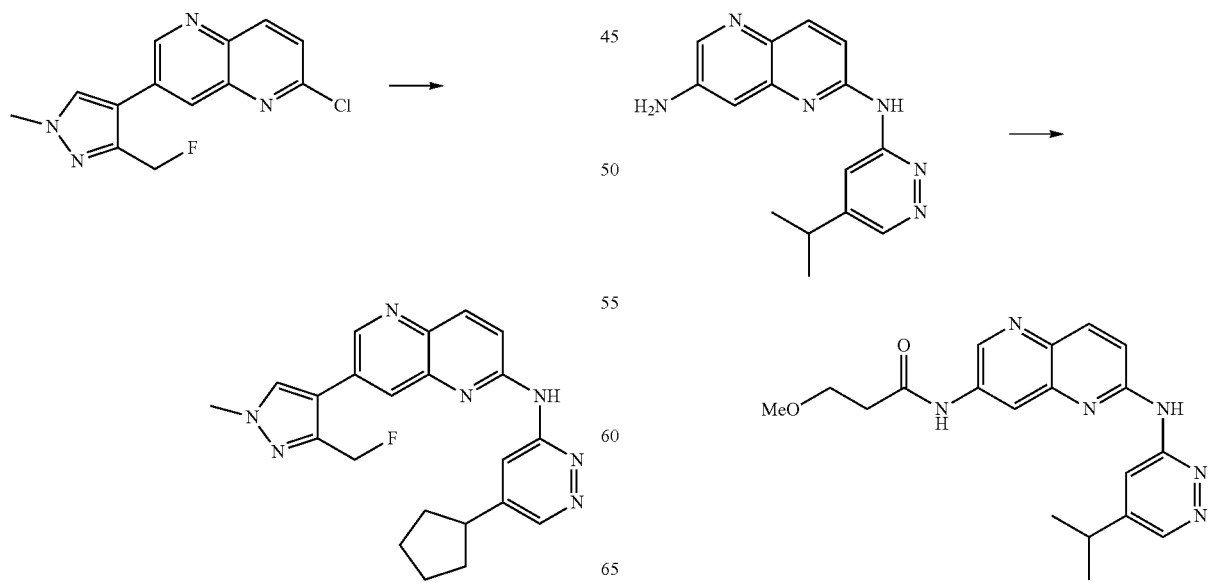

A mixture of N²-(5-isopropylpyridazin-3-yl)-1,5-naphthyridine-2,7-diamine (15 mg), N,N-dimethylformamide (1 mL), 3-methoxypropionic acid (9 μL), O-(7-azabenzotriazol-1-yl)-N,N,N',N'-tetramethyluronium hexafluorophosphate (30 mg), and N,N-diisopropylethylamine (34 μL) was stirred at room temperature for 24 hours. The solvent was distilled off under reduced pressure, and the obtained residue was purified by preparative thin layer silica gel column chromatography (chloroform-methanol, NH silica), thereby obtaining N-(6-((5-isopropylpyridazin-3-yl)amino)-1,5-naphthyridin-3-yl)-3-methoxypropanamide (6 mg) as a white solid.

¹H-NMR(DMSO-d₆)δ:10.69(1H,s),10.49(1H,s),8.85(1H,d,J=2.0 Hz),8.83(1H,d,J=2.0 Hz),8.72(1H,d,J=2.0 Hz),8.49(1H,d,J=2.0 Hz),8.17(1H,d,J=9.2 Hz),7.65(1H,d,J=9.2 Hz),3.67(2H,t,J=5.9 Hz),3.27(3H,s),3.05-2.95(1H,m),2.66(2H,t,J=5.9 Hz),1.32(6H,d,J=7.3 Hz).

MSm/z(M+H):367.

Example 0633

0633-1 and 0633-2

The following compounds were obtained in the same manner as in Examples 0585-1 and 0559-2.

| Example No. | | |
|---|---|---|
| 0633 | | |
| 0633-1 | 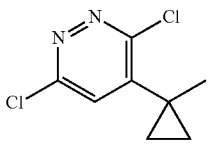 | MSm/z(M + H): 203. |
| 0633-2 | 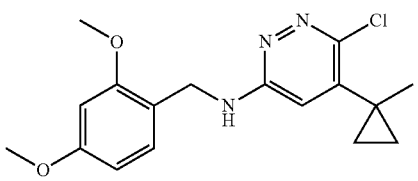 | MSm/z(M + H): 334. |

0633-3

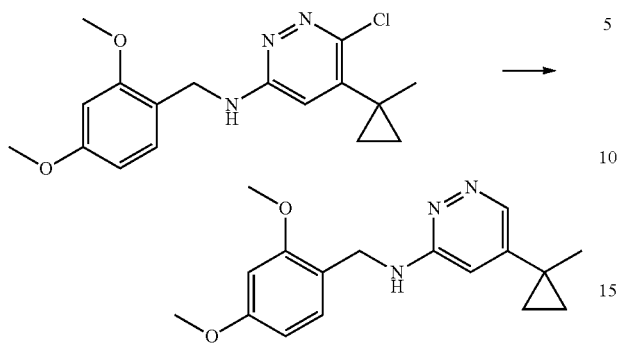

A mixture of 6-chloro-N-(2,4-dimethoxybenzyl)-5-(1-methylcyclopropyl)pyridazine-3-amine (1.98 g), ammonium formate (739 mg), tetrakis(triphenylphosphine)palladium(0) (338 mg), triethylamine (1.23 mL), and 1,2-dimethoxyethane (10 mL) was stirred at 120° C. for 4 hours using a microwave reaction apparatus. After the reaction mixture was cooled to room temperature, water and ethyl acetate were added thereto, the organic layer was collected by separation, washed with a saturated sodium chloride aqueous solution, and dried over anhydrous sodium sulfate, and the solvent was distilled off under reduced pressure. The obtained residue was purified by silica gel column chromatography (methanol-ethyl acetate-hexane), thereby obtaining N-(2,4-dimethoxybenzyl)-5-(1-methylcyclopropyl)pyridazine-3-amine (431 mg).

MSm/z(M+H):300.

0633-4 and 0633-5

The following compounds were obtained in the same manner as in Examples 0559-4 and 0015-4.

Example No.

0633

| 0633-4 | 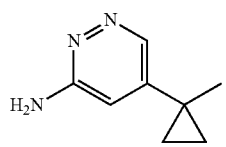 | MSm/z(M + H): 150. |
|---|---|---|
| 0633-5 | 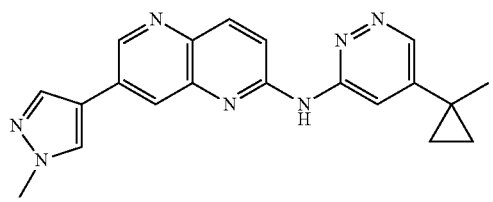 [SMILES: Cn1cc(-c2cnc3ccc(Nc4cc(C5(C)CC5)cnn4)nc3c2)cn1] | $^1$H-NMR(CDCl$_3$)δ:<br>8.87(1 H, d, J = 1.8 Hz), 8.83(1 H, brs), 8.57(1 H, brs), 6.19(1 H, d, J = 8.7 Hz), 8.10(1 H, brs), 7.95(2H, brs), 7.49(1 H, d, J = 8.7 Hz), 4.03(3H, s), 1.60(3H, s), 1.22-1.15(2H, m), 1.14-1.06(2H, m).<br>MSm/z(M + H): 358. |

Example 0634

The following compounds were obtained in the same manner as in Examples 0421-1 and 0646-3.

Example No.

0634

| 0634-1 | 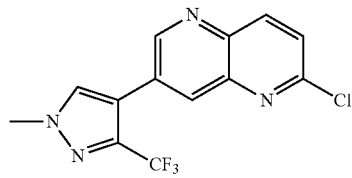 [SMILES: Cn1cc(-c2cnc3ccc(Cl)nc3c2)c(C(F)(F)F)n1] | MSm/z(M + H): 313. |
|---|---|---|

| Example No. | | |
|---|---|---|
| 0634-2 | 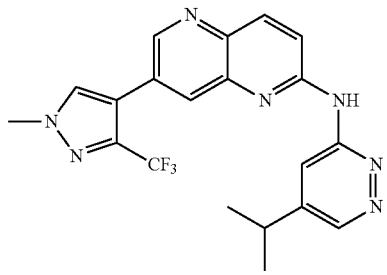 [SMILES: CC(C)c1cnnc(Nc2ccc3ncc(-c4cn(C)nc4C(F)(F)F)cc3n2)c1] | ¹H-NMR(DMSO-d₆)δ:<br>10.82(1 H, s), 8.86(1 H, d, J = 2.0 Hz), 8.80(1 H, d, J = 2.0 Hz), 8.77<br>(1 H, d, J = 2.0 Hz), 8.49(1 H, s), 8.29(1 H, d, J = 9.2 Hz), 8.10(1<br>H, d, J = 2.0 Hz), 7.79(1 H, d, J = 9.2 Hz), 4.02(3H, s), 3.06-<br>2.96(1 H, m), 1.30(6H, d, J = 7.3 Hz).<br>MSm/z(M + H): 414. |

Example 0635

0635-1

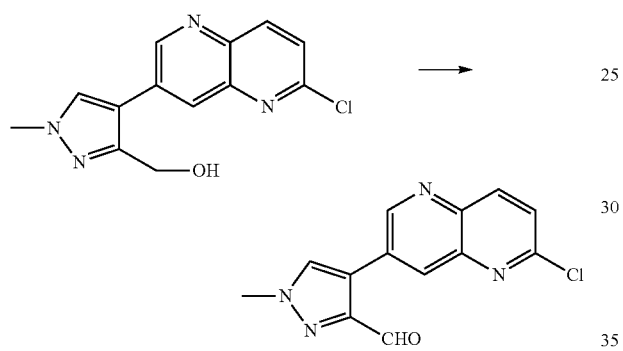

A mixture of (4-(6-chloro-1,5-naphthyridin-3-yl)-1-methyl-1H-pyrazol-3-yl)methanol (16 mg), ethyl acetate (5 mL), and manganese dioxide (16 mg) was stirred for 4.5 hours under reflux. Manganese dioxide (16 mg) was added to the reaction mixture, followed by stirring for 10.5 hours under reflux. The reaction mixture was cooled to room temperature, the insolubles were filtered off, and the solvent was distilled off under reduced pressure, thereby obtaining 4-(6-chloro-1,5-naphthyridin-3-yl)-1-methyl-1H-pyrazole-3-carbaldehyde (17 mg).

MSm/z(M+H):273.

0635-2 and 0635-3

The following compounds were obtained in the same manner as in Examples 0626-3 and 0646-3.

| Example No. | | |
|---|---|---|
| 0635 | | |
| 0635-2 | 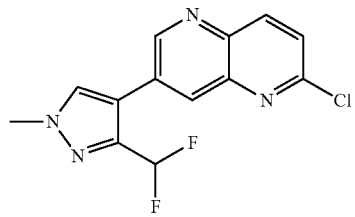 [SMILES: Cn1cc(-c2cnc3ccc(Cl)nc3c2)c(C(F)F)n1] | MSm/z(M + H): 295. |
| 0635-3 | 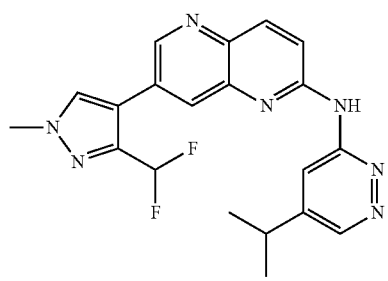 [SMILES: CC(C)c1cnnc(Nc2ccc3ncc(-c4cn(C)nc4C(F)F)cc3n2)c1] | ¹H-NMR(DMSO-d₆)δ:<br>10.79(1 H, s), 8.91(1 H, d, J = 2.0 Hz), 8.86(1 H, d, J = 2.0 Hz), 8.78<br>(1 H, d, J = 2.0 Hz), 8.49(1 H, s), 8.27(1 H, d, J = 9.2 Hz), 8.22(1<br>H, d, J = 2.0 Hz), 7.76(1 H, d, J = 9.2 Hz), 7.19(1 H, t, J = 53.5 Hz),<br>3.98(3H, s), 3.05-2.96(1 H, m), 1.31(6H, d, J = 6.6 Hz).<br>MSm/z(M + H): 396. |

Example 0636

0636-1

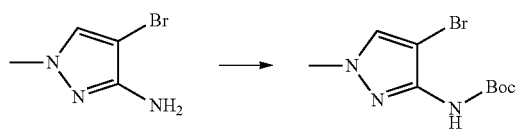

A mixture of 4-bromo-1-methyl-1H-pyrazole-3-amine (150 mg), di-tert-butyl dicarbonate (664 μL), N,N-dimethylpyridine-4-amine (11 mg), and tetrahydrofuran (5 mL) was stirred for 2.5 hours under reflux. The reaction mixture was cooled to room temperature, followed by allowing to stand overnight, and the reaction mixture was stirred for 1.5 hours under reflux. The reaction mixture was cooled to room temperature, ethyl acetate and water were added thereto, and the solvent was distilled off under reduced pressure. Ethanol (5 mL) and a 20% sodium hydroxide aqueous solution (2 mL) were added to the obtained residue, followed by stirring at room temperature for 8 hours. After water and ethyl acetate were added to the reaction mixture, the organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate), thereby obtaining tert-butyl (4-bromo-1-methyl-1H-pyrazol-3-yl)carbamate (198 mg).

$^1$H-NMR(DMSO-d$_6$)δ:8.70(1H,s),7.84(1H,s),3.75(3H,s),1.41(9H,s).

0636-2

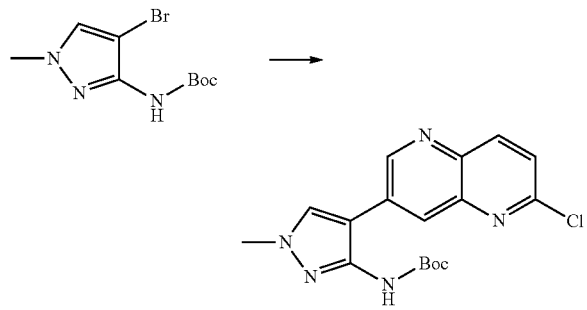

tert-Butyl (4-(6-chloro-1,5-naphthyridin-3-yl)-1-methyl-1H-pyrazol-3-yl)carbamate was obtained in the same manner as in Example 0421-1.
MSm/z(M+H):360.

0636-3

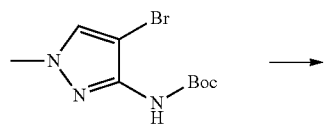

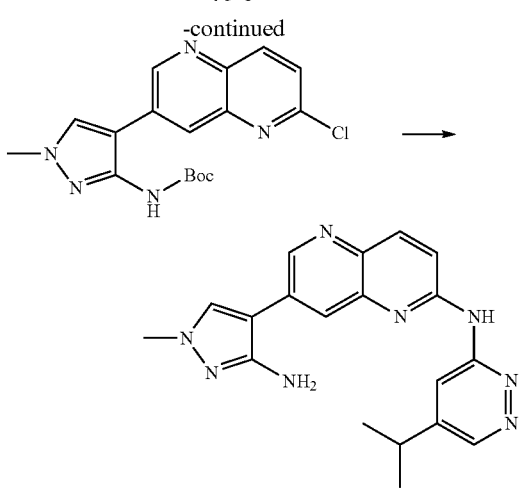

A solid matter was obtained in the same manner as in Example 0421-1.

A mixture of the obtained solid matter, 1,4-dioxane (1 mL), and 2 mol/L hydrochloric acid (0.5 mL) was stirred at 80° C. for 3 hours. The reaction mixture was cooled to room temperature, a saturated sodium hydrogen carbonate aqueous solution was added thereto, and the solvent was distilled off under reduced pressure. The obtained residue was purified by preparative thin layer silica gel column chromatography (chloroform-methanol, NH silica), thereby obtaining 7-(3-amino-1-methyl-1H-pyrazol-4-yl)-N-(5-isopropylpyridazin-3-yl)-1,5-naphthyridine-2-amine (0.6 mg) as a pale yellow solid.

$^1$H-NMR(DMSO-d$_6$)δ:10.66(1H,s),8.92(1H,d,J=2.0 Hz), 8.85(1H,d,J=2.0 Hz),8.77(1H,d,J=2.0 Hz),8.19(1H,d,J=9.2 Hz),8.16(1H,d,J=2.0 Hz),8.05(1H,s),7.66(1H,d,J=9.2 Hz), 4.97(2H,s),3.69(3H,s),3.05-2.97(1H,m),1.32(6H,d,J=6.6 Hz).

MSm/z(M+H):361.

Example 0637

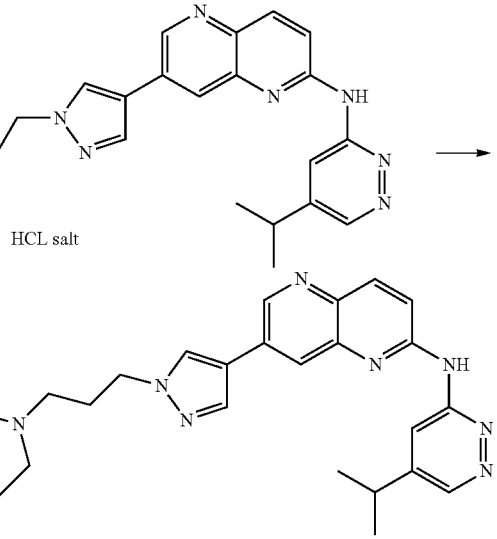

7-(1-(3-(6-Oxa-3-azabicyclo[3.1.1]heptan-3-yl)propyl)-1H-pyrazol-4-yl)-N-(5-isopropylpyridazin-3-yl)-1,5-naphthyridine-2-amine was obtained as a pale yellow solid in the same manner as in Example 0426-2.

$^1$H-NMR(DMSO-d$_6$)δ:10.70(1H,s),9.04(1H,d,J=2.0 Hz), 8.87(1H,d,J=2.0 Hz),8.73(1H,d,J=2.0 Hz),8.51(1H,s),8.32-8.19(3H,m),7.70(1H,d,J=9.2 Hz),4.43(2H,d,J=5.9 Hz),4.25 (2H,t,J=6.6 Hz),3.07-2.99(3H,m),2.88-2.81(1H,m),2.58-2.51(4H,m),2.26(1H,d,J=7.9 Hz),2.10-2.00(2H,m),1.33(6H, d,J=7.3 Hz).

MSm/z(M+H):471.

Example 0638

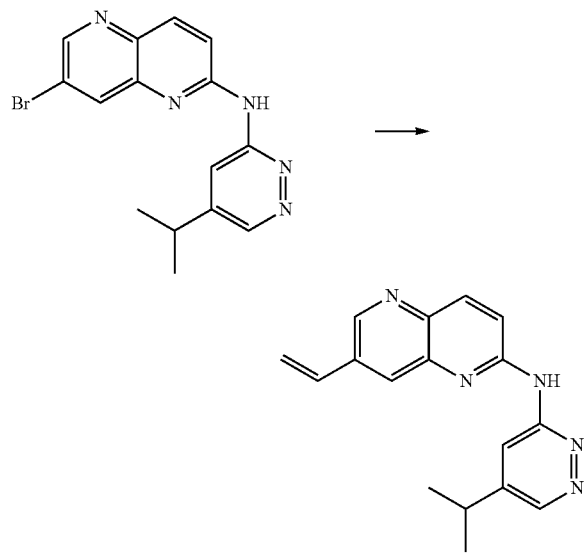

A mixture of 7-bromo-N-(5-isopropylpyridazin-3-yl)-1,5-naphthyridine-2-amine (15 mg), 4,4,5,5-tetramethyl-2-vinyl-1,3,2-dioxaborolane (8 μL), sodium carbonate (11 mg), bis(di-tert-butyl(4-dimethylaminophenyl)phosphine)dichloropalladium(II) (1 mg), 1,4-dioxane (2 mL), and water (0.2 mL) was stirred at 100° C. for 6 hours in a nitrogen atmosphere. The reaction mixture was cooled to room temperature, and the solvent was distilled off under reduced pressure. The obtained residue was purified by silica gel column chromatography (hexane-ethyl acetate-methanol), thereby obtaining N-(5-isopropylpyridazin-3-yl)-7-vinyl-1, 5-naphthyridine-2-amine (9 mg) as a pale yellow solid.

$^1$H-NMR(DMSO-d$_6$)δ:10.74(1H,s),8.94(1H,d,J=2.0 Hz), 8.86(1H,d,J=2.0 Hz),8.74(1H,d,J=2.0 Hz),8.24(1H,d,J=9.2 Hz),8.13(1H,s),7.73(1H,d,J=9.2 Hz),6.99(1H,dd,J=17.8, 11.2 Hz),6.21(1H,d,J=17.8 Hz),5.54(1H,d,J=11.2 Hz),3.08-2.97(1H,m),1.32(6H,d,J=6.6 Hz).

MSm/z(M+H):292.

Example 0639

0639-1

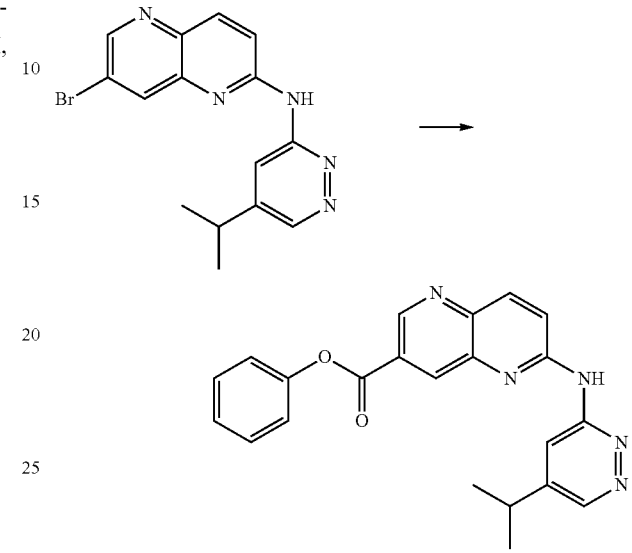

A mixture of 7-bromo-N-(5-isopropylpyridazin-3-yl)-1,5-naphthyridine-2-amine (200 mg), phenyl formate (126 μL), palladium acetate (4 mg), tri-tert-butylphosphonium tetrafluoroborate (20 mg), triethylamine (169 μL), and N,N-dimethylformamide (6 mL) was stirred at 150° C. for 30 minutes using a microwave reaction apparatus. The reaction mixture was cooled to room temperature, water was added thereto, and the solid matter was collected by filtration. The obtained solid matter was suspended by the addition of ethanol, and the solvent was distilled off under reduced pressure, thereby obtaining phenyl 6-((5-isopropylpyridazin-3-yl)amino)-1,5-naphthyridine-3-carboxylate (118 mg).

MSm/z(M+H):386.

0639-2

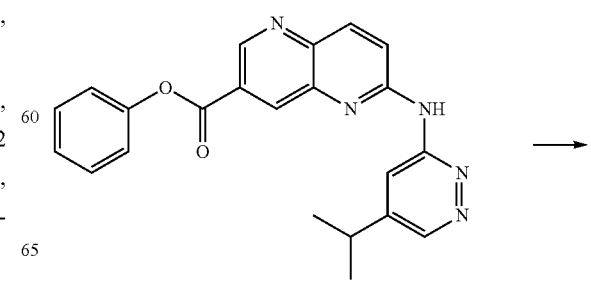

-continued

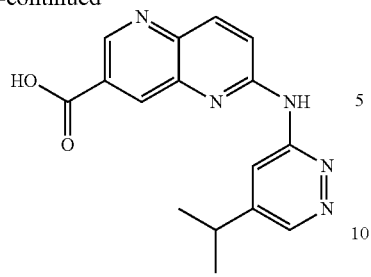

A mixture of phenyl 6-((5-isopropylpyridazin-3-yl)amino)-1,5-naphthyridine-3-carboxylate (116 mg), methanol (3 mL), and a 2 mol/L sodium hydroxide aqueous solution (1 mL) was stirred at room temperature for 17 hours. 2 mol/hydrochloric acid was added to the reaction mixture, and the solvent was distilled off under reduced pressure. The obtained residue was purified by silica gel column chromatography (hexane-ethyl acetate-methanol), thereby obtaining 6-((5-isopropylpyridazin-3-yl)amino)-1,5-naphthyridine-3-carboxylic acid (91 mg) as a pale yellow solid.

$^1$H-NMR(DMSO-d$_6$)δ:10.68(1H,s),9.14(1H,d,J=2.0 Hz),8.84(1H,d,J=2.0 Hz),8.80(1H,d,J=2.0 Hz),8.35(1H,s),8.22(1H,d,J=9.2 Hz),7.73(1H,d,J=9.2 Hz),3.08-2.98(1H,m),1.32(6H,d,J=6.6 Hz).
MSm/z(M+H):310.

Example 0640

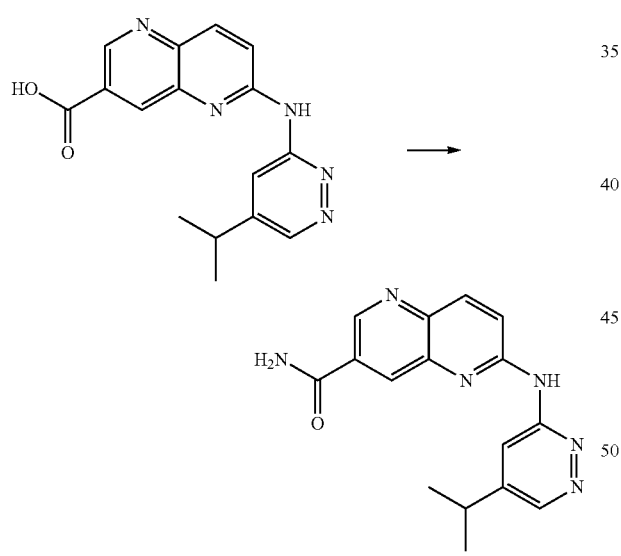

A mixture of 6-((5-isopropylpyridazin-3-yl)amino)-1,5-naphthyridine-3-carboxylic acid (40 mg), ammonium chloride (3 mg), 1-ethyl-3-(3-dimethylaminopropyl)carbodiimide hydrochloride (7 mg), 1-hydroxybenzotriazole (5 mg), N,N-diisopropylethylamine (16 μL), and N,N-dimethylformamide (1 mL) was stirred at room temperature for 17.5 hours. The solvent was distilled off under reduced pressure, and the obtained residue was purified by preparative thin layer silica gel column chromatography (chloroform-methanol, NH silica), thereby obtaining 6-((5-isopropylpyridazin-3-yl)amino)-1,5-naphthyridine-3-carboxamide (5 mg) as a pale yellow solid.

$^1$H-NMR(DMSO-d$_6$)δ:10.85(1H,s),9.13(1H,d,J=2.0 Hz),8.88(1H,d,J=2.0 Hz),8.77(1H,d,J=2.0 Hz),8.54(1H,d,J=2.0 Hz),8.42(1H,s),8.31(1H,d,J=9.2 Hz),7.83(1H,d,J=9.2 Hz),7.77(1H,s),3.08-3.00(1H,m),1.33(6H,d,J=6.6 Hz).
MSm/z(M+H):309.

Example 0641

0641-1

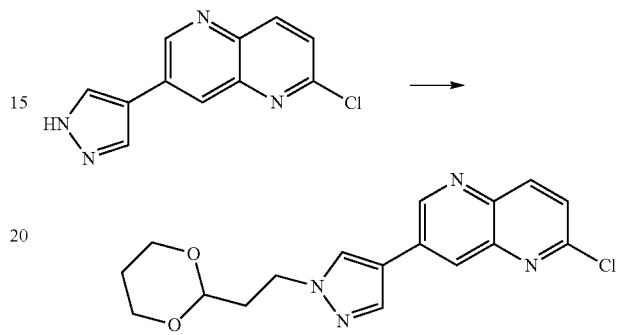

A mixture of 2-chloro-7-(1H-pyrazol-4-yl)-1,5-naphthyridine (500 mg), 2-(2-bromoethyl)-1,3-dioxane (439 μL), potassium carbonate (900 mg), and N,N-dimethylformamide (4 mL) was stirred at 80° C. for 8.5 hours. The reaction mixture was cooled to room temperature, water was added thereto, and the solid matter was collected by filtration. Ethyl acetate and hexane were added to the obtained solid matter, and the solid matter was collected by filtration, thereby obtaining 7-(1-(2-(1,3-dioxan-2-yl)ethyl)-1H-pyrazol-4-yl)-2-chloro-1,5-naphthyridine (572 mg).
MSm/z(M+H):345.

0641-2

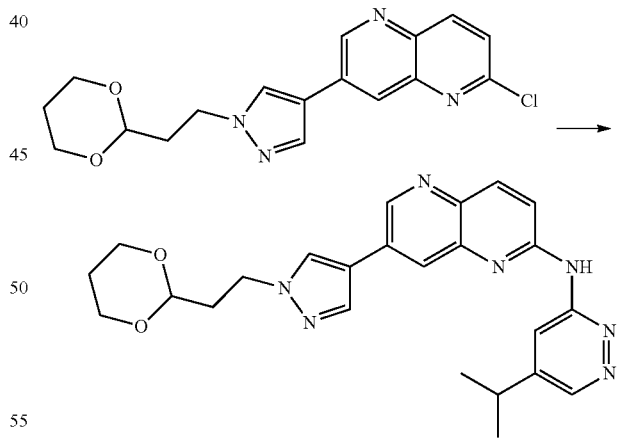

7-(1-(2-(1,3-Dioxan-2-yl)ethyl)-1H-pyrazol-4-yl)-N-(5-isopropylpyridazin-3-yl)-1,5-naphthyridine-2-amine was obtained as a pale yellow solid in the same manner as in Example 0015-4.

$^1$H-NMR(DMSO-d$_6$)δ:10.70(1H,s),9.04(1H,d,J=2.0 Hz),8.87(1H,d,J=2.0 Hz),8.73(1H,d,J=2.0 Hz),8.52(1H,s),8.23-8.19(3H,m),7.70(1H,d,J=9.2 Hz),4.58(1H,t,J=5.3 Hz),4.23(2H,t,J=7.3 Hz),4.03(2H,dd,J=10.6,4.6 Hz),3.75-3.66(2H,m),3.08-2.98(1H,m),2.12-2.03(2H,m),1.95-1.80(2H,m),1.33(6H,d,J=7.3 Hz).
MSm/z(M+H):446.

Examples 0642 and 0643

The following compounds were obtained in the same manner as in Example 0640.

| Example No. | Structure | Data |
|---|---|---|
| 0642 | | $^1$H-NMR(DMSO-$d_6$)δ: 10.85(1 H, s), 9.10(1 H, d, J = 2.0 Hz), 8.90-8.84(2H, m), 8.76(1 H, d, J = 2.0 Hz), 8.49(1 H, d, J = 2.0 Hz), 8.31(1 H, d, J = 8.2 Hz), 7.83(1 H, d, J = 9.2 Hz), 3.08-2.98(1 H, m), 2.87(3H, d, J = 4.0 Hz), 1.33(6H, d, J = 6.6 Hz). MSm/z(M + H): 323. |
| 0644 | | $^1$H-NMR(DMSO-$d_6$)δ: 10.84(1 H, s), 8.87(1 H, d, J = 2.0 Hz), 8.76(1 H, d, J = 2.0 Hz), 8.73 (1 H, d, J = 2.0 Hz), 8.29(1 H, d, J = 9.2 Hz), 8.16(1 H, d, J = 2.0 Hz), 7.62(1 H, d, J = 9.2 Hz), 3.07(3H, s), 3.07-2.99(1 H, m), 2.99(3H, s), 1.31(6H, d, J = 7.2 Hz). MSm/z(M + H): 337. |

Examples 0644 and 0645

The following compounds were obtained in the same manner as in Example 0426-2.

| Example No. | Structure | Data |
|---|---|---|
| 0644 | | $^1$H-NMR(DMSO-$d_6$)δ: 10.70(1 H, s), 9.04(1 H, d, J = 2.0 Hz), 8.87(1 H, d, J = 2.0 Hz), 8.73 (1 H, d, J = 2.0 Hz), 8.51(1 H, s), 8.23-8.19(3H, m), 7.70(1 H, d, J = 8.6 Hz), 4.21(2H, t, J = 6.9 Hz), 3.73(1 H, d, J = 9.2 Hz), 3.54-3.46(2H, m), 3.08-2.98(1 H, m), 2.75-2.64 (2H, m), 2.28(2H, t, J = 6.9 Hz), 2.05-1.90(3H, m), 1.64(1 H, t, J = 10.6 Hz), 1.33(6H, d, J = 6.6 Hz), 1.03(3H, d, J = 6.6 Hz). MSm/z(M + H): 473. |
| 0645 | | $^1$H-NMR(DMSO-$d_6$)δ: 10.70(1 H, s), 9.04(1 H, d, J = 2.0 Hz), 8.87(1 H, d, J = 2.0 Hz), 8.73 (1 H, d, J = 2.0 Hz), 8.51(1 H, s), 8.23-8.19(3H, m), 7.70(1 H, d, J = 9.2 Hz), 4.21(2H, t, J = 6.9 Hz), 3.73(1 H, d, J = 11.2 Hz), 3.54-3.45(2H, m), 3.08-3.00(1 H, m), 2.75-2.64 (2H, m), 2.28(2H, t, J = 6.9 Hz), 2.05-1.90(3H, m), 1.67-1.57(1H, m), 1.33(6H, d, J = 6.6 Hz), 1.03(3H, d, J = 6.6 Hz), MSm/z(M + H): 473. |

Example 0646

0646-1

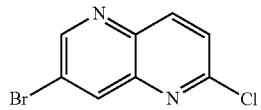

A mixture of 7-bromo-2-chloro-1,5-naphthyridine (5.0 g), 1-tert-butoxycarbonyl-4-(4,4,5,5-tetramethyl-1,3,2-dioxaborolan-2-yl)pyrazole (6.04 g), sodium carbonate (4.4 g), bis(di-tert-butyl(4-dimethylaminophenyl)phosphine)dichloropalladium(II) (366 mg), 1,4-dioxane (24 mL), and water (2.4 mL) was stirred at 110° C. for 5 hours in a nitrogen atmosphere. The reaction mixture was cooled to room temperature, water was added thereto, and the solid matter was collected by filtration. The obtained solid matter was suspended by the addition of ethyl acetate, and the solid matter was collected by filtration, thereby obtaining 2-chloro-7-(1H-pyrazol-4-yl)-1,5-naphthyridine (2.6 g) as a pale brown solid.

MSm/z(M+H):231.

0646-2

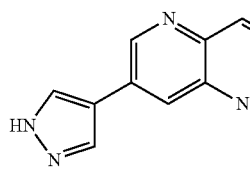
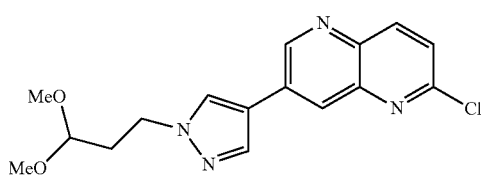

A mixture of 2-chloro-7-(1H-pyrazol-4-yl)-1,5-naphthyridine (2.5 g), potassium carbonate (3.0 g), 3-bromo-1,1-dimethoxypropane (2.2 mL), and N,N-dimethylformamide (10.8 mL) was stirred at 80° C. for 2 hours. The reaction mixture was cooled to room temperature, water was added thereto, and the solid matter was collected by filtration, thereby obtaining 2-chloro-7-(1-(3,3-dimethoxypropyl)-1H-pyrazol-4-yl)-1,5-naphthyridine (3.17 g) as a pale brown solid.

MSm/z(M+H):333.

0646-3

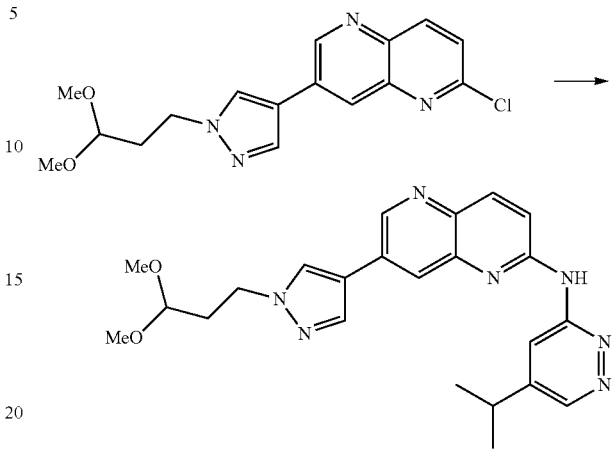

A mixture of 2-chloro-7-(1-(3,3-dimethoxypropyl)-1H-pyrazol-4-yl)-1,5-naphthyridine (3.1 g), 5-isopropylpyridazine-3-amine (1.4 g), [(2-di-cyclohexylphosphino-3,6-dimethoxy-2',4',6'-triisopropyl-1,1'-biphenyl)-2-(2'-amino-1,1'-biphenyl)]palladium(II)methanesulfonate (BRETTPHOS-PD-G3 (product name, manufactured by Sigma-Aldrich Co. LLC.)) (422 mg), cesium carbonate (7.6 g), and 1,4-dioxane (93 mL) was stirred at 110° C. for 4 hours in a nitrogen atmosphere. The reaction mixture was cooled to room temperature, and the solvent was distilled off under reduced pressure. The obtained residue was purified by silica gel column chromatography (methanol-chloroform, NH silica), thereby obtaining 7-(1-(3,3-dimethoxypropyl)-1H-pyrazol-4-yl)-N-(5-isopropylpyridazin-3-yl)-1,5-naphthyridine-2-amine (1.66 g) as a pale yellow solid.

$^1$H-NMR(CDCl$_3$)δ:9.77(1H,s),8.94(2H,dd,J=10.2,1.7 Hz),8.84(1H,d,J=2.0 Hz),8.25(1H,d,J=9.2 Hz),8.10(1H,d,J=1.3 Hz),7.98(1H,s),7.85(1H,s),7.74(1H,d,J=9.2 Hz),4.38(1H,t,J=5.6 Hz),4.30(2H,t,J=6.9 Hz),3.37(6H,s),3.13-3.03(1H,m),2.26(2H,q,J=6.6 Hz),1.43(6H,d,J=6.6 Hz).

MSm/z(M+H):434.

Example 0647

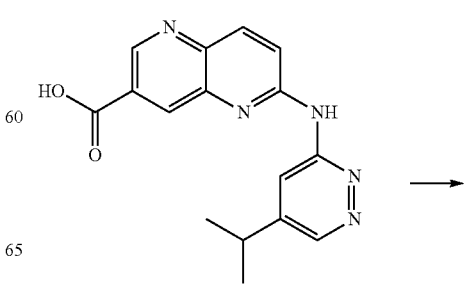

799

-continued

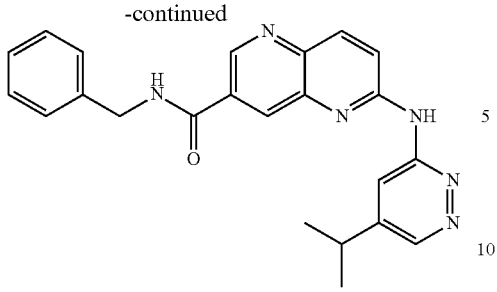

800

-continued

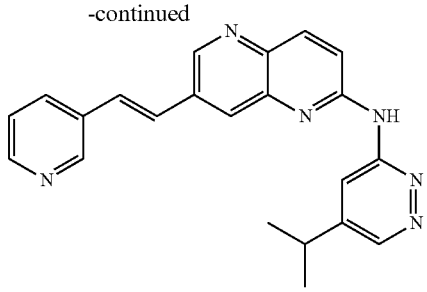

A mixture of 6-((5-isopropylpyridazin-3-yl)amino)-1,5-naphthyridine-3-carboxylic acid (15 mg), benzylamine (9 μL), 1-ethyl-3-(3-dimethylaminopropyl)carboimide hydrochloride (30 mg), N,N-diisopropylethylamine (34 μL), and N,N-dimethylformamide (1 mL) was stirred at room temperature for 2 hours. The solvent was distilled off under reduced pressure, and the obtained residue was purified by preparative thin layer silica gel column chromatography (chloroform-methanol, NH silica), thereby obtaining N-benzyl-6-((5-isopropylpyridazin-3-yl)amino)-1,5-naphthyridine-3-carboxamide (3 mg) as a white solid.

$^1$H-NMR(DMSO-d$_6$)δ:10.86(1H,s),9.48(1H,dd,J=6.0,6.0 Hz),9.16(1H,d,J=2.0 Hz),8.89(1H,d,J=2.0 Hz),8.75(1H,d,J=2.0 Hz),8.56(1H,d,J=2.0 Hz),8.32(1H,d,J=9.2 Hz),7.84 (1H,d,J=9.2 Hz),7.40-7.33(3H,m),7.28(1H,d,J=6.0 Hz),4.57 (2H,d,J=6.0 Hz),3.07-2.98(1H,m),1.32(6H,d,J=7.3 Hz).

MSm/z(M+H):399.

Example 0648

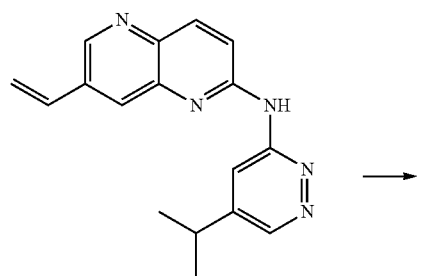

→

A mixture of N-(5-isopropylpyridazin-3-yl)-7-vinyl-1,5-naphthyridine-2-amine (15 mg), 3-bromopyridine (10 μL), palladium acetate (1 mg), tri(o-tolyl)phosphine (1 mg), triethylamine (14 μL), and N,N-dimethylformamide (1 mL) was stirred at 150° C. for 1 hour using a microwave reaction apparatus. The reaction mixture was cooled to room temperature, water was added thereto, and the solid matter was collected by filtration, thereby obtaining (E)-N-(5-isopropylpyridazin-3-yl)-7-(2-(pyridin-3-yl)vinyl)-1,5-naphthyridine-2-amine (11 mg) as a pale yellow solid.

$^1$H-NMR(DMSO-d$_6$)δ:10.76(1H,s),9.10(1H,d,J=2.0 Hz), 8.87(2H,d,J=2.0 Hz),8.76(1H,d,J=2.0 Hz),8.53-8.50(1H,m), 8.27-8.23(2H,m),8.16-8.11(1H,m),7.74(1H,d,J=9.2 Hz), 7.67(2H,s),7.49-7.45(1H,m),3.06-3.00(1H,m),1.34(6H,d, J=7.3 Hz).

MSm/z(M+H):369.

Examples 0649 to 0651

The following compounds were obtained in the same manner as in Example 0426-2.

| Example No. | | |
|---|---|---|
| 0649 | 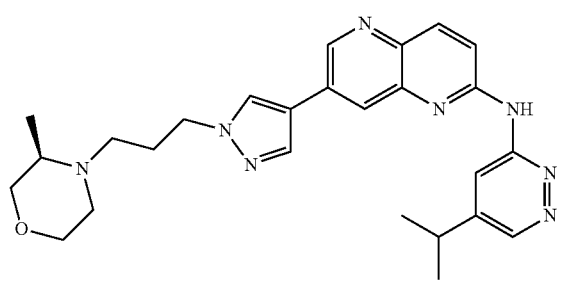 [SMILES: CC(C)c1cnnc(Nc2ccc3ncc(-c4cnn(CCCN5CCOC[C@H]5C)c4)cc3n2)c1] | $^1$H-NMR(DMSO-d$_6$)δ: 10.70(1 H, s), 9.04(1 H, d, J = 2.0 Hz), 6.87(1 H, d, J = 2.0 Hz), 8.73 (1 H, d, J = 2.0 Hz), 8.52(1 H, s), 8.32-8.19(3H, m), 7.69(1 H, d, J = 9.2 Hz), 4.20(2H, t, J = 6.6 Hz), 3.71-3.65 (1 H, m), 3.60-3.45(2H, m), 3.17-2.99(2H, m), 2.74-2.63 (2H, m), 2.33-2.26(1 H, m), 2.19-2.10(2H, m), 2.03-1.96 (2H, m), 1.34(6H, d, J = 6.6 Hz), 0.85(3H, d, J = 5.9 Hz). MSm/z(M + H): 473. |

| Example No. | | |
|---|---|---|
| 0650 | 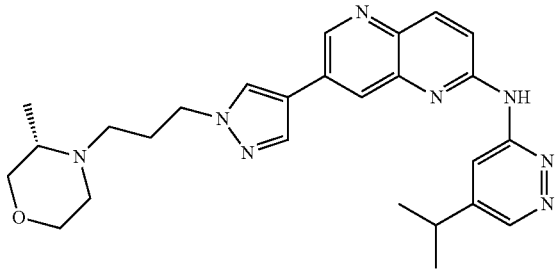 [SMILES: CC(C)c1cnnc(Nc2ccc3ncc(-c4cnn(CCCN5CCOC[C@@H]5C)c4)cc3n2)c1] | ¹H-NMR(DMSO-d₆)δ:<br>10.70(1 H, s), 9.04(1 H, d, J = 2.0 Hz), 8.87(1 H, d, J = 2.0 Hz), 8.73<br>(1 H, d, J = 2.0 Hz), 8.52(1 H, s), 8.32-8.18(3H, m),<br>7.69(1 H, d, J = 9.2 Hz), 4.20(2H, t, J = 6.6 Hz), 3.70-3.46<br>(3H, m), 3.18-3.00(2H, m), 2.75-2.63(2H, m), 2.32-2.26<br>(1 H, m), 2.19-2.10(2H, m), 2.04-1.96(2H, m),<br>1.33(6H, d, J = 7.3 Hz), 0.85(3H, d, J = 6.6 Hz).<br>MSm/z(M + H): 473. |
| 0651 |  | ¹H-NMR(DMSO-d₆)δ:<br>10.70(1 H, s), 9.05(1 H, d, J = 2.0 Hz), 8.87(1 H, d, J = 2.0 Hz), 8.73<br>(1 H, d, J = 2.0 Hz), 8.52(1 H, s), 8.31-8.17(3H, m),<br>7.70(1 H, d, J = 9.2 Hz), 4.27(2H, t, J = 6.9 Hz), 3.56-3.38<br>(5H, m), 3.08-2.99(2H, m), 2.22(2H, t, J = 6.9 Hz), 2.01-1.92<br>(2H, m), 1.82-1.74(2H, m), 1.72-1.65(2H, m),<br>1.33(6H, d, J = 6.6 Hz).<br>MSm/z(M + H): 485. |

Example 0652

Example 0653

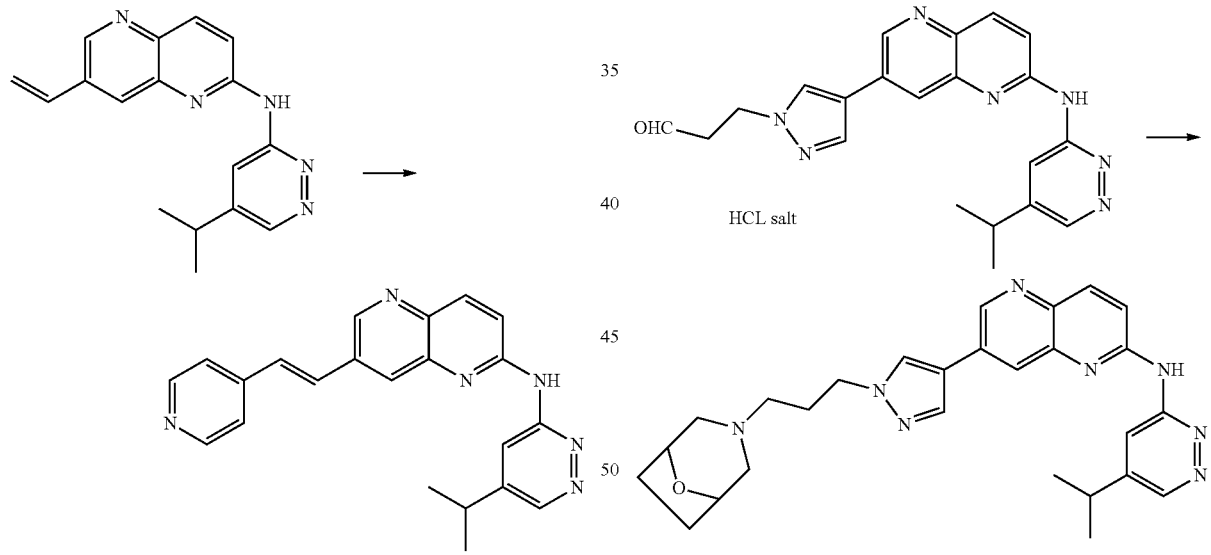

(E)-N-(5-isopropylpyridazin-3-yl)-7-(2-(pyridin-4-yl)vinyl)-1,5-naphthyridine-2-amine was obtained as a pale yellow solid in the same manner as in Example 0648.

¹H-NMR(DMSO-d₆)δ:10.78(1H,s),9.12(1H,d,J=2.0 Hz), 8.88(1H,d,J=2.0 Hz),8.76(1H,d,J=2.0 Hz),8.61(2H,d,J=5.9 Hz),8.30(1H,d,J=2.0 Hz),8.26(1H,d,J=9.2 Hz),7.78-7.73 (2H,m),7.68-7.60(3H,m),3.10-3.00(1H,m),1.34(6H,d,J=6.6 Hz).

MSm/z(M+H):369.

7-(1-(3-(8-Oxa-3-azabicyclo[3.2.1]octan-3-yl)propyl)-1H-pyrazol-4-yl)-N-(5-isopropylpyridazin-3-yl)-1,5-naphthyridine-2-amine was obtained as a pale yellow solid in the same manner as in Example 0426-2.

¹H-NMR(DMSO-d₆)δ:10.70(1H,s),9.04(1H,d,J=2.0 Hz), 8.87(1H,d,J=2.0 Hz),8.73(1H,d,J=2.0 Hz),8.48(1H,s),8.23-8.18(3H,m),7.70(1H,d,J=8.6 Hz),4.25-4.18(4H,m),3.08-3.00(1H,m),2.58-2.53(2H,m),2.23(2H,t,J=6.6 Hz),2.11(2H, d,J=9.2 Hz),1.96(2H,t,J=6.6 Hz),1.90-1.85(2H,m),1.75-1.69 (2H,m),1.34(6H,d,J=7.2 Hz).

MSm/z(M+H):485.

Example 0654

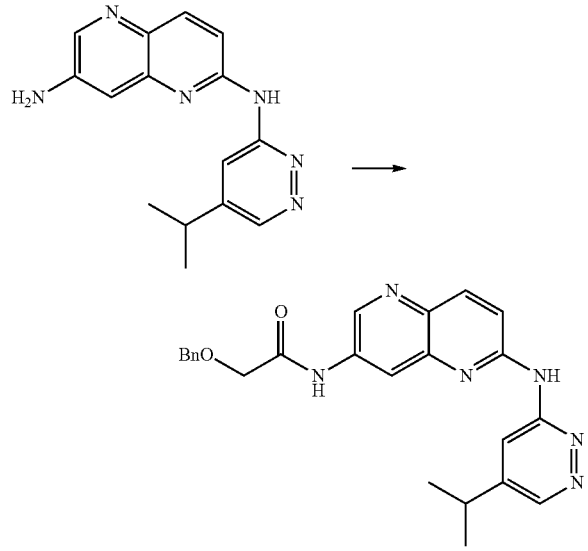

N²-(5-isopropylpyridazin-3-yl)-1,5-naphthyridine-2,7-diamine (20 mg) was added to a mixture of 2-(benzyloxy) acetic acid (49 μL), dichloromethane (5 mL), oxalyl chloride (33 μL), and N,N-dimethylformamide (1 drop), followed by stirring at room temperature for 1.5 hours, and stirring at 60° C. for 2 hours. The reaction mixture was cooled to room temperature, and purified by silica gel column chromatography (hexane-ethyl acetate-methanol), thereby obtaining 2-(benzyloxy)-N-(6-((5-isopropylpyridazin-3-yl)amino)-1, 5-naphthyridin-3-yl)acetamide (6 mg) as a pale yellow solid.

$^1$H-NMR(DMSO-d$_6$)δ:10.71(1H,s),10.38(1H,s),8.94(1H, d,J=2.0 Hz),8.85(1H,d,J=2.0 Hz),8.73(1H,d,J=2.0 Hz),8.50 (1H,d,J=2.0 Hz),8.19(1H,d,J=9.2 Hz),7.67(1H,d,J=9.2 Hz), 7.46-7.31(5H,m),4.67(2H,s),4.20(2H,s),3.05-2.95(1H,m), 1.31(6H,d,J=6.6 Hz).

MSm/z(M+H):429.

Example 0655

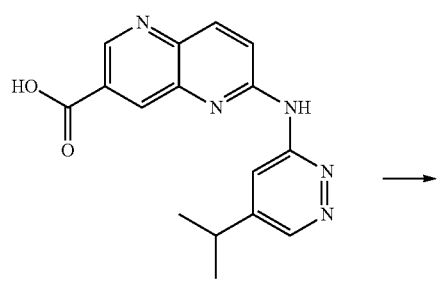

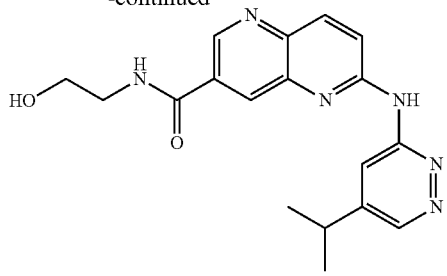

N-(2-hydroxyethyl)-6-((5-isopropylpyridazin-3-yl) amino)-1,5-naphthyridine-3-carboxamide was obtained as a pale yellow solid in the same manner as in Example 0647.

$^1$H-NMR(DMSO-d$_6$)δ:10.85(1H,s),9.12(1H,d,J=2.0 Hz), 8.94-8.87(2H,m),8.75(1H,d,J=2.0 Hz),8.52(1H,d,J=2.0 Hz), 8.31(1H,d,J=8.9 Hz),7.83(1H,d,J=8.9 Hz),4.80(1H,t,J=5.6 Hz),3.61-3.54(2H,m),3.44-3.38(2H,m),3.06-3.00(1H,m), 1.33(6H,d,J=6.6 Hz).

MSm/z(M+H):353.

Example 0656

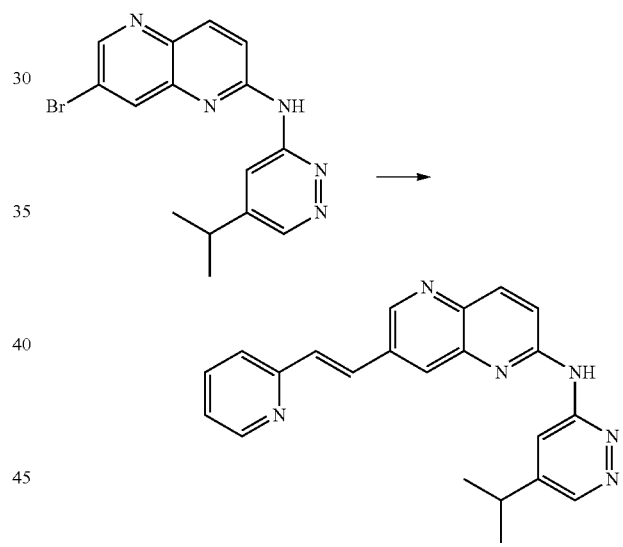

A mixture of 7-bromo-N-(5-isopropylpyridazin-3-yl)-1,5-naphthyridine-2-amine (20 mg), 2-vinylpyridine (13 μL), palladium acetate (1 mg), tri(o-tolyl)phosphine (5 mg), triethylamine (17 μL), and N,N-dimethylformamide (1 mL) was stirred at 150° C. for 1 hour using a microwave reaction apparatus. The reaction mixture was cooled to room temperature, water was added thereto, and the solid matter was collected by filtration. The obtained solid matter was purified by silica gel column chromatography (hexane-ethyl acetate-methanol), thereby obtaining (E)-N-(5-isopropylpyridazin-3-yl)-7-(2-(pyridin-2-yl)vinyl)-1,5-naphthyridine-2-amine (11 mg) as a pale yellow solid.

$^1$H-NMR(DMSO-d$_6$)δ:10.76(1H,s),9.13(1H,d,J=2.0 Hz), 8.87(1H,d,J=2.0 Hz),8.77(1H,d,J=2.0 Hz),8.63(1H,d,J=4.6 Hz),8.34(1H,d,J=2.0 Hz),8.26(1H,d,J=8.6 Hz),7.96-7.90 (1H,m),7.89-7.81(1H,m),7.77-7.62(3H,m),7.33(1H,dd, J=7.3,4.6 Hz),3.09-3.00(1H,m),1.34(6H,d,J=6.6 Hz).

MSm/z(M+H):369.

Examples 0657 to 0661

The following compounds were obtained in the same manner as in Example 0426-2.

| Example No. | | |
|---|---|---|
| 0657 | 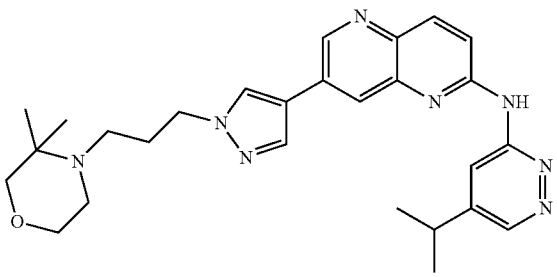 [SMILES: CC(C)c1cnnc(Nc2ccc3ncc(-c4cnn(CCCN5CCOCC5(C)C)c4)cc3n2)c1] | $^1$H-NMR(CDCl$_3$)δ:<br>9.18(1 H, s), 8.93(1 H, d, J = 2.0 Hz), 8.87(1 H, s), 8.81(1 H, s), 8.24(1 H, d, J = 8.9 Hz), 8.10(1 H, d, J = 2.0 Hz), 7.97(1 H, s), 7.88(1 H, s), 7.58(1 H, d, J = 8.9 Hz), 4.29(2H, t, J = 6.9 Hz), 3.78(2H, brs), 3.35(2H, brs), 3.11-3.01(1 H, m), 2.62-2.40(2H, m), 2.10(2H, brs), 1.42(6H, d, J = 6.6 Hz), 1.25(2H, s), 1.00(6H, s).<br>MSm/z(M + H): 487. |
| 0658 | 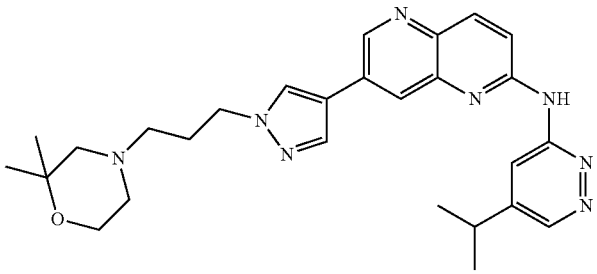 [SMILES: CC(C)c1cnnc(Nc2ccc3ncc(-c4cnn(CCCN5CCOC(C)(C)C5)c4)cc3n2)c1] | $^1$H-NMR(DMSO-d$_6$)δ:<br>10.70(1 H, s), 9.04(1 H, d, J = 2.0 Hz), 8.87(1 H, d, J = 2.0 Hz), 8.73(1 H, d, J = 2.0 Hz), 8.49(1 H, s), 8.32-8.18(3H, m), 7.70(1 H, d, J = 9.2 Hz), 4.23(2H, t, J = 6.9 Hz), 3.61(2H, t, J = 5.0 Hz), 3.08-2.99(1 H, m), 2.28-2.21 (4H, m), 2.13(2H, s), 2.05-1.95(2H, m), 1.33(6H, d, J = 6.6 Hz), 1.17(6H, s).<br>MSm/z(M + H): 488. |
| 0659 | 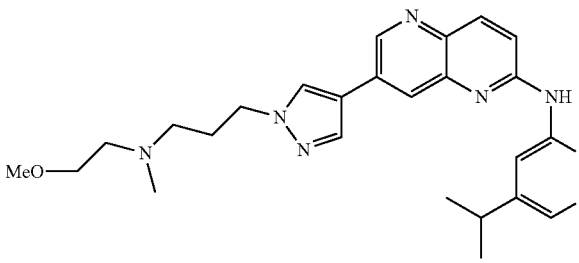 | $^1$H-NMR(DMSO-d$_6$)δ:<br>10.70(1 H, s), 9.04(1 H, d, J = 2.0 Hz), 8.87(1 H, d, J = 2.0 Hz), 8.73(1 H, d, J = 2.0 Hz), 8.50(1 H, s), 8.24-8.18(3H, m), 7.70(1 H, d, J = 9.2 Hz), 4.20(2H, t, J = 6.9 Hz), 3.40(2H, t, J = 5.9 Hz), 3.23(3H, s), 3.08-3.00(1 H, m), 2.50-2.46(2H, m), 2.33(2H, t, J = 6.9 Hz), 2.19(3H, s), 2.01-1.93(2H, m), 1.33(6H, d, J = 6.6 Hz).<br>MSm/z(M + H): 461. |
| 0660 | 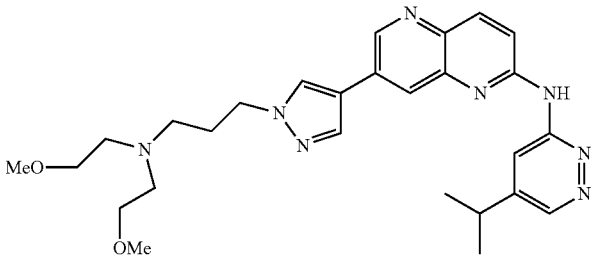 [SMILES: COCCN(CCCn1cc(-c2cnc3ccc(Nc4cc(C(C)C)cnn4)nc3c2)cn1)CCOC] | $^1$H-NMR(DMSO-d$_6$)δ:<br>10.70(1 H, s), 9.05(1 H, d, J = 2.0 Hz), 8.87(1 H, d, J = 2.0 Hz), 8.73(1 H, d, J = 2.0 Hz), 8.50(1 H, s), 8.23-8.18(3H, m), 7.69 (1 H, d, J = 9.2 Hz), 4.20(2H, t, J = 6.9 Hz), 3.38-3.30(6H, m), 3.21(6H, s), 3.08-2.98(1 H, m), 2.61 (4H, t, J = 5.9 Hz), 1.99-1.92(2H, m), 1.33(6H, d, J = 6.6 Hz).<br>MSm/z(M + H): 505. |
| 0661 | 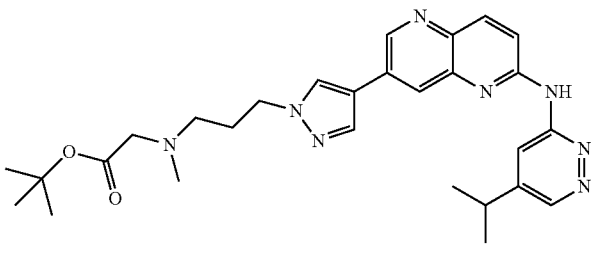 [SMILES: CC(C)c1cnnc(Nc2ccc3ncc(-c4cnn(CCCN(C)CC(=O)OC(C)(C)C)c4)cc3n2)c1] | $^1$H-NMR(DMSO-d$_6$)δ:<br>10.70(1 H, s), 9.04(1 H, d, J = 2.0 Hz), 8.87(1 H, d, J = 2.0 Hz), 8.73(1 H, d, J = 2.0 Hz), 8.51(1 H, s), 8.24-8.18(3H, m), 7.69 (1 H, d, J = 9.2 Hz), 4.20(2H, t, J = 6.9 Hz), 3.15(2H, s), 3.08-2.99(1 H, m), 2.47-2.43(2H, m), 2.28(3H, s), 2.01-1.92 (2H, m), 1.39(9H, s), 1.33(6H, d, J = 6.6 Hz).<br>MSm/z(M + H): 517. |

Example 0662

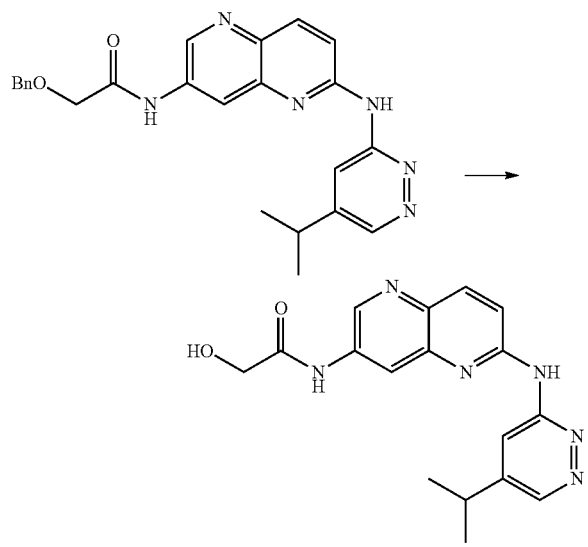

A mixture of 2-(benzyloxy)-N-(6-((5-isopropylpyridazin-3-yl)amino)-1,5-naphthyridin-3-yl)acetamide (35 mg), 10% palladium-carbon (11 mg), ammonium formate (20 mg), and methanol (5 mL) was stirred for 9 hours under reflux. The reaction mixture was cooled to room temperature, the insolubles were filtered off, and the solvent was distilled off under reduced pressure. The obtained residue was purified by silica gel column chromatography (hexane-ethyl acetate-methanol, NH silica), thereby obtaining 2-hydroxy-N-(6-((5-isopropylpyridazin-3-yl)amino)-1,5-naphthyridin-3-yl)acetamide (3 mg) as a pale yellow solid.

$^1$H-NMR(DMSO-$d_6$)δ:10.70(1H,s),10.28(1H,s),9.02(1H,d,J=2.0 Hz),8.84(1H,d,J=2.0 Hz),8.73(1H,d,J=2.0 Hz),8.57(1H,d,J=2.0 Hz),8.18(1H,d,J=9.2 Hz),7.66(1H,d,J=9.2 Hz),5.82(1H,t,J=4.6 Hz),4.10(2H,d,J=4.6 Hz),3.04-2.94(1H,m),1.31(6H,d,J=7.3 Hz).
MSm/z(M+H):339.

Examples 0663 and 0664

The following compounds were obtained in the same manner as in Example 0647.

| Example No. | | |
|---|---|---|
| 0663 | 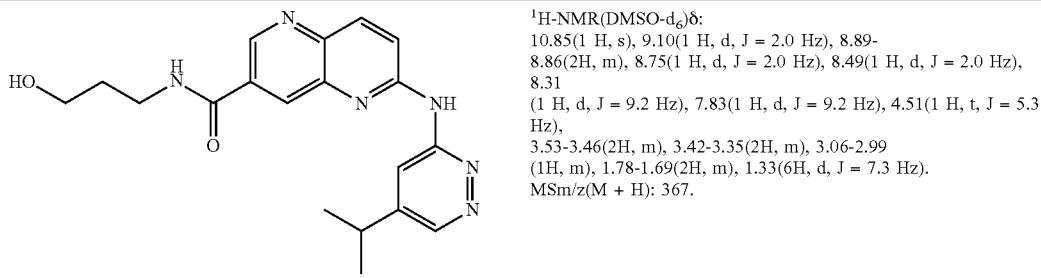 | $^1$H-NMR(DMSO-$d_6$)δ:<br>10.85(1 H, s), 9.10(1 H, d, J = 2.0 Hz), 8.89-8.86(2H, m), 8.75(1 H, d, J = 2.0 Hz), 8.49(1 H, d, J = 2.0 Hz), 8.31 (1 H, d, J = 9.2 Hz), 7.83(1 H, d, J = 9.2 Hz), 4.51(1 H, t, J = 5.3 Hz),<br>3.53-3.46(2H, m), 3.42-3.35(2H, m), 3.06-2.99 (1H, m), 1.78-1.69(2H, m), 1.33(6H, d, J = 7.3 Hz).<br>MSm/z(M + H): 367. |
| 0664 | 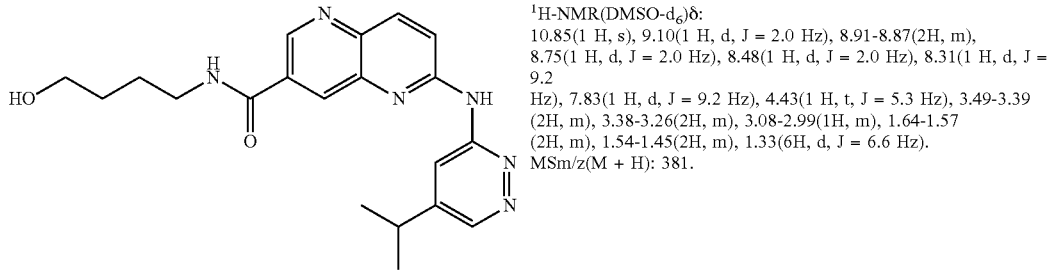 | $^1$H-NMR(DMSO-$d_6$)δ:<br>10.85(1 H, s), 9.10(1 H, d, J = 2.0 Hz), 8.91-8.87(2H, m),<br>8.75(1 H, d, J = 2.0 Hz), 8.48(1 H, d, J = 2.0 Hz), 8.31(1 H, d, J = 9.2 Hz), 7.83(1 H, d, J = 9.2 Hz), 4.43(1 H, t, J = 5.3 Hz), 3.49-3.39 (2H, m), 3.38-3.26(2H, m), 3.08-2.99(1H, m), 1.64-1.57 (2H, m), 1.54-1.45(2H, m), 1.33(6H, d, J = 6.6 Hz).<br>MSm/z(M + H): 381. |

Examples 0665 and 0666

The following compounds were obtained in the same manner as in Example 0426-2.

| Example No. | | |
|---|---|---|
| 0665 | 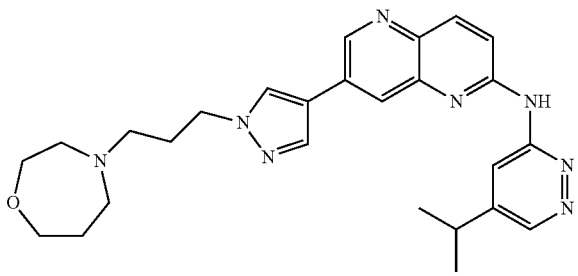 [SMILES: CC(C)c1cnnc(Nc2ccc3ncc(-c4cnn(CCCN5CCCOCC5)c4)cc3n2)c1] | ¹H-NMR(DMSO-d₆)δ:<br>10.70(1 H, s), 9.04(1 H, d, J = 2.0 Hz), 8.87(1 H, d, J = 2.0 Hz),<br>8.73(1 H, d, J = 2.0 Hz), 8.50(1 H, s), 8.24-8.18(3H, m),<br>7.70(1 H, d, J = 9.2 Hz), 4.22(2H, t, J = 6.9 Hz), 3.67(2H, t, J =<br>5.9 Hz), 3.63-3.59(2H, m), 3.08-2.99(1 H, m), 2.65-2.58<br>(4H, m), 2.45(2H, t, J = 6.9 Hz), 2.03-1.94(2H, m), 1.84-<br>1.76(2H, m), 1.33(6H, d, J = 7.3 Hz).<br>MSm/z(M + H): 473. |
| 0666 | 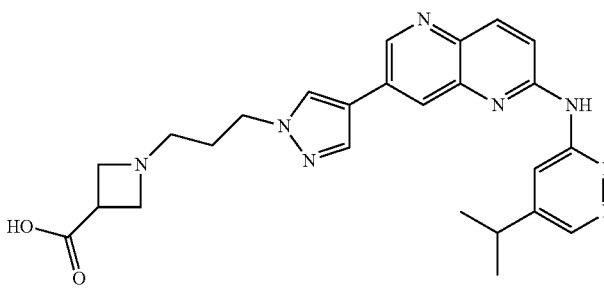 | ¹H-NMR(DMSO-d₆)δ:<br>10.70(1 H, s), 9.04(1 H, d, J = 2.0 Hz), 8.86(1 H, d, J = 2.0 Hz),<br>8.73(1 H, d, J = 2.0 Hz), 8.50(1 H, s), 8.23-8.17(3H, m),<br>7.70 (1 H, d, J = 9.2 Hz), 4.17(2H, t, J = 7.3 Hz), 3.81-3.78<br>(1H, m), 3.05-3.01(2H, m), 2.98-2.88(1 H, m), 2.35-2.28<br>(2H, m), 1.84-1.78(2H, m), 1.33(6H, d, J = 6.6 Hz),<br>0.83(2H, t, J = 7.3 Hz).<br>MSm/z(M + H): 473. |

Example 0667

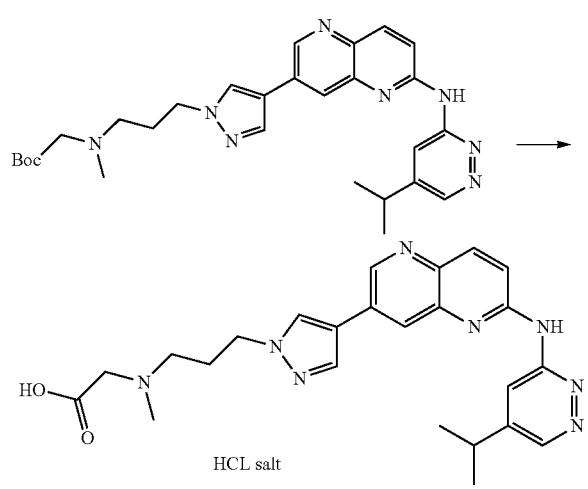

A mixture of tert-butyl 2-((3-(4-(6-((5-isopropylpyridazin-3-yl)amino)-1,5-naphthyridin-3-yl)-1H-pyrazol-1-yl)propyl) (methyl)amino)acetate (15 mg), 1,4-dioxane (2 mL), and 2 mol/L hydrochloric acid (0.5 mL) was stirred at 80° C. for 1.5 hours. The reaction mixture was cooled to room temperature, and the solvent was distilled off under reduced pressure, thereby obtaining hydrochloride (12 mg) of 2-((3-(4-(6-((5-isopropylpyridazin-3-yl)amino)-1,5-naphthyridin-3-yl)-1H-pyrazol-1-yl)propyl) (methyl)amino) acetic acid as a yellow solid.

¹H-NMR(DMSO-d₆)δ:9.95(1H,brs),9.15(1H,d,J=2.0 Hz),9.00(1H,d,J=2.0 Hz),8.56(2H,s),8.49-8.46(1H,m),8.36 (1H,d,J=8.9 Hz),8.26(1H,s),7.72(1H,d,J=8.9 Hz),4.30(2H,t, J=6.6 Hz),4.14(2H,s),3.24-3.15(2H,m),3.15-3.08(1H,m), 2.85(3H,s),2.29-2.25(2H,m),1.34(6H,d,J=6.6 Hz).

MSm/z(M+H):461.

Examples 0668 and 0669

The following compounds were obtained in the same manner as in Example 0647.

| Example No. | | |
|---|---|---|
| 0668 | 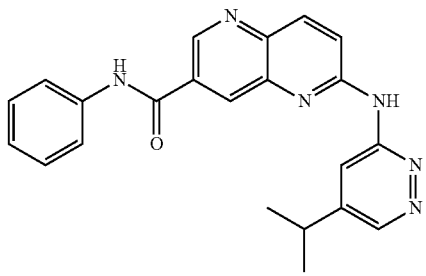 [SMILES: CC(C)c1cnnc(Nc2ccc3ncc(C(=O)Nc4ccccc4)cc3n2)c1] | ¹H-NMR(DMSO-d₆)δ:<br>10.89(1 H, s), 10.68(1 H, s), 9.18(1 H, d, J = 2.0 Hz), 8.90(1 H, d, J = 2.0 Hz), 8.78(1 H, d, J = 2.0 Hz), 8.64(1 H, d, J = 2.0 Hz),<br>8.35<br>(1 H, d, J = 9.2 Hz), 7.88-7.81(3H, m), 7.40<br>(2H, dd, J = 7.6, 7.6 Hz), 7.15(1 H, dd, J = 7.6, 7.6 Hz), 3.10-<br>3.00(1 H, m), 1.33(6H, d, J = 7.3 Hz).<br>MSm/z(M + H): 385. |

-continued

| Example No. | | |
|---|---|---|
| 0669 | 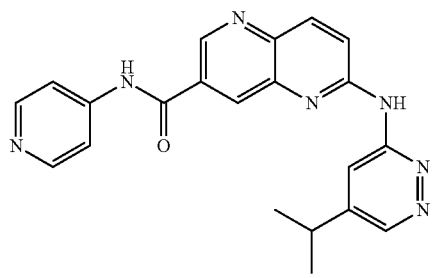 [SMILES: CC(C)c1cnnc(Nc2ccc3ncc(C(=O)Nc4ccncc4)cc3n2)c1] | ¹H-NMR(DMSO-d₆)δ: 11.02(1 H, s), 10.91(1 H, s), 9.18(1 H, d, J = 2.0 Hz), 8.90(1 H, d, J = 2.0 Hz), 8.77(1 H, d, J = 2.0 Hz), 8.67(1 H, d, J = 2.0 Hz), 6.54 (1 H, d, J = 1.3 Hz), 8.52(1 H, d, J = 1.3 Hz), 8.36(1 H, d, J = 9.2 Hz), 7.88(1 H, d, J = 9.2 Hz), 7.84-7.81(2H, m), 3.09-3.00(1 H, m), 1.33(6H, d, J = 7.3 Hz). MSm/z(M + H): 386. |

Examples 0670 and 0671

The following compounds were obtained in the same manner as in Example 0640.

| Example No. | | |
|---|---|---|
| 0670 | 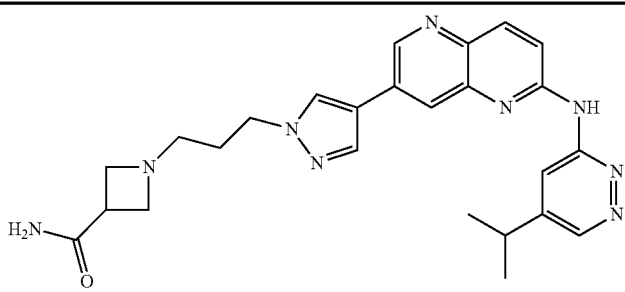 | ¹H-NMR(DMSO-d₆)δ: 10.70(1 H, s), 9.04(1 H, d, J = 2.0 Hz), 8.87(1 H, d, J = 2.0 Hz), 8.73(1 H, d, J = 2.0 Hz), 8.50(1 H, s), 8.24-8.17(3H, m), 7.70 (1 H, d, J = 9.2 Hz), 7.28(1 H, s), 6.84(1 H, s), 4.17(2H, t, J = 6.9 Hz), 3.38-3.25(1 H, m), 3.10-2.95(5H, m), 2.33 (2H, t, J = 7.3 Hz), 1.87-1.79(2H, m), 1.33(6H, d, J = 6.6 Hz). MSm/z(M + H): 472. |
| 0671 | 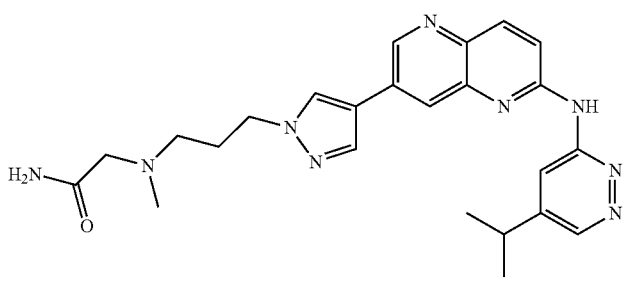 [SMILES: CC(C)c1cnnc(Nc2ccc3ncc(-c4cnn(CCCN(C)CC(N)=O)c4)cc3n2)c1] | ¹H-NMR(DMSO-d₆)δ: 10.70(1 H, s), 9.04(1 H, d, J = 2.0 Hz), 8.87(1 H, d, J = 2.0 Hz), 8.73(1 H, d, J = 2.0 Hz), 8.53(1 H, s), 8.23-8.18(3H, m), 7.70 (1 H, d, J = 9.2 Hz), 7.22(1 H, s), 7.13(1 H, s), 4.25(2H, t, J = 6.9 Hz), 3.08-2.99(1 H, m), 2.86(2H, s), 2.37(2H, t, J = 6.6 Hz), 2.21(3H, s), 2.03-1.96(2H, m), 1.33(6H, d, J = 7.3 Hz). MSm/z(M + H): 460. |

Examples 0672 to 0674

The following compounds were obtained in the same manner as in Example 0426-2.

| Example No. | | |
|---|---|---|
| 0672 | 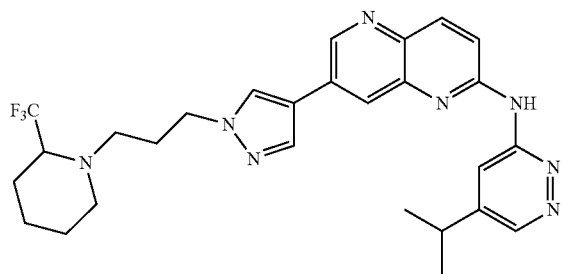 [SMILES: CC(C)c1cnnc(Nc2ccc3ncc(-c4cnn(CCCN5CCCCC5C(F)(F)F)c4)cc3n2)c1] | ¹H-NMR(DMSO-d₆)δ:<br>10.70(1 H, s), 9.04(1 H, d, J = 2.0 Hz), 8.87(1 H, d, J = 2.0 Hz), 8.74<br>(1 H, d, J = 2.0 Hz), 8.50(1 H, s), 8.24-8.18(3H, m), 7.69<br>(1 H, d, J = 9.2 Hz), 4.20(2H, t, J = 6.9 Hz), 3.08-2.96(1 H, m),<br>2.78-2.59(5H, m), 2.02-1.96(2H, m), 1.80-1.65(2H, m),<br>1.51(4H, brs), 1.33(6H, d, J = 7.3 Hz).<br>MSm/z(M + H): 525. |
| 0673 | 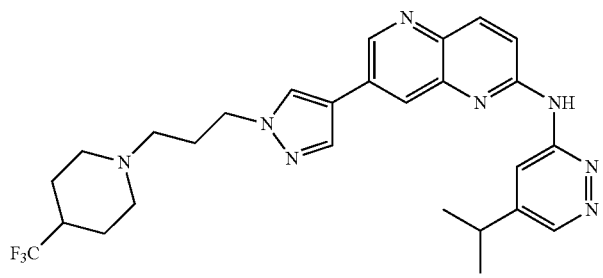 [SMILES: CC(C)c1cnnc(Nc2ccc3ncc(-c4cnn(CCCN5CCC(C(F)(F)F)CC5)c4)cc3n2)c1] | ¹H-NMR(DMSO-d₆)δ:<br>10.70(1 H, s), 9.04(1 H, d, J = 2.0 Hz), 8.87(1 H, d, J = 2.0 Hz), 8.73<br>(1 H, d, J = 2.0 Hz), 8.50(1 H, s), 8.23-8.18(3H, m), 7.69<br>(1 H, d, J = 9.2 Hz), 4.20(2H, t, J = 6.9 Hz), 3.08-2.98(1 H, m),<br>2.95-2.88(2H, m), 2.32-2.22(3H, m), 1.99(2H, t, J = 6.6 Hz),<br>1.89(2H, t, J = 10.9 Hz), 1.79-1.73(2H, m), 1.53-1.42<br>(2H, m), 1.33(6H, d, J = 6.6 Hz).<br>MSm/z(M + H): 525. |
| 0674 | 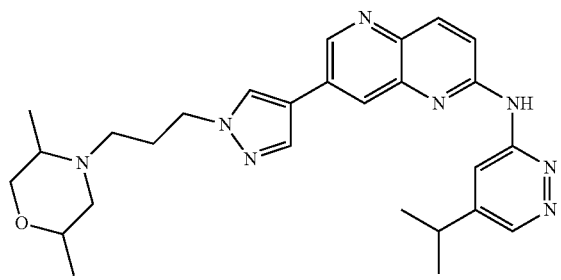 [SMILES: CC1CN(CCCn2cc(-c3cnc4ccc(Nc5cc(C(C)C)cnn5)nc4c3)cn2)C(C)CO1] | ¹H-NMR(DMSO-d₆)δ:<br>10.70(1 H, s), 9.04(1 H, d, J = 2.0 Hz), 8.87(1 H, d, J = 2.0 Hz), 8.73<br>(1 H, d, J = 2.0 Hz), 8.50(1 H, s), 8.23-8.18(3H, m), 7.69<br>(1 H, d, J = 9.2 Hz), 4.21(2H, t, J = 6.9 Hz), 3.64-3.40(4H, m),<br>3.07-2.99(1 H, m), 2.74-2.68(1 H, m), 2.43-2.31(2H, m),<br>2.20-2.12(1 H, m), 2.03-1.93(2H, m), 1.33(6H, d, J = 7.2 Hz),<br>1.06(3H, d, J = 6.62 Hz), 0.91(3H, d, J = 6.6 Hz).<br>MSm/z(M + H): 487. |

Example 0675

0675-1

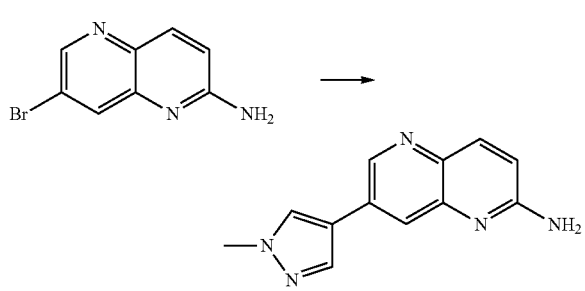 → 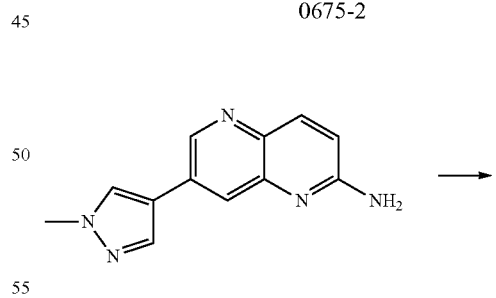

A mixture of 7-bromo-1,5-naphthyridine-2-amine (20 mg), 1-methyl-4-(4,4,5,5-tetramethyl-1,3,2-dioxaborolan-2-yl)-1H-pyrazole (154 mg), sodium carbonate (142 mg), bis(di-tert-butyl(4-dimethylaminophenyl)phosphine)dichloropalladium(II) (21 mg), 1,4-dioxane (5 mL), and water (1 mL) was stirred at 110° C. for 2 hours in a nitrogen atmosphere. The reaction mixture was cooled to room temperature, and the solvent was distilled off under reduced pressure. The obtained residue was purified by silica gel column chromatography (hexane-ethyl acetate-methanol, NH silica), thereby obtaining 7-(1-methyl-1H-pyrazol-4-yl)-1,5-naphthyridine-2-amine (150 mg).

MSm/z(M+H):226.

0675-2

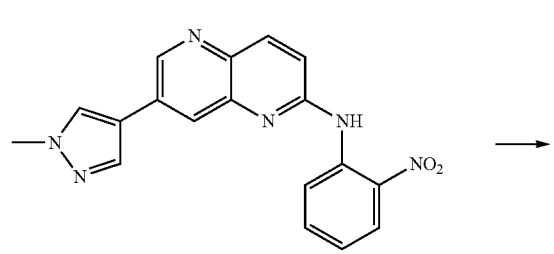 →

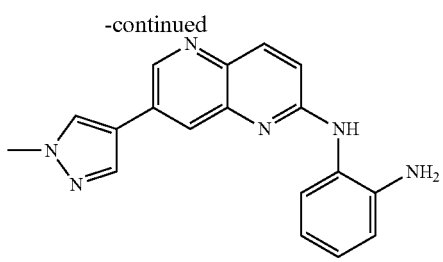

A mixture of 7-(1-methyl-1H-pyrazol-4-yl)-1,5-naphthyridine-2-amine (10 mg), 1-fluoro-2-nitrobenzene (8 µL), potassium carbonate (22 mg), and N,N-dimethylformamide (1 mL) was stirred at 90° C. for 3 hours, stirred at 110° C. for 3 hours, and stirred at 140° C. for 2 hours. The reaction mixture was cooled to room temperature, and the solvent was distilled off under reduced pressure. The obtained residue was purified by silica gel column chromatography (hexane-ethyl acetate-methanol), thereby obtaining a solid matter.

A mixture of the obtained solid matter, sodium formate (8 mg), 10% palladium-carbon (4 mg), and methanol (3 mL) was stirred at 80° C. for 1 hour. The reaction mixture was cooled to room temperature, the insolubles were filtered off, and the solvent was distilled off under reduced pressure. The obtained residue was purified by silica gel column chromatography (hexane-ethyl acetate-methanol, NH silica), thereby obtaining $N^1$-(7-(1-methyl-1H-pyrazol-4-yl)-1,5-naphthyridin-2-yl)benzene-1,2-diamine (3 mg) as a brown solid.

$^1$H-NMR(DMSO-d$_6$)δ:8.85(1H,d,J=2.0 Hz),8.57(1H,s),8.41(1H,s),8.10(1H,s),8.00-7.97(2H,m),7.49(1H,d,J=6.6 Hz),7.10(1H,d,J=9.2 Hz),6.97-6.90(1H,m),6.79(1H,dd,J=7.2,1.5 Hz),6.65-6.59(1H,m),4.93(2H,s),3.89(3H,s).

MSm/z(M+H):317.

Example 0676

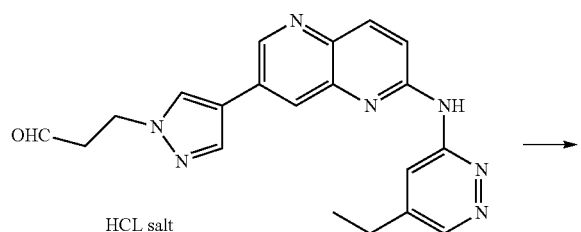

HCL salt

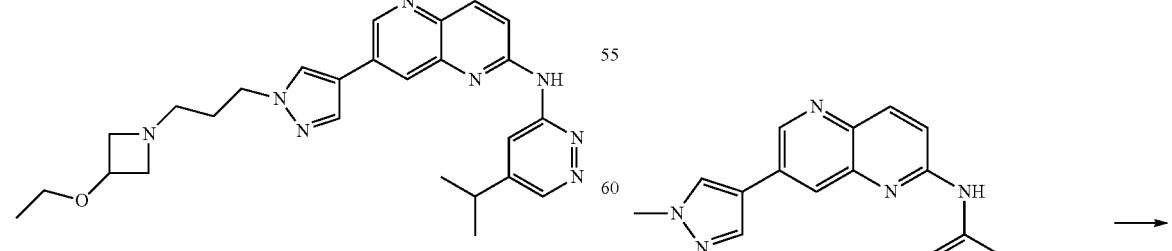

N-(5-isopropylpyridazin-3-yl)-7-(1-(3-(3-ethoxyazetidin-1-yl)propyl)-1H-pyrazol-4-yl)-1,5-naphthyridine-2-amine was obtained as a pale yellow solid in the same manner as in Example 0426-2.

$^1$H-NMR(DMSO-d$_6$)δ:10.70(1H,s),9.04(1H,d,J=2.0 Hz),8.87(1H,d,J=2.0 Hz),8.73(1H,d,J=2.0 Hz),8.50(1H,s),8.23-8.18(3H,m),7.70(1H,d,J=9.2 Hz),4.17(2H,t,J=6.9 Hz),4.06-3.98(1H,m),3.54-3.48(2H,m),3.35-3.27(2H,m),3.08-3.00(1H,m),2.75-2.70(2H,m),2.38(2H,t,J=6.6 Hz),1.87-1.80(2H,m),1.34(6H,d,J=7.9 Hz),1.08(3H,t,J=6.9 Hz).

MSm/z(M+H):473.

Example 0677

0677-1

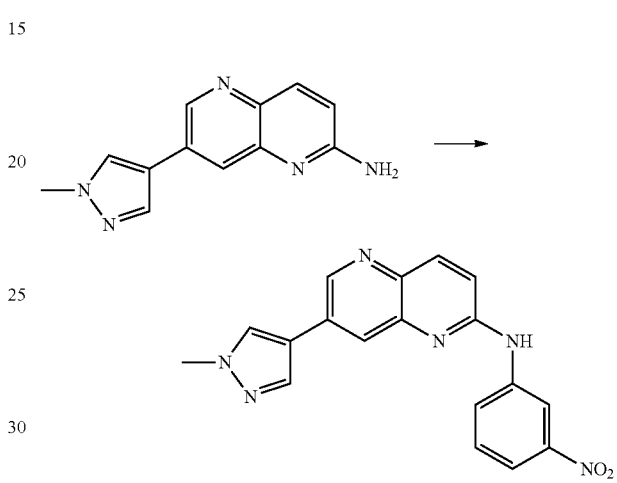

A mixture of 7-(1-methyl-1H-pyrazol-4-yl)-1,5-naphthyridine-2-amine (20 mg), 1-fluoro-3-nitrobenzene (20 mg), [(2-di-cyclohexylphosphino-3,6-dimethoxy-2',4',6'-triisopropyl-1,1'-biphenyl)-2-(2'-amino-1,1'-biphenyl)]palladium (II)methanesulfonate (BRETTPHOS-PD-G3 (product name, manufactured by Sigma-Aldrich Co. LLC.)) (5 mg), cesium carbonate (81 mg), and 1,4-dioxane (4 mL) was stirred at 110° C. for 3 hours in a nitrogen atmosphere. The reaction mixture was cooled to room temperature, and the solvent was distilled off under reduced pressure. The obtained residue was purified by silica gel column chromatography (hexane-ethyl acetate-methanol), thereby obtaining 7-(1-methyl-1H-pyrazol-4-yl)-N-(3-nitrophenyl)-1,5-naphthyridine-2-amine (27 mg).

MSm/z(M+H):347.

0677-2

-continued

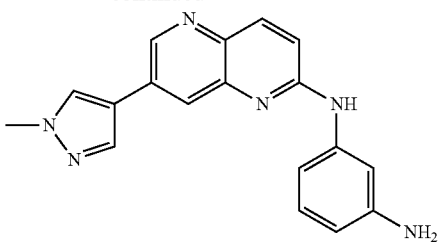

A mixture of 7-(1-methyl-1H-pyrazol-4-yl)-N-(3-nitrophenyl)-1,5-naphthyridine-2-amine (27 mg), 10% palladium-carbon (8 mg), ammonium formate (8 mg), and methanol (5 mL) was stirred for 3 hours under reflux. The reaction mixture was cooled to room temperature, the insolubles were filtered off, and the solvent was distilled off under reduced pressure, thereby obtaining $N^1$-(7-(1-methyl-1H-pyrazol-4-yl)-1,5-naphthyridin-2-yl)benzene-1,3-diamine (16 mg) as a yellow solid.

$^1$H-NMR(DMSO-d$_6$)δ:9.31(1H,s),8.88(1H,d,J=2.0 Hz), 8.42(1H,s),8.14-8.11(2H,m),8.00(1H,d,J=9.2 Hz),7.28(1H, d,J=2.0 Hz),7.20-7.14(2H,m),6.97(1H,dd,J=7.9,7.6 Hz), 6.23(1H,d,J=7.6 Hz),5.03(2H,s),3.91(3H,s).
MSm/z(M+H):317.

Examples 0678 to 0680

The following compounds were obtained in the same manner as in Example 0426-2.

| Example No. | | |
|---|---|---|
| 0678 | 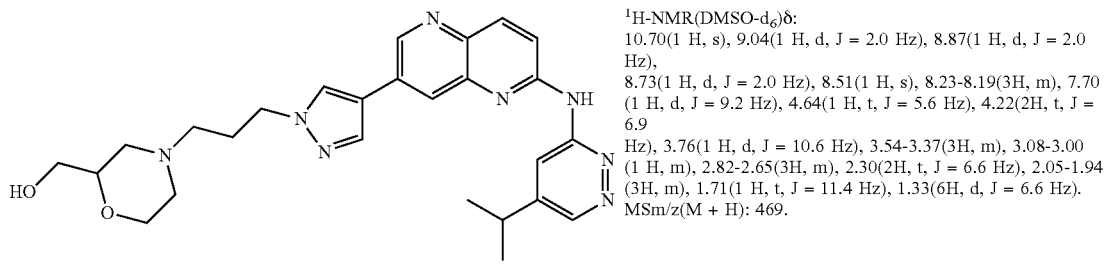 | $^1$H-NMR(DMSO-d$_6$)δ: 10.70(1 H, s), 9.04(1 H, d, J = 2.0 Hz), 8.87(1 H, d, J = 2.0 Hz), 8.73(1 H, d, J = 2.0 Hz), 8.51(1 H, s), 8.23-8.19(3H, m), 7.70 (1 H, d, J = 9.2 Hz), 4.64(1 H, t, J = 5.6 Hz), 4.22(2H, t, J = 6.9 Hz), 3.76(1 H, d, J = 10.6 Hz), 3.54-3.37(3H, m), 3.08-3.00 (1 H, m), 2.82-2.65(3H, m), 2.30(2H, t, J = 6.6 Hz), 2.05-1.94 (3H, m), 1.71(1 H, t, J = 11.4 Hz), 1.33(6H, d, J = 6.6 Hz). MSm/z(M + H): 469. |
| 0679 | 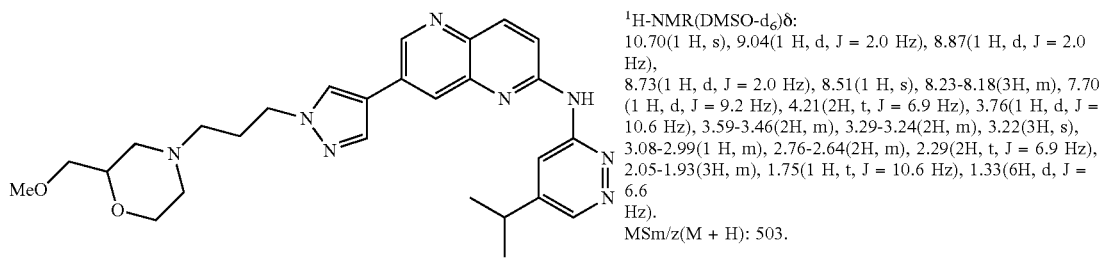 | $^1$H-NMR(DMSO-d$_6$)δ: 10.70(1 H, s), 9.04(1 H, d, J = 2.0 Hz), 8.87(1 H, d, J = 2.0 Hz), 8.73(1 H, d, J = 2.0 Hz), 8.51(1 H, s), 8.23-8.18(3H, m), 7.70 (1 H, d, J = 9.2 Hz), 4.21(2H, t, J = 6.9 Hz), 3.76(1 H, d, J = 10.6 Hz), 3.59-3.46(2H, m), 3.29-3.24(2H, m), 3.22(3H, s), 3.08-2.99(1 H, m), 2.76-2.64(2H, m), 2.29(2H, t, J = 6.9 Hz), 2.05-1.93(3H, m), 1.75(1 H, t, J = 10.6 Hz), 1.33(6H, d, J = 6.6 Hz). MSm/z(M + H): 503. |
| 0680 | 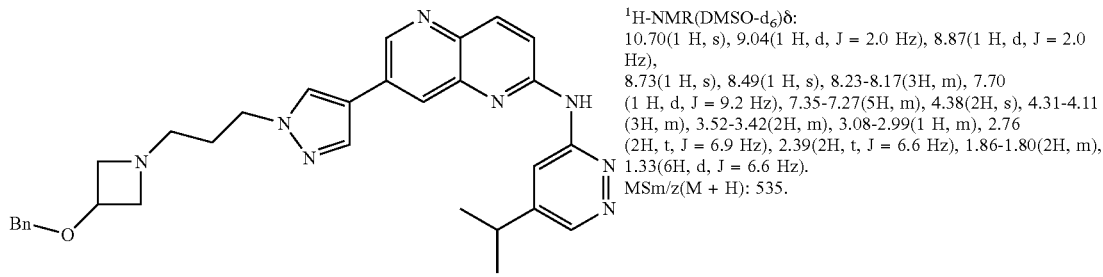 | $^1$H-NMR(DMSO-d$_6$)δ: 10.70(1 H, s), 9.04(1 H, d, J = 2.0 Hz), 8.87(1 H, d, J = 2.0 Hz), 8.73(1 H, s), 8.49(1 H, s), 8.23-8.17(3H, m), 7.70 (1 H, d, J = 9.2 Hz), 7.35-7.27(5H, m), 4.38(2H, s), 4.31-4.11 (3H, m), 3.52-3.42(2H, m), 3.08-2.99(1 H, m), 2.76 (2H, t, J = 6.9 Hz), 2.39(2H, t, J = 6.6 Hz), 1.86-1.80(2H, m), 1.33(6H, d, J = 6.6 Hz). MSm/z(M + H): 535. |

Example 0681

0681-1

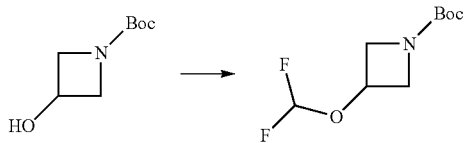 [SMILES: CC(C)(C)OC(=O)N1CC(O)C1 ; CC(C)(C)OC(=O)N1CC(OC(F)F)C1]

60% sodium hydride (42 mg) was added to a mixture of tert-butyl 3-hydroxyazetidine-1-carboxylate (150 mg), sodium 2-chloro-2,2-difluoroacetate (200 mg), and N,N-dimethylformamide (2 mL), followed by stirring at room temperature for 2 hours, stirring at 60° C. for 1 hour, and stirring at 80° C. for 4 hours. After the reaction mixture was cooled to room temperature, water and ethyl acetate were added thereto, the organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate-methanol), thereby obtaining tert-butyl 3-(difluoromethoxy)azetidine-1-carboxylate (24 mg).

$^1$H-NMR(DMSO-$d_6$)δ:5.20-5.17(1H,m),4.19-4.16(2H,m),3.80-3.76(2H,m),1.39(9H,s).

0681-2 and 0681-3

The following compounds were obtained in the same manner as in Examples 0667 and 0426-2.

| Example No. | | |
|---|---|---|
| 0681 | | |
| 0681-2 | 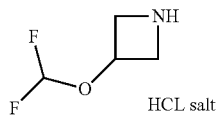 HCL salt | $^1$H-NMR(DMSO-$d_6$)δ: 5.02-5.00(1H, m), 4.52-4.49(2H, m), 4.27-4.23(2H, m). |
| 0681-3 | 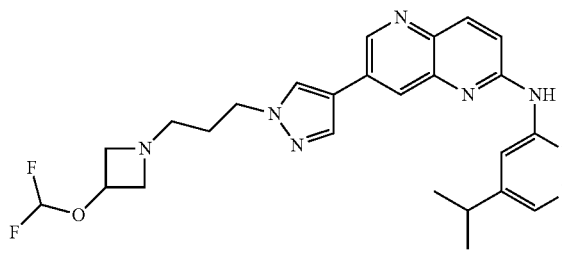 | $^1$H-NMR(DMSO-$d_6$)δ: 10.70(1 H, s), 9.04(1 H, d, J = 2.0 Hz), 8.87(1 H, d, J = 2.0 Hz), 8.73(1 H, d, J = 2.0 Hz), 8.50(1 H, s), 8.23-8.18(3H, m), 7.70(1 H, d, J = 9.2 Hz), 6.67(1 H, t, J = 75.3 Hz), 4.72-4.65(1 H, m), 4.18(2H, t, J = 6.9 Hz), 3.61-3.55(2H, m), 3.08-2.98(1 H, m), 2.97-2.91(2H, m), 2.42(2H, t, J = 6.9 Hz), 1.88-1.81(2H, m), 1.33(6H, d, J = 6.6 Hz). MSm/z(M + H): 495. |

Example 0682

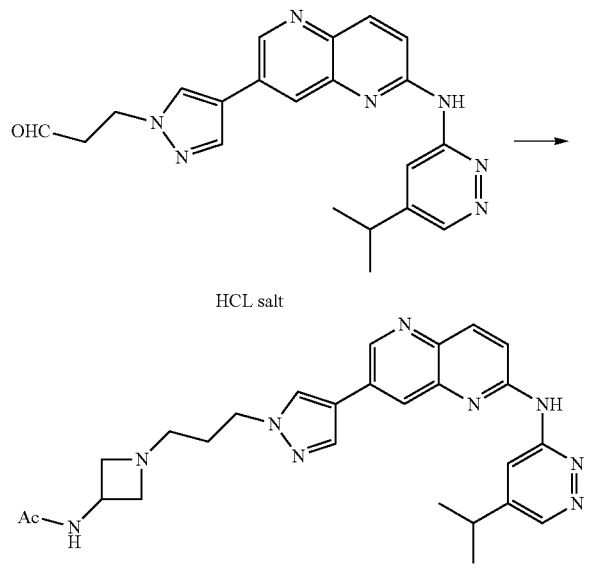

N-(1-(3-(4-(6-((5-isopropylpyridazin-3-yl)amino)-1,5-naphthyridin-3-yl)-1H-pyrazol-1-yl)propyl)azetidin-3-yl)acetamide was obtained as a pale yellow solid in the same manner as in Example 0426-2.

$^1$H-NMR(DMSO-d$_6$)δ:10.70(1H,s),9.04(1H,d,J=2.0 Hz), 8.87(1H,d,J=2.0 Hz),8.73(1H,brs),8.50(1H,s),8.27-8.17(3H, m),7.69(1H,d,J=9.2 Hz),4.28-4.16(3H,m),3.69-3.59(1H,m), 3.49(2H,t,J=7.3 Hz),3.08-2.99(1H,m),2.76-2.72(2H,m),2.36 (2H,t,J=6.9 Hz),1.86-1.81(2H,m),1.77(3H,s),1.33(6H,d, J=7.2 Hz).

MSm/z(M+H):486.

Example 0683

0683-1

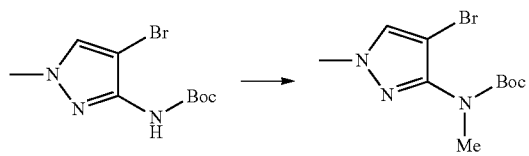 [SMILES: Cn1cc(Br)c(NC(=O)OC(C)(C)C)n1 ; CN(C(=O)OC(C)(C)C)c1nn(C)cc1Br]

60% sodium hydride (21 mg) was added to a mixture of tert-butyl (4-bromo-1-methyl-1H-pyrazol-3-yl)carbamate (130 mg), tetrahydrofuran (10 mL), and iodomethane (35 μL), followed by stirring at room temperature for 3 hours. After water and ethyl acetate were added to the reaction mixture, the organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate-methanol), thereby obtaining tert-butyl (4-bromo-1-methyl-1H-pyrazol-3-yl) (methyl)carbamate (133mg).

$^1$H-NMR(DMSO-d$_6$)δ:7.88(1H,s),3.78(3H,s),3.04(3H,s), 1.37(9H,s).

0683-2

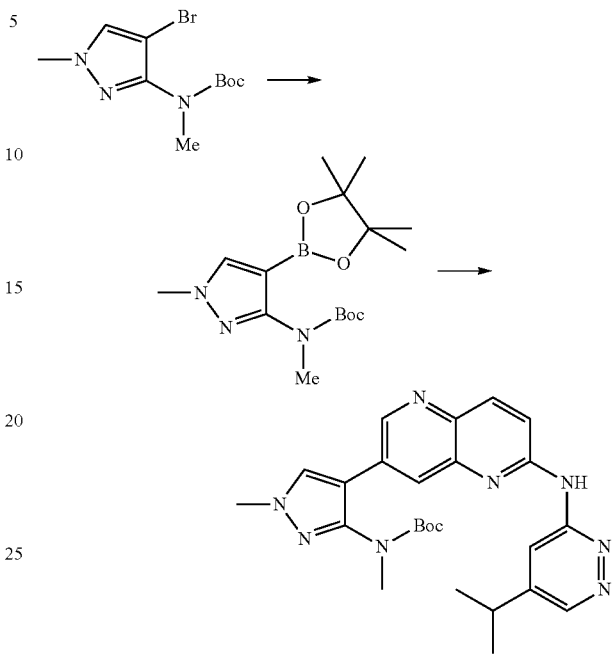

A mixture of tert-butyl (4-bromo-1-methyl-1H-pyrazol-3-yl) (methyl)carbamate (133 mg), bis(pinacolato)diboron (140 mg), a [1,1'-bis(diphenylphosphino)ferrocene]palladium(II) dichloride-dichloromethane adduct (41 mg), potassium acetate (90 mg), and 1,4-dioxane (5 mL) was stirred at 80° C. for 24 hours in a nitrogen atmosphere. The reaction mixture was cooled to room temperature, the insolubles were filtered off, and the solvent was distilled off under reduced pressure, thereby obtaining residue.

A mixture of the obtained residue, 7-bromo-N-(5-isopropylpyridazin-3-yl)-1,5-naphthyridine-2-amine (158 mg), sodium carbonate (122 mg), bis(di-tert-butyl(4-dimethylaminophenyl)phosphine)dichloropalladium(II) (14 mg), 1,4-dioxane (5 mL), and water (1 mL) was stirred at 110° C. for 6 hours in a nitrogen atmosphere. The reaction mixture was cooled to room temperature, water was added thereto, and the solid matter was collected by filtration. Chloroform and methanol were added to the obtained solid matter, the insolubles were filtered off, and the solvent was distilled off under reduced pressure. The obtained residue was purified sequentially by silica gel column chromatography (hexane-ethyl acetate-methanol), preparative thin layer silica gel column chromatography (chloroform-methanol), and preparative thin layer silica gel column chromatography (chloroform-methanol, NH silica), thereby obtaining tert-butyl (4-(6-((5-isopropylpyridazin-3-yl)amino)-1,5-naphthyridin-3-yl)-1-methyl-1H-pyrazol-3-yl) (methyl)carbamate (3 mg).

MSm/z(M+H):475.

823

0683-3

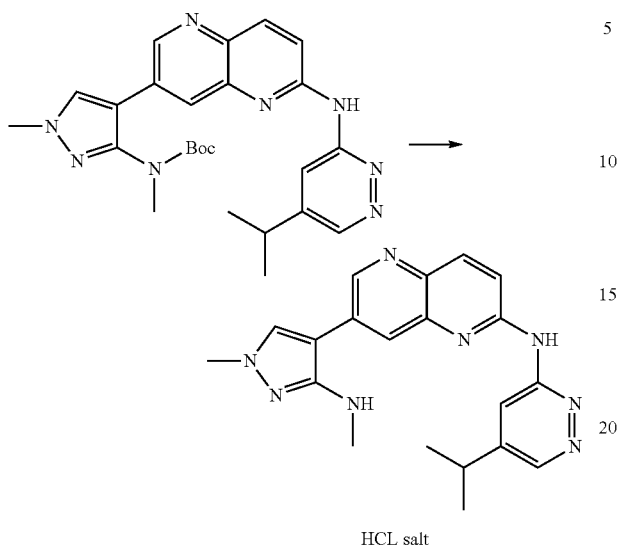

HCL salt

824

N-(5-isopropylpyridazin-3-yl)-7-(1-methyl-3-(methyl-amino)-1H-pyrazol-4-yl)-1,5-naphthyridine-2-amine hydrochloride was obtained in the same manner as in Example 0667.

$^1$H-NMR(DMSO-d$_6$)δ:9.07-9.04(2H,m),8.60(1H,s),8.44(1H,d,J=9.2 Hz),8.30(1H,brs),8.18(1H,s),7.72(1H,d,J=9.2 Hz),3.17(3H,s),2.81(3H,s),2.76-2.71(1H,m),1.33(6H,d,J=7.3 Hz).

MSm/z(M+H):375.

Examples 0684 to 0686

The following compounds were obtained in the same manner as in Example 0426-2.

| Example No. | | |
|---|---|---|
| 0684 | 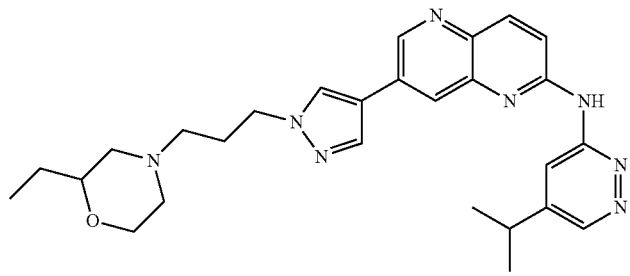 [SMILES: CCC1CN(CCCn2cc(-c3cnc4ccc(Nc5cc(C(C)C)cnn5)nc4c3)cn2)CCO1] | $^1$H-NMR (DMSO-d$_6$) δ: 10.70 (1H, s), 9.04 (1H, d, J = 2.0 Hz), 8.87 (1H, d, J = 2.0 Hz), 8.73 (1H, d, J = 2.0 Hz), 8.51 (1H, s), 8.23-8.18 (3H, m), 7.69 (1H, d, J = 9.2 Hz), 4.21 (2H, t, J = 6.9 Hz), 3.78-3.72 (1H, m), 3.51-3.45 (2H, m), 3.08-2.99 (1H, m), 2.74-2.63 (3H, m), 2.28 (2H, t, J = 6.9 Hz), 2.03-1.90 (3H, m), 1.65 (1H, t, J = 10.2 Hz), 1.40-1.32 (7H, m), 0.85 (3H, t, J = 7.6 Hz). MS m/z (M + H): 487. |
| 0685 | 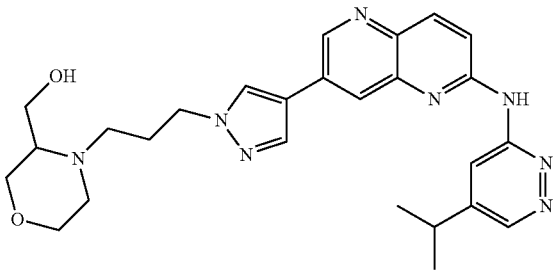 [SMILES: CC(C)c1cnnc(Nc2ccc3ncc(-c4cnn(CCCN5CCOCC5CO)c4)cc3n2)c1] | $^1$H-NMR (DMSO-d$_6$) δ: 10.70 (1H, s), 9.05 (1H, d, J = 2.0 Hz), 8.87 (1H, d, J = 2.0 Hz), 8.73 (1H, d, J = 2.0 Hz), 8.52 (1H, s), 8.23-8.19 (3H, m), 7.70 (1H, d, J = 8.2 Hz), 4.54-4.50 (1H, m), 4.21 (2H, t, J = 6.6 Hz), 3.73-3.46 (4H, m), 3.08-3.00 (1H, m), 2.77-2.70 (3H, m), 2.31-2.15 (4H, m), 2.02-1.95 (2H, m), 1.33 (6H, d, J = 6.6 Hz). MS m/z (M + H): 489. |
| 0686 | 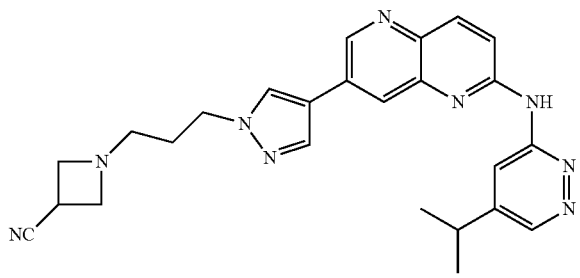 [SMILES: CC(C)c1cnnc(Nc2ccc3ncc(-c4cnn(CCCN5CC(C#N)C5)c4)cc3n2)c1] | $^1$H-NMR (DMSO-d$_6$) δ: 10.70 (1H, s), 9.04 (1H, d, J = 2.0 Hz), 8.87 (1H, d, J = 2.0 Hz), 8.73 (1H, d, J = 2.0 Hz), 8.50 (1H, s), 8.23-8.18 (3H, m), 7.70 (1H, d, J = 9.2 Hz), 4.18 (2H, t, J = 6.9 Hz), 3.46-3.30 (3H, m), 3.28-3.22 (2H, m), 3.09-2.99 (1H, m), 2.39 (2H, d, J = 6.9 Hz), 1.88-1.78 (2H, m), 1.33 (6H, d, J = 7.2 Hz). MS m/z (M + H): 454. |

Example 0687

0687-1

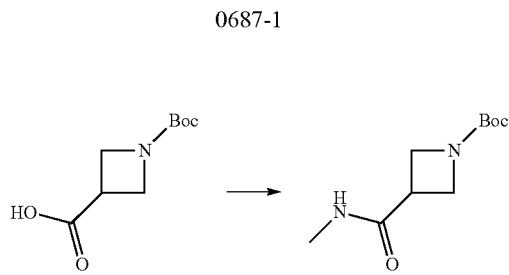

tert-Butyl 3-(methylcarbamoyl)azetidine-1-carboxylate was obtained in the same manner as in Example 0640.

¹H-NMR(DMSO-d₆)δ:3.88-3.84(4H,m),3.23-3.19(1H,m),2.59(3H,d,J=4.6 Hz),1.37(9H,s).

0687-2

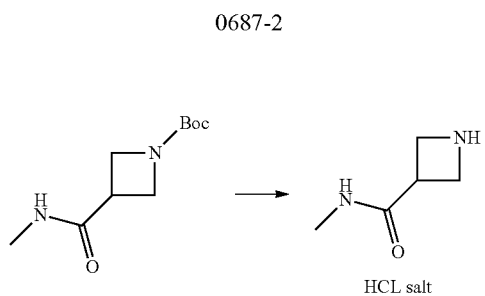

A mixture of tert-butyl 3-(methylcarbamoyl)azetidine-1-carboxylate (155 mg), 1,4-dioxane (2 mL), and a 4.0 mol/L hydrogen chloride/1,4-dioxane solution (1 mL) was stirred at room temperature for 15 hours. The solvent was distilled off under reduced pressure, thereby obtaining N-methylazetidine-3-carboxamide hydrochloride (127 mg).

¹H-NMR(DMSO-d₆)δ:4.00-3.96(4H,m),3.10-3.07(1H,m),2.63(3H,d,J=2.6 Hz).

0687-3

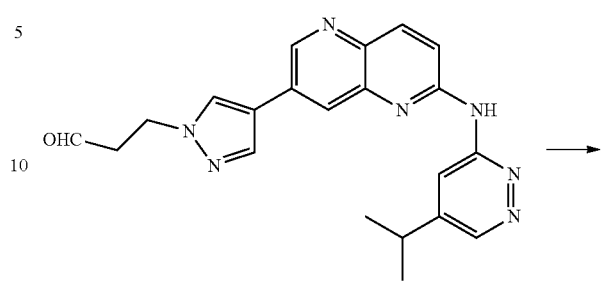

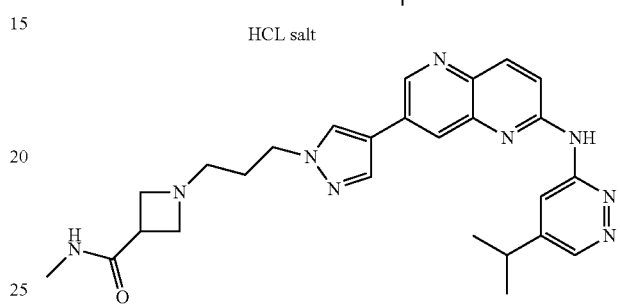

1-(3-(4-(6-((5-Isopropylpyridazin-3-yl)amino)-1,5-naphthyridin-3-yl)-1H-pyrazol-1-yl)propyl)-N-methylazetidine-3-carboxamide was obtained as a pale yellow solid in the same manner as in Example 0426-2.

¹H-NMR(DMSO-d₆)δ:10.70(1H,s),9.04(1H,d,J=2.0 Hz),8.87(1H,d,J=2.0 Hz),8.73(1H,d,J=2.0 Hz),8.50(1H,s),8.38(1H,brs),8.23-8.19(2H,m),7.70(1H,d,J=8.6 Hz),4.23(2H,t,J=6.9 Hz),3.54-3.26(5H,m),3.09-3.00(1H,m),2.67(3H,d,J=4.6 Hz),2.53-2.45(2H,m),2.00-1.94(2H,m),1.33(6H,d,J=7.3 Hz).

MSm/z(M+H):486.

Examples 0688 and 0689

The following compounds were obtained in the same manner as in Examples 0687-1, 0687-2, and 0426-2.

| Example No. | | |
|---|---|---|
| 0688 | | |
| 0688-1 | ![structure] | ¹H-NMR (DMSO-d₆) δ: 3.95-3.91 (4H, m), 3.65-3.60 (1H, m), 2.82 (6H, d, J = 1.3 Hz), 1.37 (9H, s). |
| 0688-2 | ![structure] HCL salt | ¹H-NMR (DMSO-d₆) δ: 4.06-4.04 (4H, m), 3.90-3.80 (1H, m), 2.84 (6H, d, J = 8.6 Hz). |

| Example No. | | |
|---|---|---|
| 0688-3 | 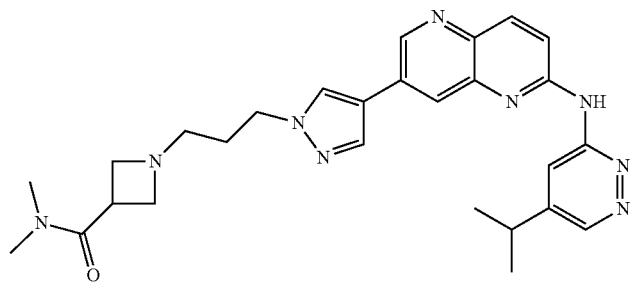 [SMILES: CC(C)c1cnnc(Nc2ccc3ncc(-c4cnn(CCCN5CC(C(=O)N(C)C)C5)c4)cc3n2)c1] | ¹H-NMR (DMSO-d₆) δ: 10.70 (1H, s), 9.04 (1H, d, J = 2.0 Hz), 8.87 (1H, d, J = 2.0 Hz), 8.73 (1H, d, J = 2.0 Hz), 8.50 (1H, s), 8.23-8.18 (3H, m), 7.70 (1H, d, J = 8.6 Hz), 4.18 (2H, t, J = 6.9 Hz), 3.49-3.43 (2H, m), 3.28-3.16 (1H, m), 3.07-2.98 (3H, m), 2.82 (3H, s), 2.79 (3H, s) 2.33 (2H, t, J = 6.9 Hz), 1.85-1.77 (2H, m), 1.33 (6H, d, J = 6.6 Hz). MS m/z (M + H): 500 |
| 0689 | | |
| 0689-1 | 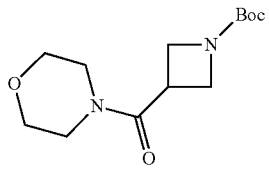 [SMILES: CC(C)(C)OC(=O)N1CC(C(=O)N2CCOCC2)C1] | ¹H-NMR (DMSO-d₆) δ: 3.98-3.95 (4H, m), 3.65-3.61 (1H, m), 3.55-3.53 (4H, m), 3.45 (2H, t, J = 4.6 Hz), 3.25 (2H, t, J = 4.6 Hz), 1.37 (9H, s). |
| 0689-2 | 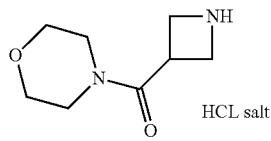 [SMILES: O=C(C1CNC1)N1CCOCC1] | ¹H-NMR (DMSO-d₆) δ: 4.11-4.02 (4H, m), 3.95-3.40 (4H, m), 3.25-3.24 (5H, m). |
| 0689-3 | 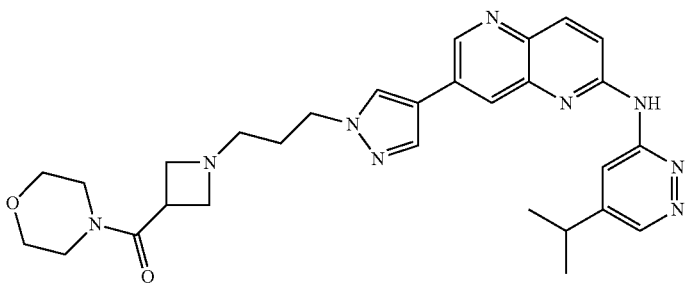 [SMILES: CC(C)c1cnnc(Nc2ccc3ncc(-c4cnn(CCCN5CC(C(=O)N6CCOCC6)C5)c4)cc3n2)c1] | ¹H-NMR (DMSO-d₆) δ: 10.70 (1H, s), 9.04 (1H, d, J = 2.0 Hz), 8.87 (1H, d, J = 2.0 Hz), 8.73 (1H, d, J = 2.0 Hz), 8.50 (1H, s), 8.23-8.18 (3H, m), 7.70 (1H, d, J = 9.2 Hz), 4.17 (2H, t, J = 6.9 Hz), 3.52-3.49 (4H, m), 3.44-3.41 (4H, m), 3.31-3.24 (3H, m), 3.13-2.99 (3H, m), 2.34 (2H, t, J = 6.6 Hz), 1.87-1.79 (2H, m), 1.33 (6H, d, J = 6.6 Hz). MS m/z (M + H): 542. |

Example 0690

0690-1

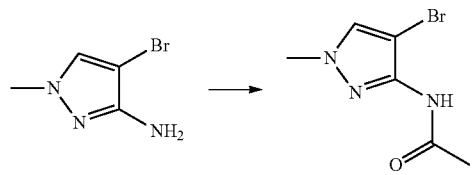

A mixture of 4-bromo-1-methyl-1H-pyrazole-3-amine (150 mg), pyridine (2 mL), acetic anhydride (241 μL), and N,N-dimethylpyridine-4-amine (11 mg) was stirred at room temperature for 3 hours. The solvent was distilled off under reduced pressure, and methanol (3 mL) and a 20% sodium hydroxide aqueous solution (1 mL) were added to the obtained residue, followed by stirring at room temperature for 3 hours. After water and ethyl acetate were added to the reaction mixture, the organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate-methanol), thereby obtaining N-(4-bromo-1-methyl-1H-pyrazol-3-yl)acetamide (79 mg).

MSm/z(M+H):218.

0690-2

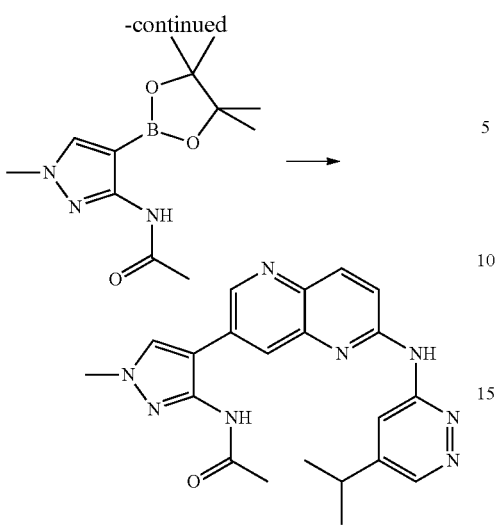

N-(4-(6-(((5-isopropylpyridazin-3-yl)amino)-1,5-naphthyridin-3-yl)-1-methyl-1H-pyrazol-3-yl)acetamide was obtained as a yellow solid in the same manner as in Example 0683-2.

$^1$H-NMR(DMSO-$d_6$)δ:10.73(1H,s),9.92(1H,s),8.86-8.84(2H,m),8.76(1H,s),8.34-8.32(1H,m),8.21(1H,d,J=9.2 Hz),8.05(1H,s),7.70(1H,d,J=9.2 Hz),3.87(3H,s),3.04-2.95(1H,m),2.04(3H,s),1.32(6H,d,J=6.6 Hz).

MS m/z (M+H):403.

Examples 0691 to 0693

The following compounds were obtained in the same manner as in Example 0426-2.

| Example No. | | |
|---|---|---|
| 0691 | 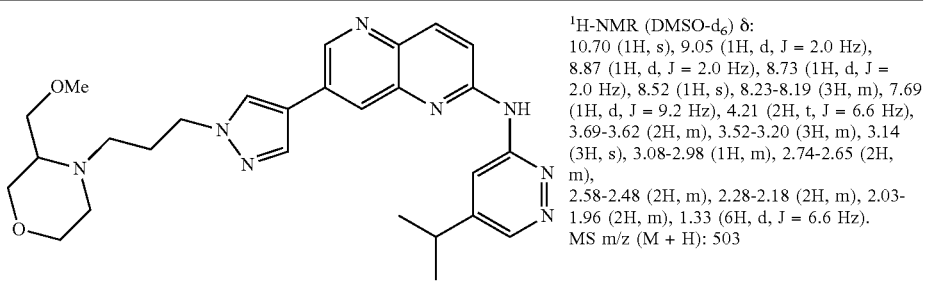 | $^1$H-NMR (DMSO-$d_6$) δ: 10.70 (1H, s), 9.05 (1H, d, J = 2.0 Hz), 8.87 (1H, d, J = 2.0 Hz), 8.73 (1H, d, J = 2.0 Hz), 8.52 (1H, s), 8.23-8.19 (3H, m), 7.69 (1H, d, J = 9.2 Hz), 4.21 (2H, t, J = 6.6 Hz), 3.69-3.62 (2H, m), 3.52-3.20 (3H, m), 3.14 (3H, s), 3.08-2.98 (1H, m), 2.74-2.65 (2H, m), 2.58-2.48 (2H, m), 2.28-2.18 (2H, m), 2.03-1.96 (2H, m), 1.33 (6H, d, J = 6.6 Hz). MS m/z (M + H): 503 |
| 0692 | 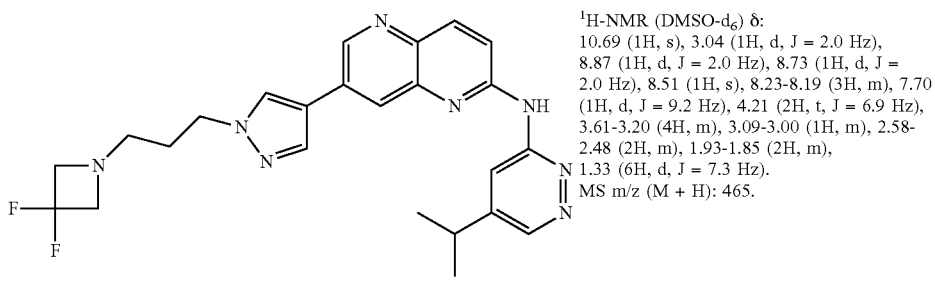 | $^1$H-NMR (DMSO-$d_6$) δ: 10.69 (1H, s), 3.04 (1H, d, J = 2.0 Hz), 8.87 (1H, d, J = 2.0 Hz), 8.73 (1H, d, J = 2.0 Hz), 8.51 (1H, s), 8.23-8.19 (3H, m), 7.70 (1H, d, J = 9.2 Hz), 4.21 (2H, t, J = 6.9 Hz), 3.61-3.20 (4H, m), 3.09-3.00 (1H, m), 2.58-2.48 (2H, m), 1.93-1.85 (2H, m), 1.33 (6H, d, J = 7.3 Hz). MS m/z (M + H): 465. |
| 0693 | 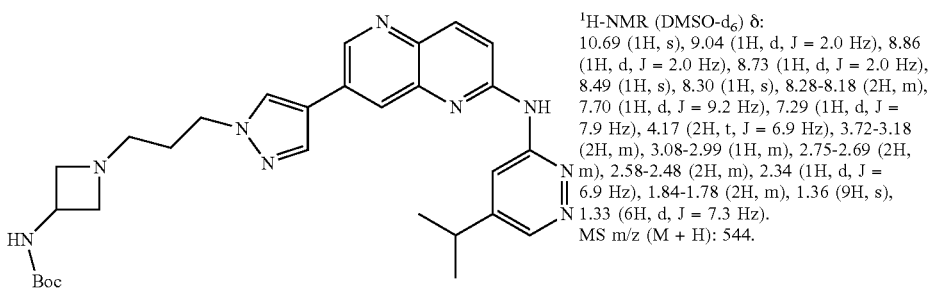 | $^1$H-NMR (DMSO-$d_6$) δ: 10.69 (1H, s), 9.04 (1H, d, J = 2.0 Hz), 8.86 (1H, d, J = 2.0 Hz), 8.73 (1H, d, J = 2.0 Hz), 8.49 (1H, s), 8.30 (1H, s), 8.28-8.18 (2H, m), 7.70 (1H, d, J = 9.2 Hz), 7.29 (1H, d, J = 7.9 Hz), 4.17 (2H, t, J = 6.9 Hz), 3.72-3.18 (2H, m), 3.08-2.99 (1H, m), 2.75-2.69 (2H, m), 2.58-2.48 (2H, m), 2.34 (1H, d, J = 6.9 Hz), 1.84-1.78 (2H, m), 1.36 (9H, s), 1.33 (6H, d, J = 7.3 Hz). MS m/z (M + H): 544. |

Example 0694

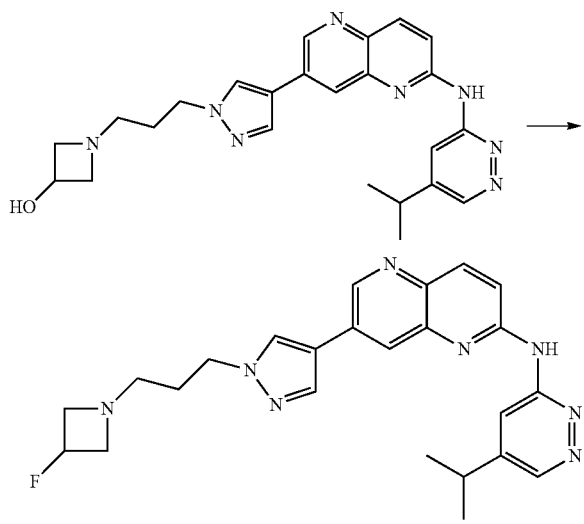

7-(1-(3-(3-Fluoroazetidin-1-yl)propyl)-1H-pyrazol-4-yl)-N-(5-isopropylpyridazin-3-yl)-1,5-naphthyridine-2-amine was obtained in the same manner as in Example 0626-3.

$^1$H-NMR(DMSO-d$_6$)δ:10.70(1H,s),9.04(1H,d,J=2.0 Hz), 8.87(1H,d,J=2.0 Hz),8.73(1H,d,J=2.0 Hz),8.50(1H,s),8.23-8.19(2H,m),7.70(1H,d,J=9.2 Hz),5.27-5.02(1H,m),4.18(2H,t,J=6.9 Hz),3.64-3.25(2H,m),3.12-2.99(3H,m),2.46-2.43(2H,m),1.90-1.82(2H,m),1.33(6H,d,J=6.9 Hz).

MSm/z(M+H):447.

Example 0695

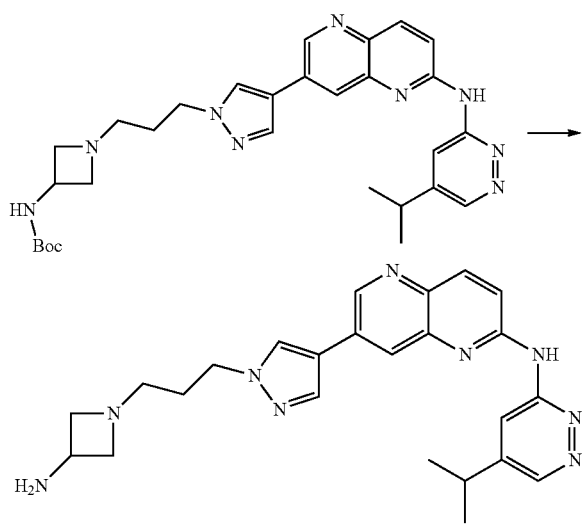

A mixture of tert-butyl (1-(3-(4-(6-((5-isopropylpyridazin-3-yl)amino)-1,5-naphthyridin-3-yl)-1H-pyrazol-1-yl)propyl)azetidin-3-yl)carbamate (17 mg), 1,4-dioxane (2 mL), methanol (1 mL), and a 4.0 mol/L hydrogen chloride/1,4-dioxane solution (1 mL) was stirred at room temperature for 1.5 hours. The solvent was distilled off under reduced pressure, a saturated sodium hydrogen carbonate aqueous solution was added to the obtained residue, and the solvent was distilled off under reduced pressure. The obtained residue was purified by preparative thin layer silica gel column chromatography (chloroform-methanol, NH silica), thereby obtaining 7-(1-(3-(3-aminoazetidin-1-yl)propyl)-1H-pyrazol-4-yl)-N-(5-isopropylpyridazin-3-yl)-1,5-naphthyridine-2-amine (10 mg) as a pale yellow solid.

$^1$H-NMR(DMSO-d$_6$)δ:10.70(1H,s),9.04(1H,d,J=2.0 Hz), 8.87(1H,d,J=2.0 Hz),8.73(1H,d,J=2.0 Hz),8.50(1H,s),8.23-8.18(3H,m),7.70(1H,d,J=9.2 Hz),4.17(2H,t,J=6.9 Hz),3.51-3.46(2H,m),3.39-3.30(2H,m),3.08-2.99(1H,m),2.51-2.45(2H,m),2.33(2H,t,J=6.9 Hz),1.86-1.77(3H,m),1.33(6H,d,J=7.2 Hz).

MSm/z(M+H):444.

Example 0696

0696-1

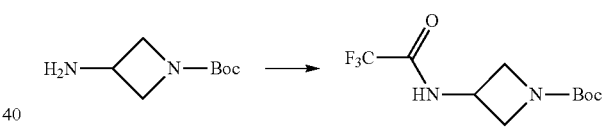

A mixture of tert-butyl 3-aminoazetidine-1-carboxylate (100 mg), triethylamine (322 μL), trifluoroacetic anhydride (244 mg), and dichloromethane (4 mL) was stirred at room temperature for 2 hours. The reaction mixture was purified by silica gel column chromatography (hexane-ethyl acetate-methanol), thereby obtaining tert-butyl 3-(2,2,2-trifluoroacetamide)azetidine-1-carboxylate (157 mg).

$^1$H-NMR(DMSO-d$_6$)δ:10.00(1H,s),4.54-4.50(1H,m), 4.09(2H,t,J=8.3 Hz),3.83(2H,t,J=8.6 Hz),1.38(9H,s).

0696-2 and 0696-3

The following compounds were obtained in the same manner as in Examples 0687-2 and 0426-2.

| Example No. | | |
|---|---|---|
| 0696 | | |
| 0696-2 | 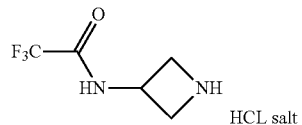 [SMILES: O=C(NC1CNC1)C(F)(F)F] HCL salt | ¹H-NMR (DMSO-d₆) δ: 10.00 (1H, brs), 4.52-4.49 (1H, m), 4.13-4.08 (2H, m), 3.84-3.82 (2H, m). |
| 0696-3 | 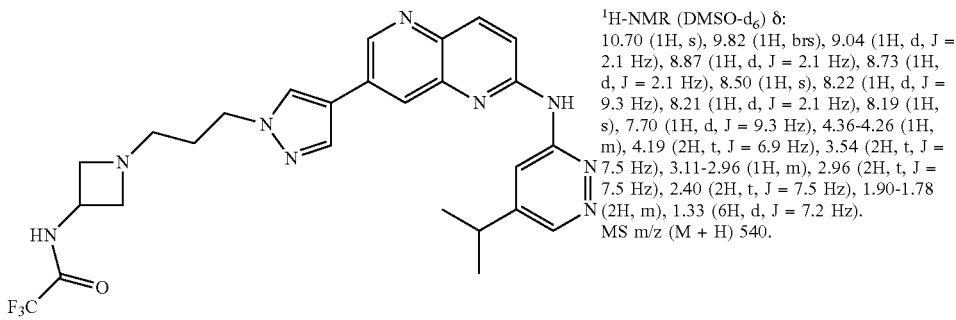 | ¹H-NMR (DMSO-d₆) δ: 10.70 (1H, s), 9.82 (1H, brs), 9.04 (1H, d, J = 2.1 Hz), 8.87 (1H, d, J = 2.1 Hz), 8.73 (1H, d, J = 2.1 Hz), 8.50 (1H, s), 8.22 (1H, d, J = 9.3 Hz), 8.21 (1H, d, J = 2.1 Hz), 8.19 (1H, s), 7.70 (1H, d, J = 9.3 Hz), 4.36-4.26 (1H, m), 4.19 (2H, t, J = 6.9 Hz), 3.54 (2H, t, J = 7.5 Hz), 3.11-2.96 (1H, m), 2.96 (2H, t, J = 7.5 Hz), 2.40 (2H, t, J = 7.5 Hz), 1.90-1.78 (2H, m), 1.33 (6H, d, J = 7.2 Hz). MS m/z (M + H) 540. |

Example 0697

0697-1

A mixture of tert-butyl 3-aminoazetidine-1-carboxylate (100 mg), triethylamine (322 μL), methanesulfonyl chloride (90 μL), and dichloromethane (4 mL) was stirred at room temperature for 2 hours. The reaction mixture was purified by silica gel column chromatography (hexane-ethyl acetate-methanol), thereby obtaining tert-butyl 3-(methane sulfonamide)azetidine-1-carboxylate (149 mg).
¹H-NMR(DMSO-d₆)δ:7.81(1H,s),4.11-4.08(3H,m),3.74-3.71(2H,m),2.89(3H,s),1.37(9H,s).

0697-2 and 0697-3

The following compounds were obtained in the same manner as in Examples 0687-2 and 0426-2.

| Example No. | | |
|---|---|---|
| 0697 | | |
| 0697-2 | 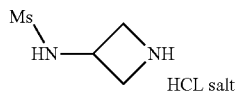 HCL salt | |
| 0697-3 | 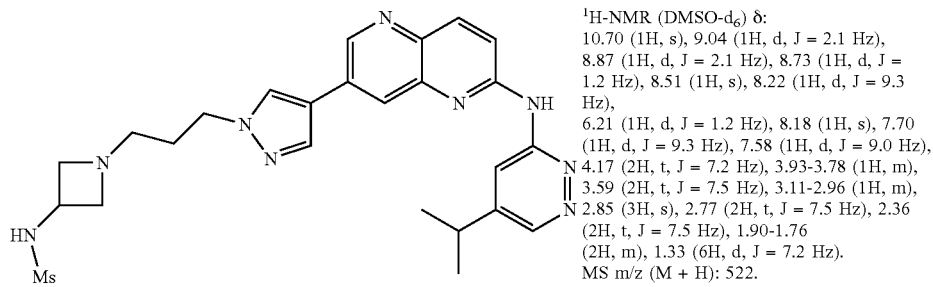 | ¹H-NMR (DMSO-d₆) δ: 10.70 (1H, s), 9.04 (1H, d, J = 2.1 Hz), 8.87 (1H, d, J = 2.1 Hz), 8.73 (1H, d, J = 1.2 Hz), 8.51 (1H, s), 8.22 (1H, d, J = 9.3 Hz), 6.21 (1H, d, J = 1.2 Hz), 8.18 (1H, s), 7.70 (1H, d, J = 9.3 Hz), 7.58 (1H, d, J = 9.0 Hz), 4.17 (2H, t, J = 7.2 Hz), 3.93-3.78 (1H, m), 3.59 (2H, t, J = 7.5 Hz), 3.11-2.96 (1H, m), 2.85 (3H, s), 2.77 (2H, t, J = 7.5 Hz), 2.36 (2H, t, J = 7.5 Hz), 1.90-1.76 (2H, m), 1.33 (6H, d, J = 7.2 Hz). MS m/z (M + H): 522. |

Example 0698

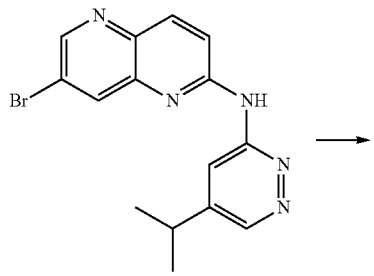

A mixture of tris(dibenzylideneacetone)dipalladium(0) (27 mg), 2-di-tert-butylphosphino-3,4,5,6-tetramethyl-2',4',6'-triisopropyl-1,1'-biphenyl (29 mg), tripotassium phosphate (96 mg), and toluene (1.5 mL) was stirred at 110° C. for 5 minutes in a nitrogen atmosphere. 7-Bromo-N-(5-isopropylpyridazin-3-yl)-1,5-naphthyridine-2-amine (50 mg) and 2,4-dimethyl-1H-imidazole (43 mg) were added to the reaction mixture, followed by stirring at 110° C. for 4 hours. The reaction mixture was cooled to room temperature, and the solvent was distilled off under reduced pressure. The obtained residue was purified sequentially by silica gel column chromatography (hexane-ethyl acetate-methanol), preparative thin layer silica gel column chromatography (chloroform-methanol, NH silica), and preparative thin layer silica gel column chromatography (chloroform-methanol), thereby obtaining 7-(2,4-dimethyl-1H-imidazol-1-yl)-N-(5-isopropylpyridazin-3-yl)-1,5-naphthyridine-2-amine (10 mg) as a pale yellow solid.

$^1$H-NMR(DMSO-d$_6$)δ:10.87(1H,s),8.87(1H,d,J=1.8 Hz),8.82(1H,d,J=1.8 Hz),8.33(1H,d,J=9.0 Hz),8.31(1H,brs),8.22(1H,brs),7.82(1H,d,J=9.0 Hz),7.21(1H,s),3.10-2.95(1H,m),2.34(3H,s),2.08(3H,s),1.30(6H,d,J=6.6 Hz).
MSm/z(M+H):360.

Example 0699

0699-1

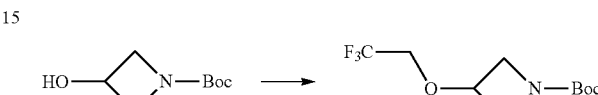

A mixture of tert-butyl 3-hydroxyazetidine-1-carboxylate (150 mg), 3,3,3-trifluoroethyl trifluoromethanesulfonate (188 μL), N,N-dimethylformamide (2 mL), and 60% sodium hydride (42 mg) was stirred at room temperature for 3 hours. After water and ethyl acetate were added to the reaction mixture, the organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate-methanol), thereby obtaining tert-butyl 3-(2,2,2-trifluoroethoxy)azetidine-1-carboxylate (114 mg).

$^1$H-NMR(DMSO-d$_6$)δ:4.44-4.41(1H,m),4.13-4.01(4H,m),3.69(2H,d,J=9.9 Hz),1.37(9H,s).

0699-2 and 0699-3

The following compounds were obtained in the same manner as in Examples 0667 and 0426-2.

| Example No. | | |
|---|---|---|
| 0699 | | |
| 0699-2 | 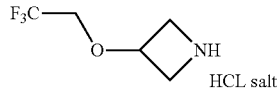 HCL salt | $^1$H-NMR (DMSO-d$_6$) δ: 4.56-4.52 (1H, m), 4.21-4.11 (4H, m), 3.87-3.83 (2H, m). |
| 0699-3 | 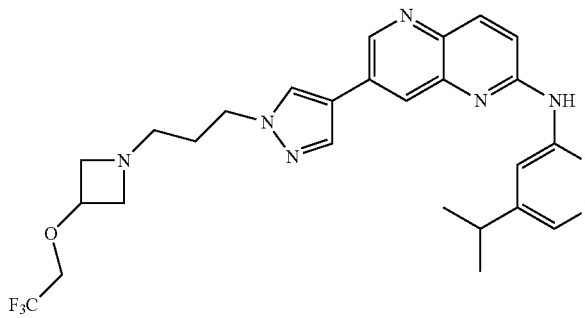 | $^1$H-NMR (DMSO-d$_6$) δ: 10.70 (1H, s), 9.04 (1H, d, J = 2.1 Hz), 8.87 (1H, d, J = 2.1 Hz), 8.73 (1H, brs), 8.49 (1H, s), 8.22 (1H, d, J = 9.0 Hz), 8.21 (1H, brs), 8.18 (1H, s), 7.70 (1H, d, J = 9.0 Hz), 4.30-4.16 (1H, m), 4.17 (2H, t, J = 7.2 Hz), 4.03 (2H, q, J = 6.6 Hz), 3.52 (2H, dd, J = 7.8, 5.7 Hz), 3.11-2.96 (1H, m), 2.81 (2H, dd, J = 7.8, 5.7 Hz), 2.39 (2H, t, J = 6.6 Hz), 1.90-1.77 (2H, m), 1.33 (6H, d, J = 6.6 Hz). MS m/z (M + H): 527. |

Example 0700

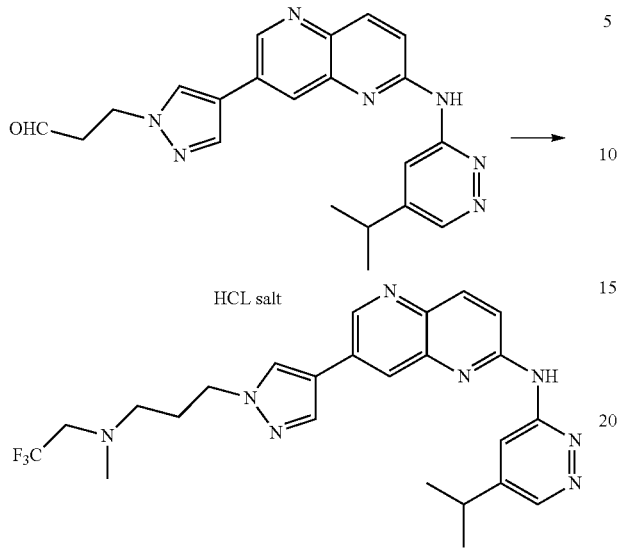

Example 0701

N-(5-isopropylpyridazin-3-yl)-7-(1-(3-(methyl (2,2,2-trifluoroethyl)amino)propyl)-1H-pyrazol-4-yl)-1,5-naphthyridine-2-amine was obtained as a pale yellow solid in the same manner as in Example 0426-2.

$^1$H-NMR(DMSO-$d_6$)δ:10.70(1H,s),9.04(1H,d,J=2.1 Hz), 8.87(1H,d,J=2.1 Hz),8.74(1H,d,J=2.1 Hz),8.48(1H,s),8.22 (1H,d,J=9.0 Hz),8.21(1H,brs)8.20(1H,brs),7.70(1H,d,J=9.0 Hz),4.20(2H,t,J=6.6 Hz),3.28-3.10(2H,m),3.11-2.96(1H,m), 2.54(2H,t,J=7.2 Hz),2.37(3H,s),2.06-1.95(2H,m),1.33(6H, d,J=7.2 Hz).

MSm/z(M+H):485.

Example 0701

Example The following compounds were obtained in the same manner as in Examples 0697-1, 0667, and 0426-2.

| Example No. | | |
|---|---|---|
| 0701 | | |
| 0701-1 | 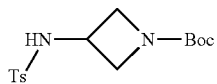 | $^1$H-NMR (DMSO-$d_6$) δ: 8.26 (1H, brs), 7.66 (2H, d, J = 8.6 Hz), 7.41 (2H, d, J = 7.9 Hz), 4.01-3.98 (1H, m), 3.85-3.82 (2H, m), 3.44-3.41 (2H, m), 2.40 (3H, s), 1.32 (9H, s) |
| 0701-2 | 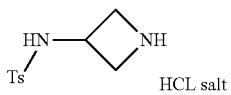 | $^1$H-NMR (DMSO-$d_6$) δ: 7.69 (2H, d, J = 8.6 Hz), 7.43 (2H, d, J = 7.9 Hz), 4.13-4.10 (1H, m), 3.89 (2H, t, J = 9.6 Hz), 3.69 (2H, t, J = 11.6 Hz), 2.40 (3H, s). |
| 0701-3 | 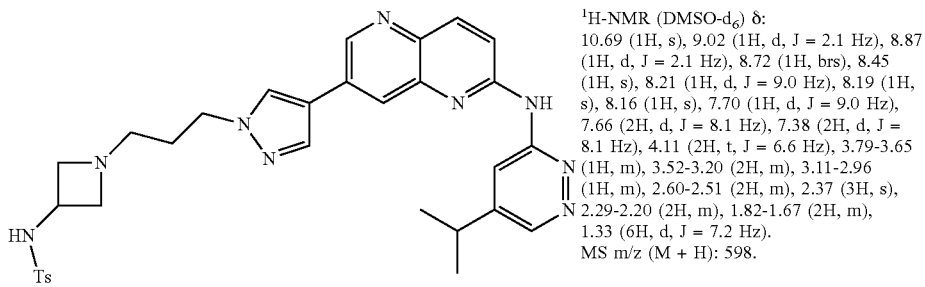 | $^1$H-NMR (DMSO-$d_6$) δ: 10.69 (1H, s), 9.02 (1H, d, J = 2.1 Hz), 8.87 (1H, d, J = 2.1 Hz), 8.72 (1H, brs), 8.45 (1H, s), 8.21 (1H, d, J = 9.0 Hz), 8.19 (1H, s), 8.16 (1H, s), 7.70 (1H, d, J = 9.0 Hz), 7.66 (2H, d, J = 8.1 Hz), 7.38 (2H, d, J = 8.1 Hz), 4.11 (2H, t, J = 6.6 Hz), 3.79-3.65 (1H, m), 3.52-3.20 (2H, m), 3.11-2.96 (1H, m), 2.60-2.51 (2H, m), 2.37 (3H, s), 2.29-2.20 (2H, m), 1.82-1.67 (2H, m), 1.33 (6H, d, J = 7.2 Hz). MS m/z (M + H): 598. |

Example 0702

The following compounds were obtained in the same manner as in Examples 0667 and 0426-2.

| Example No. | | |
|---|---|---|
| 0702 | | |
| 0702-1 | 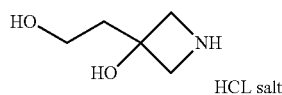 HCL salt | ¹H-NMR (DMSO-d₆) δ: 3.94-3.93 (2H, m), 3.84-3.49 (2H, m), 3.70 (2H, t, J = 7.3 Hz), 2.24 (2H, t, J = 7.3 Hz). |
| 0702-2 | 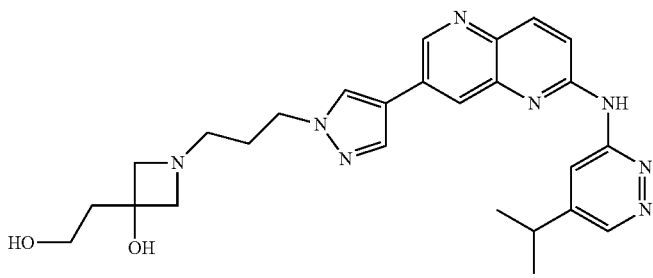 [SMILES: CC(C)c1cnnc(Nc2ccc3ncc(-c4cnn(CCCN5CC(O)(CCO)C5)c4)cc3n2)c1] | ¹H-NMR (DMSO-d₆) δ: 10.69 (1H, s), 9.04 (1H, d, J = 2.1 Hz), 8.87 (1H, d, J = 2.1 Hz), 8.72 (1H, brs), 8.50 (1H, s), 8.22 (1H, d, J = 9.0 Hz), 8.21 (1H, brs), 8.19 (1H, s), 8.70 (1H, d, J = 9.0 Hz), 4.64 (1H, brs), 4.49 (1H, brs), 4.21 (2H, t, J = 6.6 Hz), 3.47-3.37 (2H, m), 3.11-2.96 (1H, m), 2.64-2.44 (4H, m), 2.35 (2H, t, J = 7.2 Hz), 2.03-1.09 (2H, m), 1.87-1.74 (1H, m), 1.62-1.51 (1H, m), 1.33 (6H, d, J = 6.6 Hz). MS m/z (M + H): 489. |

Example 0703

0703-1

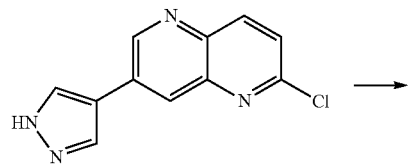

↓

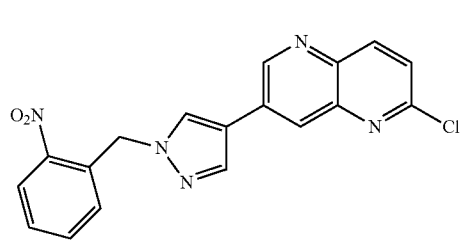

A mixture of 2-chloro-7-(1H-pyrazol-4-yl)-1,5-naphthyridine (100 mg), 1-(bromomethyl)-2-nitrobenzene (112 mg), potassium carbonate (119 mg), and N,N-dimethylformamide (4 mL) was stirred at 60° C. for 2 hours. The reaction mixture was cooled to room temperature, water was added thereto, and the solid matter was collected by filtration. The obtained solid matter was purified by silica gel column chromatography (hexane-ethyl acetate-methanol), thereby obtaining 2-chloro-7-(1-(2-nitrobenzyl)-1H-pyrazol-4-yl)-1,5-naphthyridine (134 mg).

MSm/z(M+H):366.

0703-2

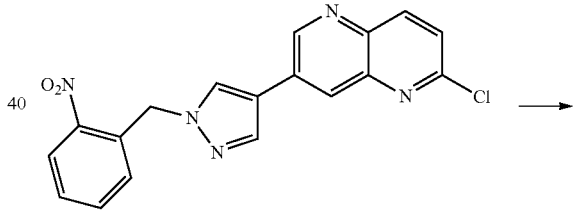

↓

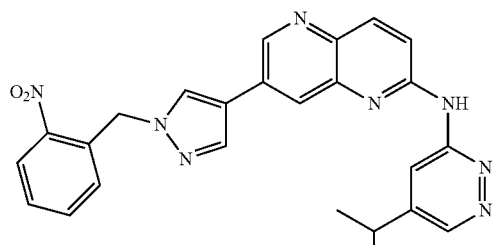

N-(5-isopropylpyridazin-3-yl)-7-(1-(2-nitrobenzyl)-1H-pyrazol-4-yl)-1,5-naphthyridine-2-amine was obtained as a pale yellow solid in the same manner as in Example 0646-3.

¹H-NMR(DMSO-d₆)δ:10.71(1H,s),9.06(1H,d,J=1.8 Hz), 8.86(1H,d,J=1.8 Hz),8.74(1H,d,J=1.8 Hz),8.64(1H,s),8.32 (1H,s),8.25(1H,brs),8.23(1H,d,J=9.0 Hz),8.14(1H,d,J=6.9 Hz),7.74(1H,t,J=6.9 Hz),7.71(1H,d,J=9.0 Hz),7.61(1H,t, J=6.9 Hz),7.01(1H,d,J=6.9 Hz),5.81(2H,s),3.11-2.96(1H, m),1.32(6H,d,J=6.6 Hz).

MSm/z(M+H):467.

841

Example 0704

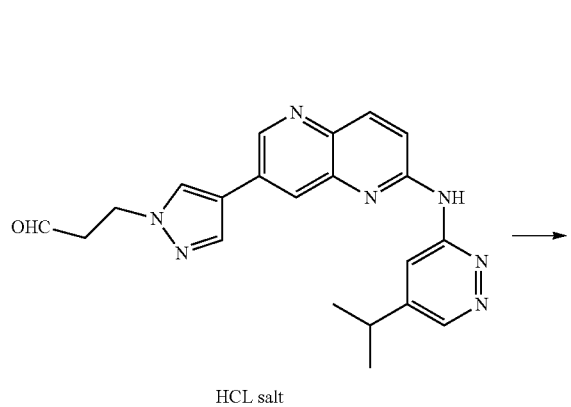

HCL salt

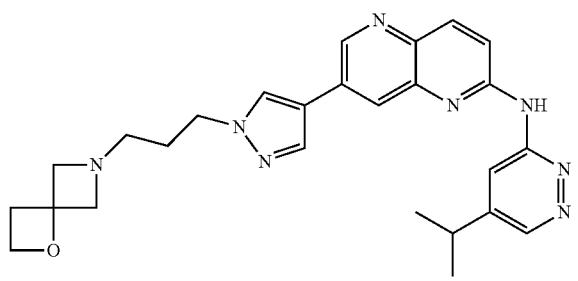

7-(1-(3-(1-Oxa-6-azaspiro[3.3]heptan-6-yl)propyl)-1H-pyrazol-4-yl)-N-(5-isopropylpyridazin-3-yl)-1,5-naphthyridine-2-amine was obtained as a pale yellow solid in the same manner as in Example 0426-2.

$^1$H-NMR(DMSO-d$_6$)δ:10.70(1H,s),9.04(1H,d,J=2.1 Hz), 8.87(1H,d,J=2.1 Hz),8.73(1H,d,J=2.1 Hz),8.49(1H,s),8.21 (1H,d,J=9.0 Hz),8.21(1H,d,J=2.1 Hz),8.18(1H,s),7.70(1H,d, J=9.0 Hz),4.36(2H,t,J=7.5 Hz),4.16(2H,t,J=6.9 Hz),3.52-3.46(2H,m),3.11-2.96(1H,m),2.99-2.95(2H,m),2.78-2.70 (2H,m),2.34(2H,t,J=6.6 Hz),1.90-1.75(2H,m),1.33(6H,d, J=7.2 Hz).

MSm/z(M+H):471.

842

Example 0705

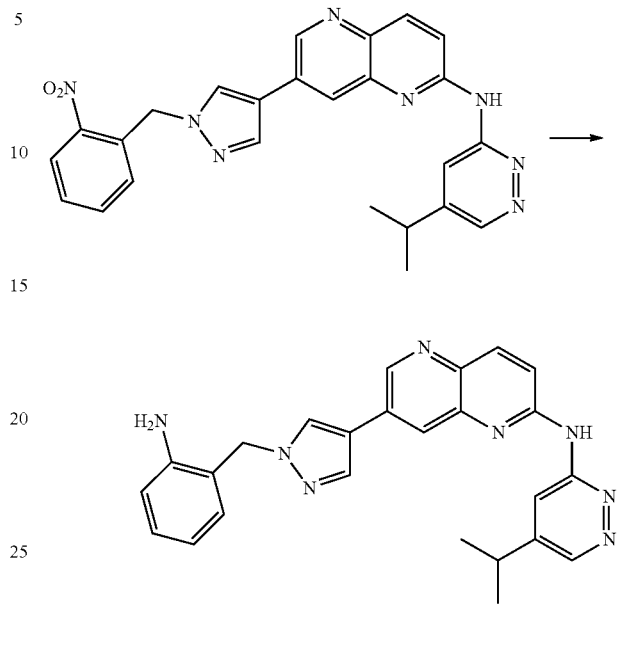

A mixture of N-(5-isopropylpyridazin-3-yl)-7-(1-(2-nitrobenzyl)-1H-pyrazol-4-yl)-1,5-naphthyridine-2-amine (50 mg), reduced iron (18 mg), ammonium chloride (6 mg), ethanol (4 mL), and water (2 mL) was stirred at 60° C. for 6 hours. The reaction mixture was cooled to room temperature, the insolubles were filtered off, and the solvent was distilled off under reduced pressure. The obtained residue was purified sequentially by silica gel column chromatography (hexane-ethyl acetate-methanol, NH silica), and silica gel column chromatography (chloroform-methanol, NH silica), thereby obtaining 7-(1-(2-aminobenzyl)-1H-pyrazol-4-yl)-N-(5-isopropylpyridazin-3-yl)-1,5-naphthyridine-2-amine (11 mg) as a pale yellow solid.

$^1$H-NMR(DMSO-d$_6$)δ:10.70(1H,s),9.03(1H,d,J=1.8 Hz), 8.87(1H,d,J=1.8 Hz),8.73(1H brs),8.57(1H,s),8.24(1H,s), 8.21(1H,d,J=9.0 Hz),8.21(1H,brs),8.70(1H,d,J=9.0 Hz), 7.02(1H,t,J=7.8 Hz),6.92(1H,d,J=7.8 Hz),6.69(1H,d,J=7.8 Hz),6.55(1H,t,J=7.8 Hz),5.26(2H,s),3.11-2.96(1H,m),1.33 (6H,d,J=6.6 Hz).

MSm/z(M+H):437.

Examples 0706 to 0708

The following compounds were obtained in the same manner as in Example 0426-2.

| Example No. | | |
|---|---|---|
| 0706 | 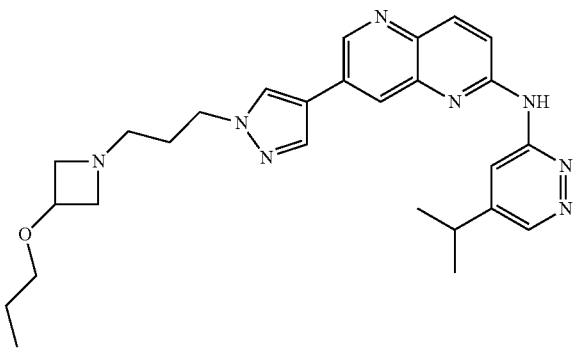 [SMILES: CCCOC1CN(CCCn2cc(-c3cnc4ccc(Nc5cc(C(C)C)cnn5)nc4c3)cn2)C1] | ¹H-NMR (DMSO-d₆) δ: 10.69 (1H, s), 9.04 (1H, d, J = 1.8 Hz), 8.87 (1H, d, J = 1.8 Hz), 8.73 (1H, d, J = 1.8 Hz), 8.49 (1H, s) 8.22 (1H, d, J = 9.3 Hz), 8.21 (1H, d, J = 1.8 Hz), 6.18 (1H, s), 7.70 (1H, d, J = 9.3 Hz), 4.18 (2H, t, J = 6.9 Hz), 4.06-3.93 (1H, m), 3.59-3.46 (2H, m), 3.24 (2H, t, J = 6.6 Hz), 3.11-2.96 (1H, m), 2.75-2.68 (2H, m), 2.38 (2H, t, J = 6.6 Hz), 1.90-1.77 (2H, m), 1.53-1.36 (2H, m), 1.33 (6H, d, J = 7.2 Hz), 0.84 (3H, t, J = 7.2 Hz). MS m/z (M + H): 487. |
| 0707 | 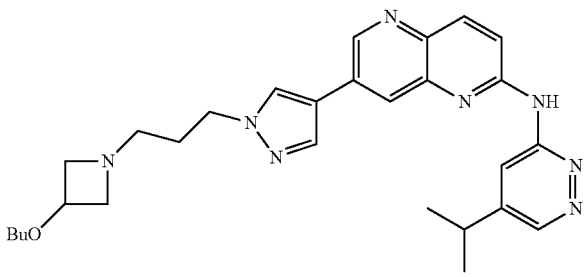 | ¹H-NMR (DMSO-d₆) δ: 10.69 (1H, s), 9.04 (1H, d, J = 1.8 Hz), 8.87 (1H, d, J = 1.8 Hz), 8.73 (1H, d, J = 1.2 Hz), 8.49 (1H, s), 8.22 (1H, d, J = 9.3 Hz), 8.21 (1H, d, J = 1.2 Hz), 8.18 (1H, s) 7.70 (1H, d, J = 9.3 Hz), 4.18 (2H, t, J = 6.9 Hz), 4.05-3.94 (1H, m), 3.55-3.47 (2H, m), 3.27 (2H, t, J = 6.6 Hz), 3.11-2.96 (1H, m), 2.75-2.67 (2H, m), 2.38 (2H, t, J = 6.6 Hz), 1.90-1.77 (2H, m), 1.50-1.37 (2H, m), 1.35-1.15 (2H, m), 1.33 (6H, d, J = 6.6 Hz), 0.58 (3H, t, J = 7.2 Hz). MS m/z (M + H) 501. |
| 0708 | 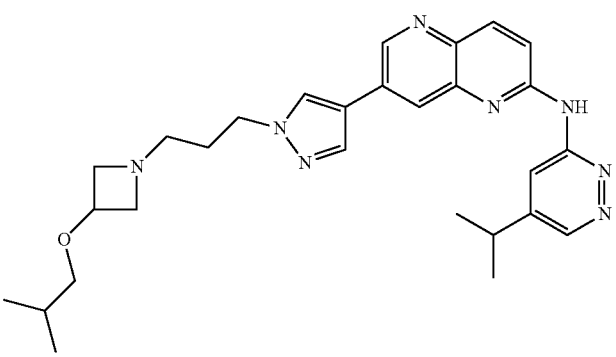 [SMILES: CC(C)COC1CN(CCCn2cc(-c3cnc4ccc(Nc5cc(C(C)C)cnn5)nc4c3)cn2)C1] | ¹H-NMR (DMSO-d₆) δ: 10.68 (1H, s), 9.04 (1H, d, J = 1.8 Hz), 8.87 (1H, d, J = 1.8 Hz), 8.73 (1H, brs), 8.49 (1H, s), 8.22 (1H, d, J = 9.3 Hz), 8.21 (1H, d, J = 1.8 Hz), 8.18 (1H, s), 7.70 (1H, d, J = 8.3 Hz), 4.18 (2H, t, J = 7.2 Hz), 4.05-3.94 (1H, m), 3.59-3.50 (2H, m), 3.11-2.96 (1H, m), 3.05 (2H, d, J = 6.6 Hz), 2.75-2.67 (2H, m), 2.38 (2H, d, J = 6.6 Hz), 1.90-1.63 (3H, m), 1.33 (6H, d, J = 7.2 Hz), 0.84 (6H, d, J = 6.6 Hz). MS m/z (M + H): 501. |

Example 0709

The following compounds were obtained in the same manner as in Examples 0699-1, 0667, and 0426-2.

| Example No. | | |
|---|---|---|
| 0709 | | |
| 0709-1 | 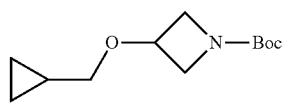 | ¹H-NMR (DMSO-d₆) δ: 4.24-4.21 (1H, m), 3.99 (2H, t, J = 7.3 Hz), 3.65 (2H, dd, J = 10.0, 5.0 Hz), 3.18 (2H, d, J = 6.6 Hz), 1.37 (9H, s), 0.98-0.95 (1H, m), 0.49-0.43 (2H, m), 0.16 (2H, td, J = 5.1, 4.0 Hz). |
| 0709-2 | 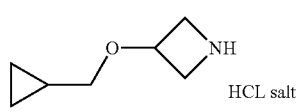 | ¹H-NMR (DMSO-d₆) δ: 4.39-4.31 (1H, m), 4.14-4.10 (2H, m), 3.86-3.76 (2H, m), 3.24 (2H, d, J = 6.6 Hz), 0.98-0.94 (1H, m), 0.51-0.45 (2H, m), 0.20-0.16 (2H, m). |

| Example No. | | |
|---|---|---|
| 0709-3 | 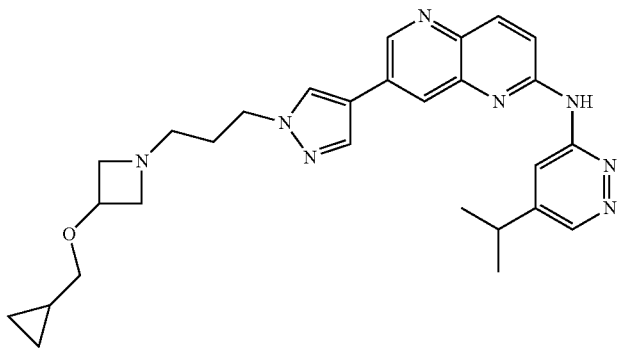 [SMILES: CC(C)c1cnnc(Nc2ccc3ncc(-c4cnn(CCCN5CC(OCC6CC6)C5)c4)cc3n2)c1] | ¹H-NMR (DMSO-d₆) δ: 10.69 (1H, s), 9.04 (1H, d, J = 1.8 Hz), 8.87 (1H, d, J = 1.8 Hz), 8.72 (1H, brs), 8.49 (1H, s), 8.22 (1H, d, J = 9.0 Hz), 8.21 (1H, d, J = 1.8 Hz), 8.18 (1H, s), 7.70 (1H, d, J = 9.0 Hz), 4.18 (2H, t, J = 7.2 Hz), 4.10-3.97 (1H, m), 3.61-3.49 (2H, m), 3.13 (2H, t, J = 7.2 Hz), 3.11-2.96 (1H, m), 2.77-2.70 (2H, m), 2.38 (2H, t, J = 6.6 Hz), 1.91-1.76 (2H, m), 1.33 (6H, d, J = 6.6 Hz), 1.00-0.83 (1H, m), 0.49-0.41 (2H, m), 0.18-0.10 (2H, m). MS m/z (M + H): 499. |

Example 0710

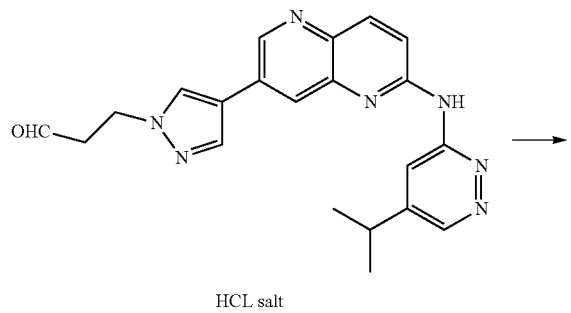

7-(1-(3-(3-Isopropoxyazetidin-1-yl)propyl)-1H-pyrazol-4-yl)-N-(5-isopropylpyridazin-3-yl)-1,5-naphthyridine-2-amine was obtained as a pale yellow solid in the same manner as in Example 0426-2.

¹H-NMR(DMSO-d₆)δ:10.68(1H,s),9.04(1H,d,J=1.8 Hz), 8.86(1H,d,J=1.8 Hz),8.72(1H,brs),8.49(1H,s),8.22(1H,d, J=9.3 Hz),8.21(1H,brs),8.18(1H,s),7.70(1H,d,J=9.3 Hz), 4.17(2H,t,J=6.9 Hz),4.12-4.00(1H,m),3.59-3.49(3H,m), 3.12-2.96(1H,m),2.71-2.63(2H,m),2.37(2H,t,J=6.6 Hz), 1.90-1.76(2H,m),1.33(6H,d,J=7.2 Hz),1.04(6H,d,J=6.0 Hz).

MSm/z(M+H):487.

Example 0711

The following compounds were obtained in the same manner as in Examples 0703-1 and 0646-3.

| Example No. | | |
|---|---|---|
| 0711 | | |
| 0711-1 | 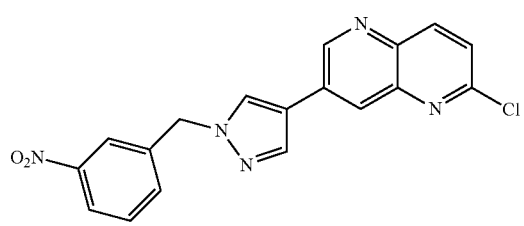 [SMILES: O=[N+]([O-])c1cccc(Cn2cc(-c3cnc4ccc(Cl)nc4c3)cn2)c1] | MS m/z (M + H): 366. |

| Example No. | | |
|---|---|---|
| 0711-2 | 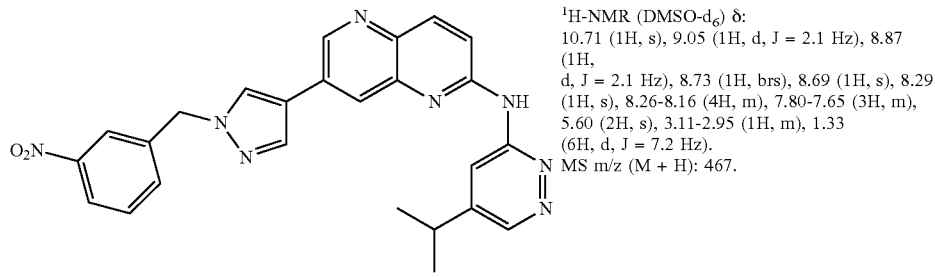 | ¹H-NMR (DMSO-d₆) δ: 10.71 (1H, s), 9.05 (1H, d, J = 2.1 Hz), 8.87 (1H, d, J = 2.1 Hz), 8.73 (1H, brs), 8.69 (1H, s), 8.29 (1H, s), 8.26-8.16 (4H, m), 7.80-7.65 (3H, m), 5.60 (2H, s), 3.11-2.95 (1H, m), 1.33 (6H, d, J = 7.2 Hz). MS m/z (M + H): 467. |

Example 0712

Example 0713

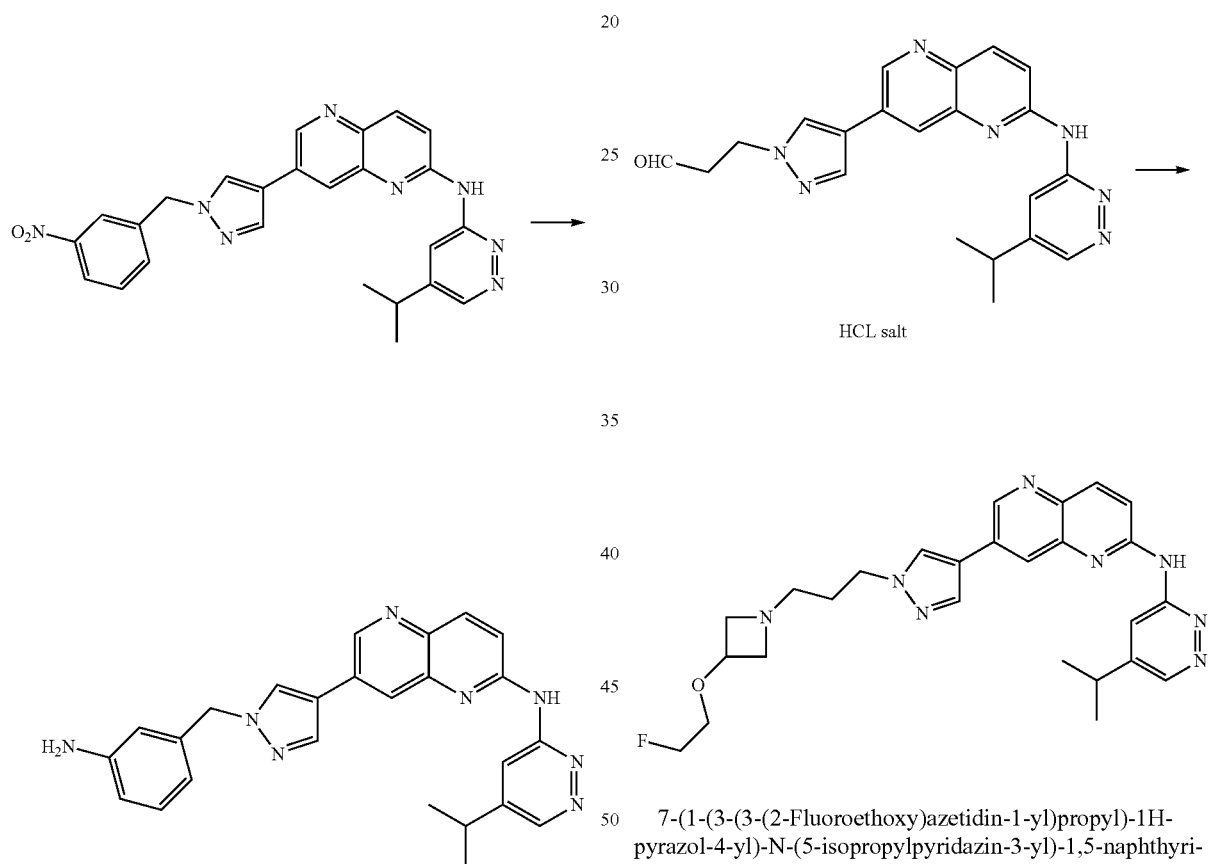

HCL salt 7-(1-(3-Aminobenzyl)-1H-pyrazol-4-yl)-N-(5-isopropylpyridazin-3-yl)-1,5-naphthyridine-2-amine was obtained as a pale yellow solid in the same manner as in Example 0705.

¹H-NMR(DMSO-d₆)δ:10.69(1H,s),9.05(1H,d,J=2.1 Hz), 8.86(1H,d,J=2.1 Hz),8.73(1H,brs),8.58(1H,s),8.22(2H,brs), 8.21(1H,d,J9.0 Hz),7.70(1H,d,J=9.0 Hz),6.98(1H,t,J=8.1 Hz),6.51-6.42(3H,m),5.23(2H,s),5.11(2H,brs),3.12-2.95 (1H,m),1.33(6H,d,J=6.6 Hz).

MSm/z(M+H):437.

7-(1-(3-(3-(2-Fluoroethoxy)azetidin-1-yl)propyl)-1H-pyrazol-4-yl)-N-(5-isopropylpyridazin-3-yl)-1,5-naphthyridine-2-amine was obtained as a pale yellow solid in the same manner as in Example 0426-2.

¹H-NMR(DMSO-d₆)δ:10.69(1H,s),9.04(1H,d,J=2.1 Hz), 8.87(1H,d,J=2.1 Hz),8.73(1H,brs),8.49(1H,s),8.21(1H,d, J=9.3 Hz),8.20(1H,d,J=2.1 Hz),8.18(1H,s),7.70(1H,d,J=9.3 Hz),4.60-4.38(2H,m),4.23-4.04(3H,m),3.64-3.44(4H,m), 3.11-2.96(1H,m),2.81-2.71(2H,m),2.39(2H,t,J=6.6 Hz), 1.90-1.78(2H m),1.33(6H,d,J=6.6 Hz).

MSm/z(M+H):491.

Example 0714

The following compounds were obtained in the same manner as in Examples 0699-1, 0667, and 0426-2.

| Example No. | | |
|---|---|---|
| 0714 | | |
| 0714-1 | 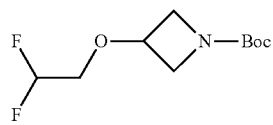 | $^1$H-NMR (DMSO-$d_6$) δ: 4.35-4.33 (1H, m), 4.03-4.00 (3H, m), 3.70-3.65 (5H, m), 1.37 (9H, s). |
| 0714-2 | 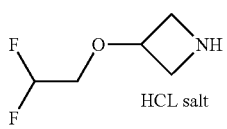 | $^1$H-NMR (DMSO-$d_6$) δ: 4.48-4.44 (1H, m), 4.14-4.12 (2H, m), 3.87 (1H, brs), 3.84-3.69 (4H, m). |
| 0714-3 | 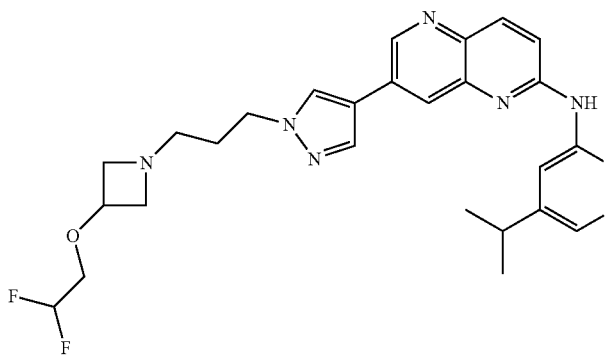 | $^1$H-NMR (DMSO-$d_6$) δ: 10.69 (1H, s), 9.04 (1H, d, J = 2.1 Hz), 8.87 (1H, d, J = 2.1 Hz), 8.73 (1H, d, J = 2.1 Hz), 8.49 (1H, s), 8.22 (1H, d, J = 9.3 Hz), 6.21 (1H, d, J = 2.1 Hz), 8.18 (1H, s), 7.70 (1H, d, J = 9.3 Hz), 6.33-5.90 (1H, m), 4.22-4.07 (3H, m), 3.72-3.47 (4H, m), 3.11-2.97 (1H, m), 2.82-2.75 (2H, m), 2.43-2.35 (2H, m), 1.93-1.76 (2H, m), 1.33 (6H, d, J = 7.2 Hz). MS m/z (M + H): 509. |

Example 0715

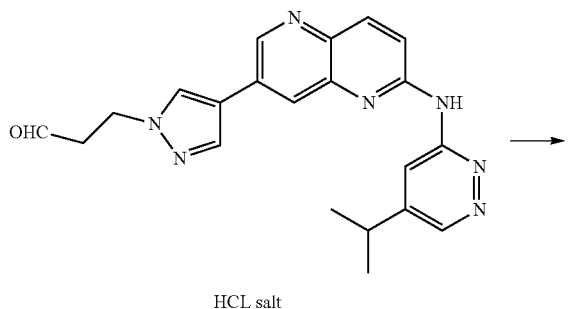

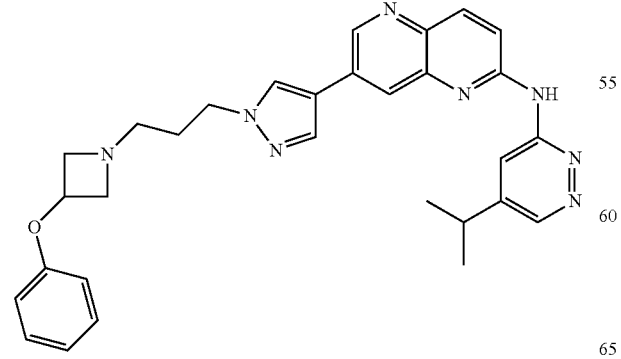

N-(5-isopropylpyridazin-3-yl)-7-(1-(3-(3-phenoxyazetidin-1-yl)propyl)-1H-pyrazol-4-yl)-1,5-naphthyridine-2-amine was obtained as a pale yellow solid in the same manner as in Example 0426-2.

$^1$H-NMR(DMSO-$d_6$)δ:10.69(1H,s),9.04(1H,d,J=2.1 Hz), 8.86(1H,d,J=2.1 Hz),8.73(1H,brs),8.24-8.16(4H,m),7.70 (1H,d,J=9.3 Hz),7.31-7.23(2H,m),6.93(1H,t,J=7.5 Hz), 6.86-6.79(2H,m),4.84-4.79(1H,m),4.20(2H,t,J=7.2 Hz),3.76 (2H,t,J=7.2 Hz),3.11-2.92(3H,m),2.50-2.43(2H,m),1.95-1.80(2H,m),1.33(6H,d,J=6.6 Hz).

MSm/z(M+H):521.

Example 0716

The following compounds were obtained in the same manner as in Examples 0703-1 and 0646-3.

| Example No. | | |
|---|---|---|
| 0716 | | |
| 0716-1 | 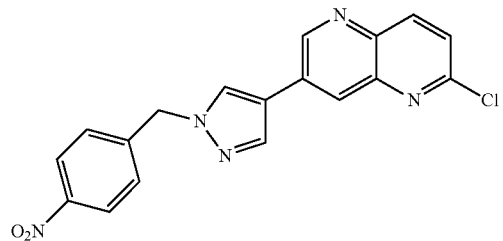 [SMILES: O=[N+]([O-])c1ccc(Cn2cc(-c3cnc4ccc(Cl)nc4c3)cn2)cc1] | MS m/z (M + H): 366. |
| 0716-2 | 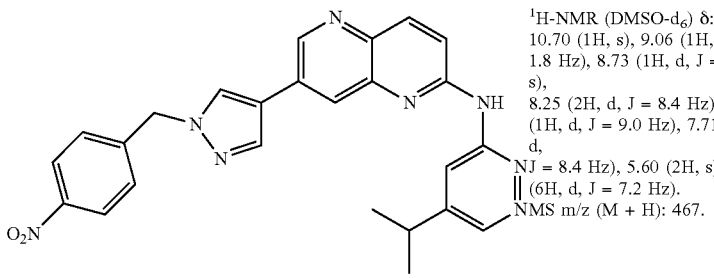 | ¹H-NMR (DMSO-d₆) δ:<br>10.70 (1H, s), 9.06 (1H, d, J = 1.8 Hz), 8.87 (1H, d, J = 1.8 Hz), 8.73 (1H, d, J = 1.8 Hz), 8.69 (1H, s), 8.30 (1H, s),<br>8.25 (2H, d, J = 8.4 Hz), 8.24 (1H, d, J = 1.8 Hz), 8.22 (1H, d, J = 9.0 Hz), 7.71 (1H, d, J = 9.0 Hz), 7.53 (2H, d,<br>J = 8.4 Hz), 5.60 (2H, s), 3.11-2.95 (1H, m), 1.33 (6H, d, J = 7.2 Hz).<br>MS m/z (M + H): 467. |

Example 0717

Example 0718

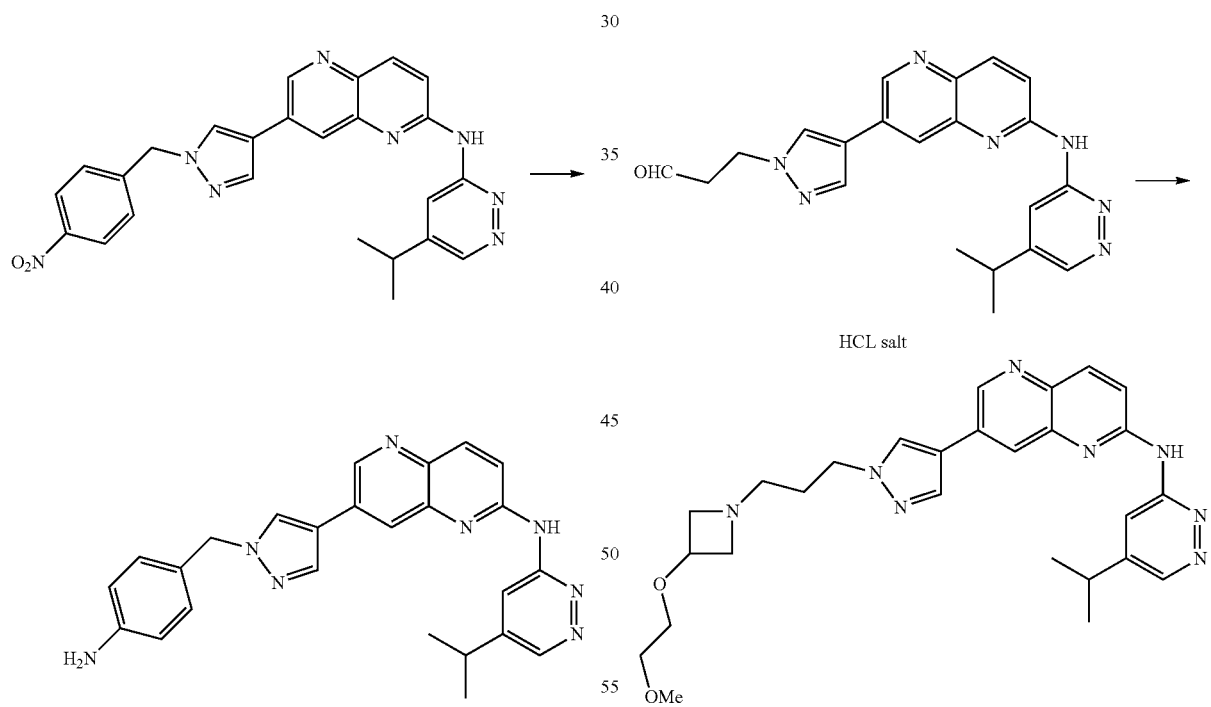

HCL salt 7-(1-(4-Aminobenzyl)-1H-pyrazol-4-yl)-N-(5-isopropylpyridazin-3-yl)-1,5-naphthyridine-2-amine was obtained as a yellow solid in the same manner as in Example 0705.

¹H-NMR(DMSO-d₆)δ:10.69(1H,s),9.03(1H,d,J=1.8 Hz), 8.86(1H,d,J=1.8 Hz),8.72(1H,brs),8.51(1H,s),8.21(1H,d, J=8.7 Hz),8.20(1H,d,J=1.8 Hz),8.17(1H,s),7.69(1H,d,J=8.7 Hz),7.04(2H,d,J=8.1 Hz),6.53(2H,d,J=8.1 Hz),5.17(2H,s), 5.10(2H,s),3.11-2.96(1H,m),1.33(6H,d,J=7.8 Hz).

MS m/z(M+H):437.

N-(5-isopropylpyridazin-3-yl)-7-(1-(3-(3-(2-methoxyethoxy)azetidin-1-yl)propyl)-1H-pyrazol-4-yl)-1,5-naphthyridine-2-amine was obtained as a pale yellow solid in the same manner as in Example 0426-2.

¹H-NMR(DMSO-d₆)δ:10.69(1H,s),9.04(1H,d,J=1.8 Hz), 8.86(1H,d,J=1.2 Hz),8.73(1H,d,J=1.2 Hz),8.49(1H,s),8.21 (1H,d,J=9.0 Hz),8.21(1H,d,J=1.8 Hz),8.18(1H,s),7.70(1H, J=9.0H),4.17(2H,d,J=7.2 Hz),4.11-3.97(1H,m),3.58-3.28

(6H,m),3.22(3H,s),3.11-2.96(1H,m),2.73(2H,dd,J=6.0,2.1 Hz),2.38(2H,d,J=6.6 Hz),1.90-1.78(2H,m),1.33(6H,d,J=6.6 Hz).

MSm/z(M+H):503.

Example 0719

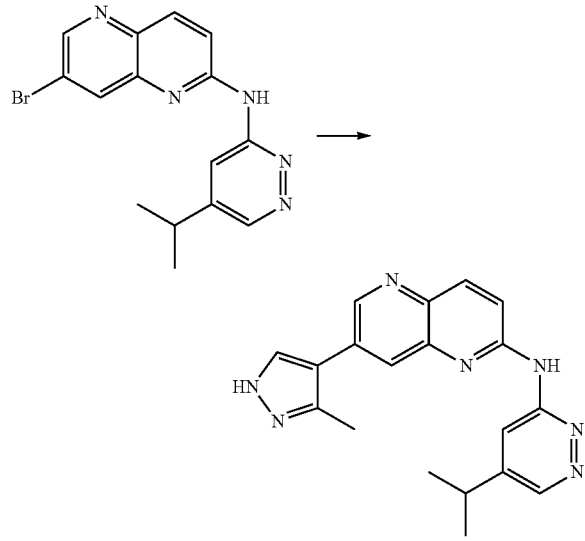

N-(5-isopropylpyridazin-3-yl)-7-(3-methyl-1H-pyrazol-4-yl)-1,5-naphthyridine-2-amine was obtained as a pale yellow solid in the same manner as in Example 0638.

$^1$H-NMR(DMSO-d$_6$)δ:12.89(1H,brs),10.71(1H,s),8.93 (1H,d,J=2.1 Hz),8.85(1H,d,J=2.1 Hz),8.73(1H,brs),8.24 (1H,d,J=9.3 Hz),8.08(2H,brs),7.74(1H,d,J=9.3 Hz),3.10-2.94(1H,m),2.50(3H,s),1.31(6H,d,J=7.2 Hz).

MSm/z(M+H):346.

Example 0720

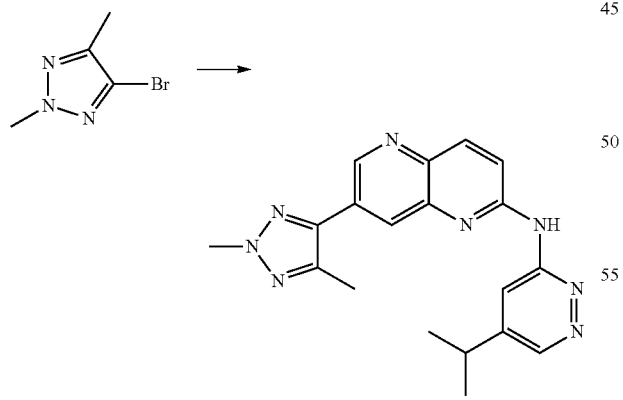

7-(2,5-Dimethyl-2H-1,2,3-triazol-4-yl)-N-(5-isopropylpyridazin-3-yl)-1,5-naphthyridine-2-amine was obtained as a pale yellow solid in the same manner as in Example 0421-1.

$^1$H-NMR(DMSO-d$_6$)δ:10.80(1H,s),9.08(1H,d,J=2.1 Hz), 8.87(1H,d,J=2.1 Hz),8.75(1H,brs),8.30(1H,brs),8.29(1H,d, J=8.1 Hz),7.81(1H,d,J=8.1 Hz),4.20(3H,s),3.13-2.96(1H, m),2.54(3H,s),1.31(6H,d,J=7.2 Hz).

MSm/z(M+H):361.

Example 0721

0721-1

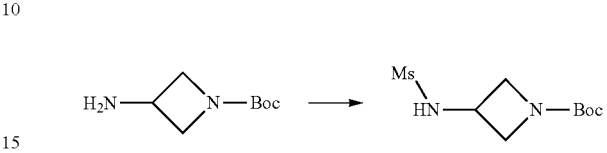

tert-Butyl 3-(methyl sulfonamide)azetidine-1-carboxylate was obtained in the same manner as in Example 0618-2.

$^1$H-NMR(DMSO-d$_6$)δ:4.24-4.22(1H,m),4.13-4.07(3H, m),3.73-3.72(2H,m),2.89(3H,s),1.37(9H,s).

0721-2

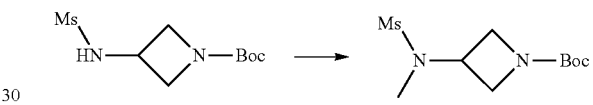

A mixture of tert-butyl 3-(methyl sulfonamide)azetidine-1-carboxylate (262 mg), iodomethane (98 μL), 60% sodium hydride (46 mg), and N,N-dimethylformamide (3 mL) was stirred at room temperature for 1 hour. After water and ethyl acetate were added to the reaction mixture, the organic layer was collected by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate-methanol), thereby obtaining tert-butyl 3-(N-methylmethyl sulfonamide)azetidine-1-carboxylate (214 mg).

$^1$H-NMR(DMSO-d$_6$)δ:4.51-4.46(1H,m),4.07-3.97(4H, m),2.86(3H,s),2.82(3H,s),1.38(9H,s).

0721-3

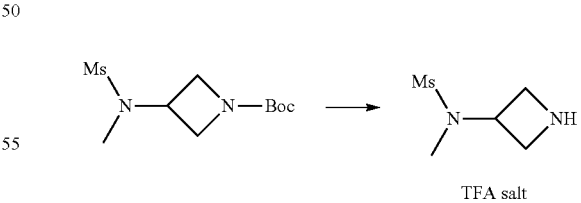

TFA salt

A mixture of tert-butyl 3-(N-methylmethyl sulfonamide) azetidine-1-carboxylate (214 mg), dichloromethane (4 mL), and trifluoroacetic acid (1.2 mL) was stirred at room temperature for 2 hours. The solvent was distilled off under reduced pressure, thereby obtaining N-(azetidin-3-yl)-N-methylmethane sulfonamide trifluoroacetate (347 mg).

$^1$H-NMR(DMSO-d$_6$)δ:4.20-4.09(4H,m),3.44(1H,q,J=7.0 Hz),2.94(3H,s),2.85(3H,s).

855
0721-4

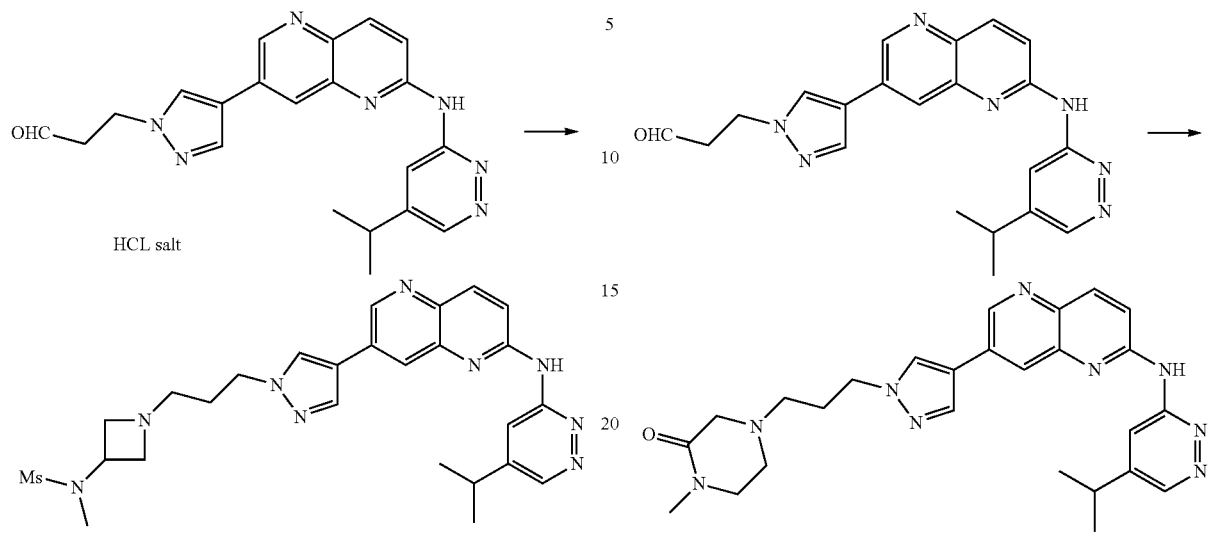

HCL salt

N-(1-(3-(4-(6-((5-isopropylpyridazin-3-yl)amino)-1,5-naphthyridin-3-yl)-1H-pyrazol-1-yl)propyl)azetidin-3-yl)-N-methylmethane sulfonamide was obtained as a pale yellow solid in the same manner as in Example 0426-2.
$^1$H-NMR(DMSO-$d_6$)δ:10.70(1H,s),9.04(1H,d,J=2.1 Hz), 8.87(1H,d,J=2.1 Hz),8.73(1H,brs),8.49(1H,s),8.31(1H,s), 8.21(1H,d,J=8.4 Hz),8.18(1H,s),7.70(1H,d,J=8.4 Hz),4.18 (2H,t,J=7.2 Hz),4.16-4.05(1H,m),3.46(2H,t,J=7.2 Hz),3.09-2.96(3H,m),2.84(3H,s),2.79(3H,s),2.40(2H,t,J=7.2 Hz), 1.92-1.78(2H,m),1.33(6H,d,J=7.2 Hz).
MSm/z(M+H):536.

Example 0722

The following compounds were obtained in the same manner as in Examples 0703-1 and 0646-3.

856
Example 0723

Triethylamine was added to a solution of hydrochloride (23 mg) of 1-methylpiperazin-2-one in dichloromethane (1 mL), followed by adjusting to pH 8. 3-(4-(6-((5-Isopropylpyridazin-3-yl)amino)-1,5-naphthyridin-3-yl)-1H-pyrazol-1-yl)propanal (19 mg), acetic acid (0.01 mL), and sodium triacetoxyborohydride (42 mg) were added thereto, followed by stirring at room temperature for 1 hour. The solvent was distilled off under reduced pressure, and the obtained residue was purified by silica gel column chromatography (ethyl acetate-methanol, NH silica), thereby obtaining 4-(3-(4-(6-((5-isopropylpyridazin-3-yl)amino)-1,5-naphthyridin-3-yl)-1H-pyrazol-1-yl)propyl)-1-methylpiperazin-2-one (4.4 mg) as a white solid.
$^1$H-NMR(DMSO-$d_6$)δ:10.70(1H,s),9.05(1H,d,J=1.8 Hz), 8.86(1H,d,J=2.1 Hz),8.72(1H,s),8.52(1H,s),8.24-8.18(3H,

| Example No. | | |
|---|---|---|
| 0722 | | |
| 0722-1 | 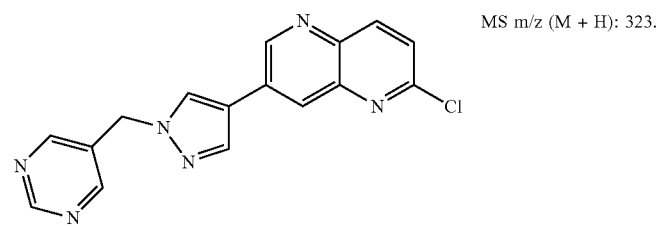 | MS m/z (M + H): 323. |
| 0722-2 | 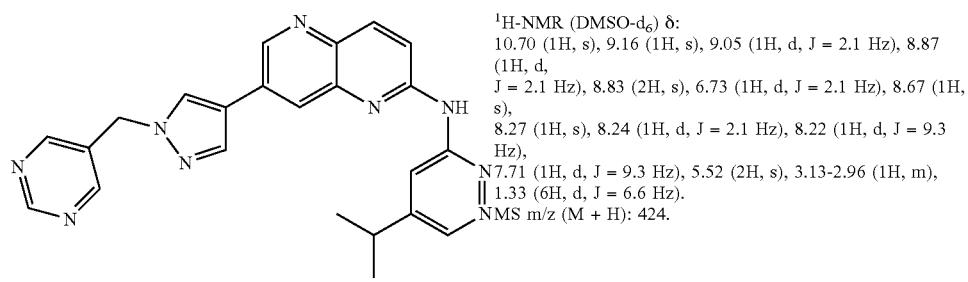 | $^1$H-NMR (DMSO-$d_6$) δ: 10.70 (1H, s), 9.16 (1H, s), 9.05 (1H, d, J = 2.1 Hz), 8.87 (1H, d, J = 2.1 Hz), 8.83 (2H, s), 6.73 (1H, d, J = 2.1 Hz), 8.67 (1H, s), 8.27 (1H, s), 8.24 (1H, d, J = 2.1 Hz), 8.22 (1H, d, J = 9.3 Hz), 7.71 (1H, d, J = 9.3 Hz), 5.52 (2H, s), 3.13-2.96 (1H, m), 1.33 (6H, d, J = 6.6 Hz). MS m/z (M + H): 424. | m),7.70(1H,d,J=9.3 Hz),4.24-4.17(2H,m),3.30-3.25(2H,m), 3.09-2.98(1H,m),2.87-2.83(2H,m),2.80(3H,s),2.66-2.60 (2H,m),2.40-2.32(2H,m),2.07-1.98(2H,m),1.34(6H,d,J=7.2 Hz).

MSm/z(M+H):486.

Example 0724

0724-1

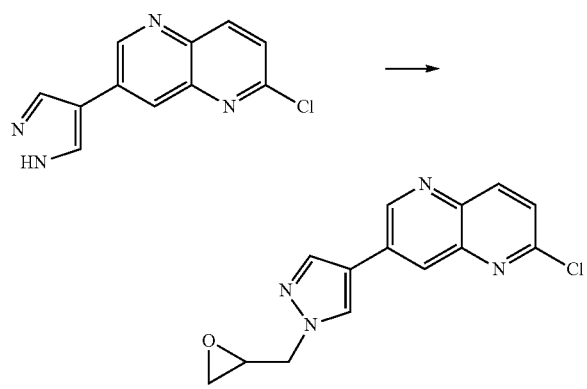

A suspension of 2-chloro-7-(1H-pyrazol-4-yl)-1,5-naphthyridine (460 mg), 2-(bromomethyl)oxirane (0.825 mL), and cesium carbonate (651 mg) in N,N-dimethylformamide (3 mL) was stirred at 50° C. for 1 hour. After the reaction mixture was cooled to room temperature, ethyl acetate and water were added thereto. The organic layer was collected by separation, washed with a saturated sodium chloride aqueous solution, and dried over anhydrous sodium sulfate, and the solvent was distilled off under reduced pressure, thereby obtaining 2-chloro-7-(1-(oxiran-2-ylmethyl)-1H-pyrazol-4-yl)-1,5-naphthyridine (561 mg) as pale yellow oily substance.

MSm/z(M+H):287.

0724-2

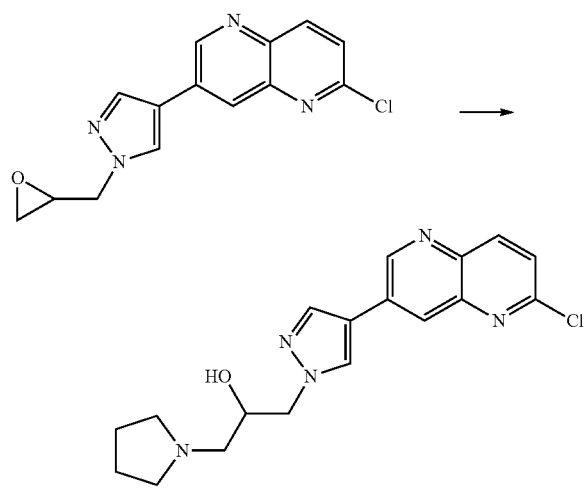

A solution of 2-chloro-7-(1-(oxiran-2-ylmethyl)-1H-pyrazol-4-yl)-1,5-naphthyridine (561 mg), and pyrrolidine (0.41 mL) in 1,4-dioxane (3 mL) was stirred at 70° C. for 1 hour. The solvent was distilled off under reduced pressure, and the obtained residue was purified by silica gel column chromatography (hexane-ethyl acetate, NH silica), thereby obtaining 1-(4-(6-chloro-1,5-naphthyridin-3-yl)-1H-pyrazol-1-yl)-3-(pyrrolidin-1-yl)propan-2-ol (192 mg) as a white solid.

MSm/z(M+H):358.

0724-3

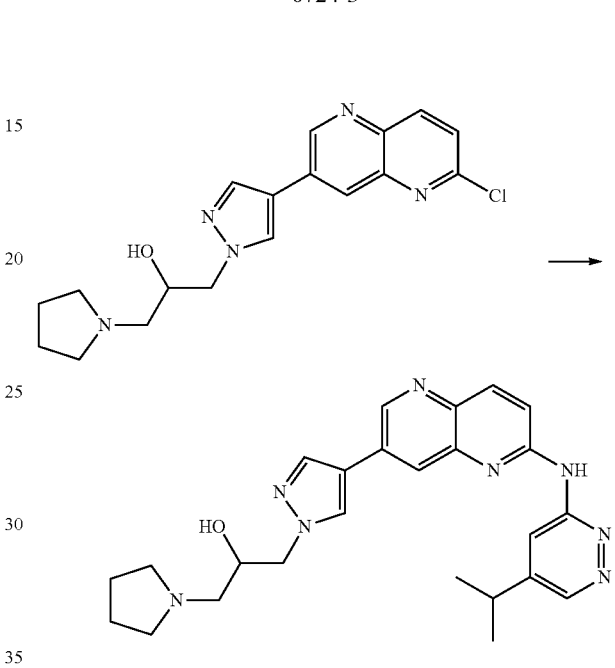

1-(4-(6-((5-Isopropylpyridazin-3-yl)amino)-1,5-naphthyridin-3-yl)-1H-pyrazol-1-yl)-3-(pyrrolidin-1-yl)propan-2-ol was obtained as a white solid in the same manner as in Example 0485-2.

$^1$H-NMR(DMSO-$d_6$)δ:10.70(1H,s),9.06(1H,d,J=1.8 Hz), 8.86(1H,d,J=1.8 Hz),8.74(1H,s),8.45(1H,s),8.24-8.18(3H, m),7.70(1H,d,J=9.3 Hz),5.04-4.90(1H,m),4.34-4.28(1H,m), 4.10-3.90(2H,m),3.48-3.31(2H,m),3.09-2.98(1H,m),2.46-2.37(4H,m),1.72-1.51(4H,m),1.34(6H,d,J=7.2 Hz).

MSm/z(M+H):459.

Example 0725

0725-1

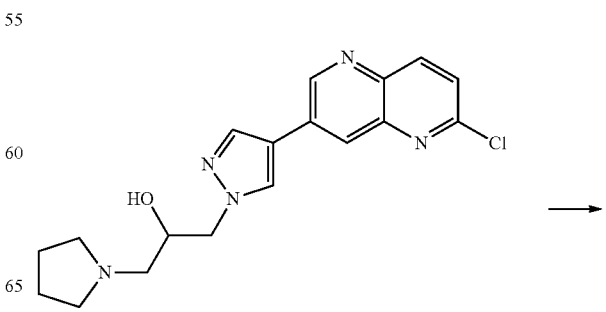

-continued

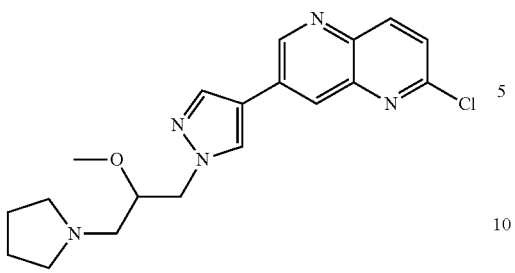

A suspension of 1-(4-(6-chloro-1,5-naphthyridin-3-yl)-1H-pyrazol-1-yl)-3-(pyrrolidin-1-yl)propan-2-ol (72 mg), and 60% sodium hydride (9.6 mg) in tetrahydrofuran (0.3 mL) was stirred at room temperature for 5 minutes. Methyl iodide (0.015 mL) was added thereto, followed by stirring at room temperature for 1 hour. The solvent was distilled off under reduced pressure, and the obtained residue was purified by silica gel column chromatography (ethyl acetate-hexane, NH silica), thereby obtaining 2-chloro-7-(1-(2-methoxy-3-(pyrrolidin-1-yl)propyl)-1H-pyrazol-4-yl)-1,5-naphthyridine (44 mg) as colorless oily substance.

MSm/z(M+H):372.

0725-2

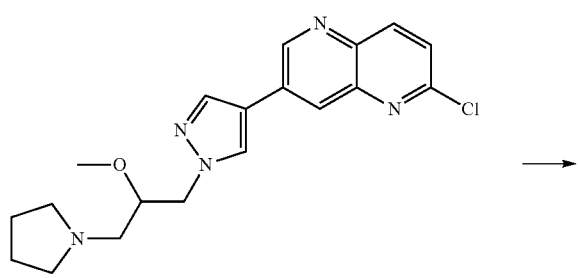

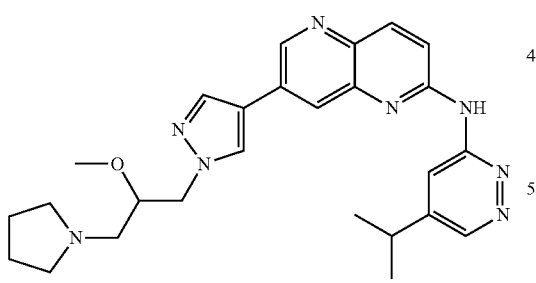

N-(5-isopropylpyridazin-3-yl)-7-(1-(2-methoxy-3-(pyrrolidin-1-yl)propyl)-1H-pyrazol-4-yl)-1,5-naphthyridine-2-amine was obtained as a white solid in the same manner as in Example 0485-2.

$^1$H-NMR(DMSO-d$_6$)δ:10.71(1H,s),9.06(1H,d,J=1.8 Hz), 8.86(1H,d,J=1.8 Hz),8.74(1H,s),8.47(1H,s),8.24-8.19(3H, m),7.71(1H,d,J=9.3 Hz),4.41-4.33(1H,m),4.24-4.51(1H,m), 3.77-3.71(1H,m),3.48-3.31(2H,m),3.23(3H,s),3.09-2.99 (1H,m),2.62-2.39(4H,m),1.72-1.52(4H,m),1.34(6H,d,J=7.2 Hz).

MSm/z(M+H):473.

Example 0726

0726-1

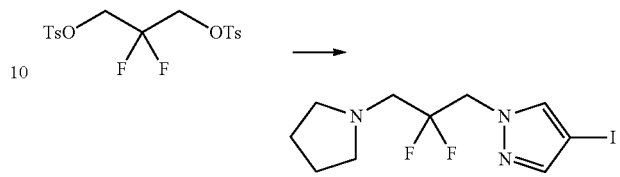

A suspension of (2,2-difluoropropane-1,3-diyl) bis(para-toluenesulfonate) (1.01 g), 4-iodo-1H-pyrazole (388 mg), and cesium carbonate (782 mg) in N,N-dimethylformamide (2 mL) was stirred at 70° C. for 1.5 hours. After the reaction mixture was cooled to room temperature, ethyl acetate and water were added thereto. The organic layer was collected by separation, washed with a saturated sodium chloride aqueous solution, and dried over anhydrous sodium sulfate, and the solvent was distilled off under reduced pressure. Pyrrolidine (1.5 mL) was added to the obtained residue, followed by stirring at 100° C. for 5 hours in a sealed tube. The solvent was distilled off under reduced pressure, and the obtained residue was purified by silica gel column chromatography (ethyl acetate-hexane, NH silica), thereby obtaining 1-(2,2-difluoro-3-(pyrrolidin-1-yl)propyl)-4-iodo-1H-pyrazole (240 mg) as colorless oily substance.

MSm/z(M+H):342.

0726-2

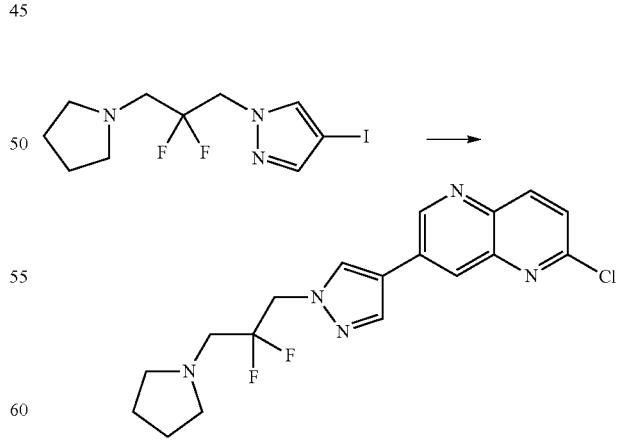

2-Chloro-7-(1-(2,2-difluoro-3-(pyrrolidin-1-yl)propyl)-1H-pyrazol-4-yl)-1,5-naphthyridine was obtained as a white solid in the same manner as in Example 0490.

MSm/z(M+H):378.

0726-3

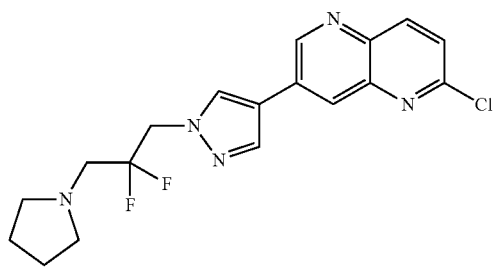

pressure. The obtained residue was purified by preparative thin layer silica gel chromatography (ethyl acetate-methanol), thereby obtaining (Z)-7-(1-(2-fluoro-3-(pyrrolidin-1-yl)-1-propen-1-yl)-1H-pyrazol-4-yl)-N-(5-isopropylpyridazin-3-yl)-1,5-naphthyridine-2-amine (7.9 mg) as a white solid.

$^1$H-NMR(DMSO-d$_6$)δ:10.74(1H,s),9.16(1H,d,J=2.1 Hz), 8.89-8.83(2H,m),8.74(1H,s),8.50(1H,s),8.39(1H,d,J=1.5 Hz),8.25(1H,d,J=9.3 Hz),7.73(1H,d,J=9.3 Hz),7.25(1H,d, J=28.2 Hz),4.09-3.97(2H,m),3.70-3.60(2H,m),3.15-3.00 (3H,m),1.94-1.88(4H,m),1.33(6H,d,J=7.2 Hz).
MSm/z(M+H):459.

Example 0727

The following compounds were obtained in the same manner as in Examples 0726, 0490, and 0485.

| Example No. | | |
|---|---|---|
| 0727 | | |
| 0727-1 | 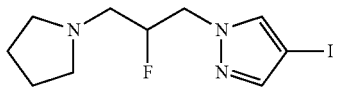 [SMILES: FC(CN1CCCC1)Cn1cc(I)cn1] | MS m/z (M + H): 324. |
| 0727-2 | 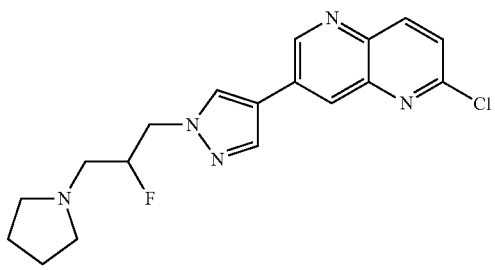 [SMILES: FC(CN1CCCC1)Cn1cc(-c2cnc3ccc(Cl)nc3c2)cn1] | MS m/z (M + H): 360. |
| 0727-3 | 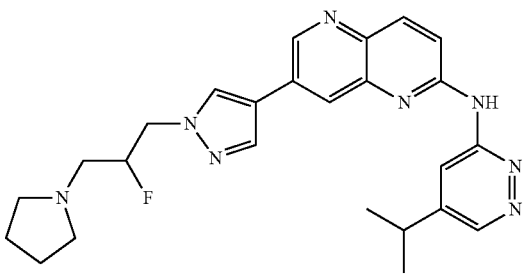 [SMILES: CC(C)c1cnnc(Nc2ccc3ncc(-c4cnn(CC(F)CN5CCCC5)c4)cc3n2)c1] | $^1$H-NMR (DMSO-d$_6$) δ: 10.71 (1H, s), 9.06 (1H, d, J = 2.1 Hz), 8.87 (1H, d, J = 1.8 Hz), 8.74 (1H, s), 8.55 (1H, s), 8.26-8.20 (3H, m), 7.71 (1H, d, J = 9.3 Hz), 5.17 (2H, d, J = 48.9 Hz), 4.62-4.44 (2H, m), 3.14-2.73 (7H, m), 1.90-1.71 (4H, m), 1.34 (6H, d, J = 7.2 Hz). MS m/z (M + H): 461. |

-continued

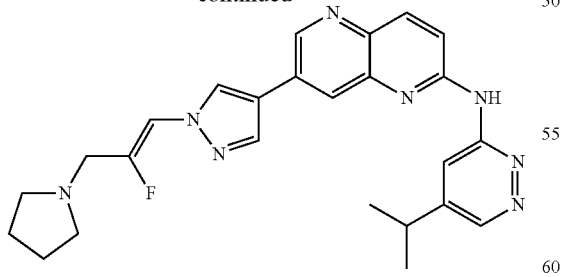

A suspension of 2-chloro-7-(1-(2,2-difluoro-3-(pyrrolidin-1-yl)propyl)-1H-pyrazol-4-yl)-1,5-naphthyridine (76 mg), 5-isopropylpyridazine-3-amine (55 mg), and potassium tert-butoxide (49 mg) in 1,4-dioxane (0.5 mL) was stirred at 120° C. for 4 hours in a sealed tube. The insolubles were filtered off, and the solvent was distilled off under reduced Example 0728

0728-1

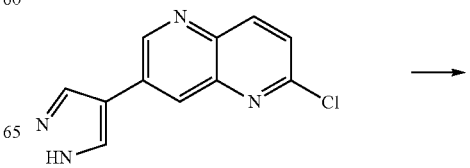

-continued

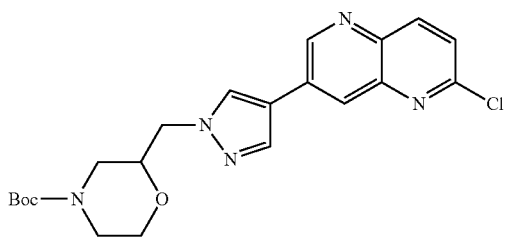

A suspension of 2-chloro-7-(1H-pyrazol-4-yl)-1,5-naphthyridine (231 mg), tert-butyl 2-((paratoluenesulfonyloxy)methyl)morpholine-4-carboxylate (371 mg), and potassium carbonate (166 mg) in N,N-dimethylformamide (1 mL) was stirred at 90° C. for 2 hours. After the reaction mixture was cooled to room temperature, ethyl acetate and water were added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-methanol), thereby obtaining tert-butyl 2-((4-(6-chloro-1,5-naphthyridin-3-yl)-1H-pyrazol-1-yl)methyl)morpholine-4-carboxylate (360 mg) as colorless oily substance.

MSm/z(M+H):430.

0728-2

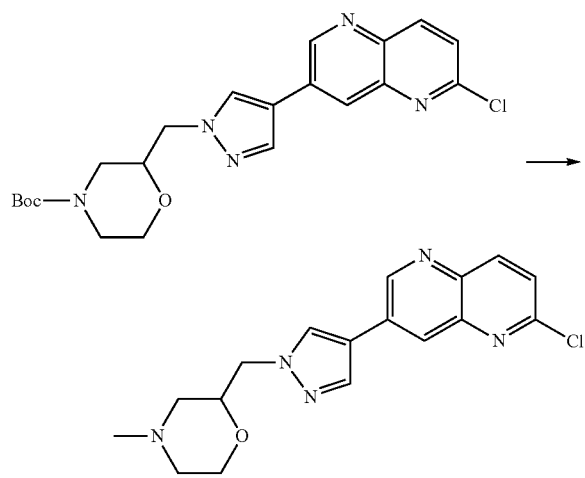

A 4 mol/L hydrogen chloride/1,4-dioxane solution (1 mL) and methanol (0.2 mL) were added to tert-butyl 2-((4-(6-chloro-1,5-naphthyridin-3-yl)-1H-pyrazol-1-yl)methyl)morpholine-4-carboxylate (360 mg), followed by stirring at room temperature for 1 hour, and the solvent was distilled off under reduced pressure. Triethylamine was added to a solution of the obtained residue in dichloromethane (1 mL), followed by adjusting to pH 8. A 37% (w/w) formaldehyde aqueous solution (0.2 mL), acetic acid (0.01 mL), and sodium triacetoxyborohydride (212 mg) was added thereto, followed by stirring at room temperature for 1 hour. The solvent was distilled off under reduced pressure, and the obtained residue was purified by silica gel column chromatography (ethyl acetate-methanol, NH silica), thereby obtaining 2-((4-(6-chloro-1,5-naphthyridin-3-yl)-1H-pyrazol-1-yl)methyl)-4-methylmorpholine (280 mg) as colorless oily substance.

MSm/z(M+H):344.

0728-3

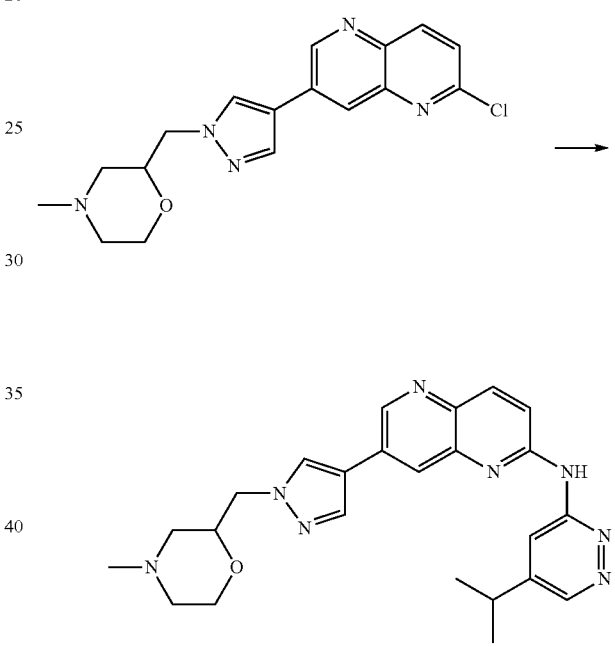

N-(5-isopropylpyridazin-3-yl)-7-(1-((4-methylmorpholin-2-yl)methyl)-1H-pyrazol-4-yl)-1,5-naphthyridine-2-amine was obtained as a white solid in the same manner as in Example 0726.

$^1$H-NMR(DMSO-d$_6$)δ:10.71(1H,s),9.05(1H,d,J=2.1 Hz), 8.87(1H,d,J=1.8 Hz),8.74(1H,s),8.48(1H,s),8.24-8.20(3H, m),7.71(1H,d,J=9.3 Hz),4.24(2H,d,J=5.7 Hz),3.92-3.77(2H, m),3.53-3.43(1H,m),3.11-2.90(1H,m),2.73-2.56(2H,m), 2.18(3H,s),2.02-1.94(1H,m)1.83-1.72(1H,m),1.34(6H,d, J=7.2 Hz).

MSm/z(M+H)445.

Example 0729

The following compounds were obtained in the same manner as in Examples 0724-2 and 0485-2.

| Example No. | | |
|---|---|---|
| 0729 | | |
| 0729-1 | 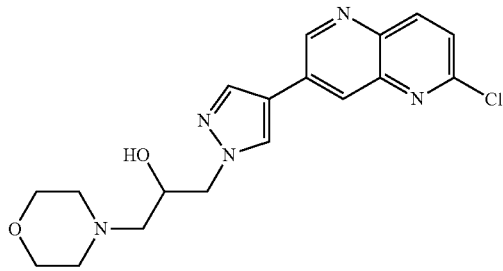 [SMILES: OC(CN1CCOCC1)Cn1cc(-c2cnc3ccc(Cl)nc3c2)cn1] | MS m/z(M + H): 374. |
| 0729-2 | 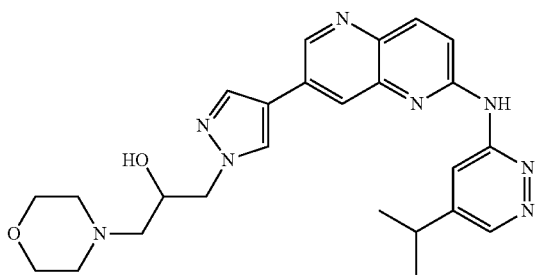 [SMILES: CC(C)c1cnnc(Nc2ccc3ncc(-c4cnn(CC(O)CN5CCOCC5)c4)cc3n2)c1] | ¹H-NMR(CDCl₃) δ: 9.39(1H, s), 8.94(1H, d, J = 2.0 Hz), 8.91(1H, d, J = 2.0 Hz), 8.83(1H, d, J = 2.0 Hz), 8.25(1H, d, J = 9.2 Hz), 8.12(1H, d, J = 2.0 Hz), 8.01(1H, s), 7.98(1H, s), 7.65(1H, d, J = 9.2 Hz), 4.39(1H, d, J = 10.6 Hz), 4.25-4.11(2H, m), 3.80-3.67(5H, m), 3.12-3.03(1H, m), 2.69-2.62(2H, m), 2.51-2.32(4H, m), 1.43(6H, d, J = 6.6 Hz). MS m/z(M + H): 475. |
Example 0730
The following compounds were obtained in the same manner as in Examples 0725-1 and 0485-2.
| Example No. | | |
|---|---|---|
| 0730 | | |
| 0730-1 | 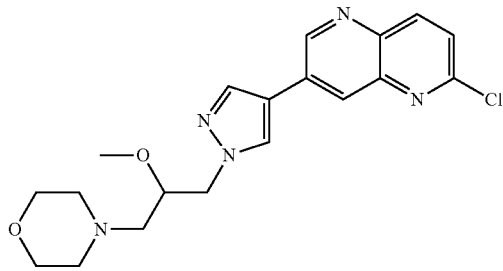 [SMILES: COC(CN1CCOCC1)Cn1cc(-c2cnc3ccc(Cl)nc3c2)cn1] | MS m/z(M + H): 388. |
| 0730-2 | 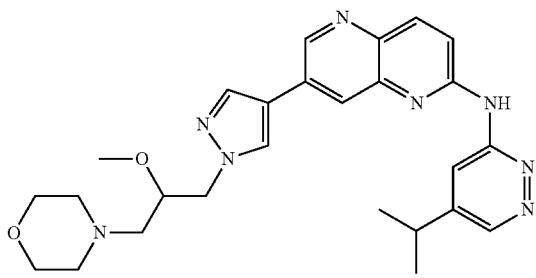 [SMILES: COC(CN1CCOCC1)Cn1cc(-c2cnc3ccc(Nc4cc(C(C)C)cnn4)nc3c2)cn1] | ¹H-NMR(CDCl₃)δ: 8.94-8.89(2H, m), 8.84(1H, s), 8.81(1H, s), 8.25 (1H, d, J = 8.6 Hz), 8.11(1H, s), 7.98(1H, s), 7.95(1H, s), 7.53(1H, d, J = 8.6 Hz), 4.50(1H, dd, J = 14.0, 3.6 Hz), 4.23(1H, dd, J = 14.0, 7.3 Hz), 3.83-3.70(5H, m), 3.36(3H, s), 3.12-3.01(1H, m), 2.58-2.42(6H, m), 1.42(6H, d, J = 6.6 Hz). MS m/z(M + H): 489. |

Example 0731

0731-1

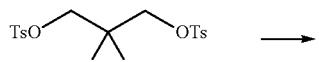

| Example No. | | |
|---|---|---|
| 0731 | | |
| 0731-2 | 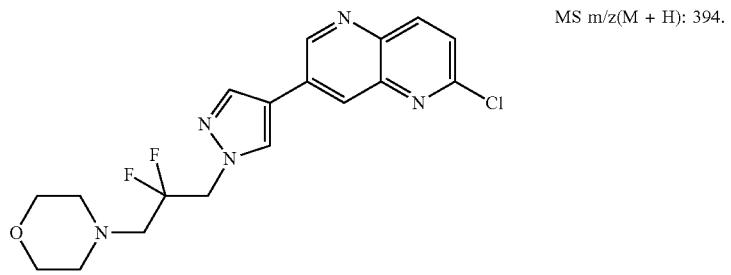 | MS m/z(M + H): 394. |
| 0731-3 | 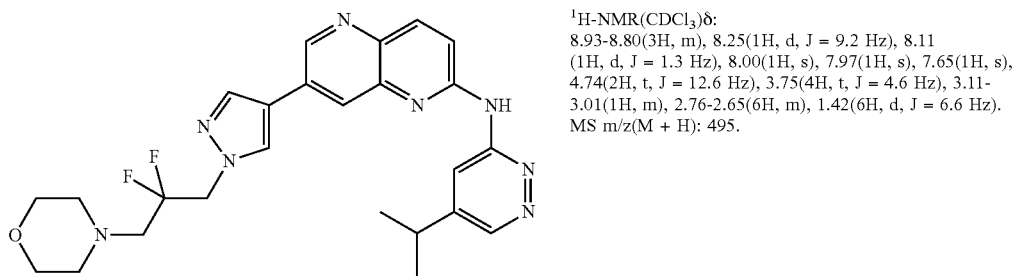 | ¹H-NMR(CDCl₃)δ:<br>8.93-8.80(3H, m), 8.25(1H, d, J = 9.2 Hz), 8.11 (1H, d, J = 1.3 Hz), 8.00(1H, s), 7.97(1H, s), 7.65(1H, s), 4.74(2H, t, J = 12.6 Hz), 3.75(4H, t, J = 4.6 Hz), 3.11-3.01(1H, m), 2.76-2.65(6H, m), 1.42(6H, d, J = 6.6 Hz).<br>MS m/z(M + H): 495. |

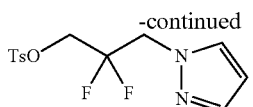

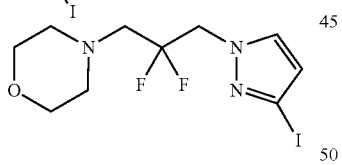

Cesium carbonate (163 mg), N,N-dimethylformamide (1 mL), and 3-iodo-1H-pyrazole (155 mg) were added to (2,2-difluoropropane-1,3-diyl) bis(4-methylbenzenesulfonate) (420 mg), followed by stirring at 70° C. for 4 hours. The reaction mixture was cooled to room temperature, and water and ethyl acetate were added thereto. The organic layer was collected by separation, washed with a saturated sodium chloride aqueous solution, and dried over anhydrous sodium sulfate, and the solvent was distilled off under reduced pressure. Morpholine (1.5 mL) was added to the obtained residue, followed by stirring at 100° C. for 4 hours. The reaction mixture was cooled to room temperature, the solvent was distilled off under reduced pressure, and the obtained residue was purified by silica gel column chromatography (hexane-ethyl acetate, NH silica), thereby obtaining 4-(2,2-difluoro-3-(3-iodo-1H-pyrazol-1-yl)propyl)morpholine (268 mg) as colorless oily substance.

MSm/z(M+H):358.

0731-2 and 0731-3

The following compounds were obtained in the same manner as in Examples 0385-7 and 0485-2.

Example 0732

0732-1

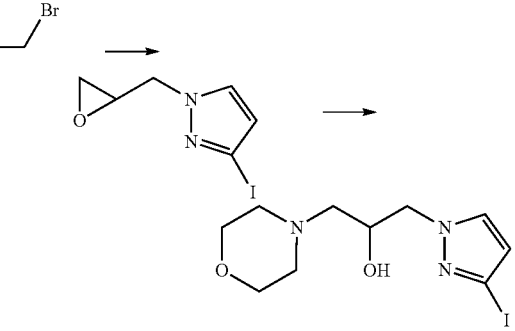

Cesium carbonate (13 g), epibromohydrin (4.92 mL), and N,N-dimethylformamide (15 mL) were added to 3-iodo-1H-pyrazole (3.88 g), followed by stirring at 50° C. for 1 hour. The reaction mixture was cooled to room temperature, and water and ethyl acetate were added thereto. The organic layer was collected by separation, washed with a saturated sodium chloride aqueous solution, and dried over anhydrous sodium sulfate, and the solvent was distilled off under reduced pressure.

1,4-Dioxane (20 mL) and morpholine (2.6 mL) were added to the obtained residue, followed by stirring at 90° C. for 1 hour. The reaction mixture was cooled to room temperature, the solvent was distilled off under reduced pressure, and the obtained residue was purified by silica gel column chromatography (hexane-ethyl acetate-methanol), thereby obtaining 1-(3-iodo-1H-pyrazol-1-yl)-3-morpholinopropan-2-ol (2.0 g) as a white solid.

MSm/z(M+H):338.

0732-2

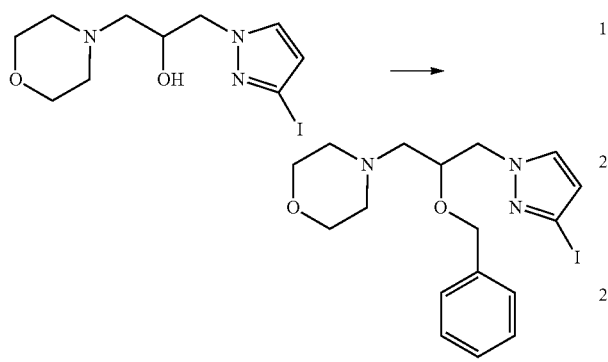

60% sodium hydride (14 mg) was added to a solution of 1-(3-iodo-1H-pyrazol-1-yl)-3-morpholinopropan-2-ol (100 mg) in N,N-dimethylformamide (1 mL) under ice-cooling, followed by stirring for 1 hour. Benzyl bromide (53 µL) was added to the reaction mixture, followed by stirring at room temperature for 1.5 hours. After water was added to the reaction mixture, the resultant product was extracted with ethyl acetate, and the organic layer was washed with a saturated sodium chloride aqueous solution, and dried over anhydrous sodium sulfate. The solvent was distilled off under reduced pressure, and the obtained residue was purified by silica gel column chromatography (hexane-ethyl acetate), thereby obtaining 4-(2-(benzyloxy)-3-(3-iodo-1H-pyrazol-1-yl)propyl)morpholine (60 mg) as colorless oily substance.

MSm/z(M+H):428.

0732-3 and 0732-4

The following compounds were obtained in the same manner as in Examples 0385-7 and 0485-2.

| Example No. |
| --- |
| 0732 |

| 0732-3 | 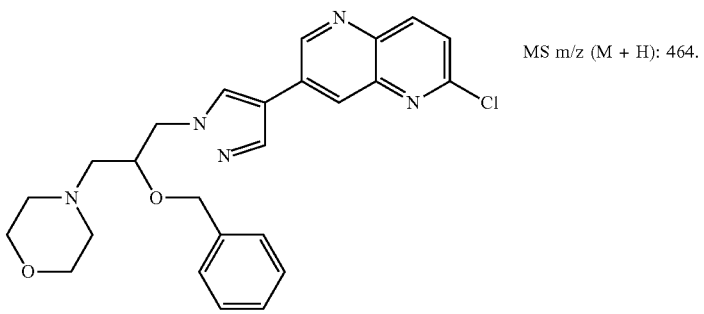 | MS m/z (M + H): 464. |
| --- | --- | --- |
| 0732-4 | 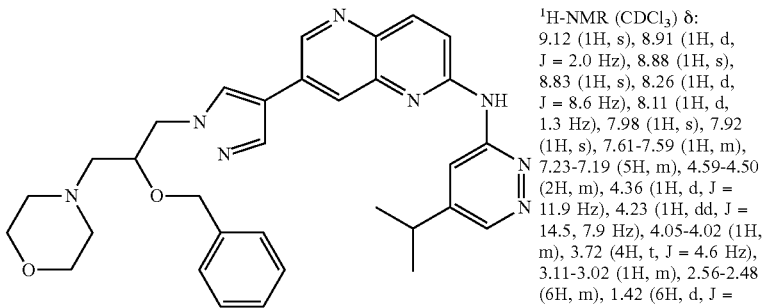 | $^1$H-NMR (CDCl$_3$) δ: 9.12 (1H, s), 8.91 (1H, d, J = 2.0 Hz), 8.88 (1H, s), 8.83 (1H, s), 8.26 (1H, d, J = 8.6 Hz), 8.11 (1H, d, 1.3 Hz), 7.98 (1H, s), 7.92 (1H, s), 7.61-7.59 (1H, m), 7.23-7.19 (5H, m), 4.59-4.50 (2H, m), 4.36 (1H, d, J = 11.9 Hz), 4.23 (1H, dd, J = 14.5, 7.9 Hz), 4.05-4.02 (1H, m), 3.72 (4H, t, J = 4.6 Hz), 3.11-3.02 (1H, m), 2.56-2.48 (6H, m), 1.42 (6H, d, J = 7.3 Hz). MS m/z (M + H): 565. |

Example 0733

The following compounds were obtained in the same manner as in Examples 0731-1, 0385-7 and 0485-2.

| Example No. | | |
|---|---|---|
| 0733 | | |
| 0733-1 | 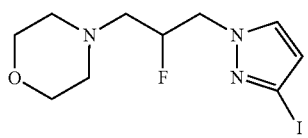 [SMILES: FC(CN1CCOCC1)Cn1ccc(I)n1] | MS m/z (M + H): 340. |
| 0733-2 | 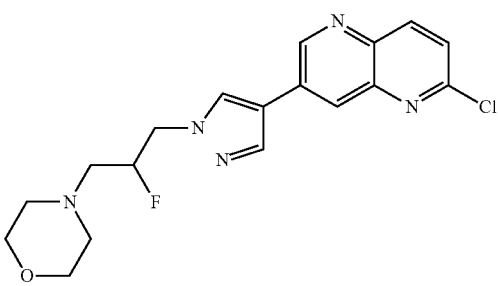 [SMILES: N=C/C(=C\NCC(F)CN1CCOCC1)c1cnc2ccc(Cl)nc2c1] | MS m/z (M + H): 376. |
| 0733-3 | 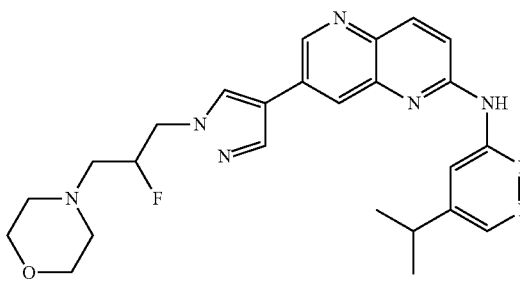 | ¹H-NMR (CDCl₃) δ: 9.22 (1H, s), 8.93 (1H, d, J = 2.0 Hz), 8.88 (1H, s), 8.83 (1H, s), 8.25 (1H, d, J = 8.6 Hz), 8.12 (1H, d, J = 2.0 Hz), 8.00 (1H, s), 7.95 (1H, s), 7.62 (1H, d, J = 8.6 Hz), 5.08 (1H, d, J = 48.2 Hz), 4.65-4.42 (2H, m), 3.74 (4H, t, J = 4.6 Hz), 3.08-3.06 (1H, m), 2.70 (1H, t, J = 5.0 Hz), 2.61-2.57 (5H, m), 1.43 (6H, d, J = 6.6 Hz). MS m/z (M + H): 477. |

Example 0734

0734-1

0734-2

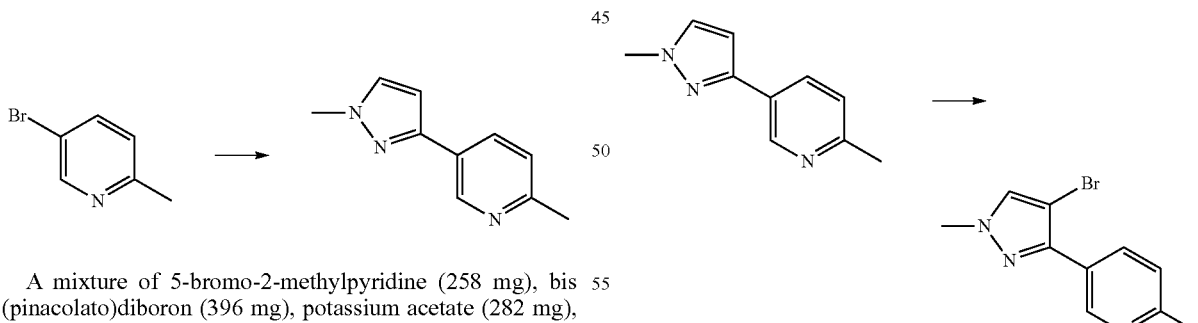

A mixture of 5-bromo-2-methylpyridine (258 mg), bis(pinacolato)diboron (396 mg), potassium acetate (282 mg), (1,1'-bis(diphenylphosphino)ferrocene)palladium(II) dichloride-dichloromethane adduct (49 mg), and 1,4-dioxane (5 mL) was stirred at 100° C. for 2.5 hours. 3-Bromo-1-methyl-1H-pyrazole (200 mg), sodium carbonate (254 mg), bis(di-tert-butyl(4-dimethylaminophenyl)phosphine)dichloropalladium(II) (42 mg), and water (0.5 mL) were added thereto, followed by stirring at 100° C. for 6 hours. The reaction mixture was cooled to room temperature, the solvent was distilled off under reduced pressure, and the obtained residue was purified by silica gel column chromatography (hexane-ethyl acetate, NH silica), thereby obtaining 2-methyl-5-(1-methyl-1H-pyrazol-3-yl)pyridine (190 mg) as yellow oily substance.

MSm/z(M+H):174.

N-bromosuccinimide (129 mg) was added to a solution of 2-methyl-5-(1-methyl-1H-pyrazol-3-yl)pyridine (190 mg) in N,N-dimethylformamide (1 mL) under ice-cooling, followed by stirring at the same temperature for 0.5 hours. After ethyl acetate and a 10% sodium hydrogen sulfite aqueous solution were added to the obtained reaction mixture, the organic layer was collected by separation, washed with a saturated sodium chloride aqueous solution, and dried over anhydrous sodium sulfate. The solvent was distilled off under reduced pressure, and the obtained residue was purified by silica gel column chromatography (ethyl acetate-hexane), thereby obtaining 5-(4-bromo-1-methyl-1H-pyrazol-3-yl)-2-methylpyridine (160 mg) as yellow oily substance.

MSm/z(M+H):252.

0734-3 and 0734-4

The following compounds were obtained in the same manner as in Examples 0385-7 and 0485-2.

| Example No. | | |
|---|---|---|
| 0734 | | |
| 0734-3 | 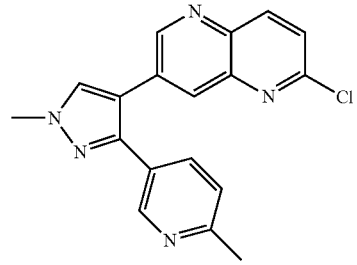 [SMILES: Cc1ccc(-c2nn(C)cc2-c2cnc3ccc(Cl)nc3c2)cn1] | MS m/z (M + H): 336. |
| 0734-4 | 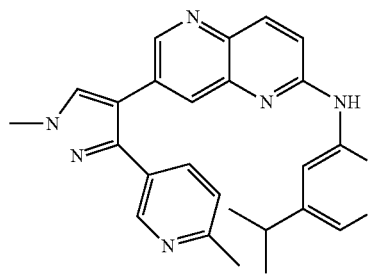 | $^1$H-NMR (CDCl$_3$) δ: 9.78 (1H, s), 8.90 (1H, s), 8.80 (1H, d, J = 2.0 Hz), 8.66 (2H, s), 8.24 (1H, d, J = 8.6 Hz), 7.94 (1H, d, J = 2.0 Hz), 7.77-7.67 (3H, m), 7.13 (1H, d, J = 8.6 Hz), 4.07 (3H, s), 3.04-2.95 (1H, m), 2.56 (3H, s), 1.34 (6H, d, J = 7.3 Hz). MS m/z (M + H): 437. |

Example 0735

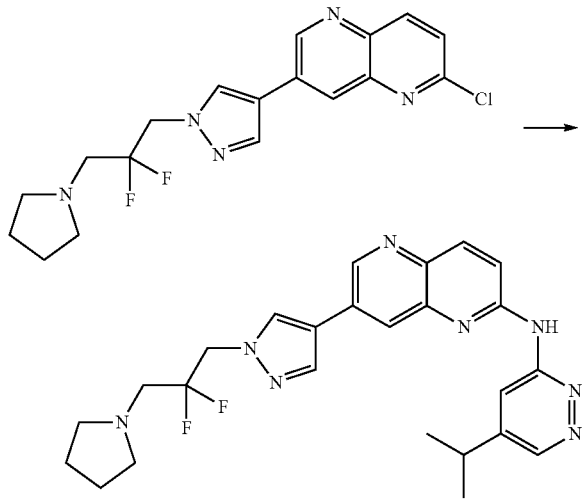

7-(1-(2,2-Difluoro-3-(pyrrolidin-1-yl)propyl)-1H-pyrazol-4-yl)-N-(5-isopropylpyridazin-3-yl)-1,5-naphthyridine-2-amine was obtained as a white solid in the same manner as in Example 0485-2.

$^1$H-NMR(CDCl$_3$)δ:8.94(1H,s),8.82(2H,s),8.72(1H,s), 8.25(1H,d,J=8.9 Hz),8.12(1H,s),8.01(1H,s),7.98(1H,s),7.52 (1H,d,J=8.9 Hz),4.72(2H,t,J=12.9 Hz),3.06(1H,s),2.87(2H, t,J=13.9 Hz),2.69(4H,t,J=3.6 Hz),1.82(4H,t,J=3.6 Hz),1.42 (6H,d,J=6.6 Hz).

MS m/z(M+H):479.

Examples 0736 to 0738

The following compounds were obtained in the same manner as in Examples 0734-1, 0734-2, 0385-7 and 0485-2.

| Example No. | | |
|---|---|---|
| 0736 | | |
| 0736-1 | 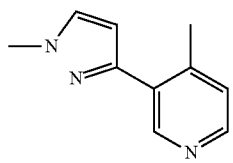 | MS m/z (M + H): 174. |
| 0736-2 | 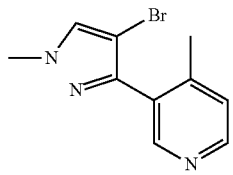 | MS m/z (M + H): 254. |
| 0736-3 | 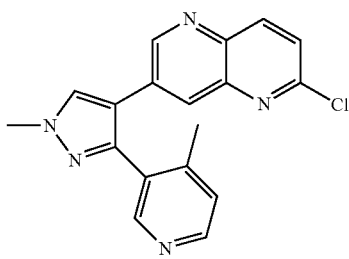 [SMILES: Cc1ccncc1-c1nn(C)cc1-c1cnc2ccc(Cl)nc2c1] | MS m/z (M + H): 336. |
| 0736-4 | 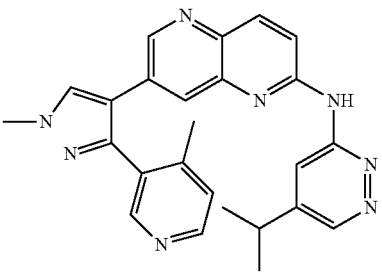 [SMILES: CN/C=C(\C(=N)c1cnccc1C)c1cnc2ccc(Nc3cc(C(C)C)cnn3)nc2c1] | $^1$H-NMR (CDCl$_3$) δ: 9.73 (1H, s), 8.83 (1H, s), 8.79 (1H, s), 8.64 (1H, s), 8.57 (1H, s), 8.50 (1H, d, J = 4.6 Hz), 8.19 (1H, d, J = 9.5 Hz), 7.86 (1H, s), 7.68 (1H, d, J = 9.5 Hz), 7.67 (1H, s), 7.17 (1H, d, J = 4.6 Hz), 4.09 (3H, s), 3.04-2.95 (1H, m), 2.14 (3H, s), 1.36 (6H, d, J = 6.6 Hz). MS m/z (M + H): 437. |

| Example No. | | |
|---|---|---|
| 0737 | | |
| 0737-1 | 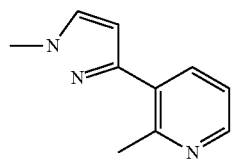 | MS m/z (M + H): 174. |
| 0737-2 | 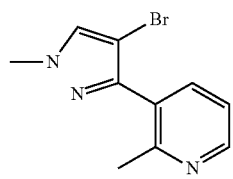 | MS m/z (M + H): 254. |
| 0737-3 | 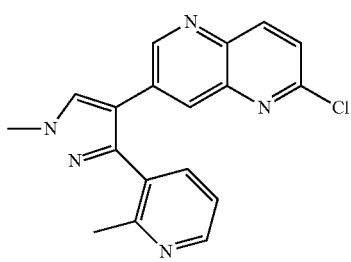 [SMILES: CN/C=C(\C(=N)c1cccnc1C)c1cnc2ccc(Cl)nc2c1] | MS m/z (M + H): 336. |
| 0737-4 | 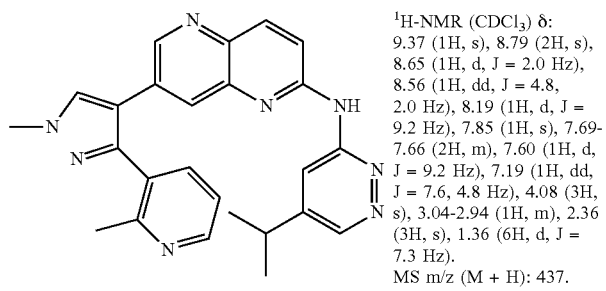 | $^1$H-NMR (CDCl$_3$) δ: 9.37 (1H, s), 8.79 (2H, s), 8.65 (1H, d, J = 2.0 Hz), 8.56 (1H, dd, J = 4.8, 2.0 Hz), 8.19 (1H, d, J = 9.2 Hz), 7.85 (1H, s), 7.69-7.66 (2H, m), 7.60 (1H, d, J = 9.2 Hz), 7.19 (1H, dd, J = 7.6, 4.8 Hz), 4.08 (3H, s), 3.04-2.94 (1H, m), 2.36 (3H, s), 1.36 (6H, d, J = 7.3 Hz).<br>MS m/z (M + H): 437. |
| 0738 | | |
| 0738-1 | 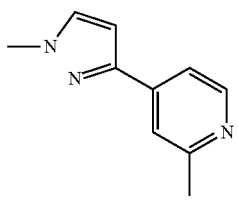 | MS m/z (M + H): 174. |

| Example No. | | |
|---|---|---|
| 0738-2 | 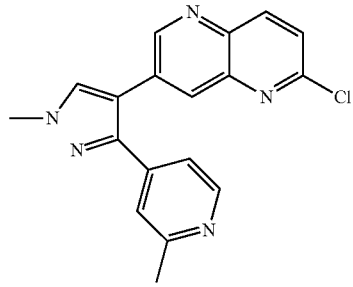 [SMILES: CN/C=C(\C(=N)c1ccnc(C)c1)c1cnc2ccc(Cl)nc2c1] | MS m/z (M + H): 336. |
| 0738-3 | 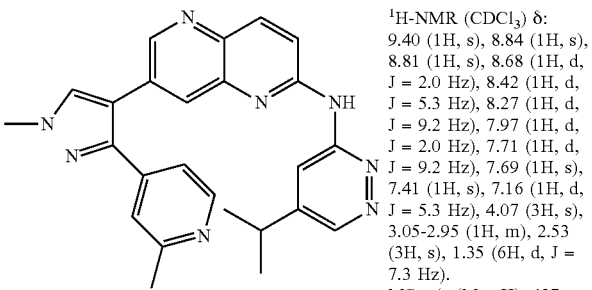 | $^1$H-NMR (CDCl$_3$) δ: 9.40 (1H, s), 8.84 (1H, s), 8.81 (1H, s), 8.68 (1H, d, J = 2.0 Hz), 8.42 (1H, d, J = 5.3 Hz), 8.27 (1H, d, J = 9.2 Hz), 7.97 (1H, d, J = 2.0 Hz), 7.71 (1H, d, J = 9.2 Hz), 7.69 (1H, s), 7.41 (1H, s), 7.16 (1H, d, J = 5.3 Hz), 4.07 (3H, s), 3.05-2.95 (1H, m), 2.53 (3H, s), 1.35 (6H, d, J = 7.3 Hz). MS m/z (M + H): 437. |

Example 0739

0739-1

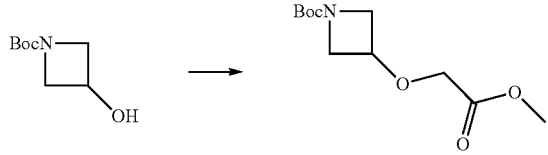 [SMILES: CC(C)(C)OC(=O)N1CC(O)C1 ; COC(=O)COC1CN(C(=O)OC(C)(C)C)C1]

60% sodium hydride (144 mg) was added to a solution of tert-butyl 3-hydroxyazetidine-1-carboxylate (520 mg) in N,N-dimethylformamide (5 mL), followed by stirring at room temperature for 0.5 hours. 2-Methyl bromoacetate (389 μL) was added thereto, followed by stirring at room temperature for 1 hour, and stirring at 50° C. for 3 hours. After water and ethyl acetate were added to the reaction mixture, the organic layer was collected by separation, washed with a saturated sodium chloride aqueous solution, and dried over anhydrous sodium sulfate. The solvent was distilled off under reduced pressure, and the obtained residue was purified by silica gel column chromatography (ethyl acetate-hexane), thereby obtaining tert-butyl 3-(2-methoxy-2-oxoethoxy)azetidine-1-carboxylate (570 mg) as colorless oily substance.

0739-2

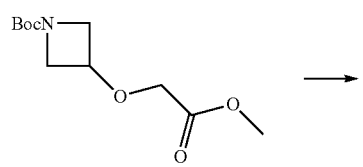

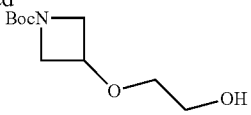

A 3 mol/L lithium borohydride/tetrahydrofuran solution (1.4 mL) was added to a solution of tert-butyl 3-(2-methoxy-2-oxoethoxy)azetidine-1-carboxylate (500 mg) in tetrahydrofuran (10 mL), followed by stirring at room temperature for 40 minutes. After water, a saturated citric acid aqueous solution, and ethyl acetate were added sequentially to the reaction mixture, the organic layer was collected by separation, washed with a saturated sodium chloride aqueous solution, and dried over anhydrous sodium sulfate. The solvent was distilled off under reduced pressure, thereby obtaining tert-butyl 3-(2-hydroxyethoxy)azetidine-1-carboxylate (281 mg) as colorless oily substance.

0739-3

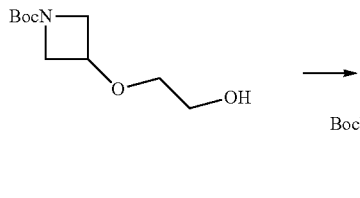

Triethylamine (345 μL) and methanesulfonyl chloride (192 μL) were added to a solution of tert-butyl 3-(2-hydroxyethoxy)azetidine-1-carboxylate (270 mg) in methylene chloride (6 mL) under ice-cooling, followed by stirring at the same temperature for 15 minutes, and stirring at 50°

C. for 15 minutes. The reaction mixture was purified by silica gel column chromatography (ethyl acetate-hexane), thereby obtaining tert-butyl 3-(2-((methylsulfonyl)oxy)ethoxy)azetidine-1-carboxylate (290 mg) as colorless oily substance.

0739-4

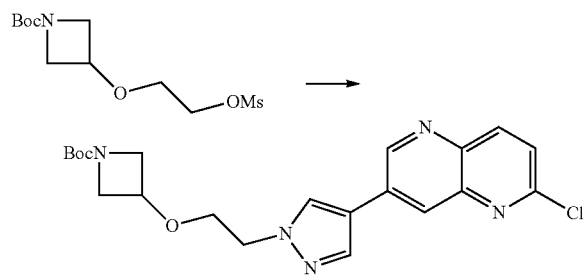

2-Chloro-7-(1H-pyrazol-4-yl)-1,5-naphthyridine (277 mg), cesium carbonate (391 mg), and N,N-dimethylformamide (3 mL) were added to tert-butyl 3-(2-((methylsulfonyl)oxy)ethoxy)azetidine-1-carboxylate (290 mg), followed by stirring at 60° C. for 1.5 hours. After the reaction mixture was cooled to room temperature, water and ethyl acetate were added thereto, the organic layer was collected by separation, washed with a saturated sodium chloride aqueous solution, and dried over anhydrous sodium sulfate. The solvent was distilled off under reduced pressure, and the obtained residue was purified by silica gel column chromatography (ethyl acetate-hexane-methanol), thereby obtaining tert-butyl 3-(2-(4-(6-chloro-1,5-naphthyridin-3-yl)-1H-pyrazol-1-yl)ethoxy)azetidine-1-carboxylate (325 mg) as colorless oily substance.
MSm/z(M+H):430.

0739-5

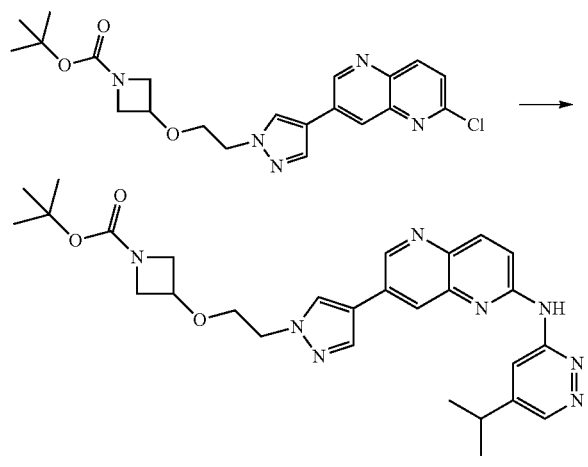

tert-Butyl 3-(2-(4-(6-((5-isopropylpyridazin-3-yl)amino)-1,5-naphthyridin-3-yl)-1H-pyrazol-1-yl)ethoxy)azetidine-1-carboxylate was obtained as a white solid in the same manner as in Example 0485-2.
$^1$H-NMR(CDCl$_3$)δ:9.11(1H,s),8.94(1H,d,J=1.5 Hz),8.87 (1H,s),8.82(1H,s),8.25(1H,d,J=9.2 Hz),8.12(1H,d,J=1.5 Hz),7.99(1H,s),7.93(1H,s),7.60(1H,d,J=9.2 Hz),4.40(2H,t,J=5.3 Hz),4.25-4.17(1H,m),4.06(1H,d,J=6.6 Hz),4.03(1H,d,J=6.6 Hz),3.84-3.75(4H,m),3.11-3.01(1H,m),1.42(6H,d,J=6.6 Hz),1.40(9H,s).
MSm/z(M+H):531.

Example 0740

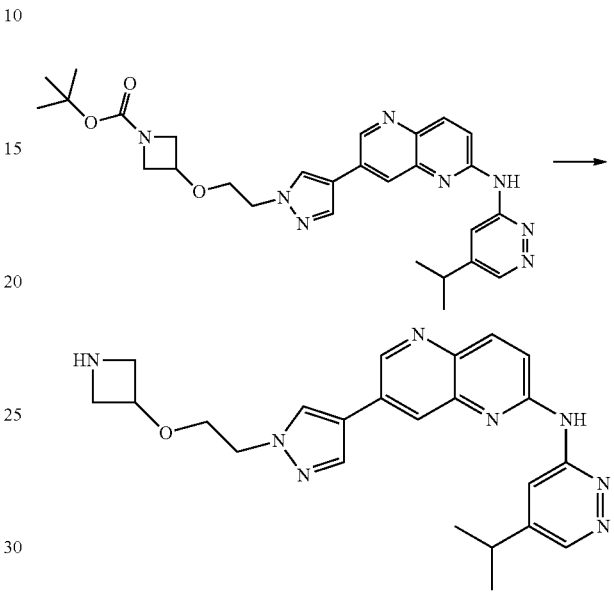

Trifluoroacetic acid (1 mL) was added to tert-butyl3-(2-(4-(6-((5-isopropylpyridazin-3-yl)amino)-1,5-naphthyridin-3-yl)-1H-pyrazol-1-yl)ethoxy)azetidine-1-carboxylate (50 mg), followed by stirring at room temperature for 20 minutes. The solvent was distilled off under reduced pressure, and the obtained residue was purified by silica gel column chromatography (ethyl acetate-methanol, NH silica), thereby obtaining 7-(1-(2-(azetidin-3-yloxy)ethyl)-1H-pyrazol-4-yl)-N-(5-isopropylpyridazin-3-yl)-1,5-naphthyridine-2-amine (8 mg) as a pale yellow solid.
$^1$H-NMR(CDCl$_3$)δ:8.94(1H,s)8.82(2H,d,J=2.0 Hz),8.74 (1H,s),8.25(1H,d,J=9.2 Hz),8.12(1H,d,J=2.0 Hz),7.98(1H,s),7.96(1H,s),7.51(1H,d,J=9.2 Hz),4.39(2H,t,J=5.0 Hz),4.33-4.31(1H,m),3.80(2H,t,J=5.0 Hz),3.70-3.64(2H,m),3.58-3.49(2H,m),3.10-3.01(1H,m),1.42(6H,d,J=7.3 Hz).
MSm/z(M+H):431.

Example 0741

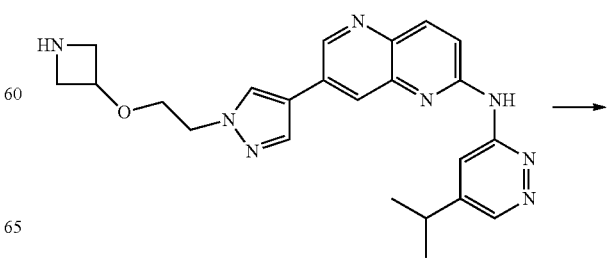

-continued

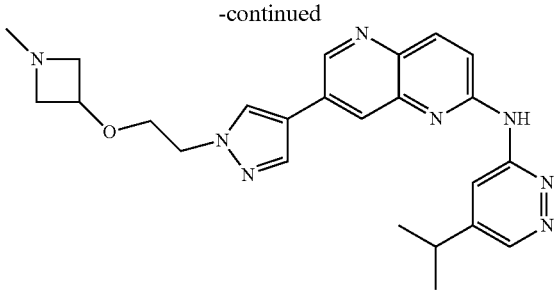

A 36.0% to 38.0% formaldehyde aqueous solution (3 µL) and sodium triacetoxyborohydride (6 mg) were added to a suspension of 7-(1-(2-(azetidin-3-yloxy)ethyl)-1H-pyrazol-4-yl)-N-(5-isopropylpyridazin-3-yl)-1,5-naphthyridine-2-amine (4 mg) in methylene chloride (0.3 mL), followed by stirring at room temperature for 20 minutes. Water was added to the reaction mixture, the solvent was distilled off under reduced pressure, and the obtained residue was purified by silica gel column chromatography (ethyl acetate-methanol, NH silica), thereby obtaining N-(5-isopropylpyridazin-3-yl)-7-(1-(2-((1-methylazetidin-3-yl)oxy)ethyl)-1H-pyrazol-4-yl)-1,5-naphthyridine-2-amine (3.74 mg) as a white solid.

$^1$H-NMR(CDCl$_3$)δ:10.02(1H,s),8.98(1H,s),8.93(1H,d,J=2.0 Hz),8.83(1H,s),8.25(1H,d,J=8.3 Hz),8.11(1H,d,J=2.0 Hz),7.98(1H,s),7.95(1H,s),7.78(1H,d,J=8.3 Hz),4.38(2H,t,J=5.3 Hz),4.12-4.04(1H,m),3.79(2H,t,J=5.3 Hz),3.59(2H,td,J=6.2,2.0 Hz),3.12-3.03(1H,m),2.88(2H,td,J=6.2,2.0 Hz),2.32(3H,s),1.43(6H,d,J=6.6 Hz).

MS m/z(M+H):445.

Examples 0742 and 0743

The following compounds were obtained in the same manner as in Example 0741.

| Example No. | | |
|---|---|---|
| 0742 | 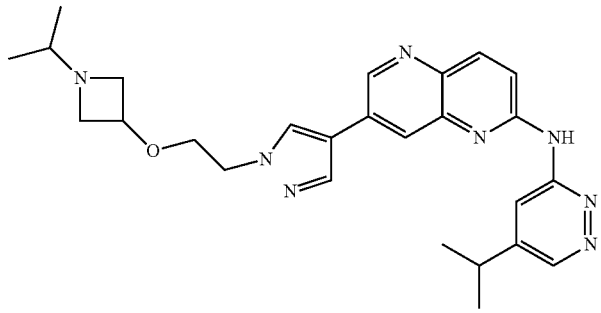 [SMILES: CC(C)c1cnnc(Nc2ccc3ncc(/C(C=N)=C/NCCOC4CN(C(C)C)C4)cc3n2)c1] | $^1$H-NMR (CDCl$_3$) δ: 9.23 (1H, s), 8.94 (1H, d, J = 2.0 Hz), 8.89 (1H, s), 8.83 (1H, s), 8.25 (1H, d, J = 9.2 Hz), 8.11 (1H, d, J = 2.0 Hz), 7.98 (1H, s), 7.95 (1H, s), 7.62 (1H, d, J = 9.2 Hz), 4.38 (2H, t, J = 5.0 Hz), 4.13-4.05 (1H, m), 3.80 (2H, t, J = 5.0 Hz), 3.62-3.53 (2H, m), 3.11-3.01 (1H, m), 2.89-2.82 (2H, m), 2.33-2.25 (1H, m), 1.43 (6H, d, J = 6.6 Hz), 0.92 (6H, d, J = 5.9 Hz). MS m/z (M + H): 473. |
| 0743 | 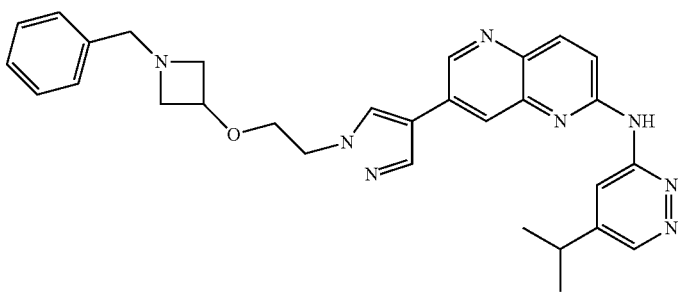 [SMILES: CC(C)c1cnnc(Nc2ccc3ncc(/C(C=N)=C/NCCOC4CN(Cc5ccccc5)C4)cc3n2)c1] | $^1$H-NMR (CDCl$_3$) δ: 9.46 (1H, s), 8.94 (1H, s), 8.92 (1H, s), 8.83 (1H, s), 8.25 (1H, d, J = 9.2 Hz), 8.11 (1H, s), 7.98 (1H, s), 7.95 (1H, s), 7.66 (1H, d, J = 9.2 Hz), 7.25-7.19 (5H, m), 4.38 (2H, t, J = 5.1 Hz), 4.18-4.10 (1H, m), 3.79 (2H, t, J = 5.1 Hz), 3.59-3.55 (4H, m), 3.11-3.01 (1H, m), 2.95-2.89 (2H, m), 1.42 (6H, d, J = 6.6 Hz). MS m/z (M + H): 521. |

Examples 0744 and 0745
The following compounds were obtained in the same manner as in Examples 0732-2, 0385-7 and 0485-2.
| Example No. | | |
|---|---|---|
| 0744 | | |
| 0744-1 | 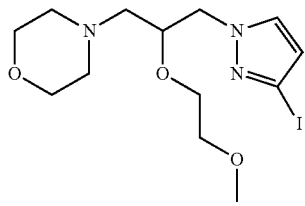 [SMILES: COCCOC(CN1CCOCC1)Cn1ccc(I)n1] | MS m/z (M + H): 396. |
| 0744-2 | 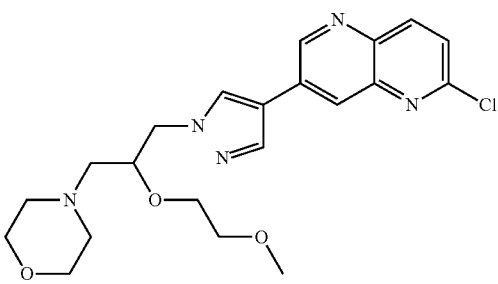 [SMILES: COCCOC(CN/C=C(\C=N)c1cnc2ccc(Cl)nc2c1)CN1CCOCC1] | MS m/z (M + H): 432. |
| 0744-3 | 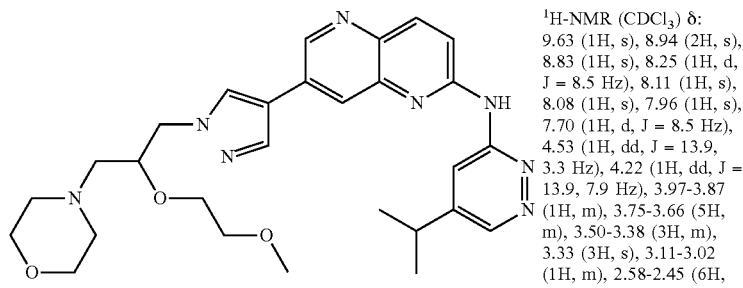 | $^1$H-NMR (CDCl$_3$) δ: 9.63 (1H, s), 8.94 (2H, s), 8.83 (1H, s), 8.25 (1H, d, J = 8.5 Hz), 8.11 (1H, s), 8.08 (1H, s), 7.96 (1H, s), 7.70 (1H, d, J = 8.5 Hz), 4.53 (1H, dd, J = 13.9, 3.3 Hz), 4.22 (1H, dd, J = 13.9, 7.9 Hz), 3.97-3.87 (1H, m), 3.75-3.66 (5H, m), 3.50-3.38 (3H, m), 3.33 (3H, s), 3.11-3.02 (1H, m), 2.58-2.45 (6H, m), 1.43 (6H, d, J = 6.6 Hz). MS m/z (M + H): 533. |
| 0745 | | |
| 0745-1 | 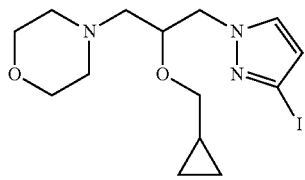 [SMILES: Ic1ccn(CC(CN2CCOCC2)OCC2CC2)n1] | MS m/z (M + H): 392. |
| 0745-2 | 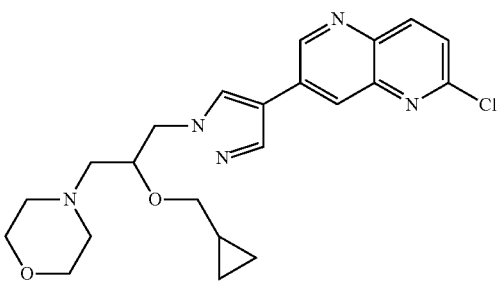 [SMILES: N=C/C(=C\NCC(CN1CCOCC1)OCC1CC1)c1cnc2ccc(Cl)nc2c1] | MS m/z (M + H): 428. |

| Example No. | | |
|---|---|---|
| 0745-3 | 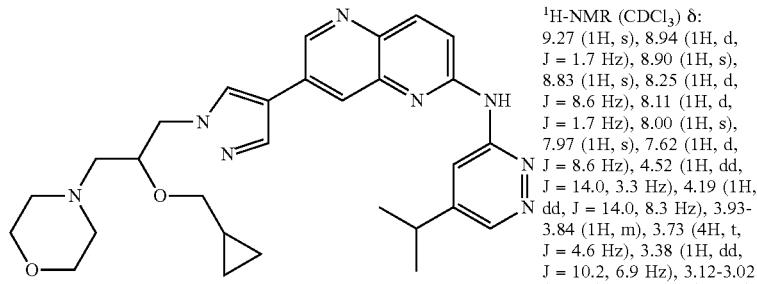 | ¹H-NMR (CDCl₃) δ: 9.27 (1H, s), 8.94 (1H, d, J = 1.7 Hz), 8.90 (1H, s), 8.83 (1H, s), 8.25 (1H, d, J = 8.6 Hz), 8.11 (1H, d, J = 1.7 Hz), 8.00 (1H, s), 7.97 (1H, s), 7.62 (1H, d, J = 8.6 Hz), 4.52 (1H, dd, J = 14.0, 3.3 Hz), 4.19 (1H, dd, J = 14.0, 8.3 Hz), 3.93-3.84 (1H, m), 3.73 (4H, t, J = 4.6 Hz), 3.38 (1H, dd, J = 10.2, 6.9 Hz), 3.12-3.02 (2H, m), 2.56-2.44 (6H, m), 1.42 (6H, d, J = 6.6 Hz), 0.98-0.91 (1H, m), 0.49-0.44 (2H, m), 0.13-0.07 (2H, m). MS m/z (M + H): 529. |

Example 0746

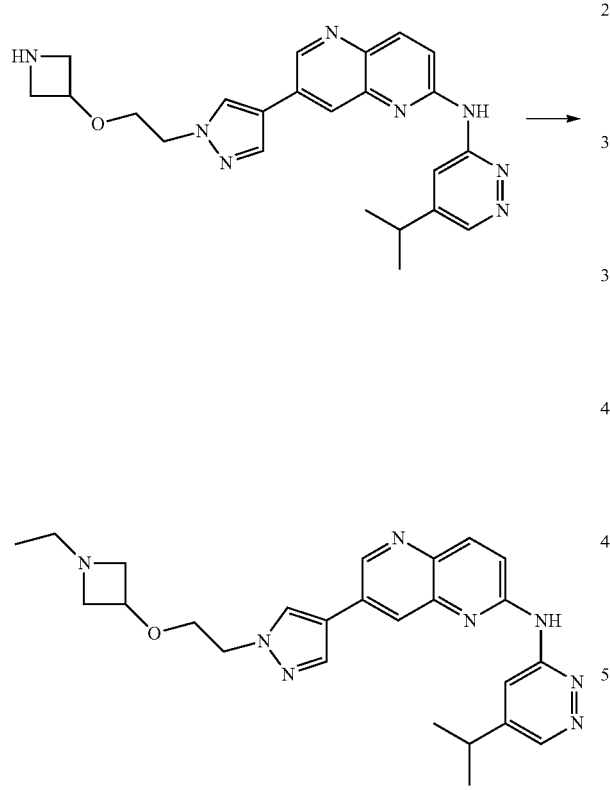

7-(1-(2-((1-Ethylazetidin-3-yl)oxy)ethyl)-1H-pyrazol-4-yl)-N-(5-isopropylpyridazin-3-yl)-1,5-naphthyridine-2-amine was obtained as a pale yellow solid in the same manner as in Example 0741.

¹H-NMR(CDCl₃)δ:8.98-8.88(2H,m),8.83(1H,s),8.25(1H,d,J=8.6 Hz),8.11(1H,s),7.98(1H,s),7.95(1H,s),7.78-7.60(1H,m),4.38(2H,t,J=5.2 Hz),4.15-4.07(1H,m),3.80(2H,t,J=5.2 Hz),3.57(2H,dd,J=6.9,3.5 Hz),3.12-3.02(1H,m),2.82(2H,dd,J=6.9,3.5 Hz),2.44(2H,q,J=7.3 Hz),1.43(6H,d,J=6.6 Hz),0.94(3H,t,J=7.3 Hz).

MSm/z(M+H):459.

Example 0747

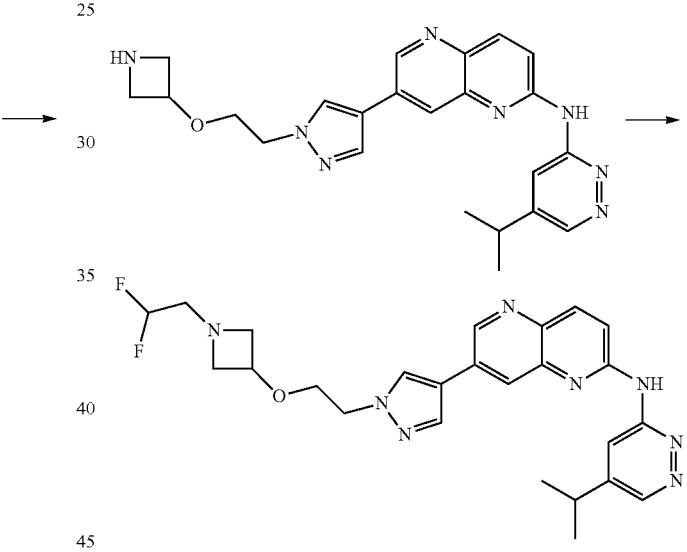

Cesium carbonate (6 mg) and 2,2-difluoroethyl trifluoromethanesulfonate (3 mg) were added to a suspension of 7-(1-(2-(azetidin-3-yloxy)ethyl)-1H-pyrazol-4-yl)-N-(5-isopropylpyridazin-3-yl)-1,5-naphthyridine-2-amine (5 mg) in tetrahydrofuran (0.5 mL), followed by stirring at room temperature for 80 minutes. Water (0.5 mL) was added to the reaction mixture, the solvent was distilled off under reduced pressure, and the obtained residue was purified by silica gel column chromatography (ethyl acetate-hexane-methanol, NH silica), thereby obtaining 7-(1-(2-((1-(2,2-difluoroethyl)azetidin-3-yl)oxy)ethyl)-1H-pyrazol-4-yl)-N-(5-isopropylpyridazin-3-yl)-1,5-naphthyridine-2-amine (3 mg) as a pale yellow solid.

¹H-NMR(CDCl₃)δ:8.94(1H,d,J=2.0 Hz),8.88-8.78(2H,m),8.25(1H,d,J=9.2 Hz),8.11(1H,s),7.98(1H,s),7.94(1H,s),7.59(1H,d,J=9.2 Hz),5.72(1H,tt,J=55.8,4.3 Hz),4.38(2H,t,J=5.0 Hz),4.17-4.09(1H,m),3.80(2H,t,J=5.0 Hz),3.66(2H,dd,J=8.3,6.3 Hz),3.08-3.03(3H,m),2.78(2H,td,J=15.0,4.3 Hz),1.42(6H,d,J=7.3 Hz).

MSm/z(M+H):495.

Example 0748

0748-1 and 0748-2

The following compounds were obtained in the same manner as in Examples 0734-1 and 0734-2.

| Example No. | | |
|---|---|---|
| 0748 | | |
| 0748-1 | 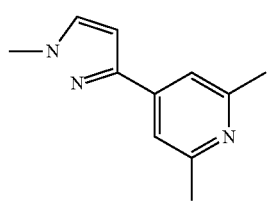 | MS m/z (M + H): 188. |
| 0748-2 | 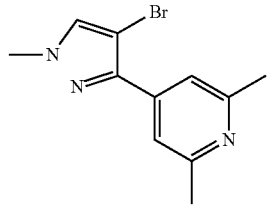 | MS m/z (M + H): 266. |

0748-3

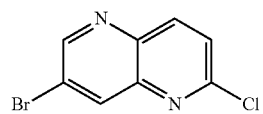

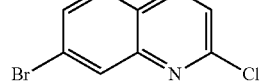

5-Isopropylpyridazine-3-amine (411 mg) and sodium tert-pentaoxide (726 mg) were added to a solution of 7-bromo-2-chloro-1,5-naphthyridine (729 mg) in N,N-dimethylacetamide (10 mL), followed by stirring at 80° C. for 10 minutes, and stirring at 100° C. for 50 minutes. After the reaction mixture was cooled to room temperature, water was added thereto, the precipitated solid was collected by filtration, and washed with ethyl acetate, thereby obtaining 7-bromo-N-(5-isopropylpyridazin-3-yl)-1,5-naphthyridine-2-amine (616 mg).

MSm/z(M+H):346.

0748-4

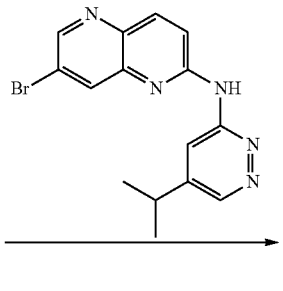

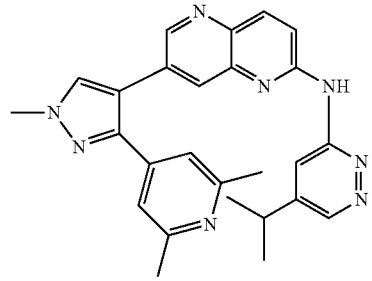

7-(3-(2,6-Dimethylpyridin-4-yl)-1-methyl-1H-pyrazol-4-yl)-N-(5-isopropylpyridazin-3-yl)-1,5-naphthyridine-2-amine was obtained in the same manner as in Example 385-7.

$^1$H-NMR(CDCl$_3$)δ:9.53(1H,s),8.85(1H,s),8.80(1H,s),8.67(1H,d,J=2.0 Hz),8.26(1H,d,J=9.2 Hz),7.97(1H,d,J=2.0 Hz),7.71(1H,d,J=9.2 Hz),7.69(1H,s),7.11(2H,s),4.07(3H,s),3.05-2.95(1H,m),2.46(6H,s),1.35(6H,d,J=7.3 Hz).

MSm/z(M+H):451.

Example 0749

The following compounds were obtained in the same manner as in Examples 0734-1 and 0734-2.

| Example No. | | |
|---|---|---|
| 0749 | | |
| 0749-1 | 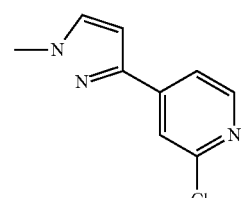 | MS m/z (M + H): 194. |
| 0749-2 | 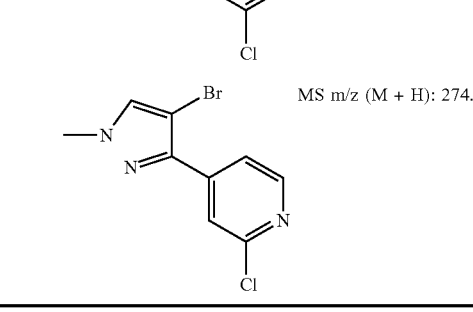 | MS m/z (M + H): 274. |

0749-3

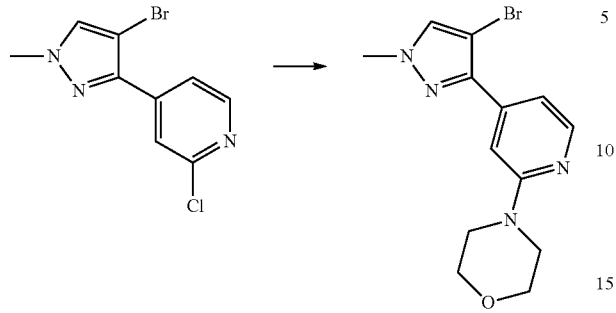

Morpholine (1 mL) was added to 4-(4-bromo-1-methyl-1H-pyrazol-3-yl)-2-chloropyridine (100 mg), followed by stirring at 150° C. for 90 minutes using a microwave reaction apparatus. The reaction mixture was cooled to room temperature, the solvent was distilled off under reduced pressure, and the obtained residue was purified by silica gel column chromatography (ethyl acetate-hexane, NH silica), thereby obtaining 4-(4-(4-bromo-1-methyl-1H-pyrazol-3-yl)pyridin-2-yl)morpholine (41 mg).

MSm/z(M+H):325.

0749-4

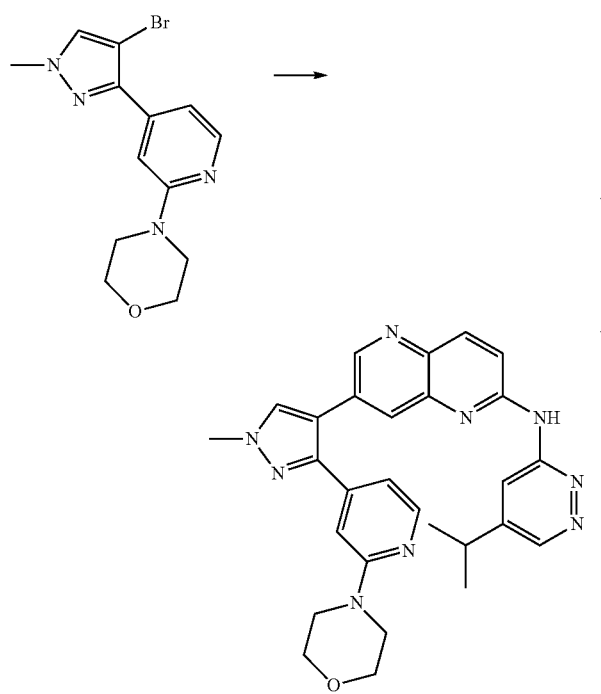

N-(5-isopropylpyridazin-3-yl)-7-(1-methyl-3-(2-morpholinopyridin-4-yl)-1H-pyrazol-4-yl)-1,5-naphthyridine-2-amine was obtained as a pale yellow solid in the same manner as in Example 0385-7.

$^1$H-NMR(CDCl$_3$)δ:9.23(1H,brs),8.85-8.77(2H,m),8.69 (1H,d,J=2.0 Hz),8.26(1H,d,J=8.6 Hz),8.12(1H,d,J=5.3 Hz), 8.00(1H,d,J=2.0 Hz),7.70-7.66(2H,m),6.87(1H,s),6.71(1H, d,J=5.3 Hz),4.06(3H,s),3.75(4H,t,J=4.6 Hz),3.44(4H,t,J=4.6 Hz),3.05-2.95(1H,m),1.36(6H,d,J=7.3 Hz).

MSm/z(M+H):508.

Example 0750

0750-1

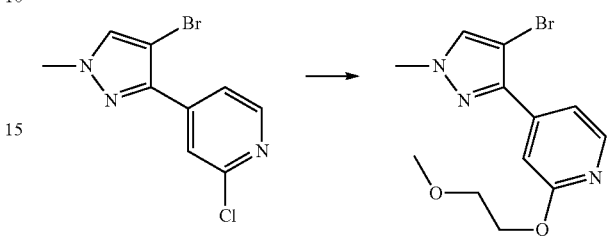

60% sodium hydride (28 mg) was added to a solution of 2-methoxyethanol (54 µL) in N,N-dimethylacetamide (1 mL) under ice-cooling, followed by stirring for 1 hour. 4-(4-Bromo-1-methyl-1H-pyrazol-3-yl)-2-chloropyridine (75 mg) was added to the reaction mixture, followed by stirring at 100° C. for 3 hours. After the reaction mixture was cooled to room temperature, water was added thereto, the resultant product was extracted with ethyl acetate, and the organic layer was washed with a saturated sodium chloride aqueous solution, and dried over anhydrous sodium sulfate. The solvent was distilled off under reduced pressure, and the obtained residue was purified by silica gel column chromatography (hexane-ethyl acetate), thereby obtaining 4-(4-bromo-1-methyl-1H-pyrazol-3-yl)-2-(2-methoxyethoxyl) pyridine (32 mg) as colorless oily substance.

MSm/z(M+H):314.

0750-2

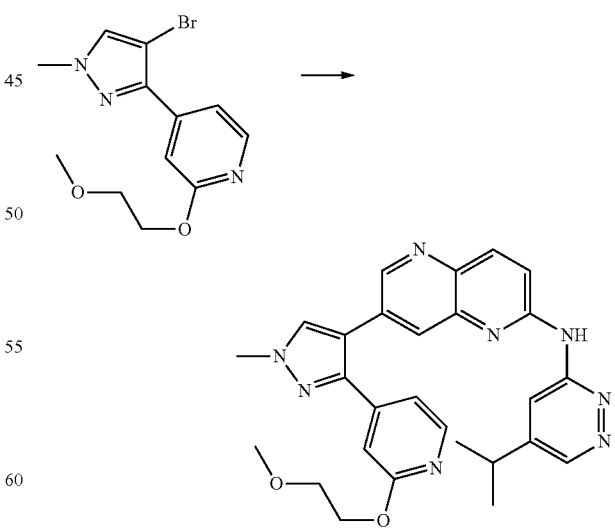

N-(5-isopropylpyridazin-3-yl)-7-(3-(2-(2-methoxyethoxyl)pyridin-4-yl)-1-methyl-1H-pyrazol-4-yl)-1,5-naphthyridine-2-amine was obtained as a pale yellow solid in the same manner as in Example 0385-7.

$^1$H-NMR(CDCl$_3$)δ:9.13(1H,s),8.82(1H,s),8.80(1H,s), 8.66(1H,d,J=1.3 Hz),8.26(1H,d,J=9.2 Hz),8.08(1H,d,J=4.9 Hz),7.98(1H,d,J=1.3 Hz),7.66(1H,s),7.63(1H,d,J=9.2 Hz), 7.01(1H,dd,J=4.9,1.3 Hz),6.96(1H,s),4.45(2H,t,J=4.6 Hz), 4.05(3H,s),3.70(2H,t,J=4.6 Hz),3.38(3H,s),3.03-2.96(1H, m),1.35(6H,d,J=7.3 Hz).

MSm/z(M+H):497.

Example 0751

The following compounds were obtained in the same manner as in Examples 0750-1 and 0385-7.

| Example No. | | |
|---|---|---|
| 0751 | | |
| 0751-1 | 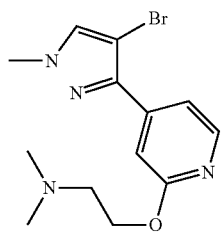 | MS m/z (M + H): 325. |
| 0751-2 | 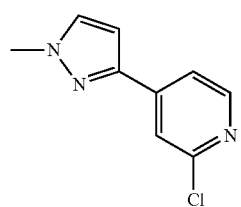 | $^1$H-NMR (CDCl$_3$) δ: 9.25 (1H, s), 8.84 (1H, s), 8.80 (1H, s), 8.66 (1H, d, J = 1.5 Hz), 8.26 (1H, d, J = 8.6 Hz), 8.09 (1H, d, J = 5.6 Hz), 7.98 (1H, d, J = 1.5 Hz), 7.69-7.63 (2H, m), 7.00 (1H, dd, J = 5.6, 1.5 Hz), 6.94 (1H, s), 4.39 (2H, t, J = 5.9 Hz), 4.05 (3H, s), 3.03-2.96 (1H, m), 2.67 (2H, t, J = 5.9 Hz), 2.28 (6H, s), 1.35 (6H, d, J = 6.6 Hz). MS m/z (M + H): 510. |

Example 0752

0752-1

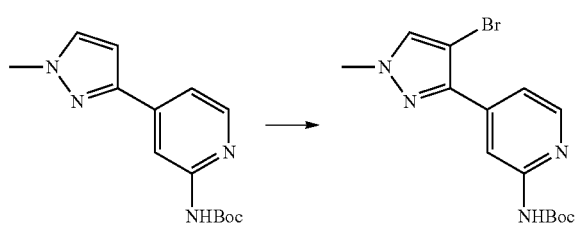

Sodium tert-butoxide (115 mg) and ((2-dicyclohexylphosphino-3,6-dimethoxy-2',4',6'-triisopropyl-1,1'-biphenyl)-2-(2'-amino-1,1'-biphenyl))palladium(II) methanesulfonate (BRETTPHOS-PD-G3, (product name, manufactured by Sigma-Aldrich Co. LLC.)) (45 mg) were added to a solution of 2-chloro-4-(1-methyl-1H-pyrazol-3-yl)pyridine (190 mg) and tert-butyl carbamate (140 mg) in 1,4-dioxane (5 mL), followed by stirring at 100° C. for 2 hours. The reaction mixture was cooled to room temperature, the solvent was distilled off under reduced pressure, and the obtained residue was purified by silica gel column chromatography (hexane-ethyl acetate), thereby obtaining tert-butyl (4-(1-methyl-1H-pyrazol-3-yl)pyridin-2-yl)carbamate.

N-bromosuccinimide (215 mg) was added to a solution of the obtained tert-butyl (4-(1-methyl-1H-pyrazol-3-yl)pyridin-2-yl)carbamate in N,N-dimethylformamide (2 mL), followed by stirring at room temperature for 50 minutes. After water was added to the reaction mixture, the resultant product was extracted with ethyl acetate, and the organic layer was washed with a saturated sodium chloride aqueous solution, and dried over anhydrous sodium sulfate. The solvent was distilled off under reduced pressure, and the obtained residue was purified by silica gel column chromatography (hexane-ethyl acetate), thereby obtaining tert-butyl (4-(4-bromo-1-methyl-1H-pyrazol-3-yl)pyridin-2-yl)carbamate (22 mg) as yellow oily substance.

MSm/z(M+H):353.

895
0752-2

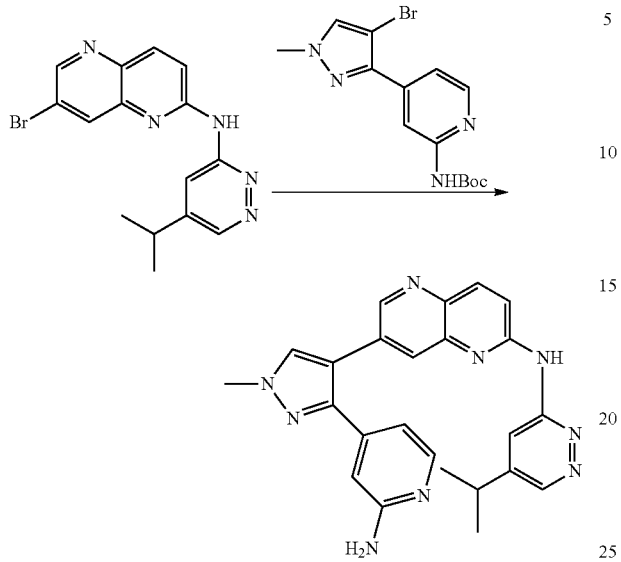

7-(3-(2-aminopyridin-4-yl)-1-methyl-1H-pyrazol-4-yl)-N-(5-isopropylpyridazin-3-yl)-1,5-naphthyridine-2-amine was obtained as a brown solid in the same manner as in Example 0385-7.

¹H-NMR(CD₃OD)δ:8.82(1H,s),8.74(1H,d,J=1.5 Hz), 8.67(1H,d,J=1.5 Hz),8.19(1H,d,J=9.2 Hz),8.11(1H,s),8.04 (1H,d,J=1.5 Hz),7.88(1H,d,J=5.3 Hz),7.62(1H,d,J=9.2 Hz), 6.70(1H,s),6.67(1H,dd,J=5.3,1.5 Hz),4.03(3H,s),3.09-2.98 (1H,m),1.33(6H,d,J=7.3 Hz).

MSm/z(M+H):438.

Example 0753

0753-1

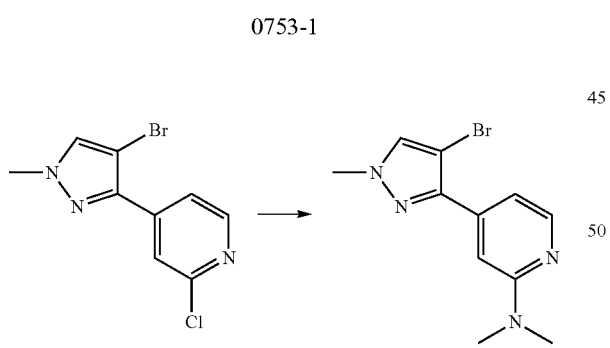

A 50% dimethylamine aqueous solution (1 mL) and 1,4-dioxane (0.5 mL) were added to 4-(4-bromo-1-methyl-1H-pyrazol-3-yl)-2-chloropyridine (75 mg), followed by stirring at 160° C. for 1 hour using a microwave reaction apparatus. The reaction mixture was cooled to room temperature, the solvent was distilled off under reduced pressure, and the obtained residue was purified by silica gel column chromatography (hexane-ethyl acetate, NH silica), thereby obtaining 4-(4-bromo-1-methyl-1H-pyrazol-3-yl)-N,N-dimethylpyridine-2-amine (41 mg).

MSm/z(M+H):281.

896
0753-2

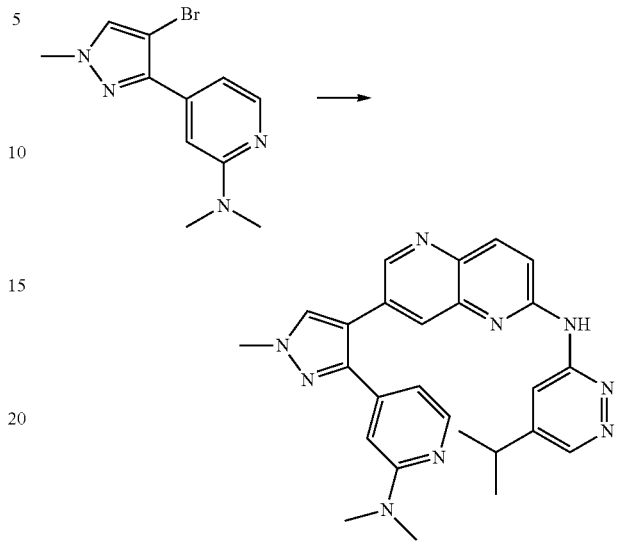

7-(3-(2-(Dimethylamino)pyridin-4-yl)-1-methyl-1H-pyrazol-4-yl)-N-(5-isopropylpyridazin-3-yl)-1,5-naphthyridine-2-amine was obtained as a yellow solid in the same manner as in Example 0385-7.

¹H-NMR(CDCl₃)δ:10.00(1H,brs),8.93(1H,s),8.81(1H,s), 8.70(1H,d,J=1.6 Hz),8.25(1H,d,J=8.6 Hz),8.11(1H,d,J=5.3 Hz),8.01(1H,d,J=1.6 Hz),7.81(1H,d,J=8.6 Hz),7.67(1H,s), 6.68(1H,s),6.65(1H,d,J=5.3 Hz),4.06(3H,s),3.05-2.94(7H, m),1.36(6H,d,J=7.2 Hz).

MSm/z(M+H):466.

Example 0754

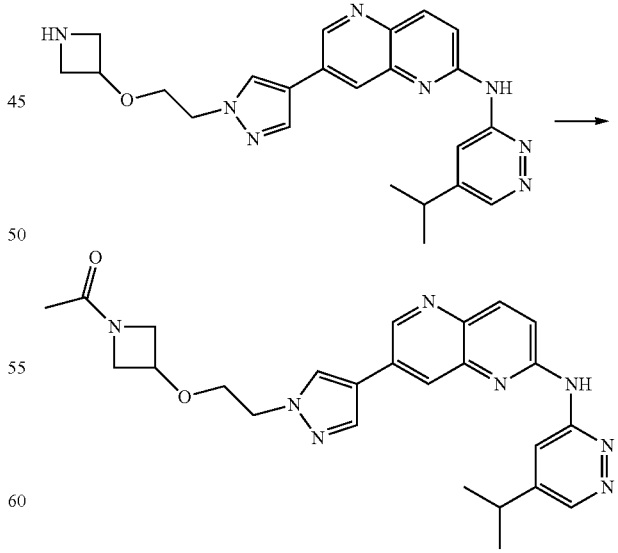

Triethylamine (2 μL) and acetic anhydride (1 μL) were added to a suspension of 7-(1-(2-(azetidin-3-yloxy)ethyl)-1H-pyrazol-4-yl)-N-(5-isopropylpyridazin-3-yl)-1,5-naphthyridine-2-amine (4 mg) in tetrahydrofuran (0.5 mL), followed by stirring at room temperature for 1 hour. The solvent was distilled off under reduced pressure, and the obtained residue was purified by silica gel column chromatography (hexane-ethyl acetate, NH silica), thereby obtaining 1-(3-(2-(4-(6-((5-isopropylpyridazin-3-yl)amino)-1,5-naphthyridin-3-yl)-1H-pyrazol-1-yl)ethoxy)azetidin-1-yl)ethanone (2 mg) as a pale yellow solid.

$^1$H-NMR(CDCl$_3$)δ:9.42(1H,s),8.93(1H,d,J=1.6 Hz),8.89(1H,s),8.83(1H,s),8.25(1H,d,J=8.9 Hz),8.12(1H,d,J=1.6 Hz),8.00(1H,s),7.92(1H,s),7.67(1H,d,J=8.9 Hz),4.41(2H,t,J=5.3 Hz),4.31-4.20(2H,m),4.17-4.10(1H,m),3.95-3.90(1H,m),3.87-3.81(3H,m),3.12-3.02(1H,m),1.84(3H,s),1.43(6H,d,J=6.6 Hz).

MSm/z(M+H):473.

Example 0755

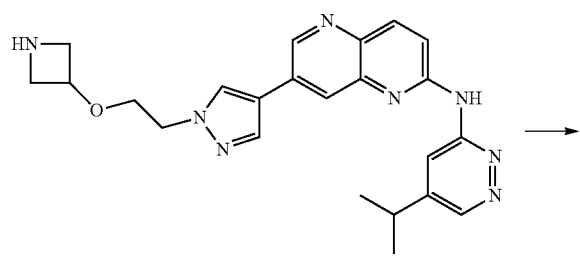

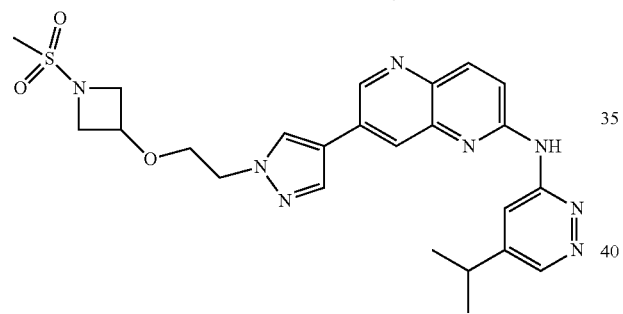

Triethylamine (2 µL) and methanesulfonyl chloride (1 µL) were added to a suspension of 7-(1-(2-(azetidin-3-yloxy)ethyl)-1H-pyrazol-4-yl)-N-(5-isopropylpyridazin-3-yl)-1,5-naphthyridine-2-amine (4 mg) in methylene chloride (0.5 mL), followed by stirring at room temperature for 1 hour. The reaction mixture was purified by silica gel column chromatography (hexane-ethyl acetate, NH silica), thereby obtaining N-(5-isopropylpyridazin-3-yl)-7-(1-(2-((1-(methylsulfonyl)azetidin-3-yl)oxy)ethyl)-1H-pyrazol-4-yl)-1,5-naphthyridine-2-amine (3 mg) as a pale yellow solid.

$^1$H-NMR(CDCl$_3$)δ:9.85(1H,s),8.94(1H,s),8.93(1H,d,J=1.6 Hz),8.83(1H,s),8.25(1H,d,J=8.9 Hz),8.11(1H,d,J=1.6 Hz),7.99(1H,s),7.92(1H,s),7.76(1H,d,J=8.9 Hz),4.40(2H,t,J=5.3 Hz),4.28-4.20(1H,m),4.07-4.00(2H,m),3.86(2H,t,J=5.3 Hz),3.79(2H,dd,J=9.2,4.6 Hz),3.12-3.03(1H,m),2.80(3H,s),1.43(6H,d,J=7.3 Hz).

MSm/z(M+H):509.

Example 0756

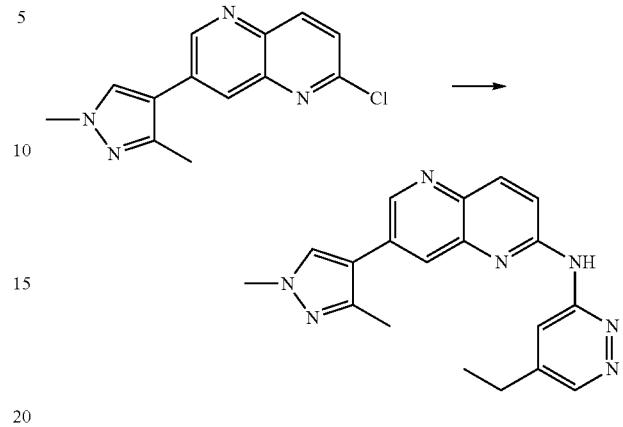

7-(1,3-Dimethyl-1H-pyrazol-4-yl)-N-(5-ethylpyridazin-3-yl)-1,5-naphthyridine-2-amine was obtained in the same manner as in Example 0757-2.

$^1$H-NMR(DMSO-d$_6$)δ:10.72(1H,s),8.88(1H,d,J=2.0 Hz),8.80(1H,d,J=2.0 Hz),8.70(1H,d,J=1.3 Hz),8.24-8.23(2H,m),8.09(1H,d,J=2.0 Hz),7.74(1H,d,J=9.2 Hz),3.85(3H,s),2.73(2H,q,J=7.5 Hz),2.42(3H,s),1.31(3H,t,J=7.5 Hz).

MSm/z(M+H):346.

Example 0757

0757-1

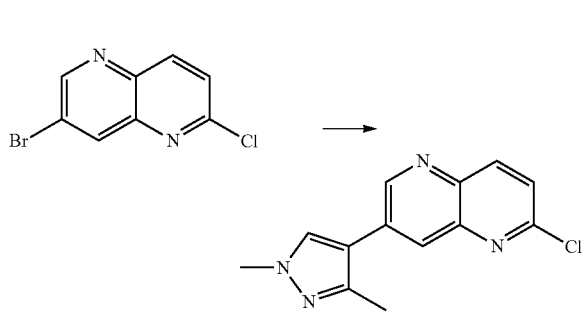

A mixture of 7-bromo-2-chloro-1,5-naphthyridine (600 mg), 1,3-dimethyl-4-(4,4,5,5-tetramethyl-1,3,2-dioxaborolan-2-yl)-1H-pyrazole (442 mg), bis(di-tert-butyl(4-dimethylaminophenyl)phosphine)dichloropalladium(II) (174 mg), sodium carbonate (522 mg), 1,4-dioxane (24 mL), and water (2.4 mL) was stirred at 100° C. for 3 hours in a nitrogen atmosphere. The reaction mixture was cooled to room temperature, and the solvent was distilled off under reduced pressure. The reaction residue was purified by silica gel column chromatography (chloroform-methanol, NH silica), thereby obtaining 2-chloro-7-(1,3-dimethyl-1H-pyrazol-4-yl)-1,5-naphthyridine (412 mg) as a white solid.

MSm/z(M+H):259.

0757-2

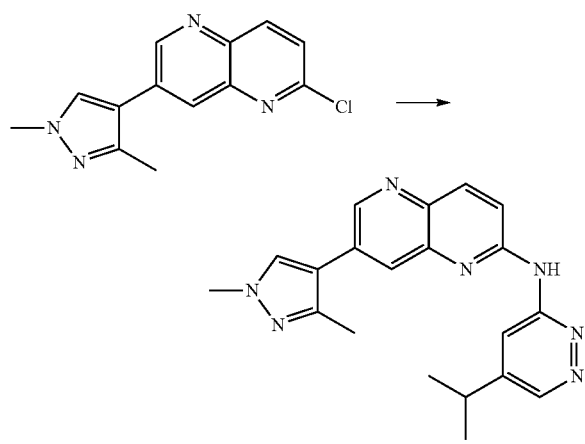

A mixture of 2-chloro-7-(1,3-dimethyl-1H-pyrazol-4-yl)-1,5-naphthyridine (30 mg), 5-isopropylpyridazine-3-amine (24 mg), tris(dibenzylideneacetone)dipalladium(0) (11 mg), 4,5-bis(diphenylphosphino)-9,9-dimethylxanthene (13 mg), cesium carbonate (76 mg), and 1,4-dioxane (1.2 mL) was stirred at 140° C. for 30 minutes using a microwave reaction apparatus. The reaction mixture was cooled to room temperature, and the solvent was distilled off under reduced pressure. The obtained residue was purified by silica gel column chromatography (chloroform-methanol, NH silica), and purified by silica gel column chromatography (chloroform-methanol), thereby obtaining 7-(1,3-dimethyl-1H-pyrazol-4-yl)-N-(5-isopropylpyridazin-3-yl)-1,5-naphthyridine-2-amine (17 mg) as a white solid.

$^1$H-NMR(DMSO-$d_6$)δ:10.72(1H,s),8.88(1H,d,J=2.0 Hz), 8.85(1H,d,J=1.3 Hz),8.74(1H,d,J=1.3 Hz),8.24-8.23(2H,m), 8.06(1H,d,J=2.0 Hz),7.74(1H,d,J=9.2 Hz),3.85(3H,s),3.03-3.00(1H,m),2.42(3H,s),1.31(6H,d,J=7.3 Hz).

MSm/z(M+H):360.

Example 0758

The following compounds were obtained in the same manner as in Examples 0757-1 and 0757-2.

| Example No. | | |
|---|---|---|
| 0758 | | |
| 0758-1 | 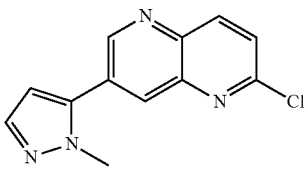 [SMILES: Cn1nccc1-c1cnc2ccc(Cl)nc2c1] | MS m/z (M + H): 245. |
| 0758-2 | 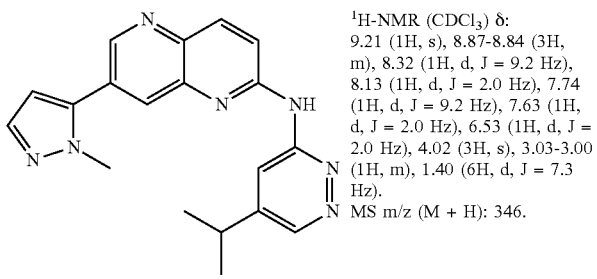 | $^1$H-NMR (CDCl$_3$) δ: 9.21 (1H, s), 8.87-8.84 (3H, m), 8.32 (1H, d, J = 9.2 Hz), 8.13 (1H, d, J = 2.0 Hz), 7.74 (1H, d, J = 9.2 Hz), 7.63 (1H, d, J = 2.0 Hz), 6.53 (1H, d, J = 2.0 Hz), 4.02 (3H, s), 3.03-3.00 (1H, m), 1.40 (6H, d, J = 7.3 Hz). MS m/z (M + H): 346. |

Example 0759
The following compounds were obtained in the same manner as in Examples 0014-1, 0014-2, 0014-3, and 0757-2.
| Example No. | | |
|---|---|---|
| 0759 | | |
| 0759-1 | 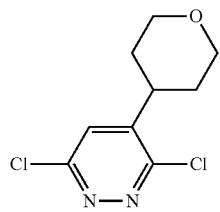 [SMILES: Clc1cc(C2CCOCC2)c(Cl)nn1] | MS m/z (M + H): 233. |
| 0759-2 | 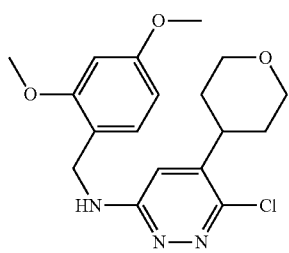 [SMILES: COc1ccc(CNc2cc(C3CCOCC3)c(Cl)nn2)c(OC)c1] | MS m/z (M + H): 364. |
| 0759-3 | 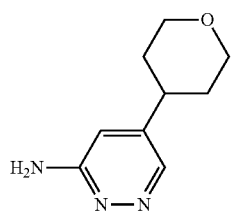 [SMILES: Nc1cc(C2CCOCC2)cnn1] | MS m/z (M + H): 180. |
| 0759-4 | 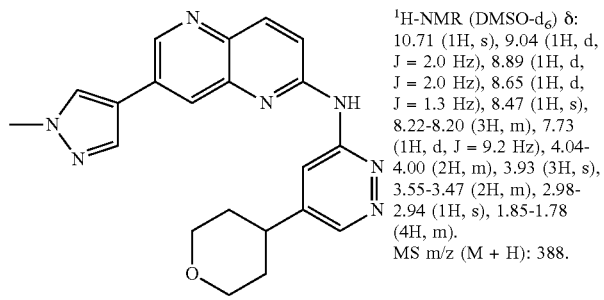 | $^1$H-NMR (DMSO-$d_6$) δ: 10.71 (1H, s), 9.04 (1H, d, J = 2.0 Hz), 8.89 (1H, d, J = 2.0 Hz), 8.65 (1H, d, J = 1.3 Hz), 8.47 (1H, s), 8.22-8.20 (3H, m), 7.73 (1H, d, J = 9.2 Hz), 4.04-4.00 (2H, m), 3.93 (3H, s), 3.55-3.47 (2H, m), 2.98-2.94 (1H, s), 1.85-1.78 (4H, m). MS m/z (M + H): 388. |
Example 0760
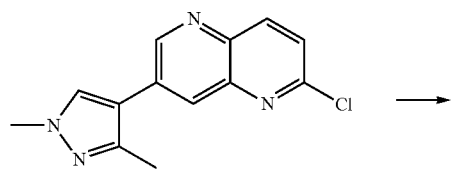 →
-continued
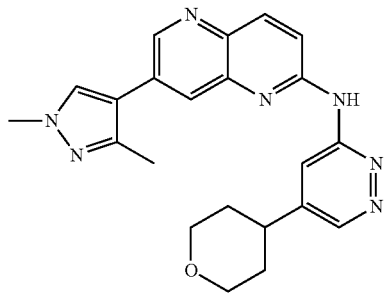 [SMILES: Cn1cc(-c2cnc3ccc(Nc4cc(C5CCOCC5)cnn4)nc3c2)cn1]
7-(1,3-Dimethyl-1H-pyrazol-4-yl)-N-(5-(tetrahydro-2H-pyran-4-yl)pyridazin-3-yl)-1,5-naphthyridine-2-amine was obtained as a white solid in the same manner as in Example 0757-2.

¹H-NMR(DMSO-d₆)δ:10.74(1H,s),9.04(1H,d,J=2.0 Hz), 8.88-8.87(2H,m),8.69(1H,s),8.25-8.24(2H,m),7.76(1H,d, J=9.2 Hz),4.01-3.98(2H,m),3.85(3H,s),3.53-3.41(2H,m), 2.97-2.93(1H,s),2.42(3H,s)1.87-1.83(4H,m).
MSm/z(M+H):402.

Example 0761

The following compounds were obtained in the same manner as in Examples 0124-2, 0757-1, and 0757-2.

| Example No. | | |
|---|---|---|
| 0761 | | |
| 0761-1 | 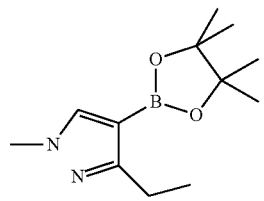 | MS m/z (M + H): 237. |
| 0761-2 | 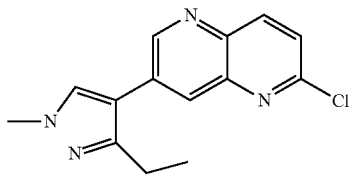 [SMILES: CCC(=N)/C(=C\NC)c1cnc2ccc(Cl)nc2c1] | MS m/z (M + H): 273. |
| 0761-3 | 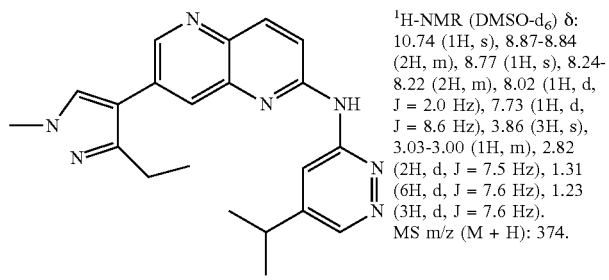 | ¹H-NMR (DMSO-d₆) δ: 10.74 (1H, s), 8.87-8.84 (2H, m), 8.77 (1H, s), 8.24-8.22 (2H, m), 8.02 (1H, d, J = 2.0 Hz), 7.73 (1H, d, J = 8.6 Hz), 3.86 (3H, s), 3.03-3.00 (1H, m), 2.82 (2H, d, J = 7.5 Hz), 1.31 (6H, d, J = 7.6 Hz), 1.23 (3H, d, J = 7.6 Hz). MS m/z (M + H): 374. |

Example 0762

0762-1

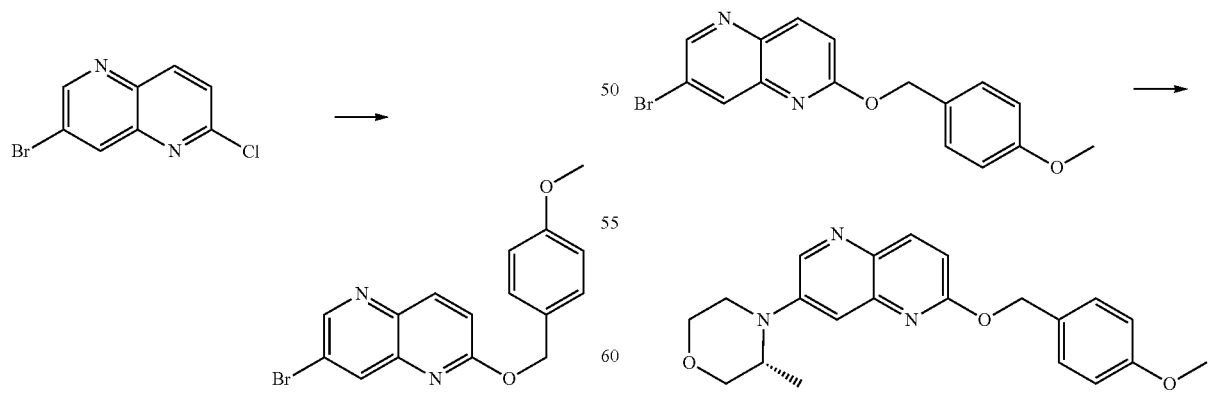

0762-2

60% sodium hydride (136 mg) was added to a mixture of 7-bromo-2-chloro-1,5-naphthyridine (300 mg), (4-methoxyphenyl)methanol, and N-methylpyrrolidone (12.3 mL) at a temperature of from 0° C. to 5° C., followed by stirring at room temperature for 2 hours in a nitrogen atmosphere. After water and ethyl acetate were added to the reaction mixture, the organic layer was washed sequentially with 0.01 mol/L hydrochloric acid and with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 7-bromo-2-((4-methoxybenzyl)oxy)-1,5-naphthyridine (204 mg) as a white solid.
MSm/z(M+H):345.

A mixture of 7-bromo-2-((4-methoxybenzyl)oxy)-1,5-naphthyridine (50 mg), (R)-3-methylmorpholine (14.7 mg), tris(dibenzylideneacetone)dipalladium(0) (11 mg), 2-dicyclohexylphosphino-2',4',6'-triisopropylbiphenyl (13 mg), sodium tert-butoxide (76 mg), and 1,4-dioxane (1.2 mL) was stirred at 100° C. for 12 hours in a nitrogen atmosphere. The reaction mixture was cooled to room temperature, and the solvent was distilled off under reduced pressure. The obtained residue was purified by silica gel column chromatography (hexane-ethyl acetate), thereby obtaining (R)-4-(6-((4-methoxybenzyl)oxy)-1,5-naphthyridin-3-yl)-3-methylmorpholine (20.2 mg) as a white solid.

MSm/z(M+H):366.

0762-3

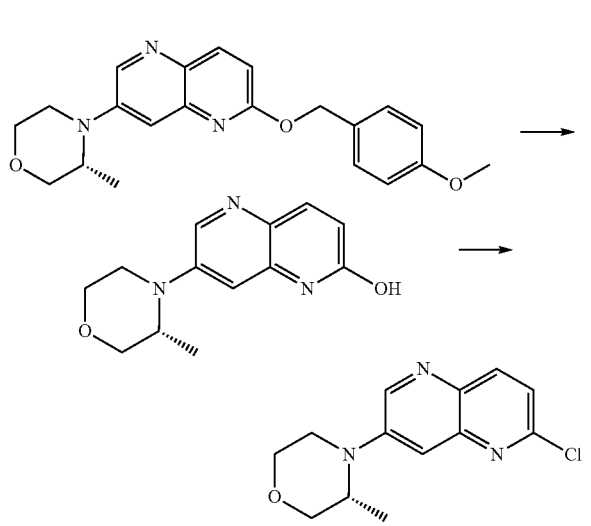

A mixture of (R)-4-(6-((4-methoxybenzyl)oxy)-1,5-naphthyridin-3-yl)-3-methylmorpholine (23.8 mg), trifluoroacetic acid (1.2 mL), and water (0.1 mL) was stirred at room temperature for 15 minutes. The solvent was distilled off under reduced pressure, and the obtained residue was purified by silica gel column chromatography (chloroform-methanol, NH silica), thereby obtaining (R)-7-(3-methylmorpholino)-1,5-naphthyridin-2-ol (14.7 mg).

A mixture of (R)-7-(3-methylmorpholino)-1,5-naphthyridin-2-ol (14.7 mg) and phosphorus oxychloride (1.0 mL) was stirred at 140° C. for 30 minutes using a microwave reaction apparatus. The reaction mixture was cooled to room temperature, and the solvent was distilled off under reduced pressure. After water and ethyl acetate were added to the obtained residue, the organic layer was washed sequentially with a saturated sodium hydrogen carbonate aqueous solution and with a saturated sodium chloride aqueous solution, and dried over anhydrous sodium sulfate, and the solvent was distilled off under reduced pressure. The obtained residue was purified by silica gel column chromatography (chloroform-methanol, NH silica), thereby obtaining (R)-4-(6-chloro-1,5-naphthyridin-3-yl)-3-methylmorpholine (14.3 mg) as a white solid.

MSm/z(M+H):264.

0762-4

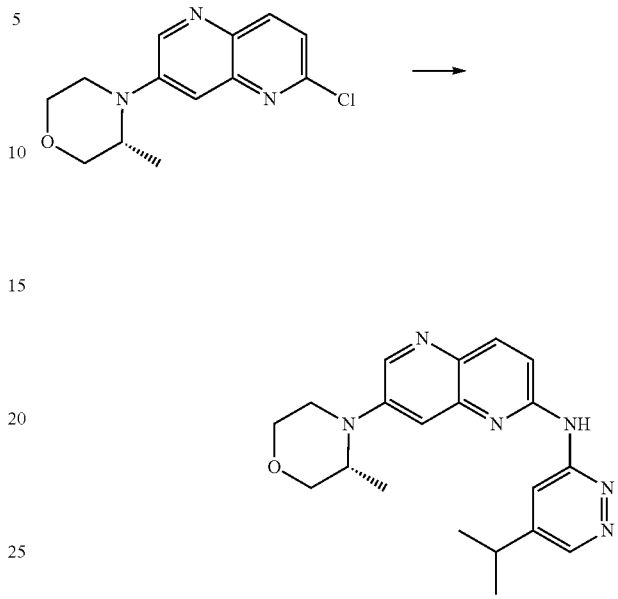

A mixture of (R)-4-(6-chloro-1,5-naphthyridin-3-yl)-3-methylmorpholine (12 mg), sodium tert-butoxide (22 mg), anhydrous sodium sulfate (12 mg), 5-isopropylpyridazine-3-amine (9.3 mg), and 1,4-dioxane (0.5 mL) was stirred at 100° C. for 30 minutes using a microwave reaction apparatus. The reaction mixture was cooled to room temperature, and sodium tert-butoxide (22 mg) and 5-isopropylpyridazine-3-amine (9.3 mg) were added thereto, followed by stirring at 150° C. for 30 minutes using a microwave reaction apparatus. The reaction mixture was cooled to room temperature, and the solvent was distilled off under reduced pressure. The obtained residue was purified by silica gel column chromatography (chloroform-methanol, NH silica), thereby obtaining (R)-N-(5-isopropylpyridazin-3-yl)-7-(3-methylmorpholino)-1,5-naphthyridine-2-amine (4.9 mg) as a white solid.

$^1$H-NMR(DMSO-d$_6$)δ:10.54(1H,s),8.83(1H,d,J=2.0 Hz), 8.69(1H,d,J=2.1 Hz),8.67(1H,d,J=2.7 Hz),8.08(1H,d,J=9.2 Hz),7.50(1H,d,J=9.2 Hz),7.23(1H,d,J=2.6 Hz),4.23-4.21 (1H,m),4.02-3.98(1H,m),3.79-3.75(2H,m),3.65-3.61(1H, m),3.49-3.40(1H,m),3.24-3.31(1H,m),3.06-2.96(1H,m), 1.30(6H,t,J=6.6 Hz),1.11(3H,t,J=6.6 Hz).

MSm/z(M+H):365.

Example 0763

The following compounds were obtained in the same manner as in Examples 0757-1, 0297-2, 0297-3, and 0015-4.

| Example No. | | |
|---|---|---|
| 0763 | | |
| 0763-1 | 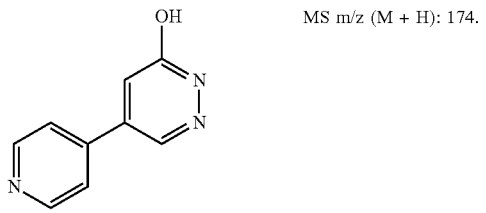 | MS m/z (M + H): 174. |
| 0763-2 | 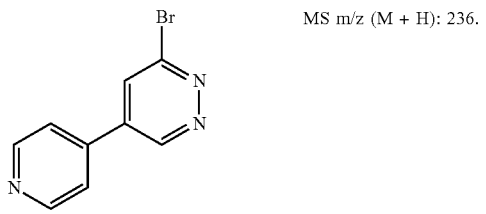 | MS m/z (M + H): 236. |
| 0763-3 | 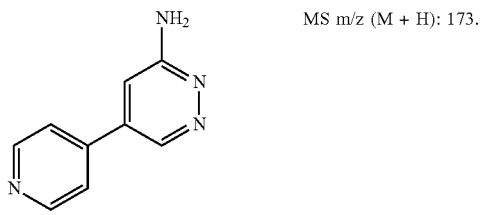 | MS m/z (M + H): 173. |
| 0763-4 | 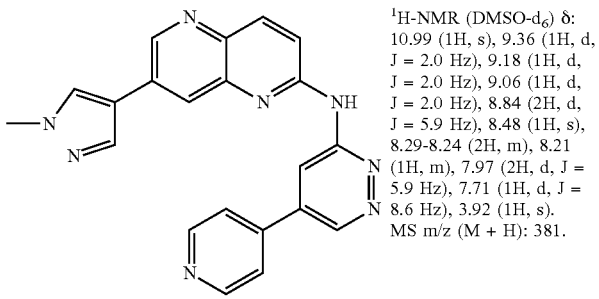 | $^{1}$H-NMR (DMSO-d$_6$) δ: 10.99 (1H, s), 9.36 (1H, d, J = 2.0 Hz), 9.18 (1H, d, J = 2.0 Hz), 9.06 (1H, d, J = 2.0 Hz), 8.84 (2H, d, J = 5.9 Hz), 8.48 (1H, s), 8.29-8.24 (2H, m), 8.21 (1H, m), 7.97 (2H, d, J = 5.9 Hz), 7.71 (1H, d, J = 8.6 Hz), 3.92 (1H, s). MS m/z (M + H): 381. |
Example 0764
The following compounds were obtained in the same manner as in Examples 0762-2, 0762-3, and 0757-2.
| Example No. | | |
|---|---|---|
| 0764 | | |
| 0764-1 | 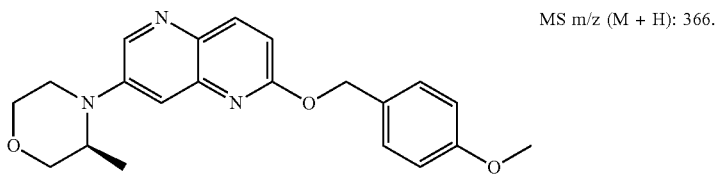 | MS m/z (M + H): 366. |
| 0764-2 | 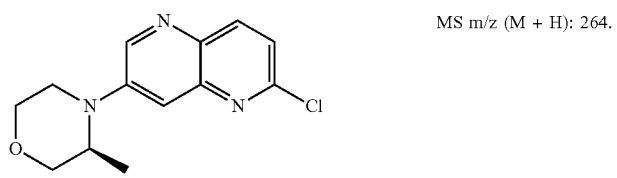 | MS m/z (M + H): 264. |

-continued

| Example No. | | |
|---|---|---|
| 0764-3 | 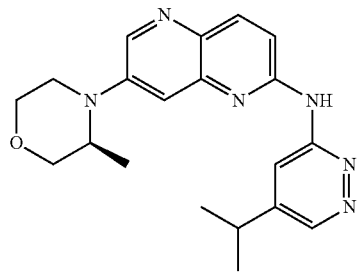 [SMILES: CC(C)c1cnnc(Nc2ccc3ncc(N4CCOC[C@@H]4C)cc3n2)c1] | $^1$H-NMR (DMSO-$d_6$) δ: 10.54 (1H, s), 8.83 (1H, d, J = 2.0 Hz), 8.69 (1H, d, J = 2.0 Hz), 8.66 (1H, d, J = 2.6 Hz), 8.08 (1H, d, J = 9.2 Hz), 7.50 (1H, d, J = 9.2 Hz), 7.28 (1H, d, J = 2.6 Hz), 4.23-4.21 (1H, m), 4.02-3.98 (1H, m), 3.79-3.74 (2H, m), 3.65-3.60 (1H, m), 3.48-3.39 (1H, m), 3.22-3.14 (1H, m), 3.05-2.96 (1H, m), 1.30 (6H, t, J = 7.3 Hz), 1.10 (3H, t, J = 6.6 Hz). MS m/z (M + H): 365. |

Examples 0765 and 0766

The following compounds were obtained in the same manner as in Example 0385-7.

| Example No. | | |
|---|---|---|
| 0765 | 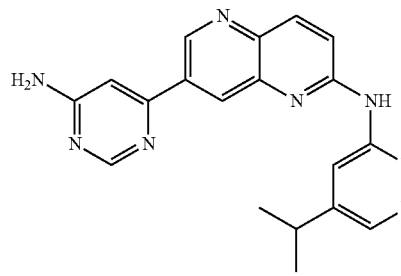 | $^1$H-NMR (DMSO-$d_6$) δ: 10.83 (1H, s), 9.29 (1H, d, J = 2.0 Hz), 8.88 (1H, d, J = 2.0 Hz), 8.79 (1H, d, J = 2.0 Hz), 8.60 (1H, d, J = 2.0 Hz), 8.55 (1H, s), 8.31 (1H, d, J = 9.2 Hz), 7.81 (1H, d, J = 9.2 Hz), 7.15-7.05 (3H, m), 3.10-3.01 (1H, m), 1.33 (6H, t, J = 6.6 Hz). MS m/z (M + H): 359. |
| 0766 | 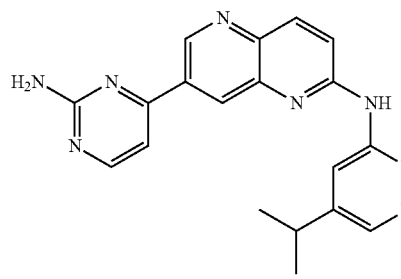 | $^1$H-NMR (DMSO-$d_6$) δ: 10.82 (1H, s), 9.38 (1H, d, J = 2.6 Hz), 8.89 (1H, d, J = 2.0 Hz), 8.75 (1H, d, J = 1.3 Hz), 8.68 (1H, d, J = 1.3 Hz), 8.43 (1H, d, J = 5.3 Hz), 8.32 (1H, d, J = 8.6 Hz) 7.83 (1H, d, J = 8.6 Hz), 7.41 (1H, d, J = 5.3 Hz), 6.86 (2H, s), 3.09-3.00 (1H, m), 1.34 (6H, d, J = 6.6 Hz). MS m/z (M + H): 359. |

Example 0767

0767-1 and 0767-2

The following compounds were obtained in the same manner as in Examples 0584-1 and 0555-2.

| Example No. | | |
|---|---|---|
| 0767 | | |
| 0767-1 | 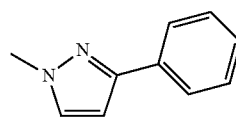 | MS m/z (M + H): 173. |

-continued

| Example No. | | |
|---|---|---|
| 0767-2 | 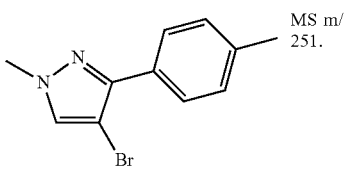 | MS m/z (M + H): 251. |

0767-3

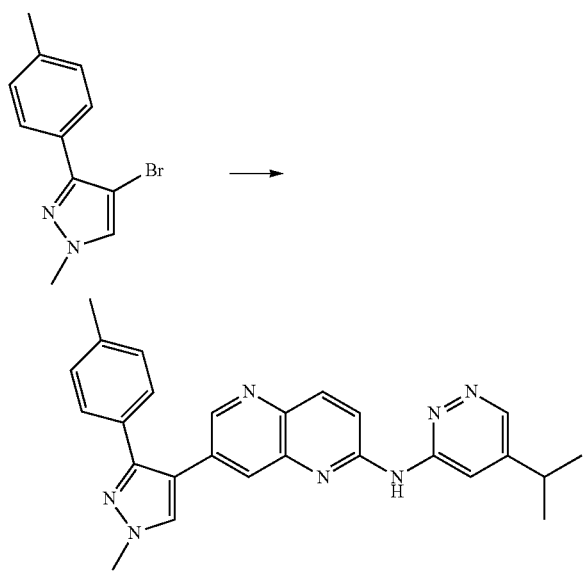

A suspension of 7-bromo-N-(5-isopropylpyridazin-3-yl)-1,5-naphthyridine-2-amine (20 mg), bis(pinacolato)diboron (29 mg), (1,1'-bis(diphenylphosphino)ferrocene)palladium (II) dichloride (5 mg), and potassium acetate (17 mg) in 1,4-dioxane (1 mL) was stirred at 100° C. for 1 hour in a nitrogen atmosphere. 4-Bromo-1-methyl-3-(4-methylphenyl)-1H-pyrazole (22 mg), water (0.1 mL), sodium carbonate (18 mg), and bis(di-tert-butyl(4-dimethylaminophenyl)phosphine)dichloropalladium(II) (4 mg) were added to the reaction mixture, followed by stirring at 100° C. for 2 hours. The reaction mixture was cooled to room temperature, insolubles were filtered off, and the solvent was distilled off under reduced pressure. The reaction residue was purified by silica gel column chromatography (methanol-ethyl acetate-hexane, NH silica), thereby obtaining N-(5-isopropylpyridazin-3-yl)-7-(1-methyl-3-(4-methylphenyl)-1H-pyrazol-4-yl)-1,5-naphthyridine-2-amine (0.6 mg).

$^1$H-NMR(CDCl$_3$)δ:8.76(2H,brs),8.68(1H,d,J=1.8 Hz), 8.22(1H,d,J=8.4 Hz),7.97(1H,brs),7.68(1H,s),7.51(1H,d,J=8.4 Hz),7.39(2H,d,J=8.7 Hz),7.14(2H,d,J=8.7 Hz),4.04 (3H,s),3.07-2.89(1H,m),2.35(3H,s),1.34(6H,d,J=6.6 Hz).

MSm/z(M+H):436.

Example 0768

Example 0584-1, The following compounds were obtained in the same manner as in Examples 0555-2, 0478-3, and 0554-3.

| Example No. |
| --- |
| 0768 |

| 0768-1 | 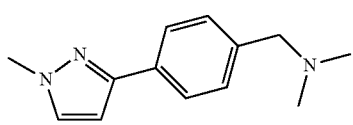 | MS m/z (M + H): 216. |
| 0768-2 | 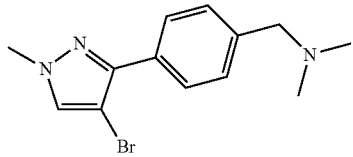 | MS m/z (M + H): 294. |
| 0768-3 | 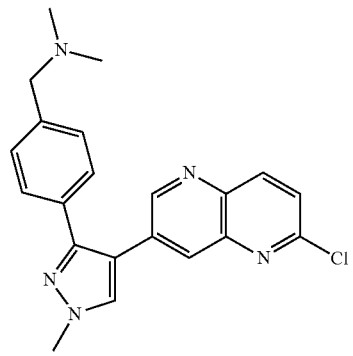 [SMILES: CN(C)Cc1ccc(-c2nn(C)cc2-c2cnc3ccc(Cl)nc3c2)cc1] | MS m/z (M + H): 376. |

| Example No. | | |
|---|---|---|
| 0768-4 | 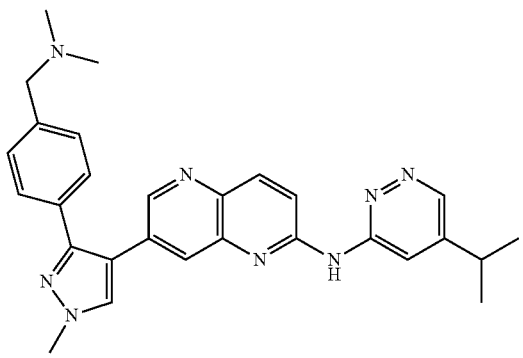 [SMILES: CC(C)c1cnnc(Nc2ccc3ncc(-c4cn(C)nc4-c4ccc(CN(C)C)cc4)cc3n2)c1] | ¹H-NMR (CDCl₃) δ:<br>8.95 (1H, bs), 8.78 (1H, brs), 8.65 (1H, d,<br>J = 2.1 Hz),8.23(1 H, d, J = 9.3 Hz),<br>7.98 (1H, brs), 7.67 (1H, s), 7.57 (1H, d, J = 9.3 Hz),<br>7.48 (2H, d, J = 7.8 Hz), 7.29 (2H, d, J = 7.8 Hz),4.05<br>(3H, s), 3.50 (2H, s), 3.06-2.90 (1H, m), 2.29<br>(6H, s), 1.34 (6H, d, J = 7.5 Hz).<br>MS m/z (M + H): 479. |

Examples 0769 and 0770

The following compounds were obtained in the same manner as in Example 0554-3.

| Example No. | | |
|---|---|---|
| 0769 | 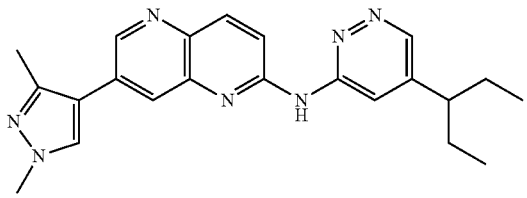 | ¹H-NMR (DMSO-d₆) δ:<br>10.70 (1H, s), 8.88 (1H, d, J = 2.1 Hz), 8.77 (1H, s), 8.62 (1H,<br>brs), 8.24 (1H, d, J = 9.3 Hz), 8.23 (1H, s), 8.00 (1H, brs),<br>7.72 (1H,d, J = 9.3 Hz), 3.84 (3H, s), 2.40 (3H, s), 2.56-2.51<br>(1H, m), 1.84-1.56 (4H, m), 0.83 (6H, t, J = 7.2 Hz).<br>MS m/z (M + H): 388. |
| 0770 | 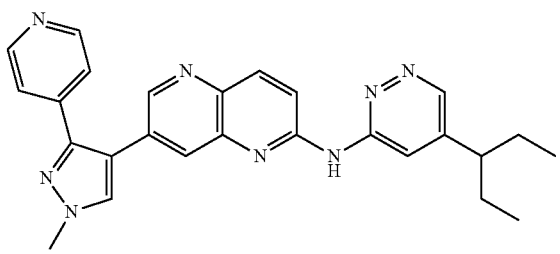 [SMILES: CCC(CC)c1cnnc(Nc2ccc3ncc(-c4cn(C)nc4-c4ccncc4)cc3n2)c1] | ¹H-NMR(CDCl₃) δ:<br>9.45 (1H, brs), 8.72 (2H, brs), 8.69 (1H, brs), 8.56 (2H, dd,<br>J = 4.8, 1.8 Hz), 8.27 (1H d, J = 9.0 Hz),<br>7.94 (1H, d, J = 1.8 Hz),<br>7.73 (1H, d, J = 9.0 Hz), 7.69 (1H, s), 7.45 (2H, dd, J = 4.8,<br>1.8 Hz), 4.07 (3H, s), 2.52-2.35 (1H, m), 1.88-1.48 (4H, m),<br>0.85 (6H, t, J = 7.8 Hz).<br>MS m/z (M + H): 451. |

Example 0771

Example 0576-2, The following compounds were obtained in the same manner as in Examples 0555-2, 0478-3, and 0554-3.

| Example No. | | |
|---|---|---|
| 0771 | | |
| 0771-1 | 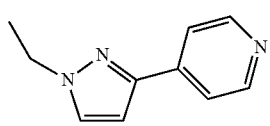 | MS m/z (M + H): 174. |

-continued
| Example No. | | |
|---|---|---|
| 0771-2 | 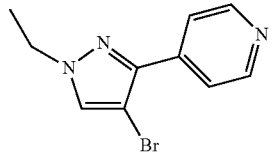 | MS m/z (M + H): 252. |
| 0771-3 | 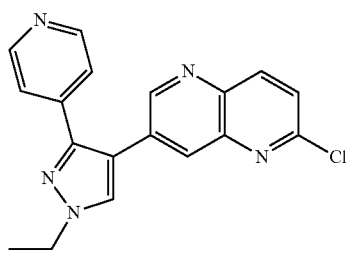 [SMILES: CCn1cc(-c2cnc3ccc(Cl)nc3c2)c(-c2ccncc2)n1] | MS m/z (M + H): 336. |
| 0771-4 | 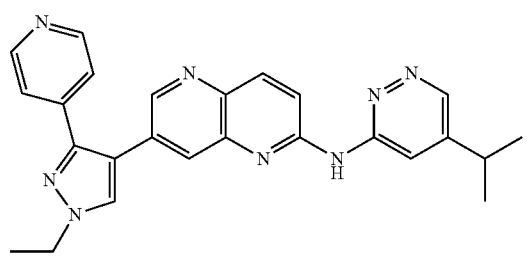 [SMILES: CCn1cc(-c2cnc3ccc(Nc4cc(C(C)C)cnn4)nc3c2)c(-c2ccncc2)n1] | $^1$H-NMR(CDCl$_3$) δ:<br>9.13(1H, brs), 8.80 (2H, brs), 8.69 (1H, brs), 8.55 (2H, dd,<br>J = 4.8, 1.5 Hz), 8.27 (1H, d, J = 9.3 Hz), 7.97 (1H, d, J =<br>1.8 Hz), 7.72 (1H, s), 7.65 (1H, d, J = 9.3 Hz),<br>7.46 (2H, dd, J = 4.8, 1.5<br>Hz), 4.33 (2H, q, J = 7.2 Hz), 3.08-2.90 (1H, m), 1.64<br>(3H, t, J = 7.2 Hz), 1.33 (6H, d, J = 7.2 Hz).<br>MS m/z (M + H): 437. |
Example 0772
Example 0115-1, Example 0110-2, Example 0110-3, The following compounds were obtained in the same manner as in Examples 0478-3 and 0554-3.
| Example No. | | |
|---|---|---|
| 0772 | | |
| 0772-1 | 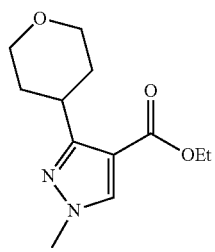 [SMILES: CCOC(=O)c1cn(C)nc1C1CCOCC1] | MS m/z (M + H): 239. |
| 0772-2 | 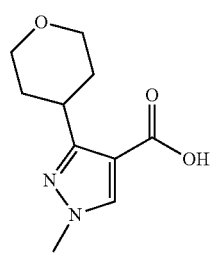 | MS m/z (M + H): 211. |

| Example No. | | |
|---|---|---|
| 0772-3 | 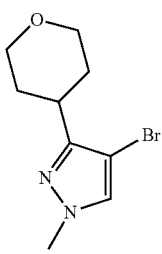 | ¹H-NMR (CDCl₃) δ:<br>7.31 (1H, s), 4.09-4.01 (2H, m), 3.84 (3H, s),<br>3.53 (2H, t, J = 9.0, 2.7 Hz) 2.98-2.86 (1H, m),<br>2.04-1.76 (4H, m) |
| 0772-4 | 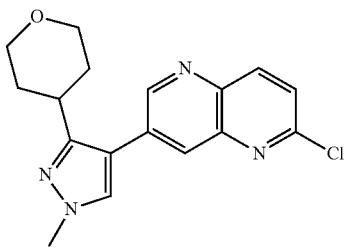 [SMILES: Cn1cc(-c2cnc3ccc(Cl)nc3c2)c(C2CCOCC2)n1] | MS m/z (M + H): 329. |
| 0772-5 | 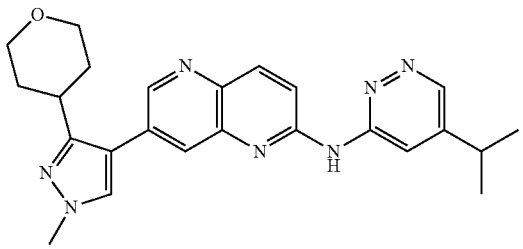 [SMILES: CC(C)c1cnnc(Nc2ccc3ncc(-c4cn(C)nc4C4CCOCC4)cc3n2)c1] | ¹H-NMR (CDCl₃) δ:<br>8.87 (1H, brs), 8.78 (2H, brs), 8.27 (1H, d, J = 9.0 Hz), 8.00 (1H,<br>brs), 7.56 (1H, s), 7.54 (1H, d, J = 9.0 Hz), 4.08-4.01<br>(2H, m), 3.96 (3H, s), 3.54-3.43 (2H, m), 3.08-2.94<br>(1H, m), 2.88-2.74 (1H, m), 2.14-1.94 (2H, m),<br>1.88-1.77 (2H, m), 1.40 (6H, d, J = 7.5 Hz).<br>MS m/z (M + H): 430 |

Example 0773

0773-1

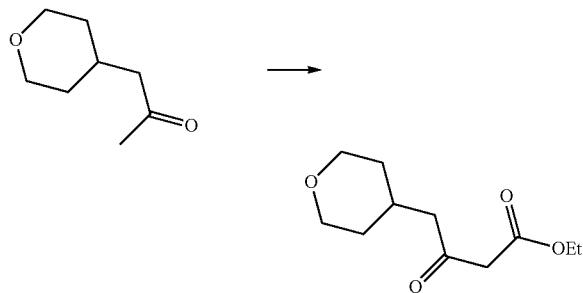

60% sodium hydride (668 mg) was added to a mixture of 1-(tetrahydro-2H-pyran-4-yl)propan-2-one (1.18 g), diethyl carbonate (1.36 mL), and tetrahydrofuran (8 mL) at room temperature, followed by stirring for 4 hours under reflux. After the reaction mixture was cooled to room temperature, a 3 mol/L potassium hydrogen sulfate aqueous solution and ethyl acetate were added thereto, and the organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining ethyl 3-oxo-4-(tetrahydro-2H-pyran-4-yl)butanoate (1.13 g).

MSm/z(M+H):215.

0773-2 to 0773-6

Example 0115-1, Example 0110-1, Example 0110-2, The following compounds were obtained in the same manner as in Examples 0478-3 and 0554-3.

| Example No. | | |
|---|---|---|
| 0773 | | |
| 0773-2 | 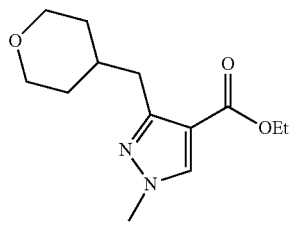 [SMILES: CCOC(=O)c1cn(C)nc1CC1CCOCC1] | MS m/z (M + H): 253. |
| 0773-3 | 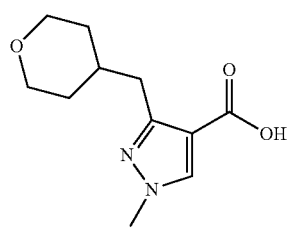 [SMILES: Cn1cc(C(=O)O)c(CC2CCOCC2)n1] | MS m/z (M + H): 225. |
| 0773-4 | 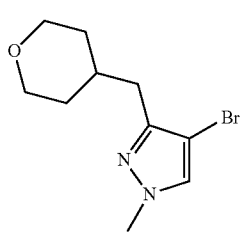 | $^1$H-NMR (CDCl$_3$) δ:<br>7.31 (1H, s), 3.96-3.91 (2H, m), 3.83 (3H, s), 3.42-3.31 (2H, m), 2.54 (2H, d, J = 6.6 Hz), 1.98-1.83 (1H, m), 1.65-1.56 (2H, m), 1.47-1.31 (2H, m). |
| 0773-5 | 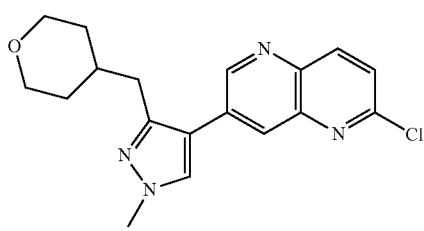 [SMILES: Cn1cc(-c2cnc3ccc(Cl)nc3c2)c(CC2CCOCC2)n1] | MS m/z (M + H): 343. |
| 0773-6 | 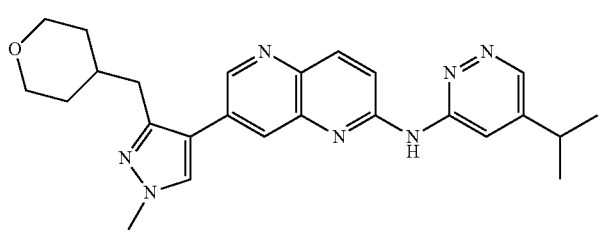 [SMILES: CC(C)c1cnnc(Nc2ccc3ncc(-c4cn(C)nc4CC4CCOCC4)cc3n2)c1] | $^1$H-NMR (CDCl$_3$) δ:<br>8.82 (1H, s), 8.80 (1H, d, J = 2.1 Hz), 8.62 (1H, brs), 8.27 (1H, d, J = 9.3 Hz), 8.03 (1H, brs), 7.59 (1 J, s), 7.52 (1H, d, J = 9.3 Hz), 3.96 (3H, s), 3.94-3.95 (2H, m), 3.38-3.25 (2H, m), 3.11-2.93 (1H, m), 2.79 (2H, d, J = 7.2 Hz),<br>2.03-1.85 (1H, m), 1.68-1.58 (2H, m), 1.45-1.29 (2H, m), 1.40 (6H, d, J = 7.2 Hz).<br>MS m/z (M + H): 444. |

Example 0774

0774-1

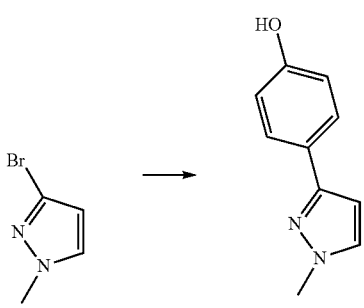

4-(1-Methyl-1H-pyrazol-3-yl)phenol was obtained in the same manner as in Example 0584-1.

MSm/z(M+H):175.

0774-2

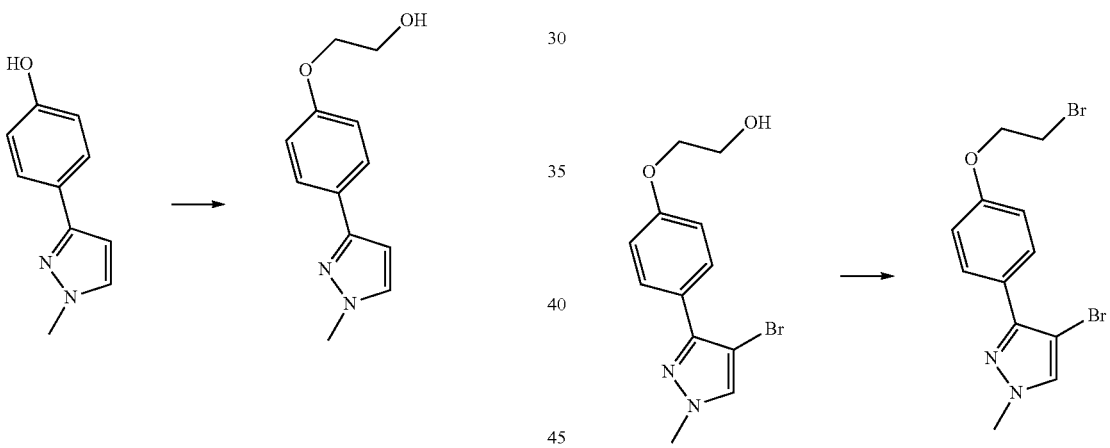

A suspension of 4-(1-methyl-1H-pyrazol-3-yl)phenol (263 mg), 2-bromoethanol (0.129 mL), and potassium carbonate (417 mg) in N,N-dimethylformamide (3 mL) was stirred at 120° C. for 19 hours. After the reaction mixture was cooled to room temperature, ethyl acetate and water were added thereto. The organic layer was collected by separation, and dried over anhydrous sodium sulfate, and the solvent was distilled off under reduced pressure. The obtained residue was purified by silica gel column chromatography (methanol-ethyl acetate-hexane), thereby obtaining 2-(4-(1-methyl-1H-pyrazol-3-yl)phenoxy)ethanol (274 mg).

MSm/z(M+H):219.

0774-3

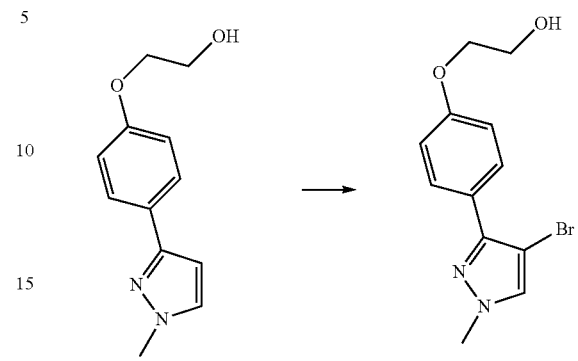

2-(4-(4-Bromo-1-methyl-1H-pyrazol-3-yl)phenoxy)ethanol was obtained in the same manner as in Example 0555-2.

MSm/z(M+H):297.

0774-4

Triphenylphosphine (490 mg) was added to a mixture of 2-(4-(4-bromo-1-methyl-1H-pyrazol-3-yl)phenoxy)ethanol (237 mg), carbon tetrabromide (621 mg), and dichloromethane (3 mL) under ice-cooling, followed by stirring at room temperature for 3 hours. The solvent of the reaction mixture was distilled off under reduced pressure, and the obtained residue was purified by silica gel column chromatography (ethyl acetate-hexane), thereby obtaining 4-bromo-3-(4-(2-bromoethoxy)phenyl)-1-methyl-1H-pyrazole (74 mg).

MSm/z(M+H):359.

923

0774-5

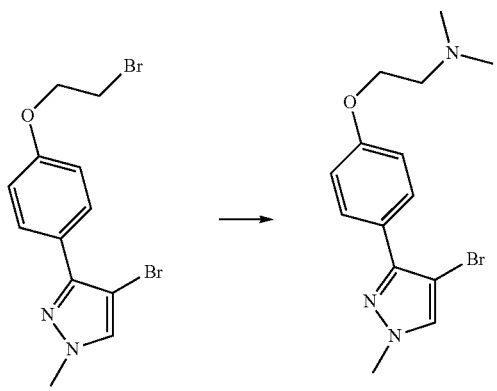 [SMILES: Cn1cc(Br)c(-c2ccc(OCCBr)cc2)n1 ; CN(C)CCOc1ccc(-c2nn(C)cc2Br)cc1]

50% dimethylamine aquaous solution (0.5 mL) was added to a mixture of 4-bromo-3-(4-(2-bromoethoxyl)phenyl)-1-methyl-1H-pyrazole (74 mg) and tetrahydrofuran (2 mL) at room temperature, followed by stirring at 50° C. for 8 hours. The solvent of the reaction mixture was distilled off under reduced pressure, thereby obtaining 2-(4-(4-bromo-1-methyl-1H-pyrazol-3-yl)phenoxy)-N,N-dimethylethan-amine (93 mg).

MSm/z(M+H):324.

0774-6 and 0774-7

The following compounds were obtained in the same manner as in Examples 0478-3 and 0554-3.

| Example No. |
| --- |
| 774 |

0774-6

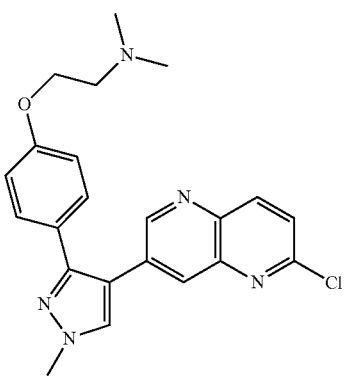 [SMILES: CN(C)CCOc1ccc(-c2nn(C)cc2-c2cnc3ccc(Cl)nc3c2)cc1]

MS m/z (M + H): 408.

0774-7

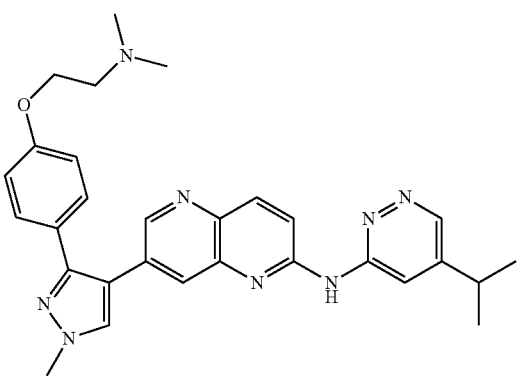 [SMILES: CC(C)c1cnnc(Nc2ccc3ncc(-c4cn(C)nc4-c4ccc(OCCN(C)C)cc4)cc3n2)c1]

$^1$H-NMR (CDCl$_3$) δ:
8.49 (1H, brs), 8.87 (1H, brs), 8.79 (1H, d, J = 2.1 Hz), 8.67
(1H, d, J = 2.1 Hz), 8.23 (1H, d, J = 9.0 Hz), 7.97 (1H, brs),
7.68 (1H, d, J = 9.0 Hz), 7.66 (1H, s), 7.43 (2H, d, J = 8.7
Hz), 6.89 (2H, d, J = 8.7 Hz), 4.05 (2H, t, J = 6.0 Hz), 4.03
(3H, s), 3.08-2.90 (1H, m), 2.72 (2H, t, J = 6.0 Hz),
2.32 (6H, s), 1.34 (6H, d, J = 6.6 Hz).
MS m/z (M + H) 509.

Example 0775

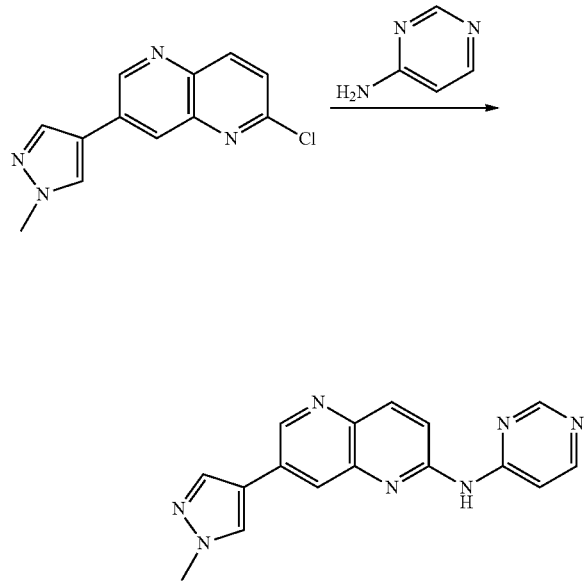

7-(1-Methyl-1H-pyrazol-4-yl)-N-(pyrimidin-4-yl)-1,5-naphthyridine-2-amine was obtained in the same manner as in Example 0015-4.

$^1$H-NMR(CDCl$_3$/CD$_3$OD=4/1)δ:8.93(1H,d,J=1.8 Hz), 8.78(1H,s),8.61(1H,d,J=6.0 Hz),8.53(1H,d,J=6.0 Hz),8.28 (1H,d,J=1.8 Hz),8.23(1H,d,J=9.3 Hz),7.99(1H,s),7.98(1H, s),7.58(1H,d,J=9.3 Hz),4.03(3H,s).

MSm/z(M+H):304.

Example 0776

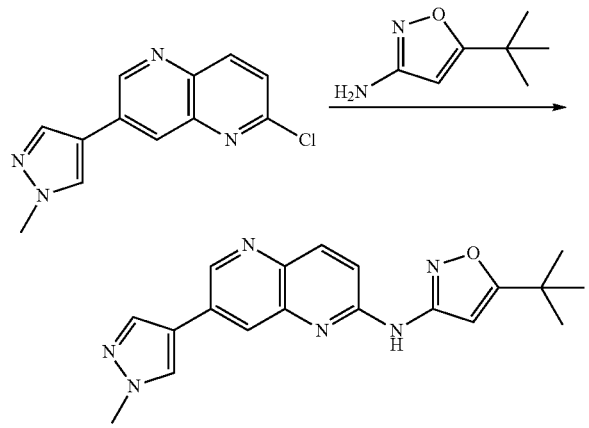

5-(tert-Butyl)-N-(7-(1-methyl-1H-pyrazol-4-yl)-1,5-naphthyridin-2-yl)isoxazole-3-amine was obtained in the same manner as in Example 0554-3.

$^1$H-NMR(CDCl$_3$)δ:9.05(1H,d,J=2.1 Hz),8.77(1H,d,J=2.1 Hz),8.05(1H,d,J=9.3 Hz),8.00(1H,s),7.90(1H,s),7.79(1H,d, J=9.3 Hz),6.72(1H,brs),4.02(3H,s),1.59(9H,s).

MSm/z(M+H):349.

Example 0777

0777-1

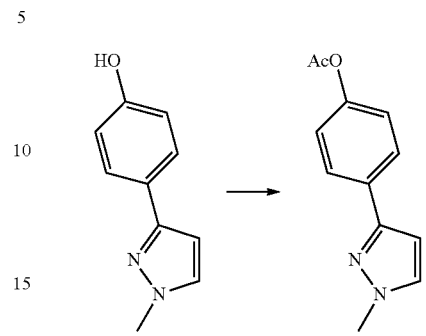

Acetyl chloride (0.143 mL) was added to a mixture of 4-(1-methyl-1H-pyrazol-3-yl)phenol (236 mg), triethylamine (0.283 mL), and tetrahydrofuran (7 mL) under ice-cooling, followed by stirring at room temperature for 1 hour. After water and ethyl acetate were added to the reaction mixture, the organic layer was collected by separation, washed with a saturated sodium chloride aqueous solution, and dried over anhydrous sodium sulfate, and the solvent was distilled off under reduced pressure. The obtained residue was purified by silica gel column chromatography (ethyl acetate-hexane), thereby obtaining 4-(1-methyl-1H-pyrazol-3-yl)phenyl acetate (249 mg).

MSm/z(M+H):217.

0777-2

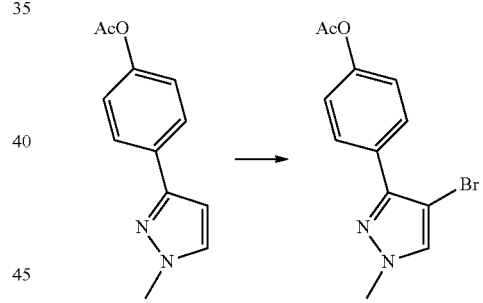

4-(4-Bromo-1-methyl-1H-pyrazol-3-yl)phenyl acetate was obtained in the same manner as in Example 0555-2.

MSm/z(M+H):295.

0777-3

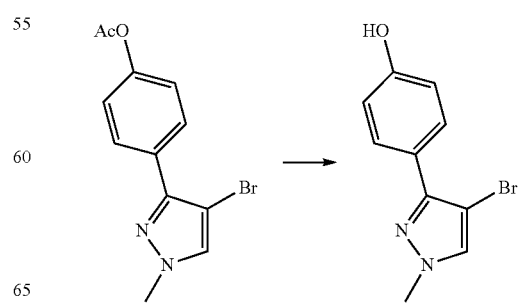

A 4 mol/L sodium hydroxide aqueous solution (0.6 mL) was added to a solution of 4-(4-bromo-1-methyl-1H-pyrazol-3-yl)phenyl acetate (381 mg) in tetrahydrofuran (2 mL), followed by stirring at room temperature for 3 hours. The reaction mixture was purified by silica gel column chromatography (ethyl acetate-hexane), thereby obtaining 4-(4-bromo-1-methyl-1H-pyrazol-3-yl)phenol (243 mg).

MSm/z(M+H):253.

0777-4

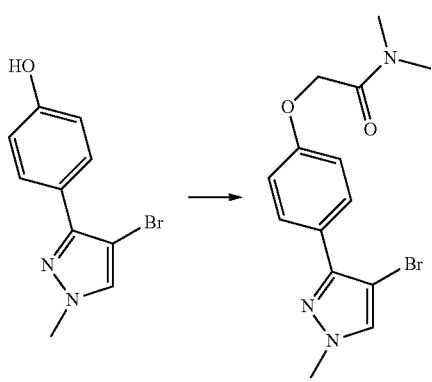 [SMILES: Cn1cc(Br)c(-c2ccc(O)cc2)n1 ; CN(C)C(=O)COc1ccc(-c2nn(C)cc2Br)cc1]

A mixture of 4-(4-bromo-1-methyl-1H-pyrazol-3-yl)phenol (45 mg), 2-chloro-N,N-dimethylacetamide (0.063 mL), cesium carbonate (252 mg), sodium iodide (77 mg), acetonitrile (1 mL), and tetrahydrofuran (0.5 mL) was stirred at 50° C. for 19 hours. The reaction mixture was cooled to room temperature, and purified by silica gel column chromatography (methanol-ethyl acetate-hexane), thereby obtaining 2-(4-(4-bromo-1-methyl-1H-pyrazol-3-yl)phenoxy)-N,N-dimethylacetamide (67 mg).

MSm/z(M+H):338.

0777-5

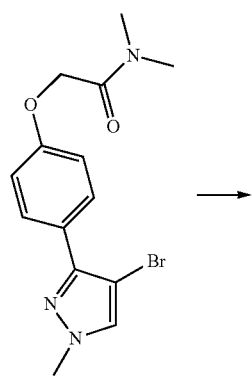

-continued

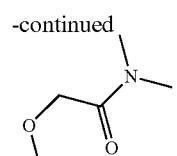
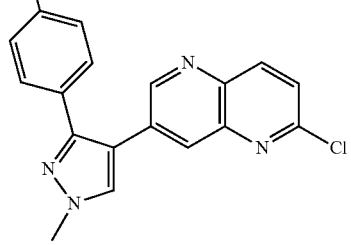

2-(4-(4-(6-Chloro-1,5-naphthyridin-3-yl)-1-methyl-1H-pyrazol-3-yl)phenoxy)-N,N-dimethylacetamide was obtained in the same manner as in Example 0478-3.

MSm/z(M+H):422.

0777-6

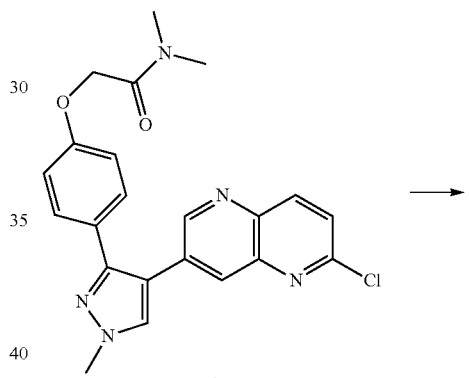

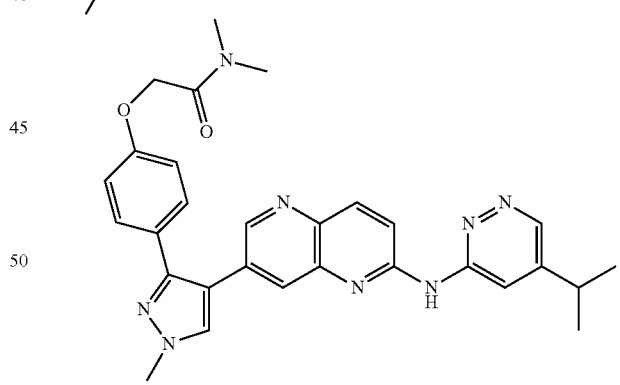

2-(4-(4-(6-((5-Isopropylpyridazin-3-yl)amino)-1,5-naphthyridin-3-yl)-1-methyl-1H-pyrazol-3-yl)phenoxy)-N,N-dimethylacetamide was obtained in the same manner as in Example 0555-4.

$^1$H-NMR(CDCl$_3$)δ:9.35(1H,brs),8.84(1H,brs),8.79(1H,d,J=2.1 Hz),8.66(1H,d,J=2.1 Hz),8.23(1H,d,J=8.7 Hz),7.98(1H,d,J=2.1 Hz),7.67(1H,d,J=8.7 Hz),7.65(1H,s),7.44(2H,d,J=8.7 Hz),6.92(2H,d,J=8.7 Hz),4.66(2H,s),4.03(3H,s),3.10-2.94(1H,m),3.07(3H,s),2.96(3H,s),1.35(6H,d,J=7.2 Hz).

MSm/z(M+H):523.

Example 0778

0778-1

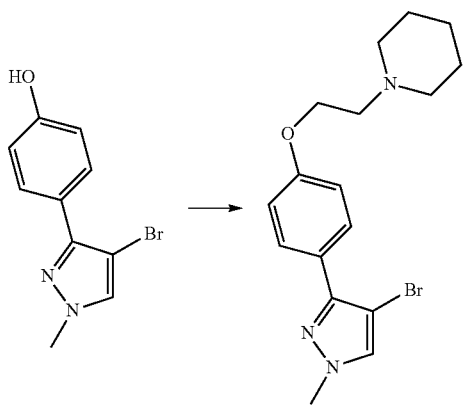 [SMILES: Cn1cc(Br)c(-c2ccc(O)cc2)n1 ; Cn1cc(Br)c(-c2ccc(OCCN3CCCCC3)cc2)n1]

A 2.2 mol/L diethyl azodicarboxylate toluene solution (0.195 mL) was added to a mixture of 4-(4-bromo-1-methyl-1H-pyrazol-3-yl)phenol (50 mg), 2-(piperidin-1-yl)ethanol (0.056 mL), triphenylphosphine (112 mg), and tetrahydrofuran (3 mL) under ice-cooling, followed by stirring at room temperature for 3 hours. The reaction mixture was purified by silica gel column chromatography (methanol-ethyl acetate-hexane), thereby obtaining 1-(2-(4-(4-bromo-1-methyl-1H-pyrazol-3-yl)phenoxy)ethyl)piperidine (70 mg).

MS m/z (M+H): 364.

0778-2 and 0778-3

The following compounds were obtained in the same manner as in Examples 0478-3 and 0554-3.

Example No.

778

0778-2

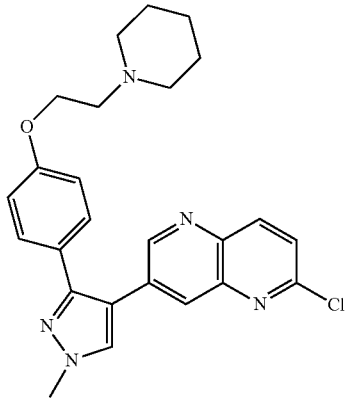 [SMILES: Cn1cc(-c2cnc3ccc(Cl)nc3c2)c(-c2ccc(OCCN3CCCCC3)cc2)n1]

MS m/z (M + H): 448.

0778-3

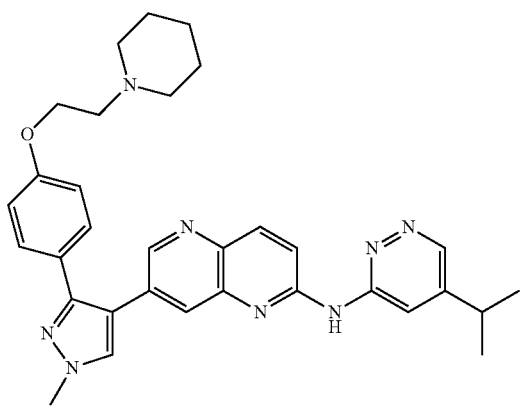 [SMILES: CC(C)c1cnnc(Nc2ccc3ncc(-c4cn(C)nc4-c4ccc(OCCN5CCCCC5)cc4)cc3n2)c1]

$^1$H-NMR (CDCl$_3$) δ:
8.23 (1H, brs), 8.84 (1H, brs), 8.78 (1H, brs), 8.66 (1H, brs), 8.23 (1H, d, J = 9.3 Hz), 7.87 (1H, brs), 7.66 (1H, s), 7.63 (1H,
d, J = 9.3 Hz), 7.42 (2H, d, J = 9.0 Hz), 6.87 (2H, d, J = 9.0 Hz),
4.15 (2H, t, J = 6.0 Hz), 4.03 (3H, s), 3.07-2.90 (1H, m), 2.86 (2H, brs), 2.60 (4H, brs), 1.82-1.42 (6H, m), 1.34 (6H, d, J = 7.2 Hz).
MS m/z (M + H) 549.

Example 0779
The following compounds were obtained in the same manner as in Examples 0115-1, 0110-1, 0110-2, 0478-3, and 0554-3.
| Example No. | | |
|---|---|---|
| 0779 | | |
| 0779-1 | 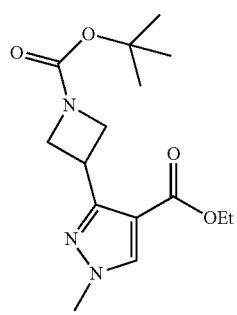 [SMILES: CCOC(=O)c1cn(C)nc1C1CN(C(=O)OC(C)(C)C)C1] | MS m/z (M + H): 310. |
| 0779-2 | 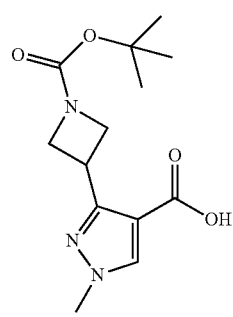 [SMILES: Cn1cc(C(=O)O)c(C2CN(C(=O)OC(C)(C)C)C2)n1] | MS m/z (M + H): 282. |
| 0779-3 | 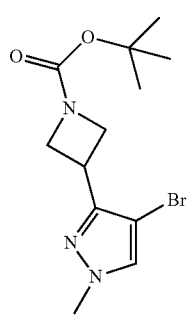 [SMILES: Cn1cc(Br)c(C2CN(C(=O)OC(C)(C)C)C2)n1] | MS m/z (M + H): 316. |
| 0779-4 | 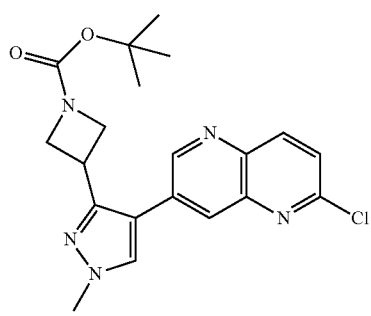 [SMILES: Cn1cc(-c2cnc3ccc(Cl)nc3c2)c(C2CN(C(=O)OC(C)(C)C)C2)n1] | MS m/z (M + H): 400. |

| Example No. | | |
|---|---|---|
| 0779-5 | 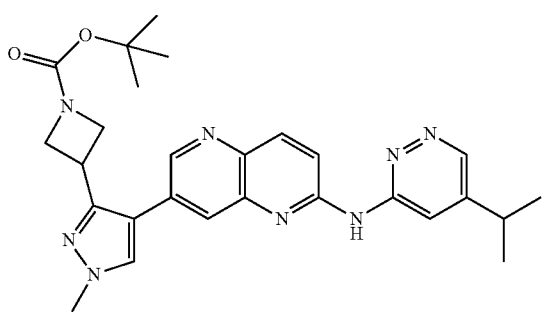 [SMILES: CC(C)c1cnnc(Nc2ccc3ncc(-c4cn(C)nc4C4CN(C(=O)OC(C)(C)C)C4)cc3n2)c1] | ¹H-NMR (CDCl₃) δ:<br>8.61 (2H, brs), 8.70 (1H, brs), 8.26 (1H, d, J = 8.7 Hz), 7.86 (1H, d, J = 2.1 Hz), 7.65 (1H, s), 7.52 (1H, d, J = 8.7 Hz), 4.76-<br>4.58 (1H, m), 4.34-4.23 (4H, m), 3.99 (3H, s), 3.11-2.95 (1H, m), 1.43 (9H, s), 1.41 (6H, d, J = 6.6 Hz).<br>MS m/z (M + H): 501. |

Example 0780

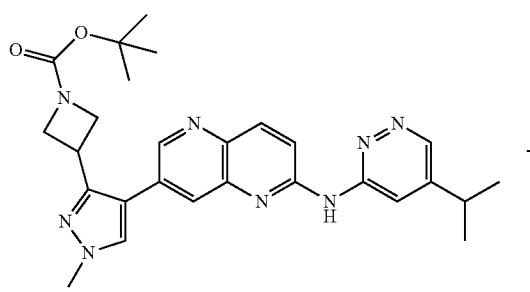

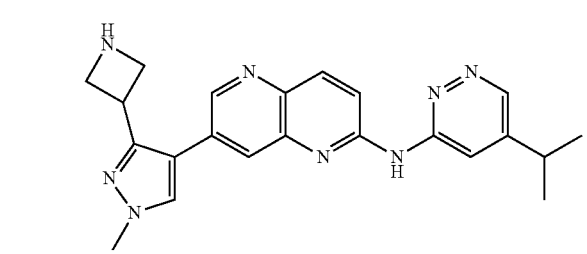

Trifluoroacetic acid (1 mL) was added to a mixture of tert-butyl 3-(4-(6-((5-isopropylpyridazin-3-yl)amino)-1,5-naphthyridin-3-yl)-1-methyl-1H-pyrazol-3-yl)azetidine-1-carboxylate (3 mg), and water (0.05 mL), followed by stirring at room temperature for 1 hour. The solvent of the reaction mixture was distilled off under reduced pressure, and the obtained residue was purified by silica gel column chromatography (methanol-ethyl acetate, NH silica), thereby obtaining 7-(3-(azetidin-3-yl)-1-methyl-1H-pyrazol-4-yl)-N-(5-isopropylpyridazin-3-yl)-1,5-naphthyridine-2-amine (1 mg).

¹H-NMR(CDCl₃)δ:8.86(1H,brs),8.81(1H,brs),8.71(1H,d, J=1.8 Hz),8.26(1H,d,J=9.0 Hz),7.89(1H,brs),7.62(1H,s), 7.58(1H,d,J=9.0 Hz),4.29-4.16(1H,m),4.11(2H,t,J=7.2 Hz), 4.00(3H,s),3.91(2H,t,J=7.2 Hz),3.10-2.95(1H,m),1.41(6H, d,J=7.2 Hz).
MSm/z(M+H):401.

Example 0781

0781-1

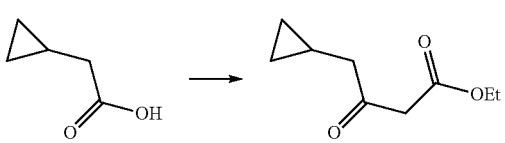 [SMILES: O=C(O)CC1CC1 ; CCOC(=O)CC(=O)CC1CC1]

Carbonyldiimidazole (1.94 g) was added to a mixture of 2-cyclopropylacetic acid (0.93 mL), Meldrum's acid (2.16 g), N,N-dimethylpyridine-4-amine (1.83 g), and dichloromethane (30 mL) under ice-cooling, followed by stirring at room temperature for 15 hours. After 1 mol/L hydrochloric acid was added to the reaction mixture, the organic layer was collected by separation, washed with a saturated sodium chloride aqueous solution, and dried over anhydrous sodium sulfate, and the solvent was distilled off under reduced pressure. Ethanol (20 mL) was added to the obtained residue, followed by stirring for 7 hours under reflux. The solvent was distilled off under reduced pressure, and the obtained residue was purified by silica gel column chromatography (ethyl acetate-hexane), thereby obtaining ethyl 4-cyclopropyl-3-oxobutanoate (528 mg).

¹H-NMR(CDCl₃)δ:4.20(2H,q,J=7.2 Hz),3.49(2H,s),2.42 (2H,d,J=6.6 Hz),1.28(3H,t,J=7.2 Hz),1.08-0.87(1H,m), 0.64-0.51(2H,m),0.18-0.11(2H,m).

0781-2 to 0781-6

Example 0115-1, Example 0110-1, Example 0110-2, The following compounds were obtained in the same manner as in Examples 0478-3 and 0554-3.

| Example No. | | |
|---|---|---|
| 0781 | | |
| 0781-2 | 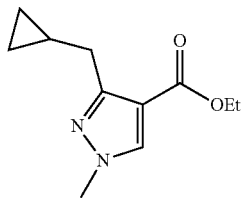 | MS m/z (M + H): 209. |
| 0781-3 | 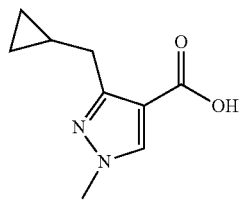 | MS m/z (M + H): 181. |
| 0781-4 | 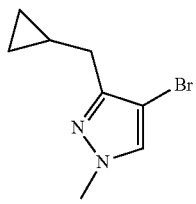 | $^1$H-NMR (CDCl$_3$) δ:<br>7.31 (1H, s), 3.84 (3H, s), 2.52 (2H, d, J = 6.6 Hz), 1.16-1.02 (1H, m), 0.52-0.44 (2H, m), 0.27-0.21 (2H, m). |
| 0781-5 | 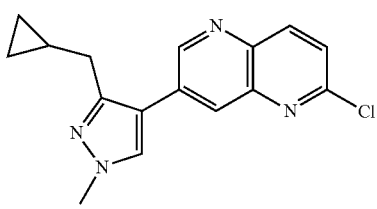 [SMILES: Cn1cc(-c2cnc3ccc(Cl)nc3c2)c(CC2CC2)n1] | MS m/z (M + H): 299. |
| 0781-6 | 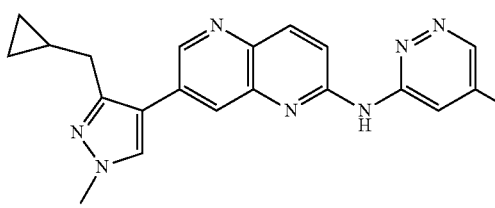 | $^1$H-NMR (CDCl$_3$) δ:<br>8.89 (1H, brs), 8.84 (1H, d, J = 2.1 Hz), 8.80 (1H, d, J = 2.1 Hz),<br>8.26 (1H, d, J = 9.0 Hz), 8.11 (1H, d, J = 2.1 Hz), 7.62 (1H, s),<br>7.53 (1H, d, J = 9.0 Hz), 3.97 (3H, s), 3.11-2.95 (1H, m),<br>2.81 (2H, d, J = 6.6 Hz), 1.40 (6H, d, J = 6.6 Hz), 1.17-1.02 (1H, m), 0.52-0.44 (2H, m), 0.23-0.16 (2H, m).<br>MS m/z (M + H): 400. |

Examples 0782 and 0783

The following compounds were obtained in the same manner as in Example 0015-4.

| Example No. | | |
|---|---|---|
| 0782 | 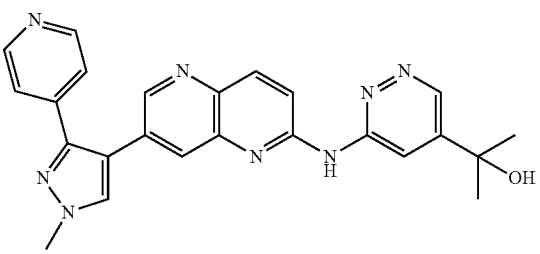 [SMILES: Cn1cc(-c2cnc3ccc(Nc4cc(C(C)(C)O)cnn4)nc3c2)c(-c2ccncc2)n1] | ¹H-NMR (CDCl₃/CD₃OD = 4/1) δ:<br>8.93 (2H, brs), 8.63 (1H, d, J = 1.8 Hz),<br>8.51 (2H, dd, J = 4.8, 1.8 Hz), 8.23 (1H, d, J = 9.3 Hz),<br>8.00 (1H, d, J = 1.8 Hz), 7.83 (1H, s), 7.59 (1H,<br>d, J = 9.3 Hz), 7.50 (2H, dd, J = 4.8, 1.8 Hz), 4.05<br>(3H, s), 1.57 (6H, s).<br>MS m/z (M + H): 439. |
| 0783 | 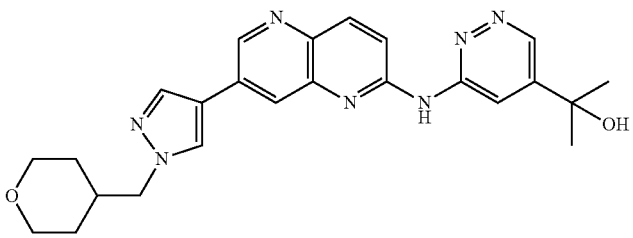 [SMILES: CC(C)(O)c1cnnc(Nc2ccc3ncc(-c4cnn(CC5CCOCC5)c4)cc3n2)c1] | ¹H-NMR (CDCl₃/CD₃OD = 4/1) δ:<br>9.05 (1H, brs), 8.90 (1H, brs),<br>8.89 (1H, d, J = 2.1 Hz), 8.23 (1H, d, J = 2.1 Hz),<br>8.21 (1H, d, J = 9.3 Hz), 8.00 (1H, s), 7.99 (1H, s),<br>7.55 (1H, d, J = 9.3 Hz), 4.12 (2H, d, J = 7.2 Hz), 4.01 (2H,<br>dd, J = 11.1, 3.6 Hz), 3.43 (2H, td, J = 11.1, 3.6 Hz),<br>2.32-<br>2.15 (1H, m), 1.72-1.34 (4H, m), 1.66 (6H, s).<br>MS m/z (M + H): 446. |

Example 0784

0784-1

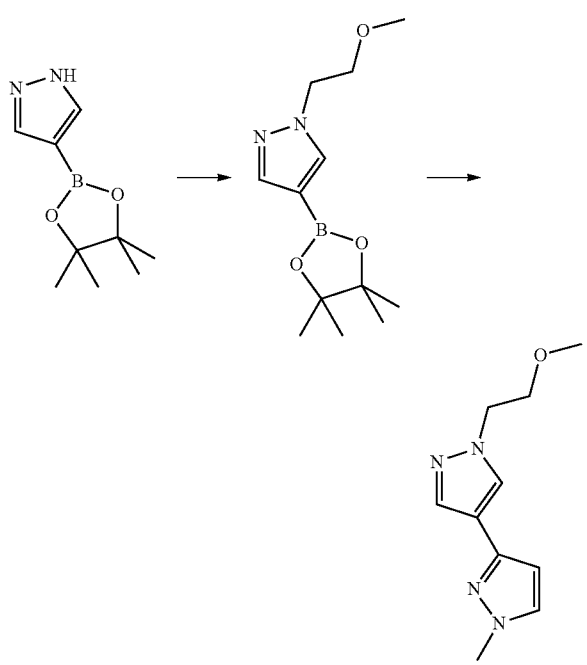

A mixture of 4-(4,4,5,5-tetramethyl-1,3,2-dioxaborolan-2-yl)-1H-pyrazole (300 mg), 1-bromo-2-methoxyethane (0.252 mL), cesium carbonate (954 mg), acetonitrile (4 mL), and 1,2-dimethoxyethane (2 mL) was stirred at 80° C. for 4 hours. The reaction mixture was cooled to room temperature, and insolubles were filtered off. The solvent was distilled off under reduced pressure, thereby obtaining 1-(2-methoxyethyl)-4-(4,4,5,5-tetramethyl-1,3,2-dioxaborolan-2-yl)-1H-pyrazole (429 mg).

A mixture of the obtained 1-(2-methoxyethyl)-4-(4,4,5,5-tetramethyl-1,3,2-dioxaborolan-2-yl)-1H-pyrazole (429 mg), 3-bromo-1-methyl-1H-pyrazole (200 mg), sodium carbonate (323 mg), bis(di-tert-butyl(4-dimethylaminophenyl)phosphine)dichloropalladium(II) (43 mg), water (1 mL), and 1,2-dimethoxyethane (5 mL) was stirred at 80° C. for 2 hours. The reaction mixture was cooled to room temperature, insolubles were filtered off, and the solvent was distilled off under reduced pressure. The obtained residue was purified by silica gel column chromatography (methanol-ethyl acetate), thereby obtaining 1'-(2-methoxyethyl)-1-methyl-1H,1'H-3,4'-bipyrazole (198 mg).

MSm/z(M+H):207.

0784-2 to 0784-4

The following compounds were obtained in the same manner as in Examples 0555-2, 0478-3, and 0554-3.

| Example No. | | |
|---|---|---|
| 0784 | | |
| 0784-2 | 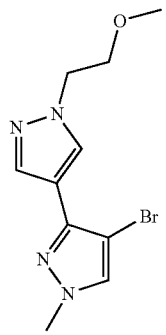 [SMILES: COCCn1cc(-c2nn(C)cc2Br)cn1] | MS m/z (M + H): 285. |
| 0784-3 | 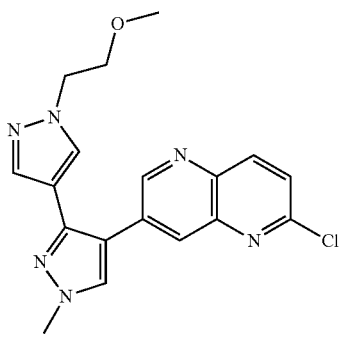 [SMILES: COCCn1cc(-c2nn(C)cc2-c2cnc3ccc(Cl)nc3c2)cn1] | MS m/z (M + H): 369. |
| 0784-4 | 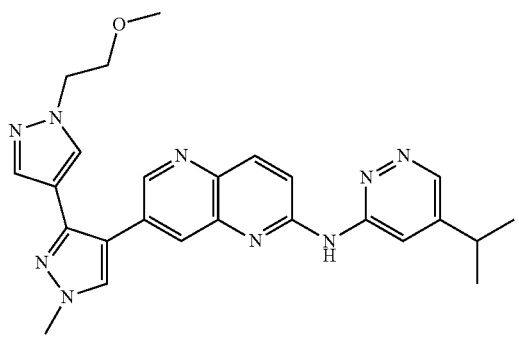 [SMILES: COCCn1cc(-c2nn(C)cc2-c2cnc3ccc(Nc4cc(C(C)C)cnn4)nc3c2)cn1] | $^1$H-NMR (CDCl$_3$) δ:<br>8.83 (1H, brs), 8.78 (1H, brs), 8.76 (1H, d, J = 1.8 Hz), 8.26 (1H, d, J = 8.4 Hz), 8.06 (1H, d, J = 1.8 Hz), 7.64 (1H, s), 7.61 (1H, d, J = 8.4 Hz), 7.59 (1H, s), 7.57 (1H, s), 4.23 (2H, t, J = 5.4 Hz), 4.01 (3H, s), 3.69 (2H, t, J = 5.4 Hz), 3.24 (3H, s), 3.09-2.93 (1H, m), 1.37 (6H, d, J = 6.6 Hz).<br>MS m/z (M + H): 470. |

Example 0785

0785-1

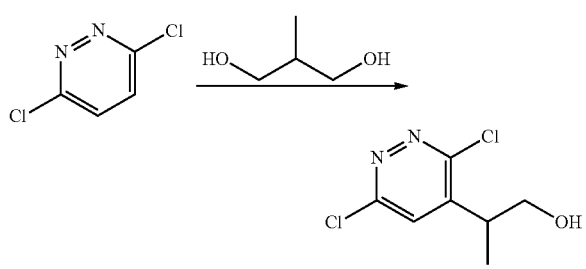

Potassium peroxodisulfate (6.72 g) was added to a mixture of 3,6-dichloropyridazine (2 g), trifluoroacetic acid (1.22 mL), 2-methylpropane-1,3-diol (2.65 g), silver nitrate (3.07 mg), and water (14 mL) at 80° C., followed by stirring at the same temperature for 30 minutes. After the reaction mixture was cooled on ice, sodium carbonate (10 g) and sodium chloride (1 g) were added thereto, followed by stirring at room temperature for 30 minutes. Insolubles were filtered off, and ethyl acetate was added thereto. The organic layer was collected by separation, washed with a saturated sodium chloride aqueous solution, and dried over anhydrous sodium sulfate, and the solvent was distilled off under reduced pressure. The obtained residue was purified by silica gel column chromatography (methanol-ethyl acetate), thereby obtaining 2-(3,6-dichloropyridazin-4-yl)propan-1-ol (1.93 g).

MSm/z(M+H):207.

0785-2 to 0785-6

Example 0562-1, Example 0559-2, The following compounds were obtained in the same manner as in Examples 0559-3, 0559-4, and 0554-3.

| Example No. | | |
|---|---|---|
| 0785 | | |
| 0785-2 | 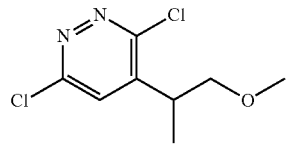 | MS m/z (M + H): 221. |
| 0785-3 | 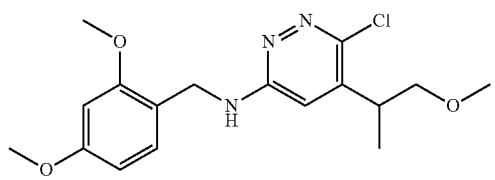 | MS m/z (M + H): 352. |
| 0785-4 | 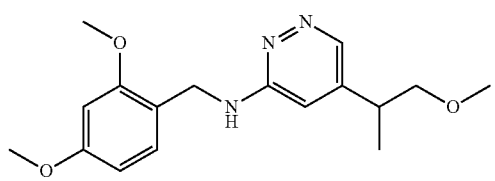 | MS m/z (M + H): 318. |
| 0785-5 | 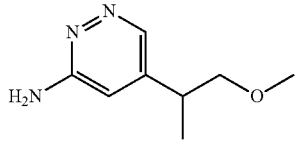 | MS m/z (M + H): 168. |
| 0785-6 | 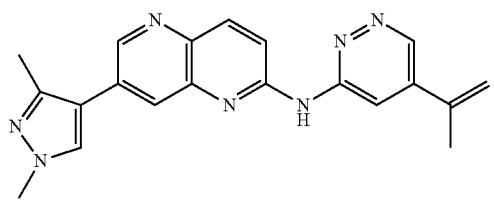 [SMILES: C=C(C)c1cnnc(Nc2ccc3ncc(-c4cn(C)nc4C)cc3n2)c1] | $^1$H-NMR (CDCl$_3$/CD$_3$OD = 4/1) δ: 9.08 (1H, brs), 8.93 (1H, brs), 8.78 (1H, d, J = 1.8 Hz), 8.23 (1H, d, J = 9.3 Hz), 8.09 (1H, brs), 7.76 (1H, s), 7.52 (1H, d, J = 9.3 Hz), 5.89 (1H, brs), 5.51 (1H, brs), 3.95 (3H, s), 2.50 (3H, s), 2.28 (3H, s) MS m/z (M + H): 358. |

Example 0786

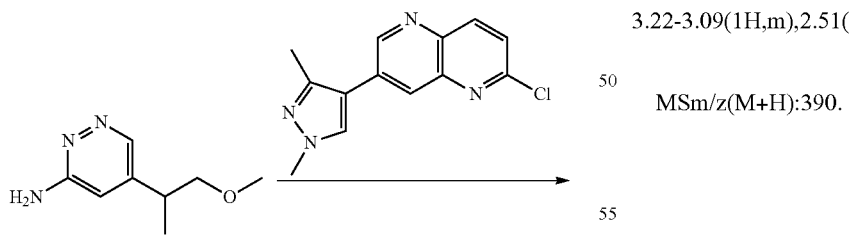

7-(1,3-dimethyl-1H-pyrazol-4-yl)-N-(5-(1-methoxypropan-2-yl)pyridazin-3-yl)-1,5-naphthyridine-2-amine was obtained in the same manner as in Example 0015-4.

$^1$H-NMR(CDCl$_3$)δ:9.83(1H,brs),8.98(1H,brs),8.84(2H, brs),8.27(1H,d,J=9.0 Hz),8.06(1H,brs),7.79(1H,d,J=9.0 Hz),7.64(1H,s),3.95(3H,s),3.61(2H,d,J=6.6 Hz),3.37(3H,s), 3.22-3.09(1H,m),2.51(3H,s),1.43(3H,d,J=7.2 Hz).

MSm/z(M+H):390.

Example 0787

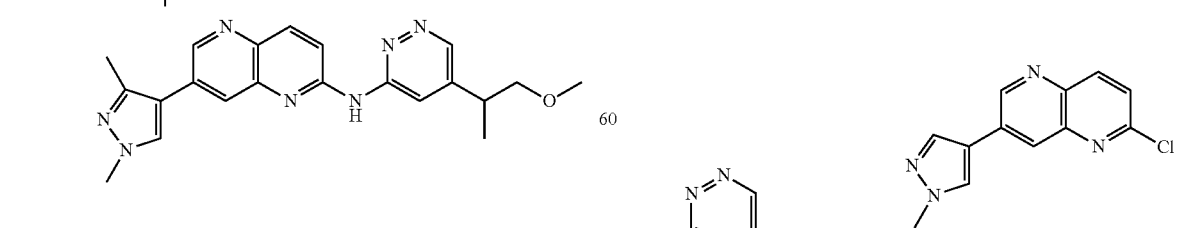

943

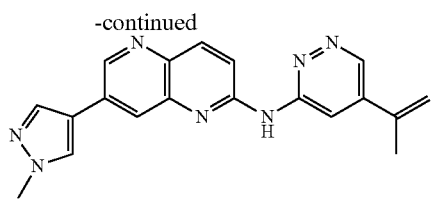

7-(1-Methyl-1H-pyrazol-4-yl)-N-(5-(prop-1-en-2-yl)pyridazin-3-yl)-1,5-naphthyridine-2-amine was obtained in the same manner as in Example 0554-3.

$^1$H-NMR(CDCl$_3$/CD$_3$OD=4/1):9.04(1H,brs),8.93(1H,brs),8.88(2H,brs),8.21(1H,d,J=9.3 Hz),8.12(1H,brs),7.95(1H,brs),7.50(1H,d,J=9.3 Hz),5.83(1H,brs),5.52(1H,brs),4.02(3H,s),2.30(3H,s).

MSm/z(M+H):344.

Example 0788

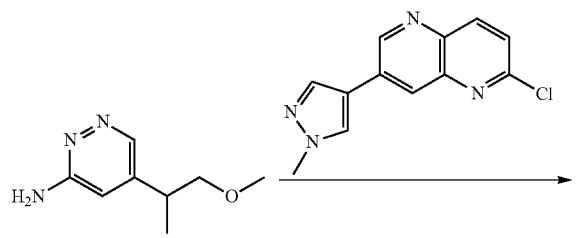

944

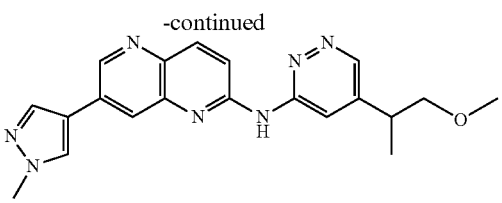

N-(5-(1-methoxypropan-2-yl)pyridazin-3-yl)-7-(1-methyl-1H-pyrazol-4-yl)-1,5-naphthyridine-2-amine was obtained in the same manner as in Example 0646-3.

$^1$H-NMR(CDCl$_3$)δ:9.44(1H,brs),8.97(1H,brs),8.92(1H,d,J=2.1 Hz),8.84(1H,brs),8.25(1H,d,J=9.3 Hz),8.10(1H,brs),7.95(1H,s),7.84(1H,s),7.67(1H,d,J=9.3 Hz),4.03(3H,s),3.62(2H,d,J=6.6 Hz),3.39(3H,s),3.25-3.11(1H,m),2.17(3H,s),1.44(3H,d,J=7.2 Hz).

MSm/z(M+H):376.

Examples 0789 to 0791

The following compounds were obtained in the same manner as in Example 0554-3.

| Example No. | | |
|---|---|---|
| 0789 | 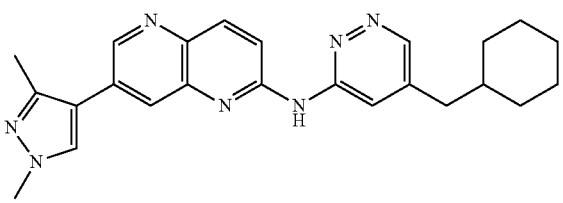 [SMILES: Cc1nn(C)cc1-c1cnc2ccc(Nc3cc(CC4CCCCC4)cnn3)nc2c1] | $^1$H-NMR (CDCl$_3$/CD$_3$OD = 4/1) δ: 8.78 (1H, d, J = 2.1 Hz), 8.76 (1H, brs), 8.62 (1H, brs), 8.21 (1H, d, J = 9.3 Hz), 8.10 (1H, d, J = 2.1 Hz), 7.74 (1H, s), 7.51 (1H, d, J = 9.3 Hz), 3.95 (3H, s), 2.61 (2H, d, J = 7.2 Hz), 2.50 (3H, s), 1.85-1.61 (8H, m), 1.35-1.00 (3H, m).<br>MS m/z (M + H): 414. |
| 0790 | 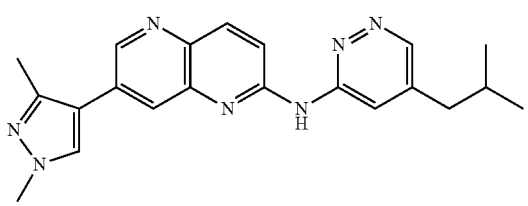 [SMILES: Cc1nn(C)cc1-c1cnc2ccc(Nc3cc(CC(C)C)cnn3)nc2c1] | $^1$H-NMR (CDCl$_3$) δ: 9.37 (1H, brs), 8.84 (1H, d, J = 1.8 Hz), 8.77 (1H, brs), 8.72 (1H, brs), 8.27 (1H, d, J = 9.3 Hz), 8.05 (1H, brs), 7.66 (1H, d, J = 9.3 Hz), 7.65 (1H, s), 3.95 (3H, s), 2.60 (2H, d, J = 7.2 Hz), 2.50 (3H, s), 2.15-2.00 (1H, m), 1.04 (6H, d, J = 6.9 Hz).<br>MS m/z (M + H:) 374. |
| 0791 | 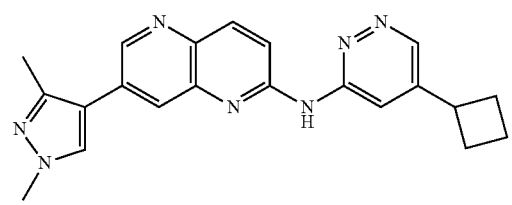 [SMILES: Cc1nn(C)cc1-c1cnc2ccc(Nc3cc(C4CCC4)cnn3)nc2c1] | $^1$H-NMR (CDCl$_3$/CD$_3$OD = 4/1)<br>δ: 8.90 (1H, brs), 8.78 (1H, d, J = 1.8 Hz), 8.65 (1H, brs), 8.22 (1H, d, J = 9.3 Hz), 8.10 (1H, d, J = 1.8 Hz), 7.75 (1H, s), 7.51 (1H, d, J = 9.3 Hz), 3.94 (3H, s), 3.75-3.56 (1H, m), 2.59-2.47 (2H, m), 2.50 (3H, s), 2.38-2.11 (4H, m).<br>MS m/z (M + H): 372. |

Example 0792

The following compounds were obtained in the same manner as in Examples 0440-1 and 0015-4.

| Example No. | | |
|---|---|---|
| 0792 | | |
| 0792-1 | 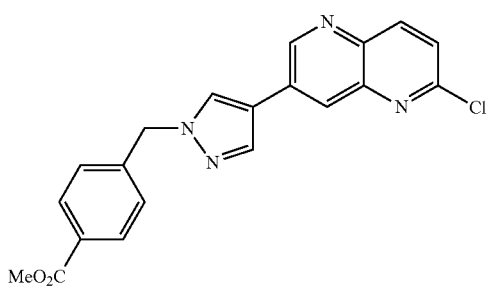 [SMILES: COC(=O)c1ccc(Cn2cc(-c3cnc4ccc(Cl)nc4c3)cn2)cc1] | MS m/z (M + H): 379. |
| 0792-2 | 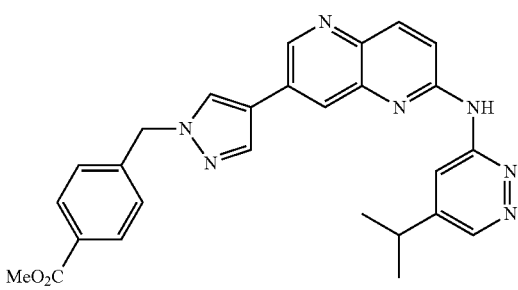 [SMILES: COC(=O)c1ccc(Cn2cc(-c3cnc4ccc(Nc5cc(C(C)C)cnn5)nc4c3)cn2)cc1] | $^1$H-NMR (DMSO-$d_6$) δ: 10.70 (1H, s), 9.06 (1H, d, J = 2.0 Hz), 8.85 (1H, d, J = 2.0 Hz), 8.73 (1H, d, J = 2.0 Hz), 8.67 (1H, s), 8.26-8.22 (3H, m), 7.97 (2H, d, J = 4.3 Hz), 7.71 (1H, d, J = 9.2 Hz), 7.41 (2H, d,= 8.6 Hz), 5.53 (2H, s), 3.84 (3H, s), 3.04-3.02 (1H, m), 1.33 (6H, d, J = 6.6 Hz). MS m/z (M + H): 480. |

Example 0793

0793-1 and 0793-2

The following compounds were obtained in the same manner as in Examples 0451-1 and 0451-2.

| Example No. | | |
|---|---|---|
| 0793 | | |
| 0793-1 | 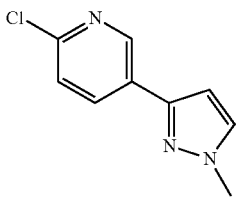 | MS m/z (M + H): 194. |
| 0793-2 | 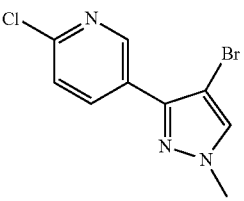 | MS m/z (M + H): 274. |

0793-3

A mixture of 5-(4-bromo-1-methyl-1H-pyrazol-3-yl)-2-chloropyridine (288 mg), 1,4-dioxane (2 mL), and a 50% dimethylamine aqueous solution (1.5 mL) was stirred at 160° C. for 1 hour using a microwave reaction apparatus. The reaction mixture was cooled to room temperature, and the solvent was distilled off under reduced pressure. The obtained residue was purified by silica gel column chromatography (hexane-ethyl acetate-methanol, NH silica), thereby obtaining 5-(4-bromo-1-methyl-1H-pyrazol-3-yl)-N,N-dimethylpyridine-2-amine (81 mg) as colorless oily substance.

MSm/z(M+H):281.

0793-4 and 0793-5

The following compounds were obtained in the same manner as in Examples 0421-1 and 0015-4.

| Example No. | | |
|---|---|---|
| 0793 | | |
| 0793-4 | 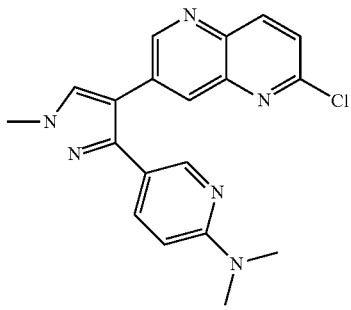 [SMILES: CN/C=C(\C(=N)c1ccc(N(C)C)nc1)c1cnc2ccc(Cl)nc2c1] | MS m/z (M + H): 365. |
| 0793-5 | 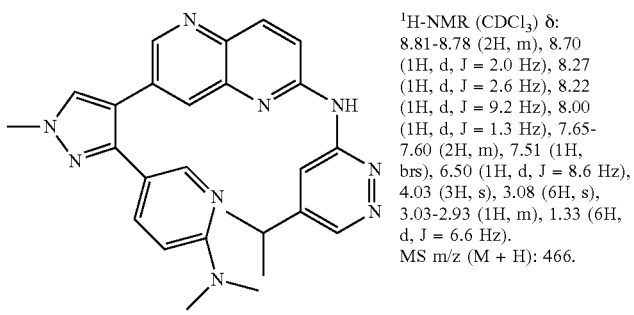 | ¹H-NMR (CDCl₃) δ: 8.81-8.78 (2H, m), 8.70 (1H, d, J = 2.0 Hz), 8.27 (1H, d, J = 2.6 Hz), 8.22 (1H, d, J = 9.2 Hz), 8.00 (1H, d, J = 1.3 Hz), 7.65-7.60 (2H, m), 7.51 (1H, brs), 6.50 (1H, d, J = 8.6 Hz), 4.03 (3H, s), 3.08 (6H, s), 3.03-2.93 (1H, m), 1.33 (6H, d, J = 6.6 Hz). MS m/z (M + H): 466. |

Example 0794

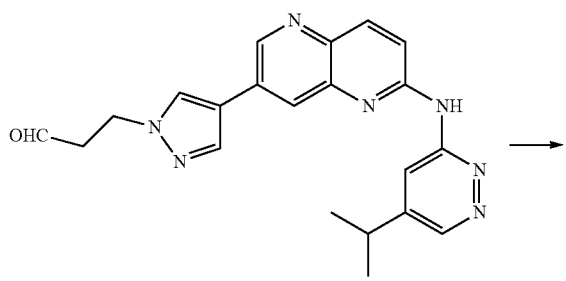

HCL salt

→

-continued

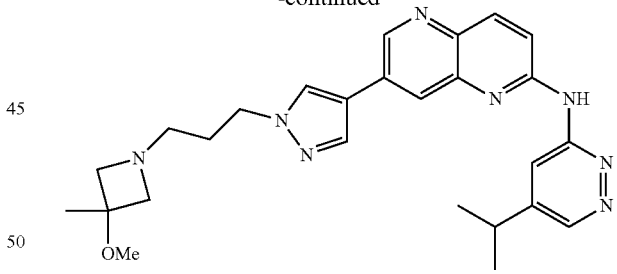

N-(5-isopropylpyridazin-3-yl)-7-(1-(3-(3-methoxy-3-methylazetidin-1-yl)propyl)-1H-pyrazol-4-yl)-1,5-naphthyridine-2-amine was obtained as a white solid in the same manner as in Example 0426-2.

¹H-NMR(CDCl₃)δ:8.93(1H,d,J=2.0 Hz),8.82(2H,m), 8.69(1H,brs),8.24(1H,d,J=9.2 Hz),8.10(1H,d,J=2.0 Hz), 7.95(1H,s),7.86(1H,s),7.50(1H,d,J=8.6 Hz),4.28(2H,t,J=6.9 Hz),3.23-3.19(5H,m),3.08-3.00(3H,m),2.52(2H,t,J=6.9 Hz), 1.99(2H,t,J=6.9 Hz),1.47(3H,s),1.42(6H,d,J=6.6 Hz).
MSm/z(M+H):473.

Example 0795

The following compounds were obtained in the same manner as in Examples 0464-1, 0440-1, and 0411-3.

| Example No. | | |
|---|---|---|
| 0795 | | |
| 0795-1 | 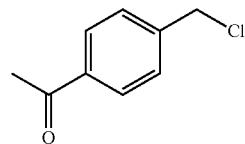 | MS m/z (M + H): 169. |
| 0795-2 | 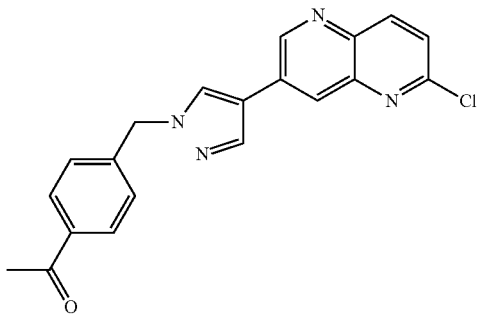 [SMILES: CC(=O)c1ccc(CN/C=C(\C=N)c2cnc3ccc(Cl)nc3c2)cc1] | MS m/z (M + H): 363. |
| 0795-3 | 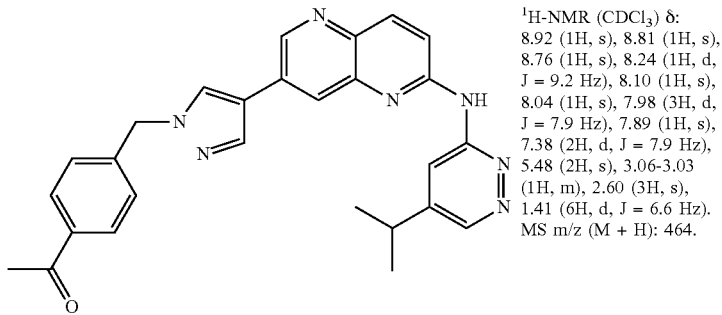 | $^1$H-NMR (CDCl$_3$) δ: 8.92 (1H, s), 8.81 (1H, s), 8.76 (1H, s), 8.24 (1H, d, J = 9.2 Hz), 8.10 (1H, s), 8.04 (1H, s), 7.98 (3H, d, J = 7.9 Hz), 7.89 (1H, s), 7.38 (2H, d, J = 7.9 Hz), 5.48 (2H, s), 3.06-3.03 (1H, m), 2.60 (3H, s), 1.41 (6H, d, J = 6.6 Hz). MS m/z (M + H): 464. |

Example 0796

0796-1

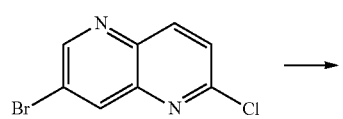

3-(4-(6-Chloro-1,5-naphthyridin-3-yl)-3-methyl-1H-pyrazol-1-yl)propan-1-ol was obtained as a brown solid in the same manner as in Example 0451-3.

MSm/z(M+H):303.

0796-2

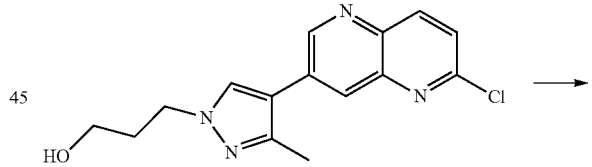

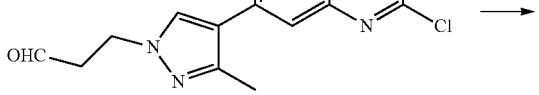

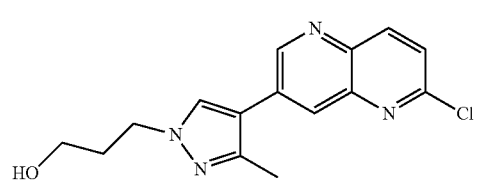

A solution of 3-(4-(6-chloro-1,5-naphthyridin-3-yl)-3-methyl-1H-pyrazol-1-yl)propan-1-ol (36 mg) in dichloromethane (1.5 mL) was added to a mixture of Dess-Martin periodinane (59 mg) and dichloromethane (1 mL) at room temperature, followed by stirring at room temperature for 7.5 hours. Ethyl acetate, a saturated sodium carbonate aqueous solution, and a saturated sodium hydrogen carbonate aqueous solution were added to the reaction mixture, followed by stirring at room temperature for 30 minutes. After water was added to the reaction mixture, the organic layer was collected by separation, washed with a saturated sodium chloride aqueous solution, and dried over anhydrous sodium sulfate, and the solvent was distilled off under reduced pressure, thereby obtaining a pale brown solid (33 mg).

A mixture of the obtained pale brown solid (16 mg), 3-methoxyazetidine hydrochloride (13 mg), triethylamine (23 μL), and dichloromethane (0.5 mL) was stirred at room temperature for 30 minutes in a nitrogen atmosphere. Acetic acid (0.1 mL) was added to the reaction mixture, followed by stirring at room temperature for 1 hour. Sodium triacetoxyborohydride (55 mg) was added to the reaction mixture, followed by stirring at room temperature for 1 hour. The solvent was distilled off under reduced pressure, a saturated sodium hydrogen carbonate aqueous solution was added to the obtained residue, and the solvent was distilled off under reduced pressure. The obtained residue was purified by silica gel column chromatography (hexane-ethyl acetate-methanol, NH silica), thereby obtaining 2-chloro-7-(1-(3-(3-methoxyazetidin-1-yl)propyl)-3-methyl-1H-pyrazol-4-yl)-1,5-naphthyridine (7.2 mg) as colorless oily substance.

MSm/z(M+H):372.

0796-3

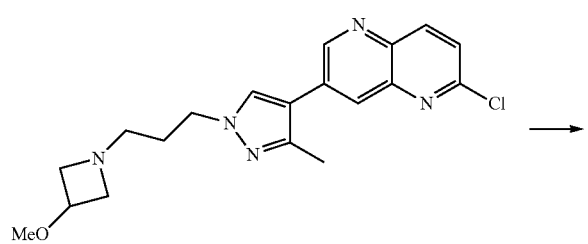

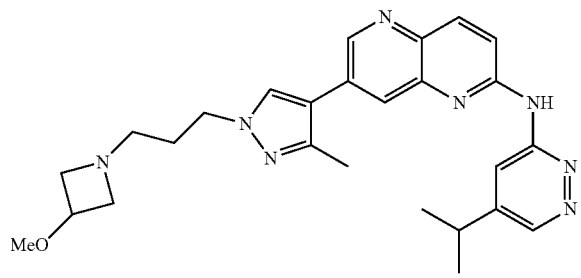

N-(5-isopropylpyridazin-3-yl)-7-(1-(3-(3-methoxyazetidin-1-yl)propyl)-3-methyl-1H-pyrazol-4-yl)-1,5-naphthyridine-2-amine was obtained as a pale brown solid in the same manner as in Example 0015-4.

$^1$H-NMR(CDCl$_3$)δ:9.10(1H,brs),8.89(1H,s),8.84-8.83 (2H,m),8.26(1H,d,J=9.2 Hz),8.06(1H,s),7.68(1H,s),7.61 (1H,d,J=8.6 Hz),4.19(2H,t,J=6.9 Hz),4.06-4.04(1H,m), 3.64-3.61(2H,m),3.27(3H,s),3.05-3.03(1H,m),2.90(2H,t, J=6.9 Hz),2.55-2.51(5H,m),1.99-1.96(2H,m),1.41(6H,d, J=6.6 Hz).

MSm/z(M+H):473.

Example 0797

The following compounds were obtained in the same manner as in Examples 0796-2 and 0421-1.

| Example No. | | |
|---|---|---|
| 0797 | | |
| 0797-1 | 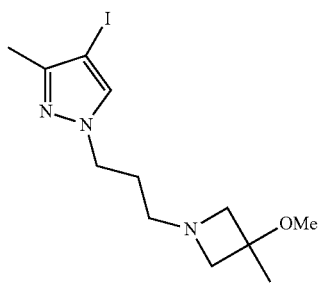 [SMILES: COC1(C)CN(CCCn2cc(I)c(C)n2)C1] | MS m/z (M + H): 350. |

| Example No. | | |
|---|---|---|
| 0797-2 | 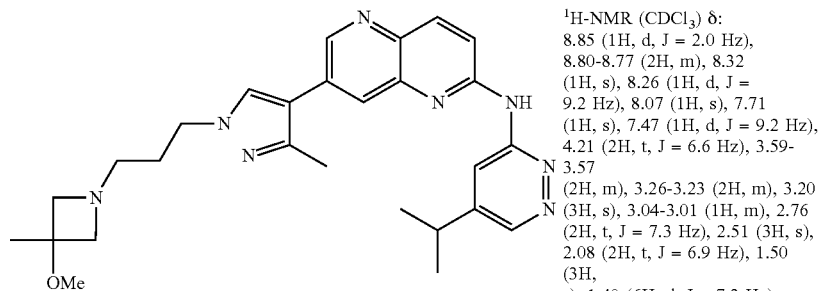 | ¹H-NMR (CDCl₃) δ: 8.85 (1H, d, J = 2.0 Hz), 8.80-8.77 (2H, m), 8.32 (1H, s), 8.26 (1H, d, J = 9.2 Hz), 8.07 (1H, s), 7.71 (1H, s), 7.47 (1H, d, J = 9.2 Hz), 4.21 (2H, t, J = 6.6 Hz), 3.59-3.57 (2H, m), 3.26-3.23 (2H, m), 3.20 (3H, s), 3.04-3.01 (1H, m), 2.76 (2H, t, J = 7.3 Hz), 2.51 (3H, s), 2.08 (2H, t, J = 6.9 Hz), 1.50 (3H, s), 1.40 (6H, d, J = 7.3 Hz). MS m/z (M + H): 487. |
Example 0798
The following compounds were obtained in the same manner as in Examples 0469-1, 0451-2, and 0421-1.
| Example No. | | |
|---|---|---|
| 0798 | | |
| 0798-1 | 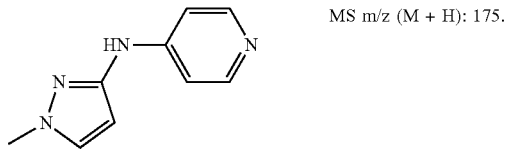 | MS m/z (M + H): 175. |
| 0798-2 | 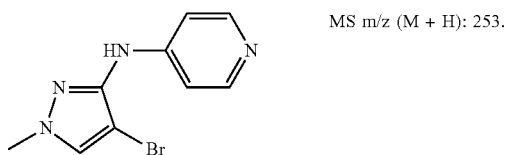 | MS m/z (M + H): 253. |
| 0798-3 | 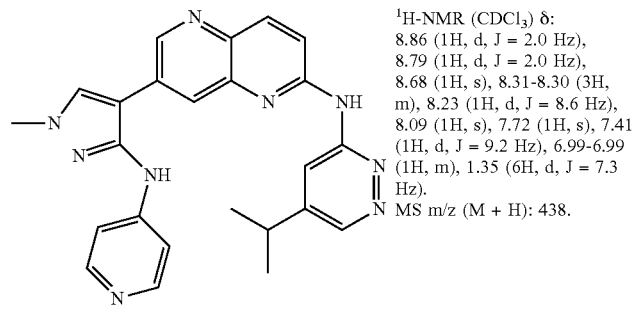 | ¹H-NMR (CDCl₃) δ: 8.86 (1H, d, J = 2.0 Hz), 8.79 (1H, d, J = 2.0 Hz), 8.68 (1H, s), 8.31-8.30 (3H, m), 8.23 (1H, d, J = 8.6 Hz), 8.09 (1H, s), 7.72 (1H, s), 7.41 (1H, d, J = 9.2 Hz), 6.99-6.99 (1H, m), 1.35 (6H, d, J = 7.3 Hz). MS m/z (M + H): 438. |

Example 0799

0799-1

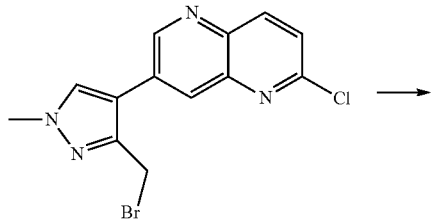

A mixture of 7-(3-(bromomethyl)-1-methyl-1H-pyrazol-4-yl)-2-chloro-1,5-naphthyridine (30 mg), pyridin-3-ol (9.8 mg), potassium carbonate (39 mg), and acetonitrile (1 mL) was stirred at room temperature for 3 hours, and stirred at 50° C. for 1 hour. The reaction mixture was cooled to room temperature, and purified by silica gel column chromatography (hexane-ethyl acetate-methanol, NH silica), thereby obtaining 2-chloro-7-(1-methyl-3-((pyridin-3-yloxy)methyl)-1H-pyrazol-4-yl)-1,5-naphthyridine (4.6 mg) as a white solid.

MSm/z(M+H):352.

0799-2

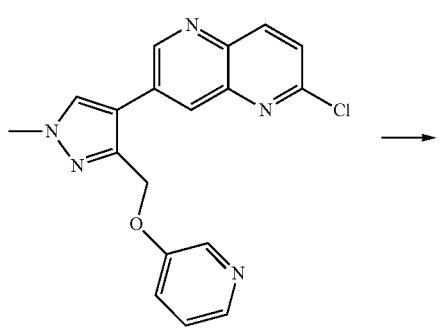

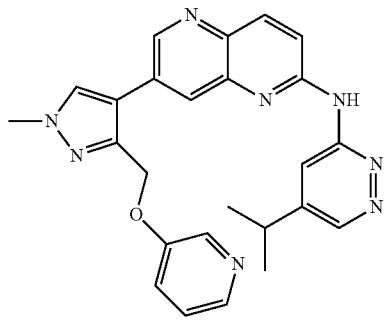

N-(5-isopropylpyridazin-3-yl)-7-(1-methyl-3-((pyridin-3-yloxy)methyl)-1H-pyrazol-4-yl)-1,5-naphthyridine-2-amine (2.4 mg) was obtained as a white solid in the same manner as in Example 0554-3.

$^1$H-NMR(CDCl$_3$)δ:8.90(1H,s),8.78(2H,s),8.62(1H,brs), 8.48(1H,d,J=3.3 Hz),8.26-8.25(3H,m),7.75(1H,s),7.52(1H, d,J=9.2 Hz),7.44-7.40(1H,m),7.22-7.21(1H,m),5.24(2H,s), 4.03(3H,s),2.96-2.87(1H,m),1.32(6H,d,J=6.6 Hz).

MSm/z(M+H):453.

Example 0800

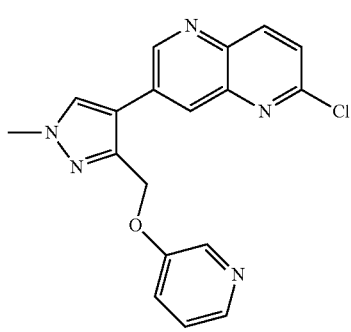

3-(4-(6-((5-Isopropylpyridazin-3-yl)amino)-1,5-naphthyridin-3-yl)-3-methyl-1H-pyrazol-1-yl)propan-1-ol was obtained as a pale yellow solid in the same manner as in Example 0015-4.

$^1$H-NMR(CDCl$_3$)δ:8.85(1H,d,J=2.0 Hz),8.81(2H,s),8.49-8.45(1H,m),8.26(1H,d,J=8.6 Hz),8.07(1H,s),7.70(1H,s), 7.49(1H,d,J=8.6 Hz),4.33(2H,t,J=6.3 Hz),3.73(2H,t,J=5.6 Hz),3.04-3.02(1H,m),2.51(3H,s),2.17-2.09(2H,m),1.40(6H, d,J=6.6 Hz).

MSm/z(M+H):404.

Example 0801

The following compounds were obtained in the same manner as in Examples 0799-1 and 0554-3.

| Example No. | | |
|---|---|---|
| 0801 | | |
| 0801-1 | 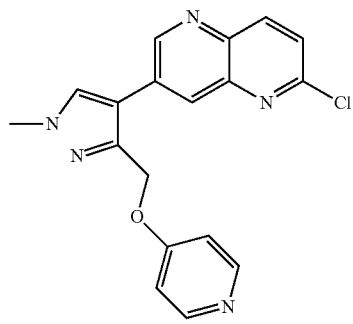 [SMILES: CN/C=C(\C(=N)COc1ccncc1)c1cnc2ccc(Cl)nc2c1] | MS m/z (M + H): 352. |
| 0801-2 | 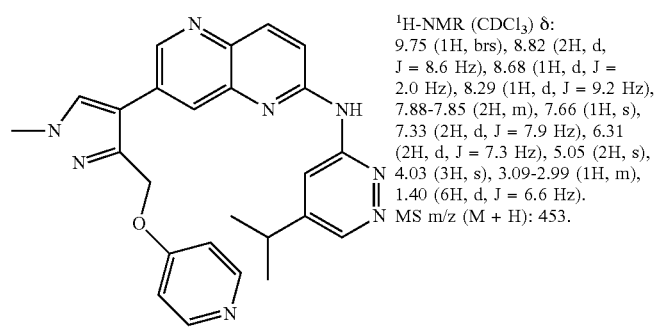 | $^1$H-NMR (CDCl$_3$) δ: 9.75 (1H, brs), 8.82 (2H, d, J = 8.6 Hz), 8.68 (1H, d, J = 2.0 Hz), 8.29 (1H, d, J = 9.2 Hz), 7.88-7.85 (2H, m), 7.66 (1H, s), 7.33 (2H, d, J = 7.9 Hz), 6.31 (2H, d, J = 7.3 Hz), 5.05 (2H, s), 4.03 (3H, s), 3.09-2.99 (1H, m), 1.40 (6H, d, J = 6.6 Hz). MS m/z (M + H): 453. |

Example 0802

0802-1

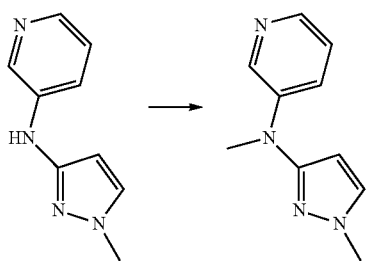

A solution of N-(1-methyl-1H-pyrazol-3-yl)pyridine-3-amine in N,N-dimethylformamide (1.9 mL) was cooled to a temperature of from 0° C. to 5° C., and 60% sodium hydride (30 mg) was added thereto in a nitrogen atmosphere, followed by stirring for 30 minutes. Iodomethane (43 μL) was added to the reaction mixture, followed by stirring at room temperature for 3 hours. After water and ethyl acetate were added to the reaction mixture, the organic layer was collected by separation, washed with a saturated sodium chloride aqueous solution, and dried over anhydrous sodium sulfate, and the solvent was distilled off under reduced pressure, thereby obtaining N-methyl-N-(1-methyl-1H-pyrazol-3-yl)pyridine-3-amine (88 mg) as yellow oily substance.

MSm/z(M+H):189.

0802-2 and 0802-3

The following compounds were obtained in the same manner as in Examples 0451-2 and 0421-1.

| Example No. | | |
|---|---|---|
| 0802 | | |
| 0802-2 | 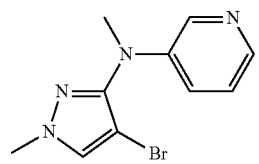 | MS m/z (M + H): 267. |

| Example No. | | |
|---|---|---|
| 0802-3 | 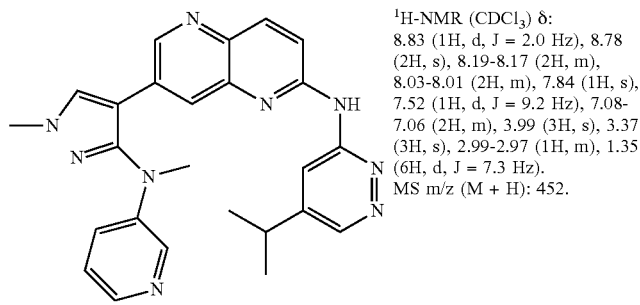 | ¹H-NMR (CDCl₃) δ:<br>8.83 (1H, d, J = 2.0 Hz), 8.78 (2H, s), 8.19-8.17 (2H, m), 8.03-8.01 (2H, m), 7.84 (1H, s), 7.52 (1H, d, J = 9.2 Hz), 7.08-7.06 (2H, m), 3.99 (3H, s), 3.37 (3H, s), 2.99-2.97 (1H, m), 1.35 (6H, d, J = 7.3 Hz).<br>MS m/z (M + H): 452. |
Example 0803
The following compounds were obtained in the same manner as in Examples 0799-1 and Example 0015-4.
| Example No. | | |
|---|---|---|
| 0803 | | |
| 0803-1 | 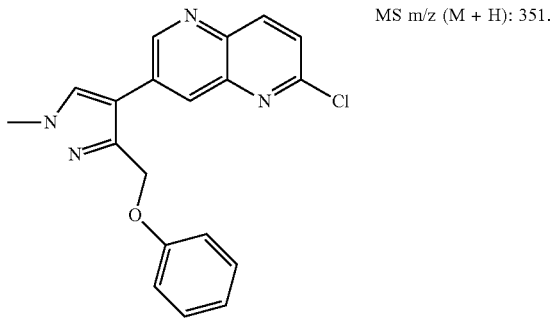 | MS m/z (M + H): 351. |
| 0803-2 | 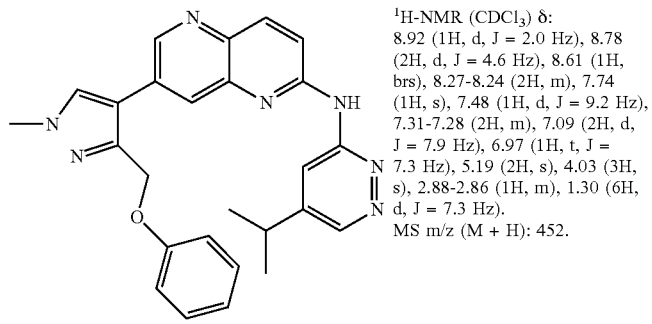 | ¹H-NMR (CDCl₃) δ:<br>8.92 (1H, d, J = 2.0 Hz), 8.78 (2H, d, J = 4.6 Hz), 8.61 (1H, brs), 8.27-8.24 (2H, m), 7.74 (1H, s), 7.48 (1H, d, J = 9.2 Hz), 7.31-7.28 (2H, m), 7.09 (2H, d, J = 7.9 Hz), 6.97 (1H, t, J = 7.3 Hz), 5.19 (2H, s), 4.03 (3H, s), 2.88-2.86 (1H, m), 1.30 (6H, d, J = 7.3 Hz).<br>MS m/z (M + H): 452. |

Examples 0804 and 0805
The following compounds were obtained in the same manner as in Examples 0799-1 and 0554-3.
| Example No. | | |
|---|---|---|
| 0804 | | |
| 0804-1 | 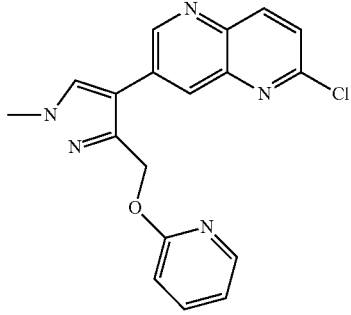 [SMILES: CN/C=C(\C(=N)COc1ccccn1)c1cnc2ccc(Cl)nc2c1] | MS m/z (M + H): 352. |
| 0804-2 | 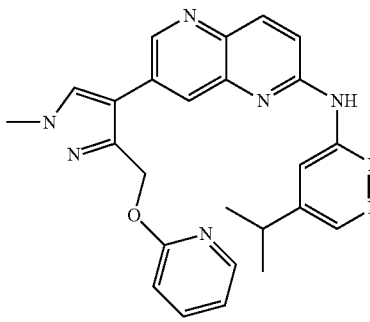 | ¹H-NMR (CDCl₃) δ: 9.47 (1H, brs), 8.93 (1H, s), 8.82 (1H, s), 8.74 (1H, d, J = 2.0 Hz), 8.25-8.22 (2H, m), 7.71 (1H, d, J = 9.2 Hz), 7.67 (1H, s), 7.42-7.41 (1H, m), 6.53 (1H, d, J = 9.2 Hz), 6.11 (1H, t, J = 6.3 Hz), 5.35 (2H, s), 3.98 (3H, s), 3.12-3.10 (1H, m), 1.41 (6H, d, J = 6.6 Hz). MS m/z (M + H): 453. |
| 0805 | | |
| 0805-1 | 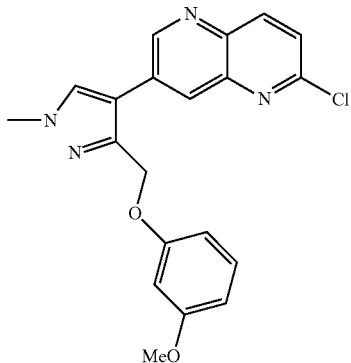 [SMILES: CN/C=C(\C(=N)COc1cccc(OC)c1)c1cnc2ccc(Cl)nc2c1] | MS m/z (M + H): 381. |
| 0805-2 |  | ¹H-NMR (CDCl₃) δ: 9.15 (1H, brs), 8.91 (1H, d, J = 2.0 Hz), 8.82 (2H, d, J = 19.2 Hz), 8.25 (2H, d, J = 7.9 Hz), 7.74 (1H, s), 7.61-7.60 (1H, m), 7.18 (1H, t, J = 8.3 Hz), 6.70-6.64 (2H, m), 6.53 (1H, dd, J = 8.3, 2.3 Hz), 5.17 (2H, s), 4.03 (3H, s), 3.76 (3H, s), 2.92-2.83 (1H, m), 1.31 (6H, d, J = 6.6 Hz). MS m/z (M + H): 482. |

Example 0806

The following compounds were obtained in the same manner as in Examples 0799-1 and 0015-4.

| Example No. | | |
|---|---|---|
| 0806 | | |
| 0806-1 | 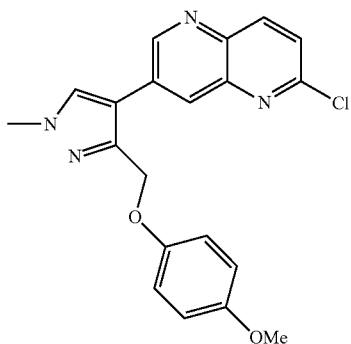 [SMILES: CN/C=C(\C(=N)COc1ccc(OC)cc1)c1cnc2ccc(Cl)nc2c1] | MS m/z (M + H): 381. |
| 0806-2 | | ¹H-NMR (CDCl₃) δ: 9.18 (1H, brs), 8.92 (1H, d, J = 2.0 Hz), 8.86 (1H, s), 8.78 (1H, d, J = 2.0 Hz), 8.30 (1H, s), 8.25 (1H, d, J = 8.6 Hz), 7.74 (1H, s), 7.61 (1H, d, J = 8.6 Hz), 7.03-7.01 (2H, m), 6.83-6.80 (2H, m), 5.13 (2H, s), 4.02 (3H, s), 3.76 (3H, s), 1.31 (6H, d, J = 6.6 Hz). MS m/z (M + H): 482. |

Example 0807

0807-1

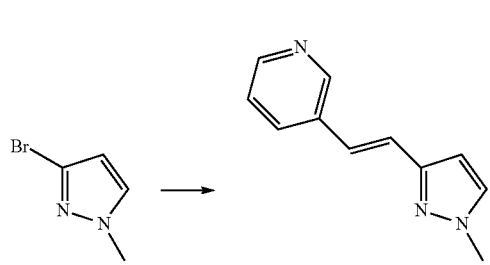

A mixture of 3-bromo-1-methyl-1H-pyrazole (100 mg), 3-vinylpyridine (100 μL), triethylamine (173 μL), palladium acetate(II) (14 mg), tri(o-tolyl)phosphine (76 mg), and N,N-dimethylformamide (3.1 mL) was stirred at 140° C. for 30 minutes using a microwave reaction apparatus. The reaction mixture was cooled to room temperature, and purified by silica gel column chromatography (hexane-ethyl acetate-methanol, NH silica), thereby obtaining (E)-3-(2-(1-methyl-1H-pyrazol-3-yl)vinyl)pyridine (18 mg) as pale yellow oily substance.

MS m/z (M+H): 186.

0807-2 and 0807-3

The following compounds were obtained in the same manner as in Examples 0451-2 and 0421-1.

| Example No. | | |
|---|---|---|
| 0807 | | |
| 0807-2 | 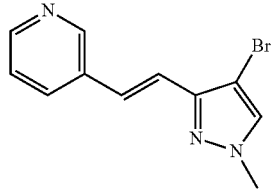 | MS m/z (M + H): 264. |
| 0807-3 | 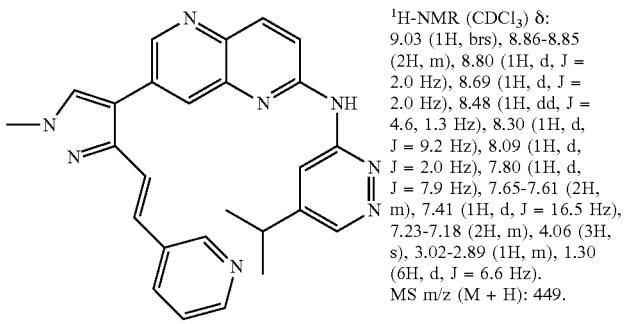 | ¹H-NMR (CDCl₃) δ: 9.03 (1H, brs), 8.86-8.85 (2H, m), 8.80 (1H, d, J = 2.0 Hz), 8.69 (1H, d, J = 2.0 Hz), 8.48 (1H, dd, J = 4.6, 1.3 Hz), 8.30 (1H, d, J = 9.2 Hz), 8.09 (1H, d, J = 2.0 Hz), 7.80 (1H, d, J = 7.9 Hz), 7.65-7.61 (2H, m), 7.41 (1H, d, J = 16.5 Hz), 7.23-7.18 (2H, m), 4.06 (3H, s), 3.02-2.89 (1H, m), 1.30 (6H, d, J = 6.6 Hz). MS m/z (M + H): 449. |
Example 0808
The following compounds were obtained in the same manner as in Examples 0799-1 and 0421-1.
| Example No. | | |
|---|---|---|
| 0808 | | |
| 0808-1 | 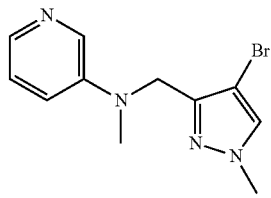 [SMILES: CN(Cc1nn(C)cc1Br)c1cccnc1] | MS m/z (M + H): 281. |
| 0808-2 | 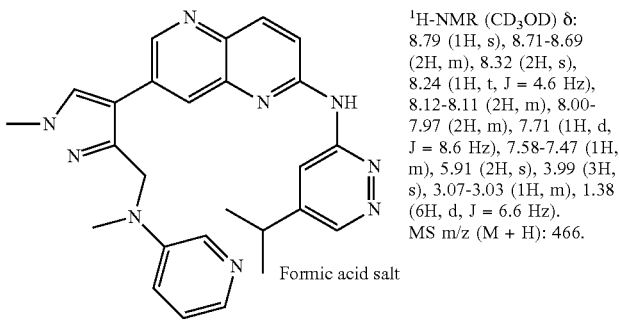  Formic acid salt | ¹H-NMR (CD₃OD) δ: 8.79 (1H, s), 8.71-8.69 (2H, m), 8.32 (2H, s), 8.24 (1H, t, J = 4.6 Hz), 8.12-8.11 (2H, m), 8.00-7.97 (2H, m), 7.71 (1H, d, J = 8.6 Hz), 7.58-7.47 (1H, m), 5.91 (2H, s), 3.99 (3H, s), 3.07-3.03 (1H, m), 1.38 (6H, d, J = 6.6 Hz). MS m/z (M + H): 466. |

Example 0809

0809-1

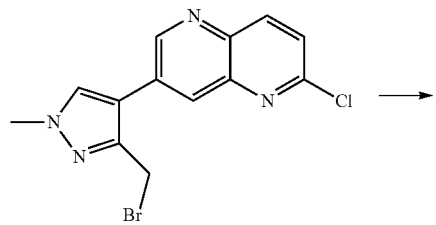

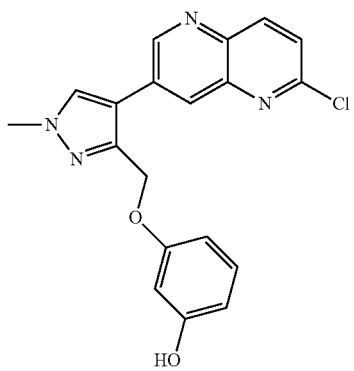

3-((4-(6-Chloro-1,5-naphthyridin-3-yl)-1-methyl-1H-pyrazol-3-yl)methoxy)phenol was obtained as a pale yellow solid in the same manner as in Example 0799-1.

MSm/z(M+H):367.

0809-2

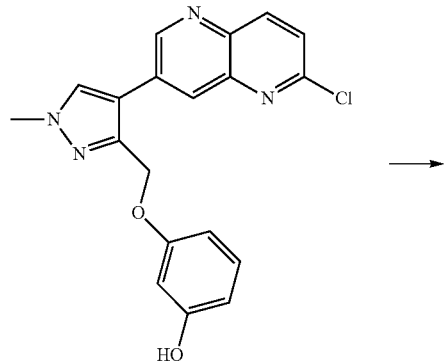

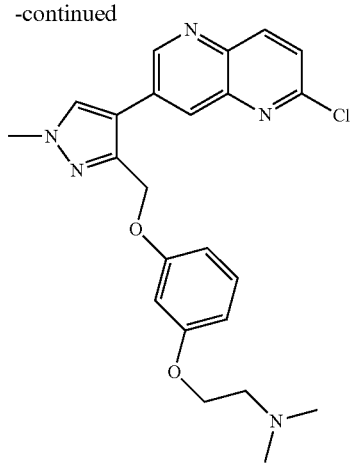

A 40% diethyl azodicarboxylate/toluene solution (5.8 μL) was added to a mixture of 3-((4-(6-chloro-1,5-naphthyridin-3-yl)-1-methyl-1H-pyrazol-3-yl)methoxy)phenol (23 mg), triphenylphosphine (34 mg), 2-(dimethylamino)ethanol (9.6 μL), and tetrahydrofuran (1 mL), followed by stirring at room temperature for 0.5 hours in a nitrogen atmosphere. Triphenylphosphine (35.1 mg) and a 40% diethyl azodicarboxylate/toluene solution (5.8 μL) were added to the reaction mixture, followed by stirring at room temperature for 1 hour. Triphenylphosphine (66.9 mg) and a 40% diethyl azodicarboxylate/toluene solution (11.6 μL) were added to the reaction mixture, followed by stirring at room temperature for 1 hour. Water was added to the reaction mixture, and the resultant product was purified by silica gel column chromatography (hexane-ethyl acetate-methanol, NH silica), thereby obtaining 2-(3-((4-(6-chloro-1,5-naphthyridin-3-yl)-1-methyl-1H-pyrazol-3-yl)methoxy)phenoxy)-N,N-dimethylethanamine (4.5 mg) as a white solid.

MSm/z(M+H):438.

0809-3

-continued

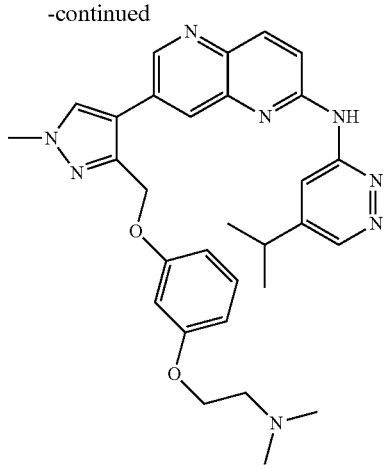

7-(3-((3-(2-(dimethylamino)ethoxy)phenoxy)methyl)-1-methyl-1H-pyrazol-4-yl)-N-(5-isopropylpyridazin-3-yl)-1,5-naphthyridine-2-amine was obtained as a white solid in the same manner as in Example 0554-3.

$^1$H-NMR(CDCl$_3$)δ:8.91(1H,d,J=2.0 Hz),8.80(1H,d,J=11.2 Hz),8.26-8.23(2H,m),7.74(1H,s),7.61-7.58(1H,m),7.19-7.08(1H,m),6.68-6.66(2H,m),6.54-6.44(2H,m),5.15(2H,s),4.07-4.00(5H,m),2.93-2.84(1H,m),2.74-2.70(2H,m),2.32(6H,s),1.31(6H,d,J=6.6 Hz).

MSm/z(M+H):539.

Example 0810

The following compounds were obtained in the same manner as in Examples 0799-1 and 0554-3.

| Example No. | | |
|---|---|---|
| 0810 | | |
| 0810-1 | 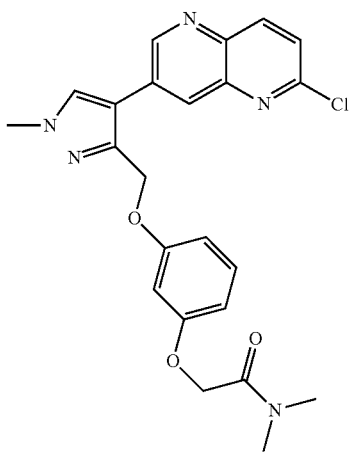 [SMILES: CN/C=C(\C(=N)COc1cccc(OCC(=O)N(C)C)c1)c1cnc2ccc(Cl)nc2c1] | MS m/z (M + H): 452. |
| 0810-2 | 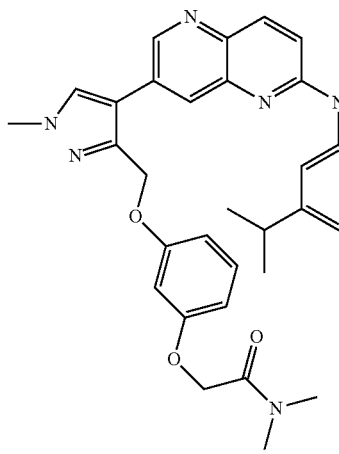 | $^1$H-NMR (CDCl$_3$) δ: 8.91 (1H, s), 8.77 (1H, s), 8.70 (1H, brs), 8.26-8.23 (2H, m), 7.73 (1H, d, J = 5.9 Hz), 7.59-7.56 (1H, m), 7.18 (2H, t, J = 8.3 Hz), 6.73-6.71 (2H, m), 6.60-6.57 (1H, m), 5.16 (2H, s), 4.65 (2H, s), 4.03 (3H, s), 3.06 (3H, s), 2.97 (3H, s), 2.92-2.86 (1H, m), 1.31-1.23 (6H, m). MS m/z (M + H): 553. |

Example 0811

The following compounds were obtained in the same manner as in Examples 0732-2 and 0385-7.

| Example No. | | |
|---|---|---|
| 0811 | | |
| 0811-1 | 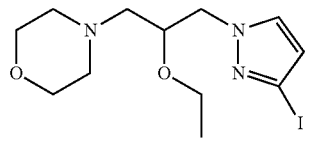 [SMILES: CCOC(CN1CCOCC1)Cn1ccc(I)n1] | MS m/z (M + H): 366. |
| 0811-2 | 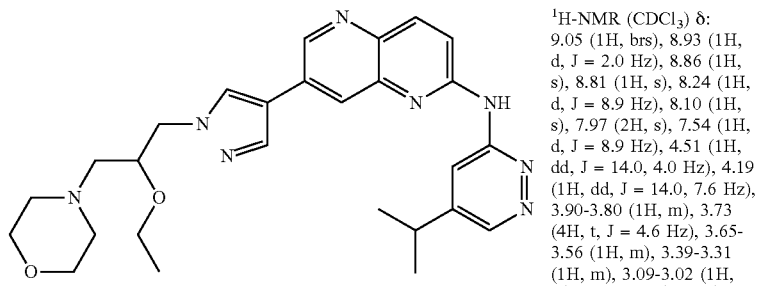 | ¹H-NMR (CDCl₃) δ: 9.05 (1H, brs), 8.93 (1H, d, J = 2.0 Hz), 8.86 (1H, s), 8.81 (1H, s), 8.24 (1H, d, J = 8.9 Hz), 8.10 (1H, s), 7.97 (2H, s), 7.54 (1H, d, J = 8.9 Hz), 4.51 (1H, dd, J = 14.0, 4.0 Hz), 4.19 (1H, dd, J = 14.0, 7.6 Hz), 3.90-3.80 (1H, m), 3.73 (4H, t, J = 4.6 Hz), 3.65-3.56 (1H, m), 3.39-3.31 (1H, m), 3.09-3.02 (1H, m), 2.56-2.46 (6H, m), 1.41 (6H, d, J = 7.2 Hz), 1.11 (3H, t, J = 6.9 Hz). MS m/z (M + H): 503. |

Example 0812

0812-1

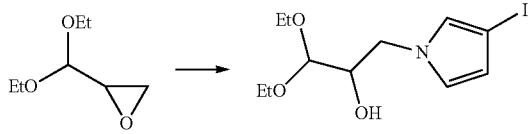 [SMILES: CCOC(OCC)C1CO1 ; CCOC(OCC)C(O)Cn1ccc(I)c1]

Cesium carbonate (424 mg), N,N-dimethylformamide (2 mL), and 3-iodo-1H-pyrazole (233 mg) were added to 2-(diethoxymethyl)oxirane (146 mg), followed by stirring at 90° C. for 1.5 hours. The reaction mixture was cooled to room temperature, water was added thereto, and the resultant product was extracted three times with ethyl acetate. An organic layer thus obtained was washed with a saturated sodium chloride aqueous solution, and dried over anhydrous sodium sulfate, and the solvent was distilled off under reduced pressure. The obtained residue was purified by silica gel column chromatography (hexane-ethyl acetate), thereby obtaining 1,1-diethoxy-3-(4-iodo-1H-pyrazol-1-yl)propan-2-ol (350 mg) as colorless oily substance.

MSm/z(M+H):341.

0812-2 and 0812-3

The following compounds were obtained in the same manner as in Examples 0725-1 and 0385-7.

| Example No. | | |
|---|---|---|
| 0812 | | |
| 0812-2 | 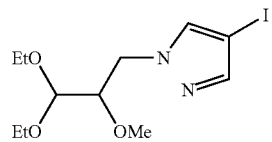 [SMILES: CCOC(OCC)C(CN/C=C(/I)C=N)OC] | MS m/z (M + H): 355. |
| 0812-3 | 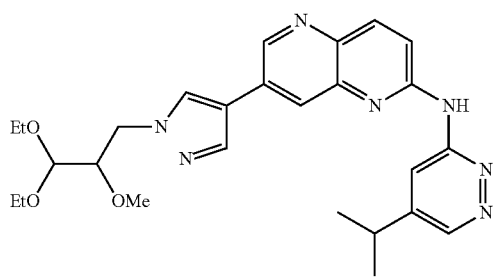 [SMILES: CCOC(OCC)C(CN/C=C(\C=N)c1cnc2ccc(Nc3cc(C(C)C)cnn3)nc2c1)OC] | MS m/z (M + H): 492. |

0812-4

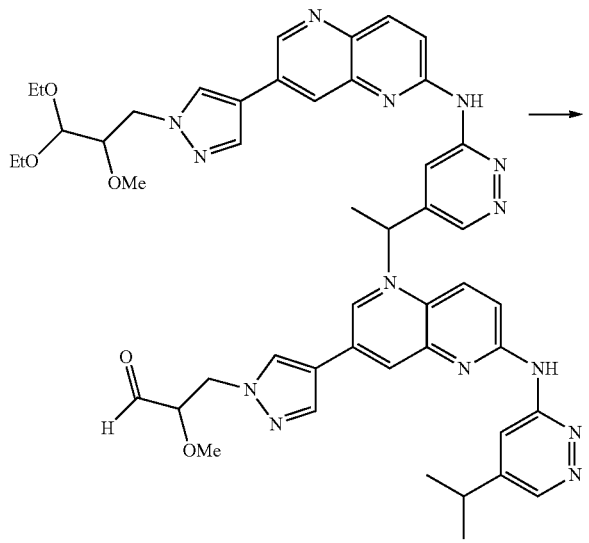

1 mol/L hydrochloric acid (1 mL) was added to a solution of 7-(1-(3,3-diethoxy-2-methoxypropyl)-1H-pyrazol-4-yl)-N-(5-isopropylpyridazin-3-yl)-1,5-naphthyridine-2-amine (50 mg) in 1,4-dioxane (1 mL), followed by stirring at 70° C. for 0.5 hours. The reaction mixture was cooled to room temperature, and the solvent was distilled off under reduced pressure. The obtained residue was dissolved in 2-propanol (1 mL), an ethyl acetate/chloroform (1/1) solution (1 mL) was added thereto, and the precipitated solid was collected by filtration, thereby obtaining 3-(4-(6-((5-isopropylpyridazin-3-yl)amino)-1,5-naphthyridin-3-yl)-1H-pyrazol-1-yl)-2-methoxypropanal hydrochloride (50 mg).

MSm/z(M+H):450. (methanol adduct)

0812-5

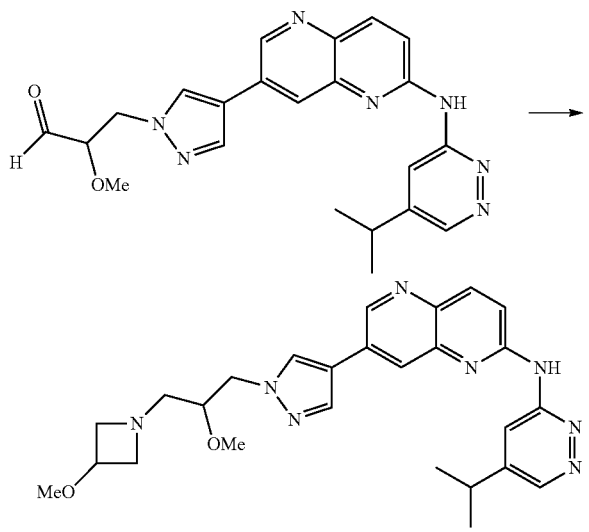

3-Methoxyazetidine hydrochloride (2 mg), triethylamine (4 μL), and sodium triacetoxyborohydride (3 mg) were added to a mixture of 3-(4-(6-((5-isopropylpyridazin-3-yl)amino)-1,5-naphthyridin-3-yl)-1H-pyrazol-1-yl)-2-methoxypropanal hydrochloride (5 mg) and dichloromethane (0.5 mL), followed by stirring at room temperature for 3 hours. Sodium triacetoxyborohydride (3 mg) was added to the reaction mixture, followed by stirring at room temperature for 1.5 hours. A drop of water was added to the reaction mixture, and the solvent was distilled off under reduced pressure. The obtained residue was purified by silica gel column chromatography (hexane-ethyl acetate, NH silica), thereby obtaining N-(5-isopropylpyridazin-3-yl)-7-(1-(2-methoxy-3-(3-methoxyazetidin-1-yl)propyl)-1H-pyrazol-4-yl)-1,5-naphthyridine-2-amine (2.7 mg) as a pale yellow solid.

$^1$H-NMR(CDCl$_3$)δ:9.35(1H,brs),8.93(1H,d,J=2.0 Hz), 8.90(1H,s),8.82(1H,s),8.25(1H,d,J=8.6 Hz),8.11(1H,s),7.97 (1H,s),7.93(1H,s),7.62(1H,d,J=8.6 Hz),4.39(1H,dd,J=13.9, 4.0 Hz),4.24-4.14(1H,m),4.11-4.03(1H,m),3.74-3.69(2H, m),3.66-3.60(1H,m),3.33(3H,s),3.27(3H,s),3.12-2.99(3H, m),2.69-2.54(2H,m),1.43(6H,d,J=6.6 Hz).

MSm/z(M+H):489.

Example 0813

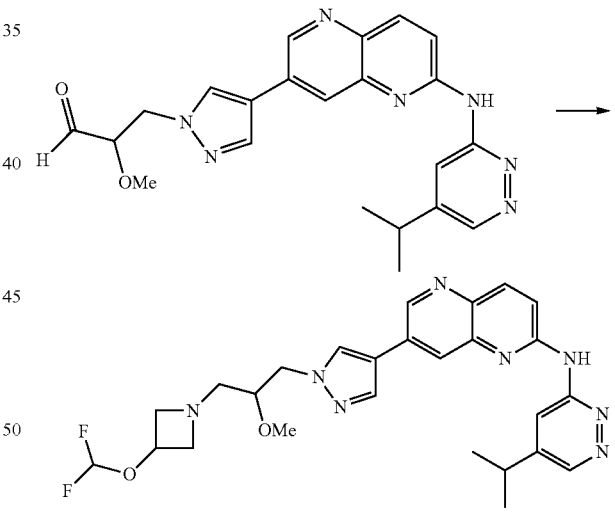

7-(1-(3-(3-(Difluoromethoxy)azetidin-1-yl)-2-methoxypropyl)-1H-pyrazol-4-yl)-N-(5-isopropylpyridazin-3-yl)-1,5-naphthyridine-2-amine was obtained as a pale yellow solid in the same manner as in Example 0812-5.

$^1$H-NMR(CDCl$_3$)δ:9.49(1H,s),8.95-8.89(2H,m),8.83(1H, s),8.25(1H,d,J=8.6 Hz),8.11(1H,d,J=1.3 Hz),7.97(1H,s), 7.92(1H,s),7.66(1H,d,J=9.2 Hz),6.18(1H,t,J=73.7 Hz),4.83-4.75(1H,m),4.38(1H,dd,J=14.2,4.3 Hz),4.22(1H,dd,J=14.2, 7.3 Hz),3.80-3.73(2H,m),3.66-3.59(1H,m),3.33(3H,s),3.15 (2H,t,J=7.3 Hz),3.09-3.04(1H,m),2.70-2.53(2H,m),1.43 (6H,d,J=7.3 Hz).

MSm/z(M+H):525.

Example 0814

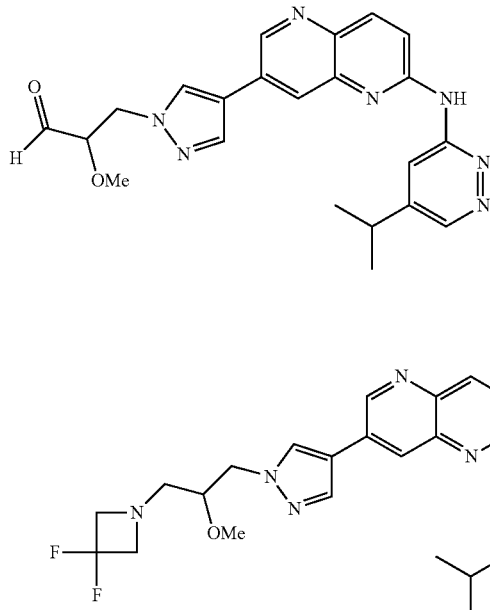

3,3-Difluoroazetidine hydrochloride (4 mg), methanol (450 μL), acetic acid (50 μL), and 2-picoline borane (3 mg) were added to 3-(4-(6-((5-isopropylpyridazin-3-yl)amino)-1,5-naphthyridin-3-yl)-1H-pyrazol-1-yl)-2-methoxypropanal hydrochloride (5 mg), followed by stirring at room temperature for 6 hours. The solvent of the reaction mixture was distilled off under reduced pressure. The obtained residue was purified by silica gel column chromatography (hexane-ethyl acetate, NH silica), thereby obtaining 7-(1-(3-(3,3-difluoroazetidin-1-yl)-2-methoxypropyl)-1H-pyrazol-4-yl)-N-(5-isopropylpyridazin-3-yl)-1,5-naphthyridine-2-amine (2.2 mg) as a pale yellow solid.

$^1$H-NMR(CDCl$_3$)δ:9.40(1H,s),8.94(1H,d,J=2.0 Hz),8.90 (1H,s),8.83(1H,d,J=2.0 Hz),8.25(1H,d,J=9.2 Hz),8.11(1H,d,J=2.0 Hz),7.98(1H,s),7.92(1H,s),7.65(1H,d,J=9.2 Hz),4.39 (1H,dd,J=14.2,4.6 Hz),4.26(1H,dd,J=14.2,6.6 Hz),3.72-3.63 (5H,m),3.34(3H,s),3.12-3.02(1H,m),2.78(1H,dd,J=12.9,4.6 Hz),2.65-2.58(1H,m),1.43(6H,d,J=7.3 Hz).

MSm/z(M+H):495.

Example 0815

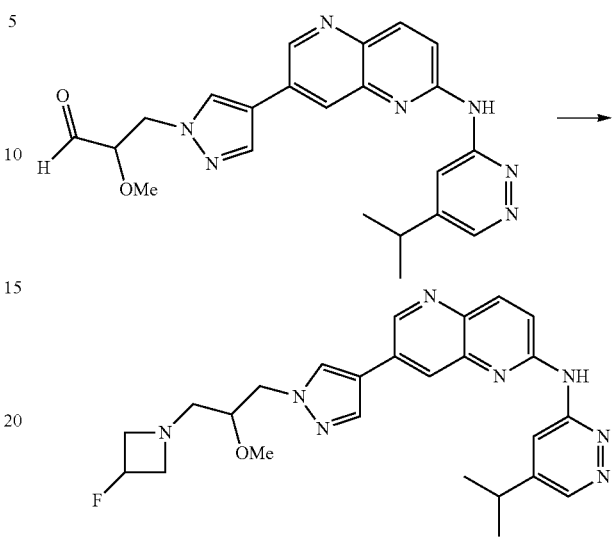

7-(1-(3-(3-Fluoroazetidin-1-yl)-2-methoxypropyl)-1H-pyrazol-4-yl)-N-(5-isopropylpyridazin-3-yl)-1,5-naphthyridine-2-amine was obtained as a white solid in the same manner as in Example 0814.

$^1$H-NMR(CDCl$_3$)δ:8.94(1H,s),8.84-8.80(3H,m),8.24(1H, d,J=9.2 Hz),8.11(1H,s),7.98(1H,s),7.93(1H,s),7.52(1H,d, J=9.2 Hz),5.14(1H,dt,J=57.2,5.1 Hz),4.39(1H,dd,J=14.2,4.0 Hz),4.22(1H,dd,J=14.2,6.9 Hz),3.80-3.71(2H,m),3.67-3.60 (1H,m),3.34(3H,s),3.31-3.18(2H,m),3.09-3.00(1H,m),2.72-2.54(2H,m),1.42(6H,d,J=7.3 Hz).

MSm/z(M+H):477.

Examples 0816 and 0817

The following compounds were obtained in the same manner as in Examples 0485-2 and 0740.

| Example No. | | |
|---|---|---|
| 0816 | | |
| 0816-1 | 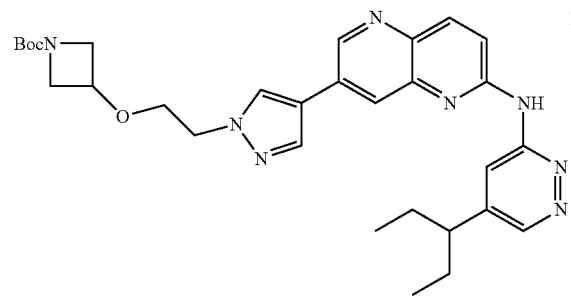 [SMILES: CCC(CC)c1cnnc(Nc2ccc3ncc(-c4cnn(CCOC5CN(C(=O)OC(C)(C)C)C5)c4)cc3n2)c1] | MS m/z (M + H): 559. |

| Example No. | | |
|---|---|---|
| 0816-2 | 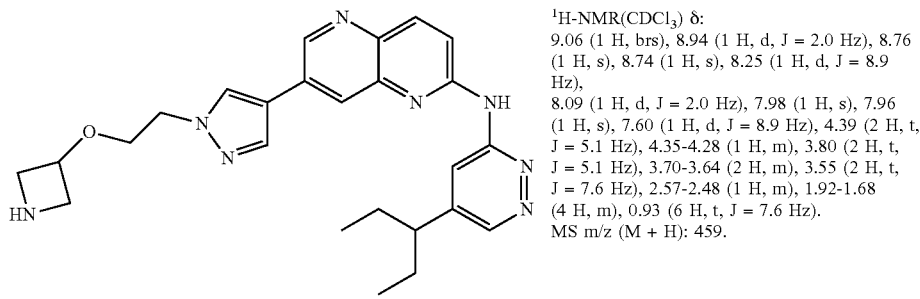 | ¹H-NMR(CDCl₃) δ:<br>9.06 (1 H, brs), 8.94 (1 H, d, J = 2.0 Hz), 8.76 (1 H, s), 8.74 (1 H, s), 8.25 (1 H, d, J = 8.9 Hz),<br>8.09 (1 H, d, J = 2.0 Hz), 7.98 (1 H, s), 7.96 (1 H, s), 7.60 (1 H, d, J = 8.9 Hz), 4.39 (2 H, t, J = 5.1 Hz), 4.35-4.28 (1 H, m), 3.80 (2 H, t, J = 5.1 Hz), 3.70-3.64 (2 H, m), 3.55 (2 H, t, J = 7.6 Hz), 2.57-2.48 (1 H, m), 1.92-1.68 (4 H, m), 0.93 (6 H, t, J = 7.6 Hz).<br>MS m/z (M + H): 459. |
| 0817 | | |
| 0817-1 | 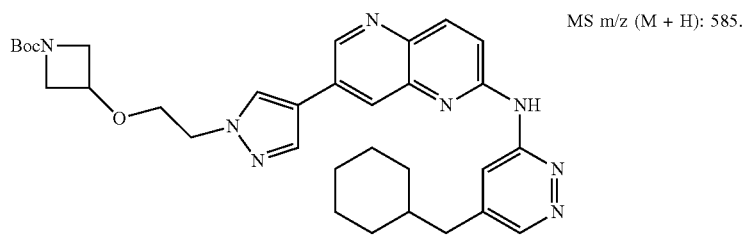 | MS m/z (M + H): 585. |
| 0817-2 | 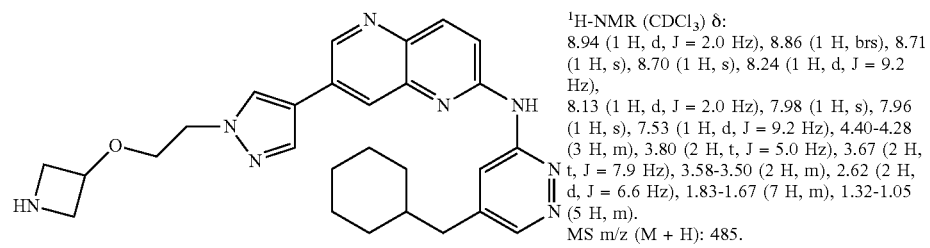 | ¹H-NMR (CDCl₃) δ:<br>8.94 (1 H, d, J = 2.0 Hz), 8.86 (1 H, brs), 8.71 (1 H, s), 8.70 (1 H, s), 8.24 (1 H, d, J = 9.2 Hz),<br>8.13 (1 H, d, J = 2.0 Hz), 7.98 (1 H, s), 7.96 (1 H, s), 7.53 (1 H, d, J = 9.2 Hz), 4.40-4.28 (3 H, m), 3.80 (2 H, t, J = 5.0 Hz), 3.67 (2 H, t, J = 7.9 Hz), 3.58-3.50 (2 H, m), 2.62 (2 H, d, J = 6.6 Hz), 1.83-1.67 (7 H, m), 1.32-1.05 (5 H, m).<br>MS m/z (M + H): 485. |

Examples 0818 and 0819

The following compounds were obtained in the same manner as in Example 0741.

| Example No. | | |
|---|---|---|
| 0818 | 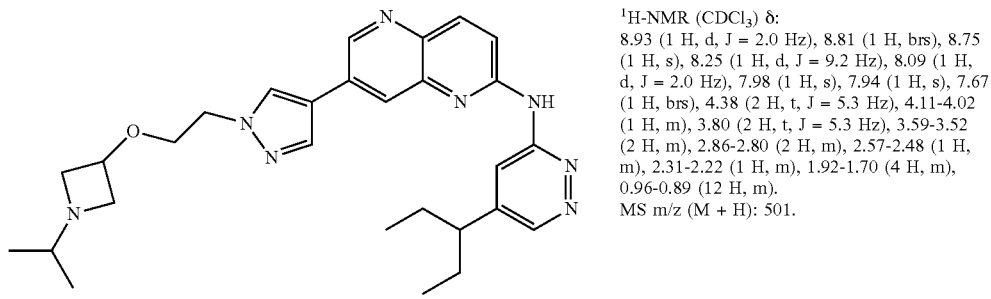 | ¹H-NMR (CDCl₃) δ:<br>8.93 (1 H, d, J = 2.0 Hz), 8.81 (1 H, brs), 8.75 (1 H, s), 8.25 (1 H, d, J = 9.2 Hz), 8.09 (1 H, d, J = 2.0 Hz), 7.98 (1 H, s), 7.94 (1 H, s), 7.67 (1 H, brs), 4.38 (2 H, t, J = 5.3 Hz), 4.11-4.02 (1 H, m), 3.80 (2 H, t, J = 5.3 Hz), 3.59-3.52 (2 H, m), 2.86-2.80 (2 H, m), 2.57-2.48 (1 H, m), 2.31-2.22 (1 H, m), 1.92-1.70 (4 H, m), 0.96-0.89 (12 H, m).<br>MS m/z (M + H): 501. |

| Example No. | | |
|---|---|---|
| 0819 | 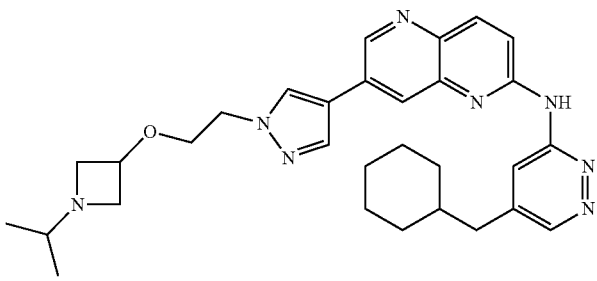 [SMILES: CC(C)N1CC(OCCn2cc(-c3cnc4ccc(Nc5cc(CC6CCCCC6)cnn5)nc4c3)cn2)C1] | ¹H-NMR (CDCl₃) δ:<br>8.93 (1 H, d, J = 2.0 Hz), 8.81 (1 H, brs), 8.74 (1 H, d, J = 2.0 Hz), 8.25 (1 H, d, J = 9.2 Hz), 8.13 (1 H, d, J = 2.0 Hz), 7.98 (1 H, s), 7.95 (1 H, s), 7.74 (1 H, brs), 4.38 (2 H, t, J = 5.3 Hz), 4.11-4.08 (1 H, m), 3.80 (2 H, t, J = 5.3 Hz), 3.58-3.52 (2 H, m), 2.85-2.79 (2 H, m), 2.64 (2 H, d, J = 6.6 Hz), 2.30-2.21 (1 H, m), 1.85-1.74 (6 H, m), 1.32-1.05 (5 H, m), 0.90 (6 H, d, J = 5.9 Hz).<br>MS m/z (M + H): 527. |

Example 0820

0820-1

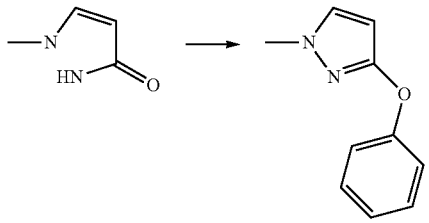

Methylene chloride (10 mL), phenylboronic acid (300 mg), triethylamine (220 μL), pyridine (254 μL), copper(II) acetate (445 mg), and molecular sieve 4A (300 mg) were added to 1-methyl-1H-pyrazol-3(2H)-one (160 mg), followed by stirring at room temperature for 18 hours. After water was added to the reaction mixture, the resultant product was extracted three times with methylene chloride, an organic layer thus obtained was washed with a saturated sodium chloride aqueous solution, and dried over anhydrous sodium sulfate. The solvent was distilled off under reduced pressure, and the obtained residue was purified by silica gel column chromatography (hexane-ethyl acetate), thereby obtaining 1-methyl-3-phenoxy-1H-pyrazole (27 mg) as colorless oily substance.

MSm/z(M+H):175.

0820-2 and 0820-3

The following compounds were obtained in the same manner as in Examples 0734-2 and 0385-7.

| Example No. | | |
|---|---|---|
| 0820 | | |
| 0820-2 | 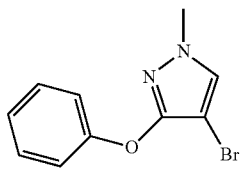 | MS m/z (M + H): 253. |
| 0820-3 | 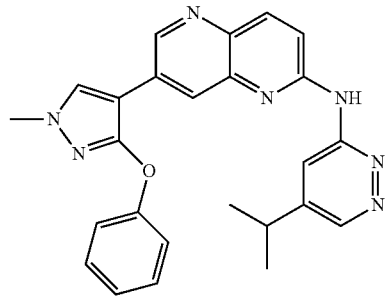 [SMILES: CC(C)c1cnnc(Nc2ccc3ncc(-c4cn(C)nc4Oc4ccccc4)cc3n2)c1] | ¹H-NMR (CDCl₃) δ:<br>9.00 (1 H, s), 8.81 (1 H, s), 8.77 (1 H, s), 8.35 (1 H, s), 8.20 (1 H, d,<br>J = 8.6 Hz), 7.80 (1 H, s), 7.36-7.30 (2 H, m), 7.22-7.19 (3 H, m),<br>7.12-7.06 (2 H, m), 3.92 (3 H, s), 3.05-2.95 (1 H, m), 1.36 (6 H, d,<br>J = 7.3 Hz).<br>MS m/z (M + H): 438. |

Example 0821

0821-1

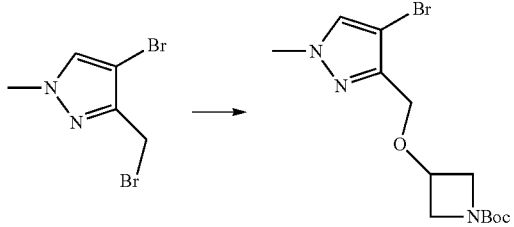

60% sodium hydride (83 mg) was added to a solution of tert-butyl 3-hydroxyazetidine-1-carboxylate (286 mg) in tetrahydrofuran (5 mL) under ice-cooling, followed by stirring for 0.5 hours. 4-Bromo-3-(bromomethyl)-1-methyl-1H-pyrazole (350 mg) was added to the reaction mixture, followed by stirring at room temperature for 1 hour, and stirring at 50° C. for 1.5 hours. Furthermore, N,N-dimethylformamide (5 mL) was added thereto, followed by stirring at 50° C. for 1 hour. After a 20% citric acid aqueous solution was added to the reaction mixture, the resultant product was extracted three times with ethyl acetate, an organic layer thus obtained was washed with a saturated sodium chloride aqueous solution, and dried over anhydrous sodium sulfate. The solvent was distilled off under reduced pressure, and the obtained residue was purified by silica gel column chromatography (hexane-acetone), thereby obtaining tert-butyl 3-((4-bromo-1-methyl-1H-pyrazol-3-yl)methoxy)azetidine-1-carboxylate (530 mg).

MSm/z(M+H):346.

0821-2

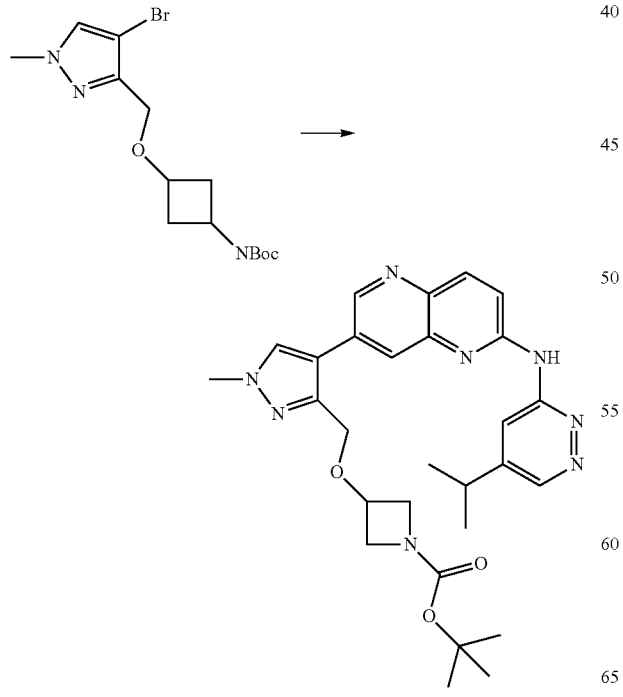

tert-Butyl 3-((4-(6-((5-isopropylpyridazin-3-yl)amino)-1,5-naphthyridin-3-yl)-1-methyl-1H-pyrazol-3-yl)methoxy)azetidine-1-carboxylate was obtained as a pale yellow solid in the same manner as in Example 0385-7.

$^1$H-NMR(CDCl$_3$)δ:9.50(1H,brs),8.90(1H,d,J=2.0 Hz), 8.80(2H,brs),8.33(1H,s),8.28(1H,d,J=9.2 Hz),7.84(1H,d,J=9.2 Hz),7.73(1H,s),4.60(2H,s),4.51-4.42(1H,m),4.14-4.05(2H,m),4.00(3H,s),3.92(2H,dd,J=9.6,4.3 Hz),3.07-2.98(1H,m),1.42(9H,s),1.41(6H,d,J=6.9 Hz).

MSm/z(M+H):531.

Example 0822

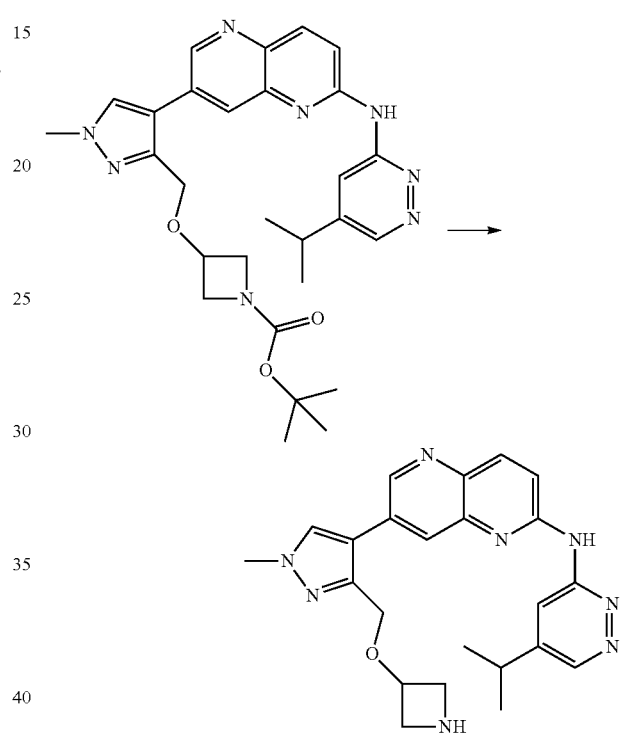

7-(3-((Azetidin-3-yloxy)methyl)-1-methyl-1H-pyrazol-4-yl)-N-(5-isopropylpyridazin-3-yl)-1,5-naphthyridine-2-amine was obtained in the same manner as in Example 0740.

$^1$H-NMR(CDCl$_3$)δ:9.00(1H,s),8.93(1H,s),8.83(1H,s), 8.30-8.25(2H,m),7.89(1H,brs),7.71(1H,s),4.57(2H,s),4.57-4.51(1H,m),3.99(3H,s),3.68(4H,d,J=6.0 Hz),3.09-3.00(1H,m),1.42(6H,d,J=7.9 Hz).

MSm/z(M+H):431.

Example 0823

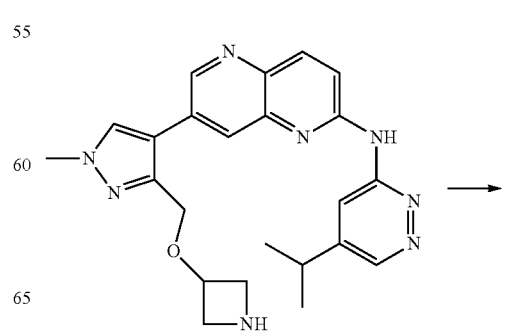

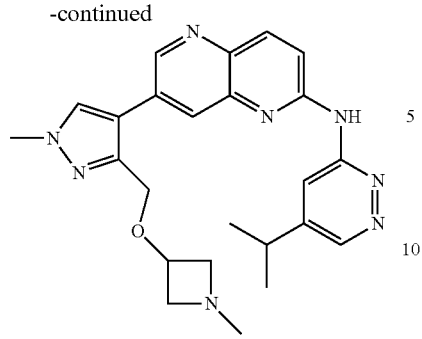

N-(5-isopropylpyridazin-3-yl)-7-(1-methyl-3-(((1-methylazetidin-3-yl)oxy)methyl)-1H-pyrazol-4-yl)-1,5-naphthyridine-2-amine was obtained as a white solid in the same manner as in Example 0741.

¹H-NMR(CDCl₃)δ:9.73(1H,brs),8.96(1H,s),8.92(1H,d,J=2.0 Hz),8.83(1H,d,J=2.0 Hz),8.28(1H,d,J=9.2 Hz),8.26(1H,s),7.76(1H,d,J=9.2 Hz),7.70(1H,s),4.56(2H,s),4.34-4.26(1H,m),4.00(3H,s),3.66(2H,dd,J=7.9,6.6 Hz),3.09-3.00(1H,m),2.94(2H,dd,J=8.3,6.6 Hz),2.32(3H,s),1.42(6H,d,J=6.6 Hz).

MSm/z(M+H):445.

Example 0824

0824-1

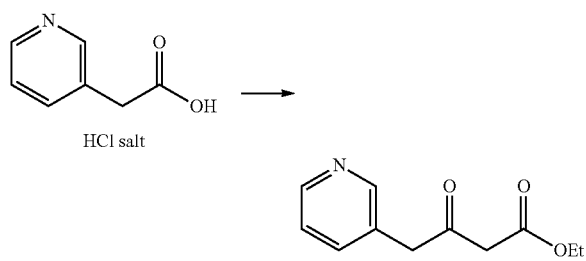

Methylene chloride (50 mL), triethylamine (2.09 mL), and 1,1'-carbonyldiimidazole (2.43 g) were added to 2-(pyridin-3-yl)acetic acid hydrochloride (1.73 g), followed by stirring at room temperature for 1.5 hours. A methylene chloride solution (50 mL) of Meldrum's acid (1.73 g) and pyridine (1.63 mL) was added to the reaction mixture under ice-cooling, followed by stirring at room temperature for 20 hours. After water was added to the reaction mixture, the resultant product was extracted two times with methylene chloride, and an organic layer thus obtained was washed with a saturated sodium chloride aqueous solution. The organic layer was dried over anhydrous sodium sulfate, and the solvent was distilled off under reduced pressure. Ethanol (100 mL) was added to the obtained residue, followed by heating under reflux for 4 days. The solvent of the reaction mixture was distilled off under reduced pressure, and the obtained residue was purified by silica gel column chromatography (hexane-ethyl acetate), thereby obtaining ethyl 3-oxo-4-(pyridin-3-yl)butanoate (480 mg) as yellow oily substance.

MSm/z(M+H):208.

0824-2

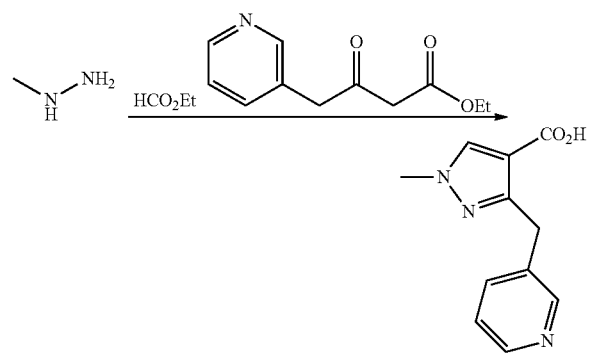

Ethyl formate (317 μL) was added to a solution of methylhydrazine (135 μL) in ethanol (1 mL), followed by heating under reflux for 3 hours under stirring. Ethyl 3-oxo-4-(pyridin-3-yl)butanoate (480 mg) was added to the reaction mixture, followed by heating under reflux for 3 hours under stirring. Furthermore, a 20% sodium ethoxide-ethanol solution (1 mL) was added thereto, followed by heating under reflux for 2 hours under stirring. A 5 mol/L sodium hydroxide aqueous solution (1 mL) was added to the reaction mixture, followed by stirring at room temperature for 1 hour. The solvent of the reaction mixture was distilled off under reduced pressure, a 4 mol/L hydrogen chloride/1,4-dioxane solution (2 mL) and ethanol (2 mL) were added to the obtained residue, and the solvent was distilled off under reduced pressure. Ethanol (2 mL) was added to the obtained residue, and the precipitated solid was collected by filtration, thereby obtaining 1-methyl-3-(pyridin-3-ylmethyl)-1H-pyrazole-4-carboxylic acid (220 mg) as a pale yellow solid.

MSm/z(M+H):218.

0824-3

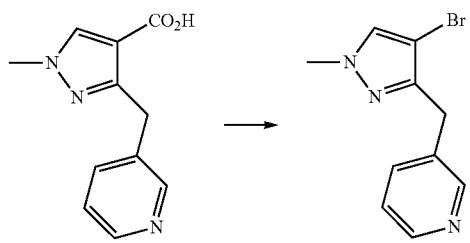 [SMILES: Cn1cc(C(=O)O)c(Cc2cccnc2)n1 ; Cn1cc(Br)c(Cc2cccnc2)n1]

Sodium hydrogen carbonate (252 mg), N,N-dimethylformamide (3 mL), and N-bromosuccinimide (178 mg) were added to 1-methyl-3-(pyridin-3-ylmethyl)-1H-pyrazole-4-carboxylic acid (220 mg), followed by stirring at room temperature for 1.5 hours. After a 1 mol/L sodium hydroxide aqueous solution was added to the reaction mixture, the resultant product was extracted three times with ethyl acetate, an organic layer thus obtained was washed with a saturated sodium chloride aqueous solution, and dried over anhydrous sodium sulfate. The solvent was distilled off under reduced pressure, and the obtained residue was purified by silica gel column chromatography (hexane-ethyl acetate), thereby obtaining 3-((4-bromo-1-methyl-1H-pyrazol-3-yl)methyl)pyridine (100 mg) as brown oily substance.

MSm/z(M+H):252.

0824-4

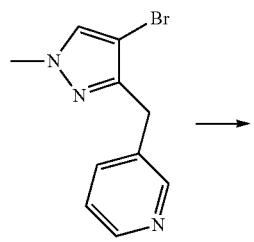

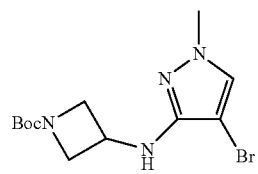 [SMILES: Cn1cc(Br)c(NC2CN(C(=O)OC(C)(C)C)C2)n1]

N-(5-isopropylpyridazin-3-yl)-7-(1-methyl-3-(pyridin-3-ylmethyl)-1H-pyrazol-4-yl)-1,5-naphthyridine-2-amine was obtained as a pale yellow solid in the same manner as in Example 0385-7.

$^1$H-NMR(CDCl$_3$)δ:8.81(2H,brs),8.73(1H,d,J=2.0 Hz), 8.50(1H,d,J=2.0 Hz),8.42(1H,d,J=5.3 Hz),8.24(1H,d,J=9.2 Hz),7.94(1H,s),7.68-7.61(2H,m),7.53(1H,d,J=7.3 Hz),7.19-7.14(1H,m),4.21(2H,s),4.00(3H,s),3.06-2.98(1H,m),1.37 (6H,d,J=7.3 Hz).

MSm/z(M+H):437.

Example 0825

The following compounds were obtained in the same manner as in Examples 0814 and 0385-7.

| Example No. | | |
|---|---|---|
| 0825 | | |
| 0825-1 | ![structure] | MS m/z (M + H): 331. |
| 0825-2 | 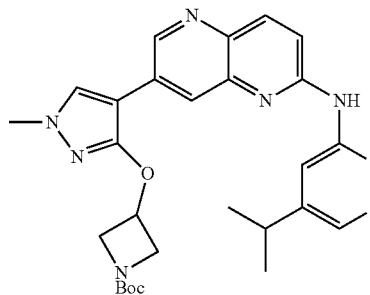 | $^1$H-NMR (CDCl$_3$) δ: 9.52 (1 H, brs), 8.93 (1 H, brs), 8.84 (1 H, s), 8.77 (1 H, s), 8.24 (1 H, d, J = 8.2 Hz), 8.11 (1 H, s), 7.69 (1 H, d, J = 8.2 Hz), 7.52 (1 H, s), 4.50-4.44 (1 H, m), 4.32 (2 H, t, J = 7.9 Hz), 4.19-4.10 (1 H, m), 3.83 (3 H, s), 3.82-3.76 (2 H, m), 3.07-2.97 (1 H, m), 1.43 (9 H, s), 1.41 (6 H, d, J = 7.2 Hz). MS m/z (M + H): 516. |

Example 0826

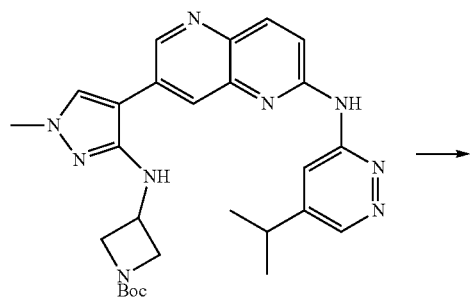

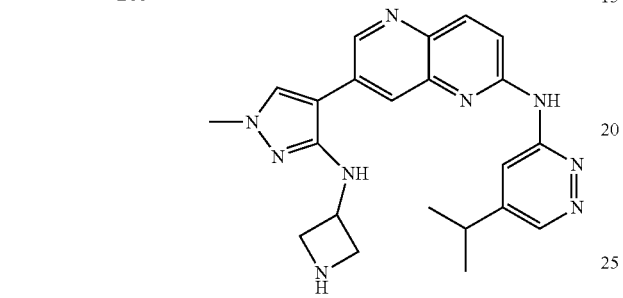

7-(3-(Azetidin-3-ylamino)-1-methyl-1H-pyrazol-4-yl)-N-((5-isopropylpyridazin-3-yl)-1,5-naphthyridine-2-amine was obtained as a white solid in the same manner as in Example 0740.
$^1$H-NMR(CDCl$_3$)δ:9.25(1H,brs),8.88(1H,s),8.86(1H,d,J=2.0 Hz),8.74(1H,d,J=2.0 Hz),8.24(1H,d,J=8.6 Hz),8.12(1H,d,J=2.0 Hz),7.61(1H,d,J=8.6 Hz),7.50(1H,s),4.69-4.60(1H,m),4.36(1H,d,J=8.6 Hz),4.03(2H,t,J=8.3 Hz),3.83(3H,s),3.58(2H,t,J=7.6 Hz),3.04-2.95(1H,m),1.38(6H,d,J=6.6 Hz).
MSm/z(M+H):416.

Example 0827

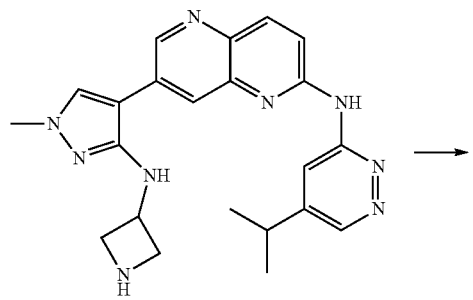

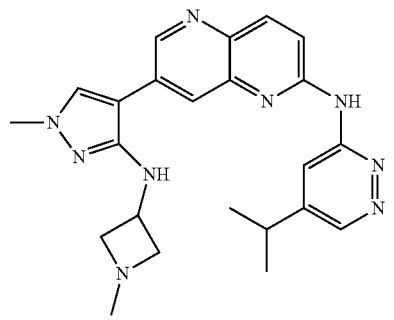

N-(5-isopropylpyridazin-3-yl)-7-(1-methyl-3-((1-methyl-azetidin-3-yl)amino)-1H-pyrazol-4-yl)-1,5-naphthyridine-2-amine was obtained as a white solid in the same manner as in Example 0741.
$^1$H-NMR(CDCl$_3$)δ:8.91(1H,s),8.85(1H,d,J=2.0 Hz),8.81(1H,d,J=2.0 Hz),8.24(1H,d,J=9.2 Hz),8.11(1H,d,J=2.0 Hz),7.61(1H,brs),7.49(1H,s),4.38-4.31(1H,m),3.83(3H,s),3.80-3.75(2H,m),3.64(1H,t,J=4.3 Hz),3.09-2.96(3H,m),2.36(3H,s),1.41(6H,d,J=7.3 Hz).
MSm/z(M+H):430.

Example 0828

0828-1

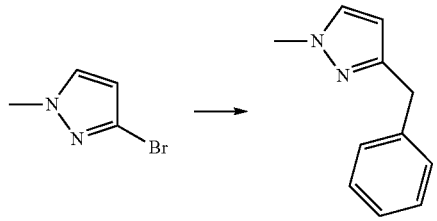

(1,3-Diisopropylimidazol-2-ylidene) (3-chloropyridyl) palladium(II) dichloride (34 mg), tetrahydrofuran (5 mL), and a 0.9 mol/L benzyl bromide-tetrahydrofuran solution (1.7 mL) were added to 3-bromo-1-methyl-1H-pyrazole (80 mg), followed by stirring at room temperature for 4 hours. Water was added to the liquid reaction mixture, and the solvent was distilled off under reduced pressure. The obtained residue was purified by silica gel column chromatography (hexane-ethyl acetate), thereby obtaining 3-benzyl-1-methyl-1H-pyrazole (41 mg) as colorless oily substance.

MSm/z(M+H):173.

0828-2 and 0828-3

The following compounds were obtained in the same manner as in Examples 0734-2 and 0385-7

| Example No. | | |
|---|---|---|
| 0828 | | |
| 0828-2 | 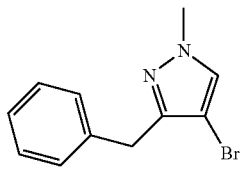 | MS m/z (M + H): 253. |
| 0828-3 | 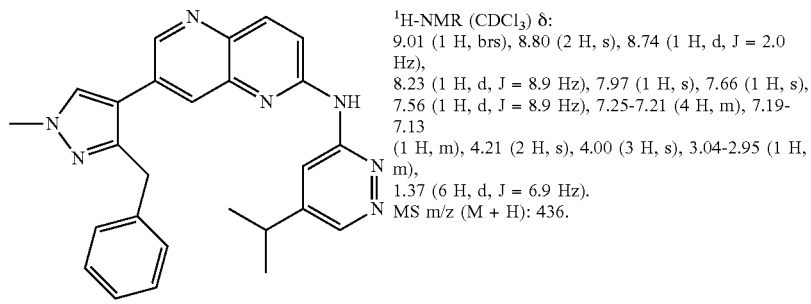 | ¹H-NMR (CDCl₃) δ:<br>9.01 (1 H, brs), 8.80 (2 H, s), 8.74 (1 H, d, J = 2.0 Hz),<br>8.23 (1 H, d, J = 8.9 Hz), 7.97 (1 H, s), 7.66 (1 H, s),<br>7.56 (1 H, d, J = 8.9 Hz), 7.25-7.21 (4 H, m), 7.19-7.13<br>(1 H, m), 4.21 (2 H, s), 4.00 (3 H, s), 3.04-2.95 (1 H, m),<br>1.37 (6 H, d, J = 6.9 Hz).<br>MS m/z (M + H): 436. |
Example 0829
The following compounds were obtained in the same manner as in Examples 0485-2 and 0385-7.
| Example No. | | |
|---|---|---|
| 0829 | | |
| 0829-1 | 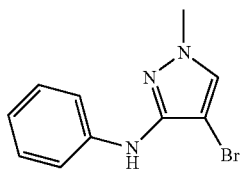 | MS m/z (M + H): 252. |
| 0829-2 | 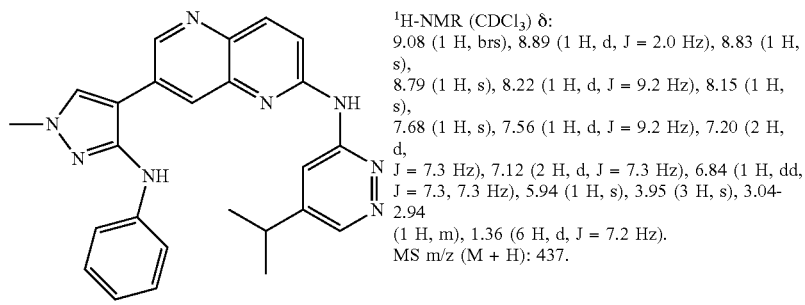 | ¹H-NMR (CDCl₃) δ:<br>9.08 (1 H, brs), 8.89 (1 H, d, J = 2.0 Hz), 8.83 (1 H, s),<br>8.79 (1 H, s), 8.22 (1 H, d, J = 9.2 Hz), 8.15 (1 H, s),<br>7.68 (1 H, s), 7.56 (1 H, d, J = 9.2 Hz), 7.20 (2 H, d,<br>J = 7.3 Hz), 7.12 (2 H, d, J = 7.3 Hz), 6.84 (1 H, dd,<br>J = 7.3, 7.3 Hz), 5.94 (1 H, s), 3.95 (3 H, s), 3.04-2.94<br>(1 H, m), 1.36 (6 H, d, J = 7.2 Hz).<br>MS m/z (M + H): 437. |

Example 0830

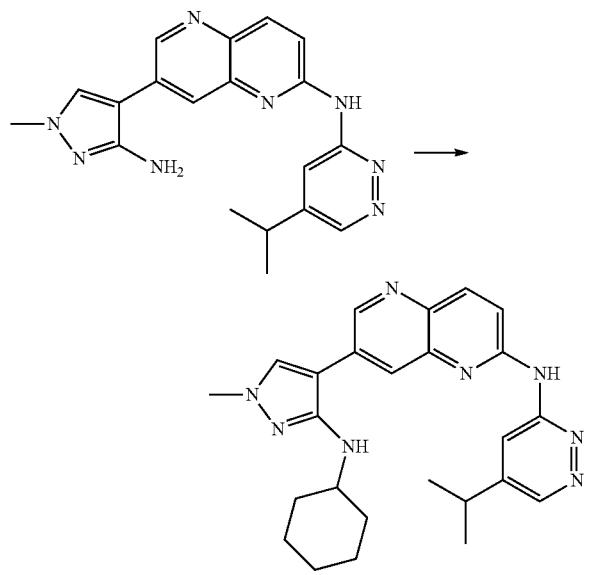

Cyclohexanone (2.1 µL), methanol (0.5 mL), acetic acid (50 µL), and 2-picoline borane (3.2 mg) were added to 7-(3-amino-1-methyl-1H-pyrazol-4-yl)-N-(5-isopropylpyridazin-3-yl)-1,5-naphthyridine-2-amine (3.6 mg), followed by stirring at room temperature for 1 hour. The solvent of the reaction mixture was distilled off under reduced pressure. The obtained residue was purified by silica gel column chromatography (hexane-ethyl acetate, NH silica), thereby obtaining 7-(3-(cyclohexylamino)-1-methyl-1H-pyrazol-4-yl)-N-(5-isopropylpyridazin-3-yl)-1,5-naphthyridine-2-amine (3.1 mg) as a pale yellow solid.

$^1$H-NMR(CDCl$_3$)δ:8.93(1H,s),8.85(1H,d,J=2.0 Hz),8.80(1H,s),8.23(1H,d,J=9.2 Hz),8.12(1H,s),7.52-7.46(2H,m),3.84(3H,s),3.68-3.62(1H,m),3.58-3.48(1H,m),3.07-2.98(1H,m),2.14(2H,d,J=13.2 Hz),1.78-1.70(4H,m),1.41(6H,d,J=6.6 Hz),1.27-1.15(4H,m).

MS m/z(M+H):443.

Examples 0831 to 0836

The following compounds were obtained in the same manner as in Example 0830.

| Example No. | | |
|---|---|---|
| 0831 | 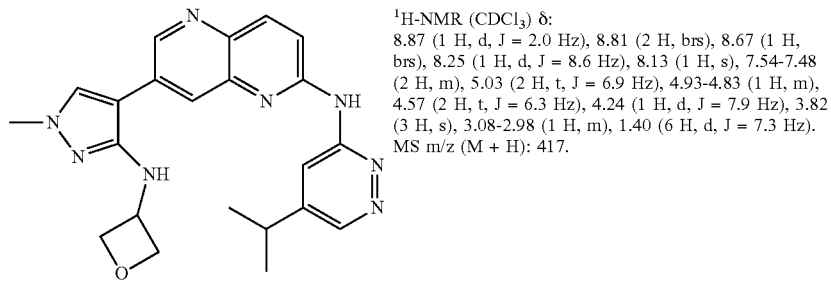 | $^1$H-NMR (CDCl$_3$) δ:<br>8.87 (1 H, d, J = 2.0 Hz), 8.81 (2 H, brs), 8.67 (1 H, brs), 8.25 (1 H, d, J = 8.6 Hz), 8.13 (1 H, s), 7.54-7.48 (2 H, m), 5.03 (2 H, t, J = 6.9 Hz), 4.93-4.83 (1 H, m), 4.57 (2 H, t, J = 6.3 Hz), 4.24 (1 H, d, J = 7.9 Hz), 3.82 (3 H, s), 3.08-2.98 (1 H, m), 1.40 (6 H, d, J = 7.3 Hz).<br>MS m/z (M + H): 417. |
| 0832 | 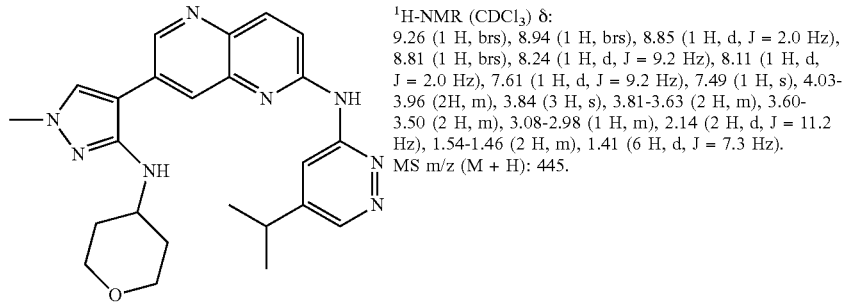 | $^1$H-NMR (CDCl$_3$) δ:<br>9.26 (1 H, brs), 8.94 (1 H, brs), 8.85 (1 H, d, J = 2.0 Hz), 8.81 (1 H, brs), 8.24 (1 H, d, J = 9.2 Hz), 8.11 (1 H, d, J = 2.0 Hz), 7.61 (1 H, d, J = 9.2 Hz), 7.49 (1 H, s), 4.03-3.96 (2H, m), 3.84 (3 H, s), 3.81-3.63 (2 H, m), 3.60-3.50 (2 H, m), 3.08-2.98 (1 H, m), 2.14 (2 H, d, J = 11.2 Hz), 1.54-1.46 (2 H, m), 1.41 (6 H, d, J = 7.3 Hz).<br>MS m/z (M + H): 445. |
| 0833 | 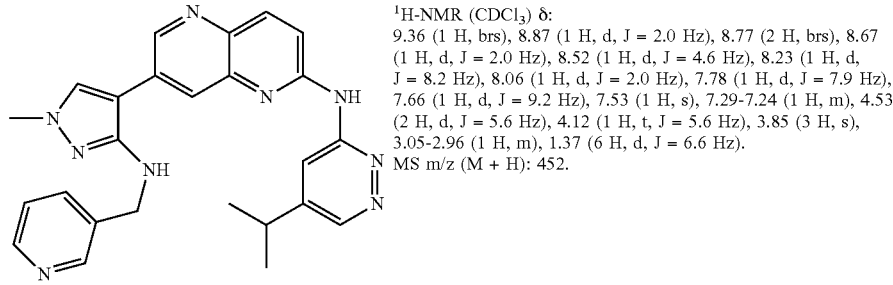 | $^1$H-NMR (CDCl$_3$) δ:<br>9.36 (1 H, brs), 8.87 (1 H, d, J = 2.0 Hz), 8.77 (2 H, brs), 8.67 (1 H, d, J = 2.0 Hz), 8.52 (1 H, d, J = 4.6 Hz), 8.23 (1 H, d, J = 8.2 Hz), 8.06 (1 H, d, J = 2.0 Hz), 7.78 (1 H, d, J = 7.9 Hz), 7.66 (1 H, d, J = 9.2 Hz), 7.53 (1 H, s), 7.29-7.24 (1 H, m), 4.53 (2 H, d, J = 5.6 Hz), 4.12 (1 H, t, J = 5.6 Hz), 3.85 (3 H, s), 3.05-2.96 (1 H, m), 1.37 (6 H, d, J = 6.6 Hz).<br>MS m/z (M + H): 452. |

| Example No. | | |
|---|---|---|
| 0834 | 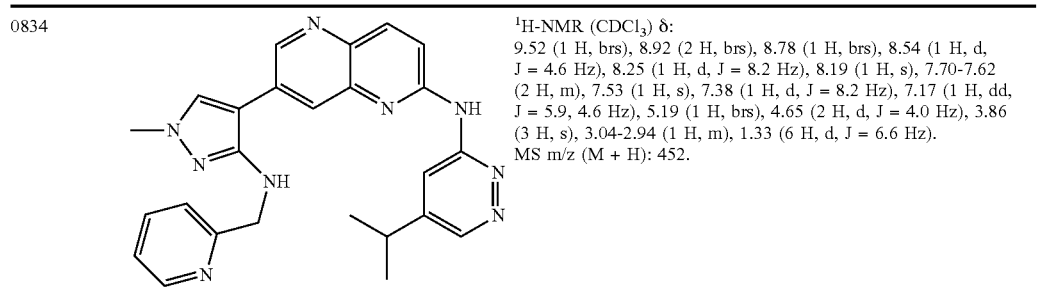 | ¹H-NMR (CDCl₃) δ:<br>9.52 (1 H, brs), 8.92 (2 H, brs), 8.78 (1 H, brs), 8.54 (1 H, d, J = 4.6 Hz), 8.25 (1 H, d, J = 8.2 Hz), 8.19 (1 H, s), 7.70-7.62 (2 H, m), 7.53 (1 H, s), 7.38 (1 H, d, J = 8.2 Hz), 7.17 (1 H, dd, J = 5.9, 4.6 Hz), 5.19 (1 H, brs), 4.65 (2 H, d, J = 4.0 Hz), 3.86 (3 H, s), 3.04-2.94 (1 H, m), 1.33 (6 H, d, J = 6.6 Hz).<br>MS m/z (M + H): 452. |
| 0835 | 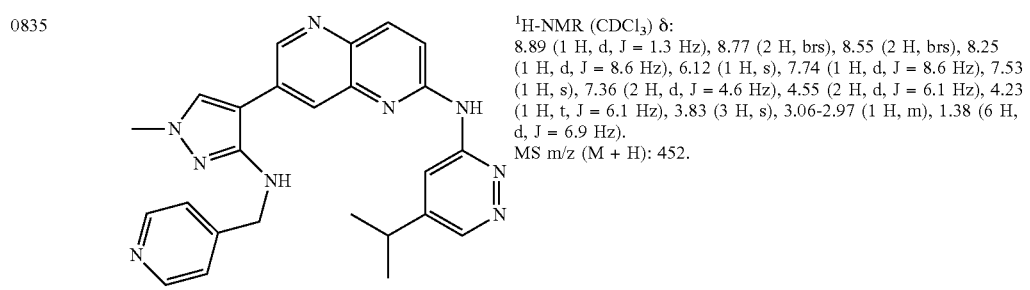 | ¹H-NMR (CDCl₃) δ:<br>8.89 (1 H, d, J = 1.3 Hz), 8.77 (2 H, brs), 8.55 (2 H, brs), 8.25 (1 H, d, J = 8.6 Hz), 6.12 (1 H, s), 7.74 (1 H, d, J = 8.6 Hz), 7.53 (1 H, s), 7.36 (2 H, d, J = 4.6 Hz), 4.55 (2 H, d, J = 6.1 Hz), 4.23 (1 H, t, J = 6.1 Hz), 3.83 (3 H, s), 3.06-2.97 (1 H, m), 1.38 (6 H, d, J = 6.9 Hz).<br>MS m/z (M + H): 452. |
| 0836 | 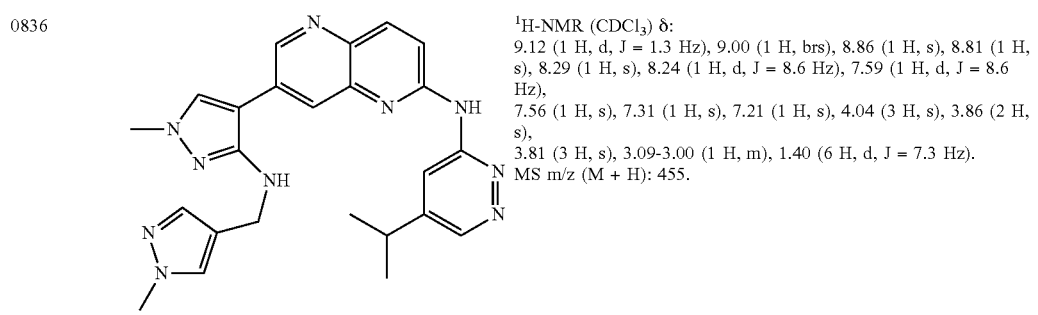 | ¹H-NMR (CDCl₃) δ:<br>9.12 (1 H, d, J = 1.3 Hz), 9.00 (1 H, brs), 8.86 (1 H, s), 8.81 (1 H, s), 8.29 (1 H, s), 8.24 (1 H, d, J = 8.6 Hz), 7.59 (1 H, d, J = 8.6 Hz), 7.56 (1 H, s), 7.31 (1 H, s), 7.21 (1 H, s), 4.04 (3 H, s), 3.86 (2 H, s), 3.81 (3 H, s), 3.09-3.00 (1 H, m), 1.40 (6 H, d, J = 7.3 Hz).<br>MS m/z (M + H): 455. |

Examples 0837 and 0838

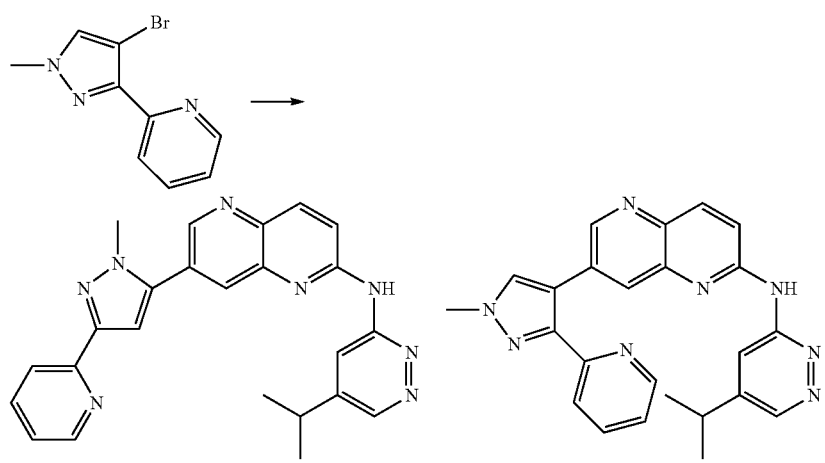

2.6 mol/L n-butyllithium (0.24 mL) was added to a mixture of 2-(4-bromo-1-methyl-1H-pyrazol-3-yl)pyridine (100 mg) and tetrahydrofuran (2 mL) at −78° C., followed by stirring at the same temperature for 1 hour. 2-Isopropoxy-4,4,5,5-tetramethyl-1,3,2-dioxaborolane (0.17 mL) was added thereto, followed by stirring at the same temperature for 1 hour. After an ammonium chloride aqueous solution and ethyl acetate were added to the reaction mixture, an organic layer was collected therefrom by separation, washed sequentially with water and a saturated sodium chloride aqueous solution, and dried over anhydrous sodium sulfate, and the solvent was distilled off under reduced pressure, thereby obtaining brown oily substance (128 mg).

A mixture of the brown oily substance (33 mg), 7-bromo-N-(5-isopropylpyridazin-3-yl)-1,5-naphthyridine-2-amine (20 mg), sodium carbonate (18 mg), bis(di-tert-butyl(4-dimethylaminophenyl)phosphine)dichloropalladium(II) (4 mg), water (0.1 mL), and 1,4-dioxane (1 mL) was stirred at 100° C. for 7 hours. The reaction mixture was cooled to room temperature, the insolubles were filtered off, and the solvent was distilled off under reduced pressure. The obtained residue was purified by silica gel column chromatography (methanol-ethyl acetate), thereby obtaining N-(5-isopropylpyridazin-3-yl)-7-(1-methyl-3-(pyridin-2-yl)-1H-pyrazol-5-yl)-1,5-naphthyridine-2-amine (1 mg) as a yellow solid and N-(5-isopropylpyridazin-3-yl)-7-(1-methyl-3-(pyridin-2-yl)-1H-pyrazol-4-yl)-1,5-naphthyridine-2-amine (7 mg) as a yellow solid.

Example 0837

N-(5-isopropylpyridazin-3-yl)-7-(1-methyl-3-(pyridin-2-yl)-1H-pyrazol-5-yl)-1,5-naphthyridine-2-amine $^1$H-NMR(CDCl$_3$)δ:9.80(1H,s),9.00-8.96(1H,m),8.92(1H, d,J=2.0 Hz),8.85(1H,d,J=2.0 Hz),8.70-8.65(1H,m),8.33(1H, d,J=9.2 Hz),8.21(1H,d,J=2.0 Hz),8.01(1H,d,J=7.9 Hz),7.82 (1H,d,J=9.2 Hz),7.80-7.75(1H,m),7.26-7.22(1H,m),7.17 (1H,s),4.09(3H,s),3.10-3.01(1H,m),1.42(6H,d,J=7.3 Hz).

MS m/z (M+H):423.

Example 0838

N-(5-isopropylpyridazin-3-yl)-7-(1-methyl-3-(pyridin-2-yl)-1H-pyrazol-4-yl)-1,5-naphthyridine-2-amine $^1$H-NMR(CDCl$_3$)δ:9.94(1H,s),8.97-8.94(1H,m),8.82-8.79(1H,m),8.76(1H,d,J=2.0 Hz),8.61-8.56(1H,m),8.25(1H, d,J=9.2 Hz),8.08(1H,d,J=2.0 Hz),7.76(1H,d,J=9.2 Hz),7.72-7.65(1H,m),7.70(1H,s),7.67-7.65(1H,m),7.24-7.18(1H,m), 4.08(3H,s),3.04-2.95(1H,m),1.36(6H,d,J=6.6 Hz).

MS m/z (M+H):423.

Example 0839

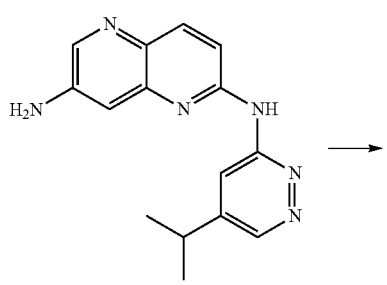

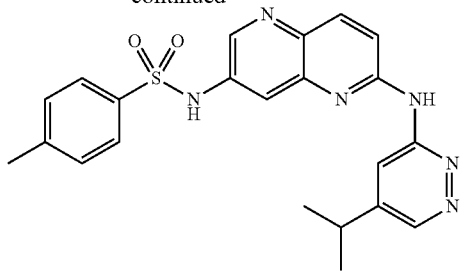

A mixture of N$^2$-(5-isopropylpyridazin-3-yl)-1,5-naphthyridine-2,7-diamine (5 mg), paratoluenesulphonyl chloride (7 mg), pyridine (4 µL), and dichloromethane (0.5 mL) was stirred at room temperature for 6 hours. The solvent of the reaction mixture was distilled off under reduced pressure. The obtained residue was purified by silica gel column chromatography (methanol-ethyl acetate), thereby obtaining N-(6-((5-isopropylpyridazin-3-yl)amino)-1,5-naphthyridin-3-yl)-4-methylbenzene sulfonamide (8 mg) as a yellow solid.

$^1$H-NMR(CDCl$_3$)δ:9.28(1H,s),8.94-8.90(1H,m),8.82(1H, d,J=2.0 Hz),8.53(1H,d,J=2.0 Hz),8.15(1H,d,J=9.2 Hz),7.97 (1H,d,J=2.0 Hz),7.77(2H,d,J=7.9 Hz),7.51(1H,d,J=8.6 Hz), 7.26-7.23(1H,m),7.25(2H,d,J=7.9 Hz),3.12-3.03(1H,m), 2.37(3H,s),1.44(6H,d,J=6.6 Hz).

MS m/z (M+H):435.

Example 0840

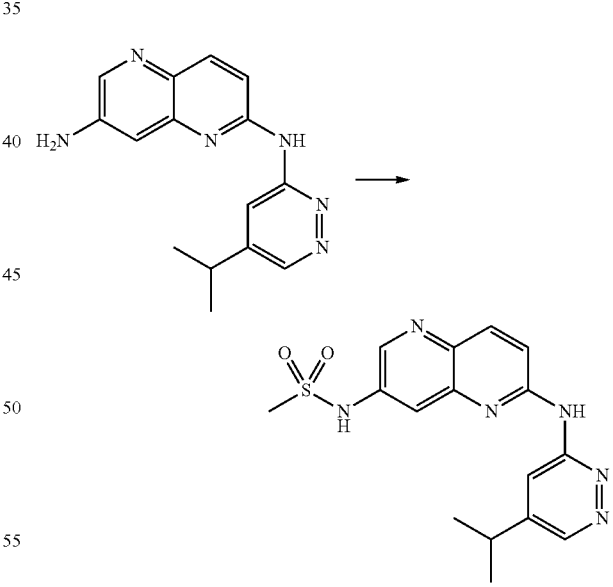

N-(6-((5-isopropylpyridazin-3-yl)amino)-1,5-naphthyridin-3-yl)methane sulfonamide was obtained as a yellow solid in the same manner as in Example 0839.

$^1$H-NMR(CDCl$_3$)δ:8.97(1H,s),8.87-8.84(1H,m),8.85-8.81(1H,m),8.67(1H,d,J=2.0 Hz),8.23(1H,d,J=8.6 Hz),8.08 (1H,d,J=2.0 Hz),7.53(1H,d,J=8.6 Hz),7.30-7.25(1H,m),3.16 (3H,s),3.11-3.02(1H,m),1.41(6H,d,J=7.3 Hz).

MS m/z (M+H):359.

Example 0841

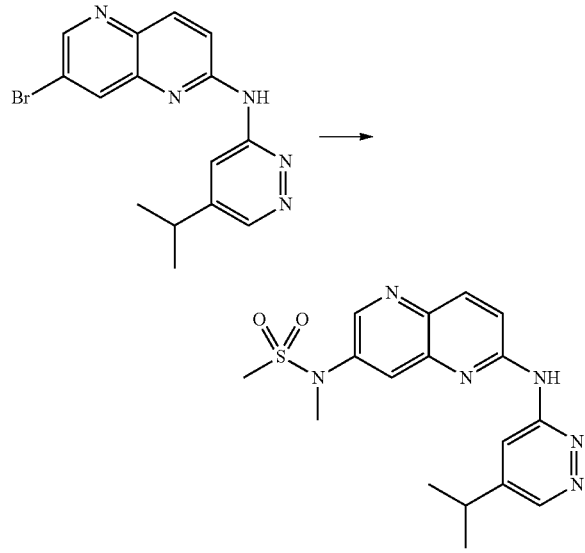

A mixture of 7-bromo-N-(5-isopropylpyridazin-3-yl)-1,5-naphthyridine-2-amine (10 mg), N-methylmethane sulfonamide (68 μL), tris(dibenzylideneacetone)dipalladium(0) (3 mg), 2-di-tert-butylphosphino-3,4,5,6-tetramethyl-2',4',6'-triisopropyl-1,1'-biphenyl (4 mg), potassium carbonate (20 mg), and tert-amyl alcohol (0.5 mL) was stirred at 100° C. for 5 hours. The reaction mixture was cooled to room temperature, the insolubles were filtered off, and the solvent was distilled off under reduced pressure. The obtained residue was purified by silica gel column chromatography (methanol-ethyl acetate), thereby obtaining N-(6-((5-isopropylpyridazin-3-yl)amino)-1,5-naphthyridin-3-yl)-N-methylmethane sulfonamide (2 mg) as a yellow solid.

$^1$H-NMR(CDCl$_3$)δ:9.82(1H,s),8.91-8.87(1H,m),8.86-8.83(1H,m),8.84-8.82(1H,m),8.27(1H,d,J=8.6 Hz),8.07-8.04(1H,m),7.80(1H,d,J=8.6 Hz),3.50(3H,s),3.10-3.02(1H,m),2.98(3H,s),1.42(6H,d,J=6.6 Hz).
MSm/z(M+H):373.

Example 0842

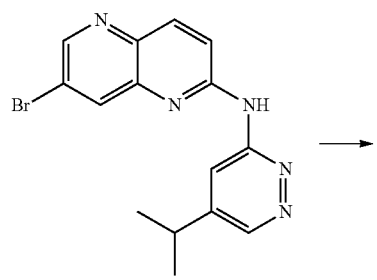

-continued

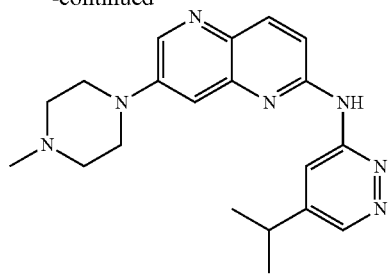

N-(5-isopropylpyridazin-3-yl)-7-(4-methylpiperazin-1-yl)-1,5-naphthyridine-2-amine was obtained as a yellow solid in the same manner as in Example 0846.

$^1$H-NMR(CDCl$_3$)δ:9.18(1H,s),8.82-8.78(2H,m),8.64(1H,d,J=2.6 Hz),8.14(1H,d,J=8.6 Hz),7.45(1H,d,J=8.6 Hz),7.32(1H,d,J=2.6 Hz),3.44-3.39(4H,m),3.09-2.98(1H,m),2.68-2.62(4H,m),2.40(3H,s),1.40(6H,d,J=7.3 Hz).
MSm/z(M+H):364.

Example 0843

0843-1

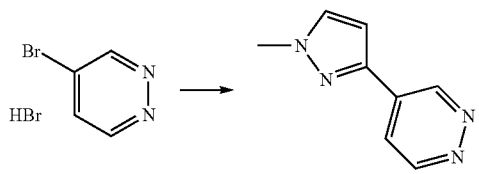

A mixture of 4-bromopyridazine hydrobromate (100 mg), bis(pinacolato)diboron (117 mg), potassium acetate (165 mg), (tris(dibenzylideneacetone)dipalladium(0) (19 mg), 2-dicyclohexylphosphino-2',4',6'-triisopropylbiphenyl (40 mg), and 1,4-dioxane (0.5 mL) was stirred at 110° C. for 0.5 hours. 3-Bromo-1-methyl-1H-pyrazole (74 mg), potassium phosphate (713 mg), water (0.2 mL), and 1,4-dioxane (0.5 mL) were added thereto, followed by stirring at 110° C. for 0.5 hours. The reaction mixture was cooled to room temperature, the solvent was distilled off under reduced pressure, and the obtained residue was purified by silica gel column chromatography (methanol-ethyl acetate), thereby obtaining 4-(1-methyl-1H-pyrazol-3-yl)pyridazine (15 mg) as a yellow solid.
MSm/z(M+H):161.

0843-2

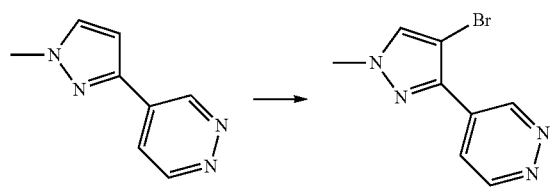

A mixture of 4-(1-methyl-1H-pyrazol-3-yl)pyridazine (15 mg), N-bromosuccinimide (18 mg), and acetonitrile (1 mL) was stirred at room temperature for 5 hours. The solvent of the reaction mixture was distilled off under reduced pressure. The obtained residue was purified by silica gel column chromatography (methanol-ethyl acetate), thereby obtaining 4-(4-bromo-1-methyl-1H-pyrazol-3-yl)pyridazine (11 mg) as a yellow solid.
MSm/z(M+H):239.

0843-3

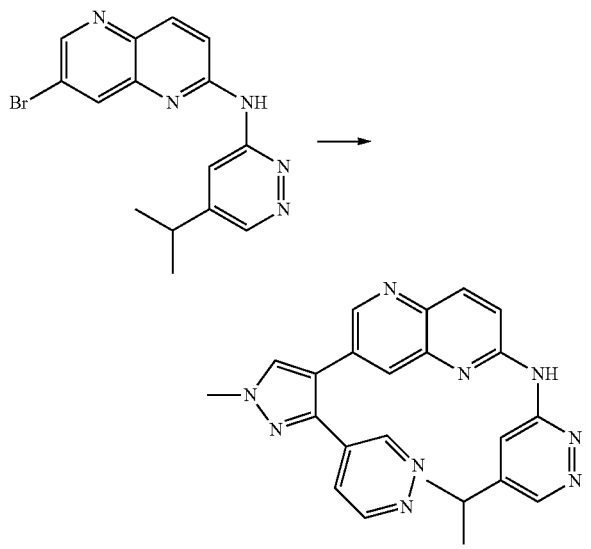

A mixture of 7-bromo-N-(5-isopropylpyridazin-3-yl)-1,5-naphthyridine-2-amine (17 mg), bis(pinacolato)diboron (14 mg), potassium acetate (9 mg), (tris(dibenzylideneacetone)dipalladium(0) (4 mg), 2-dicyclohexylphosphino-2',4',6'-triisopropylbiphenyl (9 mg), and 1,4-dioxane (0.4 mL) was stirred at 100° C. for 1 hour. 4-(4-Bromo-1-methyl-1H-pyrazol-3-yl)pyridazine (13 mg), potassium phosphate (41 mg), water (0.2 mL), and 1,4-dioxane (0.4 mL) were added thereto, followed by stirring at 100° C. for 2 hours. The reaction mixture was cooled to room temperature, the solvent was distilled off under reduced pressure, and the obtained residue was purified by silica gel column chromatography (methanol-ethyl acetate), thereby obtaining N-(5-isopropylpyridazin-3-yl)-7-(1-methyl-3-(pyridazin-4-yl)-1H-pyrazol-4-yl)-1,5-naphthyridine-2-amine (15 mg) as a yellow solid.
$^1$H-NMR(CDCl$_3$)δ:9.45-9.42(1H,m),9.10(1H,d,J=5.3 Hz),8.95(1H,s),8.82-8.78(1H,m),8.78-8.74(1H,m),8.69(1H,d,J=2.0 Hz),8.29(1H,d,J=9.2 Hz),7.96(1H,d,J=2.0 Hz),7.70(1H,s),7.63(1H,d,J=9.2 Hz),7.56(1H,dd,J=5.3,2.0 Hz),4.10(3H,s),3.03-2.94(1H,m),1.33(6H,d,J=6.6 Hz).
MSm/z(M+H):424.

Example 0844

0844-1

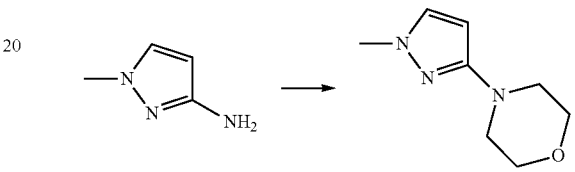

A mixture of 1-methyl-1H-pyrazole-3-amine (1 g), bis(2-bromoethyl)ether (1.2 g), potassium carbonate (4.2 g), and N,N-dimethylformamide (20 mL) was stirred at 150° C. for 1 hour. The solvent of the reaction mixture was distilled off under reduced pressure, and ethyl acetate and water were added thereto. An organic layer was collected therefrom by separation, and dried over anhydrous sodium sulfate, and the solvent was distilled off under reduced pressure. The obtained residue was purified by silica gel column chromatography (methanol-ethyl acetate), thereby obtaining 4-(1-methyl-1H-pyrazol-3-yl)morpholine (249 mg).
MSm/z(M+H):168.

0844-2 and 0844-3

The following compounds were obtained in the same manner as in Examples 0843-2 and 0843-3.

| Example No. | | |
|---|---|---|
| 0844 | | |
| 0844-2 | 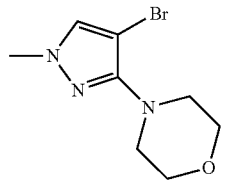 | MS m/z (M + H): 246. |
| 0844-3 | 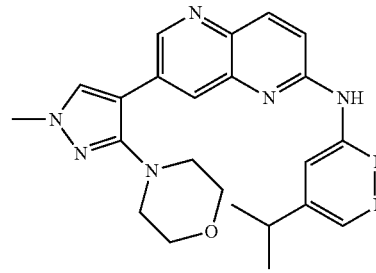 | $^1$H-NMR (CDCl$_3$) δ: 9.21 (1 H, s), 9.02-9.01 (1 H, m), 9.01-8.99 (1 H, m), 8.82-8.81 (1 H, m), 8.38-8.36 (1 H, m), 8.23 (1 H, d, J = 9.2 Hz), 7.60 (1 H, s), 7.56 (1 H, d, J = 9.2 Hz), 3.88-3.84 (4 H, m), 3.88 (3 H, s), 3.14-3.10 (4 H, m), 3.09-2.89 (1 H, m), 1.44 (6 H, d, J = 6.6 Hz). MS m/z (M + H): 431. |

Example 0845

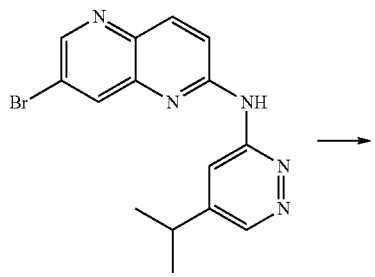

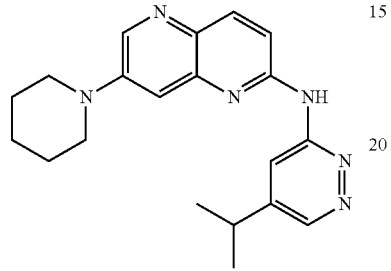

N-(5-isopropylpyridazin-3-yl)-7-(piperidin-1-yl)-1,5-naphthyridine-2-amine was obtained as a yellow solid in the same manner as in Example 0846.

$^1$H-NMR(CDCl$_3$)δ:8.79-8.75(2H,m),8.69(1H,s),8.64(1H, d,J=2.6 Hz),8.12(1H,d,J=8.6 Hz),7.34-7.30(1H,m),7.32-7.26(1H,m),3.40-3.34(4H,m),3.07-2.98(1H,m),1.83-1.75 (4H,m),1.71-1.64(2H,m),1.39(6H,d,J=7.3 Hz).

MSm/z(M+H):349.

Example 0846

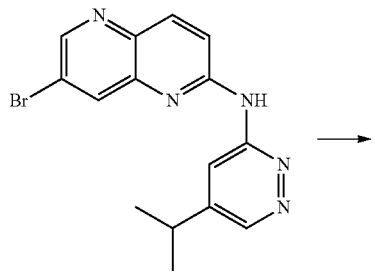

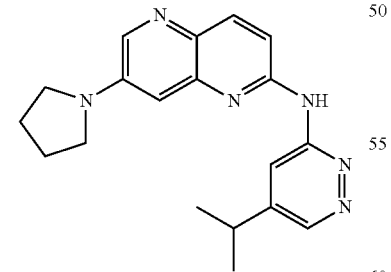

A mixture of 7-bromo-N-(5-isopropylpyridazin-3-yl)-1,5-naphthyridine-2-amine (15 mg), pyrrolidine (11 μL), tris (dibenzylideneacetone)dipalladium(0) (4 mg), 2-dicyclohexylphosphino-2',6'-diisopropoxybiphenyl (4 mg), sodium tert-butoxide (13 mg), and tert-amyl alcohol (0.5 mL) was stirred at 130° C. for 30 minutes using a microwave reaction apparatus. The reaction mixture was cooled to room temperature, the insolubles were filtered off, and the solvent was distilled off under reduced pressure. The obtained residue was purified by silica gel column chromatography (methanol-ethyl acetate), thereby obtaining N-(5-isopropylpyridazin-3-yl)-7-(pyrrolidin-1-yl)-1,5-naphthyridine-2-amine (12 mg) as a yellow solid.

$^1$H-NMR(CDCl$_3$)δ:8.79-8.75(2H,m),8.68(1H,s),8.37(1H, d,J=2.6 Hz),8.10(1H,d,J=8.6 Hz),7.22(1H,d,J=8.6 Hz),6.96 (1H,d,J=2.6 Hz),3.52-3.45(4H,m),3.06-2.97(1H,m),2.14-2.09(4H,m),1.39(6H,d,J=7.3 Hz).

MSm/z(M+H):335.

Example 0847

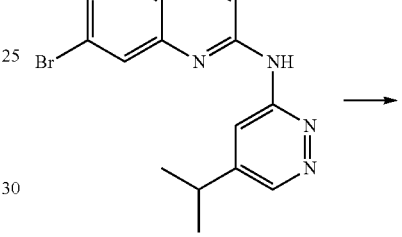

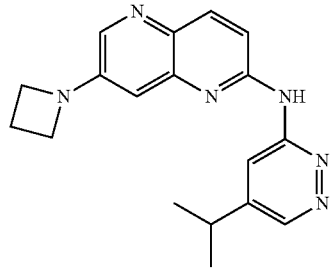

7-(Azetidin-1-yl)-N-(5-isopropylpyridazin-3-yl)-1,5-naphthyridine-2-amine was obtained as a yellow solid in the same manner as in Example 0846.

$^1$H-NMR(CDCl$_3$)δ:8.79-8.76(2H,m),8.75(1H,s),8.18-8.14(1H,m),8.11(1H,d,J=8.6 Hz),7.30-7.26(1H,m),6.88-6.84(1H,m),4.13-4.09(4H,m),3.06-2.98(1H,m),2.56-2.48 (2H,m),1.39(6H,d,J=7.3 Hz).

MSm/z(M+H):321.

Example 0848

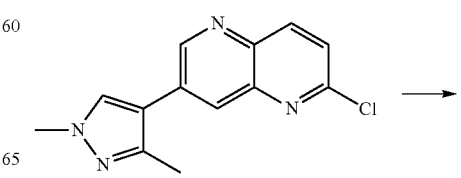

-continued

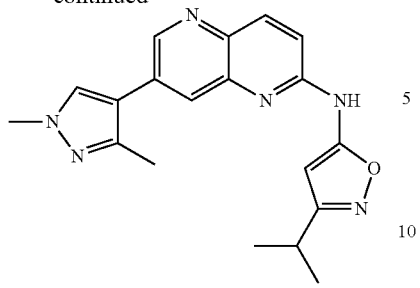

A mixture of 2-chloro-7-(1,3-dimethyl-1H-pyrazol-4-yl)-1,5-naphthyridine (20 mg), 3-isopropylisoxazole-5-amine (10 mg), tris(dibenzylideneacetone)dipalladium(0) (4 mg), 2-(dicyclohexylphosphino)-3,6-dimethoxy-2',4',6'-triisopropyl-1,1'-biphenyl (4 mg), sodium tert-butoxide (11 mg), and 1,4-dioxane (0.6 mL) was stirred at 140° C. for 30 minutes using a microwave reaction apparatus. The reaction mixture was cooled to room temperature, the insolubles were filtered off, and the solvent was distilled off under reduced pressure. The obtained residue was purified by silica gel column chromatography (ethyl acetate-methanol, chloroform-methanol, NH silica), thereby obtaining N-(7-(1,3-dimethyl-1H-pyrazol-4-yl)-1,5-naphthyridin-2-yl)-3-isopropylisoxazole-5-amine (0.8 mg) as a pale yellow solid.

$^1$H-NMR(DMSO-d$_6$)δ:8.88(1H,d,J=2.0 Hz),8.22(3H,d,J=9.9 Hz),7.31(1H,d,J=8.6 Hz),6.70(1H,s),6.55(1H,s),3.85 (3H,s),3.03-2.94(1H,m),2.43(3H,s),1.29(6H,d,J=6.6 Hz).

MSm/z(M+H):349.

Examples 0849 and 0850

0849-1 and 0850-1

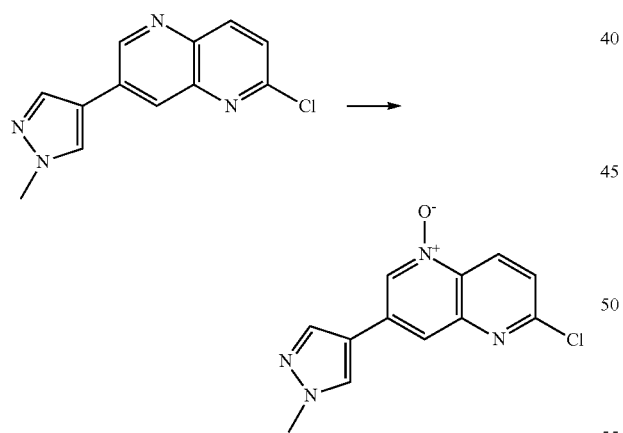

65% meta-chloroperoxybenzoic acid (672 mg) was added to a mixture of 2-chloro-7-(1-methyl-1H-pyrazol-4-yl)-1,5-naphthyridine (310 mg) and dichloromethane (10 mL) at a temperature of from 0° C. to 5° C. in a nitrogen atmosphere, followed by stirring at room temperature overnight. A sodium sulfite aqueous solution and a saturated sodium hydrogen carbonate aqueous solution were added to the reaction mixture, and the resultant product was extracted two times with chloroform. An organic layer obtained therefrom was dried over anhydrous sodium sulfate, and the solvent was distilled off under reduced pressure. The obtained residue was purified by silica gel column chromatography (hexane-ethyl acetate, chloroform-methanol), thereby obtaining 6-chloro-3-(1-methyl-1H-pyrazol-4-yl)-1,5-naphthyridine 1-oxide (341 mg) as a pale yellow solid.

MSm/z(M+H):261.

0849-2 and 0850-2

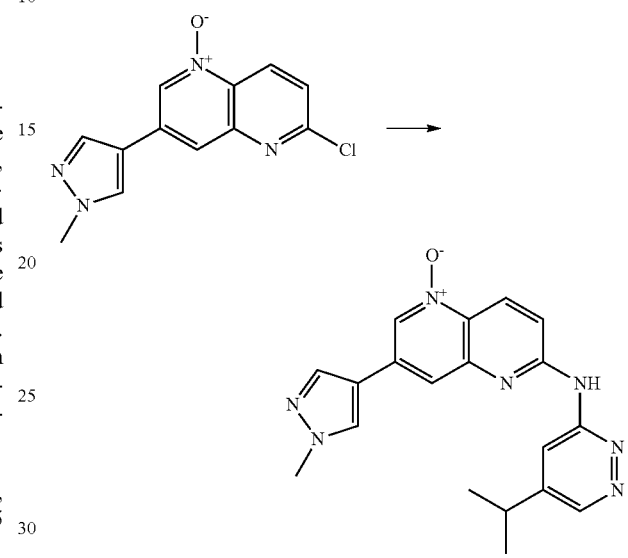

A mixture of 6-chloro-3-(1-methyl-1H-pyrazol-4-yl)-1,5-naphthyridine 1-oxide (270 mg), 2-(dicyclohexylphosphino)-3,6-dimethoxy-2',4',6'-triisopropyl-1,1'-biphenyl (56 mg), tris(dibenzylideneacetone)dipalladium(0) (48 mg), cesium carbonate (1.01 g), and 1,4-dioxane (10 mL) was stirred at 100° C. for 8 hours in a nitrogen atmosphere in a sealed tube. The reaction mixture was cooled to room temperature, and a saturated ammonium chloride aqueous solution and chloroform were added thereto. An organic layer was collected therefrom by separation, and dried over anhydrous sodium sulfate, and the solvent was distilled off under reduced pressure. The obtained residue was purified by silica gel column chromatography (hexane-ethyl acetate, chloroform-methanol), thereby obtaining 6-((5-isopropylpyridazin-3-yl)amino)-3-(1-methyl-1H-pyrazol-4-yl)-1,5-naphthyridine 1-oxide (103 mg) as a brown solid.

MSm/z(M+H):362.

0849-3 and 0850-3

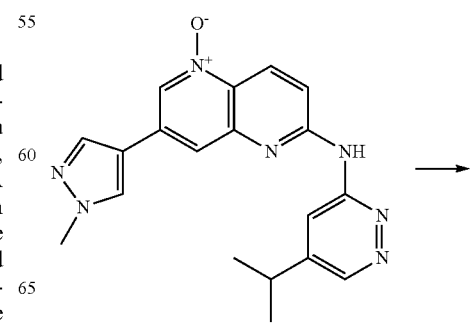

-continued

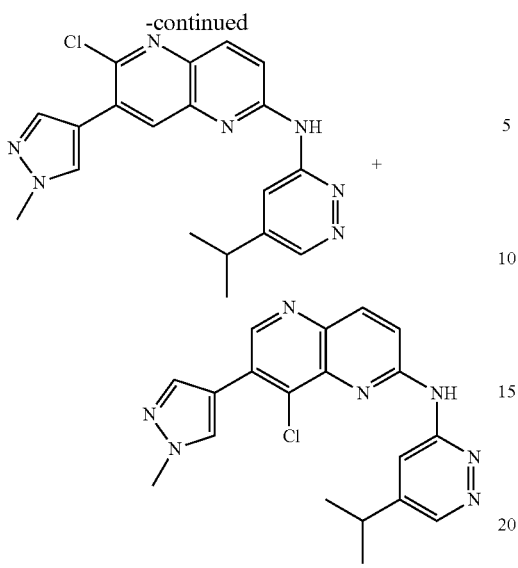

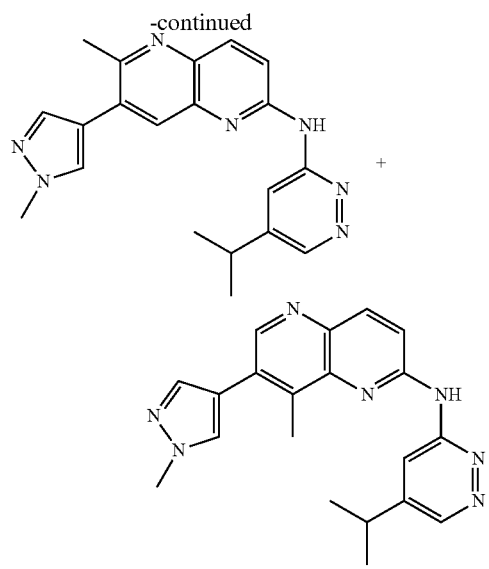

A solution of 6-((5-isopropylpyridazin-3-yl)amino)-3-(1-methyl-1H-pyrazol-4-yl)-1,5-naphthyridine 1-oxide (103 mg) in phosphorus oxychloride (4 g) was stirred at 80° C. for 2 hours. The reaction mixture was cooled to room temperature, and added dropwise to water. The obtained solution was neutralized with sodium hydrogen carbonate, and the resultant product was extracted with chloroform. An organic layer thus obtained was dried over anhydrous sodium sulfate, and the solvent was distilled off under reduced pressure. The obtained residue was purified by silica gel column chromatography (hexane-ethyl acetate, chloroform-methanol), thereby obtaining a mixture of 6-chloro-N-(5-isopropylpyridazin-3-yl)-7-(1-methyl-1H-pyrazol-4-yl)-1,5-naphthyridine-2-amine and 8-chloro-N-(5-isopropylpyridazin-3-yl)-7-(1-methyl-1H-pyrazol-4-yl)-1,5-naphthyridine-2-amine as a yellow solid.

MSm/z(M+H):380.

0849-4 and 0850-4

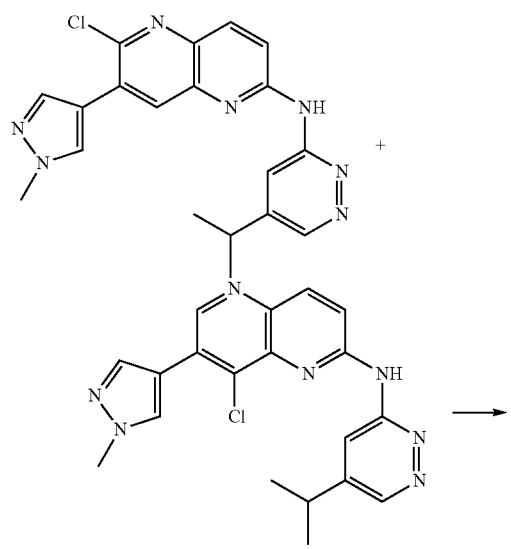

2,4,6-Trimethylboroxine (54 µL) and water (two drops) were added to a mixture of a mixture (30 mg) of 6-chloro-N-(5-isopropylpyridazin-3-yl)-7-(1-methyl-1H-pyrazol-4-yl)-1,5-naphthyridine-2-amine and 8-chloro-N-(5-isopropylpyridazin-3-yl)-7-(1-methyl-1H-pyrazol-4-yl)-1,5-naphthyridine-2-amine, potassium phosphate (48 mg), a [1,1'-bis(diphenylphosphino)ferrocene]palladium(II) dichloride-dichloromethane adduct (12 mg), and 1,2-dimethoxyethane (1.5 mL), followed by stirring at 150° C. for 30 minutes using a microwave reaction apparatus. The reaction mixture was cooled to room temperature, poured into a saturated ammonium chloride aqueous solution, and the resultant product was extracted with chloroform. An organic layer obtained therefrom was dried over anhydrous sodium sulfate, and the solvent was distilled off under reduced pressure. The obtained residue was purified sequentially by silica gel column chromatography (hexane-ethyl acetate, chloroform-methanol) and preparative reversed phase chromatography (0.1% formic acid-water, 0.1% formic acid-acetonitrile), thereby obtaining N-(5-isopropylpyridazin-3-yl)-6-methyl-7-(1-methyl-1H-pyrazol-4-yl)-1,5-naphthyridine-2-amine (12 mg) as a pale yellow solid and N-(5-isopropylpyridazin-3-yl)-8-methyl-7-(1-methyl-1H-pyrazol-4-yl)-1,5-naphthyridine-2-amine (3 mg) as a pale yellow solid.

Example 0849

N-(5-isopropylpyridazin-3-yl)-6-methyl-7-(1-methyl-1H-pyrazol-4-yl)-1,5-naphthyridine-2-amine $^1$H-NMR(CDCl$_3$)δ:9.10-8.96(1H,brs),8.86(1H,s),8.80(1H,s),8.20(1H,d,J=8.9 Hz),7.99(1H,s),7.77(1H,s),7.63(1H,s),7.57(1H,d,J=8.9 Hz),4.04(3H,s),3.08-2.98(1H,m),2.79(3H,s),1.40(6H,d,J=6.7 Hz).

MSm/z(M+H):360.

Example 0850

N-(5-isopropylpyridazin-3-yl)-8-methyl-7-(1-methyl-1H-pyrazol-4-yl)-1,5-naphthyridine-2-amine $^1$H-NMR(CDCl$_3$)δ:9.38(1H,s),9.05(1H,s),8.81(1H,d,J=2.0 Hz),8.73(1H,s),8.25(1H,d,J=8.6 Hz),7.77(1H,s),7.65

(1H,s),7.57(1H,d,J=8.6 Hz),4.04(3H,s),3.08-2.98(1H,m), 2.87(3H,s),1.41(6H,d,J=6.8 Hz).

MSm/z(M+H):360.

Examples 0851 and 0852

0851-1 and 0852-1

6-Chloro-3-(1,3-dimethyl-1H-pyrazol-4-yl)-1,5-naphthyridine 1-oxide was obtained as a yellow solid in the same manner as in Example 0849-1.

MSm/z(M+H):275.

0851-2 and 0852-2

3-(1,3-Dimethyl-1H-pyrazol-4-yl)-6-((5-isopropylpyridazin-3-yl)amino)-1,5-naphthyridine 1-oxide was obtained as a green solid in the same manner as in Example 0849-2.

MSm/z(M+H):376.

0851-3 and 0852-3

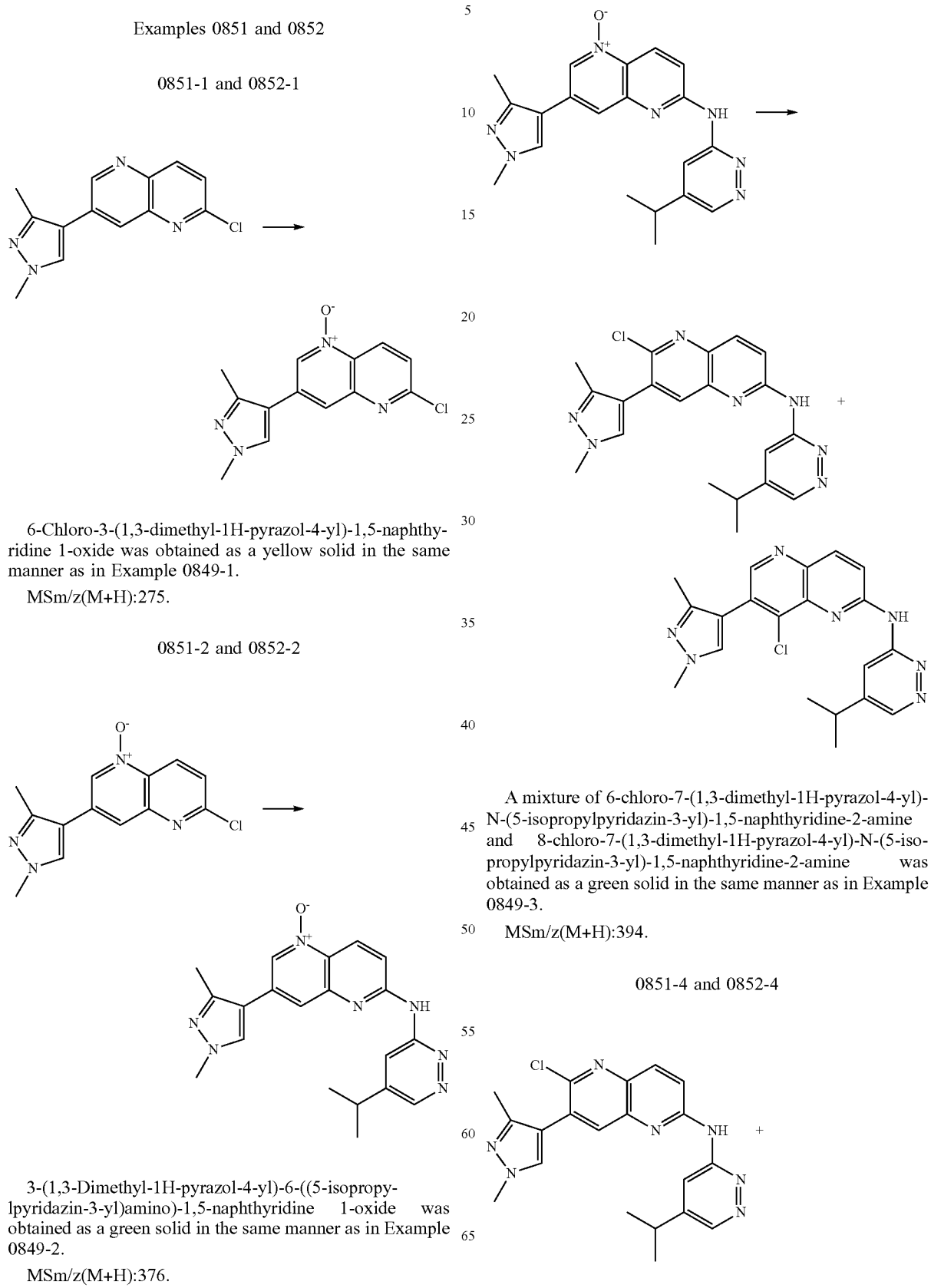

A mixture of 6-chloro-7-(1,3-dimethyl-1H-pyrazol-4-yl)-N-(5-isopropylpyridazin-3-yl)-1,5-naphthyridine-2-amine and 8-chloro-7-(1,3-dimethyl-1H-pyrazol-4-yl)-N-(5-isopropylpyridazin-3-yl)-1,5-naphthyridine-2-amine was obtained as a green solid in the same manner as in Example 0849-3.

MSm/z(M+H):394.

0851-4 and 0852-4

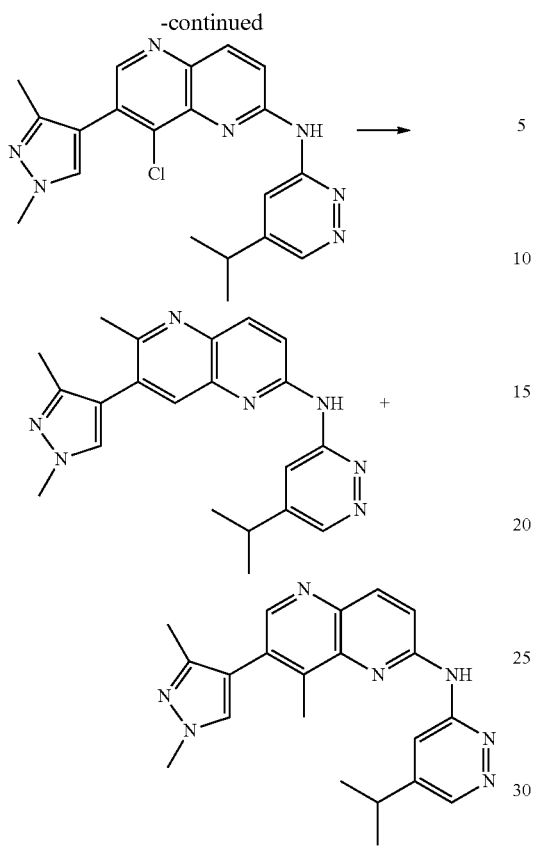

7-(1,3-Dimethyl-1H-pyrazol-4-yl)-N-(5-isopropylpyridazin-3-yl)-6-methyl-1,5-naphthyridine-2-amine as a pale yellow solid and 7-(1,3-dimethyl-1H-pyrazol-4-yl)-N-(5-isopropylpyridazin-3-yl)-8-methyl-1,5-naphthyridine-2-amine as a pale yellow solid were obtained in the same manner as in Example 0849-4.

Example 0851

7-(1,3-Dimethyl-1H-pyrazol-4-yl)-N-(5-isopropylpyridazin-3-yl)-6-methyl-1,5-naphthyridine-2-amine $^{1}$H-NMR(CDCl$_{3}$)δ:8.88-8.78(3H,m),8.22(1H,d,J=9.2 Hz),7.88(1H,s),7.55(1H,d,J=9.2 Hz),7.40(1H,s),7.26(9H,s), 3.96(3H,s),3.05-2.95(1H,m,J=6.6 Hz),2.63(3H,s),2.24(3H,s),1.38(6H,d,J=6.6 Hz).
MSm/z(M+H):374.

Example 0852

7-(1,3-Dimethyl-1H-pyrazol-4-yl)-N-(5-isopropylpyridazin-3-yl)-8-methyl-1,5-naphthyridine-2-amine $^{1}$H-NMR(CDCl$_{3}$)δ:9.43-9.35(1H,brs),9.07(1H,s),8.81 (1H,s),8.59(1H,s),8.28(1H,d,J=9.2 Hz),7.59(1H,d,J=9.2 Hz),7.40(1H,s),3.96(3H,s),3.02(1H,quint,J=6.9 Hz),2.72 (3H,s),2.23(3H,s),1.40(6H,d,J=6.6 Hz).
MSm/z(M+H):374.

Examples 0853 to 0879

The following compounds were obtained in the same manner as in Example 0846.

| Example No. | | |
|---|---|---|
| 0853 | 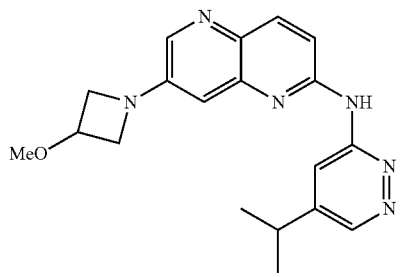 [SMILES: COC1CN(c2cnc3ccc(Nc4cc(C(C)C)cnn4)nc3c2)C1] | $^{1}$H-NMR (CDCl$_{3}$) δ:<br>10.00 (1 H, s), 8.92-8.89 (1 H, m), 8.81-8.76 (1 H, m), 8.17-8.15 (1 H, m), 8.12 (1 H, d, J = 8.6 Hz), 7.54 (1 H, d, J = 8.6 Hz), 6.91-6.88 (1 H, m), 4.48-4.41 (1 H, m), 4.31 (2 H, dd, J = 7.9, 6.6 Hz), 3.94 (2 H, dd, J = 7.9, 4.6 Hz), 3.38 (3 H, s), 3.08-2.98 (1 H, m) 1.40 (6 H, d, J = 7.3 Hz).<br>MS m/z (M + H): 351. |
| 0854 | 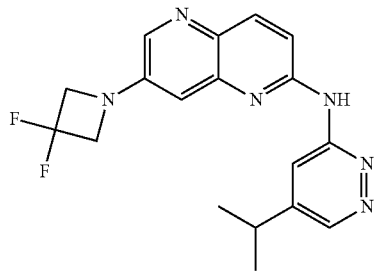 [SMILES: CC(C)c1cnnc(Nc2ccc3ncc(N4CC(F)(F)C4)cc3n2)c1] | $^{1}$H-NMR (CDCl$_{3}$) δ:<br>9.57 (1 H, s), 8.87-8.84 (1 H, m), 8.83-8.78 (1 H, m), 8.19 (1 H, d, J = 3.3 Hz), 8.16 (1 H, d, J = 8.6 Hz), 7.53 (1 H, d, J = 8.6 Hz),<br>6.99 (1 H, d, J = 3.3 Hz), 4.50-4.41 (4 H, m), 3.09-3.00 (1 H, m),<br>1.40 (6 H, d, J = 6.6 Hz).<br>MS m/z (M + H): 357. |

| Example No. | | |
|---|---|---|
| 0855 | 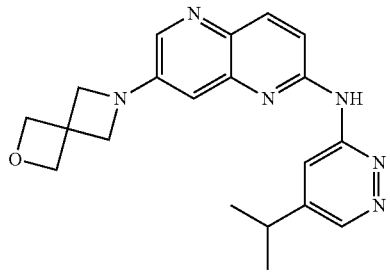 [SMILES: CC(C)c1cnnc(Nc2ccc3ncc(N4CC5(COC5)C4)cc3n2)c1] | ¹H-NMR (CDCl₃) δ:<br>8.80-8.77 (1 H, m), 8.78-8.76 (1 H, m), 8.76-8.74 (1 H, m), 8.15 (1 H, d, J = 2.6 Hz), 8.12 (1 H, d, J = 9.2 Hz), 7.31-7.27 (1 H, m)<br>6.89 (1 H, d, J = 2.6 Hz), 4.91 (4 H, s), 4.26 (4 H, s), 3.06-2.98 (1 H, m), 1.40 (6 H, d, J = 7.3 Hz).<br>MS m/z (M + H): 363. |
| 0856 | 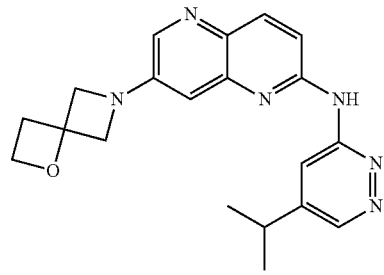 [SMILES: CC(C)c1cnnc(Nc2ccc3ncc(N4CC5(CCO5)C4)cc3n2)c1] | ¹H-NMR (CDCl₃) δ:<br>8.79-8.75 (1 H, m), 8.75-8.71 (1 H, m), 8.73-8.68 (1 H, m), 8.17-<br>8.14 (1 H, m), 8.11 (1 H, d, J = 8.6 Hz), 7.28 (1 H, d, J = 6.6 Hz),<br>6.91-6.88 (1 H, m), 4.62 (2 H, t, J = 7.3 Hz), 4.32 (2 H, d, J = 9.2<br>Hz), 4.24 (2 H, d, J = 9.2 Hz), 3.04-2.98 (1 H, m), 3.00 (2 H, t, J = 7.3 Hz), 1.39 (6 H, d, J = 6.6 Hz).<br>MS m/z (M + H): 363. |
| 0857 | 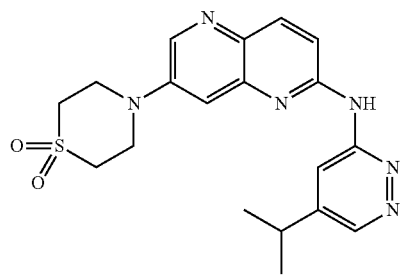 | ¹H-NMR (CDCl₃) δ:<br>8.88-8.83 (1 H, m), 8.83-8.79 (1 H, m) 8.79-8.75 (1 H, m), 8.61 (1 H, d, J = 2.6 Hz), 8.11 (1 H, d, J = 9.2 Hz), 7.52 (1 H, d, J = 9.2 Hz), 7.41-7.36 (1 H, m), 4.04-4.01 (4 H, m), 3.25-3.22 (4 H, m), 3.04-2.98 (1 H, m), 1.40 (6 H, d, J = 6.6 Hz).<br>MS m/z (M + H): 399. |
| 0858 | 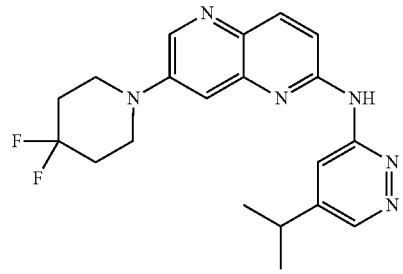 | ¹H-NMR (CDCl₃) δ:<br>9.17 (1 H, s), 8.82-8.78 (1 H, m), 8.80-8.77 (1 H, m), 8.63 (1 H, d, J = 2.6 Hz), 8.15 (1 H, d, J = 8.6 Hz), 7.48 (1 H, d, J = 8.6 Hz),<br>7.36 (1 H, d, J = 2.6 Hz), 3.58-3.52 (4 H, m), 3.08-2.99 (1 H, m),<br>2.27-2.14 (4 H, m), 1.40 (6 H, d, J = 7.4 Hz).<br>MS m/z (M + H): 385. |
| 0859 | 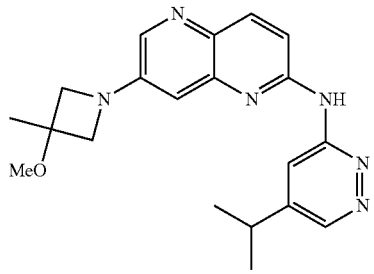 [SMILES: COC1(C)CN(c2cnc3ccc(Nc4cc(C(C)C)cnn4)nc3c2)C1] | ¹H-NMR (CDCl₃) δ:<br>9.32 (1 H, s), 8.85-8.82 (1 H, m), 8.80-8.77 (1 H, m), 8.17 (1 H, d, J = 2.6 Hz), 8.12 (1 H, d, J = 8.6 Hz), 7.39 (1 H, d, J = 8.6 Hz),<br>6.92-6.89 (1 H, m), 4.04 (2 H, d, J = 7.9 Hz), 3.92 (2 H, d, J = 7.9<br>Hz), 3.33 (3 H, s), 3.07-2.98 (1 H, m), 1.62 (3 H, s), 1.39 (6 H, d,<br>J = 7.3 Hz).<br>MS m/z (M + H): 365. |

-continued

| Example No. | | |
|---|---|---|
| 0860 | 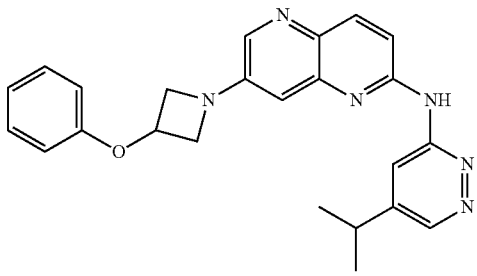 [SMILES: CC(C)c1cnnc(Nc2ccc3ncc(N4CC(Oc5ccccc5)C4)cc3n2)c1] | $^1$H-NMR (CDCl$_3$) δ:<br>8.90 (1 H, s), 8.82-879 (1 H, m), 8.60-8.76 (1 H, m), 8.20<br>(1 H, d, J = 2.6 Hz), 8.13 (1H, d, J = 8.6 Hz), 7.36-7.32 (1 H, m),<br>7.34-7.31 (2 H, m), 7.03 (1 H, t, J = 7.3 Hz), 6.95-6.91 (1 H, m),<br>6.84 (2 H, d, J = 7.3 Hz), 5.24-5.17 (1 H, m), 4.55<br>(2 H, dd, J = 8.6, 5.2 Hz) 4.15 (2 H, dd, J = 6.6, 4.0 Hz) 3.06-<br>2.98 (1 H, m), 1.39 (6 H, d, J = 6.6 Hz).<br>MS m/z (M + H): 413. |
| 0861 | 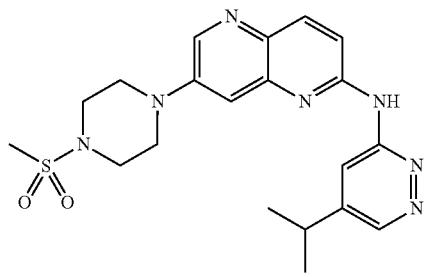 [SMILES: CC(C)c1cnnc(Nc2ccc3ncc(N4CCN(S(C)(=O)=O)CC4)cc3n2)c1] | $^1$H-NMR (CDCl$_3$) δ:<br>8.80 (1 H, s), 8.74-8.70 (1 H, m), 8.70-8.65 (1 H, m), 8.62<br>(1 H, J = 2.6 Hz), 8.16 (1 H, d, J = 9.2 Hz), 7.40 (1 H, d, J = 9.2<br>Hz), 7.35 (1 H, d, J = 2.6 Hz), 3.51-3.48 (4 H, m), 3.49-3.46<br>(4 H, m), 3.08-2.98 (1 H, m), 2.88 (3 H, s), 1.40 (6 H, d, J = 6.6 Hz).<br>MS m/z (M + H): 428. |
| 0862 | 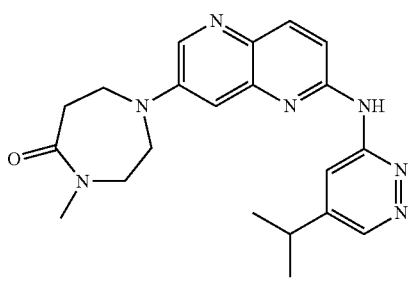 [SMILES: CC(C)c1cnnc(Nc2ccc3ncc(N4CCC(=O)N(C)CC4)cc3n2)c1] | $^1$H-NMR (CDCl$_3$) δ:<br>9.36 (1 H, s), 8.61-8.78 (1 H, m), 8.79-8.76 (1 H, m), 8.60-<br>8.56 (1 H, m), 8.15 (1 H, d, J = 9.2 Hz), 7.51 (1 H, d, J = 8.6 Hz),<br>7.29-7.26 (1 H, m), 3.71-3.68 (2 H, m), 3.69-3.66 (2 H, m),<br>3.67-3.61 (2 H, m), 3.08-2.98 (1 H, m), 3.08 (3 H, s), 2.93-2.88<br>(2 H, m), 1.40 (6 H, d, J = 6.6 Hz)<br>MS m/z (M + H): 392. |
| 0863 | 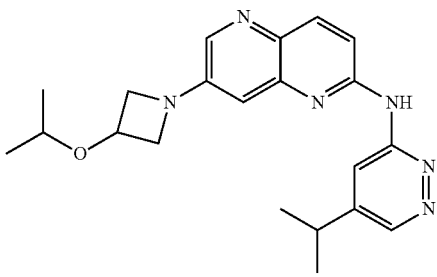 [SMILES: CC(C)OC1CN(c2cnc3ccc(Nc4cc(C(C)C)cnn4)nc3c2)C1] | $^1$H-NMR (CDCl$_3$) δ:<br>9.72 (1 H, s), 8.89-8.87 (1 H, m), 8.79 (1 H, d, J = 2.0 Hz),<br>8.16 (1 H, d, J = 2.6 Hz), 8.12 (1 H, d, J = 9.2 Hz), 7.48 (1 H, d,<br>J = 8.6 Hz), 6.90 (1 H, d, J = 2.6 Hz), 4.63-4.56 (1 H, m), 4.34<br>(2 H, dd, J = 7.9, 7.9 Hz) 3.91 (2 H, dd, J = 7.9, 5.3 Hz), 3.75-<br>3.66 (1 H, m), 3.06-2.93 (1 H, m), 1.40<br>(6 H, d, J = 6.6 Hz), 1.21 (6 H, d, J = 5.9 Hz).<br>MS m/z (M + H): 379. |
| 0864 | 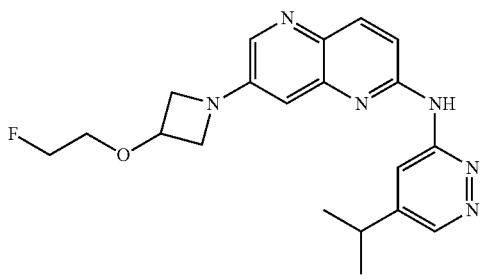 [SMILES: CC(C)c1cnnc(Nc2ccc3ncc(N4CC(OCCF)C4)cc3n2)c1] | $^1$H-NMR (CDCl$_3$) δ:<br>9.75 (1 H, s), 8.88 (1 H, s), 6.79 (1 H, d, J = 2.0 Hz), 8.16<br>(1 H, d, J = 2.6 Hz), 8.12 (1 H, d, J = 9.2 Hz), 7.49 (1 H, d,<br>J = 9.2 Hz), 6.91 (1 H, d, J = 2.6 Hz), 4.65-4.58 (1 H, m),<br>4.61 (2 H, dt, J = 46.8, 4.0 Hz), 4.34 (2 H, dd, J = 8.6, 8.6 Hz),<br>3.99 (2 H, dd, J = 8.6, 4.5 Hz), 3.76 (2 H, dt, J = 29.7, 4.0 Hz),<br>3.08-2.99 (1 H, m), 1.40 (6 H, d, J = 7.3 Hz).<br>MS m/z (M + H): 383. |

| Example No. | | |
|---|---|---|
| 0865 | 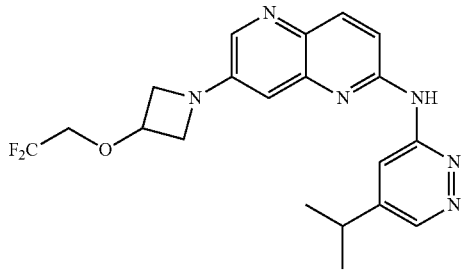 | ¹H-NMR (CDCl₃) δ:<br>9.35 (1 H, s), 8.85-8.82 (1 H, m), 8.81-8.78 (1 H, m), 8.17 (1 H, d, J = 2.6 Hz), 8.13 (1 H, d, J = 8.6 Hz), 7.43 (1 H, d, J = 8.6 Hz), 6.92 (1 H, d, J = 2.6 Hz), 4.71-4.64 (1 H, m), 4.37 (2 H, dd, J = 8.6, 8.6 Hz), 4.02 (2 H, dd, J = 6.6, 4.3 Hz), 3.95-3.88 (2 H, m), 3.08-2.99 (1 H, m), 1.40 (6 H, d, J = 7.3 Hz).<br>MS m/z (M + H): 419. |
| 0866 | 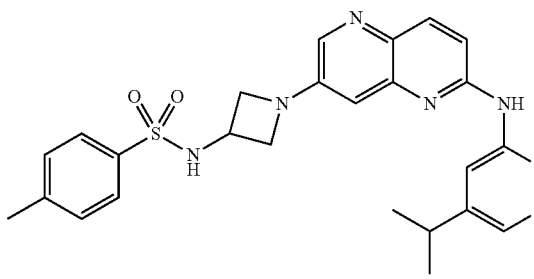 | ¹H-NMR (DMSO-d₆) δ:<br>10.52 (1 H, s), 8.83-8.82 (1 H, m), 8.65-8.64 (1 H, m), 8.45-8.33 (1 H, m), 8.08 (1 H, d, J = 2.6 Hz), 8.05 (1 H, d, J = 9.2 Hz), 7.73 (2 H, d, J = 7.9 Hz), 7.45 (2 H, d, J = 7.9 Hz), 7.44 (1 H, d, J = 9.2 Hz), 6.76 (1 H, d, J = 2.6 Hz), 4.29-4.20 (1 H, m), 4.17 (2 H, dd, J = 8.6, 8.6 Hz), 3.64 (2 H, dd, J = 6.6, 5.3 Hz), 3.05-2.96 (1 H, m), 2.43 (3 H, s), 1.29 (6 H, d, J = 6.6 Hz).<br>MS m/z (M + H): 490. |
| 0867 | 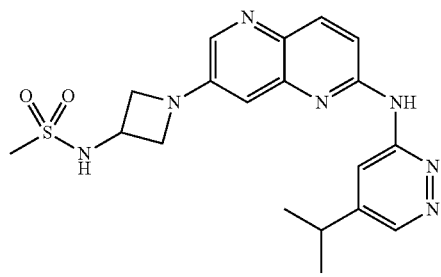 [SMILES: CC(C)c1cnnc(Nc2ccc3ncc(N4CC(NS(C)(=O)=O)C4)cc3n2)c1] | ¹H-NMR (DMSO-d₆) δ:<br>10.53 (1 H, s), 8.83 (1 H, d, J = 2.0 Hz), 8.67 (1 H, d, J = 1.3 Hz), 8.18 (1 H, d, J = 2.6 Hz), 8.07 (1 H, d, J = 9.2 Hz), 7.82 (1 H, d, J = 5.9 Hz), 7.46 (1 H, d, J = 9.2 Hz), 6.88 (1 H, d, J = 2.6 Hz), 4.44-4.39 (2 H, m), 3.89-3.85 (1 H, m), 3.40-3.36 (2 H, m), 3.04-2.88 (1 H, m), 2.97 (3 H, s), 1.31 (6 H, d, J = 6.6 Hz).<br>MS m/z (M + H): 414. |
| 0868 | 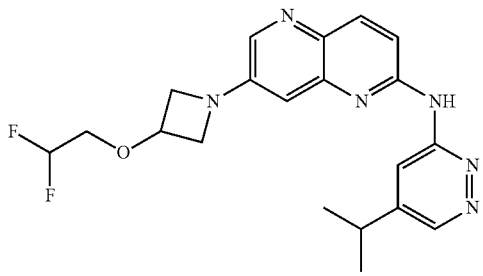 [SMILES: CC(C)c1cnnc(Nc2ccc3ncc(N4CC(OCC(F)F)C4)cc3n2)c1] | ¹H-NMR (CDCl₃) δ:<br>9.31 (1 H, s), 8.84-8.81 (1 H, m), 8.79 (1 H, d, J = 2.0 Hz), 8.17 (1 H, d, J = 2.6 Hz), 8.12 (1 H, d, J = 6.6 Hz), 7.41 (1 H, d, J = 8.6 Hz), 6.91 (1 H, d, J = 2.6 Hz), 5.92 (1 H, tt, J = 55.2, 4.0 Hz), 4.67-4.57 (1 H, m), 4.35 (2 H, dd, J = 8.6, 8.6 Hz), 3.99 (2 H, dd, J = 8.6, 4.6 Hz) 3.74 (2 H, td, J = 13.8, 4.0 Hz), 3.08-2.99 (1 H, m), 1.40 (6 H, d, J = 6.6 Hz).<br>MS m/z (M + H): 401. |
| 0869 | 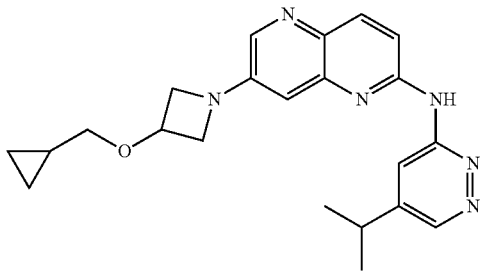 [SMILES: CC(C)c1cnnc(Nc2ccc3ncc(N4CC(OCC5CC5)C4)cc3n2)c1] | ¹H-NMR (CDCl₃) δ:<br>8.90 (1 H, s), 8.80-8.76 (1 H, m), 8.78-8.76 (1 H, m), 8.18-8.15 (1 H, m), 8.11 (1 H, d, J = 8.6 Hz), 7.32 (1 H, d, J = 8.6 Hz), 6.91-6.87 (1 H, m), 4.60-4.52 (1 H, m), 4.33 (2 H, dd, J = 8.6, 8.6 Hz), 3.97 (2 H, dd, J = 8.6, 4.6 Hz), 3.34 (2 H, d, J = 6.6 Hz), 3.06-2.96 (1 H, m), 1.39 (6 H, d, J = 6.6 Hz), 1.13-1.03 (1 H, m), 0.63-0.57 (2 H, m), 0.29-0.21 (2 H, m),<br>MS m/z (M + H): 391. |

-continued

| Example No. | | |
|---|---|---|

0870 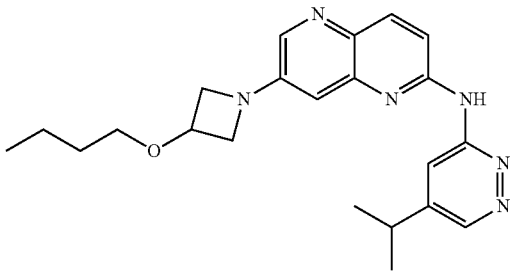 [SMILES: CCCCOC1CN(c2cnc3ccc(Nc4cc(C(C)C)cnn4)nc3c2)C1]
¹H-NMR (CDCl₃) δ:
9.70 (1 H, s), 8.89-8.86 (1 H, m), 8.80-8.77 (1 H, m), 8.16 (1 H, d, J = 2.0 Hz), 8.12 (1 H, d, J = 8.6 Hz), 7.46 (1 H, d, J = 8.6 Hz), 6.91-6.88 (1 H, m), 4.55-4.47 (1 H, m), 4.31 (2 H, dd, J = 8.6, 8.6 Hz), 3.93 (2 H, dd, J = 6.6, 4.6 Hz), 3.46 (2 H, t, J = 6.6 Hz), 3.08-2.99 (1 H, m), 1.65-1.56 (2 H, m), 1.45-1.35 (2 H, m), 1.40 (6 H, d, J = 7.0 Hz), 0.94 (3 H, t, J = 7.3 Hz)
MS m/z (M + H): 393.

0871 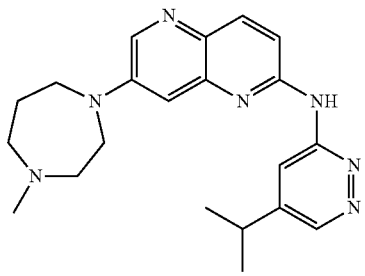 [SMILES: CC(C)c1cnnc(Nc2ccc3ncc(N4CCCN(C)CC4)cc3n2)c1]
¹H-NMR (CDCl₃) δ:
8.78-8.76 (1 H, m), 8.74-8.71 (1 H, m), 8.49 (1 H, d, J = 2.6 Hz), 8.09 (1 H, d J = 8.6 Hz), 7.28-7.25 (1 H, m), 7.27-7.22 (1 H, m), 7.10 (1 H, d, J = 2.6 Hz), 3.76-3.72 (2 H, m), 3.70-3.64 (2 H, m), 3.07-2.97 (1 H, m), 2.83-2.77 (2 H, m), 2.63-2.56 (2 H, m), 2.41 (3 H, s), 2.14-2.06 (2 H, m), 1.39 (6 H, d, J = 7.3 Hz).
MS m/z (M + H): 376.

0872 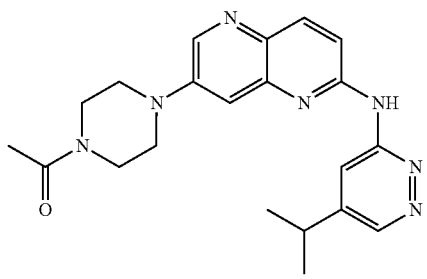 [SMILES: CC(=O)N1CCN(c2cnc3ccc(Nc4cc(C(C)C)cnn4)nc3c2)CC1]
¹H-NMR (CDCl₃) δ:
9.56 (1 H, s), 8.83-8.80 (1 H, m), 8.81-8.78 (1 H, m), 8.62 (1 H, d, J = 2.0 Hz), 8.16 (1 H, d, J = 8.6 Hz), 7.56 (1 H, d, J = 8.6 Hz), 7.33 (1 H, d, J = 2.0 Hz), 3.90-3.84 (2 H, m), 3.76-3.70 (2 H, m), 3.43-3.33 (4 H, m), 3.08-2.99 (1 H, m), 2.19 (3 H, s), 1.40 (6 H, d, J = 6.6 Hz).
MS m/z (M + H): 392.

0873 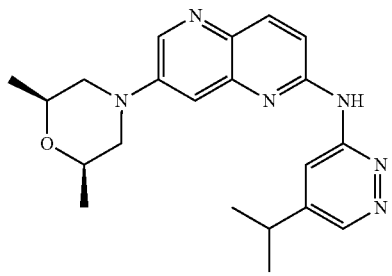 [SMILES: CC(C)c1cnnc(Nc2ccc3ncc(N4C[C@@H](C)O[C@@H](C)C4)cc3n2)c1]
¹H-NMR (CDCl₃) δ:
9.66 (1 H, s), 8.84-8.80 (1 H, m), 8.82-8.78 (1 H, m), 8.61 (1 H, d, J = 2.6 Hz), 8.15 (1 H, d, J = 8.6 Hz), 7.57 (1 H, d, J = 8.6 Hz), 7.90 (1 H, d, J = 2.6 Hz), 3.93-3.84 (2 H, m), 3.65 (2 H, d, J = 10.6 Hz), 3.10-3.01 (1 H, m), 2.61 (2 H, dd, J = 10.6, 10.6 Hz), 1.42 (6 H, d, J = 6.6 Hz), 1.32 (6 H, d, J = 6.6 Hz).
MS m/z (M + H): 379.

0874 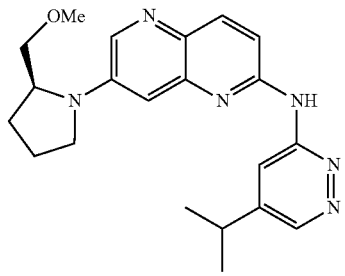 [SMILES: COC[C@@H]1CCCN1c1cnc2ccc(Nc3cc(C(C)C)cnn3)nc2c1]
¹H-NMR (CDCl₃) δ:
9.37 (1 H, s), 8.87-8.84 (1 H, m), 8.78 (1 H, d, J = 2.6 Hz), 8.45 (1 H, d, J = 2.6 Hz), 8.10 (1 H, d, J = 8.6 Hz), 7.38 (1 H, d, J = 8.6 Hz), 7.07 (1 H, d, J = 2.6 Hz), 4.16-4.09 (1 H, m), 3.65-3.60 (1 H, m), 3.61-3.54 (1 H, m), 3.41 (3 H, s), 3.38-3.28 (2 H, m), 3.07-2.97 (1 H, m), 2.17-2.03 (4 H, m), 1.40 (6 H, d, J = 7.3 Hz).
MS m/z (M + H): 379.

-continued

| Example No. | | |
|---|---|---|
| 0875 | 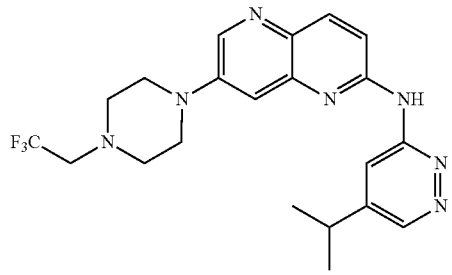 [SMILES: CC(C)c1cnnc(Nc2ccc3ncc(N4CCN(CC(F)(F)F)CC4)cc3n2)c1] | ¹H-NMR (CDCl₃) δ:<br>8.79-8.77 (1 H, m), 8.72 (1 H, d, J = 2.0 Hz), 8.63 (1 H, d, J = 2.0 Hz), 8.50 (1 H, s), 8.14 (1 H, d, J = 9.2 Hz), 7.32-7.29 (1 H, m), 7.32 (1 H, d, J = 9.2 Hz), 3.45-3.39 (4 H, m), 3.09 (2 H, q, J = 9.3 Hz), 3.06-2.98 (1 H, m), 2.96-2.89 (4 H, m), 1.39 (6 H, d, J = 7.3 Hz).<br>MS m/z (M + H): 432. |
| 0876 | 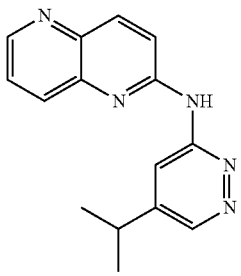 [SMILES: CC(C)c1cnnc(Nc2ccc3ncccc3n2)c1] | ¹H-NMR (CDCl₃) δ:<br>9.40 (1 H, s), 8.98-8.85 (1 H, m), 8.82 (1 H, d, J = 2.0 Hz), 8.80-8.77 (1 H, m), 8.29 (1 H, d, J = 8.6 Hz), 8.13 (1 H, d, J = 8.6 Hz), 7.70 (1 H, d, J = 8.6 Hz), 7.59-7.54 (1 H, m), 3.09-3.00 (1 H, m), 1.41 (6 H, d, J = 6.6 Hz).<br>MS m/z (M + H): 266. |
| 0877 | 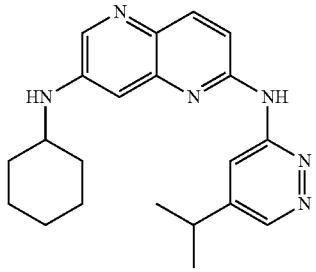 [SMILES: CC(C)c1cnnc(Nc2ccc3ncc(NC4CCCCC4)cc3n2)c1] | ¹H-NMR (CDCl₃) δ:<br>9.49 (1 H, s), 8.81-8.79 (1 H, m), 8.79-8.76 (1 H, m), 8.23 (1 H, d, J = 2.6 Hz), 8.08 (1 H, d, J = 9.2 Hz), 7.43 (1 H, d, J = 9.2 Hz), 7.00 (1 H, d, J = 2.6 Hz), 4.05 (1 H, d, J = 7.3 Hz), 3.45-3.37 (1 H, m), 3.07-2.98 (1 H, m), 2.17-2.11 (2 H, m), 1.85-1.78 (2 H, m), 1.74-1.67 (2 H, m), 1.50-1.39 (2 H, m), 1.40 (6 H, d, J = 6.6 Hz), 1.33-1.22 (2 H, m).<br>MS m/z (M + H): 363 |
| 0878 | 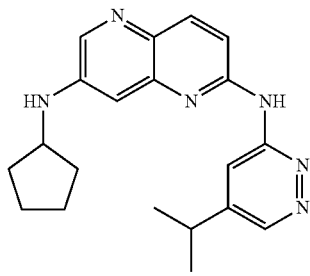 [SMILES: CC(C)c1cnnc(Nc2ccc3ncc(NC4CCCC4)cc3n2)c1] | ¹H-NMR (CDCl₃) δ:<br>9.56 (1 H, s), 8.86-8.82 (1 H, m), 8.78 (1 H, d, J = 2.0 Hz), 8.24 (1 H, d, J = 2.6 Hz), 8.09 (1 H, d, J = 9.2 Hz), 7.43 (1 H, d, J = 9.2 Hz), 7.02 (1 H, d, J = 2.6 Hz), 4.15 (1 H, d, J = 5.9 Hz), 3.96-3.88 (1 H, m), 3.07-2.98 (1 H, m), 2.17-2.07 (2 H, m), 1.79-1.68 (4 H, m), 1.69-1.56 (2 H, m), 1.40 (6 H, d, J = 6.6 Hz).<br>MS m/z (M + H): 349. |
| 0879 | 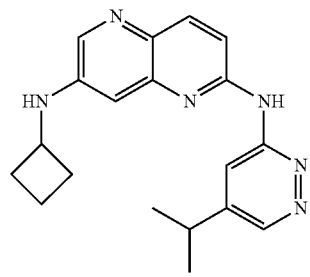 [SMILES: CC(C)c1cnnc(Nc2ccc3ncc(NC4CCC4)cc3n2)c1] | ¹H-NMR (CDCl₃) δ:<br>9.79 (1 H, s), 8.90-8.86 (1 H, m), 8.79 (1 H, d, J = 2.0 Hz), 8.23 (1 H, d, J = 2.6 Hz), 8.09 (1 H, 4, J = 8.6 Hz), 7.48 (1 H, d, J = 8.6 Hz), 6.93 (1 H, d, J = 2.6 Hz), 4.33 (1 H, d, J = 5.9 Hz), 4.10-4.01 (1 H, m), 3.08-2.98 (1 H, m), 2.58-2.47 (2 H, m) 2.03-1.84 (4 H, m), 1.41 (6 H, d, J = 6.0 Hz)<br>MS m/z (M + H): 335. |

Example 0880

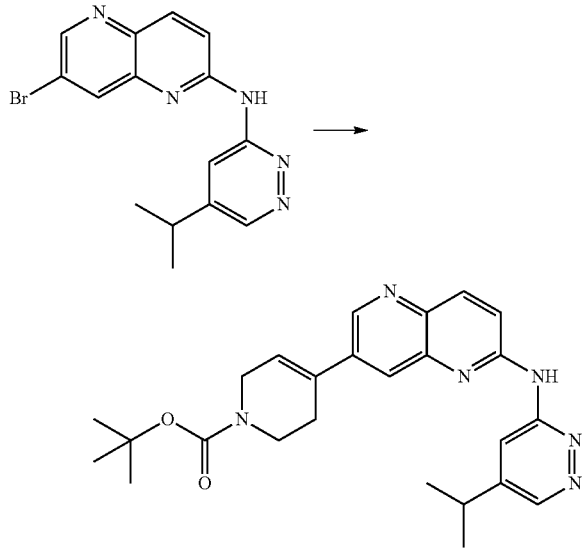

A mixture of 7-bromo-N-(5-isopropylpyridazin-3-yl)-1,5-naphthyridine-2-amine (40 mg), tert-butyl 4-(4,4,5,5-tetramethyl-1,3,2-dioxaborolan-2-yl)-5,6-dihydropyridine-1(2H)-carboxylate (72 mg), potassium phosphate (99 mg), (tris(dibenzylideneacetone)dipalladium(0) (11 mg), 2-dicyclohexylphosphino-2',4',6'-triisopropylbiphenyl (22 mg), tert-amyl alcohol (0.8 mL), and water (0.2 mL) was stirred at 100° C. for 1 hour. The reaction mixture was cooled to room temperature, the solvent was distilled off under reduced pressure, and the obtained residue was purified by silica gel column chromatography (methanol-ethyl acetate), thereby obtaining tert-butyl 4-(6-((5-isopropylpyridazin-3-yl)amino)-1,5-naphthyridin-3-yl)-5,6-dihydropyridine-1(2H)-carboxylate (36 mg) as a yellow solid.

$^1$H-NMR(CDCl$_3$)δ:9.21(1H,s),8.89-8.87(1H,m),8.88-8.86(1H,m),8.82(1H,d,J=2.0 Hz),8.25(1H,d,J=8.6 Hz),7.96(1H,d,J=2.0 Hz),7.63(1H,d,J=8.6 Hz),6.35-6.31(1H,m),4.21-4.16(2H,m),3.76-3.70(2H,m),3.10-2.99(1H,m),2.69-2.65(2H,m),1.52(9H,s),1.42(6H,d,J=7.3 Hz).

MSm/z(M+H):447.

Example 0881

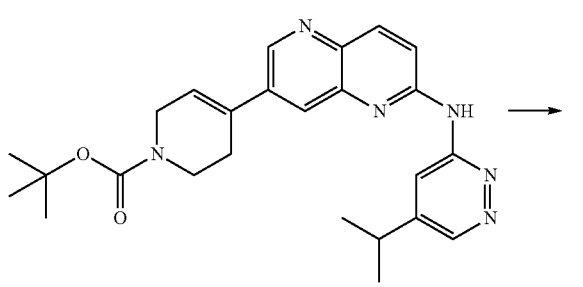

-continued

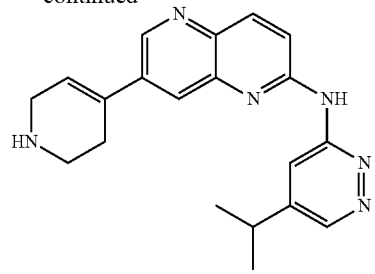

N-(5-isopropylpyridazin-3-yl)-7-(1,2,3,6-tetrahydropyridin-4-yl)-1,5-naphthyridine-2-amine was obtained as a yellow solid in the same manner as in Example 0905.

$^1$H-NMR(CDCl$_3$)δ:8.91-8.88(1H,m),8.86-8.80(1H,m),8.82-8.77(1H,m),8.24(1H,d,J=8.6 Hz),8.10-8.05(1H,m),7.96(1H,d,J=2.0 Hz),7.68(1H,d,J=8.6 Hz),6.45-6.42(1H,m),3.66-3.62(2H,m),3.22-3.18(2H,m),3.08-3.00(1H,m),2.64-2.56(2H,m),2.05-1.97(1H,m),1.41(6H,d,J=6.6 Hz).

MSm/z(M+H):347.

Example 0882

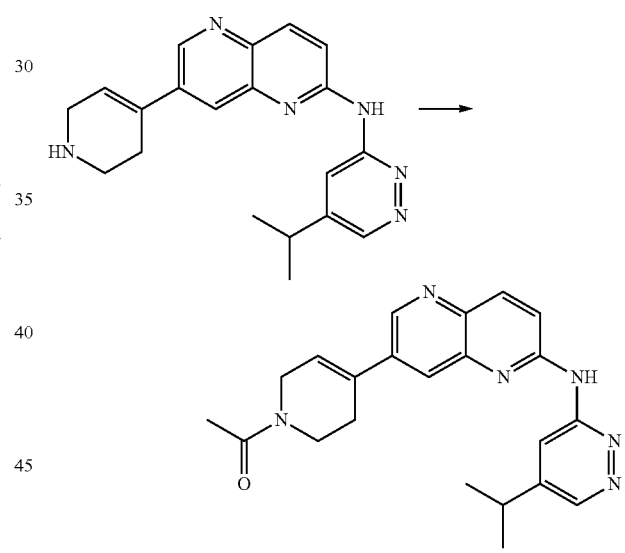

A mixture of N-(5-isopropylpyridazin-3-yl)-7-(1,2,3,6-tetrahydropyridin-4-yl)-1,5-naphthyridine-2-amine (13 mg), acetyl chloride (11 μL), N,N-diisopropylethylamine (79 μL), and dichloromethane (1 mL) was stirred at room temperature for 3 hours. A 25% sodium hydroxide aqueous solution was added to the reaction mixture, and the solvent was distilled off under reduced pressure. The obtained residue was purified by silica gel column chromatography (methanol-ethyl acetate), thereby obtaining 1-(4-(6-((5-isopropylpyridazin-3-yl)amino)-1,5-naphthyridin-3-yl)-5,6-dihydropyridine-1(2H)-yl)ethanone (3 mg) as a yellow solid.

$^1$H-NMR(CDCl$_3$)δ:8.89-8.85(1H,m),8.83-8.81(1H,m),8.81-8.79(1H,m),8.80-8.77(1H,m),8.25(1H,d,J=9.2 Hz),7.98-7.94(1H,m),7.52(1H,d,J=9.2 Hz),6.35-6.30(1H,m),4.35-4.25(2H,m),3.90-3.77(2H,m),3.08-3.00(1H,m),2.79-2.65(2H,m),2.20(3H,s),1.41(6H,d,J=6.6 Hz).

MSm/z(M+H):389.

Example 0883

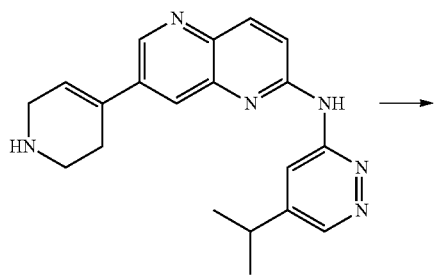

4-(6-((5-Isopropylpyridazin-3-yl)amino)-1,5-naphthyridin-3-yl)-N,N-dimethyl-5,6-dihydropyridine-1(2H)-carboxamide was obtained as a yellow solid in the same manner as in Example 0882.

¹H-NMR(CDCl₃)δ:9.02-8.99(1H,m),8.88-8.82(1H,m), 8.87(1H,d,J=2.0 Hz),8.83-8.80(1H,m),8.25(1H,d,J=8.6 Hz), 7.97(1H,d,J=2.0 Hz),7.88(1H,d,J=8.6 Hz),6.36-6.33(1H,m), 4.07-4.02(2H,m),3.58-3.53(2H,m),3.11-3.02(1H,m),2.90 (6H,s),2.78-2.69(2H,m),1.43(6H,d,J=6.6 Hz).

MSm/z(M+H):418.

Example 0884

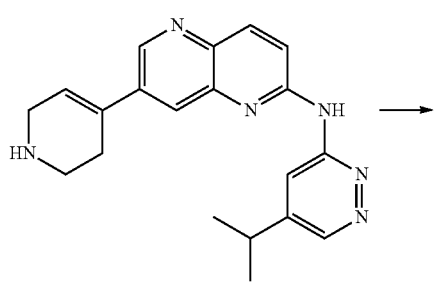

A mixture of N-(5-isopropylpyridazin-3-yl)-7-(1,2,3,6-tetrahydropyridin-4-yl)-1,5-naphthyridine-2-amine (13 mg), paraformaldehyde (20 mg), sodium triacetoxyborohydride (33 mg), acetic acid (1 μL), and methanol (0.5 mL) was stirred at room temperature for 3 hours. A saturated sodium hydrogen carbonate aqueous solution was added to the reaction mixture, and the solvent was distilled off under reduced pressure. The obtained residue was purified by silica gel column chromatography (methanol-ethyl acetate), thereby obtaining N-(5-isopropylpyridazin-3-yl)-7-(1-methyl-1,2,3,6-tetrahydropyridin-4-yl)-1,5-naphthyridine-2-amine (6 mg) as a yellow solid.

¹H-NMR(CDCl₃)δ:9.89(1H,s),8.98-8.95(1H,m),8.88(1H, d,J=2.6 Hz),8.82(1H,d,J=2.6 Hz),8.23(1H,d,J=9.2 Hz),7.96 (1H,d,J=2.6 Hz),7.76(1H,d,J=9.2 Hz),6.37-6.34(1H,m), 3.23-3.20(2H,m),3.09-3.00(2H,m),3.03-2.94(1H,m),2.77-2.72(2H,m),2.46(3H,s),1.42(6H,d,J=6.0 Hz).

MSm/z(M+H):361.

Example 0885

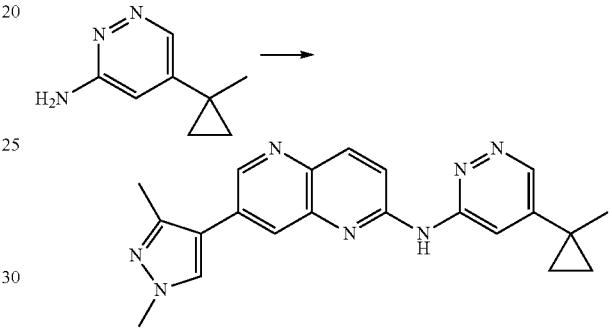

7-(1,3-Dimethyl-1H-pyrazol-4-yl)-N-(5-(1-methylcyclopropyl)pyridazin-3-yl)-1,5-naphthyridine-2-amine was obtained in the same manner as in Example 0786.

¹H-NMR(DMSO-d₆)δ:10.68(1H,s),8.89(1H,d,J=2.1 Hz), 8.73(1H,d,J=2.1 Hz),8.62(1H,d,J=2.1 Hz),8.25(1H,s),8.24 (1H,d,J=9.3 Hz),8.01(1H,d,J=2.1 Hz),7.73(1H,d,J=9.3 Hz), 3.84(3H,s),2.41(3H,s),1.51(3H,s),1.19-1.13(2H,m),1.06-1.01(2H,m).

MSm/z(M+H):372.

Example 0886

886-1

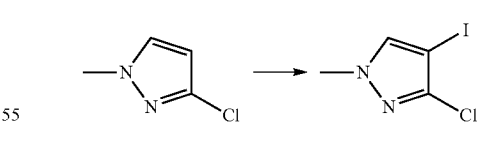

N-iodosuccinimide (225 mg) was added to a solution of 3-chloro-1-methyl-1H-pyrazole (116 mg) in acetonitrile (10 mL), followed by stirring at room temperature for 1 hour, and further stirring at 40° C. for 3 hours. The solvent of the reaction mixture was distilled off under reduced pressure, and the obtained residue was purified by silica gel column chromatography (hexane-ethyl acetate), thereby obtaining 3-chloro-4-iodo-1-methyl-1H-pyrazole (84 mg) as colorless oily substance.

MSm/z(M+H):243.

0886-2

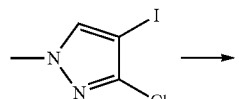

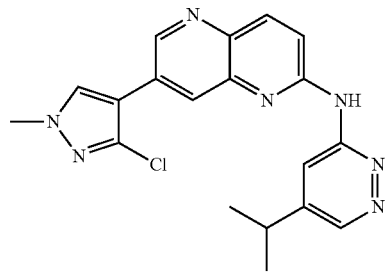

7-(3-Chloro-1-methyl-1H-pyrazol-4-yl)-N-(5-isopropylpyridazin-3-yl)-1,5-naphthyridine-2-amine was obtained as a pale yellow solid in the same manner as in Example 0935-3.

¹H-NMR(CDCl₃)δ:8.93(1H,brs),8.89(1H,d,J=2.0 Hz), 8.72(1H,brs),8.40(1H,d,J=2.0 Hz),8.22(1H,d,J=9.2 Hz), 7.94(1H,s),7.56(1H,d,J=9.2 Hz),3.99(3H,s),3.10-3.01(1H, m),1.42(6H,d,J=7.3 Hz).

MS m/z(M+H):380.

Examples 0887 to 0891

The following compounds were obtained in the same manner as in Example 0846.

| Example No. | | |
|---|---|---|
| 0887 | 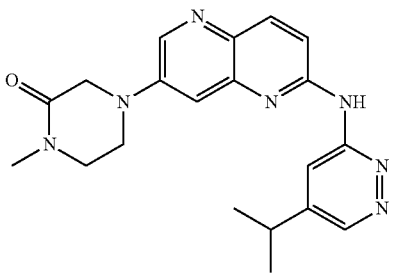 [SMILES: CC(C)c1cnnc(Nc2ccc3ncc(N4CCN(C)C(=O)C4)cc3n2)c1] | ¹H-NMR (CDCl₃) δ: 9.69 (1 H, s), 8.91-8.88 (1 H, m), 8.83-8.80 (1 H, m), 8.59 (1 H, d, J = 2.6 Hz), 8.15 (1 H, d, J = 9.2 Hz), 7.56 (1 H, d, J = 9.2 Hz), 7.30 (1 H, d, J = 2.6 Hz), 4.06 (2 H, s), 3.74-3.71 (2 H, m), 3.61-3.57 (2 H, m), 3.11-3.00 (1 H, m), 3.10 (3 H, s), 1.42 (6 H, d, J = 7.3 Hz). MS m/z (M + H): 378. |
| 0888 | 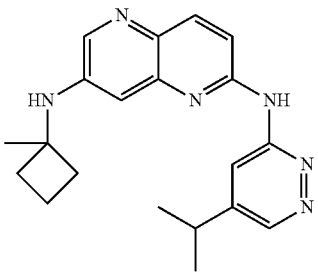 [SMILES: CC(C)c1cnnc(Nc2ccc3ncc(NC4(C)CCC4)cc3n2)c1] | ¹H-NMR (CDCl₃) δ: 8.77-8.75 (1 H, m), 8.75-8.73 (1 H, m), 8.46-8.43 (1 H, m), 8.19 (1 H, d, J = 2.6 Hz), 8.07 (1 H, d, J = 9.2 Hz), 7.21 (1 H, d, J = 9.2 Hz), 6.91 (1 H, d, J = 2.6 Hz), 4.30 (1 H, s), 3.04-2.95 (1 H, m), 2.38-2.28 (2 H, m), 2.24-2.15 (2 H, m), 2.05-1.98 (2 H, m), 1.58 (3 H, s), 1.39 (6 H, d, J = 6.5 Hz). MS m/z (M + H): 349. |
| 0889 | 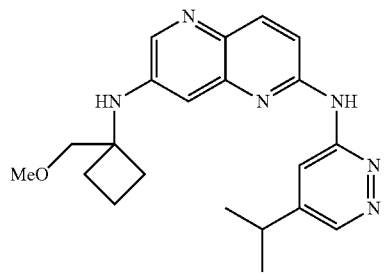 [SMILES: COCC1(Nc2cnc3ccc(Nc4cc(C(C)C)cnn4)nc3c2)CCC1] | ¹H-NMR (CDCl₃) δ: 8.69-8.68 (1 H, m), 8.63-8.62 (1 H, m), 8.16 (1 H, d, J = 2.6 Hz), 8.10-8.06 (1 H, m), 8.01 (1 H, d, J = 9.2 Hz), 7.10 (1 H, d, J = 9.2 Hz), 6.88 (1 H, d, J = 2.6 Hz), 4.42-4.39 (1 H, m), 3.62 (2 H, s), 3.30 (3 H, s), 2.97-2.88 (1 H, m), 2.32-2.23 (2 H, m), 2.25-2.18 (2 H, m), 1.98-1.89 (2 H, m), 1.31 (6 H, d, J = 6.6 Hz). MS m/z (M + H): 379. |

| Example No. | | |
|---|---|---|
| 0890 | 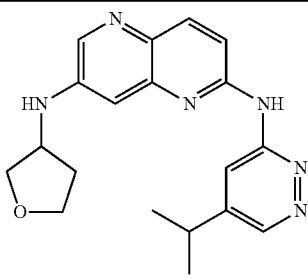 | ¹H-NMR (CDCl₃) δ:<br>9.00 (1 H, s), 8.80-8.76 (1 H, m), 8.76-8.74 (1 H, m), 8.27 (1 H, d, J = 2.0 Hz), 8.11 (1 H, d, J = 8.6 Hz), 7.36 (1 H, d, J = 8.6 Hz), 7.00 (1 H, d, J = 2.0 Hz), 4.36 (1 H, d, J = 6.6 Hz), 4.25-4.20 (1 H, m), 4.08-4.01 (1 H, m), 4.06-4.00 (1 H, m), 3.95-3.88 (1 H, m), 3.84 (1 H, dd, J = 9.2, 2.6 Hz), 3.07-2.98 (1 H, m), 2.43-2.34 (1 H, m), 2.03-1.96 (1 H, m), 1.40 (6 H, d, J = 6.6 Hz)<br>MS m/z (M + H): 351. |
| 0891 | 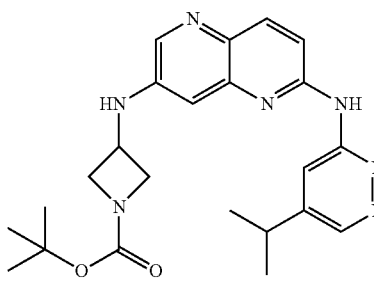 | ¹H-NMR (CDCl₃) δ:<br>8.80-8.77 (1 H, m), 8.74-8.71 (1 H, m), 8.71-8.68 (1 H, m), 8.29 (1 H, d, J = 2.0 Hz), 8.12 (1 H, d, J = 8.6 Hz), 7.33 (1 H, d, J = 8.6 Hz), 6.85 (1 H, d, J = 2.0 Hz), 4.53 (1 H, d, J = 5.3 Hz), 4.42-4.34 (1 H, m), 4.41 (2 H, dd, J = 8.6, 8.6 Hz), 3.86 (2 H, dd, J = 8.6, 4.0 Hz), 3.06-2.98 (1 H, m), 1.45 (9 H, s), 1.40 (6 H, d, J = 7.3 Hz).<br>MS m/z (M + H): 436. |

Example 0892

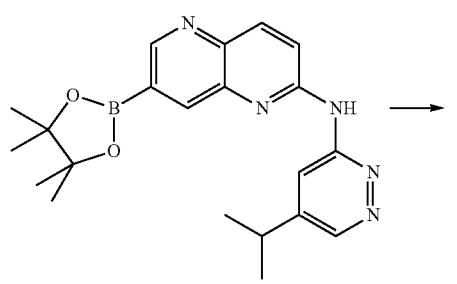

A mixture of N-(5-isopropylpyridazin-3-yl)-7-(4,4,5,5-tetramethyl-1,3,2-dioxaborolan-2-yl)-1,5-naphthyridine-2-amine (62 mg), tert-butyl 3-(((trifluoromethyl)sulfonyl)oxy)-2,5-dihydro-1H-pyrrole-1-carboxylate (50 mg), potassium phosphate (100 mg), (tris(dibenzylideneacetone)dipalladium(0) (15 mg), 2-dicyclohexylphosphino-2',4',6'-triisopropylbiphenyl (30 mg), tert-amyl alcohol (0.8 mL), and water (0.2 mL) was stirred at 100° C. for 1 hour. The reaction mixture was cooled to room temperature, the solvent was distilled off under reduced pressure, and the obtained residue was purified by silica gel column chromatography (methanol-ethyl acetate), thereby obtaining tert-butyl 3-(6-((5-isopropylpyridazin-3-yl)amino)-1,5-naphthyridin-3-yl)-2,5-dihydro-1H-pyrrole-1-carboxylate (44 mg) as a yellow solid.

¹H-NMR(CDCl₃)δ:8.98-8.95(1H,m),8.93-8.90(1H,m),8.89-8.86(1H,m),8.84-8.81(1H,m),8.24(1H,d,J=8.6 Hz),7.88-7.85(1H,m),7.57(1H,d,J=8.6 Hz),6.51-6.45(1H,m),4.68-4.63(2H,m),4.44-4.39(2H,m),3.10-3.01(1H,m),1.54 (9H,s),1.41(6H,d,J=7.3 Hz).

MS m/z(M+H):433.

Examples 0893 to 0904

The following compounds were obtained in the same manner as in Example 0846.

| Example No. | | |
|---|---|---|
| 0893 | 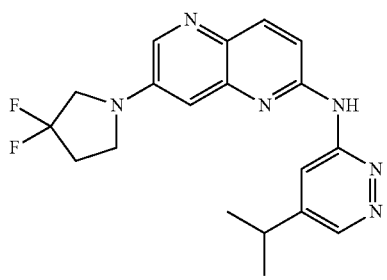 [SMILES: CC(C)c1cnnc(Nc2ccc3ncc(N4CCC(F)(F)C4)cc3n2)c1] | ¹H-NMR (CDCl₃) δ: 8.89 (1 H, s), 8.81-8.78 (1 H, m), 8.79-8.76 (1 H, m), 8.33 (1 H, d, J = 2.6 Hz), 8.14 (1 H, d, J = 9.2 Hz), 7.34 (1 H, d, J = 9.2 Hz), 7.00 (1 H, d, J = 2.6 Hz), 3.92-3.82 (2 H, m), 3.78-3.72 (2 H, m), 3.08-2.98 (1 H, m), 2.67-2.53 (2 H, m), 1.40 (6 H, d, J = 6.5 Hz). MS m/z (M + H): 371. |
| 0894 | 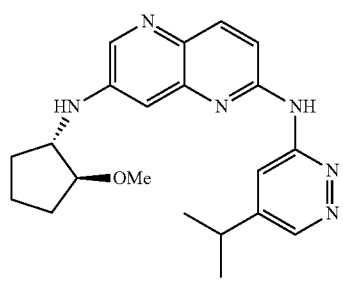 [SMILES: CO[C@H]1CCC[C@@H]1Nc1cnc2ccc(Nc3cc(C(C)C)cnn3)nc2c1] | ¹H-NMR (CDCl₃) δ: 8.83 (1 H, d, J = 2.0 Hz), 8.76 (1 H, d, J = 2.0 Hz), 8.26 (1 H, d, J = 2.6 Hz), 8.22 (1 H, s), 8.08 (1 H, d, J = 8.6 Hz), 7.16 (1 H, d, J = 2.6 Hz), 7.12 (1 H, d, J = 8.6 Hz), 4.11 (1 H, d, J = 5.9 Hz), 3.85-3.82 (1 H, m), 3.74-3.71 (1 H, m), 3.42 (3 H, s), 3.04-2.97 (1 H, m), 2.28-2.21 (2 H, m) 2.02-1.93 (2 H, m), 1.95-1.84 (2 H, m), 1.39 (6 H, d, J = 7.3 Hz). MS m/z (M + H): 379. |
| 0895 | 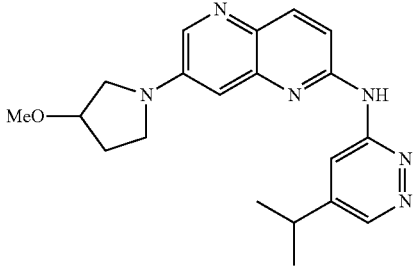 [SMILES: COC1CCN(c2cnc3ccc(Nc4cc(C(C)C)cnn4)nc3c2)C1] | ¹H-NMR (CDCl₃) δ: 8.78-8.75 (1 H, m), 8.77-8.75 (1 H, m), 8.75-8.72 (1 H, m), 8.36 (1 H, d, J = 2.6 Hz), 8.10 (1 H, d, J = 8.6 Hz), 7.22 (1 H, d, J = 8.6 Hz), 6.97 (1 H, d, J = 2.6 Hz), 4.22-4.16 (1 H, m), 3.68-3.59 (2 H, m), 3.59-3.51 (2 H, m), 3.42 (3 H, s), 3.05-2.98 (1 H, m), 2.29-2.21 (2 H, m), 1.89 (6 H, d, J = 6.6 Hz). MS m/z (M + H): 365. |
| 0896 | 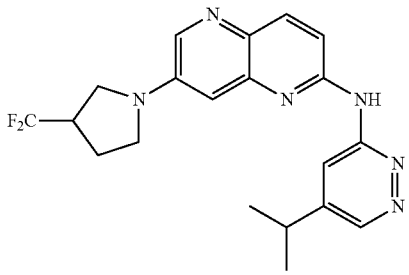 | ¹H-NMR (CDCl₃) δ: 9.52 (1 H, s), 8.87-8.84 (1 H, m), 8.80 (1 H, d, J = 2.0 Hz), 8.36 (1 H, d, J = 2.0 Hz), 8.13 (1 H, d, J = 9.2 Hz), 7.47-7.41 (1 H, m), 7.02 (1 H, d, J = 2.0 Hz), 3.79-3.72 (2 H, m), 3.68-3.55 (2 H, m), 3.22-3.13 (1 H, m), 3.09-3.00 (1 H, m), 2.48-2.26 (2 H, m), 1.41 (6 H, d, J = 6.6 Hz) MS m/z (M + H): 403. |
| 0897 | 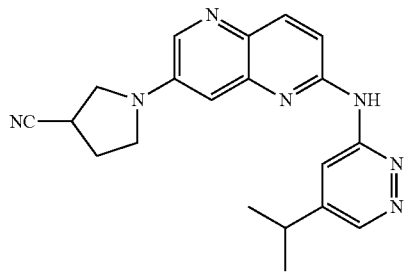 [SMILES: CC(C)c1cnnc(Nc2ccc3ncc(N4CCC(C#N)C4)cc3n2)c1] | ¹H-NMR (CDCl₃) δ: 8.80-8.76 (1 H, m), 8.73-8.70 (1 H, m), 8.40-8.36 (1 H, m), 8.37-8.34 (1 H, m), 8.13 (1 H, d, J = 9.2 Hz), 7.23 (1 H, d, J = 7.9 Hz), 7.03-7.00 (1 H, m), 3.99-3.78 (2 H, m), 3.79-3.72 (1 H, m), 3.69-3.58 (1 H, m), 3.42-3.34 (1 H, m), 3.05-2.98 (1 H, m), 2.56-2.47 (2 H, m), 1.89 (6 H, d, J = 7.3 Hz). MS m/z (M + H): 360. |

-continued

| Example No. | | |
|---|---|---|
| 0898 | 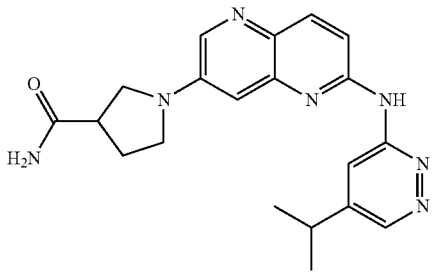 [SMILES: CC(C)c1cnnc(Nc2ccc3ncc(N4CCC(C(N)=O)C4)cc3n2)c1] | ¹H-NMR (CDCl₃) δ:<br>8.77-8.73 (1 H, m), 8.63-8.60 (1 H, m), 8.62-8.58 (1 H, m), 8.36-8.33 (1 H, m), 8.09 (1 H, d, J = 8.2 Hz), 7.21 (1 H, d, J = 8.2 Hz), 6.99-6.96 (1 H, m), 5.72-5.68 (1 H, m), 5.57-5.53 (1 H, m), 3.79-3.72 (2 H, m), 3.71-3.67 (1 H, m), 3.59-3.51 (1 H, m), 3.25-3.15 (1 H, m), 3.06-2.99 (1 H, m), 2.44-2.37 (2 H, m), 1.38 (6 H, d, J = 6.6 Hz).<br>MS m/z (M + H): 378. |
| 0899 | 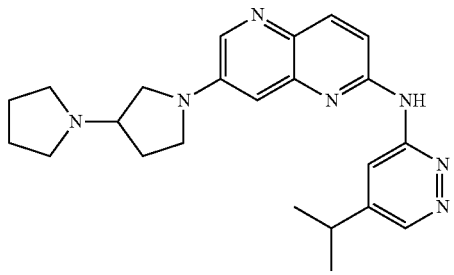 [SMILES: CC(C)c1cnnc(Nc2ccc3ncc(N4CCC(N5CCCC5)C4)cc3n2)c1] | ¹H-NMR (CDCl₃) δ:<br>9.16 (1 H, s), 8.79-8.76 (1 H, m), 8.78 (1 H, d, J = 2.6 Hz), 8.34 (1 H, d, J = 2.6 Hz), 8.10 (1 H, d, J = 9.2 Hz),<br>7.33 (1 H, d, J = 9.2 Hz), 6.95 (1 H, d, J = 2.6 Hz), 3.71-3.61 (2 H, m), 3.54-3.47 (1 H, m), 3.42-3.35 (1 H, m), 3.07-2.93 (2 H, m), 2.69-2.60 (4 H, m), 2.31-2.26 (1 H, m), 2.14-2.03 (1 H, m), 1.88-1.84 (4 H, m), 1.38 (6 H, d, J = 7.3 Hz)<br>MS m/z (M + H): 404. |
| 0900 | 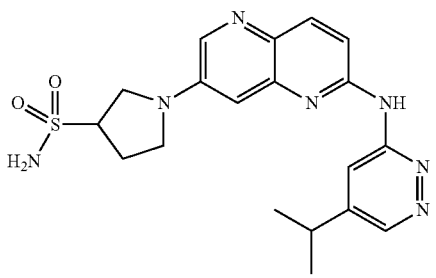 [SMILES: CC(C)c1cnnc(Nc2ccc3ncc(N4CCC(S(N)(=O)=O)C4)cc3n2)c1] | ¹H-NMR (CDCl₃) δ:<br>8.80-8.76 (1 H, m), 8.76-8.72 (1 H, m), 8.34 (1 H, d, J = 2.6 Hz), 8.04(1 H, d, J = 9.2 Hz), 7.33 (1 H, d, J = 9.2 Hz), 7.11 (1 H, d, J = 2.6 Hz), 4.09-4.01 (1 H, m), 3.92-3.86 (2 H, m), 3.77-3.71 (1 H, m), 3.62-3.59 (1 H, m), 3.08-3.02 (1 H, m), 2.60-2.54 (2 H, m), 1.40(6 H,d, J = 7.6 Hz).MS m/z (M + H): 414. |
| 0901 | 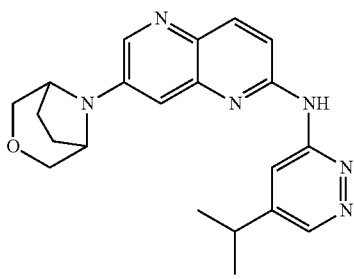 [SMILES: CC(C)c1cnnc(Nc2ccc3ncc(N4C5CCC4COC5)cc3n2)c1] | ¹H-NMR (CDCl₃) δ:<br>8.82-8.78 (1 H, m), 8.80-8.76 (1 H, m), 8.70-8.67 (1H,m), 8.51(1 H, d, J = 2.0 Hz),<br>8.12 (1 H, d, J = 8.6 Hz), 7.28 (1 H,d, J = 8.6 Hz), 7.19(1H,d, J = 2.0Hz), 4.28 (2 H, s), 3.87 (2H,d, J = 11.2Hz), 3.63(2H,d, J = 11.2Hz), 3.06-2.96 (1H,m),2.21-2.05(4H,m),1.39(6H,d, J = 6.6Hz)MSm/z (M+H):377 |
| 0902 | 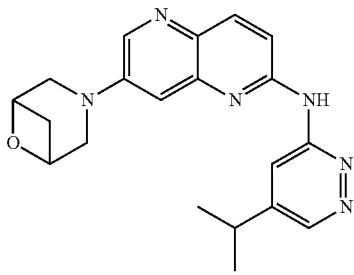 [SMILES: CC(C)c1cnnc(Nc2ccc3ncc(N4CC5CC(C4)O5)cc3n2)c1] | ¹H-NMR (CDCl₃) δ:<br>9.63-9.60 (1 H, m), 8.89-8.85 (1 H, m), 8.80-8.77 (1H,m), 8.56-8.53(1 H, m),8.15(1H,d,J = 8.6Hz), 7.47 (1 H, d, J = 8.6 Hz), 7.20-7.17 (1 H,m),4.86 (2H,d, J = 7.6Hz), 3.82-3.72(4H,m),3.36 (1H,dt, J = 8.6,7.6Hz),3.06-2.98 (1H,m),2.10(1H,d, J = 8.6Hz),1.40(6H,d,J = 7.3Hz), MSm/z(M+H):363. |

| Example No. | | |
|---|---|---|
| 0903 | 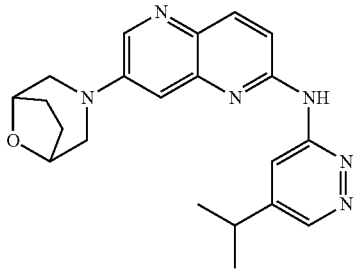 [SMILES: CC(C)c1cnnc(Nc2ccc3ncc(N4CC5CCC(C4)O5)cc3n2)c1] | ¹H-NMR (CDCl₃) δ:<br>9.40(1 H, s), 8.85-8.81 (1 H, m), 8.81-8.79 (1H,m), 8.55(1 H, d, J = 2.6 Hz),<br>8.14 (1 H, d, J = 9.2 Hz), 7.47 (1 H,d, J = 9.2 Hz), 7.22(1H,d, J = 2.6Hz), 4.60-4.57 (2 H, m), 3.52 (2H,d, J = 11.9Hz), 3.22(2H,dd, J = 11.9,2.3Hz), 3.09-2.99(1H,m),2.09-1.99(4H,m),1.40 (6H,d, J = 7.0Hz).<br>MSm/z(M+H):377. |
| 0904 | 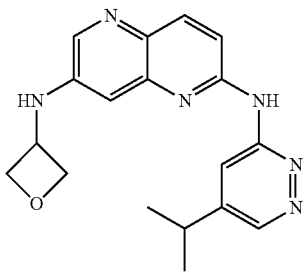 | ¹H-NMR (CDCl₃) δ:<br>9.63(1 H, s), 8.85-8.82 (1 H, m), 8.82-8.78 (1H,m), 6.30(1 H, d, J = 2.6 Hz),<br>8.12 (1 H, d, J = 9.2 Hz), 7.50 (1 H,d, J = 9.2 Hz), 6.82(1H,d, J = 2.6Hz), 5.10(2H,dd, J = 8.6,8.6Hz), 4.81-4.73(1H,m),4.72-4.63(1H,m),4.67-4.61 (2H,m),3.08-2.99(1H,m),1.41(6H,d, J = 7.3Hz)<br>MSm/z(M+H):377 |

Example 0905

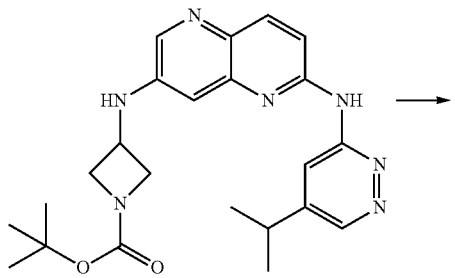

A 4 mol/L hydrogen chloride/1,4-dioxane solution (2 mL) and methanol (2 mL) were added to tert-butyl 3-((6-((5-isopropylpyridazin-3-yl)amino)-1,5-naphthyridin-3-yl)amino)azetidine-1-carboxylate (25 mg), followed by stirring at room temperature for 20 minutes. A saturated sodium hydrogen carbonate aqueous solution was added thereto, the solvent was distilled off under reduced pressure, and the obtained residue was purified by silica gel column chromatography (ethyl acetate-methanol, NH silica), thereby obtaining N⁷-(azetidin-3-yl)-N²-(5-isopropylpyridazin-3-yl)-1,5-naphthyridine-2,7-diamine (3 mg) as a pale yellow solid.

¹H-NMR(CDCl₃)δ:8.90(1H,s),8.80-8.78(1H,m),8.78-8.76(1H,m),8.27(1H,d,J=2.6 Hz),8.10(1H,d,J=9.2 Hz),7.32 (1H,d,J=9.2 Hz),6.89(1H,d,J=2.6 Hz),4.58-4.54(1H,m), 4.54-4.48(1H,m),4.09-4.02(2H,m),3.65-3.59(2H,m),3.63-3.61(1H,m),3.07-2.97(1H,m),1.40(6H,d,J=6.6 Hz).
MSm/z(M+H):336.

Example 0906

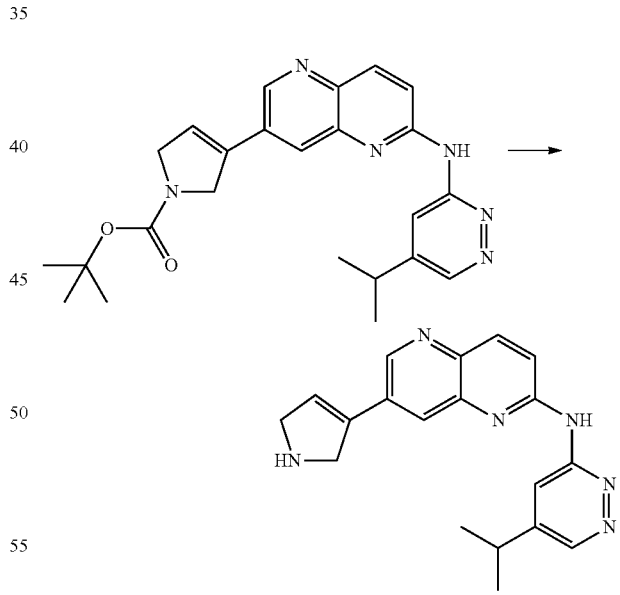

7-(2,5-Dihydro-1H-pyrrol-3-yl)-N-(5-isopropylpyridazin-3-yl)-1,5-naphthyridine-2-amine was obtained as a yellow solid in the same manner as in Example 0905.

¹H-NMR(CDCl₃)δ:10.64(1H,s),9.02-9.00(1H,m),8.93 (1H,d,J=2.0 Hz),8.84(1H,d,J=2.0 Hz),8.25(1H,d,J=9.2 Hz), 7.94(1H,d,J=9.2 Hz),7.86(1H,d,J=2.0 Hz),6.57(1H,t,J=2.0 Hz),4.31-4.26(2H,m),4.09-4.05(2H,m),3.12-3.03(1H,m), 1.88-1.85(1H,m),1.43(6H,d,J=6.6 Hz).
MSm/z(M+H):333.

Example 0907

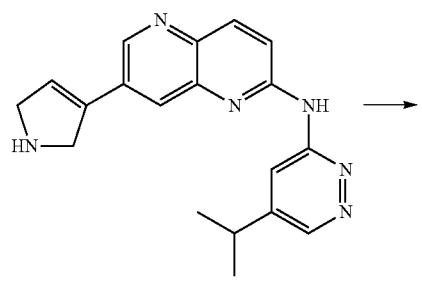

→

Example 0908

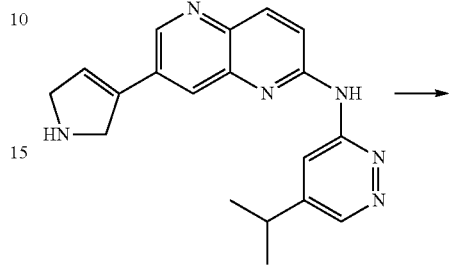

→

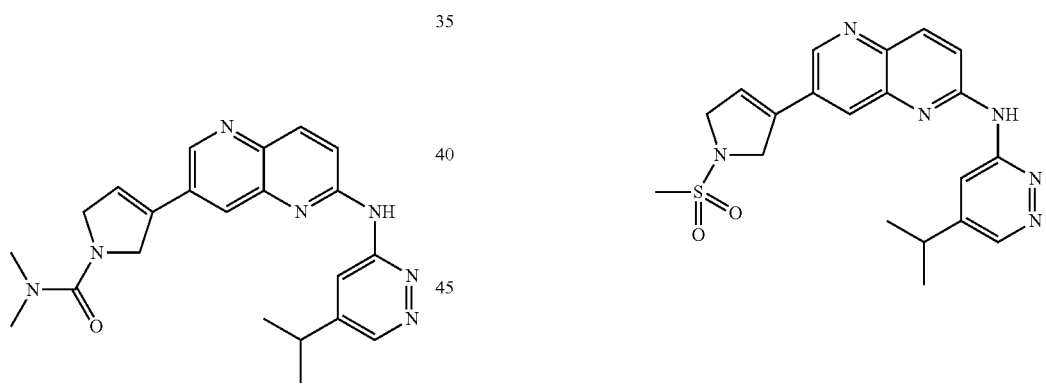

3-(6-((5-Isopropylpyridazin-3-yl)amino)-1,5-naphthyridin-3-yl)-N,N-dimethyl-2,5-dihydro-1H-pyrrole-1-carboxamide was obtained as a yellow solid in the same manner as in Example 0882.

$^1$H-NMR(CDCl$_3$)δ:9.81(1H,s),8.94(1H,d,J=2.0 Hz),8.93-8.89(1H,m),8.84(1H,d,J=2.0 Hz),8.25(1H,d,J=9.2 Hz),7.92(1H,d,J=2.0 Hz),7.78(1H,d,J=9.2 Hz),6.47-6.43(1H,m),4.82-4.77(2H,m),4.52-4.49(2H,m),3.15-3.05(1H,m),2.96(6H,s),1.43(6H,d,J=7.3 Hz).

MSm/z(M+H):404.

N-(5-Isopropylpyridazin-3-yl)-7-(1-(methylsulfonyl)-2,5-dihydro-1H-pyrrol-3-yl)-1,5-naphthyridine-2-amine was obtained as a yellow solid in the same manner as in Example 0839.

$^1$H-NMR(CDCl$_3$)δ:8.93(1H,d,J=2.0 Hz),8.83(1H,d,J=2.0 Hz),8.77(1H,d,J=2.0 Hz),8.74-8.70(1H,m),8.25(1H,d,J=8.6 Hz),7.86-7.84(1H,m),7.56(1H,d,J=8.6 Hz),6.50-6.47(1H,m),4.74-4.70(2H,m),4.50-4.46(2H,m),3.14-3.02(1H,m),2.97(3H,s),1.42(6H,d,J=6.9 Hz).

MSm/z(M+H):411.

Examples 0909 and 0910

The following compounds were obtained in the same manner as in Examples 0799-1 and 0554-3.

| Example No. | | |
|---|---|---|
| 0909 | | |
| 0909-1 | 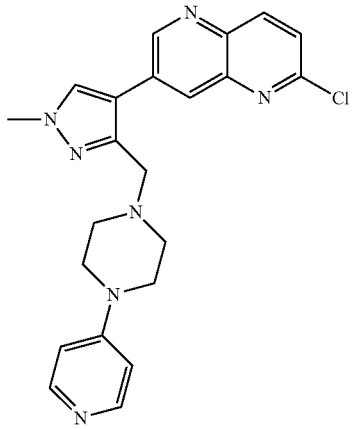 [SMILES: Cn1cc(-c2cnc3ccc(Cl)nc3c2)c(CN2CCN(c3ccncc3)CC2)n1] | MS m/z (M + H): 420. |
| 0909-2 | 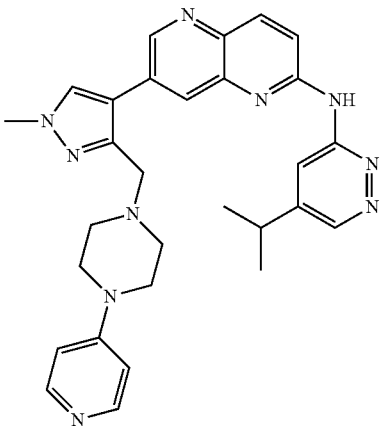 [SMILES: CC(C)c1cnnc(Nc2ccc3ncc(-c4cn(C)nc4CN4CCN(c5ccncc5)CC4)cc3n2)c1] | ¹H-NMR (CDCl₃) δ:<br>9.07 (1 H, s), 8.80-8.77 (1 H, m), 8.28-8.25 (4 H, m), 7.72-7.66<br>(2 H, m), 6.67-6.62 (2 H, m), 3.99 (3 H, d, J = 7.9 Hz), 3.70<br>(2 H, s), 3.36-3.32 (4 H, m), 3.02-2.94 (1 H, m), 2.71-2.68 (4 H,<br>m), 1.34 (6 H, d, J = 6.6 Hz).<br>MS m/z (M + H): 521. |
| 0910 | | |
| 0910-1 | 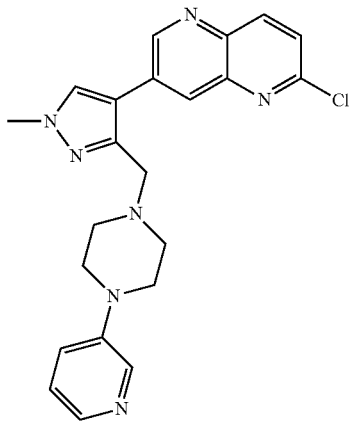 [SMILES: Cn1cc(-c2cnc3ccc(Cl)nc3c2)c(CN2CCN(c3cccnc3)CC2)n1] | MS m/z (M + H): 420. |

-continued

| Example No. | | |
|---|---|---|
| 0910-2 | 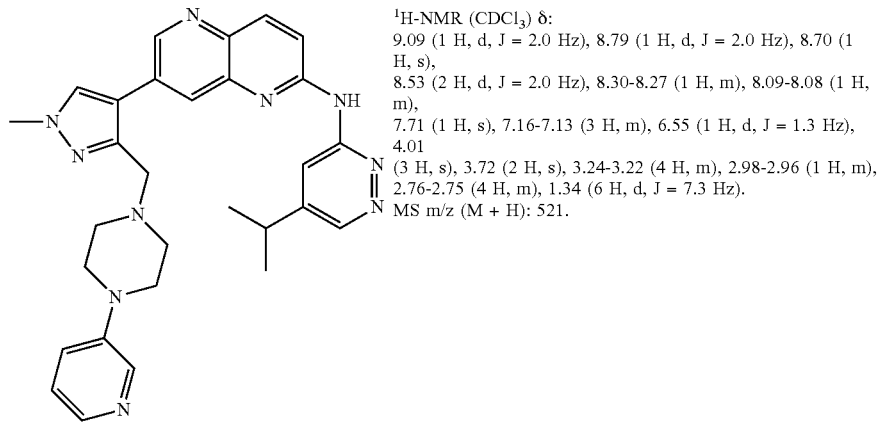 | ¹H-NMR (CDCl₃) δ:<br>9.09 (1 H, d, J = 2.0 Hz), 8.79 (1 H, d, J = 2.0 Hz), 8.70 (1 H, s),<br>8.53 (2 H, d, J = 2.0 Hz), 8.30-8.27 (1 H, m), 8.09-8.08 (1 H, m),<br>7.71 (1 H, s), 7.16-7.13 (3 H, m), 6.55 (1 H, d, J = 1.3 Hz), 4.01<br>(3 H, s), 3.72 (2 H, s), 3.24-3.22 (4 H, m), 2.98-2.96 (1 H, m), 2.76-2.75 (4 H, m), 1.34 (6 H, d, J = 7.3 Hz).<br>MS m/z (M + H): 521. |

Example 0911

0911-2

0911-1

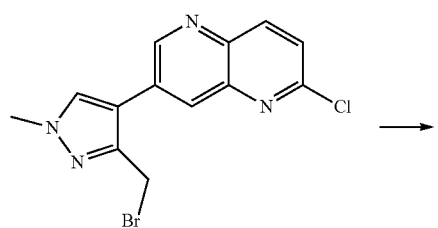

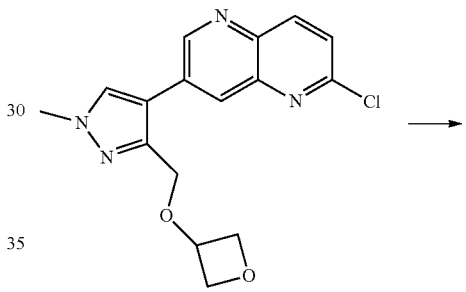

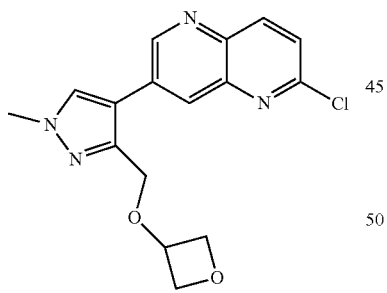

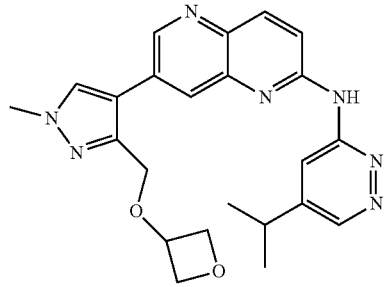

60% sodium hydride (5.8 mg) was added to a solution of oxetan-3-ol (6.5 mg) in N,N-dimethylformamide (1 mL) in a nitrogen atmosphere, followed by stirring for 30 minutes. 7-(3-(Bromomethyl)-1-methyl-1H-pyrazol-4-yl)-2-chloro-1,5-naphthyridine (20 mg) was added to the reaction mixture, followed by stirring at room temperature for 1 hour. The reaction mixture was purified by silica gel column chromatography (hexane-ethyl acetate-methanol, NH silica), thereby obtaining 2-chloro-7-(1-methyl-3-((oxetan-3-yloxy)methyl)-1H-pyrazol-4-yl)-1,5-naphthyridine (9.6 mg) as a pale yellow solid.

MS m/z (M+H): 331.

N-(5-isopropylpyridazin-3-yl)-7-(1-methyl-3-((oxetan-3-yloxy)methyl)-1H-pyrazol-4-yl)-1,5-naphthyridine-2-amine was obtained as a pale yellow solid in the same manner as in Example 0554-3.

¹H-NMR(CDCl₃)δ:8.92(1H,d,J=2.0 Hz),8.86(1H,s),8.81 (1H,s),8.63(1H,brs),8.33(1H,s),8.27(1H,d,J=8.6 Hz),7.73 (1H,s),7.55-7.52(1H,m),4.83-4.62(5H,m),4.60(2H,s),4.01 (3H,s),3.08-2.99(1H,m),1.41(6H,d,J=7.3 Hz).

MS m/z (M+H): 432.

Example 0912

0912-1

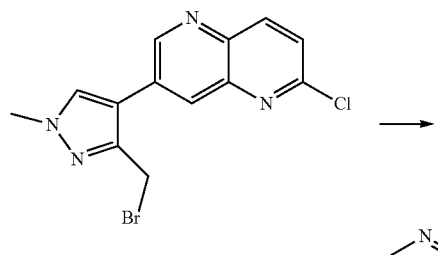

2-Chloro-7-(1-methyl-3-((4-methylpiperazin-1-yl)methyl)-1H-pyrazol-4-yl)-1,5-naphthyridine was obtained as a white solid in the same manner as in Example 0799-1.

MSm/z(M+H):357.

0912-2

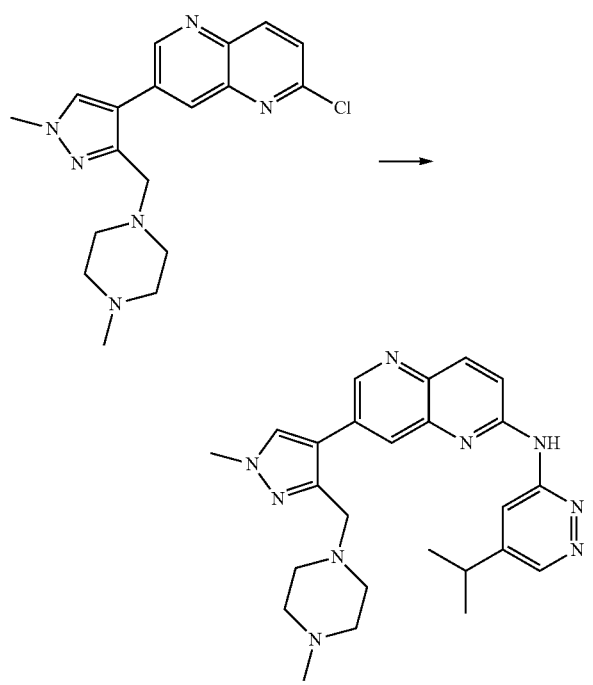

N-(5-isopropylpyridazin-3-yl)-7-(1-methyl-3-((4-methylpiperazin-1-yl)methyl)-1H-pyrazol-4-yl)-1,5-naphthyridine-2-amine was obtained as a pale yellow solid in the same manner as in Example 0554-3.

$^1$H-NMR(CDCl$_3$)δ:9.11(1H,d,J=2.0 Hz),8.81(1H,s),8.75-8.72(1H,m),8.27(1H,d,J=9.2 Hz),8.20(1H,s),7.70(1H,s),7.50-7.47(1H,m),3.99(3H,s),3.66(2H,s),3.04-3.02(1H,m),2.61-2.47(8H,m),2.27(3H,s),1.40(6H,d,J=7.3 Hz).

MSm/z(M+H):458.

Example 0913

0913-1

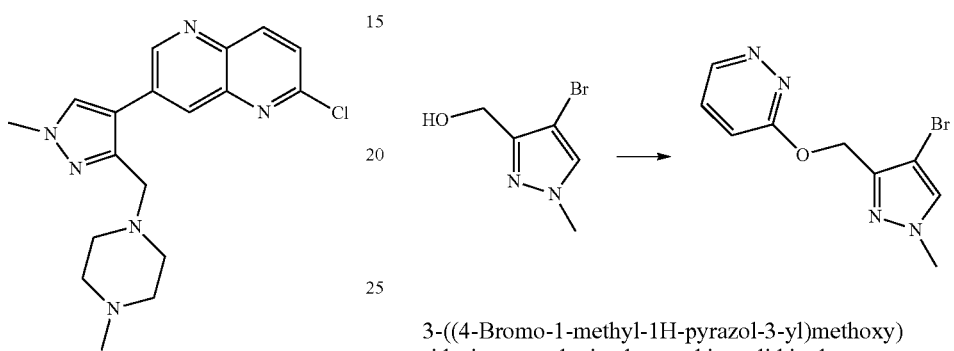

3-((4-Bromo-1-methyl-1H-pyrazol-3-yl)methoxy)pyridazine was obtained as a white solid in the same manner as in Example 0809-2.

MSm/z(M+H):269.

0913-2

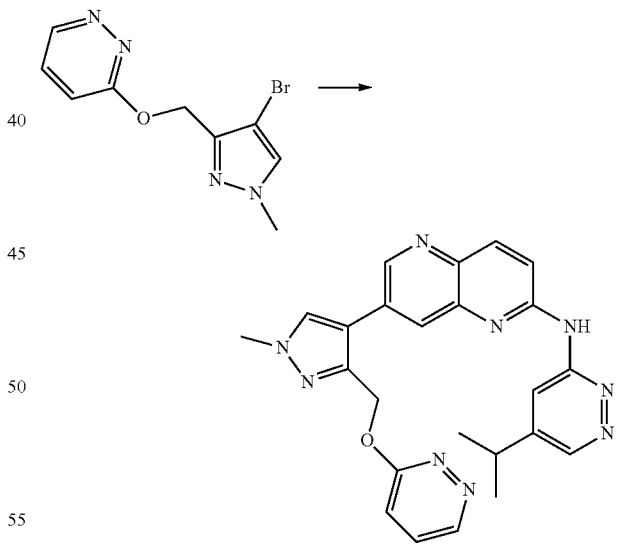

N-(5-isopropylpyridazin-3-yl)-7-(1-methyl-3-((pyridazin-3-yloxy)methyl)-1H-pyrazol-4-yl)-1,5-naphthyridine-2-amine was obtained as a yellow solid in the same manner as in Example 421-1.

$^1$H-NMR(CDCl$_3$)δ:8.89(1H,s),8.81(2H,d,J=7.3 Hz),8.26-8.24(2H,m),7.78-7.48(3H,m),7.12-7.09(1H,m),6.90-6.88(1H,m),5.57(2H,s),3.97(3H,s),3.06-3.00(1H,m),1.40(6H,d,J=6.6 Hz).

MSm/z(M+H):454.

Examples 0914 and 0915

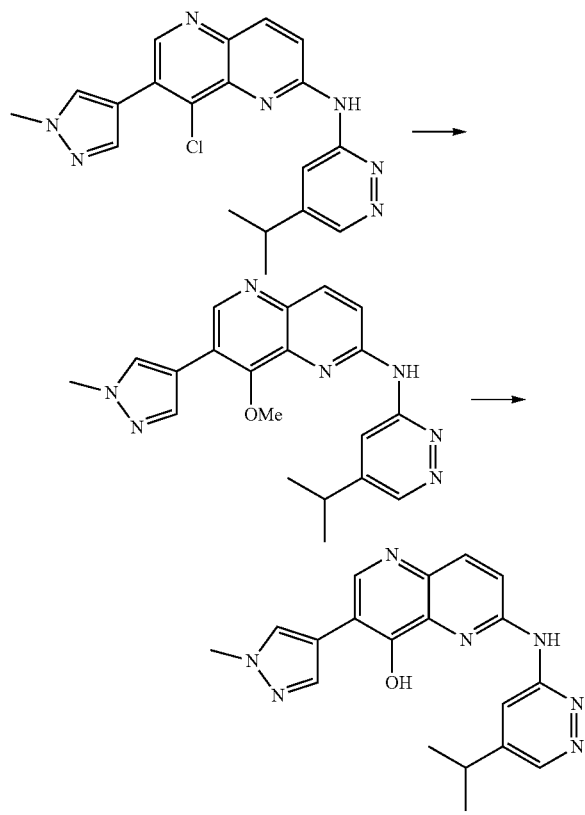

N-(5-isopropylpyridazin-3-yl)-8-methoxy-7-(1-methyl-1H-pyrazol-4-yl)-1,5-naphthyridine-2-amine as a pale yellow solid and 6-((5-isopropylpyridazin-3-yl)amino)-3-(1-methyl-1H-pyrazol-4-yl)-1,5-naphthyridin-4-ol as a pale yellow solid were obtained in the same manner as in Example 0355-1.

Example 0914

N-(5-isopropylpyridazin-3-yl)-8-methoxy-7-(1-methyl-1H-pyrazol-4-yl)-1,5-naphthyridine-2-amine $^1$H-NMR(CD$_3$OD)δ:8.95(2H,s),8.78(1H,s),8.31(1H,s),8.28(1H,brs),8.19(1H,d,J=9.2 Hz),8.13(1H,s),7.60-7.57(1H,m),4.23(3H,s),4.00(3H,s),3.09-3.06(1H,m),1.42(6H,d,J=3.3 Hz).

MSm/z(M+H):376.

Example 0915

6-((5-Isopropylpyridazin-3-yl)amino)-3-(1-methyl-1H-pyrazol-4-yl)-1,5-naphthyridine-4-ol $^1$H-NMR(CD$_3$OD)δ:8.71(1H,s),8.52(1H,brs),8.41(2H,s),8.02(3H,d,J=17.2 Hz),3.96(3H,s),3.10-3.03(1H,m),1.39(6H,d,J=6.6 Hz).

MSm/z(M+H):362.

Examples 0916 to 0919

The following compounds were obtained in the same manner as in Example 0554-3.

| Example No. | Structure | NMR / MS |
|---|---|---|
| 0916 | ![structure] | $^1$H-NMR (CDCl$_3$) δ: 8.84 (1 H, d, J = 1.8 Hz), 8.79 (1 H, brs), 8.76 (1 H, brs), 8.26 (1 H, d, J = 9.0 Hz), 8.05 (1 H, brs), 7.65 (1 H, s), 7.58 (1 H, d, J = 9.0 Hz), 3.95 (3 H, s), 2.84-2.66 (1 H, m), 2.51 (3 H, s), 1.82-1.68 (2 H, m), 1.38 (3 H, d, J = 6.6 Hz), 0.96 (3 H, t, J = 7.2 Hz). MS m/z (M + H): 374. |
| 0917 | ![structure] | $^1$H-NMR (CDCl$_3$) δ: 9.04 (1 H, brs), 8.96 (1 H, brs), 8.84 (1 H, d, J = 1.6 Hz), 8.26 (1 H, d, J = 9.3 Hz), 8.04 (1 H, brs), 7.65 (1 H, s), 7.58 (1 H, d, J = 9.3 Hz), 3.95 (3 H, s), 2.50 (3 H, s), 1.46 (9 H, s). MS m/z (M + H): 374. |
| 0918 | ![structure] | $^1$H-NMR (CDCl$_3$/CD$_3$OD = 4/1) δ: 8.88 (1 H, d, J = 2.1 Hz), 8.81 (1 H, brs), 8.66 (1 H, brs), 8.20 (1 H, d, J = 9.0 Hz), 8.17 (1 H, brs), 7.97 (2 H, brs), 7.48 (1 H, d, J = 9.0 Hz), 4.07 (3 H, s), 2.74 (2 H, t, J = 7.2 Hz), 1.87-1.77 (2 H, m), 1.08 (3 H, t, J = 7.2 Hz). MS m/z (M + H): 346. |

| Example No. | | |
|---|---|---|
| 0919 | 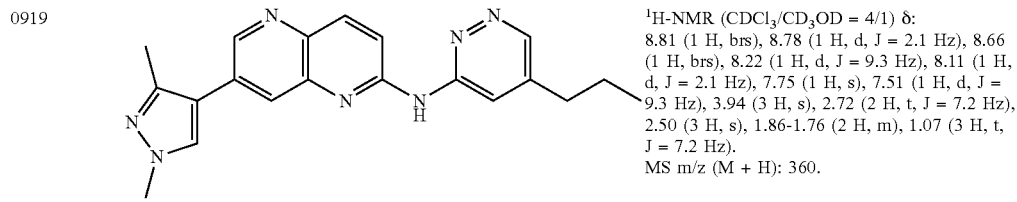 | ¹H-NMR (CDCl₃/CD₃OD = 4/1) δ: 8.81 (1 H, brs), 8.78 (1 H, d, J = 2.1 Hz), 8.66 (1 H, brs), 8.22 (1 H, d, J = 9.3 Hz), 8.11 (1 H, d, J = 2.1 Hz), 7.75 (1 H, s), 7.51 (1 H, d, J = 9.3 Hz), 3.94 (3 H, s), 2.72 (2 H, t, J = 7.2 Hz), 2.50 (3 H, s), 1.86-1.76 (2 H, m), 1.07 (3 H, t, J = 7.2 Hz). MS m/z (M + H): 360. |

Example 0920

0920-1

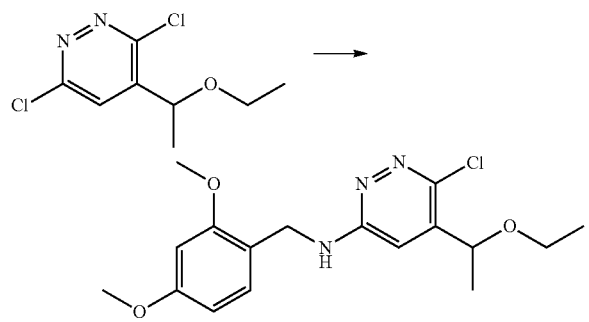

A suspension of 3,6-dichloro-4-(1-ethoxyethyl)pyridazine (240 mg), 2,4-dimethoxybenzylamine (0.280 mL), and potassium carbonate (298 mg) in pentan-2-ol (1 mL) was stirred for 17 hours under reflux. The reaction mixture was cooled to room temperature, the insolubles were filtered off, and the solvent was distilled off under reduced pressure. The obtained residue was purified by silica gel column chromatography (ethyl acetate-hexane), thereby obtaining 6-chloro-N-(2,4-dimethoxybenzyl)-5-(1-ethoxyethyl)pyridazine-3-amine (176 mg).

MSm/z(M+H):352.

0920-2 to 0920-4

The following compounds were obtained in the same manner as in Examples 0559-3, 0559-4, and 0554-3.

| Example No. | | |
|---|---|---|
| 0920 | | |
| 0920-2 | 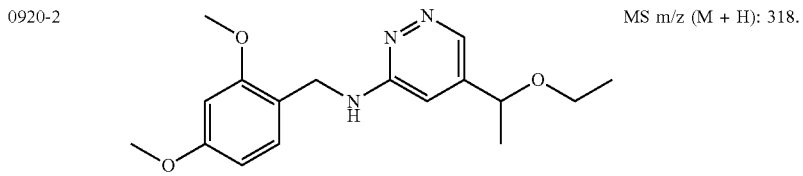 | MS m/z (M + H): 318. |
| 0920-3 | 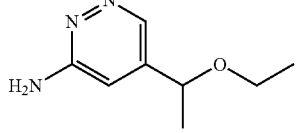 | MS m/z (M + H): 168. |
| 0920-4 | 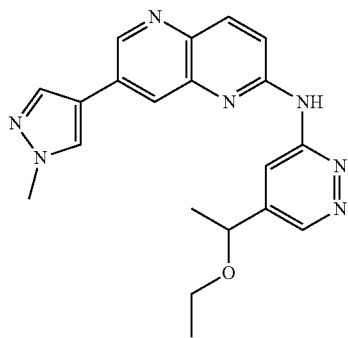 [SMILES: CCOC(C)c1cnnc(Nc2ccc3ncc(-c4cnn(C)c4)cc3n2)c1] | ¹H-NMR (CDCl₃) δ: 8.79 (1 H, brs), 9.07 (1 H, brs), 8.93 (1 H, d, J = 2.1 Hz), 8.88 (1 H, brs), 8.26 (1 H, d, J = 9.0 Hz), 8.13 (1 H, brs), 7.95 (1 H, s), 7.84 (1 H, s), 7.72 (1 H, d, J = 9.0 Hz), 4.59(1 H, q, J = 6.6 Hz), 4.02 (3 H, s), 3.65-3.49 (2 H, m), 1.58 (3 H, d, J = 6.6 Hz), 1.35 (3 H, t, J = 6.6 Hz). MS m/z (M + H): 376. |

Examples 0921 to 0923

The following compounds were obtained in the same manner as in Example 0554-3.

| Example No. | | |
|---|---|---|
| 0921 | 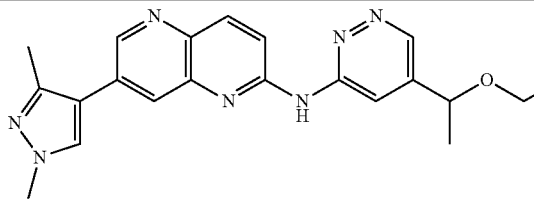 | ¹H-NMR (CDCl₃) δ:<br>9.27 (1 H, brs), 8.98 (1 H, brs), 8.85 (1 H, brs), 8.41 (1 H, brs), 8.28 (1 H, d, J = 9.3 Hz), 8.08 (1 H, brs), 7.65 (1 H, d, J = 9.3 Hz), 7.64 (1 H, s), 4.55 (1 H, q, J = 6.6 Hz), 3.95 (3 H, s), 3.60-3.48 (2 H, m), 2.50 (3 H, s), 1.55 (3 H, t, J = 6.6 Hz), 1.31 (3H, t, J = 6.6 Hz).<br>MS m/z (M + H): 390. |
| 0922 | 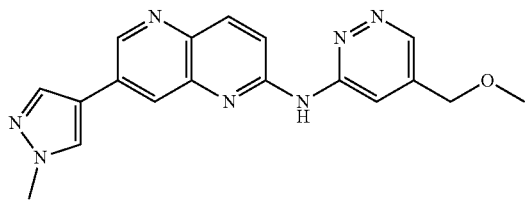 [SMILES: COCc1cnnc(Nc2ccc3ncc(-c4cnn(C)c4)cc3n2)c1] | ¹H-NMR (CDCl₃) δ:<br>8.93 (1 H, d, J = 1.8 Hz), 8.91 (1 H, brs), 8.87 (1 H, brs), 8.25 (1 H, d, J = 9.0 Hz), 8.14 (1 H, brs), 7.96 (1 H, s), 7.84, (1 H, s), 7.49 (1 H, d, J = 9.0 Hz), 4.63 (2 H, s), 4.02 (3 H, s), 3.54 (3 H, s).<br>MS m/z (M + H): 348. |
| 0923 | 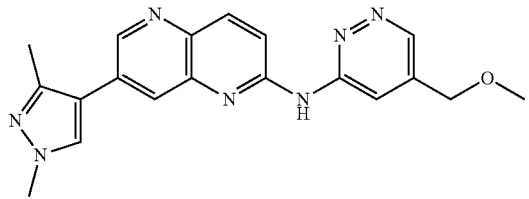 [SMILES: COCc1cnnc(Nc2ccc3ncc(-c4cn(C)nc4C)cc3n2)c1] | ¹H-NMR (CDCl₃) δ:<br>8.90 (1 H, brs), 8.85 (2 H, brs), 8.27 (1 H, d, J = 9.0 Hz), 8.09 (1 H, brs), 7.65 (1 H, s), 7.56 (1 H, d, J = 9.0 Hz), 4.60 (2 H, s), 3.95 (3 H, s), 3.54 (3 H, s), 2.52 (3 H, s).<br>MS m/z (M + H): 362. |

Example 0924

0924-1

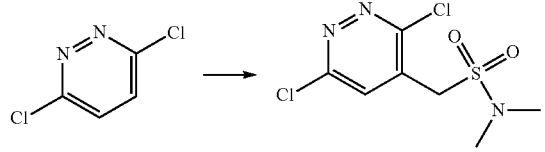

Potassium tert-butoxide (8.88 g) was added to a mixture of 3,6-dichloropyridazine (2.94 g), 1-chloro-N,N-dimethyl-methane sulfonamide (2.95 g), and tetrahydrofuran (100 mL) under ice-cooling, followed by stirring at the same temperature for 2 hours. After a saturated ammonium chloride aqueous solution and ethyl acetate were added to the reaction mixture, an organic layer was collected therefrom by separation, washed with a saturated sodium chloride aqueous solution, and dried over anhydrous sodium sulfate, and the solvent was distilled off under reduced pressure. The obtained residue was purified by silica gel chromatography (ethyl acetate-hexane), thereby obtaining 1-(3,6-dichloro-pyridazin-4-yl)-N,N-dimethylmethane sulfonamide (751 mg).

MS m/z (M+H): 270.

0924-2 to 0924-5

The following compounds were obtained in the same manner as in Examples 0920-1, 0559-3, 0559-4, and 0015-4.

| Example No. | | |
|---|---|---|
| 0924 | | |
| 0924-2 | 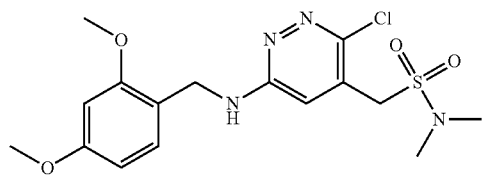 | MS m/z (M + H): 401 |

-continued

| Example No. | | |
|---|---|---|
| 0924-3 | 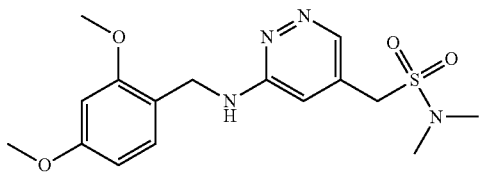 | MS m/z (M + H): 367 |
| 0924-4 | 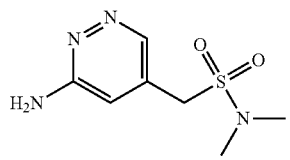 | MS m/z (M + H): 217 |
| 0924-5 | 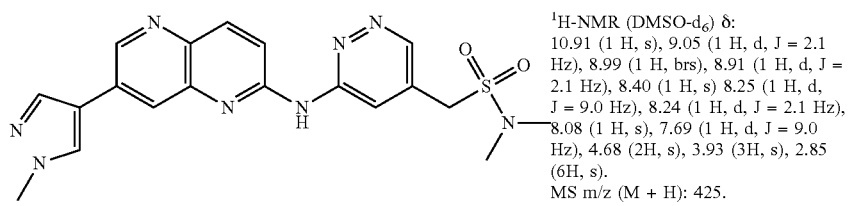 | ¹H-NMR (DMSO-d₆) δ: 10.91 (1 H, s), 9.05 (1 H, d, J = 2.1 Hz), 8.99 (1 H, brs), 8.91 (1 H, d, J = 2.1 Hz), 8.40 (1 H, s) 8.25 (1 H, d, J = 9.0 Hz), 8.24 (1 H, d, J = 2.1 Hz), 8.08 (1 H, s), 7.69 (1 H, d, J = 9.0 Hz), 4.68 (2H, s), 3.93 (3H, s), 2.85 (6H, s). MS m/z (M + H): 425. |

Example 0925

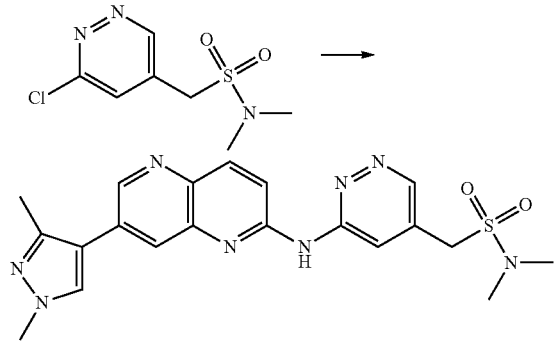

1-(6-((7-(1,3-Dimethyl-1H-pyrazol-4-yl)-1,5-naphthyridin-2-yl)amino)pyridazin-4-yl)-N,N-dimethylmethane sulfonamide was obtained in the same manner as in Example 0015-4.

¹H-NMR(DMSO-d₆)δ:10.93(1H,s),9.09(1H,brs),8.89 (2H,brs),8.26(1H,d,J=9.0 Hz),8.22(1H,s),8.16(1H,brs),7.67 (1H,d,J=9.0 Hz),4.68(2H,s),3.84(3H,s),2.83(6H,s),2.42(3H, s).

MSm/z(M+H):439.

Example 0926

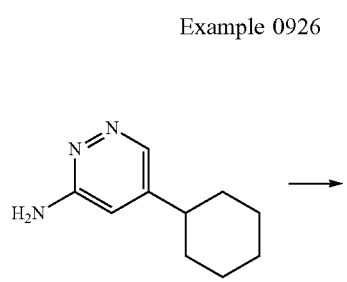

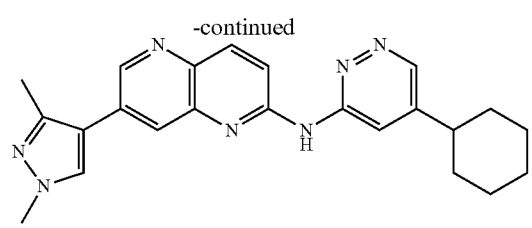

N-(5-cyclohexylpyridazin-3-yl)-7-(1,3-dimethyl-1H-pyrazol-4-yl)-1,5-naphthyridine-2-amine was obtained in the same manner as in Example 0554-3.

¹H-NMR(CDCl₃)δ:8.85(1H,brs),8.77(1H,brs),8.73(1H, brs),8.26(1H,d,J=8.7 Hz),8.08(1H,d,J=1.8 Hz),7.66(1H,s), 7.47(1H,d,J=8.7 Hz),3.95(3H,s),2.70-2.55(1H,m),2.51(3H, s),2.08-1.79(6H,m),1.62-1.20(4H,m).

MSm/z(M+H):362.

Example 0927

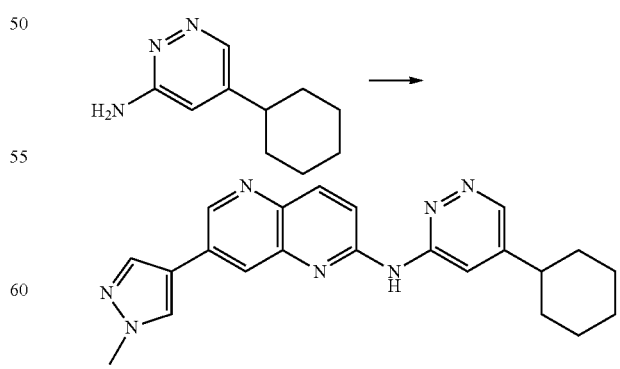

N-(5-cyclohexylpyridazin-3-yl)-7-(1-methyl-1H-pyrazol-4-yl)-1,5-naphthyridine-2-amine was obtained in the same manner as in Example 0015-4.

¹H-NMR(CDCl₃)δ:9.66(1H,brs),8.92(1H,d,J=1.8 Hz), 8.85(1H,brs),8.10(1H,d,J=1.8 Hz),8.25(1H,d,J=9.3 Hz), 8.12(1H,d,J=1.8 Hz),7.95(1H,s),7.83(1H,s),7.73(1H,d, J=9.3 Hz),4.03(3H,s),2.75-2.60(1H,m),2.10-1.79(6H,m), 1.66-1.24(4H,m).

MSm/z(M+H):386.

Example 0928

0928-1

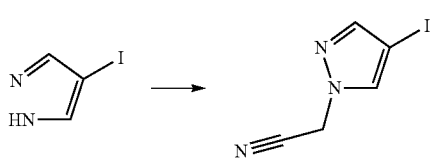 [SMILES: N=C/C(I)=C\N ; N#CCn1cc(I)cn1]

A mixture of 4-iodo-1H-pyrazole (1.00 g), bromoacetonitrile (1.03 mL), cesium carbonate (3.35 g), acetonitrile (4 mL), and 1,4-dioxane (2 mL) was stirred at 80° C. for 3 hours. The reaction mixture was cooled to room temperature, and the insolubles were filtered off. The solvent was distilled off under reduced pressure, and the obtained residue was purified by silica gel column chromatography (ethyl acetate-hexane), thereby obtaining 2-(4-iodo-1H-pyrazol-1-yl)acetonitrile (791 mg).

¹H-NMR(CDCl₃)δ:7.61(1H,s),7.60(1H,brs),5.08(2H,s).

0928-2

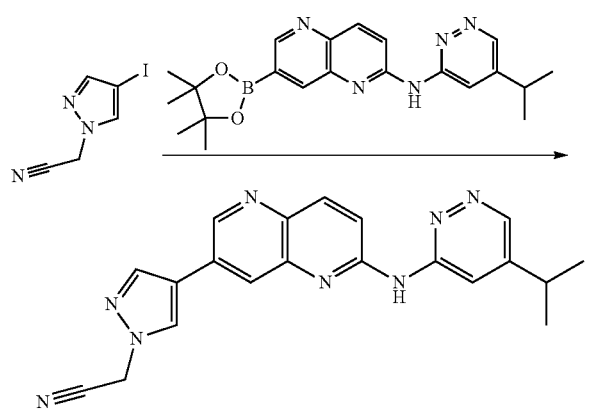

A mixture of 2-(4-iodo-1H-pyrazol-1-yl)acetonitrile (9 mg), N-(5-isopropylpyridazin-3-yl)-7-(4,4,5,5-tetramethyl-1,3,2-dioxaborolan-2-yl)-1,5-naphthyridine-2-amine (10) mg, sodium carbonate (7 mg), bis(di-tert-butyl(4-dimethylaminophenyl)phosphine)dichloropalladium(II) (2 mg), water (0.1 mL), and 1,2-dimethoxyethane (0.5 mL) was stirred at 90° C. for 2 hours. The reaction mixture was cooled to room temperature, the insolubles were filtered off, and the solvent was distilled off under reduced pressure. The obtained residue was purified by silica gel column chromatography (methanol-ethyl acetate), thereby obtaining 2-(4-(6-((5-isopropylpyridazin-3-yl)amino)-1,5-naphthyridin-3-yl)-1H-pyrazol-1-yl)acetonitrile (2.0 mg).

¹H-NMR(CDCl₃)δ:8.92(1H,brs),8.82(2H,brs),8.26(1H,d, J=8.7 Hz),8.12(1H,brs),8.05(1H,s),8.02(1H,s),7.63(1H,d, J=8.7 Hz),5.20(2H,s),3.15-2.96(1H,m),1.42(6H,d,J=6.6 Hz).

MSm/z(M+H):371.

Example 0929

N,N-dimethylacetamide (75 mL), 5-isopropylpyridazine-3-amine (5.12 g) and sodium tert-amyl oxide (9.08 g) were added to 7-bromo-2-chloro-1,5-naphthyridine (9.58 g), followed by stirring at 80° C. for 1 hour. The reaction mixture was poured into water (300 mL), and the precipitated solid was collected by filtration and washed with ethanol, thereby obtaining 7-bromo-N-(5-isopropylpyridazin-3-yl)-1,5-naphthyridine-2-amine (7.70 g) as a brown solid.

¹H-NMR(DMSO-d₆)δ:10.89(1H,s),8.88(1H,d,J=2.0 Hz), 8.80(1H,d,J=2.0 Hz),8.73(1H,d,J=2.0 Hz),8.48(1H,d,J=2.0 Hz),8.27(1H,d,J=9.2 Hz),7.79(1H,d,J=9.2 Hz),3.09-3.00 (1H,m),1.32(6H,d,J=6.6 Hz).

MSm/z(M+H):344.

Example 0930

0930-1

3-Methoxyazetidine hydrochloride (160 mg), sodium tert-butoxide (250 mg), 1,4-dioxane (10 mL), and ((2-dicyclohexylphosphino-3,6-dimethoxy-2',4',6'-triisopropyl-1,1'-biphenyl)-2-(2'-amino-1,1'-biphenyl))palladium(II) methanesulfonate (BRETTPHOS-PD-G3 (trade name, manufactured by Sigma-Aldrich Co. LLC.)) (40 mg) were added to 3-bromo-1-methyl-1H-pyrazole (160 mg), followed by stirring at 80° C. for 2 hours. The reaction mixture was cooled to room temperature, the solvent was distilled off under reduced pressure, and the obtained residue was purified by silica gel column chromatography (hexane-ethyl acetate-methanol), thereby obtaining 3-(3-methoxyazetidin-1-yl)-1-methyl-1H-pyrazole (41 mg) as yellow oily substance.

MSm/z(M+H):168.

0930-2 and 0930-3

The following compounds were obtained in the same manner as in Examples 0734-2 and 0385-7.

| Example No. | | |
|---|---|---|
| 0930 | | |
| 0930-2 | 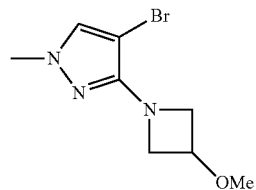 | MS m/z (M + H): 248. |
| 0930-3 | 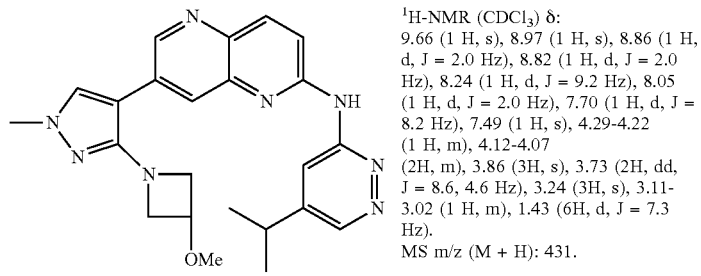 | $^1$H-NMR (CDCl$_3$) δ: 9.66 (1 H, s), 8.97 (1 H, s), 8.86 (1 H, d, J = 2.0 Hz), 8.82 (1 H, d, J = 2.0 Hz), 8.24 (1 H, d, J = 9.2 Hz), 8.05 (1 H, d, J = 2.0 Hz), 7.70 (1 H, d, J = 8.2 Hz), 7.49 (1 H, s), 4.29-4.22 (1 H, m), 4.12-4.07 (2H, m), 3.86 (3H, s), 3.73 (2H, dd, J = 8.6, 4.6 Hz), 3.24 (3H, s), 3.11-3.02 (1 H, m), 1.43 (6H, d, J = 7.3 Hz). MS m/z (M + H): 431. |

Example 0931

The following compounds were obtained in the same manner as in Examples 0886-1 and 0935-3.

| Example No. | | |
|---|---|---|
| 0931 | | |
| 0931-1 | 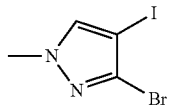 | MS m/z (M + H): 286. |
| 0931-2 | 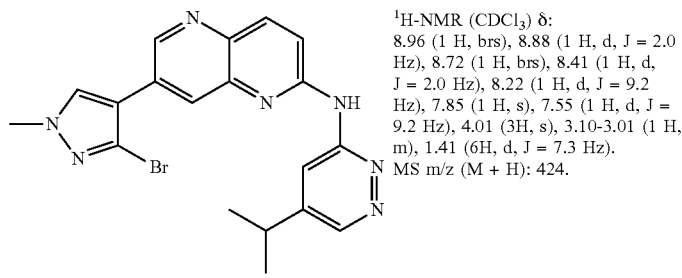 | $^1$H-NMR (CDCl$_3$) δ: 8.96 (1 H, brs), 8.88 (1 H, d, J = 2.0 Hz), 8.72 (1 H, brs), 8.41 (1 H, d, J = 2.0 Hz), 8.22 (1 H, d, J = 9.2 Hz), 7.85 (1 H, s), 7.55 (1 H, d, J = 9.2 Hz), 4.01 (3H, s), 3.10-3.01 (1 H, m), 1.41 (6H, d, J = 7.3 Hz). MS m/z (M + H): 424. |

Examples 0932 to 0934
The following compounds were obtained in the same manner as in Examples 0930-1, 0734-2, and 0385-7.
| Example No. | | |
|---|---|---|
| 0932 | | |
| 0932-1 | 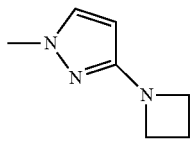 | MS m/z (M + H): 138. |
| 0932-2 | 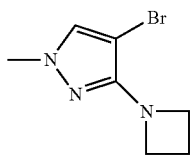 | MS m/z (M + H): 216. |
| 0932-3 | 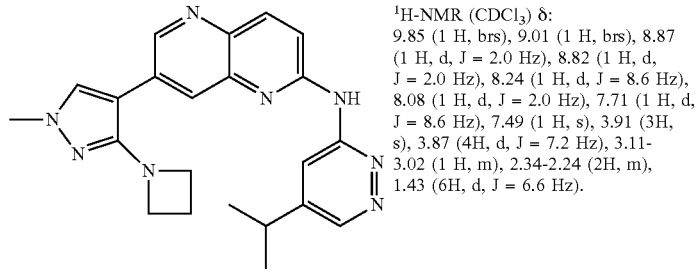 | ¹H-NMR (CDCl₃) δ: 9.85 (1 H, brs), 9.01 (1 H, brs), 8.87 (1 H, d, J = 2.0 Hz), 8.82 (1 H, d, J = 2.0 Hz), 8.24 (1 H, d, J = 8.6 Hz), 8.08 (1 H, d, J = 2.0 Hz), 7.71 (1 H, d, J = 8.6 Hz), 7.49 (1 H, s), 3.91 (3H, s), 3.87 (4H, d, J = 7.2 Hz), 3.11-3.02 (1 H, m), 2.34-2.24 (2H, m), 1.43 (6H, d, J = 6.6 Hz). |
| 0933 | | |
| 0933-1 | 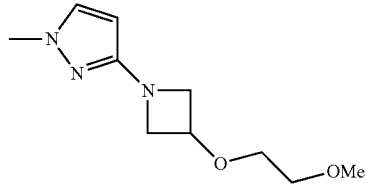 | MS m/z (M + H): 212. |
| 0933-2 | 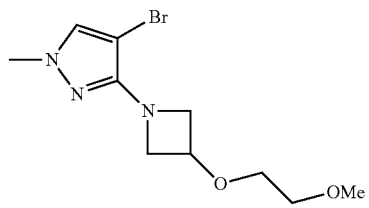 [SMILES: COCCOC1CN(c2nn(C)cc2Br)C1] | MS m/z (M + H): 290. |
| 0933-3 | 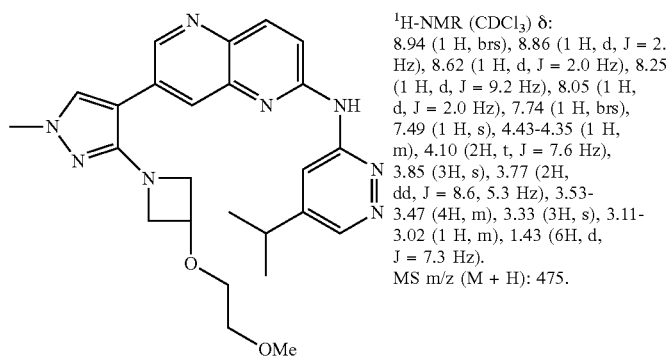 | ¹H-NMR (CDCl₃) δ: 8.94 (1 H, brs), 8.86 (1 H, d, J = 2.0 Hz), 8.62 (1 H, d, J = 2.0 Hz), 8.25 (1 H, d, J = 9.2 Hz), 8.05 (1 H, d, J = 2.0 Hz), 7.74 (1 H, brs), 7.49 (1 H, s), 4.43-4.35 (1 H, m), 4.10 (2H, t, J = 7.6 Hz), 3.85 (3H, s), 3.77 (2H, dd, J = 8.6, 5.3 Hz), 3.53-3.47 (4H, m), 3.33 (3H, s), 3.11-3.02 (1 H, m), 1.43 (6H, d, J = 7.3 Hz). MS m/z (M + H): 475. |

-continued

| Example No. | | |
|---|---|---|
| 0934 | | |
| 0934-1 | 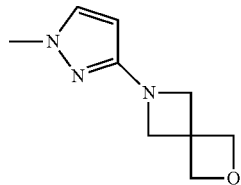 | MS m/z (M + H): 180. |
| 0934-2 | 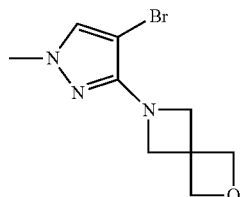 | MS m/z (M + H): 258. |
| 0934-3 | 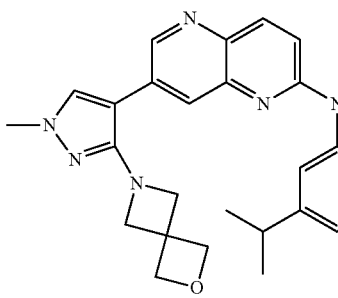 | $^1$H-NMR (CDCl$_3$) δ: 10.04 (1 H, brs), 8.98 (1 H, brs), 8.85 (1 H, d, J = 2.0 Hz), 8.83 (1 H, d, J = 2.0 Hz), 8.26 (1 H, d, J = 8.6 Hz), 8.02 (1 H, d, J = 2.0 Hz), 7.80 (1 H, d, J = 8.6 Hz), 7.49 (1 H, s), 4.77 (4H, d, J = 4.6 Hz), 4.03 (4H, s), 3.87 (3H, d, J = 9.2 Hz), 3.10-3.01 (1 H, m), 1.42 (6H, d, J = 6.6 Hz), MS m/z (M + H): 443. |

Example 0935

0935-1 and 0935-2

The following compounds were obtained in the same manner as in Examples 0930-1 and 0734-2.

| Example No. | | |
|---|---|---|
| 0935 | | |
| 0935-1 | 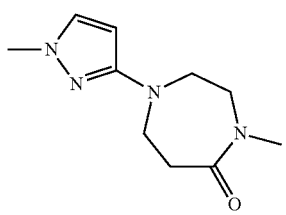 | MS m/z (M + H): 209. |
| 0935-2 | 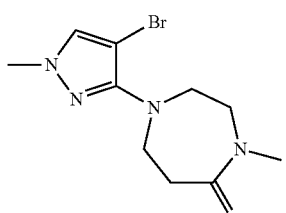 | MS m/z (M + H): 287. |

0935-3

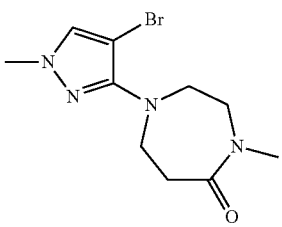

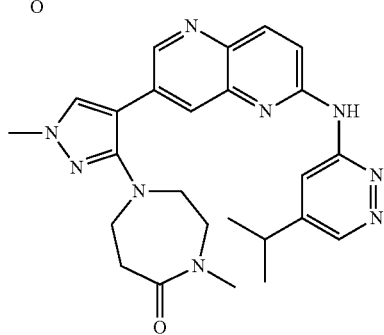

N-(5-isopropylpyridazin-3-yl)-7-(4,4,5,5-tetramethyl-1,3,2-dioxaborolan-2-yl)-1,5-naphthyridine-2-amine (13 mg), sodium carbonate (10 mg), 1,4-dioxane (0.9 mL), water (0.1 mL), and (2-dicyclohexylphosphino-2',4',6'-triisopropyl-1,1'-biphenyl) (2-(2'-amino-1,1'-biphenyl))palladium(II) methanesulfonate (XPHOS-PD-G3 (trade name, manufactured by Sigma-Aldrich Co. LLC.)) (2 mg) were added to 1-(4-bromo-1-methyl-1H-pyrazol-3-yl)-4-methyl-1,4-diazepan-5-one (9 mg), followed by stirring at 90° C. for 76 hours. The solvent of the reaction mixture was distilled off under reduced pressure, and the residue was purified by silica gel column chromatography (hexane-ethyl acetate-methanol, NH silica), thereby obtaining 1-(4-(6-((5-isopropylpyridazin-3-yl)amino)-1,5-naphthyridin-3-yl)-1-methyl-1H-pyrazol-3-yl)-4-methyl-1,4-diazepan-5-one (1.8 mg) as a yellow solid.

$^1$H-NMR(CDCl$_3$)δ:9.35(1H,brs),9.02(1H,brs),8.93(1H,brs),8.80(1H,brs),8.33(1H,brs),8.25(1H,d,J=9.2 Hz),7.65 (1H,brs),7.60(1H,s),3.87(3H,s),3.61(2H,t,J=4.8 Hz),3.33-3.26(4H,m),3.06-2.98(1H,m),3.02(3H,s),2.83(2H,t,J=4.8 Hz),1.40(6H,d,J=7.3 Hz).

MSm/z(M+H):472.

Example 0936

0936-1

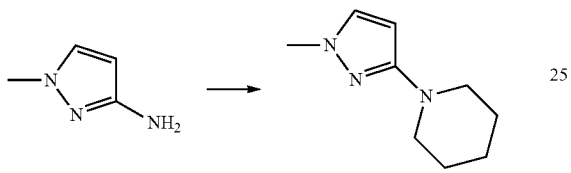

1,5-Dibromopentane (136 μL), cesium carbonate (814 mg), and N,N-dimethylacetamide (3 mL) were added to 1-methyl-1H-pyrazole-3-amine (97 mg), followed by stirring at 90° C. for 3 hours. After water was added to the reaction mixture, the resultant product was extracted three times with ethyl acetate, washed with a saturated sodium chloride aqueous solution, and dried over anhydrous sodium sulfate. The solvent of was distilled off under reduced pressure, and the residue was purified by silica gel column chromatography (hexane-ethyl acetate), thereby obtaining 1-(1-methyl-1H-pyrazol-3-yl)piperidine (91 mg) as yellow oily substance.

MSm/z(M+H):166.

0936-2 and 0936-3

The following compounds were obtained in the same manner as in Examples 0734-2 and 0935-3.

| Example No. | | |
|---|---|---|
| 0936 | | |
| 0936-2 | 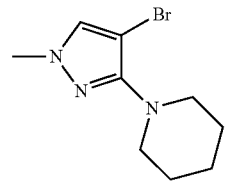 | MS m/z (M + H): 244. |
| 0936-3 | 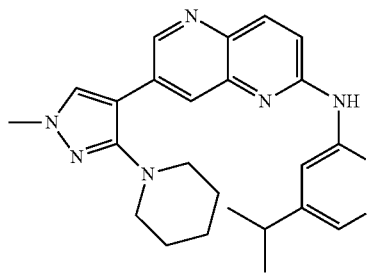 | $^1$H-NMR (CDCl$_3$) δ: 9.04 (1 H, brs), 9.00 (1 H, d, J = 2.0 Hz), 8.89 (1 H, brs), 8.79 (1 H, brs), 8.47 (1 H, brs), 8.22 (1 H, d, J = 8.9 Hz), 7.61 (1 H, s), 7.44 (1 H, d, J = 8.9 Hz), 3.87 (3H, s), 3.09-2.97 (5H, m), 1.79-1.71 (4 H, m), 1.69-1.60 (2H, m), 1.42 (6H, d, J = 7.3 Hz). MS m/z (M + H): 429. |

Example 0937

The following compounds were obtained in the same manner as in Examples 0936-1, 0734-2, and 0935-3.

| Example No. | | |
|---|---|---|
| 0937 | | |
| 0937-1 | 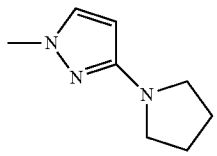 | MS m/z (M + H): 152. |
| 0937-2 | 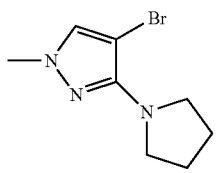 | MS m/z (M + H): 230. |
| 0937-3 | 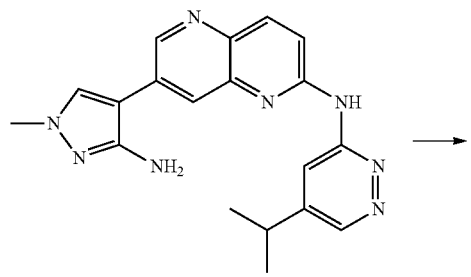 | ¹H-NMR (CDCl₃) δ: 9.20 (1 H, brs), 8.94 (1 H, d, J = 2.0 Hz), 8.88 (1 H, d, J = 2.0 Hz), 8.80 (1 H, d, J = 2.0 Hz), 8.25 (1 H, d, J = 8.6 Hz), 8.08 (1 H, d, J = 2.0 Hz), 7.58 (1 H, d, J = 8.6 Hz), 7.46 (1 H, s), 3.86 (3H, s), 3.22 (4 H, t, J = 6.6 Hz), 3.08-2.99 (1 H, m), 1.90-1.86 (4H, m), 1.40 (6H, d, J = 6.6 Hz). MS m/z (M + H): 415. |

Example 0938

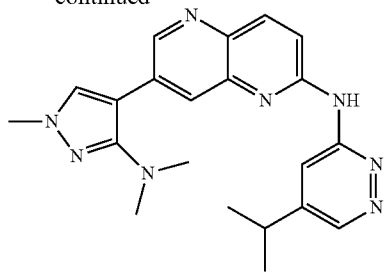

7-(3-(Dimethylamino)-1-methyl-1H-pyrazol-4-yl)-N-(5-isopropylpyridazin-3-yl)-1,5-naphthyridine-2-amine was obtained as a pale yellow solid in the same manner as in Example 0741.

¹H-NMR(CDCl₃)δ:9.24(1H,brs),9.00(1H,d,J=2.0 Hz), 8.93(1H,brs),8.81(1H,brs),8.26(1H,brs),8.24(1H,d,J=9.2

Hz),7.61(1H,d,J=9.2 Hz),7.54(1H,s),3.86(3H,s),3.09-3.00 (1H,m),2.79(6H,s),1.41(6H,d,J=6.6 Hz).

MS m/z (M+H): 389.

Examples 0939 and 0940

The following compounds were obtained in the same manner as in Example 0830.

| Example No. | | |
|---|---|---|
| 0939 | 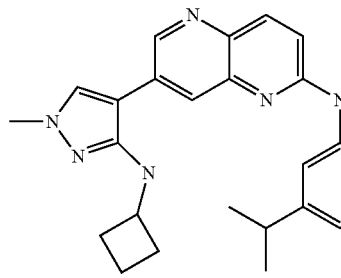 | ¹H-NMR (CDCl₃) δ: 8.91 (2H, brs), 8.85 (1 H, d, J = 2.0 Hz), 8.80 (1 H, brs), 8.24 (1 H, d, J = 9.2 Hz), 8.12 (1 H, brs), 7.53 (1 H, d, J = 9.2 Hz), 7.49 (1 H, s), 4.24-4.15 (1 H, m), 3.93 (1 H, d, J = 7.3 Hz), 3.84 (3H, s), 3.08-2.99 (1 H, m), 2.50-2.42 (2H, m), 1.89-1.69 (4H, m), 1.41 (6H, d, J = 7.3 Hz). MS m/z (M + H): 415. |
| 0940 | 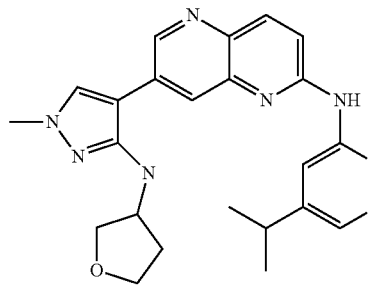 | ¹H-NMR (CDCl₃) δ: 9.86 (1 H, brs), 8.98 (1 H, brs), 8.83 (1 H, d, J = 2.0 Hz), 8.77 (1 H, brs), 8.22 (1 H, d, J = 8.9 Hz), 8.09 (1 H, d, J = 2.0 Hz), 7.71 (1 H, d, J = 8.9 Hz), 7.51 (1 H, s), 4.41-4.32 (1 H, m), 4.05-3.95 (3H, m), 3.91-3.79 (5H, m), 3.07-2.88 (1 H, m), 2.39-2.26 (2H, m), 1.41 (6H, d, J = 7.2 Hz). MS m/z (M + H): 431. |

Example 0941

The following compounds were obtained in the same manner as in Examples 0930-1, 0734-2, and 0935-3.

| Example No. | | |
|---|---|---|
| 0941 | | |
| 0941-1 | 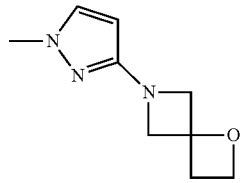 | MS m/z (M + H): 180. |
| 0941-2 | 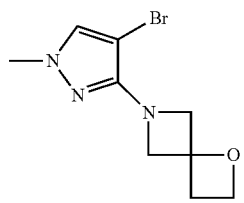 | MS m/z (M + H): 260. |

-continued

| Example No. | | |
|---|---|---|
| 0941-3 | 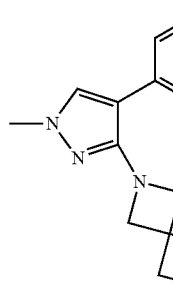 | $^1$H-NMR (CDCl$_3$) δ:<br>9.19 (1 H, brs), 8.92 (1 H, brs), 8.86 (1 H, d, J = 2.0 Hz), 8.82 (1 H, d, J = 2.0 Hz), 8.25 (1 H, d, J = 9.2 Hz), 8.03 (1 H, d, J = 2.0 Hz), 7.60 (1 H, d, J = 9.2 Hz), 7.48 (1 H, s), 4.48 (2H, t, J = 7.3 Hz), 4.12-4.00 (4H, m), 3.85 (3H, s), 3.10-3.00 (1 H, m), 2.87 (2H, t, J = 7.3 Hz), 1.41 (6H, d, J = 7.3 Hz).<br>MS m/z (M + H): 443. |

Example 0942

0942-1

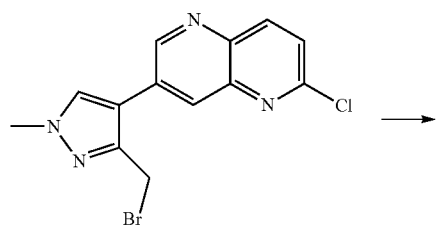

Morpholine (6 μL), potassium carbonate (16 mg), and acetonitrile (1 mL) were added to 7-(3-(bromomethyl)-1-methyl-1H-pyrazol-4-yl)-2-chloro-1,5-naphthyridine (20 mg), followed by stirring at 50° C. for 1 hour. The solvent of the reaction mixture was distilled off under reduced pressure, and the residue was purified by silica gel column chromatography (hexane-ethyl acetate-methanol), thereby obtaining 4-((4-(6-chloro-1,5-naphthyridin-3-yl)-1-methyl-1H-pyrazol-3-yl)methyl)morpholine (7 mg) as a white solid.

MS m/z (M+H):344.

0942-2

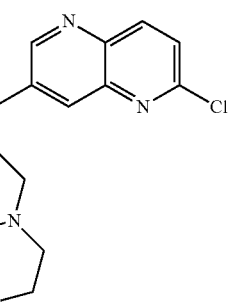

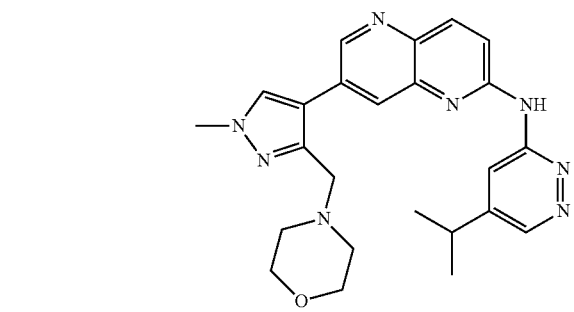

N-(5-isopropylpyridazin-3-yl)-7-(1-methyl-3-(morpholinomethyl)-1H-pyrazol-4-yl)-1,5-naphthyridine-2-amine was obtained as a white solid in the same manner as in Example 0485-2.

$^1$H-NMR(CDCl$_3$)δ:10.15(1H,brs),9.06(1H,d,J=2.0 Hz), 8.94(1H,s),8.84(1H,d,J=2.0 Hz),8.28(1H,d,J=8.9 Hz),8.26 (1H,s),7.85(1H,d,J=8.9 Hz),7.69(1H,s),3.99(3H,s),3.72(4H, t,J=4.0 Hz),3.65(2H,s),3.08-2.99(1H,m),2.58(4H,brs),1.42 (6H,d,J=6.6 Hz).

MS m/z(M+H):445.

Examples 0943 and 0944

The following compounds were obtained in the same manner as in Example 0830.

| Example No. | | |
|---|---|---|
| 0943 | 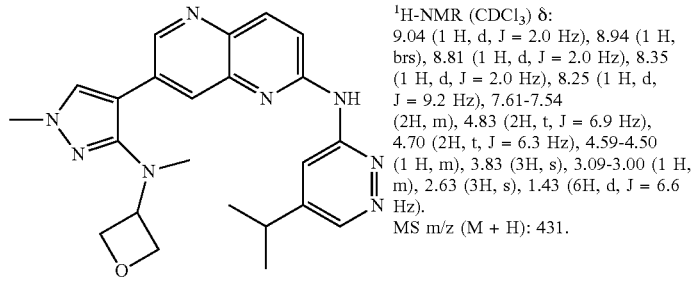 | ¹H-NMR (CDCl₃) δ: 9.04 (1 H, d, J = 2.0 Hz), 8.94 (1 H, brs), 8.81 (1 H, d, J = 2.0 Hz), 8.35 (1 H, d, J = 2.0 Hz), 8.25 (1 H, d, J = 9.2 Hz), 7.61-7.54 (2H, m), 4.83 (2H, t, J = 6.9 Hz), 4.70 (2H, t, J = 6.3 Hz), 4.59-4.50 (1 H, m), 3.83 (3H, s), 3.09-3.00 (1 H, m), 2.63 (3H, s), 1.43 (6H, d, J = 6.6 Hz). MS m/z (M + H): 431. |
| 0944 | 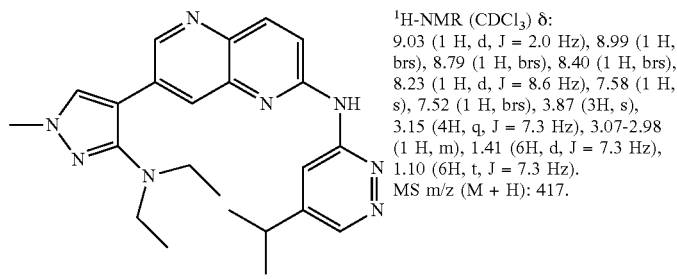 | ¹H-NMR (CDCl₃) δ: 9.03 (1 H, d, J = 2.0 Hz), 8.99 (1 H, brs), 8.79 (1 H, brs), 8.40 (1 H, brs), 8.23 (1 H, d, J = 8.6 Hz), 7.58 (1 H, s), 7.52 (1 H, brs), 3.87 (3H, s), 3.15 (4H, q, J = 7.3 Hz), 3.07-2.98 (1 H, m), 1.41 (6H, d, J = 7.3 Hz), 1.10 (6H, t, J = 7.3 Hz). MS m/z (M + H): 417. |
Example 0945
The following compounds were obtained in the same manner as in Examples 0936-1, 0741, 0734-2, and 0935-3.
| Example No. | | |
|---|---|---|
| 0945 | | |
| 0945-1 | 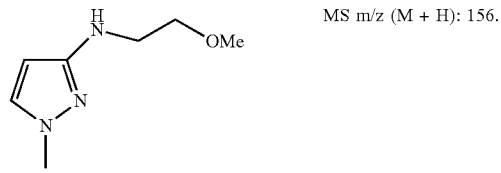 | MS m/z (M + H): 156. |
| 0945-2 | 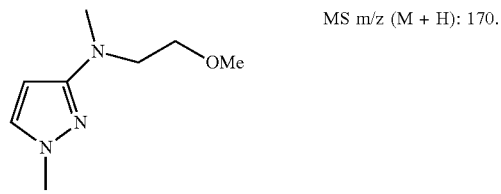 | MS m/z (M + H): 170. |
| 0945-3 | 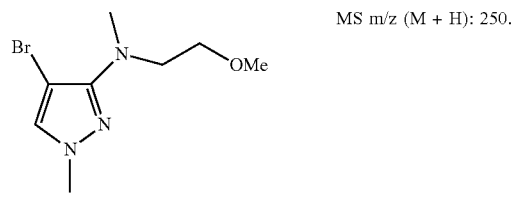 | MS m/z (M + H): 250. |

-continued

| Example No. | | |
|---|---|---|
| 0945-4 | 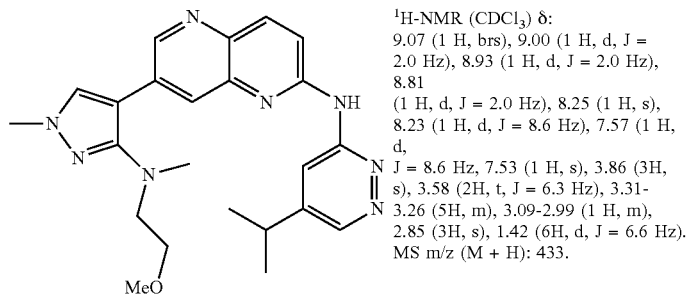 | ¹H-NMR (CDCl₃) δ: 9.07 (1 H, brs), 9.00 (1 H, d, J = 2.0 Hz), 8.93 (1 H, d, J = 2.0 Hz), 8.81 (1 H, d, J = 2.0 Hz), 8.25 (1 H, s), 8.23 (1 H, d, J = 8.6 Hz), 7.57 (1 H, d, J = 8.6 Hz), 7.53 (1 H, s), 3.86 (3H, s), 3.58 (2H, t, J = 6.3 Hz), 3.31-3.26 (5H, m), 3.09-2.99 (1 H, m), 2.85 (3H, s), 1.42 (6H, d, J = 6.6 Hz). MS m/z (M + H): 433. |

Example 0946

The following compounds were obtained in the same manner as in Examples 0734-2 and 0935-3.

| Example No. | | |
|---|---|---|
| 0946 | | |
| 0946-1 | 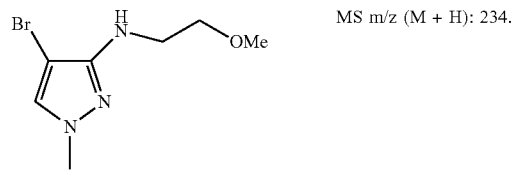 | MS m/z (M + H): 234. |
| 0946-2 | 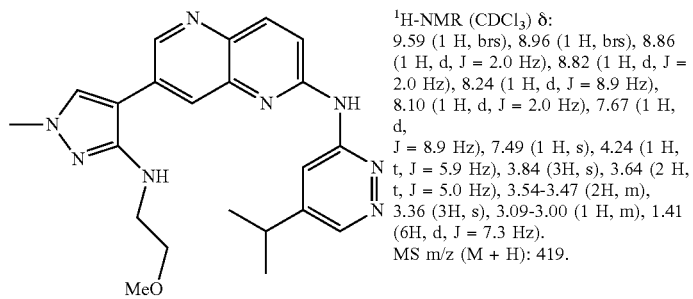 | ¹H-NMR (CDCl₃) δ: 9.59 (1 H, brs), 8.96 (1 H, brs), 8.86 (1 H, d, J = 2.0 Hz), 8.82 (1 H, d, J = 2.0 Hz), 8.24 (1 H, d, J = 8.9 Hz), 8.10 (1 H, d, J = 2.0 Hz), 7.67 (1 H, d, J = 8.9 Hz), 7.49 (1 H, s), 4.24 (1 H, t, J = 5.9 Hz), 3.84 (3H, s), 3.64 (2 H, t, J = 5.0 Hz), 3.54-3.47 (2H, m), 3.36 (3H, s), 3.09-3.00 (1 H, m), 1.41 (6H, d, J = 7.3 Hz). MS m/z (M + H): 419. |

Example 0947

The following compounds were obtained in the same manner as in Examples 0936-1, 0734-2, and 0935-3.

| Example No. | | |
|---|---|---|
| 0947 | | |
| 0947-1 | 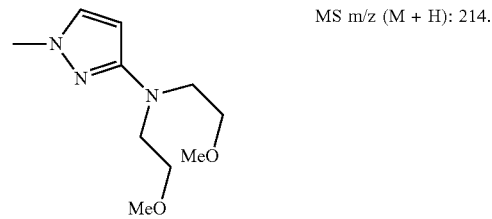 | MS m/z (M + H): 214. |

-continued

| Example No. | | |
|---|---|---|
| 0947-2 | 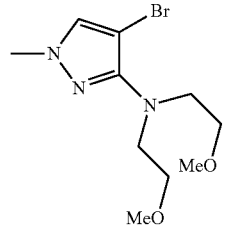 [SMILES: COCCN(CCOC)c1nn(C)cc1Br] | MS m/z (M + H): 292. |
| 0947-3 | 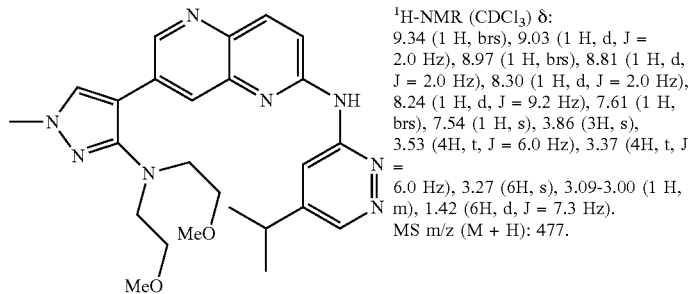 | $^1$H-NMR (CDCl$_3$) δ: 9.34 (1 H, brs), 9.03 (1 H, d, J = 2.0 Hz), 8.97 (1 H, brs), 8.81 (1 H, d, J = 2.0 Hz), 8.30 (1 H, d, J = 2.0 Hz), 8.24 (1 H, d, J = 9.2 Hz), 7.61 (1 H, brs), 7.54 (1 H, s), 3.86 (3H, s), 3.53 (4H, t, J = 6.0 Hz), 3.37 (4H, t, J = 6.0 Hz), 3.27 (6H, s), 3.09-3.00 (1 H, m), 1.42 (6H, d, J = 7.3 Hz). MS m/z (M + H): 477. |

Examples 0948 and 0949

The following compounds were obtained in the same manner as in Example 0830.

| Example No. | | |
|---|---|---|
| 0948 | 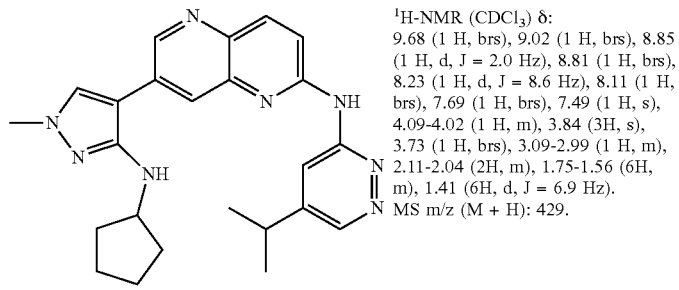 | $^1$H-NMR (CDCl$_3$) δ: 9.68 (1 H, brs), 9.02 (1 H, brs), 8.85 (1 H, d, J = 2.0 Hz), 8.81 (1 H, brs), 8.23 (1 H, d, J = 8.6 Hz), 8.11 (1 H, brs), 7.69 (1 H, brs), 7.49 (1 H, s), 4.09-4.02 (1 H, m), 3.84 (3H, s), 3.73 (1 H, brs), 3.09-2.99 (1 H, m), 2.11-2.04 (2H, m), 1.75-1.56 (6H, m), 1.41 (6H, d, J = 6.9 Hz). MS m/z (M + H): 429. |
| 0949 | 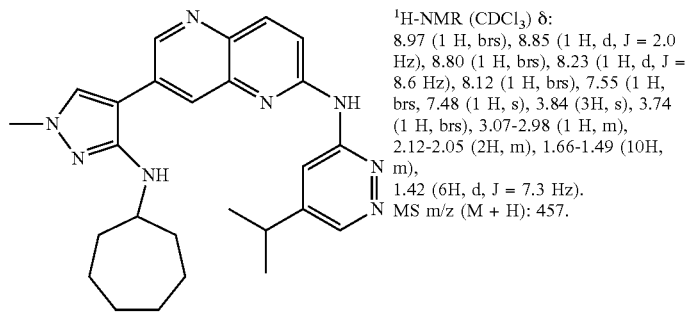 | $^1$H-NMR (CDCl$_3$) δ: 8.97 (1 H, brs), 8.85 (1 H, d, J = 2.0 Hz), 8.80 (1 H, brs), 8.23 (1 H, d, J = 8.6 Hz), 8.12 (1 H, brs), 7.55 (1 H, brs, 7.48 (1 H, s), 3.84 (3H, s), 3.74 (1 H, brs), 3.07-2.98 (1 H, m), 2.12-2.05 (2H, m), 1.66-1.49 (10H, m), 1.42 (6H, d, J = 7.3 Hz). MS m/z (M + H): 457. |

Example 0950

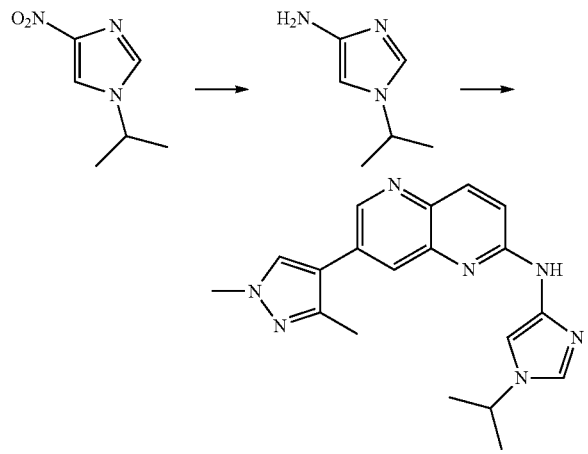

A mixture of 1-isopropyl-4-nitro-1H-imidazole (18 mg) and 2-methyltetrahydrofuran (3 mL) was reacted for 3 minutes using a flow-type hydrogenation reaction apparatus (1 bar, 1.0 mL/min, 30° C., 10% Pd/C). A mixture of tris(dibenzylideneacetone)dipalladium(0) (5 mg), 2-(dicyclohexylphosphino)-3,6-dimethoxy-2',4',6'-triisopropyl-1,1'-biphenyl (6 mg), and 2-methyltetrahydrofuran (0.5 mL)) which had been stirred at 120° C. for 5 minutes was added to the reaction mixture, followed by stirring at 80° C. for 3 hours. The reaction mixture was cooled to room temperature, the insolubles were filtered off, and the solvent was distilled off under reduced pressure. The obtained residue was purified by silica gel column chromatography (ethyl acetate-methanol, NH silica), thereby obtaining 7-(1,3-dimethyl-1H-pyrazol-4-yl)-N-(1-isopropyl-1H-imidazol-4-yl)-1,5-naphthyridine-2-amine (2.4 mg) as a yellow solid.

$^1$H-NMR(DMSO-d$_6$)δ:10.00(1H,brs),8.71(1H,d,J=2.0 Hz),8.17(1H,s),8.08(1H,s),7.99(1H,d,J=9.2 Hz),7.82(1H,s),7.71(1H,brs),7.27(1H,d,J=9.2 Hz),4.50-4.41(1H,m),3.84 (3H,s),2.41(3H,s),1.48(6H,d,J=6.6 Hz).

MSm/z(M+H):348.

Example 0951

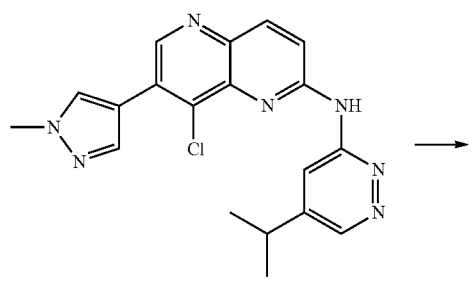

-continued

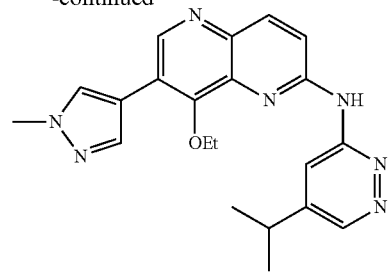

8-Ethoxy-N-(5-isopropylpyridazin-3-yl)-7-(1-methyl-1H-pyrazol-4-yl)-1,5-naphthyridine-2-amine was obtained as a a brown solid in the same manner as in Example 0355-1.

$^1$H-NMR(CD$_3$OD)δ:8.92(1H,s),8.75(2H,d,J=19.8 Hz), 8.31(1H,s),8.19-8.16(2H,m),7.63(1H,d,J=9.2 Hz),4.63(2H, q,J=7.3 Hz),4.00(3H,s),3.08-3.06(1H,m),1.41(9H,m).

MSm/z(M+H):380.

Example 0952

0952-1

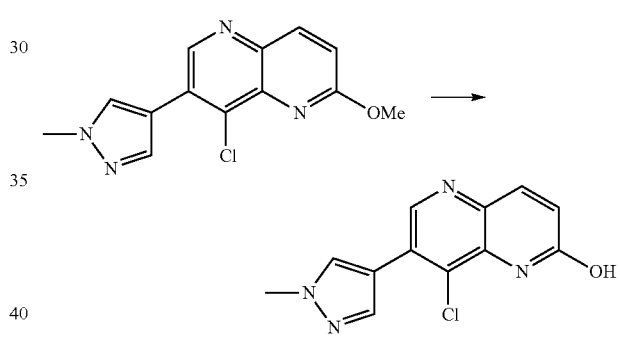

A mixture of 8-chloro-2-methoxy-7-(1-methyl-1H-pyrazol-4-yl)-1,5-naphthyridine (374 mg), 1,4-dioxane (8 mL), and 6 mol/L hydrochloric acid (5 mL) was stirred at 100° C. for 3.5 hours. The reaction mixture was cooled to room temperature, and the solvent was distilled off under reduced pressure. Water was added to the obtained residue, and the resultant product was neutralized with sodium hydrogen carbonate. The solid matter was collected by filtration, and washed with water and chloroform, thereby obtaining 8-chloro-7-(1-methyl-1H-pyrazol-4-yl)-1,5-naphthyridin-2-ol (264 mg) as a white solid.

MSm/z(M+H):261.

0952-2

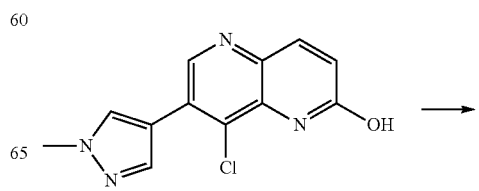

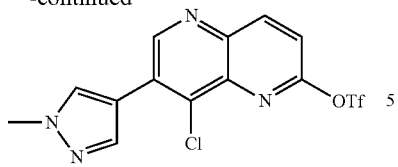

Trifluoromethanesulfonic acid anhydride (255 μL) was added to a mixture of 8-chloro-7-(1-methyl-1H-pyrazol-4-yl)-1,5-naphthyridin-2-ol (264 mg), triethylamine (0.43 mL), and dichloromethane (10 mL) at a temperature of from 0° C. to 5° C., followed by stirring at room temperature for 1 hour. After a saturated sodium hydrogen carbonate aqueous solution and ethyl acetate were added to the reaction mixture, an organic layer was collected therefrom by separation, washed with a saturated sodium chloride aqueous solution, and dried over anhydrous sodium sulfate, and the solvent was distilled off under reduced pressure. The obtained residue was purified by silica gel column chromatography (hexane-ethyl acetate-methanol), thereby obtaining 8-chloro-7-(1-methyl-1H-pyrazol-4-yl)-1,5-naphthyridin-2-yl trifluoromethanesulfonate (320 mg) as a pale brown solid.

MSm/z(M+H):393.

0952-3

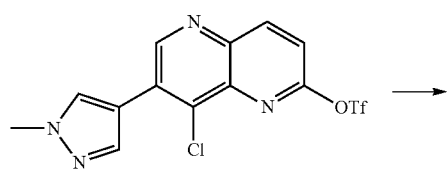

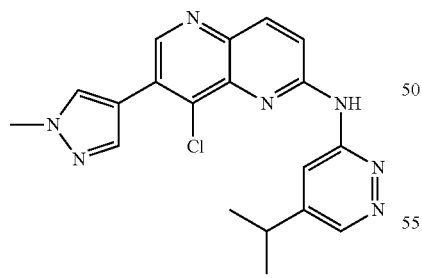

8-Chloro-N-(5-isopropylpyridazin-3-yl)-7-(1-methyl-1H-pyrazol-4-yl)-1,5-naphthyridine-2-amine was obtained as a pale yellow solid in the same manner as in Example 0646-3.

$^1$H-NMR(DMSO-d$_6$)δ:11.05(1H,s),9.26(1H,d,J=2.0 Hz), 8.99(1H,s),8.88(1H,d,J=2.0 Hz),8.57(1H,s),8.28(1H,d,J=9.2 Hz),8.19(1H,s),7.64(1H,d,J=9.2 Hz),3.97(3H,s),3.07-2.98(1H,m),1.34(6H,d,J=6.6 Hz).

MSm/z(M+H):380.

Example 0953

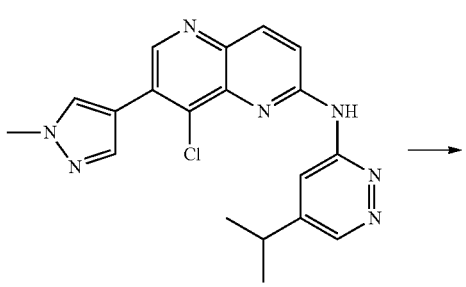

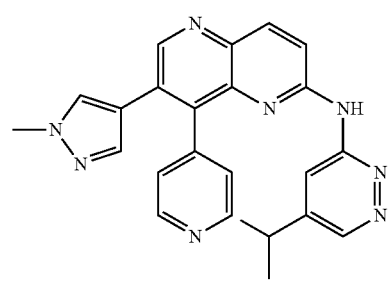

A mixture of 8-chloro-N-(5-isopropylpyridazin-3-yl)-7-(1-methyl-1H-pyrazol-4-yl)-1,5-naphthyridine-2-amine (9.6 mg), 4-pyridylboronic acid (6.9 mg), 1,1'-bis(diphenylphosphino)ferrocenepalladium(II) dichloride-dichloromethane complex (2.3 mg), tripotassium phosphate (17.1 mg), 1,2-dimethoxyethane (1.9 mL), and water (0.1 mL) was stirred at 130° C. for 1 hour using a microwave reaction apparatus. The reaction mixture was cooled to room temperature, and purified by silica gel column chromatography (methanol-ethyl acetate, NH silica), thereby obtaining N-(5-isopropylpyridazin-3-yl)-7-(1-methyl-1H-pyrazol-4-yl)-8-(pyridin-4-yl)-1,5-naphthyridine-2-amine (4.6 mg) as a brown solid.

$^1$H-NMR(CD$_3$OD)δ:8.91(1H,s),8.73-8.72(2H,m),8.66 (1H,s),8.26(1H,d,J=9.2 Hz),8.02(1H,s),7.54-7.51(4H,m), 7.13(1H,s),3.83(3H,s),2.40-2.38(1H,m),1.16(6H,d,J=6.6 Hz).

MSm/z(M+H):423.

Example 0954

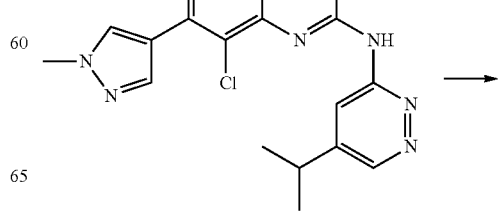

-continued

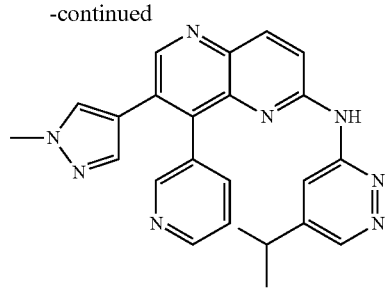

N-(5-isopropylpyridazin-3-yl)-7-(1-methyl-1H-pyrazol-4-yl)-8-(pyridin-3-yl)-1,5-naphthyridine-2-amine was obtained as a brown solid in the same manner as in Example 0953.

$^1$H-NMR(CD$_3$OD)δ:8.92(1H,s),8.71-8.66(2H,m),8.55 (1H,s),8.27(1H,d,J=9.2 Hz),8.02(1H,s),7.91-7.87(1H,m), 7.65-7.46(3H,m),7.06(1H,s),3.83(3H,s),2.48-2.45(1H,m), 1.16(6H,d,J=7.3 Hz).

MSm/z(M+H):423.

Example 0955

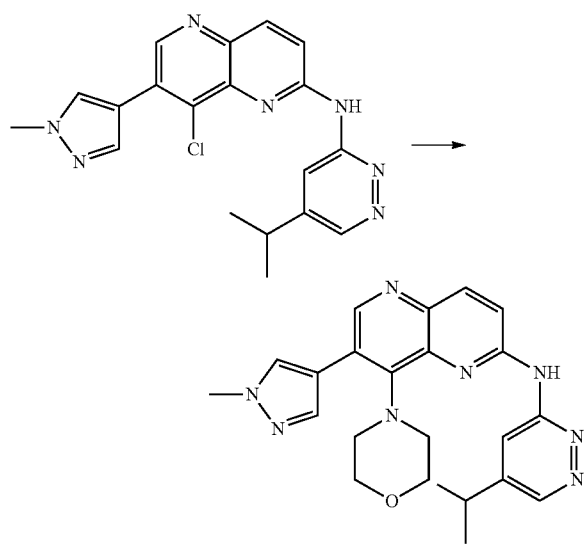

A mixture of 8-chloro-N-(5-isopropylpyridazin-3-yl)-7-(1-methyl-1H-pyrazol-4-yl)-1,5-naphthyridine-2-amine (5.3 mg) and morpholine (1 mL) was stirred at 150° C. for 1.5 hours, and further stirred at 160° C. for 14 hours, using a microwave reaction apparatus. The reaction mixture was cooled to room temperature, and purified by silica gel column chromatography (methanol-ethyl acetate, NH silica), thereby obtaining N-(5-isopropylpyridazin-3-yl)-7-(1-methyl-1H-pyrazol-4-yl)-8-morpholino-1,5-naphthyridine-2-amine (2.0 mg) as a pale brown solid.

$^1$H-NMR(CD$_3$OD)δ:8.80(1H,d,J=2.0 Hz),8.65(1H,s), 8.22(1H,s),8.19-8.17(2H,m),8.02(1H,s),7.77(1H,d,J=9.2 Hz),4.01(3H,s),3.80-3.79(4H,m),3.51-3.48(4H,m),3.19-3.14(1H,m),1.37(6H,d,J=6.6 Hz).

MSm/z(M+H):431.

Next, the utility of the compound of the invention will be described in the following Test Examples.

Test Example 1

PI3Kα Enzyme Assay

In a PI3Kα enzyme assay, a product (manufactured by Carna Biosciences, Inc.) obtained by biotinylating a human PI3Kα protein produced by using a baculovirus expression system was used. In addition, in the detection of enzyme activity, ADP-GLO KINASE ASSAY (trade name, manufactured by PROMEGA Corporation) was used.

10 μL of a reaction liquid (4.5 nmol/L PI3Kα, 40 mmol/L Tris-HCl, 20 mmol/L MgCl$_2$, 0.1% BSA, pH 7.5) including the human PI3Kα protein and a test compound having a predetermined concentration was allowed to stand at room temperature for 15 minutes. Then, 5 μL of a mixture liquid of L-α-phosphatidylinositol 4,5-diphosphate (PIP2) (manufactured by Sigma-Aldrich Co. LLC.) and ATP (manufactured by Sigma-Aldrich Co. LLC.), which are substrates, was added thereto such that final concentrations thereof became 50 μmol/L and 100 μmol/L, respectively, and an enzyme reaction was performed by allowing to stand at 25° C. for 60 minutes.

After the reaction, the enzyme reaction was stopped by adding 15 μL of an ADP-GLO REAGENT (trade name, manufactured by PROMEGA Corporation) thereto and allowing to stand at room temperature for 60 minutes. Then, 30 μL of a KINASE DETECTION REAGENT (trade name, manufactured by PROMEGA Corporation) was added thereto, followed by allowing to stand at room temperature for 40 minutes, and ADP produced by the enzyme reaction was quantified by emission intensity.

ENVISION (trade name, manufactured by Perkin Elmer Inc.) was used for the measurement of the emission intensity.

Test Example 2

ERK2 Enzyme Assay (1)

In an ERK2 enzyme assay, GLUTATHIONE S-TRANSFERASE (GST) FUSION HUMAN ERK2 PROTEIN (manufactured by Carna Biosciences, Inc.), which was produced by using an E. coli expression system, was used.

12 μL of a reaction liquid (2.5 nmol/L ERK2, 100 mmol/L Hepes, 10 mmol/L MgCl$_2$, 1.5 mmol/L DTT, 0.003% Brij35, pH 7.5) including ERK2 protein and a test compound having a predetermined concentration was allowed to stand at room temperature for 15 minutes. Then, 3 μL of a mixture liquid of FL-PEPTIDE8 (5-FAM-IPTSPITTTYFFFKKK-COOH) (manufactured by Caliper Life Sciences), which is substrate peptide, and ATP (manufactured by Sigma-Aldrich Co. LLC.) was added thereto such that the final concentrations thereof became 4.25 μmol/L and 43.1 μmol/L, respectively, and an enzyme reaction was performed by allowing to stand at 25° C. for 120 minutes.

After the reaction, the enzyme reaction was stopped by adding 30 μL of a reaction stopper liquid (100 mmol/L HEPES, 11.2 mmol/L EDTA, 5.6% Brij35, pH 7.5) including a 0.5% COATING REAGENT 8 (trade name, manufactured by Perkin Elmer Inc.) thereto. Then, phosphorylated peptide and non-phosphorylated peptide were separated using LABCHIP EZ READER (trade name, manufactured by Caliper Life Sciences), and the porportion of the phosphorylated peptide was quantified.

Test Example 2

ERK2 Enzyme Assay (2)

In an ERK2 enzyme assay, GLUTATHIONE S-TRANSFERASE (GST) FUSION HUMAN ERK2 PROTEIN (manufactured by Carna Biosciences, Inc.), which was produced by using an *E. coli* expression system, was used.

12 µL of a reaction liquid (1.25 nmol/L ERK2, 100 mmol/L Hepes, 10 mmol/L MgCl$_2$, 1.5 mmol/L DTT, 0.003% Brij35, pH 7.5) including ERK2 protein and a test compound having a predetermined concentration was allowed to stand at room temperature for 15 minutes. Then, 3 µL of a mixture liquid of FL-PEPTIDE8 (5-FAM-IP-TSPITTTYFFFKKK-COOH) (manufactured by Caliper Life Sciences), which is substrate peptide, and ATP (manufactured by Sigma-Aldrich Co. LLC.) was added thereto such that the final concentrations thereof became 4.25 µmol/L and 1 mmol/L, respectively, and an enzyme reaction was performed by allowing to stand at 25° C. for 120 minutes.

After the reaction, the enzyme reaction was stopped by adding 30 µL of a reaction stopper liquid (100 mmol/L HEPES, 11.2 mmol/L EDTA, 5.6% Brij35, pH 7.5) including a 0.5% COATING REAGENT 8 (trade name, manufactured by Perkin Elmer Inc.) thereto. Then, phosphorylated peptide and non-phosphorylated peptide were separated using LABCHIP EZ READER (trade name, manufactured by Caliper Life Sciences), and the porportion of the phosphorylated peptide was quantified.

The inhibitory activities of the compounds were evaluated using IC$_{50}$ (50% inhibitory concentration). The IC$_{50}$ was calculated using XLFIT (trade name, manufactured by ID Business Solutions).

The results are shown in Tables 1-1 to 1-10.

Evaluation Criteria
+++IC$_{50}$<1 µmol/L
++1 µmol/L≤IC$_{50}$<10 µmol/L
+10 µmol/L≤IC$_{50}$<50 µmol/L

TABLE 1-1

| Example No. | PI3Kα enzyme inhibitory activity | ERK2 enzyme inhibitory activity (1) | (2) |
|---|---|---|---|
| 0001 | +++ | +++ | |
| 0002 | +++ | +++ | |
| 0003 | ++ | +++ | |
| 0004 | +++ | +++ | |
| 0005 | +++ | | |
| 0006 | +++ | +++ | |
| 0007 | +++ | +++ | |
| 0008 | +++ | ++ | |
| 0009 | ++ | ++ | |
| 0010 | ++ | +++ | |
| 0011 | +++ | ++ | |
| 0012 | +++ | ++ | |
| 0013 | +++ | ++ | |
| 0014 | +++ | +++ | +++ |
| 0015 | +++ | +++ | +++ |
| 0016 | +++ | +++ | +++ |
| 0017 | +++ | +++ | +++ |
| 0018 | +++ | +++ | +++ |
| 0019 | +++ | +++ | |
| 0020 | +++ | +++ | |
| 0021 | +++ | +++ | +++ |
| 0022 | ++ | + | |
| 0023 | ++ | ++ | |
| 0024 | ++ | + | |
| 0025 | ++ | +++ | +++ |
| 0026 | +++ | +++ | +++ |
| 0027 | +++ | +++ | +++ |
| 0028 | | +++ | |
| 0029 | +++ | +++ | |
| 0030 | +++ | +++ | |
| 0031 | | ++ | |
| 0032 | +++ | +++ | +++ |

TABLE 1-1-continued

| Example No. | PI3Kα enzyme inhibitory activity | ERK2 enzyme inhibitory activity (1) | (2) |
|---|---|---|---|
| 0033 | ++ | ++ | |
| 0034 | ++ | | |
| 0035 | +++ | ++ | |
| 0036 | ++ | ++ | |
| 0037 | ++ | +++ | |
| 0038 | + | ++ | |
| 0039 | | +++ | |
| 0040 | + | +++ | |
| 0041 | + | +++ | |
| 0042 | | + | |
| 0043 | ++ | +++ | |
| 0044 | | ++ | |
| 0045 | + | +++ | |
| 0046 | ++ | +++ | |
| 0047 | +++ | | |
| 0048 | ++ | +++ | |
| 0049 | | ++ | |
| 0050 | ++ | +++ | |
| 0051 | ++ | +++ | |
| 0052 | ++ | +++ | |
| 0053 | ++ | +++ | |
| 0054 | +++ | +++ | |
| 0055 | ++ | +++ | |
| 0056 | + | +++ | |
| 0057 | + | ++ | |
| 0058 | ++ | +++ | |
| 0059 | ++ | +++ | |
| 0060 | + | +++ | |
| 0061 | ++ | +++ | |
| 0062 | ++ | +++ | |
| 0063 | +++ | +++ | |
| 0064 | ++ | +++ | |
| 0065 | ++ | +++ | |
| 0066 | +++ | +++ | |
| 0067 | +++ | +++ | |
| 0068 | ++ | +++ | |
| 0069 | + | ++ | |
| 0070 | +++ | +++ | |
| 0071 | +++ | +++ | +++ |
| 0072 | +++ | +++ | +++ |
| 0073 | +++ | +++ | |
| 0074 | +++ | +++ | |
| 0075 | +++ | ++ | |
| 0076 | +++ | +++ | |
| 0077 | ++ | ++ | |
| 0078 | +++ | +++ | |
| 0079 | ++ | +++ | |
| 0080 | | +++ | |
| 0081 | ++ | +++ | |
| 0082 | +++ | +++ | |
| 0083 | +++ | +++ | |
| 0084 | +++ | +++ | +++ |
| 0085 | +++ | +++ | +++ |
| 0086 | +++ | +++ | +++ |
| 0087 | +++ | +++ | +++ |
| 0088 | +++ | +++ | +++ |
| 0089 | +++ | +++ | +++ |
| 0090 | +++ | +++ | +++ |
| 0091 | +++ | +++ | +++ |
| 0092 | ++ | +++ | +++ |
| 0093 | ++ | +++ | + |
| 0094 | +++ | + | + |
| 0095 | +++ | +++ | ++ |
| 0096 | +++ | +++ | +++ |
| 0097 | +++ | +++ | |
| 0098 | +++ | +++ | |
| 0099 | +++ | +++ | |
| 0100 | ++ | +++ | |

TABLE 1-2

| Example No. | PI3Kα enzyme inhibitory activity | ERK2 enzyme inhibitory activity (1) | ERK2 enzyme inhibitory activity (2) |
|---|---|---|---|
| 0101 | +++ | +++ | |
| 0102 | +++ | +++ | |
| 0103 | +++ | +++ | |
| 0104 | ++ | +++ | |
| 0105 | +++ | +++ | |
| 0106 | +++ | +++ | |
| 0107 | +++ | +++ | |
| 0108 | ++ | +++ | |
| 0109 | +++ | ++ | |
| 0110 | +++ | +++ | |
| 0111 | | +++ | +++ |
| 0112 | +++ | +++ | +++ |
| 0113 | | +++ | +++ |
| 0114 | +++ | +++ | +++ |
| 0115 | +++ | +++ | +++ |
| 0116 | +++ | +++ | +++ |
| 0117 | +++ | +++ | +++ |
| 0118 | +++ | +++ | +++ |
| 0119 | +++ | +++ | |
| 0120 | +++ | +++ | +++ |
| 0121 | +++ | +++ | +++ |
| 0122 | +++ | +++ | +++ |
| 0123 | +++ | +++ | |
| 0124 | +++ | +++ | ++ |
| 0125 | +++ | +++ | |
| 0126 | +++ | +++ | |
| 0127 | ++ | +++ | |
| 0128 | +++ | +++ | |
| 0129 | +++ | +++ | ++ |
| 0130 | +++ | +++ | +++ |
| 0131 | +++ | +++ | +++ |
| 0132 | +++ | +++ | +++ |
| 0133 | +++ | +++ | +++ |
| 0134 | +++ | +++ | +++ |
| 0135 | +++ | +++ | ++ |
| 0136 | +++ | +++ | |
| 0137 | +++ | +++ | +++ |
| 0138 | +++ | +++ | +++ |
| 0139 | +++ | +++ | +++ |
| 0140 | +++ | +++ | +++ |
| 0141 | ++ | ++ | |
| 0142 | +++ | +++ | +++ |
| 0143 | ++ | +++ | |
| 0144 | +++ | +++ | |
| 0145 | +++ | +++ | +++ |
| 0146 | +++ | +++ | |
| 0147 | +++ | +++ | +++ |
| 0148 | +++ | +++ | +++ |
| 0149 | | ++ | |
| 0150 | +++ | +++ | ++ |
| 0151 | + | +++ | ++ |
| 0152 | ++ | +++ | |
| 0153 | ++ | +++ | |
| 0154 | ++ | +++ | |
| 0155 | ++ | +++ | |
| 0156 | +++ | +++ | |
| 0157 | +++ | +++ | +++ |
| 0158 | +++ | +++ | ++ |
| 0159 | +++ | +++ | +++ |
| 0160 | +++ | +++ | +++ |
| 0161 | +++ | +++ | +++ |
| 0162 | +++ | +++ | +++ |
| 0163 | +++ | +++ | +++ |
| 0164 | | +++ | |
| 0165 | + | +++ | |
| 0166 | ++ | +++ | |
| 0167 | +++ | +++ | +++ |
| 0168 | | +++ | |
| 0169 | | +++ | +++ |
| 0170 | ++ | +++ | |
| 0171 | + | +++ | |
| 0172 | +++ | +++ | +++ |
| 0173 | ++ | +++ | +++ |
| 0174 | | +++ | |
| 0175 | +++ | +++ | |
| 0176 | +++ | +++ | |
| 0177 | +++ | +++ | |
| 0178 | +++ | +++ | |
| 0179 | +++ | +++ | |
| 0180 | ++ | +++ | |
| 0181 | +++ | +++ | |
| 0182 | ++ | +++ | |
| 0183 | ++ | +++ | |
| 0184 | ++ | +++ | |
| 0185 | +++ | +++ | |
| 0186 | +++ | +++ | |
| 0187 | +++ | +++ | |
| 0188 | +++ | +++ | |
| 0189 | +++ | +++ | +++ |
| 0190 | ++ | +++ | |
| 0191 | +++ | +++ | |
| 0192 | +++ | +++ | |
| 0193 | +++ | +++ | |
| 0194 | ++ | +++ | |
| 0195 | ++ | +++ | |
| 0196 | ++ | +++ | |
| 0197 | +++ | +++ | |
| 0198 | | +++ | |
| 0199 | ++ | ++ | |
| 0200 | ++ | ++ | |

TABLE 1-3

| Example No. | PI3Kα enzyme inhibitory activity | ERK2 enzyme inhibitory activity (1) | ERK2 enzyme inhibitory activity (2) |
|---|---|---|---|
| 0201 | ++ | +++ | |
| 0202 | + | +++ | |
| 0203 | | +++ | |
| 0204 | | +++ | |
| 0205 | +++ | +++ | |
| 0206 | + | +++ | |
| 0207 | +++ | +++ | |
| 0208 | +++ | +++ | |
| 0209 | +++ | +++ | |
| 0210 | +++ | +++ | |
| 0211 | | +++ | |
| 0212 | | +++ | |
| 0213 | | +++ | |
| 0214 | ++ | +++ | +++ |
| 0215 | ++ | +++ | +++ |
| 0216 | | +++ | |
| 0217 | | +++ | +++ |
| 0218 | | +++ | |
| 0219 | + | ++ | |
| 0220 | +++ | ++ | |
| 0221 | +++ | +++ | |
| 0222 | +++ | +++ | |
| 0223 | ++ | +++ | |
| 0224 | +++ | +++ | |
| 0225 | ++ | +++ | |
| 0226 | ++ | +++ | +++ |
| 0227 | +++ | +++ | +++ |
| 0228 | +++ | +++ | |
| 0229 | +++ | +++ | |
| 0230 | | +++ | |
| 0231 | +++ | +++ | |
| 0232 | +++ | +++ | |
| 0233 | +++ | +++ | |
| 0234 | +++ | +++ | |
| 0235 | +++ | +++ | +++ |
| 0236 | +++ | +++ | +++ |
| 0237 | +++ | +++ | |
| 0238 | +++ | +++ | |
| 0239 | +++ | +++ | |

TABLE 1-3-continued

| Example No. | PI3Kα enzyme inhibitory activity | ERK2 enzyme inhibitory activity (1) | ERK2 enzyme inhibitory activity (2) |
| --- | --- | --- | --- |
| 0240 | +++ | +++ | +++ |
| 0241 | ++ | +++ | +++ |
| 0242 | +++ | +++ | +++ |
| 0243 | +++ | +++ | +++ |
| 0244 | +++ | +++ | |
| 0245 | +++ | +++ | |
| 0246 | ++ | +++ | +++ |
| 0247 | ++ | +++ | +++ |
| 0248 | ++ | +++ | +++ |
| 0249 | +++ | +++ | |
| 0250 | +++ | +++ | +++ |
| 0251 | ++ | +++ | +++ |
| 0252 | ++ | +++ | +++ |
| 0253 | ++ | +++ | +++ |
| 0254 | +++ | +++ | |
| 0255 | ++ | +++ | |
| 0256 | +++ | +++ | |
| 0257 | ++ | +++ | +++ |
| 0258 | +++ | +++ | +++ |
| 0259 | +++ | +++ | |
| 0260 | +++ | +++ | |
| 0261 | +++ | +++ | +++ |
| 0262 | +++ | +++ | +++ |
| 0263 | +++ | +++ | |
| 0264 | ++ | +++ | |
| 0265 | +++ | +++ | +++ |
| 0266 | +++ | +++ | +++ |
| 0267 | +++ | +++ | +++ |
| 0268 | +++ | +++ | |
| 0269 | +++ | +++ | |
| 0270 | +++ | +++ | |
| 0271 | | +++ | |
| 0272 | ++ | +++ | |
| 0273 | +++ | +++ | |
| 0274 | +++ | ++ | |
| 0275 | +++ | +++ | |
| 0276 | +++ | +++ | ++ |
| 0277 | ++ | ++ | |
| 0278 | +++ | +++ | |
| 0279 | +++ | +++ | |
| 0280 | + | ++ | |
| 0281 | ++ | ++ | |
| 0282 | ++ | ++ | |
| 0283 | +++ | +++ | |
| 0284 | +++ | ++ | |
| 0285 | +++ | +++ | |
| 0286 | ++ | ++ | |
| 0287 | +++ | +++ | |
| 0288 | +++ | +++ | |
| 0289 | +++ | ++ | |
| 0290 | +++ | +++ | +++ |
| 0291 | +++ | +++ | +++ |
| 0292 | +++ | +++ | +++ |
| 0293 | +++ | +++ | +++ |
| 0294 | +++ | +++ | +++ |
| 0295 | +++ | +++ | +++ |
| 0296 | +++ | +++ | |
| 0297 | +++ | +++ | |
| 0298 | +++ | +++ | |
| 0299 | + | +++ | |
| 0300 | ++ | +++ | |

TABLE 1-4

| Example No. | PI3Kα enzyme inhibitory activity | ERK2 enzyme inhibitory activity (1) | ERK2 enzyme inhibitory activity (2) |
| --- | --- | --- | --- |
| 0301 | +++ | +++ | |
| 0302 | +++ | +++ | |
| 0303 | +++ | +++ | +++ |
| 0304 | +++ | +++ | |
| 0305 | +++ | +++ | |
| 0306 | +++ | +++ | |
| 0307 | +++ | +++ | |
| 0308 | ++ | +++ | |
| 0309 | ++ | +++ | |
| 0310 | ++ | +++ | |
| 0311 | ++ | +++ | +++ |
| 0312 | +++ | +++ | |
| 0313 | ++ | +++ | |
| 0314 | ++ | +++ | |
| 0315 | ++ | +++ | |
| 0316 | +++ | +++ | +++ |
| 0317 | +++ | +++ | |
| 0318 | +++ | +++ | +++ |
| 0319 | +++ | +++ | |
| 0320 | +++ | +++ | +++ |
| 0321 | +++ | +++ | +++ |
| 0322 | +++ | +++ | +++ |
| 0323 | +++ | +++ | |
| 0324 | +++ | +++ | |
| 0325 | +++ | +++ | |
| 0326 | +++ | +++ | |
| 0327 | ++ | +++ | +++ |
| 0328 | | +++ | |
| 0329 | +++ | +++ | |
| 0330 | ++ | +++ | |
| 0331 | | ++ | |
| 0332 | + | +++ | |
| 0333 | ++ | +++ | |
| 0334 | +++ | +++ | |
| 0335 | + | +++ | |
| 0336 | +++ | +++ | +++ |
| 0337 | +++ | +++ | +++ |
| 0338 | +++ | +++ | +++ |
| 0339 | +++ | +++ | +++ |
| 0340 | | +++ | |
| 0341 | +++ | +++ | +++ |
| 0342 | +++ | +++ | +++ |
| 0343 | +++ | +++ | +++ |
| 0344 | +++ | +++ | +++ |
| 0345 | +++ | +++ | +++ |
| 0346 | +++ | +++ | +++ |
| 0347 | +++ | +++ | +++ |
| 0348 | ++ | +++ | +++ |
| 0349 | | +++ | ++ |
| 0350 | ++ | +++ | +++ |
| 0351 | +++ | +++ | +++ |
| 0352 | +++ | +++ | +++ |
| 0353 | +++ | +++ | +++ |
| 0354 | +++ | +++ | +++ |
| 0355 | +++ | +++ | +++ |
| 0356 | +++ | +++ | +++ |
| 0357 | | ++ | ++ |
| 0358 | +++ | +++ | +++ |
| 0359 | +++ | +++ | ++ |
| 0360 | +++ | +++ | +++ |
| 0361 | ++ | +++ | |
| 0362 | +++ | +++ | |
| 0363 | +++ | +++ | |
| 0364 | +++ | +++ | +++ |
| 0365 | +++ | +++ | +++ |
| 0366 | +++ | +++ | |
| 0367 | +++ | +++ | |
| 0368 | +++ | +++ | +++ |
| 0369 | ++ | +++ | |
| 0370 | +++ | +++ | +++ |
| 0371 | +++ | +++ | |
| 0372 | ++ | +++ | +++ |
| 0373 | +++ | +++ | |
| 0374 | +++ | +++ | |
| 0375 | +++ | +++ | |
| 0376 | +++ | +++ | |
| 0377 | +++ | +++ | |
| 0378 | +++ | +++ | |

TABLE 1-4-continued

| Example No. | PI3Kα enzyme inhibitory activity | ERK2 enzyme inhibitory activity (1) | ERK2 enzyme inhibitory activity (2) |
|---|---|---|---|
| 0379 | +++ | +++ | |
| 0380 | +++ | +++ | |
| 0381 | +++ | +++ | |
| 0382 | +++ | +++ | +++ |
| 0383 | ++ | +++ | +++ |
| 0384 | +++ | +++ | +++ |
| 0385 | +++ | +++ | |
| 0386 | +++ | +++ | |
| 0387 | +++ | +++ | |
| 0388 | ++ | +++ | |
| 0389 | +++ | +++ | |
| 0390 | +++ | +++ | |
| 0391 | +++ | +++ | |
| 0392 | +++ | +++ | |
| 0393 | ++ | +++ | |
| 0394 | +++ | +++ | |
| 0395 | +++ | +++ | |
| 0396 | + | +++ | |
| 0397 | +++ | +++ | |
| 0398 | +++ | +++ | |
| 0399 | ++ | +++ | |
| 0400 | +++ | +++ | |

TABLE 1-5

| Example No. | PI3Kα enzyme inhibitory activity | ERK2 enzyme inhibitory activity (1) | ERK2 enzyme inhibitory activity (2) |
|---|---|---|---|
| 0401 | +++ | +++ | +++ |
| 0402 | +++ | +++ | +++ |
| 0403 | +++ | +++ | +++ |
| 0404 | +++ | +++ | |
| 0405 | +++ | +++ | |
| 0406 | +++ | +++ | |
| 0407 | ++ | +++ | |
| 0408 | | +++ | |
| 0409 | +++ | ++ | |
| 0410 | +++ | | +++ |
| 0411 | +++ | | +++ |
| 0412 | +++ | | +++ |
| 0413 | +++ | | +++ |
| 0414 | +++ | | +++ |
| 0415 | +++ | | +++ |
| 0416 | +++ | | +++ |
| 0417 | +++ | | +++ |
| 0418 | +++ | | +++ |
| 0419 | +++ | | +++ |
| 0420 | +++ | | +++ |
| 0421 | +++ | | +++ |
| 0422 | +++ | | +++ |
| 0423 | +++ | | +++ |
| 0424 | +++ | | +++ |
| 0425 | +++ | | +++ |
| 0426 | +++ | | +++ |
| 0427 | +++ | | +++ |
| 0428 | +++ | | +++ |
| 0429 | +++ | | +++ |
| 0430 | +++ | | +++ |
| 0431 | +++ | | +++ |
| 0432 | +++ | | +++ |
| 0433 | +++ | | +++ |
| 0434 | +++ | | +++ |
| 0435 | +++ | | +++ |
| 0436 | +++ | | +++ |
| 0437 | +++ | | +++ |
| 0438 | +++ | | +++ |
| 0439 | +++ | | +++ |
| 0440 | +++ | | +++ |
| 0441 | +++ | | +++ |
| 0442 | +++ | | +++ |

TABLE 1-5-continued

| Example No. | PI3Kα enzyme inhibitory activity | ERK2 enzyme inhibitory activity (1) | ERK2 enzyme inhibitory activity (2) |
|---|---|---|---|
| 0443 | +++ | | +++ |
| 0444 | +++ | | +++ |
| 0445 | +++ | | +++ |
| 0446 | +++ | | +++ |
| 0447 | +++ | | ++ |
| 0448 | +++ | | ++ |
| 0449 | +++ | | +++ |
| 0450 | +++ | | +++ |
| 0451 | +++ | | +++ |
| 0452 | +++ | | +++ |
| 0453 | +++ | | +++ |
| 0454 | +++ | | +++ |
| 0455 | +++ | | +++ |
| 0456 | +++ | | +++ |
| 0457 | +++ | | + |
| 0458 | +++ | | + |
| 0459 | +++ | | +++ |
| 0460 | +++ | | +++ |
| 0461 | +++ | | +++ |
| 0462 | +++ | | +++ |
| 0463 | +++ | | +++ |
| 0464 | +++ | | +++ |
| 0465 | +++ | | +++ |
| 0466 | +++ | | +++ |
| 0467 | +++ | | +++ |
| 0468 | +++ | | +++ |
| 0469 | +++ | | +++ |
| 0470 | +++ | | +++ |
| 0471 | +++ | +++ | +++ |
| 0472 | +++ | +++ | +++ |
| 0473 | +++ | +++ | +++ |
| 0474 | +++ | +++ | +++ |
| 0475 | +++ | +++ | +++ |
| 0476 | +++ | +++ | |
| 0477 | +++ | +++ | |
| 0478 | +++ | | +++ |
| 0479 | +++ | | +++ |
| 0480 | +++ | | +++ |
| 0481 | ++ | | +++ |
| 0482 | +++ | | +++ |
| 0483 | +++ | | +++ |
| 0484 | +++ | | +++ |
| 0485 | +++ | | +++ |
| 0486 | +++ | | +++ |
| 0487 | +++ | | +++ |
| 0488 | +++ | | +++ |
| 0489 | + | | ++ |
| 0490 | +++ | | +++ |
| 0491 | +++ | | +++ |
| 0492 | +++ | | +++ |
| 0493 | +++ | | +++ |
| 0494 | +++ | | +++ |
| 0495 | +++ | | +++ |
| 0496 | +++ | | +++ |
| 0497 | ++ | | +++ |
| 0498 | +++ | | +++ |
| 0499 | +++ | | +++ |
| 0500 | +++ | | +++ |

TABLE 1-6

| Example No. | PI3Kα enzyme inhibitory activity | ERK2 enzyme inhibitory activity (1) | ERK2 enzyme inhibitory activity (2) |
|---|---|---|---|
| 0501 | ++ | | ++ |
| 0502 | +++ | | +++ |
| 0503 | +++ | | +++ |
| 0504 | +++ | | +++ |
| 0505 | ++ | | +++ |
| 0506 | ++ | | +++ |

TABLE 1-6-continued

| Example No. | PI3Kα enzyme inhibitory activity | ERK2 enzyme inhibitory activity (1) | ERK2 enzyme inhibitory activity (2) |
|---|---|---|---|
| 0507 | +++ | | +++ |
| 0508 | +++ | | +++ |
| 0509 | ++ | | +++ |
| 0510 | ++ | | +++ |
| 0511 | ++ | | +++ |
| 0512 | ++ | | +++ |
| 0513 | | | +++ |
| 0514 | ++ | | +++ |
| 0515 | +++ | | +++ |
| 0516 | + | | |
| 0517 | +++ | | +++ |
| 0518 | +++ | | +++ |
| 0519 | ++ | | +++ |
| 0520 | ++ | | +++ |
| 0521 | +++ | | +++ |
| 0522 | +++ | | +++ |
| 0523 | +++ | | +++ |
| 0524 | + | | +++ |
| 0525 | +++ | | +++ |
| 0526 | +++ | | +++ |
| 0527 | +++ | | ++ |
| 0528 | +++ | | +++ |
| 0529 | +++ | | +++ |
| 0530 | +++ | | +++ |
| 0531 | +++ | | +++ |
| 0532 | +++ | | +++ |
| 0533 | +++ | | +++ |
| 0534 | +++ | | +++ |
| 0535 | +++ | | +++ |
| 0536 | +++ | | +++ |
| 0537 | +++ | | +++ |
| 0538 | +++ | | +++ |
| 0539 | +++ | | +++ |
| 0540 | +++ | | ++ |
| 0541 | +++ | | ++ |
| 0542 | +++ | | +++ |
| 0543 | +++ | | +++ |
| 0544 | +++ | | +++ |
| 0545 | +++ | | +++ |
| 0546 | +++ | | |
| 0547 | +++ | | +++ |
| 0548 | +++ | | +++ |
| 0549 | +++ | | +++ |
| 0550 | +++ | | +++ |
| 0551 | +++ | | + |
| 0552 | +++ | | +++ |
| 0553 | +++ | | +++ |
| 0554 | +++ | | +++ |
| 0555 | +++ | | +++ |
| 0556 | +++ | | +++ |
| 0557 | +++ | | +++ |
| 0558 | +++ | | +++ |
| 0559 | + | | +++ |
| 0560 | +++ | | +++ |
| 0561 | +++ | | +++ |
| 0562 | +++ | | +++ |
| 0563 | +++ | | +++ |
| 0564 | +++ | | +++ |
| 0565 | +++ | | +++ |
| 0566 | +++ | | +++ |
| 0567 | +++ | | +++ |
| 0568 | +++ | | +++ |
| 0569 | +++ | | +++ |
| 0570 | | | +++ |
| 0571 | +++ | | +++ |
| 0572 | +++ | | +++ |
| 0573 | +++ | | +++ |
| 0574 | ++ | | +++ |
| 0575 | +++ | | +++ |
| 0576 | +++ | | +++ |
| 0577 | +++ | | +++ |
| 0578 | +++ | | +++ |
| 0579 | +++ | | +++ |
| 0580 | +++ | | +++ |
| 0581 | +++ | | +++ |
| 0582 | +++ | | +++ |
| 0583 | +++ | | +++ |
| 0584 | +++ | | +++ |
| 0585 | +++ | | +++ |
| 0586 | +++ | | +++ |
| 0587 | +++ | | +++ |
| 0588 | ++ | +++ | +++ |
| 0589 | +++ | +++ | +++ |
| 0590 | ++ | | +++ |
| 0591 | ++ | | +++ |
| 0592 | +++ | | +++ |
| 0593 | ++ | | +++ |
| 0594 | +++ | | +++ |
| 0595 | ++ | | +++ |
| 0596 | +++ | | +++ |
| 0597 | ++ | | +++ |
| 0598 | ++ | | +++ |
| 0599 | ++ | | +++ |
| 0600 | ++ | | +++ |

TABLE 1-7

| Example No. | PI3Kα enzyme inhibitory activity | ERK2 enzyme inhibitory activity (1) | ERK2 enzyme inhibitory activity (2) |
|---|---|---|---|
| 0601 | ++ | | +++ |
| 0602 | +++ | | +++ |
| 0603 | +++ | | +++ |
| 0604 | + | | +++ |
| 0605 | +++ | | +++ |
| 0606 | ++ | | +++ |
| 0607 | +++ | | +++ |
| 0608 | +++ | | +++ |
| 0609 | +++ | | +++ |
| 0610 | +++ | | +++ |
| 0611 | +++ | | +++ |
| 0612 | +++ | | +++ |
| 0613 | +++ | | +++ |
| 0614 | +++ | | +++ |
| 0615 | +++ | | +++ |
| 0616 | +++ | | +++ |
| 0617 | +++ | | +++ |
| 0618 | +++ | | +++ |
| 0619 | +++ | | +++ |
| 0620 | +++ | | +++ |
| 0621 | ++ | | +++ |
| 0622 | +++ | | +++ |
| 0623 | ++ | | ++ |
| 0624 | ++ | | +++ |
| 0625 | +++ | | ++ |
| 0626 | +++ | | +++ |
| 0627 | ++ | | +++ |
| 0628 | + | | +++ |
| 0629 | +++ | | +++ |
| 0630 | +++ | | +++ |
| 0631 | +++ | | +++ |
| 0632 | +++ | | ++ |
| 0633 | +++ | | +++ |
| 0634 | +++ | | +++ |
| 0635 | +++ | | +++ |
| 0636 | +++ | | +++ |
| 0637 | +++ | | +++ |
| 0638 | ++ | | +++ |
| 0639 | ++ | | + |
| 0640 | ++ | | +++ |
| 0641 | +++ | | +++ |
| 0642 | ++ | | +++ |
| 0643 | | | + |
| 0644 | +++ | | +++ |
| 0645 | +++ | | +++ |

TABLE 1-7-continued

| Example No. | PI3Kα enzyme inhibitory activity | ERK2 enzyme inhibitory activity (1) | ERK2 enzyme inhibitory activity (2) |
|---|---|---|---|
| 0646 | +++ | | +++ |
| 0647 | +++ | | ++ |
| 0648 | +++ | | +++ |
| 0649 | +++ | | +++ |
| 0650 | +++ | | +++ |
| 0651 | +++ | | +++ |
| 0652 | +++ | | +++ |
| 0653 | +++ | | +++ |
| 0654 | +++ | | ++ |
| 0655 | ++ | | ++ |
| 0656 | +++ | | ++ |
| 0657 | +++ | | +++ |
| 0658 | +++ | | +++ |
| 0659 | +++ | | +++ |
| 0660 | +++ | | +++ |
| 0661 | +++ | | +++ |
| 0662 | +++ | | ++ |
| 0663 | ++ | | ++ |
| 0664 | ++ | | ++ |
| 0665 | +++ | | +++ |
| 0666 | +++ | | +++ |
| 0667 | +++ | | +++ |
| 0668 | | | ++ |
| 0669 | ++ | | ++ |
| 0670 | +++ | | +++ |
| 0671 | +++ | | +++ |
| 0672 | +++ | | +++ |
| 0673 | +++ | | +++ |
| 0674 | +++ | | +++ |
| 0675 | + | | |
| 0676 | +++ | | +++ |
| 0677 | ++ | | |
| 0678 | +++ | | +++ |
| 0679 | +++ | | +++ |
| 0680 | +++ | | +++ |
| 0681 | +++ | | +++ |
| 0682 | +++ | | +++ |
| 0683 | +++ | | +++ |
| 0684 | +++ | | +++ |
| 0685 | +++ | | +++ |
| 0686 | +++ | | +++ |
| 0687 | +++ | | +++ |
| 0688 | +++ | | +++ |
| 0689 | +++ | | +++ |
| 0690 | +++ | | +++ |
| 0691 | +++ | | +++ |
| 0692 | +++ | | +++ |
| 0693 | +++ | | +++ |
| 0694 | +++ | | +++ |
| 0695 | +++ | | +++ |
| 0696 | +++ | | +++ |
| 0697 | +++ | | +++ |
| 0698 | ++ | | +++ |
| 0699 | +++ | | +++ |
| 0700 | +++ | | +++ |

TABLE 1-8

| Example No. | PI3Kα enzyme inhibitory activity | ERK2 enzyme inhibitory activity (1) | ERK2 enzyme inhibitory activity (2) |
|---|---|---|---|
| 0701 | +++ | | +++ |
| 0702 | +++ | | +++ |
| 0703 | +++ | | +++ |
| 0704 | +++ | | +++ |
| 0705 | +++ | | +++ |
| 0706 | +++ | | +++ |
| 0707 | +++ | | +++ |
| 0708 | +++ | | +++ |
| 0709 | +++ | | +++ |
| 0710 | +++ | | +++ |
| 0711 | +++ | | +++ |
| 0712 | +++ | | +++ |
| 0713 | +++ | | +++ |
| 0714 | +++ | | +++ |
| 0715 | +++ | | +++ |
| 0716 | +++ | | +++ |
| 0717 | +++ | | +++ |
| 0718 | +++ | | +++ |
| 0719 | +++ | | +++ |
| 0720 | +++ | | +++ |
| 0721 | +++ | | +++ |
| 0722 | +++ | | +++ |
| 0723 | +++ | | +++ |
| 0724 | +++ | | +++ |
| 0725 | +++ | | +++ |
| 0726 | +++ | | +++ |
| 0727 | +++ | | +++ |
| 0728 | +++ | | +++ |
| 0729 | +++ | | +++ |
| 0730 | +++ | | +++ |
| 0731 | +++ | | +++ |
| 0732 | +++ | | +++ |
| 0733 | +++ | | +++ |
| 0734 | +++ | | +++ |
| 0735 | +++ | | +++ |
| 0736 | +++ | | ++ |
| 0737 | +++ | | +++ |
| 0738 | +++ | | +++ |
| 0739 | ++ | | +++ |
| 0740 | +++ | | +++ |
| 0741 | +++ | | +++ |
| 0742 | +++ | | +++ |
| 0743 | +++ | | +++ |
| 0744 | +++ | | +++ |
| 0745 | +++ | | +++ |
| 0746 | +++ | | +++ |
| 0747 | +++ | | +++ |
| 0748 | +++ | | +++ |
| 0749 | +++ | | +++ |
| 0750 | +++ | | +++ |
| 0751 | +++ | | +++ |
| 0752 | +++ | | +++ |
| 0753 | +++ | | |
| 0754 | +++ | | +++ |
| 0755 | +++ | | +++ |
| 0756 | +++ | | +++ |
| 0757 | +++ | | +++ |
| 0758 | ++ | | +++ |
| 0759 | +++ | | +++ |
| 0760 | +++ | | +++ |
| 0761 | +++ | | +++ |
| 0762 | +++ | | |
| 0763 | | | +++ |
| 0764 | +++ | | +++ |
| 0765 | +++ | | +++ |
| 0766 | +++ | | +++ |
| 0767 | +++ | | +++ |
| 0768 | +++ | | ++ |
| 0769 | +++ | | +++ |
| 0770 | +++ | | +++ |
| 0771 | +++ | | +++ |
| 0772 | +++ | | +++ |
| 0773 | +++ | | +++ |
| 0774 | +++ | | +++ |
| 0775 | +++ | | |
| 0776 | + | | |
| 0777 | +++ | | +++ |
| 0778 | +++ | | +++ |
| 0779 | +++ | | +++ |
| 0780 | +++ | | +++ |
| 0781 | +++ | | +++ |
| 0782 | +++ | | +++ |
| 0783 | +++ | | +++ |
| 0784 | +++ | | +++ |

TABLE 1-8-continued

| Example No. | PI3Kα enzyme inhibitory activity | ERK2 enzyme inhibitory activity (1) | ERK2 enzyme inhibitory activity (2) |
|---|---|---|---|
| 0785 | +++ | | +++ |
| 0786 | +++ | | +++ |
| 0787 | +++ | | +++ |
| 0788 | +++ | | +++ |
| 0789 | +++ | | +++ |
| 0790 | +++ | | +++ |
| 0791 | +++ | | +++ |
| 0792 | +++ | | +++ |
| 0793 | +++ | | ++ |
| 0794 | +++ | | +++ |
| 0795 | +++ | | +++ |
| 0796 | +++ | | +++ |
| 0797 | +++ | | +++ |
| 0798 | +++ | | +++ |
| 0799 | +++ | | +++ |
| 0800 | +++ | | +++ |

TABLE 1-9

| Example No. | PI3Kα enzyme inhibitory activity | ERK2 enzyme inhibitory activity (1) | ERK2 enzyme inhibitory activity (2) |
|---|---|---|---|
| 0801 | ++ | | +++ |
| 0802 | +++ | | +++ |
| 0803 | +++ | | +++ |
| 0804 | +++ | | +++ |
| 0805 | +++ | | +++ |
| 0806 | +++ | | +++ |
| 0807 | +++ | | +++ |
| 0808 | ++ | | +++ |
| 0809 | +++ | | +++ |
| 0810 | +++ | | +++ |
| 0811 | +++ | | +++ |
| 0812 | +++ | | +++ |
| 0813 | +++ | | +++ |
| 0814 | +++ | | +++ |
| 0815 | +++ | | +++ |
| 0816 | +++ | | +++ |
| 0817 | +++ | | +++ |
| 0818 | +++ | | +++ |
| 0819 | +++ | | +++ |
| 0820 | +++ | | +++ |
| 0821 | +++ | | +++ |
| 0822 | +++ | | +++ |
| 0823 | +++ | | +++ |
| 0824 | +++ | | +++ |
| 0825 | +++ | | +++ |
| 0826 | +++ | | +++ |
| 0827 | +++ | | +++ |
| 0828 | +++ | | +++ |
| 0829 | +++ | | +++ |
| 0830 | +++ | | +++ |
| 0831 | +++ | | +++ |
| 0832 | +++ | | +++ |
| 0833 | +++ | | +++ |
| 0834 | +++ | | +++ |
| 0835 | +++ | | +++ |
| 0836 | +++ | | ++ |
| 0837 | ++ | | +++ |
| 0838 | +++ | | +++ |
| 0839 | + | | ++ |
| 0840 | ++ | | ++ |
| 0841 | ++ | | ++ |
| 0842 | ++ | | ++ |
| 0843 | +++ | | +++ |
| 0844 | +++ | | +++ |
| 0845 | ++ | | +++ |
| 0846 | ++ | | +++ |
| 0847 | ++ | | +++ |
| 0848 | ++ | | ++ |

TABLE 1-9-continued

| Example No. | PI3Kα enzyme inhibitory activity | ERK2 enzyme inhibitory activity (1) | ERK2 enzyme inhibitory activity (2) |
|---|---|---|---|
| 0849 | ++ | | +++ |
| 0850 | +++ | | +++ |
| 0851 | ++ | | +++ |
| 0852 | +++ | | +++ |
| 0853 | +++ | | +++ |
| 0854 | +++ | | +++ |
| 0855 | +++ | | +++ |
| 0856 | ++ | | +++ |
| 0857 | ++ | | +++ |
| 0858 | ++ | | +++ |
| 0859 | ++ | | +++ |
| 0860 | ++ | | ++ |
| 0861 | +++ | | +++ |
| 0862 | +++ | | +++ |
| 0863 | ++ | | +++ |
| 0864 | +++ | | +++ |
| 0865 | ++ | | ++ |
| 0866 | ++ | | |
| 0867 | +++ | | +++ |
| 0868 | ++ | | +++ |
| 0869 | ++ | | +++ |
| 0870 | ++ | | ++ |
| 0871 | ++ | | ++ |
| 0872 | +++ | | +++ |
| 0873 | +++ | | +++ |
| 0874 | +++ | | +++ |
| 0875 | ++ | | +++ |
| 0876 | ++ | | ++ |
| 0877 | +++ | | ++ |
| 0878 | +++ | | ++ |
| 0879 | +++ | | +++ |
| 0880 | +++ | | +++ |
| 0881 | ++ | | +++ |
| 0882 | +++ | | +++ |
| 0883 | +++ | | +++ |
| 0884 | ++ | | +++ |
| 0885 | +++ | | +++ |
| 0886 | +++ | | +++ |
| 0887 | +++ | | ++ |
| 0888 | ++ | | ++ |
| 0889 | + | | + |
| 0890 | +++ | | ++ |
| 0891 | ++ | | +++ |
| 0892 | ++ | | ++ |
| 0893 | +++ | | +++ |
| 0894 | +++ | | ++ |
| 0895 | ++ | | +++ |
| 0896 | ++ | | ++ |
| 0897 | +++ | | +++ |
| 0898 | +++ | | ++ |
| 0899 | ++ | | ++ |
| 0900 | +++ | | ++ |

TABLE 1-10

| Example No. | PI3Kα enzyme inhibitory activity | ERK2 enzyme inhibitory activity (1) | ERK2 enzyme inhibitory activity (2) |
|---|---|---|---|
| 0901 | ++ | | +++ |
| 0902 | +++ | | +++ |
| 0903 | +++ | | +++ |
| 0904 | +++ | | ++ |
| 0905 | ++ | | ++ |
| 0906 | ++ | | +++ |
| 0907 | +++ | | +++ |
| 0908 | +++ | | +++ |
| 0909 | +++ | | +++ |
| 0910 | +++ | | +++ |
| 0911 | +++ | | +++ |
| 0912 | +++ | | +++ |

TABLE 1-10-continued

| Example No. | PI3Kα enzyme inhibitory activity | ERK2 enzyme inhibitory activity (1) | ERK2 enzyme inhibitory activity (2) |
|---|---|---|---|
| 0913 | +++ | | +++ |
| 0914 | +++ | | +++ |
| 0915 | | | + |
| 0916 | +++ | | +++ |
| 0917 | +++ | | +++ |
| 0918 | +++ | | +++ |
| 0919 | +++ | | +++ |
| 0920 | +++ | | +++ |
| 0921 | +++ | | +++ |
| 0922 | ++ | | +++ |
| 0923 | +++ | | +++ |
| 0924 | +++ | | +++ |
| 0925 | +++ | | +++ |
| 0926 | +++ | | +++ |
| 0927 | +++ | | +++ |
| 0928 | +++ | | +++ |
| 0929 | ++ | | +++ |
| 0930 | +++ | | +++ |
| 0931 | +++ | | +++ |
| 0932 | +++ | | +++ |
| 0933 | +++ | | +++ |
| 0934 | +++ | | +++ |
| 0935 | +++ | | ++ |
| 0936 | +++ | | +++ |
| 0937 | +++ | | +++ |
| 0938 | +++ | | +++ |
| 0939 | +++ | | +++ |
| 0940 | +++ | | +++ |
| 0941 | +++ | | +++ |
| 0942 | +++ | | +++ |
| 0943 | +++ | | +++ |
| 0944 | +++ | | +++ |
| 0945 | +++ | | +++ |
| 0946 | +++ | | +++ |
| 0947 | ++ | | ++ |
| 0948 | +++ | | +++ |
| 0949 | ++ | | ++ |
| 0950 | +++ | | ++ |
| 0951 | +++ | | +++ |
| 0952 | +++ | | +++ |
| 0953 | +++ | | +++ |
| 0954 | +++ | | +++ |
| 0955 | +++ | | +++ |

The compound of the invention exhibited excellent inhibitory activity with respect to the PI3K-AKT pathway and/or the Ras-Raf-MEK-ERK pathway.

Test Example 3

CHO Cell Toxicity Test

In a CHO cell toxicity test, the following was used.
Cell: CHO-K1 cells (derived from Chinese hamster ovary) Test medium: F-12 MEDIUM+FCS (manufactured by Biowest) having a final concentration of 2%
Detection reagent: CELLTITER-GLO™ LUMINESCENT CELL VIABILITY ASSAY (trade name, manufactured by PROMEGA Corporation)
The CHO-K1 cells were seeded in a 96-well microplate for culture at 5,000 cells/well, and cultured in a $CO_2$ incubator (37° C.) for 24 hours. An evaluation compound (final concentration: from 25.00 μmol/L to 0.20 μmol/L, common ratio: 2.8 points) was added thereto, followed by culturing for 24 hours, and the number of viable cells was calculated from emission intensity by CELLTITER-GLO™ (trade name, manufactured by PROMEGA Corporation). In the measurement of the emission intensity, VARIOSKAN FLASH (manufactured by Thermo Fisher Scientific Inc.) was used.

An inhibition ratio was calculated from the following equation, and a concentration ($IC_{50}$ value) of compound at which the number of viable cells was suppressed to be equal to or less than 50% was determined.

Inhibition ratio (%)=100−(A/B)×100

A: Emission intensity in the presence of a test compound
B: Emission intensity in the absence of a test compound $IC_{50}$ values of the compounds of Example Nos. 0001, 0015, 0018, 0019, 0027, 0037, 0097, 0122, 0128, 0130, 0137, 0139, 0140, 0145, 0148, 0179, 0214, 0222, 0226, 0227, 0231, 0232, 0233, 0237, 0238, 0240, 0241, 0243, 0245, 0247, 0250, 0291, 0293, 0298, 0301, 0302, 0316, 0321, 0322, 0325, 0338, 0341, 0347, 0348, 0352, 0355, 0362, 0363, 0365, 0368, 0373, 0374, 0382, 0384, 0390, 0395, 0400, 0401, 0403, 0405, 0406, 0413, 0417, 0418, 0420, 0422, 0424, 0426, 0430, 0431, 0432, 0439, 0443, 0450, 0455, 0456, 0460, 0462, 0465, 0473, 0474, 0479, 0482, 0486, 0487, 0490, 0491, 0492, 0493, 0500, 0510, 0515, 0517, 0530, 0545, 0549, 0550, 0552, 0557, 0567, 0572, 0573, 0576, 0583, 0613, 0614, 0615, 0626, 0629, 0630, 0631, 0635, 0637, 0644, 0645, 0649, 0650, 0651, 0653, 0657, 0659, 0665, 0678, 0679, 0682, 0685, 0686, 0687, 0688, 0691, 0694, 0695, 0697, 0712, 0723, 0724, 0725, 0733, 0737, 0738, 0756, 0757, 0761, 0773, 0781, 0795, 0812, and 0919 were equal to or greater than 25 μmol/L.

The compound of the invention exhibited excellent safety.

INDUSTRIAL APPLICABILITY

The nitrogen-containing heterocyclic compound or salt thereof of the invention has excellent inhibitory activity with respect to the PI3K-AKT pathway and/or the Ras-Raf-MEK-ERK pathway, and is useful for a treatment such as prevention of or cure for a disease such as a malignant tumor, a cell proliferative disease, an allergic disease, an autoimmune disease, a neurodegenerative disease, a circulatory system disease, an inflammatory disease, an endocrine disorder, a metabolic disorder, or an infection.

The entirety of the disclosure of Japanese Patent Application No. 2013-003832 filed on Jan. 11, 2013, is incorporated into the present specification by reference. All documents, patent applications, and technology standards that are described in the present specification are incorporated by reference into the present specification to the same extent as in a case in which the incorporation of the individual documents, patent applications, and technology standards are specifically and individually described.

What is claimed is:
1. A nitrogen-containing heterocyclic compound represented by the following Formula [1] or salt thereof:

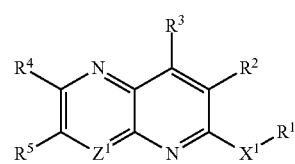

wherein, in Formula [1]:
$Z^1$ represents N or $CR^{6d}$;
$R^{6d}$ represents a hydrogen atom, a halogen atom, a $C_{1-6}$ alkyl group which may be substituted, a $C_{1-6}$ alkoxy group which may be substituted, or $NHR^{8d}$;

$R^{8d}$ represents a hydrogen atom or a $C_{1-6}$ alkyl group which may be substituted;

$X^1$ represents $NR^9$ or S;

$R^9$ represents a hydrogen atom, a $C_{1-6}$ alkyl group which may be substituted, or an amino protecting group;

$R^1$ represents a monocyclic nitrogen-containing heteroaryl group which may be substituted, a monocyclic nitrogen- and oxygen-containing heteroaryl group which may be substituted, a monocyclic nitrogen- and sulfur-containing heteroaryl group which may be substituted, a bicyclic nitrogen-containing heteroaryl group which may be substituted, a bicyclic nitrogen- and oxygen-containing heteroaryl group which may be substituted, or a bicyclic nitrogen- and sulfur-containing heteroaryl group which may be substituted;

$R^2$ represents a hydrogen atom or a halogen atom;

$R^3$ represents a hydrogen atom or a halogen atom;

$R^4$ represents a hydrogen atom, a halogen atom, an amino group which may be protected, a hydroxyl group which may be protected, a $C_{1-6}$ alkyl group which may be substituted, or a $C_{1-6}$ alkoxy group which may be substituted;

$R^5$ represents a $C_{3-8}$ cycloalkyl group which may be substituted, an aryl group which may be substituted, a heteroaryl group which may be substituted, a heterocyclyl group which may be substituted, or $NR^{12a}R^{13a}$, provided that in a case in which $Z^1$ represents N and $R^4$ represents a hydrogen atom, $R^5$ represents a $C_{3-8}$ cycloalkyl group which may be substituted, a heteroaryl group which may be substituted, a heterocyclyl group which may be substituted, or $NR^{12a}R^{13a}$;

$R^{12a}$ presents a hydrogen atom or a $C_{1-6}$ alkyl group which may be substituted; and $R^{13a}$ represents a $C_{3-8}$ cycloalkyl group which may be substituted, an aryl group which may be substituted, a heteroaryl group which may be substituted, or a heterocyclyl group which may be substituted.

2. The nitrogen-containing heterocyclic compound or salt thereof according to claim 1, wherein $R^4$ represents a hydrogen atom, a halogen atom, an amino group which may be protected, or a $C_{1-6}$ alkoxy group which may be substituted.

3. The nitrogen-containing heterocyclic compound or salt thereof according to claim 1, wherein:

$Z^1$ represents $CR^{6d}$; and $R^{6d}$ has the same meaning as in claim 1.

4. The nitrogen-containing heterocyclic compound or salt thereof according to claim 1, wherein $R^2$ is a hydrogen atom.

5. The nitrogen-containing heterocyclic compound or salt thereof according to claim 1, wherein $R^3$ is a hydrogen atom.

6. The nitrogen-containing heterocyclic compound or salt thereof according to claim 1, wherein $X^1$ represents $NR^{9a}$ or S, and $R^{9a}$ represents a hydrogen atom or an amino protecting group.

7. The nitrogen-containing heterocyclic compound or salt thereof according to claim 1, wherein $R^1$ represents a pyrazolyl group which may be substituted, an imidazolyl group which may be substituted, a triazolyl group which may be substituted, a thiazolyl group which may be substituted, an oxadiazolyl group which may be substituted, a thiadiazolyl group which may be substituted, a pyridyl group which may be substituted, or a pyridazinyl group which may be substituted.

8. The nitrogen-containing heterocyclic compound or salt thereof according to claim 1, wherein:

$R^1$ represents a pyrazolyl group which may be substituted with one or more substituents selected from a substituent group $A_1$, an imidazolyl group which may be substituted with one or more substituents selected from the substituent group $A_1$, a triazolyl group which may be substituted with one or more substituents selected from the substituent group $A_1$, a thiazolyl group which may be substituted with one or more substituents selected from the substituent group $A_1$, an oxadiazolyl group which may be substituted with one or more substituents selected from the substituent group $A_1$, a thiadiazolyl group which may be substituted with one or more substituents selected from the substituent group $A_1$, a pyridyl group which may be substituted with one or more substituents selected from the substituent group $A_1$, or a pyridazinyl group which may be substituted with one or more substituents selected from the substituent group $A_1$;

the substituent group $A_1$ consists of a halogen atom, a hydroxyl group which may be protected, an amino group which may be protected, a carboxyl group which may be protected, a cyano group, a carbamoyl group which may be substituted with one or more substituents selected from a substituent group $B_1$, a sulfamoyl group which may be substituted with one or more substituents selected from the substituent group $B_1$, a $C_{1-6}$ alkyl group which may be substituted with one or more substituents selected from the substituent group $B_1$, a $C_{2-6}$ alkenyl group which may be substituted with one or more substituents selected from the substituent group $B_1$, a $C_{3-8}$ cycloalkyl group which may be substituted with one or more substituents selected from the substituent group $B_1$, an aryl group which may be substituted with one or more substituents selected from the substituent group $B_1$, a $C_{1-6}$ alkoxy group which may be substituted with one or more substituents selected from the substituent group $B_1$, a $C_{3-8}$ cycloalkoxy group which may be substituted with one or more substituents selected from the substituent group $B_1$, an aryloxy group which may be substituted with one or more substituents selected from the substituent group $B_1$, a $C_{1-6}$ alkylthio group which may be substituted with one or more substituents selected from the substituent group $B_1$, an arylthio group which may be substituted with one or more substituents selected from the substituent group $B_1$, a $C_{1-6}$ alkylamino group which may be substituted with one or more substituents selected from the substituent group $B_1$, a di($C_{1-6}$ alkyl)amino group which may be substituted with one or more substituents selected from the substituent group $B_1$, an acyl group which may be substituted with one or more substituents selected from the substituent group $B_1$, a heteroaryl group which may be substituted with one or more substituents selected from the substituent group $B_1$, a heterocyclyl group which may be substituted with one or more substituents selected from the substituent group $B_1$, and an oxo group;

the substituent group $B_1$ consists of a halogen atom, a hydroxyl group which may be protected, an amino group which may be protected, a carboxyl group which may be protected, a cyano group, a carbamoyl group which may be substituted with one or more substituents selected from a substituent group $C_1$, a sulfamoyl group which may be substituted with one or more substituents selected from the substituent group $C_1$, a $C_{1-6}$ alkyl group which may be substituted with one or more substituents selected from the substituent group $C_1$, a $C_{3-8}$ cycloalkyl group which may be substituted with one or more substituents selected from the substituent group $C_1$, an aryl group which may be substituted with one or more substituents selected from the substituent group C₁, a C₁₋₆ alkoxy group which may be substituted with one or more substituents selected from the substituent group C₁, a C₁₋₆ alkylamino group which may be substituted with one or more substituents selected from the substituent group C₁, a di(C₁₋₆ alkyl) amino group which may be substituted with one or more substituents selected from the substituent group C₁, a C₁₋₆ alkylsulfonyl group which may be substituted with one or more substituents selected from the substituent group C₁, an arylsulfonyl group which may be substituted with one or more substituents selected from the substituent group C₁, an acyl group which may be substituted with one or more substituents selected from the substituent group C₁, a heteroaryl group which may be substituted with one or more substituents selected from the substituent group C₁, a heterocyclyl group which may be substituted with one or more substituents selected from the substituent group C₁, and an oxo group; and the substituent group C₁ consists of a halogen atom, a hydroxyl group which may be protected, an amino group which may be protected, a carboxyl group which may be protected, a cyano group, a carbamoyl group which may be substituted with a C₁₋₆ alkyl group, a C₁₋₆ alkyl group which may be substituted with a halogen atom, an aryl group which may be substituted with a halogen atom or a C₁₋₆ alkyl group, a C₁₋₆ alkoxy group which may be substituted with a halogen atom, and an oxo group.

9. The nitrogen-containing heterocyclic compound or salt thereof according to claim 1, wherein:

R¹ represents a pyrazolyl group which may be substituted with one or more substituents selected from a substituent group α₁, an imidazolyl group which may be substituted with one or more substituents selected from the substituent group α₁, a triazolyl group which may be substituted with one or more substituents selected from the substituent group α₁, a thiazolyl group which may be substituted with one or more substituents selected from the substituent group α₁, an oxadiazolyl group which may be substituted with one or more substituents selected from the substituent group α₁, a thiadiazolyl group which may be substituted with one or more substituents selected from the substituent group α₁, a pyridyl group which may be substituted with one or more substituents selected from the substituent group α₁, or a pyridazinyl group which may be substituted with one or more substituents selected from the substituent group α₁;

the substituent group α₁ consists of a halogen atom, a hydroxyl group which may be protected, an amino group which may be protected, a carboxyl group which may be protected, a cyano group, a carbamoyl group which may be substituted with one or more substituents selected from a substituent group β₁, a sulfamoyl group which may be substituted with one or more substituents selected from the substituent group β₁, a C₁₋₆ alkyl group which may be substituted with one or more substituents selected from the substituent group β₁, a C₃₋₈ cycloalkyl group which may be substituted with one or more substituents selected from the substituent group β₁, an aryl group which may be substituted with one or more substituents selected from the substituent group β₁, a C₁₋₆ alkoxy group which may be substituted with one or more substituents selected from the substituent group β₁, an aryloxy group which may be substituted with one or more substituents selected from the substituent group β₁, a C₁₋₆ alkylthio group which may be substituted with one or more substituents selected from the substituent group β₁, an arylthio group which may be substituted with one or more substituents selected from the substituent group β₁, a C₁₋₆ alkylamino group which may be substituted with one or more substituents selected from the substituent group β₁, a di(C₁₋₆ alkyl)amino group which may be substituted with one or more substituents selected from the substituent group β₁, an acyl group which may be substituted with one or more substituents selected from the substituent group β₁, a heteroaryl group which may be substituted with one or more substituents selected from the substituent group β₁, a heterocyclyl group which may be substituted with one or more substituents selected from the substituent group β₁, and an oxo group;

the substituent group β₁ consists of a halogen atom, a hydroxyl group which may be protected, an amino group which may be protected, a carboxyl group which may be protected, a cyano group, a carbamoyl group which may be substituted with one or more substituents selected from a substituent group γ₁, a C₁₋₆ alkyl group which may be substituted with one or more substituents selected from the substituent group γ₁, a C₃₋₈ cycloalkyl group which may be substituted with one or more substituents selected from the substituent group γ₁, an aryl group which may be substituted with one or more substituents selected from the substituent group γ₁, a C₁₋₆ alkoxy group which may be substituted with one or more substituents selected from the substituent group γ₁, a C₁₋₆ alkylamino group which may be substituted with one or more substituents selected from the substituent group γ₁, a di(C₁₋₆ alkyl)amino group which may be substituted with one or more substituents selected from the substituent group γ₁, a C₁₋₆ alkylsulfonyl group which may be substituted with one or more substituents selected from the substituent group γ₁, an arylsulfonyl group which may be substituted with one or more substituents selected from the substituent group γ₁, an acyl group which may be substituted with one or more substituents selected from the substituent group γ₁, a heteroaryl group which may be substituted with one or more substituents selected from the substituent group γ₁, a heterocyclyl group which may be substituted with one or more substituents selected from the substituent group γ₁, and an oxo group; and the substituent group γ₁ consists of a halogen atom, a hydroxyl group which may be protected, an amino group which may be protected, a carboxyl group which may be protected, a cyano group, a carbamoyl group which may be substituted with a C₁₋₆ alkyl group, a C₁₋₆ alkyl group which may be substituted with a halogen atom, a C₁₋₆ alkoxy group which may be substituted with a halogen atom, and an oxo group.

10. A nitrogen-containing heterocyclic compound represented by the following Formula [1] or salt thereof:

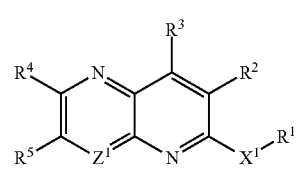

[1]

wherein, in Formula [1]:

$Z^1$ represents $CR^{6a}$;

$R^{6a}$ represents an aryl group which may be substituted, a heteroaryl group which may be substituted, a heterocyclyl group which may be substituted, or $NHR^{8a}$; and $R^{8a}$ represents an aryl group which may be substituted, a heteroaryl group which may be substituted, or a heterocyclyl group which may be substituted;

$X^1$ represents $NR^9$ or S;

$R^9$ represents a hydrogen atom, a $C_{1-6}$ alkyl group which may be substituted, or an amino protecting group;

$R^1$ represents a monocyclic nitrogen-containing heteroaryl group which may be substituted, a monocyclic nitrogen- and oxygen-containing heteroaryl group which may be substituted, a monocyclic nitrogen- and sulfur-containing heteroaryl group which may be substituted, a bicyclic nitrogen-containing heteroaryl group which may be substituted, a bicyclic nitrogen- and oxygen-containing heteroaryl group which may be substituted, or a bicyclic nitrogen- and sulfur-containing heteroaryl group which may be substituted;

$R^2$ represents a hydrogen atom or a halogen atom;

$R^3$ represents a hydrogen atom or a halogen atom;

$R^4$ represents a hydrogen atom, a halogen atom, an amino group which may be protected, a hydroxyl group which may be protected, a $C_{1-6}$ alkyl group which may be substituted, or a $C_{1-6}$ alkoxy group which may be substituted; and $R^5$ represents a hydrogen atom or a halogen atom.

11. A nitrogen-containing heterocyclic compound represented by the following Formula [1] or salt thereof:

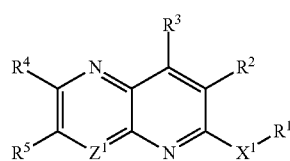

[1]

wherein, in Formula [1]:

$X^1$ represents $NR^9$ or S;

$R^9$ represents a hydrogen atom, a $C_{1-6}$ alkyl group which may be substituted, or an amino protecting group;

$R^1$ represents a monocyclic nitrogen-containing heteroaryl group which may be substituted, a monocyclic nitrogen- and oxygen-containing heteroaryl group which may be substituted, a monocyclic nitrogen- and sulfur-containing heteroaryl group which may be substituted, a bicyclic nitrogen-containing heteroaryl group which may be substituted, a bicyclic nitrogen- and oxygen-containing heteroaryl group which may be substituted, or a bicyclic nitrogen- and sulfur-containing heteroaryl group which may be substituted;

$R^2$ represents a hydrogen atom or a halogen atom;

$R^3$ represents a hydrogen atom or a halogen atom;

$R^4$ represents a hydrogen atom, a halogen atom, an amino group which may be protected, a hydroxyl group which may be protected, a $C_{1-6}$ alkyl group which may be substituted, or a $C_{1-6}$ alkoxy group which may be substituted;

$R^5$ represents a hydrogen atom or a halogen atom;

$Z^1$ represents $CR^{6b}$;

$R^{6b}$ represents an aryl group which may be substituted with one or more substituents selected from a substituent group $\alpha_2$, a heteroaryl group which may be substituted with one or more substituents selected from the substituent group $\alpha_2$, a heterocyclyl group which may be substituted with one or more substituents selected from the substituent group $\alpha_2$, or $NHR^{8b}$;

$R^{8b}$ represents an aryl group which may be substituted with one or more substituents selected from the substituent group $\alpha_2$, a heteroaryl group which may be substituted with one or more substituents selected from the substituent group $\alpha_2$, or a heterocyclyl group which may be substituted with one or more substituents selected from the substituent group $\alpha_2$;

the substituent group $\alpha_2$ consists of a halogen atom, a hydroxyl group which may be protected, an amino group which may be protected, a carboxyl group which may be protected, a cyano group, a carbamoyl group which may be substituted with one or more substituents selected from a substituent group $\beta_2$, a $C_{1-6}$ alkyl group which may be substituted with one or more substituents selected from the substituent group $\beta_2$, a $C_{1-6}$ alkoxy group which may be substituted with one or more substituents selected from the substituent group $\beta_2$, and an oxo group;

the substituent group $\beta_2$ consists of a halogen atom, a $C_{1-6}$ alkyl group which may be substituted with one or more substituents selected from a substituent group $\gamma_2$, a $C_{3-8}$ cycloalkyl group which may be substituted with one or more substituents selected from the substituent group $\gamma_2$, an aryl group which may be substituted with one or more substituents selected from the substituent group $\gamma_2$, a heteroaryl group which may be substituted with one or more substituents selected from the substituent group $\gamma_2$, and a heterocyclyl group which may be substituted with one or more substituents selected from the substituent group $\gamma_2$; and the substituent group $\gamma_2$ consists of a halogen atom, a hydroxyl group which may be protected, an amino group which may be protected, a carboxyl group which may be protected, a cyano group, a $C_{1-6}$ alkyl group which may be substituted with a halogen atom, a $C_{1-6}$ alkoxy group which may be substituted with a halogen atom, and an oxo group.

12. A nitrogen-containing heterocyclic compound represented by the following Formula [1] or salt thereof:

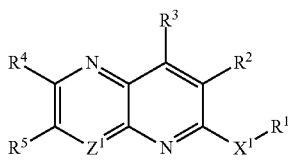

[1]

wherein, in Formula: [1]:

$X^1$ represents $NR^9$ or S;

$R^9$ represents a hydrogen atom, a $C_{1-6}$ alkyl group which may be substituted, or an amino protecting group;

$R^1$ represents a monocyclic nitrogen-containing heteroaryl group which may be substituted, a monocyclic nitrogen- and oxygen-containing heteroaryl group which may be substituted, a monocyclic nitrogen- and sulfur-containing heteroaryl group which may be substituted, a bicyclic nitrogen-containing heteroaryl group which may be substituted, a bicyclic nitrogen- and oxygen-containing heteroaryl group which may be substituted, or a bicyclic nitrogen- and sulfur-containing heteroaryl group which may be substituted;

R² represents a hydrogen atom or a halogen atom;
R³ represents a hydrogen atom or a halogen atom;
R⁴ represents a hydrogen atom, a halogen atom, an amino group which may be protected, a hydroxyl group which may be protected, a $C_{1-6}$ alkyl group which may be substituted, or a $C_{1-6}$ alkoxy group which may be substituted;
R⁵ represents a hydrogen atom or a halogen atom;
Z¹ represents $CR^{6c}$;
$R^{6c}$ represents a phenyl group which may be substituted with one or more substituents selected from a substituent group $α_2$, a pyrazolyl group which may be substituted with one or more substituents selected from the substituent group $α_2$, a pyridyl group which may be substituted with one or more substituents selected from the substituent group $α_2$, a pyrimidinyl group which may be substituted with one or more substituents selected from the substituent group $α_2$, a pyrazinyl group which may be substituted with one or more substituents selected from the substituent group $α_2$, a pyridazinyl group which may be substituted with one or more substituents selected from the substituent group $α_2$, a morpholinyl group which may be substituted with one or more substituents selected from the substituent group $α_2$, or $NHR^{8c}$;
$R^{8c}$ represents a phenyl group which may be substituted with one or more substituents selected from the substituent group $α_2$, a pyridyl group which may be substituted with one or more substituents selected from the substituent group $α_2$, a pyrimidinyl group which may be substituted with one or more substituents selected from the substituent group $α_2$, a pyrazinyl group which may be substituted with one or more substituents selected from the substituent group $α_2$, or a pyridazinyl group which may be substituted with one or more substituents selected from the substituent group $α_2$;
the substituent group $α_2$ consists of a halogen atom, a hydroxyl group which may be protected, an amino group which may be protected, a carboxyl group which may be protected, a cyano group, a carbamoyl group which may be substituted with one or more substituents selected from a substituent group $β_2$, a $C_{1-6}$ alkyl group which may be substituted with one or more substituents selected from the substituent group $β_2$, a $C_{1-6}$ alkoxy group which may be substituted with one or more substituents selected from the substituent group $β_2$, and an oxo group;
the substituent group $β_2$ consists of a halogen atom, a $C_{1-6}$ alkyl group which may be substituted with one or more substituents selected from a substituent group $γ_2$, a $C_{3-8}$ cycloalkyl group which may be substituted with one or more substituents selected from the substituent group $γ_2$, an aryl group which may be substituted with one or more substituents selected from the substituent group $γ_2$, a heteroaryl group which may be substituted with one or more substituents selected from the substituent group $γ_2$, and a heterocyclyl group which may be substituted with one or more substituents selected from the substituent group $γ_2$; and
the substituent group $γ_2$ consists of a halogen atom, a hydroxyl group which may be protected, an amino group which may be protected, a carboxyl group which may be protected, a cyano group, a $C_{1-6}$ alkyl group which may be substituted with a halogen atom, a $C_{1-6}$ alkoxy group which may be substituted with a halogen atom, and an oxo group.

13. A nitrogen-containing heterocyclic compound represented by the following Formula [1] or salt thereof:

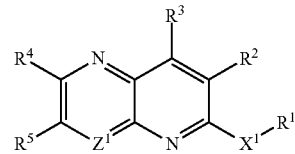

[1]

wherein, in Formula [1]:
Z¹ represents N or CH;
X¹ represents $NR^9$ or S;
R⁹ represents a hydrogen atom, a $C_{1-6}$ alkyl group which may be substituted, or an amino protecting group;
R¹ represents a monocyclic nitrogen-containing heteroaryl group which may be substituted, a monocyclic nitrogen- and oxygen-containing heteroaryl group which may be substituted, a monocyclic nitrogen- and sulfur-containing heteroaryl group which may be substituted, a bicyclic nitrogen-containing heteroaryl group which may be substituted, a bicyclic nitrogen- and oxygen-containing heteroaryl group which may be substituted, or a bicyclic nitrogen- and sulfur-containing heteroaryl group which may be substituted;
R² represents a hydrogen atom or a halogen atom;
R³ represents a hydrogen atom or a halogen atom;
R⁴ represents a hydrogen atom, a halogen atom, an amino group which may be protected, a hydroxyl group which may be protected, a $C_{1-6}$ alkyl group which may be substituted, or a $C_{1-6}$ alkoxy group which may be substituted;
R⁵ represents a $C_{3-8}$ cycloalkyl group which may be substituted with one or more substituents selected from a substituent group $A_3$, an aryl group which may be substituted with one or more substituents selected from the substituent group $A_3$, a heteroaryl group which may be substituted with one or more substituents selected from the substituent group $A_3$, a heterocyclyl group which may be substituted with one or more substituents selected from the substituent group $A_3$, or $NR^{12b}R^{13b}$, provided that in a case in which Z¹ represents N and R⁴ represents a hydrogen atom, R⁵ represents a $C_{3-8}$ cycloalkyl group which may be substituted with one or more substituents selected from a substituent group $A_3$, a heteroaryl group which may be substituted with one or more substituents selected from the substituent group $A_3$, a heterocyclyl group which may be substituted with one or more substituents selected from the substituent group $A_3$, or $NR^{12b}R^{13b}$;
$R^{12b}$ represents a hydrogen atom or a $C_{1-6}$ alkyl group;
$R^{13b}$ represents a $C_{3-8}$ cycloalkyl group which may be substituted with one or more substituents selected from the substituent group $A_3$, an aryl group which may be substituted with one or more substituents selected from the substituent group $A_3$, a heteroaryl group which may be substituted with one or more substituents selected from the substituent group $A_3$, or a heterocyclyl group which may be substituted with one or more substituents selected from the substituent group $A_3$;
the substituent group $A_3$ consists of a halogen atom, a hydroxyl group which may be protected, an amino group which may be protected, an amino group which may be substituted with one or more substituents selected from a substituent group $E_3$, a carboxyl group which may be protected, a cyano group, a carbamoyl group which may be substituted with one or more substituents selected from a substituent group $B_3$, a sulfamoyl group which may be substituted with one or more substituents selected from the substituent group $B_3$, a $C_{1-6}$ alkyl group which may be substituted with one or more substituents selected from the substituent group $B_3$, a $C_{2-6}$ alkenyl group which may be substituted with one or more substituents selected from the substituent group $B_3$, a $C_{3-8}$ cycloalkyl group which may be substituted with one or more substituents selected from the substituent group $B_3$, an aryl group which may be substituted with one or more substituents selected from the substituent group $B_3$, a $C_{1-6}$ alkoxy group which may be substituted with one or more substituents selected from the substituent group $B_3$, an aryloxy group which may be substituted with one or more substituents selected from the substituent group $B_3$, a $C_{1-6}$ alkylthio group which may be substituted with one or more substituents selected from the substituent group $B_3$, an arylthio group which may be substituted with one or more substituents selected from the substituent group $B_3$, a $C_{1-6}$ alkyl amino group which may be substituted with one or more substituents selected from the substituent group $B_3$, a di($C_{1-6}$ alkyl) amino group which may be substituted with one or more substituents selected from the substituent group $B_3$, a $C_{1-6}$ alkylsulfonyl group which may be substituted with one or more substituents selected from the substituent group $B_3$, an arylsulfonyl group which may be substituted with one or more substituents selected from the substituent group $B_3$, an acyl group which may be substituted with one or more substituents selected from the substituent group $B_3$, a heteroaryl group which may be substituted with one or more substituents selected from the substituent group $B_3$, a heterocyclyl group which may be substituted with one or more substituents selected from the substituent group $B_3$, a heterocyclyloxy group which may be substituted with one or more substituents selected from the substituent group $B_3$, and an oxo group;

the substituent group $B_3$ consists of a halogen atom, a hydroxyl group which may be protected, an amino group which may be protected, a carboxyl group which may be protected, a cyano group, a carbamoyl group which may be substituted with one or more substituents selected from a substituent group $C_3$, a $C_{1-6}$ alkyl group which may be substituted with one or more substituents selected from the substituent group $C_3$, a $C_{3-8}$ cycloalkyl group which may be substituted with one or more substituents selected from the substituent group $C_3$, an aryl group which may be substituted with one or more substituents selected from the substituent group $C_3$, a $C_{1-6}$ alkoxy group which may be substituted with one or more substituents selected from the substituent group $C_3$, an aryloxy group which may be substituted with one or more substituents selected from the substituent group $C_3$, a $C_{1-6}$ alkylamino group which may be substituted with one or more substituents selected from the substituent group $C_3$, a di($C_{1-6}$ alkyl)amino group which may be substituted with one or more substituents selected from the substituent group $C_3$, a $C_{1-6}$ alkylsulfonyl group which may be substituted with one or more substituents selected from the substituent group $C_3$, an arylsulfonyl group which may be substituted with one or more substituents selected from the substituent group $C_3$, an acyl group which may be substituted with one or more substituents selected from the substituent group $C_3$, a heteroaryl group which may be substituted with one or more substituents selected from the substituent group $C_3$, a heterocyclyl group which may be substituted with one or more substituents selected from the substituent group $C_3$, a heteroaryloxy group which may be substituted with one or more substituents selected from the substituent group $C_3$, a heterocyclyloxy group which may be substituted with one or more substituents selected from the substituent group $C_3$, and an oxo group;

the substituent group $C_3$ consists of a halogen atom, a hydroxyl group which may be protected, an amino group which may be protected, a carboxyl group which may be protected, a nitro group, cyano group, a carbamoyl group which may be substituted with one or more substituents selected from a substituent group $D_3$, a $C_{1-6}$ alkyl group which may be substituted with one or more substituents selected from the substituent group $D_3$, a $C_{3-8}$ cycloalkyl group which may be substituted with one or more substituents selected from the substituent group $D_3$, an aryl group which may be substituted with one or more substituents selected from the substituent group $D_3$, a $C_{1-6}$ alkoxy group which may be substituted with one or more substituents selected from the substituent group $D_3$, an aryloxy group which may be substituted with one or more substituents selected from the substituent group $D_3$, a $C_{1-6}$ alkylamino group which may be substituted with one or more substituents selected from the substituent group $D_3$, a di($C_{1-6}$ alkyl)amino group which may be substituted with one or more substituents selected from the substituent group $D_3$, a $C_{1-6}$ alkylsulfonyl group which may be substituted with one or more substituents selected from the substituent group $D_3$, an acyl group which may be substituted with one or more substituents selected from the substituent group $D_3$, a heteroaryl group which may be substituted with one or more substituents selected from the substituent group $D_3$, a heterocyclyl group which may be substituted with one or more substituents selected from the substituent group $D_3$, a silyl group which may be substituted with one or more substituents selected from the substituent group $D_3$, and an oxo group;

the substituent group $D_3$ consists of a halogen atom, a hydroxyl group which may be protected, a $C_{1-6}$ alkyl group, a $C_{3-8}$ cycloalkyl group, an aryl group, a $C_{1-6}$ alkoxy group, a $C_{1-6}$ alkylamino group, a di($C_{1-6}$ alkyl) amino group, a $C_{1-6}$ alkylsulfonyl group, a heteroaryl group, a heterocyclyl group, and an oxo group;

the substituent group $E_3$ consists of a $C_{3-8}$ cycloalkyl group which may be substituted with one or more substituents selected from a substituent group $F_3$, an aryl group which may be substituted with one or more substituents selected from the substituent group $F_3$, a heteroaryl group which may be substituted with one or more substituents selected from the substituent group $F_3$, and a heterocyclyl group which may be substituted with one or more substituents selected from the substituent group $F_3$; and the substituent group $F_3$ consists of a halogen atom, a carboxyl group which may be protected, and a $C_{1-6}$ alkyl group.

14. A nitrogen-containing heterocyclic compound represented by the following Formula [1] or salt thereof:

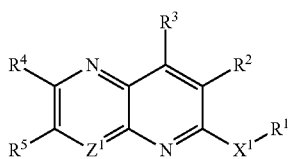

[1]

wherein, in Formula [1]:
$Z^1$ represents N or CH;
$X^1$ represents $NR^9$ or S;
$R^9$ represents a hydrogen atom, a $C_{1-6}$ alkyl group which may be substituted, or an amino protecting group;
$R^1$ represents a monocyclic nitrogen-containing heteroaryl group which may be substituted, a monocyclic nitrogen- and oxygen-containing heteroaryl group which may be substituted, a monocyclic nitrogen- and sulfur-containing heteroaryl group which may be substituted, a bicyclic nitrogen-containing heteroaryl group which may be substituted, a bicyclic nitrogen- and oxygen-containing heteroaryl group which may be substituted, or a bicyclic nitrogen- and sulfur-containing heteroaryl group which may be substituted;
$R^2$ represents a hydrogen atom or a halogen atom;
$R^3$ represents a hydrogen atom or a halogen atom;
$R^4$ represents a hydrogen atom, a halogen atom, an amino group which may be protected, a hydroxyl group which may be protected, a $C_{1-6}$ alkyl group which may be substituted, or a $C_{1-6}$ alkoxy group which may be substituted;
$R^5$ represents a $C_{3-8}$ cycloalkyl group which may be substituted with one or more substituents selected from a substituent group $\alpha_3$, an aryl group which may be substituted with one or more substituents selected from the substituent group $\alpha_3$, a heteroaryl group which may be substituted with one or more substituents selected from the substituent group $\alpha_3$, a heterocyclyl group which may be substituted with one or more substituents selected from the substituent group $\alpha_3$, or $NR^{12b}R^{13c}$, provided that in a case in which $Z^1$ represents N and $R^4$ represents a hydrogen atom, $R^5$ represents a $C_{3-8}$ cycloalkyl group which may be substituted with one or more substituents selected from a substituent group $\alpha_3$, a heteroaryl group which may be substituted with one or more substituents selected from the substituent group $\alpha_3$, a heterocyclyl group which may be substituted with one or more substituents selected from the substituent group $\alpha_3$, or $NR^{12b}R^{13c}$;
$R^{12b}$ represents a hydrogen atom or a $C_{1-6}$ alkyl group;
$R^{13c}$ represents a $C_{3-8}$ cycloalkyl group which may be substituted with one or more substituents selected from the substituent group $\alpha_3$, an aryl group which may be substituted with one or more substituents selected from the substituent group $\alpha_3$, a heteroaryl group which may be substituted with one or more substituents selected from the substituent group $\alpha_3$, or a heterocyclyl group which may be substituted with one or more substituents selected from the substituent group $\alpha_3$;
the substituent group $\alpha_3$ consists of a halogen atom, a hydroxyl group which may be protected, an amino group which may be protected, a carboxyl group which may be protected, a cyano group, a carbamoyl group which may be substituted with one or more substituents selected from a substituent group $\beta_3$, a $C_{1-6}$ alkyl group which may be substituted with one or more substituents selected from the substituent group $\beta_3$, a $C_{3-8}$ cycloalkyl group which may be substituted with one or more substituents selected from the substituent group $\beta_3$, an aryl group which may be substituted with one or more substituents selected from the substituent group $\beta_3$, a $C_{1-6}$ alkoxy group which may be substituted with one or more substituents selected from the substituent group $\beta_3$, an aryloxy group which may be substituted with one or more substituents selected from the substituent group $\beta_3$, a $C_{1-6}$ alkylthio group which may be substituted with one or more substituents selected from the substituent group $\beta_3$, an arylthio group which may be substituted with one or more substituents selected from the substituent group $\beta_3$, a $C_{1-6}$ alkylamino group which may be substituted with one or more substituents selected from the substituent group $\beta_3$, a di($C_{1-6}$ alkyl)amino group which may be substituted with one or more substituents selected from the substituent group $\beta_3$, a $C_{1-6}$ alkylsulfonyl group which may be substituted with one or more substituents selected from the substituent group $\beta_3$, an arylsulfonyl group which may be substituted with one or more substituents selected from the substituent group $\beta_3$, an acyl group which may be substituted with one or more substituents selected from the substituent group $\beta_3$, a heteroaryl group which may be substituted with one or more substituents selected from the substituent group $\beta_3$, a heterocyclyl group which may be substituted with one or more substituents selected from the substituent group $\beta_3$, a heterocyclyloxy group which may be substituted with one or more substituents selected from the substituent group $\beta_3$, and an oxo group;
the substituent group $\beta_3$ consists of a halogen atom, a hydroxyl group which may be protected, an amino group which may be protected, a carboxyl group which may be protected, a cyano group, a carbamoyl group which may be substituted with one or more substituents selected from a substituent group $\gamma_3$, a $C_{1-6}$ alkyl group which may be substituted with one or more substituents selected from the substituent group $\gamma_3$, a $C_{3-8}$ cycloalkyl group which may be substituted with one or more substituents selected from the substituent group $\gamma_3$, an aryl group which may be substituted with one or more substituents selected from the substituent group $\gamma_3$, a $C_{1-6}$ alkoxy group which may be substituted with one or more substituents selected from the substituent group $\gamma_3$, a $C_{1-6}$ alkylamino group which may be substituted with one or more substituents selected from the substituent group $\gamma_3$, a di($C_{1-6}$ alkyl)amino group which may be substituted with one or more substituents selected from the substituent group $\gamma_3$, a $C_{1-6}$ alkylsulfonyl group which may be substituted with one or more substituents selected from the substituent group $\gamma_3$, an arylsulfonyl group which may be substituted with one or more substituents selected from the substituent group $\gamma_3$, a heteroaryl group which may be substituted with one or more substituents selected from the substituent group $\gamma_3$, a heterocyclyl group which may be substituted with one or more substituents selected from the substituent group $\gamma_3$, a heterocyclyloxy group which may be substituted with one or more substituents selected from the substituent group $\gamma_3$, and an oxo group; and
the substituent group $\gamma_3$ consists of a halogen atom, a hydroxyl group which may be protected, an amino group which may be protected, a carboxyl group which may be protected, a cyano group, a $C_{1-6}$ alkyl group which may be substituted with a halogen atom, a $C_{1-6}$ alkoxy group which may be substituted with a halogen atom, and an oxo group.

15. A nitrogen-containing heterocyclic compound represented by the following Formula [1] or salt thereof:

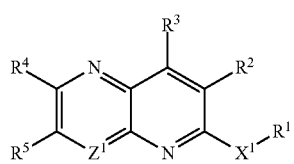

[1]

wherein, in Formula [1]:
$Z^1$ represents N or CH;
$X^1$ represents $NR^9$ or S;
$R^9$ represents a hydrogen atom, a $C_{1-6}$ alkyl group which may be substituted, or an amino protecting group;
$R^1$ represents a monocyclic nitrogen-containing heteroaryl group which may be substituted, a monocyclic nitrogen- and oxygen-containing heteroaryl group which may be substituted, a monocyclic nitrogen- and sulfur-containing heteroaryl group which may be substituted, a bicyclic nitrogen-containing heteroaryl group which may be substituted, a bicyclic nitrogen- and oxygen-containing heteroaryl group which may be substituted, or a bicyclic nitrogen- and sulfur-containing heteroaryl group which may be substituted;
$R^2$ represents a hydrogen atom or a halogen atom;
$R^3$ represents a hydrogen atom or a halogen atom;
$R^4$ represents a hydrogen atom, a halogen atom, an amino group which may be protected, a hydroxyl group which may be protected, a $C_{1-6}$ alkyl group which may be substituted, or a $C_{1-6}$ alkoxy group which may be substituted;
$R^5$ represents a phenyl group which may be substituted with one or more substituents selected from a substituent group $\alpha_3$, a pyrazolyl group which may be substituted with one or more substituents selected from the substituent group $\alpha_3$, an isoxazolyl group which may be substituted with one or more substituents selected from the substituent group $\alpha_3$, a pyridyl group which may be substituted with one or more substituents selected from the substituent group $\alpha_3$, a pyrimidinyl group which may be substituted with one or more substituents selected from the substituent group $\alpha_3$, a pyrazinyl group which may be substituted with one or more substituents selected from the substituent group $\alpha_3$, a pyridazinyl group which may be substituted with one or more substituents selected from the substituent group $\alpha_3$, an azetidinyl which may be substituted with one or more substituents selected from the substituent group $\alpha_3$, a pyrrolidinyl group which may be substituted with one or more substituents selected from the substituent group $\alpha_3$, a piperidinyl group which may be substituted with one or more substituents selected from the substituent group $\alpha_3$, a piperazinyl group which may be substituted with one or more substituents selected from the substituent group $\alpha_3$, a morpholinyl group which may be substituted with one or more substituents selected from the substituent group $\alpha_3$, a homopiperazinyl group which may be substituted with one or more substituents selected from the substituent group $\alpha_3$, or $NR^{12b}R^{13d}$, provided that in a case in which $Z^1$ represents N and $R^4$ represents a hydrogen atom, $R^5$ represents a pyrazolyl group which may be substituted with one or more substituents selected from the substituent group $\alpha_3$, an isoxazolyl group which may be substituted with one or more substituents selected from the substituent group $\alpha_3$, a pyridyl group which may be substituted with one or more substituents selected from the substituent group $\alpha_3$, a pyrimidinyl group which may be substituted with one or more substituents selected from the substituent group $\alpha_3$, a pyrazinyl group which may be substituted with one or more substituents selected from the substituent group $\alpha_3$, a pyridazinyl group which may be substituted with one or more substituents selected from the substituent group $\alpha_3$, an azetidinyl which may be substituted with one or more substituents selected from the substituent group $\alpha_3$, a pyrrolidinyl group which may be substituted with one or more substituents selected from the substituent group $\alpha_3$, a piperidinyl group which may be substituted with one or more substituents selected from the substituent group $\alpha_3$, a piperazinyl group which may be substituted with one or more substituents selected from the substituent group $\alpha_3$, a morpholinyl group which may be substituted with one or more substituents selected from the substituent group $\alpha_3$, a homopiperazinyl group which may be substituted with one or more substituents selected from the substituent group $\alpha_3$, or $NR^{12b}R^{13d}$;
$R^{12b}$ represents a hydrogen atom or a $C_{1-6}$ alkyl group;
$R^{13d}$ represents a phenyl group which may be substituted with one or more substituents selected from the substituent group $\alpha_3$, a pyrazolyl group which may be substituted with one or more substituents selected from the substituent group $\alpha_3$, an isoxazolyl group which may be substituted with one or more substituents selected from the substituent group $\alpha_3$, a pyridyl group which may be substituted with one or more substituents selected from the substituent group $\alpha_3$, a pyrimidinyl group which may be substituted with one or more substituents selected from the substituent group $\alpha_3$, a pyrazinyl group which may be substituted with one or more substituents selected from the substituent group $\alpha_3$, a pyridazinyl group which may be substituted with one or more substituents selected from the substituent group $\alpha_3$, a pyrrolidinyl group which may be substituted with one or more substituents selected from the substituent group $\alpha_3$, a piperidinyl group which may be substituted with one or more substituents selected from the substituent group $\alpha_3$, or a tetrahydropyridyl group which may be substituted with one or more substituents selected from the substituent group $\alpha_3$;
the substituent group $\alpha_3$ consists of a halogen atom, a hydroxyl group which may be protected, an amino group which may be protected, a carboxyl group which may be protected, a cyano group, a carbamoyl group which may be substituted with one or more substituents selected from a substituent group $\beta_3$, a $C_{1-6}$ alkyl group which may be substituted with one or more substituents selected from the substituent group $\beta_3$, a $C_{3-8}$ cycloalkyl group which may be substituted with one or more substituents selected from the substituent group $\beta_3$, an aryl group which may be substituted with one or more substituents selected from the substituent group $\beta_3$, a $C_{1-6}$ alkoxy group which may be substituted with one or more substituents selected from the substituent group $\beta_3$, an aryloxy group which may be substituted with one or more substituents selected from the substituent group $\beta_3$, a $C_{1-6}$ alkylthio group which may be substituted with one or more substituents selected from the substituent group β₃, an arylthio group which may be substituted with one or more substituents selected from the substituent group β₃, a $C_{1-6}$ alkylamino group which may be substituted with one or more substituents selected from the substituent group β₃, a di($C_{1-6}$ alkyl) amino group which may be substituted with one or more substituents selected from the substituent group β₃, a $C_{1-6}$ alkylsulfonyl group which may be substituted with one or more substituents selected from the substituent group β₃, an arylsulfonyl group which may be substituted with one or more substituents selected from the substituent group β₃, an acyl group which may be substituted with one or more substituents selected from the substituent group β₃, a heteroaryl group which may be substituted with one or more substituents selected from the substituent group β₃, a heterocyclyl group which may be substituted with one or more substituents selected from the substituent group β₃, a heterocyclyloxy group which may be substituted with one or more substituents selected from the substituent group β₃, and an oxo group;

the substituent group β₃ consists of a halogen atom, a hydroxyl group which may be protected, an amino group which may be protected, a carboxyl group which may be protected, a cyano group, a carbamoyl group which may be substituted with one or more substituents selected from a substituent group γ₃, a $C_{1-6}$ alkyl group which may be substituted with one or more substituents selected from the substituent group γ₃, a $C_{3-8}$ cycloalkyl group which may be substituted with one or more substituents selected from the substituent group γ₃, an aryl group which may be substituted with one or more substituents selected from the substituent group γ₃, a $C_{1-6}$ alkoxy group which may be substituted with one or more substituents selected from the substituent group γ₃, a $C_{1-6}$ alkylamino group which may be substituted with one or more substituents selected from the substituent group γ₃, a di($C_{1-6}$ alkyl)amino group which may be substituted with one or more substituents selected from the substituent group γ₃, a $C_{1-6}$ alkylsulfonyl group which may be substituted with one or more substituents selected from the substituent group γ₃, an arylsulfonyl group which may be substituted with one or more substituents selected from the substituent group γ₃, a heteroaryl group which may be substituted with one or more substituents selected from the substituent group γ₃, a heterocyclyl group which may be substituted with one or more substituents selected from the substituent group γ₃, a heterocyclyloxy group which may be substituted with one or more substituents selected from the substituent group γ₃, and an oxo group; and the substituent group γ₃ consists of a halogen atom, a hydroxyl group which may be protected, an amino group which may be protected, a carboxyl group which may be protected, a cyano group, a $C_{1-6}$ alkyl group which may be substituted with a halogen atom, a $C_{1-6}$ alkoxy group which may be substituted with a halogen atom, and an oxo group.

16. A nitrogen-containing heterocyclic compound represented by the following Formula [1a] or a salt thereof:

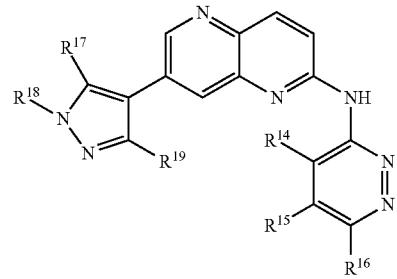

[1a]

wherein, in Formula [1a]:

each of $R^{14}$, $R^{15}$, and $R^{16}$ independently represents a hydrogen atom, a halogen atom, a hydroxyl group which may be protected, an amino group which may be protected, a carboxyl group which may be protected, a cyano group, a carbamoyl group which may be substituted with one or more substituents selected from a substituent group $B_1$, a sulfamoyl group which may be substituted with one or more substituents selected from the substituent group $B_1$, a $C_{1-6}$ alkyl group which may be substituted with one or more substituents selected from the substituent group $B_1$, a $C_{2-6}$ alkenyl group which may be substituted with one or more substituents selected from the substituent group $B_1$, a $C_{3-8}$ cycloalkyl group which may be substituted with one or more substituents selected from the substituent group $B_1$, an aryl group which may be substituted with one or more substituents selected from the substituent group $B_1$, a $C_{1-6}$ alkoxy group which may be substituted with one or more substituents selected from the substituent group $B_1$, a $C_{3-8}$ cycloalkoxy group which may be substituted with one or more substituents selected from the substituent group $B_1$, an aryloxy group which may be substituted with one or more substituents selected from the substituent group $B_1$, a $C_{1-6}$ alkylthio group which may be substituted with one or more substituents selected from the substituent group $B_1$, an arylthio group which may be substituted with one or more substituents selected from the substituent group $B_1$, a $C_{1-6}$ alkylamino group which may be substituted with one or more substituents selected from the substituent group $B_1$, a di($C_{1-6}$ alkyl)amino group which may be substituted with one or more substituents selected from the substituent group $B_1$, an acyl group which may be substituted with one or more substituents selected from the substituent group $B_1$, a heteroaryl group which may be substituted with one or more substituents selected from the substituent group $B_1$, or a heterocyclyl group which may be substituted with one or more substituents selected from the substituent group $B_1$;

each of $R^{17}$, $R^{18}$, and $R^{19}$ independently represents a hydrogen atom, a halogen atom, a hydroxyl group which may be protected, an amino group which may be protected, an amino group which may be substituted with one or more substituents selected from a substituent group $E_3$, a carboxyl group which may be protected, a cyano group, a carbamoyl group which may be substituted with one or more substituents selected from a substituent group $B_3$, a sulfamoyl group which may be substituted with one or more substituents selected from the substituent group $B_3$, a $C_{1-6}$ alkyl group which may be substituted with one or more substituents selected from the substituent group $B_3$, a $C_{2-6}$ alkenyl group which may be substituted with one or more substituents selected from the substituent group $B_3$, a $C_{3-8}$ cycloalkyl group which may be substituted with one or more substituents selected from the substituent group $B_3$, an aryl group which may be substituted with one or more substituents selected from the substituent group $B_3$, a $C_{1-6}$ alkoxy group which may be substituted with one or more substituents selected from the substituent group $B_3$, an aryloxy group which may be substituted with one or more substituents selected from the substituent group $B_3$, a $C_{1-6}$ alkylthio group which may be substituted with one or more substituents selected from the substituent group $B_3$, an arylthio group which may be substituted with one or more substituents selected from the substituent group $B_3$, a $C_{1-6}$ alkyl amino group which may be substituted with one or more substituents selected from the substituent group $B_3$, a di($C_{1-6}$ alkyl)amino group which may be substituted with one or more substituents selected from the substituent group $B_3$, a $C_{1-6}$ alkylsulfonyl group which may be substituted with one or more substituents selected from the substituent group $B_3$, an arylsulfonyl group which may be substituted with one or more substituents selected from the substituent group $B_3$, an acyl group which may be substituted with one or more substituents selected from the substituent group $B_3$, a heteroaryl group which may be substituted with one or more substituents selected from the substituent group $B_3$, a heterocyclyl group which may be substituted with one or more substituents selected from the substituent group $B_3$, or a heterocyclyloxy group which may be substituted with one or more substituents selected from the substituent group $B_3$;

the substituent group $B_1$ consists of a halogen atom, a hydroxyl group which may be protected, an amino group which may be protected, a carboxyl group which may be protected, a cyano group, a carbamoyl group which may be substituted with one or more substituents selected from a substituent group $C_1$, a sulfamoyl group which may be substituted with one or more substituents selected from the substituent group $C_1$, a $C_{1-6}$ alkyl group which may be substituted with one or more substituents selected from the substituent group $C_1$, a $C_{3-8}$ cycloalkyl group which may be substituted with one or more substituents selected from the substituent group $C_1$, an aryl group which may be substituted with one or more substituents selected from the substituent group $C_1$, a $C_{1-6}$ alkoxy group which may be substituted with one or more substituents selected from the substituent group $C_1$, a $C_{1-6}$ alkylamino group which may be substituted with one or more substituents selected from the substituent group $C_1$, a di($C_{1-6}$ alkyl)amino group which may be substituted with one or more substituents selected from the substituent group $C_1$, a $C_{1-6}$ alkylsulfonyl group which may be substituted with one or more substituents selected from the substituent group $C_1$, an arylsulfonyl group which may be substituted with one or more substituents selected from the substituent group $C_1$, an acyl group which may be substituted with one or more substituents selected from the substituent group $C_1$, a heteroaryl group which may be substituted with one or more substituents selected from the substituent group $C_1$, a heterocyclyl group which may be substituted with one or more substituents selected from the substituent group $C_1$, and an oxo group;

the substituent group $C_1$ consists of a halogen atom, a hydroxyl group which may be protected, an amino group which may be protected, a carboxyl group which may be protected, a cyano group, a carbamoyl group which may be substituted with a $C_{1-6}$ alkyl group, a $C_{1-6}$ alkyl group which may be substituted with a halogen atom, an aryl group which may be substituted with a halogen atom or a $C_{1-6}$ alkyl group, a $C_{1-6}$ alkoxy group which may be substituted with a halogen atom, and an oxo group;

the substituent group $B_3$ consists of a halogen atom, a hydroxyl group which may be protected, an amino group which may be protected, a carboxyl group which may be protected, a cyano group, a carbamoyl group which may be substituted with one or more substituents selected from a substituent group $C_3$, a $C_{1-6}$ alkyl group which may be substituted with one or more substituents selected from the substituent group $C_3$, a $C_{3-8}$ cycloalkyl group which may be substituted with one or more substituents selected from the substituent group $C_3$, an aryl group which may be substituted with one or more substituents selected from the substituent group $C_3$, a $C_{1-6}$ alkoxy group which may be substituted with one or more substituents selected from the substituent group $C_3$, an aryloxy group which may be substituted with one or more substituents selected from the substituent group $C_3$, a $C_{1-6}$ alkylamino group which may be substituted with one or more substituents selected from the substituent group $C_3$, a di($C_{1-6}$ alkyl)amino group which may be substituted with one or more substituents selected from the substituent group $C_3$, a $C_{1-6}$ alkylsulfonyl group which may be substituted with one or more substituents selected from the substituent group $C_3$, an arylsulfonyl group which may be substituted with one or more substituents selected from the substituent group $C_3$, an acyl group which may be substituted with one or more substituents selected from the substituent group $C_3$, a heteroaryl group which may be substituted with one or more substituents selected from the substituent group $C_3$, a heterocyclyl group which may be substituted with one or more substituents selected from the substituent group $C_3$, a heteroaryloxy group which may be substituted with one or more substituents selected from the substituent group $C_3$, a heterocyclyloxy group which may be substituted with one or more substituents selected from the substituent group $C_3$, and an oxo group;

the substituent group $C_3$ consists of a halogen atom, a hydroxyl group which may be protected, an amino group which may be protected, a carboxyl group which may be protected, a nitro group, cyano group, a carbamoyl group which may be substituted with one or more substituents selected from a substituent group $D_3$, a $C_{1-6}$ alkyl group which may be substituted with one or more substituents selected from the substituent group $D_3$, a $C_{3-8}$ cycloalkyl group which may be substituted with one or more substituents selected from the substituent group $D_3$, an aryl group which may be substituted with one or more substituents selected from the substituent group $D_3$, a $C_{1-6}$ alkoxy group which may be substituted with one or more substituents selected from the substituent group $D_3$, an aryloxy group which may be substituted with one or more substituents selected from the substituent group $D_3$, a $C_{1-6}$ alkylamino group which may be substituted with one or more substituents selected from the substituent group $D_3$, a di($C_{1-6}$ alkyl)amino group which may be substituted with one or more substituents selected from the substituent group D₃, a C₁₋₆ alkylsulfonyl group which may be substituted with one or more substituents selected from the substituent group D₃, an acyl group which may be substituted with one or more substituents selected from the substituent group D₃, a heteroaryl group which may be substituted with one or more substituents selected from the substituent group D₃, a heterocyclyl group which may be substituted with one or more substituents selected from the substituent group D₃, a silyl group which may be substituted with one or more substituents selected from the substituent group D₃, and an oxo group;

the substituent group D₃ consists of a halogen atom, a hydroxyl group which may be protected, a C₁₋₆ alkyl group, a C₃₋₈ cycloalkyl group, an aryl group, a C₁₋₆ alkoxy group, a C₁₋₆ alkylamino group, a di(C₁₋₆ alkyl) amino group, a C₁₋₆ alkylsulfonyl group, a heteroaryl group, a heterocyclyl group, and an oxo group;

the substituent group E₃ consists of a C₃₋₈ cycloalkyl group which may be substituted with one or more substituents selected from a substituent group F₃, an aryl group which may be substituted with one or more substituents selected from the substituent group F₃, a heteroaryl group which may be substituted with one or more substituents selected from the substituent group F₃, and a heterocyclyl group which may be substituted with one or more substituents selected from the substituent group F₃; and the substituent group F₃ consists of a halogen atom, a carboxyl group which may be protected, and a C₁₋₆ alkyl group.

17. The nitrogen-containing heterocyclic compound or salt thereof according to claim 16, wherein each of R¹⁴, R¹⁶ and R¹⁷ represents a hydrogen atom.

18. A pharmaceutical composition comprising the nitrogen-containing heterocyclic compound or salt thereof according to claim 1 and a pharmacologically acceptable additive.

19. A nitrogen-containing heterocyclic compound or salt thereof, the compound being any one of the compounds set forth below:

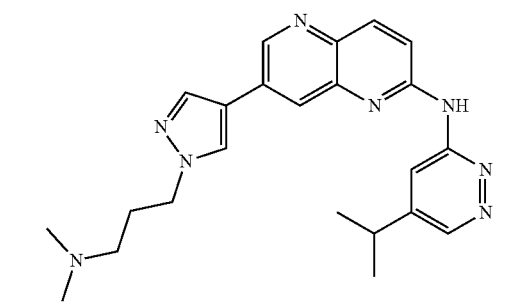

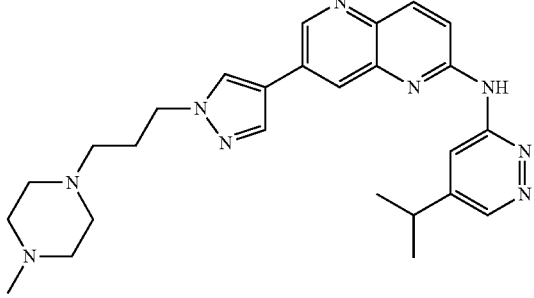

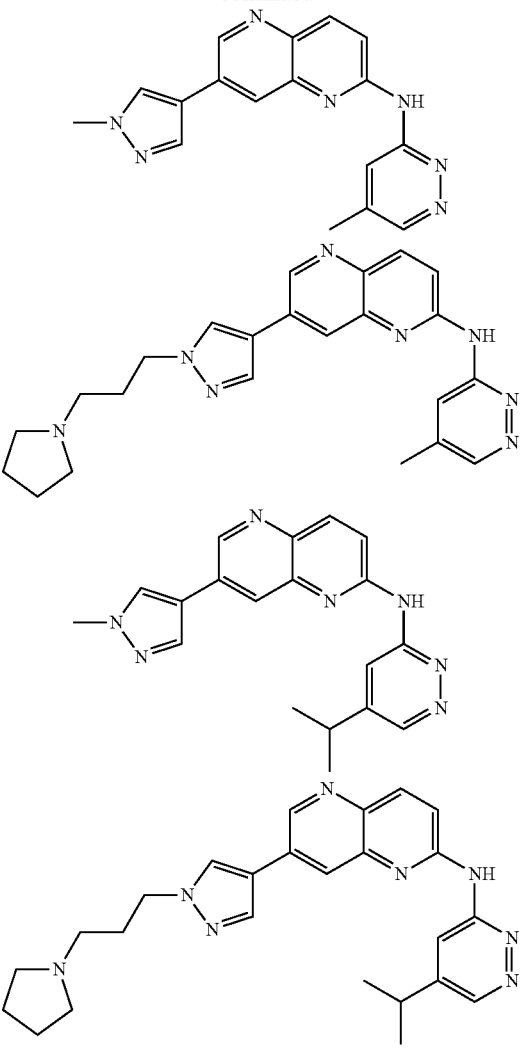

-continued

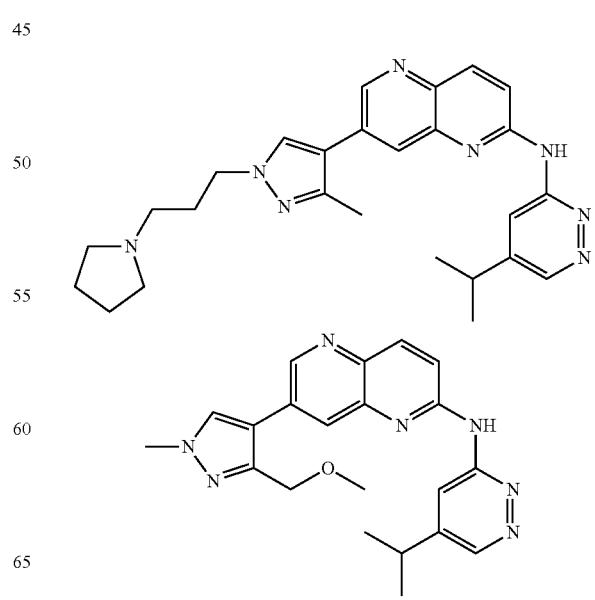

1115
-continued
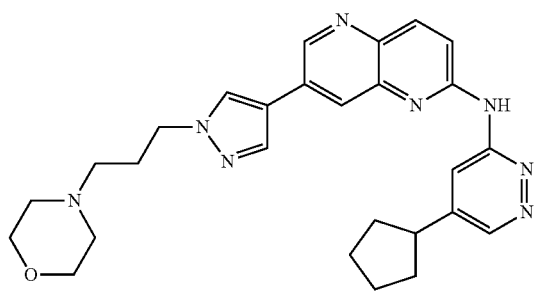
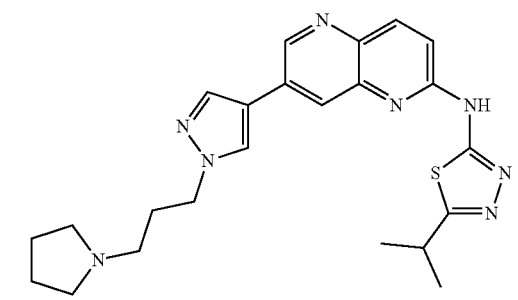
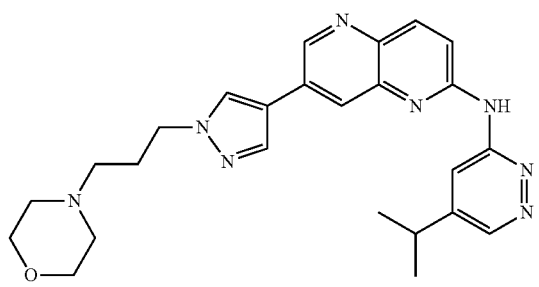
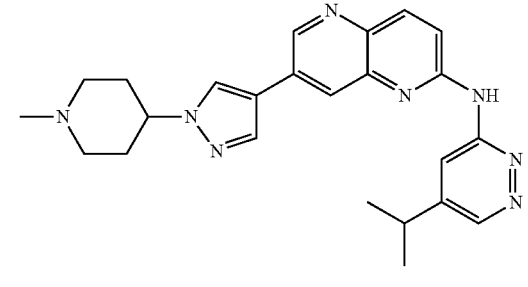
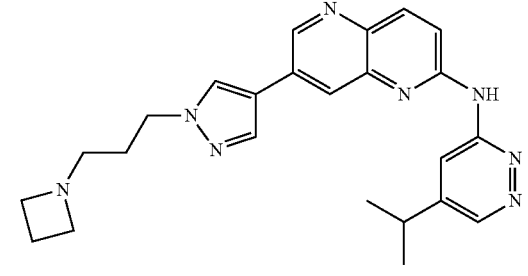
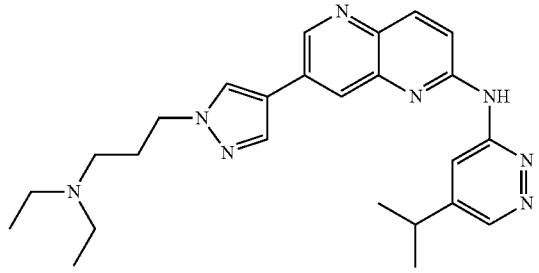
1116
-continued
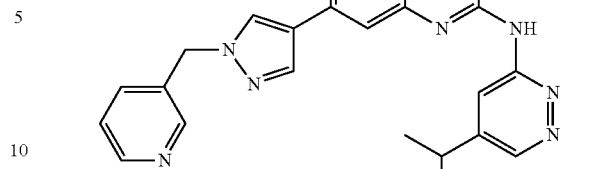
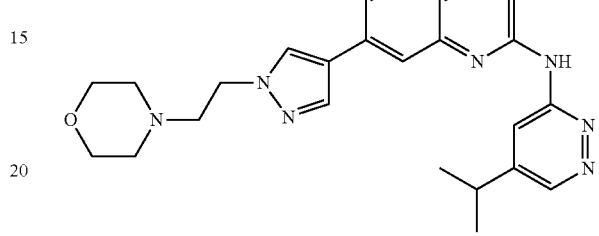
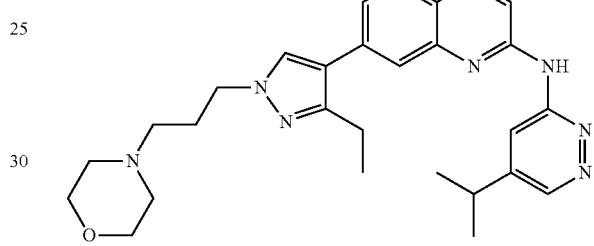
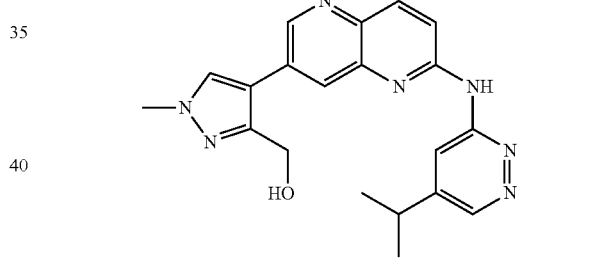
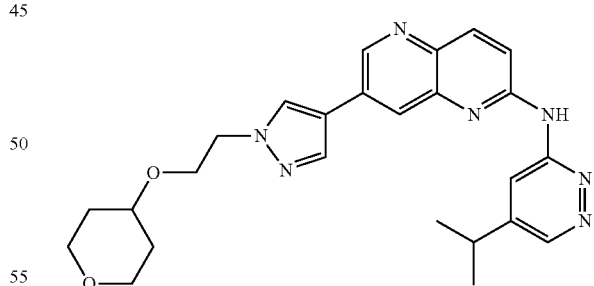
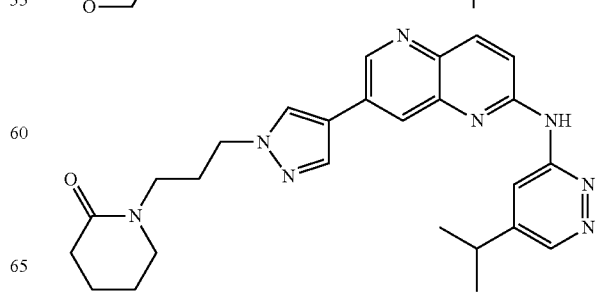

1117
-continued
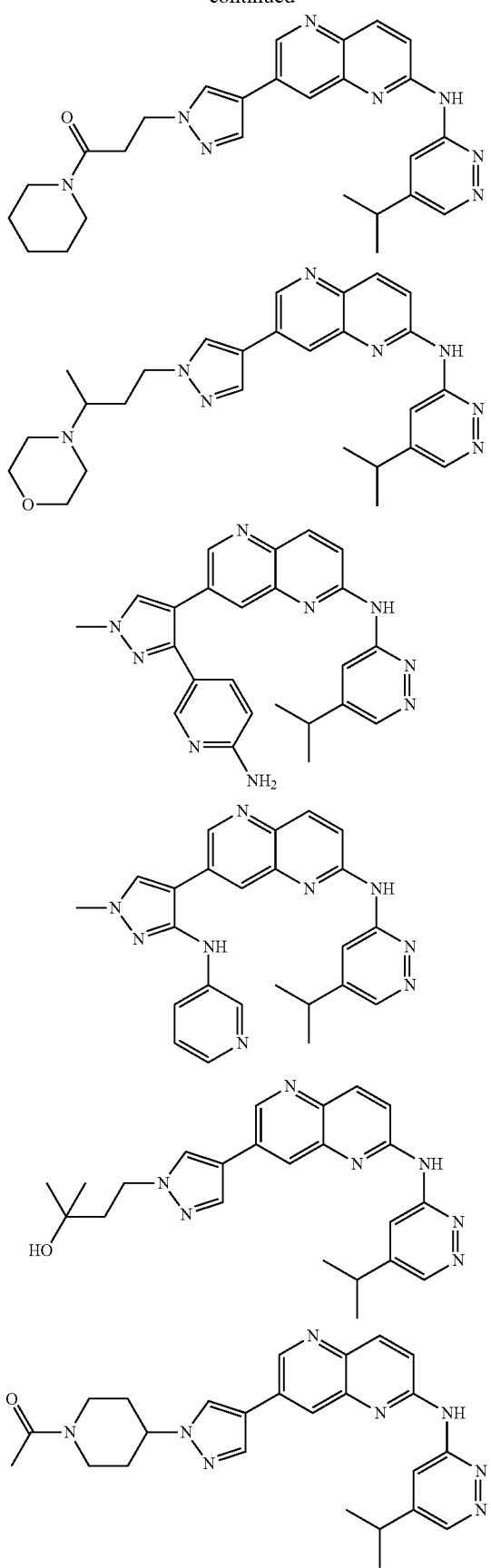
1118
-continued
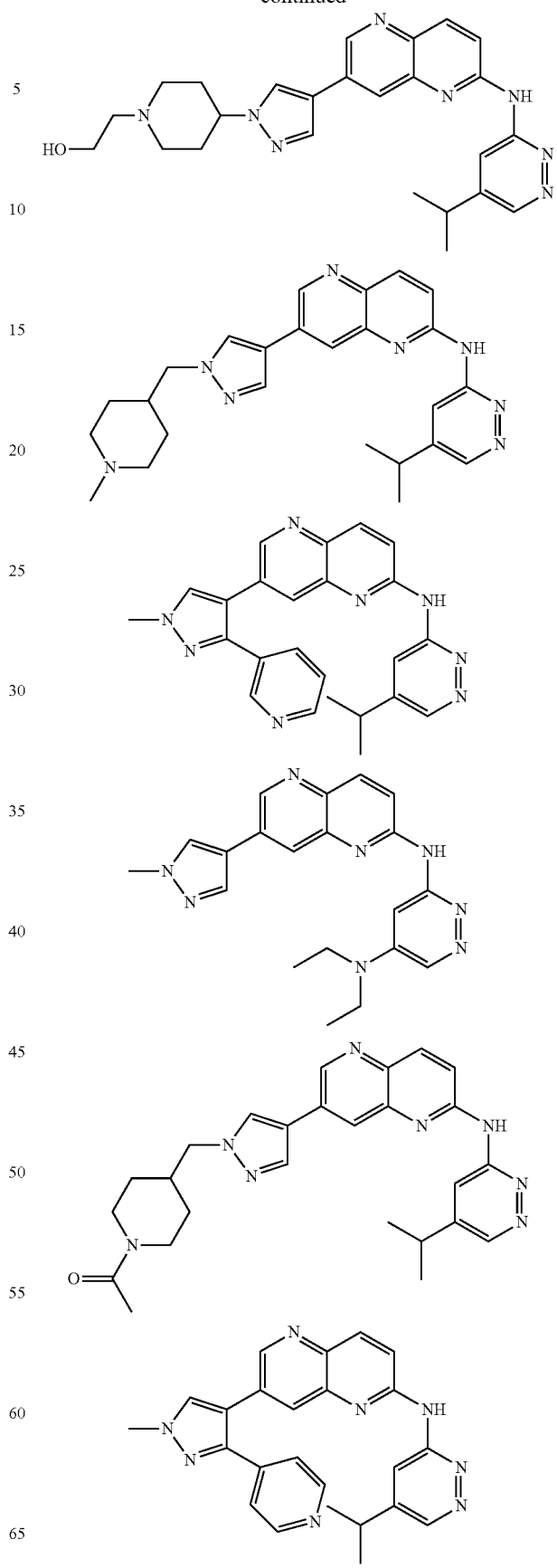

1119
-continued
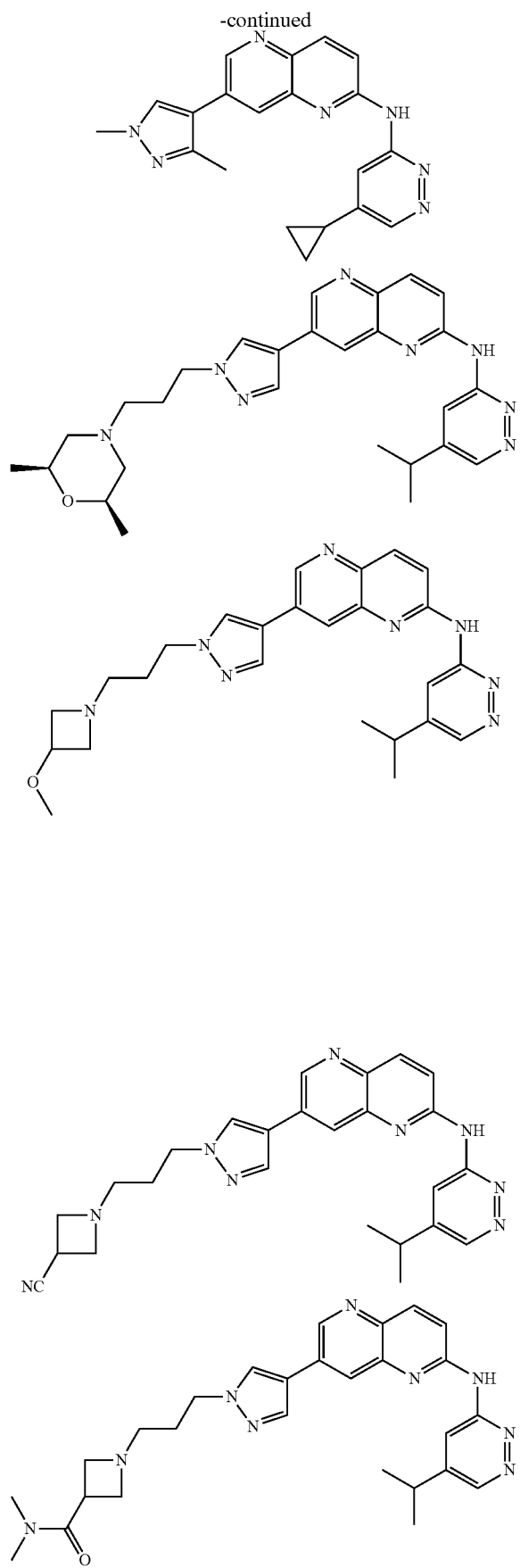
1120
-continued
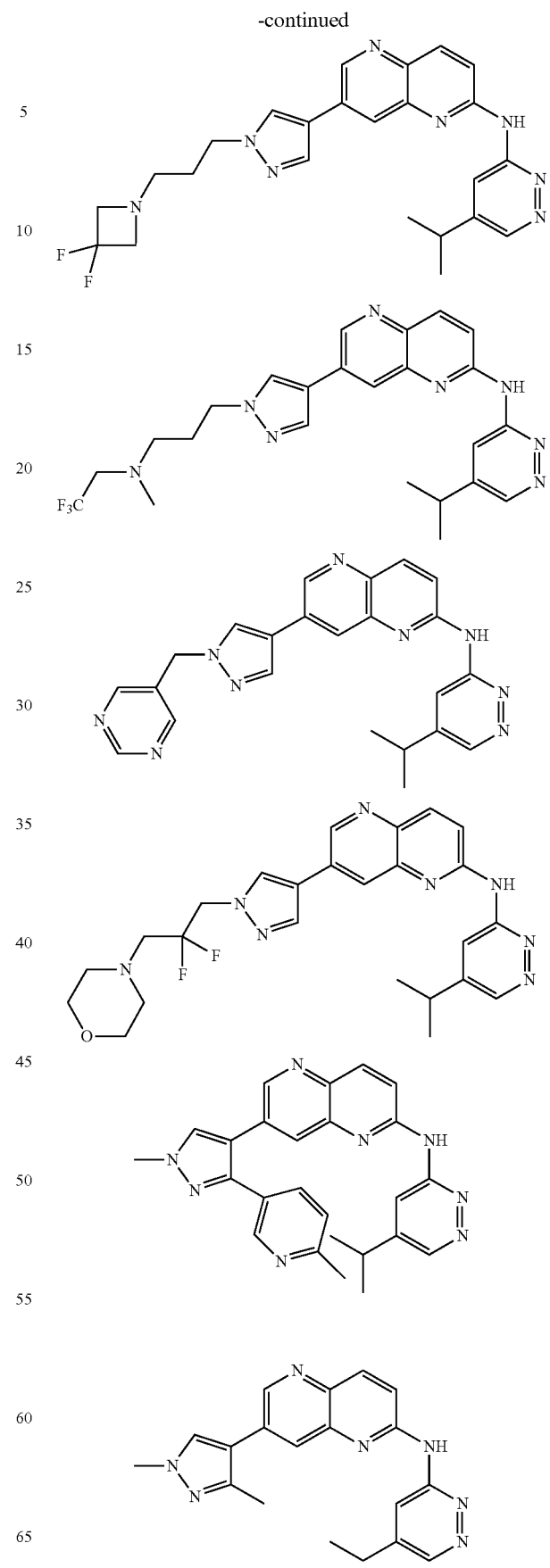

1121
-continued
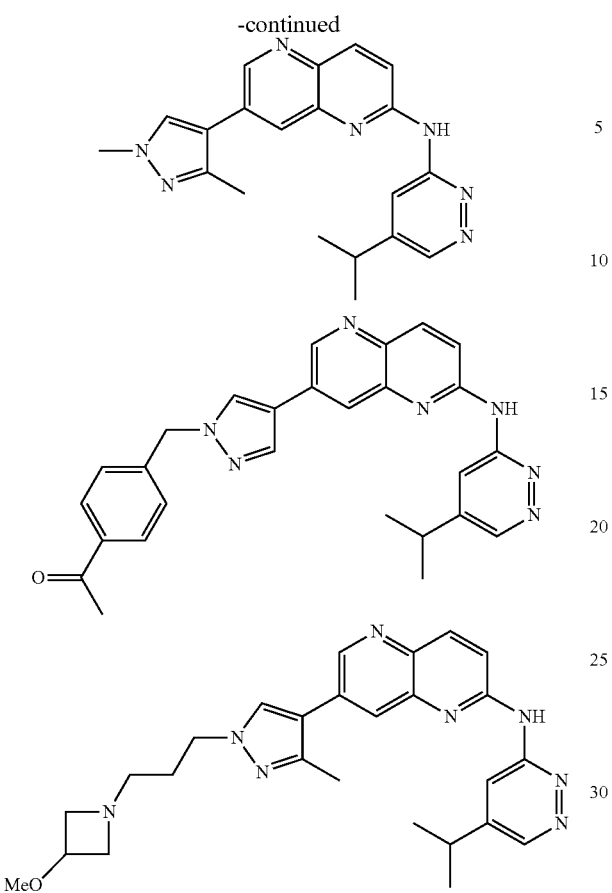
1122
-continued
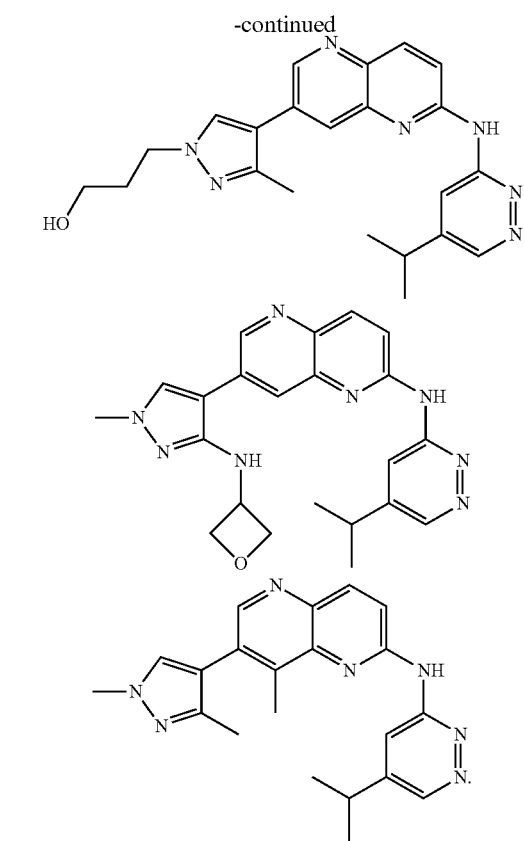
* * * * *